US008728790B2

(12) United States Patent
Basler et al.

(10) Patent No.: US 8,728,790 B2
(45) Date of Patent: *May 20, 2014

(54) COMPOSITIONS AND METHODS COMPRISING PROTEASE VARIANTS

(75) Inventors: Joshua R Basler, Palo Alto, CA (US); Luis G Cascão-Pereira, Redwood City, CA (US); David A Estell, San Francisco, CA (US); James T Kellis, Jr., Woodside, CA (US); Alexander Pisarchik, Belmont, CA (US); Ayrookaran J. Poulose, Belmont, CA (US); Daniel E. Torres Pazmino, Leiden (NL)

(73) Assignee: Danisco US Inc., Palo Alto, CA (US)

( * ) Notice: Subject to any disclaimer, the term of this patent is extended or adjusted under 35 U.S.C. 154(b) by 34 days.

This patent is subject to a terminal disclaimer.

(21) Appl. No.: 12/963,930

(22) Filed: Dec. 9, 2010

(65) Prior Publication Data

US 2011/0262999 A1    Oct. 27, 2011

Related U.S. Application Data

(60) Provisional application No. 61/285,127, filed on Dec. 9, 2009, provisional application No. 61/392,373, filed on Oct. 12, 2010.

(51) Int. Cl.
C12N 9/64 (2006.01)

(52) U.S. Cl.
USPC .......................................................... 435/226

(58) Field of Classification Search
None
See application file for complete search history.

(56) References Cited

U.S. PATENT DOCUMENTS

| | | |
|---|---|---|
| 4,246,612 A | 1/1981 | Berry et al. |
| 4,430,243 A | 2/1984 | Bragg |
| 4,683,195 A | 7/1987 | Mullis et al. |
| 4,683,202 A | 7/1987 | Mullis |
| 4,760,025 A | 7/1988 | Estell et al. |
| 4,810,410 A | 3/1989 | Diakun et al. |
| 5,227,084 A | 7/1993 | Martens et al. |
| 5,264,366 A | 11/1993 | Ferrari et al. |
| RE34,606 E | 5/1994 | Estell et al. |
| 5,340,735 A | 8/1994 | Christianson et al. |
| 5,352,604 A | 10/1994 | Wilson et al. |
| 5,486,303 A | 1/1996 | Capeci et al. |
| 5,489,392 A | 2/1996 | Capeci et al. |
| 5,500,364 A | 3/1996 | Christianson et al. |
| 5,516,448 A | 5/1996 | Capeci et al. |
| 5,565,422 A | 10/1996 | Del Greco et al. |
| 5,569,645 A | 10/1996 | Dinniwell et al. |
| 5,574,005 A | 11/1996 | Welch et al. |
| 5,576,282 A | 11/1996 | Miracle et al. |
| 5,595,967 A | 1/1997 | Miracle et al. |
| 5,597,936 A | 1/1997 | Perkins et al. |
| 5,691,297 A | 11/1997 | Nassano et al. |
| 5,700,676 A | 12/1997 | Bott et al. |
| 5,801,039 A | 9/1998 | Maurer et al. |
| 5,855,625 A | 1/1999 | Maurer et al. |
| 5,879,584 A | 3/1999 | Bianchetti et al. |
| 5,888,954 A | 3/1999 | Haerer et al. |
| 5,955,340 A | 9/1999 | Bott et al. |
| 6,225,464 B1 | 5/2001 | Hiler, II et al. |
| 6,306,812 B1 | 10/2001 | Perkins et al. |
| 6,312,936 B1 | 11/2001 | Poulose et al. |
| 6,326,348 B1 | 12/2001 | Vinson et al. |
| 6,376,450 B1 | 4/2002 | Ghosh et al. |
| 6,472,184 B1 | 10/2002 | Hegemann |
| 6,482,628 B1 | 11/2002 | Poulose et al. |
| 6,566,112 B2 | 5/2003 | Jones et al. |
| 6,586,223 B1 | 7/2003 | Sikorski et al. |
| 6,605,458 B1 | 8/2003 | Hansen et al. |
| 6,610,642 B2 | 8/2003 | Ghosh et al. |
| 8,224,578 B2 | 7/2012 | Raab et al. |
| 2002/0081703 A1 | 6/2002 | Estell |
| 2003/0118605 A1 | 6/2003 | Estell et al. |
| 2004/0209343 A1 | 10/2004 | Svendsen et al. |
| 2005/0054843 A1 | 3/2005 | Estell et al. |
| 2005/0148059 A1 | 7/2005 | Estell et al. |
| 2005/0239043 A1 | 10/2005 | Harding |
| 2006/0089284 A1 | 4/2006 | Miracle et al. |
| 2008/0090747 A1 | 4/2008 | Augustinus et al. |

FOREIGN PATENT DOCUMENTS

| | | |
|---|---|---|
| CA | 2162459 | 11/1994 |
| EP | 0 201 184 | 12/1992 |
| EP | 0 200 362 | 12/1996 |
| EP | 2 100 949 | 9/2009 |
| WO | WO 89/06270 | 7/1989 |
| WO | WO 92/21760 | 12/1992 |
| WO | WO 95/23221 | 8/1995 |
| WO | WO 95/29979 | 11/1995 |
| WO | WO 95/30010 | 11/1995 |
| WO | WO 99/06521 | 2/1999 |
| WO | WO 99/34011 | 7/1999 |
| WO | WO 00/32601 | 6/2000 |
| WO | WO 2007/044993 | 4/2007 |

(Continued)

OTHER PUBLICATIONS

Christianson, T., et al., "Peptide Mapping of Subtilisins as a Practical Tool for Locating Protein Sequence Errors During Extensive Protein Engineering Projects." *Anal. Biochem.* 223: 119-129 (1994).

Heinz, D.W., et al., "Changing the Inhibitory Specificity and Function of the Proteinase Inhibitor Eglin *c* by Site-Directed Mutagenesis: Functional and Structural Investigation." *Biochemistry* 31: 8755-8766, 1992.

Hsia, C.Y., et al., "Active-Site Titration of Serine Proteases Using a Fluoride Ion Selective Electrode and Sulfonyl Fluoride Inhibitors." *Anal. Biochem.* 242: 221-227, 1996.

Maddox, D.E., et al., "Elevated Serum Levels in Human Pregnancy of a Molecule Immunochemically Similar to Eosinophil Granule Major Basic Protein." *J. Exp. Med.* 158: 1211-1226, 1983.

McKenzie, T., et al., "The Nucleotide Sequence of pUB110: Some Salient Features in Relation to Replication and Its Regulation." *Plasmid* 15(2): 93-103, 1986.

(Continued)

*Primary Examiner* — Sheridan Swope
(74) *Attorney, Agent, or Firm* — Danisco US Inc.

(57) ABSTRACT

The present invention provides protease variants, compositions comprising protease variants, and methods of using such protease variants and compositions.

3 Claims, 8 Drawing Sheets

(56) References Cited

FOREIGN PATENT DOCUMENTS

| WO | WO 2007/145964 | 12/2007 |
|---|---|---|
| WO | WO 2009/149144 | 12/2009 |
| WO | WO 2009/149200 | 12/2009 |

OTHER PUBLICATIONS

Ottesen, M., et al. "Subtilisin." In *Methods of Enzymatic Analysis—Third Edition; Enzymes 3: Peptidases, Proteinases and Their Inhibitors*, vol. 5, Chapter 2.7, pp. 159-163, Bergmeyer, et al., eds., Verlag Chemie, Weinham, Germany, 1984.

Pisarchik, A., et al., "Probing the structural plasticity of an archaeal primordial cobaltochelatase CbiX$^s$." *Prot. Eng. Des. Select.* 20: 257-265, 2007.

Rawlings, N.D., et al., "Evolutionary Family of Peptides." *Biochem. J.* 290: 205-218, 1993.

Rawlings, N.D., et al., "MEROPS: the peptidase database." *Nucl. Acids Res.* 34 Database issue, D270-D272, 2006.

Walter, H.-E., et al., "Method with Haemoglobin, Casein and Azocoll as Substrate." In *Methods of Enzymatic Analysis—Third Edition; Enzymes 3: Peptidases, Proteinases and Their Inhibitors*, vol. 5, Chapter 2.15.2, pp. 270-277, Bergmeyer, et al., eds., Verlag Chemie, Weinham, Germany, 1984.

Ward, O.P., "Proteinases." In *Microbial Enzymes and Biotechnology*, Fogarty, W.M., ed., Applied Science Publishers, London, England, Chapter 6, pp. 251-317, 1983.

Wells, J.A., et al., "Cloning, sequencing, and secretion of *Bacillus amyloliquefaciens* subtilisin in *Bacillus subtilis*." *Nucleic Acids Res.* 11(22): 7911-7925, 1983.

International Search Report and the Written Opinion of the International Searching Authority for International Application No. PCT/US10/59628 dated Aug. 3, 2011.

Brode, P.F., III, et al., "Subtilisin BPN' variants: Increased hydrolytic activity on surface-bound substrates via decreased surface activity." *Biochemistry* 35(10):3162-3169, 1996.

Supplementary European Search Report for European Patent Application No. 10 83 6666 mailed May 17, 2013.

FIGURE 5

```
BPN'    1   AQSVPYGVSQ IKAPALHSQG YTGSNVKVAV IDSGIDSSHP DLKVAGGASM VPSETNPFQD
GG36    1   AQSVPWGISR VQAPAAHNRG LTGSGVKVAV LDTGIS-THP DLNIRGGASF VPGEPST-QD

BPN'    61  NNSHGTHVAG TVAALNNSIG VLGVAPSASL YAVKVLGADG SGQYSWIING IEWAIANNMD
GG36    59  GNGHGTHVAG TIAALNNSIG VLGVAPSAEL YAVKVLGASG SGSVSSIAQG LEWAGNNGMH

161
BPN'    121 VINMSLGGPS GSAALKAAVD KAVASGVVVV AAAGNEGTSG SSSTVGYPGK YPSVIAVGAV
GG36    119 VANLSLGSPS PSATLEQAVN SATSRGVLVV AASGNSGAGS ----ISYPAR YANAMAVGAT

BPN'    181 DSSNQRASFS QYGPELDVMA PGVSIQSTLP GNKYGAYNGT SMASPHVAGA AALILSKHPN
GG36    175 DQNNNRASFS QYGAGLDIVA PGVNVQSTYP GSTYASLNGT SMATPHVAGA AALVKQKNPS

BPN'    241 WTNTQVRSSL ENTTTKLGDS FYYGKGLINV QAAAQ
GG36    235 WSNVQIRNHL KNTATSLGST NLYGSGLVNA EAATR
```

COMPOSITIONS AND METHODS COMPRISING PROTEASE VARIANTS

CROSS-REFERENCES TO RELATED APPLICATIONS

This application claims priority to and benefit of U.S. Provisional Patent Application No. 61/285,127, filed on Dec. 9, 2009, and U.S. Provisional Patent Application No. 61/392,373, filed on Oct. 12, 2010, the disclosure of each of which is incorporated herein by reference in its entirety for all purposes.

SEQUENCE LISTING

The sequence listing submitted via EFS, in compliance with 37 C.F.R. §1.52(e), is incorporated herein by reference. The sequence listing text file submitted via EFS contains the file "31488US-2-seqlist.txt" created on Jan. 31, 2011, which is 263,237 bytes in size.

FIELD OF THE INVENTION

The present invention provides protease variants, compositions comprising protease variants, and methods of using such protease variants and compositions thereof.

BACKGROUND OF THE INVENTION

Although proteases have long been known in the art of industrial enzymes, there remains a need for engineered proteases that are suitable for particular conditions and uses. The present invention fills these and other needs.

SUMMARY OF THE INVENTION

In a first aspect, the invention provides an isolated protease variant of a parent protease enzyme, the protease variant having proteolytic activity and comprising an amino acid sequence which comprises an alteration at one or more amino acid positions corresponding to amino acid positions of SEQ ID NO:2 selected from the group consisting of positions 24, 53, 78, 97, 101, 128, and 217, wherein the at least one alteration is independently (i) an insertion of one or more amino acid residues upstream or downstream of the amino acid residue which occupies the position, (ii) a deletion of the amino acid residue which occupies the position, or (iii) a substitution of the amino acid residue which occupies the position with a different amino acid residue, wherein each amino acid position is numbered by correspondence with an amino acid position in the amino acid sequence of *Bacillus amyloliquefaciens* subtilisin protease BPN' set forth in SEQ ID NO:2 as determined by alignment of the amino acid sequence of the variant with SEQ ID NO:2.

In a second aspect, the invention provides an isolated protease variant of a parent protease, the variant comprising an amino acid sequence comprising three amino acid substitutions selected from the group consisting of X024G/R, X053G, X078N, X101N, X128A/S, and X217L/Q, wherein the variant has proteolytic activity and each amino acid position of the variant is numbered by correspondence to an amino acid position in the amino acid sequence of SEQ ID NO:2 as determined by alignment of the amino acid sequence of the variant with SEQ ID NO:2.

In a third aspect, the invention provides an isolated polypeptide having protease activity, said polypeptide comprising an amino acid sequence having at least 85% sequence identity to a polypeptide sequence selected from the group consisting of:
a) BPN'-S024G+S053G+S078N+S101N+G128A+Y217Q+A088T+N109G+A116T+G131H+N243V+L257G;
b) BPN'-S024G+S053G+S078N+S101N+G128A+Y217Q+S033T+N076D;
c) BPN'-S024G+S053G+S078N+S101N+G128S+Y217Q+S009T+N109G+K141R+N243V;
d) BPN'-S024G+S053G+S078N+S101N+G128A+Y217Q+S162G+K256R;
e) BPN'-S024G+S053G+S078N+S101N+G128A+Y217Q+N109G+A116T;
f) BPN'-S024G+S053G+S078N+S101N+G128A+Y217Q+N109G+L257G;
g) BPN'-S024G+S053G+S078N+S101N+G128A+Y217Q+S162G+L257G;
h) BPN'-S024G+S053G+S078N+S101N+G128A+Y217Q+N061G+N109G+N243V;
i) BPN'-S024G+S053G+S078N+S101N+G128S+Y217Q+N109G+N243V+S248A;
j) BPN'-S024G+S053G+S078N+S101N+G128S+Y217Q+S033T+N076D+N109G+N218S+N243V+S248N+K256R;
k) BPN'-S024G+S053G+S078N+S101N+G128A+Y217Q+N109G+A116T+N243V+K256R;
l) BPN'-S024G+S053G+S078N+S101N+G128A+Y217Q+A088T+N109G+A116T+G131H+N243V;
m) BPN'-S024G+S053G+S078N+S101N+G128A+Y217Q+A088T+N109G;
n) BPN'-S024G+S053G+S078N+S101N+G128A+Y217Q+N109G+N243V;
o) BPN'-S024G+S053G+S078N+S101N+G128A+Y217Q+T158S+L257G;
p) BPN'-S024G+S053G+S078N+S101N+G128A+Y217Q+N061S+N109G+N243V;
q) BPN'-S024G+S053G+S078N+S101N+G128S+Y217Q+P040A+N109G+N243V+S248N+K256R;
r) BPN'-S024G+S053G+S078N+S101N+G128S+Y217Q+S009T+S018T+Y021N+N109G+K141R;
s) BPN'-S024G+S053G+S078N+S101N+G128A+Y217Q+A088T+N109G+A116T+T158S+N243V+K256R;
t) BPN'-S024G+S053G+S078N+S101N+G128A+Y217Q+A088T+N109G+A116T+T158S+N218S+L257G;
u) BPN'-S024G+S053G+S078N+S101N+G128A+Y217Q+N109G+K256R;
v) BPN'-S024G+S053G+S078N+S101N+G128S+Y217Q+N109G+N243V+K256R;
w) BPN'-S024G+S053G+S078N+S101N+G128A+Y217Q+S063G+K256R;
x) BPN'-S024G+S053G+S078N+S101N+G128A+Y217Q+S063G+N109G;
y) BPN'-S024G+S053G+S078N+S101N+G128S+Y217Q+S063G;
z) BPN'-S024G+S053G+S078N+S101N+G128A+Y217Q+S063G+N076D;
aa) BPN'-S024G+S053G+S078N+S101N+G128S+Y217Q+S033T+N076D+N218S;
bb) BPN'-S024G+S053G+S078N+S101N+G128A+Y217Q+N076D+N218S; and
cc) BPN'-S024G+S053G+S078N+S101N+G128A+Y217Q,
wherein each amino acid position of the variant is numbered by correspondence with an amino acid position of the sequence of SEQ ID NO:2.

In a fourth aspect, the invention provides an isolated polypeptide having protease activity selected from the group consisting of: (a) a polypeptide comprising an amino acid sequence having at least 95%, 96%, 97%, 98%, or 99% sequence identity to the polypeptide sequence of SEQ ID NO:6; (b) a polypeptide encoded by a polynucleotide that hybridizes under at least high stringency conditions with (i) the polynucleotide sequence of SEQ ID NO:5 or (ii) a complementary polynucleotide sequence of (i); and (c) a polypeptide encoded by a polynucleotide comprising a polynucleotide sequence having at least 95% sequence identity to the polynucleotide sequence of SEQ ID NO:5.

In a fifth aspect, the invention provides an isolated protease variant of a parent protease, wherein: (a) the variant comprises an amino acid sequence having no more than 20, 15, or 10 alterations relative to the parent protease, wherein (i) the alterations are independently selected from an insertion, a deletion, or a substitution, and (ii) the alterations include a substitution of glycine at positions 24 and 53, a substitution of asparagine at positions 78 and 101, a substitution of alanine or serine at position 128, and a substitution of glutamine at position 217, (b) the parent protease has at least 90% sequence identity to SEQ ID NO:2, (c) the amino acid sequence of SEQ ID NO:2 is used for determining position numbering; and (d) the variant has increased proteolytic activity relative to the parent protease, wherein each amino acid position is numbered by correspondence with an amino acid position of the sequence of SEQ ID NO:2.

In a sixth aspect, the invention provides an isolated protease variant of a parent protease, wherein (a) the variant comprises an amino acid sequence (i) having at least 85% identity to the sequence of SEQ ID NO:2 and (ii) comprising a substitution of glycine at positions 24 and 53, a substitution of asparagine at positions 78 and 101, a substitution of alanine or serine at position 128, and a substitution of glutamine at position 217; (b) the parent protease has at least 85% sequence identity to SEQ ID NO:2; (c) each amino acid position of the variant is numbered by correspondence with an amino acid position of the sequence of SEQ ID NO:2; and (d) the variant has increased proteolytic activity relative to the parent protease.

In another aspect, the invention provides an isolated or recombinant nucleic acid comprising a polynucleotide sequence encoding at least one polypeptide variant (e.g., protease variant) of the invention, or a complementary polynucleotide sequence thereof.

In another aspect, the invention provides an isolated or recombinant nucleic acid comprising a polynucleotide sequence having at least 80% sequence identity to the polynucleotide sequence set forth in SEQ ID NO:3 or SEQ ID NO:5, or a complementary polynucleotide sequence thereof.

In another aspect, the invention provides an expression vector comprising at least one nucleic acid of the invention. Also provided is a recombinant host cell or cell culture comprising at least one nucleic acid or an expression vector of the invention.

In another aspect, the invention provides a method of producing at least one polypeptide (e.g., protease variant) of the invention, the method comprising: (a) introducing a recombinant expression vector of the invention which encodes a polypeptide (e.g., protease variant) of the invention into a population of cells; (b) culturing the cells in a culture medium under conditions conducive to produce the polypeptide (e.g., protease variant) encoded by the expression vector; and optionally (c) isolating or recovering the variant from the cells or from the culture medium.

In another aspect, the invention provides a composition comprising at least one protease variant or polypeptide of the invention, optionally in combination with another enzyme. Such composition may comprise an adjunct ingredient, such as a surfactant and/or builder, or a carrier. Such composition may be a cleaning composition or a detergent composition and may be useful in cleaning methods described elsewhere herein. Such composition may be a fabric and home care product or such composition may not be a fabric and home care product.

In another aspect, the invention provides a method for cleaning an item, object, or surface in need of cleaning, the method comprising contacting the item, object, or surface with a polypeptide or protease variant of the invention or a composition of the invention, and optionally rinsing the item, object, or surface with water.

In another aspect, the invention provides a method for cleaning an item or surface (e.g., hard surface), the method comprising contacting at least a portion of the item or surface (e.g., hard surface) to be cleaned with a polypeptide or protease variant of the invention or a composition of the invention for a sufficient time and/or under conditions sufficient or effective to clean or wash the item or surface (e.g., hard surface) to a desired degree, and optionally comprising rinsing the item or surface (e.g., hard surface) with water.

Other aspects of the invention are described below.

BRIEF DESCRIPTION OF THE DRAWINGS

FIG. 5 provides an alignment of the mature reference subtilisin proteases including: BPN' (SEQ ID NO:2) and GG36 (SEQ ID NO:755). Each amino acid position of each protease variant described herein, including each cold water protease variant, is numbered according to the numbering of the corresponding amino acid position in the amino acid sequence of *Bacillus amyloliquefaciens* subtilisin protease BPN' (SEQ ID NO:2), as shown in FIG. 5, as determined by alignment of the protease variant amino acid sequence with the *Bacillus amyloliquefaciens* subtilisin protease BPN' amino acid sequence. Thus, unless otherwise specified herein, substitution positions are given in relationship to BPN'.

DESCRIPTION OF THE INVENTION

Definitions

Figure 1:
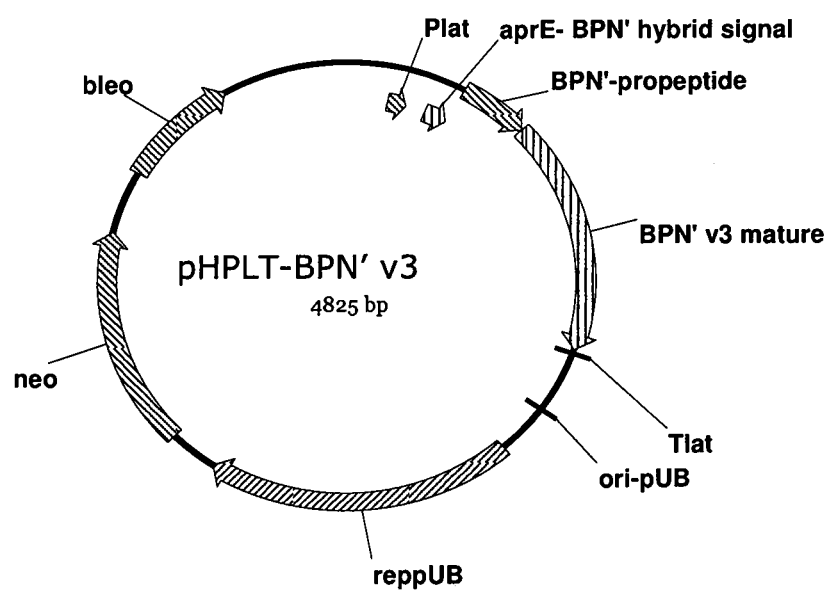
FIG. 1 provides a plasmid map of pHPLT-BPN'-v3.

Unless otherwise indicated, the practice of the present invention involves conventional techniques commonly used in molecular biology, protein engineering, microbiology, and recombinant DNA, which are within the skill of the art. Such techniques are known to those of skill in the art and are described in numerous texts and reference works well known to those of skill in the art. All patents, patent applications, articles and publications mentioned herein, both supra and infra, are hereby expressly incorporated herein by reference.

Unless defined otherwise herein, all technical and scientific terms used herein have the same meaning as commonly understood by one of ordinary skill in the art to which this invention pertains. Many technical dictionaries are known to those of skill in the art. Although any methods and materials similar or equivalent to those described herein find use in the practice of the present invention, some suitable methods and materials are described herein. Accordingly, the terms defined immediately below are more fully described by reference to the specification as a whole. Numeric ranges are inclusive of the numbers defining the range. Unless otherwise indicated, nucleic acids are written left to right in 5' to 3' orientation; amino acid sequences are written left to right in amino to carboxy orientation, respectively. It is to be understood that this invention is not limited to the particular methodology, protocols, and reagents described, as these may vary, depending upon the context they are used by those of skill in the art.

The practice of the present invention employs, unless otherwise indicated, conventional techniques of protein purification, molecular biology, microbiology, recombinant DNA techniques and protein sequencing, all of which are within the skill of those in the art.

Furthermore, the headings provided herein are not limitations of the various aspects of the invention which can be had by reference to the specification as a whole. Accordingly, the terms defined immediately below are more fully defined by reference to the specification as a whole. Nonetheless, in order to facilitate understanding of the invention, a number of terms are defined below.

As used herein, the terms "protease" and "proteinase" refer to an enzyme protein that has the ability to break down other proteins. A protease has the ability to conduct "proteolysis," which begins protein catabolism by hydrolysis of peptide bonds that link amino acids together in a peptide or polypeptide chain forming the protein. This activity of a protease as a protein-digesting enzyme is referred to as "proteolytic activity." Many well known procedures exist for measuring proteolytic activity (see, e.g., Kalisz, "Microbial Proteinases," In: Fiechter (ed.), *Advances in Biochemical Engineering/Biotechnology* (1988)). For example, proteolytic activity may be ascertained by comparative assays which analyze the respective protease's ability to hydrolyze a commercial substrate. Exemplary substrates useful in the analysis of protease or proteolytic activity, include, but are not limited to, dimethyl casein (Sigma C-9801), bovine collagen (Sigma C-9879), bovine elastin (Sigma E-1625), and bovine keratin (ICN Biomedical 902111). Colorimetric assays utilizing these substrates are well known in the art (see, e.g., WO 99/34011 and U.S. Pat. No. 6,376,450, both of which are incorporated herein by reference). The pNA assay (see, e.g., Del Mar et al., Anal. Biochem. 99:316-320 [1979]) also finds use in determining the active enzyme concentration for fractions collected during gradient elution. This assay measures the rate at which p-nitroaniline is released as the enzyme hydrolyzes the soluble synthetic substrate, succinyl-alanine-alanine-proline-phenylalanine-p-nitroanilide (suc-AAPF-pNA). The rate of production of yellow color from the hydrolysis reaction is measured at 410 nm on a spectrophotometer and is proportional to the active enzyme concentration. In addition, absorbance measurements at 280 nanometers (nm) can be used to determine the total protein concentration. The active enzyme/total protein ratio gives the enzyme purity.

As used herein, the term "subtilisin" refers any member of the S8 serine protease family as described in MEROPS—The Peptidase Data base (see Rawlings et al., MEROPS: the peptidase database, Nucl. Acids Res., 34 Database issue, D270-272 [2006]). As described therein, the peptidase family S8 contains the serine endopeptidase subtilisin and its homologues (Rawlings and Barrett, Biochem. J. 290:205-218, [1993]). Family S8, also known as the subtilase family, is the second largest family of serine peptidases. The tertiary structures for several members of family S8 have now been determined. A typical S8 protein structure consists of three layers with a seven-stranded β sheet sandwiched between two layers of helices. Subtilisin (S08.001) is the type structure for clan SB (SB). Despite the different structure, the active sites of subtilisin and chymotrypsin (S01.001) can be superimposed, which suggests the similarity is the result of convergent rather than divergent evolution.

A "protease variant" (or "variant protease") may refer to a protease that differs in its amino acid sequence from the amino acid sequence of a reference protease or parent protease by at least one amino acid residue. A parent protease or reference protease need not be a wild-type protease, but may itself be a variant of a wild-type protease. It is not intended that the reference or parent protease be limited to any particular amino acid sequence. A protease variant of a reference or parent protease may comprise an amino acid sequence comprising at least 60%, 70%, 80%, 85%, 90%, 91%, 92%, 93%, 94%, 95%, 96%, 97%, 98%, or 99% identity to the amino acid sequence of the parent protease or reference protease and at least one amino acid substitution, insertion, or deletion relative to the amino acid sequence of the parent protease or reference protease. In one aspect, the invention includes a variant of a serine protease, wherein the variant has at least one mutation relative to the serine protease. In one aspect, the present invention includes a "BPN' variant" (or "BPN' subtilisin variant") comprising an amino acid sequence comprising one or more mutations relative to the mature BPN' sequence of SEQ ID NO:2.

A parent protease or reference protease can be, but is not limited to, e.g., a known protease (including, but not limited to, e.g., BPN') or a commercially available protease or a variant of the commercially available protease. A parent protease or reference protease may itself be a variant of a known or commercially available protease. A protease variant can be derived from a parent protease that is commercially available or a variant of such commercially available parent protease. Commercially available proteases, include, but are not limited to, e.g., proteases sold under the tradenames SAVINASE®, POLARZYME®, KANNASE®, LIQUANASE®, LIQUANASE ULTRA®, SAVINASE ULTRA®, OVOZYME®, (by Novozymes A/S); MAXACAL®, PROPERASE®, PURAFECT®, FN3®, FN4® and PURAFECT OXP®, PURAFAST™, PURAFECT® PRIME, PURAMAX® (by Danisco US Inc., formerly Genencor International, Inc.); and those available from Henkel/Kemira, namely BLAP (amino acid sequence shown in FIG. 29 of U.S. Pat. No. 5,352,604 with the following mutations S99D+S101R+S103A+V104I+G159S, hereinafter referred to as BLAP) and BLAP X (BLAP with S3T+V4I+V205I).

As used herein, a "cold water protease" is an enzyme that exhibits one or more of the following four criteria: (a) a performance index of at least 1.1, at least 1.2, at least 1.3, at least 1.4, at least 1.5, at least 1.6, at least 1.7, at least 1.8, at least 1.9, at least 2, from 1.1 to about 10, from 1.1 to about 8, or even from 1.1 to about 5 on BMI at pH 8 and 16° C. (60° F.) when compared to PURAFECT® Prime (SEQ ID NO:2 with the amino acid substitution Y217L), as defined in the "Test Method" set forth herein in Part I Example 1; (b) a performance index of at least 1.3, at least 1.4, at least 1.5, at least 1.6, at least 1.7, at least 1.8, at least 1.9, at least 2, from 1.3 to about 10, from 1.3 to about 8, or even from 1.3 to about 5 on BMI at pH 8 and 16° C. (60° F.) when compared to BPN' (SEQ ID NO:2), as defined in the "Test Method" set forth herein in Part I Example 1; (c) a performance index of at least 0.9, at least 1.0, at least 1.1, at least 1.2, at least 1.3, at least 1.4, at least 1.5, at least 1.6, at least 1.7, at least 1.8, at least 1.9, at least 2, from 0.9 to about 10, from 0.9 to about 8, or even from 0.9 to about 5 on BMI at pH 8 and 16° C. (60° F.) when compared to BPN'-v3 (SEQ ID NO:4), as defined in the "Test Method" set forth herein in Part I Example 1; and/or (d) a performance index of at least 0.9, at least 1.0, at least 1.1, at least 1.2, at least 1.3, at least 1.4, at least 1.5, at least 1.6, at least 1.7, at least 1.8, at least 1.9, at least 2, from 0.9 to about 10, from 0.9 to about 8, from 0.9 to about 5, from 1.0 to about 10, from 1.0 to about 8, or even from 1.0 to about 5 on BMI at pH 8 and 16° C. (60° F.) when compared to BPN'-v36 (SEQ ID NO:6), as defined in the "Test Method" set forth herein in Part I Example 1.

Some suitable cold water proteases are derived from subtilisins, particularly those derived from subtilisin BPN' (SEQ ID NO:2). A cold water protease can be a variant of BPN' having the amino acid sequence of SEQ ID NO:2 (e.g., "BPN' variant" or "BPN' subtilisin variant"). Some such cold water proteases comprise one or more of the amino acid substitutions set forth herein.

As used herein, the genus $Bacillus$ includes all species within the genus $Bacillus$, as known to those of skill in the art, including but not limited to $B.$ $subtilis,$ $B.$ $licheniformis,$ $B.$ $lentus,$ $B.$ $brevis,$ $B.$ $stearothermophilus,$ $B.$ $alkalophilus,$ $B.$ $amyloliquefaciens,$ $B.$ $clausii,$ $B.$ $halodurans,$ $B.$ $megaterium,$ $B.$ $coagulans,$ $B.$ $circulans,$ $B.$ $lautus,$ and $B.$ $thuringiensis.$ It is recognized that the genus $Bacillus$ continues to undergo taxonomical reorganization. Thus, it is intended that the genus include species that have been reclassified, including but not limited to such organisms as $B.$ $stearothermophilus,$ which is now named "$Geobacillus$ $stearothermophilus.$" The production of resistant endospores in the presence of oxygen is considered the defining feature of the genus $Bacillus$, although this characteristic also applies to the recently named $Alicyclobacillus,$ $Amphibacillus,$ $Aneurinibacillus,$ $Anoxybacillus,$ $Brevibacillus,$ $Filobacillus,$ $Gracilibacillus,$ $Halobacillus,$ $Paenibacillus,$ $Salibacillus,$ $Thermobacillus,$ $Ureibacillus$, and $Virgibacillus$.

The terms "polynucleotide" and "nucleic acid," which are used interchangeably herein, refer to a polymer of any length of nucleotide monomers covalently bonded in a chain. DNA (deoxyribonucleic acid), a polynucleotide comprising deoxyribonucleotides, and RNA (ribonucleic acid), a polymer of ribonucleotides, are examples of polynucleotides or nucleic acids having distinct biological function. Polynucleotides or nucleic acids include, but are not limited to, a single-, double- or triple-stranded DNA, genomic DNA, cDNA, RNA, DNA-RNA hybrid, or a polymer comprising purine and pyrimidine bases, or other natural, chemically, biochemically modified, non-natural or derivatized nucleotide bases. The following are non-limiting examples of polynucleotides: genes, gene fragments, chromosomal fragments, expressed sequence tag(s) (EST(s)), exons, introns, messenger RNA (mRNA), transfer RNA (tRNA), ribosomal RNA (rRNA), ribozymes, complementary DNA (cDNA), recombinant polynucleotides, branched polynucleotides, plasmids, vectors, isolated DNA of any sequence, isolated RNA of any sequence, nucleic acid probes, and primers. Some polynucleotides comprise modified nucleotides, such as methylated nucleotides and nucleotide analogs, uracyl, other sugars and linking groups such as fluororibose and thioate, and nucleotide branches. A sequence of nucleotides may be interrupted by non-nucleotide components.

As used herein, the term "vector" refers to a nucleic acid construct or polynucleotide construct used to introduce or transfer nucleic acid(s) or polynucleotide(s) into a target cell or tissue. A vector is typically used to introduce foreign DNA into another cell or tissue. A vector generally comprises a DNA sequence that is a transgene and a larger polynucleotide sequence that serves as the "backbone" of the vector. The vector typically serves to transfers genetic information, such as the inserted transgene, to a target cell or tissue so as to isolate, multiply, or express the insert in the target cell or tissue. Vectors include plasmids, cloning vectors, bacteriophages, viruses (e.g., viral vector), cosmids, expression vectors, shuttle vectors, cassettes, and the like. A vector typically includes an origin of replication, a multicloning site, and a selectable marker. The process of inserting a vector into a target cell is typically referred to as transformation in bacterial and yeast cells and as transfection in mammalian cells. The present invention includes a vector that comprises a DNA sequence encoding a protease variant (e.g., precursor or mature protease variant) that is operably linked to a suitable prosequence (e.g., secretory, signal peptide sequence, etc.) capable of effecting the expression of the DNA sequence in a suitable host.

As used herein, the term "expression cassette" or "expression vector" refers to a nucleic acid construct or vector generated recombinantly or synthetically for the expression of a nucleic acid of interest (e.g., a foreign nucleic acid or transgene) in a target cell. The nucleic acid of interest typically expresses a protein of interest. An expression vector or expression cassette typically comprises a promoter nucleotide sequence that drives or promotes expression of the foreign nucleic acid. The expression vector or cassette also typically includes any other specified nucleic acid elements that permit transcription of a particular nucleic acid in a target cell. A recombinant expression cassette can be incorporated into a plasmid, chromosome, mitochondrial DNA, plastid DNA, virus, or nucleic acid fragment. Some expression vectors have the ability to incorporate and express heterologous DNA fragments in a host cell. Many prokaryotic and eukaryotic expression vectors are commercially available. Selection of appropriate expression vectors is within the knowledge of those of skill in the art. Selection of appropriate expression vectors for expression of a protein from a nucleic acid sequence incorporated into the expression vector is within the knowledge of those of skill in the art.

A DNA construct is an artificially constructed segment of nucleic acid that may be introduced into a target cell or tissue. A DNA construct typically comprises a DNA insert comprising a nucleotide sequence encoding a protein of interest that has been subcloned into a vector. The vector may contain bacterial resistance genes for growth in bacteria and a promoter for expression of the protein of interest in an organism. The DNA may be generated in vitro by PCR or any other suitable technique(s) known to those in the art. The DNA construct may comprise a nucleic acid sequence of interest. In one aspect, the sequence is operably linked to additional elements such as control elements (e.g., promoters, etc.). The DNA construct may further comprise a selectable marker and may further comprise an incoming sequence flanked by homology boxes. The construct may comprise other non-homologous sequences, added to the ends (e.g., stuffer sequences or flanks). The ends of the sequence may be closed such that the DNA construct forms a closed circle. The nucleic acid sequence of interest, which is incorporated into the DNA construct, using techniques well known in the art, may be a wild-type, mutant, or modified nucleic acid. The DNA construct may comprise one or more nucleic acid sequences homologous to the host cell chromosome. The DNA construct may comprise one or more non-homologous nucleotide sequences. Once the DNA construct is assembled in vitro, it may be used, e.g., to: 1) insert heterologous sequences into a desired target sequence of a host cell; and/or 2) mutagenize a region of the host cell chromosome (i.e., replace an endogenous sequence with a heterologous sequence); 3) delete target genes; and/or 4) introduce a replicating plasmid into the host. "DNA construct" is used interchangeably herein with "expression cassette."

As used herein, a "plasmid" refers to an extrachromosomal DNA molecule which is capable of replicating independently from the chromosomal DNA. A plasmid is double stranded (ds) and may be circular and is typically used as a cloning vector.

As used herein in the context of introducing a nucleic acid sequence into a cell, the term "introduced" refers to any method suitable for transferring the nucleic acid sequence into the cell. Such methods for introduction include but are not limited to protoplast fusion, transfection, transformation, electroporation, conjugation, and transduction (see, e.g., Ferrari et al., "Genetics," in Hardwood et al. (eds.), *Bacillus*, Plenum Publishing Corp., pp. 57-72 [1989]).

Transformation refers to the genetic alteration of a cell which results from the uptake, genomic incorporation, and expression of genetic material (e.g., DNA).

As used herein, a nucleic acid is "operably linked" with another nucleic acid sequence when it is placed into a functional relationship with another nucleic acid sequence. For example, a promoter or enhancer is operably linked to a nucleotide coding sequence if the promoter affects the transcription of the coding sequence. A ribosome binding site may be operably linked to a coding sequence if it is positioned so as to facilitate translation of the coding sequence. Typically, "operably linked" DNA sequences are contiguous. However, enhancers do not have to be contiguous. Linking is accomplished by ligation at convenient restriction sites. If such sites do not exist, synthetic oligonucleotide adaptors or linkers may be used in accordance with conventional practice.

As used herein, "recombinant" when used with reference to a cell typically indicates that the cell has been modified by the introduction of a heterologous nucleic acid sequence or that the cell is derived from a cell so modified. For example, a recombinant cell may comprise a gene not found in identical form within the native (non-recombinant) form of the cell, or a recombinant cell may comprise a native gene (found in the native form of the cell) but which has been modified and re-introduced into the cell. A recombinant cell may comprise a nucleic acid endogenous to the cell that has been modified without removing the nucleic acid from the cell; such modifications include those obtained by gene replacement, site-specific mutation, and related techniques known to those of ordinary skill in the art. Recombinant DNA (rDNA) is a form of artificial DNA that is created by combining two or more nucleotide sequences that would not normally occur together through the process of gene splicing. Recombinant DNA technology includes techniques for the production of recombinant DNA in vitro and transfer of the recombinant DNA into cells where it may be expressed or propagated, thereby producing a recombinant polypeptide.

As used herein, the term nucleic acid or gene "amplification" refers to a process by which specific DNA sequences are disproportionately replicated such that the amplified nucleic acid or gene becomes present in a higher copy number than was initially present in the genome. Selection of cells by growth in the presence of a drug (e.g., an inhibitor of an inhibitable enzyme) may result in the amplification of either the endogenous gene encoding the gene product required for growth in the presence of the drug or by amplification of exogenous (i.e., input) sequences encoding this nucleic acid or gene product or both.

As used herein, the term "primer" refers to an oligonucleotide (a polymer of nucleotide residues), whether occurring naturally as in a purified restriction digest or produced synthetically, which is capable of acting as a point of initiation of synthesis when placed under conditions in which synthesis of a primer extension product which is complementary to a nucleic acid strand is induced (i.e., in the presence of nucleotides and an inducing agent such as DNA polymerase and at a suitable temperature and pH). A primer is preferably single stranded for maximum efficiency in amplification, but may alternatively be double stranded. If double stranded, the primer is first treated to separate its strands before being used to prepare extension products. The primer may comprise an oligodeoxyribonucleotide. The primer must be sufficiently long to prime the synthesis of extension products in the presence of the inducing agent. The exact length of a primer depends on a variety of factors, including temperature, source of primer, and the use of the method.

As used herein, the term "probe" refers to an oligonucleotide, whether occurring naturally as in a purified restriction digest or produced synthetically, recombinantly or by PCR amplification, which is typically capable of hybridizing to another oligonucleotide of interest. A probe may be single-stranded or double-stranded. Probes are useful in the detection, identification and isolation of particular gene sequences. It is contemplated that any probe used in the present invention will be labeled with any "reporter molecule," so that it is detectable in any detection system, including, but not limited to enzyme (e.g., ELISA, as well as enzyme-based histochemical assays), fluorescent, radioactive, and luminescent systems. It is not intended that the invention be limited to any particular detection system or label.

As used herein, the term "polymerase chain reaction" (PCR) refers to the methods of U.S. Pat. Nos. 4,683,195 4,683,202, and 4,965,188, hereby incorporated by reference, which include methods for increasing the concentration of a segment of a target sequence in a mixture of genomic DNA without cloning or purification. This process for amplifying the target sequence is well known in the art.

As used herein, the term "amplification reagents" refers to those reagents (e.g., deoxyribonucleotide triphosphates, buffer, etc.) needed for amplification except for primers, nucleic acid template, and the amplification enzyme. Typically, amplification reagents along with other reaction components are placed and contained in a reaction vessel (test tube, microwell, etc.).

As used herein, the term "restriction endonuclease" or "restriction enzyme" refers to an enzyme (e.g., bacterial enzyme) that is capable of cutting double-stranded or single-stranded DNA at or near a specific sequence of nucleotides known as a restriction site. The nucleotide sequence comprising the restriction site is recognized and cleaved by a given restriction endonuclease or restriction enzyme and is frequently the site for insertion of DNA fragments. A restriction site can be engineered into an expression vector or DNA construct.

As is known in the art, a DNA sequence can be transcribed by an RNA polymerase to produce an RNA sequence, but an RNA sequence can be reverse transcribed by reverse transcriptase to produce a DNA sequence.

"Host strain" or "host cell" refers to a suitable host for an expression vector comprising a DNA sequence of interest. A DNA sequence of interest may express a protein of interest in the host strain or host cell.

A "protein" or "polypeptide" or "peptide" is a polymeric sequence of amino acid residues. A carboxyl group of one amino acid is linked to the amino group of another. The terms "protein" and "polypeptide" and "peptide" may be used interchangeably herein. A peptide comprises two or more amino acids. Peptides typically contain fewer amino acids than do polypeptides or proteins. The single and 3-letter code for amino acids as defined in conformity with the IUPAC-IUB Joint Commission on Biochemical Nomenclature (JCBN) is used through out this disclosure. The single letter X refers to any of the twenty amino acids. It is also understood that a polypeptide may be coded for by more than one nucleotide sequence due to the degeneracy of the genetic code.

In describing enzyme variants, the following nomenclature is used typically for ease of reference: Original amino acid(s):position(s):substituted amino acid(s). The accepted IUPAC single letter or triple letter amino acid abbreviation is employed. The single letter "X" refers to any amino acid residue However, when in the context of an amino acid substitution (e.g. "X003C"), it is to be understood that "X" refers to an amino acid residue other than the amino acid residue resulting from the substitution (e.g., X is an amino acid residue other than C). Mutations are typically named by the one letter code for the parent amino acid, followed by a three or two or one digit amino acid position number in an amino acid sequence and then the one letter code for the substituted amino acid. For example, mutating the amino acid glycine (G) at amino acid position 87 in an amino acid sequence by substituting to the amino acid serine (S) for glycine (G) is represented as "G087S" or "G87S". Typically, the substitution of a glycine at position 2 with a threonine is represented as G002T; however, such substitution may also be represented as G02T or G2T. One or two leading zeroes ("0") may be included simply to provide a convenient three number designation for each amino acid position. The amino acid position "001" is the same as "1" and thus "A001C" is the same as "A1C". "X001G" refers to the substitution of glycine (G) at amino acid position 1 in an amino acid sequence, wherein the amino acid that is to be replaced by glycine is any amino acid. Multiple mutations are indicated by inserting a "–" between the mutations or by using a plus (+) sign between the mutations. For example, amino acid substitutions at amino acid residue positions 87 and 90 in an amino acid sequence are represented as either "G087S-A090Y" or "G87S-A90Y" or "G87S+A90Y" or "G087S+A090Y". For deletions, the one letter code "Z" is used. For an insertion relative to the parent sequence, the one letter code "Z" is on the left side of the position number. For a deletion, the one letter code "Z" is on the right side of the position number. For insertions, the position number is the position number before the inserted amino acid(s), plus 0.01 for each amino acid. For example, an insertion of three amino acids alanine (A), serine (S) and tyrosine (Y) between position 87 and 88 is shown as "Z087.01A-Z087.02S-Z087.03Y." Thus, combining all the mutations above plus a deletion at position 100 is: "G087S-Z087.01A-Z087.02S-Z087.03Y-A090Y-A100Z."

A "prosequence" or "propeptide sequence" refers to an amino acid sequence between the signal peptide sequence and mature protease sequence that is necessary for the secretion of the protease. Cleavage of the prosequence or propeptide sequence results in a mature active protease.

The term "signal sequence" or "signal peptide" refers to a sequence of amino acid residues that may participate in the secretion or direct transport of the mature or precursor form of a protein. The signal sequence is typically located N-terminal to the precursor or mature protein sequence. The signal sequence may also be referred to as a leader sequence. The signal sequence may be endogenous or exogenous. One exemplary exogenous signal sequence comprises the first seven amino acid residues of the signal sequence from *Bacillus subtilis* subtilisin fused to the remainder of the signal sequence of the subtilisin from *Bacillus lentus* (ATCC 21536). A signal sequence is normally absent from the mature protein. A signal sequence is typically cleaved from the protein by a signal peptidase after the protein is transported.

The term "hybrid signal sequence" refers to signal sequences in which part of sequence is obtained from the expression host fused to the signal sequence of the gene to be expressed. Synthetic sequences can be utilized.

The term "mature" form of a protein, polypeptide, or peptide refers to the functional form of the protein, polypeptide, or peptide without the signal peptide sequence and propeptide sequence.

The term "precursor" form of a protein or peptide refers to a mature form of the protein having a prosequence operably linked to the amino or carbonyl terminus of the protein. The precursor may also have a "signal" sequence operably linked to the amino terminus of the prosequence. The precursor may also have additional polynucleotides that are involved in post-translational activity (e.g., polynucleotides cleaved therefrom to leave the mature form of a protein, polypeptide, or peptide).

The term "wild-type" in reference to an amino acid sequence or nucleic acid sequence indicates that the amino acid sequence or nucleic acid sequence is native or naturally occurring sequence. As used herein, the term "naturally-occurring" refers to anything (e.g., proteins, amino acids, or nucleic acid sequences) that is found in nature (e.g., has not been manipulated by means of recombinant or chemical methods). As used herein, the term "non-naturally occurring" refers to anything that is not found in nature (e.g., recombinant or chemically synthesized nucleic acids produced in the laboratory).

An amino acid residue in a particular amino acid sequence may be numbered by correspondence with an amino acid residue in a position of a reference amino acid sequence. An amino acid residue of an amino acid sequence of interest which is in a position that "corresponds to" or is "corresponding to" or in "correspondence with" the position of an amino acid residue of a reference amino acid sequence indicates that the amino acid residue of the sequence of interest is located at a position that is equivalent or homologous to the position of an amino acid residue in the reference amino acid sequence. One skilled in the art can determine whether a particular residue position in a polypeptide corresponds to a position of a homologous reference sequence. For example, a protease variant may be aligned with that of a reference sequence (e.g., BPN' sequence of SEQ ID NO:2) using known techniques. The positions of the amino acid residues in the reference sequence are used for numbering of the amino acid residues in the sequence of interest. Accordingly, the amino acid residues of the protease variant may be numbered according to the corresponding amino acid residue position numbering of the reference sequence. For example, the amino acid residues in the reference sequence of SEQ ID NO: 2 may be used for determining amino acid residue position numbering of each amino acid residue of a protease variant of interest.

As used herein, "homology" refers to sequence similarity or identity, with identity being preferred. Homology may be determined using standard techniques known in the art (see, e.g., Smith and Waterman, Adv. Appl. Math. 2:482 [1981]; Needleman and Wunsch, J. Mol. Biol. 48:443 [1970; Pearson and Lipman, Proc. Natl. Acad. Sci. USA 85:2444 [1988]; software programs such as GAP, BESTFIT, FASTA, and TFASTA in the Wisconsin Genetics Software Package (Genetics Computer Group, Madison, Wis.); and Devereux et al., Nucl. Acid Res. 12:387-395 [1984]). One example of a useful algorithm is PILEUP. PILEUP creates a multiple sequence alignment from a group of related sequences using progressive, pair-wise alignments. It can also plot a tree showing the clustering relationships used to create the alignment. PILEUP uses a simplification of the progressive alignment method of Feng and Doolittle (see Feng and Doolittle, J. Mol. Evol. 35:351-360 [1987]). The method is similar to that described by Higgins and Sharp (see Higgins and Sharp, CABIOS 5:151-153 [1989]). Useful PILEUP parameters including a default gap weight of 3.00, a default gap length weight of 0.10, and weighted end gaps. Another example of a useful algorithm is the BLAST algorithm, described by Altschul et al., (see Altschul et al., J. Mol. Biol. 215:403-410 [1990]; and Karlin and Altschul, Proc. Natl. Acad. Sci. USA 90:5873-5787 [1993]). A particularly useful BLAST program is the WU-BLAST-2 program (see Altschul et al., Meth. Enzymol. 266:460-480 [1996]). WU-BLAST-2 uses several search parameters, most of which are set to the default values. The adjustable parameters are set with the following values: overlap span=1, overlap fraction=0.125, word threshold (T)=11. The HSP S and HSP S2 parameters are dynamic values and are established by the program itself depending upon the composition of the particular sequence and composition of the particular database against which the sequence of interest is being searched. However, the values may be adjusted to increase sensitivity.

The percent sequence identity (% sequence identity or simply % identity) between a subject polypeptide sequence and a reference polypeptide sequence means that the subject amino acid sequence is identical on an amino acid residue-by-amino acid residue basis by a specified percentage to the reference polypeptide sequence over a comparison length when the sequences are optimally aligned, as determined, for example, by an amino acid sequence comparison algorithm or visual inspection. The percent sequence identity between a subject nucleic acid sequence and a reference nucleic acid sequence similarly means the subject nucleotide sequence is identical on a nucleic acid residue-by-nucleic acid residue basis by a specified percentage to the reference nucleotide sequence over a comparison length when the sequences are optimally aligned.

The percent sequence identity (percent identity or % sequence identity or % identity) between a reference sequence and a subject sequence of interest may be readily determined by one skilled in the art. The percent identity shared by two polypeptide sequences can be determined, for example, by direct comparison of the amino acid residues in each sequence by aligning the residues of the respective sequences for maximum similarity and determining the number of identical amino acid residues between the sequences by using a sequence comparison algorithm known in the art or by visual inspection. The two optimally aligned polypeptide sequences can be compared over the comparison length and the number of positions in the optimal alignment at which identical amino acid residues occur in both polypeptide sequences can be determined, thereby providing the number of matched positions, and the number of matched positions is then divided by the total number of positions over the comparison length. The resulting number is multiplied by 100 to yield the percent identity of the subject polypeptide sequence to the reference (or query) polypeptide sequence. The percent identity shared by two nucleic acid sequences can be similarly determined by direct comparison of the nucleotide residues in each sequence by aligning the residues of the respective sequences for maximum similarity and determining the number of identical nucleic acid residues between the nucleic acid sequences by using a sequence comparison algorithm or by visual inspection. The percent identity between two or more sequences may also be described as the sequences being a particular percent identical.

An example of an algorithm that is suitable for determining sequence identity is the BLAST algorithm, (see Altschul, et al., J. Mol. Biol., 215:403-410 [1990]). Software for performing BLAST analyses is publicly available through the National Center for Biotechnology Information. This algorithm involves first identifying high scoring sequence pairs (HSPs) by identifying short words of length W in the query sequence that either match or satisfy some positive-valued threshold score T when aligned with a word of the same length in a database sequence. These initial neighborhood word hits act as starting points to find longer HSPs containing them. The word hits are expanded in both directions along each of the two sequences being compared for as far as the cumulative alignment score can be increased. Extension of the word hits is stopped when: the cumulative alignment score falls off by the quantity X from a maximum achieved value; the cumulative score goes to zero or below; or the end of either sequence is reached. The BLAST algorithm parameters W, T, and X determine the sensitivity and speed of the alignment. The BLAST program uses as defaults a wordlength (W) of 11, the BLOSUM62 scoring matrix (see Henikoff and Henikoff, Proc. Natl. Acad. Sci. USA 89:10915 [1992]) alignments (B) of 50, expectation (E) of 10, M'S, N'-4, and a comparison of both strands.

The BLAST algorithm then performs a statistical analysis of the similarity between two sequences (see, e.g., Karlin and Altschul, supra). One measure of similarity provided by the BLAST algorithm is the smallest sum probability (P(N)), which provides an indication of the probability by which a match between two nucleotide or amino acid sequences would occur by chance. For example, a nucleic acid is considered similar to a protease-encoding nucleic acid of this invention if the smallest sum probability in a comparison of the test nucleic acid to a protease-encoding nucleic acid is less than about 0.1, more preferably less than about 0.01, and most preferably less than about 0.001. Where the test nucleic acid encodes a protease polypeptide, it is considered similar to a specified protease-encoding nucleic acid if the comparison results in a smallest sum probability of less than about 0.5, and more preferably less than about 0.2.

"Optimal alignment" or "optimally aligned" refers to the alignment of two (or more) sequences giving the highest percent identity score. For example, optimal alignment of two polypeptide sequences can be achieved by manually aligning the sequences such that the maximum number of identical amino acid residues in each sequence are aligned together or by using software programs or procedures described herein or known in the art. Optimal alignment of two nucleic acid sequences can be achieved by manually aligning the sequences such that the maximum number of identical nucleotide residues in each sequence are aligned together or by using software programs or procedures described herein or known in the art.

Two sequences (e.g., polypeptide sequences) may be deemed "optimally aligned" when they are aligned using defined parameters, such as a defined amino acid substitution matrix, gap existence penalty (also termed gap open penalty), and gap extension penalty, so as to achieve the highest identity score possible for that pair of sequences. The BLOSUM62 scoring matrix (see Henikoff and Henikoff, supra) is often used as a default scoring substitution matrix in polypeptide sequence alignment algorithms (e.g., BLASTP). The gap existence penalty is imposed for the introduction of a single amino acid gap in one of the aligned sequences, and the gap extension penalty is imposed for each residue position in the gap. Exemplary alignment parameters employed are: BLOSUM62 scoring matrix, gap existence penalty=11, and gap extension penalty=1. The alignment score is defined by the amino acid positions of each sequence at which the alignment begins and ends (e.g., the alignment window), and optionally by the insertion of a gap or multiple gaps into one or both sequences, so as to achieve the highest possible similarity score.

Optimal alignment between two or more sequences can be determined manually by visual inspection or by using a computer, such as, but not limited to e.g., the BLASTP program for amino acid sequences and the BLASTN program for nucleic acid sequences (see, e.g., Altschul et al., Nucleic Acids Res. 25(17):3389-3402 (1997); see also the National Center for Biotechnology Information (NCBI) website) or CLUSTALW program.

A polypeptide of interest may be said to be "substantially identical" to a reference polypeptide if the polypeptide of interest comprises an amino acid sequence having at least about 60%, 70%, 75%, 80%, 85%, 90%, 91%, 92%, 93%, 94%, 95%, 96%, 97%, 98%, 99%, or 99.5% sequence identity to the amino acid sequence of the reference polypeptide. The percent identity between two such polypeptides can be determined manually by inspection of the two optimally aligned polypeptide sequences or by using software programs or algorithms (e.g., BLAST, ALIGN, CLUSTAL) using standard parameters. One indication that two polypeptides are substantially identical is that the first polypeptide is immunologically cross-reactive with the second polypeptide. Typically, polypeptides that differ by conservative amino acid substitutions are immunologically cross-reactive. Thus, a polypeptide is substantially identical to a second polypeptide, e.g., where the two peptides differ only by a conservative amino acid substitution or one or more conservative amino acid substitutions.

A nucleic acid of interest may be said to be "substantially identical" to a reference nucleic acid if the nucleic acid of interest comprises a nucleotide sequence having at least about 60%, 70%, 75%, 80%, 85%, 90%, 91%, 92%, 93%, 94%, 95%, 96%, 97%, 98%, 99%, or 99.5% sequence identity to the nucleotide sequence of the reference nucleic acid. The percent identity between two such nucleic acids can be determined manually by inspection of the two optimally aligned nucleic acid sequences or by using software programs or algorithms (e.g., BLAST, ALIGN, CLUSTAL) using standard parameters. One indication that two nucleic acid sequences are substantially identical is that the two nucleic acid molecules hybridize to each other under stringent conditions (e.g., within a range of medium to high stringency).

As used herein, "isolated" in reference to a particular component of interest means that component is essentially or substantially free of other components. For example, an "isolated" polypeptide means the polypeptide is essentially or substantially free of other components, including, but not limited to, e.g., other polypeptides and cellular components. An "isolated" nucleic acid means the nucleic acid is essentially or substantially free of other components, including, but not limited to, e.g., other nucleic acids and cellular components. For purposes of this application, "isolated" refers to nucleic acids or polypeptides that are not part of a library (e.g., screening library).

Purity and homogeneity are typically determined using analytical chemistry techniques, such as polyacrylamide gel electrophoresis or high-performance liquid chromatography. A protein or nucleic acid that is the predominant species present in a preparation is substantially purified. The term "purified" denotes that a nucleic acid or protein gives rise to essentially one band in an electrophoretic gel, chromatographic eluate, and/or a media subjected to density gradient centrifugation. Particularly, "purified" means that when isolated, the isolate contains at least 85%, 90%, 91%, 92%, 93%, 94%, 95%, 96%, 97%, 98%, 99%, or 99.5% or more of nucleic acid or protein by weight of the isolate. Purified polypeptides may be obtained by a number of methods including, but not limited to, e.g., laboratory synthesis, chromatography (e.g., high-performance liquid chromatography) preparative electrophoresis, polyacrylamide gel electrophoresis followed by visualization upon staining, centrifugation, precipitation, affinity purification, etc. (see, generally, R Scopes, Protein Purification, Springer-Verlag, N.Y. (1982), Deutscher, Methods in Enzymol., Vol. 182: Guide to Protein Purification, Academic Press, Inc. N.Y. (1990)). The invention includes an isolated or purified polypeptides (e.g., isolated protease variants or subtilisin variants of the invention) and isolated or purified nucleic acids (e.g., nucleic acids encoding protease variants or subtilisin variants of the invention).

In a related sense, the invention provides methods of enriching compositions for one or more molecules of the invention, such as one or more polypeptides of the invention (e.g., one or more protease variants of the invention) or one or more nucleic acids of the invention (e.g., one or more nucleic acids encoding one or more protease variants of the invention). A composition is enriched for a molecule when there is a substantial increase in the concentration of the molecule after application of a purification or enrichment technique. A substantially pure polypeptide or nucleic acid will typically comprise at least about 60%, 70%, 80%, 85%, 90%, 91%, 92%, 93%, 94%, 95%, 96%, 97%, 98, 99%, 99.5% or more by weight (on a molar basis) of all macromolecular species in a particular composition.

As used herein, the term "combinatorial mutagenesis" refers to methods in which libraries of nucleic acid variants of a reference nucleic acid sequence are generated. In these libraries, the variants contain one or several mutations chosen from a predefined set of mutations. The methods also provide means to introduce random mutations which were not members of the predefined set of mutations. Some such methods include those set forth in U.S. Pat. No. 6,582,914, hereby incorporated by reference. Some such combinatorial mutagenesis methods include and/or encompass methods embodied in commercially available kits (e.g., QUIKCHANGE® Multi Site-Directed Mutagenesis Kit (Stratagene)).

As used herein, having "improved properties" used in connection with a protease variant refers to a protease variant having improved properties compared to a reference or parent protease. Protease variants of the invention may exhibit one of more of the following properties: enhanced or improved proteolytic activity, enhanced or improved stability, enhanced or improved ability to clean a surface or item, enhanced or improved cleaning performance, enhanced or improved fabric or laundry cleaning performance or wash performance, enhanced or improved hand wash performance, enhanced or improved hand or manual dishwashing performance, enhanced or improved automatic dishwashing performance, enhanced or improved laundry performance compared to a reference protease or parent protease of interest.

As used herein, the term "functional assay" refers to an assay that provides an indication of a protein's activity. The term typically refers to assay systems in which a protein is analyzed for its ability to function in its usual capacity. For example, in the case of enzymes, a functional assay involves determining the effectiveness of the enzyme in catalyzing a reaction.

The term "property" or grammatical equivalents thereof in the context of a molecule may refer to any characteristic or attribute of the molecule that can be selected or detected. For example, in the context of a polypeptide, a property may be enzymatic activity (e.g., proteolytic activity), stability, or other property.

A "mutant" nucleic acid sequence typically refers to a nucleic acid sequence that has an alteration in at least one codon occurring in a host cell's wild-type sequence such that the expression product of the mutant nucleic acid sequence is a protein with an altered amino acid sequence relative to the wild-type protein. The expression product may have an altered functional capacity (e.g., enhanced enzymatic activity).

As used herein, the term "net charge" is defined as the sum of all charges present in a molecule. "Net charge changes" can be made to a parent protein molecule to provide a protein variant that has a net charge that differs from that of the parent protein molecule (i.e., the variant has a net charge that is not the same as that of the parent molecule). For example, substitution of a neutral amino acid of a protein with a negatively charged amino acid or substitution of a positively charged amino acid of a protein with a neutral amino acid results in net charge of −1 with respect to the unmodified protein. Substitution of a positively charged amino acid of a protein with a negatively charged amino acid results in a net charge of −2 with respect to the unmodified protein. Substitution of a neutral amino acid of a protein with a positively charged amino acid or substitution of a negatively charged amino acid of a protein with a neutral amino acid results in net charge of +1 with respect to the parent. Substitution of a negatively charged amino acid of a protein with a positively charged amino acid results in a net charge of +2 with respect to the unmodified protein. The net charge of a parent protein can also be altered by deletion and/or insertion of one or more charged amino acids.

The terms "thermally stable" and "thermostable" and "thermostability" in reference to a polypeptide indicates that the polypeptide is resistant to a permanent change in its activity caused solely by heat, such as, e.g., via exposure to higher temperature. For example, a thermally stable enzyme means that the enzyme is resistant to a permanent change in its enzymatic activity caused solely by heat, such as, e.g., via exposure to higher temperature. Typically, a protease that is thermally stable is able to retain at least about 50%, 60%, 70%, 75%, 80%, 85%, 90%, 92%, 95%, 96%, 97%, 98%, or 99% of its proteolytic activity after exposure to increased temperatures over a given time period, e.g., at least about 60 minutes, 120 minutes, 180 minutes, 240 minutes, 300 minutes, etc.

Cleaning activity of a polypeptide or protease may refer to a cleaning performance achieved by a protease. Cleaning activity may be determined by using various assays for cleaning one or more of various enzyme-sensitive stains on an object, item, or surface (e.g., a stain resulting from food, grass, blood, ink, blood/milk/ink, milk/oil/pigment, egg yolk, milk, oil, and/or egg protein). Cleaning performance of a polypeptide (e.g., a polypeptide of the invention (such as a protease variant) or a reference polypeptide (e.g., reference protease) may be determined by subjecting the stain on the object, item, or surface to standard wash condition(s) and assessing the degree to which the stain is removed by using various chromatographic, spectrophotometric, or other quantitative methodologies. Exemplary cleaning assays and methods are known in the art and include, but are not limited to those described in WO 99/34011 and U.S. Pat. No. 6,605,458, both of which are herein incorporated by reference, as well as those cleaning assays and methods included in the Part I Examples and Part II Examples provided below.

The term "cleaning effective amount" of a protease variant or reference protease refers to the amount of protease that achieves a desired level of enzymatic activity in a specific cleaning composition. Such effective amounts are readily ascertained by one of ordinary skill in the art and are based on many factors, such as the particular protease used, the cleaning application, the specific composition of the cleaning composition, and whether a liquid or dry (e.g., granular, tablet, bar) composition is required, etc.

The term "cleaning adjunct material" refers to any liquid, solid, or gaseous material included in cleaning composition other than a protease variant of the invention. The cleaning compositions of the present invention may include one of more cleaning adjunct materials. Each cleaning adjunct material is typically selected depending on the particular type and form of cleaning composition (e.g., liquid, granule, powder, bar, paste, spray, tablet, gel, foam, or other composition). Preferably, each cleaning adjunct material is compatible with the protease enzyme used in the composition.

The term "enhanced performance" in the context of cleaning activity refers to an increased or greater cleaning activity by an enzyme on certain enzyme sensitive stains such as egg, milk, grass, ink, oil, and/or blood, as determined by usual evaluation after a standard wash cycle and/or multiple wash cycles.

The term "diminished performance" in the context of cleaning activity refers to a decreased or lesser cleaning activity by an enzyme on certain enzyme sensitive stains such as egg, milk, grass or blood, as determined by usual evaluation after a standard wash cycle.

As used herein, the term "institutional cleaning composition" refers to products suitable for use in institutions including but not limited to schools, hospitals, factories, stores, corporations, buildings, restaurants, office complexes and buildings, processing and/or manufacturing plants, veterinary hospitals, factory farms, factory ranches, etc.

As used herein, "fabric and home care product" refers to a product or device generally intended to be used or consumed in the form in which it is sold and that is for treating fabric, hard surface and any other surface in the area of fabric and home care, including: air care including air freshener and scent delivery systems, car care, dishwashing, fabric conditioning (including softening and/or freshening), laundry detergency, laundry and rinse additive and/or care, hard surface cleaning and/or treatment including floor and toilet bowl cleaners, and other cleaning products for consumer and institutional use.

As used herein, the terms "cleaning composition" and "cleaning formulation" refer to compositions that find use in the removal of undesired compound(s) from an item(s) to be cleaned, such as, but not limited to, e.g., fabric, laundry, dishes, dishware, contact lenses, other solid substrates, hair (including human or animal hair) (shampoos), skin (soaps, cosmetics, and creams), teeth (mouthwashes, toothpastes), non-fabric and home care objects, filters, membranes (e.g., filtration membrane, including, but not limited to, ultrafiltration membranes), hard surfaces and other surfaces, including, but not limited to, e.g., the hard surface of a table (table top or legs), wall, another furniture item or object, floor, ceiling, etc. A cleaning composition or cleaning formulation may be useful in a personal care application and/or in personal care item, including, e.g., but not limited to, shampoo (for cleaning human or animal hair); soap, cream or cosmetics (for skin cleaning and/or skin care); mouthwash (for oral care); toothpaste (for cleaning teeth and/or oral care). The terms encompass any material/compound selected for the particular type of cleaning composition or formulation desired and the form of the product (e.g., liquid, gel, granule, or spray composition), as long as the composition or formulation is compatible with the protease and/or other enzyme(s) used in the composition or formulation. The specific selection of cleaning composition or formulation materials are readily made by considering the surface, object, or item (e.g., fabric) to be cleaned, and the desired form of the composition or formulation for the cleaning conditions during use. In one aspect, a cleaning composition or formulation may be a fabric and home care product (e.g., a cleaning composition for cleaning laundry). In another aspect, a cleaning composition or formulation is not a fabric and home care product (e.g., a cleaning composition for cleaning contact lens, hair, teeth, or skin, or useful in personal care applications and/or personal care items).

Cleaning compositions and cleaning formulations include any composition that is suited for cleaning, bleaching, disinfecting, and/or sterilizing any object, item, and/or surface. Such compositions and formulations include, but are not limited to, for example, liquid and/or solid compositions, including cleaning or detergent compositions (e.g., liquid, tablet, gel, bar, granule, and/or solid laundry cleaning or detergent compositions and fine fabric detergent compositions; hard surface cleaning compositions and formulations, such as for glass, wood, ceramic and metal counter tops and windows; carpet cleaners; oven cleaners; fabric fresheners; fabric softeners; and textile, laundry booster cleaning or detergent compositions, laundry additive cleaning compositions, and laundry pre-spotter cleaning compositions; dishwashing compositions, including hand or manual dishwash compositions (e.g., "hand" or "manual" dishwashing detergents) and automatic dishwashing compositions (e.g., "automatic dishwashing detergents").

Cleaning compositions or cleaning formulations, as used herein, include, unless otherwise indicated, granular or powder-form all-purpose or heavy-duty washing agents, especially cleaning detergents; liquid, granular, gel, solid, tablet, or paste-form all-purpose washing agents, especially the so-called heavy-duty liquid (HDL) detergent or heavy-duty powder detergent (HDD) types; liquid fine-fabric detergents; hand or manual dishwashing agents, including those of the high-foaming type; hand or manual dishwashing, automatic dishwashing, or dishware or tableware washing agents, including the various tablet, powder, solid, granular, liquid, gel, and rinse-aid types for household and institutional use; liquid cleaning and disinfecting agents, including antibacterial hand-wash types, cleaning bars, mouthwashes, denture cleaners, car shampoos, carpet shampoos, bathroom cleaners; personal care items, such as, but not limited to, e.g., hair shampoos and/or hair-rinses for humans (and other animals), shower gels and foam baths, skin care items, cosmetics, creams, bath and personal human soaps; metal cleaners; as well as cleaning auxiliaries, such as bleach additives and "stain-stick" or pre-treat types. Some granular compositions are in "compact" form; some liquid compositions are in a "concentrated" form.

In one aspect, the invention provides a cleaning composition or detergent composition comprising at least one protease variant or polypeptide of the invention, wherein the cleaning composition or detergent composition is useful for cleaning contact lens(es). In another aspect, the invention provides a cleaning composition or detergent composition comprising at least one protease variant or polypeptide of the invention, wherein the cleaning composition or detergent composition is useful in a personal care application. In another aspect, the invention provides a cleaning composition or detergent composition comprising at least one protease variant or polypeptide of the invention, wherein the cleaning composition or detergent composition is useful for cleaning or rinsing hair, including human hair and/or animal hair (e.g., hair shampoo and/or hair-rinse). In another aspect, the invention provides a cleaning composition or detergent composition comprising at least one protease variant or polypeptide of the invention, wherein the cleaning composition or detergent composition is useful for cleaning or treating skin (e.g., human and/or animal skin) (e.g., shower gel, foam bath, skin care cleaner, cosmetic, cream, and/or bath soap). In another aspect, the invention provides a cleaning composition or detergent composition comprising at least one protease variant or polypeptide of the invention, wherein the cleaning composition or detergent composition is useful for cleaning teeth and/or dentures and/or for oral care. Such cleaning compositions or detergent compositions may comprise at least one adjunct ingredient or carrier, at least one additional enzyme, at least one builder, and/or at least one surfactant and may be formulated or in a form appropriate to their use. Such cleaning or detergent compositions may contain phosphate or may be phosphate-free. Additional details regarding compositions of the invention are provided elsewhere herein.

As used herein, "fabric cleaning compositions" include hand and machine laundry detergent compositions including laundry additive compositions and compositions suitable for use in the soaking and/or pretreatment of stained fabrics (e.g., clothes, linens, and other textile materials).

As used herein, "non-fabric cleaning compositions" include non-textile (i.e., non-fabric) surface cleaning compositions, including, but not limited to, for example, hand or manual or automatic dishwashing detergent compositions, oral cleaning compositions, denture cleaning compositions, and personal cleansing compositions.

As used herein, the term "detergent composition" or "detergent formulation" is used in reference to a composition intended for use in a wash medium for the cleaning of soiled or dirty objects, including particular fabric and/or non-fabric objects or items. Such compositions of the present invention are not limited to any particular detergent composition or formulation. Indeed, the detergents of the invention may comprise at least one protease variant of the invention and, in addition, one or more surfactants, transferase(s), hydrolytic enzymes, perhydrolases, oxido reductases, builders (e.g., a builder salt), bleaching agents, bleach activators, bluing agents, fluorescent dyes, caking inhibitors, masking agents, enzyme activators, antioxidants, and/or solubilizers. In some instances, a builder salt is a mixture of a silicate salt and a phosphate salt, preferably with more silicate (e.g., sodium metasilicate) than phosphate (e.g., sodium tripolyphosphate). Some compositions of the invention, such as, but not limited to, cleaning compositions or detergent compositions, do not contain any phosphate (e.g., phosphate salt or phosphate builder).

As used herein, "dishwashing composition" refers to all forms of compositions for cleaning dishware, including cutlery, including, but not limited to, granular and liquid forms. In some aspects, the dishwashing composition is an "automatic dishwashing" composition that finds use in automatic dishwashing machines. It is not intended that the present invention be limited to any particular type of dishware composition. Indeed, the present invention finds use in cleaning dishware (e.g., dishes, including, but not limited to plates, cups, glasses, bowls, etc.) and cutlery (e.g., utensils, including, but not limited to, spoons, knives, forks, serving utensils, etc.) of any material, including, but not limited to, ceramics, plastics, metals, china, glass, acrylics, etc. The term "dishware" is used herein in reference to both dishes and cutlery.

As used herein, the term "bleaching" refers to the treatment of a material (e.g., fabric, laundry, pulp, etc.) or surface for a sufficient length of time and/or under appropriate pH and/or temperature conditions to effect a brightening (i.e., whitening) and/or cleaning of the material. Examples of chemicals suitable for bleaching include, but are not limited to, for example, $ClO_2$, $H_2O_2$, peracids, $NO_2$, etc.

As used herein, "wash performance" of a protease (e.g., a protease variant of the invention) refers to the contribution of a protease variant to washing that provides additional cleaning performance to the detergent as compared to the detergent without the addition of the protease variant to the composition. Wash performance is compared under relevant washing conditions. In some test systems, other relevant factors, such as detergent composition, sud concentration, water hardness, washing mechanics, time, pH, and/or temperature, can be controlled in such a way that condition(s) typical for household application in a certain market segment (e.g., hand or manual dishwashing, automatic dishwashing, dishware cleaning, tableware cleaning, fabric cleaning, etc.) are imitated.

The term "relevant washing conditions" is used herein to indicate the conditions, particularly washing temperature, time, washing mechanics, sud concentration, type of detergent and water hardness, actually used in households in a hand dishwashing, automatic dishwashing, or laundry detergent market segment.

The term "improved wash performance" is used to indicate that a better end result is obtained in stain removal under relevant washing conditions, or that less protease variant, on weight basis, is needed to obtain the same end result relative to the corresponding wild-type or starting parent protease.

As used herein, the term "disinfecting" refers to the removal of contaminants from the surfaces, as well as the inhibition or killing of microbes on the surfaces of items. It is not intended that the present invention be limited to any particular surface, item, or contaminant(s) or microbes to be removed.

The "compact" form of the cleaning compositions herein is best reflected by density and, in terms of composition, by the amount of inorganic filler salt. Inorganic filler salts are conventional ingredients of detergent compositions in powder form. In conventional detergent compositions, the filler salts are present in substantial amounts, typically about 17 to about 35% by weight of the total composition. In contrast, in compact compositions, the filler salt is present in amounts not exceeding about 15% of the total composition. The filler salt can be present in amounts that do not exceed about 10%, or more preferably, about 5%, by weight of the composition. The inorganic filler salts can be selected from the alkali and alkaline-earth-metal salts of sulfates and chlorides. The filler salt may be sodium sulfate.

The position of an amino acid residue in a given amino acid sequence is typically numbered herein using the numbering of the position of the corresponding amino acid residue of the *B. amyloliquefaciens* subtilisin BPN' amino acid sequence shown in SEQ ID NO:2. The *B. amyloliquefaciens* subtilisin BPN' amino acid sequence of SEQ ID NO:2 thus serves as a reference sequence. A given amino acid sequence, such as a protease variant amino acid sequence described herein, can be aligned with the BPN' sequence (SEQ ID NO:2) using an alignment algorithm as described herein, and an amino acid residue in the given amino acid sequence that aligns (preferably optimally aligns) with an amino acid residue in the BPN' sequence can be conveniently numbered by reference to the corresponding amino acid residue in the subtilisin BPN' sequence.

Generally, the nomenclature used herein and many of the laboratory procedures in cell culture, molecular genetics, molecular biology, nucleic acid chemistry, and protein chemistry described below are well known and commonly employed by those of ordinary skill in the art. Methods for production and manipulation of recombinant nucleic acid methods, nucleic acid synthesis, cell culture methods, and transgene incorporation (e.g., transfection, electroporation) are known to those skilled in the art and are described in numerous standard texts. Oligonucleotide synthesis and purification steps are typically performed according to specifications. Techniques and procedures are generally performed according to conventional methods well known in the art and various general references that are provided throughout this document. Procedures therein are believed to be well known to those of ordinary skill in the art and are provided for the convenience of the reader.

A fabric and home care product may comprise a protease (including a protease variant), including one or more protease variants of the invention and a material selected from the group consisting of an encapsulate comprising a perfume, a hueing agent, an amphiphilic cleaning polymer and mixtures thereof, with the balance of any aspects of the aforementioned composition is made up of one or more adjunct materials, is disclosed. In one aspect of the aforementioned fabric and home care product, said fabric and home care product may comprise, based on total fabric and home care product weight, from about 0.005 weight percent (0.0005 wt %) to about 0.1 wt %, from about 0.001 wt % to about 0.05 wt %, or even from about 0.002 wt % to about 0.03 wt % of said protease. In one aspect of the aforementioned fabric and home care product, said fabric and home care product may comprise, based on total fabric and home care product weight, about 0.00003 wt % to about 0.1 wt %, from about 0.00008 wt % to about 0.05 wt %, or even from about 0.0001 wt % to about 0.04 wt % fabric hueing agent. In one aspect of the aforementioned fabric and home care product, said fabric and home care product may comprise, based on total fabric and home care product weight, from about 0.001 wt % to about 5 wt %, from about 0.01 wt % to about 2 wt %, or even from about 0.03 wt % to about 0.5 wt %, perfume capsules. In one aspect of the aforementioned fabric and home care product, said fabric and home care product may comprise, based on total fabric and home care product weight, from about 0.1 wt % to about 5 wt %, from about 0.25 wt % to about 2.5 wt %, or even from about 0.3 wt % to about 1.5 wt % amphiphilic cleaning polymer.

Polypeptides of the Invention

The present invention provides novel polypeptides, which may be collectively referred to as "polypeptides of the invention". Polypeptides of the invention include isolated, recombinant, substantially pure, or non-naturally occurring protease variants, including, for example, subtilisin protease variant polypeptides, which have enzymatic activity (e.g., proteolytic activity) and/or additional properties discussed in greater detail elsewhere herein (e.g., cleaning activity, stability, etc.). Polypeptides of the invention include isolated, recombinant, substantially pure, or non-naturally occurring cold water proteases having proteolytic activities, cleaning activities, stability, and other properties discussed elsewhere herein. Such polypeptides, including cold water proteases, of the invention may have enhanced performance relative to known proteases (e.g., enhanced proteolytic activity, enhanced cleaning performance or activity, enhanced stability, etc). Polypeptides of the invention are useful in cleaning applications and may be incorporated into cleaning compositions that are useful in methods of cleaning an item or a surface (e.g., of surface of an item) in need of cleaning Polypeptides of the invention having proteolytic activity are useful in fabric and home care products, including, e.g., fabric and home care cleaning compositions. Some polypeptides of the invention having proteolytic activity are useful in personal care compositions. Polypeptides of the invention having proteolytic activity are also useful in non-fabric and home care products (i.e., those products that are not fabric and home care products are described herein). A protease variant of the invention may be a subtilisin protease variant. The invention includes *Bacillus* species protease variants and *Bacillus* species subtilisin protease variants.

Polypeptides of the invention are disclosed throughout this specification, including, but not limited to, Part I Examples and Part II Examples provided below. The invention includes an isolated, recombinant, substantially pure, or non-naturally occurring protease variant (e.g., a subtilisin variant) having proteolytic activity, which polypeptide comprises an amino acid sequence having at least about 60%, 70%, 80%, 85%, 86%, 87%, 88%, 89%, 90%, 91%, 92%, 93%, 94%, 95%, 96%, 97%, 98%, 99%, 99.5%, or 100% sequence identity to a specific protease variant amino acid sequence set forth in any of the Part I and Part II Examples below. In one aspect, the invention includes an isolated, recombinant, substantially pure, or non-naturally occurring subtilisin polypeptide having proteolytic activity, wherein said polypeptide is a protease variant of the BPN' sequence of SEQ ID NO:2 and said polypeptide comprises an amino acid sequence having at least about 60%, 70%, 80%, 85%, 86%, 87%, 88%, 89%, 90%, 91%, 92%, 93%, 94%, 95%, 96%, 97%, or 98% sequence identity to SEQ ID NO:2 and a set of amino acid substitutions set forth in any of Part I Examples. In one aspect, the invention includes an isolated, recombinant, substantially pure, or non-naturally occurring subtilisin polypeptide having proteolytic activity, wherein said polypeptide is a protease variant of the GG36 sequence of SEQ ID NO:755 and said polypeptide comprises an amino acid sequence having at least about 60%, 70%, 80%, 85%, 86%, 87%, 88%, 89%, 90%, 91%, 92%, 93%, 94%, 95%, 96%, 97%, or 98% sequence identity to SEQ ID NO:755 and a set of amino acid substitutions set forth in any of Part II Examples.

In a first aspect, the invention provides an isolated or non-naturally occurring polypeptide protease variant of a parent protease enzyme, the variant having proteolytic activity and comprising an amino acid sequence which comprises an alteration at one or more amino acid positions corresponding to amino acid positions of SEQ ID NO:2 selected from the group consisting of positions 24, 53, 78, 97, 101, 128, and 217, wherein the at least one alteration is independently (i) an insertion of one or more amino acid residues upstream or downstream of the amino acid residue which occupies the position, (ii) a deletion of the amino acid residue which occupies the position, or (iii) a substitution of the amino acid residue which occupies the position with a different amino acid residue, wherein each amino acid position is numbered by correspondence with an amino acid position in the amino acid sequence of *Bacillus amyloliquefaciens* subtilisin protease BPN' set forth in SEQ ID NO:2 as determined by alignment of the amino acid sequence of the variant with SEQ ID NO:2. A variant of a protease enzyme according to the first aspect of the invention may be termed a protease variant. A variant according to the first aspect of the invention may be a non-naturally occurring protease. A variant according to the first aspect of the invention may be isolated or purified. A variant according to the first aspect of the invention may be a subtilisin variant. A variant according to the first aspect of the invention may have proteolytic activity. A variant according to the first aspect of the invention may have enhanced proteolytic activity compared to the proteolytic activity of the BPN' amino acid sequence set forth in SEQ ID NO:2.

A variant according to the first aspect of the invention may be a variant of a parent protease that is a subtilisin protease, and the subtilisin protease may be a *Bacillus* species protease. A parent *Bacillus* protease according to the first aspect of the invention may be selected from the group consisting of *B. amyloliquefaciens* subtilisin protease BPN' (SEQ ID NO:2), *B. stearothermophilus, B. subtilis, B. licheniformis, B. lentus, B. brevis, B. stearothermophilus, B. alkalophilus, B. amyloliquefaciens, B. clausii, B. halodurans, B. megaterium, B. coagulans, B. circulans, B. lautus, B.* species TS-23, *B. thuringiensis*, BPN'-v3 (SEQ ID NO4:), and BPN'-v36 (SEQ ID NO:6). A parent protease according to the first aspect of the invention may comprise an amino acid sequence having at least 60%, 70%, 80%, 85%, 90%, 91%, 92%, 93%, 94%, 95%, 96%, 97%, 98%, 99% or 100% sequence identity to the amino acid sequence of SEQ ID NO:2, SEQ ID NO:4, or SEQ ID NO:6.

A variant according to the first aspect of the invention may be a protease variant having a mature form. A variant according to the first aspect of the invention may be a protease variant having a mature form.

A variant according to the first aspect of the invention may comprise an amino acid sequence comprising an alteration at two amino acid positions selected from the group consisting of positions 24, 53, 78, 97, 101, 128, and 217. A variant according to the first aspect of the invention may comprise an amino acid sequence comprising an alteration at three amino acid positions selected from the group consisting of positions 24, 53, 78, 97, 101, 128, and 217. A variant according to the first aspect of the invention may comprise an amino acid sequence comprising an alteration at four amino acid positions selected from the group consisting of positions 24, 53, 78, 97, 101, 128, and 217. A variant according to the first aspect of the invention may comprise an amino acid sequence comprising an alteration at five amino acid positions selected from the group consisting of positions 24, 53, 78, 97, 101, 128, and 217. A variant according to the first aspect of the invention may comprise an amino acid sequence comprising an alteration at six amino acid positions selected from the group consisting of positions 24, 53, 78, 97, 101, 128, and 217. A variant according to the first aspect of the invention may comprise an amino acid sequence comprising an alteration at each of the amino acid positions corresponding to positions of SEQ ID NO:2 selected from the group consisting of positions 24, 53, 78, 97, 101, 128, and 217. A variant according to the first aspect of the invention may comprise an amino acid sequence comprising a substitution of an amino acid residue with a different amino acid residue at a position selected from the group consisting of positions 24, 53, 78, 97, 101, 128, and 217.

A variant according to the first aspect of the invention may comprise an amino acid sequence comprising a substitution of an amino acid residue with a different amino acid residue at each of two or three positions selected from the group consisting of positions 24, 53, 78, 97, 101, 128, and 217. A variant according to the first aspect of the invention may comprise an amino acid sequence comprising a substitution of an amino acid residue with a different amino acid residue at each of four positions selected from the group consisting of positions 24, 53, 78, 97, 101, 128, and 217. A variant according to the first aspect of the invention may comprise an amino acid sequence comprising a substitution of an amino acid residue with a different amino acid residue at each of five positions selected from the group consisting of positions 24, 53, 78, 97, 101, 128, and 217. A variant according to the first aspect of the invention may comprises an amino acid sequence comprising a substitution of an amino acid residue with a different amino acid residue at each of six or seven positions selected from the group consisting of positions 24, 53, 78, 97, 101, 128, and 217. A variant according to the first aspect of the invention may comprise an amino acid sequence comprising a substitution of an amino acid residue with a different amino acid residue at each of positions 24, 53, 78, 101, 128, and 217, wherein each position is numbered by correspondence with a position in SEQ ID NO:2.

A variant according to the first aspect of the invention may comprise an amino acid sequence comprising at least one amino acid substitution selected from the group consisting of X024G/R, X053G, X078N, X097A, X101N, X128A/S, and X217Q/L. A variant according to the first aspect of the invention may comprise an amino acid sequence comprising at least two amino acid substitutions selected from the group consisting of X024G/R, X053G, X078N, X097A, X101N, X128A/S, and X217Q/L. A variant according to the first aspect of the invention may comprise an amino acid sequence comprising at least three amino acid substitutions selected from the group consisting of X024G/R, X053G, X078N, X097A, X101N, X128A/S, and X217Q/L. A variant according to the first aspect of the invention may comprise an amino acid sequence comprising at least four amino acid substitutions selected from the group consisting of X024G/R, X053G, X078N, X097A, X101N, X128A/S, and X217Q/L. A variant according to the first aspect of the invention may comprise an amino acid sequence comprising at least five amino acid substitutions selected from the group consisting of X024G/R, X053G, X078N, X097A, X101N, X128A/S, and X217Q/L. A variant according to the first aspect of the invention may comprise an amino acid sequence comprising at least six amino acid substitutions selected from the group consisting of X024G/R, X053G, X078N, X097A, X101N, X128A/S, and X217Q/L. A variant according to the first aspect of the invention may comprise an amino acid sequence comprising a set of substitutions selected from the group consisting of: (a) X128A/S and/or X217L/Q, (b) G128A/S and/or Y217L/Q, and (c) G097A, G128A/S, and Y217L/Q. A variant according to the first aspect of the invention may comprise an amino acid sequence comprising amino acid substitutions X024G/R+X053G+X078N+X101N+X128A/S+X217Q/L, wherein the variant has proteolytic activity; and wherein optionally the variant has enhanced proteolytic activity or enhanced cleaning activity compared to the protease set forth in SEQ ID NO:2, SEQ ID NO:4, or SEQ ID NO:6 or a performance index in a proteolytic assay (e.g., AAPF assay) or cleaning assay (e.g., BMI, grass, or egg microswatch assay) that is greater than that of the protease set forth in SEQ ID NO:2, SEQ ID NO:4, or SEQ ID NO:6.

A variant according to the first aspect of the invention may comprise at least one amino acid substitution selected from the group of S024G, S053G, S078N, S101N, G128A/S, and Y217Q. A variant according to the first aspect of the invention may comprise an amino acid sequence comprising amino acid substitutions S024G+S053G+S078N+S101N+G128A+Y217Q.

A variant according to the first aspect of the invention may comprise an amino acid sequence having at least 60%, 65%, 70%, 80%, or 85% sequence identity to the amino acid sequence of SEQ ID NO:2. A variant according to the first aspect of the invention may comprise an amino acid sequence having at least 90% sequence identity to SEQ ID NO:2. A variant according to the first aspect of the invention may comprise an amino acid sequence having at least 91%, 92%, 93%, 94%, 95%, 96%, 97%, 98%, or 99% sequence identity to SEQ ID NO:2. A variant according to the first aspect of the invention may comprise an amino acid sequence having at least 95% sequence identity to SEQ ID NO:2.

A variant according to the first aspect of the invention may have enhanced proteolytic activity compared to the proteolytic activity of the protease set forth in SEQ ID NO:2. A variant according to the first aspect of the invention may have enhanced proteolytic activity compared to the proteolytic activity of the protease set forth in SEQ ID NO:4. A variant according to the first aspect of the invention may have enhanced proteolytic activity compared to the proteolytic activity of the protease set forth in SEQ ID NO:6. A variant according to the first aspect of the invention may have enhanced cleaning activity compared to the cleaning activity of the protease set forth in SEQ ID NO:2, SEQ ID NO:4, or SEQ ID NO:6. A variant according to the first aspect of the invention may a performance index in a proteolytic assay (e.g., AAPF assay) or cleaning assay (e.g., BMI, grass, or egg microswatch assay) that is greater than that of the protease set forth in SEQ ID NO:2, SEQ ID NO:4, or SEQ ID NO:6.

In a second aspect, the invention provides an isolated or non-naturally occurring polypeptide protease variant of a parent protease, the variant comprising an amino acid sequence comprising three amino acid substitutions selected from the group consisting of X024G/R, X053G, X078N, X101N, X128A/S, and X217L/Q, wherein the variant has proteolytic activity and each amino acid position of the variant is numbered by correspondence to an amino acid position in the amino acid sequence of SEQ ID NO:2 as determined by alignment of the amino acid sequence of the variant with SEQ ID NO:2. A variant according to the first aspect of the invention may have enhanced proteolytic activity or enhanced cleaning activity compared to the protease set forth in SEQ ID NO:2, SEQ ID NO:4, or SEQ ID NO:6. A variant according to the first aspect of the invention may have a performance index in a proteolytic assay (e.g., AAPF assay) or cleaning assay (e.g., BMI, grass, or egg microswatch assay) that is greater than that of the protease set forth in SEQ ID NO:2, SEQ ID NO:4, or SEQ ID NO:6.

A variant according to the second aspect of the invention may comprise an amino acid sequence comprising three amino acid substitutions selected from the group consisting of X024G/R, X053G, X078N, X101N, X128A/S, and X217L/Q, wherein the variant has proteolytic activity and each amino acid position of the variant is numbered by correspondence to an amino acid position in the amino acid sequence of SEQ ID NO:2 as determined by alignment of the amino acid sequence of the variant with SEQ ID NO:2. A variant according to the second aspect of the invention may comprise an amino acid sequence comprising four amino acid substitutions selected from the group consisting of X024G/R, X053G, X078N, X101N, X128A/S, and X217L/Q. A variant according to the second aspect of the invention may comprise an amino acid sequence comprising five amino acid substitutions selected from the group consisting of X024G/R, X053G, X078N, X101N, X128A/S, and X217L/Q. A variant according to the second aspect of the invention may comprise an amino acid sequence comprising six amino acid substitutions selected from the group consisting of X024G/R, X053G, X078N, X101N, X128A/S, and X217L/Q. A variant according to the second aspect of the invention may comprise an amino acid sequence further comprising amino acid substitution X097A. A variant according to the second aspect of the invention may comprise an amino acid sequence comprising amino acid substitutions X024G/R+X053G+X078N+X101N+X128A/S+X217L/Q or X097A+X128A/S+X217L/Q.

A variant according to the second aspect of the invention may comprise an amino acid sequence comprising amino acid substitutions S024G/R+S053G+S078N+S101N+G128A/S+Y217L/Q or G097A+G128A/S+Y217L/Q. A variant according to the second aspect of the invention may comprise an amino acid sequence comprising amino acid substitutions S024G+S053G+S078N+S101N+G128S+Y217Q or S024G+S053G+S078N+S101N+G128A+Y217Q.

The amino acid sequence of a variant according to the second aspect of the invention may further comprise the substitution N109G. The amino acid sequence of a variant according to the second aspect of the invention may further comprise the substitution N076D. The amino acid sequence of a variant according to the second aspect of the invention may further comprise the substitution S033T. The amino acid sequence of a variant according to the second aspect of the invention may further comprise the substitution N243V. The amino acid sequence of a variant according to the second aspect of the invention may further comprise the substitution S248A. The amino acid sequence of a variant according to the second aspect of the invention may further comprise the substitution A088T. The amino acid sequence of a variant according to the second aspect of the invention may further comprise the substitution S063G. The amino acid sequence of the variant according to the second aspect of the invention may further comprise two or more substitutions selected from the group consisting of N109G, N076D, S033T, N243V, S248A, A088T, and S063G.

The amino acid sequence of a variant according to the second aspect of the invention may comprise an amino acid sequence comprising amino acid substitutions S024G+S053G+S078N+S101N+G128S+Y217Q or S024G+S053G+S078N+S101N+G128A+Y217Q and may further comprise a set of amino acid substitutions selected from the group consisting of: A088T+N109G+A116T+G131H+N243V+L257G, S033T+N076D, S009T+N109G+K141R+N243V, S162G+K256R, N109G+A116T, N109G+L257G, S162G+L257G, N061G+N109G+N243V, N109G+N243V+S248A, S033T+N076D+N109G+N218S+N243V+S248N+K256R, N109G+A116T+N243V+K256R, A088T+N109G+A116T+G131H+N243V, A088T+N109G, N109G+N243V, T158S+L257G, N061S+N109G+N243V, P040A+N109G+N243V+S248N+K256R, S009T+S018T+Y021N+N109G+K141R, A088T+N109G+A116T+T158S+N243V+K256R, A088T+N109G+A116T+T158S+N218S+L257G, N109G+K256R, N109G+N243V+K256R, S063G+K256R, S063G+N109G, S063G, S063G+N076D, S033T+N076D+N218S, and N076D+N218S.

A variant according to the second aspect of the invention may comprise an amino acid sequence comprising amino acid substitutions S024G+S053G+S078N+S101N+G128A+Y217Q and may further comprise a set of amino acid substitutions selected from the group consisting of: A088T+N109G+A116T+G131H+N243V+L257G, S033T+N076D, S009T+N109G+A128S+K141R+N243V, S162G+K256R, N109G+A116T, N109G+L257G, S162G+L257G, N061G+N109G+N243V, N109G+A128S+N243V+S248A, S033T+N076D+N109G+A128S+N218S+N243V+S248N+K256R, N109G+A116T+N243V+K256R, A088T+N109G+A116T+G131H+N243V, A088T+N109G, N109G+N243V, T158S+L257G, N061S+N109G+N243V, P040A+N109G+A128S+N243V+S248N+K256R, S009T+S018T+Y021N+N109G+A128S+K141R, A088T+N109G+A116T+T158S+N243V+K256R, A088T+N109G+A116T+T158S+N218S+L257G, N109G+K256R, N109G+A128S+N243V+K256R, S063G+K256R, S063G+N109G, S063G+A128S, S063G+N076D, S033T+N076D+A128S+N218S, and N076D+N218S, wherein the variant has proteolytic activity and each amino acid position of the variant is numbered by correspondence to an amino acid position in the amino acid sequence of SEQ ID NO:2 as determined by alignment of the amino acid sequence of the variant with SEQ ID NO:2. Notably, for example, a variant according to the second aspect of the invention which comprises a sequence comprising substitutions S024G+S053G+S078N+S101N+G128A+Y217Q, and which further comprises the set of substitutions S009T+N109G+A128S+K141R+N243V, has a serine (S) at position 128 because the alanine in position 128 (i.e., G128A substitution) is substituted with S (A128S substitution).

The amino acid sequence of a variant according to the second aspect of the invention may have at least 60%, 65%, or 70% sequence identity to the amino acid sequence of SEQ ID NO:2, SEQ ID NO:4, or SEQ ID NO:6. The amino acid sequence of a variant according to the second aspect of the invention may have at least 80% or 85% sequence identity to the amino acid sequence of SEQ ID NO:2, SEQ ID NO:4, or SEQ ID NO:6. The amino acid sequence of a variant according to the second aspect of the invention may have at least 90%, 91%, 92%, 93%, 94%, 95%, 96%, 97%, or 98% sequence identity to the amino acid sequence of SEQ ID NO:2, SEQ ID NO:4, or SEQ ID NO:6.

The patent protease according to the second aspect of the invention may be a subtilisin protease. The parent protease according to the second aspect of the invention may comprise an amino acid sequence having at least 60%, 70%, 80%, 85%, 90%, 91%, 92%, 93%, 94%, 95%, 96%, 97%, 98%, 99% or 100% sequence identity to the amino acid sequence of SEQ ID NO:2, SEQ ID NO:4, or SEQ ID NO:6. A variant according to the second aspect of the invention may be a protease variant having a mature form. A variant according to the first aspect of the invention may be a protease variant having a mature form.

The invention also provides an isolated polypeptide (e.g., protease variant) according to the second aspect of the invention comprising an amino acid sequence having at least 80%, 85%, 90%, 91%, 92%, 93%, 94%, 95%, 96%, 97%, 98%, 99% or 100% sequence identity to the amino acid sequence of SEQ ID NO:6 and comprising a set of amino acid substitutions selected from the group consisting of:
A088T+N109G+A116T+G131H+N243V+L257G,
S033T+N076D,
S009T+N109G+A128S+K141R+N243V,
S162G+K256R,
N109G+A116T,
N109G+L257G,
S162G+L257G,
N061G+N109G+N243V,
N109G+A128S+N243V+S248A,
S033T+N076D+N109G+A128S+N218S+N243V+S248N+K256R,
N109G+A116T+N243V+K256R,
A088T+N109G+A116T+G131H+N243V,
A088T+N109G,
N109G+N243V,
T158S+L257G,
N061S+N109G+N243V,
P040A+N109G+A128S+N243V+S248N+K256R,
S009T+S018T+Y021N+N109G+A128S+K141R,
A088T+N109G+A116T+T158S+N243V+K256R, A088T+N109G+A116T+T158S+N218S+L257G,
N109G+K256R,
N109G+A128S+N243V+K256R,
S063G+K256R,
S063G+N109G,
S063G+A128S,
S063G+N076D,
S033T+N076D+A128S+N218S, and
N076D+N218S,
wherein the variant has proteolytic activity and each amino acid position of the variant is numbered by correspondence to an amino acid position in the amino acid sequence of SEQ ID NO:2 as determined by alignment of the amino acid sequence of the variant with SEQ ID NO:2. Such polypeptide may have enhanced proteolytic activity or enhanced cleaning activity compared to the protease set forth in SEQ ID NO:2, SEQ ID NO:4, or SEQ ID NO:6. Such polypeptide may have a performance index in a proteolytic assay (e.g., AAPF assay) or cleaning assay (e.g., BMI, grass, or egg microswatch assay) that is greater than that of the protease set forth in SEQ ID NO:2, SEQ ID NO:4, or SEQ ID NO:6. A variant according to the second aspect of the invention may have enhanced proteolytic activity compared to the proteolytic activity of the BPN' protease having the sequence of SEQ ID NO:2. A variant according to the second aspect of the invention may have enhanced proteolytic activity compared to the proteolytic activity of the protease having the sequence of SEQ ID NO:4 or SEQ ID NO:6. The parent protease of a variant according to the second aspect of the invention may be a subtilisin protease, and optionally the subtilisin protease may be a *Bacillus* species. The parent subtilisin protease of a variant according to the second aspect of the invention may be selected from the group consisting of *B. amyloliquefaciens* subtilisin protease BPN' (SEQ ID NO:2), *B. stearothermophilus, B. subtilis, B. licheniformis, B. lentus, B. brevis, B. stearothermophilus, B. alkalophilus, B. amyloliquefaciens, B. clausii, B. halodurans, B. megaterium, B. coagulans, B. circulans, B. lautus, B.* species TS-23, *B. thuringiensis*, BPN'-v3 (SEQ ID NO4:), and BPN'-v36 (SEQ ID NO:6). A parent protease according to the second aspect of the invention may comprise an amino acid sequence having at least 60%, 65%, 70%, 75%, 80%, 85%, 90%, 91%, 92%, 93%, 94%, 95%, 96%, 97%, 98%, 99% or 100% sequence identity to the amino acid sequence of SEQ ID NO:2, SEQ ID NO:4, or SEQ ID NO:6.

A variant according to the second aspect of the invention may be a protease variant having a mature form. A parent protease according to the second aspect of the invention may be protease having a mature form.

A variant according to the second aspect of the invention may comprise an amino acid sequence having at least 60%, 65%, 70%, 75%, 80%, 85%, 90%, 91%, 92%, 93%, 94%, 95%, 96%, 97%, 98%, 99% or 100% sequence identity to SEQ ID NO:2, SEQ ID NO:6, or SEQ ID NO:4.

In a third aspect, the invention provides an isolated or non-naturally occurring polypeptide having protease activity, said polypeptide comprising an amino acid sequence having at least 80%, 85%, 90%, 91%, 92%, 93%, 94%, 95%, 96%, 97%, 98%, 99%, or 100% sequence identity to a polypeptide sequence selected from the group consisting of:
a) BPN'-S024G+S053G+S078N+S101N+G128A+Y217Q+A088T+N109G+A116T+G131H+N243V+L257G;
b) BPN'-S024G+S053G+S078N+S101N+G128A+Y217Q+S033T+N076D;
c) BPN'-S024G+S053G+S078N+S101N+G128S+Y217Q+S009T+N109G+K141R+N243V;
d) BPN'-S024G+S053G+S078N+S101N+G128A+Y217Q+S162G+K256R;
e) BPN'-S024G+S053G+S078N+S101N+G128A+Y217Q+N109G+A116T;
f) BPN'-S024G+S053G+S078N+S101N+G128A+Y217Q+N109G+L257G;
g) BPN'-S024G+S053G+S078N+S101N+G128A+Y217Q+S162G+L257G;
h) BPN'-S024G+S053G+S078N+S101N+G128A+Y217Q+N061G+N109G+N243V;
i) BPN'-S024G+S053G+S078N+S101N+G128S+Y217Q+N109G+N243V+S248A;
j) BPN'-S024G+S053G+S078N+S101N+G128S+Y217Q+S033T+N076D+N109G+N218S+N243V+S248N+K256R;
k) BPN'-S024G+S053G+S078N+S101N+G128A+Y217Q+N109G+A116T+N243V+K256R;
l) BPN'-S024G+S053G+S078N+S101N+G128A+Y217Q+A088T+N109G+A116T+G131H+N243V;
m) BPN'-S024G+S053G+S078N+S101N+G128A+Y217Q+A088T+N109G;
n) BPN'-S024G+S053G+S078N+S101N+G128A+Y217Q+N109G+N243V;
o) BPN'-S024G+S053G+S078N+S101N+G128A+Y217Q+T158S+L257G;
p) BPN'-S024G+S053G+S078N+S101N+G128A+Y217Q+N061S+N109G+N243V;
q) BPN'-S024G+S053G+S078N+S101N+G128S+Y217Q+P040A+N109G+N243V+S248N+K256R;
r) BPN'-S024G+S053G+S078N+S101N+G128S+Y217Q+S009T+S018T+Y021N+N109G+K141R;
s) BPN'-S024G+S053G+S078N+S101N+G128A+Y217Q+A088T+N109G+A116T+T158S+N243V+K256R;
t) BPN'-S024G+S053G+S078N+S101N+G128A+Y217Q+A088T+N109G+A116T+T158S+N218S+L257G;
u) BPN'-S024G+S053G+S078N+S101N+G128A+Y217Q+N109G+K256R;
v) BPN'-S024G+S053G+S078N+S101N+G128S+Y217Q+N109G+N243V+K256R;
w) BPN'-S024G+S053G+S078N+S101N+G128A+Y217Q+S063G+K256R;
x) BPN'-S024G+S053G+S078N+S101N+G128A+Y217Q+S063G+N109G;
y) BPN'-S024G+S053G+S078N+S101N+G128S+Y217Q+S063G;
z) BPN'-S024G+S053G+S078N+S101N+G128A+Y217Q+S063G+N076D;
aa) BPN'-S024G+S053G+S078N+S101N+G128S+Y217Q+S033T+N076D+N218S;
bb) BPN'-S024G+S053G+S078N+S101N+G128A+Y217Q+N076D+N218S; and
cc) BPN'-S024G+S053G+S078N+S101N+G128A+Y217Q, wherein each amino acid position of the variant is numbered by correspondence with an amino acid position of the sequence of SEQ ID NO:2. A variant according to the third aspect of the invention may have enhanced proteolytic activity or enhanced cleaning activity compared to the protease set forth in SEQ ID NO:2, SEQ ID NO:4, or SEQ ID NO:6. A variant according to the third aspect of the invention may have a performance index in a proteolytic assay (e.g., AAPF assay) or cleaning assay (e.g., BMI, grass, or egg microswatch assay) that is greater than that of the protease set forth in SEQ ID NO:2, SEQ ID NO:4, or SEQ ID NO:6.

A polypeptide according to the third aspect of the invention may comprise or consist of the amino acid sequence set forth in any of a) through cc) above or a fragment of any thereof having proteolytic activity. A variant or parent protease according to the third aspect of the invention may be in a mature form.

In a fourth aspect, the invention provides an isolated or non-naturally occurring polypeptide having protease activity selected from the group consisting of: (a) a polypeptide comprising an amino acid sequence having at least 85%, 90%, 95%, 96%, 97%, 98%, 99%, or 100% sequence identity to the polypeptide sequence of SEQ ID NO:6; (b) a polypeptide encoded by a polynucleotide that hybridizes under at least high stringency conditions with (i) the polynucleotide sequence of SEQ ID NO:5 or (ii) a complementary polynucleotide sequence of (i); and (c) a polypeptide encoded by a polynucleotide comprising a nucleotide sequence having at least 90%, 95%, 96%, 97%, 98%, 99%, or 100% sequence identity to the polynucleotide sequence of SEQ ID NO:5. A polypeptide according to the fourth aspect of the invention may comprise or consist of the amino acid sequence of SEQ ID NO:6, or a fragment thereof having proteolytic activity. The variant according to the fourth aspect of the invention may have increased proteolytic activity and/or cleaning performance or activity compared to that of mature BPN' (SEQ ID NO:2). The variant according to the fourth aspect of the invention may have increased proteolytic activity and/or cleaning performance or activity compared to that of SEQ ID NO:4 or SEQ ID NO:6. A variant or parent protease according to the fourth aspect of the invention may be in a mature form.

In a fifth aspect, the invention provides an isolated or non-naturally occurring protease variant of a parent protease, wherein: (a) the variant comprises an amino acid sequence having no more than 25, 20, 15, or 10 alterations relative to the parent protease, wherein (i) the alterations are independently selected from an insertion, a deletion, or a substitution, and (ii) the alterations include a substitution of glycine at positions 24 and 53, a substitution of asparagine at positions 78 and 101, a substitution of alanine or serine at position 128, and a substitution of glutamine at position 217, (b) the parent protease has at least 90% sequence identity to SEQ ID NO:2, (c) the amino acid sequence of SEQ ID NO:2 is used for determining position numbering; and (d) the variant has increased proteolytic activity relative to the parent protease, wherein each amino acid position is numbered by correspondence with an amino acid position of the sequence of SEQ ID NO:2. The amino acid sequence of a variant according to the fifth aspect of the invention may have at least 80%, 85%, 90%, 91%, 92%, 93%, 94%, 95%, 96%, 97%, or 98% sequence identity to the amino acid sequence of SEQ ID NO:2, SEQ ID NO:4, or SEQ ID NO:6.

The parent protease according to the fifth aspect of the invention may have at least 80%, 85%, 95%, 96%, 97%, 98%, 99%, or 100% identity to the sequence of SEQ ID NO:2, SEQ ID NO:4, or SEQ ID NO:6. The parent protease according to the fifth aspect of the invention may be a protease having the amino acid sequence of SEQ ID NO:2. A variant or parent protease according to the fifth aspect of the invention may be in a mature form.

The amino acid sequence of a variant according to the fifth aspect of the invention may further comprise the substitution N109G. The amino acid sequence of a variant according to the fifth aspect of the invention may further comprise the substitution N076D. The amino acid sequence of a variant according to the fifth aspect of the invention may further comprise the substitution S033T. The amino acid sequence of a variant according to the fifth aspect of the invention may further comprise the substitution N243V. The amino acid sequence of a variant according to the fifth aspect of the invention may further comprise the substitution S248A. The amino acid sequence of a variant according to the fifth aspect of the invention may further comprise the substitution A088T. The amino acid sequence of a variant according to the fifth aspect of the invention may further comprise the substitution S063G.

The amino acid sequence of a variant according to the fifth aspect of the invention may further comprise a set of amino acid substitutions selected from the group consisting of: A088T+N109G+A116T+G131H+N243V+L257G, S033T+N076D, S009T+N109G+K141R+N243V, S162G+K256R, N109G+A116T, N109G+L257G, S162G+L257G, N061G+N109G+N243V, N109G+N243V+S248A, S033T+N076D+N109G+N218S+N243V+S248N+K256R, N109G+A116T+N243V+K256R, A088T+N109G+A116T+G131H+N243V, A088T+N109G, N109G+N243V, T158S+L257G, N061S+N109G+N243V, P040A+N109G+N243V+S248N+K256R, S009T+S018T+Y021N+N109G+K141R, A088T+N109G+A116T+T158S+N243V+K256R, A088T+N109G+A116T+T158S+N218S+L257G, N109G+K256R, N109G+N243V+K256R, S063G+K256R, S063G+N109G, S063G, S063G+N076D, S033T+N076D+N218S, and N076D+N218S.

The parent protease according to the fifth aspect of the invention may be a subtilisin protease. The parent protease according to the fifth aspect of the invention may be BPN' set forth in SEQ ID NO:2. The variant according to the fifth aspect of the invention may have increased proteolytic activity and/or cleaning performance or activity compared to that of SEQ ID NO:4 or SEQ ID NO:6.

In a sixth aspect, the invention provides an isolated or non-naturally occurring protease variant of a parent protease, wherein (a) the variant comprises an amino acid sequence (i) having at least 80%, 85%, 90%, 91%, 92%, 93%, 94%, 95%, 96%, or 97% identity to the sequence of SEQ ID NO:2 and (ii) comprising a substitution of glycine at positions 24 and 53, a substitution of asparagine at positions 78 and 101, a substitution of alanine or serine at position 128, and a substitution of glutamine at position 217; (b) the parent protease has at least 80%, 85%, 90%, 91%, 92%, 93%, 94%, 95%, 96%, 97%, 98%, 99%, or 100% sequence identity to SEQ ID NO:2; (c) each amino acid position of the variant is numbered by correspondence with an amino acid position of the sequence of SEQ ID NO:2; and (d) the variant has increased proteolytic activity relative to the parent protease. The parent protease according to the sixth aspect of the invention may be a subtilisin protease. The parent protease according to the sixth aspect of the invention may be a protease having the amino acid sequence of SEQ ID NO:2. The variant according to the sixth aspect of the invention may have increased proteolytic activity and/or cleaning activity compared to the proteolytic activity and/or cleaning activity, respectively, of the parent protease.

The amino acid sequence of a variant according to the sixth aspect of the invention may further comprise the substitution N109G. The amino acid sequence of a variant according to the sixth aspect of the invention may further comprise the substitution N076D. The amino acid sequence of a variant according to the sixth aspect of the invention may further comprise the substitution S033T. The amino acid sequence of a variant according to the sixth aspect of the invention may further comprise the substitution N243V. The amino acid sequence of a variant according to the sixth aspect of the invention may further comprise the substitution S248A. The amino acid sequence of a variant according to the sixth aspect of the invention may further comprise the substitution A088T. The amino acid sequence of a variant according to the sixth aspect of the invention may further comprise the substitution S063G.

The amino acid sequence of a variant according to the sixth aspect of the invention may further comprise a set of amino acid substitutions selected from the group consisting of: A088T+N109G+A116T+G131H+N243V+L257G, S033T+N076D, S009T+N109G+K141R+N243V, S162G+K256R, N109G+A116T, N109G+L257G, S162G+L257G, N061G+N109G+N243V, N109G+N243V+S248A, S033T+N076D+N109G+N218S+N243V+S248N+K256R, N109G+A116T+N243V+K256R, A088T+N109G+A116T+G131H+N243V, A088T+N109G, N109G+N243V, T158S+L257G, N061S+N109G+N243V, P040A+N109G+N243V+S248N+K256R, S009T+S018T+Y021N+N109G+K141R, A088T+N109G+A116T+T158S+N243V+K256R, A088T+N109G+A116T+T158S+N218S+L257G, N109G+K256R, N109G+N243V+K256R, S063G+K256R, S063G+N109G, S063G, S063G+N076D, S033T+N076D+N218S, and N076D+N218S.

The variant according to the sixth aspect of the invention may have increased proteolytic activity and/or cleaning performance or activity compared to that of SEQ ID NO:2, SEQ ID NO:4, or SEQ ID NO:6. A variant according to the sixth aspect of the invention may have a performance index in a proteolytic assay (e.g., AAPF assay) or cleaning assay (e.g., BMI, grass, or egg microswatch assay) that is greater than that of the protease set forth in SEQ ID NO:2, SEQ ID NO:4, or SEQ ID NO:6. A variant or parent protease according to the sixth aspect of the invention may be in a mature form.

In a seventh aspect, the invention provides an isolated or non-naturally occurring protease variant of BPN' subtilisin protease having the amino acid sequence shown in SEQ ID NO:2, said protease variant selected from the group consisting of:

(a) a protease variant comprising an amino acid sequence having at least 80%, 85%, 90%, 95%, 96%, 97%, 98%, or 99% identity to the amino acid sequence of SEQ ID NO:2, said variant having increased proteolytic activity and/or increased cleaning activity compared to the protease of SEQ ID NO:2 and/or SEQ ID NO:4, wherein amino acid positions of the variant are numbered by correspondence with the sequence of SEQ ID NO:2 and wherein said variant comprises at least one set of amino acid substitution(s) relative to SEQ ID NO:2 selected from groups (i) through (x):

(i) G097A-G128A-P210S-Y217Q-N218A and G097A-G128A-P210S-Y217Q;

(ii) S063T-S078N-G097A-S101A-G128A-S183T-Y217Q-T244N, N061A-S078N-G097A-G128A-Y217Q-S224A, S053G-S078N-G097A-G128A-P129T-Q185T-Y217Q, S063T-S078N-G097A-S101A-G128A-S183T-Y217Q, S063T-S078N-G097A-S101A-G128A-Y217Q, S063T-S078N-G097A-S101A-G128A-Y217Q-T244I, and S078N-G097A-G128A-P129T-Y217Q;

(iii) S063T-S078N-G097A-S101A-G128A-S183T-Y217Q, S063T-S078N-G097A-S101A-G128A-S183T-Y217Q-T244N, S063T-S078N-G097A-S101A-G128A-Y217Q, and S063T-S078N-G097A-S101A-G128A-Y217Q-T244I;

(iv) G097A-I111V-M124V-Y217Q, G097A-I111V-Y167A-Y217Q, S024G-N025G-N061P-G097A-S101N-G128S-Y217Q, S024G-N025G-S053G-N061P-G097A-S101N-G128A-V203Y-Y217Q, S024G-N025G-S053G-T055P-N061P-G097A-S101N-G128S-V203Y-Y217Q, and V068A-A092G-Y217Q;

(v) N061P-G097A-S101N-G128A-P210S-Y217Q, S024G-N025G-S053G-N061P-G097A-S101N-G128A-P210S-Y217Q, S024G-N025G-S053G-N061P-G097A-S101N-G128S-Y217Q, S024G-N025G-S053G-N061P-S078N-G097A-S101N-I111V-G128S-Y217Q;

(vi) N061P-G097A-G128S-Y217Q, N061P-G097A-S101N-G128A-P210S-Y217Q, N061P-N062Q-G097A-S101N-I111V-Y217Q, S024G-N025G-N061P-G097A-S101N-G128A-P210S-Y217Q, S024G-N025G-S053G-N061P-G097A-S101N-G128A-P210S-Y217Q, S024G-N025G-S053G-N061P-G097A-S101N-G128S-Y217Q, and S024G-N025G-S053G-N061P-S078N-G097A-S101N-I111V-G128S-Y217Q;

(vii) N061P-G097A-S101N-G128A-P210S-Y217Q, S024G-N025G-S053G-T055P-N061P-G097A-S101N-G128A-Y217Q, N025G-G097A-S101N-G128A-Y217Q, N025G-S038G-S053G-N061P-S078N-G097A-S101N-G128A-Y217Q, N025G-S053G-N061P-S078N-G128A-Y217Q, N025G-S053G-N061P-S078N-S101N-G128A-Y217Q, N025G-S053G-T055P-N061P-S078N-G097A-S101N-G128A-Y217Q, N025G-S053G-T055P-S078N-G097A-S101N-G128A-Y217Q, N025G-S078N-G097A-S101N-G128A-Y217Q, N025G-T055P-N061P-S078N-G097A-S101N-G128A-Y217Q, N025G-T055P-N061P-S078N-S101N-G128A-Y217Q, N061P-S101N-G128A-Y217Q, S024G-N025G-N061P-G097A-G128A-Y217Q, S024G-N025G-N061P-G097A-S101N-G128A-Y217Q, S024G-N025G-S053G-N061P-S078N-G097A-S101N-G128A-Y217Q, S024G-N025G-S053G-N061P-S078N-S101N-G128A-Y217Q, S024G-N025G-S053G-T055P-G097A-S101N-G128A-Y217Q, S024G-N025G-S053G-T055P-N061P-G128A-Y217Q, S024G-N025G-T055P-G097A-G128A-Y217Q, S024G-N025G-T055P-N061P-S078N-G097A-S101N-G128A-Y217Q, S024G-N061P-S078N-G097A-S101N-G128A-Y217Q, S024G-S053G-N061P-G097A-G128A-Y217Q, S024G-S053G-N061P-S078N-G097A-G128A-Y217Q, S024G-S053G-T055P-G097A-S101N-G128A-Y217Q, S024G-S053G-T055P-N061P-G097A-S101N-G128A-Y217Q, S024G-S053G-T055P-N061P-S078N-G097A-S101N-G128A-Y217Q, S024G-S053G-T055P-N061P-S101N-G128A-Y217Q, S024G-T055P-N061P-G097A-G128A-Y217Q, S053G-G097A-S101N-G128A-Y217Q, S053G-N061P-G097A-S101N-G128A-Y217Q-S249N, S053G-N061P-S078N-G097A-G128A-Y217Q, S053G-S078N-G097A-S101N-G128A-Y217Q, S053G-T055P-G097A-S101N-G128A-Y217Q, S053G-T055P-N061P-S101N-G128A-Y217Q, S053G-T055P-S078N-G097A-S101N-G128A-Y217Q, T055P-G097A-S101N-G128A-Y217Q, and T055P-N061P-S078N-G097A-S101N-G128A-Y217Q;

(viii) S024G-N025G-N061P-S078N-G097A-S101N-G128A-Y217Q, S024G-N025G-S053G-N061P-S078N-S101N-G128A-Y217Q, S024G-N025G-S053G-T055P-N061P-G097A-S101N-G128A-Y217Q, S024G-S053G-T055P-N061P-G097A-S101N-G128A-Y217Q, S024G-S053G-T055P-N061P-S078N-G097A-S101N-G128A-Y217Q, S024G-T055P-N061P-S078N-S101N-G128A-Y217Q, S053G-G097A-S101N-G128A-Y217Q, and T055P-N061P-S078N-G128A-Y217Q;

(ix) N025G-T055P-N061P-S078N-G097A-S101N-G128A-Y217Q, N061P-S101N-G128A-Y217Q, S024G-N025G-S053G-N061P-S078N-S101N-G128A-Y217Q, S024G-N025G-S053G-T055P-S101N-G128A-Y217Q, S024G-N025G-S053G-T055P-N061P-G128A-Y217Q, S024G-N025G-T055P-N061P-S078N-G097A-S101N-G128A-Y217Q, N025G-S053G-N061P-S078N-G128A-Y217Q, S024G-N025G-S053G-T055P-G097A-S101N-G128A-Y217Q, S024G-N025G-N061P-S078N-G097A-S101N-G128A-Y217Q, S024G-S053G-T055P-G097A-S101N-G128A-Y217Q, S053G-N061P-S078N-G097A-

G128A-Y217Q, S024G-N025G-T055P-G097A-G128A-Y217Q, S024G-N025G-S053G-T055P-G097A-G128A-Y217Q; and (x) S024G-G097A-S101N-G128A-Y217Q, S101N-G128A-Y217Q, N025G-T055P-N061P-S078N-S101N-G128A-Y217Q, S053G-T055P-N061P-S101N-G128A-Y217Q, S024G-T055P-N061P-G097A-S101N-G128A, S053G-T055P-S078N-G097A-S101N-G128A-Y217Q, N025G-S053G-N061P-S078N-S101N-G128A-Y217Q, S024G-S053G-T055P-N061P-S101N-G128A-Y217Q, S024G-N025G-S053G-T055P-N061P-G097A-S101N-G128A-Y217Q, S024G-N025G-N061P-S078N-G097A-S101N-G128A, N061P-S101N-G128A-Y217Q, S024G-N025G-S053G-N061P-S078N-S101N-G128A-Y217Q, S024G-T055P-N061P-S078N-S101N-G128A-Y217Q, N025G-S053G-T055P-N061P-S078N-G097A-S101N-G128A-Y217Q, S024G-N025G-S053G-T055P-S101N-G128A-Y217Q, N025G-T055P-N061P-S078N-G097A-S101N-G128A-Y217Q, S024G-N025G-N061P-S078N-S101N-G128A-Y217Q, S024G-N025G-S053G-T055P-N061P-G128A-Y217Q, S024G-S053G-T055P-N061P-G097A-S101N-G128A-Y217Q, S024G-N025G-S053G-N061P-S078N-G097A-S101N-G128A-Y217Q, T055P-N061P-S078N-G128A-Y217Q, S024G-S053G-T055P-N061P-S078N-G097A-S101N-G128A-Y217Q, N025G-S038G-S053G-N061P-S078N-G097A-S101N-G128A-Y217Q, S024G-N025G-T055P-N061P-S078N-G097A-S101N-G128A-Y217Q, S024G-N025G-S053G-N061P-G128A-Y217Q, N025G-S053G-N061P-S078N-G128A-Y217Q, S024G-N025G-S053G-T055P-G097A-S101N-G128A-Y217Q, S024G-N025G-S053G-T055P-S078N-S101N-G128A-Y217Q, T055P-N061P-S078N-G097A-S101N-G128A-Y217Q, S024G-N025G-S053G-T055P-N061P-S078N-G128A-Y217Q, S024G-N025G-N061P-G097A-S101N-G128A-Y217Q, S053G-N061P-G097A-S101N-G128A-Y217Q-S249N, N025G-S053G-T055P-S078N-G097A-S101N-G128A-Y217Q, S024G-T055P-G097A-G128A-Y217Q, T055P-N061P-G097A-A116S-G128A, S024G-N025G-T055P-G097A-S101N-G128A-Y217Q, S024G-N025G-N061P-S078N-G097A-S101N-G128A-Y217Q, S053G-T055P-G097A-S101N-G128A-Y217Q, T055P-G097A-S101N-G128A-Y217Q, S024G-N061P-G097A-S101N-G128A-Y217Q, S024G-S053G-T055P-G097A-S101N-G128A-Y217Q, G097A-G128S-Y217Q, S024G-S053G-N061P-G097A-G128A-Y217Q, S024G-N025G-N061P-G097A-G128A-Y217Q, S024G-N061P-S078N-G097A-S101N-G128A-Y217Q, S024G-S053G-T055P-N061P-S078N-G097A-G128A-Y217Q, S024G-S053G-S078N-S101N-G128A-Y217Q, S024G-N025G-S053G-T055P-N061P-S078N-G097A-G128A-Y217Q, S053G-N061P-S078N-G097A-G128A-Y217Q, S024G-T055P-N061P-G097A-G128A-Y217Q, S024G-S038G-S053G-S078N-S101N-G128A-Y217Q, S053G-G097A-S101N-G128A-Y217Q, N025G-T055P-G097A-G128A-Y217Q, S024G-T055P-S078N-G097A-S101N-G128A-Y217Q, S053G-S078N-G097A-S101N-G128A-Y217Q, S024G-N025G-T055P-G097A-G128A-Y217Q, S024G-N025G-S053G-T055P-G097A-G128A-Y217Q, N025G-S078N-G097A-S101N-G128A-Y217Q, N025G-G097A-S101N-G128A-Y217Q, S024G-S053G-N061P-S078N-G097A-G128A-Y217Q, S024G-S053G-S078N-G097A-S101N-G128A-Y217Q, N025G-S078N-G097A-G128A-Y217Q, and S024G-N025G-S053G-N061P-G097A-G128A-S130G-Y217Q; and (b) a protease variant comprising an amino acid sequence having at least 80%, 85%, 90%, 95%, 96%, 97%, 98%, or 99% identity to the amino acid sequence of SEQ ID NO:6, said variant having increased proteolytic activity and/or increased cleaning activity compared to SEQ ID NO:2, SEQ ID NO:4 and/or SEQ ID NO:6, wherein amino acid positions of the variant are numbered by correspondence with the sequence of SEQ ID NO:2 and wherein said variant comprises at least one set of amino acid substitution(s) relative to SEQ ID NO:6 selected from groups (i) through (xv):

(i) at least one substitution relative to SEQ ID NO:6 selected from the group consisting of A116V, G160S, I111L, I115V, N109S, N117M, P005G, Q059V, T164S, Y262M, A015Q, A015S, A098E, A098N, A098S, A098T, A098V, A098Y, A114S, A114T, A116G, A116L, A116S, A116T, A116W, A133G, A133H, A133T, A133V, A137G, A137I, A137L, A137S, A137T, A138E, A216E, A216F, A216V, D099S, D181E, F261A, F261Q, G024F, G024I, G024Q, G024Y, G097S, G160T, G211L, G211V, H017F, H017W, H039V, H226A, I031V, I111V, I268V, K170R, K265R, L016Q, L016T, L135M, L209T, L209V, L233M, L257T, L257V, L267A, L267V, N025A, N025I, N025Q, N025R, N025T, N025V, N101I, N101Q, N101S, N109A, N109G, N109H, N109L, N109M, N109Q, N109T, N117Q, N184A, N184L, N184T, N184W, N212G, N212L, N212V, N243P, N252G, N252M, P005T, P014S, P040G, P040L, P040Q, P129A, P129S, P172G, P172S, P194Q, P210A, P210S, Q185F, Q185G, Q185I, Q185M, Q185N, Q185S, Q275H, R186K, S009A, S009G, S009H, S009M, S018T, S130T, S132N, S145K, S159T, S161I, S161K, S161N, S161T, S162I, S162M, S162Y, S163G, S182F, S182G, S182V, S182W, S183F, S183L, S183M, S183T, S183V, S183W, S224A, S236T, S249V, T022A, T022G, T022Q, T022V, T208V, T242S, T253N, T253S, T254A, T254T, T255L, T255S, T255V, V004A, V004P, V004W, V084C, V139C, V165M, V203F, Y021K, Y021N, Y021T, Y021V, Y167F, Y171F, Y214F, Y262F, and Y262T;

(ii) at least one substitution relative to SEQ ID NO:6 selected from the group consisting of A216E, L090I, A098R, A098W, A098Y, A116G, A116R, A116S, A133M, I107L, I115V, M124L, N101I, N109H, N109S, N109T, N117R, P005G, Q185L, S089V, V095A, A015Y, A029G, A098D, A098E, A098G, A098N, A098S, A098T, A098V, A114S, A114T, A116E, A116L, A116T, A116V, A133H, A133L, A133S, A137G, A137I, A137L, A137S, A137V, A138S, A144S, A144V, A176S, A176T, A187T, A216E, A216P, A216Q, A216R, A216S, A216T, A216V, A216Y, D041E, D120A, D120E, D120Q, D120R, D120S, D181S, G020A, G020S, G024A, G097A, G097D, G097S, G131Q, G160S, G166I, G211L, G215N, H039N, H238N, I111L, I111V, I122A, L075I, L075Q, L135M, L209T, L209V, L233V, L235M, L235R, L257A, M119I, N025A, N025G, N025T, N061K, N101F, N101H, N101L, N101Q, N101R, N101S, N101T, N109A, N109G, N109K, N109L, N117E, N117H, N117K, N117S, N212G, N212S, N218F, N218G, N218H, N218L, N218S, N218W, N240Q, N252M, N252R, N252S, P005T, P040A, P040G, P040T, P129D, P129S, P194S, P210R, Q019R, Q019W, Q103L, Q103W, Q185A, Q185G, Q185M, Q185R, Q185T, Q206G, Q206Y, Q217A, Q217E, Q217R, Q217S, Q217T, S003Q, S009H, S018M, S033T, S130A, S130F, S130G, S130T, S130V, S145T, S159A, S161N, S161T, S162V, S162Y, S182L, S182W, S183F, S183L, S183V, S183W, S188K, S188W, S236Q, S236T, S248L, T022H, T022K, T208C, T253H, T255V, V044I, V121I, V139C, V143H, V143Q, V143T, V143W, V143Y, Y006K, Y021A, Y104W, A001F, A001G, A001H, A001K, A001L, A001Q, A001S, A001Y, A013V, A015G, A015K, A015R, A015S, A015T, A015W, A048S, A073N, A073S, A092S, A098K, A098P, A116D, A116W, A128S, A133P, A133T, A133V, A134G, A134S, A137H, A137N, A137T, A144D, A144K, A144L, A144M, A144N, A144R, A179G, A179S, A187V, A216G, A216L, A216W, A223S, A230C, A272K, A272L, A272P, A272S, A272T, A272W, A273G, A273S, A274G, A274M, A274T, D120K, D140E, D181A, D181E, D181G, D181H, D181I, D181T, D259E, D259N, D259Q, E054D, E156D, E156T, E251L, E251T, E251V, F058Y, F189W, F261K, F261Q, F261R, G007A, G007S, G020F, G020H, G020N, G020Q, G020T, G020Y, G024F, G024Q, G024R, G024T, G024V, G024W, G024Y, G053T, G097K, G097M, G097R, G097T, G131A, G131H, G131P, G131R, G131T, G131V, G160H, G160T, G166C, G166Q, G166S, G166T, G211A, G211D, G211K, G211M, G211N, G211Q, G211R, G211V, G211W, G215S, G215T, G215W, H017T, H017W, H017Y, H039V, H226A, H226F, H226I, H226L, H226M, H226V, I035V, I079A, I079S, I108V, I205V, I234L, I234V, I268V, K012S, K043P, K136H, K136R, K141A, K141F, K141T, K141W, K170A, K170G, K170R, K213A, K213R, K213S, K237A, K237H, K237L, K237S, K237V, K256A, K256G, K256H, K256M, K256P, K256Q, K256R, L016A, L016Q, L016T, L016V, L042V, L075M, L075T, L082M, L082V, L135F, L196I, L209H, L209Q, L209R, L209S, L209W, L233A, L233M, L233Q, L235I, L235K, L250I, L257S, L257T, L257V, L267A, L267Q, L267T, L267V, M119C, M199V, N025C, N025E, N025F, N025I, N025K, N025L, N025M, N025Q, N025V, N025Y, N061F, N061P, N061S, N061T, N076G, N078S, N101A, N109M, N109Q, N109R, N117A, N117M, N117Q, N118D, N118G, N118H, N118Q, N118R, N118S, N184A, N184C, N184G, N184L, N184R, N184S, N184T, N184V, N184W, N212C, N212F, N212I, N212K, N212L, N212P, N212Q, N212R, N212V, N212W, N212Y, N218A, N218P, N218T, N240A, N240E, N240G, N240H, N240L, N240R, N240S, N240T, N243C, N243Q, N243T, N243V, N252A, N252G, N252K, N252Q, P014G, P014Q, P014R, P014S, P014T, P040F, P040L, P040Q, P040S, P040V, P086C, P086H, P086S, P129A, P129E, P129G, P129K, P129R, P172A, P172K, P172Q, P172S, P194A, P194G, P194H, P194L, P194M, P194Q, P194R, P194V, P194W, P194Y, P210A, P210G, P210L, P210S, P239K, P239R, Q002A, Q002S, Q010A, Q010N, Q010R, Q010T, Q019A, Q019C, Q019D, Q019G, Q019S, Q019T, Q019V, Q059I, Q059V, Q103S, Q185F, Q185H, Q185I, Q185K, Q185N, Q185S, Q185Y, Q206H, Q206L, Q206P, Q206W, Q217F, Q217H, Q217I, Q217K, Q217L, Q217N, Q217V, Q271G, Q271R, Q271T, Q275F, Q275P, Q275R, R186I, R186K, S003A, S003F, S003G, S003H, S003K, S003R, S003T, S009T, S018N, S018T, S037G, S037T, S037V, S038G, S038Q, S063N, S063Q, S063T, S089M, S089N, S130K, S130L, S130R, S130W, S132N, S145G, S145K, S145M, S145R, S145V, S159C, S159H, S159L, S159Q, S159R, S159T, S159W, S161A, S161C, S161G, S161H, S161I, S161K, S161P, S161Q, S161R, S162F, S162G, S162I, S162L, S162M, S162N, S162P, S162R, S163G, S173A, S173G, S173N, S182F, S182G, S182K, S182N, S182Q, S182V, S183A, S183M, S183Q, S183R, S183T, S188A, S188F, S188G, S188P, S188R, S188T, S188V, S190C, S204A, S204G, S204I, S204L, S204Q, S204R, S204V, S207G, S224A, S224T, S236C, S236D, S236E, S236G, S236N, S248A, S248F, S248K, S248M, S248T, S249A, S249R, S249T, S249V, S249W, S249Y, S260G, S260H, S260K, S260N, T022A, T022G, T022Q, T022S, T022V, T022Y, T055A, T055K, T158A, T158S, T208L, T208S, T208V, T220S, T242D, T242N, T242S, T244E, T244G, T244I, T244R, T244V, T244W, T253A, T253G, T253N, T253S, T254S, T254V, T255H, T255I, T255K, T255L, T255Q, T255R, T255S, T255Y, V004A, V004N, V004P, V004W, V008A, V008M, V026I, V045S, V045W, V051I, V081Q, V081T, V084C, V093I, V095C, V143A, V143E, V143F, V143N, V143S, V147I, V147L, V147S, V147T, V148I, V149C, V149I, V165M, V180A, V180C, V180I, V180L, V180T, V192A, V192C, V192I, V192S, V192T, V192Y, V198L, V203A, V203F, V203K, V203L, V203M, V203N, V203Y, W241Y, Y006A, Y006G, Y006H, Y006L, Y006N, Y006P, Y006Q, Y006T, Y021E, Y021K, Y021L, Y021N, Y021Q, Y021R, Y021S, Y021T, Y104F, Y104I, Y104V, Y171F, Y214F, Y214L, Y214W, Y262F, and Y262S;

(iii) at least one set of amino acid substitutions relative to SEQ ID NO:6 selected from the group consisting of A088T-L257G, A116T-A128S, N061S-N109G-A128S-N243V-S260P, S009T-N109G-A128S-K141R-N243V, S009T-S018T-Y021N-N109G-A128S-K141R, and S162G-K256R;

(iv) at least one set of amino acid substitution(s) relative to SEQ ID NO:6 selected from the group consisting of A116T, A088T-N243V, G024E-A116T, K043Y, N076D-A116T, N218S-S248N, S033T-N243V, S033T-S063G, S248N-L257G, A001E-S249A, A088T-A116T, A088T-A128S, A088T-G131H, A088T-L257G, A088T-N109G, A088T-S248N, A088T-S249A, A116T-N243V, A116T-T158S, A128S, A128S-K256R, A128S-L257G, A128S-N243V, A128S-S248N, A128S-T158S, G024E-A088T, G024E-A128S, G024E-G131H, G024E-K256R, G024E-L257G, G024E-N218S, G024E-N243V, G024E-S162G, G024E-S249A, G024E-T158S, G131H, G131H-K256R, G131H-S249A, K043Y-A088T, K043Y-A116T, K256R, N076D-K256R, N109G, N109G-A116T, N109G-A128S, N109G-A128S-N243V-K256R, N109G-A128S-N243V-S248A, N109G-G131H, N109G-K256R, N109G-L257G, N109G-N218S, N109G-N243V, N109G-S248N, N218S-L257G, N243V, N243V-K256R, N243V-L257G, N243V-S248N, N243V-S249A, Q103H-A128S, Q103H-G131H, Q103H-K256R, Q103H-L257G, Q103H-N243V, Q103H-S248N, Q103H-S249A, Q103H-T158S, Q206D-N243V, S033T-A128S, S033T-K256R, S033T-N076D, S033T-N218S, S033T-S248N, S033T-T158S, S063G-A128S, S063G-K256R, S063G-N243V, S063G-S162G, S063G-T158S, S162G-K256R, S248N-K256R, S249A, T158S-N243V, and T158S-S249A;

(v) at least one set of amino acid substitution(s) relative to SEQ ID NO:6 selected from the group consisting of A088T-L257G, G024E-K256R, G024E-L257G, N109G-A116T, N109G-L257G, N243V-K256R, S033T-N109G, S033T-T158S, S063G-L257G, A001E-L257G, A088T-A128S, A088T-G169A, A088T-K256R, A088T-N109G, A088T-N218S, A088T-N243V, A088T-S248N, A088T-T158S, A116T, A116T-A128S, A116T-G131H, A116T-K256R, A116T-L257G, A116T-N218S, A116T-S162G, A116T-T158S, A128S, A128S-G169A, A128S-K256R, A128S-L257G, A128S-N218S, G024E, G024E-A128S, G024E-G131H, G024E-N109G, G024E-N243V, G024E-S033T, G024E-S063G, G024E-S248N, G024E-S249A, G024E-T158S, G131H, G131H-G169A, G131H-K256R, G131H-N218S, G131H-S249A, G169A, G169A-L257G, G169A-N243V, K043Y-A088T, K043Y-N109G, K256R, K256R-L257G, N061G-N109G-N243V, N076D-N109G, N109G, N109G-A128S, N109G-G131H, N109G-K256R, N109G-N218S, N109G-S162G, N109G-S248N, N109G-S249A, N109G-T158S, N218S, N218S-K256R, N218S-L257G, N218S-S248N, N243V, N243V-L257G, N243V-S248N, N243V-S249A, P040A-N109G-A128S-N243V-S248N-K256R, Q103H-K256R, Q103H-L257G, Q103H-N109G, S009T-S018T-Y021N-N109G-A128S-K141R, S033T-A088T, S033T-A116T, S033T-A128S, S033T-G131H, S033T-K043Y, S033T-K256R, S033T-L257G, S033T-N076D, S033T-N218S, S033T-N243V, S033T-Q103H, S033T-S063G, S033T-S162G, S033T-S248N, S033T-S249A, S063G, S063G-A088T, S063G-A116T, S063G-A128S, S063G-G131H, S063G-K256R, S063G-N109G, S063G-N218S, S063G-N243V, S063G-S248N, S063G-S249A, S063G-T158S, S162G-K256R, S162G-N218S, S162G-N243V, S162G-S248N, S162G-S249A, S248N, S249A, S249A-L257G, T158S, T158S-L257G, and T158S-N243V;

(vi) at least one set of amino acid substitution(s) relative to SEQ ID NO:6 selected from the group consisting of T158S-L257G, K256R, L257G, S033T-N109G, S162G-K256R, S162G-L257G, G024E-K256R, G024E-L257G, G024E-S033T, N109G-A116T, N218S-L257G, S033T-A088T, S033T-A116T, S033T-N243V, S033T-Q103H, S162G-N218S, S162G-N243V, T158S, T158S-N218S, T158S-N243V, A088T, A088T-G169A, A088T-K256R, A088T-L257G, A088T-S162G, A088T-T158S, A116T-K256R, A116T-L257G, A116T-N243V, A128S-L257G, A128S-N218S, A128S-N243V, A128S-S248N, G024E-A116T, G024E-A128S, G024E-G131H, G024E-N243V, G024E-S248N, G024E-S249A, G024E-T158S, G131H-N243V, G131H-T158S, G169A-N218S, G169A-N243V, G169A-S248N, K256R-L257G, N109G-A128S, N109G-G131H, N109G-N218S, N109G-N243V, N109G-S249A, N109G-S248N, N218S-K256R, N218S-N243V, N218S-S249A, N243V, N243V-K256R, N243V-L257G, N243V-S248N, Q103H-N109G, Q103H-N218S, S033T-A128S, S033T-L257G, S033T-N218S, S033T-S162G, S033T-S248N, S033T-T158S, S063G-K256R, S063G-L257G, S162G, S162G-G169A, S162G-S248N, S248N, S248N-K256R, S248N-L257G, S249A, T158S-S162G, and T158S-S248N;

(vii) at least one set of amino acid substitutions relative to SEQ ID NO:6 selected from the group consisting of S033T-N076D-A128S-N218S, A001E-S033T-N109G-N218S, S033T-N218S, S033T-S063G-Q103H-N109Q-A128S-G131H-G169A-N243V, A128S-G169A, S033T-S063G-Q103H-N109Q-A128S-G131H-G169A-N243P, S018T-Y021N-S033T-N109G-A128S-N243V-S248N-K256R, S033T-A128S-G131H-N243P, P040E-N109G-A128S-G131H, S033T-A128S, S033T-N109G-A128S-N243V-S248N-K256R, N109G-G169A, S063G-N109G-A128S-G131H, G169A, N109G-A128S-G131H-N243V-S248N-K256R, S033T-A128S-G131H-N243V, A128S-N218S, A001E-G169A, A088T-G169A, G169A-L257G, N109G-N218S, S033T-N109G-A128S-N243P-S248N-K256R, G169A-K256R, N076D-G169A, A001E-G131H-G169A-N243V, G169A-S249A, S033T-N109G, G169A-S248N, K043Y-G169A, K043Y-N218S, N218S-L257G, N218S-N243V, S063G-G169A, A001E-A128S-G131H-N243V, A001E-S033T-N109G-N243V, A088T-N218S, G024E-N218S, G024E-S033T, G169A-Q206D, N076D-N218S, S033T-L257G, S162G-G169A, A001E-N218S, A116T-N218S, G169A-N243V, N218S, P040A-N109G-A128S-N243V-S248N-K256R, S033T-N076D, A001E-S033T, A128S-G131H, N218S-S248N, S018T-Y021N-N109G-A128S, S033T-K043Y, S033T-N243V, S033T-Q206D, S063G-N218S, S162G-N218S, T158S-G169A, A116T-G169A, G131H-G169A, N061S-N109G-A128S-S260P, N109G-A128S-N243V-K256R, N109G-A128S-N243V-S248A, N109G-A128S-N243V-S248A-K256R, N109G-A128S-N243V-S248N-K256R-L257G, N218S-K256R, S009T-N109G-A128S-K141R, S009T-S018T-Y021N-N109G-A128S-K141R, S033T-A088T, S033T-S063G, S033T-S162G, T158S-N218S, A001E-N076D-N109G-A128S, N109G-A128S-N243V-S248N-K256R, N109G-A128S-S248N-K256R, S009T-N109G-A128S-K141R-N243V, S018T-Y021N-N061S-N109G-A128S-S260P, S033T-A116T, S033T-S248N, S033T-S249A, S033T-T158S, G131H-N218S, N109A-A128S-N243V-K256R, N109G-A128S, N109G-A128S-S162G-N243V-S248N-K256R, N109G-A128S-T158S-N243V-S248N-K256R, N218S-S249A, Q206D-N218S, S018T-Y021N-N109G-A128S-N243V, S018T-Y021N-N109G-A128S-N243V-S248N-K256R, S033T-K256R, A116T-A128S, N061S-N109G-A128S-N243V-S260P, N109G-A128S-N243V-S248N, S009T-N109G-A128S-K141R-N243V-S248N-K256R, G024E-A128S, N061S-N109G-A128S-N243V-S248N-K256R-S260P, N109S-A128S-N243V-K256R, S033T, S033T-G131H, A001E-A128S, A128S, A128S-L257G, A128S-Q206D, N109Q-A128S-N243V-K256R, S009T-A128S-K141R-N243V, S009T-S018T-Y021N-A128S-K141R-N243V, A088T-A128S, A128S-K256R, A128S-N243V, N061P-N109G-N243V, N061S-A128S-N243V-S260P, S018T-Y021N-A128S-N243V, A128S-N243V-S248N-K256R, A128S-S248N, A128S-S249A, N076D-A128S, S063G-A128S, A128S-S162G, A128S-T158S, S018T-Y021N-N061S-A128S-N243V-S260P, S033T-Q103H-A128S-G131H, N061S-N109G-N243V, K043Y-A128S, N061P-N109G-G131H-N243V, N109G-L257G, A001E-G024E-S204E-Q206D, A001E-L257G, A088T-N109G, G024E-N109G, K043Y-N109G, N061G-N109G-N243V, N076D-N109G, N109G, N109G-A116T, N109G-K256R, N109G-N243V-K256R, N109G-N243V-S248A-K256R, N109G-Q206D, S063G-N109G, A001E-A116T, A001E-N109G, A001E-Q206D, A088T-A116T, A088T-N243V, A116T-L257G, G024E-A116T, G024E-L257G, G024E-N243V, G024E-Q206D, N109G-G131H, N109G-N243V, N109G-S162G, N109G-S248N, N109G-S248N-K256R, N109G-S249A, N109G-T158S, N243V-L257G, A001E-A088T, A001E-G024E, A001E-K256R, A001E-N076D, A001E-N243V, A088T, A088T-L257G, A088T-Q206D, A116T, A116T-K256R, A116T-N243V, G024E-A088T, G024E-K043Y, G024E-K256R, G024E-N076D, G024E-S162G, G024E-S248N, K043Y-A088T, K043Y-A116T, K043Y-L257G, K043Y-N243V, K043Y-Q206D, K256R-L257G, N076D-A116T, N076D-L257G, N076D-N243V, N076D-Q206D, N109G-N243V-S248N, N109G-N243V-S248N-K256R, N243V-K256R, Q206D, Q206D-L257G, Q206D-N243V, Q206D-S248N, S063G-K256R, S063G-L257G, T158S-L257G, A001E, A001E-K043Y, A001E-S162G, A001E-S248N, A001E-S249A, A001E-T158S, A088T-K256R, A088T-S162G, A088T-S248N, A088T-S249A, A116T-Q206D, A116T-S248N, A116T-S249A, G024E, G024E-G131H, G024E-S249A, G024E-T158S, G131H, G131H-K256R, G131H-L257G, K043Y-K256R, K043Y-N076D, K256R, L257G, N076D-A088T, N076D-K256R, N076D-S162G, N076D-S248N, N076D-S249A, N109G-N243P-S248A-K256R, N109G-N243P-S248N-K256R, N243V, Q206D-K256R, S033T-P040E-Q103H-N109G, S063G, S063G-A116T, S063G-Q206D, S162G-K256R, S162G-L257G, S162G-N243V, S162G-Q206D, S162G-S248N, S248N, S248N-L257G, S249A, S249A-L257G, T158S, T158S-N243V, and T158S-Q206D;

(viii) at least one set of amino acid substitution(s) relative to SEQ ID NO:6 selected from the group consisting of A088T-A116T-N243V-K256R-L257G, A088T-A116T-N243V-L257G, A088T-T158S-N218S-K256R, A088T-T158S-N218S-N243V-L257G, A088T-A116T-T158S-N218S-N243V-K256R-L257G, A088T-N109G-A116T-G131H-A153S-N218S-S248N-L257G, A088T-N109G-A116T-T158S-S248N-K256R-L257G, A088T-N109G-T158S-L257G, A114S-A116T-N218S-N243V-S248N-K256R-L257G, A116T-T158S-K256R, A088T-A116T-

G131H-T158S-S248N-L257G, A088T-A116T-T158S, A088T-N109G-A116T-G131H-L257G, A088T-N109G-A116T-T158S-N243V-S248N-L257G, A088T-N109G-N243V-L257G, A088T-N109G-N243V-S248N, A088T-N109G-T158S-N243V-L257G, A088T-N109G-T158S-N243V-S248N-L257G, A116T-T158S-S248N-L257G, Y006H-A116T-G131H-S248N, A088T-A116T-G131H-T158S-N218S-N243V, A088T-A116T-G131H-T158S-N243V, A088T-A116T-G131H-T158S-N243V-K256R-L257G, A088T-A116T-N218S-N243V-K256R-L257G, A088T-A116T-S248N-K256R-L257G, A088T-A116T-T158S-N218S-N243V, A088T-A116T-T158S-N243V-K256R-L257G, A088T-A116T-T158S-N243V-S248N-L257G, A088T-G131H-N243V-S248N-K256R-L257G, A088T-N109G-A116T-T158S-L257G, A088T-N109G-A116T-T158S-N212D-N243V-K256R-L257G, A088T-N109G-A116T-T158S-N218S-N243V-S248N-K256R, A088T-N109G-A116T-T158S-S248N-L257G, A088T-N109G-G131H-V148A-N218S-N243V-K256R-L257G, A088T-N109G-K256R, A088T-N109G-N243V-S248N-L257G, A088T-N109G-T158S-K256R, A088T-N109G-T158S-N243V, A088T-T158S-N243V-K256R-L257G, A116T, A116T-N218S-N243V-L257G-N269S, A116T-T158S-K256R-L257G, N109G-A116T-K256R-L257G, N109G-A116T-N243V, N109G-A116T-T158S-N243V-K256R-L257G, N109G-G131H-L257G, N109G-G131H-S248N-K256R-L257G, N109G-G131H-T158S-K256R-L257G, S003P-A116T-T158S-S248N-K256R, T158S-S248N-K256R, A088T-A116T-G131H-N243V-K256R, A088T-A116T-G131H-S248N-K256R-L257G, A088T-A116T-G131H-V147A-T158S-N218S-N243V-S248N-L257G, A088T-A116T-S248N-L257G, A088T-A116T-T158S-N218S, A088T-A116T-T158S-N218S-K256R-L257G, A088T-A116T-T158S-N218S-L257G, A088T-G131H-N243V-L257G, A088T-G131H-T158S-S248N-L257G, A088T-L257G, A088T-N109G-A116T, A088T-N109G-A116T-G131H-N218S, A088T-N109G-A116T-G131H-N218S-S248N-L257G, A088T-N109G-A116T-G131H-N243V-S248N-K256R-L257G, A088T-N109G-A116T-G131H-T158S-S248N-K256R-L257G, A088T-N109G-A116T-N218S-N243V-K256R, A088T-N109G-A116T-N218S-N243V-L257G, A088T-N109G-A116T-N243V-S248N-K256R, A088T-N109G-A116T-N243V-S248N-K256R-L257G, A088T-N109G-A116T-T158S-L257G, A088T-N109G-A116T-T158S-N243V-L257G, A088T-N109G-G131H-T158S-N243V-S248N-K256R, A088T-N109G-G131H-T158S-W241R-S248N-K256R, A088T-N109G-K256R-L257G, A088T-N109G-L257G, A088T-N109G-N243V, A088T-N109G-N243V-K256R, A088T-N109G-N243V-K256R-L257G, A088T-N109G-S248N-K256R, A088T-N109G-T158S-N218S-K256R-L257G, A088T-N109G-T158S-N218S-N243V-S248N-K256R, A088T-N109G-T158S-N243V-K256R, A088T-N109G-T158S-N243V-K256R-L257G, A088T-N109G-T158S-N243V-S248N-A274D, A088T-N109G-T158S-S248N-L257G, A088T-T158S-K256R, A088T-T158S-N218S-N243V-K256R-L257G, A088T-T158S-N243V-L257G, A116T-G131H-N218S-N243V-S248N, A116T-G131H-S248N-L257G, A116T-S248N-K256R-L257G, A116T-T158S-N218S-N243V-K256R, A116T-T158S-N218S-S248N-L257G-Q271R, A116T-T158S-N243V-K256R-L257G, A116T-T158S-N243V-S248N-L257G, G131H-S248N, G131H-T158S-I234T-N243V-K256R, G131H-W241L-N243V-S248N-K256R, N109G-A116T-G131H-A137V-T158S-S248N-K256R-L257G, N109G-A116T-G131H-A151S-N218S-K256R-L257G, N109G-A116T-G131H-T158S-N218S-N243V-K256R, N109G-A116T-G131H-T158S-N218S-S248N, N109G-A116T-G131H-T158S-N243V-S248N, N109G-A116T-S248N, N109G-A116T-T158S-L257G, N109G-A116T-T158S-N218S-W241R-N243V, N109G-A116T-T158S-N243V-S248N-L257G, N109G-A116T-T158S-S248N-K256R-L257G, N109G-A116T-T158S-S248N-L257G, N109G-G131H-N218S-L257G, N109G-G131H-N218S-S248N-K256R-L257G, N109G-G131H-T158S-N218S-S248N-K256R-L257G-A274T, N109G-K256R, N109G-N243V-L257G, N109G-T158S-N218S-K256R-L257G, N109G-T158S-N218S-L257G, N109G-T158S-S248N-K256R, P014L-A015L-L016C-H017T-S018L-Q019K-G020A-Y021T-T022L-G023E, S003F-A088T-N109G-A116T-T158S-N243V-K256R-L257G, V004A-A088T-A116T-T158S-N218S, V004A-N109G-A116T-G131H-S248N-K256R-L257G, V004L-A116T-N218S-N243V-S248N-L257G, Y006H-N109G-N218S-N243V-S248N, A001T-A116T-T158S-N243V-L257G, A088T-A116T, A088T-A116T-G131H-L257G, A088T-A116T-G131H-N218S-L257G, A088T-A116T-G131H-N218S-S248N-K256R-L257G, A088T-A116T-G131H-N218S-S248N-L257G, A088T-A116T-G131H-N243V-K256R-L257G, A088T-A116T-G131H-N243V-L257G, A088T-A116T-G131H-N243V-S248N, A088T-A116T-G131H-T158S-K256R-L257G, A088T-A116T-G131H-T158S-L257G, A088T-A116T-G131H-T158S-N218S, A088T-A116T-G131H-T158S-N218S-N243V-K256R-A273T, A088T-A116T-G131H-T158S-N218S-S248N-K256R, A088T-A116T-G131H-T158S-N218S-S248N-L257G, A088T-A116T-G131H-T158S-N243V-S248N-K256R, A088T-A116T-G131H-T158S-S248N, A088T-A116T-G131H-T158S-S248N-L257G, A088T-A116T-K256R, A088T-A116T-K256R-L257G, A088T-A116T-N218S-N243V-L257G, A088T-A116T-N243V-K256R, A088T-A116T-N243V-L257G, A088T-A116T-N243V-S248N-K256R-L257G, A088T-A116T-S248N-K256R, A088T-A116T-T158S-K256R, A088T-A116T-T158S-N218S, A088T-A116T-T158S-N218S-N243V-K256R, A088T-A116T-T158S-N218S-N243V-K256R-N269S, A088T-A116T-T158S-N218S-N243V-S248N, A088T-A116T-T158S-N218S-N243V-S248N, A088T-A116T-T158S-N218S-N243V-S248N-K256R-L257G, A088T-A116T-T158S-N243V-K256R, A088T-A116T-T158S-N243V-L257G, A088T-A116T-T158S-N243V-S248N-K256R, A088T-A116T-T158S-N243V-S248N-K256R-L257G, A088T-A116T-T158S-S248N-K256R, A088T-A116T-V143A-N218S-S248N-K256R, A088T-A116T-V147I-T158S-N218S-N243V-L257G, A088T-G131H-K256R-L257G, A088T-G131H-N218S-N243V-S248N, A088T-G131H-N218S-S248N-L257G, A088T-G131H-S248N-K256R-L257G, A088T-G131H-T158S-L257G, A088T-G131H-T158S-N218S-K256R, A088T-G131H-T158S-N218S-N243V-K256R-L257G, A088T-G131H-T158S-N218S-N243V-L257G, A088T-G131H-T158S-N218S-S248N, A088T-G131H-T158S-N243V, A088T-G131H-T158S-N243V, A088T-G131H-T158S-N243V-S248N, A088T-G131H-T158S-N243V-S248N-K256R, A088T-G131H-T158S-N243V-S248N-L257G, A088T-I107T-N109G-A116T-G131H-T158S-N218S-N243V-S248N, A088T-N109G-A116T-G131H-L257G, A088T-N109G-A116T-G131H-N218S, A088T-N109G-A116T-G131H-N218S-L257G, A088T-N109G-A116T-G131H-N218S-N243V, A088T-N109G-A116T-G131H-N218S-N243V-K256R-L257G, A088T-N109G-A116T-G131H-N218S-N243V-L257G, A088T-N109G-A116T-G131H-N218S-S248N-K256R-L257G, A088T-N109G-A116T-G131H-N243V, A088T-N109G-A116T-G131H-N243V-L257G, A088T-N109G-

A116T-G131H-N243V-S248N-L257G, A088T-N109G-A116T-G131H-S248N, A088T-N109G-A116T-G131H-S248N-K256R, A088T-N109G-A116T-G131H-S248N-L257G, A088T-N109G-A116T-G131H-T158S-L257G, A088T-N109G-A116T-G131H-T158S-N218S, A088T-N109G-A116T-G131H-T158S-N218S-S248N-K256R, A088T-N109G-A116T-G131H-T158S-N218T-N243V, A088T-N109G-A116T-G131H-T158S-N243V-K256R, A088T-N109G-A116T-G131H-T158S-N243V-K256R-L257G, A088T-N109G-A116T-G131H-T158S-N243V-S248N, A088T-N109G-A116T-G131H-T158S-N243V-S248N-K256R, A088T-N109G-A116T-G131H-T158S-S248N-K256R-L257G, A088T-N109G-A116T-G131H-T158S-S248N-L257G, A088T-N109G-A116T-N218S, A088T-N109G-A116T-N218S-L257G, A088T-N109G-A116T-N218S-N243V, A088T-N109G-A116T-N218S-N243V-S248N-L257G, A088T-N109G-A116T-N218S-S248N-K256R, A088T-N109G-A116T-N218T-K256R, A088T-N109G-A116T-N218T-K256R-L257G, A088T-N109G-A116T-N243V, A088T-N109G-A116T-N243V-K256R-L257G, A088T-N109G-A116T-N243V-K256R-L257G-N269D, A088T-N109G-A116T-S248N-K256R, A088T-N109G-A116T-T158S, A088T-N109G-A116T-T158S-N218S-L257G, A088T-N109G-A116T-T158S-N218S-N243V, A088T-N109G-A116T-T158S-N218S-N243V-K256R, A088T-N109G-A116T-T158S-N218S-N243V-K256R-L257G, A088T-N109G-A116T-T158S-N218S-N243V-K256R-L257G, A088T-N109G-A116T-T158S-N218S-N243V-L257G, A088T-N109G-A116T-T158S-N218S-S248N, A088T-N109G-A116T-T158S-N243V, A088T-N109G-A116T-T158S-N243V-K256R, A088T-N109G-A116T-T158S-N243V-K256R-L257G, A088T-N109G-A116T-T158S-S248N-L257G, A088T-N109G-G131H-L257G, A088T-N109G-G131H-N218S-K256R-L257G, A088T-N109G-G131H-N218S-N243V-K256R, A088T-N109G-G131H-N218S-N243V-L257G, A088T-N109G-G131H-N218S-N243V-S248N-K256R-L257G, A088T-N109G-G131H-N243V, A088T-N109G-G131H-N243V-L257G, A088T-N109G-G131H-N243V-S248N-K256R, A088T-N109G-G131H-N243V-S248N-L257G, A088T-N109G-G131H-S248N-L257G, A088T-N109G-G131H-T158S-L257G, A088T-N109G-G131H-T158S-N218S-N243V-S248N-K256R, A088T-N109G-G131H-T158S-N243V, A088T-N109G-G131H-T158S-N243V-K256R, A088T-N109G-G131H-T158S-N243V-K256R-L257G, A088T-N109G-G131H-T158S-N243V-L257G, A088T-N109G-L257G, A088T-N109G-N218S-K256R, A088T-N109G-N218S-N243V-S248N-L257G, A088T-N109G-N218S-S248N-K256R-L257G, A088T-N109G-N243V-K256R-L257G, A088T-N109G-N243V-S248N-K256R-L257G, A088T-N109G-N243V-S248N-L257G-I268V, A088T-N109G-S248N-K256R-L257G, A088T-N109G-T158S-N218S-K256R, A088T-N109G-T158S-N218S-N243V-L257G, A088T-N109G-T158S-N218S-N243V-L257G, A088T-N109G-T158S-N243V-K256R-I268V, A088T-N109G-T158S-N243V-S248N-Q275R, A088T-N218S-N243V, A088T-N218S-N243V-S248N-K256R-L257G, A088T-N218S-S248N, A088T-N218S-S248N-L257G, A088T-N243V, A088T-N243V, A088T-N243V-K256R, A088T-N243V-L257G, A088T-S145T-T158S-S248N, A088T-T158S-L257G, A088T-T158S-N218S-S248N-L257G, A088T-T158S-N243V-K256R-L257G-Q271H, A088T-T158S-S248N, A088T-V143A-T158S-K256R, A116T-G131H-K256R, A116T-G131H-N218S, A116T-G131H-N243V, A116T-G131H-N243V-K256R, A116T-G131H-N243V-L257G, A116T-G131H-S248N-K256R, A116T-G131H-T158S-N218-I234T-N243V-S248N-K256R, A116T-G131H-T158S-N243V-L257G, A116T-G131H-T158S-N243V-S248N-K256R, A116T-G131H-V143F-T158S-N218S, A116T-L257G, A116T-N218S, A116T-N218S-L257G, A116T-N218S-N243V-L257G, A116T-N243V, A116T-N243V-K256R, A116T-N243V-S248N, A116T-N243V-S248N-K256R-L257G, A116T-S248N, A116T-T158S, A116T-T158S-N218S-N243V, A116T-T158S-N218S-S248N, A116T-T158S-N243V, A116T-T158S-N243V-K256R, A116T-T158S-N243V-L257G, A116T-T158S-N243V-S248N, A116T-T158S-S248N-K256R-L257G, A116T-V149I-T158S-N243V-S248N-K256R-Q271H, G131H-N218S-N243V-L257G, G131H-N243V, G131H-N243V-S248N-K256R, G131H-T158S, G131H-T158S-N218S-N243V-K256R, G131H-T158S-N243V-K256R-L257G, G131H-T158S-N243V-S248N-L257G, N109G-A116T-G131H-N218S-K256R-L257G, N109G-A116T-G131H-N218S-L257G, N109G-A116T-G131H-N218S-N243V-K256R-L257G, N109G-A116T-G131H-N218S-S248N-K256R, N109G-A116T-G131H-N243V-K256R, N109G-A116T-G131H-N243V-L257G, N109G-A116T-G131H-N243V-S248N-K256R-L257G, N109G-A116T-G131H-S248N, N109G-A116T-G131H-S248N-I268V, N109G-A116T-G131H-T158S-N218S-N243V-S248N-K256R, N109G-A116T-G131H-T158S-N218S-S248N-L257G, N109G-A116T-G131H-T158S-S248N, N109G-A116T-G131H-T158S-S248N-K256R, N109G-A116T-N218S, N109G-A116T-N218S-N243V-K256R, N109G-A116T-N218S-K256R-L257G, N109G-A116T-N218S-S248N-L257G, N109G-A116T-N243V-K256R, N109G-A116T-N243V-S248N-K256R-L257G, N109G-A116T-S248N-L257G, N109G-A116T-T158S-G211V-N243V-S248N-K256R, N109G-A116T-T158S-K256R-L257G, N109G-A116T-T158S-N218S, N109G-A116T-T158S-N218S-N243V-K256R-L257G, N109G-A116T-T158S-N218S-N243V-L257G, N109G-A116T-T158S-N218S-N243V-S248N-L257G, N109G-A116T-T158S-N218S-S248N-K256R-L257G, N109G-A116T-T158S-N243V, N109G-A116T-T158S-Q275R, N109G-G131H-A137V-T158S-N218S-S248N, N109G-G131H-N218S-K237N, N109G-G131H-N218S-N243V-K256R-L257G, N109G-G131H-N218S-S248N-K256R, N109G-G131H-N243V-K256R-L257G, N109G-G131H-S145F-N218S-N243V-K256R-L257G, N109G-G131H-S248N-K256R, N109G-G131H-S248N-L257G, N109G-G131H-T158S-K256R, N109G-G131H-T158S-N218S-N243V-K256R, N109G-G131H-T158S-N243V, N109G-G131H-T158S-N243V-K256R-L257G, N109G-G131H-T158S-N243V-L257G, N109G-G131H-T158S-S248N-L257G, N109G-G131H-T158S-S248N-Q271R, N109G-N218S-L257G, N109G-N218S-N243V, N109G-N243V-K256R-L257G, N109G-N243V-S248N-K256R-L257G, N109G-T158S-I268V, N109G-T158S-K256R, N109G-T158S-N218S-N243V-K256R-L257G, N109G-T158S-N218S-S248N-L257G, N109G-T158S-N243V, N109G-T158S-N243V-K256R-L257G, N109G-T158S-N243V-S248N, N109S-A116T-S248N, N218S, N218S-N243V-S248N-K256R-L257G, N218S-S248N-L257G, N243V, N243V-K256R, N243V-S248N-K256R, N243V-S248N-K256R-L257G, S105P-A116T-T158S-N218S-N243V-S248N-K256R, S248N, T158S-N243V-K256R, and T158S-N243V-L257G;

(ix) at least one set of amino acid substitution(s) relative to SEQ ID NO:6 selected from the group consisting of A088T-N109G-A116T-T158S-N243V-L257G, A116T-N218S-N243V-L257G-N269S, A088T-A116T-K256R, A088T-G131H-K256R, A088T-N109G-A116T-T158S-S248N-K256R-L257G, A088T-N109G-T158S-L257G, A088T-

A116T-G131H-T158S-N218S-N243V-K256R-A273T, A088T-A116T-N243V-L257G, A088T-A116T-S248N-K256R-L257G, A088T-A116T-T158S-N243V-L257G, A088T-A116T-T158S-N243V-S248N-L257G, A088T-N109G-A116T-G131H-N218S-N243V-S248N-K256R-L257G, A088T-N109G-A116T-G131H-N243V-L257G, A088T-N109G-A116T-G131H-T158S-L257G, A088T-N109G-A116T-T158S-N218S-L257G, A088T-N109G-A116T-T158S-N218S-N243V-S248N-K256R-L257G, A088T-N109G-G131H-N218S-K256R-L257G, A088T-N109G-N218S-S248N-L257G, A088T-T158S-N218S-N243V-K256R-I268V, A088T-T158S-N218S-S248N-L257G, A116T-N218S-K256R-L257G, N109G-A116T, N109G-A116T-G131H-T158S-L257G, N109G-A116T-N243V, N109G-A116T-N243V-K256R, N109G-A116T-T158S-L257G, N109G-K256R, N109G-N243V-K256R-L257G, S003P-N109G-G131H-T158S-K256R, A088T-A116T, A088T-A116T-G131H-N218S-K256R-L257G, A088T-A116T-G131H-N218S-L257G, A088T-A116T-G131H-N218S-N243V-S248N-L257G, A088T-A116T-G131H-N243V-K256R-L257G, A088T-A116T-G131H-N243V-S248N-K256R-L257G, A088T-A116T-G131H-T158S-N218S-N243V, A088T-A116T-G131H-T158S-N218S-N243V-K256R-L257G, A088T-A116T-G131H-T158S-N218S-N243V-S248N, A088T-A116T-G131H-T158S-S248N-K256R-L257G, A088T-A116T-G131H-T158S-S248N-L257G, A088T-A116T-N218S-N243V-L257G, A088T-A116T-N218S-N243V-S248N-K256R-L257G, A088T-A116T-N218S-N243V-S248N-K256R-Q275R, A088T-A116T-T158S-A216S-N218S-N243V-K256R-L257G, A088T-A116T-T158S-K256R, A088T-A116T-T158S-N218S-L257G, A088T-A116T-T158S-N218S-N243V, A088T-A116T-T158S-N218S-N243V-K256R, A088T-A116T-T158S-N218S-N243V-K256R-L257G, A088T-A116T-T158S-N218S-N243V-K256R-N269S, A088T-A116T-T158S-N243V, A088T-A116T-T158S-N243V-K256R, A088T-A116T-V147I-T158S-N218S-N243V-L257G, A088T-G131H-K256R-L257G, A088T-G131H-N218S-N243V-S248N-K256R-L257G, A088T-G131H-S248N-K256R-L257G, A088T-G131H-T158S-N218S-L257G, A088T-G131H-T158S-N218S-N243V-L257G, A088T-I107T-N109G-A116T-G131H-T158S-N218S-N243V-S248N, A088T-I107T-N109G-G131H-N218S-S248N-K256R, A088T-N109G-A116T-G131H-A153S-N218S-S248N-L257G, A088T-N109G-A116T-G131H-K256R-L257G, A088T-N109G-A116T-G131H-N218S-K256R-L257G, A088T-N109G-A116T-G131H-N218S-L257G, A088T-N109G-A116T-G131H-N218S-N243V-K256R, A088T-N109G-A116T-G131H-N218S-N243V-L257G, A088T-N109G-A116T-G131H-N243V-L257G, A088T-N109G-A116T-G131H-S248N-L257G, A088T-N109G-A116T-G131H-T158S-N218S, A088T-N109G-A116T-G131H-T158S-N218S-N243V-S248N-K256R, A088T-N109G-A116T-G131H-T158S-N218S-N243V-S248N-L257G, A088T-N109G-A116T-N218S-K256R-L257G, A088T-N109G-A116T-N218S-L257G, A088T-N109G-A116T-N218S-N243V, A088T-N109G-A116T-N218S-N243V-L257G, A088T-N109G-A116T-N218T-K256R, A088T-N109G-A116T-N218T-K256R-L257G, A088T-N109G-A116T-N243V, A088T-N109G-A116T-N243V-K256R-L257G, A088T-N109G-A116T-N243V-K256R-L257G-N269D, A088T-N109G-A116T-T158S, A088T-N109G-A116T-T158S, A088T-N109G-A116T-T158S-L257G, A088T-N109G-A116T-T158S-N218S-N243V-K256R-L257G, A088T-N109G-A116T-T158S-N218S-N243V-K256R-L257G, A088T-N109G-A116T-T158S-N218S-N243V-S248N, A088T-N109G-A116T-T158S-N243V-S248N-L257G, A088T-N109G-G131H-A138V-T158S-N218S-N243V-S248N-L257G, A088T-N109G-G131H-L257G, A088T-N109G-G131H-N218S, A088T-N109G-G131H-N218S-N243V-L257G, A088T-N109G-G131H-N218S-N243V-S248N-K256R-L257G, A088T-N109G-G131H-N218S-S248N-K256R-L257G, A088T-N109G-G131H-T158S-N218S-K256R, A088T-N109G-G131H-T158S-N218S-N243V, A088T-N109G-G131H-T158S-N243V-K256R-L257G, A088T-N109G-G131H-T158S-N243V-L257G, A088T-N109G-G131H-T158S-N243V-S248N-L257G, A088T-N109G-G131H-V149A-K256R-L257G, A088T-N109G-N218S-N243V-L257G, A088T-N109G-N218S-N243V-S248N-L257G, A088T-N109G-N218S-S248N-K256R-L257G, A088T-N109G-N243V, A088T-N109G-N243V-K256R-L257G, A088T-N109G-N243V-L257G, A088T-N109G-N243V-S248N-L257G, A088T-N109G-S248N-K256R-L257G, A088T-N109G-T158S-K256R, A088T-N109G-T158S-N218S-N243V-K256R-Q275R, A088T-N109G-T158S-N243V, A088T-N109G-T158S-N243V-K256R-I268V, A088T-N109G-T158S-N243V-L257G, A088T-N109G-T158S-N243V-S248N-L257G, A088T-N218S-N243V-L257G, A088T-N218S-N243V-S248N-K256R-L257G, A088T-N218S-S248N, A088T-T158S-N218S-N243V-K256R-L257G, A088T-V143A-T158S-K256R, A088T-V147I-N218S-N243V-K256R-L257G, A114S-A116T-N218S-N243V-S248N-K256R-L257G, A116T-G131H-N218S-N243V-S248N-K256R-L257G, A116T-G131H-N218S-N243V-S248N-L257G, A116T-G131H-N243V-K256R, A116T-G131H-N243V-L257G, A116T-G131H-N243V-S248N-K256R, A116T-G131H-S248N-L257G, A116T-G131H-T158S-N218-I234T-N243V-S248N-K256R, A116T-G131H-T158S-N218S-N243V-S248N-L257G, A116T-N218S-L257G, A116T-T158S-N218S-K256R-L257G, A116T-T158S-N218S-S248N, A116T-T158S-N218S-S248N-L257G-Q271R, A116T-T158S-N243V-S248N-L257G, A116T-T158S-S248N-L257G, G131H-N218S-S248N-K256R-L257G, I107T-N109G-A116T-G131H-T158S-N218S-N243V-S248N-K256R-L257G, N109G-A116T-G131H-A137V-T158S-S248N-K256R-L257G, N109G-A116T-G131H-A151S-N218S-K256R-L257G, N109G-A116T-G131H-N218S-K256R-L257G, N109G-A116T-G131H-N218S-N243V-L257G, N109G-A116T-G131H-N243V-L257G, N109G-A116T-G131H-S248N-L257G, N109G-A116T-G131H-T158S-N218S-N243V-K256R-L257G, N109G-A116T-G131H-T158S-N218S-N243V-S248N-K256R-L257G, N109G-A116T-K256R-L257G, N109G-A116T-N218S-N243V-K256R, N109G-A116T-N218S-N243V-S248N-K256R-L257G, N109G-A116T-N218S-N243V-S248N-L257G, N109G-A116T-N243V-S248N-K256R, N109G-A116T-S248N-L257G, N109G-A116T-T158S-G211V-N243V-S248N-K256R, N109G-A116T-T158S-N218S, N109G-A116T-T158S-N218S-N243V-L257G, N109G-A116T-T158S-N218S-N243V-S248N, N109G-G131H-N218S-K237N, N109G-G131H-N218S-K256R-L257G, N109G-G131H-N218S-L257G, N109G-G131H-N218S-N243V-L257G, N109G-G131H-N243V-K256R-L257G, N109G-G131H-N243V-S248N-L257G, N109G-G131H-S248N-K256R, N109G-G131H-T158S-K256R-L257G, N109G-G131H-T158S-N218S-K256R-L257G, N109G-G131H-T158S-N243V, N109G-N218S, N109G-N218S-N243V-L257G, N109G-T158S-N218S-K256R-L257G, N109G-T158S-N218S-L257G, N109G-T158S-N218S-N243V-K256R, N109G-T158S-N243V-L257G, N243V-K256R-L257G, N243V-L257G, S003F-A088T-N109G-A116T-T158S-N243V-K256R-L257G, T158S-

N218S-L233S, T158S-N218S-N243V-S248N-K256R, V004A-N109G-A116T-T158S-N218S-S248N-L257G, Y006H-A116T-G131H-T158S-N218S-N243V-S248N-K256R-A272G, A088T-A098S-N218S-K256R, A088T-A116T-G131H-K256R-L257G-L267M, A088T-A116T-G131H-L257G, A088T-A116T-G131H-N218S-A274T, A088T-A116T-G131H-N218S-K256R, A088T-A116T-G131H-N218S-N243V-K256R, A088T-A116T-G131H-N218S-N243V-K256R-L257G, A088T-A116T-G131H-N218S-N243V-K256R-L257G, A088T-A116T-G131H-N218S-N243V-L257G, A088T-A116T-G131H-N218S-N243V-S248N-K256R, A088T-A116T-G131H-N218S-N243V-S248N-K256R-L257G, A088T-A116T-G131H-N218S-S248N-L257G, A088T-A116T-G131H-N243V-K256R, A088T-A116T-G131H-N243V-L257G, A088T-A116T-G131H-N243V-S248N, A088T-A116T-G131H-N243V-S248N-A274V, A088T-A116T-G131H-N243V-S248N-K256R-L257G, A088T-A116T-G131H-S248N-K256R-L257G, A088T-A116T-G131H-S248N-L257G, A088T-A116T-G131H-T158S-K256R-L257G, A088T-A116T-G131H-T158S-K256R-L257G, A088T-A116T-G131H-T158S-L257G, A088T-A116T-G131H-T158S-N218S, A088T-A116T-G131H-T158S-N218S-K256R, A088T-A116T-G131H-T158S-N218S-K256R-L257G, A088T-A116T-G131H-T158S-N218S-K256R-L257G, A088T-A116T-G131H-T158S-N218S-L257G, A088T-A116T-G131H-T158S-N218S-N243V-K256R, A088T-A116T-G131H-T158S-N218S-N243V-S248N-K256R, A088T-A116T-G131H-T158S-N218S-S248N-K256R, A088T-A116T-G131H-T158S-N218S-S248N-L257G, A088T-A116T-G131H-T158S-N243V-K256R-L257G, A088T-A116T-G131H-T158S-N243V-L257G, A088T-A116T-G131H-T158S-N243V-S248N-K256R, A088T-A116T-G131H-T158S-N243V-S248N-K256R-L257G, A088T-A116T-K256R, A088T-A116T-N218S-K256R, A088T-A116T-N218S-N243V-K256R, A088T-A116T-N218S-N243V-K256R-L257G, A088T-A116T-N218S-N243V-S248N-K256R, A088T-A116T-N218S-N243V-S248N-L257G, A088T-A116T-N243V-K256R, A088T-A116T-N243V-L257G, A088T-A116T-N243V-S248N-K256R, A088T-A116T-N243V-S248N-K256R-L257G, A088T-A116T-S248N, A088T-A116T-S248N-K256R, A088T-A116T-S248N-L257G, A088T-A116T-T158S-N218S, A088T-A116T-T158S-N218S-K256R, A088T-A116T-T158S-N218S-K256R, A088T-A116T-T158S-N218S-K256R-L257G, A088T-A116T-T158S-N218S-N243V-K256R, A088T-A116T-T158S-N218S-N243V-S248N, A088T-A116T-T158S-N218S-N243V-S248N, A088T-A116T-T158S-N218S-N243V-S248N-K256R, A088T-A116T-T158S-N218S-N243V-S248N-K256R-L257G, A088T-A116T-T158S-N218S-N243V-S248N-L257G, A088T-A116T-T158S-N243V-K256R-L257G, A088T-G131H, A088T-G131H-N218S-K256R-L257G, A088T-G131H-N218S-N243V-K256R, A088T-G131H-N218S-N243V-K256R, A088T-G131H-N218S-N243V-L257G, A088T-G131H-N218S-N243V-L257G, A088T-G131H-N218S-S248N, A088T-G131H-N218S-S248N-K256R, A088T-G131H-N218S-S248N-K256R-L257G, A088T-G131H-N218S-S248N-L257G, A088T-G131H-N218T-L257G, A088T-G131H-N243V-L257G, A088T-G131H-N243V-S248N-K256R, A088T-G131H-S248N, A088T-G131H-S248N-L257G, A088T-G131H-T158S-N218S-K256R, A088T-G131H-T158S-N218S-K256R-L257G, A088T-G131H-T158S-N218S-N243V-K256R, A088T-G131H-T158S-N218S-N243V-K256R, A088T-G131H-T158S-N218S-N243V-K256R-L257G, A088T-G131H-T158S-N218S-N243V-K256R-L257G, A088T-G131H-T158S-N218S-S248N, A088T-G131H-T158S-N218S-S248N-K256R, A088T-G131H-T158S-N218S-S248N-K256R, A088T-G131H-T158S-N218S-S248N-L257G-I268V, A088T-G131H-T158S-N243V, A088T-G131H-T158S-N243V-S248N, A088T-G131H-T158S-N243V-S248N, A088T-G131H-T158S-N243V-S248N-K256R-L257G, A088T-N109G-A116T, A088T-N109G-A116T-G131H-D140G-T158S-N218S-N243V-K256R, A088T-N109G-A116T-G131H-K256R, A088T-N109G-A116T-G131H-N218S, A088T-N109G-A116T-G131H-N218S, A088T-N109G-A116T-G131H-N218S-K256R, A088T-N109G-A116T-G131H-N218S-L257G, A088T-N109G-A116T-G131H-N218S-N243V, A088T-N109G-A116T-G131H-N218S-N243V-K256R-L257G, A088T-N109G-A116T-G131H-N218S-N243V-L257G, A088T-N109G-A116T-G131H-N218S-N243V-S248N-K256R, A088T-N109G-A116T-G131H-N218S-S248N-K256R-L257G, A088T-N109G-A116T-G131H-N218S-S248N-L257G, A088T-N109G-A116T-G131H-N218S-S248N-L257G, A088T-N109G-A116T-G131H-N243V-K256R-L257G, A088T-N109G-A116T-G131H-N243V-S248N, A088T-N109G-A116T-G131H-N243V-S248N-K256R-L257G, A088T-N109G-A116T-G131H-N243V-S248N-L257G, A088T-N109G-A116T-G131H-S248N-K256R, A088T-N109G-A116T-G131H-S248N-K256R-L257G, A088T-N109G-A116T-G131H-S248N-L257G, A088T-N109G-A116T-G131H-T158S, A088T-N109G-A116T-G131H-T158S-N218S, A088T-N109G-A116T-G131H-T158S-N218S-L257G, A088T-N109G-A116T-G131H-T158S-N218S-N243V-K256R, A088T-N109G-A116T-G131H-T158S-N218S-N243V-K256R, A088T-N109G-A116T-G131H-T158S-N218S-N243V-K256R-L257G, A088T-N109G-A116T-G131H-T158S-N218S-N243V-S248N-K256R, A088T-N109G-A116T-G131H-T158S-N218S-S248N, A088T-N109G-A116T-G131H-T158S-N218S-S248N-K256R, A088T-N109G-A116T-G131H-T158S-N218S-S248N-L257G, A088T-N109G-A116T-G131H-T158S-N218S-S248N-L257G, A088T-N109G-A116T-G131H-T158S-N218T-N243V, A088T-N109G-A116T-G131H-T158S-N243V-K256R-L257G, A088T-N109G-A116T-G131H-T158S-N243V-S248N, A088T-N109G-A116T-G131H-T158S-N243V-S248N-K256R, A088T-N109G-A116T-G131H-T158S-N243V-S248N-L257G, A088T-N109G-A116T-G131H-T158S-S248N-K256R-L257G, A088T-N109G-A116T-G131H-T158S-S248N-L257G, A088T-N109G-A116T-K256R, A088T-N109G-A116T-N218S, A088T-N109G-A116T-N218S-N243V, A088T-N109G-A116T-N218S-N243V-K256R, A088T-N109G-A116T-N218S-N243V-K256R-L257G, A088T-N109G-A116T-N218S-N243V-L257G, A088T-N109G-A116T-N218S-N243V-S248N-K256R-L257G, A088T-N109G-A116T-N243V-S248N, A088T-N109G-A116T-N243V-S248N-K256R, A088T-N109G-A116T-N243V-S248N-K256R-L257G, A088T-N109G-A116T-N243V-S248N-K256R-L257G, A088T-N109G-A116T-N243V-S248N-L257G, A088T-N109G-A116T-S248N-K256R, A088T-N109G-A116T-S248N-K256R-L257G, A088T-N109G-A116T-T158S-K256R, A088T-N109G-A116T-T158S-N218S, A088T-N109G-A116T-T158S-N218S-K256R-L257G, A088T-N109G-A116T-T158S-N218S-L257G, A088T-N109G-A116T-T158S-N218S-N243V, A088T-N109G-A116T-T158S-N218S-N243V-L257G, A088T-N109G-A116T-T158S-N218S-N243V-S248N, A088T-N109G-A116T-T158S-N218S-N243V-S248N-K256R, A088T-N109G-A116T-T158S-N218S-N243V-S248N-L257G, A088T-N109G-A116T-T158S-N218S-S248N, A088T-N109G-A116T-T158S-N218S-

S248N-K256R, A088T-N109G-A116T-T158S-N218S-S248N-L257G, A088T-N109G-A116T-T158S-N243V-K256R, A088T-N109G-A116T-T158S-N243V-S248N, A088T-N109G-A116T-T158S-S248N, A088T-N109G-A116T-T158S-S248N-K256R, A088T-N109G-A116T-T158S-S248N-L257G, A088T-N109G-G131H-N218S-K256R, A088T-N109G-G131H-N218S-K256R, A088T-N109G-G131H-N218S-N243V-K256R, A088T-N109G-G131H-N218S-N243V-K256R, A088T-N109G-G131H-N218S-N243V-K256R-L257G, A088T-N109G-G131H-N218S-N243V-S248N-K256R, A088T-N109G-G131H-N218S-S248N, A088T-N109G-G131H-N218S-S248N-L257G, A088T-N109G-G131H-N243V-K256R-L257G, A088T-N109G-G131H-N243V-K256R-L257G, A088T-N109G-G131H-N243V-L257G, A088T-N109G-G131H-N243V-L257G, A088T-N109G-G131H-N243V-S248N-K256R, A088T-N109G-G131H-N243V-S248N-K256R-L257G, A088T-N109G-G131H-N243V-S248N-L257G, A088T-N109G-G131H-S248N-L257G, A088T-N109G-G131H-T158S-K256R-L257G, A088T-N109G-G131H-T158S-N218S-L257G, A088T-N109G-G131H-T158S-N218S-L257G, A088T-N109G-G131H-T158S-N218S-N243V-S248N, A088T-N109G-G131H-T158S-N218S-N243V-S248N-K256R, A088T-N109G-G131H-T158S-N218S-S248N-K256R, A088T-N109G-G131H-T158S-N218S-S248N-L257G, A088T-N109G-G131H-T158S-N243V, A088T-N109G-G131H-T158S-N243V-S248N, A088T-N109G-G131H-T158S-N243V-S248N-K256R, A088T-N109G-G131H-T158S-N243V-S248N-K256R, A088T-N109G-G131H-T158S-N243V-S248N-K256R-L257G, A088T-N109G-G131H-T158S-S248N-K256R-L257G, A088T-N109G-G131H-T158S-W241R-S248N-K256R, A088T-N109G-G131H-V148A-N218S-N243V-K256R-L257G, A088T-N109G-G154A-N155P-E156T-G157L-T158M-S159E-G160E-S161L, A088T-N109G-N218S-K256R, A088T-N109G-N218S-N243V-L257G, A088T-N109G-N218S-N243V-S248N, A088T-N109G-N243V-K256R, A088T-N109G-N243V-S248N, A088T-N109G-N243V-S248N-K256R-L257G, A088T-N109G-S248N, A088T-N109G-T158S-N218S, A088T-N109G-T158S-N218S-K256R, A088T-N109G-T158S-N218S-K256R-L257G, A088T-N109G-T158S-N218S-L257G, A088T-N109G-T158S-N218S-N243V-S248N-K256R, A088T-N109G-T158S-N218S-N243V-S248N-K256R-L257G, A088T-N109G-T158S-N218S-S248N-K256R, A088T-N109G-T158S-N218S-S248N-K256R-L257G, A088T-N109G-T158S-N243V-K256R, A088T-N109G-T158S-N243V-K256R, A088T-N109G-T158S-N243V-S248N-L257G, A088T-N109G-T158S-S248N-K256R-L257G, A088T-N109G-T158S-S248N-L257G, A088T-N109G-T158S-S248N-L257G, A088T-N109G-V147A-N218S-N243V-K256R, A088T-N218S-L257G-I268V, A088T-N218S-N243V, A088T-N218S-N243V-S248N, A088T-N218S-N243V-S248N-N269S, A088T-N218S-S248N-K256R, A088T-N218S-S248N-L257G-Q271R, A088T-N243V, A088T-N243V, A088T-N243V-K256R, A088T-N243V-S248N-K256R, A088T-N243V-S248N-K256R-L257G, A088T-S248N, A088T-T158S-N218S-K256R-L257G, A088T-T158S-N218S-N243V-K256R, A088T-T158S-N218S-N243V-L257G, A088T-T158S-N218S-N243V-S248N-K256R-L257G, A088T-T158S-N218S-N243V-S248N-K256R-L257G, A088T-T158S-N243V-K256R-L257G, A088T-T158S-N243V-K256R-L257G-Q271H, A088T-T158S-N243V-S248N, A088T-T158S-N243V-S248N-L257G, A088T-T158S-S248N, A088T-V147A-K256R, A116T-G131H-K256R, A116T-G131H-N218S, A116T-G131H-N218S-K256R-L257G, A116T-G131H-N218S-L257G, A116T-G131H-N218S-N243V, A116T-G131H-N218S-S248N-K256R, A116T-G131H-N218S-S248N-K256R-L257G, A116T-G131H-N243V-S248N, A116T-G131H-N243V-S248N-L257G, A116T-G131H-S248N-K256R, A116T-G131H-T158S-A231V-N243V-L257G, A116T-G131H-T158S-N218S-K256R, A116T-G131H-T158S-N218S-K256R-L257G, A116T-G131H-T158S-N218S-N243V-K256R-L257G, A116T-G131H-T158S-N218S-N243V-S248N-K256R, A116T-G131H-T158S-N218S-N243V-S248N-K256R-L257G, A116T-G131H-T158S-N218S-S248N, A116T-G131H-T158S-N243V-L257G, A116T-G131H-T158S-N243V-S248N-K256R, A116T-G131H-T158S-S248N-K256R, A116T-G131H-T158S-S248N-L257G, A116T-G131H-V143F-T158S-N218S, A116T-K256R, A116T-N218S, A116T-N218S-K256R, A116T-N218S-N243V-L257G, A116T-N218S-N243V-S248N-K256R, A116T-N218S-N243V-S248N-K256R-L257G, A116T-N218S-N243V-S248N-L257G, A116T-N218S-S248N-L257G, A116T-N243V, A116T-N243V-K256R-L257G, A116T-N243V-S248N, A116T-N243V-S248N-K256R-L257G, A116T-S248N-K256R-L257G, A116T-T158S-K256R-L257G, A116T-T158S-N218S, A116T-T158S-N218S-K256R, A116T-T158S-N218S-N243V, A116T-T158S-N218S-N243V-S248N, A116T-T158S-N218S-S248N-K256R, A116T-T158S-N218S-S248N-K256R-L257G, A116T-T158S-N243V-K256R, A116T-T158S-N243V-L257G, A116T-T158S-N243V-S248N, A116T-T158S-S248N-K256R-L257G, G131H-K141R-T158S-N218S-K256R, G131H-N218S, G131H-N218S-K256R, G131H-N218S-N243V-K256R-L257G, G131H-N218S-N243V-S248N, G131H-N218S-N243V-S248N-L257G, G131H-N243V-S248N-K256R, G131H-N243V-S248N-K256R-L257G, G131H-S248N, G131H-T158S-I234T-N243V-K256R, G131H-T158S-N218S-K256R-L257G, G131H-T158S-N218S-N243V, G131H-T158S-N218S-N243V-S248N-L257G, G131H-T158S-N218S-S248N-K256R-L257G, G131H-T158S-N218S-S248N-L257G, G131H-T158S-N243V-K256R, G131H-T158S-N243V-S248N-L257G, N109G, N109G-A116T-G131H-A144V-T158S-S248N-K256R-L257G, N109G-A116T-G131H-K256R-L257G, N109G-A116T-G131H-N218S-N243V-K256R, N109G-A116T-G131H-N218S-N243V-K256R-L257G, N109G-A116T-G131H-N218S-S248N-K256R, N109G-A116T-G131H-N218S-S248N-L257G, N109G-A116T-G131H-N243V-K256R, N109G-A116T-G131H-N243V-S248N, N109G-A116T-G131H-N243V-S248N-K256R-L257G, N109G-A116T-G131H-S248N, N109G-A116T-G131H-S248N-K256R, N109G-A116T-G131H-T158S-K256R, N109G-A116T-G131H-T158S-K256R-L257G, N109G-A116T-G131H-T158S-N218S-K256R, N109G-A116T-G131H-T158S-N218S-K256R-L257G, N109G-A116T-G131H-T158S-N218S-L257G, N109G-A116T-G131H-T158S-N218S-N243V-K256R, N109G-A116T-G131H-T158S-N218S-N243V-S248N-L257G, N109G-A116T-G131H-T158S-N218S-S248N, N109G-A116T-G131H-T158S-N243V-L257G, N109G-A116T-G131H-T158S-N243V-S248N, N109G-A116T-G131H-T158S-S248N, N109G-A116T-G131H-T158S-S248N-K256R, N109G-A116T-G131H-T158S-S248N-K256R-L257G, N109G-A116T-G131H-V149A-T158S-N218S-N243V-S248N-L257G, N109G-A116T-N218S, N109G-A116T-N218S-K256R, N109G-A116T-N218S-N243V-K256R-L257G, N109G-A116T-N218S-N243V-S248N-I268V, N109G-A116T-N243V-K256R-L257G, N109G-A116T-N243V-S248N, N109G-A116T-N243V-S248N-L257G, N109G-A116T-T158S, N109G-A116T-T158S-N218S-

N243V-K256R-L257G, N109G-A116T-T158S-N218S-N243V-S248N-K256R-L257G, N109G-A116T-T158S-N218S-N243V-S248N-L257G, N109G-A116T-T158S-N218S-S248N-K256R-L257G, N109G-A116T-T158S-N243V-K256R-L257G, N109G-A116T-T158S-N243V-L257G, N109G-A116T-T158S-N243V-S248N-L257G, N109G-A116T-T158S-Q275R, N109G-A116T-T158S-S248N-K256R-L257G, N109G-G131H-L257G, N109G-G131H-N218S-N243V-S248N-K256R-L257G, N109G-G131H-N218S-N243V-S248N-L257G, N109G-G131H-N218S-S248N-K256R-L257G, N109G-G131H-N243V-K256R, N109G-G131H-S145F-N218S-N243V-K256R-L257G, N109G-G131H-S248N-K256R-L257G, N109G-G131H-S248N-L257G, N109G-G131H-T158S-K256R, N109G-G131H-T158S-N218S-L257G, N109G-G131H-T158S-N218S-N243V, N109G-G131H-T158S-N218S-N243V-K256R, N109G-G131H-T158S-N218S-N243V-K256R-L257G, N109G-G131H-T158S-N218S-N243V-S248N-L257G, N109G-G131H-T158S-N218S-S248N-K256R, N109G-G131H-T158S-N218S-S248N-K256R-L257G-A274T, N109G-G131H-T158S-N218S-S248N-L257G, N109G-G131H-T158S-N243V-S248N, N109G-G131H-T158S-N243V-S248N-K256R-L257G, N109G-G131H-T158S-S248N-K256R-L257G, N109G-G131H-T158S-S248N-L257G, N109G-N218S-K256R-L257G, N109G-N218S-L257G, N109G-N218S-N243V-K256R, N109G-N218S-N243V-S248N-S260F, N109G-N218S-S248N, N109G-N243V-K256R, N109G-N243V-L257G, N109G-N243V-S248N, N109G-N243V-S248N-K256R-L257G, N109G-S182F-S204F-S207L-N218S-S236F-S248N-L257G, N109G-S248N-K256R, N109G-T158S-K256R, N109G-T158S-N218S-N243V-K256R-L257G, N109G-T158S-N218S-S248N-L257G, N109G-T158S-N243V, N109G-T158S-N243V-K256R, N109G-T158S-N243V-S248N, N109G-T158S-N243V-S248N-K256R, N109G-T158S-S248N-K256R, N109G-T158S-S248N-L257G, N218S, N218S-N243V-S248N-K256R, N218S-S248N-L257G, N243V-K256R, N243V-S248N-K256R, N243V-S248N-K256R-L257G, N243V-S248N-L257G-Q271R, S003P-A116T-T158S-S248N-K256R, S248N, T158S-N218S, T158S-N218S-A272V, T158S-N218S-L257G, T158S-N218S-N243V-K256R-L257G, T158S-N218S-N243V-L257G, T158S-N218S-S248N-K256R-L257G, T158S-N243V-K256R, T158S-N243V-K256R-L257G, T158S-N243V-S248N-K256R, V004A-N109G-A116T-G131H-S248N-K256R-L257G, and Y006H-A116T-G131H-S248N;

(x) at least one set of amino acid substitutions relative to SEQ ID NO:6 selected from the group consisting of S018F-S162L, S018P-D120N, P014T-S037T, S009T-K141R, and S161P-S162L;

(xi) at least one set of amino acid substitutions selected relative to SEQ ID NO:6 from the group consisting of I031V-S038W, P014T-S037T, S018F-S162L, S018P-D120N, and S162L-D181H;

(xii) at least one set of amino acid substitutions relative to SEQ ID NO:6 selected from the group consisting of Y21H-D259G, S183T-S249R, N61D-Q206R, Y262N-Q275R, K043R-N076S, A133V-D259N, and I079V-Q217H;

(xiii) at least one set of amino acid substitutions relative to SEQ ID NO:6 selected from the group consisting of N61P-S63G-N109Q-A128S-S224A-N243V, A88T-N109G-A114S-A116T-A128S-N243V, A88T-N109G-A114S-A116T-A128S-S183L-S224A-N243V, N109G-A128S-S183V, N109G-A128S-N243V-K256R, N109M-A128S-S224A, A88T-N109S-A116T-A128S-S224A-N243V, N109Q-A128S-S224A-N243V, A88T-N109M-A116T-A128S-S224A-N243V, N109S-A128S-S224A-N243V, A88T-N109G-A116T-N243V, N101Q-N109Q-A128S-S224A-N243V, N109G-A116T-N243V-K256R, N109G-A128S-P129S-S130T-S224A-N243V, and A88T-N109Q-A116T-A128S-S224A-N243V;

(xiv) at least one set of amino acid substitutions relative to SEQ ID NO:6 selected from the group consisting of S33T-T55P-N61P-S63G-A88T-N109G-A116T-A128S-G131H-S224A-N243V, S33T-N61G-S63G-N109G-A128S-N218S-N243V, S33T-S63G-N109G-A128S-N218S-N243V, N61P-S63G-N109Q-A128S-G131H-G169A-S224A-N243V-S249Q, S33T-N61G-A88T-N109G-A116T-A128S-N218S-N243V, S33T-N109G-A128S-N218S-N243V, S33T-A128S-N218S, A1G-N61P-S63G-N109Q-A128S-G131H-S224A-N243V, N61P-S63G-N109Q-A128S-G131H-S224A-N243V-S249Q, S63G-N109Q-A128S-G131H-S224A-N243V, N61P-S63G-N109Q-A128S-S224A-N243V, A88T-N109G-A114S-A116T-A128S-N243V, A88T-N109G-A114S-A116T-A128S-S183L-S224A-N243V, N109G-A114S-A128S, N109G-A114S-A128S-S183L-S224A, N109G-A114S-A128S-S224A, N109G-A114S-A128S-S224A-N243V, A88T-N109G-A116T-A128S-S224A-N243V, N61G-A88T-N109G-A116T-A128S-S224A-N243V, N109G-A128S-S183V, N109G-A114S-A128S-N243V, N109G-A128S-N243V-S248A, N109G-A128S-S224A-N243V, N109G-A128S-N243V-K256R, N109G-A128S-S224A, N109G-A128S-S183L-S224A, N61G-N109G-A128S-S224A, N109M-A128S-S224A, A88T-N109S-A116T-A128S-S224A-N243V, N109M-A128S-S224A-N243V, S63G-A128S, A88T-N109G-A116T-N243V, N101Q-N109Q-A128S-S224A-N243V, N109G-A116T-N243V-K256R, N109G-A116T, S63G-N109G, A88T-N109G, N109G-K256R, N61G-N109G-N243V, S33T-N109G-A128S-G169A-N218S-N243V, S33T-N109G-A128S-N218S-S224A-N243V, N109G-A128S-P129S-S130T-S224A-N243V, and A88T-N109Q-A116T-A128S-S224A-N243V; and (xv) at least one set of amino acid substitutions relative to SEQ ID NO:6 selected from the group consisting of G24S-G53S-N78S-G97A-N101S-A128S, I31L-S33T-S63G-N109G-A128S-G169A-N218S-N243V, A1G-I31L-S33T-T55P-N61P-S63G-A88T-N109G-A116T-A128S-G131H-G169A-S224A-N243V-S249Q, S33T-N61G-S63G-N109G-A128S-G131H-G169A-N218S-N243V, S33T-S63G-N109G-A128S-G169A-N218S-N243V, S33T-T55P-N61P-S63G-A88T-N109G-A116T-A128S-G131H-S224A-N243V, S33T-T55P-N61P-S63G-A88T-N109G-A116T-A128S-G131H-S224A-N243V-S249Q, S33T-N61G-S63G-N109G-A128S-N218S-N243V, S33T-S63G-N109G-A128S-N218S-N243V, S33T-T55P-N61P-S63G-N109Q-A128S-G131H-S224A-N243V, N61P-S63G-N109Q-A128S-G131H-G169A-S224A-N243V-S249Q, S33T-N61G-A88T-N109G-A116T-A128S-N218S-N243V, S33T-N109G-A128S-N218S-N243V, S33T-N76D-N109G-A128S-N218S-N243V, S33T-N76D-N109G-A128S-N218S-N243V-S248N-K256R, S33T-N61G-N109G-A128S-N218S-N243V, S33T-N76D-A128S-N218S, S33T-A128S-N218S, A1G-N61P-S63G-N109Q-A128S-G131H-S224A-N243V, N61P-S63G-N109Q-A128S-G131H-S224A-N243V-S249Q, N61P-S63G-N109Q-A128S-G131H-S224A-N243V, S63G-N109Q-A128S-G131H-S224A-N243V, N61P-S63G-N109Q-A128S-S224A-N243V, A88T-N109G-A114S-A116T-A128S-N243V, A88T-N109G-A114S-A116T-A128S-S183L-S224A-N243V, N109G-A114S-A128S, N109G-A114S-A128S-S183L-S224A, N109G-A114S-A128S-S224A, N109G-A114S-A128S-S224A-N243V, A88T-N109G-A116T-

A128S-S224A-N243V, N109G-A128S-S224A-N243V, N109G-A114S-A128S-N243V, N109G-A128S-S224A-N243V, N109G-A128S-N243V-K256R, N109G-A128S-S224A, N109G-A128S-S183L-S224A, N61G-N109G-A128S-S224A, N76D-N109G-A128S-S224A, N109M-A128S-S224A, N109G-A128S-S183L, S33T-N76D, A88T-N109S-A116T-A128S-S224A-N243V, N109Q-A128S-S224A-N243V, N109S-A128S-S224A, A88T-N109M-A116T-A128S-S224A-N243V, N101Q-N109Q-A128S-P129S-S130T-S224A-N243V, S63G-N109Q-A128S-S224A-N243V, N109M-A128S-S224A-N243V, S63G-A128S, N109S-A128S-S224A-N243V, A88T-N109G-A116T-N243V, N61S-N109G-N243V, N101Q-N109Q-A128S-S224A-N243V, N109G-A116T-N243V-K256R, A88T-N109G-A116T-T158S-N243V-K256R, N109G-A116T, S63G-N109G, A88T-N109G, N109G-K256R, N61G-N109G-N243V, S33T-N61P-S63G-N109G-A128S-G131H-G169A-N218S-N243V, S33T-N109G-A128S-G169A-N218S-N243V, S33T-N109G-A128S-N218S-S224A-N243V, N109G-A128S-P129S-S130T-S224A-N243V, and A88T-N109Q-A116T-A128S-S224A-N243V.

In an eighth aspect, the invention provides an isolated or non-naturally occurring protease variant of a BPN' subtilisin protease having the amino acid sequence of SEQ ID NO:2, said variant having proteolytic activity and comprising at least one set of amino acid substitution(s) selected from the group consisting of: S182E, N109I, N109D-Y217L-S248R, N109D-S188R-Y217L, S87D-Y217L-S248R, S87R-N109D-Y217L-S248R, S87R-N109D-S188D-Y217L-S248R, G128A-Y217Q, I111V-M124V, M124V-Y217Q, N62Q-G97A, S89Y-M124V, V68A, V68A-A92G, V68A-G97A, V68A-I111V, V68A-S89Y, V68A-V227T, V68A-Y217Q, W106F-Y217Q, G97A-G128A-Y217Q, G97A-L126A-Y217Q, G97A-M124V-L126A-Y217Q, G97A-N123G-Y217Q, L96T-G97A-Y217Q, M124V-L126A-Y217Q, N62Q-G128A-Y217Q, N62Q-G97A-Y217Q, G97N-G128A-Y217M, G97G-G128S-Y217E, G97A-G128A-Y217Q, G97M-G128S-Y217E, G97A-G128S-Y217Q, G97D-G128S-Y217Q, G97M-G128G-Y217M, G97G-G128S-Y217Q, G97S-G128S-Y217Q, G97G-G128A-Y217Q, G97S-G128A-Y217E, G97A-G128S-Y217L, G97A-G128A-Y217N, G97Q-G128S-Y217L, G97A-G128A-Y217M, G97A-G128A-Y217S, G97D-G128A-Y217Q, G97M-G128S-Y217Q, G97Q-G128G-Y217D-S87Y, G97S-G128A-Y217N, G97A-G128S-Y217T, G97D-G128S-Y217E, G97D-G128A-Y217L, G97G-G128S-Y217E-S78P-A272T, G97T-G128S-Y217D, G97D-G128A-Y217I, G97Q-G128S-Y217Q, G97G-G128A-Y217D, G97Q-G128A-Y217N, G97S-G128A-Y217M, G97S-G128S-Y217N, G97S-G128S-Y217M, G97E-G128S-Y217M, G97S-G128P-Y217Q, G97T-G128S-Y217Q, G97D-G128S-Y217Q-A73T, G97E-G128S-Y217N, G97G-G128A-Y217I, G97Q-G128A-Y217D, G97Q-G128S-Y217M, G97R-G128T-Y217Q-S162P, G97S-G128S-Y217D, G97T-G128P-Y217I, G97Q-G128G-Y217E, G97C-G128G-Y217N, G97D-G128S-Y217H, G97M-G128S-Y217L, G97M-G128S-Y217N, G97S-G128S-Y217E, G97M-G128S-Y217I, G97A-G128P-Y217A, G97R-G128S-Y217D, G97A-G128A-Y217Q-S145D, G97A-G128A-Y217Q-P239R, G97A-G128A-Y217Q-N61E-P129E-S162K-K213L-N240K, G97A-G128A-Y217Q-N61E, G97A-G128A-Y217Q-P40E-A144K-K213L, G97A-G128A-Y217Q-P129E, G97A-G128A-Y217Q-N61E-P129E-S159K, G97A-G128A-Y217Q-K213L, G97A-G128A-Y217Q-S87D, G97A-G128A-Y217Q-Q206E, G97A-G128A-Y217Q-S24R-P40E-S145D-S159K-K213L, G97A-G128A-Y217Q-K265N, G97A-G128A-Y217Q-S24R, G97A-G128A-Y217Q-P40E, G97A-G128A-Y217Q-Q275E, G97A-G128A-Y217Q-P129E-S145D-N240K, G97A-G128A-Y217Q-A144K, G97A-G128A-Y217Q-S159K, G97A-G128A-Y217Q-S162K, G97A-G128A-Y217Q-N240K, G97A-G128A-Y217Q-S53G, G97A-G128A-Y217Q-S78N, G97A-G128A-Y217Q-S53G-S78N, G97A-G128A-Y217Q-S53G-I111V, G97A-G128A-Y217Q-S53G-N117S, G97A-G128A-Y217Q-S53G-S132N, G97A-G128A-Y217Q-Y104N-S132N, G97A-G128A-Y217Q-S53G-S78N-I111V, G97A-G128A-Y217Q-S53G-S78N-N117S, G97A-G128A-Y217Q-S53G-S78N-S132N, G97A-G128A-Y217Q-S53G-Y104N-S132N, G97A-G128A-Y217Q-S78N-Y104N-S132N, Y217L-V068C-A069G, Y217L-I079F-A098G, Y217L-P086T-S101D-Q103S-V147I, Y217L-A088T-P129S-G146D, Y217L-V093I-G128D-P129R, Y217L-Z096.01D-A098R, Y217L-Z096.01H-A098G, Y217L-G097S-Z097.01S-A098G-A273T, Y217L-A098S-D099G-G100D, Y217L-Z098.01N, Y217L-D099G-Z099.01N, Y217L-D099G-Z099.01S, Y217L-D099V-S101D, Y217L-Z099.01S, Y217L-G100D, Y217L-S101D-Q103H, Y217L-S101G-A151V, Y217L-S101H-G102S, Y217L-S101H-Q103D, Y217L-G102R-Q103C-Y104C-V192I, Y217L-Q103D, Y217L-V121I-I122S-N123C, Y217L-V121I-N123C, Y217L-I122S-N123S, Y217L-M124I, Y217L-M124V, Y217L-L126F-P129Z-S182N, Y217L-L126Y, Y217L-G127S-P129D, Y217L-Z127.01N-G128S-P129S, Y217L-G128H-P129Y, Y217L-G128S-P129D, Y217L-G128S-P129D-S248R, Y217L-G128S-P129G, Y217L-P129G-G131Z, Y217L-P129G-S130H-S132Z, Y217L-P129H-G131Z, Y217L-P129L, Y217L-P129S-S130H-S132Z, Y217L-P129Z, Y217L-P129Z-S130G, Y217L-P129Z-S130G-G131H-S132H, Y217L-P129Z-S130H, Y217L-S130V-G131D-S132I, S87T-A88L-S89G-G97A-G128A-Y217Q, N61P-S63H-G97A-G128A-Y217Q, S87G-A88V-S89A-G97A-G128A-Y217Q, P86S-S87G-A88V-G97A-G128A-Y217Q, Q59S-N61P-G97A-G128A-Y217Q, S24G-N25G-G97A-G128A-Y217Q, N61P-N62S-G97A-G128A-Y217Q, G97A-G128A-P129Q-S130G-G131S-Y217Q, L75S-N76Y-G97A-G128A-Y217Q, G97A-G128A-V203Y-Y217Q, T55P-G97A-G128A-Y217Q, A88V-L90I-G97A-G128A-Y217Q, G97A-G128A-G211R-N212S-K213V-Y217Q, G23A-S24G-N25G-G97A-G128A-Y217Q, T22N-S24A-G97A-G128A-Y217Q, S24R-G97A-G128A-Y217Q, G97A-A98S-G128A-Y217Q, G97A-G128A-T158G-S159G-Y217Q, Q59E-N61P-G97A-G128A-Y217Q, G97A-A98E-G128A-Y217Q, G97A-G128A-Y217Q-P86S-S87G-A88V-A116N-N117S-N118G, G97A-G128A-Y217Q-S63T-P86S-S87G-A88V, G97A-G128A-Y217Q-P86S-S87G-A88V-P239R, G97A-G128A-Y217Q-S24G-N25G-N61P-N62S-P194L-A232T, G97A-G128A-Y217Q-P129Q-S130G-G131S-A133V-L267V, G97A-G128A-Y217Q-A134T-L267V, G97A-G128A-Y217Q-S24R-P40E-P129E-S159K-K265R, G97A-G128A-Y217Q-A134T-G211T, G97A-G128A-Y217Q-S24R-P129E, G97A-G128A-Y217Q-I111V-S161P, G97A-G128A-Y217Q-T55P-P129Q, G97A-G128A-Y217Q-I115V-L267V, G97A-G128A-Y217Q-P86S-S87G-A88V-A116N-N117G-N118R, G97A-G128A-Y217Q-V203Y-L267V, G97A-G128A-Y217Q-S24G-N25G-S78N-S101N-V203Y, G97A-G128A-Y217Q-P52S-T55P-V203Y, G97A-G128A-Y217Q-Q59S-N61P-A116S-N117G-N118R, G97A-G128A-Y217Q-S24G-N25G-P129Q-S130G-G131S, G97A-G128A-Y217Q-P86S-S87G-A88V-T242R, G97A-G128A-Y217Q-P40E-T55P-N269K, G97A-G128A-Y217Q-G23A-S24G-

N25G-A116N-N117S-N118G, V8L-N25Y-P129Q-S130G-G131S, G97A-G128A-Y217Q-S24G-N25G-S53G-S78N-S87T-A88L-S89G-S101N, G97A-G128A-Y217Q-G211T-L267V, G97A-G128A-Y217Q-S24R-A116N-N117S-N118G, G97A-G128A-Y217Q-S24R-A128S-P129G, G97A-G128A-Y217Q-P129Q-S130G-G131S-N240K, G97A-G128A-Y217Q-N25Y-P129Q-S130G-G131S, G97A-G128A-Y217Q-S87T-A88L-S89G-A134T, G97A-G128A-Y217Q-P129Q-S130G-G131S-L267V, G97A-G128A-Y217Q-S87G-A88V-S89A-A116N-N117S-N118G, G97A-G128A-Y217Q-N61P-P129Q-S130G-G131S, G97A-G128A-Y217Q-N61P-S78N-S87T-A88L-S89G-S101N, G97A-G128A-Y217Q-T55P-P129V-P194S, G97A-G128A-Y217Q-T55P-P129V, G97A-G128A-Y217Q-S24G-N25G-T55P-S78N-S101N, G97A-G128A-Y217Q-T55P-S78N-I115V, G97A-G128A-Y217Q-N25Y-S87G-A88V-S89A, G97A-G128A-Y217Q-A134T-N240K, G97A-G128A-Y217Q-S24R-Q59S-N61P, G97A-G128A-Y217Q-G23A-S24G-N25G-P239R, G97A-G128A-Y217Q-T55P-A116S-N117G-N118R, G97A-G128A-Y217Q-A134T-S161P, G97A-G128A-Y217Q-S24G-N25G-S53G-N61P-S101N-V203Y, G97A-G128A-Y217Q-N25Y-Q59S-N61P, G97A-G128A-Y217Q-N25Y-P129Q-S130G-G131S-A137T, G97A-G128A-Y217Q-G23A-S24G-N25G-N61P-S63H, G97A-G128A-Y217Q-T55P-N61P-S78N-S101N-V203Y, G97A-G128A-Y217Q-P129Q-N240K, G97A-G128A-Y217Q-T55P-A134T, G97A-G128A-Y217Q-N25Y-N61P-S63H, G97A-G128A-Y217Q-S87T-A88L-S89G-P129S, G97A-G128A-Y217Q-T55P-L75H-N76G, G97A-G128A-Y217Q-S524G-N25G-S53G-S78N-S87T-A88L-S89G-S101N-V203Y, G97A-G128A-Y217Q-T55P-I115V, G97A-G128A-Y217Q-T55P-A116N-N117S-N118G, G97A-G128A-Y217Q-S24G-N25G-A116N-N117S-N118G, G97A-G128A-Y217Q-S24R-P129Q-S130G-G131S, G97A-G128A-Y217Q-G23A-S24G-N25G-G211R-N212S-K213V, G97A-G128A-Y217Q-S24G-N25G-T55P-N61P-S78N-S101N-V203Y, G97A-G128A-Y217Q-T55P-S78N-S87T-A88L-S89G-S101N, G97A-G128A-Y217Q-I115V-A273S, G97A-G128A-Y217Q-N25Y-T55P, G97A-G128A-Y217Q-S24G-N25G-S53G-T55P-N61P-S78N-S87T-A88L-S89G-S101N-V203Y, G97A-G128A-Y217Q-Q59S-N61P-N240K, G97A-G128A-Y217Q-S161P-L267V, G97A-G128A-Y217Q-S24G-N25G-S53G-T55P-N61P-S78N-S87T-A88L-S89G-S101N, G97A-G128A-Y217Q-S87T-A88L-S89G-S101N, G97A-G128A-Y217Q-S24G-N25G-N61P-S101N, G97A-G128A-Y217Q-S24G-N25G-S53G-T55P-S101N-V203Y, G97A-G128A-Y217Q-N240K, G97A-G128A-Y217Q-S24G-N25G-S53G-T55P-S87T-A88L-S89G-S101N-V203Y, G97A-G128A-Y217Q-S24G-N25G-T55P-S101N, G97A-G128A-Y217Q-N61P-S63H-A128S-P129Q, G97A-G128A-Y217Q-S89Y-P129Q-S130G-G131S, G97A-G128A-Y217Q-P129Q-S130G-G131S-V203Y, G97A-G128A-Y217Q-I115V-N240K, G97A-G128A-Y217Q-S53G-N61P-S87T-A88L-S89G-S101N-V203Y, G97A-G128A-Y217Q-S161P-V203Y, G97A-G128A-Y217Q-S87T-A88L-S89G-N240K, G97A-G128A-Y217Q-S87T-A88L-S89G-P239R, G97A-G128A-Y217Q-T55P-N61P-S78N-S87T-A88L-S89G-S101N-V203Y, G97A-G128A-Y217Q-S24G-N25G-I115V-A134T, G97A-G128A-Y217Q-Y6Q-P129Q-S130G-G131S, G97A-G128A-Y217Q-T55P-S78N-S89Y, G97A-G128A-Y217Q-S24G-N25G-T55P-S78N-A88V-S101N, G97A-G128A-Y217Q-N61P-S63H-S78N-I111V-A134T, G97A-G128A-Y217Q-S24G-N25G-S53G-T55P-S78N-S101N, G97A-G128A-Y217Q-S24G-N25G-S53G-S78N-S101N-V203Y, G97A-G128A-Y217Q-S53G-N61P-S101N-V203Y, G97A-G128A-Y217Q-S53G-T55P-S78N-S101N-V203Y, G97A-G128A-Y217Q-S53G-T55P-N61P-S78N-S87T-A88L-S89G-S101N, G97A-G128A-Y217Q-N240K-A273S, G97A-G128A-Y217Q-S78N-S87T-A88L-S89G-S101N, G97A-G128A-Y217Q-Q59S-N61P-S87T-A88L-S89G, G97A-G128A-Y217Q-N61P-S63H-S78N-S161P, G97A-G128A-Y217Q-N61P-S63H-S78N-I111V, G97A-G128A-Y217Q-T55P-A128S-P129Q, G97A-G128A-Y217Q-N61P-S78N-S101N-V203Y, G97A-G128A-Y217Q-N61E-A144K, G97A-G128A-Y217Q-A134T-P239R, G97A-G128A-Y217Q-S24G-N25G-S53G-S78N-S87T-A88L-S101N-V203Y, G97A-G128A-Y217Q-S24G-N25G-S53G-T55P-N61P-S101N-V203Y, G97A-G128A-Y217Q-N61P-S78N-S87T-A88L-S89G-S101N-V203Y, G97A-G128A-Y217Q-T55P-N240K, G97A-G128A-Y217Q-S24G-N25G-S87T-A88L-S89G-S101N, G97A-G128A-Y217Q-P129Q-S130G-G131S-P239R, G97A-G128S-Y217Q, G97A-G128A-Y217Q-S53G-N61P-S101N, G97A-G128A-Y217Q-I111V-P129Q-G211T, G97A-G128A-Y217Q-S24G-N25G-S53G-S101N-V203Y, G97A-G128A-Y217Q-Q59S-N61P-S87G-A88V-S89A, G97A-G128A-Y217Q-S24G-N25G-S78N-S87T-A88L-S89G-S101N, G97A-G128A-Y217Q-P129Q-S130G-G131S-S162K, G97A-G128A-Y217Q-T55P-P129Q-S130G-G131S, G97A-G128A-Y217Q-T55P-V203Y, G97A-G128A-Y217Q-S87G-A88V-S89A-P129Q-S130G-G131S, G97A-G128A-Y217Q-S24G-N25G-S53G-T55P-N61P-S78N-S87T-A88L-S89G, G97A-G128A-Y217Q-I111V-P129Q-S130G-G131S, G97A-G128A-Y217Q-I111V-A273S, G97A-G128A-Y217Q-N61P-S87T-A88L-S89G, G97A-G128A-Y217Q-T22N-S24A-N61P-S63H, G97A-G128A-Y217Q, G97A-G128A-Y217Q-S53G-S78N-S87T-A88L-S89G-S101N-P129S-V203Y, G97A-G128A-Y217Q-S159K-L267V, G97A-G128A-Y217Q-P40E-S53Y-S78Y-P86S-S87G-A88V, G97A-G128A-Y217Q-S24R-S145D, G97A-G128A-Y217Q-I111V-S159K, G97A-G128A-Y217Q-T55P-P129L, G97A-G128A-Y217Q-Q59S-N61P-V203Y, G97A-G128A-Y217Q-T55P-S78N-S87T-A88L-S89G-S101N-V203Y, G97A-G128A-Y217Q-S24G-N25G-S53G-S78N-S101N, G97A-G128A-Y217Q-S53G-N61P-S78N-S87T-A88L-S89G-S101N-V203Y, G97A-G128A-Y217Q-S89Y, G97A-G128A-Y217Q-S24R-P129V, G97A-G128A-Y217Q-S87G-A88V-S89A-A116N-N117S-N118G-P172H, G97A-G128A-Y217Q-I111V-A134T, G97A-G128A-Y217Q-Q59S-N61P-P129Q-S130G-G131S, G97A-G128A-Y217Q-P5S-S87G-A88V-S89A-A116G-N117R, Y217Q-N61P-A97G-G102A-A128G-P129S, G97A-G128A-Y217Q-S24G-N25G-S53G-N61P-S78N, G97A-G128A-Y217Q-S145D-S159K-N240K-Q275E, G97A-G128A-Y217Q-T55P-A128S-P129D, G97A-G128A-Y217Q-G23A-S24G-N25G-A128S-P129D, G97A-G128A-Y217Q-S24G-N25G-S53G-S78N-S87T-A88L-S89G-V203Y, G97A-G128A-Y217Q-I111V-P239R, G97A-G128A-Y217Q-S87G-A88V-S89A-S162K, G97A-G128A-Y217Q-S87T-A88L-S89G-I115V, G97A-G128A-Y217Q-S24G-N25G-T55P-S78N, G97A-G128A-Y217Q-T55P-A92G, G97A-G128A-Y217Q-S24G-N25G-S53G-S87T-A88L-S89G-V203Y, G97A-G128A-Y217Q-T22N-S24A-T55P, G97A-G128A-Y217Q-S53G-S87T-A88L-S89G-S101N-V203Y, G97A-G128A-Y217Q-S24G-N25G-S53G-T55P-S78N-S87T-A88L-S89G, G97A-G128A-Y217Q-P129Q-S130G-G131S-S159K, G97A-Y217Q-N61P-N62Q-G100N-A128G, G97A-G128A-Y217Q-S24R-S78N-S182P-L267V, G97A-G128A-Y217Q-P239R-A273S, G97A-G128A-Y217Q-S53G-S78N-S87T-A88L-S89G-S101N-V203Y, G97A-G128A-Y217Q-P129Q-S130G-G131S-T242R, G97A-G128A-Y217Q-S3F-S87T-A88L-S89G-G211T,

G97A-G128A-Y217Q-S24G-N25G-L75H-N76G, G97A-G128A-Y217Q-S53G-T55P-N61P-S78N-S87T-A88L-S89G, G97A-G128A-Y217Q-S87T-A88L-S89G-A144K, G97A-G128A-Y217Q-S78N-S87T-A88L-S89G-V203Y, G97A-G128A-Y217Q-Q59S-N61P-A116N-N117S-N118G, G97A-G128A-Y217Q-S87T-A88L-S89G-I111V, G97A-G128A-Y217Q-S24R-S145D-P239R-Q275E, G97A-G128A-Y217Q-S145D-A273S, G97A-G128A-Y217Q-S24G-N25G-K141E-T242R, G97A-G128A-Y217Q-S87T-A88L-S89G-S101N-V203Y, G97A-G128A-Y217Q-A116N-N117S-N118G-P129Q-S130G-G131S, G97A-G128A-Y217Q-S89Y-G211T, G97A-G128A-Y217Q-S87G-A88V-S89A-A116N-N117S-N118G-A144T, G97A-G128A-Y217Q-S24G-N25G-S78N-S87T-A88L-S89G-S101N-V203Y, G97A-G128A-Y217Q-S24G-N25G-P129V, G97A-Y217Q-N61P-A128G-P129S-S130P, G97A-G128A-Y217Q-T55P-N61P-S87T-A88L-S89G-G110C-S130P, G97A-Y217Q-N123G-A128G, G97A-G128A-Y217Q-N61P-N62Q-G100N-G102A-M124I, S78N-G97A-G128A-Y217Q, G97A-S101N-G128A-Y217Q, G97A-G128A-A137V-Y217Q, N61P-G97A-G128A-Y217Q, G97A-G128A-S130P-Y217Q, G97A-Q103N-G128A-Y217Q, S63T-G97A-G128A-Y217Q, G97A-G102A-G128A-Y217Q, G97A-N109D-G128A-Y217Q-S248R, S87R-G97A-G128A-Y217Q, G97A-G128A-S188D-Y217Q, S87D-G97A-G128A-Y217Q-S248R, G97A-G128A-S188D-S248R-Y217Q, G97A-G128A-S248D-Y217Q, S78N-G97A-G128A-Y217Q-L267V, S78N-G97A-G128A-Y217Q-S161P, S78N-G97A-G128A-Y217Q-I115V, S78N-G97A-G128A-Y217Q-A273S, S78N-G97A-G128A-Y217Q-G211T, S78N-G97A-G128A-Y217Q, S78N-G97A-G128A-Y217Q-I111V, S78N-G97A-G128A-Y217Q-V147L, S78N-G97A-G128A-Y217Q-I108V, S78N-G97A-G128A-Y217Q-S89Y, S78N-G97A-G128A-Y217Q-A138T, G97A-G128A-Y217Q-A134T-K213L, G97A-G128A-Y217Q-G23A-S24G-N25G-P129V, G97A-G128A-Y217Q-S24R-P239R, and G97A-G128A-Y217Q-S24R-S87T-A88L-S89G, wherein amino acid positions of the variant are numbered by correspondence with the amino acid sequence of SEQ ID NO:2.

A variant according to the eighth aspect of the invention may have increased proteolytic activity and/or increased cleaning activity compared to the protease having the sequence of SEQ ID NO:2 and/or SEQ ID NO:4 and may be in a mature form. A variant according to the eighth aspect of the invention may comprise an amino acid sequence having at least 80%, 85%, 90%, 91%, 92%, 93%, 94%, 95%, 96%, 97%, 98%, or 99% identity to SEQ ID NO:2 or SEQ ID NO:4, wherein the variant has proteolytic activity and optionally has enhanced proteolytic activity and/or enhanced cleaning activity compared to the protease having the sequence of SEQ ID NO:2 or SEQ ID NO:4.

A variant according to the eighth aspect of the invention may comprise three, four, five, six, seven, eight, nine, 10, 11, 12, 13, 14 or 15 amino acid substitutions at positions selected from the group of consisting of positions 24, 25, 40, 52, 53, 55, 58, 59, 61, 62, 63, 68, 78, 86, 87, 88, 89, 92, 96, 97, 100, 101, 103, 104, 106, 111, 114, 115, 116, 117, 118, 123, 124, 125, 126, 128, 129, 130, 131, 132, 133, 134, 144, 145, 159, 161, 162, 167, 194, 203, 206, 213, 217, 227, 232, 239, 240, 242, 265, 267, and 275. A variant according to the eighth aspect may comprise a total of three, four, five, six, seven, eight, nine, 10, 11, 12, 13, 14 or 15 amino acid substitutions selected from groups (a) and (b): (a) charged amino acid substitutions selected from the group consisting of N61E, A144K, P129E, P239R, P40E, Q103E, Q206E, Q7275E, S145D, S159K, S162K, S24R, S63H, S87D and T242R; and (b) neutral amino acid substitutions selected from the group consisting of A114G, A116N, A133V, A134T, A232T, A88V, A92G, F58G, G100T, G128A, G131S, G97A, I111V, I115V, K213L, K265N, L126A, L267V, L96T, M124V, N117S, N118G, N123G, N240K, N25G, N61P, N62Q, N62R, N62S, P129Q, P129V, P194L, P239V, P52L, P86S, Q59S, S101N, S125A, S130G, S132N, S161P, S24G, S53G, S78N, S87G, S89Y, T55P, V203Y, V227T, V68A, W106F, Y104N, Y167A, and Y217Q. A variant according to the eighth aspect may comprise an amino acid sequence having at least 85%, 90%, 91%, 92%, 93%, 94%, 95%, 96%, 97%, 98%, or 99% sequence identity to SEQ ID NO:2.

In a ninth aspect, the invention provides an isolated or non-naturally occurring protease variant selected from the group of:

(a) a protease variant having proteolytic activity, the variant comprising an amino acid sequence having at least 60%, 70%, 80%, 85%, 90%, 95%, 96%, 97%, or 98% identity to SEQ ID NO:2, and comprising at least one set of amino acid substitution(s) relative to SEQ ID NO:2 selected from groups (i) through (vii):

(i) Q059V-S078N-G097A-I108V-G128A-V147Q-G211A-Y217Q-N252Q, S078N-G097A-I108V-G128A-V147Q-G211A-Y217Q, S078N-G097A-I108V-G128A-V147Q/-G211A-Y217Q-N252Q, S078N-G097A-I108V-G128A-V147Q-Y217Q-N252Q, and S078N-S087E-G097A-M124I-G128A-Y217Q-S224A;

(ii) Q059V-S078N-G097A-I108V-G128A-V147Q-G211A-Y217Q-N252Q, S078N-G097A-I108V-G128A-V147Q-G211A-Y217Q, S078N-G097A-I108V-G128A-V147Q-G211A-Y217Q-N252Q, S078N-G097A-I108V-G128A-V147Q-Y217Q-N252Q, and S078N-S087E-G097A-M124I-G128A-Y217Q-S224A;

(iii) G097A-M124V-Y167A-Y217Q, V068A-Y167A-Y217Q, G097A-I111V-M124V-Y167A, I111V-M124V-Y167A-Y217Q, V068A-I111V-Y167A-Y217Q, G097A-I111V-M124V-Y167A-Y217Q, and P052L-V068A-I111V;

(iv) G097A-N123A-Y217Q, G097A-N123V-Y217Q, N061P-G102A-G128S-Y217Q, N061P-S101N-G102A-G128S-Y217Q, Y217Q, S078N-G097A-I111V-N123Q-Y217Q, and G102A-N123Q-Y217Q;

(v) G097A-N123A-Y217Q, G097A-N123V-Y217Q, N061P-N062Q-G097A-G100D-Y217Q, N061P-S101N-G102A-G128S-Y217Q, Y217Q, N061P-G102A-G128S-Y217Q, S078N-G097A-I111V-N123Q-Y217Q, and G102A-N123Q-Y217Q;

(vi) N061P-N062Q-G097A-G100N-Y217Q, N061P-G097A-M124I-Y217Q, G102A-N123Q-Y217Q, S024G-N025G-S053G-N061P-G097A-S101N-N123Q-Y217Q, S053G-N061P-G097A-S101N-N123Q-Y217Q, N061P-G097A-S101N-N123Q-Y217Q, N061P-N062Q-G097A-G100Q-P210S-Y217Q, S053G-N061P-G102A-P129S-P210S-Y217Q, G097A-I111V-M124V-P210S-Y217Q, G097A-N123Q-P210S-Y217Q, N061P-G097A-N123Q-Y217Q, S024G-N025G-S053G-N061P-G097A-S101N-M124I-Y217Q, S053G-N061P-G097A-S101N-M124I-Y217Q, S053G-N061P-G097A-M124I-Y217Q, N061P-S078N-G097A-I111V-M124I-Y217Q, N061P-G097A-M124V-Y217Q, N061P-N062Q-G100N-G102A-Y217Q, N061P-N062Q-G097A-G100Q-S101N-Y217Q, S024G-N025G-S053G-N061P-N062Q-G097A-G100N-S101N-Y217Q, S078N-G097A-I111V-N123Q-Y217Q, S053G-N061P-N062Q-G097A-G100N-S101N-Y217Q, N061P-N062Q-G097A-G100N-S101N-Y217Q, N061P-N062Q-S078N-G097A-G100N-I111V-Y217Q, N061P-N062Q-G097A-G100D-Y217Q, N061P-N062Q-G097A-G100Q-Y217Q, N061P-S101N-G102A-G128S-Y217Q, N061P-

G102A-G128S-Y217Q, S024G-N025G-S053G-N061P-S101N-G102A-P129S-Y217Q, S053G-N061P-S101N-G102A-P129S-Y217Q, N061P-S078N-G102A-I111V-P129S-Y217Q, G097A-N123V-Y217Q, S053G-N061P-G102A-P129S-Y217Q, S024G-N025G-S053G-N061P-N062Q-G097A-S101N-I111V-Y217Q, S053G-N061P-N062Q-G097A-S101N-I111V-Y217Q, N061P-N062Q-G097A-S101N-I111V-Y217Q, N061P-N062Q-G097A-I111V-Y217Q, N062Q-S078N-G097A-I111V-Y217Q, N062Q-G097A-I111V-Y217Q, S024G-N025G-S053G-N061P-G097A-S101N-I111V-M124V-Y217Q, S053G-N061P-G097A-S101N-I111V-M124V-Y217Q, N061P-G097A-S101N-I111V-M124V-Y217Q, G097A-N123Q-Y217Q, N061P-G097A-I111V-M124V-Y217Q, S078N-G097A-I111V-M124V-Y217Q, G097A-I111V-M124I-Y217Q, S053G-S078N-G097A-I111V-G128S-Y217Q, S078N-G097A-G128S-Y217Q, S053G-N061P-G097A-G128S-Y217Q, G097A-N123A-Y217Q. and Y217Q; and (vii) S101N-G128A-Y217Q, S024G-T055P-N061P-G097A-S101N-G128A, S024G-N025G-N061P-S078N-G097A-S101N-G128A, S024G-T055P-N061P-S078N-S101N-G128A-Y217Q, S024G-N025G-S053G-N061P-S078N-G097A-S101N-G128A-Y217Q, S024G-S053G-T055P-N061P-S078N-G097A-S101N-G128A-Y217Q, S053G-N061P-G097A-S101N-G128A-Y217Q-S249N, N025G-S053G-T055P-S078N-G097A-S101N-G128A-Y217Q, S024G-N025G-T055P-G097A-S101N-G128A-Y217Q, S024G-S053G-N061P-G097A-G128A-Y217Q, S024G-N061P-S078N-G097A-S101N-G128A-Y217Q, S024G-S053G-T055P-N061P-S078N-G097A-G128A-Y217Q, S024G-T055P-N061P-G097A-G128A-Y217Q, S024G-S038G-S053G-S078N-S101N-G128A-Y217Q, S053G-S078N-G097A-S101N-G128A-Y217Q, N025G-S078N-G097A-G128A-Y217Q, S024G-N025G-S053G-N061P-G097A-G128A-S130G-Y217Q, and S024G-S053G-S078N-G097A-S101N-G128A-Y217Q; and (b) a protease variant having proteolytic activity, the variant comprising an amino acid sequence having at least 60%, 70%, 80%, 85%, 90%, 95%, 96%, 97%, 98%, or 99% identity to the amino acid sequence of SEQ ID NO:6 and comprising at least one set of amino acid substitution(s) relative to SEQ ID NO:6 selected from groups (i) through (xii):

(i) A001C, A001D, A001E, A001F, A001H, A001K, A001L, A001M, A001N, A001P, A001Q, A001R, A001S, A001T, A001V, A013C, A013S, A015C, A015D, A015E, A015L, A015R, A048C, A048E, A048S, A073N, A073T, A074G, A074S, A085C, A085G, A085S, A085T, A085V, A088M, A088S, A092S, A098G, A114G, A133E, A133P, A133R, A137E, A137H, A137R, A142C, A144D, A144G, A144H, A144K, A144L, A144N, A144R, A152S, A153G, A153S, A153V, A176C, A179G, A187C, A187F, A187G, A187L, A187N, A187P, A187Q, A187S, A187T, A187V, A187W, A200G, A216C, A216H, A216R, A216W, A223S, A228S, A230G, A230S, A230T, A230V, A231V, A232C, A232V, A272E, A272G, A272K, A272P, A272R, A273D, A273G, A273H, A273L, A273P, A273Q, A273R, A273T, A273V, A274H, A274M, A274R, D036E, D036N, D036Q, D036S, D041C, D060G, D099A, D099H, D099Q, D120E, D181A, D181G, D181H, D181T, D197T, D259A, D259G, D259H, D259N, D259P, D259Q, D259S, D259T, E156A, E156C, E156G, E156H, E156L, E156Q, E156S, E156V, E195G, E251C, E251I, E251L, E251Q, E251T, F058Y, F189A, F189G, F189H, F189L, F189R, F189S, F189T, F189W, F189Y, F261C, F261D, F261E, F261K, F261P, G020C, G020E, G020F, G020H, G020L, G020N, G020Q, G020R, G020T, G020Y, G024A, G024D, G024P, G046D, G053A, G053D, G053E, G053F, G053L, G053M, G053Q, G053R, G053S, G053Y, G097K, G097M, G097R, G131C, G131D, G131R, G146A, G157A, G157N, G157P, G157S, G157T, G160A, G160L, G160R, G160V, G166C, G166I, G166L, G166Q, G166V, G166W, G169A, G178A, G211E, G211K, G215C, G215D, G215E, G215H, G215L, G215S, G215T, G215W, G258A, G258D, G258P, G258S, H017I, H039S, H226L, H238N, H238Y, I107L, I011T, I011V, I031C, I031F, I031L, I079E, I079F, I079K, I079L, I079M, I079Q, I079R, I107L, I111M, I175L, I205A, I205C, I205V, I268L, I268M, K012A, K012C, K012E, K012F, K012G, K012H, K012L, K012N, K012S, K012T, K012W, K027A, K027N, K027S, K027T, K043A, K043C, K043D, K043E, K043F, K043G, K043H, K043I, K043L, K043M, K043N, K043P, K043Q, K043R, K043T, K043V, K043W, K043Y, K136G, K136H, K141A, K141G, K141H, K141L, K141M, K141N, K141Q, K141R, K141T, K141V, K141W, K170A, K170C, K170G, K170Q, K170S, K213A, K213G, K213H, K213I, K213L, K213N, K213Q, K213R, K213S, K213T, K213V, K237A, K237H, K237I, K237L, K237N, K237S, K237T, K237V, K256A, K256C, K256D, K256E, K256G, K256H, K256M, K256P, K256Q, K256S, K256T, K256V, K256W, K265G, K265H, K265N, K265S, K265Y, L016E, L042C, L042F, L042M, L042V, L075G, L075H, L075I, L075T, L082A, L082E, L082F, L082I, L082R, L082S, L082T, L090M, L135F, L196M, L209A, L209C, L209E, L209G, L209H, L209R, L209S, L233E, L233G, L233S, L235M, L235R, L235V, L235W, L257C, L257D, L257E, L257G, L257P, L257R, L257W, L267E, L267F, M050L, M050Y, M119C, M119I, M124L, M222A, M222F, M222L, M222S, M222T, N025C, N025E, N025P, N056D, N056S, N061A, N061C, N061D, N061G, N061I, N061K, N061L, N061Q, N061R, N062A, N062C, N062H, N062L, N062Q, N062R, N062S, N062T, N062V, N062Y, N076A, N076D, N076E, N076L, N076M, N076P, N076Q, N076S, N076T, N076V, N078D, N078E, N078F, N078G, N078H, N078K, N078P, N078Q, N078R, N101D, N101F, N101R, N117G, N117R, N117S, N118A, N118D, N118H, N118Q, N118R, N118S, N118T, N184C, N184E, N184P, N184R, N212C, N212D, N212E, N212R, N212W, N218C, N218D, N218E, N218F, N218G, N218M, N218P, N218R, N218T, N218V, N218W, N240A, N240G, N240Q, N240S, N240W, N243C, N243G, N243S, N252D, N252E, N252V, N269C, N269H, P005A, P005D, P005M, P005Q, P005V, P005W, P014A, P014D, P014F, P014K, P014M, P014R, P014V, P040F, P040R, P040W, P057A, P057W, P129E, P129R, P129V, P172E, P172K, P172R, P194E, P194H, P194R, P194W, P201A, P201G, P201T, P210E, P210L, P239A, P239G, P239H, P239K, P239N, P239R, P239T, Q002D, Q002E, Q002G, Q002I, Q002K, Q002L, Q002P, Q002R, Q002V, Q010D, Q010R, Q010W, Q019C, Q019D, Q019E, Q019H, Q019L, Q019P, Q019R, Q059A, Q059C, Q059D, Q059E, Q059L, Q059R, Q059S, Q059T, Q059W, Q103W, Q185D, Q185E, Q185K, Q185R, Q185W, Q206D, Q206G, Q206H, Q206L, Q206V, Q206W, Q217A, Q217C, Q217E, Q217F, Q217G, Q217H, Q217K, Q217L, Q217R, Q217V, Q245A, Q245D, Q245E, Q245H, Q245M, Q245R, Q271A, Q271C, Q271D, Q271E, Q271F, Q271G, Q271L, Q271P, Q271R, Q271T, Q271W, Q271Y, Q275A, Q275F, Q275G, Q275I, Q275L, Q275P, Q275R, R186A, R186H, R186I, R186L, R186M, R186V, R186W, S003D, S003E, S003F, S003K, S003R, S009C, S009E, S009K, S018C, S018D, S018R, S037A, S037D, S037E, S037G, S037H, S037K, S037L, S037R, S037S, S037Y, S038D, S038M, S038P, S038R, S038Y, S049C, S049I, S063A, S063C, S063D, S063F, S063L, S063M, S063R, S063Y, S087C, S087D, S087K, S087L, S087M, S087N, S087R, S087Y, S089A, S089C, S089D, S089E, S089F, S089G, S089H, S089I, S089K,

S089P, S089R, S089V, S089Y, S105T, S125A, S130C, S130D, S130E, S130K, S130R, S130W, S145D, S145G, S145L, S145R, S145T, S159C, S159D, S159L, S159P, S159W, S161C, S161E, S161R, S162C, S162E, S162W, S163A, S173T, S173V, S182C, S182E, S182R, S183C, S183D, S183P, S183R, S188C, S188D, S188E, S188F, S188K, S188L, S188P, S188R, S188W, S190A, S190C, S190G, S190T, S191G, S204E, S204G, S204R, S204Y, S207G, S224G, S224T, S236C, S236D, S236E, S236G, S248C, S248D, S248E, S248H, S248R, S249E, S249L, S249R, S260A, S260C, S260E, S260G, S260K, S260Q, S260R, S260V, S260Y, T022L, T022P, T055C, T055D, T055E, T055I, T055K, T055M, T055R, T055S, T055V, T055W, T055Y, T071A, T158A, T158D, T158E, T158G, T158L, T158P, T158Q, T158R, T158V, T158Y, T164A, T164G, T164K, T164Q, T164R, T208S, T220A, T242D, T242G, T244D, T244E, T244R, T253E, T253R, T253Y, T254G, T255C, T255D, T255E, T255K, T255R, V004D, V004E, V004T, V026A, V028I, V028L, V030I, V044A, V044C, V044P, V044T, V045C, V045D, V045E, V045G, V045I, V045N, V045R, V045T, V051H, V072L, V081A, V081G, V081H, V081R, V081S, V084I, V084M, V095A, V095C, V143A, V143C, V143E, V143F, V143G, V143H, V143Q, V143T, V143W, V147A, V147Q, V147S, V148I, V148L, V149C, V149I, V149L, V165C, V165L, V180A, V180C, V180M, V180S, V192C, V192F, V192G, V192I, V192Q, V192Y, V203A, V203C, V203D, V203E, V203G, V203K, V203M, V203R, V203S, V270C, V270G, V270L, V270P, W241F, W241L, Y006A, Y006C, Y006D, Y006E, Y006M, Y006N, Y006R, Y006S, Y021C, Y091W, Y104T, Y104V, Y104W, Y214H, Y214Q, Y262C, Y262D, Y262E, Y262H, Y262I, Y262R, and Y262V;

(ii) A001C, A001E, A001P, A015C, A015E, A048C, A048E, A073T, A085C, A085G, A088I, A088M, A114G, A128H, A137R, A142C, A187C, A187F, A187L, A187N, A187P, A187W, A216C, A216H, A230G, A230S, A273D, A273H, A273P, A273Q, A273R, A273T, A274H, D036N, D036Q, D036S, D041C, D041N, D099A, D099H, D099N, D099Q, D099S, D197T, D259H, E156C, E156G, E156H, E156L, E156Q, F058G, F189A, F189G, F189H, F189L, F189R, F189S, F189T, F261C, F261D, F261E, G046D, G053E, G053L, G053M, G053Q, G053R, G131C, G131D, G146A, G157N, G157P, G157T, G160V, G178A, G215C, G215L, G258A, G258P, H039A, H067T, H238T, I011L, I031F, I079E, I111M, I175L, I268M, K012A, K012C, K012E, K012F, K012G, K012H, K012L, K012N, K012W, K027N, K027S, K027T, K043C, K043D, K043G, K043L, K043R, K043W, K136E, K136G, K141G, K141L, K141M, K141N, K141R, K170C, K170Q, K213V, K256D, K265G, K265N, K265Q, K265S, K265Y, L042C, L042F, L075G, L075V, L082A, L082E, L082F, L082H, L082R, L082S, L090M, L090T, L126W, L233E, L233G, L233S, L235V, L257D, L257E, L257G, L257P, L257R, L257W, M050L, M222A, M222F, M222L, M222S, M222T, N025R, N056S, N062C, N062H, N062L, N062Q, N062R, N062T, N062Y, N076D, N076P, N078D, N078E, N078F, N078R, N078V, N117G, N118L, N184P, N269C, N269H, N269Q, P005V, P005W, P014K, P057A, P057W, P086F, P129V, P201T, P225G, P225S, P239A, P239G, P239H, P239N, P239T, Q002D, Q002I, Q002K, Q002L, Q002P, Q002R, Q002V, Q010W, Q019L, Q019P, Q059C, Q059D, Q059E, Q059W, Q185W, Q217C, Q245A, Q245H, Q271C, Q271D, Q271E, Q271L, Q271W, Q275A, Q275G, R186M, S009C, S009L, S018C, S018D, S037E, S037H, S037K, S037L, S037Y, S038P, S038Y, S049C, S049N, S063C, S063D, S063F, S063L, S063Y, S087C, S087K, S087L, S087N, S087R, S087Y, S089C, S089K, S089L, S089N, S089R, S089Y, S089D, S089E, S089F, S089G, S089P, S089W, S105T, S125A, S130C, S145D, S159D, S159P, S163A, S173V, S182P, S183P, S190A, S190G, S191G, S204E, S224G, S248E, S248H, S249E, S260V, S260Y, T022P, T055E, T055M, T055R, T055V, T158D, T158E, T164A, T164G, T164K, T164Q, T164R, T220A, T242G, T242P, T253E, T255C, T255G, V004D, V004T, V044A, V044L, V044P, V044T, V045C, V045G, V045I, V045K, V045L, V045N, V045R, V045T, V045V, V051H, V081A, V081G, V081H, V081R, V084S, V143G, V147A, V148L, V165C, V180S, V203D, V203G, V203S, V270C, V270G, V270P, V270S, W241L, Y104T, Y214H, Y214Q, Y262D, Y262E, Y262G, Y262H, Y262L, Y262N, Y263G, and Y263W;

(iii) A001E, A001E-A088T, A001E-A116T, A001E-A128S, A001E-A128S-G131H-N243V, A001E-G024E, A001E-G131H, A001E-G131H-G169A-N243V, A001E-G169A, A001E-K043Y, A001E-K256R, A001E-L257G, A001E-N076D, A001E-N076D-N109G-A128S, A001E-N109G, A001E-N218S, A001E-N243V, A001E-Q103H, A001E-Q206D, A001E-S033T, A001E-S033T-N109G-N218S, A001E-S033T-N109G-N243V, A001E-S063G, A001E-S162G, A001E-S248N, A001E-S249A, A001E-T158S, A088T-A128S, A088T-G169A, A088T-N218S, A088T-Q206D, A116T-G169A, A116T-N218S, A116T-Q206D, A128S, A128S-G131H, A128S-G169A, A128S-N218S, A128S-N243V, A128S-Q206D, G024E, G024E-A088T, G024E-A128S, G024E-G131H, G024E-K043Y, G024E-N076D, G024E-N218S, G024E-Q103H, G024E-Q206D, G024E-S033T, G024E-S063G, G024E-S162G, G024E-S248N, G024E-S249A, G131H-G169A, G131H-N218S, G131H-N243V, G131H-Q206D, G169A, G169A-K256R, G169A-L257G, G169A-N218S, G169A-N243V, G169A-Q206D, G169A-S248N, G169A-S249A, K043Y, K043Y-A116T, K043Y-A128S, K043Y-G131H, K043Y-G169A, K043Y-L257G, K043Y-N076D, K043Y-N109G, K043Y-N218S, K043Y-Q103H, K043Y-Q206D, K043Y-S063G, K043Y-S162G, K043Y-S248N, K043Y-S249A, K043Y-T158S, N076D, N076D-A088T, N076D-A116T, N076D-A128S, N076D-G131H, N076D-G169A, N076D-N218S, N076D-N243V, N076D-Q103H, N076D-Q206D, N076D-S162G, N076D-S248N, N076D-S249A, N109G-G169A, N109G-Q206D, N109G-S248N, N218S, N218S-K256R, N218S-L257G, N218S-S248N, N218S-S249A, P040E-N109G-A128S-G131H, Q103H, Q103H-G169A, Q103H-Q206D, Q206D, Q206D-K256R, Q206D-L257G, Q206D-N218S, Q206D-N243V, Q206D-S248N, Q206D-S249A, S018T-Y021N-S033T-N109G-A128S-N243V-S248N-K256R, S033T, S033T-A088T, S033T-A116T, S033T-A128S, S033T-A128S-G131H-N243P, S033T-G131H, S033T-G169A, S033T-K043Y, S033T-K256R, S033T-L257G, S033T-N076D, S033T-N076D-A128S-N218S, S033T-N076D-N109G-A128S-N218S-N243V-S248N-K256R, S033T-N109G, S033T-N109G-A128S-N243V-S248N-K256R, S033T-N218S, S033T-P040E-Q103H-N109G, S033T-Q103H-A128S-G131H, S033T-Q206D, S033T-S063G, S033T-S063G-Q103H-N109Q-A128S-G131H-G169A-N243P, S033T-S063G-Q103H-N109Q-A128S-G131H-G169A-N243V, S033T-S162G, S033T-S248N, S033T-S249A, S063G-A116T, S063G-G131H, S063G-G169A, S063G-N109G-A128S-G131H, S063G-N218S, S063G-N243V, S063G-Q206D, S063G-S249A, S162G-G169A, S162G-N218S, S162G-Q206D, S162G-S249A, S248N-K256R, S248N-S249A, S249A-K256R, S249A-L257G, T158S-G169A, T158S-K256R, T158S-Q206D, and T158S-S162G;

(iv) A001E, A001E-A088T, A001E-A116T, A001E-A128S-G131H-N243V, A001E-G024E, A001E-G131H-G169A-N243V, A001E-G169A, A001E-K043Y, A001E-

L257G, A001E-N076D, A001E-N076D-N109G-A128S, A001E-N109G, A001E-Q103H, A001E-Q206D, A001E-S033T-N109G-N218S, A001E-S033T-N109G-N243V, A001E-S248N, A001E-T158S, A088T-G169A, A088T-Q206D, A116T-G169A, A116T-N218S, A116T-Q206D, A128S-G131H, A128S-N243V-S248N-K256R, A128S-Q206D, G024E-K043Y, G024E-N076D, G024E-Q206D, G131H-G169A, G131H-N218S, G131H-N243V-K256R, G131H-Q206D, G131H-S248N, G169A-K256R, G169A-N218S, G169A-N243V, G169A-Q206D, G169A-S249A, K043Y-G169A, K043Y-N076D, K043Y-N218S, K043Y-Q206D, N061P-N109G-G131H-N243V, N061P-N109G-N243V, N061S-N109G-A128S-N243V-S248N-K256R-S260P, N061S-N109G-N243V, N076D, N076D-G131H, N076D-L257G, N076D-N109G, N076D-Q103H, N076D-Q206D, N076D-S249A, N109G-A128S-N243V-S248N, N109G-A128S-N243V-S248N-K256R, N109G-A128S-S248N-K256R, N109G-G169A, N109G-N243P-S248A-K256R, N109G-N243P-S248N-K256R, N109G-N243V-K256R, N109G-N243V-S248A-K256R, N109G-N243V-S248N, N109G-N243V-S248N-K256R, N109G-S248N-K256R, N218S-S249A, N243V-S248N-K256R, P040E-N109G-A128S-G131H, Q103H-Q206D, Q206D, Q206D-K256R, Q206D-L257G, Q206D-N218S, Q206D-S248N, Q206D-S249A, S009T-N109G-A128S-K141R-N243V-S248N-K256R, S009T-S018T-Y021N-A128S-K141R-N243V, S018T-Y021N-A128S-N243V, S018T-Y021N-N061S-A128S-N243V-S260P, S018T-Y021N-N061S-N109G-A128S-S260P, S018T-Y021N-S033T-N109G-A128S-N243V-S248N-K256R, S033T, S033T-A128S-G131H-N243P, S033T-A128S-G131H-N243V, S033T-G169A, S033T-N076D-A128S-N218S, S033T-N076D-N109G-A128S-N218S-N243V-S248N-K256R, S033T-N109G-A128S-N243P-S248N-K256R, S033T-N109G-A128S-N243V-S248N-K256R, S033T-P040E-Q103H-N109G, S033T-Q103H-A128S-G131H, S033T-S063G-Q103H-N109Q-A128S-G131H-G169A-N243P, S033T-S063G-Q103H-N109Q-A128S-G131H-G169A-N243V, S063G-G131H, S063G-G169A, S063G-N109G-A128S-G131H, S063G-Q206D, S162G-Q206D, T158S-Q206D, and T158S-S162G;

(v) A001E-A088T, A001E-A128S, A001E-A128S-G131H-N243V, A001E-G024E, A001E-G024E-S204E-Q206D, A001E-G131H-G169A-N243V, A001E-K043Y, A001E-N076D, A001E-N076D-N109G-A128S, A001E-N218S, A001E-N243V, A001E-Q103H, A001E-Q206D, A001E-S033T, A001E-S033T-N109G-N218S, A001E-S162G, A116T-Q206D, A128S-N243V-S248N-K256R, A128S-Q206D, G024E-Q206D, G131H-Q206D, K043Y-G131H, K043Y-Q103H, K043Y-Q206D, K043Y-S162G, N061S-N109G-A128S-N243V-S260P, N076D-A128S, N076D-Q206D, N076D-S162G, N076D-S248N, N109G-A128S-S248N-K256R, N109G-A128S-T158S-N243V-S248N-K256R, N109G-N243P-S248N-K256R, N109G-Q206D, N243V-S248N-K256R, P040E-N109G-A128S-G131H, Q103H-Q206D, Q206D-K256R, Q206D-N243V, Q206D-S248N, Q206D-S249A, S018T-Y021N-N061S-A128S-N243V-S260P, S018T-Y021N-N061S-N109G-A128S-S260P, S033T-A128S-G131H-N243P, S033T-N076D-A128S-N218S, S033T-N076D-N109G-A128S-N218S-N243V-S248N-K256R, S033T-P040E-Q103H-N109G, S033T-S063G-Q103H-N109Q-A128S-G131H-G169A-N243P, S063G-Q206D, S162G-Q206D, and T158S-Q206D;

(vi) A001E, A001E-A128S, A001E-G024E, A001E-G131H, A001E-G169A, A001E-K043Y, A001E-K256R, A001E-L257G, A001E-N076D, A001E-N109G, A001E-N218S, A001E-N243V, A001E-Q103H, A001E-Q206D, A001E-S033T, A001E-S063G, A001E-S162G, A001E-S248N, A001E-S249A, A001E-T158S, A088T-A116T, A088T-G131H, A088T-N109G, A088T-N218S, A088T-Q206D, A116T-A128S, A116T-G131H, A116T-Q206D, A116T-S248N, A128S, A128S-G131H, A128S-Q206D, G024E, G024E-N076D, G024E-N109G, G024E-Q206D, G131H, G131H-L257G, G131H-Q206D, G169A-K256R, G169A-Q206D, K043Y, K043Y-A088T, K043Y-A116T, K043Y-A128S, K043Y-G131H, K043Y-G169A, K043Y-K256R, K043Y-L257G, K043Y-N076D, K043Y-N109G, K043Y-N218S, K043Y-N243V, K043Y-Q103H, K043Y-S063G, K043Y-S162G, K043Y-S248N, K043Y-S249A, K043Y-T158S, N076D-A088T, N076D-A116T, N076D-A128S, N076D-G131H, N076D-G169A, N076D-N109G, N076D-N218S, N076D-N243V, N076D-Q103H, N076D-Q206D, N076D-S248N, N076D-T158S, N109G, N109G-G169A, N109G-Q206D, N109G-S162G, N109G-T158S, N218S-S248N, Q103H, Q103H-A128S, Q103H-G131H, Q103H-Q206D, Q103H-S248N, Q103H-S249A, Q103H-T158S, Q206D, Q206D-K256R, Q206D-L257G, Q206D-N218S, Q206D-N243V, Q206D-S248N, Q206D-S249A, S033T, S033T-K256R, S033T-S063G, S033T-S249A, S063G-A088T, S063G-G131H, S063G-G169A, S063G-N076D, S063G-N109G, S063G-N218S, S063G-Q103H, S063G-Q206D, S162G-Q206D, S162G-S249A, S248N-S249A, S249A-K256R, T158S-Q206D, and T158S-S249A;

(vii) G131H-S162G, G131H-S248N, G131H-T158S, K043Y-G131H, K043Y-S162G, Q103H-A128S, Q103H-N218S, S033T-Q103H, S063G-A088T, S063G-G131H, S063G-S248N, and T158S-S162G;

(viii) A015S-A088T-N109G-G131H-T158S-N218S-S248N, A088T-A098S-G131H-S248N-K256R-L257G, A088T-A098S-N218S-K256R, A088T-A116T-G131H-G146C, A088T-A116T-G131H-K256R, A088T-A116T-G131H-K256R-L257G-L267M, A088T-A116T-G131H-N218S-N243V-K256R, A088T-A116T-G131H-N218S-N243V-K256R-L257G, A088T-A116T-G131H-N218S-N243V-K256R-L257G, A088T-A116T-G131H-N218S-N243V-S248N, A088T-A116T-G131H-N218S-S248N, A088T-A116T-G131H-N218S-S248N-K256R, A088T-A116T-G131H-N218S-S248N-K256R, A088T-A116T-G131H-N243V, A088T-A116T-G131H-S248N, A088T-A116T-G131H-S248N-L257G, A088T-A116T-G131H-S248N-L257G, A088T-A116T-G131H-T158S-L257G, A088T-A116T-G131H-T158S-N218S, A088T-A116T-G131H-T158S-N218S-K256R-L257G, A088T-A116T-G131H-T158S-N218S-L257G, A088T-A116T-G131H-T158S-N218S-N243V-S248N-K256R, A088T-A116T-G131H-T158S-N218S-N243V-S248N-K256R-L257G, A088T-A116T-G131H-T158S-N218S-N243V-S248N-L257G, A088T-A116T-G131H-T158S-N218S-N243V-S248N-L257G, A088T-A116T-G131H-T158S-N218S-S248N, A088T-A116T-G131H-T158S-N218S-S248N-K256R, A088T-A116T-K256R-L257G, A088T-A116T-N218S, A088T-A116T-N218S-I268V, A088T-A116T-N218S-K256R, A088T-A116T-N218S-L257G, A088T-A116T-N218S-N243V-Q271R, A088T-A116T-N218S-N243V-S248N-K256R, A088T-A116T-N218S-N243V-S248N-K256R-Q275R, A088T-A116T-N218S-S248N, A088T-A116T-N218S-S248N-K256R, A088T-A116T-N243V-S248N-K256R, A088T-A116T-T158S, A088T-A116T-T158S-K256R, A088T-A116T-T158S-K256R-L257G, A088T-A116T-T158S-N218S-K256R, A088T-A116T-T158S-N218S-N243V-L257G, A088T-T158S-N218S-N243V-S248N-E251K-K256R-L257G, A088T-A116T-T158S-N218S-N243V-S248N-K256R, A088T-A116T-T158S-N218S-N243V-S248N-L257G, A088T-A116T-T158S-N218S-S248N, A088T-A116T-T158S-N218S-S248N-K256R, A088T-A116T-T158S-N218S-S248N-K256R-L257G, A088T-A116T-T158S-N218S-S248N-L257G, A088T-A116T-T158S-N243V, A088T-A116T-T158S-N243V-K256R-L257G, A088T-A116T-T158S-S248N-K256R-L257G, A088T-A116T-T158S-S248N-L257G, A088T-A138E-N218S-N243V-K256R, A088T-G131H, A088T-G131H, A088T-G131H-K141E-N218S-N243V-S248N-L257G, A088T-G131H-K256R, A088T-G131H-N218S-K237R-K256R-L257G, A088T-G131H-N218S-K256R, A088T-G131H-N218S-K256R, A088T-G131H-N218S-K256R-L257G, A088T-G131H-N218S-N243V-K256R-L257G, A088T-G131H-N218S-N243V-L257G, A088T-G131H-N218S-N243V-L257G, A088T-G131H-N218S-N243V-S248N, A088T-G131H-N218S-N243V-S248N-K256R, A088T-G131H-N218S-N243V-S248N-K256R, A088T-G131H-N218S-N243V-S248N-K256R-L257G, A088T-G131H-N218S-N243V-S248N-K256R-L257G, A088T-G131H-N218S-N243V-S248N-L257G, A088T-G131H-N218S-S248N, A088T-G131H-N218S-S248N-K256R, A088T-G131H-N218S-S248N-K256R, A088T-G131H-N243V, A088T-G131H-N243V-K256R, A088T-G131H-N243V-K256R-L257G, A088T-G131H-N243V-S248N, A088T-G131H-N243V-S248N, A088T-G131H-N243V-S248N-K256R, A088T-G131H-S248N, A088T-G131H-S248N-K256R, A088T-G131H-T158S-N218S-I234T-S248N-L257G, A088T-G131H-T158S-N218S-K256R-L257G, A088T-G131H-T158S-N218S-L257G, A088T-G131H-T158S-N218S-N243V, A088T-G131H-T158S-N218S-N243V-K256R-L257G, A088T-G131H-T158S-N218S-N243V-S248N-K256R, A088T-G131H-T158S-N218S-N243V-S248N-K256R, A088T-G131H-T158S-N218S-N243V-S248N-K256R-L257G, A088T-G131H-T158S-N218S-N243V-S248N-K256R-L257G, A088T-G131H-T158S-N218S-N243V-S248N-L257G, A088T-G131H-T158S-N218S-S248N-K256R, A088T-G131H-T158S-N218S-S248N-K256R-L257G, A088T-G131H-T158S-S248N-K256R, A088T-G131H-T158S-S248N-K256R-L257G, A088T-G131H-T158S-S248N-K256R-L257G, A088T-G131H-V149L-T158S-N243V-S248N-K256R-L257G, A088T-I107T-N109G-G131H-N218S-A223G-S248N-K256R, A088T-I107T-N109G-G131H-N218S-S248N-K256R, A088T-I108T-N109G-G131H-T158S-N218S-S248N-K256R-L257G, A088T-K213N-N243V-S248N-K256R, A088T-K256R-L257G, A088T-L257G, A088T-N109G-A116T-G131H-A232S-N243V-K256R, A088T-N109G-A116T-G131H-D140G-S248N-L257G, A088T-N109G-A116T-G131H-D140G-T158S-N218S-N243V-K256R, A088T-N109G-A116T-G131H-K141E-N218S, A088T-N109G-A116T-G131H-N218S-L257G, A088T-N109G-A116T-G131H-N218S-N243V-K256R, A088T-N109G-A116T-G131H-N218S-N243V-S248N-K256R, A088T-N109G-A116T-G131H-N218S-N243V-S248N-K256R, A088T-N109G-A116T-G131H-N218S-N243V-S248N-K256R-L257G, A088T-N109G-A116T-G131H-N218S-N243V-S248N-K256R-L257G, A088T-N109G-A116T-G131H-N218S-N243V-S248N-N269D, A088T-N109G-A116T-G131H-N218S-N243V-S248N-Q275R, A088T-N109G-A116T-G131H-N218S-S248N-K256R-L257G, A088T-N109G-A116T-G131H-N243V-S248N, A088T-N109G-A116T-G131H-T158S, A088T-N109G-A116T-G131H-T158S-N218S-L257G-I268V, A088T-N109G-A116T-G131H-T158S-N218S-N243F-S248N, A088T-N109G-A116T-G131H-T158S-N218S-N243V-K256R, A088T-N109G-A116T-G131H-T158S-N218S-N243V-K256R-L257G, A088T-N109G-A116T-G131H-T158S-N218S-N243V-S248N, A088T-N109G-A116T-G131H-T158S-N218S-N243V-S248N, A088T-N109G-A116T-G131H-T158S-N218S-N243V-S248N-L257G, A088T-N109G-A116T-G131H-T158S-N218S-S248N-L257G, A088T-N109G-A116T-G131H-T158S-N218S-S248N-L257G, A088T-N109G-A116T-G131H-T158S-N243V-S248N-K256R-I268V, A088T-N109G-A116T-G131H-T158S-N243V-S248N-L257G, A088T-N109G-A116T-G131H-T158S-S248N, A088T-N109G-A116T-G131H-T158S-S248N, A088T-N109G-A116T-G131H-V149A-N218S-S248N-K256R-L257G, A088T-N109G-A116T-G131H-W241L-S248N-K256R-L257G, A088T-N109G-A116T-K256R, A088T-N109G-A116T-M124I-G131H-T158S-N218S-S248N-L257G, A088T-N109G-A116T-N218S-K256R-L257G, A088T-N109G-A116T-N218S-N243V-S248N-K256R, A088T-N109G-A116T-N218S-N243V-S248N-K256R-L257G, A088T-N109G-A116T-N218S-S248N, A088T-N109G-A116T-T158S-K256R-L257G, A088T-N109G-A116T-T158S-N218S, A088T-N109G-A116T-T158S-N218S-K256R-L257G, A088T-N109G-A116T-T158S-N218S-N243V-L257G, A088T-N109G-A116T-T158S-N218S-N243V-S248N-L257G, A088T-N109G-A116T-T158S-N243V-S248N, A088T-N109G-A116T-T158S-N243V-S248N-K256R, A088T-N109G-A116T-V148A-N218S-N243V, A088T-N109G-D140G-N243V, A088T-N109G-G131H-A138V-T158S-N218S-N243V-S248N-L257G, A088T-N109G-G131H-D140G-T158S-N243V-S248N-K256R, A088T-N109G-G131H-K141E-T158S-N218S-K256R, A088T-N109G-G131H-K256R-L257G, A088T-N109G-G131H-N218S-N243V, A088T-N109G-G131H-N218S-N243V-S248N, A088T-N109G-G131H-N218S-N243V-S248N-L257G, A088T-N109G-G131H-N218S-S248N, A088T-N109G-G131H-N218S-S248N-K256R-L257G, A088T-N109G-G131H-N218S-S248N-K256R-L257G-Q275R, A088T-N109G-G131H-N218S-S248N-K256R-Q271R, A088T-N109G-G131H-N218S-S248N-L257G, A088T-N109G-G131H-N243V-S248N, A088T-N109G-G131H-N243V-S248N-K256R-L257G, A088T-N109G-G131H-T158S, A088T-N109G-G131H-T158S-K256R, A088T-N109G-G131H-T158S-L233S-N243V-S248N, A088T-N109G-G131H-T158S-N218S-N243V-K256R, A088T-N109G-G131H-T158S-N218S-N243V-K256R-L257G, A088T-N109G-G131H-T158S-N218S-N243V-S248N-K256R-L257G, A088T-N109G-G131H-T158S-N218S-N243V-S248N-K256R-L257G, A088T-N109G-G131H-T158S-N218S-N243V-S248N-L257G, A088T-N109G-G131H-T158S-N218S-S248N-K256R, A088T-N109G-G131H-T158S-N218S-S248N-K256R, A088T-N109G-G131H-T158S-N243V-S248N-K256R, A088T-N109G-G131H-T158S-S248N-K256R, A088T-N109G-G131H-T158S-S248N-K256R-L257G, A088T-N109G-G131H-V149A-K256R-L257G, A088T-N109G-G131H-V149L-T158S-K256R-L257G, A088T-N109G-N218S-K256R-L257G, A088T-N109G-N218S-N243V-K256R, A088T-N109G-N218S-N243V-L257G, A088T-N109G-N218S-N243V-S248N, A088T-N109G-N218S-N243V-S248N-K256R-L257G, A088T-N109G-N218S-S248N-K256R, A088T-N109G-N218S-S248N-T255K-K256R-L257G, A088T-N109G-N243V-K256R, A088T-N109G-N243V-S248N-K256R, A088T-N109G-S248N-K256R-L257G, A088T-N109G-T158S, A088T-N109G-T158S-K256R-L257G, A088T-N109G-T158S-N218S, A088T-N109G-T158S-N218S-K256R-L257G-Q271K, A088T-N109G-T158S-N218S-L257G, A088T-N109G-T158S-N218S-N243V-K256R, A088T-N109G-T158S-N218S-N243V-

K256R-L257G, A088T-N109G-T158S-N218S-N243V-S248N-K256R, A088T-N109G-T158S-N218S-N243V-S248N-L257G, A088T-N109G-T158S-N218S-S248N, A088T-N109G-T158S-S248N, A088T-N109G-T158S-S248N-K256R, A088T-N109G-W241R-S248N-K256R, A088T-N218S-N243V-K256R, A088T-N218S-N243V-L257G, A088T-N218S-N243V-S248N, A088T-N218S-N243V-S248N-K256R, A088T-N218S-N243V-S248N-K256R, A088T-N218S-S248N, A088T-N218S-S248N-L257G, A088T-N218S-S248N-L257G-Q271R, A088T-S248N-K256R-L257G, A088T-T158S-K256R, A088T-T158S-N218S-K256R-L257G, A088T-T158S-N218S-L257G, A088T-T158S-N218S-N243V-K256R, A088T-T158S-N218S-N243V-K256R, A088T-T158S-N218S-N243V-L257G, A088T-T158S-N218S-N243V-S248N, A088T-T158S-N218S-N243V-S248N-K256R, A088T-T158S-N218S-N243V-S248N-K256R-L257G, A088T-T158S-N218S-N243V-S248N-K256R-L257G, A088T-T158S-N218S-N243V-S248N-L257G, A088T-T158S-N218S-Q245K-S248N-K256R, A088T-T158S-N218S-S248N, A088T-T158S-N218S-S248N-K256R, A088T-T158S-N218S-S248N-K256R, A088T-T158S-N218S-S248N-L257G, A088T-T158S-N218S-S248N-L257G-Q275K, A088T-T158S-N243V, A088T-T158S-N243V-K256R, A088T-T158S-N243V-S248N, A088T-T158S-S248N-K256R-L257G, A088T-T158S-S248N-L257G, A088T-T158S-V203I-N218S-K256R-L257G, A088T-V147I-N218S-N243V-K256R-L257G, A088T-Y104H-A116T-G131H-N218S-N243V, A116T-D140G-T158S-N218S-N243V-S248N, A116T-G131H-K141E-N218S-N243V-S248N-L257G, A116T-G131H-L257G, A116T-G131H-N218S-N243V, A116T-G131H-N218S-N243V-K256R, A116T-G131H-N218S-N243V-K256R-L257G, A116T-G131H-N218S-N243V-S248N-K256R, A116T-G131H-N218S-N243V-S248N-K256R-L257G, A116T-G131H-N218S-S248N, A116T-G131H-N218S-S248N-K256R, A116T-G131H-N218S-W241R-N243V-S248N-K256R-L257G, A116T-G131H-N243V-S248N-K256R, A116T-G131H-T158S-N218S-L257G, A116T-G131H-T158S-N218S-N243V-S248N, A116T-G131H-T158S-N218S-S248N, A116T-G131H-T158S-N218S-S248N-L257G-N269D, A116T-G131H-T158S-N218S-S248N-Q271R, A116T-G131H-T158S-N243V-K256R, A116T-G131H-T158S-N243V-S248N, A116T-G131H-V139I-N218S-N243V-S248N, A116T-G131H-V150A-T158S-N243V-S248N-K256R-L257G, A116T-G157E-T158S-N243V-S248N-K256R, A116T-K141E-N218S-N243V-S248N-K256R-L257G, A116T-K256R, A116T-N218S-N243V-S248N, A116T-N218T-N243V-S248N, A116T-N243V-K256R-L257G, A116T-S248N-K256R, A116T-T158S-N218S, A116T-T158S-N218S-K256R, A116T-T158S-N218S-K256R-L257G, A116T-T158S-N218S-N243V-L257G, A116T-T158S-N218S-N243V-S248N, A116T-T158S-N218S-S248N-L257G, G024S-G053S-N078S-G097A-N101S, G053S-A088T-N109G-A116T-G131H-T158S-G169S-N218S-S248N-K256R-L257G, G065D-A088T-G131H-N243V-S248N, G131H-K141R-T158S-N218S-K256R, G131H-K256R, G131H-N218S-K256R-L257G, G131H-N218S-L257G, G131H-N218S-N243V-S248N-L257G, G131H-N218S-S248N, G131H-N218S-S248N-K256R, G131H-N243V-S248N, G131H-N243V-S248N-L257G, G131H-T158S-N218S, G131H-T158S-N218S-N240H-N243V-S248N-K256R-L257G, G131H-T158S-N218S-N243V, G131H-T158S-N218S-N243V-S248N-K256R-L257G, G131H-T158S-N218S-N243V-S248N-L257G, G131H-T158S-N218S-S248N-I268V, G131H-T158S-N218S-S248N-K256R-L257G-N269S, G131H-T158S-N243V-L257G, G131H-T158S-N243V-S248N, G131H-T158S-S248N, I107T-G131H-T158S-N243V-S248N-K256R-L257G, I107T-N109G-G131H-N218S-L257G, K256R, K256R-L257G, L090I-N109G-T158S-N243V, L257G, N109G-A116T-G131H-N218S-N243V, N109G-A116T-G131H-N218S-N243V-L257G, N109G-A116T-G131H-N218S-S248N-L257G, N109G-A116T-G131H-N218S-W241R-N243V-K256R, N109G-A116T-G131H-S248N-L257G, N109G-A116T-G131H-T158S-N218S-K256R, N109G-A116T-G131H-T158S-N218S-K256R-L257G-Q271R, N109G-A116T-G131H-T158S-N218S-N243V-K256R-L257G, N109G-A116T-G131H-T158S-N218S-N243V-S248N, N109G-A116T-G131H-T158S-N218S-N243V-S248N-L257G, N109G-A116T-G131H-T158S-N243V-K256R-L257G, N109G-A116T-G131H-T158S-N243V-S248N-K256R, N109G-A116T-G131H-T158S-S248N-K256R-L257G, N109G-A116T-I234T-N243V-S248N-K256R-L257G, N109G-A116T-K141E-T158S-N218S-N243V-L257G, N109G-A116T-N218S-N243V-S248N, N109G-A116T-N218S-W241R-N243V-S248N-K256R-L257G, N109G-A116T-N243V-K256R-L257G, N109G-A116T-T158S-N218S-K237R-N243V-S248N, N109G-A116T-T158S-N218S-N243V-S248N, N109G-G131H-K141E-L257G, N109G-G131H-N218S-N243V, N109G-G131H-N218S-N243V-S248N, N109G-G131H-S248N, N109G-G131H-T158S, N109G-G131H-T158S-L257G, N109G-G131H-T158S-N218S-N243V-S248N-K256R, N109G-G131H-T158S-N218S-S248N-K256R, N109G-G131H-T158S-N218S-S248N-L257G, N109G-G131H-T158S-N243V-S248N-K256R-L257G, N109G-G131H-T158S-S248N-K256R, N109G-N218S-K256R-L257G, N109G-N218S-N243V-S248N-K256R, N109G-N218S-S248N-L257G, N109G-S248N, N109G-T158S-N218S, N109G-T158S-N218S-N243V, N109G-T158S-N218S-N243V-L257G, N109G-T158S-N218S-S248N-K256R, N109G-T158S-N243V-L257G, N109G-T158S-N243V-S248N-K256R-L257G, N218S-K256R, N218S-N243V-K256R, N218S-N243V-S248N, N218S-S248N, N218S-S248N-K256R, N218S-S248N-K256R-L257G, N243V-L257G, S003P-N109G-A116T-G131H-N218S-N243V-S248N, S003P-N109G-A116T-G131H-T158S-N218S-K256R, S003P-N109G-G131H-T158S-L257G, S003P-S248N-L257G, S105H-W106G-I107L-I108S-N109A-G110A-I111S-E112N-W113G-A114P, S248N-L257G, T158S, T158S-K256R, T158S-N218S, T158S-N218S-K256R, T158S-N218S-L233S-S248N, T158S-N218S-L257G, T158S-N218S-N243V-K256R, T158S-N218S-N243V-S248N, T158S-N218S-N243V-S248N-L257G, T158S-N218S-S248N-K256R-L257G, T158S-N218S-S248N-L257G, T158S-N243V-S248N-K256R, T158S-N243V-S248N-K256R-L257G, T158S-N243V-S248N-L257G, T158S-S248N, T158S-S248N-K256R-L257G, V004A-A088T-G131H-N218S-N243V-S248N-L257G, V004L-A088T-G131H-T158S-N218S-S248N-L257G, Y006H-N218S-N243V-S248N, and Y104H-N109G-G131H-N243V-S248N;

(ix) A088T-A098S-G131H-S248N-K256R-L257G, A088T-A116T-G131H-K256R, A088T-A116T-G131H-L257G, A088T-A116T-G131H-N218S-N243V, A088T-A116T-G131H-N218S-S248N-K256R, A088T-A116T-G131H-N218S-S248N-K256R, A088T-A116T-G131H-N218S-S248N-L257G, A088T-A116T-G131H-N243V-S248N-L257G, A088T-A116T-G131H-S248N, A088T-A116T-G131H-S248N-K256R-L257G, A088T-A116T-G131H-T158S-K256R, A088T-A116T-G131H-T158S-L257G, A088T-A116T-G131H-T158S-N218S-L257G,

A088T-A116T-G131H-T158S-N218S-N243V-L257G, A088T-A116T-G131H-T158S-N218S-N243V-S248N-K256R-L257G, A088T-A116T-G131H-T158S-N243V-K256R-L257G, A088T-A116T-G131H-T158S-N243V-S248N-L257G, A088T-A116T-G131H-V150A-N218S-S248N-L257G, A088T-A116T-K256R-L257G, A088T-A116T-K256R-L257G, A088T-A116T-L257G, A088T-A116T-N218S, A088T-A116T-N218S, A088T-A116T-N218S-N243V-Q271R, A088T-A116T-N218S-N243V-S248N, A088T-A116T-N218S-S248N-K256R, A088T-A116T-T158S, A088T-A116T-T158S, A088T-A116T-T158S-K256R, A088T-A116T-T158S-K256R-L257G, A088T-A116T-T158S-N218S-N243V-L257G, A088T-A116T-T158S-N218S-S248N, A088T-A116T-T158S-N218S-S248N-K256R, A088T-A116T-T158S-N243V-K256R-L257G, A088T-A116T-T158S-N243V-S248N-K256R, A088T-A138E-N218S-N243V-K256R, A088T-G131D-T158S-N243V-S248N, A088T-G131H, A088T-G131H-L257G, A088T-G131H-N218S-K237R-K256R-L257G, A088T-G131H-N218S-K256R, A088T-G131H-N218S-N243V-S248N-K256R, A088T-G131H-N218S-N243V-S248N-L257G, A088T-G131H-N243V-K256R, A088T-G131H-N243V-L257G, A088T-G131H-N243V-S248N, A088T-G131H-N243V-S248N-K256R, A088T-G131H-T158S-N218S-I234T-S248N-L257G, A088T-G131H-T158S-N218S-N243V-S248N-K256R-L257G, A088T-G131H-T158S-N243V-K256R-L257G, A088T-G131H-T158S-S248N, A088T-G131H-T158S-S248N-K256R, A088T-G131H-T158S-S248N-K256R, A088T-G131H-T158S-S248N-K256R-L257G, A088T-G131H-V149L-T158S-N243V-S248N-K256R-L257G, A088T-I108T-N109G-G131H-T158S-N218S-S248N-K256R-L257G, A088T-K213N-N243V-S248N-K256R, A088T-K256R-L257G, A088T-N109G-A116T-G131H-D140G-S248N-L257G, A088T-N109G-A116T-G131H-K141E-N218S, A088T-N109G-A116T-G131H-L257G, A088T-N109G-A116T-G131H-N218S-N243V-S248N-K256R-L257G, A088T-N109G-A116T-G131H-N218S-N243V-S248N-Q275R, A088T-N109G-A116T-G131H-N218S-S248N, A088T-N109G-A116T-G131H-N218S-S248N-K256R-L257G, A088T-N109G-A116T-G131H-N243V-S248N-K256R, A088T-N109G-A116T-G131H-N243V-S248N-K256R, A088T-N109G-A116T-G131H-T158S-K256R, A088T-N109G-A116T-G131H-T158S-N218S-L257G-I268V, A088T-N109G-A116T-G131H-T158S-N218S-N243V-S248N, A088T-N109G-A116T-G131H-T158S-N218S-N243V-S248N, A088T-N109G-A116T-G131H-T158S-N243V-S248N-K256R-L257G, A088T-N109G-A116T-G131H-T158S-S248N, A088T-N109G-A116T-G131H-V149A-T158S-N218S-K256R, A088T-N109G-A116T-G131H-W241L-S248N-K256R-L257G, A088T-N109G-A116T-M124I-G131H-T158S-N218S-S248N-L257G, A088T-N109G-A116T-N218S-N243V-S248N-K256R, A088T-N109G-A116T-N218S-S248N-K256R-L257G, A088T-N109G-A116T-N243V-K256R, A088T-N109G-A116T-N243V-S248N-L257G, A088T-N109G-A116T-S248N-L257G, A088T-N109G-A116T-T158S-K256R-L257G, A088T-N109G-A116T-T158S-N212D-N243V-K256R-L257G, A088T-N109G-A116T-T158S-N218S-N243V-K256R, A088T-N109G-A116T-T158S-N218S-N243V-L257G, A088T-N109G-A116T-T158S-N218S-N243V-S248N, A088T-N109G-A116T-T158S-N243V-K256R-L257G, A088T-N109G-A116T-T158S-N243V-S248N, A088T-N109G-A116T-T158S-S248N-L257G-Q271P, A088T-N109G-A116T-V148A-N218S-N243V, A088T-N109G-A137E-T158S-N218S-N243V-S248N-K256R-L257G, A088T-N109G-D140G-N243V, A088T-N109G-G131H-A152S-T158S-N218S-S248N-K256R, A088T-N109G-G131H-D140G-T158S-N243V-S248N-K256R, A088T-N109G-G131H-K256R-L257G, A088T-N109G-G131H-K256R-L257G, A088T-N109G-G131H-N218S, A088T-N109G-G131H-N218S-L257G, A088T-N109G-G131H-N218S-N243V, A088T-N109G-G131H-N218S-N243V-S248N-L257G, A088T-N109G-G131H-N218S-S248N, A088T-N109G-G131H-N243V-S248N, A088T-N109G-G131H-T158S-L233S-N243V-S248N, A088T-N109G-G131H-T158S-L257G, A088T-N109G-G131H-T158S-N218S-N243V-S248N-K256R-L257G, A088T-N109G-G131H-T158S-N218S-S248N-K256R, A088T-N109G-G131H-T158S-N218S-W241R-S248N-L257G, A088T-N109G-G131H-T158S-N243V-S248N-L257G, A088T-N109G-G131H-T158S-S248N-K256R, A088T-N109G-L257G, A088T-N109G-N218S-K256R-L257G, A088T-N109G-N218S-S248N-K256R, A088T-N109G-N218S-S248N-T255K-K256R-L257G, A088T-N109G-N243V-K256R-L257G, A088T-N109G-N243V-S248N-K256R, A088T-N109G-S248N-K256R-L257G, A088T-N109G-T158S, A088T-N109G-T158S-N218S-N243V, A088T-N109G-T158S-N218S-N243V-S248N-L257G, A088T-N109G-T158S-N218S-N243V-S248N-L257G, A088T-N109G-T158S-N218S-S248N, A088T-N109G-T158S-N218S-S248N, A088T-N109G-T158S-N243V-S248N-K256R, A088T-N109G-T158S-N243V-S248N-Q275R, A088T-N109G-T158S-S248N, A088T-N109G-T158S-S248N-K256R, A088T-N109G-W241R-S248N-K256R, A088T-N218S-N243V-S248N-K256R-L257G, A088T-N218S-S248N-L257G, A088T-N243V-L257G, A088T-S248N, A088T-S248N-K256R-L257G, A088T-S248N-L257G, A088T-S248N-L257G-I268V, A088T-T158S-K256R, A088T-T158S-N218S-K256R, A088T-T158S-N218S-L257G, A088T-T158S-N218S-L257G, A088T-T158S-N218S-N243V-S248N, A088T-T158S-N218S-N243V-S248N-L257G, A088T-T158S-N218S-Q245K-S248N-K256R, A088T-T158S-N218S-S248N-K256R, A088T-T158S-N218S-S248N-L257G, A088T-T158S-N218S-S248N-L257G-Q275K, A088T-T158S-N243V-K256R, A088T-T158S-N243V-K256R-L257G, A088T-T158S-N243V-L257G, A088T-T158S-N243V-S248N-K256R, A088T-T158S-S248N, A088T-T158S-S248N-K256R-L257G, A088T-T158S-S248N-L257G, A088T-T158S-V203I-N218S-K256R-L257G, A088T-Y104H-A116T-G131H-N218S-N243V, A088T-Y104H-N109G-A116T-A153S-N218S-N243V-S248N-L257G-N269D, A088T-Y104H-N109G-G131H-A137E-T158S-N218S-N243V-S248N-K256R, A098S-G131H-T158S-N218S-N243V-S248N-K256R-L257G, A116T-D140G-T158S-N218S-N243V-S248N, A116T-G131H-K141E-N218S-N243V-S248N-L257G, A116T-G131H-N218S-W241R-N243V-S248N-K256R-L257G, A116T-G131H-N243V, A116T-G131H-T158S-K256R-L257G, A116T-G131H-T158S-N218S-N243V, A116T-G131H-T158S-N218S-S248N-K256R, A116T-G131H-T158S-N243V-S248N, A116T-G131H-V139I-N218S-N243V-S248N, A116T-G157E-T158S-N243V-S248N-K256R, A116T-N218S-S248N, A116T-N218S-S248N-K256R, A116T-N243V-K256R, A116T-S248N-K256R, A116T-T158S, A116T-T158S-L257G-Q271R, A116T-T158S-N218S-N243V-K256R-L257G, G053S-A088T-N109G-A116T-G131H-T158S-G169S-N218S-S248N-K256R-L257G, G065D-A088T-G131H-N243V-S248N, G131H-N218S-L257G, G131H-N218S-S248N, G131H-N243V-K256R, G131H-S248N-K256R, G131H-T158S, G131H-T158S-K256R, G131H-

T158S-N243V-L257G, K256R, K256R-L257G, L090I-N109G-T158S-N243V, L257G, N109G-A116T-G131H, N109G-A116T-G131H-N243V, N109G-A116T-G131H-N243V-K256R-L257G, N109G-A116T-G131H-T158S-N218S-N243V-S248N, N109G-A116T-G131H-T158S-N218S-N243V-S248N-K256R, N109G-A116T-I234T-N243V-S248N-K256R-L257G, N109G-A116T-N218S-N243V-L257G, N109G-A116T-N218S-W241R-N243V-S248N-K256R-L257G, N109G-A116T-S248N-K256R, N109G-A116T-T158S-K256R-L257G, N109G-A116T-T158S-N218S-K237R-N243V-S248N, N109G-A116T-T158S-N218S-S248N-K256R, N109G-A116T-T158S-N243V, N109G-A116T-T158S-S248N, N109G-A116T-T158S-S248N-K256R, N109G-G131H-A137V-T158S-N218S-S248N, N109G-G131H-K141E-L257G, N109G-G131H-T158S, N109G-G131H-T158S-N243V-K256R-L257G, N109G-G131H-T158S-N243V-S248N-L257G, N109G-G131H-T158S-S248N-Q271R, N109G-N218S-S248N-K256R, N109G-N243V-S248N-L257G, N109G-S248N, N109G-T158S-K256R-L257G, N109G-T158S-N218S-N243V-L257G, N109G-T158S-N243V-K256R-L257G, N109G-T158S-N243V-S248N-K256R-L257G, N218S-N243V-S248N-K256R-L257G, N243V, P014L-A015L-L016C-H017T-S018L-Q019K-G020A-Y021T-T022L-G023E, S003P-N109G-A116T-G131H-T158S-N218S-K256R, S003P-N109G-G131H-T158S-L257G, S003P-S248N-L257G, S105H-W106G-I107L-I108S-N109A-G110A-I111S-E112N-W113G-A114P, T158S-N218S-N243V-K256R, T158S-N218S-N243V-S248N, T158S-N218S-S248N-K256R, T158S-N243V-S248N, T158S-S248N, T158S-S248N-K256R, T158S-S248N-K256R-L257G, V004A-A088T-A116T-T158S-N218S, V004A-A088T-G131H-N218S-N243V-S248N-L257G, V004M-A116T-V148A-T158S-N243V-S248N-K256R, Y006H-N109G-N218S-N243V-S248N, Y104H-A116T-T158S-S248N, Y104H-N109G-G131H-N243V-S248N, and Y104H-N218S-L257G;

(x) A045S-S236G, A045S-S236Y, A134T-S260G, G024A-S037W, I031V-S038W, I115T-S183T, I115V-N184Y, N025K-P129K, N025K-P129R, N025K-S037P, N061D-S260I, Q010L-S037P, Q010R-S037T, Q019L-S260N, Q019L-S260P, S037P-T254S, S161P-T253A, and S162L-D181H;

(xi) A045S-S236G, A045S-S236Y, A133V-S260N, A134T-S260G, G024A-S037W, I031V-S038W, I115T-S183T, I115V-N184Y, N025K-P129R, N025K-S037P, N061D-S260I, Q010R-S037T, Q019L-S260N, Q019L-S260P, and S162L-D181H; and (xii) A045S-S236G, A045S-S236Y, I115T-S183T, N025K-S037P, N061S-S260P, Q010L-S037P, Q010R-S037T, Q019L-S260N, S037P-T254S, and S161P-S260P; wherein each amino acid position of the variant is numbered by correspondence to an amino acid position in the amino acid sequence of SEQ ID NO:2.

A variant according to the ninth aspect of the invention may have enhanced proteolytic activity and/or enhanced cleaning activity compared to the protease set forth in SEQ ID NO:2, SEQ ID NO:4, or SEQ ID NO:6, respectively. A variant according to the ninth aspect of the invention may have a performance index in a proteolytic assay (e.g., AAPF assay) or cleaning assay (e.g., BMI, grass, or egg microswatch assay) that is greater than that of the protease set forth in SEQ ID NO:2, SEQ ID NO:4, or SEQ ID NO:6. A variant according to the ninth aspect of the invention may be a protease variant of BPN' subtilisin protease (SEQ ID NO:2).

In a twenty-first aspect, the invention provides an isolated or non-naturally occurring cold water protease that is a variant of a parent protease, said cold water protease comprising a total of three, four, five, six, seven, eight, nine, 10, 11, 12, 13, 14 or 15 mutations selected from groups (a) and (b) below, wherein at least one mutation is selected from group (a):

(a) 1, 9, 14, 15, 16, 17, 18, 19, 20, 21, 22, 23, 33, 43, 76, 102, 109, 137, 141, 158, 169, 204, 210, 218, 243, 248, 249, 256, 257, 260, and 269; and (b) 24, 25, 40, 52. 53, 55, 58, 59, 61, 62, 63, 68, 78, 86, 87, 88, 89, 92, 96, 97, 100, 101, 103, 104, 106, 111, 114, 115, 116, 117, 118, 123, 124, 125, 126, 128, 129, 130, 131, 132, 133, 134, 144, 145, 159, 161, 162, 167, 194, 203, 206, 213, 217, 227, 232, 239, 240, 242, 265, 267, and 275, wherein amino acid positions are numbered by correspondence with SEQ ID NO:2. The parent protease according to the twenty-first aspect of the invention may comprise an amino acid sequence having at least 80%, 85%, 90%, 91%, 92%, 93%, 94%, 95%, 96%, 97%, 98%, 99%, or 100% identity to the amino acid sequence of SEQ ID NO:2 and the variant according to the twenty-first aspect of the invention, may comprise a total of three, four, five, six, seven, eight, nine, 10, 11, 12, 13, 14 or 15 mutations selected from groups (a) and (b) below, wherein at least one mutation is selected from group (a):

(a) A1E/T, S9/T, P14L, A15L, L16C, H17T, S18L/T, Q19K, G20A, Y21N/T, T22L, G23E, S33T, K43Y, N76D, G102A, N109A/S/G, A137V, K141R, T158S, G169A, S204E, P210S, N218S, N243P/V, S248N/A, S249A, K256R, L257G, S260P, and N269D; and (b) S24G/R/E, N25G, P40A/E, P52L, S53G, T55P, F58G, Q59S, N61E/P/G/S, N62Q/R/S, S63G/H, V68A, S78N, P86S, S87D/G, A88T/V, S89Y, A92G, L96T, G97A, G100N/Q/T, S101N, Q103E/H, Y104N, W106F, I111V, A114G, I115V, A116N/T, N117S, N118G, N123A/G/Q/V, M124I/V, S125A, L126A, G128A/S, P129E/Q/S/V, S130G, G131S/H, S132N, A133V, A134T, A144K, S145D, S159K, S161P, S162G/K, Y167A, P194L, V203Y, Q206D/E, K213L, Y217Q/L/D, V227T, A232T, P239R/V, N240K, T242R, K265N, L267V, and Q275E. A variant and parent protease according to the second aspect of the invention may be in a mature form.

A variant according to the twenty-first aspect of the invention may have a total net charge of −1, 0 or +1 relative to the BPN' wild-type.

In the first, second, fourth, fifth, sixth, seventh, eighth, ninth, or twenty-first aspect of the invention, the variant may be a subtilisin protease variant having improved wash performance or cleaning performance in a detergent as compared to that of the parent subtilisin protease, which may be a subtilisin protease. In the third aspect of the invention, the polypeptide may have improved wash performance or cleaning performance in a detergent as compared to that of the protease of SEQ ID NO:2, SEQ ID NO:4 or SEQ ID NO:6. Exemplary detergents for such aspects are shown in the Part I Examples and Part II Examples.

A protease variant according to the first, second, third, fourth, fifth, sixth, seventh, eighth, ninth, or twenty-first aspect of the invention may be a cold water protease. In one aspect, a protease variant according to the first, second, third, fourth, fifth, sixth, seventh, eighth, ninth, or twenty-first aspect of the invention may be a cold water protease having: (i) a performance index (PI) greater than 1, at least 1.1, at least 1.2, at least 1.3, at least 1.4, at least 1.5, at least 1.6, at least 1.7, at least 1.8, at least 1.9, at least 2, from at least 1 to about 10, from at least 1 to about 8, or from at least 1 to about 5 on BMI at pH 8 and 60° F. when compared to an enzyme having the amino acid sequence of SEQ ID NO:4, as defined in the Test Method set forth in Part I Example 1; or (ii) a performance index of at least 1, at least 1.1, at least 1.2, at least 1.3, at least 1.4, at least 1.5, at least 1.6, at least 1.7, at least 1.8, at least 1.9, at least 2, from at least 1 to about 10, from at least 1 to about 8, or from at least 1 to about 5 on BMI at pH 8 and 60° F. when compared to an enzyme having the amino acid sequence of SEQ ID NO:6, as defined in the Test Method set forth in Part I Example 1.

As noted above, the protease variant polypeptides of the invention have enzymatic activities (e.g., proteolytic activities) and thus are useful in cleaning applications, including but not limited to, methods for cleaning dishware items, tableware items, fabrics, and items having hard surfaces (e.g., the hard surface of a table, table top, wall, furniture item, floor, ceiling, etc.). Exemplary cleaning compositions comprising one or more protease variant polypeptides of the invention are described infra. The enzymatic activity (e.g., protease activity) of a protease variant polypeptide of the invention can be determined readily using procedures well known to those of ordinary skill in the art. The Examples presented infra describe methods for evaluating the enzymatic activity, cleaning performance, and/or washing performance. The performance of protease variants of the invention in removing stains (e.g., a proteinaceous stain), cleaning hard surfaces, or cleaning laundry, dishware or tableware item(s) can be readily determined using procedures well known in the art and/or by using procedures set forth in the Part I Examples and/or Part II Examples.

A polypeptide of the invention can be subject to various changes, such as one or more amino acid insertions, deletions, and/or substitutions, either conservative or non-conservative, including where such changes do not substantially alter the enzymatic activity of the polypeptide. Similarly, a nucleic acid of the invention can also be subject to various changes, such as one or more substitutions of one or more nucleic acids in one or more codons such that a particular codon encodes the same or a different amino acid, resulting in either a silent variation (e.g., mutation in a nucleotide sequence results in a silent mutation in the amino acid sequence, for example when the encoded amino acid is not altered by the nucleic acid mutation) or non-silent variation, one or more deletions of one or more nucleic acids (or codons) in the sequence, one or more additions or insertions of one or more nucleic acids (or codons) in the sequence, and/or cleavage of or one or more truncations of one or more nucleic acids (or codons) in the sequence. Many such changes in the nucleic acid sequence may not substantially alter the enzymatic activity of the resulting encoded protease variant compared to the protease variant encoded by the original nucleic acid sequence. A nucleic acid of the invention can also be modified to include one or more codons that provide for optimum expression in an expression system (e.g., bacterial expression system), while, if desired, said one or more codons still encode the same amino acid(s).

The present invention includes a genus of polypeptides comprising protease variant polypeptides having the desired enzymatic activity (e.g., protease activity or cleaning performance activity) which comprise sequences having the amino acid substitutions described herein and also which comprise one or more additional amino acid substitutions, such as conservative and non-conservative substitutions, wherein the polypeptide exhibits, maintains, or approximately maintains the desired enzymatic activity (e.g., protease activity or subtilisin activity, as reflected in the cleaning activity or performance of the protease variant). Amino acid substitutions in accordance with the invention may include, but are not limited to, one or more non-conservative substitutions and/or one or more conservative amino acid substitutions. A conservative amino acid residue substitution typically involves exchanging a member within one functional class of amino acid residues for a residue that belongs to the same functional class (identical amino acid residues are considered functionally homologous or conserved in calculating percent functional homology). A conservative amino acid substitution typically involves the substitution of an amino acid in an amino acid sequence with a functionally similar amino acid. For example, alanine, glycine, serine, and threonine are functionally similar and thus may serve as conservative amino acid substitutions for one another. Aspartic acid and glutamic acid may serve as conservative substitutions for one another. Asparagine and glutamine may serve as conservative substitutions for one another. Arginine, lysine, and histidine may serve as conservative substitutions for one another. Isoleucine, leucine, methionine, and valine may serve as conservative substitutions for one another. Phenylalanine, tyrosine, and tryptophan may serve as conservative substitutions for one another.

Other conservative amino acid substitution groups can be envisioned. For example, amino acids can be grouped by similar function or chemical structure or composition (e.g., acidic, basic, aliphatic, aromatic, sulfur-containing). For instance, an aliphatic grouping may comprise: Glycine (G), Alanine (A), Valine (V), Leucine (L), Isoleucine (I). Other groups containing amino acids that are considered conservative substitutions for one another include: aromatic: Phenylalanine (F), Tyrosine (Y), Tryptophan (W); sulfur-containing: Methionine (M), Cysteine (C); Basic: Arginine (R), Lysine (K), Histidine (H); Acidic: Aspartic acid (D), Glutamic acid (E); non-polar uncharged residues, Cysteine (C), Methionine (M), and Proline (P); hydrophilic uncharged residues: Serine (S), Threonine (T), Asparagine (N), and Glutamine (Q). Additional groupings of amino acids are well-known to those of skill in the art and described in various standard textbooks. Listing of a polypeptide sequence herein, in conjunction with the above substitution groups, provides an express listing of all conservatively substituted polypeptide sequences.

More conservative substitutions exist within the amino acid residue classes described above, which also or alternatively can be suitable. Conservation groups for substitutions that are more conservative include: valine-leucine-isoleucine, phenylalanine-tyrosine, lysine-arginine, alanine-valine, and asparagine-glutamine. Thus, for example, the invention includes an isolated or recombinant protease variant polypeptide (e.g., subtilisin variant) having proteolytic activity, said protease variant polypeptide comprising an amino acid sequence having at least about 80%, 85%, 90%, 95%, 96%, 97%, 98%, 99%, or 99.5% sequence identity to the amino acid sequence of SEQ ID NO:2. A conservative substitution of one amino acid for another in a protease variant of the invention is not expected to alter significantly the enzymatic activity or cleaning performance activity of the protease variant. Enzymatic activity or cleaning performance activity of the resultant protease can be readily determined using the standard assays and the assays described herein.

Conservatively substituted variations of a polypeptide sequence of the invention (e.g., protease variants of the invention) include substitutions of a small percentage, sometimes less than about 25%, 20%, 15%, 14%, 13%, 12%, 11%, 10%, 9%, 8%, 7%, or 6% of the amino acids of the polypeptide sequence, or less than about 5%, 4%, 3%, 2%, or 1%, of the amino acids of the polypeptide sequence, with a conservative amino acid.

As described elsewhere herein in greater detail and in the Examples provided herein, polypeptides of the invention may have cleaning abilities that may be compared to known proteases, including known subtilisins. Exemplary known subtilisin proteases include, but are not limited to, for example, *B. lentus* subtilisin GG36, *B. amyloliquefaciens* subtilisin BPN', *B. amyloliquefaciens* subtilisin BPN'-Y217L, and *B. clausii* PB92.

Numerous polypeptides of the invention, including protease variants, such as, e.g., subtilisin protease variants described and set forth throughout the specification, including, but not limited to, in the Examples. Part I Examples describe protease variants of the invention, including, e.g., but not limited to, BPN' protease variants. Part II Examples describe additional protease variants of the invention, including, e.g., but not limited to, GG36 protease variants.

The present invention provides protease variants, including serine protease variants, having one or more substitutions as compared to a reference serine protease. In one aspect, the present invention provides cold water proteases. In addition, the present invention provides compositions comprising one or more such protease variants, e.g., serine protease variants. A composition may comprise at least one such protease variant of the invention and an adjunct ingredient, as described elsewhere herein. In one aspect, the present invention provides cleaning compositions comprising at least one of these protease variants, e.g., serine protease variants. A cleaning composition may be a detergent composition. The trend in cleaning is to use lower wash temperatures to save energy. Enzymes have lower activity at lower temperatures resulting in reduced cleaning performance. There is a need in the art for enzymes with enhanced performance at coldwater washing conditions over those currently known in the art. The present invention addresses this need.

The present invention provides cleaning compositions comprising at least one serine protease variant described herein, such as a subtilisin protease variant. The subtilisin protease variant may be a BPN' protease variant. As discussed in further detail supra, the invention includes a composition comprising a BPN' protease variant and a GG36 protease variant. Some protease variants, including, but not limited to, e.g., subtilisin variants of the invention, are cold water proteases. The cleaning composition may be a laundry detergent. The laundry detergent may be a detergent having a pH between 3 and 11 (e.g., between pH 4, pH 5, pH 6, pH 7, pH 7.5, pH 8, pH 9, pH 10, pH 10.5, etc.) cold water detergent, a low pH detergent (e.g., pH 3-6), neutral pH detergent (e.g., pH 6.5-7.5), alkaline pH detergent (e.g., pH 9-11) or a compact detergent. A detergent may include phosphate or be without phosphate. The cleaning composition may be a dishwashing detergent. In one aspect, the dishwashing detergent is a phosphate-free detergent, while in another aspect, the dishwashing detergent is a phosphate-containing detergent. In one aspect, the cleaning composition of the invention further comprises at least one additional enzyme, which may optionally be selected from the group of a neutral metalloprotease, lipase, cutinase, amylase, carbohydrase, cellulase, pectinase, mannanase, arabinase, galactanase, xylanase, perhydrolase, oxidase, and peroxidase. Also provided are isolated nucleic acids encoding a serine protease variant of the invention, expression vectors comprising one or more such nucleic acids of the invention, and host cells comprising at least one such expression vector of the invention.

Throughout the specification, for ease of reference, a "set of amino acid substitutions" or "set of substitutions" may refer to a set of multiple amino acid substitutions (i.e., G097A+G128A+Y217Q) or set of a single amino acid substitution (i.e., Y217Q). Thus, a BPN' variant comprising the BPN' sequence (SEQ ID NO:2) comprising at least one set of amino acid substitutions selected from the group consisting of G097A-G128A-Y217Q and Y217Q indicates the BPN' variant comprises an amino acid sequence comprising BPN'-G097A-G128A-Y217Q or BPN'-Y217Q.

The amino acid sequence of the mature BPN'-v3 subtilisin protease variant, which is set forth in SEQ ID NO:4, can be represented as BPN'-G097A-G128A-Y217Q, which means the BPN' amino acid sequence of SEQ ID NO:2 with the three substitutions G097A, G128A, and Y217Q. In this format, each dash (-) is equivalent to using a plus sign (+). Thus, BPN'-G097A-G128A-Y217Q can be written alternatively as BPN'+G097A+G128A+Y217Q. The amino acid sequence of the mature BPN'-v36 subtilisin protease variant, which is set forth in SEQ ID NO:6, can be written as BPN'-S24G-S53G-S78N-S101N-G128A-Y217Q or BPN'+S24G+S53G+S78N+S101N+G128A+Y217Q. BPN' variants of the invention may be depicted using these formats.

In addition, the present invention provides subtilisin variants, wherein each such variant is a mature form having proteolytic activity and comprises the BPN'-v3 amino acid sequence (SEQ ID NO:4) comprising at least one set of amino acid substitutions selected from the group consisting of S87T-A88L-S89G, N61P-S63H, S87G-A88V-S89A, P86S-S87G-A88V, Q59S-N61P, S24G-N25G, N61P-N62S, P129Q-S130G-G131S, L75S-N76Y, V203Y, T55P, A88V-L90I, G211R-N212S-K213V, G23A-S24G-N25G, T22N-S24A, S24R, A98S, T158G-S159G, Q59E-N61P, and A98E, and wherein the amino acid positions are numbered by correspondence with the amino acid sequence of *B. amyloliquefaciens* subtilisin BPN' set forth as SEQ ID NO:2.

Note that the BPN'-v3 amino acid sequence, which is set forth as SEQ ID NO:4, may be written as BPN'-G97A-G128A-Y217Q. The invention includes a protease variant having proteolytic activity, wherein said variant comprises the amino acid sequence of SEQ ID NO:4 having an amino acid substitution A128S in SEQ ID NO:4. Thus, the invention includes the amino acid sequence BPN'-G97A-G128A-Y217Q. Throughout this specification, polypeptide variants of the invention may be described as a variant of a reference polypeptide comprising one or more particular amino acid substitutions at one or more specified positions in the reference polypeptide sequence, respectively.

The present invention also provides subtilisin variants, wherein each such variant is a mature form having proteolytic activity and comprises the BPN'-v3 amino acid sequence (SEQ ID NO:4) comprising at least one set of amino acid substitutions selected from the group consisting of P86S-S87G-A88V-A116N-N117S-N118G, S24G-N25G-N61P-S101N, S24G-N25G-S53G-T55P-S87T-A88L-S89G-S101N-V203Y, N61P-S78N-S101N-V203Y, T55P-N61P-S78N-S101N-V203Y, S53G-T55P-N61P-S78N-S87T-A88L-S89G-S101N, V203Y-L267V, S24G-N25G-T55P-S101N, A134T-L267V, S24G-N25G-S53G-T55P-N61P-S78N-S87T-A88L-S89G, S24G-N25G-S53G-N61P-S101N-V203Y, N25Y-Q59S-N61P, I111V-S161P, I115V-L267V, T55P-S78N-S87T-A88L-S89G-S101N-V203Y, N25Y-P129Q-S130G-G131S-A137T, N61P-S63H-A128S-P129Q, S53G-N61P-S101N-V203Y, S24G-N25G-S53G-S78N-S87T-A88L-S89G-S101N, N61P-S78N-S87T-A88L-S89G-S101N, N25Y-N61P-S63H, Q59S-N61P-V203Y, V8L-N25Y-P129Q-S130G-G131S, P86S-S87G-A88V-P239R, S24G-N25G-S53G-T55P-N61P-S101N-V203Y, S24G-N25G-P129Q-S130G-G131S, N240K, G23A-S24G-N25G-G211R-N212S-K213V, N61P-S63H-S78N-I111V-A134T, S63T-P86S-S87G-A88V, G23A-S24G-N25G-A116N-N117S-N118G, S78N-S87T-A88L-S89G-S101N, S24G-N25G-A116N-N117S-N118G, T55P-N240K, T55P-P129V-P194S, N25Y-S87G-A88V-S89A, S24G-N25G-

S87T-A88L-S89G-S101N, P129Q-S130G-G131S-V203Y, Q59S-N61P-N240K, S24R-P40E-P129E-S159K-K265R, P52S-T55P-V203Y, S24R-P129E, S24G-N25G-S53G-N61P-S78N, S24G-N25G-T55P-S78N-S101N, P86S-S87G-A88V-A116S-N117G-N118R, N61P-S87T-A88L-S89G, S24G-N25G-S53G-T55P-S78N-S87T-A88L-S89G, G23A-S24G-N25G-N61P-S63H, S24R-Q59S-N61P, N61P-P129Q-S130G-G131S, S24G-N25G-S53G-T55P-N61P-S78N-S87T-A88L-S89G-S101N, S24G-N25G-S53G-T55P-S101N-V203Y, N61P-S78N-S87T-A88L-S89G-S101N-V203Y, S24G-N25G-S53G-T55P-S78N-S101N, S24G-N25G-S53G-S101N-V203Y, S24G-N25G-S78N-S101N-V203Y, P129Q-S130G-G131S-A133V-L267V, S87T-A88L-S89G-S101N, G23A-S24G-N25G-P239R, S87G-A88V-S89A-A116N-N117S-N118G, Q59S-N61P-A116S-N117G-N118R, Q59S-N61P-S87T-A88L-S89G, S24G-N25G-S53G-S87T-A88L-S89G-V203Y, A134T-G211T, T55P-A128S-P129Q, T55P-S78N-S87T-A88L-S89G-S101N, P86S-S87G-A88V-T242R, S161P-V203Y, S24G-N25G-T55P-N61P-S78N-S101N-V203Y, G211T-L267V, P40E-T55P-N269K, S24R-A128S-P129G, S24G-N25G-N61P-N62S-P194L-A232T, T55P-A116S-N117G-N118R, S24G-N25G-S53G-S78N-S101N-V203Y, P129Q-S130G-G131S-N240K, S53G-T55P-N61P-S78N-S87T-A88L-S89G, N25Y-P129Q-S130G-G131S, T55P-I115V, N25Y-T55P, G23A-S24G-N25G-A128S-P129D, S53G-S78N-S87T-A88L-S89G-S101N-P129S-V203Y, T55P-A134T, N61P-S63H-S78N-I111V, N61P-A97G-G102A-A128G-P129S, S53G-N61P-S101N, Q59S-N61P-S87G-A88V-S89A, S53G-S87T-A88L-S89G-S101N-V203Y, S87T-A88L-S89G-P129S, S53G-T55P-S78N-S101N-V203Y, T55P-P129Q-S130G-G131S, Q59S-N61P-P129Q-S130G-G131S, A134T-P239R, T55P-V203Y, T55P-S78N-S89Y, T22N-S24A-N61P-S63H, S161P-L267V, T55P-L75H-N76G, A134T-S161P, S87T-A88L-S89G-A134T, T55P-A116N-N117S-N118G, A128S, T55P-S78N-I115V, Y6Q-P129Q-S130G-G131S, S24R-P129Q-S130G-G131S, S24G-N25G-S53G-S78N-S101N, T55P-P129V, N61P-N62Q-G100N-A128G, T55P-P129Q, S24G-N25G-S53G-T55P-N61P-S78N-S87T-A88L-S89G-S101N-V203Y, S87T-A88L-S89G-N240K, A134T-N240K, S87T-A88L-S89G-P239R, P129Q-S130G-G131S-L267V, P129Q-N240K, S78N-S87T-A88L-S89G-V203Y, I111V-A273S, S24G-N25G-T55P-S78N-A88V-S101N, S24G-N25G-T55P-S78N, S24G-N25G-S53G-S78N-S87T-A88L-S101N-V203Y, S24G-N25G-S53G-S78N-S87T-A88L-S89G-V203Y, S24G-N25G-S53G-S78N-S87T-A88L-S89G-S101N-V203Y, S87G-A88V-S89A-P129Q-S130G-G131S, N61P-S63H-S78N-S161P, T55P-N61P-S78N-S87T-A88L-S89G-S101N-V203Y, I111V-P129Q-S130G-G131S, T22N-S24A-T55P, I115V-N240K, S87G-A88V-S89A-A116N-N117S-N118G-P172H, S24G-N25G-S78N-S87T-A88L-S89G-S101N, S24G-N25G-I115V-A134T, T55P-A128S-P129D, I111V-S159K, N240K-A273S, S159K-L267V, I111V-P129Q-G211T, I115V-A273S, S89Y, S24R-A116N-N117S-N118G, N61E-A144K, P129Q-S130G-G131S-P239R, S87T-A88L-S89G-I115V, T55P-A92G, S145D-S159K-N240K-Q275E, S89Y-P129Q-S130G-G131S, P129Q-S130G-G131S-S162K, I111V-A134T, P40E-S53Y-S78Y-P86S-S87G-A88V, S24G-N25G-L75H-N76G, N61P-A128G-P129S-S130P, S24R-S145D, S24R-S145D-P239R-Q275E, S24R-S78N-S182P-L267V, S53G-N61P-S87T-A88L-S89G-S101N-V203Y, P5S-S87G-A88V-S89A-A116G-N117R, S53G-N61P-S78N-S87T-A88L-S89G-S101N-V203Y, Q59S-N61P-A116N-N117S-N118G, P239R-A273S, S53G-S78N-S87T-A88L-S89G-S101N-V203Y, S24R-P129V, I111V-P239R, S87T-A88L-S89G-S101N-V203Y, T55P-P129L, S87T-A88L-S89G-I111V, S145D-A273S, P129Q-S130G-G131S-T242R, S3F-S87T-A88L-S89G-G211T, S87G-A88V-S89A-S162K, S89Y-G211T, S87T-A88L-S89G-A144K, P129Q-S130G-G131S-S159K, A116N-N117S-N118G-P129Q-S130G-G131S, S24G-N25G-P129V, S24G-N25G-S78N-S87T-A88L-S89G-S101N-V203Y, N123G-A128G, N61P-N62Q-G100N-G102A-M124I, S24G-N25G-K141E-T242R, S87G-A88V-S89A-A116N-N117S-N118G-A144T, T55P-N61P-S87T-A88L-S89G-G110C-S130P, L75S-N76Y-A116S-N117G-N118R, S145D-S159K-K213L-P239R-N240K, S24R-S87T-A88L-S89G, G23A-S24G-N25G-P129V, A134T-K213L, S89Y-A273S, S24R-P239R, N123G-A128G-P129S, S89Y-P239R, S24G-N25G-A92G, N61P-S63H-I115V-A228V, A97G-A128G-Q217L, L75S-N76Y-P129V, S24R-P129L, S87G-A88V-S89A-P129Q-S182Y-S204Y-P239Q, S24R-A92G, S24R-A116S-N117G-N118R, G23A-S24G-N25G-A116G-N117R, S24G-N25G-P129L, S87T-A88L-S89G-S101G, G23A-S24G-N25G-P129L, S53G-N61P-G102A-V203Y, T55P-V147P, Y6Q-L75S-N76Y, N61P-S63H-V147P, S24R-V147P, S24G-N25G-V68C-A69G, S24G-N25G-N61P-L75S-N76Y-S101N-V203Y, L75S-N76Y-S78N-S101N-V203Y, L75S-N76Y-S78N-S87T-A88L-S89G-S101N-S130P, S24G-N25G-S53G-S101N-S130P-V203Y, G47E-M50I-L75S-N76Y-S162K, S53G-T55P-S87T-A88L-S89G-S101N-S130P-V203Y, S24G-N25G-L75S-N76Y-A128T-P129T-S130G-G131Q-S132C-A133G-A134T, P129Q-S130G-G131S-V147P, S53G-T55P-N61P-L75S-N76Y-S87T-A88L-S89G-G102A-S130P-V203Y, and S53G-T55P-N61P-L75S-N76Y-S101N-S130P-V203Y, and wherein the amino acid positions are numbered by correspondence with the amino acid sequence of *B. amyloliquefaciens* subtilisin BPN' set forth as SEQ ID NO:2.

The present invention also provides subtilisin variants, wherein the variant is a mature form having proteolytic activity and comprises the BPN'-v3 amino acid sequence (SEQ ID NO:4) comprising at least one set of amino acid substitutions selected from the group consisting of P40E-S78N-S87D-Y217L, P40E-Y217L, T22V-S78N-Q206E-K213N-Y217L, T22V-S78N-K213N-Y217L, S87D-Y217L, S78N-Y217L, K213N-Y217L, Q206E-Y217L, and T22V-Y217L, and wherein the amino acid positions are numbered by correspondence with the amino acid sequence of *B. amyloliquefaciens* subtilisin BPN' of SEQ ID NO:2.

The present invention also provides subtilisin variants, wherein each such variant is a mature form having proteolytic activity and the variant comprises the BPN'-v3 amino acid sequence (SEQ ID NO:4) comprising at least one set of amino acid substitutions selected from the group consisting of S87D-N76D-S78N, P40E-S78N-S87D, P40E-S87D, S78N-P40E, S87D-N76D, P40E, S78N-S87D, S87D, and S78N, and wherein the amino acid positions are numbered by correspondence with the amino acid sequence of *B. amyloliquefaciens* subtilisin BPN' of SEQ ID NO:2. In one aspect, the substitutions confer improved enzyme stability.

The present invention also provides subtilisin variants, wherein each such variant is a mature form having proteolytic activity and comprises the BPN'-v3 amino acid sequence (SEQ ID NO:4) comprising at least one set of amino acid substitutions selected from the group consisting of S101N, A137V, N61P, S130P, Q103N, S63T, G102A, N109D-S248R, S87R, S188D, S87D-S248R, S188D-S248R, S248D, N109D-S188D-S248R, N109D, S87R-S248R, N109D-S188R, N76D, 587D-N109D-S188D-S248R, S87R-N109D-S188D-S248R, S87R-S188R-S248R, A187D, N109D-S248D, S87R-N109R-S188R-S248R, F189D, G100N, S87R-N109D-S188D, S87D-N109D-S188D, S87R-S188D-S248D, N62D, and S87D-N109D-S188D-S248D, and wherein the amino acid positions are numbered by correspondence the positions of with the amino acid sequence of *B. amyloliquefaciens* subtilisin BPN' of SEQ ID NO:2.

The present invention also provides subtilisin variants, wherein each such variant is a mature form having proteolytic activity and comprises the BPN'-v3 amino acid sequence (SEQ ID NO:4) comprising at least one set of amino acid substitutions selected from S78N-L267V, S78N-S161P, S78N-I115V, S78N-A273S, S78N-G211T, S78N, S78N-I111V, S78N-V147L, S78N-I108V, S78N-S89Y, S78N-A138T, S78N-P172V, S78N-Q59G, P129T-V147Q-S159D-S161P-S183T-Q185T-G211A-S224A, Q059V-I108V-V147Q-G211A-N252Q, S78N-Y167A, S78N-A92G, S78N-P129L, N061A-S087E-M124I-S161P-S224A, S78N-N62Q, S78N-V68A, S063T-S101A-L126V-S183T-T244N, S78N-M124T, P040L-S053G-Q059V-N061A-N062Q-S063T-S087E-G100N, N062Q-G100N-S125A-S159D-N240S, V68A-G102A-G211A-S125A, and S053G-V068A-G102A-P129T-Q185T, and wherein the amino acid positions are numbered by correspondence with the amino acid residue positions of the amino acid sequence of *B. amyloliquefaciens* subtilisin BPN' set forth as SEQ ID NO:2.

The present invention also provides subtilisin variants, wherein each such variant is a mature form having proteolytic activity and comprises an amino acid sequence comprising at least one set of amino acid substitutions selected from the group consisting of G97A-G128S-Y217Q-S24G-N25G-N61P-S101N, G97A-G128S-Y217Q-S53G-N61P-S101N-V203Y, G97A-G128S-Y217Q-S24G-N25G-S53G-T55P-N61P-S101N-V203Y, G97A-G128A-Y217Q-S24G-N25G-S53G-N61P-S101N-V203Y, P52L-V68A-G97A-I111V, I111V-M124V-Y167A-Y217Q, Y104N-G128A-Y217Q, M124V-Y167A-Y217Q, I111V-M124V-Y217Q, P52L-V68A-G97A, G97A-I111V-M124V, V68A-A92G-G97A, G97A-I111V-M124V-Y167A-Y217Q, P52L-V68A-I111V-Y217Q, P52L-V68A-I111V, V68A-A92G-I111V, P52L-V68A-G97A-I111V-Y217Q, V68A-G97A-I111V, G97A-I111V-Y217Q, G97A-I111V-M124V-Y167A, S89Y-I111V-M124V, V68A-S89Y-I111V, V68A-A92G-Y217Q, I111V-Y167A-Y217Q, G97A-I111V-Y167A-Y217Q, G97A-I111V-M124V-Y217Q, V68A-I111V-Y167A-Y217Q, I111V-G128A-Y217Q, G97A-M124V-Y217Q, V68A-Y167A-Y217Q, I111V-M124V-Y167A, N62Q-G97A-I111V, G97A-M124V-Y167A-Y217Q, G97A-L126A-Y217Q, V68A-I111V-Y217Q, S89Y-M124V-Y217Q, and L96T-G97A-Y217Q, and wherein the positions are numbered by correspondence with the amino acid residue positions of the amino acid sequence of *B. amyloliquefaciens* subtilisin BPN' set forth as SEQ ID NO:2. Some such variants comprise the BPN' amino acid sequence (SEQ ID NO:2) comprising at least one set of amino acid substitutions selected from said group.

The present invention also provides subtilisin variants, wherein each such variant is a mature form having proteolytic activity and comprises a BPN' amino acid sequence comprising at least one, two, three, four, five, six, seven, eight, nine, ten, eleven or more substitutions selected from S182E, N109I, N117H, K237D, L257Q, P225N, S105H, S236I, L235H, S249E, N76E, S145N, N243D, R247N, E195N, A98K, S182N, S161H, G83H, G131D, T71C, K136Q, P40D, A187H, L250K, S9I, N76M, S132D, Q19F, E112H, S249P, S53D, V68E, D41I, K43H, V4H, A13Y, N62P, L196E, and V44D, and wherein the positions are numbered by correspondence with the amino acid residue positions of amino acid sequence of *B. amyloliquefaciens* subtilisin BPN' set forth as SEQ ID NO:2.

The present invention also provides dishwashing compositions comprising the subtilisin variant(s), and fabric cleaning compositions comprising the subtilisin variant(s). In some preferred aspects, the dishwashing and fabric cleaning compositions further comprise at least one additional enzyme. In some preferred aspects, the additional enzyme is selected from: a protease (e.g., a neutral metalloprotease, a wild type serine protease, or a second variant serine protease) a lipase, a cutinase, an amylase, a carbohydrase, a cellulase, a pectinase, a mannanase, an arabinase, a galactanase, a xylanase, a perhydrolase, an oxidase, and a peroxidase. Moreover, the present invention provides dishwashing methods, comprising the steps of: providing i) the dishwashing composition comprising the subtilisin variant, and ii) dishware in need of cleaning; and contacting the dishware with the dishwashing composition under conditions effective to provide cleaning of the dishware. Similarly, the present invention provides fabric cleaning methods, comprising the steps of: providing i) the fabric cleaning composition comprising the subtilisin variant, and ii) laundry in need of cleaning; and contacting the laundry with the fabric cleaning composition under conditions effective to provide cleaning of the laundry. In still further aspects, the present invention provides an isolated nucleic acid encoding the variant, an expression vector comprising the isolated nucleic acid in operable combination with a promoter, and/or host cells comprising the expression vector are provided.

The present invention also provides cleaning compositions comprising the subtilisin variants provided herein. In one aspect, the cleaning compositions comprise a liquid, gel, tablet, powder and/or granule detergent. In some further aspects, the cleaning compositions are selected from laundry detergents and dish detergents. In some preferred aspects, the cleaning compositions comprise laundry detergents. In some particularly preferred aspects, the cleaning compositions are heavy duty detergents. In some additional aspects, the cleaning compositions comprise dish detergents selected from hand dishwashing and automatic dishwashing detergents. In some further preferred aspects, the cleaning compositions provided herein further comprise at least one bleaching agent. In some additional aspects, the cleaning compositions provided herein are phosphate-free, while in some alternative aspects, the cleaning compositions provided herein are phosphate-containing detergents. In some still further aspects, the cleaning compositions provided herein are cold water detergents. In yet some additional aspects, the cleaning compositions provided herein further comprise at least one additional enzyme. In one aspect, the cleaning compositions comprise at least one additional enzyme selected from the group consisting of a hemicellulase, cellulase, peroxidase, protease, metalloprotease, xylanase, lipase, phospholipase, esterase, perhydrolase, cutinase, pectinase, pectate lyase, mannanase, keratinase, reductase, oxidase, phenoloxidase, lipoxygenase, ligninase, pullulanase, tannase, pentosanase, malanase, β-glucanase, arabinosidase, hyaluronidase, chondroitinase, laccase, and amylase; or mixtures of any thereof.

The present invention also provides methods for cleaning, comprising providing an item to be cleaned and a composition comprising at least one cleaning composition provided herein, and contacting them with the composition, under conditions effective to provide cleaning of the item. In one aspect, the methods further comprise the step of rinsing the item after contacting the item with the cleaning composition. In some preferred aspects, the item to be cleaned comprises dishware. In some alternative aspects, the item to be cleaned comprises fabric.

In some further aspects, any of the above mutations, deletions, insertions or combinations thereof can be applied to either the enzyme of SEQ ID NO:2 containing the mutation Y217L or the enzyme of SEQ ID NO:2 containing the mutations G97A-G128A-Y217Q.

In one aspect, the present invention provides a suitable cold water protease derived from a subtilisin, particularly subtilisin BPN' (SEQ ID NO:2) (i.e., a BPN' subtilisin variant). In one aspect, a cold water protease one, two, three, four, five, six, seven, eight, nine, ten, eleven or more of the following amino acid substitutions relative to SEQ ID NO:2: Q002W, P005K, P005L, P005Y, G007T, V008G, V008K, V008P, I011G, I011H, I011S, K012L, A013M, L016W, G023S, V026H, V026W, V026Y, K027P, V028Q, V028S, V028T, A029C, A029D, A029S, A029T, A029V, V030D, V030E, V030G, V030T, I031E, I031G, I031H, I031K, I031N, I031Q, I031S, I031Y, S033F, S033H, D036L, S037P, D041A, D041C, D041M, D041N, D041S, L042S, L042Y, V044H, V044Q, V044T, G046F, G046L, G046M, G046V, G047T, G047W, S049I, S049V, M050D, M050I, M050R, V051A, V051G, V051S, P052C, P052I, P052L, P052M, P052V, P052W, P052Y, E054R, N056G, N056I, N056K, N056M, N056Q, N056R, N056V, N056Y, P057I, P057K, P057L, P057R, P057T, P057V, F058T, Q059P, Q059W, N061P, N062D, N062M, N062Q, S063C, S063Q, S063T, G065Q, V068A, V068G, V068M, V068S, A069C, A069D, A069F, A069H, A069M, A069N, A069P, A069Q, A069R, A069T, T071D, T071E, T071G, T071K, T071M, V072D, V072G, V072K, V072Q, V072S, V072T, A073E, A073I, A073K, A073M, A073Q, A073S, A073V, A074E, A074F, A074H, A074I, A074L, A074M, A074Q, A074R, A074V, A074W, A074Y, L075A, N076A, N077G, N077L, N077P, N077Q, N077R, N077S, N077T, S078W, G080H, V081D, V081F, V081H, V081N, V081Q, V081R, V081W, L082G, L082N, L082W, A085I, A085T, A085V, P086A, P086G, P086M, P086Q, P086R, P086T, P086W, P086Y, S087F, S087I, S087L, S087M, S087Q, S087V, S087W, A088D, A088E, A088K, A088P, A088Q, S089D, S089Q, S089V, L090D, L090E, L090F, L090H, L090P, L090S, L090T, Y091L, Y091Q, Y091T, A092C, A092I, A092M, A092N, A092P, A092V, V093D, V093F, V093L, V093T, K094C, K094R, K094S, V095I, L096F, L096H, L096I, L096M, L096N, L096Q, L096S, L096T, L096V, L096W, L096Y, G097A, G097C, G097D, G097E, G097F, G097L, G097M, G097P, G097Q, G097S, G097V, G097W, G097Y, D099C, D099E, D099I, D099M, D099P, D099V, D099Y, G100D, G100E, G100H, G100I, G100K, G100M, G100Q, G100T, G100V, G100Y, S101A, S101E, S101G, S101N, S101P, S101Q, S101T, S101V, G102A, G102S, Q103E, Q103G, Q103H, Q103K, Q103N, Y104L, Y104M, Y104N, Y104T, Y104V, S105D, S105I, S105R, S105V, W106A, W106C, W106E, W106F, W106G, W106I, W106L, W106M, W106S, W106T, W106V, I107R, I107S, I107T, I108S, I108T, G110S, G110T, I111A, I111C, I111F, I111L, I111M, I111T, I111V, E112I, E112L, E112T, W113H, A114I, A114V, I115A, I115E, I115F, I115H, I115M, I115N, I115P, I115Q, I115R, I115S, I115T, I115V, I115Y, N117K, N117V, N117W, N118I, N118L, N118V, M119F, M119N, D120Y, I122R, I122S, I122T, N123A, N123C, N123G, N123S, M124A, M124H, M124N, M124Q, M124S, M124T, M124V, S125A, L126A, L126Q, L126S, L126T, L126Y, G128E, G128N, G128T, P129V, S130P, S132I, S132N, S132P, S132Q, S132V, A134I, A134L, A134M, L135I, L135T, L135V, L135W, L135Y, K136D, K136F, K136I, K136V, K136Y, A137P, A138D, A138E, A138F, A138H, A138Q, A138Y, A142G, A142I, A142T, A142V, V143W, A144P, G146L, G146T, G146Y, V147D, V147P, V147W, V147Y, V148N, V148Y, V149E, A151T, A153T, A153V, S159K, T164W, V165T, Y167A, Y167D, Y167E, Y167M, Y167P, Y167S, Y167T, P168L, P168T, G169C, K170E, K170N, K170P, K170Q, K170S, K170T, K170Y, Y171C, Y171D, Y171L, Y171N, Y171W, P172E, P172G, P172I, P172L, P172V, P172Y, S173H, S173W, S173Y, V174A, V174I, V174L, V174S, I175A, I175F, I175R, I175T, I175V, A176V, V177W, V180F, V180H, V180Q, S182W, N184A, N184L, N184V, Q185D, Q185E, Q185I, Q185S, Q185T, R186C, R186D, R186E, R186F, R186G, R186I, R186L, R186N, R186P, R186Q, R186S, R186T, R186V, R186W, R186Y, A187D, A187E, A187Q, S190G, S190N, Y192D, Y192E, Y192L, Y192Q, G193H, G193Q, G193T, G193V, P194E, P194I, P194L, P194M, P194N, P194T, P194V, E195C, E195K, E195W, L196I, L196M, L196T, L196V, D197I, D197M, M199F, M199Q, A200C, A200H, A200N, A200T, A200V, A200Y, P201L, P201T, P201V, V203G, I205L, I205T, T208C, T208L, T208M, T208P, T208V, L209C, L209W, P210C, P210D, P210E, P210F, P210G, P210Q, P210R, P210S, P210V, G211A, G211D, G211E, G211P, G211T, G211V, G211W, N212E, N212T, K213Q, K213T, Y214A, Y214D, Y214N, Y214P, Y214S, G215D, G215Q, G215V, A216E, Y217E, Y217L, Y217M, N218P, A223W, S224D, S224N, S224Q, H226E, H226T, V227G, V227L, V227S, A230H, A230N, A231W, A231Y, A232N, I234W, L235N, S236W, H238A, H238G, H238I, P239H, P239S, W241G, W241Q, R247H, R247L, R247W, R247Y, L250E, L250T, N252Q, T253Y, T254D, T254Q, T254R, T255L, T255P, K256G, K256R, G258P, Y263D, Y263K, Y263R, K265P, I268S, I268T, I268W, V270F, A273K, A273P, A273R, A273V, A273W, A274W, S182E, and N109I, wherein positions of the variant sequence are numbered by correspondence to positions of SEQ ID NO:2.

In another aspect, the invention provides suitable cold water proteases, including subtilisin variants, particularly variant of mature BPN' (SEQ ID NO:2), comprising one, two, three, four, five, six, seven, eight, nine, ten, eleven or more of the following sets of mutations relative to SEQ ID NO:2: N109D-Y217L-S248R, N109D-S188R-Y217L, S87D-Y217L-S248R, S87R-N109D-Y217L-S248R, S87R-N109D-S188D-Y217L-S248R, G128A-Y217Q, I111V-M124V, M124V-Y217Q, N62Q-G97A, S89Y-M124V, V68A, V68A-A92G, V68A-G97A, V68A-I111V, V68A-S89Y, V68A-V227T, V68A-Y217Q, W106F-Y217Q, G97A-G128A-Y217Q, G97A-L126A-Y217Q, G97A-M124V-L126A-Y217Q, G97A-N123G-Y217Q, L96T-G97A-Y217Q, M124V-L126A-Y217Q, N62Q-G128A-Y217Q, N62Q-G97A-Y217Q, G97N-G128A-Y217M, G97G-G128S-Y217E, G97A-G128A-Y217Q, G97M-G128S-Y217E, G97A-G128S-Y217Q, G97D-G128S-Y217Q, G97M-G128G-Y217M, G97G-G128S-Y217Q, G97S-G128S-Y217Q, G97G-G128A-Y217Q, G97S-G128A-Y217E, G97A-G128S-Y217L, G97A-G128A-Y217N, G97Q-G128S-Y217L, G97A-G128A-Y217M, G97A-G128A-Y217S, G97D-G128A-Y217Q, G97M-G128S-Y217Q, G97Q-G128G-Y217D-S87Y, G97S-G128A-Y217N, G97A-G128S-Y217T, G97D-G128S-Y217E, G97D-G128A-Y217L, G97G-G128S-Y217E-S78P-A272T, G97T-G128S-Y217D, G97D-G128A-Y217I, G97Q-G128S-Y217Q, G97G-G128A-Y217D, G97Q-G128A-Y217N, G97S-G128A-Y217M, G97S-G128S-Y217N, G97S-G128S-Y217M, G97E-G128S-Y217M, G97S-G128P-Y217Q, G97T-G128S-Y217Q, G97D-G128S-Y217Q-A73T, G97E-G128S-Y217N, G97G-G128A-Y217I, G97Q-

G128A-Y217D, G97Q-G128S-Y217M, G97R-G128T-Y217Q-S162P, G97S-G128S-Y217D, G97T-G128P-Y217I, G97Q-G128G-Y217E, G97C-G128G-Y217N, G97D-G128S-Y217H, G97M-G128S-Y217L, G97M-G128S-Y217N, G97S-G128S-Y217E, G97M-G128S-Y217I, G97A-G128P-Y217A, G97R-G128S-Y217D, G97A-G128A-Y217Q-S145D, G97A-G128A-Y217Q-P239R, G97A-G128A-Y217Q-N61E-P129E-S162K-K213L-N240K, G97A-G128A-Y217Q-N61E, G97A-G128A-Y217Q-P40E-A144K-K213L, G97A-G128A-Y217Q-P129E, G97A-G128A-Y217Q-N61E-P129E-S159K, G97A-G128A-Y217Q-K213L, G97A-G128A-Y217Q-S87D, G97A-G128A-Y217Q-Q206E, G97A-G128A-Y217Q-S24R-P40E-S145D-S159K-K213L, G97A-G128A-Y217Q-K265N, G97A-G128A-Y217Q-S24R, G97A-G128A-Y217Q-P40E, G97A-G128A-Y217Q-Q275E, G97A-G128A-Y217Q-P129E-S145D-N240K, G97A-G128A-Y217Q-A144K, G97A-G128A-Y217Q-S159K, G97A-G128A-Y217Q-S162K, G97A-G128A-Y217Q-N240K, G97A-G128A-Y217Q-S53G, G97A-G128A-Y217Q-S78N, G97A-G128A-Y217Q-S53G-S78N, G97A-G128A-Y217Q-S53G-I111V, G97A-G128A-Y217Q-S53G-N117S, G97A-G128A-Y217Q-S53G-S132N, G97A-G128A-Y217Q-Y104N-S132N, G97A-G128A-Y217Q-S53G-S78N-I111V, G97A-G128A-Y217Q-S53G-S78N-N117S, G97A-G128A-Y217Q-S53G-S78N-S132N, G97A-G128A-Y217Q-S53G-Y104N-S132N, G97A-G128A-Y217Q-S78N-Y104N-S132N, Y217L-V068C-A069G, Y217L-I079F-A098G, Y217L-P086T-S101D-Q103S-V147I, Y217L-A088T-P129S-G146D, Y217L-V093I-G128D-P129R, Y217L-Z096.01D-A098R, Y217L-Z096.01H-A098G, Y217L-G097S-Z097.01S-A098G-A273T, Y217L-A098S-D099G-G100D, Y217L-Z098.01N, Y217L-D099G-Z099.01N, Y217L-D099G-Z099.01S, Y217L-D099V-S101D, Y217L-Z099.01S, Y217L-G100D, Y217L-S101D-Q103H, Y217L-S101G-A151V, Y217L-S101H-G102S, Y217L-S101H-Q103D, Y217L-G102R-Q103C-Y104C-V192I, Y217L-Q103D, Y217L-V121I-I122S-N123C, Y217L-V121L-N123C, Y217L-I122S-N123S, Y217L-M124I, Y217L-M124V, Y217L-L126F-P129Z-S182N, Y217L-L126Y, Y217L-G127S-P129D, Y217L-Z127.01N-G128S-P129S, Y217L-G128H-P129Y, Y217L-G128S-P129D, Y217L-G128S-P129D-S248R, Y217L-G128S-P129G, Y217L-P129G-G131Z, Y217L-P129G-S130H-S132Z, Y217L-P129H-G131Z, Y217L-P129L, Y217L-P129S-S130H-S132Z, Y217L-P129Z, Y217L-P129Z-S130G, Y217L-P129Z-S130G-G131H-S132H, Y217L-P129Z-S130H, Y217L-S130V-G131D-S132I, G97A-G128A-Y217Q-A134T-K213L, G97A-G128A-Y217Q-G23A-S24G-N25G-P129V, G97A-G128A-Y217Q-S24R-P239R, and G97A-G128A-Y217Q-S24R-S87T-A88L-S89G, wherein positions of the variant sequence are numbered by correspondence to positions of SEQ ID NO:2.

In another aspect, the invention provides suitable cold water proteases, including subtilisin variants, particularly variants of mature BPN' (SEQ ID NO:2) comprise one, two, three, four, five, six, seven, eight, nine, ten, eleven or more of the following sets of mutations relative to SEQ ID NO:2: S87T-A88L-S89G-G97A-G128A-Y217Q, N61P-S63H-G97A-G128A-Y217Q, S87G-A88V-S89A-G97A-G128A-Y217Q, P86S-S87G-A88V-G97A-G128A-Y217Q, Q59S-N61P-G97A-G128A-Y217Q, S24G-N25G-G97A-G128A-Y217Q, N61P-N62S-G97A-G128A-Y217Q, G97A-G128A-P129Q-S130G-G131S-Y217Q, L75S-N76Y-G97A-G128A-Y217Q, G97A-G128A-V203Y-Y217Q, T55P-G97A-G128A-Y217Q, A88V-L90I-G97A-G128A-Y217Q, G97A-G128A-G211R-N212S-K213V-Y217Q, G23A-S24G-N25G-G97A-G128A-Y217Q, T22N-S24A-G97A-G128A-Y217Q, S24R-G97A-G128A-Y217Q, G97A-A98S-G128A-Y217Q, G97A-G128A-T158G-S159G-Y217Q, Q59E-N61P-G97A-G128A-Y217Q, G97A-A98E-G128A-Y217Q, G97A-G128A-Y217Q-P86S-S87G-A88V-A116N-N117S-N118G, G97A-G128A-Y217Q-S63T-P86S-S87G-A88V, G97A-G128A-Y217Q-P86S-S87G-A88V-P239R, G97A-G128A-Y217Q-S24G-N25G-N61P-N62S-P194L-A232T, G97A-G128A-Y217Q-P129Q-S130G-G131S-A133V-L267V, G97A-G128A-Y217Q-A134T-L267V, G97A-G128A-Y217Q-S24R-P40E-P129E-S159K-K265R, G97A-G128A-Y217Q-A134T-G211T, G97A-G128A-Y217Q-S24R-P129E, G97A-G128A-Y217Q-I111V-S161P, G97A-G128A-Y217Q-T55P-P129Q, G97A-G128A-Y217Q-I115V-L267V, G97A-G128A-Y217Q-P86S-S87G-A88V-A116S-N117G-N118R, G97A-G128A-Y217Q-V203Y-L267V, G97A-G128A-Y217Q-S24G-N25G-S78N-S101N-V203Y, G97A-G128A-Y217Q-P52S-T55P-V203Y, G97A-G128A-Y217Q-Q59S-N61P-A116S-N117G-N118R, G97A-G128A-Y217Q-S24G-N25G-P129Q-S130G-G131S, G97A-G128A-Y217Q-P86S-S87G-A88V-T242R, G97A-G128A-Y217Q-P40E-T55P-N269K, G97A-G128A-Y217Q-G23A-S24G-N25G-A116N-N117S-N118G, G97A-G128A-Y217Q-V8L-N25Y-P129Q-S130G-G131S, G97A-G128A-Y217Q-S24G-N25G-S53G-S78N-S87T-A88L-S89G-S101N, G97A-G128A-Y217Q-G211T-L267V, G97A-G128A-Y217Q-S24R-A116N-N117S-N118G, G97A-G128A-Y217Q-S24R-A128S-P129G, G97A-G128A-Y217Q-P129Q-S130G-G131S-N240K, G97A-G128A-Y217Q-N25Y-P129Q-S130G-G131S, G97A-G128A-Y217Q-S87T-A88L-S89G-A134T, G97A-G128A-Y217Q-P129Q-S130G-G131S-L267V, G97A-G128A-Y217Q-S87G-A88V-S89A-A116N-N117S-N118G, G97A-G128A-Y217Q-N61P-P129Q-S130G-G131S, G97A-G128A-Y217Q-N61P-S78N-S87T-A88L-S89G-S101N, G97A-G128A-Y217Q-T55P-P129V-P194S, G97A-G128A-Y217Q-T55P-P129V, G97A-G128A-Y217Q-S24G-N25G-T55P-S78N-S101N, G97A-G128A-Y217Q-T55P-S78N-I115V, G97A-G128A-Y217Q-N25Y-S87G-A88V-S89A, G97A-G128A-Y217Q-A134T-N240K, G97A-G128A-Y217Q-S24R-Q59S-N61P, G97A-G128A-Y217Q-G23A-S24G-N25G-P239R, G97A-G128A-Y217Q-T55P-A116S-N117G-N118R, G97A-G128A-Y217Q-A134T-S161P, G97A-G128A-Y217Q-S24G-N25G-S53G-N61P-S101N-V203Y, G97A-G128A-Y217Q-N25Y-Q59S-N61P, G97A-G128A-Y217Q-N25Y-P129Q-S130G-G131S-A137T, G97A-G128A-Y217Q-G23A-S24G-N25G-N61P-S63H, G97A-G128A-Y217Q-T55P-N61P-S78N-S101N-V203Y, G97A-G128A-Y217Q-P129Q-N240K, G97A-G128A-Y217Q-T55P-A134T, G97A-G128A-Y217Q-N25Y-N61P-S63H, G97A-G128A-Y217Q-S87T-A88L-S89G-P129S, G97A-G128A-Y217Q-T55P-L75H-N76G, G97A-G128A-Y217Q-S24G-N25G-S53G-S78N-S87T-A88L-S89G-S101N-V203Y, G97A-G128A-Y217Q-T55P-I115V, G97A-G128A-Y217Q-T55P-A116N-N117S-N118G, G97A-G128A-Y217Q-S24G-N25G-A116N-N117S-N118G, G97A-G128A-Y217Q-S24R-P129Q-S130G-G131S, G97A-G128A-Y217Q-G23A-S24G-N25G-G211R-N212S-K213V, G97A-G128A-Y217Q-S24G-N25G-T55P-N61P-S78N-S101N-V203Y, G97A-G128A-Y217Q-T55P-S78N-S87T-A88L-S89G-S101N, G97A-G128A-Y217Q-I115V-A273S, G97A-G128A-Y217Q-N25Y-T55P, G97A-G128A-Y217Q-S24G-N25G-S53G-T55P-N61P-S78N-S87T-A88L-S89G-S101N-V203Y, G97A-G128A-Y217Q-Q59S-N61P-N240K, G97A-G128A-Y217Q-S161P-L267V, G97A-G128A-Y217Q-S24G-

N25G-S53G-T55P-N61P-S78N-S87T-A88L-S89G-S101N, G97A-G128A-Y217Q-S87T-A88L-S89G-S101N, G97A-G128A-Y217Q-S24G-N25G-N61P-S101N, G97A-G128A-Y217Q-S24G-N25G-S53G-T55P-S101N-V203Y, G97A-G128A-Y217Q-N240K, G97A-G128A-Y217Q-S24G-N25G-S53G-T55P-S87T-A88L-S89G-S101N-V203Y, G97A-G128A-Y217Q-S24G-N25G-T55P-S101N, G97A-G128A-Y217Q-N61P-S63H-A128S-P129Q, G97A-G128A-Y217Q-S89Y-P129Q-S130G-G131S, G97A-G128A-Y217Q-P129Q-S130G-G131S-V203Y, G97A-G128A-Y217Q-I115V-N240K, G97A-G128A-Y217Q-S53G-N61P-S87T-A88L-S89G-S101N-V203Y, G97A-G128A-Y217Q-S161P-V203Y, G97A-G128A-Y217Q-S87T-A88L-S89G-N240K, G97A-G128A-Y217Q-S87T-A88L-S89G-P239R, G97A-G128A-Y217Q-T55P-N61P-S78N-S87T-A88L-S89G-S101N-V203Y, G97A-G128A-Y217Q-S24G-N25G-I115V-A134T, G97A-G128A-Y217Q-Y6Q-P129Q-S130G-G131S, G97A-G128A-Y217Q-T55P-S78N-S89Y, G97A-G128A-Y217Q-S24G-N25G-T55P-S78N-A88V-S101N, G97A-G128A-Y217Q-N61P-S63H-S78N-I111V-A134T, G97A-G128A-Y217Q-S24G-N25G-S53G-T55P-S78N-S101N, G97A-G128A-Y217Q-S24G-N25G-S53G-S78N-S101N-V203Y, G97A-G128A-Y217Q-S53G-N61P-S101N-V203Y, G97A-G128A-Y217Q-S53G-T55P-S78N-S101N-V203Y, G97A-G128A-Y217Q-S53G-T55P-N61P-S78N-S87T-A88L-S89G-S101N, G97A-G128A-Y217Q-N240K-A273S, G97A-G128A-Y217Q-S78N-S87T-A88L-S89G-S101N, G97A-G128A-Y217Q-Q59S-N61P-S87T-A88L-S89G, G97A-G128A-Y217Q-N61P-S63H-S78N-S161P, G97A-G128A-Y217Q-N61P-S63H-S78N-I111V, G97A-G128A-Y217Q-T55P-A128S-P129Q, G97A-G128A-Y217Q-N61P-S78N-S101N-V203Y, G97A-G128A-Y217Q-N61E-A144K, G97A-G128A-Y217Q-A134T-P239R, G97A-G128A-Y217Q-S24G-N25G-S53G-S78N-S87T-A88L-S101N-V203Y, G97A-G128A-Y217Q-S24G-N25G-S53G-T55P-N61P-S101N-V203Y, G97A-G128A-Y217Q-N61P-S78N-S87T-A88L-S89G-S101N-V203Y, G97A-G128A-Y217Q-T55P-N240K, G97A-G128A-Y217Q-S24G-N25G-S87T-A88L-S89G-S101N, G97A-G128A-Y217Q-P129Q-S130G-G131S-P239R, G97A-G128S-Y217Q, G97A-G128A-Y217Q-S53G-N61P-S101N, G97A-G128A-Y217Q-I111V-P129Q-G211T, G97A-G128A-Y217Q-S24G-N25G-S53G-S101N-V203Y, G97A-G128A-Y217Q-Q59S-N61P-S87G-A88V-S89A, G97A-G128A-Y217Q-S24G-N25G-S78N-S87T-A88L-S89G-S101N, G97A-G128A-Y217Q-P129Q-S130G-G131S-S162K, G97A-G128A-Y217Q-T55P-P129Q-S130G-G131S, G97A-G128A-Y217Q-T55P-V203Y, G97A-G128A-Y217Q-S87G-A88V-S89A-P129Q-S130G-G131S, G97A-G128A-Y217Q-S24G-N25G-S53G-T55P-N61P-S78N-S87T-A88L-S89G, G97A-G128A-Y217Q-I111V-P129Q-S130G-G131S, G97A-G128A-Y217Q-I111V-A273S, G97A-G128A-Y217Q-N61P-S87T-A88L-S89G, G97A-G128A-Y217Q-T22N-S24A-N61P-S63H, G97A-G128A-Y217Q, G97A-G128A-Y217Q-S53G-S78N-S87T-A88L-S89G-S101N-P129S-V203Y, G97A-G128A-Y217Q-S159K-L267V, G97A-G128A-Y217Q-P40E-S53Y-S78Y-P86S-S87G-A88V, G97A-G128A-Y217Q-S24R-S145D, G97A-G128A-Y217Q-I111V-S159K, G97A-G128A-Y217Q-T55P-P129L, G97A-G128A-Y217Q-Q59S-N61P-V203Y, G97A-G128A-Y217Q-T55P-S78N-S87T-A88L-S89G-S101N-V203Y, G97A-G128A-Y217Q-S24G-N25G-S53G-S78N-S101N, G97A-G128A-Y217Q-S53G-N61P-S78N-S87T-A88L-S89G-S101N-V203Y, G97A-G128A-Y217Q-S89Y, G97A-G128A-Y217Q-S24R-P129V, G97A-G128A-Y217Q-S87G-A88V-S89A-A116N-N117S-N118G-P172H, G97A-G128A-Y217Q-I111V-A134T, G97A-G128A-Y217Q-Q59S-N61P-P129Q-S130G-G131S, G97A-G128A-Y217Q-P5S-S87G-A88V-S89A-A116G-N117R, Y217Q-N61P-A97G-G102A-A128G-P129S, G97A-G128A-Y217Q-S24G-N25G-S53G-N61P-S78N, G97A-G128A-Y217Q-S145D-S159K-N240K-Q275E, G97A-G128A-Y217Q-T55P-A128S-P129D, G97A-G128A-Y217Q-G23A-S24G-N25G-A128S-P129D, G97A-G128A-Y217Q-S24G-N25G-S53G-S78N-S87T-A88L-S89G-V203Y, G97A-G128A-Y217Q-I111V-P239R, G97A-G128A-Y217Q-S87G-A88V-S89A-S162K, G97A-G128A-Y217Q-S87T-A88L-S89G-I115V, G97A-G128A-Y217Q-S24G-N25G-T55P-S78N, G97A-G128A-Y217Q-T55P-A92G, G97A-G128A-Y217Q-S24G-N25G-S53G-S87T-A88L-S89G-V203Y, G97A-G128A-Y217Q-T22N-S24A-T55P, G97A-G128A-Y217Q-S53G-S87T-A88L-S89G-S101N-V203Y, G97A-G128A-Y217Q-S24G-N25G-S53G-T55P-S78N-S87T-A88L-S89G, G97A-G128A-Y217Q-P129Q-S130G-G131S-S159K, G97A-Y217Q-N61P-N62Q-G100N-A128G, G97A-G128A-Y217Q-S24R-S78N-S182P-L267V, G97A-G128A-Y217Q-P239R-A273S, G97A-G128A-Y217Q-S53G-S78N-S87T-A88L-S89G-S101N-V203Y, G97A-G128A-Y217Q-P129Q-S130G-G131S-T242R, G97A-G128A-Y217Q-S3F-S87T-A88L-S89G-G211T, G97A-G128A-Y217Q-S24G-N25G-L75H-N76G, G97A-G128A-Y217Q-S53G-T55P-N61P-S78N-S87T-A88L-S89G, G97A-G128A-Y217Q-S87T-A88L-S89G-A144K, G97A-G128A-Y217Q-S78N-S87T-A88L-S89G-V203Y, G97A-G128A-Y217Q-Q59S-N61P-A116N-N117S-N118G, G97A-G128A-Y217Q-S87T-A88L-S89G-I111V, G97A-G128A-Y217Q-S24R-S145D-P239R-Q275E, G97A-G128A-Y217Q-S145D-A273S, G97A-G128A-Y217Q-S24G-N25G-K141E-T242R, G97A-G128A-Y217Q-S87T-A88L-S89G-S101N-V203Y, G97A-G128A-Y217Q-A116N-N117S-N118G-P129Q-S130G-G131S, G97A-G128A-Y217Q-S89Y-G211T, G97A-G128A-Y217Q-S87G-A88V-S89A-A116N-N117S-N118G-A144T, G97A-G128A-Y217Q-S24G-N25G-S78N-S87T-A88L-S89G-S101N-V203Y, G97A-G128A-Y217Q-S24G-N25G-P129V, G97A-Y217Q-N61P-A128G-P129S-S130P, G97A-G128A-Y217Q-T55P-N61P-S87T-A88L-S89G-G110C-S130P, G97A-Y217Q-N123G-A128G, G97A-G128A-Y217Q-N61P-N62Q-G100N-G102A-M124I, S78N-G97A-G128A-Y217Q, G97A-S101N-G128A-Y217Q, G97A-G128A-A137V-Y217Q, N61P-G97A-G128A-Y217Q, G97A-G128A-S130P-Y217Q, G97A-Q103N-G128A-Y217Q, S63T-G97A-G128A-Y217Q, G97A-G102A-G128A-Y217Q, G97A-N109D-G128A-Y217Q-S248R, S87R-G97A-G128A-Y217Q, G97A-G128A-S188D-Y217Q, S87D-G97A-G128A-Y217Q-S248R, G97A-G128A-S188D-S248R-Y217Q, G97A-G128A-S248D-Y217Q, S78N-G97A-G128A-Y217Q-L267V, S78N-G97A-G128A-Y217Q-S161P, S78N-G97A-G128A-Y217Q-I115V, S78N-G97A-G128A-Y217Q-A273S, S78N-G97A-G128A-Y217Q-G211T, S78N-G97A-G128A-Y217Q, S78N-G97A-G128A-Y217Q-I111V, S78N-G97A-G128A-Y217Q-V147L, S78N-G97A-G128A-Y217Q-I108V, S78N-G97A-G128A-Y217Q-S89Y, and S78N-G97A-G128A-Y217Q-A138T, wherein positions of the variant sequence are numbered by correspondence to positions of SEQ ID NO:2.

In another aspect, the cold water protease is variant of subtilisin BPN' having SEQ ID NO:2, wherein the variant comprises three, four, five, six, seven, eight, nine, ten, eleven, twelve, thirteen, fourteen, fifteen, or more mutations selected from amino acid positions 24, 25, 40, 52, 53, 55, 58, 59, 61, 62, 63, 68, 78, 86, 87, 88, 89, 92, 96, 97, 100, 101, 103, 104, 106, 111, 114, 115, 116, 117, 118, 123, 124, 125, 126, 128, 129, 130, 131, 132, 133, 134, 144, 145, 159, 161, 162, 167, 194, 203, 206, 213, 217, 227, 232, 239, 240, 242, 265, 267, and 275, wherein the positions of the variant sequence are numbered by correspondence to positions in the amino acid sequence of SEQ ID NO:2.

In another aspect, the cold water protease is variant of subtilisin BPN' comprising SEQ ID NO:2 (i.e., a BPN' subtilisin variant), wherein the variant comprises a total of three, four, five, six, seven, eight, nine, ten, eleven, twelve, thirteen, fourteen, fifteen or more mutations selected from groups (a) and (b): (a) charged mutations selected from the group consisting of N61E, A144K, P129E, P239R, P40E, Q103E, Q206E, Q7275E, S145D, S159K, S162K, S24R, S63H, S87D and T242R; and (b) neutral mutations selected from the group consisting of A114G, A116N, A133V, A134T, A232T, A88V, A92G, F58G, G100T, G128A, G131S, G97A, I111V, I115V, K213L, K265N, L126A, L267V, L96T, M124V, N117S, N118G, N123G, N240K, N25G, N61P, N62Q, N62R, N62S, P129Q, P129V, P194L, P239V, P52L, P86S, Q59S, S101N, S125A, S130G, S132N, S161P, S24G, S53G, S78N, S87G, S89Y, T55P, V203Y, V227T, V68A, W106F, Y104N, Y167A, and Y217Q, wherein the positions of the variant sequence are numbered by correspondence to positions in the amino acid sequence of SEQ ID NO:2.

Nucleic Acids of the Invention

The invention provides isolated, non-naturally occurring, or recombinant nucleic acids (also referred to herein as "polynucleotides"), which may be collectively referred to as "nucleic acids of the invention" or "polynucleotides of the invention", which encode polypeptides (e.g., protease variants) of the invention. Nucleic acids of the invention, including all described below, are useful in recombinant production (e.g., expression) of polypeptides of the invention, typically through expression of a plasmid expression vector comprising a sequence encoding the polypeptide of interest or fragment thereof. As discussed above, polypeptides include protease variant polypeptides, including subtilisin variant polypeptides having enzymatic activity (e.g., proteolytic activity) which are useful in cleaning applications and cleaning compositions for cleaning an item or a surface (e.g., surface of an item) in need of cleaning.

The invention includes an isolated, recombinant, substantially pure, or non-naturally occurring nucleic acid comprising a polynucleotide sequence encoding any protein, polypeptide, or protease variant (including any fusion protein, etc.) of the invention described above in the section entitled "Polypeptides of the Invention" and elsewhere herein, including, but not limited to, the Examples, including Part I Examples and Part II Examples, or a complementary polynucleotide sequence thereof. The invention also provides an isolated, recombinant, substantially pure, or non-naturally-occurring nucleic acid comprising a polynucleotide sequence encoding a combination of two or more of any polypeptides, proteins, or protease variants (including any fusion protein) of the invention described above and elsewhere herein, including, but not limited to, the Examples, including Part I Examples and Part II Examples.

In a tenth aspect, the invention provides an isolated, non-naturally occurring, or recombinant nucleic acid comprising a polynucleotide sequence encoding a variant (or polypeptide as in the third aspect) of the first, second, third, fourth, fifth, sixth, seventh, eighth, or ninth aspect of the invention, or a complementary polynucleotide sequence thereof.

In an eleventh aspect, the invention provides an isolated, non-naturally-occurring, or recombinant nucleic acid comprising a polynucleotide sequence having at least 60%, 70%, 80%, 85%, 90%, 91%, 92%, 93%, 94%, 95%, 96%, 97%, 98%, 99% or 100% sequence identity to the polynucleotide sequence set forth in SEQ ID NO:3 or SEQ ID NO:5, or a complementary polynucleotide sequence thereof.

The present invention further provides nucleic acid encoding a protease variant comprising an amino acid sequence which differs from the amino acid sequence of SEQ ID NO:2, and wherein the total net charge of the protease variant is +1, +2, +3, +4, +5, 0, −1, −2, −3, −4, or −5 relative to the total net charge of the *B. amyloliquefaciens* BPN' subtilisin protease, and wherein amino acid positions of the protease variant are numbered according to the numbering of corresponding amino acid positions in the amino acid sequence of *Bacillus amyloliquefaciens* subtilisin BPN' shown in SEQ ID NO:2 as determined by alignment of the protease variant amino acid sequence with the *Bacillus amyloliquefaciens* subtilisin BPN' amino acid sequence.

The present invention provides nucleic acids encoding a subtilisin variant of *B. amyloliquefaciens* BPN' subtilisin protease, wherein the BPN' subtilisin protease comprises the amino acid sequence shown in SEQ ID NO:2, and wherein the protease variant comprises an amino acid sequence which differs from the amino acid sequence of SEQ ID NO:2 in no more than two, three, four, five, six, seven, eight, nine, 10, 11, 12, 13, 14, 15, 16, 17, 18, 19, 20, 21, 22, 23, 24, or 25 mutations at amino acid positions selected from amino acid positions 1-275, wherein the amino acid positions of the subtilisin variant are numbered by correspondence with the amino acid sequence of *B. amyloliquefaciens* subtilisin BPN' set forth as SEQ ID NO:2, wherein amino acid positions of the protease variant are numbered according to the numbering of corresponding amino acid positions in the amino acid sequence of *Bacillus amyloliquefaciens* subtilisin BPN' shown in SEQ ID NO:2 as determined by alignment with the protease variant.

The present invention provides nucleic acids encoding a subtilisin variant comprising an amino acid sequence which differs from the amino acid sequence of SEQ ID NO:2, and wherein the total net charge of the protease variant is +1, +2, +3, +4, +5, 0, −1, −2, −3, −4, or −5 relative to the total net charge of the *Bacillus lentus* subtilisin BPN' protease, and wherein amino acid positions of the protease variant are numbered according to the numbering of corresponding amino acid positions in the amino acid sequence of *Bacillus amyloliquefaciens* subtilisin BPN' shown in SEQ ID NO:2 as determined by alignment of the protease variant amino acid sequence with the *Bacillus amyloliquefaciens* subtilisin BPN' amino acid sequence.

The above low ionic strength protease variants may form part of a detergent composition that is diluted in water, typically within a laundry washing machine, to form a laundry detergent wash liquor, whose conductivity is from about 0.1 mS/cm to about 3 mS/cm, from about 0.3 mS/cm to about 2.5 mS/cm, or even from about 0.5 mS/cm to about 2 mS/cm. The protease variants may be high ionic strength protease variants. Such high ionic strength protease variants comprise two or more mutations, and have a total net charge of +5, +4, +3, +2, +1 or 0 relative to wild-type BPN' subtilisin protease wild-type shown in SEQ ID NO:2.

The above high ionic strength protease variants may form part of a detergent composition that is diluted in water, typically within a laundry washing machine, to form a laundry detergent wash liquor, whose conductivity is from about 3 mS/cm to about 30 mS/cm, from about 3.5 mS/cm to about 20 mS/cm, or even from about 4mS/cm to about 10 mS/cm.

The charge of the protease variants is expressed relative to BPN' having the amino acid sequence of SEQ ID NO:2. The amino acids that impart a single negative charge are D and E and those that impart a single positive charge are R, H and K. Any amino acid change versus SEQ ID NO:2 that changes a charge is used to calculate the charge of the protease variant. For example, introducing a negative charge mutation from a wild-type neutral position will add a net charge of −1 to the protease variant, whereas introducing a negative charge mutation (D or E) from a wild-type positive amino acid residue (R, H or K) will add a net charge of −2. Summing the charge changes from all the amino acid residues that are different for the protease variant versus BPN' having the amino acid sequence of SEQ ID NO:2 gives the charge change of the protease variant. Without wishing to be bound by theory, it is believed that: the preferred charge range for cold water proteases to be used in low conductivity laundry detergent solutions is −5, −4, −3, −2, −1, 0, particularly −2, −1; the preferred charge range for cold water proteases to be used in high conductivity laundry detergent solutions is +5, +4, +3, +2, +1, 0, particularly +2, +1. By correctly selecting the charge unexpectedly improved levels of cold water cleaning performance can be obtained. "Low conductivity laundry detergent solutions" are defined as having a conductivity of from about 0.1 mS/cm to about 3 mS/cm, from about 0.3 mS/cm to about 2.5 mS/cm, or even from about 0.5 mS/cm to about 2 mS/cm. "High conductivity laundry detergent solutions" are defined as having a conductivity of from about 3 mS/cm to about 30 mS/cm, from about 3.5 mS/cm to about 20 mS/cm, or even from about 4 mS/cm to about 10 mS/cm. It is intended that the above examples be non-limiting. Once mutations are combined to optimize cold water performance, the enzyme charge can also be balanced by mutations in further positions.

The invention includes cold water proteases and products comprising at least one cold water protease. In one aspect, the cold water protease is a variant of subtilisin BPN' having SEQ ID NO:2, said variant comprising an amino acid sequence having one or more mutations, and having a total net charge of −1, 0 or +1 relative to wild-type BPN' (SEQ ID NO:2). The amino acids that impart negative charge are typically D and E and those that impart positive charge are typically R, H and K. Without wishing to be bound by theory, it is believed that this charge range (−1, 0, +1) is the optimal charge to deliver cold water performance. However, these examples should be viewed as non-limiting. In one aspect, once mutations are combined to optimize cold water performance, the enzyme charge is balanced by mutations in further positions.

The invention provides an isolated, recombinant, substantially pure, or non-naturally occurring protease variant (e.g., subtilisin variant) having proteolytic activity, said protease variant comprising an amino acid sequence which differs from the amino acid sequence shown in SEQ ID NO:2 by 50, 45, 40, 35, 30, 25, 20, 19, 18, 17, 16, 15, 14, 13, 12, 11, 10, 9, or 8 amino acid residues, wherein amino acid positions are numbered according to the numbering of corresponding amino acid positions in the amino acid sequence of *Bacillus amyloliquefaciens* subtilisin BPN' shown in SEQ ID NO:2, as determined by alignment of the protease variant amino acid sequence with the *Bacillus amyloliquefaciens* subtilisin BPN' amino acid sequence, wherein the subtilisin variant includes the amino acid sequence of BPN'-v3 (SEQ ID NO:4) or BPN'-v36 (SEQ ID NO:6).

In one aspect, the invention provides an isolated, recombinant, substantially pure, or non-naturally occurring protease variant (e.g., subtilisin variant) having proteolytic activity, said protease variant comprising an amino acid sequence which differs from the amino acid sequence shown in SEQ ID NO:2 by no more than 50, 45, 40, 35, 30, 25, 20, 19, 18, 17, 16, 15, 14, 13, 12, 11, 10, 9, 6, 5, 4, 3, 2 amino acid residues, wherein amino acid positions are numbered according to the numbering of corresponding amino acid positions in the amino acid sequence of *Bacillus amyloliquefaciens* subtilisin BPN' shown in SEQ ID NO:2, as determined by alignment of the protease variant amino acid sequence with the *Bacillus amyloliquefaciens* subtilisin BPN' amino acid sequence, as set forth herein.

The invention includes an isolated, recombinant, or non-naturally occurring nucleic acid comprising a polynucleotide sequence encoding: (a) at least one protease variant of the invention, including any protease variant described herein, including, but not limited to, those protease variants set forth in the Part I Examples, (b) at least one cold water protease of the invention, or (c) at least one protease variant of the invention, including any protease variant described herein, including, but not limited to, a Series I GG36 variant set forth in the Part II Examples, or a complementary polynucleotide sequence of any thereof. In another aspect, the invention provides an expression vector comprising at least one nucleic acid of the invention. The expression vector may be operably linked to a promoter.

In another aspect, the invention provides a nucleic acid comprising a polynucleotide sequence having at least 60%, 70%, 80%, 85%, 90%, 91%, 92%, 93%, 94%, 95%, 96%, 97%, 98%, 99% or 100% sequence identity to the polynucleotide sequence set forth in SEQ ID NO:3 or SEQ ID NO:5, or a complementary polynucleotide sequence thereof.

Nucleic acids of the invention can be generated by using any suitable synthesis, manipulation, and/or isolation techniques, or combinations thereof. For example, a polynucleotide of the invention may be produced using standard nucleic acid synthesis techniques, such as solid-phase synthesis techniques that are well-known to those skilled in the art. In such techniques, fragments of up to 50 or more nucleotide bases are typically synthesized, then joined (e.g., by enzymatic or chemical ligation methods, or polymerase mediated recombination methods) to form essentially any desired continuous nucleic acid sequence. The synthesis of the nucleic acids of the invention can be also facilitated (or alternatively accomplished) by any suitable method known in the art, including but not limited to chemical synthesis using the classical phosphoramidite method (see, e.g., Beaucage et al. Tetrahedron Letters 22:1859-69 (1981)); or the method described by Matthes et al., EMBO J. 3:801-805 (1984), as is typically practiced in automated synthetic methods. Nucleic acids of the invention also can be produced by using an automatic DNA synthesizer. Customized nucleic acids can be ordered from a variety of commercial sources (e.g., The Midland Certified Reagent Company, the Great American Gene Company, Operon Technologies Inc., and DNA2.0). Other techniques for synthesizing nucleic acids and related principles are known in the art (see, e.g., Itakura et al., Ann. Rev. Biochem. 53:323 (1984); and Itakura et al., Science 198:1056 (1984)).

As indicated above, recombinant DNA techniques useful in modification of nucleic acids are well known in the art. For example, techniques such as restriction endonuclease digestion, ligation, reverse transcription and cDNA production, and polymerase chain reaction (e.g., PCR) are known and readily employed by those of skill in the art. Nucleotides of the invention may also be obtained by screening cDNA libraries (e.g., cDNA libraries generated using mutagenesis techniques commonly used in the art, including those described herein) using one or more oligonucleotide probes that can hybridize to or PCR-amplify polynucleotides which encode a protease variant polypeptide(s) of the invention. Procedures for screening and isolating cDNA clones and PCR amplification procedures are well known to those of skill in the art and described in standard references known to those skilled in the art. Some nucleic acids of the invention can be obtained by altering a naturally occurring polynucleotide backbone (e.g., that encodes an enzyme or parent protease) by, for example, a known mutagenesis procedure (e.g., site-directed mutagenesis, site saturation mutagenesis, and in vitro recombination).

The invention includes nucleic acids that hybridize to a target nucleic acid of the invention (e.g., SEQ ID NO:3 or 5), or a complementary polynucleotide sequence thereof, wherein hybridization is over substantially the entire length of the target nucleic acid. The hybridizing nucleic acid may hybridize to a nucleotide sequence of the invention under at least stringent conditions or under at least high stringency conditions. Moderately stringent, stringent, and highly stringent hybridization conditions for nucleic acid hybridization experiments are known. Examples of factors that can be combined to achieve such levels of stringency are briefly discussed herein.

Nucleic acids hybridize due to a variety of well-characterized physico-chemical forces, such as hydrogen bonding, solvent exclusion, base stacking and the like. An extensive guide to the hybridization of nucleic acids is found in P. Tijssen (1993) Laboratory Techniques in Biochemistry and Molecular Biology—Hybridization with Nucleic Acid Probes, vol. 24, part I, chapter 2, "Overview of principles of hybridization and the strategy of nucleic acid probe assays," (Elsevier, N.Y.) (hereinafter "Tijssen"). See also Hames and Higgins (1995) Gene Probes 1 and 2. An indication that two nucleic acid sequences are substantially identical is that the two molecules hybridize to each other under at least stringent conditions. Stringent hybridization conditions in the context of nucleic acid hybridization experiments, such as Southern and northern hybridizations, are sequence dependent, and are different under different environmental parameters. High stringency conditions are typically selected such that hybridization occurs at about 5° C. or less than the thermal melting point (Tm) for the specific sequence at a defined ionic strength and pH. The Tm is the temperature (under defined ionic strength and pH) at which 50% of the test sequence hybridizes to a perfectly matched probe. The Tm indicates the temperature at which the nucleic acid duplex is 50% denatured under the given conditions and its represents a direct measure of the stability of the nucleic acid hybrid. Thus, the Tm corresponds to the temperature corresponding to the midpoint in transition from helix to random coil; it depends on length, nucleotide composition, and ionic strength for long stretches of nucleotides. Under stringent conditions, a probe will typically hybridize to its target subsequence, but to no other sequences. Very stringent condition" are selected to be equal to the Tm for a particular probe.

The Tm of a DNA-DNA duplex can be estimated using equation (1): Tm (° C.)=81.5° C.+16.6 ($\log_{10}$M)+0.41(% G+C)−0.72(% f)−500/n, where M is the molarity of the monovalent cations (usually Na+), (% G+C) is the percentage of guanosine (G) and cytosine (C) nucleotides, (% f) is the percentage of formalize and n is the number of nucleotide bases (i.e., length) of the hybrid. The Tm of an RNA-DNA duplex can be estimated using equation (2): Tm (° C.)=79.8° C.+18.5 ($\log_{10}$M)+0.58(% G+C)−11.8(% G+C)$^2$−0.56(% f)−820/n, where M is the molarity of the monovalent cations (usually Na+), (% G+C) is the percentage of guanosine (G) and cytosine (C) nucleotides, (% f) is the percentage of formamide and n is the number of nucleotide bases (i.e., length) of the hybrid. Equations 1 and 2 above are typically accurate only for hybrid duplexes longer than about 100-200 nucleotides. The Tm of nucleic acid sequences shorter than 50 nucleotides can be calculated as follows: Tm (° C.)=4G+C)+2(A+T), where A (adenine), C, T (thymine), and G are the numbers of the corresponding nucleotides.

Non-hybridized nucleic acid material is typically removed by a series of washes, the stringency of which can be adjusted depending upon the desired results, in conducting hybridization analysis. Low stringency washing conditions (e.g., using higher salt and lower temperature) increase sensitivity, but can product nonspecific hybridization signals and high background signals. Higher stringency conditions (e.g., using lower salt and higher temperature that is closer to the hybridization temperature) lower the background signal, typically with only the specific signal remaining. For additional guidance, see Hames and Higgins, supra.

Exemplary stringent conditions for analysis of at least two nucleic acids comprising at least 100 nucleotides include incubation in a solution or on a filter in a Southern or northern blot comprises 50% formalin (or formamide) with 1 milligram (mg) of heparin at 42° C., with the hybridization being carried out overnight. A regular stringency wash can be carried out using a solution comprising 0.2×SSC buffer wash at about 65° C. for about 15 minutes (see Sambrook et al. (1989) Molecular Cloning: A Laboratory Manual, Cold Spring Harbor Press, and the third edition thereof (2001) for a description of SSC buffer). The regular stringency wash can be preceded by a low stringency wash to remove background probe signal. A low stringency wash can be carried out in, for example, a solution comprising 2×SSC buffer at about 40° C. for about 15 minutes. A highly stringent wash can be carried out using a solution comprising 0.15 M NaCl at about 72° C. for about 15 minutes. Exemplary moderate stringency conditions include overnight incubation at 37° C. in a solution comprising 20% formalin (or formamide), 0.5×SSC, 50 mM sodium phosphate (pH 7.6), 5×Denhardt's solution, 10% dextran sulfate, and 20 mg/ml denatured sheared salmon sperm DNA, followed by washing the filters in 1×SSC at about 37-50° C. High stringency conditions are conditions that (a) use low ionic strength and high temperature for washing, such as 0.015 M sodium chloride/0.0015 M sodium citrate/0.1% sodium dodecyl sulfate (SDS) at 50° C., (b) employ a denaturing agent during hybridization, such as formamide, e.g., 50% (v/v) formamide with 0.1% bovine serum albumin (BSA)/0.1% Ficoll/0.1% polyvinylpyrrolidone (PVP)/50 mM sodium phosphate buffer at pH 6.5 with 750 mM sodium chloride, 75 mM sodium citrate at 42° C., or (c) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42° C. with washes at (1) 42° C. in 0.2×SSC, (2) 55° C. in 50% formamide, and (3) 55° C. in 0.1×SSC (preferably with EDTA). A signal to noise ratio of 2× or 2.5×-5× that observed for an unrelated probe in the particular hybridization assay indicates detection of a specific hybridization. Detection of at least stringent hybridization between two sequences in the context of the present invention indicates relatively strong structural similarity or homology to a nucleic acid of the invention.

Vectors, Cells, and Methods for Making Protease Variant Polypeptides of the Invention A variety of methods are known in the art that are suitable for generating modified polynucleotides of the invention that encode protease variants of the invention (such as cold water proteases of the invention), including, but not limited to, e.g., site-saturation mutagenesis, scanning mutagenesis, insertional mutagenesis, deletion mutagenesis, random mutagenesis, site-directed mutagenesis, and directed-evolution, as well as various other recombinatorial approaches. Methods for making modified polynucleotides and proteins (e.g., protease variants) include DNA shuffling methodologies (see, e.g., Stemmer W P, Proc. Natl. Acad. Sci. USA 91(22):10747-51 (1994)); methods based on non-homologous recombination of genes, e.g., ITCHY (Ostermeier et al., Bioorg. Med. Chem. 7:2139-44 [1999]); SCRATCHY (Lutz et al., Proc. Natl. Acad. Sci. USA 98:11248-53 [2001]); SHIPREC (Sieber et al., Nat. Biotechnol. 19:456-60 [2001]); NRR (Bittker et al., Nat. Biotechnol. 20:1024-9 [2001]; Bittker et al., Proc Natl. Acad. Sci. USA 101:7011-6 [2004]); methods that rely on the use of oligonucleotides to insert random and targeted mutations, deletions and/or insertions (Ness et al., Nat. Biotechnol. 20:1251-5 [2002]; Coco et al., Nat. Biotechnol. 20:1246-50 [2002]; Zha et al., Chembiochem. 4:34-9 [2003]; Glaser et al., J. Immunol. 149:3903-13 [1992]); see also Arkin and Youvan, Biotechnology 10:297-300 (1992); Reidhaar-Olson et al., Methods Enzymol. 208:564-86 (1991).

In one aspect, a full-length parent polynucleotide is ligated into an appropriate expression plasmid, and the following mutagenesis method is used to facilitate the construction of the modified protease of the present invention, although other methods may be used. The method is based on that described by Pisarchik et al. (Pisarchik et al., Prot. Eng. Des. Select. 20:257-265 [2007]). In one aspect, an added advantage is provided in that the restriction enzyme cuts outside its recognition sequence, which allows digestion of practically any nucleotide sequence and precludes formation of a restriction site scar.

In one approach, a naturally-occurring gene encoding a full-length protease is obtained and sequenced and scanned for one or more points at which it is desired to make a mutation (e.g., deletion, insertion, substitution) at one or more amino acids. Mutation of the gene in order to change its sequence to conform to the desired sequence is accomplished by primer extension in accord with generally known methods. Fragments to the left and to the right of the desired point(s) of mutation are amplified by PCR and to include the Eam1104I restriction site. The left and right fragments are digested with Eam1104I to generate a plurality of fragments having complementary three base overhangs, which are then pooled and ligated to generate a library of modified sequences containing one or more mutations. This method avoids the occurrence of frame-shift mutations. This method also simplifies the mutagenesis process because all of the oligonucleotides can be synthesized so as to have the same restriction site, and no synthetic linkers are necessary to create the restriction sites as is required by some other methods.

In one aspect, the invention includes a method of making a cold water protease, the method comprising: (a) providing a library of nucleic acid variants of a DNA substrate molecule that encodes a parent protease; (b) transforming the library of nucleic acid variants into host cells; (c) expressing the library to provide polypeptide expression products; (d) screening the polypeptide expression products to identify a mutant protease having at least one property selected from the group consisting of: (i) having a performance index of from 1.1 to 10 on a blood/milk/ink (BMI) stain at pH 8 and 16° C. compared to PURAFECT® Prime (SEQ ID NO:2 with the amino acid substitution Y217L) as defined in the "Test Method" set forth in Part I Example 1; (ii) a performance index of from 1.3 to 10 on BMI stain at pH 8 and 16° C. compared to BPN' (SEQ ID NO:2), as defined in the "Test Method" set forth herein in Part I Example 1; (iii) a performance index of from 0.9 to about 10 on BMI stain at pH 8 and 16° C. compared to BPN'-v3 (SEQ ID NO:4), as defined in the "Test Method" set forth herein in Part I Example 1; and (d) a performance index of from 1.0 to about 10 on BMI at pH 8 and 16° C. compared to BPN'-v36 (SEQ ID NO:6), as defined in the "Test Method" set forth herein in Part I Example 1, wherein a cold water protease is identified.

In another aspect, the invention provides an expression vector comprising at least one nucleic acid of the invention. Such nucleic acid may comprise a polynucleotide sequence encoding: (a) at least one protease variant of the invention, including any protease variant described herein, including, but not limited to, those protease variants set forth in the Part I Examples, (b) at least one cold water protease of the invention, or (c) at least one protease variant of the invention, including any protease variant described herein, including, but not limited to, a Series I GG36 variant set forth in the Part II Examples, or a complementary polynucleotide sequence of any thereof. Such expression vector may be operably linked to a promoter.

In another aspect, the invention provides a recombinant host cell comprising: (a) a nucleic acid of the invention, (b) an expression vector comprising a nucleic acid of the invention, (c) a protease variant of the invention, including, but not limited to, e.g., a cold water protease of the invention. The recombinant host cell may be a bacterial cell, such as, but not limited to, e.g., a *Bacillus* cell. An exemplary *Bacillus* cell is a *Bacillus subtilis* cell.

In another aspect, the invention provides a cell culture comprising: (a) a nucleic acid of the invention, (b) an expression vector comprising a nucleic acid of the invention, (c) a protease variant of the invention, including, but not limited to, e.g., a cold water protease of the invention variant.

In another aspect, the invention provides isolated or recombinant vectors comprising at least one polynucleotide of the invention described herein (e.g., a polynucleotide encoding a protease variant of the invention described herein), isolated or recombinant expression vectors or expression cassettes comprising at least one nucleic acid or polynucleotide of the invention, isolated, substantially pure, or recombinant DNA constructs comprising at least one nucleic acid or polynucleotide of the invention, isolated or recombinant cells comprising at least one polynucleotide of the invention, cell cultures comprising cells comprising at least one polynucleotide of the invention, cell cultures comprising at least one nucleic acid or polynucleotide of the invention, and compositions comprising one or more such vectors, nucleic acids, expression vectors, expression cassettes, DNA constructs, cells, cell cultures, or any combination or mixtures thereof.

In another aspect, the invention provides recombinant cells comprising at least one vector (e.g., expression vector or DNA construct) of the invention which comprises at least one nucleic acid or polynucleotide of the invention. Some such recombinant cells are transformed or transfected with such at least one vector. Such cells are typically referred to as host cells. Some such cells comprise bacterial cells, including, but are not limited to, e.g., *Bacillus* sp. cells, such as, e.g., *Bacillus subtilis* cells. The invention also provides recombinant cells (e.g., recombinant host cells) comprising at least one protease variant of the invention.

In another aspect, the invention provides a vector comprising a nucleic acid or polynucleotide of the invention. The vector may be an expression vector or expression cassette in which a polynucleotide sequence of the invention which encodes a protease variant of the invention is operably linked to one or additional nucleic acid segments required for efficient gene expression (e.g., a promoter operably linked to the polynucleotide of the invention which encodes a protease variant of the invention). A vector may include a transcription terminator and/or a selection gene, such as an antibiotic resistance gene that enables continuous cultural maintenance of plasmid-infected host cells by growth in antimicrobial-containing media.

An expression vector may be derived from plasmid or viral DNA, or in alternative aspects, contains elements of both. Exemplary vectors include, but are not limited to pXX, pC194, pJH101, pE194, pHP13 (Harwood and Cutting (eds.)), *Molecular Biological Methods for Bacillus*, John Wiley & Sons (1990), see, e.g., chapter 3; suitable replicating plasmids for *B. subtilis* include those listed on p. 92; Perego, M. (1993) Integrational Vectors for Genetic Manipulations in *Bacillus subtilis*, pp. 615-624; A. L. Sonenshein, J. A. Hoch, and R. Losick (ed.), *Bacillus subtilis* and other Gram-positive bacteria: biochemistry, physiology and molecular genetics, American Society for Microbiology, Washington, D.C.

For expression and production of a protein of interest (e.g., protease variant) in a cell, at least one expression vector comprising at least one copy of a polynucleotide encoding the modified protease, and preferably comprising multiple copies, is transformed into the cell under conditions suitable for expression of the protease. In one aspect, a polynucleotide sequence encoding the protease variant (as well as other sequences included in the vector) is integrated into the genome of the host cell, while in another aspect, a plasmid vector comprising a polynucleotide sequence encoding the protease variant remains as autonomous extra-chromosomal element within the cell. The invention provides both extrachromosomal nucleic acid elements as well as incoming nucleotide sequences that are integrated into the host cell genome. The vectors described herein are useful for production of the protease variants of the invention. In one aspect, a polynucleotide construct encoding the protease variant is present on an integrating vector that enables the integration and optionally the amplification of the polynucleotide encoding the protease variant into the bacterial chromosome. Examples of sites for integration include are well known to those skilled in the art. In one aspect, transcription of a polynucleotide encoding a protease variant of the invention is effectuated by a promoter that is the wild-type promoter for the selected precursor protease. In some other aspects, the promoter is heterologous to the precursor protease, but is functional in the host cell. Specifically, examples of suitable promoters for use in bacterial host cells include, but are not limited to, e.g., the amyE, amyQ, amyL, pstS, sacB, pSPAC, pAprE, pVeg, pHpaII promoters, the promoter of the *B. stearothermophilus* maltogenic amylase gene, the *B. amyloliquefaciens* (BAN) amylase gene, the *B. subtilis* alkaline protease gene, the *B. clausii* alkaline protease gene the *B. pumilis* xylosidase gene, the *B. thuringiensis* cryIIIA, and the *B. licheniformis* alpha-amylase gene. Additional promoters include, but are not limited to the A4 promoter, as well as phage Lambda $P_R$ or $P_L$ promoters, and the *E. coli* lac, trp or tac promoters.

Protease variants of the invention can be produced in host cells of any suitable Gram-positive microorganism, including bacteria and fungi. For example, in one aspect, the protease variant is produced in host cells of fungal and/or bacterial origin. In one aspect, the host cells are *Bacillus* sp., *Streptomyces* sp., *Escherichia* sp. or *Aspergillus* sp. In one aspect, the protease variants are produced by *Bacillus* sp. host cells. Examples of *Bacillus* sp. host cells that find use in the production of the protease variants of the invention include, but are not limited to *B. licheniformis, B. lentus, B. subtilis, B. amyloliquefaciens, B. lentus, B. brevis, B. stearothermophilus, B. alkalophilus, B. coagulans, B. circulans, B. pumilis, B. thuringiensis, B. clausii,* and *B. megaterium*, as well as other organisms within the genus *Bacillus*. In one aspect, *B. subtilis* host cells are used for production of protease variants. U.S. Pat. Nos. 5,264,366 and 4,760,025 (RE 34,606) describe various *Bacillus* host strains that can be used for producing protease variants of the invention, although other suitable strains can be used.

Several industrial bacterial strains that can be used to produce protease variants of the invention include non-recombinant (i.e., wild-type) *Bacillus* sp. strains, as well as variants of naturally-occurring strains and/or recombinant strains. In one aspect, the host strain is a recombinant strain, wherein a polynucleotide encoding a polypeptide of interest has been introduced into the host. In one aspect, the host strain is a *B. subtilis* host strain and particularly a recombinant *Bacillus subtilis* host strain. Numerous *B. subtilis* strains are known, including, but not limited to, e.g., 1A6 (ATCC 39085), 168 (1A01), SB19, W23, Ts85, B637, PB1753 through PB1758, PB3360, JH642, 1A243 (ATCC 39,087), ATCC 21332, ATCC 6051, MI113, DE100 (ATCC 39,094), GX4931, PBT 110, and PEP 211strain (see, e.g., Hoch et al., Genetics 73:215-228 (1973)) (see also U.S. Pat. Nos. 4,450,235 and 4,302,544, and EP 0134048, each of which is incorporated by reference in its entirety). The use of *B. subtilis* as an expression host cells is well known in the art (see, e.g., Palva et al., Gene 19:81-87 (1982); Fahnestock and Fischer, J. Bacteriol. 165:796-804 (1986); and Wang et al., Gene 69:39-47 (1988)).

In one aspect, the *Bacillus* host cell is a *Bacillus* sp. that includes a mutation or deletion in at least one of the following genes, degU, degS, degR and degQ. The mutation may be in a degU gene, and in some instances the mutation may be degU(Hy)32. See, e.g., Msadek et al., J. Bacteriol. 172:824-834 (1990) and Olmos et al., Mol. Gen. Genet. 253:562-567 (1997)). A typical host strain is a *Bacillus subtilis* carrying a degU32(Hy) mutation. The *Bacillus* host may comprise an amino acid mutation (e.g., substitution) or deletion in scoC4 (see, e.g., Caldwell et al., J. Bacteriol. 183:7329-7340 (2001)); spoIIE (see, e.g., Arigoni et al., Mol. Microbiol. 31:1407-1415 (1999)); and/or oppA or other genes of the opp operon (see, e.g., Perego et al., Mol. Microbiol. 5:173-185 (1991)). Indeed, it is contemplated that any mutation in the opp operon that causes the same phenotype as a mutation in the oppA gene will find use in one aspect of the altered *Bacillus* strain of the invention. Such mutations may occur alone or combinations of mutations may be present. In one aspect, an altered *Bacillus* host cell strain that can be used to produce a protease variant of the invention is a *Bacillus* host strain that already includes a mutation in one or more of the above-mentioned genes. In addition, *Bacillus* sp. host cells that comprise mutation(s) and/or deletions of endogenous protease genes find use. The *Bacillus* host cell may comprise a deletion of the aprE and the nprE genes. The *Bacillus* sp. host cell may comprise a deletion of 5 protease genes, or the *Bacillus* sp. host cell may comprise a deletion of 9 protease genes (see, e.g., U.S. Pat. Appn. Pub. No. 2005/0202535).

Host cells are transformed with at least one nucleic acid encoding at least one protease variant of the invention using any suitable method known in the art. Whether the nucleic acid is incorporated into a vector or is used without the presence of plasmid DNA, it is typically introduced into a microorganism, in one aspect, preferably an *E. coli* cell or a competent *Bacillus* cell. Methods for introducing a nucleic acid (e.g., DNA) into *Bacillus* cells or *E. coli* cells utilizing plasmid DNA constructs or vectors and transforming such plasmid DNA constructs or vectors into such cells are well known. In one aspect, the plasmids are subsequently isolated from *E. coli* cells and transformed into *Bacillus* cells. However, it is not essential to use intervening microorganisms such as *E. coli*, and in one aspect, a DNA construct or vector is directly introduced into a *Bacillus* host.

Those of skill in the art are well aware of suitable methods for introducing nucleic acid or polynucleotide sequences of the invention into *Bacillus* cells (see, e.g., Ferrari et al., "Genetics," in Harwood et al. (ed.), *Bacillus*, Plenum Publishing Corp. (1989), pp. 57-72; Saunders et al., J. Bacteriol. 157:718-726 (1984); Hoch et al., J. Bacteriol. 93:1925-1937 (1967); Mann et al., Current Microbiol. 13:131-135 (1986); and Holubova, Folia Microbiol. 30:97 (1985); Chang et al., Mol. Gen. Genet. 168:11-115 (1979); Vorobjeva et al., FEMS Microbiol. Lett. 7:261-263 (1980); Smith et al., Appl. Env. Microbiol. 51:634 (1986); Fisher et al., Arch. Microbiol. 139:213-217 (1981); and McDonald, J. Gen. Microbiol. 130: 203 (1984)). Indeed, such methods as transformation, including protoplast transformation and congression, transduction, and protoplast fusion are well known and suited for use in the present invention. Methods of transformation are used to introduce a DNA construct or vector comprising a nucleic acid encoding a protease variant of the present invention into a host cell. Methods known in the art to transform *Bacillus* cells include such methods as plasmid marker rescue transformation, which involves the uptake of a donor plasmid by competent cells carrying a partially homologous resident plasmid (Contente et al., Plasmid 2:555-571 (1979); Haima et al., Mol. Gen. Genet. 223:185-191 (1990); Weinrauch et al., J. Bacteriol. 154:1077-1087 (1983); and Weinrauch et al., J. Bacteriol. 169:1205-1211 (1987)). In this method, the incoming donor plasmid recombines with the homologous region of the resident "helper" plasmid in a process that mimics chromosomal transformation.

In addition to commonly used methods, in one aspect, host cells are directly transformed with a DNA construct or vector comprising a nucleic acid encoding a protease variant of the invention (i.e., an intermediate cell is not used to amplify, or otherwise process, the DNA construct or vector prior to introduction into the host cell). Introduction of the DNA construct or vector of the invention into the host cell includes those physical and chemical methods known in the art to introduce a nucleic acid sequence (e.g., DNA sequence) into a host cell without insertion into a plasmid or vector. Such methods include, but are not limited to calcium chloride precipitation, electroporation, naked DNA, liposomes and the like. In additional aspects, DNA constructs or vector are co-transformed with a plasmid, without being inserted into the plasmid. In further aspects, a selective marker is deleted from the altered *Bacillus* strain by methods known in the art (see Stahl et al., J. Bacteriol. 158:411-418 (1984); and Palmeros et al., Gene 247:255-264 (2000)).

In one aspect, the transformed cells of the present invention are cultured in conventional nutrient media. The suitable specific culture conditions, such as temperature, pH and the like are known to those skilled in the art. In addition, some culture conditions may be found in the scientific literature such as Hopwood (2000) *Practical Streptomyces Genetics*, John Innes Foundation, Norwich UK; Hardwood et al., (1990) *Molecular Biological Methods for Bacillus*, John Wiley and from the American Type Culture Collection (ATCC). In one aspect, the invention provides a culture (e.g., cell culture) comprising at least one protease variant or at least one nucleic acid of the invention. Also provided is a composition comprising at least one nucleic acid, vector, or DNA construct of the invention.

Host cells transformed with at least one polynucleotide sequence encoding at least one protease variant of the invention may be cultured in a suitable nutrient medium under conditions permitting the expression of the present protease, after which the resulting protease is recovered from the culture. The medium used to culture the cells comprises any conventional medium suitable for growing the host cells, such as minimal or complex media containing appropriate supplements. Suitable media are available from commercial suppliers or may be prepared according to published recipes (e.g., in catalogues of the American Type Culture Collection). The protease produced by the cells may be recovered from the culture medium by conventional procedures, including, but not limited to, e.g., separating the host cells from the medium by centrifugation or filtration, precipitating the proteinaceous components of the supernatant or filtrate by means of a salt (e.g., ammonium sulfate), chromatographic purification (e.g., ion exchange, gel filtration, affinity, etc.). Any method suitable for recovering or purifying a protease variant of the invention can be used.

In one aspect, a protease variant produced by a recombinant host cell is secreted into the culture medium. A nucleic acid sequence that encodes a purification facilitating domain may be used to facilitate purification of soluble proteins. A vector or DNA construct comprising a polynucleotide sequence encoding a protease variant may further comprise a nucleic acid sequence encoding a purification facilitating domain to facilitate purification of the protease variant (see, e.g., Kroll, D. J. et al., DNA Cell Biol. 12:441-53 (1993)). Such purification facilitating domains include, but are not limited to, e.g., metal chelating peptides such as histidine-tryptophan modules that allow purification on immobilized metals (Porath J., Protein Expr. Purif. 3:263-281 (1992)), protein A domains that allow purification on immobilized immunoglobulin, and the domain utilized in the FLAGS extension/affinity purification system (Immunex Corp., Seattle, Wash.). The inclusion of a cleavable linker sequence such as Factor XA or enterokinase (Invitrogen, San Diego, Calif.) between the purification domain and the heterologous protein also find use to facilitate purification.

Assays for detecting and measuring the enzymatic activity of an enzyme, such as a protease variant of the invention, are well known. Various assays for detecting and measuring activity of proteases, such as, e.g., protease variants of the invention, are also known to those of ordinary skill in the art. In particular, assays are available for measuring protease activity that are based on the release of acid-soluble peptides from casein or hemoglobin, measured as absorbance at 280 nm or colorimetrically using the Folin method (see, e.g., Bergmeyer et al., "Methods of Enzymatic Analysis" vol. 5, *Peptidases, Proteinases and their Inhibitors*, Verlag Chemie, Weinheim (1984)). Other exemplary assays involve the solubilization of chromogenic substrates (see, e.g., Ward, "Proteinases," in Fogarty (ed.). *Microbial Enzymes and Biotechnology*, Applied Science, London, (1983), pp. 251-317). Other exemplary assays include, but are not limited to succinyl-Ala-Ala-Pro-Phe-para nitroanilide assay (SAAPFpNA) and the 2,4,6-trinitrobenzene sulfonate sodium salt assay (TNBS assay). Numerous additional references known to those in the art provide suitable methods (see, e.g., Wells et al., Nucleic Acids Res. 11:7911-7925 (1983); Christianson et al., Anal. Biochem. 223:119-129 (1994); and Hsia et al., Anal Biochem. 242:221-227 (1999)).

A variety of methods can be used to determine the level of production of a mature protease (e.g., mature protease variant of the invention) in a host cell. Such methods include, but are not limited to, e.g., methods that utilize either polyclonal or monoclonal antibodies specific for the protease. Exemplary methods include, but are not limited, e.g., to enzyme-linked immunosorbent assays (ELISA), radioimmunoassays (RIA), fluorescent immunoassays (FIA), and fluorescent activated cell sorting (FACS). These and other assays are well known in the art (see, e.g., Maddox et al., J. Exp. Med. 158:1211 (1983)).

In another aspect, the invention provides methods for making or producing a mature protease variant of the invention. A mature protease variant does not include a signal peptide or a propeptide sequence. Some such methods comprising making or producing a protease variant of the invention in a recombinant bacterial host cell, such as, e.g., a *Bacillus* sp. cell, including, e.g., *Bacillus subtilis* cell. In one aspect, the invention provides a method of producing a protease variant of the invention, the method comprising cultivating a recombinant host cell comprising a recombinant expression vector comprising a nucleic acid encoding a protease variant of the invention under conditions conducive to the production of the protease variant. Some such methods further comprise recovering the protease variant from the culture.

In one aspect, the invention provides a method of producing a protease variant of the invention, the method comprising: (a) introducing a recombinant expression vector comprising a nucleic acid encoding a protease variant of the invention into a population of cells (e.g., bacterial cells, such as *Bacillus subtilis* cells); and (b) culturing the cells in a culture medium under conditions conducive to produce the protease variant encoded by the expression vector. Some such methods further comprise: (c) isolating the protease variant from the cells or from the culture medium.

In addition to recombinant production, the protease variant polypeptides of the invention may be produced by direct peptide synthesis using solid-phase techniques (see, e.g., Stewart et al. (1969) Solid-Phase Peptide Synthesis, W.H. Freeman Co, San Francisco; Merrifield (1963) J. Am. Chem. Soc 85:2149-2154). Peptide synthesis may be performed using manual or automated techniques. Automated synthesis may be achieved, for example, using Applied Biosystems 431A Peptide Synthesizer (Perkin Elmer, Foster City, Calif.) in accordance with the instructions provided by the manufacturer. For example, subsequences may be chemically synthesized separately and combined using chemical methods to provide protease variants or functional fragments thereof. Alternatively, such variant polypeptide sequences may be ordered from any number of companies that specialize in production of polypeptides. Most commonly, polypeptides of the invention are produced by expressing coding nucleic acids and recovering polypeptides, e.g., as described above and in the Examples.

In another aspect, the invention provides a method of producing a protease variant, the method comprising cultivating a recombinant host cell of the invention, said host cell comprising an expression vector which comprising at least one nucleic acid of the invention, under conditions conducive to produce the variant. The method may further comprise recovering the variant from the culture.

In another aspect, the invention includes a method of producing a protease variant, the method comprising: (a) introducing the recombinant expression vector of the invention into a population of cells; and (b) culturing the cells in a culture medium under conditions conducive to produce the subtilisin variant encoded by the expression vector. The method may further comprise (c) isolating the variant from the cells or from the culture medium.

In another aspect, the invention provides methods for producing a serine protease variant of a *Bacillus* serine protease, comprising: transforming a host cell with an expression vector comprising a nucleic acid encoding the serine protease variant; and cultivating the transformed host cell under conditions suitable for the production of the serine protease variant. In one aspect, the methods further comprise the step of harvesting the produced serine protease variant. In one aspect, the host cell is a *Bacillus* cell, and in a subset of these aspects, the *Bacillus* cell is a *B. subtilis* cell. Furthermore, the present invention provides methods of cleaning, comprising the step of contacting a surface and/or an article comprising a fabric with a cleaning composition comprising a serine protease variant. In some alternative methods, the present invention provides methods of cleaning, comprising the step of contacting a surface and/or an article comprising dishware with a cleaning composition comprising a serine protease variant.

In another aspect, the invention provides a method for identifying a wild-type subtilisin protease, said subtilisin protease comprising an amino acid sequence which comprises the following amino acids: a glycine or arginine at amino acid position 24, a glycine at amino acid position 53, an asparagine at amino acid position 78, an alanine at amino acid position 97, an asparagine at amino acid position 101, an alanine or serine at amino acid position 128, and/or a leucine or glutamine at amino acid position 217, wherein said amino acid positions are numbered by correspondence with amino acid positions in the amino acid sequence of BPN' set forth in SEQ ID NO:2, said method comprising: a) providing a sample comprising at least one wild-type subtilisin protease or a library of wild-type subtilisin proteases, or providing a DNA sample comprising one or more DNA sequences encoding wild-type subtilisin proteases; and b) identifying a wild-type subtilisin protease or DNA sequence that encodes a wild-type protease.

In a twelfth aspect, the invention provides an expression vector comprising at least one nucleic acid of the tenth or eleventh aspect of the invention. An expression vector according to the twelfth aspect of the invention may be operably linked to a promoter. Such expression vector may be in isolated or purified form.

In a thirteenth aspect, the invention provides a recombinant host cell comprising: (a) a nucleic acid of the tenth or eleventh aspect of the invention or (b) an expression vector of the twelfth aspect of the invention. A recombinant host cell of the thirteenth aspect of the invention may be a bacterial cell, which may optionally be a *Bacillus* cell. A recombinant host cell of the thirteenth aspect of the invention may be a *Bacillus subtilis* cell.

In a fourteenth aspect, the invention provides a cell culture comprising: (a) a nucleic acid of the tenth or eleventh aspect of the invention or (b) an expression vector of the twelfth aspect of the invention.

In a fifteenth aspect, the invention provides a method of producing a protease variant, the method comprising cultivating a recombinant host cell of the thirteenth aspect of the invention under conditions conducive to produce the variant. A method according to the fifteenth aspect of the invention may further comprise isolating or recovering the variant from the culture.

In a sixteenth aspect, the invention provides a method of producing a protease variant, the method comprising: (a) introducing the recombinant expression vector of the twelfth aspect of the invention into a population of cells; and (b) culturing the cells in a culture medium under conditions conducive to produce the protease variant encoded by the expression vector. The method according to the sixteenth aspect of the invention may further comprise (c) isolating or recovering the variant from the cells or from the culture medium.

Compositions of the Invention

The invention includes a composition comprising at least one polypeptide (e.g., at least one protease variant) of the invention. Polypeptides of the invention are described infra and supra, including in the Part I Examples and Part II Examples. Such compositions may comprise at least one excipient, carrier, adjunct ingredient, or other substituent, component, or material.

For example, in one aspect, the invention includes a composition comprising at least one protease variant and at least one excipient, carrier, adjunct ingredient, or other substituent, component, or material. Such at least one protease variant may be any one of those set forth herein, including, but not limited to, in the Part I Examples. Such at least one protease variant may be a BPN' protease variant. For example, a composition of the invention may be a BPN' protease variant, such as BPN'-v36 (SEQ ID NO:6) or BPN'-v3 (SEQ ID NO:4) or any protease variant set forth herein or in Part I Examples 2-23. Such composition may be a fabric and home care product or fabric and home care composition. Alternatively, such composition may be a fabric and home care product or fabric and home care composition.

Such composition may further comprise (in addition to a BPN' protease variant) at least one GG36 protease variant, such as at least one Series I GG36 protease variant described in the Part II Examples. Such compositions are useful in a variety of applications as described elsewhere herein.

In a seventeenth aspect, the invention provides a composition comprising a variant (or polypeptide as in the third aspect) of the first, second, third, fourth, fifth, sixth, seventh, eighth, or ninth aspect of the invention. A composition according to the seventeenth aspect of the invention may comprise an adjunct ingredient or carrier as described in greater detail elsewhere herein. A composition according to the seventeenth aspect of the invention may comprise at least one builder and/or at least one surfactant. A composition according to the seventeenth aspect of the invention may comprise phosphate or may not comprise phosphate.

A composition according to the seventeenth aspect of the invention may be a cleaning composition or a detergent composition. A composition according to the seventeenth aspect of the invention may be a fabric or home care product. A composition according to the seventeenth aspect of the invention may not be a fabric or home care product. A composition according to the seventeenth aspect of the invention may be a cleaning composition or detergent composition that is a fabric or home care product. A composition according to the seventeenth aspect of the invention may be a cleaning composition or detergent composition that is not a fabric or home care product.

A composition according to the seventeenth aspect of the invention may comprise may further comprise one, two, three, four, five or more additional enzymes. Such additional enzyme(s) may be selected from the group consisting of additional enzymes selected from the group consisting of hemicellulase, cellulase, amylase, peroxidase, protease, xylanase, lipase, phospholipase, esterase, cutinase, pectinase, pectate lyase, mannanase, keratinase, reductase, oxidase, phenoloxidase, lipoxygenase, ligninase, pullulanase, tannase, pentosanase, malanase, β-glucanase, arabinosidase, hyaluronidase, chondroitinase, and laccase.

The additional enzyme according to the seventeenth aspect of the invention may be a GG36 protease variant having proteolytic activity, such as, e.g., a Series I GG36 protease variant, which Series I GG36 protease variant may comprise an amino acid sequence having at least 60%, 70%, 80%, 85%, 90%, 91%, 92%, 93%, 94%, 95%, 96%, 97%, or 98% sequence identity to the subtilisin *Bacillus lentus* GG36 of SEQ ID NO:755 and at least one amino acid substitution selected from the group consisting of A1R, Q2S, V4R, V4S, S9A, R10S, P14K, A16S, H17R, N18R, G20R, T22A, T22R, S24R, S24W, G25R, G25V, V26F, L42I, N43R, N43A, G46R, P52F, P52E, P52N, T57R, Q59A, N62E, N62Q, V68A, V68C, T71G, I72C, A74C, L75A, L75F, L75R, N76D, S78R, L82R, P86W, E89P, E89T, E89G, E89H, E89I, E89V, E89W, Y91N, K94N, G100S, S101A, S101N, S101G, S101D, S103G, S103N, V104L, V104I, S106V, S106G, A108I, L111V, E112V, G115K, G115R, N117F, G118I, V121F, S128D, S128F, S128L, S128N, P129E, S144R, L148I, A158E, G159E, S160D, S166D, N185E, N185I, R186H, S188E, S188D, D197F, V203E, Y209S, Y209N, Y209F, Y209T, Y209E, Y209H, Y209G, P210R, S212I, S212F, Y214F, A215N, A215D, A215E, L217E, L217N, T224A, A230E, A231I, Q236F, N238R, N238K, P239K, P239G, P239R, P239S, W241R, S242R, S242L, N243R, V244R, N248I, N248V, H249R, L250I, N252R, T253R, L262D, Y263F, S265F, L267V, L267N. N269I, N269R, E271F, E271I, E271H, E271P, E271T, E271V, E271L, and A272F, wherein each amino acid position of the variant is numbered by correspondence to an amino acid position in the amino acid sequence of *Bacillus amyloliquefaciens* subtilisin BPN' protease set forth in SEQ ID NO:2. A composition according to the seventeenth aspect of the invention that comprises an additional enzyme (such as a protease, such as, e.g., a Series I G36 protease variant as described herein) may be a fabric and home care product. Alternatively, such composition may not be a fabric and home care product.

A composition according to the seventeenth aspect of the invention may comprise a Series I GG36 protease variant which comprises an amino acid sequence having at least 60%, 70%, 80%, 85%, 90%, 91%, 92%, 93%, 94%, 95%, 96%, 97%, 98%, or 99% sequence identity to the subtilisin *Bacillus lentus* GG36 of SEQ ID NO:755 and at least one amino acid substitution selected from the group consisting of T022R-S024R, S009A-E271L, N018R-W241R, N018R-G115R, N043R-H249R, G020R-H249R, V004R-H249R, G020R-S024R, N018R-H249R, S009A-G020R, G020R-W241R, S009A-S078R, G020R-G115R, N018R-S024R, S024R-S242R, T022R-G115R, N018R-N043R, G020R-N043R, N018R-S242R, S242R-N269R, N018R-V244R, S024R-N269R, G020R-E271L, S024R-E271L, V004R-S009A, G020R-N269R, A001R-S024R, V244R-E271L, S009A-N018R, W241R-E271L, V004R-S024R, S009A-H249R, S009A-T022R, N062E-P129E, N062E-G159E, A016S-L148I, A158E-H249R, A016S-N062E, L111V-S188D, T022A-N062E, N062E-L148I, T022A-P129E, N062E-E271F, N062E-A158E, A016S-G159E, N062E-R186H, S128N-G159E, N062E-S188D, N062E-S128N, L148I-G159E, S103G-A158E, L111V-G159E, A158E-E271F, A016S-S188D, T022A-L111V, S128N-A158E, A016S-A158E, V104L-A158E, S128N-R186H, G159E-Y209E, N062E-S101A, L111V-Y209E, I148I-S188D, S101A-Y209E, T022A-S188D, A016S-T022A, S128N-P129E, A016S-Y209E, A016S-S128N, T022A-E089P, S128N-Y209E, E089P-A158E, N062E-S103G, R186H-E271F, A016S-P129E, E089P-G159E, L111V-H249R, S101A-P129E, L148I-Y209E, T022A-G159E, P129E-H249R, P129E-Y209E, V104L-P129E, S128N-S188D, L111V-A158E, T022A-A158E, N062E-Y209E, N062E-H249R, S101A-R186H, E089P-P129E, P129E-E271, T22A-L111V-

G159E, S101A-S103G-V104L-Y209E, S101A-S103G-V104L-G159E, S101A-S103G-V104L-S188D, S101G-S103A-V104I-G159D, T22A-S103G-G159E, T22A-S128N-E271F-Y209E, T22A-Y209E-E271F, T22A-S101A-Y209E, S101A-Y209E-E271F, T22A-L111V-S128N, T22A-S101A-G159E, S101A-S103G-V104L, T22A-S101A-S103G-V104L, S101A-S103G-V104L, S101G-S103A-V104I, S101A-S103G-V104L-S128N, S103A-V104I-G159D-A232V-Q236H-Q245R-N248D-N252K, S101G-V104I-G159D-A232V-Q236H-Q245R-N248D-N252K, S101G-S103A-G159D-A232V-Q236H-Q245R-N248D-N252K, S101G-S103A-V104L-A232V-Q236H-Q245R-N248D-N252K, S101G-S103A-V104L-G159D-Q236H-Q245R-N248D-N252K, S101G-S103A-V104L-G159D-A232V-Q245R-N248D-N252K, S101G-S103A-V104L-G159D-A232V-Q236H-N248D-N252K, S101G-S103A-V104L-G159D-A232V-Q236H-Q245R-N252K, S101G-S103A-V104L-G159D-A232V-Q236H-Q245R-N248D, N62E-S101G-S103A-V104I-G159D-A232V-Q245R-N248D-E271F, N62E-S101G-S103A-V104I-G159D-A232V-Q245R-N248D-H249R, T22A-S101G-S103A-V104I-G159D-A232V-Q245R-N248D-H249R, S101G-S103A-V104I-G159D-A232V-Q245R-N248D-S24R, S101G-S103A-V104I-G159D-A232V-Q245R-N248D-T253R, S101G-S103A-V104I-A158E-A232V-Q245R-N248D-H249R, T22A-S101G-S103A-V104I-G159D-A232V-Q245R-N248D-E271F, S101G-S103A-V104I-G159E-A232V-Q245R-N248D-H249R, S101G-S103A-V104I-G159D-A232V-Q245R-N248D-N238R, S101G-S103A-V104I-A158E-A232V-Q245R-N248D-E271F, S101G-S103A-V104I-G159D-A232V-Q245R-N248D, S101G-S103A-V104I-G159D-A232V-Q245R-N248D-E271F, S101G-S103A-V104I-G159D-A232V-Q245R-N248D-N76D, and S101G-S103A-V104I-G159E-A232V-Q245R-N248D-E271F, wherein each amino acid position of the variant is numbered by correspondence to an amino acid position in the amino acid sequence of *Bacillus amyloliquefaciens* subtilisin BPN' protease set forth in SEQ ID NO:2. Such composition may be a fabric and home care product or fabric and home care composition. In another aspect, such composition may not be a fabric and home care product or fabric and home care composition.

A composition according to the seventeenth aspect of the invention may comprise an Series I GG36 protease variant which comprises an amino acid sequence having at least 60%, 70%, 80%, 85%, 90%, 91%, 92%, 93%, 94%, 95%, 96%, 97%, or 98% sequence identity to the subtilisin *Bacillus lentus* GG36 of SEQ ID NO:755 and comprises three, four, five, six, seven, eight, nine, 10, 11, 12, 13, 14, 15, 16, 17, 18, 19, 20, 21, 22, 23, 24, or even 25 amino acid substitutions selected from the group consisting of: A1R, Q2S, V4R, V4S, S9A, R10S, P14K, A16S, H17R, N18R, G20R, T22A, T22R, S24R, S24W, G25R, G25V, V26F, L42I, N43R, N43A, G46R, P52F, P52E, P52N, T57R, Q59A, N62E, N62Q, V68A, V68C, T71G, I72C, A74C. L75A, L75F, L75R, N76D, S78R, L82R, P86W, E89P, E89T, E89G, E89H, E89I, E89V, E89W, Y91N, K94N, G100S, S101A, S101N, S101G, S101D, S103G, S103N, V104L, V104I, S106V, S106G, A108I, L111V, E112V, G115K, G115R, N117F, G118I, V121F, S128D, S128F, S128L, S128N, P129E, S144R, L148I, A158E. G159E, S160D, S166D, N185E, N185I, R186H, S188E, S188D, D197F, V203E, Y209S, Y209N, Y209F, Y209T, Y209E, Y209H, Y209G, P210R, S212I, S212F, Y214F, A215N, A215D, A215E, L217E, L217N, T224A, A230E, A231I, Q236F, N238R, N238K, P239K, P239G, P239R, P239S, W241R, S242R, S242L, N243R, V244R, N248I, N248V, H249R, L250I, N252R, T253R, L262D, Y263F, S265F, L267V, L267N, N269I, N269R, E271F, E271I, E271H, E271P, E271T, E271V, E271L, and A272F; and optionally at least one amino acid substitution selected from the group consisting of: S103A, G159D, Q236H, Q245R, N248D, and N252K, wherein each amino acid position of the variant is numbered by correspondence to an amino acid position in the amino acid sequence of *Bacillus amyloliquefaciens* subtilisin BPN' protease set forth in SEQ ID NO:2. Such composition may be a fabric and home care product or fabric and home care composition. In another aspect, such composition may not be a fabric and home care product or fabric and home care composition.

A composition according to the seventeenth aspect of the invention may comprise a Series I GG36 protease variant which comprises an amino acid sequence having at least 60%, 70%, 80%, 85%, 90%, 91%, 92%, 93%, 94%, 95%, 96%, 97%, or 98% sequence identity to the subtilisin *Bacillus lentus* GG36 of SEQ ID NO:755 and (a) two or more substitutions selected from the group consisting of A1R, Q2S, V4R, V4S, S9A, R10S, P14K, A16S, T22A, T22R, S24R, G25V, V26F, L42I, P52F, P52E, P52N, N62E, N62Q, V68A, V68C, T71G, I72C, A74C. L75A, L75F, S78R, E89P, E89T, E89G, E89H, E89W, Y91N, K94N, G100S, S101A, S101N, S101G, S101D, S103G, S103N, V104L, V104I, A108I, L111V, E112V, G115K, N117F, V121F, S128D, S128F, S128L, S128N, P129E, L148I, A158E. G159E, S160D, S166D, N185E, R186H, S188E, S188D, V203E, Y209S, Y209N, Y209F, Y209T, Y209E, Y209H, Y209G, P210R, S212I, S212F, Y214F, A215N, A215D, A215E, L217E, L217N, T224A, A230E, A231I, Q236F, N238R, N238K, P239K, P239G, P239R, N248V, H249R, L250I, L262D, Y263F, S265F, L267V, L267N. N269I, N269R, E271F, E271I, E271H and A272F, and/or (b) one or more sets of substitutions selected from the group consisting of N062E-P129E, N062E-G159E, A016S-L148I, A158E-H249R, A016S-N062E, L111V-S188D, T022A-N062E, N062E-L148I, T022A-P129E, N062E-E271F, N062E-A158E, A016S-G159E, N062E-R186H, S128N-G159E, N062E-S188D, N062E-S128N, L148I-G159E, S103G-A158E, L111V-G159E, A158E-E271F, A016S-S188D, T022A-L111V, S128N-A158E, A016S-A158E, V104L-A158E, S128N-R186H, G159E-Y209E, N062E-S101A, L111V-Y209E, L148I-S188D, S101A-Y209E, T022A-S188D, A016S-T022A, S128N-P129E, A016S-Y209E, A016S-S128N, T022A-E089P, S128N-Y209E, E089P-A158E, N062E-S103G, R186H-E271F, A016S-P129E, E089P-G159E, L111V-H249R, S101A-P129E, L148I-Y209E, T022A-G159E, P129E-H249R, P129E-Y209E, V104L-P129E, S128N-S188D, L111V-A158E, T022A-A158E, N062E-Y209E, N062E-H249R, S101A-R186H, E089P-P129E, P129E-E271F, T22A-L111V-G159E, S101A-S103G-V104L-Y209E, S101A-S103G-V104L-G159E, S101A-S103G-V104L-S188D, S101G-S103A-V104I-G159D, T22A-S103G-G159E, T22A-S128N-E271F-Y209E, T22A-Y209E-E271F, T22A-S101A-Y209E, S101A-Y209E-E271F, T22A-L111V-S128N, T22A-S101A-G159E, S101A-S103G-V104L, T22A-S101A-S103G-V104L, S101A-S103G-V104L, S101G-S103A-V104I, S101A-S103G-V104L-S128N, S103A-V104I-G159D-A232V-Q236H-Q245R-N248D-N252K, S101G-V104I-G159D-A232V-Q236H-Q245R-N248D-N252K, S101G-S103A-G159D-A232V-Q236H-Q245R-N248D-N252K, S101G-S103A-V104L-A232V-Q236H-Q245R-N248D-N252K, S101G-S103A-V104L-G159D-Q236H-Q245R-N248D-N252K, S101G-S103A-V104L-G159D-A232V-Q245R-N248D-N252K, S101G-S103A-V104L-G159D-A232V-Q236H-N248D-N252K, S101G-S103A-V104L-G159D-A232V-

Q236H-Q245R-N252K, S101G-S103A-V104L-G159D-A232V-Q236H-Q245R-N248D, N62E-S101G-S103A-V104I-G159D-A232V-Q245R-N248D-E271F, N62E-S101G-S103A-V104I-G159D-A232V-Q245R-N248D-H249R, T22A-S101G-S103A-V104I-G159D-A232V-Q245R-N248D-H249R, S101G-S103A-V104I-G159D-A232V-Q245R-N248D-S24R, S101G-S103A-V104I-G159D-A232V-Q245R-N248D-T253R, S101G-S103A-V104I-A158E-A232V-Q245R-N248D-H249R, T22A-S101G-S103A-V104I-G159D-A232V-Q245R-N248D-E271F, S101G-S103A-V104I-G159E-A232V-Q245R-N248D-H249R, S101G-S103A-V104I-G159D-A232V-Q245R-N248D-N238R, S101G-S103A-V104I-A158E-A232V-Q245R-N248D-E271F, S101G-S103A-V104I-G159D-A232V-Q245R-N248D, S101G-S103A-V104I-G159D-A232V-Q245R-N248D-E271F, S101G-S103A-V104I-G159D-A232V-Q245R-N248D-N76D, and S101G-S103A-V104I-G159E-A232V-Q245R-N248D-E271F, wherein each amino acid position of the variant is numbered by correspondence to an amino acid position in the amino acid sequence of *Bacillus amyloliquefaciens* subtilisin BPN' protease set forth in SEQ ID NO:2. Such composition may be a fabric and home care product or fabric and home care composition. In another aspect, such composition may not be a fabric and home care product or fabric and home care composition.

A composition according to the seventeenth aspect of the invention may comprise a Series I GG36 protease variant which comprises an amino acid sequence having at least 60%, 70%, 80%, 85%, 90%, 91%, 92%, 93%, 94%, 95%, 96%, 97%, or 98% sequence identity to the subtilisin *Bacillus lentus* GG36 of SEQ ID NO:755 and (a) two or more substitutions selected from the group of consisting of V4R, H17R, N18R, G20R, T22R, S24R, S24W, G25R, N43R, N43A, G46R, P52F, P52N, T57R, Q59A, N62Q, T71G, L75R, N76D, S78R, L82R, P86W, E89P, E89W, E89T, E89I, E89H, E89V, V104L, S106V, S106G, G115R, G118I, V121F, S144R, N185I, D197F, Y209N, Y209S, L217E, A231I, P239R, P239S, W241R, S242R, S242L, N243R, V244R, N248I, H249R, N252R, T253R, E271T, E271V, E271L, E271H, E271F, E271P, A1R, S9A, S212F, and N269R; and/or (b) one or more sets of substitutions selected from the group consisting of T022R-S024R, S009A-E271L, N018R-W241R, N018R-G115R, N043R-H249R, G020R-H249R, V004R-H249R, G020R-S024R, N018R-H249R, S009A-G020R, G020R-W241R, S009A-S078R, G020R-G115R, N018R-S024R, S024R-S242R, T022R-G115R, N018R-N043R, G020R-N043R, N018R-S242R, S242R-N269R, N018R-V244R, S024R-N269R, G020R-E271L, S024R-E271L, V004R-S009A, G020R-N269R, A001R-S024R, V244R-E271L, S009A-N018R, W241R-E271L, V004R-S024R, S009A-H249R, S009A-T022R, S101G-S103A-V104I-G159D-A232V-Q245R-N248D-E271F, S101G-S103A-V104I-A158E-A232V-Q245R-N248D-E271F, S101G-S103A-V104I-A158E-A232V-Q245R-N248D-H249R, S101G-S103A-V104I-G159D-A232V-Q245R-N248D-S24R, S101G-S103A-V104L-G159D-A232V-Q236H-Q245R-N252K, and S101G-S103A-V104L-A232V-Q236H-Q245R-N248D-N252K, wherein each amino acid position of the variant is numbered by correspondence to an amino acid position in the amino acid sequence of *Bacillus amyloliquefaciens* subtilisin BPN' protease set forth in SEQ ID NO:2. Such composition may be a fabric and home care product or fabric and home care composition. In another aspect, such composition may not be a fabric and home care product or fabric and home care composition.

A composition according to the seventeenth aspect of the invention may comprise at least one additional enzyme selected from the group consisting of hemicellulase, cellulase, amylase, peroxidase, protease, xylanase, lipase, phospholipase, esterase, cutinase, pectinase, pectate lyase, mannanase, keratinase, reductase, oxidase, phenoloxidase, lipoxygenase, ligninase, pullulanase, tannase, pentosanase, malanase, β-glucanase, arabinosidase, hyaluronidase, chondroitinase, and laccase. A composition according to the seventeenth aspect of the invention may comprise two or more additional enzymes selected from the group consisting of hemicellulase, cellulase, amylase, peroxidase, protease, xylanase, lipase, phospholipase, esterase, cutinase, pectinase, pectate lyase, mannanase, keratinase, reductase, oxidase, phenoloxidase, lipoxygenase, ligninase, pullulanase, tannase, pentosanase, malanase, β-glucanase, arabinosidase, hyaluronidase, chondroitinase, and laccase.

A composition according to the seventeenth aspect of the invention may comprise phosphate or may not contain phosphate. A composition according to the seventeenth aspect of the invention may comprise at least one builder and/or at least one surfactant.

As further elsewhere herein, the polypeptides of the invention, including the protease variants of the invention, are useful in a variety of cleaning applications, including laundry cleaning applications, automatic dishwashing applications, hand dishwashing applications, hard surface cleaning applications, personal care applications, and other applications described herein. Thus, for example, in one aspect, the invention provides cleaning compositions comprising at least one polypeptide (e.g., protease variant) of the invention. As noted above, such cleaning compositions include, but are not limited to, e.g., automatic and hand dishwashing detergent compositions, laundry detergent compositions (including, e.g., liquid and powder laundry detergent compositions), fabric cleaning compositions, hard surface cleaning compositions (including, but not limited to, e.g., hard surface of a non-dishware item, non-tableware item, table, table top, furniture item, wall, floor, ceiling, etc.). Such cleaning compositions, which are useful in methods of cleaning an item or a surface in need of cleaning, may comprise, e.g., but not limited to, at least one excipient, carrier, and/or other substituent, component, or material.

In another aspect, the invention provides a composition comprising any polypeptide of the invention (e.g., any protease variant or subtilisin variant of the invention) described herein, wherein said composition is a fabric and home care composition or a fabric and home care product.

In another aspect, the invention provides a composition comprising any polypeptide of the invention (e.g., any protease variant or subtilisin variant of the invention) described herein, wherein said composition is not a fabric and home care composition or not a fabric and home care product. A composition of the invention comprising a protease variant of the invention may further comprise at least one adjunct material selected from perfume encapsulate; fabric hueing agent; cold-water soluble brightener; a bleach catalyst that may comprise a material selected from an iminium cation, iminium polyion, iminium zwitterion; modified amine; modified amine oxide; N-sulphonyl imine; N-phosphonyl imine; N-acyl imine; thiadiazole dioxide; perfluoroimine; cyclic sugar ketone; first wash lipase; bacterial cleaning cellulase; Guerbet nonionic surfactant; and mixture of any thereof. Compositions of the invention may further comprise at least one additional non-immunoequivalent protease selected from subtilisins (EC 3.4.21.62); trypsin-like or chymotrypsin-like proteases; metalloproteases; and mixtures thereof.

Compositions of the invention may further comprise at least one additional non-immunoequivalent protease selected from: subtilisins (EC 3.4.21.62) derived from *B. subtilis, B. amyloliquefaciens, B. pumilus* and *B. gibsonii*; trypsin proteases and/or chymotrypsin proteases derived from *Cellulomonas*; metalloproteases derived from *B. amyloliquefaciens*; and mixtures thereof.

Compositions of the invention further comprise at least one additional enzyme selected from first-wash lipases; alpha-amylases; bacterial cleaning cellulases; and mixtures thereof.

A composition of the invention may further comprise at least one of the following: an encapsulate comprising a perfume comprises a perfume micro capsule; a hueing agent comprising a material selected from basic, acid, hydrophobic, direct and polymeric dyes, and dye-conjugates having a peak absorption wavelength of from 550 nm to 650 nm and mixtures thereof; a detersive surfactant comprising a material selected from anionic detersive surfactants, non-ionic detersive surfactant, cationic detersive surfactants, zwitterionic detersive surfactants and amphoteric detersive surfactants and mixtures thereof; a builder comprising a material selected from zeolites, phosphates and mixtures thereof; a silicate salt comprising a material selected from sodium silicate, potassium silicate and mixtures thereof; a brightener comprising a material selected from cold-water soluble brightener and mixtures thereof; a carboxylate polymer comprising a material selected from maleate/acrylate random copolymer or polyacrylate homopolymer and mixtures thereof; a soil release polymer comprising a material selected from terephthalate co-polymer and mixtures thereof; a cellulosic polymer comprising a material selected from alkyl cellulose, alkyl alkoxyalkyl cellulose, carboxyalkyl cellulose, alkyl carboxyalkyl cellulose and mixtures thereof; a bleach catalyst comprising a material selected from an iminium cation; iminium polyion; iminium zwitterion; modified amine; modified amine oxide; N-sulphonyl imine; N-phosphonyl imine; N-acyl imine; thiadiazole dioxide; perfluoroimine; cyclic sugar ketone and any mixture thereof; a bleach activator comprising a material selected from dodecanoyl oxybenzene sulphonate, decanoyl oxybenzene sulphonate, decanoyl oxybenzoic acid or salt thereof, 3,5,5-trimethyl hexanoyloxybenzene sulphonate, tetraacetyl ethylene diamine (TAED), nonanoyloxybenzene sulphonate (NOBS) and mixtures thereof; a source of hydrogen peroxide comprising a material selected from an inorganic perhydrate salt, including an alkali metal salt, such as sodium salts of perborate (usually mono- or tetra-hydrate), percarbonate, persulphate, perphosphate, persilicate salt, and any mixture thereof; a chelant comprising a material selected from DTPA (diethylene triamine pentaacetic acid), HEDP (hydroxyethane diphosphonic acid), DTPMP (diethylene triamine penta(methylene phosphonic acid)), ethylenediaminedisuccinic acid (EDDS), 1,2-dihydroxybenzene-3,5-disulfonic acid disodium salt hydrate, derivative of said chelant; and any mixture thereof.

A composition of the invention may comprise a fabric hueing agent selected from the group consisting of a dye; dye-clay conjugate comprising at least one cationic-basic dye and a smectite clay; and any mixture thereof.

A composition of the invention may comprise at least one fabric hueing agent selected from small molecule dye, polymeric dye, and any mixture thereof; dye-clay conjugate comprising at least one cationic-basic dye and a smectite clay; and any mixture thereof.

A composition comprising a protease of the invention may be provided in single or multiple-compartment unit doses. The composition may be a multi-compartment unit dose, wherein the protease variant is in a different compartment than any source of hydrogen peroxide and/or chelant and/or additional enzyme. A composition comprising at least one protease variant or polypeptide of the invention may comprise a wash liquor.

A composition comprising at least one protease variant of the invention may comprise one or more of the following ingredients (based on total composition weight): from about 0.0005 wt % to about 0.1 wt %, from about 0.001 wt % to about 0.05 wt %, or even from about 0.002 wt % to about 0.03 wt % of said protease variant; and one or more of the following: from about 0.00003 wt % to about 0.1 wt % fabric hueing agent; from about 0.001 wt % to about 5 wt %, perfume capsules; from about 0.001 wt % to about 1 wt %, cold-water soluble brighteners; from about 0.00003 wt % to about 0.1 wt % bleach catalysts; from about 0.00003 wt % to about 0.1 wt % first wash lipases; from about 0.00003 wt % to about 0.1 wt % bacterial cleaning cellulases; and/or from about 0.05 wt % to about 20 wt % Guerbet nonionic surfactants.

A composition may be a granular or powder laundry detergent comprising a cold water protease or comprising a protease variant that is not a cold water protease.

A composition of the invention may be provided in any suitable form, including a fluid or solid. The composition may be in the form of a unit dose pouch, especially when in the form of a liquid, and the composition may be at least partially, or even completely, enclosed by a water-soluble pouch. In addition, the composition may have any combination of parameters and/or characteristics detailed above.

Unless otherwise noted, all component or composition levels provided herein are made in reference to the active level of that component or composition, and are exclusive of impurities, for example, residual solvents or by-products, which may be present in commercially available sources. Enzyme components weights are based on total active protein. All percentages and ratios are calculated by weight unless otherwise indicated. All percentages and ratios are calculated based on the total composition unless otherwise indicated. In the exemplified detergent compositions, the enzymes levels are expressed by pure enzyme by weight of the total composition and, unless otherwise specified, the detergent ingredients are expressed by weight of the total compositions.

As indicated herein, in one aspect, the cleaning compositions of the present invention may further comprise one or more adjunct materials or ingredients including, but not limited to, e.g., one or more surfactants, builders, bleaches, bleach activators, bleach catalysts, other enzymes, enzyme stabilizing systems, chelants, optical brighteners, soil release polymers, dye transfer agents, dispersants, suds suppressors, dyes, perfumes, perfume capsules, colorants, filler salts, hydrotropes, photoactivators, fluorescers, fabric conditioners, fabric softeners, hydrolyzable surfactants, preservatives, anti-oxidants, anti-shrinkage agents, anti-wrinkle agents, germicides, fungicides, color speckles, silvercare, anti-tarnish and/or anti-corrosion agents, alkalinity sources, solubilizing agents, carriers, excipients, processing aids, pigments, rinse aid (e.g., a rinse aid containing at least one surfactant to prevent water droplet formation by making water drain from the surface of the item being cleaned in a thin sheet, rather than forming droplets), solvents, and/or pH control agents (see, e.g., U.S. Pat. Nos. 6,610,642, 6,605,458, 5,705,464, 5,710,115, 5,698,504, 5,695,679, 5,686,014 and 5,646,101, all of which are incorporated herein by reference). Aspects of specific cleaning composition materials are exemplified in detail below. If a cleaning adjunct material(s) is not compatible with a protease variant of the present invention in a desired cleaning composition, then a suitable method of keeping the cleaning adjunct material(s) and the protease variant(s) separated (i.e., not in contact with one anther) until combination of the two components is appropriate is used. Such separation methods include any suitable method known in the art (e.g., gelcaps, encapsulation, tablets, physical separation, etc.).

The cleaning compositions of the present invention are advantageously employed, for example, in laundry applications, hard surface cleaning applications, hand or manual dishwashing applications, automatic dishwashing applications, eyeglass cleaning applications, as well as cosmetic applications, such as for cleaning dentures, teeth, hair, and skin. Due to the unique advantages of increased effectiveness in lower temperature solutions, the protease variant enzymes of the present invention are suited for laundry applications and dishwashing applications, including hand and automatic dishwashing applications. Furthermore, the protease variant enzymes of the present invention find use in solid, gel, granular, and/or liquid compositions, including solid, gel, granular, and/or liquid detergent compositions and/or formulations.

The protease variants of the present invention also find use cleaning additive product compositions. In one aspect, a protease variant of the invention is useful in low temperature solution cleaning applications and methods. In one aspect, the invention provides cleaning additive product compositions which include at least one protease variant enzyme of the present invention and which are ideally suited for inclusion in a wash process when additional bleaching effectiveness is desired. Such instances include, but are not limited to, e.g., low temperature solution cleaning applications. In one aspect, the additive product composition is in its simplest form—i.e., one or more protease variants of the invention. In one aspect, the additive product composition is packaged in dosage form for addition to a cleaning process. In one aspect, the additive product composition is packaged in dosage form for addition to a cleaning process where a source of peroxygen is employed and increased bleaching effectiveness is desired. Any suitable single dosage unit form may be used, including but not limited to, e.g., pills, tablets, gelcaps, or other single dosage units, such as pre-measured powders or liquids. Thus, in one aspect, the invention provides a cleaning product composition comprising at least one protease variant of the invention, wherein the product is formulated in suitable form (e.g., as a liquid, powder solid, pill, tablet, gelcap or other suitable form) in a suitable single dosage unit such that a single dose of the protease variant is provided. Such cleaning products are useful in a variety of cleaning methods and applications, including but not limited to, e.g., machine or hand laundry methods and applications, automatic dishwashing or hand dishwashing methods and applications, etc. Such cleaning methods and applications may be conducted at low temperature or low pH conditions. In one aspect, at least one filler and/or at least one carrier material is included to increase the volume of such compositions. Suitable filler or carrier materials include, but are not limited to, e.g., various salts of sulfate, carbonate and silicate as well as talc, clay and the like. Suitable filler or carrier materials for liquid compositions include, but are not limited to, e.g., water or low molecular weight primary and secondary alcohols including polyols and diols. Examples of such alcohols include, but are not limited to, e.g., methanol, ethanol, propanol and isopropanol. In one aspect, the compositions contain from about 5% to about 90% of such filler or carrier materials. Acidic fillers may be included in such compositions to reduce the pH of the resulting solution in the cleaning method or application. Alternatively, in one aspect, the cleaning additive includes one or more adjunct ingredients, as more fully described below.

The present cleaning compositions and cleaning additives require an effective amount of at least one protease variant of the invention, alone or in combination with other proteases and/or additional enzymes. The required level of enzyme is achieved by the addition of one or more protease variants of the invention. Typically, a cleaning composition comprises at least about 0.0001 weight percent to about 20 weight percent, from about 0.0001 to about 10 weight percent, from about 0.0001 to about 1 weight percent, from about 0.001 to about 1 weight percent, or from about 0.01 to about 0.1 weight percent of at least one protease variant of the invention. In one aspect, a composition of the invention (e.g., cleaning composition of the invention) comprises from about 0.01 milligram (mg) to about 10 mg, about 0.01 to about 5 mg, about 0.01 mg to about 2 mg, about 0.01 to about 1 mg, about 0.5 mg to about 10 mg, about 0.5 to about 5 mg, about 0.5 to about 4 mg, about 0.5 to about 4 mg, about 0.5 to about 3 mg, about 0.5 to about 2 mg, about 0.5 to about 1 mg, about 0.1 to about 10 mg, about 0.1 to about 5 mg, about 0.1 to about 4 mg, about 0.1 to about 3 mg, about 0.1 to about 2 mg, about 0.1 to about 2 mg, about 0.1 to about 1 mg, about 0.1 to about 0.5 mg of at least one active protease variant of the invention per gram of the composition.

The invention includes a cleaning composition comprising an amount of a protease variant of the invention (said composition optionally comprising one or more adjunct ingredients) such that when the cleaning composition is added to wash water the resultant protease concentration in the resultant wash liquor is 0.01 ppm to 10 ppm, including, e.g., 0.1 ppm to 1 ppm, 0.1 to 5 ppm, 1 to 5 ppm, 1 ppm to 10 ppm, 5 ppm to 10 ppm, 5 ppm to 7 ppm.

The cleaning compositions of the invention are typically formulated such that, during use in aqueous cleaning operations, the wash water will have a pH of from about 5.0 to about 11.5 or even from about 7.5 to about 10.5. Liquid product compositions or formulations are typically formulated to have a neat pH from about 3.0 to about 9.0 or from about 3.0 to about 5.0. Granular laundry product compositions are typically formulated to have a pH from about 9 to about 11. Hand dishwashing and automatic dishwashing detergent compositions are typically formulated to have a pH from about 8 to about 11.5, including, but not limited to, e.g., pH ranges of about 8 to about 10, from about 9 to about 11.5, and from about 9.5 to about 11.5 depending on the method and specific application. Techniques for controlling pH at recommended usage levels include the use of buffers, alkalis, acids, etc., and are well known to those skilled in the art.

Suitable low pH cleaning compositions typically have a neat pH of from about 3 to about 5, and are typically free of surfactants that hydrolyze in such a pH environment. Such surfactants include sodium alkyl sulfate surfactants that comprise at least one ethylene oxide moiety or even from about 1 to about 16 moles of ethylene oxide. Such cleaning compositions typically comprise a sufficient amount of a pH modifier, such as sodium hydroxide, monoethanolamine, or hydrochloric acid, to provide such cleaning composition with a neat pH of from about 3 to about 5. Such compositions typically comprise at least one acid stable enzyme. In one aspect, the compositions are liquids, while in other aspects, they are solids. The pH of such liquid compositions is typically measured as a neat pH. The pH of such solid compositions is measured as a 10% solids solution of said composition wherein the solvent is distilled water. In these aspects, all pH measurements are taken at 20° C., unless otherwise indicated.

In one aspect, when the protease variant(s) of the invention is/are employed in a granular composition or liquid, it is desirable for the protease variant to be in the form of an encapsulated particle to protect the protease variant from other components of the granular composition during storage. In addition, encapsulation is also a means of controlling the availability of the protease variant during the cleaning process. In one aspect, encapsulation enhances the performance of the protease variant(s) and/or additional enzymes. In this regard, the protease variants of the present invention are encapsulated with any suitable encapsulating material known in the art. In one aspect, the encapsulating material typically encapsulates at least part of the catalyst for the protease variant(s) of the invention. Typically, the encapsulating material is water-soluble and/or water-dispersible. In one aspect, the encapsulating material has a glass transition temperature (Tg) of 0° C. or higher. Glass transition temperature is described in more detail in WO 97/11151. The encapsulating material is typically selected from consisting of carbohydrates, natural or synthetic gums, chitin, chitosan, cellulose and cellulose derivatives, silicates, phosphates, borates, polyvinyl alcohol, polyethylene glycol, paraffin waxes, and combinations thereof. When the encapsulating material is a carbohydrate, it is typically selected from monosaccharides, oligosaccharides, polysaccharides, and combinations thereof. In some typical aspects, the encapsulating material is a starch (see, e.g., EP 0 922 499; U.S. Pat. Nos. 4,977,252, 5,354,559, and 5,935,826). In one aspect, the encapsulating material is a microsphere made from plastic such as thermoplastics, acrylonitrile, methacrylonitrile, polyacrylonitrile, polymethacrylonitrile and mixtures thereof; commercially available microspheres that find use include, but are not limited to those supplied by EXPANCEL® (Stockviksverken, Sweden), and PM 6545, PM 6550, PM 7220, PM 7228, EXTENDOSPHERES®, LUXSIL®, Q-CEL®, and SPHERICEL® (PQ Corp., Valley Forge, Pa.).

As described herein, the protease variants of the invention find particular use in the cleaning methods and applications, including, but not limited to, e.g., cleaning, laundry, hand dishwashing, and automatic dishwashing detergent compositions. These applications place enzymes under various environmental stresses. The protease variants of the invention provide advantages over many currently used enzymes in such cleaning applications due to their proteolytic activity and stability under various conditions.

There are a variety of wash conditions including varying detergent formulations, wash water volumes, wash water temperatures, and lengths of wash time, to which proteases involved in washing are exposed. In addition, detergent formulations used in different geographical areas have different concentrations of their relevant components present in the wash water. For example, European detergents typically have about 4500-5000 parts per million (ppm) of detergent components in the wash water, while Japanese detergents typically have approximately 667 ppm of detergent components in the wash water. In North America, particularly the United States, detergents typically have about 975 ppm of detergent components present in the wash water.

A low detergent concentration system includes detergents where less than about 800 ppm of the detergent components are present in the wash water. Japanese detergents are typically considered low detergent concentration system as they have approximately 667 ppm of detergent components present in the wash water.

A medium detergent concentration includes detergents where between about 800 ppm and about 2000 ppm of the detergent components are present in the wash water. North American detergents are generally considered to be medium detergent concentration systems as they have approximately 975 ppm of detergent components present in the wash water. Brazil typically has approximately 1500 ppm of detergent components present in the wash water.

A high detergent concentration system includes detergents where greater than about 2000 ppm of the detergent components are present in the wash water. European detergents are generally considered to be high detergent concentration systems as they have approximately 4500-5000 ppm of detergent components in the wash water.

Latin American detergents are generally high suds phosphate builder detergents and the range of detergents used in Latin America can fall in both the medium and high detergent concentrations as they range from 1500 ppm to 6000 ppm of detergent components in the wash water. As mentioned above, Brazil typically has approximately 1500 ppm of detergent components present in the wash water. However, other high suds phosphate builder detergent geographies, not limited to other Latin American countries, may have high detergent concentration systems up to about 6000 ppm of detergent components present in the wash water.

In light of the foregoing, it is evident that concentrations of detergent compositions in typical wash solutions throughout the world varies from less than about 800 ppm of detergent composition ("low detergent concentration geographies"), e.g., about 667 ppm in Japan, to between about 800 ppm to about 2000 ppm ("medium detergent concentration geographies"), e.g., about 975 ppm in U.S. and about 1500 ppm in Brazil, to greater than about 2000 ppm ("high detergent concentration geographies"), e.g., about 4500 ppm to about 5000 ppm in Europe and about 6000 ppm in high suds phosphate builder geographies.

The concentrations of the typical wash solutions are determined empirically. For example, in the U.S., a typical washing machine holds a volume of about 64.4 L of wash solution. Accordingly, in order to obtain a concentration of about 975 ppm of detergent within the wash solution about 62.79 g of detergent composition must be added to the 64.4 L of wash solution. This amount is the typical amount measured into the wash water by the consumer using the measuring cup provided with the detergent.

As a further example, different geographies use different wash temperatures. The temperature of the wash water in Japan is typically less than that used in Europe. For example, the temperature of the wash water in North America and Japan is typically between about 10 and about 30° C. (e.g., about 20° C.), whereas the temperature of wash water in Europe is typically between about 30 and about 60° C. (e.g., about 40° C.). However, in the interest of saving energy, many consumers are switching to using cold water washing. In addition, in some further regions, cold water is typically used for laundry, as well as in dishwashing applications. In one aspect, the "cold water washing" of the present invention utilizes washing at temperatures from about 4° C. to about 10° C., from about 10° C. to about 40° C., or from about 20° C. to about 30° C., from about 15° C. to about 25° C., from about 10° C. to about 20° C., from about 14° C. to about 18° C., as well as all other combinations within the range of about 15° C. to about 35° C., and all ranges within 10° C. to 40° C., and about 16° C.

As a further example, different geographies typically have different water hardness. Water hardness is usually described in terms of the grains per gallon mixed $Ca^{2+}/Mg^{2+}$. Hardness is a measure of the amount of calcium ($Ca^{2+}$) and magnesium ($Mg^{2+}$) in the water. Most water in the United States is hard, but the degree of hardness varies. Moderately hard (60-120 ppm) to hard (121-181 ppm) water has 60 to 181 parts per million (parts per million converted to grains per U.S. gallon is ppm # divided by 17.1 equals grains per gallon) of hardness minerals.

| Water | Grains per gallon | Parts per million |
|---|---|---|
| Soft | less than 1.0 | less than 17 |
| Slightly hard | 1.0 to 3.5 | 17 to 60 |
| Moderately hard | 3.5 to 7.0 | 60 to 120 |
| Hard | 7.0 to 10.5 | 120 to 180 |
| Very hard | greater than 10.5 | greater than 180 |

European water hardness is typically greater than about 10.5 (e.g., about 10.5 to about 20.0) grains per gallon mixed $Ca^{2+}/Mg^{2+}$ (e.g., about 15 grains per gallon mixed $Ca^{2+}/Mg^{2+}$). North American water hardness is typically greater than Japanese water hardness, but less than European water hardness. For example, North American water hardness can be between about 3 to about 10 grains, about 3 to about 8 grains or about 6 grains Japanese water hardness is typically lower than North American water hardness, usually less than about 4, for example about 3 grains per gallon mixed $Ca^{2+}/Mg^{2+}$.

Accordingly, in one aspect, the invention provides protease variants that show surprising wash performance in at least one set of wash conditions (e.g., water temperature, water hardness, and/or detergent concentration). In one aspect, the protease variants of the invention are comparable in wash performance to other subtilisin proteases. In one aspect, the protease variants of the present invention exhibit enhanced wash performance as compared to subtilisin proteases currently commercially available. Thus, in one aspect of the invention, the protease variants provided herein exhibit enhanced oxidative stability, enhanced thermal stability, enhanced cleaning capabilities under various conditions, and/or enhanced chelator stability. In addition, the protease variants of the invention find use in cleaning compositions that do not include detergents, again either alone or in combination with builders and stabilizers.

In one aspect, the invention provides a cleaning composition comprising at least one protease variant of the present invention that is present at a level from about 0.00001% to about 10% by weight of the composition with the balance (e.g., about 99.999% to about 90.0%) comprising one or more cleaning adjunct materials by weight of composition. In another aspect, the invention provides a cleaning composition comprising at least one protease variant of the invention that is present at a level of about 0.0001% to about 10%, about 0.001% to about 5%, about 0.001% to about 2%, or about 0.005% to about 0.5% by weight of the composition with the balance of the cleaning composition (e.g., about 99.9999% to about 90.0%, about 99.999% to about 98%, about 99.995% to about 99.5% by weight) comprising one or more cleaning adjunct materials.

In one aspect, a cleaning composition of the invention comprises, in addition to at least one protease variant of the invention, one or more additional enzymes, which provide cleaning performance and/or fabric care and/or hand or manual dishwashing and/or automatic dishwashing benefits. Examples of suitable enzymes include, but are not limited to, e.g., hemicellulases, cellulases, peroxidases, proteases, xylanases, lipases, phospholipases, esterases, perhydrolases, cutinases, pectinases, pectate lyases, mannanases, keratinases, reductases, oxidases, phenoloxidases, lipoxygenases, ligninases, pullulanases, tannases, pentosanases, malanases, β-glucanases, arabinosidases, hyaluronidase, chondroitinase, laccase, and/or amylases, neutral metalloprotease enzymes (abbreviated as "nprE"), or mixtures of any thereof. In one aspect, the cleaning composition comprises, in addition to at least one protease variant of the invention, a combination of additional enzymes (i.e., a "cocktail") comprising conventional applicable enzymes such as, e.g., at least one additional protease, lipase, cutinase, cellulose, and/or amylase.

In addition to the protease variants provided herein, any other suitable protease may find use and be included in a composition of the invention. In one aspect, the invention provides a composition (e.g., cleaning composition) comprising at least one protease variant of the invention and at least one additional protease. Suitable proteases include those of animal, vegetable, or microbial origin. In one aspect, a microbial protease may be included. A chemically or genetically modified mutant of a protease may be included. In one aspect, the at least one additional protease is a serine protease, preferably an alkaline microbial protease or a trypsin-like protease. Examples of alkaline proteases include subtilisins, especially those derived from Bacillus (e.g., subtilisin, B. lentus subtilisin (i.e., GG36), B. amyloliquefaciens subtilisin (i.e., BPN'), subtilisin Carlsberg, subtilisin 309, subtilisin 147, PB92, and subtilisin 168). Additional examples include those mutant proteases (i.e., protease variants) described in U.S. Pat. Nos. RE 34,606, 5,955,340, 5,700,676, 6,312,936, and 6,482,628, all of which are incorporated herein by reference. Additional proteases include, but are not limited to trypsin (e.g., of porcine or bovine origin), and the Fusarium protease described in WO 89/06270. A composition of the invention comprising at least one protease variant of the invention may also comprise at least one commercially available protease enzyme. Commercially available protease enzymes that find use in compositions of the invention include, but are not limited to, e.g., MAXATASE®, MAXACAL™, MAXAPEM™, OPTICLEAN®, OPTIMASE®, PROPERASE®, PURAFECT®, PURAFECT® OXP, PURAMAX™, EXCELLASE™, and PURAFAST™ (Genencor); ALCALASE®, SAVINASE®, PRIMASE®, DURAZYM™, POLARZYME®, OVOZYME®, KANNASE®, LIQUANASE®, NEUTRASE®, RELASE® and ESPERASE® (Novozymes); KAP Bacillus alkalophilus subtilisin with A230V+S256G+S259N (Kao); and BLAP™ B. lentus protease, BLAP X, and BLAP S (Henkel Kommanditgesellschaft auf Aktien, Duesseldorf, Germany). Additional proteases that may be included in compositions of the invention include those described in WO95/23221, WO 92/21760, U.S. Pat. Pub. No. 2008/0090747, and U.S. Pat. Nos. 5,801,039, 5,340,735, 5,500,364, 5,855,625, RE 34,606, 5,955,340, 5,700,676, 6,312,936, and 6,482,628, and various other patents. Metalloproteases may be included in compositions of the invention. Such metalloproteases, include, but are not limited to, e.g., the neutral metalloprotease enzyme (nprE) described in WO 07/044,993.

In one aspect, the invention provides a composition (e.g., cleaning composition) comprising at least one protease variant of the invention and at least one lipase. Suitable lipases include, but are not limited to, e.g., those of bacterial or fungal origin. A chemically or genetically modified mutant of a lipase may be included in the composition. Examples of useful lipases include Humicola lanuginosa lipase (see, e.g., EP 258 068, and EP 305 216), Rhizomucor miehei lipase (see, e.g., EP 238 023), Candida lipase, such as C. antarctica lipase (e.g., C. antarctica lipase A or B; see, e.g., EP 214 761), Pseudomonas lipases such as P. alcaligenes lipase and P. pseudoalcaligenes lipase (see, e.g., EP 218 272), P. cepacia lipase (see, e.g., EP 331 376), P. stutzeri lipase (see, e.g., GB 1,372,034), P. fluorescens lipase, Bacillus lipase (e.g., B.

*subtilis* lipase (Dartois et al., Biochem. Biophys. Acta 1131: 253-260 (1993)); *B. stearothermophilus* lipase (see, e.g., JP 64/744992); and *B. pumilus* lipase (see, e.g., WO 91/16422)).

Furthermore, a number of cloned lipases find use in compositions (e.g., cleaning compositions) of the present invention, including, but not limited to, e.g., *Penicillium camembertii* lipase (Yamaguchi et al., Gene 103:61-67 (1991)), *Geotricum candidum* lipase (Schimada et al., J. Biochem. 106:383-388 (1989)), and various *Rhizopus* lipases such as *R. delemar* lipase (Hass et al., Gene 109:117-113 (1991)), a *R. niveus* lipase (Kugimiya et al., Biosci. Biotech. Biochem. 56:716-719 (1992)) and *R. oryzae* lipase.

Other types of lipolytic enzymes, such as cutinases, also find use in one aspect of the present invention, including, but not limited to, e.g., the cutinase derived from *Pseudomonas mendocina* (see WO 88/09367), and the cutinase derived from *Fusarium solani pisi* (see WO 90/09446).

Additional suitable lipases include commercially available lipases such as M1 LIPASE™, LUMA FAST™, and LIPOMAX™ (Genencor); LIPOLASE® and LIPOLASE® ULTRA (Novozymes); and LIPASE P™ "Amano" (Amano Pharmaceutical Co. Ltd., Japan).

In one aspect, the invention provides compositions (e.g., cleaning compositions) comprising at least one protease variant of the invention and at least one lipase that is present at a level from about 0.00001% to about 10% of additional lipase by weight of the composition and the balance of one or more cleaning adjunct materials by weight of composition. In one aspect, a cleaning composition of the present invention comprises, in addition to at least one protease variant of the invention, at least one lipase at a level of about 0.0001% to about 10%, about 0.001% to about 5%, about 0.001% to about 2%, or about 0.005% to about 0.5% lipase by weight of the composition.

Also included is a composition (e.g., cleaning composition) comprising at least one variant of the invention and at least one amylase. Any amylase (e.g., alpha and/or beta) suitable for use in alkaline solutions may be useful to include in such a composition. Suitable amylases include, but are not limited to, e.g., those of bacterial or fungal origin. A chemically or genetically modified mutant of an amylase may be included. Amylases that find use in compositions of the invention, include, but are not limited to, e.g., α-amylases obtained from *B. licheniformis* (see, e.g., GB 1,296,839). Commercially available amylases that find use in compositions of the invention include, but are not limited to, e.g., DURAMYL®, TERMAMYL®, FUNGAMYL®, STAINZYME®, STAINZYME PLUS®, STAINZYME ULTRA®, and BAN™ (Novozymes), as well as POWERASE™, RAPIDASE® and MAXAMYL® P (Genencor).

In one aspect, the invention provides a cleaning composition comprising at least one protease variant or at least one amylase, wherein the amylase is present at a level from about 0.00001% to about 10% of additional amylase by weight of the composition and the balance of one or more cleaning adjunct materials by weight of composition. In another aspect, the invention includes a cleaning composition comprising at least one protease variant and at least one amylase that is present at a level of about 0.0001% to about 10%, about 0.001% to about 5%, about 0.001% to about 2%, about 0.005% to about 0.5% amylase by weight of the composition.

Any suitable cellulase may find used in a cleaning composition of the present invention. In one aspect, the invention provides a cleaning composition comprising at least one protease variant of the invention and one or at least one cellulase. Suitable cellulases include, but are not limited to, e.g., those of bacterial or fungal origin. A chemically or genetically modified mutant of a cellulase may be included in a composition of the invention. Suitable cellulases include, but are not limited to, e.g., *Humicola insolens* cellulases (see, e.g., U.S. Pat. No. 4,435,307) and cellulases having color care benefits (see, e.g., EP 0 495 257). Additional suitable cellulases are known in the art. Commercially available cellulases that find use and may be included in a composition of the invention include, but are not limited to, e.g., CELLUZYME®, CAREZYME® (Novozymes), and KAC-500(B)™ (Kao Corporation), Puradax 7000L, Puradax HA 4000G (Genencor). In one aspect, cellulases are incorporated as portions or fragments of mature wild-type or variant cellulases, wherein a portion of the N-terminus is deleted (see, e.g., U.S. Pat. No. 5,874,276). In one aspect, a cleaning composition of the invention comprises at least one protease variant of the invention and at least one cellulase at a level from about 0.00001% to about 10% of additional cellulase by weight of the composition and the balance of one or more cleaning adjunct materials by weight of composition. In another aspect, the invention provides a cleaning composition comprising at least one protease variant of the invention and at least one cellulase at a level of about 0.0001% to about 10%, about 0.001% to about 5%, about 0.001% to about 2%, about 0.005% to about 0.5% cellulase by weight of the composition.

Any mannanase suitable for use in detergent compositions also finds use in and thus may be included in a cleaning composition of the invention. In one aspect, the invention provides a cleaning composition comprising at least one protease variant of the invention and least one mannanase. Suitable mannanases include, but are not limited to, e.g., those of bacterial or fungal origin. A chemically or genetically modified mutant of a mannanase may be included in a composition of the invention. Various mannanases are known which are useful and may be included in a composition of invention (see, e.g., mannanases described in U.S. Pat. Nos. 6,566,114, 6,602,842, and 6,440,991, all of which are incorporated herein by reference). In one aspect, the invention provides a cleaning composition comprising at least one protease variant of the invention and at least one mannanase at a level from about 0.00001% to about 10% of additional mannanase by weight of the composition and the balance of one or more cleaning adjunct materials by weight of composition. In some such cleaning compositions, each mannanase is present at a level of about 0.0001% to about 10%, about 0.001% to about 5%, about 0.001% to about 2%, or about 0.005% to about 0.5% mannanase by weight of the composition.

A peroxidase may be used in combination with hydrogen peroxide or a source thereof (e.g., a percarbonate, perborate or persulfate) in a composition of the invention. An oxidase may be used in combination with oxygen in a composition of the invention. Both such types of enzymes are used for "solution bleaching" (i.e., to prevent transfer of a textile dye from a dyed fabric to another fabric when the fabrics are washed together in a wash liquor), preferably together with an enhancing agent (see, e.g., WO 94/12621 and WO 95/01426). Suitable peroxidases/oxidases that may be included in compositions of the invention include, but are not limited to, e.g., those of plant, bacterial, or fungal origin. A chemically or genetically modified mutant of a peroxidase or oxidase may be included in a composition of the invention. In one aspect, the invention provides a cleaning composition comprising at least one protease variant of the invention and at least one peroxidase and/or at least one oxidase enzyme. Each such peroxidase or oxidase may be present in the composition at a level from about 0.00001% to about 10% of peroxidase or oxidase by weight of the composition and the balance of one or more cleaning adjunct materials by weight of composition.

In another aspect, the invention provides a cleaning composition comprising at least one protease variant of the invention and at least one peroxidase and/or at least one oxidase enzyme, wherein each such peroxidase or oxidase is present at a level of about 0.0001% to about 10%, about 0.001% to about 5%, about 0.001% to about 2%, or about 0.005% to about 0.5% peroxidase or oxidase enzyme, respectively, by weight of the composition.

In one aspect, the invention provides a composition (e.g., cleaning composition) comprising at least one protease variant of the invention and one or more additional enzymes find use, including but not limited to, e.g., one or more perhydrolases (see, e.g., WO 05/056782).

In another aspect, the invention provides a composition (e.g., cleaning composition) comprising at least one protease variant of the invention and one or more mixtures of the above-mentioned enzymes are encompassed, such as, e.g., one or more additional proteases, amylases, lipases, mannanases, and/or cellulases. Indeed, it is contemplated that various mixtures of these enzymes will find use in compositions of the present invention. It is also contemplated that the varying levels of the protease variant(s) and one or more additional enzymes may both independently range to about 10%, the balance of the cleaning composition being one or more cleaning adjunct materials. The specific selection of a cleaning adjunct material is readily made by considering the surface or item (e.g., dishware item, tableware item, or fabric item) or fabric to be cleaned, and the desired form of the composition for the cleaning conditions during use (e.g., through the hand or automatic dishwashing detergent use).

In one aspect, the invention provides a composition (e.g., cleaning composition) comprising at least one protease variant of the invention (and optionally at least one additional enzyme, if desired) and one or more cleaning adjunct materials. Examples of suitable cleaning adjunct materials include, but are not limited to, e.g., surfactants, builders, bleaches, bleach activators, bleach catalysts, other enzymes, enzyme stabilizing systems, chelants, optical brighteners, soil release polymers, dye transfer agents, dye transfer inhibiting agents, catalytic materials, hydrogen peroxide, sources of hydrogen peroxide, preformed peracids, polymeric dispersing agents, clay soil removal agents, structure elasticizing agents, dispersants, suds suppressors, dyes, perfumes, colorants, filler salts, hydrotropes, perfume, perfume capsule, photoactivators, fluorescers, fabric conditioners, fabric softeners, carriers, hydrotropes, processing aids, solvents, pigments, hydrolyzable surfactants, preservatives, anti-oxidants, anti-shrinkage agents, anti-wrinkle agents, germicides, fungicides, color speckles, silvercare, anti-tarnish and/or anti-corrosion agents, alkalinity sources, solubilizing agents, carriers, processing aids, pigments, and pH control agents (see, e.g., U.S. Pat. Nos. 6,610,642, 6,605,458, 5,705,464, 5,710,115, 5,698,504, 5,695,679, 5,686,014 and 5,646,101, all of which are incorporated herein by reference). Aspects of specific cleaning composition materials are exemplified in detail below. As noted above, if a cleaning adjunct material is not compatible with a protease variant of the present invention included in a desired cleaning composition, then a suitable method of keeping the cleaning adjunct material(s) and the protease(s) separated (i.e., not in contact with each other) until combination of the components is appropriate is used. Such separation methods include any suitable method known in the art (e.g., gelcap, encapsulation, tablets, physical separation, etc.).

In one aspect, a composition (e.g., cleaning composition) of the invention comprises an effective amount of at least one protease variant of the invention that is useful or effective for cleaning a surface in need of proteinaceous stain removal. Such cleaning compositions include cleaning compositions for such applications as cleaning hard surfaces, laundry, fabrics, dishes, tableware, or dishware (e.g., by hand or manual dishwashing or automatic dishwashing). Indeed, in one aspect, the present invention provides fabric cleaning compositions, while in another aspect, the invention provides non-fabric cleaning compositions. Notably, the invention also provides cleaning compositions comprising at least one protease variant of the invention, wherein such cleaning compositions are suitable for personal care, including oral care (including dentifrices, toothpastes, mouthwashes, etc., as well as denture cleaning compositions), suitable for cleaning skin and hair, and suitable for cleaning eyeglasses. It is intended that the present invention encompass detergent compositions in any form (i.e., liquid, granular, bar, solid, semi-solid, gels, emulsions, tablets, capsules, etc.).

By way of example, several cleaning compositions wherein the protease variants of the invention find use are described in greater detail below. In one aspect in which the cleaning compositions of the invention are formulated as compositions suitable for use in laundry machine washing method(s), the compositions of the invention preferably contain at least one surfactant and at least one builder compound, as well as one or more cleaning adjunct materials, including, e.g., one or more cleaning adjunct materials selected from the group of organic polymeric compounds, bleaching agents, additional enzymes, suds suppressors, dispersants, lime-soap dispersants, soil suspension and anti-redeposition agents, and corrosion inhibitors. In one aspect, laundry compositions also contain one or more softening agents (i.e., as additional cleaning adjunct materials). Additional exemplary laundry or fabric cleaning compositions and formulations to which one or more protease variants of the invention can be added are presented in the Examples below.

The compositions of the invention also find use as detergent additive products in solid or liquid form. Such additive products are intended to supplement and/or boost the performance of conventional detergent compositions and can be added at any stage of the cleaning process. In one aspect, the density of the laundry detergent composition ranges from about 400 to about 1200 g/liter, while in other aspects, it ranges from about 500 to about 950 g/liter of composition measured at 20° C.

In one aspect, the invention provides cleaning compositions, such as those described in U.S. Pat. No. 6,605,458, comprising at least protease variant of the invention. In one aspect, the composition comprising at least one protease variant of the invention is a compact granular fabric cleaning composition, while in other aspects, the composition is a granular fabric cleaning composition useful in the laundering of colored fabrics; in another aspect, the composition is a granular fabric cleaning composition which provides softening through the wash capacity. In another aspect, the composition is a heavy duty liquid fabric cleaning composition. In another aspect, the invention provides a composition comprising at least one protease variant of the invention, wherein the composition is a fabric cleaning composition, such as one described in U.S. Pat. Nos. 6,610,642 and 6,376,450. Also provided are granular laundry detergent compositions of particular utility under European or Japanese washing conditions (see, e.g., U.S. Pat. No. 6,610,642) which comprise at least one protease variant of the invention.

In one aspect, the invention provides hard surface cleaning compositions comprising at least one protease variant provided herein. Some such compositions comprise hard surface cleaning compositions such as those described in U.S. Pat.

Nos. 6,610,642, 6,376,450, and 6,376,450 that include at least one such protease variant.

The invention includes hand dishwashing or automatic dishwashing detergent compositions comprising at least one protease variant provided herein. Some such compositions comprise hard surface cleaning compositions, such as those described in U.S. Pat. Nos. 6,610,642 and 6,376,450.

In one aspect, the invention provides cleaning compositions for use in manual or hand dishwashing or automatic dishwashing methods comprising at least one protease variant of the invention and/or at least one surfactant and/or at least one additional cleaning adjunct material selected from the group of organic polymeric compounds, suds enhancing agents, group II metal ions, solvents, hydrotropes, and additional enzymes.

In one aspect in which the cleaning compositions of the invention are formulated as compositions suitable for use in automatic dishwashing machine method(s), the compositions of the invention typically contain at least one surfactant and/or at least one builder compound and may contain one or more cleaning adjunct materials preferably selected from organic polymeric compounds, bleaching agents, additional enzymes, suds suppressors, dispersants, lime-soap dispersants, soil suspension and anti-redeposition agents and corrosion inhibitors. Additional exemplary dishwashing compositions and formulations to which one or more protease variants of the invention can be added are presented in the Examples below.

In another aspect, the invention provides oral care compositions comprising at least one protease variant of the present invention that are useful for oral care (e.g., cleaning teeth and dentures); components of oral care compositions that may be useful and included in such compositions include those described in U.S. Pat. No. 6,376,450. Compositions of the invention may further comprise cleaning adjunct materials and compounds described in the U.S. Pat. Nos. 6,376,450, 6,605,458, and 6,610,642, all of which are incorporated by reference herein.

The cleaning compositions of the invention are formulated into any suitable form and prepared by any process chosen by the formulator, non-limiting examples of which are described in U.S. Pat. Nos. 5,879,584, 5,691,297, 5,574,005, 5,569,645, 5,565,422, 5,516,448, 5,489,392, and 5,486,303, all of which are incorporated herein by reference. When a low pH cleaning composition is desired, the pH of such composition is adjusted via the addition of a material such as monoethanolamine or an acidic material such as hydrogen chloride (HCl).

While not essential for the purposes of the present invention, the non-limiting list of adjuncts illustrated hereinafter are suitable for use in the instant cleaning compositions. In one aspect, these adjuncts are incorporated, e.g., to assist or enhance cleaning performance for treatment of the substrate to be cleaned or to modify the aesthetics of the cleaning composition as is the case with perfumes, colorants, dyes or the like. It is understood that such adjuncts are in addition to the protease variants of the present invention. The precise nature of these additional components, and levels of incorporation thereof, will depend on the physical form of the composition and the nature of the cleaning operation for which it is to be used. Suitable adjunct materials include, but are not limited to, e.g., surfactants, builders, chelating agents, dye transfer inhibiting agents, deposition aids, dispersants, additional enzymes, and enzyme stabilizers, catalytic materials, bleach activators, bleach boosters, hydrogen peroxide, sources of hydrogen peroxide, preformed peracids, polymeric dispersing agents, clay soil removal/anti-redeposition agents, brighteners, suds suppressors, dyes, perfumes, structure elasticizing agents, fabric softeners, carriers, hydrotropes, processing aids and/or pigments. In addition to the disclosure below, suitable examples of such other adjuncts and levels of use are found in U.S. Pat. Nos. 5,576,282, 6,306,812, and 6,326,348, incorporated by reference. The aforementioned adjunct ingredients may constitute the balance of the cleaning compositions of the present invention.

In one aspect, cleaning compositions of the invention comprise at least one surfactant and/or a surfactant system, wherein the surfactant is selected from nonionic surfactants, anionic surfactants, cationic surfactants, ampholytic surfactants, zwitterionic surfactants, semi-polar nonionic surfactants and mixtures thereof. In some low pH cleaning composition aspects (e.g., compositions having a neat pH of from about 3 to about 5), the composition typically does not contain alkyl ethoxylated sulfate, as it is believed that such surfactant may be hydrolyzed by such compositions the acidic contents. In one aspect, the surfactant is present at a level of from about 0.1% to about 60%, while in alternative aspects the level is from about 1% to about 50%, while in still further aspects the level is from about 5% to about 40%, by weight of the cleaning composition.

In one aspect, cleaning compositions of the invention comprise one or more detergent builders or builder systems. In some such compositions incorporating at least one builder, the cleaning compositions comprise at least about 1%, from about 3% to about 60% or even from about 5% to about 40% builder by weight of the cleaning composition. Builders include, but are not limited to, e.g., alkali metal, ammonium and alkanolammonium salts of polyphosphates, alkali metal silicates, alkaline earth and alkali metal carbonates, aluminosilicates, polycarboxylate compounds, ether hydroxypolycarboxylates, copolymers of maleic anhydride with ethylene or vinyl methyl ether, 1,3,5-trihydroxy benzene-2,4,6-trisulphonic acid, and carboxymethyloxysuccinic acid, the various alkali metal, ammonium and substituted ammonium salts of polyacetic acids such as ethylenediamine tetraacetic acid and nitrilotriacetic acid, as well as polycarboxylates, such as mellitic acid, succinic acid, citric acid, oxydisuccinic acid, polymaleic acid, benzene 1,3,5-tricarboxylic acid, carboxymethyloxysuccinic acid, and soluble salts thereof. It is contemplated that any suitable builder will find use in various compositions of the invention.

In some such compositions, the builders form water-soluble hardness ion complexes (e.g., sequestering builders), such as citrates and polyphosphates (e.g., sodium tripolyphosphate and sodium tripolyphosphate hexahydrate, potassium tripolyphosphate, and mixed sodium and potassium tripolyphosphate, etc.). It is contemplated that any suitable builder will find use in the present invention, including those known in the art (see, e.g., EP 2 100 949).

Some cleaning compositions of the invention comprise at least one chelating agent in addition to at least one protease variant. Suitable chelating agents include, but are not limited to, e.g., copper, iron, and/or manganese chelating agents and mixtures thereof. In aspects in which at least one chelating agent is used, the cleaning compositions of the present invention comprise from about 0.1% to about 15% or even from about 3% to about 10% chelating agent by weight of the subject cleaning composition.

Some cleaning compositions provided herein comprise at least one deposition aid in addition to at least one protease variant. Suitable deposition aids include, but are not limited to, e.g., polyethylene glycol, polypropylene glycol, polycarboxylate, soil release polymers such as polytelephthalic acid, clays such as kaolinite, montmorillonite, atapulgite, illite, bentonite, halloysite, and mixtures thereof.

As indicated herein, in one aspect, anti-redeposition agents find use in one aspect of the present invention. In one aspect, non-ionic surfactants find use. These non-ionic surfactants also find use in preventing the re-deposition of soils. In one aspect, the anti-redeposition agent is a non-ionic surfactant as known in the art (see, e.g., EP 2 100 949).

In one aspect, the cleaning compositions of the present invention include one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof. In aspects in which at least one dye transfer inhibiting agent is used, the cleaning compositions of the present invention comprise from about 0.0001% to about 10%, from about 0.01% to about 5%, or even from about 0.1% to about 3% by weight of the cleaning composition.

In one aspect, silicates are included within the compositions of the present invention. In some such aspects, sodium silicates (e.g., sodium disilicate, sodium metasilicate, and crystalline phyllosilicates) find use. In one aspect, silicates are present at a level of from about 1% to about 20%. In one aspect, silicates are present at a level of from about 5% to about 15% by weight of the composition.

In one aspect, the cleaning compositions of the invention also comprise dispersants. Suitable water-soluble organic materials include, but are not limited to, e.g., the homo- or co-polymeric acids or their salts, in which the polycarboxylic acid comprises at least two carboxyl radicals separated from each other by not more than two carbon atoms.

In one aspect, the enzymes (e.g., protease variants of the invention or other additional enzymes) used in the cleaning compositions are stabilized any suitable technique. In one aspect, the enzymes employed herein are stabilized by the presence of water-soluble sources of calcium and/or magnesium ions in the finished compositions that provide such ions to the enzymes. In one aspect, the enzyme stabilizers include oligosaccharides, polysaccharides, and inorganic divalent metal salts, including alkaline earth metals, such as calcium salts. It is contemplated that various techniques for enzyme stabilization will find use in the present invention. For example, in one aspect, the enzymes employed herein are stabilized by the presence of water-soluble sources of zinc (II), calcium (II) and/or magnesium (II) ions in the finished compositions that provide such ions to the enzymes, as well as other metal ions (e.g., barium (II), scandium (II), iron (II), manganese (II), aluminum (III), Tin (II), cobalt (II), copper (II), nickel (II), and oxovanadium (IV). Chlorides and sulfates also find use in one aspect of the present invention. Examples of suitable oligosaccharides and polysaccharides (e.g., dextrins) are known in the art (see, e.g., WO 07/145,964). In one aspect, reversible protease inhibitors also find use, such as boron-containing compounds (e.g., borate, phenyl boronic acid, 4-formyl phenyl boronic acid, other phenyl boronic acid derivatives, peptide inhibitors, and the like) and/or a tripeptide aldehyde find use in compositions of the invention to further improve stability, as desired.

In one aspect, one or more bleaches, bleach activators, and/or bleach catalysts are included in the compositions of the invention. In one aspect, the cleaning compositions of the invention comprise inorganic and/or organic bleaching compound(s). Inorganic bleaches include, but are not limited to perhydrate salts (e.g., perborate, percarbonate, perphosphate, persulfate, and persilicate salts). In one aspect, inorganic perhydrate salts are alkali metal salts. In one aspect, inorganic perhydrate salts are included as the crystalline solid, without additional protection, although in some other aspects, the salt is coated. Any suitable salt known in the art finds use in the compositions of the invention (see, e.g., EP 2 100 949).

In one aspect, bleach activators are used in the compositions of the invention. Bleach activators are typically organic peracid precursors that enhance the bleaching action in the course of cleaning at temperatures of 60° C. and below. Bleach activators suitable for use herein include compounds which, under perhydrolysis conditions, give aliphatic peroxycarboxylic acids having preferably from about 1 to about 10 carbon atoms, in particular from about 2 to about 4 carbon atoms, and/or optionally substituted perbenzoic acid. Additional bleach activators are known in the art and find use in the composition of the invention (see, e.g., EP 2 100 949).

In one aspect and as further described herein, the cleaning compositions of the invention further comprise at least one bleach catalyst. In one aspect, the manganese triazacyclononane and related complexes find use, as well as cobalt, copper, manganese, and iron complexes. Additional bleach catalysts find use in the present invention (see, e.g., U.S. Pat. Nos. 4,246,612, 5,227,084, and 4,810410; WO 99/06521; and EP 2 100 949).

In one aspect, the cleaning compositions of the invention comprise one or more catalytic metal complexes. In one aspect, a metal-containing bleach catalyst finds use. In some aspects, the metal bleach catalyst comprises a catalyst system comprising a transition metal cation of defined bleach catalytic activity (e.g., copper, iron, titanium, ruthenium, tungsten, molybdenum, or manganese cations), an auxiliary metal cation having little or no bleach catalytic activity (e.g., zinc or aluminum cations), and a sequestrate having defined stability constants for the catalytic and auxiliary metal cations, particularly ethylenediaminetetraacetic acid, ethylenediaminetetra (methylenephosphonic acid) and water-soluble salts thereof are used (see, e.g., U.S. Pat. No. 4,430,243). In one aspect, the cleaning compositions of the invention are catalyzed by means of a manganese compound. Such compounds and levels of use are well known in the art (see, e.g., U.S. Pat. No. 5,576,282). In additional aspects, cobalt bleach catalysts find use and are included in the cleaning compositions of the invention. Various cobalt bleach catalysts are known in the art (see, e.g., U.S. Pat. Nos. 5,597,936 and 5,595,967) and are readily prepared by known procedures.

In one aspect, the cleaning compositions of the invention include a transition metal complex of a macropolycyclic rigid ligand (MRL). As a practical matter, and not by way of limitation, in one aspect, the compositions and cleaning processes provided by the invention are adjusted to provide on the order of at least one part per hundred million of the active MRL species in the aqueous washing medium, and in one aspect, provide from about 0.005 ppm to about 25 ppm, from about 0.05 ppm to about 10 ppm, and from about 0.1 ppm to about 5 ppm, of the MRL in the wash liquor.

In one aspect, transition-metals in the instant transition-metal bleach catalyst include, but are not limited to, e.g., manganese, iron and chromium. Preferred MRLs also include, but are not limited to, e.g., special ultra-rigid ligands that are cross-bridged (e.g., 5,12-diethyl-1,5,8,12-tetraazabicyclo(6.6.2)hexadecane). Suitable transition metal MRLs are readily prepared by known procedures (see, e.g., WO 2000/32601 and U.S. Pat. No. 6,225,464).

In one aspect, the invention provides an automatic dishwashing detergent composition formulated as a detergent tablet. Such tablet comprises at least one protease variant of the invention and a builder, such as, e.g., a builder salt. Some such tablets have an alkalinity of at least equivalent to 3 grams (g) of sodium hydroxide per 100 grams of the tablet composition and a density of at least 1.4 grams/cubic centimeter. The builder salt can comprise a mixture of a silicate salt and a phosphate salt, preferably with more silicate (e.g., sodium metasilicate) than phosphate (e.g., sodium tripolyphosphate). Some such tablets are free of surfactant materials and are especially adapted for use in automatic dishwashing machines.

In one aspect, the cleaning compositions of the present invention comprise metal care agents. Metal care agents are useful in preventing and/or reducing the tarnishing, corrosion, and/or oxidation of metals, including aluminum, stainless steel, and non-ferrous metals (e.g., silver and copper). Suitable metal care agents include those described in EP 2 100 949, WO 9426860, and WO 94/26859). In some such cleaning compositions, the metal care agent is a zinc salt. Some such cleaning compositions comprise from about 0.1% to about 5% by weight of one or more metal care agent.

As indicated above, the cleaning compositions of the present invention are formulated into any suitable form and prepared by any process chosen by the formulator, non-limiting examples of which are described in U.S. Pat. Nos. 5,879,584, 5,691,297, 5,574,005, 5,569,645, 5,516,448, 5,489,392, and 5,486,303, all of which are incorporated herein by reference. In one aspect in which a low pH cleaning composition is desired, the pH of such composition is adjusted via the addition of an acidic material such as hydrogen chloride (HCl).

The cleaning compositions disclosed herein find use in cleaning a situs (e.g., a surface, dishware, tableware, or fabric). Typically, at least a portion of the situs is contacted with a present cleaning composition of the invention in neat form or diluted in a wash liquor, and then the situs is optionally washed and/or rinsed. For purposes of the present invention, "washing" includes, but is not limited to, e.g., scrubbing and mechanical agitation. In one aspect, the cleaning compositions are employed at concentrations of from about 500 ppm to about 15,000 ppm in solution. When the wash solvent is water, the water temperature typically ranges from about 5° C. to about 90° C. and when the situs comprises a fabric, the water to fabric mass ratio is typically from about 1:1 to about 30:1.

Processes of Making and Using Compositions

The compositions of the invention described herein and throughout, including, e.g., cleaning compositions, can be formulated into any suitable form and prepared by any suitable process chosen by the formulator (see, e.g., U.S. Pat. Nos. 5,879,584, 5,691,297, 5,574,005, 5,569,645, 5,565,422, 5,516,448, 5,489,392, 5,486,303, 4,515,705, 4,537,706, 4,515,707, 4,550,862, 4,561,998, 4,597,898, 4,968,451, 5,565,145, 5,929,022, 6,294,514 and 6,376,445).

In one aspect, the cleaning compositions of the invention are provided in unit dose form, including tablets, capsules, sachets, pouches, and multi-compartment pouches. In one aspect, the unit dose format is designed to provide controlled release of the ingredients within a multi-compartment pouch (or other unit dose format). Suitable unit dose and controlled release formats are known in the art (see, e.g., EP 2 100 949, WO 02/102955, U.S. Pat. Nos. 4,765,916 and 4,972,017, and WO 04/111178 for materials suitable for use in unit dose and controlled release formats). In one aspect, the unit dose form is provided by tablets wrapped with a water-soluble film or water-soluble pouches. Various formats for unit doses are provided in EP 2 100 947, and are known in the art.

Additional aspects of the invention relating to processes of making and using compositions of the invention are described elsewhere herein.

Methods of the Invention

The invention provides methods for cleaning or washing an item or surface (e.g., hard surface) in need of cleaning, including, but not limited to, e.g., methods for cleaning or washing a dishware item, a tableware item, a fabric item, a laundry item, personal care item, eye glass, etc., or the like, and methods for cleaning or washing a hard or soft surface, such as, e.g., a hard surface of an item.

In one aspect, the invention provides a method for cleaning an item, object, or surface in need of cleaning, the method comprising contacting the item or surface (or a portion of the item or surface desired to be cleaned) with a protease variant of any of the invention or a composition of the invention for a sufficient time and/or under conditions suitable or effective to clean the item, object, or surface to a desired degree. Some such methods further comprise rinsing the item, object, or surface with water. For some such methods, the cleaning composition is a dishwashing detergent composition and the item or object to be cleaned is a dishware item or tableware item. A dishware item is a dish item generally used in serving or eating food. A dishware item can be, but is not limited to, e.g., a dish, plate, cup, bowl, etc., and the like. Tableware is a broader term that includes, but is not limited, to, e.g., dishes, cutlery, knives, forks, spoons, chopsticks, glassware, pitchers, sauce boats, drinking vessels, etc., and the like; a tableware item includes any of these or similar items for serving or eating food. For some such methods, the cleaning composition is an automatic dishwashing detergent composition or a hand dishwashing detergent composition and the item or object to be cleaned is a dishware or tableware item. For some such methods, the cleaning composition is a laundry detergent composition, such as, e.g., a power laundry detergent composition or a liquid laundry detergent composition, and the item to be cleaned is a fabric item.

In one aspect, the invention provides methods for cleaning or washing a fabric item optionally in need of cleaning or washing, respectively. Some such methods comprise providing a composition comprising the protease variant (such as, but not limited to, e.g., a fabric or laundry cleaning composition) and a fabric item or laundry item in need of cleaning, and contacting the fabric item or laundry item (or a portion of the item desired to be cleaned) with the composition under conditions sufficient or effective to clean or wash the fabric or laundry item to a desired degree.

In one aspect, the invention provides a method for cleaning or washing an item or surface (e.g., hard surface) optionally in need of cleaning, the method comprising providing an item or surface to be cleaned or washed and contacting the item or surface (or a portion of the item or surface desired to be cleaned or washed) with at least one protease variant of the invention or a composition of the invention comprising at least one such protease variant for a sufficient time and/or under conditions sufficient or effective to clean or wash the item or surface to a desired degree. Such compositions include, but are not limited to, e.g., a cleaning composition or detergent composition of the invention (including, but not limited to, e.g., hand dishwashing detergent composition, hand dishwashing cleaning composition, laundry detergent or fabric detergent or laundry or fabric cleaning composition, liquid laundry detergent, liquid laundry cleaning composition, powder laundry detergent composition, powder laundry cleaning composition, automatic dishwashing detergent composition, laundry booster cleaning or detergent composition, laundry cleaning additive, and laundry pre-spotter composition, etc.). In some instances, if desired, the method can be repeated one or more times, particularly if additional cleaning or washing is desired. For example, in some instance, the method optionally further comprises allowing the item or surface to remain in contact with the at least one protease variant or composition for a period of time sufficient or effective to clean or wash the item or surface to the desired degree. Some such methods further comprise rinsing the item or surface with water. Some such methods further comprise contacting the item or surface with at least one protease variant of the invention or a composition of the invention again and allowing the item or surface to remain in contact with the at least one protease variant or composition for a period of time sufficient to clean or wash the item or surface to the desired degree. For some such methods, the cleaning composition is a dishwashing detergent composition and the item to be cleaned is a dishware or tableware item. For some such methods, the cleaning composition is an automatic dishwashing detergent composition or a hand dishwashing detergent composition and the item to be cleaned is a dishware or tableware item. For some such methods, the cleaning composition is a laundry detergent composition and the item to be cleaned is a fabric item.

In one aspect, the invention provides a method of cleaning a tableware or dishware item in an automatic dishwashing machine, the method comprising providing an automatic dishwashing machine, placing an amount of an automatic dishwashing composition comprising at least one protease variant of the invention or a composition of the invention sufficient to clean the tableware or dishware item in the machine (e.g., by placing the composition in an appropriate or provided detergent compartment or dispenser in the machine), putting a dishware or tableware item in the machine, and operating the machine so as to clean the tableware or dishware item (e.g., as per the manufacturer's instructions). Such method can include any automatic dishwashing composition described herein, which comprises, but is not limited to, e.g., any protease variant described herein. The amount of automatic dishwashing composition to be used can be readily determined according to manufacturer's instructions or suggestions and any form of automatic dishwashing composition comprising at least one protease variant of the invention (e.g., liquid, powder, solid, gel, table, etc.), including any described herein, may be employed.

In one aspect, the invention provides a method for cleaning a surface, item or object optionally in need of cleaning, the method comprises contacting the item or surface (or a portion of the item or surface desired to be cleaned) with at least one protease variant of the invention or a cleaning composition of the invention in neat form or diluted in a wash liquor for a sufficient time and/or under conditions sufficient or effective to clean or wash the item or surface to a desired degree. The surface, item, or object may then be (optionally) washed and/or rinsed if desired. For purposes of the present invention, "washing" includes, but is not limited to, e.g., scrubbing and mechanical agitation. In one aspect, the cleaning compositions are employed at concentrations of from about 500 ppm to about 15,000 ppm in solution (e.g., aqueous solution). When the wash solvent is water, the water temperature typically ranges from about 5° C. to about 90° C. and when the situs comprises a fabric, the water to fabric mass ratio is typically from about 1:1 to about 30:1.

In one aspect, the invention provides a method of cleaning a laundry or fabric item in an washing machine, the method comprising providing an washing machine, placing an amount of a laundry detergent composition comprising at least one protease variant of the invention sufficient to clean the laundry or fabric item in the machine (e.g., by placing the composition in an appropriate or provided detergent compartment or dispenser in the machine), putting the laundry or fabric item in the machine, and operating the machine so as to clean the tableware or dishware item (e.g., as per the manufacturer's instructions). Such method can include any laundry washing detergent composition described herein, which comprises, but is not limited to, e.g., any protease variant described herein. The amount of laundry detergent composition to be used can be readily determined according to manufacturer's instructions or suggestions and any form of laundry detergent composition comprising at least one protease variant of the invention (e.g., solid, powder, liquid, tablet, gel, etc.), including any described herein, may be employed.

In an eighteenth aspect, the invention provides a method for cleaning an item, object, or surface in need of cleaning, the method comprising contacting the item, object, or surface with (i) a variant (or polypeptide as in the third aspect) of the first, second, third, fourth, fifth, sixth, seventh, eighth, or ninth aspect of the invention or (ii) a composition of the seventeenth aspect of the invention. A method of the eighteenth aspect of the invention may further comprise rinsing the item, object, or surface with water.

In a nineteenth aspect, the invention provides a method for cleaning an item or hard surface, the method comprising contacting at least a portion of the item or hard surface to be cleaned with (i) a variant (or polypeptide as in the third aspect) of the first, second, third, fourth, fifth, sixth, seventh, eighth, or ninth aspect of the invention or (ii) a composition of the seventeenth aspect of the invention for a sufficient time and/or under conditions sufficient or effective to clean or wash the item or hard surface to a desired degree, and optionally comprising rinsing the item or hard surface with water.

In a twentieth aspect, the invention provides a method of treating and/or cleaning a surface or fabric comprising the steps of optionally washing and/or rinsing said surface or fabric, contacting said surface or fabric with (i) a variant (or polypeptide as in the third aspect) of the first, second, third, fourth, fifth, sixth, seventh, eighth, or ninth aspect of the invention or (ii) a composition of the seventeenth aspect of the invention, and then optionally washing and/or rinsing said surface or fabric.

Included is a use of a protease variant or polypeptide of the invention in a detergent composition, including, but not limited to, in a laundry and/or dishwashing detergent composition.

Additional exemplary cleaning methods are provided throughout and in the Examples below.

EXPERIMENTAL

In the experimental disclosure of Part I Examples and Part I Examples which follow, the following abbreviations apply: PI (Performance Index), ppm (parts per million); M (molar); mM (millimolar); μM (micromolar); nM (nanomolar); mol (moles); mmol (millimoles); μmol (micromoles); nmol (nanomoles); gm (grams); mg (milligrams); μg (micrograms); pg (picograms); L (liters); ml and mL (milliliters); μl and μL, (microliters); cm (centimeters); mm (millimeters); μm (micrometers); nm (nanometers); U (units); V (volts); MW (molecular weight); sec (seconds); min(s) (minute/minutes); h(s) and hr(s) (hour/hours); ° C. (degrees Centigrade); QS (quantity sufficient); ND (not done); rpm (revolutions per minute); GH (degrees German hardness); $H_2O$ (water); $dH_2O$ (deionized water); HCl (hydrochloric acid); aa (amino acid); bp (base pair); kb (kilobase pair); kD (kilodaltons); cDNA (copy or complementary DNA); DNA (deoxyribonucleic acid); ssDNA (single stranded DNA); dsDNA (double stranded DNA); dNTP (deoxyribonucleotide triphosphate); RNA (ribonucleic acid); $MgCl_2$ (magnesium chloride); NaCl (sodium chloride); w/v (weight to volume); v/v (volume to volume); w/w (weight to weight); g (gravity); OD (optical density); ppm (parts per million); Dulbecco's phosphate buffered solution (DPBS); SOC (2% Bacto-Tryptone, 0.5% Bacto Yeast Extract, 10 mM NaCl, 2.5 mM KCl); Terrific Broth (TB; 12 g/l Bacto-Tryptone, 24 g/l glycerol, 2.31 g/l $KH_2PO_4$, and 12.54 g/l $K_2HPO_4$); $OD_{280}$ (optical density at 280 nm); $OD_{600}$ (optical density at 600 nm); $A_{405}$ (absorbance at 405 nm); Vmax (the maximum initial velocity of an enzyme catalyzed reaction); PAGE (polyacrylamide gel electrophoresis); PBS (phosphate buffered saline [150 mM NaCl, 10 mM sodium phosphate buffer, pH 7.2]); PBST (PBS+0.25% TWEEN®-20); PEG (polyethylene glycol); PCR (polymerase chain reaction); RT-PCR (reverse transcription PCR); SDS (sodium dodecyl sulfate); Tris (tris(hydroxymethyl) aminomethane); HEPES (N-[2-Hydroxyethyl]piperazine-N-[2-ethanesulfonic acid]); HBS (HEPES buffered saline); Tris-HCl (tris[Hydroxymethyl]aminomethane-hydrochloride); Tricine (N[tris-(hydroxymethyl)-methyl]-glycine); CHES (2-(N-cyclo-hexylamino) ethane-sulfonic acid); TAPS (3-{[tris-(hydroxymethyl)-methyl]-amino}-propanesulfonic acid); CAPS (3-(cyclo-hexylamino)-propane-sulfonic acid; DMSO (dimethyl sulfoxide); DTT (1,4-dithio-DL-threitol); SA (sinapinic acid (s,5-dimethoxy-4-hydroxy cinnamic acid); TCA (trichloroacetic acid); Glut and GSH (reduced glutathione); GSSG (oxidized glutathione); TCEP (Tris[2-carboxyethyl]phosphine); Ci (Curies); mCi (milliCuries); μCi (microCuries); HPLC (high-performance liquid chromatography); RP-HPLC (reverse phase high pressure liquid chromatography); TLC (thin layer chromatography); MALDI-TOF (matrix-assisted laser desorption/ionization—time of flight); Ts (tosyl); Bn (benzyl); Ph (phenyl); Ms (mesyl); Et (ethyl); Me (methyl); Taq (*Thermus aquaticus* DNA polymerase); Klenow (DNA polymerase I large (Klenow) fragment); EGTA (ethylene glycol-bis(β-aminoethyl ether) N,N,N',N'-tetraacetic acid); EDTA (ethylenediaminetetracetic acid); bla (β-lactamase or ampicillin-resistance gene); HDL (heavy duty liquid); HDD (heavy duty powder detergent); HSG (high suds granular detergent); CEE (Central and Eastern Europe); WE (Western Europe); NA, when used in reference to detergents (North America); Japan and JPN, when used in reference to detergents (Japan); MTP (microtiter plate); MJ Research (MJ Research, Reno, Nev.); Baseclear (Baseclear BV, Inc., Leiden, The Netherlands); PerSeptive (PerSeptive Biosystems, Framingham, Mass.); ThermoFinnigan (ThermoFinnigan, San Jose, Calif.); Argo (Argo BioAnalytica, Morris Plains, N.J.); Seitz EKS (SeitzSchenk Filtersystems GmbH, Bad Kreuznach, Germany); Pall (Pall Corp., East Hills, N.Y. and Bad Kreuznach, Germany); Spectrum (Spectrum Laboratories, Dominguez Rancho, Calif.); Molecular Structure (Molecular Structure Corp., Woodlands, Tex.); Accelrys (Accelrys, Inc., San Diego, Calif.); Chemical Computing (Chemical Computing Corp., Montreal, Canada); New Brunswick (New Brunswick Scientific, Co., Edison, N.J.); CFT (Center for Test Materials, Vlaardingen, The Netherlands); P&G and Procter & Gamble (Procter & Gamble, Inc., Cincinnati, Ohio); GE Healthcare (GE Healthcare, Chalfont St. Giles, United Kingdom); DNA2.0 (DNA2.0, Menlo Park, Calif.); OXOID (Oxoid, Basingstoke, Hampshire, UK); Megazyme (Megazyme International Ireland Ltd., Bray Business Park, Bray, Co., Wicklow, Ireland); Finnzymes (Finnzymes Oy, Espoo, Finland); Kelco (CP Kelco, Wilmington, Del.); Corning (Corning Life Sciences, Corning, N.Y.); (NEN (NEN Life Science Products, Boston, Mass.); Pharma AS (Pharma AS, Oslo, Norway); Dynal (Dynal, Oslo, Norway); Bio-Synthesis (Bio-Synthesis, Lewisville, Tex.); ATCC (American Type Culture Collection, Rockville, Md.); Gibco/BRL (Gibco/BRL, Grand Island, N.Y.); Sigma (Sigma Chemical Co., St. Louis, Mo.); Pharmacia (Pharmacia Biotech, Piscataway, N.J.); NCBI (National Center for Biotechnology Information); Applied Biosystems (Applied Biosystems, Foster City, Calif.); BD Biosciences and/or Clontech (BD Biosciences CLONTECH Laboratories, Palo Alto, Calif.); Operon Technologies (Operon Technologies, Inc., Alameda, Calif.); MWG Biotech (MWG Biotech, High Point, N.C.); Oligos Etc (Oligos Etc. Inc, Wilsonville, Oreg.); Bachem (Bachem Bioscience, Inc., King of Prussia, Pa.); Difco (Difco Laboratories, Detroit, Mich.); Mediatech (Mediatech, Herndon, Va.; Santa Cruz (Santa Cruz Biotechnology, Inc., Santa Cruz, Calif.); Oxoid (Oxoid Inc., Ogdensburg, N.Y.); Worthington (Worthington Biochemical Corp., Freehold, N.J.); GIBCO BRL or Gibco BRL (Life Technologies, Inc., Gaithersburg, Md.); Millipore (Millipore, Billerica, Mass.); Bio-Rad (Bio-Rad, Hercules, Calif.); Invitrogen (Invitrogen Corp., San Diego, Calif.); NEB (New England Biolabs, Beverly, Mass.); Sigma (Sigma Chemical Co., St. Louis, Mo.); Pierce (Pierce Biotechnology, Rockford, Ill.); Takara (Takara Bio Inc. Otsu, Japan); Roche (Hoffmann-La Roche, Basel, Switzerland); Gene Oracle (Gene Oracle, Inc., Mountain View, Calif.); EM Science (EM Science, Gibbstown, N.J.); Qiagen (Qiagen, Inc., Valencia, Calif.); Biodesign (Biodesign Intl., Saco, Me.); Aptagen (Aptagen, Inc., Herndon, Va.); Sorvall (Sorvall brand, from Kendro Laboratory Products, Asheville, N.C.); Molecular Devices (Molecular Devices, Corp., Sunnyvale, Calif.); R&D Systems (R&D Systems, Minneapolis, Minn.); Siegfried Handel (Siegfried Handel AG, Zofingen, Switzerland); Stratagene (Stratagene Cloning Systems, La Jolla, Calif.); Marsh (Marsh Biosciences, Rochester, N.Y.); Geneart (Geneart GmbH, Regensburg, Germany); Bio-Tek (Bio-Tek Instruments, Winooski, Vt.); (Biacore (Biacore, Inc., Piscataway, N.J.); PeproTech (PeproTech, Rocky Hill, N.J.); SynPep (SynPep, Dublin, Calif.); New Objective (New Objective brand; Scientific Instrument Services, Inc., Ringoes, N.J.); Waters (Waters, Inc., Milford, Mass.); Matrix Science (Matrix Science, Boston, Mass.); Dionex (Dionex, Corp., Sunnyvale, Calif.); Monsanto (Monsanto Co., St. Louis, Mo.); Wintershall (Wintershall AG, Kassel, Germany); BASF (BASF Co., Florham Park, N.J.); Huntsman (Huntsman Petrochemical Corp., Salt Lake City, Utah); Shell Chemicals (Shell Chemicals, Inc., London, UK); Stepan (Stepan, Northfield, Ill.); Clariant (Clariant, Sulzbach, Germany); Industrial Zeolite (Industrial Zeolite Ltd., Grays, Essex, UK); Jungbunzlauer (Jungbunzlauer, Basel, Switzerland); Solvay (Solvay, Brussels, Belgium); 3V Sigma (3V Sigma, Bergamo, Italy); Innospec (Innospec, Ellesmere Port, UK); Thermphos (Thermphos, Vlissiggen-Ost, The Netherlands); Ciba Specialty (Ciba Specialty Chemicals, Basel, Switzerland); Dow Corning (Dow Corning, Barry, UK); Enichem (Enichem Iberica, Barcelona, Spain); Fluka Chemie AG (Fluka Chemie AG, Buchs, Switzerland); Gist-Brocades (Gist-Brocades, NV, Delft, The Netherlands); Dow Corning (Dow Corning Corp., Midland, Mich.); Mettler-Toledo (Mettler-Toledo Inc, Columbus, Ohio); RB (Reckitt-Benckiser, Slough, UK); and Microsoft (Microsoft, Inc., Redmond, Wash.).

In the exemplified detergent compositions provided herein, the enzymes levels are expressed by pure enzyme by weight of the total composition and unless otherwise specified, the detergent ingredients are expressed by weight of the total compositions. The abbreviated component identifications therein have the following meanings:

| Abbreviation | Ingredient |
| --- | --- |
| LAS | Sodium linear $C_{11-13}$ alkyl benzene sulfonate |
| NaC16-17HSAS | Sodium $C_{16-17}$ highly soluble alkyl sulfate |
| TAS | Sodium tallow alkyl sulphate |
| CxyAS | Sodium $C_{1x}$-$C_{1y}$ alkyl sulfate |
| CxyEz | $C_{1x}$-$C_{1y}$ predominantly linear primary alcohol condensed with an average of z moles of ethylene oxide |
| CxyAEzS | $C_{1x}$-$C_{1y}$ sodium alkyl sulfate condensed with an average of z moles of ethylene oxide. Added molecule name in the examples. |
| Nonionic | Mixed ethoxylated/propoxylated fatty alcohol e.g. Plurafac LF404 being an alcohol with an average degree of ethoxylation of 3.8 and an average degree of propoxylation of 4.5. |
| QAS | $R_2 \cdot N^+(CH_3)_2(C_2H_4OH)$ with $R_2 = C_{12}$-$C_{14}$ |
| Silicate | Amorphous Sodium Silicate ($SiO_2$:$Na_2O$ ratio = 1.6-3.2:1) |
| Metasilicate | Sodium metasilicate ($SiO_2$:$Na_2O$ ratio = 1.0) |
| Zeolite A | Hydrated aluminosilicate of formula $Na_{12}(AlO_2SiO_2)_{12} \cdot 27H_2O$ |
| SKS-6 | Crystalline layered silicate of formula $\delta$-$Na_2Si_2O_5$ |
| Sulfate | Anhydrous sodium sulphate |
| STPP | Sodium Tripolyphosphate |
| MA/AA | Random copolymer of 4:1 acrylate/maleate, average molecular weight about 70,000-80,000 |
| AA | Sodium polyacrylate polymer of average molecular weight (MW) 4,500 |
| Polycarboxylate | Copolymer comprising mixture of carboxylated monomers such as acrylate, maleate and methyacrylate with a MW ranging between 2,000-80,000 such as Sokolan commercially available from BASF, being a copolymer of acrylic acid, MW 4,500 |
| BB1 | 3-(3,4-Dihydroisoquinolinium)propane sulfonate |
| BB2 | 1-(3,4-dihydroisoquinolinium)-decane-2-sulfate |
| PB1 | Sodium perborate monohydrate |
| PB4 | Sodium perborate tetrahydrate of nominal formula $NaBO_3 \cdot 4H_2O$ |
| Percarbonate | Sodium percarbonate of nominal formula $2Na_2CO_3 \cdot 3H_2O_2$ |
| TAED | Tetraacetyl ethylene diamine |
| NOBS | Nonanoyloxybenzene sulfonate in the form of the sodium salt |
| DTPA | Diethylene triamine pentaacetic acid |
| HEDP | 1,1-hydroxyethane diphosphonic acid |
| DETPMP | Diethyltriamine penta (methylene) phosphonate, marketed by Monsanto under the Trade name Dequest 2060 |
| EDDS | Ethylenediamine-N,N'-disuccinic acid, (S,S) isomer in the form of its sodium salt |
| Diamine | Dimethyl aminopropyl amine; 1,6-hezane diamine; 1,3-propane diamine; 2-methyl-1,5-pentane diamine; 1,3-pentanediamine; 1-methyl-diaminopropane |
| DETBCHD | 5, 12- diethyl-1,5,8,12-tetraazabicyclo [6,6,2] hexadecane, dichloride, Mn(II) SALT |
| PAAC | Pentaamine acetate cobalt(III) salt |
| Paraffin | Paraffin oil sold under the tradename Winog 70 by Wintershall |
| Paraffin Sulfonate | A Paraffin oil or wax in which some of the hydrogen atoms have been replaced by sulfonate groups |
| Aldose oxidase | Oxidase enzyme sold under the tradename Aldose Oxidase by Novozymes A/S |
| Galactose oxidase | Galactose oxidase from Sigma |
| nprE | The recombinant form of neutral metalloprotease expressed in *Bacillus subtilis* (see, e.g., WO 07/044993) |
| PMN | Purified neutral metalloprotease from *Bacillus amyloliquefaciens* |
| Amylase | A suitable amylolytic enzyme, such as those sold under the tradenames PURAFECT ® Ox described in WO 94/18314, WO96/05295 sold by Genencor; NATALASE ®, TERMAMYL ®, FUNGAMYl ® and DURAMYL ™, all available from Novozymes A/S. |
| Lipase | A suitable lipolytic enzyme such as those sold under the tradenames LIPEX ®, LIPOLASE ®, LIPOLASE ® Ultra by Novozymes A/S and Lipomax ™ by Gist-Brocades. |
| Cellulase | A suitable cellulytic enzyme such as those sold under the tradenames CAREZYME ®, CELLUZYME ®, and/or ENDOLASE ® by Novozymes A/S. |
| Pectin Lyase | A suitable pectin lyase, such as those sold under the tradenames XPECT ®, PECTAWAY ® and PECTAWASH ® available from Novozymes A/S. |
| PVP | Polyvinylpyrrolidone with an average molecular weight of 60,000 |
| PVNO | Polyvinylpyridine-N-Oxide, with an average molecular weight of 50,000 |
| PVPVI | Copolymer of vinylimidazole and vinylpyrrolidone, with an average molecular weight of 20,000 |
| Brightener 1 | Disodium 4,4'-bis(2-sulphostyryl)biphenyl |
| Silicone antifoam | Polydimethylsiloxane foam controller with siloxane-oxyalkylene copolymer as dispersing agent with a ratio of said foam controller to said dispersing agent of 10:1 to 100:1 |
| Suds Suppressor | 12% Silicone/silica, 18% stearyl alcohol, 70% starch in granular form |
| SRP 1 | Anionically end capped poly esters |
| PEG X | Polyethylene glycol of a molecular weight of x |
| PVP K60 ® | Vinylpyrrolidone homopolymer (average MW 160,000) |

-continued

| Abbreviation | Ingredient |
|---|---|
| Jeffamine ® ED-2001 | Capped polyethylene glycol from Huntsman |
| Isachem ® AS | A branched alcohol alkyl sulphate from Enichem |
| MME PEG (2000) | Monomethyl ether polyethylene glycol (MW 2000) from Fluka Chemie AG |
| DC3225C | Silicone suds suppresser, mixture of Silicone oil and Silica from Dow Corning |
| TEPAE | Tetreaethylenepentaamine ethoxylate |
| BTA | Benzotriazole |
| Betaine | $(CH_3)_3N^+CH_2COO^-$ |
| Sugar | Industry grade D-glucose or food grade sugar |
| CFAA | $C_{12}$-$C_{14}$ alkyl N-methyl glucamide |
| TPKFA | $C_{12}$-$C_{14}$ topped whole cut fatty acids |
| Clay | A hydrated aluminumu silicate in a general formula $Al_2O_3SiO_2 \cdot xH_2O$. Types: Kaolinite, montmorillonite, atapulgite, illite, bentonite, halloysite |
| pH | Measured as a 1% solution in distilled water at 20° C. |

For North American (NA) and Western European (WE) heavy duty liquid laundry (HDL) detergents, heat inactivation of the enzymes present in commercially-available detergents is performed by placing pre-weighed liquid detergent (in a glass bottle) in a water bath at 95° C. for 2 hours. The incubation time for heat inactivation of NA and WE auto dish washing (ADW) detergents is 8 hours. Both un-heated and heated detergents are assayed within 5 minutes of dissolving the detergent to accurately determine percentage deactivated. Enzyme activity is tested by the AAPF assay.

For testing of enzyme activity in heat-inactivated detergents, working solutions of detergents are made from the heat inactivated stocks. Appropriate amounts of water hardness (e.g., 6 gpg or 12 gpg) and buffer are added to the detergent solutions to match the desired conditions. The solutions are mixed by vortexing or inverting the bottles. The following Table provides information regarding some of the commercially-available detergents and test conditions used herein. In some experiments, additional and/or other commercially available detergents find use in the following Examples.

TABLE 1.1

Laundry and Dish Washing Conditions

| Region | Form | Dose | Detergent* | Buffer | gpg | pH | T (° C.) |
|---|---|---|---|---|---|---|---|
| Laundry (Heavy Duty Liquid and Granular) | | | | | | | |
| NA | HDL | 0.78 g/l | P&G TIDE ® 2X | 5 mM HEPES | 6 | 8.0 | 20 |
| WE | HDL | 5.0 g/L | Henkel PERSIL ™ | 5 mM HEPES | 12 | 8.2 | 40 |
| WE | HDG | 8.0 g/L | P&G ARIEL ® | 2 mM $Na_2CO_3$ | 12 | 10.5 | 40 |
| JPN | HDG | 0.7 g/L | P&G TIDE ® | 2 mM $Na_2CO_3$ | 6 | 10.0 | 20 |
| NA | HDG | 1.0 g/L | P&G TIDE ® | 2 mM $Na_2CO_3$ | 6 | 10.0 | 20 |
| Automatic Dish Washing | | | | | | | |

TABLE 1.1-continued

Laundry and Dish Washing Conditions

| Region | Form | Dose | Detergent* | Buffer | gpg | pH | T (° C.) |
|---|---|---|---|---|---|---|---|
| WE | ADW | 3.0 g/L | RB CALGONIT ™ | 2 mM $Na_2CO_3$ | 21 | 10.0 | 40 |
| NA | ADW | 3.0 g/L | P&G CASCADE ® | 2 mM $Na_2CO_3$ | 9 | 10.0 | 40 |

In some additional aspects, the following solutions find use:

TABLE 1-2

Working Detergent Solutions

| Detergent | Temp (C.) | Detergent g/L | pH | Buffer | gpg |
|---|---|---|---|---|---|
| TIDE ® 2X Cold | 16 | 0.98 | 8 | 5 mM HEPES | 6 |
| TIDE ® 2X Cold | 32 | 0.98 | 8 | 5 mM HEPES | 6 |
| TIDE ® 2X Cold | 16 | 0.98 | 7 | 5 mM MOPS | 6 |

The examples, which are intended to be purely exemplary of the invention and should therefore not be considered to limit the invention in any way, also describe and detail aspects and embodiments of the invention discussed above. The foregoing examples and detailed description are offered by way of illustration and not by way of limitation.

Part I
Table of Detergents

The compositions of the detergents used in the assays in Part I Examples are shown in Table 1-3. BPN' variant protein samples were added to the detergent compositions as described in Part I Example 1 to assay for the various properties tested.

The following are liquid laundry detergent compositions suitable for top-loading automatic washing machines (1, 2 & 4) and front loading washing machines (3).

TABLE 1-3

Composition of Detergents Used in the Assays to Test BPN' Variants

| Ingredient | Composition (wt % of composition) | | | |
|---|---|---|---|---|
| | 1 | 2 | 3 | 4 |
| $C_{12-15}$ Alkylethoxy(1.8)sulfate | 14.7 | 11.6 | | 16.31 |
| $C_{11.8}$ Alkylbenzene sulfonate | 4.3 | 11.6 | 8.3 | 7.73 |

TABLE 1-3-continued

Composition of Detergents Used in the Assays to Test BPN' Variants

| Ingredient | Composition (wt % of composition) | | | |
| --- | --- | --- | --- | --- |
| | 1 | 2 | 3 | 4 |
| $C_{16-17}$ Branched alkyl sulfate | 1.7 | 1.29 | | 3.09 |
| $C_{12-14}$ Alkyl -9-ethoxylate | 0.9 | 1.07 | | 1.31 |
| $C_{12}$ dimethylamine oxide | 0.6 | 0.64 | | 1.03 |
| Citric acid | 3.5 | 0.65 | 3 | 0.66 |
| $C_{12-18}$ fatty acid | 1.5 | 2.32 | 3.6 | 1.52 |
| Sodium Borate (Borax) | 2.5 | 2.46 | 1.2 | 2.53 |
| Sodium $C_{12-14}$ alkyl ethoxy 3 sulfate | | | 2.9 | |
| $C_{14-15}$ alkyl 7-ethoxylate | | | 4.2 | |
| $C_{12-14}$ Alkyl -7-ethoxylate | | | 1.7 | |
| Ca formate | 0.09 | 0.09 | | 0.09 |
| A compound having the following general structure: bis(($C_2H_5O$)($C_2H_4O$)n)($CH_3$)—$N^+$—$C_xH_{2x}$—$N^+$—($CH_3$)-bis(($C_2H_5O$)($C_2H_4O$)n), wherein n = from 20 to 30, and x = from 3 to 8, or sulphated or sulphonated variants thereof | | | 1.2 | |
| Random graft co-polymer [1] | | 1.46 | 0.5 | |
| Ethoxylated Polyethylenimine [2] | 1.5 | 1.29 | | 1.44 |
| Diethylene triamine pentaacetic acid | 0.34 | 0.64 | | 0.34 |
| Diethylene triamine penta(methylene phosphonic acid) | | | 0.3 | |
| Tinopal AMS-GX | | 0.06 | | |
| Tinopal CBS-X | 0.2 | 0.17 | | 0.29 |
| Amphiphilic alkoxylated grease cleaning polymer [3] | 1.28 | 1 | 0.4 | 1.93 |
| Ethanol | 2 | 1.58 | 1.6 | 5.4 |
| Propylene Glycol | 3.9 | 3.59 | 1.3 | 4.3 |
| Diethylene glycol | 1.05 | 1.54 | | 1.15 |
| Polyethylene glycol | 0.06 | 0.04 | | 0.1 |
| Monoethanolamine | 3.05 | 2.41 | 0.4 | 1.26 |
| NaOH | 2.44 | 1.8 | | 3.01 |
| Sodium Cumene Sulphonate | | | 1 | |
| Sodium Formate | | 0.11 | | 0.09 |
| Water, Aesthetics (Dyes, perfumes) and Minors (Enzymes, solvents, structurants) | balance | balance | balance | |

[1] Random graft copolymer is a polyvinyl acetate grafted polyethylene oxide copolymer having a polyethylene oxide backbone and multiple polyvinyl acetate side chains. The molecular weight of the polyethylene oxide backbone is about 6000 and the weight ratio of the polyethylene oxide to polyvinyl acetate is about 40 to 60 and no more than 1 grafting point per 50 ethylene oxide units.
[2] Polyethylenimine (MW = 600) with 20 ethoxylate groups per —NH.
[3] Amphiphilic alkoxylated grease cleaning polymer is a polyethylenimine (MW = 600) with 24 ethoxylate groups per —NH and 16 propoxylate groups per —NH Part I Examples Example 1

Assays

Various assays were used as set forth below. Any deviations from the protocols provided below are indicated in the subsequent Examples.

A. TCA Assay for Protein Content Determination in 96-Well Microtiter Plates

For BPN' and BPN' variants, this assay was started using filtered *B. subtilis* bacterial culture supernatant from microtiter plates grown 3-4 days at 33-37° C. with shaking at 230-250 rpm and humidified aeration. A fresh 96-well flat bottom microtiter plate (MTP) was used for the assay. First, 100 μL/well of 0.25 N HCl was placed in each well. Then, 25 μL of filtered culture broth was added. The light scattering/absorbance at 405 nm (use 5 sec mixing mode in the plate reader) was then determined in order to provide the "blank" reading. For the test, 100 μL/well of 30% (w/v) trichloroacetic acid (TCA) was placed in the plates and incubated for 10 minutes at room temperature. The light scattering/absorbance at 405 nm (use 5 sec mixing mode in the plate reader) was then determined. The equipment used was a Biomek FX Robot (Beckman Coulter) and a SpectraMAX (type 340; Molecular Devices) MTP Reader; the MTPs were from Costar (type 9017).

The calculations were performed by subtracting the blank (no TCA) from the test reading with TCA to provide a relative measure of the protein content in the samples. If desired, a standard curve can be created by calibrating the TCA readings with AAPF assays of clones with known conversion factors. However, the TCA results are linear with respect to protein concentration from 250 to 2500 micrograms protein per ml (ppm) and can thus be plotted directly against enzyme performance for the purpose of choosing good-performing variants. The turbidity/light scatter increase in the samples correlates to the total amount of precipitable protein in the culture supernatant.

B. AAPF Protease Assay in 96-Well Microtiter Plates

In order to determine the protease activity of the proteases and variants thereof of the present invention, the hydrolysis of N-succinyl-L-alanyl-L-alanyl-L-prolyl-L-phenyl-p-nitroanilide (suc-AAPF-pNA) was measured. The reagent solutions used were: 100 mM Tris/HCl, pH 8.6, containing 0.005% TWEEN®-80 (Tris dilution buffer); 100 mM Tris buffer, pH 8.6, containing 10 mM $CaCl_2$ and 0.005% TWEEN®-80 (Tris/Ca buffer); and 160 mM suc-AAPF-pNA in DMSO (suc-AAPF-pNA stock solution) (Sigma: S-7388). To prepare a suc-AAPF-pNA working solution, 1 ml suc-AAPF-pNA stock solution was added to 100 ml Tris/Ca buffer and mixed well for at least 10 seconds. The assay was performed by adding 10 μl of diluted protease solution to each well, immediately followed by the addition of 190 μl 1 mg/ml suc-AAPF-pNA working solution. The solutions were mixed for 5 sec., and the absorbance change in kinetic mode (25 readings in 5 minutes) was read at 405 nm in an MTP reader, at 25° C. The protease activity was expressed as AU (activity=$\Delta$OD min$^{-1}$ ml$^{-1}$).

C. BMI Microswatch Assay

Blood, milk and ink (BMI) stained microswatches of 5.5 millimeter circular diameter were obtained from CFT. Before cutting the swatches, the fabric (EMPA 116) was washed with water. One microswatch was placed in each well of a 96-well non-binding microtiter plate (Corning 3641). The detergents used for the assays included Detergent Composition 1, Detergent Composition 2, and Detergent Composition 4. The detergents were diluted in Milli-Q (deionized) water to a working strength concentration of 0.788 g/L. These detergents were buffered with 5 mM HEPES pH 8.2 or pH 7.2, which upon addition to detergent, buffers at pH 8 or pH 7, respectively. Additionally, 6 grains per gallon (gpg) water hardness (3:1 Ca:Mg—CaCl$_2$:MgCl$_2$.6H$_2$O) was added. The detergent solution was pre-equilibrated in an ice-water bath for 16° C. assays (room temperature for 32° C. assays) and pumped into a circulating reservoir (Beckman FX). Then, 190 µl of the desired detergent solution was added to each well of the MTP that contained microswatches. To this mixture, 10 µl of the diluted enzyme master dilution solution was added, providing an approximate enzyme concentration of 0.4-0.5 µg/mL. The master dilution was prepared from the culture supernatants at 8 µg/mL, where the approximate enzyme concentrations of the culture supernatants and BPN'-v3 or BPN'-v36 parent controls were determined using the AAPF protease activity assay, basing the concentration on a purified BPN'-v3 or BPN'-v36 standard of known concentration. The MTP was sealed with tape and placed in the iEMS incubator/shaker (Thermo/Labsystems) pre-set at 16° C. in a refrigerated dairy case or at 32° C. on the benchtop for 20 minutes, with agitation at 1400 rpm. Following incubation under the appropriate conditions, the sealing tape was removed from each plate and 125 µl (150 µl if pipetting by hand for smaller screens) of the solution from each well was transferred into a fresh MTP (Corning 9017). The new MTP containing 125 µl-150 µl of solution/well was read at 600 nm (with 5 sec mixing mode in the plate reader) using a MTP SpectraMax reader (type 340; Molecular Devices). Blank controls containing a microswatch and detergent but no enzyme were also included. The absorbance value obtained was corrected for the blank value (substrate without enzyme), providing a measure of hydrolytic activity. For each sample (variant), the performance index was calculated as described below. This BMI Microswatch Assay, run at 60° F. (16° C.) and pH 8, is referred to herein as the "Test Method."

D. Egg Microswatch Assay

CS38 aged egg yolk with pigment stained cotton microswatches of 5.5 millimeter circular diameter were obtained from CFT. These swatches were not pre-rinsed in water. One microswatch was placed in each well of a 96-well non-binding microtiter plate (Corning 3641). Detergent Composition 4 was diluted in Milli-Q (deionized) water to a working strength concentration of 0.788 g/L. The detergents were buffered with 5 mM HEPES pH 8.2 which upon addition to detergent, buffers at pH 8. Additionally 6 grains per gallon (gpg) water hardness (3:1 Ca:Mg—CaCl$_2$:MgCl$_2$.6H$_2$O); was added. The detergent solution was pre-equilibrated in an ice-water bath for 16° C. assays (room temperature for 32° C. assays) and pumped into a circulating reservoir (Beckman FX). Then, 185 µl of the desired detergent solution was added to each well of the MTP, containing microswatches. To this mixture, 15 µl of the diluted enzyme master dilution solution was added, providing an approximate enzyme concentration of 0.6 µg/mL in the reaction. The master dilution was prepared from the culture supernatants at 8 µg/mL, where the approximate enzyme concentration of the culture supernatants and BPN'-v3 or BPN'-v36 parent control was determined using the AAPF protease activity assay, basing the concentration on a purified BPN'-v3 or BPN'-v36 standard of known concentration. The MTP was sealed with tape and placed in the iEMS incubator/shaker (Thermo/Labsystems) pre-set at 16° C. in a refrigerated dairy case or at 32° C. on the benchtop for 30 minutes, with agitation at 1400 rpm. Following incubation under the appropriate conditions, the sealing tape was removed from each plate and 125 µl (150 µl if pipetting by hand for smaller screens) of the solution from each well was transferred into a fresh MTP (Corning 9017). The new MTP containing 125 µl-150 µl of solution/well was read at 405 nm (with 5 sec mixing mode in the plate reader) using a MTP SpectraMax reader (type 340; Molecular Devices). Blank controls containing a microswatch and detergent but no enzyme were also included. The absorbance value obtained was corrected for the blank value (substrate without enzyme), providing a measure of hydrolytic activity. For each sample (variant), the performance index was calculated as described below.

E. Grass Microswatch Assay

Warwick Equest scrubbed grass on woven cotton swatches were obtained from Warwick. These swatches were cut into 5.5 millimeter circular diameter microswatches using a custom made 96-well punch machine that places one microswatch in each well of a 96-well non-binding microtiter plate (Corning 3641). After cutting of the swatches, the fabric was washed in the wells (pre-rinsed) with 100 µL per well of 50% working strength Detergent Composition 4 diluted in water. After 20 minutes of pre-rinsing the 100 µl of 50% detergent rinse was removed carefully pipetting by hand. Detergent Composition 4 was diluted in Milli-Q (deionized) water to a working strength concentration of 0.788 g/L. These detergents were buffered with 5 mM HEPES pH 8.2, which upon addition to detergent, buffers at pH 8. Additionally 6 grains per gallon (gpg) water hardness (3:1 Ca:Mg—CaCl$_2$:MgCl$_2$.6H$_2$O); was added. The detergent solution was pre-equilibrated in an ice-water bath for 16° C. assays (room temperature for 32° C. assays). Then, 180 µl of the desired detergent solution was added to each well of the MTP containing the microswatches, immediately after the pre-rinsing was complete. To this mixture, 20 µl of the diluted enzyme master dilution solution was added making the approximate enzyme in the reaction at 0.8 µg/mL. The master dilution was prepared from the culture supernatants at 8 µg/mL where the approximate enzyme concentration of the culture supernatants and BPN'-v36 parent control was determined using the AAPF protease assay basing the concentration on a purified BPN'-v36 standard of known concentration. The MTP was sealed with tape and placed in the iEMS incubator/shaker (Thermo/Labsystems) pre-set at 16° C. in a refrigerated dairy case or at 32° C. on the benchtop for 30 minutes, with agitation at 1400 rpm. Following incubation under the appropriate conditions, the sealing tape was removed from each plate and 125 µl (150 µl if pipetting by hand for smaller screens) of the solution from each well was transferred into a fresh MTP (Corning 9017). The new MTP containing 125 µl-150 µl of solution/well was read at both 430 nm and 670 nm (with 5 sec mixing mode in the plate reader) using a MTP SpectraMax reader (type 340; Molecular Devices). Blank controls containing a microswatch and detergent but no enzyme were also included. The absorbance value obtained was corrected for the blank value (substrate without enzyme), providing a measure of hydrolytic activity. For each sample (variant), the performance index was calculated as described below.

F. Stability Assay

The stability of protease variants was determined in the presence of 40% concentrated Detergent Composition 3 diluted in water. The reagents used were Detergent Composition 3 diluted to 50% in Milli-Q water, 10 mM MES 0.01% TWEEN®-80 pH 5.8 master dilution buffer, AAPF reagents: see protocol AAPF assay. The equipment used was F-bottom MTP (Corning 9017) for dilution of diluted enzyme into detergent as well as for suc-AAPF-pNA plates, Biomek FX (Beckman Coulter), Spectramax Plus 384 MTP Reader (Molecular Devices), iEMS Incubator/Shaker (1 mm amplitude) (Thermo Electron Corporation), sealing tape: Nunc (236366), circulating reservoir (Beckman Fx).

Detergent Composition 3 was initially diluted to 50% in water. This detergent was kept at room temperature and cycled through the circulating reservoir. The iEMS incubators/shakers (Thermo/Labsystems) were pre-set at 43° C. Culture supernatants were diluted into plates containing master dilution buffer to a concentration of ~20 ppm (master dilution plate). Then, 40 µl of sample from the master dilution plate was added to plates containing 160 µl 50% Detergent Composition 3 to give a final incubation concentration of 4 ppm. The contents were mixed and kept at room temperature and triplicate AAPF assays were performed immediately on these plates and recorded as unstressed reads. The AAPF assay was modified such that 20 µL of sample from the step above was added to 190 µL of suc-AAPF-pNA working solution. The plates were immediately covered with sealing tape and placed in 43° C. iEMS shakers for 30 min at 650 rpm. Following 30 minutes of incubation, triplicate AAPF assays were performed on these stress plates and recorded as stressed reads. The stability of the samples was determined by calculating the ratio of the residual and initial AAPF activity as follows: Residual Activity (%)=[mOD·min$^{-1}$ stressed]*100/[mOD·min$^{-1}$ unstressed]. For each sample (variant), the performance index was calculated as described below.

G. LAS/EDTA Stability Assay

The stability of protease variants in the presence of a representative anionic surfactant (LAS=linear alkylbenzene sulfonate, specifically, sodium dodecylbenzenesulfonate-DOBS) and di-sodium EDTA was measured after incubation under defined conditions and the residual activity was determined using the AAPF assay. The reagents used were dodecylbenzene sulfonate, sodium salt (DOBS, Sigma No. D-2525), TWEEN®-80 (Sigma No. P-8074), di-sodium EDTA (Siegfried Handel No. 164599-02), HEPES (Sigma No. H-7523), unstressed buffer: 50 mM HEPES (11.9 g/l)+0.005% TWEEN®-80, pH 8.0, Stress buffer: 50 mM HEPES (11.9 g/l), 0.1% (w/v) DOBS (1 g/l), 10 mM EDTA (3.36 g/l), pH 8.0, reference protease and protease variant culture supernatants, containing 200-400 µg/ml protein. The equipment used was V- or U-bottom MTPs as dilution plates (Greiner 651101 and 650161, respectively), F-bottom MTPs (Corning 9017) for unstressed and LAS/EDTA buffer as well as for suc-AAPF-pNA plates, Biomek FX (Beckman Coulter), Spectramax Plus 384 MTP Reader (Molecular Devices), iEMS Incubator/Shaker (1 mm amplitude) (Thermo Electron Corporation), and Nunc sealing tape (236366).

The iEMS incubator/shaker (Thermo/Labsystems) was set at 29° C. Culture supernatants were diluted into plates containing unstressed buffer to a concentration of ~25 ppm (master dilution plate). Then, 20 µl of sample from the master dilution plate was added to plates containing 180 µl unstressed buffer to give a final incubation concentration of 2.5 ppm. The contents were mixed and kept at room temperature and an AAPF assay was performed on this plate. Then, 20 µl of sample from the master dilution plate was also added to plates containing 180 µl stress buffer (50 mM HEPES (11.9 g/l), 0.1% (w/v) DOBS (1 g/l), 10 mM EDTA (3.36 g/l), pH 8.0). The solutions were mixed and immediately placed in 29° C. iEMS shaker for 30 min at 400 rpm. Following 30 minutes of incubation, an AAPF assay was performed on the stress plate. The stability of the samples was determined by calculating the ratio of the residual and initial AAPF activity as follows: Residual Activity (%)=[mOD·min-1 stressed]*100/[mOD·min-1 unstressed]. For each sample (variant), the performance index was calculated as described below.

Performance Index

The performance index provides a comparison of the performance of a variant (actual value) and a standard or reference protease enzyme (theoretical value) at the same protein concentration. The theoretical values can be calculated using the parameters of a performance dose response curve (i.e. using a Langmuir equation to generate the performance curve) of the standard/reference protease. A performance index (PI) that is greater than 1 (PI>1) identifies a better variant as compared to the standard or reference protease (which may be, e.g., wild-type protease or another protease variant), while a PI of 1 (PI=1) identifies a variant that performs the same as the standard or reference protease, and a PI that is less than 1 (PI<1) identifies a variant that performs worse than the standard or reference protease. Thus, the PI identifies winners (e.g., variants having enhanced proteolytic activity compared to that of the standard/reference protease) as well as variants that may be less desirable for use under certain circumstances (e.g., variants having proteolytic activity lower than the proteolytic activity of the standard/reference protease).

It is important to note that protease variants of the invention having performance index values lower than that of a reference or standard protease are nevertheless useful in the applications and methods described herein. For example, protease variants of the invention having performance index values lower than that of a reference or standard protease have proteolytic activity and thus are useful in the compositions of the invention, such as, but not limited to, e.g., cleaning compositions (including, but not limited, to, e.g., detergent cleaning compositions) for cleaning a variety of surfaces and items, including, but not limited to, e.g., laundry, fabrics, and dishware, and in personal care applications and compositions as described elsewhere herein; such protease variants are also useful in fabric and home care products and compositions and in non-fabric and home care products and compositions described elsewhere herein and in methods of the invention, including, but not limited, to, e.g., cleaning methods, methods for personal care, etc., described elsewhere herein.

Various terms set forth below are used to describe the variant: non-deleterious variants have a PI>0.05; deleterious variants have a PI less than or equal to 0.05; combinable variants are those for which the variant has performance index values greater than or equal to 0.2 for at least one property, and >0.05 for all properties. Combinable variants are those that can be combined to deliver proteins with appropriate performance indices for one or more desired properties. These data find use in engineering any subtilisin/subtilase or protease. Even if the subtilase or protease to be engineered has an amino acid different from that of subtilisin BPN' at one or more particular positions, these data find use in identifying amino acid substitutions that alter the desired properties by identifying the best choices for substitutions, including substitutions of the BPN' wild type amino acid.

Example 2

Construction of BPN' Library and Cleaning Performance of BPN' Variants a) Description of the BPN'-v3 Expression Cassette Used for Library Construction The BPN'-v3 (BPN' protease containing G097A-G128A-Y217Q substitutions) expression cassette used for combinatorial library construction was generated using the BPN' expression cassette, which comprises the aprE-BPN' hybrid leader sequence (i.e., signal sequence), BPN' pro and BPN' mature sequence from *B. amyloliquefaciens*. The DNA sequence is shown below as SEQ ID NO:1 and encodes the BPN' precursor protein shown below as SEQ ID NO:168.

```
                                                              (SEQ ID NO: 1)
GTGAGAAGCAAAAAATTGTGGATCAGTTTGCTGTTTGCTTTAGCGTTAATCTTTACGATGGC

GTTCGGCAGCACATCCTCTGCCCAGGCGGCAGGGAAATCAAACGGGGAAAAGAAATATATT

GTCGGGTTTAAACAGACAATGAGCACGATGAGCGCCGCTAAGAAGAAAGATGTCATTTCTG

AAAAAGGCGGGAAAGTGCAAAAGCAATTCAAATATGTAGACGCAGCTTCAGCTACATTAAA

CGAAAAAGCTGTAAAAGAATTGAAAAAAGACCCGAGCGTCGCTTACGTTGAAGAAGATCAC

GTAGCACATGCGTACGCGCAGTCCGTGCCTTACGGCGTATCACAAATTAAAGCCCCTGC

TCTGCACTCTCAAGGCTACACTGGATCAAATGTTAAAGTAGCGGTTATCGACAGCGGT

ATCGACTCGAGCCATCCAGATCTTAAAGTCGCTGGAGGGGCTTCTATGGTGCCGTCCG

AAACAAACCCGTTTCAAGATAACAATTCTCATGGCACACACGTCGCAGGAACGGTTGC

GGCGTTAAACAATTCTATTGGCGTGCTTGGTGTAGCCCCGTCTGCTTCGCTCTACGCC

GTTAAAGTTCTTGGCGCAGACGGATCAGGCCAATACTCATGGATTATCAACGGCATCG

AATGGGCCATCGCGAATAACATGGATGTAATCAACATGAGCCTGGGAGGACCAAGCG

GCAGTGCGGCACTTAAAGCAGCAGTTGATAAAGCTGTTGCATCTGGTGTCGTCGTAGT

AGCGGCAGCTGGGAATGAGGGAACATCCGGATCATCGAGTACCGTCGGTTATCCAGG

CAAGTACCCTTCAGTGATTGCAGTGGGCGCTGTAGACTCTTCAAATCAACGTGCCTCT

TTTTCCTCCGTGGGACCGGAGCTGGATGTCATGGCCCCTGGCGTTTCTATTCAATCGA

CGCTTCCAGGGAACAAGTATGGTGCGTATAACGGGACTTCCATGGCCTCGCCGCATGT

AGCTGGGGCGGCCGCATTGATTCTTTCTAAGCACCCGAACTGGACAAACACTCAAGTC

CGCAGCAGTTTAGAAAACACCACTACAAAACTTGGTGATTCTTTCTACTATGGAAAAG

GGCTGATCAACGTACAGGCGGCAGCTCAG
```

In the nucleotide sequence of SEQ ID NO:1, the DNA sequence encoding the mature protease is shown in bold, the nucleotide sequence encoding leader sequence (aprE-BPN' hybrid leader sequence) is shown in standard (non-underlined) text, and the nucleotide sequence encoding the pro sequence (BPN') is underlined. In the amino acid sequence (aprE-BPN' hybrid leader sequence, BPN' pro sequence, and BPN' mature protein sequence) of the BPN' precursor protein set forth in SEQ ID NO:168, the bolded portion indicates the mature BPN' subtilisin protease.

```
                                                            (SEQ ID NO: 168)
VRSKKLWISLLFALALIFTMAFGSTSSAQAAGKSNGEKKYIVGFKQTMST

MSAAKKKDVISEKGGKVQKQFKYVDAASATLNEKAVKELKKDPSVAYVEE

DHVAHAYAQSVPYGVSQIKAPALHSQGYTGSNVKVAVIDSGIDSSHPDLK

VAGGASMVPSETNPFQDNNSHGTHVAGTVAALNNSIGVLGVAPSASLYAV

KVLGADGSGQYSWIINGIEWAIANNMDVINMSLGGPSGSAALKAAVDKAV

ASGVVVVAAAGNEGTSGSSSTVGYPGKYPSVIAVGAVDSSNQRASFSSVG

PELDVMAPGVSIQSTLPGNKYGAYNGTSMASPHVAGAAALILSKHPNWTN

TQVRSSLENTTTKLGDSFYYGKGLINVQAAAQ
```

Thus, the amino acid sequence of the mature BPN' subtilisin protease is:

```
                                                              (SEQ ID NO: 2)
AQSVPYGVSQIKAPALHSQGYTGSNVKVAVIDSGIDSSHPDLKVAGGASM

VPSETNPFQDNNSHGTHVAGTVAALNNSIGVLGVAPSASLYAVKVLGADG

SGQYSWIINGIEWAIANNMDVINMSLGGPSGSAALKAAVDKAVASGVVVV

AAAGNEGTSGSSSTVGYPGKYPSVIAVGAVDSSNQRASFSSVGPELDVMA

PGVSIQSTLPGNKYGAYNGTSMASPHVAGAAALILSKHPNWTNTQVRSS

LENTTTKLGDSFYYGKGLINVQAAAQ
```

The nucleotide sequence of the mature BPN'-v3 gene is shown below (the signal sequence and propeptide sequence used in the BPN'-v3 expression cassette is the same as that for BPN' shown in SEQ ID NO:1):

(SEQ ID NO: 3)
GCGCAGTCCGTGCCTTACGGCGTATCACAAATTAAAGCCCCTGCTCTGCA

CTCTCAAGGCTACACTGGATCAAATGTTAAAGTAGCGGTTATCGACAGCG

GTATCGACTCGAGCCATCCAGATCTTAAAGTCGCTGGAGGGGCTTCTATG

GTGCCGTCCGAAACAAACCCGTTTCAAGATAACAATTCTCATGGCACACA

CGTCGCAGGAACGGTTGCGGCGTTAAACAATTCTATTGGCGTGCTTGGTG

TAGCCCCGTCTGCTTCGCTCTACGCCGTTAAAGTTCTTGCAGCAGACGGA

TCAGGCCAATACTCATGGATTATCAACGGCATCGAATGGGCCATCGCGAA

TAACATGGATGTAATCAACATGAGCCTGGGAGCACCAAGCGGCAGTGCGG

CACTTAAAGCAGCAGTTGATAAAGCTGTTGCATCTGGTGTCGTCGTAGTA

GCGGCAGCTGGGAATGAGGGAACATCCGGATCATCGAGTACCGTCGGTTA

TCCAGGCAAGTACCCTTCAGTGATTGCAGTGGGCGCTGTAGACTCTTCAA

ATCAACGTGCCTCTTTTTCCTCCGTGGGACCGGAGCTGGATGTCATGGCC

CCTGGCGTTTCTATTCAATCGACGCTTCCAGGGAACAAGTATGGTGCGCA

AAACGGGACTTCCATGGCCTCGCCGCATGTAGCTGGGGCGGCCGCATTG

ATTCTTTCTAAGCACCCGAACTGGACAAACACTCAAGTCCGCAGCAGTTT

AGAAAACACCACTACAAAACTTGGTGATTCTTTCTACTATGGAAAAGGGC

TGATCAACGTACAGGCGGCAGCTCAG

The protein sequence of the mature BPN'-v3 protease variant is shown below (the signal sequence and propeptide sequence used in the BPN'-v3 expression cassette is the same as that for BPN' shown in SEQ ID NO:168):

(SEQ ID NO: 4)
AQSVPYGVSQIKAPALHSQGYTGSNVKVAVIDSGIDSSHPDLKVAGGASM

VPSETNPFQDNNSHGTHVAGTVAALNNSIGVLGVAPSASLYAVKVLAADG

SGQYSWIINGIEWAIANNMDVINMSLGAPSGSAALKAAVDKAVASGVVVV

AAAGNEGTSGSSSTVGYPGKYPSVIAVGAVDSSNQRASFSSVGPELDVMA

PGVSIQSTLPGNKYGAQNGTSMASPHVAGAAALILSKHPNWTNTQVRSSL

ENTTTKLGDSFYYGKGLINVQAAAQ b) Construction of Combinatorial Library Using pHPLT-BPN'-v3 Plasmid The pHPLT-BPN'-v3 plasmid (see FIG. 1) containing the BPN'-v3 expression cassette described above served as template DNA for cloning to provide variants derived from BPN'-v3. The vector pHPLT (FIG. 4 in U.S. Pat. No. 6,566,112) contains the *B. licheniformis* LAT promoter ("Plat"); a sequence encoding the LAT signal peptide ("preLAT"). Additional plasmid elements from plasmid pUB110 disclosed in McKenzie et al., *Plasmid* 15(2): 93-103 (1986): "ori-pUB" is the origin of replication from pUB110; "neo" is the neomycin/kanamycin resistance gene from pUB110; "Terminator" is the transcriptional terminator from *B. licheniformis* amylase.

A combinatorial DNA library was synthesized at DNA 2.0 and delivered as individual ligation reactions. In some instances for efficient transformation of *B. subtilis*, the DNA from the ligation reaction mixtures was amplified by rolling circle amplification (RCA) using the Illustra Templiphi kit (GE Healthcare). The reaction was performed according to the manufacturer's protocol. One microliter of ten-fold diluted amplified DNA was used to transform 50 µL of competent *B. subtilis* cells (ΔaprE, ΔnprE, amyE::xylRPxylA-comK-phleo). The transformation mixture was shaken at 37° C. for 1 hour. Ten micro-liter aliquots of the transformation mixture were plated on skim milk (1.6%) Luria agar plates supplemented with 10 µg/ml of neomycin (Teknova).

The transformants that formed halos on the skim milk plates were picked into microtiter plates containing 150 µl Luria broth (LB) medium supplemented with 10 µg/ml neomycin. Plates were grown overnight at 37° C. with 250-300 rpm shaking and 70-80% humidity using Enzyscreen lids for microtiter plates (Enzyscreen). Using a 96 pin replicating tool, (Enzyscreen) the overnight culture plate was used to inoculate a new microtiter plate containing 180 µl of MBD medium (a MOPS based defined medium) with 2.5 µg/ml neomycin. MBD medium was prepared essentially as known in the art (see Neidhardt et al., J. Bacteriol. 119:736-747 [1974]), except that $NH_4Cl_2$, $FeSO_4$, and $CaCl_2$ were omitted from the base medium, 3 mM $K_2HPO_4$ was used, and the base medium was supplemented with 60 mM urea, and 100 ml of a solution made of 210 g/L glucose, and 350 g/L maltodextrin. 1 g/L of BD Bacto Yeast Extract was added and the pH was adjusted to 7.4 with KOH. The micronutrients were made up as a 100× stock solution containing in one liter, 400 mg $FeSO_4.7H_2O$, 100 mg $MnSO_4.H_2O$, 100 mg $ZnSO_4.7H_2O$, 50 mg $CuCl_2.2H_2O$, 100 mg $CoCl_2.6H_2O$, 100 mg $NaMoO_4.2H_2O$, 100 mg $Na_2B_4O_7.10H_2O$, 10 ml of 1M $CaCl_2$, and 10 ml of 0.5 M sodium citrate. The MBD medium containing microtiter plates were grown for 64 hours at 37° C., 250-300 rpm, and 70-80% humidity using Enzyscreen lids (Enzyscreen) for protease variant expression. The next day, cultures were filtered through a micro-filter plate (0.22 um; Millipore) and the resulting filtrates containing protease variants were used for biochemical analysis.

The protease variants were tested for cleaning performance using a BMI microswatch assay in Detergent Composition 1 at 16° C. and pH 8 and BMI microswatch assay in Detergent Composition 2 at 16° C. and pH 8. Protein content was determined using the TCA assay. Assays were performed as described in Example 1 and Performance Indices were calculated relative to BPN'-v3 (with a PI value of 1.0).

The following BPN' subtilisin protease variant was determined to have a PI value greater than 1.0, at least 1.1, at least 1.2, at least 1.3, at least 1.4, at least 1.5, at least 1.6, at least 1.7, at least 1.8, at least 1.9, at least 2 to about 5, or from greater than 1.0 to about 5 relative to BPN'-v3 (SEQ ID NO:4) in a BMI microswatch cleaning assay in Detergent Composition 1 at pH 8 and 16° C.: BPN' amino acid sequence (SEQ ID NO:2) comprising the set of amino acid substitutions G097A-G128A-P210S-Y217Q, wherein amino acid positions of the variant are numbered by correspondence with the sequence of SEQ ID NO:2. Such variant has a PI value of 1.1 relative to BPN'-v3 in this BMI microswatch cleaning assay, and enhanced proteolytic activity compared to BPN' (SEQ ID NO:2) and a greater PI value than that of BPN' in this assay. The invention includes a protease variant having enhanced proteolytic activity compared to BPN' (SEQ ID NO:2) in this assay, the variant having an amino acid sequence comprising amino acid substitutions G097A-G128A-P210S-Y217Q, wherein amino acid positions of the variant are numbered by correspondence with the sequence of SEQ ID NO:2. Also included is a protease variant having enhanced proteolytic activity compared to SEQ ID NO:2 in this assay, the variant comprising an amino acid sequence having at least 60%, 70%, 80%, 85%, 90%, 91%, 92%, 93%, 94%, 95%, 96%, 97%, or 98% identity to the sequence of SEQ ID NO:2 and comprising amino acid substitutions G097A-G128A-P210S-Y217Q, wherein amino acid positions of the variant are numbered by correspondence with amino acid positions of the SEQ ID NO:2 sequence. Also provided is a subtilisin protease variant having enhanced proteolytic activity compared to BPN' and/or a PI value greater than that of BPN' (SEQ ID NO:2) and/or BPN'-v3 in a BMI microswatch cleaning assay, the variant comprising an amino acid sequence having at least 90%, 91%, 92%, 93%, 94%, 95%, 96%, 97%, or 98% identity to SEQ ID NO:2, wherein the variant comprises substitutions X097A-X128A-X210S-X217Q, wherein positions of the variant are numbered by correspondence with the sequence of SEQ ID NO:2, and optionally wherein the variant comprises at least one substitution selected from the group of G097A, G128A, P210S, and Y217Q. Such protease variant may be an isolated, recombinant, substantially pure, or non-naturally occurring protease variant. Also included are compositions, including, but not limited to, e.g., cleaning compositions, comprising such protease variant and methods for cleaning utilizing such variant as described in greater detail elsewhere herein.

The following BPN' variants were determined to have a PI value of about 1.0 relative to BPN'-v3 in a BMI microswatch cleaning assay in Detergent Composition 1 at pH 8 and 16° C.: BPN' amino acid sequence (SEQ ID NO:2) comprising at least one set of amino acid substitutions selected from the group consisting of G097A-G128A-Y217Q, G097A-G128A-E156S-P210S-Y217Q, G097A-G128A-P210S-Y217Q-N218A, G097A-G128A-P210S-Y217Q-N218S, and G097A-Y104F-G128A-E156S-P210I-Y217Q, wherein amino acid positions of the variant are numbered by correspondence with the sequence of SEQ ID NO:2. Such variants have enhanced proteolytic activity compared to BPN' (SEQ ID NO:2) and a greater PI value than that of BPN' in this assay. The invention includes a protease variant having enhanced proteolytic activity compared to BPN' (SEQ ID NO:2) or a PI value of about 1.0 relative to BPN'-v3 in this BMI microswatch cleaning assay, the variant comprising an amino acid sequence having at least 60%, 70%, 80%, 85%, 90%, 91%, 92%, 93%, 94%, 95%, 96%, 97%, or 98% identity to the sequence of SEQ ID NO:2 and comprising at least one set of amino acid substitutions selected from said group above, wherein amino acid positions of the variant are numbered by correspondence with amino acid positions of the SEQ ID NO:2 sequence. Also provided is a subtilisin protease variant having enhanced proteolytic activity compared to BPN' and/or a PI value of about 1.0 compared to BPN'-v3 in this BMI microswatch cleaning assay, the variant comprising an amino acid sequence having at least 90%, 91%, 92%, 93%, 94%, 95%, 96%, 97%, 98%, or 99% identity to SEQ ID NO:2, wherein the variant comprises at least one substitution selected from the group of X097A, X104F, X128A, X156A/S, X210I/S, X217Q, X218A/S, and optionally at least one substitution selected from the group of G097A, Y104F, G128A, E156A/S, P210I/S, Y217Q, and N218A/S, wherein positions of the variant are numbered by correspondence with the sequence of SEQ ID NO:2. Also included are compositions, including, but not limited to, e.g., cleaning compositions, comprising at least one such variant and methods for cleaning utilizing at least one such variant as described in greater detail elsewhere herein.

The following BPN' variants were determined to have a PI value of about 0.9 relative to BPN'-v3 in a BMI microswatch cleaning assay in Detergent Composition 1 at pH 8 and 16° C.: BPN' amino acid sequence (SEQ ID NO:2) comprising at least one set of amino acid substitutions selected from the group consisting of G097A-G128A-E156A-P210S-Y217Q-N218S and G097A-G128A-Y217Q-N218A, wherein positions of the variant are numbered by correspondence with the sequence of SEQ ID NO:2. Such variants have proteolytic activity. The invention includes a protease variant having proteolytic activity, a PI value of about 0.9 relative to BPN'-v3, and/or enhanced proteolytic activity compared to BPN' in this assay, the variant comprising an amino acid sequence having at least 60%, 70%, 80%, 85%, 90%, 91%, 92%, 93%, 94%, 95%, 96%, 97%, or 98% identity to the sequence of SEQ ID NO:2 and at least one set of amino acid substitutions selected from said group above, wherein amino acid positions of the variant are numbered by correspondence with positions of the SEQ ID NO:2 sequence. Also included are compositions, including, but not limited to, e.g., cleaning compositions, comprising at least one such variant and methods for cleaning utilizing at least one such variant as described in greater detail elsewhere herein.

The following BPN' variants were determined to have a PI value of greater than 1.0 to about 5 relative to BPN'-v3 in a BMI microswatch cleaning assay in Detergent Composition 2 at pH 8 and 16° C.: BPN' amino acid sequence (SEQ ID NO:2) comprising at least one set of amino acid substitutions selected from the group consisting of G097A-G128A-P210S-Y217Q-N218A and G097A-G128A-P210S-Y217Q, wherein amino acid positions of the variant are numbered by correspondence with the sequence of SEQ ID NO:2. The invention includes a protease variant having enhanced proteolytic activity compared to BPN' (SEQ ID NO:2) and/or a PI value of greater than 1.0 to about 5 relative to BPN'-v3 in this BMI microswatch cleaning assay, the variant comprising an amino acid sequence having at least 60%, 70%, 80%, 85%, 90%, 91%, 92%, 93%, 94%, 95%, 96%, 97%, or 98% identity to the sequence of SEQ ID NO:2 and comprising at least one set of amino acid substitutions selected from said group above, wherein amino acid positions of the variant are numbered by correspondence with amino acid positions of the SEQ ID NO:2 sequence. Such variants have enhanced proteolytic activity compared to BPN' (SEQ ID NO:2) and a greater PI value than that of BPN' in this assay. Also provided is a subtilisin protease variant having enhanced proteolytic activity compared to BPN' and/or a PI value of greater than 1, at least 1.1, at least 1.2, at least 1.3, at least 1.4, at least 1.5, at least 1.6, at least 1.7, at least 1.8, at least 1.9 to about 5 compared to BPN'-v3 in this BMI microswatch cleaning assay, the variant comprising an amino acid sequence having at least 85%, 90%, 91%, 92%, 93%, 94%, 95%, 96%, 97%, 98%, or 99% identity to SEQ ID NO:2, wherein the variant comprises at least one substitution selected from the group of X097A, X104F, X128A, X156A/S, X210I/S, X217Q, X218A/S, and optionally at least one substitution selected from the group of G097A, Y104F, G128A, E156A/S, P210I/S, Y217Q, and N218A/S, wherein amino acid positions of the variant are numbered by correspondence with position of the sequence of SEQ ID NO:2. Such variants have enhanced proteolytic activity compared to BPN' (SEQ ID NO:2) and a greater PI value than that of BPN' in this assay. Also included are compositions, including, but not limited to, e.g., cleaning compositions, comprising at least one such variant and methods for cleaning utilizing at least one such variant as described in greater detail elsewhere herein.

The following BPN' variants were determined to have a PI value of about 1.0 relative to BPN'-v3 in a BMI microswatch cleaning assay in Detergent Composition 2 at pH 8 and 16° C.: BPN' amino acid sequence (SEQ ID NO:2) comprising at least one set of amino acid substitutions selected from the group consisting of G097A-G128A-Y217Q (i.e., BPN'-v3), G097A-G128A-E156S-P210S-Y217Q, and G097A-G128A-P210S-Y217Q-N218S, wherein positions of the variant are numbered by correspondence with the sequence of SEQ ID NO:2. Such variants have proteolytic activity and enhanced proteolytic activity compared to BPN' in this assay. The invention includes a protease variant having proteolytic activity, PI value of 1.0 relative to BPN'-v3, and/or enhanced proteolytic activity compared to BPN' in this assay, the variant comprising an amino acid sequence having at least 60%, 70%, 80%, 85%, 90%, 91%, 92%, 93%, 94%, 95%, 96%, 97%, or 98% identity to the sequence of SEQ ID NO:2 and at least one set of amino acid substitutions selected from said group above, wherein positions of the variant are numbered by correspondence with positions of the SEQ ID NO:2 sequence. Also included are compositions, including, but not limited to, e.g., cleaning compositions, comprising at least one such variant and methods for cleaning utilizing at least one such variant as described in greater detail elsewhere herein.

The following BPN' variants were determined to have a PI value of about 0.9 relative to BPN'-v3 in a BMI microswatch cleaning assay in Detergent Composition 2 at pH 8 and 16° C.: BPN' amino acid sequence (SEQ ID NO:2) comprising at least one set of amino acid substitutions selected from the group consisting of G097A-G128A-E156A-P210S-Y217Q-N218S, G097A-G128A-Y217Q-N218A, and G097A-Y104F-G128A-E156S-P210I-Y217Q, wherein positions of the variant are numbered by correspondence with the sequence of SEQ ID NO:2. Such variants have proteolytic activity. The invention includes a protease variant having proteolytic activity, a PI value of about 0.9 relative to BPN'-v3, and/or enhanced proteolytic activity compared to BPN' in this assay, the variant comprising an amino acid sequence having at least 60%, 70%, 80%, 85%, 90%, 91%, 92%, 93%, 94%, 95%, 96%, 97%, or 98% identity to the sequence of SEQ ID NO:2 and at least one set of amino acid substitutions selected from said group above, wherein amino amino acid positions of the variant are numbered by correspondence with positions of the SEQ ID NO:2 sequence. Also included are compositions, including, but not limited to, e.g., cleaning compositions, comprising at least one such variant and methods for cleaning utilizing at least one such variant as described in greater detail elsewhere herein.

Example 3

Figure 2:
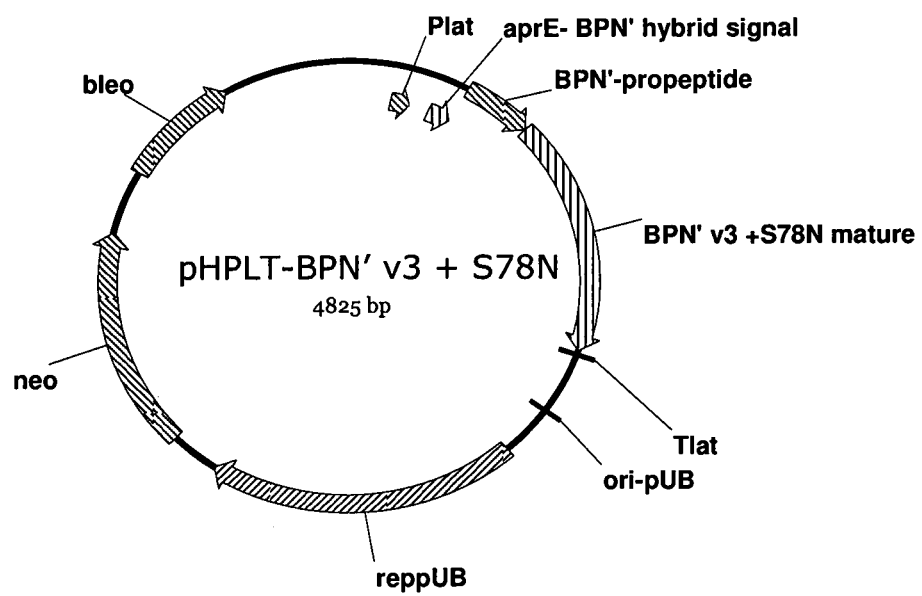
FIG. 2 provides a plasmid map of pHPLT-BPN'-v3+S78N.

Generation of Combinatorial Libraries and Cleaning Performance of Variants of BPN'-v3+S78N a) Description of BPN'-v3+S78N Variant and Synthetic Gene Sequences Derived from this Variant Gene Oracle synthesized and cloned eight genes into the pHPLT-BPN'-v3+S78N (BPN'-S78N-G97A-G128A-Y217Q) parent plasmid (see FIG. 2). Some of these genes were used as templates (parents) to create combinatorial libraries. The BPN'-v3+S78N variant was generated using standard molecular biology methods known in the art. The nucleotide sequence encoding the BPN'-v3+S78N variant is shown below:

```
(SEQ ID NO: 7)
GCGCAGTCCGTGCCTTACGGCGTATCACAAATTAAAGCCCCTGCTCTGCA

CTCTCAAGGCTACACTGGATCAAATGTTAAAGTAGCGGTTATCGACAGCG

GTATTGATTCGAGCCATCCAGATCTTAAAGTCGCTGGAGGGGCTTCTATG

GTGCCGTCCGAAACAAACCCGTTTCAAGATAACAATTCTCATGGCACACA

CGTCGCAGGAACGGTTGCGGCGTTAAACAATAATATTGGCGTGCTTGGTG

TAGCCCCGTCTGCTTCGCTCTACGCCGTTAAAGTTCTTGCAGCAGACGG

ATCAGGCCAATACTCATGGATTATCAACGGCATCGAATGGGCCATCGCGA

ATAACATGGATGTAATCAACATGAGCCTGGGAGCACCAAGCGGCAGTGCG

GCACTTAAAGCAGCAGTTGATAAAGCTGTTGCATCTGGTGTCGTCGTAGT

AGCGGCAGCTGGGAATGAGGGAACATCCGGATCATCGAGTACCGTCGGTT

ATCCAGGCAAGTACCCTTCAGTGATTGCAGTGGGCGCTGTAGACTCTTCA

AATCAACGTGCCTCTTTTTCCTCCGTGGGACCGGAGCTGGATGTCATGGC

CCCTGGCGTTTCTATTCAATCGACGCTTCCAGGGAACAAGTATGGTGCGC

AAAACGGGACTTCCATGGCCTCGCCGCATGTAGCTGGGGCGGCCGCATTG

ATTCTTTCTAAGCACCCGAACTGGACAAACACTCAAGTCCGCAGCAGTTT

AGAAAACACCACTACAAAACTTGGTGATTCTTTCTACTATGGAAAAGGGC

TGATCAACGTACAGGCGGCAGCTCAG
```

The amino acid sequence of the BPN'-v3+S78N variant is shown below:

```
(SEQ ID NO: 8)
AQSVPYGVSQIKAPALHSQGYTGSNVKVAVIDSGIDSSHPDLKVAGGASM

VPSETNPFQDNNSHGTHVAGTVAALNNNIGVLGVAPSASLYAVKVLAADG

SGQYSWIINGIEWAIANNMDVINMSLGAPSGSAALKAAVDKAVASGVVVV

AAAGNEGTSGSSSTVGYPGKYPSVIAVGAVDSSNQRASFSSVGPELDVM

APGVSIQSTLPGNKYGAQNGTSMASPHVAGAAALILSKHPNWTNTQVRS

SLENTTTKLGDSFYYGKGLINVQAAAQ
```

The nucleotide and protein sequences of genes GcM90-96, and GcM100 are shown below. The nucleotide sequence of synthesized gene GcM90 is:

```
(SEQ ID NO: 9)
GCGCAGTCCGTGCCTTACGGCGTATCACAAATTAAAGCCCCTGCTCTGCA

CTCTCAAGGCTACACTGGATCAAATGTTAAAGTAGCGGTTATCGACAGCG

GTATCGACTCGAGCCATCCAGATCTTAAAGTCGCTGGAGGGGCTTCTATG

GTGCCGGGAGAAACAAACCCGTTTCAAGATAACAATTCTCATGGCACACA

CGCAGCAGGAACGGTTGCGGCGTTAAACAATAATATTGGCGTGCTTGGTG

TAGCCCCGTCTGCTTCGCTCTACGCCGTTAAAGTTCTTGCAGCAGACGGA

TCAGCACAATACTCATGGATTATCAACGGCATCGAATGGGCCATCGCGAA

TAACATGGATGTAATCAACATGAGCCTGGGAGCAACAAGCGGCAGTGCGG

CACTTAAAGCAGCAGTTGATAAAGCTGTTGCATCTGGTGTCGTCGTAGTA

GCGGCAGCTGGGAATGAGGGAACATCCGGATCATCGAGTACCGTCGGTTA

TCCAGGCAAGTACCCTTCAGTGATTGCAGTGGGCGCTGTAGACTCTTCAA

ATACACGTGCCTCTTTTTCCTCCGTGGGACCGGAGCTGGATGTCATGGCC

CCTGGCGTTTCTATTCAATCGACGCTTCCAGGGAACAAGTATGGTGCGCA

AAACGGGACTTCCATGGCCTCGCCGCATGTAGCTGGGGCGGCCGCATTGA
```

-continued

TTCTTTCTAAGCACCCGAACTGGACAAACACTCAAGTCCGCAGCAGTTTA

GAAAACACCACTACAAAACTTGGTGATTCTTTCTACTATGGAAAAGGGCT

GATCAACGTACAGGCGGCAGCTCAGTAA

The amino acid sequence of GcM90 is provided below:

(SEQ ID NO: 10)
AQSVPYGVSQIKAPALHSQGYTGSNVKVAVIDSGIDSSHPDLKVAGGASM

VPGETNPFQDNNSHGTHAAGTVAALNNNIGVLGVAPSASLYAVKVLAADG

SAQYSWIINGIEWAIANNMDVINMSLGATSGSAALKAAVDKAVASGVVVV

AAAGNEGTSGSSSTVGYPGKYPSVIAVGAVDSSNTRASFSSVGPELDVMA

PGVSIQSTLPGNKYGAQNGTSMASPHVAGAAALILSKHPNWTNTQVRSS

LENTTTKLGDSFYYGKGLINVQAAAQ

The nucleotide sequence of synthesized gene GcM91 is provided below:

(SEQ ID NO: 11)
GCGCAGTCCGTGCCTTACGGCGTATCACAAATTAAAGCCCCTGCTCTG

CACTCTCAAGGCTACACTGGATCAAATGTTAAAGTAGCGGTTATCGACAG

CGGTATCGACTCGAGCCATCCAGATCTTAAAGTCGCTGGAGGGGCTTCTA

TGGTGCCGTCCGAAACAAACCCGTTTGTCGATAACAATTCTCATGGCACA

CACGTCGCAGGAACGGTTGCGGCGTTAAACAATAATATTGGCGTGCTTGG

TGTAGCCCCGTCTGCTTCGCTCTACGCCGTTAAAGTTCTTGCAGCAGACG

GATCAGGCCAATACTCATGGATTGTCAACGGCATCGAATGGGCCATCGCG

AATAACATGGATGTAATCAACATGAGCCTGGGAGCACCAAGCGGCAGTGC

GGCACTTAAAGCAGCAGTTGATAAAGCTGTTGCATCTGGTCAAGTCGTAG

TAGCGGCAGCTGGGAATGAGGGAACATCCGGATCATCGAGTACCGTCGGT

TATCCAGGCAAGTACCCTTCAGTGATTGCAGTGGGCGCTGTAGACTCTTC

AAATCAACGTGCCTCTTTTTCCTCCGTGGGACCGGAGCTGGATGTCATGG

CCCCTGGCGTTTCTATTCAATCGACGCTTCCAGCAAACAAGTATGGTGCG

CAAAACGGGACTTCCATGGCCTCGCCGCATGTAGCTGGGCGGCCGCATT

GATTCTTTCTAAGCACCCGAACTGGACAAACACTCAAGTCCGCAGCAGTT

TAGAACAAACCACTACAAAACTTGGTGATTCTTTCTACTATGGAAAAGGG

CTGATCAACGTACAGGCGGCAGCTCAGTAA

The amino acid sequence of GcM91 is provided below:

(SEQ ID NO: 12)
AQSVPYGVSQIKAPALHSQGYTGSNVKVAVIDSGIDSSHPDLKVAGGAS

MVPSETNPFVDNNSHGTHVAGTVAALNNNIGVLGVAPSASLYAVKVLAAD

GSGQYSWIVNGIEWAIANNMDVINMSLGAPSGSAALKAAVDKAVASGQV

VVAAAGNEGTSGSSSTVGYPGKYPSVIAVGAVDSSNQRASFSSVGPELDV

MAPGVSIQSTLPANKYGAQNGTSMASPHVAGAAALILSKHPNWTNTQVRS

SLEQTTTKLGDSFYYGKGLINVQAAAQ

The nucleotide sequence of synthesized gene GcM92 is provided below:

(SEQ ID NO: 13)
GCGCAGTCCGTGCCTTACGGCGTATCACAAATTAAAGCCCCTGCTCTGCA

CTCTCAAGGCTACACTGGATCAAATGTTAAAGTAGCGGTTATCGACAGCG

GTATCGACTCGAGCCATCCAGATCTTAAAGTCGCTGGAGGGGCTTCTATG

GTGCCGTCCGAAACAAACCCGTTTCAAGATGCAAATTCTCATGGCACACA

CGTCGCAGGAACGGTTGCGGCGTTAAACAATAATATTGGCGTGCTTGGTG

TAGCCCCGGAAGCTTCGCTCTACGCCGTTAAAGTTCTTGCAGCAGACGGA

TCAGGCCAATACTCATGGATTATCAACGGCATCGAATGGGCCATCGCGAA

TAACATGGATGTAATCAACATCAGCCTGGGAGCACCAAGCGGCAGTGCGG

CACTTAAAGCAGCAGTTGATAAAGCTGTTGCATCTGGTGTCGTCGTAGTA

GCGGCAGCTGGGAATGAGGGAACATCCGGACCTTCGAGTACCGTCGGTTA

TCCAGGCAAGTACCCTTCAGTGATTGCAGTGGGCGCTGTAGACTCTTCAA

ATCAACGTGCCTCTTTTTCCTCCGTGGGACCGGAGCTGGATGTCATGGCC

CCTGGCGTTTCTATTCAATCGACGCTTCCAGGGAACAAGTATGGTGCGCA

AAACGGGACTTCCATGGCCGCACCGCATGTAGCTGGGGCGGCCGCATTGA

TTCTTTCTAAGCACCCGAACTGGACAAACACTCAAGTCCGCAGCAGTTTA

GAAAACACCACTACAAAACTTGGTGATTCTTTCTACTATGGAAAAGGGC

TGATCAACGTACAGGCGGCAGCTCAGTAA

The amino acid sequence of GcM92 is provided below:

(SEQ ID NO: 14)
AQSVPYGVSQIKAPALHSQGYTGSNVKVAVIDSGIDSSHPDLKVAGGASM

VPSETNPFQDANSHGTHVAGTVAALNNNIGVLGVAPEASLYAVKVLAADG

SGQYSWIINGIEWAIANNMDVINISLGAPSGSAALKAAVDKAVASGVVVV

AAAGNEGTSGPSSTVGYPGKYPSVIAVGAVDSSNQRASFSSVGPELDVMA

PGVSIQSTLPGNKYGAQNGTSMAAPHVAGAAALILSKHPNWTNTQVRSS

LENTTTKLGDSFYYGKGLINVQAAAQ

The nucleotide sequence of synthesized gene of GcM93 is provided below:

(SEQ ID NO: 15)
GCGCAGTCCGTGCCTTACGGCGTATCACAAATTAAAGCCCCTGCTCTGC

ACTCTCAAGGCTACACTGGATCAAATGTTAAAGTAGCGGTTATCGACAGC

GGTATCGACTCGAGCCATCCAGATCTTAAAGTCGCTGGAGGGGCTTCTAT

GGTGCCGTCCGAAACAAACCCGTTTCAAGATAACCAATCTCATGGCACAC

ACGTCGCAGGAACGGTTGCGGCGTTAAACAATAATATTGGCGTGCTTGGT

GTAGCCCCGTCTGCTTCGCTCTACGCCGTTAAAGTTCTTGCAGCAGACAA

CTCAGGCCAATACTCATGGATTATCAACGGCATCGAATGGGCCATCGCGA

ATAACATGGATGTAATCAACATGGCACTGGGAGCACCAAGCGGCAGTGCG

GCACTTAAAGCAGCAGTTGATAAAGCTGTTGCATCTGGTGTCGTCGTAGT

AGCGGCAGCTGGGAATGAGGGAACAGATGGATCATCGAGTACCGTCGGTT

ATCCAGGCAAGTACCCTTCAGTGATTGCAGTGGGCGCTGTAGACTCTTCA

AATCAACGTGCCTCTTTTTCCTCCGTGGGACCGGAGCTGGATGTCATGGC

```
CCCTGGCGTTTCTATTCAATCGACGCTTCCAGGGAACAAGTATGGTGCGC

AAAACGGGACTTCCATGGCCTCGCCGCATGTAGCTGGGGCGGCCGCATT

GATTCTTTCTAAGCACCCGTCATGGACAAACACTCAAGTCCGCAGCAGT

TTAGAAAACACCACTACAAAACTTGGTGATTCTTTCTACTATGGAAAAG

GGCTGATCAACGTACAGGCGGCAGCTCAGTAA
```

The amino acid sequence of GcM93 is provided below:

(SEQ ID NO: 16)
```
AQSVPYGVSQIKAPALHSQGYTGSNVKVAVIDSGIDSSHPDLKVAGGASM

VPSETNPFQDNQSHGTHVAGTVAALNNNIGVLGVAPSASLYAVKVLAADN

SGQYSWIINGIEWAIANNMDVINMALGAPSGSAALKAAVDKAVASGVVVV

AAAGNEGTDGSSSTVGYPGKYPSVIAVGAVDSSNQRASFSSVGPELDVM

APGVSIQSTLPGNKYGAQNGTSMASPHVAGAAALILSKHPSWTNTQVRS

SLENTTTKLGDSFYYGKGLINVQAAAQ
```

The nucleotide sequence of synthesized gene GcM94 is provided below:

(SEQ ID NO: 17)
```
GCGCAGTCCGTGCCTTACGGCGTATCACAAATTAAAGCCCCTGCTCTGCA

CTCTCAAGCTACACTGGATCAAATGTTAAAGTAGCGGTTATCGACAGCGG

TATCGACTCGAGCCATCCAGATCTTAAAGTCGCTGGAGGGGCTTCTATGG

TGCCGTCCGAAACAAACCCGTTTCAAGATAACAATACACATGGCACACAC

GTCGCAGGAACGGTTGCGGCGTTAAACAATAATATTGGCGTGCTTGGTGT

AGCCCCGTCTGCTTCGCTCTACGCCGTTAAAGTTCTTGCAGCAGACGGAG

CAGGCCAATACTCATGGATTATCAACGGCATCGAATGGGCCATCGCGAAT

AACATGGATGTAATCAACATGAGCGTCGGAGCACCAAGCGGCAGTGCGGC

ACTTAAAGCAGCAGTTGATAAAGCTGTTGCATCTGGTGTCGTCGTAGTAG

CGGCAGCTGGGAATGAGGGAACATCCGGATCATCGAGTACCGTCGGTTAT

CCAGGCAAGTACCCTTCAGTGATTGCAGTGGGCGCTGTAGACTCTACAAA

TCAACGTGCCTCTTTTTCCTCCGTGGGACCGGAGCTGGATGTCATGGCCC

CTGGCGTTTCTATTCAATCGACGCTTCCAGGGAACAAGTATGGTGCGCAA

AACGGGACTTCCATGGCCTCGCCGCATGTAGCTGGGGCGGCCGCATTGAT

TCTTTCTAAGCACCCGAACTGGACAAACACCAAGTCCGCAGCAGTTTAG

AAAACACCACTACAAAACTTGGTGATTCTTTCTACTATGGAAAAGGGCTG

ATCAACGTACAGGCGGCAGCTCAGTAA
```

The amino acid sequence of GcM94 is provided below:

(SEQ ID NO: 18)
```
AQSVPYGVSQIKAPALHSQGYTGSNVKVAVIDSGIDSSHPDLKVAGGASM

VPSETNPFQDNNTHGTHVAGTVAALNNNIGVLGVAPSASLYAVKVLAADG

AGQYSWIINGIEWAIANNMDVINMSVGAPSGSAALKAAVDKAVASGVVVV

AAAGNEGTSGSSSTVGYPGKYPSVIAVGAVDSTNQRASFSSVGPELDVMA

PGVSIQSTLPGNKYGAQNGTSMASPHVAGAAALILSKHPNWTNNQVRSSL

ENTTTKLGDSFYYGKGLINVQAAAQ
```

The nucleotide sequence of synthesized gene GcM 95 is provided below:

(SEQ ID NO: 19)
```
GCGCAGTCCGTGCCTTACGGCGTATCACAAATTAAAGCCCCTGCTCTGCA

CTCTCAAGGCTACACTGGATCAAATGTTAAAGTAGCGGTTATCGACAGCG

GTATCGACTCGAGCCATCTGGATCTTAAAGTCGCTGGAGGGGCTTCTATG

GTGCCGGGAGAAACAAACCCGTTTGTCGATGCACAAACACATGGCACACA

CGTCGCAGGAACGGTTGCGGCGTTAAACAATAATATTGGCGTGCTTGGTG

TAGCCCCGGAAGCTTCGCTCTACGCCGTTAAAGTTCTTGCAGCAGACAAC

GCAGCACAATACTCATGGATTGTCAACGGCATCGAATGGGCCATCGCGAA

TAACATGGATGTAATCAACATGAGCCTGGGAGCACCAAGCGGCAGTGCGG

CACTTAAAGCAGCAGTTGATAAAGCTGTTGCATCTGGTGTCGTCGTAGTA

GCGGCAGCTGGGAATGAGGGAACATCCGGATCATCGAGTACCGTCGGTTA

TCCAGGCAAGTACCCTTCAGTGATTGCAGTGGGCGCTGTAGACTCTTCAA

ATCAACGTGCCTCTTTTTCCTCCGTGGGACCGGAGCTGGATGTCATGGCC

CCTGGCGTTTCTATTCAATCGACGCTTCCAGGGAACAAGTATGGTGCGCA

AAACGGGACTTCCATGGCCTCGCCGCATGTAGCTGGGGCGGCCGCATTGA

TTCTTTCTAAGCACCCGAACTGGACAAACACTCAAGTCCGCAGCAGTTTA

GAAAACACCACTACAAAACTTGGTGATTCTTTCTACTATGGAAAAGGGCT

GATCAACGTACAGGCGGCAGCTCAGTAA
```

The amino acid sequence of GcM 95 is provided below:

(SEQ ID NO: 20)
```
AQSVPYGVSQIKAPALHSQGYTGSNVKVAVIDSGIDSSHLDLKVAGGASM

VPGETNPFVDAQTHGTHVAGTVAALNNNIGVLGVAPEASLYAVKVLAADN

AAQYSWIVNGIEWAIANNMDVINMSLGAPSGSAALKAAVDKAVASGVVVV

AAAGNEGTSGSSSTVGYPGKYPSVIAVGAVDSSNQRASFSSVGPELDVMA

PGVSIQSTLPGNKYGAQNGTSMASPHVAGAAALILSKHPNWTNTQVRSSL

ENTTTKLGDSFYYGKGLINVQAAAQ
```

The nucleotide sequence of synthesized gene GcM96 is provided below:

(SEQ ID NO: 21)
```
GCGCAGTCCGTGCCTTACGGCGTATCACAAATTAAAGCCCCTGCTCTGCA

CTCTCAAGGCTACACTGGATCAAATGTTAAAGTAGCGGTTATCGACAGCG

GTATCGACTCGAGCCATCCAGATCTTAAAGTCGCTGGAGGGGCTTCTATG

GTGCCGTCCGAAACAAACCCGTTTCAAGATAACAATTCTCATGGCACACA

CGTCGCAGGAACGGTTGCGGCGTTAAACAATAATATTGGCGTGCTTGGTG

TAGCCCCGTCTGCTTCGCTCTACGCCGTTAAAGTTCTTGCAGCAGACGGA

TCAGGCCAATACTCATGGATTATCAACGGCATCGAATGGGCCATCGCGAA
```

```
TAACATGGATGTAATCAACATGAGCCTGGGAGCAACAAGCGGCAGTGCGG

CACTTAAAGCAGCAGTTGATAAAGCTGTTGCATCTGGTCAAGTCGTAGTA

GCGGCAGCTGGGAATGAGGGAACAGATGGACCTTCGAGTACCGTCGGTTA

TCCAGGCAAGTACCCTTCAGTGATTGCAGTGGGCGCTGTAGACTCTACAA

ATACACGTGCCTCTTTTTCCTCCGTGGGACCGGAGCTGGATGTCATGGCC

CCTGGCGTTTCTATTCAATCGACGCTTCCAGCAAACAAGTATGGTGCGCA

AAACGGGACTTCCATGGCCGCACCGCATGTAGCTGGGGCGGCCGCATTGA

TTCTTTCTAAGCACCCGTCATGGACAAACAACCAAGTCCGCAGCAGTTTA

GAACAAACCACTACAAAACTTGGTGATTCTTTCTACTATGGAAAAGGGCT

GATCAACGTACAGGCGGCAGCTCAGTAA
```

The amino acid sequence of GcM96 is provided below:

```
                                                    (SEQ ID NO: 22)
AQSVPYGVSQIKAPALHSQGYTGSNVKVAVIDSGIDSSHPDLKVAGGASM

VPSETNPFQDNNSHGTHVAGTVAALNNNIGVLGVAPSASLYAVKVLAADG

SGQYSWIINGIEWAIANNMDVINMSLGATSGSAALKAAVDKAVASGQVVV

AAAGNEGTDGPSSTVGYPGKYPSVIAVGAVDSTNTRASFSSVGPELDVMA

PGVSIQSTLPANKYGAQNGTSMAAPHVAGAAALILSKHPSWTNNQVRSSL

EQTTTKLGDSFYYGKGLINVQAAAQ
```

The nucleotide sequence of synthesized gene GcM100 is provided below:

```
                                                    (SEQ ID NO: 23)
GCGCAGTCCGTGCCTTACGGCGTATCACAAATTAAAGCCCCTGCTCTGCA

CTCTCAAGGCTACACTGGATCAAATGTTAAAGTAGCGGTTATCGACAGCG

GTATCGACTCGAGCCATCCAGATCTTAAAGTCGCTGGAGGGGCTTCTATG

GTGCCGTCCGAAACAAACCCGTTTCAAGATAACAATTCTCATGGCACACA

CGCAGCAGGAACGGTTGCGGCGTTAAACAATAATATTGGCGTGCTTGGTG

TAGCCCCGTCTGCTTCGCTCTACGCCGTTAAAGTTCTTGCAGCAGACGGA

TCAGCACAATACTCATGGATTATCAACGGCATCGAATGGGCCATCGCGAA

TAACATGGATGTAATCAACATGGCACTGGGAGCACCAAGCGGCAGTGCGG

CACTTAAAGCAGCAGTTGATAAAGCTGTTGCATCTGGTGTCGTCGTAGTA

GCGGCAGCTGGGAATGAGGGAACATCCGGATCATCGAGTACCGTCGGTTA

TCCAGGCAAGTACCCTTCAGTGATTGCAGTGGGCGCTGTAGACTCTTCAA

ATCAACGTGCCTCTTTTTCCTCCGTGGGACCGGAGCTGGATGTCATGGCC

CCTGGCGTTTCTATTCAATCGACGCTTCCAGCAAACAAGTATGGTGCGCA

AAACGGGACTTCCATGGCCTCGCCGCATGTAGCTGGGGCGGCCGCATTGA

TTCTTTCTAAGCACCCGAACTGGACAAACACTCAAGTCCGCAGCAGTTTA

GAAAACACCACTACAAAACTTGGTGATTCTTTCTACTATGGAAAAGGGCT

GATCAACGTACAGGCGGCAGCTCAGTAA
```

The amino acid sequence of GcM100 is provided below:

```
                                                    (SEQ ID NO: 24)
AQSVPYGVSQIKAPALHSQGYTGSNVKVAVIDSGIDSSHPDLKVAGGASM

VPSETNPFQDNNSHGTHAAGTVAALNNNIGVLGVAPSASLYAVKVLAADG

SAQYSWIINGIEWAIANNMDVINMALGAPSGSAALKAAVDKAVASGVVVV

AAAGNEGTSGSSSTVGYPGKYPSVIAVGAVDSSNQRASFSSVGPELDVMA

PGVSIQSTLPANKYGAQNGTSMASPHVAGAAALILSKHPNWTNTQVRSSL

ENTTTKLGDSFYYGKGLINVQAAAQ
``` b) Construction of Combinatorial Libraries CG1-CG5 and CG8 Using the Synthetic Genes GcM90-94 and GcM100

TABLE 3-1

List of Possible Substitutions Introduced and Primers Used for the Construction of Combinatorial Libraries CG1-CG5 and CG8

| Synthesized Genes (template or parent) | Library Name | Substitutions Introduced | Primer Name | Primer Sequence |
|---|---|---|---|---|
| GcM90 | CG1 | G53S | 1 S53 f | /5Phos/CTTCTATGGTGCCG<u>TCC</u>GAAACA AACCCGTTTCAAG (SEQ ID NO: 25) |
| | | A68V | 1 V68 f | /5Phos/TCATGGCACACAC<u>GTC</u>GCAGGAA CGGTTGCGGCG (SEQ ID NO: 26) |
| | | A102G | 1 G102 f | /5Phos/AGCAGACGGATCA<u>GGC</u>CAATACT CATGGATTATCAAC (SEQ ID NO: 27) |
| | | T129P | 1 P129 f | /5Phos/TGAGCCTGGGAGCA<u>CC</u>AAGCGGC AGTGCGGCACTTAAAG (SEQ ID NO: 28) |
| | | T185Q | 1 Q185 f | /5Phos/TAGACTCTTCAAATCAA<u>C</u>GTGCC TCTTTTTCCTCCGTG (SEQ ID NO: 29) |
| GcM91 | CG2 | V59Q | 2 Q59 f | /5Phos/GAAACAAACCCGTTT<u>C</u>AAGATAA CAATTCTCATG (SEQ ID NO: 30) |
| | | V108I | 2 I108 f | /5Phos/ATACTCATGGATT<u>ATC</u>AACGGCA TCGAATGGGCCATC (SEQ ID NO: 31) |
| | | Q147V | 2 V147 f | /5Phos/TGTTGCATCTGGT<u>GTC</u>GTCGTAGT AGCGGCAGCTGG (SEQ ID NO: 32) |
| | | A211G | 2 G211 f | /5Phos/ATCGACGCTTCCA<u>GGG</u>AACAAGT ATGGTGCGCAAAAC (SEQ ID NO: 33) |
| | | Q252N | 2 N252 f | /5Phos/CAGCAGTTTAGAA<u>AAC</u>ACCACTA CAAAACTTGGTG (SEQ ID NO: 34) |

TABLE 3-1-continued

List of Possible Substitutions Introduced and Primers Used for the Construction of Combinatorial Libraries CG1-CG5 and CG8

| Synthesized Genes (template or parent) | Library Name | Substitutions Introduced | Primer Name | Primer Sequence |
|---|---|---|---|---|
| GcM92 | CG3 | A61N | 3 N61 f | /5Phos/CAAACCCGTTTCAAGAT<u>AAC</u>AAT TCTCATGGCACACAC (SEQ ID NO: 35) |
| | | E87S | 3 S87 f | /5Phos/TTGGTGTAGCCCCG<u>TCT</u>GCTTCGC TCTACGCCGTTAAAG (SEQ ID NO: 36) |
| | | I124M | 3 M124 f | /5Phos/TGGATGTAATCAAC<u>ATG</u>AGCCTG GGAGCACCAAGCG (SEQ ID NO: 37) |
| | | P161S | 3 S161 f | /5Phos/AGGGAACATCCGGATCA<u>TC</u>GAGT ACCGTCGGTTATCCAG (SEQ ID NO: 38) |
| | | A224S | 3 S224 f | /5Phos/GACTTCCATGGCC<u>TCG</u>CCGCATG TAGCTGGGCGGC (SEQ ID NO: 39) |
| GcM93 | CG4 | Q62N | 4 N62 f | /5Phos/GTTTCAAGATAAC<u>AAT</u>TCTCATG GCACACACGTCGC (SEQ ID NO: 40) |
| | | N100G | 4 G100 f | /5Phos/GTTCTTGCAGCAGAC<u>GGA</u>TCAGG CCAATACTCATG (SEQ ID NO: 41) |
| | | A125S | 4 S125 f | /5Phos/ATGTAATCAACATG<u>AGC</u>CTGGGA GCACCAAGCGGCAG (SEQ ID NO: 42) |
| | | D159S | 4 S159 f | /5Phos/GGAATGAGGGAACAT<u>CC</u>GGATCA TCGAGTACCGTCGG (SEQ ID NO: 43) |
| | | S240N | 4 N240 f | /5Phos/CTTTCTAAGCACCCG<u>AAC</u>TGGAC AAACACTCAAGTCCG (SEQ ID NO: 44) |
| GcM94 | CG5 | T63S | 5 S63 f | /5Phos/TCAAGATAACAAT<u>TCT</u>CATGGCA CACACGTCGCAGG (SEQ ID NO: 45) |
| | | A101S | 5 S101 f | /5Phos/TGCAGCAGACGGA<u>TC</u>AGGCCAAT ACTCATGGATTATC (SEQ ID NO: 46) |
| | | V126L | 5 L126 f | /5Phos/AATCAACATGAGC<u>CTG</u>GGAGCAC CAAGCGGCAGTG (SEQ ID NO: 47) |
| | | T183S | 5 S183 f | /5Phos/CGCTGTAGACTCT<u>TC</u>AAATCAAC GTGCCTCTTTTTCC (SEQ ID NO: 48) |
| | | N244T | 5 T244 f | /5Phos/GAACTGGACAAAC<u>ACT</u>CAAGTCC GCAGCAGTTTAG (SEQ ID NO: 49) |
| GcM100 | CG8 | A68V | 1 V68 f | /5Phos/TCATGGCACACAC<u>GTC</u>GCAGGAA CGGTTGCGGCG (SEQ ID NO: 50) |
| | | A102G | 1 G102 f | /5Phos/AGCAGACGGATCA<u>GGC</u>CAATACT CATGGATTATCAAC (SEQ ID NO: 51) |
| | | A211G | 2 G211 f | /5Phos/ATCGACGCTTCC<u>AGGG</u>AACAAGT ATGGTGCGCAAAAC (SEQ ID NO: 52) |
| | | A125S | 4 S125 f | /5Phos/ATGTAATCAACATG<u>AGC</u>CTGGGA GCACCAAGCGGCAG (SEQ ID NO: 53) |

Each synthesized gene was built into the pHPLT-BPN'-S78N-G97A-G128A-Y217Q parent molecule. Resulting plasmids containing the six synthesized genes GcM90-94, and GcM100 served as templates to make combinatorial libraries at the respective positions (Table 3-1). Two additional genes, GcM95 and GcM96, were also synthesized for analysis, but did not serve as parental DNA for libraries. These genes each have nine mutations on top of the pHPLT-BPN'-S78N-G97A-G128A-Y217Q parent molecule.

The parent plasmids (template DNA) containing the synthetic genes GcM90-94, and GcM100 were methylated were methylated using two micrograms of DNA and methylase (NEB), according to the NEB protocol. Methylated DNA was then purified using DNA Clean and Concentrator kit (Zymo Research). Combinatorial libraries CG1-5 and CG8 were made using a QUIKCHANGE® Multi Site-Directed Mutagenesis kit ("QCMS kit"; Stratagene) following the manufacturer's protocol (see Table 3-1 for respective template and primer combinations), with the exception of libraries CG3 and CG4, which used 86.5 ng of each primer in place of the 50 ng suggested in the protocol. All primers used for introducing the desired substitutions in each library are listed in Table 3-1. They were synthesized and provided by Integrated DNA Technologies. After the QCMS reactions were completed for each library, the template DNA was digested by the addition of 0.5-1 μl DpnI (from the QCMS kit) and incubated at 37° C. for 1-4 hours, followed by another addition of 0.5-1 μl DpnI and another incubation at 37° C. for 1-4 hours. For efficient transformation of *B. subtilis*, DNA from the QCMS reaction mixtures were amplified before transformation and transformants grown as described in Example 2.

Additional variants of BPN'-v3+S78N were produced by DNA2.0. The following substitutions were introduced individually into the BPN'-v3+S78N parent molecule: Q59G, N62Q, V68A, S89Y, A92G, I108V, I115V, M124T, P129L, A138T, V147L, S161P, Y167A, P172V, G211T, L267V, and A273S.

All of the combinatorial library variants described above and the variants synthesized at DNA2.0 were tested for cleaning performance using a BMI microswatch assay in Detergent Composition 1 at 16° C. and pH 8 and BMI microswatch assay in Detergent Composition 2 at 16° C. and pH 8. Protein content was determined using the TCA assay. Assays were performed as described in Example 1 and Performance Indices were calculated relative to BPN'-v3 (with a PI value of 1.0).

The following BPN' variants were determined to have a PI value greater than 1.0, at least 1.1, at least 1.2, at least 1.3, at least 1.4, at least 1.5, at least 1.6, at least 1.7, at least 1.8, at least 1.9, at least 2, from greater than 1.0 to about 10, from greater than 1.0 to about 8, or from greater than 1.0 to about 5 relative to BPN'-v3 in a BMI microswatch cleaning assay in Detergent Composition 1 at pH 8 and 16° C.: BPN' amino acid sequence (SEQ ID NO:2) comprising at least one set of amino acid substitutions selected from the group consisting of S063T-S078N-G097A-S101A-G128A-S183T-Y217Q-T244N, N061A-S078N-G097A-G128A-Y217Q-S224A, S053G-S078N-G097A-G128A-P129T-Q185T-Y217Q, S063T-S078N-G097A-S101A-G128A-S183T-Y217Q, S063T-S078N-G097A-S101A-G128A-Y217Q, S063T-S078N-G097A-S101A-G128A-Y217Q-T244I, and S078N-G097A-G128A-P129T-Y217Q, wherein amino acid positions of the variant are numbered by correspondence with the sequence of SEQ ID NO:2. Such variants have enhanced proteolytic activity compared to BPN' (SEQ ID NO:2) and a greater PI value than that of BPN' and BPN'-v3 in this assay. The invention includes a protease variant having enhanced proteolytic activity compared to BPN' (SEQ ID NO:2) and/or a PI value of greater than 1 to about 5 relative to BPN'-v3 in this BMI microswatch cleaning assay, the variant comprising an amino acid sequence having at least 60%, 70%, 80%, 85%, 90%, 91%, 92%, 93%, 94%, 95%, 96%, 97%, or 98% identity to the sequence of SEQ ID NO:2 and comprising at least one set of amino acid substitutions selected from said group above, wherein amino acid positions of the variant are numbered by correspondence with amino acid positions of the SEQ ID NO:2 sequence. Also included are compositions, including, but not limited to, e.g., cleaning compositions, comprising at least one such variant and methods for cleaning utilizing at least one such variant as described in greater detail elsewhere herein.

Also provided is a subtilisin protease variant having enhanced proteolytic activity compared to BPN' and/or a PI value of greater than 1.0 to about 5 relative to BPN'-v3 in this BMI microswatch cleaning assay, the variant comprising an amino acid sequence having at least 85%, 90%, 91%, 92%, 93%, 94%, 95%, 96%, 97%, 98%, or 99% identity to SEQ ID NO:2, wherein the variant comprises at least one substitution selected from the group of X040E, X053G, X059V, X061A, X062H/Q, X068A, X078N, X087E, X101A, X102A, X108V, X124I, X125A, X126V, X129T, X147Q, X159D, X183T, X185T, X211A, X224A, X244I/N, X252Q, and X274D, and optionally at least one substitution selected from the group of X040E, X053G, X059V, X061A, X062H/Q, X068A, X078N, X087E, X101A, X102A, X108V, M124I, S125A, L126V, P129T, V147Q, S159D, S183T, Q185T, G211A, S224A, T244I/N, N252Q, and A274D, wherein amino acid positions of the variant are numbered by correspondence with positions of the sequence of SEQ ID NO:2. Also included are compositions, including, but not limited to, e.g., cleaning compositions, comprising at least one such variant and methods for cleaning utilizing at least one such variant as described in greater detail elsewhere herein.

The following BPN' variants were determined to have a PI value of about 1.0 relative to BPN'-v3 in a BMI microswatch cleaning assay in Detergent Composition 1 at pH 8 and 16° C.: BPN' amino acid sequence (SEQ ID NO:2) comprising at least one set of amino acid substitutions selected from the group consisting of G097A-G128A-Y217Q, N061A-S078N-S087E-G097A-G128A-Y217Q-S224A, Q059V-S078N-G097A-G128A-G211A-Y217Q, Q059V-S078N-G097A-G128A-V147Q-Y217Q, Q059V-S078N-G097A-G128A-Y217Q, Q059V-S078N-G097A-I108V-G128A-Y217Q-N252Q, S053G-S078N-G097A-G128A-P129T-Y217Q, S078N-G097A-G128A-G211A-Y217Q, S078N-G097A-G128A-Q185T-Y217Q, S078N-G097A-G128A-V147Q-Y217Q, S078N-G097A-G128A-Y217Q, S078N-G097A-G128A-Y217Q-S224A, and S078N-G097A-G128A-Y217Q-S224A-A274D, wherein amino acid positions of the variant are numbered by correspondence with the sequence of SEQ ID NO:2. Such variants have enhanced proteolytic activity compared to BPN' (SEQ ID NO:2) and a greater PI value than that of BPN' in this assay. The invention includes a protease variant having enhanced proteolytic activity compared to BPN' (SEQ ID NO:2) and/or a PI value of about 1.0 relative to BPN'-v3 in this BMI microswatch cleaning assay, the variant comprising an amino acid sequence having at least 60%, 70%, 80%, 85%, 90%, 91%, 92%, 93%, 94%, 95%, 96%, 97%, or 98% identity to the sequence of SEQ ID NO:2 and comprising at least one set of amino acid substitutions selected from said group above, wherein amino acid positions of the variant are numbered by correspondence with amino acid positions of the SEQ ID NO:2 sequence. Also included are compositions, including, but not limited to, e.g., cleaning compositions, comprising at least one such variant and methods for cleaning utilizing at least one such variant as described in greater detail elsewhere herein.

The following BPN' variant was determined to have a PI value of about 0.9 relative to BPN'-v3 in a BMI microswatch cleaning assay in Detergent Composition 1 at pH 8 and 16° C.: BPN' amino acid sequence (SEQ ID NO:2) comprising the set of amino acid substitutions S078N-G097A-I108V-G128A-V147Q-Y217Q, wherein positions of the variant are numbered by correspondence with the sequence of SEQ ID NO:2. Such variants have proteolytic activity. The invention includes a protease variant having proteolytic activity, a PI value of about 0.9 relative to BPN'-v3, and/or enhanced proteolytic activity compared to BPN' in this assay, the variant comprising an amino acid sequence having at least 60%, 70%, 80%, 85%, 90%, 91%, 92%, 93%, 94%, 95%, 96%, 97%, or 98% identity to the sequence of SEQ ID NO:2 and comprising said set of amino acid substitutions above, wherein amino acid positions of the variant are numbered by correspondence with positions of the SEQ ID NO:2 sequence. Also included are compositions, including, but not limited to, e.g., cleaning compositions, comprising at least one such variant and methods for cleaning utilizing at least one such variant as described in greater detail elsewhere herein.

The following BPN' variants were determined to a PI value equal to or greater than 0.5 and less than 0.9 relative to BPN'-v3 in a BMI microswatch cleaning assay in Detergent Composition 1 at pH 8 and 16° C.: BPN' amino acid sequence (SEQ ID NO:2) comprising at least one set of amino acid substitutions selected from the group consisting of Q059V-S078N-G097A-I108V-G128A-V147Q-G211A-Y217Q-N252Q, S078N-G097A-I108V-G128A-V147Q-G211A-Y217Q, S078N-G097A-I108V-G128A-V147Q-G211A-Y217Q-N252Q, S078N-G097A-I108V-G128A-V147Q-Y217Q-N252Q, and S078N-S087E-G097A-M124I-G128A-Y217Q-S224A, wherein amino acid positions of the variant are numbered by correspondence with positions of the SEQ ID NO:2 sequence. Such variants have proteolytic activity. The invention includes a protease variant having proteolytic activity, the variant comprising an amino acid sequence having at least 60%, 70%, 80%, 85%, 90%, 91%, 92%, 93%, 94%, 95%, 96%, 97%, or 98% identity to the sequence of SEQ ID NO:2 and at least one set of amino acid substitutions selected from said group above, wherein positions of the variant are numbered by correspondence with positions of the SEQ ID NO:2 sequence. Also included are compositions, including, but not limited to, e.g., cleaning compositions, comprising at least one such variant and methods for cleaning utilizing at least one such variant as described in greater detail elsewhere herein.

The following BPN' variants were determined to have a PI value greater than 1.0, at least 1.1, at least 1.2, at least 1.3, at least 1.4, at least 1.5, at least 1.6, at least 1.7, at least 1.8, at least 1.9, at least 2, from greater than 1.0 to about 10, from greater than 1.0 to about 8, or from greater than 1.0 to about 5 relative to BPN'-v3 in a BMI microswatch cleaning assay in Detergent Composition 2 at pH 8 and 16° C.: BPN' amino acid sequence (SEQ ID NO:2) comprising at least one set of amino acid substitutions selected from the group consisting of S063T-S078N-G097A-S101A-G128A-S183T-Y217Q, S063T-S078N-G097A-S101A-G128A-S183T-Y217Q-T244N, S063T-S078N-G097A-S101A-G128A-Y217Q, and S063T-S078N-G097A-S101A-G128A-Y217Q-T244I, wherein amino acid positions of the variant are numbered by correspondence with the sequence of SEQ ID NO:2. Such variants have enhanced proteolytic activity compared to BPN' (SEQ ID NO:2) and a greater PI value than that of BPN' in this assay. The invention includes a protease variant having enhanced proteolytic activity compared to BPN' (SEQ ID NO:2) and/or a PI value of greater than about 1.0 to about 5 relative to BPN'-v3 in this BMI microswatch cleaning assay, the variant comprising an amino acid sequence having at least 60%, 70%, 80%, 85%, 90%, 91%, 92%, 93%, 94%, 95%, 96%, 97%, or 98% identity to the sequence of SEQ ID NO:2 and comprising at least one set of amino acid substitutions selected from said group above, wherein amino acid positions of the variant are numbered by correspondence with amino acid positions of the SEQ ID NO:2 sequence. Also included are compositions, including, but not limited to, e.g., cleaning compositions, comprising at least one such variant and methods for cleaning utilizing at least one such variant as described in greater detail elsewhere herein.

The following BPN' variants were determined to have a PI value of about 1.0 relative to BPN'-v3 in a BMI microswatch cleaning assay in Detergent Composition 2 at pH 8 and 16° C.: BPN' amino acid sequence (SEQ ID NO:2) comprising at least one set of amino acid substitutions selected from the group consisting of G097A-G128A-Y217Q, N061A-S078N-G097A-G128A-Y217Q-S224A, N061A-S078N-S087E-G097A-G128A-Y217Q-S224A, Q059V-S078N-G097A-G128A-G211A-Y217Q, Q059V-S078N-G097A-G128A-V147Q-Y217Q, Q059V-S078N-G097A-G128A-Y217Q, Q059V-S078N-G097A-I108V-G128A-Y217Q-N252Q, S053G-S078N-G097A-G128A-P129T-Q185T-Y217Q, S053G-S078N-G097A-G128A-P129T-Y217Q, S078N-G097A-G128A-G211A-Y217Q, S078N-G097A-G128A-P129T-Y217Q, S078N-G097A-G128A-Q185T-Y217Q, S078N-G097A-G128A-Y217Q, S078N-G097A-G128A-Y217Q-S224A, and S078N-G097A-G128A-Y217Q-S224A-A274D, wherein amino acid positions of the variant are numbered by correspondence with the sequence of SEQ ID NO:2. Such variants have enhanced proteolytic activity compared to BPN' (SEQ ID NO:2) and a greater PI value than that of BPN' in this assay. The invention includes a protease variant having enhanced proteolytic activity compared to BPN' (SEQ ID NO:2) and/or a PI value of about 1 relative to BPN'-v3 in this BMI microswatch cleaning assay, the variant comprising an amino acid sequence having at least 60%, 70%, 80%, 85%, 90%, 91%, 92%, 93%, 94%, 95%, 96%, 97%, or 98% identity to the sequence of SEQ ID NO:2 and comprising at least one set of amino acid substitutions selected from said group above, wherein amino acid positions of the variant are numbered by correspondence with amino acid positions of the SEQ ID NO:2 sequence. Also included are compositions, including, but not limited to, e.g., cleaning compositions, comprising at least one such variant and methods for cleaning utilizing at least one such variant as described in greater detail elsewhere herein.

The following BPN' variants were determined to have a PI value of about 0.9 relative to BPN'-v3 in a BMI microswatch cleaning assay in Detergent Composition 2 at pH 8 and 16° C.: BPN' amino acid sequence (SEQ ID NO:2) comprising at least one set of amino acid substitutions selected from the group consisting of S078N-G097A-G128A-V147Q-Y217Q and S078N-G097A-I108V-G128A-V147Q-Y217Q, wherein positions of the variant are numbered by correspondence with the sequence of SEQ ID NO:2. Such variants have proteolytic activity. The invention includes a protease variant having proteolytic activity, a PI value of about 0.9 relative to BPN'-v3, and/or an enhanced proteolytic activity compared to BPN' in this assay, the variant comprising an amino acid sequence having at least 60%, 70%, 80%, 85%, 90%, 91%, 92%, 93%, 94%, 95%, 96%, 97%, or 98% identity to the sequence of SEQ ID NO:2 and at least one set of amino acid substitutions selected from said group above, wherein amino acid positions of the variant are numbered by correspondence with positions of the SEQ ID NO:2 sequence. Also included are compositions, including cleaning compositions, comprising at least one such variant and methods for cleaning an item or surface in need of cleaning utilizing at least one such variant as described in greater detail elsewhere herein.

The following BPN' variants were determined to a PI value equal to or greater than 0.5 and less than 0.9 relative to BPN'-v3 in a BMI microswatch cleaning assay in Detergent Composition 2 at pH 8 and 16° C.: BPN' amino acid sequence (SEQ ID NO:2) comprising at least one set of amino acid substitutions selected from the group consisting of Q059V-S078N-G097A-I108V-G128A-V147Q-G211A-Y217Q-N252Q, S078N-G097A-I108V-G128A-V147Q-G211A-Y217Q, S078N-G097A-I108V-G128A-V147Q-G211A-Y217Q-N252Q, S078N-G097A-I108V-G128A-V147Q-Y217Q-N252Q, and S078N-S087E-G097A-M124I-G128A-Y217Q-S224A, wherein amino acid positions of the variant are numbered by correspondence with positions of the SEQ ID NO:2 sequence. Such variants have proteolytic activity. The invention includes a protease variant having proteolytic activity, the variant comprising an amino acid sequence having at least 60%, 70%, 80%, 85%, 90%, 91%, 92%, 93%, 94%, 95%, 96%, 97%, or 98% identity to the sequence of SEQ ID NO:2 and at least one set of amino acid substitutions selected from said group above, wherein positions of the variant are numbered by correspondence with positions of the SEQ ID NO:2 sequence. Also included are compositions, including cleaning compositions, comprising at least one such variant and methods for cleaning an item or surface in need of cleaning utilizing at least one such variant as described in greater detail elsewhere herein.

Example 4

Generation and Cleaning Performance of BPN' Variants

Generation of BPN' Variants LC1-LC4 via QUIKCHANGE® Multi Site-Directed Mutagenesis BPN' variants were constructed from different parental plasmids using QUIKCHANGE® Multi Site-Directed Mutagenesis kits. The parental plasmids (Table 4-1) were methylated using a NEB Dam Methylase Kit in a reaction containing 77.5 μL H20+10 μL Buffer 10×+0.25 μL SAM+2 μL DAM methylase+10 μL miniprep DNA (~150 ng/μL) at 37° C. overnight. The methylated plasmid DNA was purified using a QIAGEN® PCR purification kit. QUIKCHANGE® Multi Site-Directed Mutagenesis reactions were set up for each of the DNA templates in a reaction mix containing 2.5 μL Buffer 5×+0.5 μL primer 1 (25 μM)+0.5 μL primer 2 (25 μM)+1 μL dNTP's+1 μL enzyme blend+18 μL H₂O+1.5 μL DNA. The PCR program used was: 95° C. for 1 min; (95° C. for 1 min, 53° C. for 1 min, 65° C. for 9:39 min)×29 cycles; 65° C. for 10 min, 4° C. hold. Primer sequences are shown in Table 4-2. In all reactions, PCR was performed using a MJ Research PTC-200 Peltier thermal cycler. Parental DNA from the PCR samples was removed by addition of 1 μL of DpnI to QUIKCHANGE® Multi Site-Directed Mutagenesis reactions at 37° C. overnight. To increase transformation frequency, the DpnI-digested reactions were amplified using rolling circle amplification (RCA) using the Illustra TempliPhi kit according to the manufacturer's protocol. *B. subtilis* cells (ΔaprE, ΔnprE, amyE::xylRPxylAcomK-phleo) were transformed with 1 μL each of the RCA reaction and the transformed cells were plated onto LA+1.6% skim milk plates containing 10 ppm neomycin and incubated at 37° C. overnight. Colonies from overnight growth were selected to perform colony PCR for sequencing using "puReTaq Ready-To-Go PCR Beads" (Amersham). The PCR and sequencing primers used were pHPLT F1 (/5PHOS/TACATATGAGT-TATGCAGTTTG (SEQ ID NO:54)) and pHPLT seq R1 (/5PHOS/TTATCCTTTACCTTGTCTC (SEQ ID NO:55)). Clones with appropriate sequences were frozen. BPN' variant proteins were produced by growing *B. subtilis* transformants in 96 well microtiter plates at 37° C. for 68 hours in a MOPS based medium containing urea as described in Example 2.

TABLE 4-1

Parental Plasmids and Primers Used for Generation of BPN' Variants LC1-LC4

| Parental Plasmid | Mutations Introduced | Primers Used |
|---|---|---|
| BPN'-G097A-G128A-Y217Q-S024G-N025G-N061P-S101N (termed LC1) | A128S | A128Sf, A128Sr |
| BPN'-G097A-G128A-Y217Q-S053G-N061P-S101N-V203Y (termed LC2) | A128S | A128Sf, A128Sr |
| BPN'-G097A-G128A-Y217Q-S024G-N025G-S053G-T055P-N061P-S101N-V203Y (termed LC3) | A128S | A128Sf, A128Sr |
| BPN'-G097A-G128A-Y217Q-S024G-N025G-S053G-T055P-N061P-S101N-V203Y (termed LC4) | P55T | P55Tf, P55Tr |

TABLE 4-2

Sequences of Primers Used for QUIKCHANGE ® Multi Site-Directed Mutagenesis Reactions to Make BPN' variants LC1-LC4

| Primer Name | Primer Sequence (5' to 3') |
|---|---|
| A128Sf | /5Phos/CAACATGAGCCTGGGATCACCAAGCGGCAGTGCGG (SEQ ID NO: 56) |
| A128Sr | /5Phos/CCGCACTGCCGCTTGGTGATCCCAGGCTCATGTTG (SEQ ID NO: 57) |
| P55Tf | /5Phos/CTATGGTGCCGGGCGAAACAAACCCGTTTCAAGATCCG (SEQ ID NO: 58) |
| P55Tr | /5Phos/CGGATCTTGAAACGGGTTTGTTTCGCCCGGCACCATAG (SEQ ID NO: 59) |

Generation of Additional BPN' Variants LC5-LC37

Figure 3:
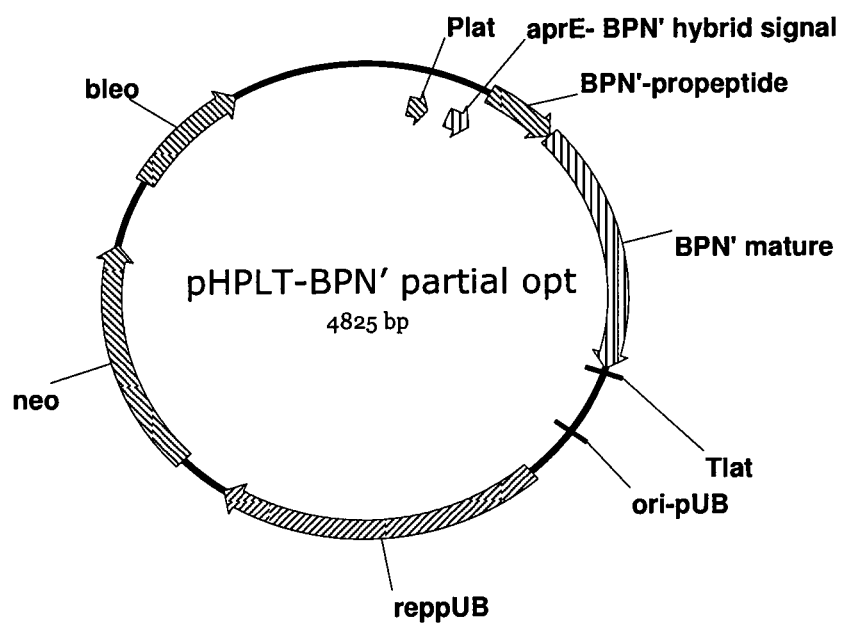
FIG. 3 provides a plasmid map of pHPLT-BPN' partial opt.

An additional 33 BPN' variants termed successively LC5 through LC37 were produced by DNA 2.0 using the BPN' nucleic acid as the parent gene contained in the expression plasmid pHPLT-BPN' partial opt (see FIG. 3). LC5 through LC37 BPN' variants are as follows, respectively: BPN'-P52L-V68A-G97A-I111V, BPN'-I111V-M124V-Y167A-Y217Q, BPN'-Y104N-G128A-Y217Q, BPN'-M124V-Y167A-Y217Q, BPN'I111V-M124V-Y217Q, BPN'-P52L-V68A-G97A, BPN'-G97A-I111V-M124V, BPN'-V68A-A92G-G97A, BPN'-G97A-I111V-M124V-Y167A-Y217Q, BPN'-P52L-V68A-I111V-Y217Q, BPN'-P52L-V68A-I111V, BPN'-V68A-A92G-I111V, BPN'-P52L-V68A-G97A-I111V-Y217Q, BPN'-V68A-G97A-I111V, BPN'-G97A-I111V-Y217Q, BPN'-G97A-I111V-M124V-Y167A, BPN'-S89Y-I111V-M124V, BPN'-V68A-S89Y-I111V, BPN'-V68A-A92G-Y217Q, BPN'-I111V-Y167A-Y217Q, BPN'-G97A-I111V-Y167A-Y217Q, BPN'-G97A-I111V-M124V-Y217Q, BPN'-V68A-I111V-Y167A-Y217Q, BPN'-I111V-G128A-Y217Q, BPN'-G97A-M124V-Y217Q, BPN'-V68A-Y167A-Y217Q, BPN'-I111V-M124V-Y167A, BPN'-N62Q-G97A-I111V, BPN'-G97A-M124V-Y167A-Y217Q, BPN'-G97A-L126A-Y217Q, BPN'-V68A-I111V-Y217Q, BPN'-S89Y-M124V-Y217Q, and BPN'-L96T-G97A-Y217Q. Plasmid pHPLT-BPN' partial opt was also created by DNA 2.0.

Transformants were picked into microtiter plates and grown as described in Example 2. The variants were assayed for cleaning performance using a BMI microswatch assay in Detergent Composition 2 at 16° C. and pH 8. Protein content was determined using the TCA assay. The assays were performed as described in Example 1 and the Performance Indices were calculated relative to BPN'-v3 (with a PI value of 1.0).

The following BPN' variants were determined to have a PI value greater than 1.0, at least 1.1, at least 1.2, at least 1.3, at least 1.4, at least 1.5, at least 1.6, at least 1.7, at least 1.8, at least 1.9, at least 2, from greater than 1.0 to about 10, from greater than 1.0 to about 8, or from greater than 1.0 to about 5 relative to BPN'-v3 in a BMI microswatch cleaning assay in Detergent Composition 2 at pH 8 and 16° C.: BPN' amino acid sequence (SEQ ID NO:2) comprising at least one set of amino acid substitutions selected from the group consisting of G097A-I111V-M124V-Y217Q, G097A-I111V-Y167A-Y217Q, S024G-N025G-N061P-G097A-S101N-G128S-Y217Q, S024G-N025G-S053G-N061P-G097A-S101N-G128A-V203Y-Y217Q, S024G-N025G-S053G-T055P-N061P-G097A-S101N-G128S-V203Y-Y217Q, and V068A-A092G-Y217Q, wherein amino acid positions of the variant are numbered by correspondence with the sequence of SEQ ID NO:2. Such variants have enhanced proteolytic activity compared to BPN' (SEQ ID NO:2) and a greater PI value than that of BPN' in this assay. The invention includes a protease variant having enhanced proteolytic activity compared to BPN' (SEQ ID NO:2) and/or a PI value of greater than 1.0 to about 5 relative to BPN'-v3 in this BMI microswatch cleaning assay, the variant comprising an amino acid sequence having at least 60%, 70%, 80%, 85%, 90%, 91%, 92%, 93%, 94%, 95%, 96%, 97%, or 98% identity to the sequence of SEQ ID NO:2 and comprising at least one set of amino acid substitutions selected from said group above, wherein amino acid positions of the variant are numbered by correspondence with amino acid positions of the SEQ ID NO:2 sequence. Also provided is a subtilisin protease variant having enhanced proteolytic activity compared to BPN' and/or a PI value of greater than 1.0 to about 5 compared to BPN'-v3 in this BMI microswatch cleaning assay, the variant comprising an amino acid sequence having at least 85%, 90%, 91%, 92%, 93%, 94%, 95%, 96%, 97%, 98%, or 99% identity to SEQ ID NO:2, wherein the variant comprises at least one substitution selected from the group of X024G, X025G, X052L, X053G, X055P, X061P, X062Q, X068A, X089Y, X092G, X096T, X097A, X101N, X104N, X111V, X124V, X126A, X128A/S, X167A, X203Y, and X217Q, and optionally at least one substitution selected from the group of S024G, N025G, P052L, S053G, T055P, N061P, N062Q, V068A, S089Y, A092G, L096T, G097A, S101N, Y104N, I111V, M124V, L126A, G128A/S, Y167A, V203Y, and Y217Q, and wherein amino acid positions of the variant are numbered by correspondence with positions of the sequence of SEQ ID NO:2. Also included are compositions, including, but not limited to, e.g., cleaning compositions, comprising at least one such variant and methods for cleaning utilizing at least one such variant as described in greater detail elsewhere herein.

The following BPN' variants were determined to have a PI value of about 1.0 relative to BPN'-v3 in a BMI microswatch cleaning assay in Detergent Composition 2 at pH 8 and 16° C.: BPN' amino acid sequence (SEQ ID NO:2) comprising at least one set of amino acid substitutions selected from the group consisting of G097A-G128A-Y217Q, G097A-G128S-Y217Q, G097A-I111V-Y217Q, I111V-G128A-Y217Q, I111V-M124V-Y167A, I111V-M124V-Y217Q, L096T-G097A-Y217Q, N062Q-G097A-I111V, S053G-N061P-G097A-S101N-G128S-V203Y-Y217Q, S089Y-M124V-Y217Q, and V068A-I111V-Y217Q, wherein amino acid positions of the variant are numbered by correspondence with the sequence of SEQ ID NO:2. The invention includes a protease variant having enhanced proteolytic activity compared to BPN' (SEQ ID NO:2) and/or a PI value of about 1.0 relative to BPN'-v3 in this BMI microswatch cleaning assay, the variant comprising an amino acid sequence having at least 60%, 70%, 80%, 85%, 90%, 91%, 92%, 93%, 94%, 95%, 96%, 97%, or 98% identity to the sequence of SEQ ID NO:2 and comprising at least one set of amino acid substitutions selected from said group above, wherein amino acid positions of the variant are numbered by correspondence with amino acid positions of the SEQ ID NO:2 sequence. Such variants have enhanced proteolytic activity compared to BPN' (SEQ ID NO:2), a greater PI value than that of BPN', and a PI value of about 1.0 compared to BPN'-v3 in this assay. Also included are compositions, including, but not limited to, e.g., cleaning compositions, comprising at least one such variant and methods for cleaning utilizing at least one such variant as described in greater detail elsewhere herein.

The following BPN' variants were determined to have a PI value of about 0.9 relative to BPN'-v3 in a BMI microswatch cleaning assay in Detergent Composition 2 at pH 8 and 16° C.: BPN' amino acid sequence (SEQ ID NO:2) comprising at least one set of amino acid substitutions selected from the group consisting of G097A-I111V-M124V, G097A-L126A-Y217Q, G097A-M124V-Y217Q, I111V-Y167A-Y217Q, M124V-Y167A-Y217Q, P052L-V068A-G097A, S089Y-I111V-M124V, V068A-A092G-G097A, V068A-A092G-I111V, V068A-G097A-I111V, V068A-S089Y-I111V, and Y104N-G128A-Y217Q, wherein positions of the variant are numbered by correspondence with the sequence of SEQ ID NO:2. Such variants have proteolytic activity. The invention includes a protease variant having proteolytic activity, a PI value of about 0.9 relative to BPN'-v3, and/or an enhanced proteolytic activity compared to BPN' in this assay, the variant comprising an amino acid sequence having at least 60%, 70%, 80%, 85%, 90%, 91%, 92%, 93%, 94%, 95%, 96%, 97%, or 98% identity to the sequence of SEQ ID NO:2 and at least one set of amino acid substitutions selected from said group above, wherein amino acid positions of the variant are numbered by correspondence with positions of the SEQ ID NO:2 sequence. Also included are compositions, including, but not limited to, e.g., cleaning compositions, comprising at least one such variant and methods for cleaning utilizing at least one such variant as described in greater detail elsewhere herein.

The following BPN' variants were determined to a PI value equal to or greater than 0.5 and less than 0.9 relative to BPN'-v3 in a BMI microswatch cleaning assay in Detergent Composition 2 at pH 8 and 16° C.: BPN' amino acid sequence (SEQ ID NO:2) comprising at least one set of amino acid substitutions selected from the group consisting of G097A-M124V-Y167A-Y217Q, V068A-Y167A-Y217Q, G097A-I111V-M124V-Y167A, I111V-M124V-Y167A-Y217Q, V068A-I111V-Y167A-Y217Q, G097A-I111V-M124V-Y167A-Y217Q, and P052L-V068A-I111V, wherein positions of the variant are numbered by correspondence with the sequence of SEQ ID NO:2. Such variants have proteolytic activity. The invention includes a protease variant having proteolytic activity, the variant comprising an amino acid sequence having at least 60%, 70%, 80%, 85%, 90%, 91%, 92%, 93%, 94%, 95%, 96%, 97%, or 98% identity to the sequence of SEQ ID NO:2 and at least one set of amino acid substitutions selected from said group above, wherein positions of the variant are numbered by correspondence with positions of the SEQ ID NO:2 sequence. Such variants have proteolytic activity. Also included are compositions, including, but not limited to, e.g., cleaning compositions, comprising at least one such variant and methods for cleaning utilizing at least one such variant as described in greater detail elsewhere herein.

Example 5

Cleaning Performance of BPN' Variants

Variants based on parent BPN' were made by DNA 2.0. The variants were grown as described in Example 2 and tested for cleaning performance on BMI microswatch assay in Detergent Composition 1 at 16° C. and pH 8, BMI microswatch assay in Detergent Composition 4 at 16° C. and pH 8, and egg microswatch assay in Detergent Composition 4 at 16° C. and pH 8. The protein content was determined using the TCA assay. The assays were performed as described in Example 1 and the Performance Indices were calculated relative to BPN'-v3 (with a PI value of 1.0).

The following BPN' variants were determined to have a PI value greater than 1.0, at least 1.1, at least 1.2, at least 1.3, at least 1.4, at least 1.5, at least 1.6, at least 1.7, at least 1.8, at least 1.9, at least 2, from greater than 1.0 to about 10, from greater than 1.0 to about 8, or from greater than 1.0 to about 5 relative to BPN'-v3 in a BMI microswatch cleaning assay in Detergent Composition 4 at pH 8 and 16° C.: BPN' amino acid sequence (SEQ ID NO:2) comprising at least one set of amino acid substitutions selected from the group consisting of N061P-G097A-S101N-G128A-P210S-Y217Q, S024G-N025G-S053G-N061P-G097A-S101N-G128A-P210S-Y217Q, S024G-N025G-S053G-N061P-G097A-S101N-G128S-Y217Q, and S024G-N025G-S053G-N061P-S078N-G097A-S101N-I111V-G128S-Y217Q, wherein amino acid positions of the variant are numbered by correspondence with the sequence of SEQ ID NO:2. Such variants have enhanced proteolytic activity compared to BPN' (SEQ ID NO:2) and a greater PI value than that of BPN' in this assay. The invention includes a protease variant having enhanced proteolytic activity compared to BPN' (SEQ ID NO:2) and/or a PI value of greater than 1.0 to about 5 relative to BPN'-v3 in this BMI microswatch cleaning assay, the variant comprising an amino acid sequence having at least 60%, 70%, 80%, 85%, 90%, 91%, 92%, 93%, 94%, 95%, 96%, 97%, or 98% identity to the sequence of SEQ ID NO:2 and comprising at least one set of amino acid substitutions selected from said group above, wherein amino acid positions of the variant are numbered by correspondence with amino acid positions of the SEQ ID NO:2 sequence. Also included are compositions, including, but not limited to, e.g., cleaning compositions, comprising at least one such variant and methods for cleaning utilizing at least one such variant as described in greater detail elsewhere herein.

The following BPN' variants were determined to have a PI value of about 1.0 relative to BPN'-v3 in a BMI microswatch cleaning assay in Detergent Composition 4 at pH 8 and 16° C.: BPN' amino acid sequence (SEQ ID NO:2) comprising at least one set of amino acid substitutions selected from the group consisting of G097A-G128A-Y217Q, G097A-G128A-P210S-Y217Q, G097A-G128S-P210S-Y217Q, G097A-I111V-M124I-Y217Q, G097A-I111V-M124V-P210S-Y217Q, G097A-N123Q-P210S-Y217Q, G097A-N123Q-Y217Q, N061P-G097A-G128A-P210S-Y217Q, N061P-G097A-G128S-Y217Q, N061P-G097A-I111V-M124V-Y217Q, N061P-G097A-N123Q-Y217Q, N061P-G097A-S101N-I111V-M124V-Y217Q, N061P-G097A-S101N-N123Q-Y217Q, N061P-G102A-P129S-Y217Q, N061P-N062Q-G097A-G100N-S101N-Y217Q, N061P-N062Q-G097A-G100N-Y217Q, N061P-N062Q-G097A-G100Q-P210S-Y217Q, N061P-N062Q-G097A-I111V-Y217Q, N061P-N062Q-G097A-S101N-I111V-Y217Q, N061P-S078N-G097A-I111V-M124I-Y217Q, N061P-S078N-G102A-I111V-P129S-Y217Q, N062Q-G097A-I111V-P210S-Y217Q, N062Q-G097A-I111V-Y217Q, N062Q-S078N-G097A-I111V-Y217Q, S024G-N025G-N061P-G097A-S101N-G128A-P210S-Y217Q, S024G-N025G-S053G-N061P-G097A-S101N-I111V-M124V-Y217Q, S024G-N025G-S053G-N061P-G097A-S101N-N123Q-Y217Q, S024G-N025G-S053G-N061P-N062Q-G097A-G100N-S101N-Y217Q, S024G-N025G-S053G-N061P-N062Q-G097A-S101N-I111V-Y217Q, S024G-N025G-S053G-N061P-S101N-G102A-P129S-Y217Q, S053G-N061P-G097A-G128S-Y217Q, S053G-N061P-G097A-M124I-Y217Q, S053G-N061P-G097A-S101N-I111V-M124V-Y217Q, S053G-N061P-G102A-P129S-P210S-Y217Q, S053G-N061P-G102A-P129S-Y217Q, S053G-N061P-N062Q-G097A-G100N-S101N-Y217Q, S053G-N061P-N062Q-G097A-S101N-I111V-Y217Q, S053-N061P-S101N-G102A-P129S-Y217Q, S053G-S078N-G097A-I111V-G128S-Y217Q, S078N-G097A-G128S-Y217Q, and S078N-G097A-I111V-M124V-Y217Q, wherein amino acid positions of the variant are numbered by correspondence with the sequence of SEQ ID NO:2. Such variants have enhanced proteolytic activity compared to BPN' (SEQ ID NO:2) and a greater PI value than that of BPN' in this assay. The invention includes a protease variant having enhanced proteolytic activity compared to BPN' (SEQ ID NO:2) and/or a PI value of about 1.0 relative to BPN'-v3 in this BMI microswatch cleaning assay, the variant comprising an amino acid sequence having at least 60%, 70%, 80%, 85%, 90%, 91%, 92%, 93%, 94%, 95%, 96%, 97%, or 98% identity to the sequence of SEQ ID NO:2 and comprising at least one set of amino acid substitutions selected from said group above, wherein amino acid positions of the variant are numbered by correspondence with amino acid positions of the SEQ ID NO:2 sequence. Also included are compositions, including, but not limited to, e.g., cleaning compositions, comprising at least one such variant and methods for cleaning utilizing at least one such variant as described in greater detail elsewhere herein.

The following BPN' variants were determined to have a PI value of about 0.9 relative to BPN'-v3 in a BMI microswatch cleaning assay in Detergent Composition 4 at pH 8 and 16° C.: BPN' amino acid sequence (SEQ ID NO:2) comprising at least one set of amino acid substitutions selected from the group consisting of N061P-G097A-M124I-Y217Q, N061P-G097A-M124V-Y217Q, N061P-N062Q-G097A-G100D-Y217Q, N061P-N062Q-G097A-G100Q-S101N-Y217Q, N061P-N062Q-G097A-G100Q-Y217Q, N061P-N062Q-G100N-G102A-Y217Q, N061P-N062Q-S078N-G097A-G100N-I111V-Y217Q, S024G-N025G-S053G-N061P-G097A-S101N-M124I-Y217Q, S053G-N061P-G097A-S101N-M124I-Y217Q, and S053G-N061P-G097A-S101N-N123Q-Y217Q, wherein positions of the variant are numbered by correspondence with the sequence of SEQ ID NO:2. Such variants have proteolytic activity. The invention includes a protease variant having proteolytic activity, a PI value of about 0.9 relative to BPN'-v3, and/or an enhanced proteolytic activity compared to BPN' in this assay, the variant comprising an amino acid sequence having at least 60%, 70%, 80%, 85%, 90%, 91%, 92%, 93%, 94%, 95%, 96%, 97%, or 98% identity to the sequence of SEQ ID NO:2 and at least one set of amino acid substitutions selected from said group above, wherein amino acid positions of the variant are numbered by correspondence with positions of the SEQ ID NO:2 sequence. Also included are compositions, including, but not limited to, e.g., cleaning compositions, comprising at least one such variant and methods for cleaning utilizing at least one such variant as described in greater detail elsewhere herein.

Also provided is a subtilisin protease variant having enhanced proteolytic activity compared to BPN' and/or a PI value of greater than 1.0 to about 5 compared to BPN'-v3 in a BMI microswatch cleaning assay in Detergent Composition 1 or 4 at pH 8 and 16° C., the variant comprising an amino acid sequence having at least 85%, 90%, 91%, 92%, 93%, 94%, 95%, 96%, 97%, 98%, or 99% identity to SEQ ID NO:2, wherein the variant comprises at least one substitution selected from the group of X024G, X025G, X053G, X061P, X062Q, X078N, X097A, X100D/N/Q, X101N, X102A, X111V, X123A/Q/V, X124I/V, X128A/S, X129S, X210S, X217Q, and optionally at least one substitution selected from the group of S024G, N025G, S053G, N061P, N062Q, S078N, G097A, G100D/N/Q, S101N, G102A, I111V, N123A/Q/V, M124I/V, G128A/S, P129S, P210S, and Y217Q, wherein amino acid positions of the variant are numbered by correspondence with positions of the sequence of SEQ ID NO:2.

Such variants have enhanced proteolytic activity compared to BPN' (SEQ ID NO:2) and a greater PI value than that of BPN' in this assay. Also included are compositions, including, but not limited to, e.g., cleaning compositions, comprising at least one such variant and methods for cleaning utilizing at least one such variant as described in greater detail elsewhere herein.

The following BPN' variants were determined to have a PI value equal to or greater than 0.5 and less than 0.9 relative to BPN'-v3 in a BMI microswatch cleaning assay in Detergent Composition 4 at pH 8 and 16° C.: BPN' amino acid sequence (SEQ ID NO:2) comprising at least one set of amino acid substitutions selected from the group consisting of G097A-N123A-Y217Q, G097A-N123V-Y217Q, N061P-G102A-G128S-Y217Q, N061P-S101N-G102A-G128S-Y217Q, Y217Q, S078N-G097A-I111V-N123Q-Y217Q, and G102A-N123Q-Y217Q, wherein positions of the variant are numbered by correspondence with positions of the SEQ ID NO:2 sequence. Such variants have proteolytic activity. The invention includes a protease variant having proteolytic activity, the variant comprising an amino acid sequence having at least 60%, 70%, 80%, 85%, 90%, 91%, 92%, 93%, 94%, 95%, 96%, 97%, or 98% identity to the sequence of SEQ ID NO:2 and at least one set of amino acid substitutions selected from said group above, wherein positions of the variant are numbered by correspondence with positions of the SEQ ID NO:2 sequence. Also included are compositions, including, but not limited to, e.g., cleaning compositions, comprising at least one such variant and methods for cleaning utilizing at least one such variant as described in greater detail elsewhere herein.

The following BPN' variants were determined to have a PI value greater than 1.0, at least 1.1, at least 1.2, at least 1.3, at least 1.4, at least 1.5, at least 1.6, at least 1.7, at least 1.8, at least 1.9, at least 2, from greater than 1.0 to about 10, from greater than 1.0 to about 8, or from greater than 1.0 to about 5 relative to BPN'-v3 in a BMI microswatch cleaning assay in Detergent Composition 1 at pH 8 and 16° C.: BPN' amino acid sequence (SEQ ID NO:2) comprising at least one set of amino acid substitutions selected from the group consisting of N061P-G097A-G128S-Y217Q, N061P-G097A-S101N-G128A-P210S-Y217Q, N061P-N062Q-G097A-S101N-I111V-Y217Q, S024G-N025G-N061P-G097A-S101N-G128A-P210S-Y217Q, S024G-N025G-S053G-N061P-G097A-S101N-G128A-P210S-Y217Q, S024G-N025G-S053G-N061P-G097A-S101N-G128S-Y217Q, and S024G-N025G-S053G-N061P-S078N-G097A-S101N-I111V-G128S-Y217Q, wherein amino acid positions of the variant are numbered by correspondence with the sequence of SEQ ID NO:2. Such variants have enhanced proteolytic activity compared to BPN' (SEQ ID NO:2) and a greater PI value than that of BPN' in this assay. The invention includes a protease variant having enhanced proteolytic activity compared to BPN' (SEQ ID NO:2) and/or a PI value of greater than 1.0 to about 5 relative to BPN'-v3 in this BMI microswatch cleaning assay, the variant comprising an amino acid sequence having at least 60%, 70%, 80%, 85%, 90%, 91%, 92%, 93%, 94%, 95%, 96%, 97%, or 98% identity to the sequence of SEQ ID NO:2 and comprising at least one set of amino acid substitutions selected from said group above, wherein amino acid positions of the variant are numbered by correspondence with amino acid positions of the SEQ ID NO:2 sequence. Also included are compositions, including, but not limited to, e.g., cleaning compositions, comprising at least one such variant and methods for cleaning utilizing at least one such variant as described in greater detail elsewhere herein.

The following BPN' variants were determined to have a PI value of about 1.0 relative to BPN'-v3 in a BMI microswatch cleaning assay in Detergent Composition 1 at pH 8 and 16° C.: BPN' amino acid sequence (SEQ ID NO:2) comprising at least one set of amino acid substitutions selected from the group consisting of G097A-G128A-Y217Q, G097A-G128A-P210S-Y217Q, G097A-G128S-P210S-Y217Q, G097A-I111V-M124I-Y217Q, G097A-I111V-M124V-P210S-Y217Q, G097A-N123Q-P210S-Y217Q, G097A-N123Q-Y217Q, N061P-G097A-G128A-P210S-Y217Q, N061P-G097A-I111V-M124V-Y217Q, N061P-G097A-M124V-Y217Q, N061P-G097A-N123Q-Y217Q, N061P-G097A-S101N-I111V-M124V-Y217Q, N061P-G102A-P129S-Y217Q, N061P-N062Q-G097A-G100N-S101N-Y217Q, N061P-N062Q-G097A-G100Q-Y217Q, N061P-N062Q-G097A-I111V-Y217Q, N061P-N062Q-S078N-G097A-G100N-I111V-Y217Q, N061P-S078N-G097A-I111V-M124I-Y217Q, N061P-S078N-G102A-I111V-P129S-Y217Q, N062Q-G097A-I111V-P210S-Y217Q, N062Q-G097A-I111V-Y217Q, N062Q-S078N-G097A-I111V-Y217Q, S024G-N025G-S053G-N061P-G097A-S101N-I111V-M124V-Y217Q, S024G-N025G-S053G-N061P-G097A-S101N-N123Q-Y217Q, S024G-N025G-S053G-N061P-N062Q-G097A-G100N-S101N-Y217Q, S024G-N025G-S053G-N061P-N062Q-G097A-S101N-I111V-Y217Q, S024G-N025G-S053G-N061P-S101N-G102A-P129S-Y217Q, S053G-N061P-G097A-G128S-Y217Q, S053G-N061P-G102A-P129S-P210S-Y217Q, S053G-N061P-G102A-P129S-Y217Q, S053G-N061P-N062Q-G097A-S101N-I111V-Y217Q, S053G-N061P-S101N-G102A-P129S-Y217Q, S053G-S078N-G097A-I111V-G128S-Y217Q, S078N-G097A-G128S-Y217Q, and S078N-G097A-I111V-M124V-Y217Q, wherein amino acid positions of the variant are numbered by correspondence with the sequence of SEQ ID NO:2. Such variants have enhanced proteolytic activity compared to BPN' (SEQ ID NO:2) and a greater PI value than that of BPN' in this assay. The invention includes a protease variant having enhanced proteolytic activity compared to BPN' (SEQ ID NO:2) and/or a PI value of about 1.0 relative to BPN'-v3 in this BMI microswatch cleaning assay, the variant comprising an amino acid sequence having at least 60%, 70%, 80%, 85%, 90%, 91%, 92%, 93%, 94%, 95%, 96%, 97%, or 98% identity to the sequence of SEQ ID NO:2 and comprising at least one set of amino acid substitutions selected from said group above, wherein amino acid positions of the variant are numbered by correspondence with amino acid positions of the SEQ ID NO:2 sequence. Also included are compositions, including, but not limited to, e.g., cleaning compositions, comprising at least one such variant and methods for cleaning utilizing at least one such variant as described in greater detail elsewhere herein.

The following BPN' variants were determined to have a PI value of about 0.9 relative to BPN'-v3 in a BMI microswatch cleaning assay in Detergent Composition 1 at pH 8 and 16° C.: BPN' amino acid sequence (SEQ ID NO:2) comprising at least one set of amino acid substitutions selected from the group consisting of N061P-G097A-M124I-Y217Q, N061P-G097A-S101N-N123Q-Y217Q, N061P-N062Q-G097A-G100N-Y217Q, N061P-N062Q-G097A-G100N-P210S-Y217Q, N061P-N062Q-G097A-G100S-S101N-Y217Q, N061P-N062Q-G100N-G102A-Y217Q, S024G-N025G-S053G-N061P-G097A-S101N-M124I-Y217Q, S053G-N061P-G097A-M124I-Y217Q, S053G-N061P-G097A-S101N-I111V-M124V-Y217Q, S053G-N061P-G097A-S101N-M124I-Y217Q, S053G-N061P-G097A-S101N-N123Q-Y217Q, and S053G-N061P-N062Q-G097A-G100N-S101N-Y217Q, wherein positions of the variant are numbered by correspondence with the sequence of SEQ ID NO:2. Such variants have proteolytic activity. The invention includes a protease variant having proteolytic activity, a PI value of about 0.9 relative to BPN'-v3, and/or an enhanced proteolytic activity compared to BPN' in this assay, the variant comprising an amino acid sequence having at least 60%, 70%, 80%, 85%, 90%, 91%, 92%, 93%, 94%, 95%, 96%, 97%, or 98% identity to the sequence of SEQ ID NO:2 and at least one set of amino acid substitutions selected from said group above, wherein amino acid positions of the variant are numbered by correspondence with positions of the SEQ ID NO:2 sequence. Also included are compositions, including, but not limited to, e.g., cleaning compositions, comprising at least one such variant and methods for cleaning utilizing at least one such variant as described in greater detail elsewhere herein.

The following BPN' variants were determined to have a PI value equal to or greater than 0.5 and less than 0.9 relative to BPN'-v3 in a BMI microswatch cleaning assay in Detergent Composition 1 at pH 8 and 16° C.: BPN' amino acid sequence (SEQ ID NO:2) comprising at least one set of amino acid substitutions selected from the group consisting of G097A-N123A-Y217Q, G097A-N123V-Y217Q, N061P-N062Q-G097A-G100D-Y217Q, N061P-S101N-G102A-G128S-Y217Q, Y217Q, N061P-G102A-G128S-Y217Q, S078N-G097A-I111V-N123Q-Y217Q, and G102A-N123Q-Y217Q, wherein positions of the variant are numbered by correspondence with positions of the SEQ ID NO:2 sequence. Such variants have proteolytic activity. The invention includes a protease variant having proteolytic activity, the variant comprising an amino acid sequence having at least 60%, 70%, 80%, 85%, 90%, 91%, 92%, 93%, 94%, 95%, 96%, 97%, or 98% identity to the sequence of SEQ ID NO:2 and at least one set of amino acid substitutions selected from said group above, wherein positions of the variant are numbered by correspondence with positions of the SEQ ID NO:2 sequence. Also included are compositions, including, but not limited to, e.g., cleaning compositions, comprising at least one such variant and methods for cleaning utilizing at least one such variant as described in greater detail elsewhere herein.

The following BPN' variants were determined to have a PI value greater than 1.0 to about 5 relative to BPN'-v3 in an egg microswatch cleaning assay in Detergent Composition 4 at 16° C. and pH 8: BPN' amino acid sequence (SEQ ID NO:2) comprising the set of amino acid substitutions N061P-G097A-S101N-G128A-P210S-Y217Q, wherein amino acid positions of the variant are numbered by correspondence with the sequence of SEQ ID NO:2. Such variants have enhanced proteolytic activity compared to BPN' (SEQ ID NO:2) and a greater PI value than that of BPN' in this assay. The invention includes a protease variant having enhanced proteolytic activity compared to BPN' (SEQ ID NO:2) and/or a PI value of greater than 1.0 to about 5 relative to BPN'-v3 in this egg microswatch cleaning assay, the variant comprising an amino acid sequence having at least 60%, 70%, 80%, 85%, 90%, 91%, 92%, 93%, 94%, 95%, 96%, 97%, or 98% identity to the sequence of SEQ ID NO:2 and comprising amino acid substitutions N061P-G097A-S101N-G128A-P210S-Y217Q, wherein amino acid positions of the variant are numbered by correspondence with the sequence of SEQ ID NO:2. Also included are compositions, including, but not limited to, e.g., cleaning compositions, comprising at least one such variant and methods for cleaning utilizing at least one such variant as described in greater detail elsewhere herein.

The following BPN' variants were determined to have a PI value of about 1.0 relative to BPN'-v3 in an egg microswatch cleaning assay in Detergent Composition 4 at pH 8 and 16° C.: BPN' amino acid sequence (SEQ ID NO:2) comprising at least one set of amino acid substitutions selected from the group consisting of G097A-G128A-Y217Q, N061P-G102A-P129S-Y217Q, N062Q-G097A-I111V-P210S-Y217Q, S024G-N025G-S053G-N061P-G097A-S101N-G128A-P210S-Y217Q, S024G-N025G-N061P-G097A-S101N-G128A-P210S-Y217Q, N061P-G097A-G128A-P210S-Y217Q, G097A-G128S-P210S-Y217Q, S024G-N025G-S053G-N061P-S078N-G097A-S101N-I111V-G128S-Y217Q, S024G-N025G-S053G-N061P-G097A-S101N-G128S-Y217Q, N061P-G097A-G128S-Y217Q, and G097A-G128A-P210S-Y217Q, wherein amino acid positions of the variant are numbered by correspondence with the sequence of SEQ ID NO:2. Such variants have enhanced proteolytic activity compared to BPN' (SEQ ID NO:2) and a greater PI value than that of BPN' in this assay. The invention includes a protease variant having enhanced proteolytic activity compared to BPN' (SEQ ID NO:2) and/or a PI value of about 1.0 relative to BPN'-v3 in this egg microswatch cleaning assay, the variant comprising an amino acid sequence having at least 60%, 70%, 80%, 85%, 90%, 91%, 92%, 93%, 94%, 95%, 96%, 97%, or 98% identity to the sequence of SEQ ID NO:2 and comprising at least one set of amino acid substitutions selected from said group above, wherein amino acid positions of the variant are numbered by correspondence with amino acid positions of the SEQ ID NO:2 sequence. Also included are compositions, including, but not limited to, e.g., cleaning compositions, comprising at least one such variant and methods for cleaning utilizing at least one such variant as described in greater detail elsewhere herein.

The following BPN' variants were determined to have a PI value equal to or greater than 0.5 and equal to or less than 0.9 relative to BPN'-v3 in an egg microswatch cleaning assay in Detergent Composition 4 at pH 8 and 16° C.: BPN' amino acid sequence (SEQ ID NO:2) comprising at least one set of amino acid substitutions selected from the group consisting of N061P-G097A-M124I-Y217Q, S053G-N061P-G097A-S101N-N123Q-Y217Q, S053G-N061P-G102A-P129S-P210S-Y217Q, G097A-I111V-M124V-P210S-Y217Q, G097A-N123Q-P210S-Y217Q, S053G-N061P-S101N-G102A-P129S-Y217Q, S053G-N061P-N062Q-G097A-S101N-I111V-Y217Q, N061P-N062Q-G097A-S101N-I111V-Y217Q, N061P-N062Q-G097A-I111V-Y217Q, N062Q-G097A-I111V-Y217Q, N061P-G097A-S101N-I111V-M124V-Y217Q, G097A-N123Q-Y217Q, N061P-G097A-I111V-M124V-Y217Q, S078N-G097A-I111V-M124V-Y217Q, S053G-S078N-G097A-I111V-G128S-Y217Q, S078N-G097A-G128S-Y217Q, S053G-N061P-G097A-G128S-Y217Q, N061P-N062Q-G097A-G100N-Y217Q, S024G-N025G-S053G-N061P-G097A-S101N-N123Q-Y217Q, N061P-G097A-S101N-N123Q-Y217Q, N061P-N062Q-G097A-G100Q-P210S-Y217Q, N061P-G097A-N123Q-Y217Q, S024G-N025G-S053G-N061P-G097A-S101N-M124I-Y217Q, S053G-N061P-G097A-S101N-M124I-Y217Q, S053G-N061P-G097A-M124I-Y217Q, N061P-S078N-G097A-I111V-M124I-Y217Q, N061P-G097A-M124V-Y217Q, S024G-N025G-S053G-N061P-N062Q-G097A-G100N-S101N-Y217Q, S024G-N025G-S053G-N061P-S101N-G102A-P129S-Y217Q, N061P-S078N-G102A-I111V-P129S-Y217Q, S053G-N061P-G102A-P129S-Y217Q, S024G-N025G-S053G-N061P-N062Q-G097A-S101N-I111V-Y217Q, N062Q-S078N-G097A-I111V-Y217Q, S024G-N025G-S053G-N061P-G097A-S101N-I111V-M124V-Y217Q, S053G-N061P-G097A-S101N-I111V-M124V-Y217Q, G097A-I111V-M124I-Y217Q, Y217Q, N061P-N062Q-G100N-

G102A-Y217Q, S053G-N061P-N062Q-G097A-G100N-S101N-Y217Q, N061P-N062Q-G097A-G100N-S101N-Y217Q, N061P-N062Q-S078N-G097A-G100N-I111V-Y217Q, N061P-N062Q-G097A-G100Q-Y217Q, N061P-S101N-G102A-G128S-Y217Q, G097A-N123V-Y217Q, G097A-N123A-Y217Q, G102A-N123Q-Y217Q, N061P-N062Q-G097A-G100Q-S101N-Y217Q, S078N-G097A-I111V-N123Q-Y217Q, N061P-N062Q-G097A-G100D-Y217Q, and N061P-G102A-G128S-Y217Q, wherein positions of the variant are numbered by correspondence with the sequence of SEQ ID NO:2. Such variants have proteolytic activity. The invention includes a protease variant having proteolytic activity and/or a PI value of equal to or greater than 0.5 and equal to or less than 0.9 relative to BPN'-v3 in this egg microswatch cleaning assay, the variant comprising an amino acid sequence having at least 60%, 70%, 80%, 85%, 90%, 91%, 92%, 93%, 94%, 95%, 96%, 97%, or 98% identity to the sequence of SEQ ID NO:2 and at least one set of amino acid substitutions selected from said group above, wherein amino acid positions of the variant are numbered by correspondence with positions of the SEQ ID NO:2 sequence. Also included are compositions, including, but not limited to, e.g., cleaning compositions, comprising at least one such variant and methods for cleaning utilizing at least one such variant as described in greater detail elsewhere herein.

Also provided is a subtilisin protease variant having enhanced proteolytic activity compared to BPN' and/or a PI value of greater than 1.0 to about 5 compared to BPN'-v3 in this egg microswatch cleaning assay in Detergent Composition 4 at pH 8 and 16° C., the variant comprising an amino acid sequence having at least 85%, 90%, 91%, 92%, 93%, 94%, 95%, 96%, 97%, 98%, or 99% identity to SEQ ID NO:2, wherein the variant comprises at least one substitution selected from the group of X024G, X025G, X053G, X061P, X062Q, X078N, X097A, X100D/N/Q, X101N, X102A, X111V, X123A/Q/V, X124I/V, X128A/S, X129S, X210S, and X217Q, and optionally at least one substitution selected from the group of S024G, N025G, S053G, N061P, N062Q, S078N, G097A, G100D/N/Q, S101N, G102A, I111V, N123A/Q/V, M124I/V, G128A/S, P129S, P210S, and Y217Q, wherein amino acid positions of the variant are numbered by correspondence with positions of the sequence of SEQ ID NO:2. Such variants have enhanced proteolytic activity compared to BPN' (SEQ ID NO:2) and a greater PI value than that of BPN' in this assay. Also included are compositions, including, but not limited to, e.g., cleaning compositions, comprising at least one such variant and methods for cleaning utilizing at least one such variant as described in greater detail elsewhere herein.

Example 6

Construction and Cleaning Performance of BPN' Variants

A BPN' combinatorial library based on BPN' parent was made by DNA2.0 and delivered as a ligation reaction. For efficient transformation of *B. subtilis*, DNA from the ligation reaction mixtures was amplified before transformation and transformants grown as described in Example 2. These variants were tested for cleaning performance using BMI microswatch assay in Detergent Composition 1 and Detergent Composition 4 at 16° C. and pH 8 as well as egg microswatch assay in Detergent Composition 4 at 16° C. and pH 8. Protein content was determined using the TCA assay and protease activity was assayed using the AAPF assay. The assays were performed as described in Example 1 and the Performance Indices were calculated relative to BPN'-v3 (with a PI value of 1.0).

The following BPN' variants were determined to have a PI value greater than 1.0, at least 1.1, at least 1.2, at least 1.3, at least 1.4, at least 1.5, at least 1.6, at least 1.7, at least 1.8, at least 1.9, at least 2, from greater than 1.0 to about 10, from greater than 1.0 to about 8, or from greater than 1.0 to about 5 relative to BPN'-v3 in a BMI microswatch cleaning assay in Detergent Composition 1 at pH 8 and 16° C.: BPN' amino acid sequence (SEQ ID NO:2) comprising at least one set of amino acid substitutions selected from the group consisting of S024G-N025G-S053G-T055P-N061P-G097A-S101N-G128A-Y217Q, N025G-G097A-S101N-G128A-Y217Q, N025G-S038G-S053G-N061P-S078N-G097A-S101N-G128A-Y217Q, N025G-S053G-N061P-S078N-G128A-Y217Q, N025G-S053G-N061P-S078N-S101N-G128A-Y217Q, N025G-S053G-T055P-N061P-S078N-G097A-S101N-G128A-Y217Q, N025G-S053G-T055P-S078N-G097A-S101N-G128A-Y217Q, N025G-S078N-G097A-S101N-G128A-Y217Q, N025G-T055P-N061P-S078N-G097A-S101N-G128A-Y217Q, N025G-T055P-N061P-S078N-S101N-G128A-Y217Q, N061P-S101N-G128A-Y217Q, S024G-N025G-N061P-G097A-G128A-Y217Q, S024G-N025G-N061P-G097A-S101N-G128A-Y217Q, S024G-N025G-S053G-N061P-S078N-G097A-S101N-G128A-Y217Q, S024G-N025G-S053G-N061P-S078N-S101N-G128A-Y217Q, S024G-N025G-S053G-T055P-G097A-S101N-G128A-Y217Q, S024G-N025G-S053G-T055P-N061P-G128A-Y217Q, S024G-N025G-T055P-G097A-G128A-Y217Q, S024G-N025G-T055P-N061P-S078N-G097A-S101N-G128A-Y217Q, S024G-N061P-S078N-G097A-S101N-G128A-Y217Q, S024G-S053G-N061P-G097A-G128A-Y217Q, S024G-S053G-N061P-S078N-G097A-G128A-Y217Q, S024G-S053G-T055P-G097A-S101N-G128A-Y217Q, S024G-S053G-T055P-N061P-G097A-S101N-G128A-Y217Q, S024G-S053G-T055P-N061P-S078N-G097A-S101N-G128A-Y217Q, S024G-S053G-T055P-N061P-S101N-G128A-Y217Q, S024G-T055P-N061P-G097A-G128A-Y217Q, S053G-G097A-S101N-G128A-Y217Q, S053G-N061P-G097A-S101N-G128A-Y217Q-S249N, S053G-N061P-S078N-G097A-G128A-Y217Q, S053G-S078N-G097A-S101N-G128A-Y217Q, S053G-T055P-G097A-S101N-G128A-Y217Q, S053G-T055P-N061P-S101N-G128A-Y217Q, S053G-T055P-S078N-G097A-S101N-G128A-Y217Q, T055P-G097A-S101N-G128A-Y217Q, and T055P-N061P-S078N-G097A-S101N-G128A-Y217Q, wherein amino acid positions of the variant are numbered by correspondence with the sequence of SEQ ID NO:2. Such variants have enhanced proteolytic activity compared to BPN' (SEQ ID NO:2) and a greater PI value than that of BPN' in this assay. The invention includes a protease variant having enhanced proteolytic activity compared to BPN' (SEQ ID NO:2) and/or a PI value of greater than 1.0 to about 5 relative to BPN'-v3 in this BMI microswatch cleaning assay, the variant comprising an amino acid sequence having at least 60%, 70%, 80%, 85%, 90%, 91%, 92%, 93%, 94%, 95%, 96%, 97%, or 98% identity to the sequence of SEQ ID NO:2 and comprising at least one set of amino acid substitutions selected from said group above, wherein amino acid positions of the variant are numbered by correspondence with amino acid positions of the SEQ ID NO:2 sequence.

The following BPN' variants were determined to have a PI value of about 1.0 relative to BPN'-v3 in a BMI microswatch cleaning assay in Detergent Composition 1 at pH 8 and 16° C.: BPN' amino acid sequence (SEQ ID NO:2) comprising at least one set of amino acid substitutions selected from the group consisting of G097A-G128S-Y217Q, G097A-G128A-Y217Q, N025G-S078N-G097A-G128A-Y217Q, N025G-T055P-G097A-G128A-Y217Q, S024G-G097A-S101N-G128A-Y217Q, S024G-I035V-T055P-N061P-S078N-G097A-Y217Q, S024G-N025G-N061P-S078N-G097A-S101N-G128A, S024G-N025G-N061P-S078N-G097A-S101N-G128A-Y217Q, S024G-N025G-N061P-S078N-S101N-G128A-Y217Q, S024G-N025G-S053G-N061P-G097A-G128A-S130G-Y217Q, S024G-N025G-S053G-N061P-G128A-Y217Q, S024G-N025G-S053G-T055P-G097A-G128A-Y217Q, S024G-N025G-S053G-T055P-N061P-S078N-G097A-G128A-Y217Q, S024G-N025G-S053G-T055P-N061P-S078N-G128A-Y217Q, S024G-N025G-S053G-T055P-S078N-S101N-G128A-Y217Q, S024G-N025G-S053G-T055P-S101N-G128A-Y217Q, S024G-N025G-T055P-G097A-S101N-G128A-Y217Q, S024G-N025G-T055P-N061P-S078N-G097A-Y217Q, S024G-N061P-G097A-S101N-G128A-Y217Q, S024G-S038G-S053G-S078N-S101N-G128A-Y217Q, S024G-S053G-S078N-G097A-S101N-G128A-Y217Q, S024G-S053G-S078N-S101N-G128A-Y217Q, S024G-S053G-T055P-N061P-S078N-G097A-G128A-Y217Q, S024G-T055P-G097A-G128A-Y217Q, S024G-T055P-N061P-G097A-S101N-G128A, S024G-T055P-N061P-S078N-S101N-G128A-Y217Q, S024G-T055P-S078N-G097A-S101N-G128A-Y217Q, S101N-G128A-Y217Q, T055P-N061P-G097A-A116S-G128A, and T055P-N061P-S078N-G128A-Y217Q, wherein amino acid positions of the variant are numbered by correspondence with the sequence of SEQ ID NO:2. Such variants have enhanced proteolytic activity compared to BPN' and a greater PI value than that of BPN' in this assay. The invention includes a protease variant having enhanced proteolytic activity compared to BPN' (SEQ ID NO:2) and/or a PI value of about 1.0 relative to BPN'-v3 in this BMI microswatch cleaning assay, the variant comprising an amino acid sequence having at least 60%, 70%, 80%, 85%, 90%, 91%, 92%, 93%, 94%, 95%, 96%, 97%, or 98% identity to the sequence of SEQ ID NO:2 and comprising at least one set of amino acid substitutions selected from said group above, wherein amino acid positions of the variant are numbered by correspondence with amino acid positions of the SEQ ID NO:2 sequence. Also included are compositions, including, but not limited to, e.g., cleaning compositions, comprising at least one such variant and methods for cleaning utilizing at least one such variant as described in greater detail elsewhere herein.

Also provided is a subtilisin protease variant having enhanced proteolytic activity compared to BPN' and/or a PI value of greater than 1.0 to about 5 compared to BPN'-v3 in this BMI microswatch cleaning assay in Detergent Composition 1 at pH 8 and 16° C., the variant comprising an amino acid sequence having at least 85%, 90%, 91%, 92%, 93%, 94%, 95%, 96%, 97%, 98%, or 99% identity to SEQ ID NO:2, wherein the variant comprises at least one substitution selected from the group of X024G, X025G, X035V, X038G, X053G, X055P, X061P, X078N, X097A, X101N, X116S, X128A/S, X130G, X216Q, X217Q, and X249N, and optionally at least one substitution selected from the group of S024G, N025G, I035V, S038G, S053G, T055P, N061P, S078N, G097A, S101N, A116S, G128A/S, S130G, Y216Q, Y217Q, and S249N, and wherein amino acid positions of the variant are numbered by correspondence with positions of the sequence of SEQ ID NO:2. Also included are compositions, including, but not limited to, e.g., cleaning compositions, comprising at least one such variant and methods for cleaning utilizing at least one such variant as described in greater detail elsewhere herein.

The following BPN' variants were determined to have a PI value greater than 1.0, at least 1.1, at least 1.2, at least 1.3, at least 1.4, at least 1.5, at least 1.6, at least 1.7, at least 1.8, at least 1.9, at least 2, from greater than 1.0 to about 10, from greater than 1.0 to about 8, or from greater than 1.0 to about 5 relative to BPN'-v3 in a BMI microswatch cleaning assay in Detergent Composition 4 at pH 8 and 16° C.: BPN' amino acid sequence (SEQ ID NO:2) comprising at least one set of amino acid substitutions selected from the group consisting of S024G-N025G-N061P-S078N-G097A-S101N-G128A-Y217Q, S024G-N025G-S053G-N061P-S078N-S101N-G128A-Y217Q, S024G-N025G-S053G-T055P-N061P-G097A-S101N-G128A-Y217Q, S024G-S053G-T055P-N061P-G097A-S101N-G128A-Y217Q, S024G-S053G-T055P-N061P-S078N-G097A-S101N-G128A-Y217Q, S024G-T055P-N061P-S078N-S101N-G128A-Y217Q, S053G-G097A-S101N-G128A-Y217Q, and T055P-N061P-S078N-G128A-Y217Q, wherein amino acid positions of the variant are numbered by correspondence with the sequence of SEQ ID NO:2. Such variants have enhanced proteolytic activity compared to BPN' (SEQ ID NO:2) and a greater PI value than that of BPN' in this assay. The invention includes a protease variant having enhanced proteolytic activity compared to BPN' (SEQ ID NO:2) and/or a PI value of greater than 1.0 to about 5 relative to BPN'-v3 in this BMI microswatch cleaning assay, the variant comprising an amino acid sequence having at least 60%, 70%, 80%, 85%, 90%, 91%, 92%, 93%, 94%, 95%, 96%, 97%, or 98% identity to the sequence of SEQ ID NO:2 and comprising at least one set of amino acid substitutions selected from said group above, wherein amino acid positions of the variant are numbered by correspondence with amino acid positions of the SEQ ID NO:2 sequence.

The following BPN' variants were determined to have a PI value of about 1.0 relative to BPN'-v3 in a BMI microswatch cleaning assay in Detergent Composition 4 at pH 8 and 16° C.: BPN' amino acid sequence (SEQ ID NO:2) comprising at least one set of amino acid substitutions selected from the group consisting of G097A-G128S-Y217Q, G097A-G128A-Y217Q, N025G-G097A-S101N-G128A-Y217Q, N025G-S038G-S053G-N061P-S078N-G097A-S101N-G128A-Y217Q, N025G-S053G-N061P-S078N-G128A-Y217Q, N025G-S053G-N061P-S078N-S101N-G128A-Y217Q, N025G-S053G-T055P-N061P-S078N-G097A-S101N-G128A-Y217Q, N025G-S053G-T055P-S078N-G097A-S101N-G128A-Y217Q, N025G-S078N-G097A-G128A-Y217Q, N025G-S078N-G097A-S101N-G128A-Y217Q, N025G-T055P-G097A-G128A-Y217Q, N025G-T055P-N061P-S078N-G097A-S101N-G128A-Y217Q, N025G-T055P-N061P-S078N-S101N-G128A-Y217Q, N061P-S101N-G128A-Y217Q, S024G-G097A-S101N-G128A-Y217Q, S024G-I035V-T055P-N061P-S078N-G097A-Y217Q, S024G-N025G-N061P-G097A-G128A-Y217Q, S024G-N025G-N061P-G097A-S101N-G128A-Y217Q, S024G-N025G-N061P-S078N-G097A-S101N-G128A, S024G-N025G-N061P-S078N-S101N-G128A-Y217Q, S024G-N025G-S053G-N061P-G097A-G128A-S130G-Y217Q, S024G-N025G-S053G-N061P-G128A-Y217Q, S024G-N025G-S053G-N061P-S078N-G097A-S101N-G128A-Y217Q, S024G-N025G-S053G-T055P-G097A-G128A-Y217Q, S024G-N025G-S053G-T055P-G097A-S101N-G128A-Y217Q, S024G-N025G-S053G-T055P-N061P-G128A-Y217Q, S024G-N025G-S053G-T055P-N061P-S078N-G097A-G128A-Y217Q, S024G-N025G-

S053G-T055P-N061P-S078N-G128A-Y217Q, S024G-N025G-S053G-T055P-S078N-S101N-G128A-Y217Q, S024G-N025G-S053G-T055P-S101N-G128A-Y217Q, S024G-N025G-T055P-G097A-G128A-Y217Q, S024G-N025G-T055P-G097A-S101N-G128A-Y217Q, S024G-N025G-T055P-N061P-S078N-G097A-S101N-G128A-Y217Q, S024G-N061P-G097A-S101N-G128A-Y217Q, S024G-N061P-S078N-G097A-S101N-G128A-Y217Q, S024G-S038G-S053G-S078N-S101N-G128A-Y217Q, S024G-S053G-N061P-G097A-G128A-Y217Q, S024G-S053G-N061P-S078N-G097A-G128A-Y217Q, S024G-S053G-S078N-G097A-S101N-G128A-Y217Q, S024G-S053G-S078N-S101N-G128A-Y217Q, S024G-S053G-T055P-G097A-S101N-G128A-Y217Q, S024G-S053G-T055P-N061P-S078N-G097A-G128A-Y217Q, S024G-S053G-T055P-N061P-S101N-G128A-Y217Q, S024G-T055P-G097A-G128A-Y217Q, S024G-T055P-N061P-G097A-G128A-Y217Q, S024G-T055P-N061P-G097A-S101N-G128A, S024G-T055P-S078N-G097A-S101N-G128A-Y217Q, S053G-N061P-G097A-S101N-G128A-Y217Q-S249N, S053G-N061P-S078N-G097A-G128A-Y217Q, S053G-S078N-G097A-S101N-G128A-Y217Q, S053G-T055P-G097A-S101N-G128A-Y217Q, S053G-T055P-N061P-S101N-G128A-Y217Q, S053G-T055P-S078N-G097A-S101N-G128A-Y217Q, S101N-G128A-Y217Q, T055P-G097A-S101N-G128A-Y217Q, and T055P-N061P-S078N-G097A-S101N-G128A-Y217Q, wherein amino acid positions of the variant are numbered by correspondence with the sequence of SEQ ID NO:2. Such variants have enhanced proteolytic activity compared to BPN' (SEQ ID NO:2) and a greater PI value than that of BPN' in this assay. The invention includes a protease variant having enhanced proteolytic activity compared to BPN' (SEQ ID NO:2) and/or a PI value of about 1.0 relative to BPN'-v3 in this BMI microswatch cleaning assay, the variant comprising an amino acid sequence having at least 60%, 70%, 80%, 85%, 90%, 91%, 92%, 93%, 94%, 95%, 96%, 97%, or 98% identity to the sequence of SEQ ID NO:2 and comprising at least one set of amino acid substitutions selected from said group above, wherein amino acid positions of the variant are numbered by correspondence with amino acid positions of the SEQ ID NO:2 sequence. Also included are compositions, including, but not limited to, e.g., cleaning compositions, comprising at least one such variant and methods for cleaning utilizing at least one such variant as described in greater detail elsewhere herein.

The following BPN' variants were determined to have a PI value of about 0.9 relative to BPN'-v3 in a BMI microswatch cleaning assay in Detergent Composition 4 at pH 8 and 16° C.: BPN' amino acid sequence (SEQ ID NO:2) comprising at least one set of amino acid substitutions selected from the group consisting of T055P-N061P-G097A-A116S-G128A and S024G-N025G-T055P-N061P-S078N-G097A-Y217Q, wherein positions of the variant are numbered by correspondence with the sequence of SEQ ID NO:2. Such variants have proteolytic activity and may have enhanced proteolytic activity compared to BPN' (SEQ ID NO:2) in this assay. The invention includes a protease variant having proteolytic activity, a PI value of about 0.9 relative to BPN'-v3, and/or an enhanced proteolytic activity compared to BPN' in this assay, the variant comprising an amino acid sequence having at least 60%, 70%, 80%, 85%, 90%, 91%, 92%, 93%, 94%, 95%, 96%, 97%, or 98% identity to the sequence of SEQ ID NO:2 and at least one set of amino acid substitutions selected from said group above, wherein amino acid positions of the variant are numbered by correspondence with positions of the SEQ ID NO:2 sequence. Also included are compositions, including, but not limited to, e.g., cleaning compositions, comprising at least one such variant and methods for cleaning utilizing at least one such variant as described in greater detail elsewhere herein.

The following BPN' variants were determined to have a PI value greater than 1.0, at least 1.1, at least 1.2, at least 1.3, at least 1.4, at least 1.5, at least 1.6, at least 1.7, at least 1.8, at least 1.9, at least 2, from greater than 1.0 to about 10, from greater than 1.0 to about 8, or from greater than 1.0 to about 5 relative to BPN'-v3 in an egg microswatch cleaning assay in Detergent Composition 4 at pH 8 and 16° C.: BPN' amino acid sequence (SEQ ID NO:2) comprising at least one set of amino acid substitutions selected from the group consisting of N025G-T055P-N061P-S078N-G097A-S101N-G128A-Y217Q, N061P-S101N-G128A-Y217Q, S024G-N025G-S053G-N061P-S078N-S101N-G128A-Y217Q, S024G-N025G-S053G-T055P-S101N-G128A-Y217Q, S024G-N025G-S053G-T055P-N061P-G128A-Y217Q, S024G-N025G-T055P-N061P-S078N-G097A-S101N-G128A-Y217Q, N025G-S053G-N061P-S078N-G128A-Y217Q, S024G-N025G-S053G-T055P-G097A-S101N-G128A-Y217Q, S024G-N025G-N061P-S078N-G097A-S101N-G128A-Y217Q, S024G-S053G-T055P-G097A-S101N-G128A-Y217Q, S053G-N061P-S078N-G097A-G128A-Y217Q, S024G-N025G-T055P-G097A-G128A-Y217Q, and S024G-N025G-S053G-T055P-G097A-G128A-Y217Q, wherein amino acid positions of the variant are numbered by correspondence with the sequence of SEQ ID NO:2. Such variants have enhanced proteolytic activity compared to BPN' (SEQ ID NO:2) and a greater PI value than that of BPN' in this assay. The invention includes a protease variant having enhanced proteolytic activity compared to BPN' (SEQ ID NO:2) and/or a PI value of greater than 1.0 to about 5 relative to BPN'-v3 in this egg microswatch cleaning assay, the variant comprising an amino acid sequence having at least 60%, 70%, 80%, 85%, 90%, 91%, 92%, 93%, 94%, 95%, 96%, 97%, or 98% identity to the sequence of SEQ ID NO:2 and comprising at least one set of amino acid substitutions selected from said group above, wherein amino acid positions of the variant are numbered by correspondence with amino acid positions of the SEQ ID NO:2 sequence.

The following BPN' variants were determined to have a PI value of about 1.0 relative to BPN'-v3 in an egg microswatch cleaning assay in Detergent Composition 4 at pH 8 and 16° C.: BPN' amino acid sequence (SEQ ID NO:2) comprising at least one set of amino acid substitutions selected from the group consisting of G097A-G128S-Y217Q, G097A-G128A-Y217Q, S024G-G097A-S101N-G128A-Y217Q, N025G-T055P-N061P-S078N-S101N-G128A-Y217Q, S053G-T055P-N061P-S101N-G128A-Y217Q, S053G-T055P-S078N-G097A-S101N-G128A-Y217Q, N025G-S053G-N061P-S078N-S101N-G128A-Y217Q, S024G-S053G-T055P-N061P-S101N-G128A-Y217Q, S024G-N025G-S053G-T055P-N061P-G097A-S101N-G128A-Y217Q, N025G-S053G-T055P-N061P-S078N-G097A-S101N-G128A-Y217Q, S024G-N025G-N061P-S078N-S101N-G128A-Y217Q, S024G-S053G-T055P-N061P-G097A-S101N-G128A-Y217Q, T055P-N061P-S078N-G128A-Y217Q, N025G-S038G-S053G-N061P-S078N-G097A-S101N-G128A-Y217Q, S024G-N025G-S053G-N061P-G128A-Y217Q, S024G-N025G-S053G-T055P-S078N-S101N-G128A-Y217Q, T055P-N061P-S078N-G097A-S101N-G128A-Y217Q, S024G-N025G-S053G-T055P-N061P-S078N-G128A-Y217Q, S024G-N025G-N061P-G097A-S101N-G128A-Y217Q, S024G-T055P-G097A-G128A-Y217Q, T055P-N061P-G097A-A116S-G128A, S053G-T055P-G097A-S101N-G128A-Y217Q, T055P-

G097A-S101N-G128A-Y217Q, S024G-N061P-G097A-S101N-G128A-Y217Q, S024G-N025G-N061P-G097A-G128A-Y217Q, S024G-S053G-S078N-S101N-G128A-Y217Q, S024G-N025G-S053G-T055P-N061P-S078N-G097A-G128A-Y217Q, S053G-G097A-S101N-G128A-Y217Q, N025G-T055P-G097A-G128A-Y217Q, S024G-T055P-S078N-G097A-S101N-G128A-Y217Q, N025G-S078N-G097A-S101N-G128A-Y217Q, N025G-G097A-S101N-G128A-Y217Q, S024G-S053G-N061P-S078N-G097A-G128A-Y217Q, S024G-N025G-T055P-N061P-S078N-G097A-Y217Q, and S024G-I035V-T055P-N061P-S078N-G097A-Y217Q, wherein amino acid positions of the variant are numbered by correspondence with the sequence of SEQ ID NO:2. Such variants have enhanced proteolytic activity compared to BPN' (SEQ ID NO:2) and a greater PI value than that of BPN' in this assay. The invention includes a protease variant having enhanced proteolytic activity compared to BPN' (SEQ ID NO:2) and/or a PI value of about 1.0 relative to BPN'-v3 in this egg microswatch cleaning assay, the variant comprising an amino acid sequence having at least 60%, 70%, 80%, 85%, 90%, 91%, 92%, 93%, 94%, 95%, 96%, 97%, or 98% identity to the sequence of SEQ ID NO:2 and comprising at least one set of amino acid substitutions selected from said group above, wherein amino acid positions of the variant are numbered by correspondence with amino acid positions of the SEQ ID NO:2 sequence. Also included are compositions, including, but not limited to, e.g., cleaning compositions, comprising at least one such variant and methods for cleaning comprising utilizing at least one such variant as described in greater detail elsewhere herein.

The following BPN' variants were determined to have a PI value of about 0.9 relative to BPN'-v3 in an egg microswatch cleaning assay in Detergent Composition 4 at pH 8 and 16° C.: BPN' amino acid sequence (SEQ ID NO:2) comprising at least one set of amino acid substitutions selected from the group consisting of S101N-G128A-Y217Q, S024G-T055P-N061P-G097A-S101N-G128A, S024G-N025G-N061P-S078N-G097A-S101N-G128A, S024G-T055P-N061P-S078N-S101N-G128A-Y217Q, S024G-N025G-S053G-N061P-S078N-G097A-S101N-G128A-Y217Q, S024G-S053G-T055P-N061P-S078N-G097A-S101N-G128A-Y217Q, S053G-N061P-G097A-S101N-G128A-Y217Q-S249N, N025G-S053G-T055P-S078N-G097A-S101N-G128A-Y217Q, S024G-N025G-T055P-G097A-S101N-G128A-Y217Q, S024G-S053G-N061P-G097A-G128A-Y217Q, S024G-N061P-S078N-G097A-S101N-G128A-Y217Q, S024G-S053G-T055P-N061P-S078N-G097A-G128A-Y217Q, S024G-T055P-N061P-G097A-G128A-Y217Q, S024G-S038G-S053G-S078N-S101N-G128A-Y217Q, S053G-S078N-G097A-S101N-G128A-Y217Q, N025G-S078N-G097A-G128A-Y217Q, and S024G-N025G-S053G-N061P-G097A-G128A-S130G-Y217Q, wherein positions of the variant are numbered by correspondence with the sequence of SEQ ID NO:2. Such variants have proteolytic activity. The invention includes a protease variant having proteolytic activity, a PI value of about 0.9 relative to BPN'-v3, and/or an enhanced proteolytic activity compared to BPN' in this assay, the variant comprising an amino acid sequence having at least 60%, 70%, 80%, 85%, 90%, 91%, 92%, 93%, 94%, 95%, 96%, 97%, or 98% identity to the sequence of SEQ ID NO:2 and at least one set of amino acid substitutions selected from said group above, wherein amino acid positions of the variant are numbered by correspondence with positions of the SEQ ID NO:2 sequence. Also included are compositions, including, but not limited to, e.g., cleaning compositions, comprising at least one such variant and methods for cleaning utilizing at least one such variant as described in greater detail elsewhere herein.

The following BPN' variant was determined to have a PI value of about 0.8 relative to BPN'-v3 in an egg microswatch cleaning assay in Detergent Composition 4 at pH 8 and 16° C.: BPN' amino acid sequence (SEQ ID NO:2) comprising amino acid substitutions S024G-S053G-S078N-G097A-S101N-G128A-Y217Q, wherein positions of the variant are numbered by correspondence with the sequence of SEQ ID NO:2. The invention includes a protease variant having proteolytic activity, a PI value of about 0.8 relative to BPN'-v3, and/or an enhanced proteolytic activity compared to BPN' in this assay, the variant comprising an amino acid sequence having at least 60%, 70%, 80%, 85%, 90%, 91%, 92%, 93%, 94%, 95%, 96%, 97%, or 98% identity to the sequence of SEQ ID NO:2 and comprising amino acid substitutions S024G-S053G-S078N-G097A-S101N-G128A-Y217Q, wherein amino acid positions of the variant are numbered by correspondence with positions of the SEQ ID NO:2 sequence. Also included are compositions, including, but not limited to, e.g., cleaning compositions, comprising at least one such variant and methods for cleaning utilizing at least one such variant as described in greater detail elsewhere herein.

The following BPN' variants were determined to have a PI value greater than 1.0, at least 1.1, at least 1.2, at least 1.3, at least 1.4, at least 1.5, at least 1.6, at least 1.7, at least 1.8, at least 1.9, at least 2, from greater than 1.0 to about 10, from greater than 1 to about 12, from greater than 4 to about 12, from greater than 1.0 to about 8, or from greater than 1.0 to about 5 relative to BPN'-v3 in an AAPF proteolytic assay: BPN' amino acid sequence (SEQ ID NO:2) comprising at least one set of amino acid substitutions selected from the group consisting of S024G-G097A-S101N-G128A-Y217Q, S101N-G128A-Y217Q, N025G-T055P-N061P-S078N-S101N-G128A-Y217Q, S053G-T055P-N061P-S101N-G128A-Y217Q, S024G-T055P-N061P-G097A-S101N-G128A, S053G-T055P-S078N-G097A-S101N-G128A-Y217Q, N025G-S053G-N061P-S078N-S101N-G128A-Y217Q, S024G-S053G-T055P-N061P-S101N-G128A-Y217Q, S024G-N025G-S053G-T055P-N061P-G097A-S101N-G128A-Y217Q, S024G-N025G-N061P-S078N-G097A-S101N-G128A, N061P-S101N-G128A-Y217Q, S024G-N025G-S053G-N061P-S078N-S101N-G128A-Y217Q, S024G-T055P-N061P-S078N-S101N-G128A-Y217Q, N025G-S053G-T055P-N061P-S078N-G097A-S101N-G128A-Y217Q, S024G-N025G-S053G-T055P-S101N-G128A-Y217Q, N025G-T055P-N061P-S078N-G097A-S101N-G128A-Y217Q, S024G-N025G-N061P-S078N-S101N-G128A-Y217Q, S024G-N025G-S053G-T055P-N061P-G128A-Y217Q, S024G-S053G-T055P-N061P-G097A-S101N-G128A-Y217Q, S024G-N025G-S053G-N061P-S078N-G097A-S101N-G128A-Y217Q, T055P-N061P-S078N-G128A-Y217Q, S024G-S053G-T055P-N061P-S078N-G097A-S101N-G128A-Y217Q, N025G-S038G-S053G-N061P-S078N-G097A-S101N-G128A-Y217Q, S024G-N025G-T055P-N061P-S078N-G097A-S101N-G128A-Y217Q, S024G-N025G-S053G-N061P-G128A-Y217Q, N025G-S053G-N061P-S078N-G128A-Y217Q, S024G-N025G-S053G-T055P-G097A-S101N-G128A-Y217Q, S024G-N025G-S053G-T055P-S078N-S101N-G128A-Y217Q, T055P-N061P-S078N-G097A-S101N-G128A-Y217Q, S024G-N025G-S053G-T055P-N061P-S078N-G128A-Y217Q, S024G-N025G-N061P-G097A-S101N-G128A-Y217Q, S053G-N061P-G097A-S101N-G128A-Y217Q-S249N, N025G-S053G-T055P-S078N-G097A-S101N-G128A-Y217Q, S024G-T055P-G097A-G128A-Y217Q, T055P-N061P-G097A-

A116S-G128A, S024G-N025G-T055P-G097A-S101N-G128A-Y217Q, S024G-N025G-N061P-S078N-G097A-S101N-G128A-Y217Q, S053G-T055P-G097A-S101N-G128A-Y217Q, T055P-G097A-S101N-G128A-Y217Q, S024G-N061P-G097A-S101N-G128A-Y217Q, S024G-S053G-T055P-G097A-S101N-G128A-Y217Q, G097A-G128S-Y217Q, S024G-S053G-N061P-G097A-G128A-Y217Q, S024G-N025G-N061P-G097A-G128A-Y217Q, S024G-N061P-S078N-G097A-S101N-G128A-Y217Q, S024G-S053G-T055P-N061P-S078N-G097A-G128A-Y217Q, S024G-S053G-S078N-S101N-G128A-Y217Q, S024G-N025G-S053G-T055P-N061P-S078N-G097A-G128A-Y217Q, S053G-N061P-S078N-G097A-G128A-Y217Q, S024G-T055P-N061P-G097A-G128A-Y217Q, S024G-S038G-S053G-S078N-S101N-G128A-Y217Q, S053G-G097A-S101N-G128A-Y217Q, N025G-T055P-G097A-G128A-Y217Q, S024G-T055P-S078N-G097A-S101N-G128A-Y217Q, S053G-S078N-G097A-S101N-G128A-Y217Q, S024G-N025G-T055P-G097A-G128A-Y217Q, S024G-N025G-S053G-T055P-G097A-G128A-Y217Q, N025G-S078N-G097A-S101N-G128A-Y217Q, N025G-G097A-S101N-G128A-Y217Q, S024G-S053G-N061P-S078N-G097A-G128A-Y217Q, S024G-S053G-S078N-G097A-S101N-G128A-Y217Q, N025G-S078N-G097A-G128A-Y217Q, and S024G-N025G-S053G-N061P-G097A-G128A-S130G-Y217Q, wherein amino acid positions of the variant are numbered by correspondence with the sequence of SEQ ID NO:2. Such variants have enhanced proteolytic activity compared to BPN' protease (SEQ ID NO:2) and a greater PI value than that of BPN' in this assay. The invention includes a protease variant having enhanced proteolytic activity compared to BPN' (SEQ ID NO:2) and/or a PI value of greater than 1.0 to about 5 relative to BPN'-v3 in this AAPF assay, the variant comprising an amino acid sequence having at least 60%, 70%, 80%, 85%, 90%, 91%, 92%, 93%, 94%, 95%, 96%, 97%, or 98% identity to the sequence of SEQ ID NO:2 and comprising at least one set of amino acid substitutions selected from said group above, wherein amino acid positions of the variant are numbered by correspondence with amino acid positions of the SEQ ID NO:2 sequence.

The following BPN' variant was determined to have a PI value of about 1.0 relative to BPN'-v3 in an AAPF proteolytic assay: BPN' amino acid sequence (SEQ ID NO:2) comprising amino acid substitutions G097A-G128A-Y217Q, wherein amino acid positions of the variant are numbered by correspondence with the sequence of SEQ ID NO:2. Such variants have enhanced proteolytic activity compared to BPN' protease (SEQ ID NO:2) and a greater PI value than that of BPN' in this assay. The invention includes a protease variant having enhanced proteolytic activity compared to BPN' (SEQ ID NO:2) and/or a PI value of about 1.0 relative to BPN'-v3 in this AAPF assay, the variant comprising an amino acid sequence having at least 60%, 70%, 80%, 85%, 90%, 91%, 92%, 93%, 94%, 95%, 96%, 97%, or 98% identity to the sequence of SEQ ID NO:2 and comprising amino acid substitutions G097A-G128A-Y217Q, wherein amino acid positions of the variant are numbered by correspondence with amino acid positions of the SEQ ID NO:2 sequence. Also included are compositions, including, but not limited to, e.g., cleaning compositions, comprising at least one such variant and methods for cleaning utilizing at least one such variant as described in greater detail elsewhere herein.

Example 7

Construction of Site Evaluation Libraries of BPN'-v36 and Cleaning Performance of BPN'-v36 Variants Construction of the Site Evaluation Libraries of BPN'-v36

The amino acid sequence of BPN'-v36 is set forth in SEQ ID NO:6 below:

(SEQ ID NO: 6)
AQSVPYGVSQIKAPALHSQGYTGGNVKVAVIDSGIDSSHPDLKVAGGASM

VPGETNPFQDNNSHGTHVAGTVAALNNNIGVLGVAPSASLYAVKVLGADG

NGQYSWIINGIEWAIANNMDVINMSLGAPSGSAALKAAVDKAVASGVVVV

AAAGNEGTSGSSSTVGYPGKYPSVIAVGAVDSSNQRASFSSVGPELDVMA

PGVSIQSTLPGNKYGAQNGTSMASPHVAGAAALILSKHPNWTNTQVRSSL

ENTTTKLGDSFYYGKGLINVQAAAQ

The nucleic acid sequence encoding the BPN'-v36 protease variant is:

(SEQ ID NO: 5)
Gcgcagtccgtgccttacggcgtatcacaaattaaagccctgctctgca ctctcaaggctacactggaggcaatgttaaagtagcggttatcgacagcg gtatcgactcgagccatccagatcttaaagtcgctggaggggcttctatg gtgccgggcgaaacaaacccgtttcaagataacaattctcatgcacaca cgtcgcaggaacggttgcggcgttaaacaataatattggcgtgcttggtg tagccccgtctgcttcgctctacgccgttaaagttcttggcgcagacgga aatggccaatactcatggattatcaacggcatcgaatgggccatcgcgaa taacatggatgtaatcaacatgagcctgggagcaccaagcggcagtgcgg cacttaaagcagcagttgataaagctgttgcatctggtgtcgtcgtagta gcggcagctgggaatgagggaacatccggatcatcgagtaccgtcggtta tccaggcaagtaccttcagtgattgcagtgggcgctgtagactcttcaa atcaacgtgcctcttttcctccgtgggaccggagctggatgtcatggcc cctggcgtttctattcaatcgacgcttccagggaacaagtatggtgcgca aaacgggacttccatggcctcgccgcatgtagctggggcggccgcattga ttctttctaagcacccgaactggacaaacactcaagtccgcagcagttta gaaaacaccactacaaaacttggtgattctttctactatggaaaagggct gatcaacgtacaggcggcagctcag The amino acid sequence of BPN'-v36 may be represented by reference to the subtilisin BPN' amino acid sequence of SEQ ID NO:2. That is, BPN'-v36 may be represented as the subtilisin BPN' sequence of SEQ ID NO:2 with the six amino acid substitutions S024G-S053G-S078N-S101N-G128A-Y217Q. The BPN'-v36 amino acid sequence may be conveniently designated as BPN'-S024G-S053G-S078N-S101N-G128A-Y217Q or BPN'+S024G+S053G+S078N+S101N+G128A+Y217Q. Throughout this specification, unless otherwise indicated, each amino acid position of an amino acid sequence is numbered according to the numbering of a corresponding amino acid position in the amino acid sequence of *Bacillus amyloliquefaciens* subtilisin BPN' shown in SEQ ID NO:2 as determined by alignment of the variant amino acid sequence with the *Bacillus amyloliquefaciens* subtilisin BPN' amino acid sequence.

Site evaluation libraries (SELs) were created at every single amino acid position in mature BPN'-v36 (i.e., BPN'-S24G-S53G-S78N-S101N-G128A-Y217Q) protein by PCR fusion.

For each codon to be mutated in the BPN'-v36 protease, a pair of partially overlapping, complementary (mutagenic forward and reverse) primers were designed. Each mutagenic primer contained the NNS (N=A, C, G, or T and S=G or C) mutagenic codon in the center flanked by at least 15 nucleotides on each side. To create a library at a given position, two PCR reactions were carried out using either a common forward gene-flanking primer (P4974, GCCTCACATTTGTGCCACCTA; SEQ ID NO:60) and a mutagenic NNS reverse primer, or the common reverse gene-flanking primer (P4976, CCTCTCGGTTATGAGTTAGTTC; SEQ ID NO:61) and a mutagenic NNS forward primer. These PCR reactions generated two PCR fragments, one encoding the 5' half of the mutant BPN'-v36 gene (5' gene fragment) and the other encoding the 3' half of the mutant BPN'-v36 gene (3' gene fragment).

Figure 4:
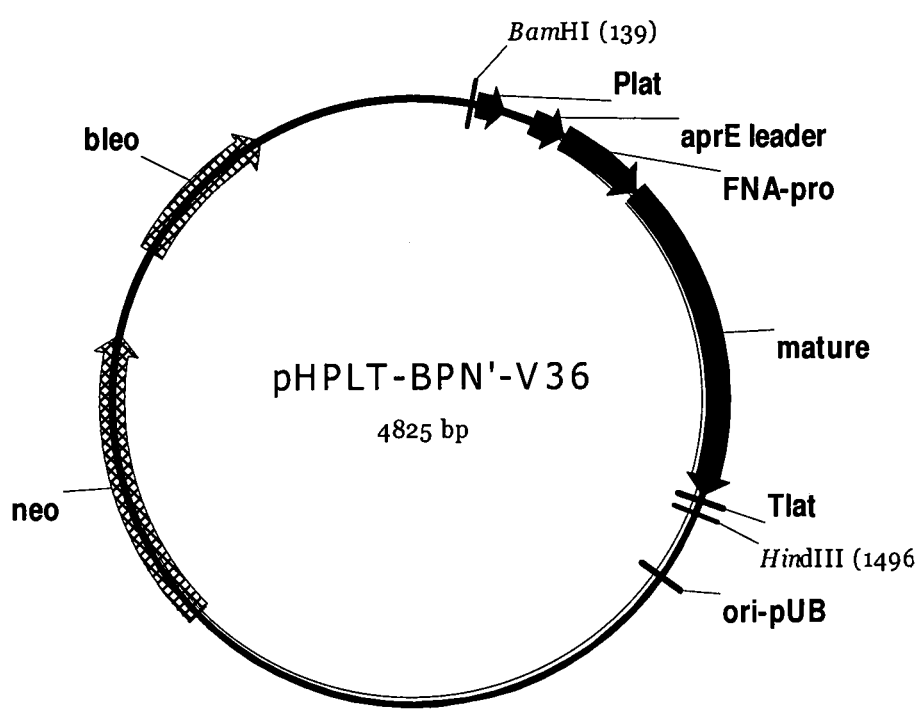
FIG. 4 provides a plasmid map of pHPLT-BPN'-v36.

Each PCR amplification reaction contained 30 pmol of each primer and 100 ng of the BPN'-v36 parent template DNA (plasmid pHPLT-BPN'-v36, see FIG. 4). Amplifications were carried out using Vent DNA polymerase (NEB). The PCR reaction (20 μL) was initially heated at 95° C. for 2.5 min followed by 30 cycles of denaturation at 94° C. for 15 sec., annealing at 55° C. for 15 sec. and extension at 72° C. for 40 sec. Following amplification, the 5' and 3' gene fragments were gel-purified by the QIAGEN® gel-band purification kit, mixed (50 ng of each fragment), mixed and amplified by PCR once again using the primers P4973 (AAAGGATCCTAATCGGCGCTTTTC; SEQ ID NO:62) and P4950 (CTTGTCTCCAAGCTTAAAATAAAA; SEQ ID NO:63) to generate the full-length gene fragment. The PCR conditions were same as described above, except the extension phase, which was carried out at 72° C. for 2 min. The full-length DNA fragment was gel-purified by the QIAGEN® gel-band purification kit, digested by the BamHI and HindIII restriction enzymes and ligated with the pHPLT-BPN' partial opt vector that also was digested with the same restriction enzymes. Ligation mixtures were amplified using rolling circle amplification in an Illustra Templiphi kit according to the manufacturer's recommendation (GE Healthcare) to generate multimeric DNA for transformation into *Bacillus subtilis*. For this purpose, 1 μl of the ligation mixture was mixed with 5 μl of the sample buffer, heated to 95° C. for 3 min and cooled on ice. Next, 5 μl of the reaction buffer and 0.2 μl of the enzyme were added to each tube, followed by incubation at 30° C. for 10 hours. Products of the rolling circle amplification were diluted 100 times and used to transform *B. subtilis* cells (ΔaprE, ΔnprE, amyE::xylRPxylAcomK-phleo). An aliquot of the transformation mix was plated on LB plates containing 1.6% skim milk and 10 μg/mL neomycin and incubated overnight at 37° C. Subsequently, the colonies with halos were inoculated in 150 μl of LB media containing 10 μg/mL neomycin. The next day, cultures were either frozen with 15% glycerol or grown in MBD medium for biochemical analysis as described in Example 2.

Cleaning Performance of the BPN'-v36 Variants

Protein variants from BPN'-v36 SEL were tested for cleaning performance using a BMI microswatch assay in Detergent Composition 4 at 16° C. and egg microswatch assay in Detergent Composition 4 at 16° C. and pH 8. Protein content was determined using the TCA assay. The assays were performed as described in Example 1 and the Performance Indices were calculated relative to BPN'-v36 (i.e., BPN'-S24G-S53G-S78N-S101N-G128A-Y217Q) (with a PI value of 1.0).

The following BPN'-v36 variants were determined to have a PI value greater than 1.0, at least 1.1, at least 1.2, at least 1.3, at least 1.4, at least 1.5, at least 1.6, at least 1.7, at least 1.8, at least 1.9, at least 2, from greater than 1.0 to about 10, from greater than 1.0 to about 8, or from greater than 1.0 to about 5 relative to BPN'-v36 in a BMI microswatch cleaning assay in Detergent Composition 4 at pH 8 and 16° C.: BPN'-S024G-S053G-S078N-S101N-G128A-Y217Q (SEQ ID NO:6) (i.e., BPN'-v36) comprising at least one amino acid substitution selected from the group consisting of A116V, G160S, I111L, I115V, N109S, N117M, P005G, Q059V, T164S, Y262M, A015Q, A015S, A098E, A098N, A098S, A098T, A098V, A098Y, A114S, A114T, A116G, A116L, A116S, A116T, A116W, A133G, A133H, A133T, A133V, A137G, A137I, A137L, A137S, A137T, A138S, A216E, A216F, A216V, D099S, D181E, F261A, F261Q, G024F, G024I, G024Q, G024Y, G097S, G160T, G211L, G211V, H017F, H017W, H039V, H226A, I031V, I111V, I268V, K170R, K265R, L016Q, L016T, L135M, L209T, L209V, L233M, L257T, L257V, L267A, L267V, N025A, N025I, N025Q, N025R, N025T, N025V, N101I, N101Q, N101S, N109A, N109G, N109H, N109L, N109M, N109Q, N109T, N117Q, N184A, N184L, N184T, N184W, N212G, N212L, N212V, N243P, N252G, N252M, P005T, P014S, P040G, P040L, P040Q, P129A, P129S, P172G, P172S, P194Q, P210A, P210S, Q185F, Q185G, Q185I, Q185M, Q185N, Q185S, Q275H, R186K, S009A, S009G, S009H, S009M, S018T, S130T, S132N, S145K, S159T, S161I, S161K, S161N, S161T, S162I, S162M, S162Y, S163G, S182F, S182G, S182V, S182W, S183F, S183L, S183M, S183T, S183V, S183W, S224A, S236T, S249V, T022A, T022G, T022Q, T022V, T208V, T242S, T253N, T253S, T254A, T254S, T255L, T255S, T255V, V004A, V004P, V004W, V084C, V139C, V165M, V203F, Y021K, Y021N, Y021T, Y021V, Y167F, Y171F, Y214F, Y262F, and Y262T, wherein amino acid positions of the variant are numbered by correspondence with the sequence of SEQ ID NO:2. Such variants have enhanced proteolytic activity compared to BPN' (SEQ ID NO:2) and a greater PI value than that of BPN' in this assay. The invention includes a protease variant having enhanced proteolytic activity compared to BPN' (SEQ ID NO:2), enhanced proteolytic activity compared to BPN'-v3 and BPN'-v36, a PI value greater than that of BPN'-v3, and/or a PI value greater than 1 to about 5 relative to BPN'-v36 in this BMI microswatch cleaning assay, the variant comprising an amino acid sequence having at least 60%, 70%, 80%, 85%, 90%, 91%, 92%, 93%, 94%, 95%, 96%, 97%, 98%, or 99% identity to the sequence of SEQ ID NO:2 or SEQ ID NO:6 and comprising at least one, two, three, four, five, six or more amino acid substitutions selected from said group above, wherein amino acid positions of the variant are numbered by correspondence with amino acid positions of the SEQ ID NO:2 sequence. Also included are compositions, including, but not limited to, e.g., cleaning compositions, comprising at least one such variant and methods for cleaning utilizing at least one such variant as described in greater detail elsewhere herein.

The following BPN'-v36 variants were determined to have a PI value of about 1.0 relative to BPN'-v36 in a BMI microswatch cleaning assay in Detergent Composition 4 at pH 8 and 16° C.: BPN'-S024G-S053G-S078N-S101N-G128A-Y217Q amino acid sequence (SEQ ID NO:6) comprising at least one amino acid substitution selected from the group consisting of A001G, A001Y, A013G, A013V, A015F, A015G, A015K, A015M, A015P, A015T, A015W, A015Y, A029G, A073S, A088C, A088I, A088L, A088T, A088V, A098D, A098K, A098P, A098R, A098W, A116D, A116E, A116R, A128S, A133L, A133M, A133S, A134G, A134S, A137N, A137V, A144M, A144Q, A144S, A144T, A144V, A151C, A176S, A176T, A179S, A216G, A216L, A216P, A216Q, A216S, A216T, A216Y, A228T, A230C, A231C, A272I, A272L, A272Q, A272S, A272T, A272W, A273S, A274G, A274L, A274Q, A274T, A274V, D041E, D099G, D099N, D120A, D120K, D120Q, D120R, D120S, D140E, D181S, D259E, E054D, E156D, E156T, E251V, F261G, F261H, F261L, F261R, F261S, F261T, F261V, F261W, G007A, G007S, G020A, G020D, G020S, G024N, G024R, G024S, G024T, G024V, G024W, G053H, G053K, G053N, G053T, G097A, G097D, G097T, G131A, G131H, G131P, G131Q, G131T, G131V, G160H, G160P, G166A, G166S, G166T, G211A, G211D, G211M, G211N, G211P, G211Q, G211R, G211W, G215A, G215N, G215V, H017L, H017M, H017T, H017V, H017Y, H039A, H039C, H039N, H226F, H226I, H226M, H226S, H226V, H226Y, I035V, I079A, I079S, I079T, I079V, I079W, I108V, I115L, I122A, I234L, I234V, K012R, K027R, K136R, K141F, K213W, K237R, K256R, K265Q, L016A, L016F, L016I, L016S, L016V, L042I, L075A, L075M, L075Q, L075V, L075Y, L082K, L082M, L082Q, L082V, L090I, L196I, L196V, L209Q, L209W, L233A, L233Q, L233V, L235I, L235K, L250I, L257A, L257H, L257L, L257S, L257Y, L267Q, L267R, L267S, L267T, M199V, N025F, N025G, N025H, N025K, N025L, N025M, N025S, N025Y, N061F, N061H, N061P, N061S, N061T, N061V, N061W, N076G, N076W, N078S, N078T, N078V, N101A, N101H, N101L, N101T, N109K, N109R, N117A, N117E, N117H, N117K, N118G, N184G, N184H, N184I, N184S, N184V, N212A, N212F, N212I, N212K, N212P, N212Q, N212S, N212Y, N218A, N218H, N218L, N218S, N240E, N240H, N240L, N240R, N240T, N243A, N243Q, N243T, N243V, N252A, N252K, N252L, N252Q, N252R, N252S, N252T, N269Q, N269S, P014G, P014Q, P014T, P040A, P040H, P040S, P040T, P040V, P040Y, P086A, P086C, P086F, P086H, P086S, P129D, P129G, P129K, P129T, P172A, P172Q, P194A, P194G, P194L, P194M, P194S, P194V, P194Y, P210G, P210R, P210V, Q002A, Q002S, Q010A, Q010F, Q010H, Q010I, Q010L, Q010N, Q010S, Q010T, Q019A, Q019G, Q019N, Q019S, Q019T, Q019V, Q019W, Q059I, Q103L, Q103S, Q185A, Q185H, Q185L, Q185Y, Q206P, Q206S, Q206Y, Q217I, Q217N, Q217S, Q217T, Q245K, Q275D, Q275S, Q275W, S003A, S003G, S003H, S003M, S003P, S003Q, S003T, S003V, S009I, S009L, S009P, S009T, S009W, S018A, S018G, S018I, S018L, S018M, S018N, S018P, S018V, S018W, S033T, S037Q, S037T, S037V, S038G, S038H, S038K, S038Q, S038T, S063K, S063N, S063Q, S063T, S087A, S087F, S087G, S087Q, S087T, S089L, S089M, S089N, S089Q, S089T, S089W, S130A, S130F, S130G, S130L, S130V, S145A, S145H, S145M, S145V, S159A, S159G, S159H, S159Q, S159R, S161A, S161G, S161H, S161L, S161M, S161P, S161Q, S161W, S162A, S162F, S162G, S162L, S162N, S162P, S162R, S162V, S163P, S173A, S173G, S182A, S182H, S182K, S182L, S182N, S182P, S182Q, S182T, S183A, S183G, S183H, S183Q, S188A, S188G, S188T, S188V, S191A, S204A, S204I, S204L, S204Q, S204V, S224C, S236A, S236N, S236Q, S248A, S248F, S248G, S248I, S248K, S248L, S248M, S248N, S248Q, S248T, S248V, S249A, S249C, S249H, S249Q, S249T, S249W, S249Y, S260H, S260N, S260P, S260T, T022H, T022K, T022N, T022R, T022S, T022Y, T055A, T055G, T055L, T055N, T055P, T055Q, T071S, T158H, T158S, T164N, T208C, T208L, T220S, T242N, T244A, T244G, T244H, T244I, T244Q, T244S, T244V, T244W, T253A, T253G, T253H, T253Q, T254V, T255A, T255G, T255H, T255I, T255Q, T255Y, V004G, V004N, V004R, V008A, V008C, V008M, V026I, V044I, V044L, V045H, V045K, V045L, V045M, V045Q, V045S, V045V, V045W, V045Y, V051I, V081L, V081Q, V081T, V084A, V084S, V084T, V093I, V121I, V143N, V143S, V143Y, V147C, V147I, V147L, V147T, V180I, V180L, V180T, V192A, V192S, V192T, V198I, V198L, V198M, V203H, V203I, V203L, V203N, V203Q, V203T, V203W, V203Y, V270A, V270S, V270T, W241M, W241Y, Y006G, Y006H, Y006I, Y006K, Y006L, Y006P, Y006Q, Y006T, Y006V, Y006W, Y021A, Y021D, Y021E, Y021L, Y021Q, Y021R, Y021S, Y104F, Y104I, Y214L, Y214V, Y214W, Y262A, Y262G, Y262L, Y262N, Y262S, Y262W, Y263G, and Y263W, wherein amino acid positions of the variant are numbered by correspondence with the sequence of SEQ ID NO:2. Thus, e.g., the invention includes BPN'-S024G-S053G-S078N-S101N-G128A-Y217Q amino acid sequence (SEQ ID NO:6) comprising substitution A128S, e.g., BPN'-S024G-S053G-S078N-S101N-G128S-Y217Q. Such variants have enhanced proteolytic activity compared to BPN' (SEQ ID NO:2) and a greater PI value than that of BPN' in this assay. The invention includes a protease variant having enhanced proteolytic activity compared to BPN' (SEQ ID NO:2), a PI value of about 1.0 relative to BPN'-v3, and/or a PI value of about 1.0 relative to BPN'-v36 in this BMI microswatch cleaning assay, the variant comprising an amino acid sequence having at least 60%, 70%, 80%, 85%, 90%, 91%, 92%, 93%, 94%, 95%, 96%, 97%, 98%, or 99% identity to the sequence of SEQ ID NO:2 or SEQ ID NO:6 and comprising at least one, two, three, four, five, six or more amino acid substitutions selected from said group above, wherein amino acid positions of the variant are numbered by correspondence with amino acid positions of the SEQ ID NO:2 sequence. Also included are compositions, including, but not limited to, e.g., cleaning compositions, comprising at least one such variant and methods for cleaning utilizing at least one such variant as described in greater detail elsewhere herein.

The following BPN'-v36 variants were determined to have a PI value of about 0.9 relative to BPN'-v36 in a BMI microswatch cleaning assay in Detergent Composition 4 at pH 8 and 16° C.: BPN'-S024G-S053G-S078N-S101N-G128A-Y217Q amino acid sequence (SEQ ID NO:6) comprising at least one amino acid substitution selected from the group consisting of A001F, A001K, A001L, A001M, A001Q, A001R, A001S, A001T, A001V, A013C, A013S, A015D, A015E, A015L, A015R, A048S, A073N, A073T, A074G, A074S, A085C, A085G, A085S, A085V, A088M, A088S, A092S, A098G, A114G, A133P, A137E, A137H, A144G, A144H, A144K, A144L, A144N, A153S, A153V, A176C, A179G, A187G, A187S, A200G, A216W, A223S, A228S, A230T, A230V, A231V, A232C, A232V, A272E, A272G, A272K, A272P, A273G, A273L, A273V, A274M, A274R, D036E, D099A, D099Q, D120E, D181A, D181G, D259A, D259G, D259Q, D259T, E156A, E156S, E251I, E251L, E251Q, E251T, F058Y, F261C, F261D, F261K, F261P, G020E, G020F, G020H, G020L, G020N, G020Q, G020R, G020T, G020Y, G024A, G024P, G053A, G053D, G053E, G053F, G053L, G053Q, G053S, G053Y, G097K, G097M, G157A, G157S, G160A, G160L, G166C, G166I, G166Q, G169A, G211K, G215H, G215L, G215S, G215T, G215W, G258S, H017I, H039S, H226L, H238N, H238Y, I011L, I011V, I031L, I079F, I079K, I079L, I079M, I079Q, I205A, I205V, I268L, I268M, K012G, K043F, K043H, K043I, K043N, K043Q, K043T, K141A, K141R, K141W, K170A, K213A, K213G, K213H, K213I, K213L, K213N, K213Q, K213R, K213S, K213T, K213V, K237A, K237H, K237I, K237L, K237N, K237S, K256A, K256G, K256H, K256M, K256P, K256Q, K256W, K265H, L016E, L042V, L075G, L075H, L075I, L075T, L082A, L082F, L082H, L082R, L082S, L082T, L090M, L135F, L196M, L209C, L209H, L209S, L233S, L235M, L235R, L235W, L257C, L257G, L267F, M050Y, M119C, M119I, M124L, N025C, N025E, N025P, N061A, N061G, N061I, N061K, N061L, N061Q, N061R, N062S, N062T, N076A, N076P, N076Q, N076S, N076T, N076V, N078G, N078H, N078K, N078P, N078Q, N078R, N101F, N117R, N117S, N118D, N118H, N118Q, N118R, N118S, N118T, N184C, N184E, N184R, N212D, N212R, N212W, N218F, N218G, N218M, N218P, N218T, N218V, N218W, N240A, N240G, N240Q, N240S, N240W, N243C, N243G, N243S, N252V, N269H, P005A, P005D, P005M, P005Q, P014A, P014M, P014R, P014V, P040F, P040R, P040W, P129E, P129R, P172E, P172K, P194H, P194R, P194W, P201A, P201G, P210L, P239K, P239R, Q002D, Q002E, Q002G, Q002I, Q002P, Q002V, Q010D, Q010R, Q019C, Q019D, Q019E, Q019H, Q019L, Q019P, Q019R, Q059A, Q059E, Q059L, Q059S, Q059T, Q103W, Q185D, Q185K, Q185R, Q185W, Q206G, Q206H, Q206L, Q206V, Q206W, Q217E, Q217F, Q217H, Q217L, Q217V, Q245M, Q271A, Q271D, Q271G, Q271L, Q271P, Q271T, Q271Y, Q275F, Q275L, Q275P, Q275R, S003D, S003F, S003K, S003R, S009K, S018D, S018R, S037A, S037G, S037K, S037L, S037P, S038M, S063A, S063F, S063G, S063M, S063R, S063Y, S087C, S087K, S087L, S087M, S087N, S087Y, S089A, S089D, S089F, S089G, S089H, S089I, S089K, S089R, S089V, S089Y, S130D, S130E, S130K, S130W, S145G, S145L, S145R, S145T, S159D, S159L, S159W, S161E, S161R, S162C, S162E, S162W, S163A, S182E, S182R, S183C, S183D, S183P, S183R, S188D, S188P, S204G, S204Y, S207G, S224G, S224T, S236C, S236G, S248D, S248H, S248R, S249E, S249L, S249R, S260A, S260G, S260K, S260Q, S260V, S260Y, T022L, T055D, T055E, T055I, T055K, T055M, T055S, T055V, T055Y, T158A, T158G, T158L, T158Q, T158V, T164K, T164Q, T208S, T244D, T244E, T244R, T253E, T253R, T253Y, T254G, T255D, T255E, T255K, T255R, V026A, V028I, V028L, V030I, V044C, V044P, V045E, V045G, V045N, V072L, V081A, V081G, V081H, V081S, V084I, V084M, V095A, V095C, V143A, V143F, V143H, V143Q, V143T, V143W, V147A, V147Q, V147S, V148I, V148L, V149C, V149I, V149L, V165L, V180A, V180C, V180M, V192C, V192F, V192I, V192Q, V192Y, V203A, V203G, V203K, V203S, V270C, V270L, V270P, W241F, Y006A, Y006M, Y006N, Y006R, Y006S, Y021C, Y091W, Y104V, Y104W, Y262C, Y262D, Y262E, Y262H, Y262I, Y262R, and Y262V, wherein amino acid positions of the variant are numbered by correspondence with the sequence of SEQ ID NO:2. Such variants may have enhanced proteolytic activity compared to BPN' (SEQ ID NO:2) and/or a greater PI value than that of BPN' in this assay. The invention includes a protease variant having proteolytic activity and/or a PI value of about 0.9 relative to BPN'-v36 in this BMI microswatch cleaning assay, the variant comprising an amino acid sequence having at least 60%, 70%, 80%, 85%, 90%, 91%, 92%, 93%, 94%, 95%, 96%, 97%, 98%, or 99% identity to the sequence of SEQ ID NO:2 or SEQ ID NO:6 and comprising at least one, two, three, four, five, six or more amino acid substitutions selected from said group above, wherein amino acid positions of the variant are numbered by correspondence with amino acid positions of the SEQ ID NO:2 sequence. Also included are compositions, including, but not limited to, e.g., cleaning compositions, comprising at least one such variant and methods for cleaning utilizing at least one such variant as described in greater detail elsewhere herein.

The following BPN'-v36 variants were determined to have a PI value equal to or greater than 0.5 and less than 0.9 relative to BPN'-v36 in a BMI microswatch cleaning assay in Detergent Composition 4 at pH 8 and 16° C.: BPN'-S24G-S53G-S78N-S101N-G128A-Y217Q amino acid sequence (SEQ ID NO:6) comprising at least one amino acid substitution selected from the group consisting of A001D, A001H, A001N, A015C, A048C, A048E, A085T, A133R, A137R, A142C, A144D, A144R, A152S, A153G, A187P, A187Q, A187T, A187V, A216R, A230S, A272R, A273H, A273T, A274H, D036N, D036S, D181H, D181T, D259N, D259P, D259S, E156G, E156H, E156L, E156Q, E156V, E251C, F189S, F189T, F189W, F189Y, F261E, G020C, G024D, G053M, G053R, G097R, G131R, G131E, G157N, G160R, G160V, G166L, G166W, G211E, G215D, G258A, G258D, G258P, I011T, I031C, I079E, I079R, I175L, I205C, K012H, K012N, K027A, K027N, K027S, K043A, K043D, K043E, K043G, K043L, K043M, K043P, K043V, K043W, K043Y, K136H, K141H, K141L, K141M, K141N, K141Q, K141T, K141V, K170G, K170S, K237T, K237V, K256D, K256S, K256T, K256V, K265N, K265S, L042F, L042M, L082E, L209A, L209E, L209G, L209R, L233G, L235V, L257D, L257E, L257P, L257R, L257W, L267E, M050L, N056D, N056S, N061C, N061D, N062A, N062H, N062L, N062V, N062Y, N076D, N076L, N076M, N078D, N078F, N101D, N101R, N118A, N212C, N212E, N218C, N218D, N218E, N252D, N252E, P014F, P014K, P057A, P057W, P172R, P194E, P201T, P210E, Q059C, Q059D, Q059R, Q185E, Q206D, Q217A, Q217K, Q217R, Q245A, Q245D, Q245E, Q245H, Q245R, Q271E, Q271F, Q271R, Q271W, Q275G, Q275I, R186I, R186L, R186V, R186W, S003E, S009C, S009E, S018C, S037D, S037E, S037H, S037R, S037Y, S038D, S038P, S038R, S038Y, S063L, S087D, S087R, S089C, S089E, S130C, S130W, S145D, S159C, S159P, S161C, S173T, S182C, S188E, S188F, S188K, S188L, S188R, S188W, S190A, S190G, S190T, S204R, S236D, S236E, S248C, S248E, S260C, S260E, S260R, T022P, T055C, T055W, T071A, T158D, T158E, T158P, T158R, T158Y, T164R, T242D, T242G, T255C, V004E, V004T, V045C, V045D, V045R, V045T, V051H, V081R, V143C, V143E, V143G, V192G, V203C, V203D, V203E, V203M, V203R, V270G, W241L, Y214H, Y214Q, A001E, A133E, A187L, A187N, A216C, A216H, A273Q, D099H, D259H, E156C, E195G, F189H, G131C, G146A, G166V, G215C, G215E, I107L, K012A, K012S, K012T, K043C, K170C, K256C, K256E, K265G, K265Y, L233E, M222F, M222S, N062Q, N076E, N078E, N184P, N218R, P005V, P014D, Q002K, Q002L, Q002R, Q010W, Q271C, R186H, S049C, S063C, S063D, S105T, S188C, S190C, S204E, T055R, T164G, V004D, V044T, V045I, V165C, V180S, Y006C, Y006D, Y006E, Y104T, A001C, A187C, A230G, A273D, A273P, D036Q, F189G, F189L, F189R, G157T, G178A, I031F, I111M, K012F, K012L, K027T, K043R, K136G, K141G, K170Q, M222A, M222L, N062R, N117G, N269C, P005W, P129V, P239A, P239H, P239T, Q059W, Q217G, Q275A, R186A, S191G, T164A, T220A, A001P, A187F, A187W, A273R, D041C, D060G, D197T, F189A, G046D, G157P, K012C, K012E, K012W, L042C, M222T, N062C, P239G, P239N, Q217C, R186M, S049T, S089P, S125A, S173V, and V044A, wherein amino acid positions of the variant are numbered by correspondence with amino acid positions of the SEQ ID NO:2 sequence. Such variants have proteolytic activity. The invention includes a protease variant having proteolytic activity and/or a PI value equal to or greater than 0.5 and less than 0.9 relative to BPN'-v36 in this BMI microswatch cleaning assay, the variant comprising an amino acid sequence having at least 60%, 70%, 80%, 85%, 90%, 91%, 92%, 93%, 94%, 95%, 96%, 97%, 98%, or 99% identity to the sequence of SEQ ID NO:2 or SEQ ID NO:6 and comprising at least one, two, three, four, five, six or more amino acid substitutions selected from said group above, wherein amino acid positions of the variant are numbered by correspondence with amino acid positions of the SEQ ID NO:2 sequence. Also included are compositions, including, but not limited to, e.g., cleaning compositions, comprising at least one such variant and methods for cleaning utilizing at least one such variant as described in greater detail elsewhere herein.

The following BPN'-v36 variants were determined to have a PI value greater than 1.0, at least 1.1, at least 1.2, at least 1.3, at least 1.4, at least 1.5, at least 1.6, at least 1.7, at least 1.8, at least 1.9, at least 2, from greater than 1.0 to about 10, from greater than 1.0 to about 8, or from greater than 1.0 to about 5 relative to BPN'-v36 in an egg microswatch cleaning assay in Detergent Composition 4 at 16° C. and pH 8: BPN'-S024G-S053G-S078N-S101N-G128A-Y217Q amino acid sequence (SEQ ID NO:6) comprising at least one amino acid substitution selected from the group consisting of A216E, L090I, A098R, A098W, A098Y, A116G, A116R, A116S, A133M, I107L, I115V, M124L, N101I, N109H, N109S, N109T, N117R, P005G, Q185L, S089V, V095A, A015Y, A029G, A098D, A098E, A098G, A098N, A098S, A098T, A098V, A114S, A114T, A116E, A116L, A116T, A116V, A133H, A133L, A133S, A137G, A137I, A137L, A137S, A137V, A138S, A144S, A144V, A176S, A176T, A187T, A216F, A216P, A216Q, A216R, A216S, A216T, A216V, A216Y, D041E, D120A, D120E, D120Q, D120R, D120S, D181S, G020A, G020S, G024A, G097A, G097D, G097S, G131Q, G160S, G166I, G211L, G215N, H039N, H238N, I111L, I111V, I122A, L075I, L075Q, L135M, L209T, L209V, L233V, L235M, L235R, L257A, M119I, N025A, N025G, N025T, N061K, N101F, N101H, N101L, N101Q, N101R, N101S, N101T, N109A, N109G, N109K, N109L, N117E, N117H, N117K, N117S, N212G, N212S, N218F, N218G, N218H, N218L, N218S, N218W, N240Q, N252M, N252R, N252S, P005T, P040A, P040G, P040T, P129D, P129S, P194S, P210R, Q019R, Q019W, Q103L, Q103W, Q185A, Q185G, Q185M, Q185R, Q185T, Q206G, Q206Y, Q217A, Q217E, Q217R, Q217S, Q217T, S003Q, S009H, S018M, S033T, S130A, S130F, S130G, S130T, S130V, S145T, S159A, S161N, S161T, S162V, S162Y, S182L, S182W, S183F, S183L, S183V, S183W, S188K, S188W, S236Q, S236T, S248L, T022H, T022K, T208C, T253H, T255V, V044I, V121I, V139C, V143H, V143Q, V143T, V143W, V143Y, Y006K, Y021A, Y104W, A001F, A001G, A001H, A001K, A001L, A001Q, A001S, A001Y, A013V, A015G, A015K, A015R, A015S, A015T, A015W, A048S, A073N, A073S, A092S, A098K, A098P, A116D, A116W, A128S, A133P, A133T, A133V, A134G, A134S, A137H, A137N, A137T, A144D, A144K, A144L, A144M, A144N, A144R, A179G, A179S, A187V, A216G, A216L, A216W, A223S, A230C, A272K, A272L, A272P, A272S, A272T, A272W, A273G, A273S, A274G, A274M, A274T, D120K, D140E, D181A, D181E, D181G, D181H, D181T, D259E, D259N, D259Q, E054D, E156D, E156T, E251L, E251T, E251V, F058Y, F189W, F261K, F261Q, F261R, G007A, G007S, G020F, G020H, G020N, G020Q, G020T, G020Y, G024F, G024Q, G024R, G024T, G024V, G024W, G024Y, G053T, G097K, G097M, G097R, G097T, G131A, G131H, G131P, G131R, G131T, G131V, G160H, G160T, G166C, G166Q, G166S, G166T, G211A, G211D, G211K, G211M, G211N, G211Q, G211R, G211V, G215S, G215T, G215W, H017T, H017W, H017Y, H039V, H226A, H226F, H226I, H226L, H226M, H226V, I035V, I079A, I079S, I108V, I205V, I234L, I234V, I268V, K012S, K043P, K136H, K136R, K141A, K141F, K141T, K141W, K170A, K170G, K170R, K213A, K213R, K213S, K237A, K237H, K237L, K237S, K237V, K256A, K256G, K256H, K256M, K256P, K256Q, K256R, L016A, L016Q, L016T, L016V, L042V, L075M, L075T, L082M, L082V, L135F, L196I, L209H, L209Q, L209R, L209S, L209W, L233A, L233M, L233Q, L235I, L235K, L250I, L257S, L257T, L257V, L267A, L267Q, L267T, L267V, M119C, M199V, N025C, N025E, N025F, N025I, N025K, N025L, N025M, N025Q, N025V, N025Y, N061F, N061P, N061S, N061T, N076G, N078S, N101A, N109M, N109Q, N109R, N117A, N117M, N117Q, N118D, N118G, N118H, N118Q, N118R, N118S, N184A, N184C, N184G, N184L, N184R, N184S, N184T, N184V, N184W, N212C, N212F, N212I, N212K, N212L, N212P, N212Q, N212R, N212V, N212W, N212Y, N218A, N218P, N218T, N240A, N240E, N240G, N240H, N240L, N240R, N240S, N240T, N243C, N243Q, N243T, N243V, N252A, N252G, N252K, N252Q, P014G, P014Q, P014R, P014S, P014T, P040F, P040L, P040Q, P040S, P040V, P086C, P086H, P086S, P129A, P129E, P129G, P129K, P129R, P172A, P172K, P172Q, P172S, P194A, P194G, P194H, P194L, P194M, P194Q, P194R, P194V, P194W, P194Y, P210A, P210G, P210L, P210S, P239K, P239R, Q002A, Q002S, Q010A, Q010N, Q010R, Q010T, Q019A, Q019C, Q019D, Q019G, Q019S, Q019T, Q019V, Q059I, Q059V, Q103S, Q185F, Q185H, Q185I, Q185K, Q185N, Q185S, Q185Y, Q206H, Q206L, Q206P, Q206W, Q217F, Q217H, Q217I, Q217K, Q217L, Q217N, Q217V, Q271G, Q271R, Q271T, Q275F, Q275P, Q275R, R186A, R186I, R186K, S003A, S003F, S003G, S003H, S003K, S003R, S003T, S009T, S018N, S018T, S037G, S037T, S037V, S038G, S038Q, S063N, S063Q, S063T, S089M, S089N, S130K, S130L, S130R, S130W, S132N, S145G, S145K, S145M, S145R, S145V, S159C, S159H, S159L, S159Q, S159R, S159T, S159W, S161A, S161C, S161G, S161H, S161I, S161K, S161P, S161Q, S161R, S162F, S162G, S162I, S162L, S162M, S162N, S162P, S162R, S163G, S173A, S173G, S182F, S182G, S182K, S182N, S182Q, S182V, S183A, S183M, S183Q, S183R, S183T, S188A, S188F, S188G, S188P, S188R, S188T, S188V, S190C, S204A, S204G, S204I, S204L, S204Q, S204R, S204V, S207G, S224A, S224T, S236C, S236D, S236E, S236G, S236N, S248A, S248F, S248K, S248M, S248T, S249A, S249R, S249T, S249V, S249W, S249Y, S260G, S260H, S260K, S260N, T022A, T022G, T022Q, T022S, T022V, T022Y, T055A, T055K, T158A, T158S, T208L, T208S, T208V, T220S, T242D, T242N, T242S, T244E, T244G, T244I, T244R, T244V, T244W, T253A, T253G, T253N, T253S, T254S, T254V, T255H, T255I, T255K, T255L, T255Q, T255R, T255S, T255Y, V004A, V004N, V004P, V004W, V008A, V008M, V026I, V045S, V045W, V051I, V081Q, V081T, V084C, V093I, V095C, V143A, V143E, V143F, V143N, V143S, V147I, V147L, V147S, V147T, V148I, V149C, V149I, V165M, V180A, V180C, V180I, V180L, V180T, V192A, V192C, V192I, V192S, V192T, V192Y, V198L, V203A, V203F, V203K, V203L, V203M, V203N, V203Y, W241Y, Y006A, Y006G, Y006H, Y006L, Y006N, Y006P, Y006Q, Y006T, Y021E, Y021K, Y021L, Y021N, Y021Q, Y021R, Y021S, Y021T, Y104F, Y104I, Y104V, Y171F, Y214F, Y214L, Y214W, Y262F, and Y262S, wherein amino acid positions of the variant are numbered by correspondence with the sequence of SEQ ID NO:2. Such variants have enhanced proteolytic activity compared to BPN' (SEQ ID NO:2) and a greater PI value than that of BPN' in this assay. The invention includes a protease variant having enhanced proteolytic activity compared to BPN' (SEQ ID NO:2), enhanced proteolytic activity compared to BPN'-v3 and BPN'-v36, a PI value greater than 1.0 to about 5 relative to BPN'-v3, and/or a PI value of greater than 1.0 to about 5 relative to BPN'-v36 in this egg microswatch cleaning assay, the variant comprising an amino acid sequence having at least 60%, 70%, 80%, 85%, 90%, 91%, 92%, 93%, 94%, 95%, 96%, 97%, 98%, or 99% identity to the sequence of SEQ ID NO:2 or SEQ ID NO:6 and comprising at least one, two, three, four, five, six or more amino acid substitutions selected from said group above, wherein amino acid positions of the variant are numbered by correspondence with amino acid positions of the SEQ ID NO:2 sequence. Also included are compositions, including, but not limited to, e.g., cleaning compositions, comprising at least one such variant and methods for cleaning utilizing at least one such variant as described in greater detail elsewhere herein.

The following BPN'-v36 variants were determined to have a PI value of about 1.0 relative to BPN'-v36 in an egg microswatch cleaning assay in Detergent Composition 4 at pH 8 and 16° C.: BPN'-S024G-S053G-S078N-S101N-G128A-Y217Q amino acid sequence (SEQ ID NO:6) comprising at least one amino acid substitution selected from the group consisting of A001D, A001M, A001N, A001R, A001T, A001V, A013C, A013G, A013S, A015D, A015F, A015L, A015M, A015P, A015Q, A074G, A074S, A085S, A085T, A085V, A088C, A088L, A088S, A088T, A088V, A133E, A133G, A133R, A137E, A144G, A144H, A144Q, A144T, A151C, A152S, A153G, A153S, A153V, A176C, A187G, A187Q, A187S, A200G, A228S, A228T, A230T, A230V, A231C, A231V, A232C, A232V, A272E, A272G, A272I, A272Q, A272R, A273L, A273V, A274L, A274Q, A274R, A274V, D036E, D259A, D259G, D259P, D259S, D259T, E156A, E156S, E156V, E195G, E251C, E251I, E251Q, F189Y, F261A, F261G, F261H, F261L, F261P, F261S, F261T, F261V, F261W, G020C, G020D, G020E, G020L, G020R, G024D, G024I, G024N, G024P, G024S, G053A, G053D, G053F, G053H, G053K, G053N, G053S, G053Y, G157A, G157S, G160A, G160L, G160P, G160R, G166A, G166L, G166V, G166W, G169A, G211E, G211P, G215A, G215D, G215E, G215H, G215V, G258D, G258S, H017F, H017I, H017L, H017M, H017V, H039C, H226S, H226Y, I011T, I011V, I031C, I031L, I031V, I079F, I079K, I079L, I079M, I079Q, I079R, I079T, I079V, I079W, I115L, I205A, I205C, I268L, K012R, K012T, K027R, K043A, K043E, K043F, K043H, K043I, K043M, K043N, K043Q, K043T, K043V, K043Y, K141H, K141Q, K141V, K170S, K213G, K213H, K213I, K213L, K213N, K213Q, K213T, K213W, K237I, K237N, K237R, K237T, K256C, K256E, K256S, K256T, K256V, K256W, K265H, K265R, L016E, L016F, L016I, L016S, L042I, L042M, L075A, L075H, L075Y, L082K, L082Q, L082T, L196M, L196V, L209A, L209C, L209E, L209G, L235W, L257C, L257H, L257Q, L257Y, L267E, L267F, L267R, L267S, M050Y, N025H, N025P, N025S, N056D, N061A, N061C, N061D, N061G, N061H, N061I, N061L, N061Q, N061R, N061V, N061W, N062A, N062S, N062V, N076A, N076E, N076L, N076M, N076Q, N076S, N076T, N076W, N078G, N078H, N078K, N078P, N078Q, N078T, N101D, N118A, N118T, N184E, N184H, N184I, N212A, N212D, N212E, N218C, N218D, N218E, N218M, N218R, N218V, N240W, N243A, N243G, N243P, N243S, N252D, N252E, N252L, N252T, N252V, N269S, P005A, P005D, P005M, P005Q, P014A, P014D, P014F, P014M, P014V, P040H, P040R, P040W, P040Y, P086A, P129T, P172E, P172G, P172R, P194E, P201A, P201G, P210E, P210V, Q002E, Q002G, Q010D, Q010F, Q010H, Q010I, Q010L, Q010S, Q019E, Q019H, Q019N, Q059A, Q059L, Q059R, Q059S, Q059T, Q185D, Q185E, Q206D, Q206S, Q206V, Q217G, Q245D, Q245E, Q245K, Q245M, Q245R, Q271A, Q271F, Q271P, Q271Y, Q275D, Q275H, Q275I, Q275L, Q275S, Q275W, R186H, R186L, R186V, R186W, S003D, S003E, S003M, S003P, S003V, S009A, S009E, S009G, S009I, S009K, S009M, S009P, S009W, S018A, S018G, S018I, S018L, S018P, S018R, S018V, S018W, S037A, S037D, S037Q, S037R, S037Y, S038D, S038H, S038K, S038M, S038R, S038T, S063A, S063G, S063K, S063M, S063R, S087A, S087D, S087F, S087G, S087Q, S087T, S089A, S089C, S089H, S089I, S089K, S089L, S089Q, S089R, S089T, S089Y, S130D, S130E, S145A, S145H, S145L, S159G, S161E, S161L, S161M, S161W, S162A, S162C, S162E, S162W, S163P, S173T, S182A, S182C, S182E, S182H, S182R, S182T, S183C, S183D, S183G, S183H, S188C, S188D, S188E, S188L, S190T, S191A, S204Y, S224C, S236A, S248C, S248D, S248G, S248I, S248N, S248Q, S248R, S248V, S249C, S249H, S249L, S249Q, S260A, S260C, S260E, S260P, S260Q, S260R, S260T, T022L, T022N, T022R, T055C, T055D, T055G, T055I, T055L, T055N, T055Q, T055S, T055V, T055Y, T071A, T071S, T158G, T158H, T158L, T158P, T158Q, T158R, T158V, T158Y, T164N, T164S, T244A, T244D, T244H, T244Q, T244S, T253Q, T253R, T253Y, T254A, T254G, T255A, T255D, T255E, V004E, V004G, V004R, V008C, V026A, V028L, V030I, V044C, V045D, V045E, V045H, V045M, V045Q, V045Y, V072L, V081L, V081S, V084A, V084I, V084M, V084T, V143C, V147C, V147Q, V149L, V165L, V180M, V192F, V192G, V192Q, V198I, V198M, V203C, V203E, V203H, V203I, V203Q, V203R, V203T, V203W, V270A, V270L, V270T, W241F, W241M, Y006C, Y006D, Y006E, Y006I, Y006M, Y006R, Y006S, Y006V, Y006W, Y021C, Y021D, Y021V, Y091W, Y167F, Y214V, Y262A, Y262C, Y262I, Y262M, Y262R, Y262T, Y262V, and Y262W, wherein amino acid positions of the variant are numbered by correspondence with the sequence of SEQ ID NO:2. Such variants have enhanced proteolytic activity compared to BPN' (SEQ ID NO:2) and a greater PI value than that of BPN' in this assay. The invention includes a protease variant having enhanced proteolytic activity compared to BPN' (SEQ ID NO:2), a PI value of about 1.0 relative to BPN'-v3, and/or a PI value of about 1.0 relative to BPN'-v36 in this egg microswatch cleaning assay, the variant comprising an amino acid sequence having at least 60%, 70%, 80%, 85%, 90%, 91%, 92%, 93%, 94%, 95%, 96%, 97%, 98%, or 99% identity to the sequence of SEQ ID NO:2 or SEQ ID NO:6 and comprising at least one, two, three, four, five, six or more amino acid substitutions selected from said group above, wherein amino acid positions of the variant are numbered by correspondence with amino acid positions of the SEQ ID NO:2 sequence. Also included are compositions, including, but not limited to, e.g., cleaning compositions, comprising at least one such variant and methods for cleaning utilizing at least one such variant as described in greater detail elsewhere herein.

The following BPN'-v36 variants were determined to have a PI value of about 0.9 relative to BPN'-v36 in an egg microswatch cleaning assay in Detergent Composition 4 at pH 8 and 16° C.: BPN'-S024G-S053G-S078N-S101N-G128A-Y217Q amino acid sequence (SEQ ID NO:6) comprising at least one amino acid substitution selected from the group consisting of A001E, A015C, A015E, A048C, A048E, A073T, A085C, A085G, A088I, A088M, A114G, A137R, A187L, A187N, A187P, A187W, A216C, A230S, A273D, A273H, A273T, D036N, D099N, D259H, E156C, E156G, E156H, E156Q, F189H, F189R, F189S, F189T, F261C, F261D, F261E, G053E, G053M, G053Q, G131C, G131D, G157N, G160V, G215C, G215L, G258A, H039A, I011L, I079E, I268M, K012A, K012G, K012H, K012N, K027N, K043C, K043D, K043G, K043L, K043W, K136G, K141G, K141L, K141M, K141N, K141R, K170C, K170Q, K213V, K256D, K265G, K265N, K265Q, K265S, L082A, L082F, L082H, L082R, L082S, L090M, L233S, L235V, L257E, L257G, L257R, L257W, M222S, N025R, N062H, N062T, N076D, N076P, N078D, N078E, N078F, N078R, N078V, N269H, N269Q, P014K, P057A, P086F, P201T, Q002D, Q002I, Q002P, Q002V, Q019L, Q019P, Q059C, Q059D, Q059E, Q185W, Q271C, Q271D, Q271E, Q271L, Q271W, Q275G, R186M, S009C, S009L, S018D, S037E, S037H, S037K, S037L, S037P, S038P, S063C, S063D, S063F, S063L, S063Y, S087L, S087N, S087R, S087Y, S089D, S089F, S089G, S089W, S105T, S125A, S130C, S159D, S159P, S163A, S182P, S183P, S190A, S190G, S204E, S224G, S248E, S248H, S249E, S260V, S260Y, T055M, T055R, T055W, T158D, T158E, T164G, T164K, T164Q, T220A, T242G, T253E, T255C, T255G, V004D, V044L, V044P, V045C, V045G, V045L, V045N, V045R, V045V, V081A, V081G, V081H, V084S, V147A, V203D, V203G, V270C, V270P, V270S, W241L, Y104T, Y214Q, Y262D, Y262E, Y262G, Y262H, Y262L, Y262N, Y263G, and Y263W, wherein amino acid positions of the variant are numbered by correspondence with the sequence of SEQ ID NO:2. Such variants have proteolytic activity. The invention includes a protease variant having enhanced proteolytic activity compared to BPN' (SEQ ID NO:2), and/or a PI value of about 0.9 relative to BPN'-v36 in this egg microswatch cleaning assay, the variant comprising an amino acid sequence having at least 60%, 70%, 80%, 85%, 90%, 91%, 92%, 93%, 94%, 95%, 96%, 97%, 98%, or 99% identity to the sequence of SEQ ID NO:2 or SEQ ID NO:6 and comprising at least one, two, three, four, five, six or more amino acid substitutions selected from said group above, wherein amino acid positions of the variant are numbered by correspondence with amino acid positions of the SEQ ID NO:2 sequence. Also included are compositions, including, but not limited to, e.g., cleaning compositions, comprising at least one such variant and methods for cleaning utilizing at least one such variant as described in greater detail elsewhere herein.

The following BPN'-v36 variants were determined to have a PI value equal to or greater than 0.5 and less than 0.9 relative to BPN'-v36 in an egg microswatch cleaning assay in Detergent Composition 4 at pH 8 and 16° C.: BPN'-S024G-S053G-S078N-S101N-G128A-Y217Q amino acid sequence (SEQ ID NO:6) comprising at least one amino acid substitution selected from the group consisting of A001C, A142C, A187C, A216H, A273Q, A274H, D036Q, D036S, D099S, D197T, E156L, F189A, F189L, G053L, G053R, G157P, G178A, G258P, H039S, H238Y, K012C, K012E, K012L, K012W, K136E, K265Y, L075G, L075V, L082E, L126W, L257D, L257P, M050L, M222A, M222F, M222L, N056S, N062C, N062L, N062Y, N269C, P057W, Q002K, Q002L, Q217C, Q245A, Q245H, S018C, S038Y, S049C, S087C, S087K, S145D, S191G, T022P, T055E, T164A, T164R, V045K, V051H, V081R, V143G, V148L, V180S, V203S, V270G, Y214H, A187F, A273P, F189G, G046D, G146A, G157T, I031F, I175L, K012F, K027T, L042F, L233E, L233G, M222T, N062R, N184P, P005V, P005W, P129V, P239N, P239T, Q010W, Q059W, Q275A, V004T, V165C, A128H, A230G, D041C, H067T, K027S, K043R, L090T, N062Q, N117G, P225G, P225S, P239G, P239H, Q002R, S089E, V044A, V045I, A001P, A273R, D041N, D099A, D099H, D099Q, F058G, I111M, L042C, N118L, P239A, S049N, S089P, S173V, T242P, V044T, and V045T, wherein amino acid positions of the variant are numbered by correspondence with the sequence of SEQ ID NO:2. Such variants have proteolytic activity. The invention includes a protease variant having proteolytic activity and/or a PI value of equal to or greater than 0.5 and less than 0.9 relative to BPN'-v36 in this egg microswatch cleaning assay, the variant comprising an amino acid sequence having at least 60%, 70%, 80%, 85%, 90%, 91%, 92%, 93%, 94%, 95%, 96%, 97%, 98%, or 99% identity to the sequence of SEQ ID NO:2 or SEQ ID NO:6 and comprising at least one, two, three, four, five, six or more amino acid substitutions selected from said group above, wherein amino acid positions of the variant are numbered by correspondence with amino acid positions of the SEQ ID NO:2 sequence. Also included are compositions, including, but not limited to, e.g., cleaning compositions, comprising at least one such variant and methods for cleaning utilizing at least one such variant as described in greater detail elsewhere herein.

Example 8

Cleaning Performance of Additional Combinatorial Variants Based on BPN'-v36 Parent Additional combinatorial variants based on parent BPN'-v36 (BPN'-S24G-S53G-S78N-S101N-G128A-Y217Q) were made and provided by DNA 2.0. These variants were tested for their cleaning performance using BMI microswatch assay in Detergent Composition 4 at 16° C. and pH 8, BMI microswatch assay in Detergent Composition 4 at 16° C. and pH 7, Egg microswatch assay in Detergent Composition 4 at 16° C. and pH 8, and Grass microswatch assay in Detergent Composition 4 at 16° C. and pH 8. Protein content was determined using TCA assay and protease activity was assayed using AAPF assay. All assays were performed as described in Example 1 and the Performance Indices were calculated relative to BPN'-v36 (with a PI value of 1.0).

The following BPN'-v36 variants were determined to have a PI value greater than 1.0, at least 1.1, at least 1.2, at least 1.3, at least 1.4, at least 1.5, at least 1.6, at least 1.7, at least 1.8, at least 1.9, at least 2, from greater than 1.0 to about 10, from greater than 1.0 to about 8, or from greater than 1.0 to about 5 relative to BPN'-v36 in a BMI microswatch cleaning assay in Detergent Composition 4 at pH 8 and 16° C.: BPN'-S024G-S053G-S078N-S101N-G128A-Y217Q amino acid sequence (SEQ ID NO:6) comprising at least one set of amino acid substitutions selected from the group consisting of A088T-L257G, A116T-A128S, N061S-N109G-A128S-N243V-S260P, S009T-N109G-A128S-K141R-N243V, S009T-S018T-Y021N-N109G-A128S-K141R, and S162G-K256R, wherein amino acid positions of the variant are numbered by correspondence with the sequence of SEQ ID NO:2. Such variants have enhanced proteolytic activity compared to BPN', BPN'-v3, and BPN'-v36, and a greater PI value than that of BPN', BPN'-v3 and BPN'-v36 in this assay. The invention includes a protease variant having enhanced proteolytic activity compared to BPN', BPN'-v3, and BPN'-v36, a PI value of greater than 1.0 to about 5 relative to BPN'-v3, and/or a PI value of greater than 1.0 to about 5 relative to BPN'-v36 in this BMI microswatch cleaning assay, the variant comprising an amino acid sequence having at least 60%, 70%, 80%, 85%, 90%, 91%, 92%, 93%, 94%, 95%, 96%, 97%, or 98% identity to the sequence of SEQ ID NO:2 or SEQ ID NO:6 and comprising at least one set of amino acid substitutions selected from said group above, wherein amino acid positions of the variant are numbered by correspondence with amino acid positions of the SEQ ID NO:2 sequence.

The following BPN'-v36 variants were determined to have a PI value of about 1.0 relative to BPN'-v36 in a BMI microswatch cleaning assay in Detergent Composition 4 at pH 8 and 16° C.: BPN'-S024G-S053G-S078N-S101N-G128A-Y217Q amino acid sequence (SEQ ID NO:6) comprising at least one set of amino acid substitutions selected from the group consisting of A088T, A088T-A116T, A088T-G131H, A088T-K256R, A088T-N109G, A088T-N243V, A088T-Q103H, A088T-S162G, A088T-S248N, A088T-S249A, A088T-T158S, A116T, A116T-G131H, A116T-K256R, A116T-L257G, A116T-N243V, A116T-S162G, A116T-S248N, A116T-S249A, A116T-T158S, A128S-K256R, A128S-L257G, A128S-N243V-S248N-K256R, A128S-S162G, A128S-S248N, A128S-S249A, A128S-T158S, G024E-A116T, G024E-K256R, G024E-L257G, G024E-N109G, G024E-N243V, G024E-T158S, G131H, G131H-K256R, G131H-L257G, G131H-N243V-K256R, G131H-S162G, G131H-S248N, G131H-S249A, G131H-T158S, K043Y-A088T, K043Y-K256R, K043Y-N243V, K256R, K256R-L257G, L257G, N061G-N109G-N243V, N061P-N109G-G131H-N243V, N061P-N109G-N243V, N061S-A128S-N243V-S260P, N061S-N109G-A128S-N243V-S248N-K256R-S260P, N061S-N109G-A128S-S260P, N061S-N109G-N243V, N076D-K256R, N076D-L257G, N076D-N109G, N076D-T158S, N109A-A128S-N243V-K256R, N109G, N109G-A116T, N109G-A128S, N109G-A128S-G131H-N243V-S248N-K256R, N109G-A128S-N243V-K256R, N109G-A128S-N243V-S248A, N109G-A128S-N243V-S248A-K256R, N109G-A128S-N243V-S248N, N109G-A128S-N243V-S248N-K256R, N109G-A128S-N243V-S248N-K256R-L257G, N109G-A128S-S162G-N243V-S248N-K256R, N109G-A128S-S248N-K256R, N109G-A128S-T158S-N243V-S248N-K256R, N109G-G131H, N109G-K256R, N109G-L257G, N109G-N218S, N109G-N243P-S248A-K256R, N109G-N243P-S248N-K256R, N109G-N243V, N109G-N243V-K256R, N109G-N243V-S248A-K256R, N109G-N243V-S248N, N109G-N243V-S248N-K256R, N109G-S162G, N109G-S248N-K256R, N109G-S249A, N109G-T158S, N109Q-A128S-N243V-K256R, N109S-A128S-N243V-K256R, N218S-N243V, N243V, N243V-K256R, N243V-L257G, N243V-S248N, N243V-S248N-K256R, N243V-S249A, P040A-N109G-A128S-N243V-S248N-K256R, Q103H-A116T, Q103H-A128S, Q103H-G131H, Q103H-K256R, Q103H-L257G, Q103H-N109G, Q103H-N218S, Q103H-N243V, Q103H-S162G, Q103H-S248N, Q103H-S249A, Q103H-T158S, S009T-A128S-K141R-N243V, S009T-N109G-A128S-K141R, S009T-N109G-A128S-K141R-N243V-S248N-K256R, S009T-S018T-Y021N-A128S-K141R-N243V, S018T-Y021N-A128S-N243V, S018T-Y021N-N061S-A128S-N243V-S260P, S018T-Y021N-N061S-N109G-A128S-S260P, S018T-Y021N-N109G-A128S, S018T-Y021N-N109G-A128S-N243V, S018T-Y021N-N109G-A128S-N243V-S248N-K256R, S033T-N109G-A128S-N243P-S248N-K256R, S033T-N243V, S033T-Q103H, S033T-T158S, S063G, S063G-A088T, S063G-A128S, S063G-K256R, S063G-L257G, S063G-N076D, S063G-N109G, S063G-Q103H, S063G-S162G, S063G-S248N, S063G-T158S, S162G, S162G-L257G, S162G-N243V, S162G-S248N, S248N, S248N-L257G, S249A, T158S, T158S-L257G, T158S-N218S, T158S-N243V, T158S-S248N, and T158S-S249A, wherein amino acid positions of the variant are numbered by correspondence with the sequence of SEQ ID NO:2. Such variants have enhanced proteolytic activity compared to BPN' (SEQ ID NO:2) and a greater PI value than that of BPN' in this assay. The invention includes a protease variant having enhanced proteolytic activity compared to BPN' (SEQ ID NO:2), a PI value of about 1.0 relative to BPN'-v3, and a PI value of about 1.0 relative to BPN'-v36 in this BMI microswatch cleaning assay, the variant comprising an amino acid sequence having at least 60%, 70%, 80%, 85%, 90%, 91%, 92%, 93%, 94%, 95%, 96%, 97%, or 98% identity to the sequence of SEQ ID NO:2 or SEQ ID NO:6 and comprising at least one set of amino acid substitutions selected from said group above, wherein amino acid positions of the variant are numbered by correspondence with amino acid positions of the SEQ ID NO:2 sequence. Also included are compositions, including, but not limited to, e.g., cleaning compositions, comprising at least one such variant and methods for cleaning utilizing at least one such variant as described in greater detail elsewhere herein.

The following BPN'-v36 variants were determined to have a PI value of about 0.9 relative to BPN'-v36 in a BMI microswatch cleaning assay in Detergent Composition 4 at pH 8 and 16° C.: BPN'-S024G-S053G-S078N-S101N-G128A-Y217Q amino acid sequence (SEQ ID NO:6) comprising at least one set of amino acid substitutions selected from the group consisting of A001E-A088T, A001E-A116T, A001E-A128S-G131H-N243V, A001E-G131H-G169A-N243V, A001E-K256R, A001E-N109G, A001E-N243V, A001E-S033T, A001E-S033T-N109G-N218S, A001E-S033T-N109G-N243V, A001E-S162G, A001E-T158S, A088T-A128S, A088T-G169A, A088T-N218S, A088T-Q206D, A116T-G169A, A116T-N218S, A116T-Q206D, A128S, A128S-G131H, A128S-G169A, A128S-N218S, A128S-N243V, A128S-Q206D, G024E, G024E-A088T, G024E-A128S, G024E-G131H, G024E-K043Y, G024E-N218S, G024E-Q103H, G024E-S033T, G024E-S063G, G024E-S162G, G024E-S248N, G024E-S249A, G131H-G169A, G131H-N218S, G131H-N243V, G131H-Q206D, G169A, G169A-K256R, G169A-L257G, G169A-N218S, G169A-N243V, G169A-Q206D, G169A-S248N, G169A-S249A, K043Y, K043Y-A116T, K043Y-A128S, K043Y-G131H, K043Y-G169A, K043Y-L257G, K043Y-N109G, K043Y-N218S, K043Y-Q103H, K043Y-S063G, K043Y-S162G, K043Y-S248N, K043Y-S249A, K043Y-T158S, N076D, N076D-A088T, N076D-A128S, N076D-G131H, N076D-N218S, N076D-N243V, N076D-Q103H, N076D-S162G, N076D-S248N, N076D-S249A, N109G-G169A, N109G-Q206D, N109G-S248N, N218S, N218S-K256R, N218S-L257G, N218S-S248N, N218S-S249A, P040E-N109G-A128S-G131H, Q103H, Q103H-G169A, Q206D, Q206D-K256R, Q206D-L257G, Q206D-N218S, Q206D-N243V, Q206D-S248N, Q206D-S249A, S018T-Y021N-S033T-N109G-A128S-N243V-S248N-K256R, S033T, S033T-A088T, S033T-A116T, S033T-A128S, S033T-A128S-G131H-N243P, S033T-G131H, S033T-K043Y, S033T-K256R, S033T-L257G, S033T-N076D, S033T-N076D-A128S-N218S, S033T-N076D-N109G-A128S-N218S-N243V-S248N-K256R, S033T-N109G, S033T-N109G-A128S-N243V-S248N-K256R, S033T-N218S, S033T-P040E-Q103H-N109G, S033T-Q103H-A128S-G131H, S033T-Q206D, S033T-S063G, S033T-S162G, S033T-S248N, S033T-S249A, S063G-A116T, S063G-G131H, S063G-G169A, S063G-N109G-A128S-G131H, S063G-N218S, S063G-N243V, S063G-Q206D, S063G-S249A, S162G-G169A, S162G-N218S, S162G-Q206D, S162G-S249A, S248N-K256R, S248N-S249A, S249A-K256R, S249A-L257G, T158S-G169A, T158S-K256R, T158S-Q206D, and T158S-S162G, wherein amino acid positions of the variant are numbered by correspondence with the sequence of SEQ ID NO:2. Such variants have proteolytic activity. The invention includes a protease variant having enhanced proteolytic activity compared to BPN' (SEQ ID NO:2), and/or a PI value of about 0.9 relative to BPN'-v36 in this BMI microswatch cleaning assay, the variant comprising an amino acid sequence having at least 60%, 70%, 80%, 85%, 90%, 91%, 92%, 93%, 94%, 95%, 96%, 97%, 98%, or 99% identity to the sequence of SEQ ID NO:2 or SEQ ID NO:6 and comprising at least one set of acid substitutions selected from said group above, wherein amino acid positions of the variant are numbered by correspondence with amino acid positions of the SEQ ID NO:2 sequence. Also included are compositions, including, but not limited to, e.g., cleaning compositions, comprising at least one such variant and methods for cleaning utilizing at least one such variant as described in greater detail elsewhere herein.

The following BPN'-v36 variants were determined to have a PI value equal to or greater than 0.5 and less than 0.9 relative to BPN'-v36 in a BMI microswatch cleaning assay in Detergent Composition 4 at pH 8 and 16° C.: BPN'-S024G-S053G-S078N-S101N-G128A-Y217Q amino acid sequence (SEQ ID NO:6) comprising at least one set of amino acid substitutions selected from the group consisting of A001E, A001E-A128S, A001E-G024E, A001E-G131H, A001E-G169A, A001E-L257G, A001E-N218S, A001E-Q103H, A001E-S063G, A001E-S248N, A001E-S249A, G024E-N076D, K043Y-N076D, K043Y-Q206D, N076D-A116T, N076D-G169A, N076D-Q206D, Q103H-Q206D, S033T-G169A, S033T-S063G-Q103H-N109Q-A128S-G131H-G169A-N243P, S033T-S063G-Q103H-N109Q-A128S-G131H-G169A-N243V, A001E-K043Y, A001E-N076D, A001E-N076D-N109G-A128S, A001E-Q206D, and G024E-Q206D, wherein amino acid positions of the variant are numbered by correspondence with the sequence of SEQ ID NO:2. Such variants have proteolytic activity. The invention includes a protease variant having proteolytic activity and/or a PI value equal to or greater than 0.5 and less than 0.9 relative to BPN'-v36 in this BMI microswatch cleaning assay, the variant comprising an amino acid sequence having at least 60%, 70%, 80%, 85%, 90%, 91%, 92%, 93%, 94%, 95%, 96%, 97%, 98%, or 99% identity to the sequence of SEQ ID NO:2 or SEQ ID NO:6 and comprising at least one set of acid substitutions selected from said group above, wherein amino acid positions of the variant are numbered by correspondence with amino acid positions of the SEQ ID NO:2 sequence. Also included are compositions, including, but not limited to, e.g., cleaning compositions, comprising at least one such variant and methods for cleaning utilizing at least one such variant as described in greater detail elsewhere herein.

The following BPN'-v36 variants were determined to have a PI value greater than 1.0, at least 1.1, at least 1.2, at least 1.3, at least 1.4, at least 1.5, at least 1.6, at least 1.7, at least 1.8, at least 1.9, at least 2, from greater than 1.0 to about 10, from greater than 1.0 to about 8, or from greater than 1.0 to about 5 relative to BPN'-v36 in a BMI microswatch cleaning assay in Detergent Composition 4 at pH 7 and 16° C.: BPN'-S024G-S053G-S078N-S101N-G128A-Y217Q amino acid sequence (SEQ ID NO:6) comprising at least one set of amino acid substitutions selected from the group consisting of A116T, A088T-N243V, G024E-A116T, K043Y, N076D-A116T, N218S-S248N, S033T-N243V, S033T-S063G, S248N-L257G, A001E-S249A, A088T-A116T, A088T-A128S, A088T-G131H, A088T-L257G, A088T-N109G, A088T-S248N, A088T-S249A, A116T-N243V, A116T-T158S, A128S, A128S-K256R, A128S-L257G, A128S-N243V, A128S-S248N, A128S-T158S, G024E-A088T, G024E-A128S, G024E-G131H, G024E-K256R, G024E-L257G, G024E-N218S, G024E-N243V, G024E-S162G, G024E-S249A, G024E-T158S, G131H, G131H-K256R, G131H-S249A, K043Y-A088T, K043Y-A116T, K256R, N076D-K256R, N109G, N109G-A116T, N109G-A128S, N109G-A128S-N243V-K256R, N109G-A128S-N243V-S248A, N109G-G131H, N109G-K256R, N109G-L257G, N109G-N218S, N109G-N243V, N109G-S248N, N218S-L257G, N243V, N243V-K256R, N243V-L257G, N243V-S248N, N243V-S249A, Q103H-A128S, Q103H-G131H, Q103H-K256R, Q103H-L257G, Q103H-N243V, Q103H-S248N, Q103H-S249A, Q103H-T158S, Q206D-N243V, S033T-A128S, S033T-K256R, S033T-N076D, S033T-N218S, S033T-S248N, S033T-T158S, S063G-A128S, S063G-K256R, S063G-N243V, S063G-S162G, S063G-T158S, S162G-K256R, S248N-K256R, S249A, T158S-N243V, and T158S-S249A, wherein amino acid positions of the variant are numbered by correspondence with the sequence of SEQ ID NO:2. Such variants have enhanced proteolytic activity compared to BPN', BPN'-v3, and BPN'-v36, and a greater PI value than that of BPN', BPN'-v3 and BPN'-v36 in this assay. The invention includes a protease variant having enhanced proteolytic activity compared to BPN' (SEQ ID NO:2), enhanced proteolytic activity compared to BPN', BPN'-v3, and BPN'-v36, a PI value of greater than 1.0 to about 5 relative to BPN'-v3, and/or a PI value of greater than 1.0 to about 5 relative to BPN'-v36 in this BMI microswatch cleaning assay, the variant comprising an amino acid sequence having at least 60%, 70%, 80%, 85%, 90%, 91%, 92%, 93%, 94%, 95%, 96%, 97%, 98%, or 99% identity to the sequence of SEQ ID NO:2 or SEQ ID NO:6 and comprising at least one set of amino acid substitutions selected from said group above, wherein amino acid positions of the variant are numbered by correspondence with amino acid positions of the SEQ ID NO:2 sequence. Also included are compositions, including, but not limited to, e.g., cleaning compositions, comprising at least one such variant and methods for cleaning utilizing at least one such variant as described in greater detail elsewhere herein.

The following BPN'-v36 variants were determined to have a PI value of about 1.0 relative to BPN'-v36 in a BMI microswatch cleaning assay in Detergent Composition 4 at pH 7 and 16° C.: BPN'-S024G-S053G-S078N-S101N-G128A-Y217Q amino acid sequence (SEQ ID NO:6) comprising at least one set of amino acid substitutions selected from the group consisting of A001E-A128S, A001E-G131H, A001E-K256R, A001E-N218S, A001E-N243V, A001E-S033T, A001E-S063G, A001E-S162G, A088T, A088T-K256R, A088T-N218S, A088T-Q103H, A088T-S162G, A088T-T158S, A116T-A128S, A116T-G131H, A116T-K256R, A116T-L257G, A116T-S162G, A116T-S248N, A116T-S249A, A128S-G169A, A128S-N218S, A128S-S162G, A128S-S249A, G024E, G024E-N109G, G024E-Q103H, G024E-S033T, G024E-S063G, G024E-S248N, G131H-L257G, G131H-N243V, G131H-S162G, G131H-T158S, G169A, G169A-L257G, G169A-S248N, K043Y-A128S, K043Y-G131H, K043Y-K256R, K043Y-L257G, K043Y-N109G, K043Y-N243V, K043Y-Q103H, K043Y-S063G, K043Y-S162G, K043Y-S248N, K043Y-S249A, K043Y-T158S, K256R-L257G, L257G, N061G-N109G-N243V, N061S-A128S-N243V-S260P, N061S-N109G-A128S-N243V-S260P, N061S-N109G-A128S-S260P, N076D-A088T, N076D-A128S, N076D-G169A, N076D-N218S, N076D-N243V, N076D-S162G, N076D-S248N, N076D-T158S, N109A-A128S-N243V-K256R, N109G-A128S-G131H-N243V-S248N-K256R, N109G-A128S-N243V-S248A-K256R, N109G-A128S-N243V-S248N-K256R-L257G, N109G-A128S-S162G-N243V-S248N-K256R, N109G-A128S-T158S-N243V-S248N-K256R, N109G-Q206D, N109G-S162G, N109G-S249A, N109G-T158S, N109Q-A128S-N243V-K256R, N109S-A128S-N243V-K256R, N218S, N218S-K256R, N218S-N243V, P040A-

N109G-A128S-N243V-S248N-K256R, Q103H, Q103H-A116T, Q103H-G169A, Q103H-N109G, Q103H-N218S, Q103H-S162G, S009T-A128S-K141R-N243V, S009T-N109G-A128S-K141R, S009T-N109G-A128S-K141R-N243V, S009T-S018T-Y021N-N109G-A128S-K141R, S018T-Y021N-N109G-A128S, S018T-Y021N-N109G-A128S-N243V, S018T-Y021N-N109G-A128S-N243V-S248N-K256R, S033T-A088T, S033T-A116T, S033T-G131H, S033T-K043Y, S033T-L257G, S033T-N109G, S033T-Q103H, S033T-Q206D, S033T-S162G, S033T-S249A, S063G, S063G-A088T, S063G-A116T, S063G-L257G, S063G-N076D, S063G-N109G, S063G-N218S, S063G-Q103H, S063G-S248N, S063G-S249A, S162G, S162G-G169A, S162G-L257G, S162G-N218S, S162G-N243V, S162G-S248N, S162G-S249A, S248N, S248N-S249A, S249A-K256R, S249A-L257G, T158S, T158S-G169A, T158S-K256R, T158S-L257G, T158S-N218S, and T158S-S248N, wherein amino acid positions of the variant are numbered by correspondence with the sequence of SEQ ID NO:2. Such variants have enhanced proteolytic activity compared to BPN' protease (SEQ ID NO:2) and a greater PI value than that of BPN' in this assay. The invention includes a protease variant having enhanced proteolytic activity compared to BPN' (SEQ ID NO:2), a PI value of 1.0 relative to BPN'-v3, and a PI value of about 1.0 relative to BPN'-v36 in this BMI microswatch cleaning assay, the variant comprising an amino acid sequence having at least 60%, 70%, 80%, 85%, 90%, 91%, 92%, 93%, 94%, 95%, 96%, 97%, 98%, or 99% identity to the sequence of SEQ ID NO:2 or SEQ ID NO:6 and comprising at least one set of amino acid substitutions selected from said group above, wherein amino acid positions of the variant are numbered by correspondence with amino acid positions of the SEQ ID NO:2 sequence. Also included are compositions, including, but not limited to, e.g., cleaning compositions, comprising at least one such variant and methods for cleaning utilizing at least one such variant as described in greater detail elsewhere herein.

The following BPN'-v36 variants were determined to have a PI value of about 0.9 relative to BPN'-v36 in a BMI microswatch cleaning assay in Detergent Composition 4 at pH 7 and 16° C.: BPN'-S024G-S053G-S078N-S101N-G128A-Y217Q amino acid sequence (SEQ ID NO:6) comprising at least one set of amino acid substitutions selected from the group consisting of A001E, A001E-A088T, A001E-A116T, A001E-G169A, A001E-L257G, A001E-N109G, A001E-S033T-N109G-N243V, A001E-T158S, A088T-G169A, A088T-Q206D, A116T-N218S, A128S-G131H, A128S-N243V-S248N-K256R, A128S-Q206D, G024E-K043Y, G024E-N076D, G024E-Q206D, G131H-G169A, G131H-N218S, G131H-N243V-K256R, G131H-Q206D, G131H-S248N, G169A-K256R, G169A-N218S, G169A-N243V, G169A-Q206D, K043Y-N076D, K043Y-N218S, N061P-N109G-G131H-N243V, N061P-N109G-N243V, N061S-N109G-A128S-N243V-S248N-K256R-S260P, N061S-N109G-N243V, N076D, N076D-G131H, N076D-L257G, N076D-N109G, N076D-Q103H, N076D-S249A, N109G-A128S-N243V-S248N, N109G-A128S-N243V-S248N-K256R, N109G-A128S-S248N-K256R, N109G-N243P-S248A-K256R, N109G-N243P-S248N-K256R, N109G-N243V-K256R, N109G-N243V-S248A-K256R, N109G-N243V-S248N, N109G-N243V-S248N-K256R, N109G-S248N-K256R, N218S-S249A, N243V-S248N-K256R, Q103H-Q206D, Q206D, Q206D-K256R, Q206D-N218S, Q206D-S248N, Q206D-S249A, S009T-N109G-A128S-K141R-N243V-S248N-K256R, S009T-S018T-Y021N-A128S-K141R-N243V, S018T-Y021N-A128S-N243V, S018T-Y021N-N061S-A128S-N243V-S260P, S018T-Y021N-N061S-N109G-A128S-S260P, S018T-Y021N-S033T-N109G-A128S-N243V-S248N-K256R, S033T, S033T-G169A, S033T-N076D-A128S-N218S, S033T-N076D-N109G-A128S-N218S-N243V-S248N-K256R, S033T-N109G-A128S-N243P-S248N-K256R, S033T-N109G-A128S-N243V-S248N-K256R, S063G-G131H, S063G-G169A, S162G-Q206D, and T158S-S162G, wherein amino acid positions of the variant are numbered by correspondence with the sequence of SEQ ID NO:2. Such variants have proteolytic activity. The invention includes a protease variant having proteolytic activity and/or a PI value of about 0.9 relative to BPN'-v36 in this BMI microswatch cleaning assay, the variant comprising an amino acid sequence having at least 60%, 70%, 80%, 85%, 90%, 91%, 92%, 93%, 94%, 95%, 96%, 97%, 98%, or 99% identity to the sequence of SEQ ID NO:2 or SEQ ID NO:6 and comprising at least one set of acid substitutions selected from said group above, wherein amino acid positions of the variant are numbered by correspondence with amino acid positions of the SEQ ID NO:2 sequence. Also included are compositions, including, but not limited to, e.g., cleaning compositions, comprising at least one such variant and methods for cleaning utilizing at least one such variant as described in greater detail elsewhere herein.

The following BPN'-v36 variants were determined to have a PI value equal to or greater than 0.5 and less than 0.9 relative to BPN'-v36 in a BMI microswatch cleaning assay in Detergent Composition 4 at pH 7 and 16° C.: BPN'-S024G-S053G-S078N-S101N-G128A-Y217Q amino acid sequence (SEQ ID NO:6) comprising at least one set of amino acid substitutions selected from the group consisting of A001E-A128S-G131H-N243V, A001E-G024E, A001E-G131H-G169A-N243V, A001E-Q103H, A001E-S033T-N109G-N218S, A001E-S248N, A116T-G169A, A116T-Q206D, G169A-S249A, K043Y-G169A, N109G-G169A, P040E-N109G-A128S-G131H, Q206D-L257G, S033T-A128S-G131H-N243P, S033T-A128S-G131H-N243V, S033T-P040E-Q103H-N109G, S033T-Q103H-A128S-G131H, S063G-N109G-A128S-G131H, S063G-Q206D, T158S-Q206D, A001E-K043Y, A001E-N076D, A001E-Q206D, S033T-S063G-Q103H-N109Q-A128S-G131H-G169A-N243P, S033T-S063G-Q103H-N109Q-A128S-G131H-G169A-N243V, A001E-N076D-N109G-A128S, K043Y-Q206D, and N076D-Q206D, wherein amino acid positions of the variant are numbered by correspondence with the sequence of SEQ ID NO:2. Such variants have proteolytic activity. The invention includes a protease variant having proteolytic activity and/or a PI value equal to or greater than 0.5 and less than 0.9 relative to BPN'-v36 in this assay, the variant comprising an amino acid sequence having at least 60%, 70%, 80%, 85%, 90%, 91%, 92%, 93%, 94%, 95%, 96%, 97%, 98%, or 99% identity to the sequence of SEQ ID NO:2 or SEQ ID NO:6 and comprising at least one set of acid substitutions selected from said group above, wherein amino acid positions of the variant are numbered by correspondence with amino acid positions of the SEQ ID NO:2 sequence. Also included are compositions, including, but not limited to, e.g., cleaning compositions, comprising at least one such variant and methods for cleaning utilizing at least one such variant as described in greater detail elsewhere herein.

The following BPN'-v36 variants were determined to have a PI value greater than 1.0, at least 1.1, at least 1.2, at least 1.3, at least 1.4, at least 1.5, at least 1.6, at least 1.7, at least 1.8, at least 1.9, at least 2, from greater than 1.0 to about 10, from greater than 1.0 to about 8, or from greater than 1.0 to about 5 relative to BPN'-v36 in an egg microswatch cleaning assay in Detergent Composition 4 at pH 8 and 16° C.: BPN'-S024G-

S053G-S078N-S101N-G128A-Y217Q amino acid sequence (SEQ ID NO:6) comprising at least one set of amino acid substitutions selected from the group consisting of A088T-L257G, G024E-K256R, G024E-L257G, N109G-A116T, N109G-L257G, N243V-K256R, S033T-N109G, S033T-T158S, S063G-L257G, A001E-L257G, A088T-A128S, A088T-G169A, A088T-K256R, A088T-N109G, A088T-N218S, A088T-N243V, A088T-S248N, A088T-T158S, A116T, A116T-A128S, A116T-G131H, A116T-K256R, A116T-L257G, A116T-N218S, A116T-S162G, A116T-T158S, A128S, A128S-G169A, A128S-K256R, A128S-L257G, A128S-N218S, G024E, G024E-A128S, G024E-G131H, G024E-N109G, G024E-N243V, G024E-S033T, G024E-S063G, G024E-S248N, G024E-S249A, G024E-T158S, G131H, G131H-G169A, G131H-K256R, G131H-N218S, G131H-S249A, G169A, G169A-L257G, G169A-N243V, K043Y-A088T, K043Y-N109G, K256R, K256R-L257G, N061G-N109G-N243V, N076D-N109G, N109G, N109G-A128S, N109G-G131H, N109G-K256R, N109G-N218S, N109G-S162G, N109G-S248N, N109G-S249A, N109G-T158S, N218S, N218S-K256R, N218S-L257G, N218S-S248N, N243V, N243V-L257G, N243V-S248N, N243V-S249A, P040A-N109G-A128S-N243V-S248N-K256R, Q103H-K256R, Q103H-L257G, Q103H-N109G, S009T-S018T-Y021N-N109G-A128S-K141R, S033T-A088T, S033T-A116T, S033T-A128S, S033T-G131H, S033T-K043Y, S033T-K256R, S033T-L257G, S033T-N076D, S033T-N218S, S033T-N243V, S033T-Q103H, S033T-S063G, S033T-S162G, S033T-S248N, S033T-S249A, S063G, S063G-A088T, S063G-A116T, S063G-A128S, S063G-G131H, S063G-K256R, S063G-N109G, S063G-N218S, S063G-N243V, S063G-S248N, S063G-S249A, S063G-T158S, S162G-K256R, S162G-N218S, S162G-N243V, S162G-S248N, S162G-S249A, S248N, S249A, S249A-L257G, T158S, T158S-L257G, and T158S-N243V, wherein amino acid positions of the variant are numbered by correspondence with the sequence of SEQ ID NO:2. Such variants have enhanced proteolytic activity compared to BPN', BPN'-v3, and BPN'-v36, and a greater PI value than that of BPN', BPN'-v3 and BPN'-v36 in this assay. The invention includes a protease variant having enhanced proteolytic activity compared to BPN' (SEQ ID NO:2), enhanced proteolytic activity compared to BPN', BPN'-v3, and BPN'-v36, a PI value of greater than 1.0 to about 5 relative to BPN'-v3, and/or a PI value of greater than 1.0 to about 5 relative to BPN'-v36 in this egg microswatch cleaning assay, the variant comprising an amino acid sequence having at least 60%, 70%, 80%, 85%, 90%, 91%, 92%, 93%, 94%, 95%, 96%, 97%, 98%, or 99% identity to the sequence of SEQ ID NO:2 or SEQ ID NO:6 and comprising at least one set of amino acid substitutions selected from said group above, wherein amino acid positions of the variant are numbered by correspondence with amino acid positions of the SEQ ID NO:2 sequence. Also included are compositions, including, but not limited to, e.g., cleaning compositions, comprising at least one such variant and methods for cleaning utilizing at least one such variant as described in greater detail elsewhere herein.

The following BPN'-v36 variants were determined to have a PI value of about 1.0 relative to BPN'-v36 in an egg microswatch cleaning assay in Detergent Composition 4 at pH 8 and 16° C.: BPN'-S024G-S053G-S078N-S101N-G128A-Y217Q amino acid sequence (SEQ ID NO:6) comprising at least one set of amino acid substitutions selected from the group consisting of A001E, A001E-A116T, A001E-G131H, A001E-G169A, A001E-K256R, A001E-N109G, A001E-S033T-N109G-N243V, A001E-S063G, A001E-S248N, A001E-S249A, A001E-T158S, A088T, A088T-A116T, A088T-G131H, A088T-Q103H, A088T-Q206D, A088T-S162G, A088T-S249A, A116T-G169A, A116T-N243V, A116T-S248N, A116T-S249A, A128S-G131H, A128S-N243V, A128S-S162G, A128S-S248N, A128S-S249A, A128S-T158S, G024E-A088T, G024E-A116T, G024E-K043Y, G024E-N076D, G024E-N218S, G024E-Q103H, G024E-S162G, G131H-L257G, G131H-N243V, G131H-N243V-K256R, G131H-S162G, G131H-S248N, G131H-T158S, G169A-K256R, G169A-N218S, G169A-Q206D, G169A-S248N, G169A-S249A, K043Y, K043Y-A116T, K043Y-A128S, K043Y-G169A, K043Y-K256R, K043Y-L257G, K043Y-N076D, K043Y-N218S, K043Y-N243V, K043Y-S063G, K043Y-S248N, K043Y-S249A, K043Y-T158S, L257G, N061P-N109G-G131H-N243V, N061P-N109G-N243V, N061S-A128S-N243V-S260P, N061S-N109G-A128S-N243V-S248N-K256R-S260P, N061S-N109G-A128S-S260P, N061S-N109G-N243V, N076D, N076D-A088T, N076D-A116T, N076D-G131H, N076D-G169A, N076D-K256R, N076D-L257G, N076D-N218S, N076D-N243V, N076D-Q103H, N076D-S249A, N076D-T158S, N109A-A128S-N243V-K256R, N109G-A128S-G131H-N243V-S248N-K256R, N109G-A128S-N243V-K256R, N109G-A128S-N243V-S248A, N109G-A128S-N243V-S248A-K256R, N109G-A128S-N243V-S248N, N109G-A128S-N243V-S248N-K256R, N109G-A128S-N243V-S248N-K256R-L257G, N109G-A128S-S162G-N243V-S248N-K256R, N109G-G169A, N109G-N243P-S248A-K256R, N109G-N243V-K256R, N109G-N243V-S248A-K256R, N109G-N243V-S248N, N109G-N243V-S248N-K256R, N109G-S248N-K256R, N109Q-A128S-N243V-K256R, N109S-A128S-N243V-K256R, N218S-N243V, N218S-S249A, Q103H, Q103H-A116T, Q103H-A128S, Q103H-G131H, Q103H-G169A, Q103H-N218S, Q103H-N243V, Q103H-S162G, Q103H-S248N, Q103H-S249A, Q103H-T158S, Q206D, Q206D-L257G, Q206D-N218S, S009T-A128S-K141R-N243V, S009T-N109G-A128S-K141R, S009T-N109G-A128S-K141R-N243V, S009T-N109G-A128S-K141R-N243V-S248N-K256R, S009T-S018T-Y021N-A128S-K141R-N243V, S018T-Y021N-A128S-N243V, S018T-Y021N-N109G-A128S, S018T-Y021N-N109G-A128S-N243V, S018T-Y021N-N109G-A128S-N243V-S248N-K256R, S018T-Y021N-S033T-N109G-A128S-N243V-S248N-K256R, S033T, S033T-A128S-G131H-N243V, S033T-G169A, S033T-N109G-A128S-N243P-S248N-K256R, S033T-N109G-A128S-N243V-S248N-K256R, S033T-Q103H-A128S-G131H, S033T-Q206D, S033T-S063G-Q103H-N109Q-A128S-G131H-G169A-N243V, S063G-G169A, S063G-N076D, S063G-N109G-A128S-G131H, S063G-Q103H, S063G-S162G, S162G, S162G-G169A, S162G-L257G, S248N-K256R, S248N-L257G, S248N-S249A, S249A-K256R, T158S-G169A, T158S-K256R, T158S-N218S, T158S-S162G, T158S-S248N, and T158S-S249A, wherein amino acid positions of the variant are numbered by correspondence with the sequence of SEQ ID NO:2. Such variants have enhanced proteolytic activity compared to BPN' protease (SEQ ID NO:2) and a greater PI value than that of BPN' in this assay. The invention includes a protease variant having enhanced proteolytic activity compared to BPN' (SEQ ID NO:2), a PI value of about 1.0 relative to BPN'-v3, and a PI value of 1.0 relative to BPN'-v36 in this egg microswatch cleaning assay, the variant comprising an amino acid sequence having at least 60%, 70%, 80%, 85%, 90%, 91%, 92%, 93%, 94%, 95%, 96%, 97%, 98%, or 99% identity to the sequence of SEQ ID NO:2 or SEQ ID NO:6 and comprising at least one set of amino acid substitutions selected from said group above, wherein amino acid positions of the variant are numbered by correspondence with amino acid positions of the SEQ ID NO:2 sequence. Also included are compositions, including, but not limited to, e.g., cleaning compositions, comprising at least one such variant and methods for cleaning utilizing at least one such variant as described in greater detail elsewhere herein.

The following BPN'-v36 variants were determined to have a PI value equal to or greater than 0.5 and less than 0.9 relative to BPN'-v36 in an egg microswatch cleaning assay in Detergent Composition 4 at pH 8 and 16° C.: BPN'-S024G-S053G-S078N-S101N-G128A-Y217Q amino acid sequence (SEQ ID NO:6) comprising at least one set of amino acid substitutions selected from the group consisting of A001E-A088T, A001E-A128S, A001E-A128S-G131H-N243V, A001E-G024E, A001E-G024E-S204E-Q206D, A001E-G131H-G169A-N243V, A001E-K043Y, A001E-N076D, A001E-N076D-N109G-A128S, A001E-N218S, A001E-N243V, A001E-Q103H, A001E-Q206D, A001E-S033T, A001E-S033T-N109G-N218S, A001E-S162G, A116T-Q206D, A128S-N243V-S248N-K256R, A128S-Q206D, G024E-Q206D, G131H-Q206D, K043Y-G131H, K043Y-Q103H, K043Y-Q206D, K043Y-S162G, N061S-N109G-A128S-N243V-S260R, N076D-A128S, N076D-Q206D, N076D-S162G, N076D-S248N, N109G-A128S-S248N-K256R, N109G-A128S-T158S-N243V-S248N-K256R, N109G-N243P-S248N-K256R, N109G-Q206D, N243V-S248N-K256R, P040E-N109G-A128S-G131H, Q103H-Q206D, Q206D-K256R, Q206D-N243V, Q206D-S248N, Q206D-S249A, S018T-Y021N-N061S-A128S-N243V-S260P, S018T-Y021N-N061S-N109G-A128S-S260P, S033T-A128S-G131H-N243P, S033T-N076D-A128S-N218S, S033T-N076D-N109G-A128S-N218S-N243V-S248N-K256R, S033T-P040E-Q103H-N109G, S033T-S063G-Q103H-N109Q-A128S-G131H-G169A-N243P, S063G-Q206D, S162G-Q206D, and T158S-Q206D, wherein amino acid positions of the variant are numbered by correspondence with the sequence of SEQ ID NO:2. Such variants have proteolytic activity. The invention includes a protease variant having proteolytic activity and/or a PI value equal to or greater than 0.5 and less than 0.9 relative to BPN'-v36 in this assay, the variant comprising an amino acid sequence having at least 60%, 70%, 80%, 85%, 90%, 91%, 92%, 93%, 94%, 95%, 96%, 97%, 98%, or 99% identity to the sequence of SEQ ID NO:2 or SEQ ID NO:6 and comprising at least one set of acid substitutions selected from said group above, wherein amino acid positions of the variant are numbered by correspondence with amino acid positions of the SEQ ID NO:2 sequence. Also included are compositions, including, but not limited to, e.g., cleaning compositions, comprising at least one such variant and methods for cleaning utilizing at least one such variant as described in greater detail elsewhere herein.

The following BPN'-v36 variants were determined to have a PI value greater than 1.0, at least 1.1, at least 1.2, at least 1.3, at least 1.4, at least 1.5, at least 1.6, at least 1.7, at least 1.8, at least 1.9, at least 2, from greater than 1.0 to about 10, from greater than 1.0 to about 8, or from greater than 1.0 to about 5 relative to BPN'-v36 in a grass microswatch cleaning assay in Detergent Composition 4 at pH 8 and 16° C.: BPN'-S024G-S053G-S078N-S101N-G128A-Y217Q amino acid sequence (SEQ ID NO:6) comprising at least one set of amino acid substitutions selected from the group consisting of T158S-L257G, K256R, L257G, S033T-N109G, S162G-K256R, S162G-L257G, G024E-K256R, G024E-L257G, G024E-S033T, N109G-A116T, N218S-L257G, S033T-A088T, S033T-A116T, S033T-N243V, S033T-Q103H, S162G-N218S, S162G-N243V, T158S, T158S-N218S, T158S-N243V, A088T, A088T-G169A, A088T-K256R, A088T-L257G, A088T-S162G, A088T-T158S, A116T-K256R, A116T-L257G, A116T-N243V, A128S-L257G, A128S-N218S, A128S-N243V, A128S-S248N, G024E-A116T, G024E-A128S, G024E-G131H, G024E-N243V, G024E-S248N, G024E-S249A, G024E-T158S, G131H-N243V, G131H-T158S, G169A-N218S, G169A-N243V, G169A-S248N, K256R-L257G, N109G-A128S, N109G-G131H, N109G-N218S, N109G-N243V, N109G-S249A, N218S, N218S-K256R, N218S-N243V, N218S-S249A, N243V, N243V-K256R, N243V-L257G, N243V-S248N, Q103H-N109G, Q103H-N218S, S033T-A128S, S033T-L257G, S033T-N218S, S033T-S162G, S033T-S248N, S033T-T158S, S063G-K256R, S063G-L257G, S162G, S162G-G169A, S162G-S248N, S248N, S248N-K256R, S248N-L257G, S249A, T158S-S162G, and T158S-S248N, wherein amino acid positions of the variant are numbered by correspondence with the sequence of SEQ ID NO:2. Such variants have enhanced proteolytic activity compared to BPN', BPN'-v3, and BPN'-v36, and a greater PI value than that of BPN', BPN'-v3 and BPN'-v36 in this assay. The invention includes a protease variant having enhanced proteolytic activity compared to BPN' (SEQ ID NO:2), enhanced proteolytic activity compared to BPN', BPN'-v3, and BPN'-v36, a PI value of greater than 1.0 to about 5 relative to BPN'-v3, and/or a PI value of greater than 1.0 to about 5 relative to BPN'-v36 in this BMI microswatch cleaning assay, the variant comprising an amino acid sequence having at least 60%, 70%, 80%, 85%, 90%, 91%, 92%, 93%, 94%, 95%, 96%, 97%, 98%, or 99% identity to the sequence of SEQ ID NO:2 or SEQ ID NO:6 and comprising at least one set of amino acid substitutions selected from said group above, wherein amino acid positions of the variant are numbered by correspondence with amino acid positions of the SEQ ID NO:2 sequence. Also included are compositions, including, but not limited to, e.g., cleaning compositions, comprising at least one such variant and methods for cleaning utilizing at least one such variant as described in greater detail elsewhere herein.

The following BPN'-v36 variants were determined to have a PI value of about 1.0 relative to BPN'-v36 in a grass microswatch cleaning assay in Detergent Composition 4 at pH 8 and 16° C.: BPN'-S024G-S053G-S078N-S101N-G128A-Y217Q amino acid sequence (SEQ ID NO:6) comprising at least one set of amino acid substitutions selected from the group consisting of A001E-A088T, A001E-A116T, A088T-A128S, A088T-N243V, A088T-Q103H, A088T-S248N, A088T-S249A, A116T, A116T-G169A, A116T-N218S, A116T-S162G, A116T-S249A, A116T-T158S, A128S-G169A, A128S-K256R, A128S-S162G, A128S-S249A, A128S-T158S, G024E-A088T, G024E-K043Y, G024E-N218S, G024E-Q103H, G024E-S063G, G024E-S162G, G131H-G169A, G131H-K256R, G131H-N218S, G131H-S162G, G131H-S248N, G131H-S249A, G169A, G169A-L257G, G169A-S249A, N076D, N076D-K256R, N076D-L257G, N076D-S162G, N076D-S249A, N109G-K256R, N109G-L257G, N109G-S248N, N243V-S249A, Q103H-A116T, Q103H-G169A, Q103H-K256R, Q103H-L257G, Q103H-N243V, Q103H-S162G, S033T-G131H, S033T-G169A, S033T-K043Y, S033T-N076D, S033T-Q206D, S063G, S063G-A116T, S063G-A128S, S063G-N243V, S063G-S162G, S063G-S248N, S063G-S249A, S063G-T158S, S249A-L257G, T158S-G169A, and T158S-K256R, wherein amino acid positions of the variant are numbered by correspondence with the sequence of SEQ ID NO:2. Such variants have enhanced proteolytic activity compared to BPN' (SEQ ID NO:2) and a greater PI value than that of BPN' in this assay. The invention includes a protease variant having enhanced proteolytic activity compared to BPN' (SEQ ID NO:2), a PI value of 1.0 relative to BPN'-v3, and a PI value of about 1.0 relative to BPN'-v36 in this BMI microswatch cleaning assay, the variant comprising an amino acid sequence having at least 60%, 70%, 80%, 85%, 90%, 91%, 92%, 93%, 94%, 95%, 96%, 97%, 98%, or 99% identity to the sequence of SEQ ID NO:2 or SEQ ID NO:6 and comprising at least one set of amino acid substitutions selected from said group above, wherein amino acid positions of the variant are numbered by correspondence with amino acid positions of the SEQ ID NO:2 sequence. Also included are compositions, including, but not limited to, e.g., cleaning compositions, comprising at least one such variant and methods for cleaning utilizing at least one such variant as described in greater detail elsewhere herein.

The following BPN'-v36 variants were determined to have a PI value equal to or greater than 0.5 and less than 0.9 relative to BPN'-v36 in a grass microswatch cleaning assay in Detergent Composition 4 at pH 8 and 16° C.: BPN'-S024G-S053G-S078N-S101N-G128A-Y217Q amino acid sequence (SEQ ID NO:6) comprising at least one set of amino acid substitutions selected from the group consisting of A001E-G169A, A001E-K256R, A001E-N109G, A001E-N218S, A088T-A116T, A088T-G131H, A088T-N109G, A088T-N218S, A116T-A128S, A116T-G131H, A116T-S248N, A128S, A128S-G131H, G024E, G024E-N109G, G131H, G131H-L257G, G169A-K256R, G169A-Q206D, K043Y, K043Y-A088T, K043Y-L257G, K043Y-N109G, N076D-A088T, N076D-G131H, N076D-G169A, N076D-N243V, N076D-T158S, N109G, N109G-S162G, N109G-T158S, N218S-S248N, Q103H-A128S, Q103H-S248N, Q103H-S249A, Q103H-T158S, Q206D-K256R, Q206D-L257G, Q206D-N218S, Q206D-N243V, Q206D-S248N, S033T, S033T-K256R, S033T-S063G, S033T-S249A, S063G-A088T, S063G-G131H, S063G-G169A, S063G-N109G, S162G-Q206D, S162G-S249A, S248N-S249A, S249A-K256R, T158S-Q206D, T158S-S249A, A001E-L257G, A001E-N243V, A001E-Q103H, A001E-S063G, A001E-S162G, A001E-T158S, G024E-N076D, G131H-Q206D, K043Y-A116T, K043Y-G169A, K043Y-K256R, K043Y-N076D, K043Y-S063G, K043Y-S162G, K043Y-S248N, K043Y-S249A, K043Y-T158S, N076D-A116T, N076D-A128S, N076D-S248N, N109G-G169A, Q103H, Q103H-G131H, Q206D-S249A, S063G-N076D, S063G-N218S, S063G-Q103H, A001E-A128S, A001E-G024E, A001E-G131H, A001E-N076D, A001E-Q206D, A001E-S033T, A001E-S248N, A001E-S249A, A088T-Q206D, A116T-Q206D, A128S-Q206D, G024E-Q206D, K043Y-A128S, K043Y-G131H, K043Y-N218S, K043Y-Q103H, N076D-N109G, N076D-N218S, N076D-Q103H, N109G-Q206D, Q103H-Q206D, Q206D, A001E, A001E-K043Y, K043Y-N243V, and S063G-Q206D, N076D-Q206D, wherein amino acid positions of the variant are numbered by correspondence with the sequence of SEQ ID NO:2. Such variants have proteolytic activity. The invention includes a protease variant having proteolytic activity and/or a PI value equal to or greater than 0.5 and less than 0.9 relative to BPN'-v36 in this grass microswatch cleaning assay, the variant comprising an amino acid sequence having at least 60%, 70%, 80%, 85%, 90%, 91%, 92%, 93%, 94%, 95%, 96%, 97%, 98%, or 99% identity to the sequence of SEQ ID NO:2 or SEQ ID NO:6 and comprising at least one set of acid substitutions selected from said group above, wherein amino acid positions of the variant are numbered by correspondence with amino acid positions of the SEQ ID NO:2 sequence. Also included are compositions, including, but not limited to, e.g., cleaning compositions, comprising at least one such variant and methods for cleaning utilizing at least one such variant as described in greater detail elsewhere herein.

The following BPN'-v36 variants were determined to have a PI value greater than 1.0, at least 1.1, at least 1.2, at least 1.3, at least 1.4, at least 1.5, at least 1.6, at least 1.7, at least 1.8, at least 1.9, at least 2, from greater than 1.0 to about 10, from greater than 1.0 to about 8, or from greater than 1.0 to about 5 relative to BPN'-v36 in an AAPF proteolytic assay: BPN'-S024G-S053G-S078N-S101N-G128A-Y217Q amino acid sequence (SEQ ID NO:6) comprising at least one set of amino acid substitutions selected from the group consisting of S033T-N076D-A128S-N218S, A001E-S033T-N109G-N218S, S033T-N218S, S033T-S063G-Q103H-N109Q-A128S-G131H-G169A-N243V, A128S-G169A, S033T-S063G-Q103H-N109Q-A128S-G131H-G169A-N243P, S018T-Y021N-S033T-N109G-A128S-N243V-S248N-K256R, S033T-A128S-G131H-N243P, P040E-N109G-A128S-G131H, S033T-A128S, S033T-N109G-A128S-N243V-S248N-K256R, N109G-G169A, S063G-N109G-A128S-G131H, G169A, N109G-A128S-G131H-N243V-S248N-K256R, S033T-A128S-G131H-N243V, A128S-N218S, A001E-G169A, A088T-G169A, G169A-L257G, N109G-N218S, S033T-N109G-A128S-N243P-S248N-K256R, G169A-K256R, N076D-G169A, A001E-G131H-G169A-N243V, G169A-S249A, S033T-N109G, G169A-S248N, K043Y-G169A, K043Y-N218S, N218S-L257G, N218S-N243V, S063G-G169A, A001E-A128S-G131H-N243V, A001E-S033T-N109G-N243V, A088T-N218S, G024E-N218S, G024E-S033T, G169A-Q206D, N076D-N218S, S033T-L257G, S162G-G169A, A001E-N218S, A116T-N218S, G169A-N243V, N218S, P040A-N109G-A128S-N243V-S248N-K256R, S033T-N076D, A001E-S033T, A128S-G131H, N218S-S248N, S018T-Y021N-N109G-A128S, S033T-K043Y, S033T-N243V, S033T-Q206D, S063G-N218S, S162G-N218S, T158S-G169A, A116T-G169A, G131H-G169A, N061S-N109G-A128S-S260P, N109G-A128S-N243V-K256R, N109G-A128S-N243V-S248A, N109G-A128S-N243V-S248A-K256R, N109G-A128S-N243V-S248N-K256R-L257G, N218S-K256R, S009T-N109G-A128S-K141R, S009T-S018T-Y021N-N109G-A128S-K141R, S033T-A088T, S033T-S063G, S033T-S162G, T158S-N218S, A001E-N076D-N109G-A128S, N109G-A128S-N243V-S248N-K256R, N109G-A128S-S248N-K256R, S009T-N109G-A128S-K141R-N243V, S018T-Y021N-N061S-N109G-A128S-S260P, S033T-A116T, S033T-S248N, S033T-S249A, S033T-T158S, G131H-N218S, N109A-A128S-N243V-K256R, N109G-A128S, N109G-A128S-S162G-N243V-S248N-K256R, N109G-A128S-T158S-N243V-S248N-K256R, N218S-S249A, Q206D-N218S, S018T-Y021N-N109G-A128S-N243V, S018T-Y021N-N109G-A128S-N243V-S248N-K256R, S033T-K256R, A116T-A128S, N061S-N109G-A128S-N243V-S260P, N109G-A128S-N243V-S248N, S009T-N109G-A128S-K141R-N243V-S248N-K256R, G024E-A128S, N061S-N109G-A128S-N243V-S248N-K256R-S260P, N109S-A128S-N243V-K256R, S033T, S033T-G131H, A001E-A128S, A128S, A128S-L257G, A128S-Q206D, N109Q-A128S-N243V-K256R, S009T-A128S-K141R-N243V, S009T-S018T-Y021N-A128S-K141R-N243V, A088T-A128S, A128S-K256R, A128S-N243V, N061P-N109G-N243V, N061S-A128S-N243V-S260P, S018T-Y021N-A128S-N243V, A128S-N243V-S248N-K256R, A128S-S248N, A128S-S249A, N076D-A128S, S063G-A128S, A128S-S162G, A128S-T158S, S018T-Y021N-N061S-A128S-N243V-S260P, S033T-Q103H-A128S-G131H, N061S-N109G-

N243V, K043Y-A128S, N061P-N109G-G131H-N243V, N109G-L257G, A001E-G024E-S204E-Q206D, A001E-L257G, A088T-N109G, G024E-N109G, K043Y-N109G, N061G-N109G-N243V, N076D-N109G, N109G, N109G-A116T, N109G-K256R, N109G-N243V-K256R, N109G-N243V-S248A-K256R, N109G-Q206D, S063G-N109G, A001E-A116T, A001E-N109G, A001E-Q206D, A088T-A116T, A088T-N243V, A116T-L257G, G024E-A116T, G024E-L257G, G024E-N243V, G024E-Q206D, N109G-G131H, N109G-N243V, N109G-S162G, N109G-S248N, N109G-S248N-K256R, N109G-S249A, N109G-T158S, N243V-L257G, A001E-A088T, A001E-G024E, A001E-K256R, A001E-N076D, A001E-N243V, A088T, A088T-L257G, A088T-Q206D, A116T, A116T-K256R, A116T-N243V, G024E-A088T, G024E-K043Y, G024E-K256R, G024E-N076D, G024E-S162G, G024E-S248N, K043Y-A088T, K043Y-A116T, K043Y-L257G, K043Y-N243V, K043Y-Q206D, K256R-L257G, N076D-A116T, N076D-L257G, N076D-N243V, N076D-Q206D, N109G-N243V-S248N, N109G-N243V-S248N-K256R, N243V-K256R, Q206D, Q206D-L257G, Q206D-N243V, Q206D-S248N, S063G-K256R, S063G-L257G, T158S-L257G, A001E, A001E-K043Y, A001E-S162G, A001E-S248N, A001E-S249A, A001E-T158S, A088T-K256R, A088T-S162G, A088T-S248N, A088T-S249A, A116T-Q206D, A116T-S248N, A116T-S249A, G024E, G024E-G131H, G024E-S249A, G024E-T158S, G131H, G131H-K256R, G131H-L257G, K043Y-K256R, K043Y-N076D, K256R, L257G, N076D-A088T, N076D-K256R, N076D-S162G, N076D-S248N, N076D-S249A, N109G-N243P-S248A-K256R, N109G-N243P-S248N-K256R, N243V, Q206D-K256R, S033T-P040E-Q103H-N109G, S063G, S063G-A116T, S063G-Q206D, S162G-K256R, S162G-L257G, S162G-N243V, S162G-Q206D, S162G-S248N, S248N, S248N-L257G, S249A, S249A-L257G, T158S, T158S-N243V, and T158S-Q206D, wherein amino acid positions of the variant are numbered by correspondence with the sequence of SEQ ID NO:2. Such variants have enhanced proteolytic activity compared to BPN', BPN'-v3, and BPN'-v36, and a greater PI value than that of BPN', BPN'-v3 and BPN'-v36 in this assay. The invention includes a protease variant having enhanced proteolytic activity compared to BPN' (SEQ ID NO:2), enhanced proteolytic activity compared to BPN', BPN'-v3, and BPN'-v36, a PI value of greater than 1.0 to about 5 relative to BPN'-v3, and/or a PI value of greater than 1.0 to about 5 relative to BPN'-v36 in this assay, the variant comprising an amino acid sequence having at least 60%, 70%, 80%, 85%, 90%, 91%, 92%, 93%, 94%, 95%, 96%, 97%, 98%, or 99% identity to the sequence of SEQ ID NO:2 or SEQ ID NO:6 and comprising at least one set of amino acid substitutions selected from said group above, wherein amino acid positions of the variant are numbered by correspondence with amino acid positions of the SEQ ID NO:2 sequence. Also included are compositions, including, but not limited to, e.g., cleaning compositions, comprising at least one such variant and methods for cleaning utilizing at least one such variant as described in greater detail elsewhere herein.

The following BPN'-v36 variants were determined to have a PI value of about 1.0 relative to BPN'-v36 in an AAPF proteolytic assay: BPN'-S024G-S053G-S078N-S101N-G128A-Y217Q amino acid sequence (SEQ ID NO:6) comprising at least one set of amino acid substitutions selected from the group consisting of A001E-G131H, A001E-S063G, A088T-G131H, A088T-T158S, A116T-G131H, A116T-S162G, A116T-T158S, G024E-S063G, G131H-N243V, G131H-N243V-K256R, G131H-Q206D, G131H-S249A, K043Y, K043Y-S063G, K043Y-S248N, K043Y-S249A, K043Y-T158S, N076D, N076D-G131H, N076D-T158S, N243V-S248N, N243V-S248N-K256R, N243V-S249A, Q103H-G169A, Q206D-S249A, S063G-N076D, S063G-N243V, S063G-S162G, S063G-S249A, S063G-T158S, S162G, S162G-S249A, S248N-K256R, S248N-S249A, S249A-K256R, T158S-K256R, T158S-S248N, and T158S-S249A, wherein amino acid positions of the variant are numbered by correspondence with the sequence of SEQ ID NO:2. Such variants have enhanced proteolytic activity compared to BPN' (SEQ ID NO:2) and a greater PI value than that of BPN' in this assay. The invention includes a protease variant having enhanced proteolytic activity compared to BPN' (SEQ ID NO:2), a PI value of about 1.0 relative to BPN'-v3, and a PI value of 1.0 relative to BPN'-v36 in this assay, the variant comprising an amino acid sequence having at least 60%, 70%, 80%, 85%, 90%, 91%, 92%, 93%, 94%, 95%, 96%, 97%, or 98% identity to the sequence of SEQ ID NO:2 or SEQ ID NO:6 and comprising at least one set of amino acid substitutions selected from said group above, wherein amino acid positions of the variant are numbered by correspondence with amino acid positions of the SEQ ID NO:2 sequence. Also included are compositions, including, but not limited to, e.g., cleaning compositions, comprising at least one such variant and methods for cleaning utilizing at least one such variant as described in greater detail elsewhere herein.

The following BPN'-v36 variants were determined to have a PI value of about 0.9 relative to BPN'-v36 in an AAPF proteolytic assay: BPN'-S024G-S053G-S078N-S101N-G128A-Y217Q amino acid sequence (SEQ ID NO:6) comprising at least one set of amino acid substitutions selected from the group consisting of G131H-S162G, G131H-S248N, G131H-T158S, K043Y-G131H, K043Y-S162G, S063G-A088T, S063G-G131H, S063G-S248N, T158S-S162G, Q103H-N218S, S033T-Q103H, and Q103H-A128S, wherein amino acid positions of the variant are numbered by correspondence with the sequence of SEQ ID NO:2. Such variants have proteolytic activity. The invention includes a protease variant having proteolytic activity and/or a PI value of about 0.9 relative to BPN'-v36 in this proteolytic assay, the variant comprising an amino acid sequence having at least 60%, 70%, 80%, 85%, 90%, 91%, 92%, 93%, 94%, 95%, 96%, 97%, or 98% identity to the sequence of SEQ ID NO:2 or SEQ ID NO:6 and comprising at least one set of acid substitutions selected from said group above, wherein amino acid positions of the variant are numbered by correspondence with amino acid positions of the SEQ ID NO:2 sequence. Also included are compositions, including, but not limited to, e.g., cleaning compositions, comprising at least one such variant and methods for cleaning utilizing at least one such variant as described in greater detail elsewhere herein.

Also provided is a subtilisin protease variant having proteolytic activity, enhanced proteolytic activity compared to BPN', or a PI value greater than that of BPN' (SEQ ID NO:2) in a BMI microswatch cleaning assay, the variant comprising an amino acid sequence having at least 90%, 91%, 92%, 93%, 94%, 95%, 96%, 97%, 98%, or 99% identity to SEQ ID NO:2 or SEQ ID NO:6, wherein the variant comprises at least one substitution selected from the group of X001E, X009T, X018T, X021N, X024G, X033T, X040A, X043Y, X061G/P/S, X063G, X076D, X088T, X103H, X109A/G/Q/S, X116T, X128S, X131H, X141R, X158S, X162G, X169A, X204E, X206D, X218S, X243P/V, X248A/N, X249A, X256R, X257G, and X260P, wherein positions of the variant are numbered by correspondence with the sequence of SEQ ID NO:2, and optionally wherein the variant comprises at least one substitution selected from the group of A001E, S009T, S018T, Y021N, S024G, S033T, P040A, K043Y, N061G/P/S, S063G, N076D, A088T, Q103H, N109A/G/Q/S, A116T, G128S, G131H, K141R, T158S, S162G, G169A, S204E, Q206D, N218S, N243P/V, S248A/N, S249A, K256R, L257G, and S260P, and wherein amino acid positions of the variant are numbered by correspondence with amino acid positions of the SEQ ID NO:2 sequence. Also included are compositions, including cleaning compositions, comprising at least one such protease variant and methods for cleaning utilizing at least one such protease variant as described in greater detail elsewhere herein.

Example 9

Construction and Cleaning Performance of Variants from a Combinatorial Library Based on BPN'-v36 Parent A BPN' combinatorial library based on the BPN'-v36 parent molecule was made by DNA 2.0 and delivered as a ligation reaction. For efficient transformation of *B. subtilis*, DNA from the ligation reaction mixture was amplified before transformation and transformants grown as described in Example 2. The variants were tested for cleaning performance using BMI microswatch assay in Detergent Composition 4 at 16° C. and pH 8 and egg microswatch assay in Detergent Composition 4 at 16° C. and pH 8. Protein content was determined using the TCA assay. Assays were performed as in Example 1 and Performance Indices were calculated relative to BPN'-v36 (i.e., BPN'-S24G-S53G-S78N-S101N-G128A-Y217Q) (with a PI value of 1.0).

The following BPN'-v36 variants were determined to have a PI value greater than 1.0, at least 1.1, at least 1.2, at least 1.3, at least 1.4, at least 1.5, at least 1.6, at least 1.7, at least 1.8, at least 1.9, at least 2, from greater than 1.0 to about 10, from greater than 1.0 to about 8, or from greater than 1.0 to about 5 relative to BPN'-v36 in a BMI microswatch cleaning assay in Detergent Composition 4 at pH 8 and 16° C.: BPN'-S024G-S053G-S078N-S101N-G128A-Y217Q amino acid sequence (SEQ ID NO:6) comprising at least one set of amino acid substitutions selected from the group consisting of A088T-A116T-N243V-K256R-L257G, A088T-A116T-N243V-L257G, A088T-T158S-N218S-K256R, A088T-T158S-N218S-N243V-L257G, A088T-A116T-T158S-N218S-N243V-K256R-L257G, A088T-N109G-A116T-G131H-A153S-N218S-S248N-L257G, A088T-N109G-A116T-T158S-S248N-K256R-L257G, A088T-N109G-T158S-L257G, A114S-A116T-N218S-N243V-S248N-K256R-L257G, A116T-T158S-K256R, A088T-A116T-G131H-T158S-S248N-L257G, A088T-A116T-T158S, A088T-N109G-A116T-G131H-L257G, A088T-N109G-A116T-T158S-N243V-S248N-L257G, A088T-N109G-N243V-L257G, A088T-N109G-N243V-S248N, A088T-N109G-T158S-N243V-L257G, A088T-N109G-T158S-N243V-S248N-L257G, A116T-T158S-S248N-L257G, Y006H-A116T-G131H-S248N, A088T-A116T-G131H-T158S-N218S-N243V, A088T-A116T-G131H-T158S-N243V, A088T-A116T-G131H-T158S-N243V-K256R-L257G, A088T-A116T-N218S-N243V-K256R-L257G, A088T-A116T-S248N-K256R-L257G, A088T-A116T-T158S-N218S-N243V, A088T-A116T-T158S-N243V-K256R-L257G, A088T-A116T-T158S-N243V-S248N-L257G, A088T-G131H-N243V-S248N-K256R-L257G, A088T-N109G-A116T-T158S-L257G, A088T-N109G-A116T-T158S-N212D-N243V-K256R-L257G, A088T-N109G-A116T-T158S-N218S-N243V-S248N-K256R, A088T-N109G-A116T-T158S-S248N-L257G, A088T-N109G-G131H-V148A-N218S-N243V-K256R-L257G, A088T-N109G-K256R, A088T-N109G-N243V-S248N-L257G, A088T-N109G-T158S-K256R, A088T-N109G-T158S-N243V, A088T-T158S-N243V-K256R-L257G, A116T, A116T-N218S-N243V-L257G-N269S, A116T-T158S-K256R-L257G, N109G-A116T-K256R-L257G, N109G-A116T-N243V, N109G-A116T-T158S-N243V-K256R-L257G, N109G-G131H-L257G, N109G-G131H-S248N-K256R-L257G, N109G-G131H-T158S-K256R-L257G, S003P-A116T-T158S-S248N-K256R, T158S-S248N-K256R, A088T-A116T-G131H-N243V-K256R, A088T-A116T-G131H-S248N-K256R-L257G, A088T-A116T-G131H-V147A-T158S-N218S-N243V-S248N-L257G, A088T-A116T-S248N-L257G, A088T-A116T-T158S-N218S, A088T-A116T-T158S-N218S-K256R-L257G, A088T-A116T-T158S-N218S-L257G, A088T-G131H-N243V-L257G, A088T-G131H-T158S-S248N-L257G, A088T-L257G, A088T-N109G-A116T, A088T-N109G-A116T-G131H-N218S, A088T-N109G-A116T-G131H-N218S-S248N-L257G, A088T-N109G-A116T-G131H-N243V-S248N-K256R-L257G, A088T-N109G-A116T-G131H-T158S-S248N-K256R-L257G, A088T-N109G-A116T-N218S-N243V-K256R, A088T-N109G-A116T-N218S-N243V-L257G, A088T-N109G-A116T-N243V-S248N-K256R, A088T-N109G-A116T-N243V-S248N-K256R-L257G, A088T-N109G-A116T-T158S-L257G, A088T-N109G-A116T-T158S-N243V-L257G, A088T-N109G-G131H-T158S-N243V-S248N-K256R, A088T-N109G-G131H-T158S-W241R-S248N-K256R, A088T-N109G-K256R-L257G, A088T-N109G-L257G, A088T-N109G-N243V, A088T-N109G-N243V-K256R, A088T-N109G-N243V-K256R-L257G, A088T-N109G-S248N-K256R, A088T-N109G-T158S-N218S-K256R-L257G, A088T-N109G-T158S-N218S-N243V-S248N-K256R, A088T-N109G-T158S-N243V-K256R, A088T-N109G-T158S-N243V-K256R-L257G, A088T-N109G-T158S-N243V-S248N-A274D, A088T-N109G-T158S-S248N-L257G, A088T-T158S-K256R, A088T-T158S-N218S-N243V-K256R-L257G, A088T-T158S-N243V-L257G, A116T-G131H-N218S-N243V-S248N, A116T-G131H-S248N-L257G, A116T-S248N-K256R-L257G, A116T-T158S-N218S-N243V-K256R, A116T-T158S-N218S-S248N-L257G-Q271R, A116T-T158S-N243V-K256R-L257G, A116T-T158S-N243V-S248N-L257G, G131H-S248N, G131H-T158S-I234T-N243V-K256R, G131H-W241L-N243V-S248N-K256R, N109G-A116T-G131H-A137V-T158S-S248N-K256R-L257G, N109G-A116T-G131H-A151S-N218S-K256R-L257G, N109G-A116T-G131H-T158S-N218S-N243V-K256R, N109G-A116T-G131H-T158S-N218S-S248N, N109G-A116T-G131H-T158S-N243V-S248N, N109G-A116T-S248N, N109G-A116T-T158S-L257G, N109G-A116T-T158S-N218S-W241R-N243V, N109G-A116T-T158S-N243V-S248N-L257G, N109G-A116T-T158S-S248N-K256R-L257G, N109G-A116T-T158S-S248N-L257G, N109G-G131H-N218S-L257G, N109G-G131H-N218S-S248N-K256R-L257G, N109G-G131H-T158S-N218S-S248N-K256R-L257G-A274T, N109G-K256R, N109G-N243V-L257G, N109G-T158S-N218S-K256R-L257G, N109G-T158S-N218S-L257G, N109G-T158S-S248N-K256R, P014L-A015L-L016C-H017S-S018L-Q019K-G020A-Y021T-T022L-G023E, S003F-A088T-N109G-A116T-T158S-N243V-K256R-L257G, V004A-A088T-A116T-T158S-N218S, V004A-N109G-A116T-G131H-S248N-K256R-L257G, V004L-A116T-N218S-N243V-S248N-L257G, Y006H-N109G-N218S-N243V-S248N, A001T-A116T-T158S-N243V-L257G, A088T-A116T, A088T-A116T-G131H-L257G, A088T-A116T-G131H-N218S-L257G, A088T-A116T-G131H-N218S-S248N-K256R-L257G, A088T-A116T-G131H-N218S-S248N-L257G, A088T-A116T-G131H-N243V-K256R-L257G, A088T-A116T-G131H-N243V-L257G, A088T-A116T-G131H-N243V-S248N, A088T-A116T-G131H-T158S-K256R-L257G, A088T-A116T-G131H-T158S-L257G, A088T-A116T-G131H-T158S-N218S, A088T-A116T-G131H-T158S-N218S-N243V-K256R-A273T, A088T-A116T-G131H-T158S-N218S-S248N-K256R, A088T-A116T-G131H-T158S-N218S-S248N-L257G, A088T-A116T-G131H-T158S-N243V-S248N-K256R, A088T-A116T-G131H-T158S-S248N, A088T-A116T-G131H-T158S-S248N-L257G, A088T-A116T-K256R, A088T-A116T-K256R-L257G, A088T-A116T-N218S-N243V-L257G, A088T-A116T-N243V-K256R, A088T-A116T-N243V-L257G, A088T-A116T-N243V-S248N-K256R-L257G, A088T-A116T-S248N-K256R, A088T-A116T-T158S-K256R, A088T-A116T-T158S-N218S, A088T-A116T-T158S-N218S-N243V-K256R, A088T-A116T-T158S-N218S-N243V-K256R-N269S, A088T-A116T-T158S-N218S-N243V-S248N, A088T-A116T-T158S-N218S-N243V-S248N, A088T-A116T-T158S-N218S-N243V-S248N-K256R-L257G, A088T-A116T-T158S-N218S-N243V-K256R, A088T-A116T-T158S-N243V-L257G, A088T-A116T-T158S-N243V-S248N-K256R, A088T-A116T-T158S-N243V-S248N-K256R-L257G, A088T-A116T-T158S-S248N-K256R, A088T-A116T-V143A-N218S-S248N-K256R, A088T-A116T-V147I-T158S-N218S-N243V-L257G, A088T-G131H-K256R-L257G, A088T-G131H-N218S-N243V-S248N, A088T-G131H-N218S-S248N-L257G, A088T-G131H-S248N-K256R-L257G, A088T-G131H-T158S-L257G, A088T-G131H-T158S-N218S-K256R, A088T-G131H-T158S-N218S-N243V-K256R-L257G, A088T-G131H-T158S-N218S-N243V-L257G, A088T-G131H-T158S-N218S-S248N, A088T-G131H-T158S-N243V, A088T-G131H-T158S-N243V, A088T-G131H-T158S-N243V-S248N, A088T-G131H-T158S-N243V-S248N-K256R, A088T-G131H-T158S-N243V-S248N-L257G, A088T-I107T-N109G-A116T-G131H-T158S-N218S-N243V-S248N, A088T-N109G-A116T-G131H-L257G, A088T-N109G-A116T-G131H-N218S, A088T-N109G-A116T-G131H-N218S-L257G, A088T-N109G-A116T-G131H-N218S-N243V, A088T-N109G-A116T-G131H-N218S-N243V-K256R-L257G, A088T-N109G-A116T-G131H-N218S-N243V-L257G, A088T-N109G-A116T-G131H-N218S-S248N-K256R-L257G, A088T-N109G-A116T-G131H-N243V, A088T-N109G-A116T-G131H-N243V-L257G, A088T-N109G-A116T-G131H-N243V-S248N-L257G, A088T-N109G-A116T-G131H-S248N, A088T-N109G-A116T-G131H-S248N-K256R, A088T-N109G-A116T-G131H-S248N-L257G, A088T-N109G-A116T-G131H-T158S-L257G, A088T-N109G-A116T-G131H-T158S-N218S, A088T-N109G-A116T-G131H-T158S-N218S-S248N-K256R, A088T-N109G-A116T-G131H-T158S-N218T-N243V, A088T-N109G-A116T-G131H-T158S-N243V-K256R, A088T-N109G-A116T-G131H-T158S-N243V-K256R-L257G, A088T-N109G-A116T-G131H-T158S-N243V-S248N, A088T-N109G-A116T-G131H-T158S-N243V-S248N-K256R, A088T-N109G-A116T-G131H-T158S-S248N-K256R-L257G, A088T-N109G-A116T-G131H-T158S-S248N-L257G, A088T-N109G-A116T-N218S, A088T-N109G-A116T-N218S-L257G, A088T-N109G-A116T-N218S-N243V, A088T-N109G-A116T-N218S-N243V-S248N-L257G, A088T-N109G-A116T-N218S-S248N-K256R, A088T-N109G-A116T-N218T-K256R, A088T-N109G-A116T-N243V, A088T-N109G-A116T-N243V-K256R-L257G, A088T-N109G-A116T-N243V-K256R-L257G-N269D, A088T-N109G-A116T-S248N-K256R, A088T-N109G-A116T-T158S, A088T-N109G-A116T-T158S-N218S-L257G, A088T-N109G-A116T-T158S-N218S-N243V, A088T-N109G-A116T-T158S-N218S-N243V-K256R, A088T-N109G-A116T-T158S-N218S-N243V-K256R-L257G, A088T-N109G-A116T-T158S-N218S-N243V-K256R-L257G, A088T-N109G-A116T-T158S-N218S-N243V-L257G, A088T-N109G-A116T-T158S-N218S-S248N, A088T-N109G-A116T-T158S-N243V, A088T-N109G-A116T-T158S-N243V-K256R, A088T-N109G-A116T-T158S-N243V-K256R-L257G, A088T-N109G-A116T-T158S-S248N-L257G, A088T-N109G-G131H-L257G, A088T-N109G-G131H-N218S-K256R-L257G, A088T-N109G-G131H-N218S-N243V-K256R, A088T-N109G-G131H-N218S-N243V-L257G, A088T-N109G-G131H-N218S-N243V-S248N-K256R-L257G, A088T-N109G-G131H-N243V, A088T-N109G-G131H-N243V-L257G, A088T-N109G-G131H-N243V-S248N-K256R, A088T-N109G-G131H-N243V-S248N-L257G, A088T-N109G-G131H-S248N-L257G, A088T-N109G-G131H-T158S-L257G, A088T-N109G-G131H-T158S-N218S-N243V-S248N-K256R, A088T-N109G-G131H-T158S-N243V, A088T-N109G-G131H-T158S-N243V-K256R, A088T-N109G-G131H-T158S-N243V-K256R-L257G, A088T-N109G-G131H-T158S-N243V-L257G, A088T-N109G-L257G, A088T-N109G-N218S-K256R, A088T-N109G-N218S-N243V-S248N-L257G, A088T-N109G-N218S-S248N-K256R-L257G, A088T-N109G-N243V-K256R-L257G, A088T-N109G-N243V-S248N-K256R-L257G, A088T-N109G-N243V-S248N-L257G-I268V, A088T-N109G-S248N-K256R-L257G, A088T-N109G-T158S-N218S-K256R, A088T-N109G-T158S-N218S-N243V-L257G, A088T-N109G-T158S-N218S-N243V-L257G, A088T-N109G-T158S-N243V-K256R-I268V, A088T-N109G-T158S-N243V-S248N-Q275R, A088T-N218S-N243V, A088T-N218S-N243V-S248N-K256R-L257G, A088T-N218S-S248N, A088T-N218S-S248N-L257G, A088T-N243V, A088T-N243V, A088T-N243V-K256R, A088T-N243V-L257G, A088T-S145T-T158S-S248N, A088T-T158S-L257G, A088T-T158S-N218S-S248N-L257G, A088T-T158S-N243V-K256R-L257G-Q271H, A088T-T158S-S248N, A088T-V143A-T158S-K256R, A116T-G131H-K256R, A116T-G131H-N218S, A116T-G131H-N243V, A116T-G131H-N243V-K256R, A116T-G131H-N243V-L257G, A116T-G131H-S248N-K256R, A116T-G131H-T158S-N218S-I234T-N243V-S248N-K256R, A116T-G131H-T158S-N243V-L257G, A116T-G131H-T158S-N243V-S248N-K256R, A116T-G131H-V143F-T158S-N218S, A116T-L257G, A116T-N218S, A116T-N218S-L257G, A116T-N218S-N243V-L257G, A116T-N243V, A116T-N243V-K256R, A116T-N243V-S248N, A116T-N243V-S248N-K256R-L257G, A116T-S248N, A116T-T158S, A116T-T158S-N218S-N243V, A116T-T158S-N218S-S248N, A116T-T158S-N243V, A116T-T158S-N243V-K256R, A116T-T158S-N243V-L257G, A116T-T158S-N243V-S248N, A116T-T158S-S248N-K256R-L257G, A116T-V149I-T158S-N243V-S248N-K256R-Q271H, G131H-N218S-N243V-L257G, G131H-N243V, G131H-N243V-S248N-K256R, G131H-T158S, G131H-T158S-N218S-N243V-K256R, G131H-T158S-N243V-K256R-L257G, G131H-T158S-N243V-S248N-L257G, N109G-A116T-G131H-N218S-K256R-L257G, N109G-A116T-G131H-N218S-L257G, N109G-A116T-G131H-N218S-N243V-K256R-L257G, N109G-A116T-G131H-N218S-S248N-K256R,

N109G-A116T-G131H-N243V-K256R, N109G-A116T-G131H-N243V-L257G, N109G-A116T-G131H-N243V-S248N-K256R-L257G, N109G-A116T-G131H-S248N, N109G-A116T-G131H-S248N-I268V, N109G-A116T-G131H-T158S-N218S-N243V-S248N-K256R, N109G-A116T-G131H-T158S-N218S-S248N-L257G, N109G-A116T-G131H-T158S-S248N, N109G-A116T-G131H-T158S-S248N-K256R, N109G-A116T-N218S, N109G-A116T-N218S-N243V-K256R, N109G-A116T-N218S-N243V-K256R-L257G, N109G-A116T-N218S-S248N-L257G, N109G-A116T-N243V-K256R, N109G-A116T-N243V-S248N-K256R-L257G, N109G-A116T-S248N-L257G, N109G-A116T-T158S-G211V-N243V-S248N-K256R, N109G-A116T-T158S-K256R-L257G, N109G-A116T-T158S-N218S, N109G-A116T-T158S-N218S-N243V-K256R-L257G, N109G-A116T-T158S-N218S-N243V-L257G, N109G-A116T-T158S-N218S-N243V-S248N-L257G, N109G-A116T-T158S-N218S-S248N-K256R-L257G, N109G-A116T-T158S-N243V, N109G-A116T-T158S-Q275R, N109G-G131H-A137V-T158S-N218S-S248N, N109G-G131H-N218S-K237N, N109G-G131H-N218S-N243V-K256R-L257G, N109G-G131H-N218S-S248N-K256R, N109G-G131H-N243V-K256R-L257G, N109G-G131H-S145F-N218S-N243V-K256R-L257G, N109G-G131H-S248N-K256R, N109G-G131H-S248N-L257G, N109G-G131H-T158S-K256R, N109G-G131H-T158S-N218S-N243V-K256R, N109G-G131H-T158S-N243V, N109G-G131H-T158S-N243V-K256R-L257G, N109G-G131H-T158S-N243V-L257G, N109G-G131H-T158S-S248N-L257G, N109G-G131H-T158S-S248N-Q271R, N109G-N218S-L257G, N109G-N218S-N243V, N109G-N243V-K256R-L257G, N109G-N243V-S248N-K256R-L257G, N109G-T158S-I268V, N109G-T158S-K256R, N109G-T158S-N218S-N243V-K256R-L257G, N109G-T158S-N218S-S248N-L257G, N109G-T158S-N243V, N109G-T158S-N243V-K256R-L257G, N109G-T158S-N243V-S248N, N109S-A116T-S248N, N218S, N218S-N243V-S248N-K256R-L257G, N218S-S248N-L257G, N243V, N243V-K256R, N243V-S248N-K256R, N243V-S248N-K256R-L257G, S105P-A116T-T158S-N218S-N243V-S248N-K256R, S248N, T158S-N243V-K256R, and T158S-N243V-L257G, wherein amino acid positions of the variant are numbered by correspondence with the sequence of SEQ ID NO:2. Such variants have enhanced proteolytic activity compared to BPN', BPN'-v3, and BPN'-v36, and a greater PI value than that of BPN', BPN'-v3 and BPN'-v36 in this assay. The invention includes a protease variant having enhanced proteolytic activity compared to BPN' (SEQ ID NO:2), enhanced proteolytic activity compared to BPN', BPN'-v3, and BPN'-v36, a PI value of greater than 1.0 to about 5 relative to BPN'-v3, and/or a PI value of greater than 1.0 to about 5 relative to BPN'-v36 in this assay, the variant comprising an amino acid sequence having at least 60%, 70%, 80%, 85%, 90%, 91%, 92%, 93%, 94%, 95%, 96%, 97%, or 98% identity to the sequence of SEQ ID NO:2 or SEQ ID NO:6 and comprising at least one set of amino acid substitutions selected from said group above, wherein amino acid positions of the variant are numbered by correspondence with amino acid positions of the SEQ ID NO:2 sequence. Also included are compositions, including, but not limited to, e.g., cleaning compositions, comprising at least one such variant and methods for cleaning utilizing at least one such variant as described in greater detail elsewhere herein.

The following BPN'-v36 variants were determined to have a PI value of about 1.0 relative to BPN'-v36 in a BMI microswatch cleaning assay in Detergent Composition 4 at pH 8 and 16° C.: BPN'-S024G-S053G-S078N-S101N-G128A-Y217Q amino acid sequence (SEQ ID NO:6) comprising at least one set of amino acid substitutions selected from the group consisting of A088T, A088T-A116T-G131H-L257G, A088T-A116T-G131H-N218S-A274T, A088T-A116T-G131H-N218S-K256R, A088T-A116T-G131H-N218S-K256R-L257G, A088T-A116T-G131H-N218S-N243V, A088T-A116T-G131H-N218S-N243V-L257G, A088T-A116T-G131H-N218S-N243V-S248N-K256R, A088T-A116T-G131H-N218S-N243V-S248N-K256R-L257G, A088T-A116T-G131H-N218S-N243V-S248N-L257G, A088T-A116T-G131H-N218S-S248N, A088T-A116T-G131H-N218S-S248N-L257G, A088T-A116T-G131H-N243V, A088T-A116T-G131H-N243V-K256R, A088T-A116T-G131H-N243V-S248N, A088T-A116T-G131H-N243V-S248N-A274V, A088T-A116T-G131H-N243V-S248N-K256R-L257G, A088T-A116T-G131H-N243V-S248N-K256R-L257G, A088T-A116T-G131H-N243V-S248N-L257G, A088T-A116T-G131H-S248N-K256R, A088T-A116T-G131H-S248N-K256R-L257G, A088T-A116T-G131H-T158S-K256R, A088T-A116T-G131H-T158S-K256R-L257G, A088T-A116T-G131H-T158S-N218S-K256R, A088T-A116T-G131H-T158S-N218S-K256R-L257G, A088T-A116T-G131H-T158S-N218S-L257G, A088T-A116T-G131H-T158S-N218S-N243V-K256R, A088T-A116T-G131H-T158S-N218S-N243V-K256R-L257G, A088T-A116T-G131H-T158S-N218S-N243V-L257G, A088T-A116T-G131H-T158S-N218S-N243V-S248N, A088T-A116T-G131H-T158S-N218S-N243V-S248N, A088T-A116T-G131H-T158S-N218S-N243V-S248N-K256R, A088T-A116T-G131H-T158S-N243V-K256R, A088T-A116T-G131H-T158S-N243V-K256R, A088T-A116T-G131H-T158S-N243V-K256R-L257G, A088T-A116T-G131H-T158S-N243V-L257G, A088T-A116T-G131H-T158S-N243V-S248N, A088T-A116T-G131H-T158S-N243V-S248N-K256R-L257G, A088T-A116T-G131H-T158S-N243V-S248N-K256R-L257G, A088T-A116T-G131H-T158S-N243V-S248N-L257G, A088T-A116T-G131H-T158S-S248N-K256R, A088T-A116T-G131H-T158S-S248N-K256R-L257G, A088T-A116T-K256R, A088T-A116T-L257G, A088T-A116T-N218S, A088T-A116T-N218S-N243V-K256R, A088T-A116T-N218S-N243V-N269D, A088T-A116T-N218S-N243V-S248N, A088T-A116T-N218S-N243V-S248N-K256R-L257G, A088T-A116T-N218S-N243V-S248N-L257G, A088T-A116T-N218S-S248N, A088T-A116T-N218S-S248N-L257G, A088T-A116T-N243V-K256R-L257G, A088T-A116T-N243V-S248N-K256R, A088T-A116T-S248N, A088T-A116T-S248N-K256R, A088T-A116T-T158S-A216S-N218S-N243V-K256R-L257G, A088T-A116T-T158S-N218S-K256R, A088T-A116T-T158S-N218S-N243V-K256R, A088T-A116T-T158S-N218S-N243V-S248N-K256R-L257G, A088T-A116T-T158S-N218S-S248N, A088T-A116T-T158S-N243V-K256R, A088T-A116T-T158S-N243V-S248N, A088T-A116T-T158S-N243V-S248N-K256R, A088T-A116T-T158S-N243V-S248N-L257G, A088T-A116T-T158S-S248N, A088T-G131D-T158S-N243V-S248N, A088T-G131H-A138V-N218S-L257G, A088T-G131H-K256R, A088T-G131H-N218S-N243V-K256R, A088T-G131H-N218S-N243V-K256R, A088T-G131H-N218S-S248N, A088T-G131H-N218S-S248N-K256R-L257G, A088T-G131H-N218T-L257G, A088T-G131H-N243V-L257G, A088T-G131H-N243V-S248N-K256R, A088T-G131H-S248N, A088T-G131H-S248N-L257G, A088T-G131H-T158S-K256R, A088T-G131H-T158S-K256R-L257G, A088T-G131H-T158S-N218S, A088T-G131H-

T158S-N218S, A088T-G131H-T158S-N218S-K256R-L257G, A088T-G131H-T158S-N218S-N243V-K256R, A088T-G131H-T158S-N218S-N243V-K256R, A088T-G131H-T158S-N218S-N243V-S248N, A088T-G131H-T158S-N218S-S248N, A088T-G131H-T158S-N218S-S248N-K256R, A088T-G131H-T158S-N218S-S248N-L257G-I268V, A088T-G131H-T158S-N243V-K256R, A088T-G131H-T158S-N243V-K256R-L257G, A088T-G131H-T158S-N243V-S248N, A088T-G131H-T158S-N243V-S248N-K256R-L257G, A088T-G131H-T158S-S248N, A088T-G131H-T158S-S248N-K256R, A088T-N109G-A116T-G131H-K256R, A088T-N109G-A116T-G131H-K256R-L257G, A088T-N109G-A116T-G131H-K256R-L257G, A088T-N109G-A116T-G131H-N218S-K256R, A088T-N109G-A116T-G131H-N218S-K256R, A088T-N109G-A116T-G131H-N218S-K256R-L257G, A088T-N109G-A116T-G131H-N218S-N243V-L257G, A088T-N109G-A116T-G131H-N218S-S248N, A088T-N109G-A116T-G131H-N218S-S248N-L257G, A088T-N109G-A116T-G131H-N243V-K256R, A088T-N109G-A116T-G131H-N243V-K256R-L257G, A088T-N109G-A116T-G131H-N243V-S248N-K256R, A088T-N109G-A116T-G131H-N243V-S248N-K256R, A088T-N109G-A116T-G131H-S248N-K256R-L257G, A088T-N109G-A116T-G131H-S248N-K256R-L257G, A088T-N109G-A116T-G131H-S248N-L257G, A088T-N109G-A116T-G131H-T158S-K256R, A088T-N109G-A116T-G131H-T158S-L257G, A088T-N109G-A116T-G131H-T158S-N218S, A088T-N109G-A116T-G131H-T158S-N218S-L257G, A088T-N109G-A116T-G131H-T158S-N218S-N243V, A088T-N109G-A116T-G131H-T158S-N218S-N243V-K256R, A088T-N109G-A116T-G131H-T158S-N218S-N243V-L257G, A088T-N109G-A116T-G131H-T158S-N218S-N243V-S248N-K256R, A088T-N109G-A116T-G131H-T158S-N218S-N243V-S248N-K256R, A088T-N109G-A116T-G131H-T158S-N218S-N243V-S248N-K256R-L257G, A088T-N109G-A116T-G131H-T158S-N218S-S248N, A088T-N109G-A116T-G131H-T158S-N218T-K256R, A088T-N109G-A116T-G131H-T158S-N243V, A088T-N109G-A116T-G131H-T158S-N243V-S248N, A088T-N109G-A116T-G131H-T158S-N243V-S248N-K256R-L257G, A088T-N109G-A116T-G131H-T158S-N243V-S248N-L257G, A088T-N109G-A116T-G131H-V149A-T158S-N218S-K256R, A088T-N109G-A116T-K256R, A088T-N109G-A116T-N218S-K256R, A088T-N109G-A116T-N218S-N243V, A088T-N109G-A116T-N218S-N243V-K256R-L257G, A088T-N109G-A116T-N218S-N243V-L257G, A088T-N109G-A116T-N218S-N243V-S248N-K256R, A088T-N109G-A116T-N218S-S248N, A088T-N109G-A116T-N218S-S248N-K256R-L257G, A088T-N109G-A116T-N243V-K256R, A088T-N109G-A116T-N243V-S248N-K256R-L257G, A088T-N109G-A116T-N243V-S248N-L257G, A088T-N109G-A116T-N243V-S248N-L257G, A088T-N109G-A116T-S248N, A088T-N109G-A116T-S248N-K256R-L257G, A088T-N109G-A116T-S248N-L257G, A088T-N109G-A116T-T158S, A088T-N109G-A116T-T158S-K256R, A088T-N109G-A116T-T158S-N218S, A088T-N109G-A116T-T158S-N218S-L257G, A088T-N109G-A116T-T158S-N218S-N243V-S248N, A088T-N109G-A116T-T158S-N218S-N243V-S248N, A088T-N109G-A116T-T158S-N218S-N243V-S248N-K256R, A088T-N109G-A116T-T158S-N218S-N243V-S248N-K256R-L257G, A088T-N109G-A116T-T158S-N218S-S248N, A088T-N109G-A116T-T158S-N218S-S248N-K256R, A088T-N109G-A116T-T158S-N218S-S248N-L257G, A088T-N109G-A116T-T158S-N218S-S248N-L257G, A088T-N109G-A116T-T158S-N243V-K256R, A088T-N109G-A116T-T158S-N243V-S248N, A088T-N109G-A116T-T158S-S248N, A088T-N109G-A116T-T158S-S248N-K256R, A088T-N109G-A137E-T158S-N218S-N243V-S248N-K256R-L257G, A088T-N109G-G131H-A152S-T158S-N218S-S248N-K256R, A088T-N109G-G131H-K256R-L257G, A088T-N109G-G131H-N218S, A088T-N109G-G131H-N218S, A088T-N109G-G131H-N218S-K256R, A088T-N109G-G131H-N218S-K256R, A088T-N109G-G131H-N218S-L257G, A088T-N109G-G131H-N218S-N243V, A088T-N109G-G131H-N218S-N243V-K256R, A088T-N109G-G131H-N218S-N243V-K256R-L257G, A088T-N109G-G131H-N218S-N243V-S248N-K256R, A088T-N109G-G131H-N218S-S248N, A088T-N109G-G131H-N218S-S248N-K256R, A088T-N109G-G131H-N218S-S248N-K256R, A088T-N109G-G131H-N218S-S248N-K256R-L257G, A088T-N109G-G131H-N243V-K256R, A088T-N109G-G131H-N243V-K256R-L257G, A088T-N109G-G131H-N243V-K256R-L257G, A088T-N109G-G131H-N243V-L257G, A088T-N109G-G131H-N243V-S248N-K256R, A088T-N109G-G131H-S248N-K256R, A088T-N109G-G131H-S248N-L257G, A088T-N109G-G131H-T158S, A088T-N109G-G131H-T158S-K256R, A088T-N109G-G131H-T158S-K256R-L257G, A088T-N109G-G131H-T158S-N218S-K256R, A088T-N109G-G131H-T158S-N218S-K256R, A088T-N109G-G131H-T158S-N218S-L257G, A088T-N109G-G131H-T158S-N218S-L257G, A088T-N109G-G131H-T158S-N218S-N243V, A088T-N109G-G131H-T158S-N218S-N243V-K256R, A088T-N109G-G131H-T158S-N218S-N243V-S248N, A088T-N109G-G131H-T158S-N218S-S248N-L257G, A088T-N109G-G131H-T158S-N243V-K256R-L257G, A088T-N109G-G131H-T158S-N243V-S248N, A088T-N109G-G131H-T158S-N243V-S248N-K256R-L257G, A088T-N109G-G131H-T158S-N243V-S248N-K256R-L257G, A088T-N109G-G131H-T158S-N243V-S248N-L257G, A088T-N109G-G131H-T158S-N243V-S248N-L257G, A088T-N109G-G131H-T158S-S248N, A088T-N109G-G131H-T158S-S248N-L257G, A088T-N109G-G131H-V149A-K256R-L257G, A088T-N109G-G154A-N155P-E156T-G157L-T158M-S159E-G160E-S161L, A088T-N109G-K256R-L257G, A088T-N109G-N218S-K256R, A088T-N109G-N218S-N243V-L257G, A088T-N109G-N218S-N243V-S248N-K256R, A088T-N109G-N218S-N243V-S248N-K256R, A088T-N109G-N218S-S248N, A088T-N109G-N218S-S248N-L257G, A088T-N109G-N218S-S248N-L257G, A088T-N109G-N243V-S248N-K256R, A088T-N109G-S248N, A088T-N109G-S248N, A088T-N109G-T158S-N218S, A088T-N109G-T158S-N218S-K256R-Q271H, A088T-N109G-T158S-N218S-N243V, A088T-N109G-T158S-N218S-N243V-K256R-Q275R, A088T-N109G-T158S-N218S-N243V-S248N-K256R-L257G, A088T-N109G-T158S-N218S-S248N, A088T-N109G-T158S-N218S-S248N-K256R, A088T-N109G-T158S-N218S-S248N-N269D, A088T-N109G-T158S-N243V-K256R, A088T-N109G-T158S-N243V-S248N-K256R, A088T-N109G-T158S-N243V-S248N-K256R-L257G-N269D, A088T-N109G-T158S-N243V-S248N-L257G, A088T-N109G-T158S-S248N-K256R-L257G, A088T-N109G-T158S-S248N-L257G, A088T-N109G-V147A-N218S-N243V-K256R, A088T-N218S, A088T-N218S-K256R, A088T-N218S-L257G-I268V, A088T-N218S-N243V, A088T-N218S-N243V-K256R, A088T-N218S-N243V-K256R-L257G, A088T-N218S-N243V-L257G, A088T-N218S-N243V-S248N-K256R-L257G, A088T-N218S-N243V-S248N-L257G, A088T-N218S-

N243V-S248N-N269S, A088T-N218S-S248N-K256R, A088T-N243V-S248N, A088T-N243V-S248N-K256R, A088T-N243V-S248N-K256R, A088T-N243V-S248N-K256R-L257G, A088T-N243V-S248N-L257G, A088T-S248N, A088T-S248N, A088T-S248N-K256R-L257G, A088T-S248N-L257G, A088T-S248N-L257G-I268V, A088T-T158S, A088T-T158S, A088T-T158S-N218S, A088T-T158S-N218S-K256R, A088T-T158S-N218S-L257G, A088T-T158S-N218S-N243V-K256R-I268V, A088T-T158S-N218S-N243V-K256R-L257G, A088T-T158S-N218S-N243V-S248N-L257G, A088T-T158S-N218S-S248N, A088T-T158S-N243V-K256R, A088T-T158S-N243V-K256R-L257G, A088T-T158S-N243V-S248N-K256R, A088T-T158S-N243V-S248N-L257G, A088T-T158S-N243V-S248N-L257G, A088T-T158S-S248N, A088T-T158S-S248N-L257G, A088T-V147A-K256R, A098S-G131H-T158S-N218S-N243V-S248N-K256R-L257G, A116T-G131H-N218S-K256R, A116T-G131H-N218S-K256R-L257G, A116T-G131H-N218S-L257G, A116T-G131H-N218S-N243V-S248N-L257G, A116T-G131H-N218S-S248N-K256R-L257G, A116T-G131H-N243V-S248N, A116T-G131H-N243V-S248N-L257G, A116T-G131H-T158S-A231V-N243V-L257G, A116T-G131H-T158S-K256R, A116T-G131H-T158S-K256R-L257G, A116T-G131H-T158S-N218S-K256R, A116T-G131H-T158S-N218S-K256R-L257G, A116T-G131H-T158S-N218S-N243V, A116T-G131H-T158S-N218S-N243V-K256R, A116T-G131H-T158S-N218S-N243V-K256R-L257G, A116T-G131H-T158S-N218S-N243V-L257G, A116T-G131H-T158S-N218S-N243V-S248N-K256R, A116T-G131H-T158S-N218S-N243V-S248N-K256R-L257G, A116T-G131H-T158S-N218S-N243V-S248N-L257G, A116T-G131H-T158S-N218S-S248N-K256R, A116T-G131H-T158S-N218T-L257G, A116T-G131H-T158S-S248N-K256R, A116T-G131H-T158S-S248N-L257G, A116T-N218S-K256R, A116T-N218S-K256R-L257G, A116T-N218S-N243V-S248N-K256R, A116T-N218S-N243V-S248N-K256R-L257G, A116T-N218S-N243V-S248N-L257G, A116T-N218S-S248N, A116T-N218S-S248N-K256R, A116T-N218S-S248N-L257G, A116T-N243V-S248N-L257G, A116T-S248N-L257G, A116T-T158S-L257G-Q271R, A116T-T158S-N218S-L257G, A116T-T158S-N218S-N243V-K256R-L257G, A116T-T158S-N218S-S248N-K256R, A116T-T158S-N218S-S248N-K256R-L257G, A116T-T158S-N243V-S248N-K256R, A116T-T158S-N243V-S248N-K256R-L257G, G024S-G053S-N078S-G097A-N101S-A128S, G131H, G131H-N218S, G131H-N218S-K256R, G131H-N218S-N243V-K256R, G131H-N218S-N243V-K256R-L257G, G131H-N218S-N243V-S248N, G131H-N218S-N243V-S248N-K256R, G131H-N218S-S248N-K256R-L257G, G131H-N218S-S248N-L257G, G131H-N243V-K256R, G131H-N243V-K256R-L257G, G131H-N243V-S248N-K256R-L257G, G131H-S248N-K256R, G131H-T158S-K256R, G131H-T158S-K256R-L257G, G131H-T158S-N218S-K256R, G131H-T158S-N218S-K256R-L257G, G131H-T158S-N218S-N243V-K256R-L257G, G131H-T158S-N218S-N243V-S248N, G131H-T158S-N218S-S248N-K256R-L257G, G131H-T158S-N218S-S248N-L257G, G131H-T158S-N243V-K256R, G131H-T158S-N243V-S248N-K256R, G131H-T158S-S248N, G131H-V147I-N218S-S248N-K256R, I107T-N109G-A116T-G131H-T158S-N218S-N243V-S248N-K256R-L257G, I107T-N109G-G131H-N218S-N243V-K256R-L257G, N109G, N109G-A116T-G131H, N109G-A116T-G131H-A144V-T158S-S248N-K256R-L257G, N109G-A116T-G131H-K256R-L257G, N109G-A116T-G131H-L257G, N109G-A116T-G131H-N218S-N243V-K256R, N109G-A116T-G131H-N218S-N243V-S248N-K256R, N109G-A116T-G131H-N243V, N109G-A116T-G131H-N243V-K256R-L257G, N109G-A116T-G131H-N243V-S248N, N109G-A116T-G131H-N243V-S248N-K256R, N109G-A116T-G131H-S248N-K256R, N109G-A116T-G131H-T158S-K256R, N109G-A116T-G131H-T158S-K256R-L257G, N109G-A116T-G131H-T158S-L257G, N109G-A116T-G131H-T158S-N218S, N109G-A116T-G131H-T158S-N218S-K256R-L257G, N109G-A116T-G131H-T158S-N218S-L257G, N109G-A116T-G131H-T158S-N218S-N243V-S248N-K256R-L257G, N109G-A116T-G131H-T158S-N218S-S248N-K256R, N109G-A116T-G131H-T158S-N218S-S248N-K256R-L257G, N109G-A116T-G131H-T158S-N243V-L257G, N109G-A116T-G131H-T158S-S248N-L257G, N109G-A116T-G131H-V147A-T158S-N218S-K256R-L257G, N109G-A116T-G131H-V149A-T158S-N218S-N243V-S248N-L257G, N109G-A116T-K256R, N109G-A116T-N218S-K256R, N109G-A116T-N218S-N243V, N109G-A116T-N218S-N243V-L257G, N109G-A116T-N218S-N243V-S248N-I268V, N109G-A116T-N218S-N243V-S248N-K256R-L257G, N109G-A116T-N218S-N243V-S248N-L257G, N109G-A116T-N243V-S248N, N109G-A116T-N243V-S248N-K256R, N109G-A116T-N243V-S248N-L257G, N109G-A116T-S248N-K256R, N109G-A116T-T158S, N109G-A116T-T158S-N218S-N243V-S248N-K256R, N109G-A116T-T158S-N218S-N243V-S248N-K256R-L257G, N109G-A116T-T158S-N218S-S248N-K256R, N109G-A116T-T158S-N243V-L257G, N109G-A116T-T158S-N243V-S248N, N109G-A116T-T158S-S248N, N109G-A116T-T158S-S248N-K256R, N109G-G131H, N109G-G131H-K256R, N109G-G131H-N218S-K256R, N109G-G131H-N218S-K256R-L257G, N109G-G131H-N218S-N243V-L257G, N109G-G131H-N218S-N243V-S248N-K256R, N109G-G131H-N218S-N243V-S248N-K256R-L257G, N109G-G131H-N218S-N243V-S248N-L257G, N109G-G131H-N218S-S248N-L257G, N109G-G131H-N243V, N109G-G131H-N243V-K256R, N109G-G131H-N243V-S248N, N109G-G131H-N243V-S248N-K256R-L257G, N109G-G131H-N243V-S248N-L257G, N109G-G131H-T158S-N218S-K256R-L257G, N109G-G131H-T158S-N218S-L257G, N109G-G131H-T158S-N218S-N243V, N109G-G131H-T158S-N218S-N243V-K256R-L257G, N109G-G131H-T158S-N218S-N243V-S248N, N109G-G131H-T158S-N218S-N243V-S248N-K256R-L257G, N109G-G131H-T158S-N218S-N243V-S248N-L257G, N109G-G131H-T158S-N218S-S248N-K256R-L257G, N109G-G131H-T158S-N243V-K256R-I268V, N109G-G131H-T158S-N243V-S248N, N109G-G131H-T158S-N243V-S248N-K256R, N109G-G131H-T158S-N243V-S248N-L257G, N109G-G131H-T158S-S248N, N109G-G131H-T158S-S248N-K256R-L257G, N109G-K141E-N218S-S248N-L257G, N109G-N218S, N109G-N218S-N243V-K256R, N109G-N218S-N243V-L257G, N109G-N218S-N243V-S248N-S260F, N109G-N218S-S248N, N109G-N218S-S248N-K256R, N109G-N243V-K256R, N109G-N243V-S248N, N109G-N243V-S248N-K256R, N109G-N243V-S248N-L257G, N109G-N243V-S248N-L257G-Q275R, N109G-S182F-S204F-S207L-N218S-S236F-S248N-L257G, N109G-S248N-K256R, N109G-T158S-K256R-L257G, N109G-T158S-L257G, N109G-T158S-N218S-N243V-K256R, N109G-T158S-N218S-N243V-S248N, N109G-T158S-N218S-N243V-S248N-L257G, N109G-T158S-N243V-K256R, N109G-T158S-N243V-S248N-K256R, N109G-T158S-N243V-S248N-L257G,

N109G-T158S-S248N-L257G, N218S-N243V-L257G, N218S-N243V-S248N-K256R, N243V-K256R-L257G, N243V-S248N-L257G-Q271R, P057Q-A088T-N109G-A116T-G131H-T158S-N218S-S248N, S003P-A116T-N218S-K256R, S003P-N109G-G131H-N218S-N243V-S248N-K256R-L257G, S248N-K256R-L257G, T158S-K256R-L257G, T158S-N218S-A272V, T158S-N218S-K256R-L257G, T158S-N218S-L233S, T158S-N218S-N243V, T158S-N218S-N243V-K256R-L257G, T158S-N218S-N243V-L257G, T158S-N218S-N243V-S248N-K256R, T158S-N218S-S248N-K256R, T158S-N243V, T158S-N243V-K256R-L257G, T158S-N243V-S248N, T158S-N243V-S248N-K256R-N269D, and V004A-N109G-A116T-T158S-N218S-S248N-L257G, wherein amino acid positions of the variant are numbered by correspondence with the sequence of SEQ ID NO:2. Such variants have enhanced proteolytic activity compared to BPN' (SEQ ID NO:2) and a greater PI value than that of BPN' in this assay. The invention includes a protease variant having enhanced proteolytic activity compared to BPN' (SEQ ID NO:2), a PI value of 1.0 relative to BPN'-v3, and a PI value of about 1.0 relative to BPN'-v36 in this assay, the variant comprising an amino acid sequence having at least 60%, 70%, 80%, 85%, 90%, 91%, 92%, 93%, 94%, 95%, 96%, 97%, or 98% identity to the sequence of SEQ ID NO:2 or SEQ ID NO:6 and comprising at least one set of amino acid substitutions selected from said group above, wherein amino acid positions of the variant are numbered by correspondence with amino acid positions of the SEQ ID NO:2 sequence. Also included are compositions, including, but not limited to, e.g., cleaning compositions, comprising at least one such variant and methods for cleaning utilizing at least one such variant as described in greater detail elsewhere herein.

The following BPN'-v36 variants were determined to have a PI value of about 0.9 relative to BPN'-v36 in a BMI microswatch cleaning assay in Detergent Composition 4 at pH 8 and 16° C.: BPN'-S024G-S053G-S078N-S101N-G128A-Y217Q amino acid sequence (SEQ ID NO:6) comprising at least one set of amino acid substitutions selected from the group consisting of A088T-A098S-N218S-K256R, A088T-A116T-G131H-K256R, A088T-A116T-G131H-K256R-L257G-L267M, A088T-A116T-G131H-N218S-N243V-K256R, A088T-A116T-G131H-N218S-N243V-K256R-L257G, A088T-A116T-G131H-N218S-N243V-S248N, A088T-A116T-G131H-N218S-S248N, A088T-A116T-G131H-N218S-S248N-K256R, A088T-A116T-G131H-N218S-S248N-K256R, A088T-A116T-G131H-N243V, A088T-A116T-G131H-S248N, A088T-A116T-G131H-S248N-L257G, A088T-A116T-G131H-S248N-L257G, A088T-A116T-G131H-T158S-N218S, A088T-A116T-G131H-T158S-N218S-K256R-L257G, A088T-A116T-G131H-T158S-N218S-N243V-S248N-K256R, A088T-A116T-G131H-T158S-N218S-N243V-S248N-L257G, A088T-A116T-G131H-T158S-N218S-S248N, A088T-A116T-G131H-T158S-N218S-S248N-K256R, A088T-A116T-K256R-L257G, A088T-A116T-N218S-I268V, A088T-A116T-N218S-K256R, A088T-A116T-N218S-N243V-Q271R, A088T-A116T-N218S-N243V-S248N-K256R, A088T-A116T-N218S-N243V-S248N-K256R-Q275R, A088T-A116T-N218S-S248N, A088T-A116T-N218S-S248N-K256R, A088T-A116T-N243V-S248N-K256R, A088T-A116T-T158S, A088T-A116T-T158S-N218S-K256R, A088T-A116T-T158S-N218S-N243V-L257G, A088T-A116T-T158S-N218S-N243V-S248N-L257G, A088T-A116T-T158S-N218S-S248N, A088T-A116T-T158S-N218S-S248N-K256R, A088T-A116T-T158S-N218S-S248N-K256R-L257G, A088T-A116T-T158S-N218S-S248N-L257G, A088T-A116T-T158S-S248N-L257G, A088T-G131H, A088T-G131H, A088T-G131H-N218S-K237R-K256R-L257G, A088T-G131H-N218S-K256R, A088T-G131H-N218S-K256R-L257G, A088T-G131H-N218S-N243V-K256R-L257G, A088T-G131H-N218S-N243V-L257G, A088T-G131H-N218S-N243V-L257G, A088T-G131H-N218S-N243V-S248N, A088T-G131H-N218S-N243V-S248N-K256R, A088T-G131H-N218S-N243V-S248N-K256R-L257G, A088T-G131H-N218S-N243V-S248N-K256R-L257G, A088T-G131H-N218S-S248N, A088T-G131H-N243V, A088T-G131H-N243V-K256R, A088T-G131H-N243V-K256R-L257G, A088T-G131H-N243V-S248N, A088T-G131H-N243V-S248N, A088T-G131H-N243V-S248N-K256R, A088T-G131H-S248N, A088T-G131H-S248N-K256R, A088T-G131H-T158S-N218S-K256R-L257G, A088T-G131H-T158S-N218S-L257G, A088T-G131H-T158S-N218S-N243V, A088T-G131H-T158S-N218S-N243V-K256R-L257G, A088T-G131H-T158S-N218S-N243V-S248N-K256R, A088T-G131H-T158S-N218S-N243V-S248N-K256R-L257G, A088T-G131H-T158S-N218S-N243V-S248N-K256R-L257G, A088T-G131H-T158S-N218S-N243V-S248N-L257G, A088T-G131H-T158S-N218S-S248N-K256R, A088T-G131H-T158S-N218S-S248N-K256R-L257G, A088T-G131H-T158S-S248N-K256R-L257G, A088T-L257G, A088T-N109G-A116T-G131H-N218S-L257G, A088T-N109G-A116T-G131H-N218S-N243V-S248N-K256R, A088T-N109G-A116T-G131H-N218S-N243V-S248N-K256R-L257G, A088T-N109G-A116T-G131H-N218S-N243V-S248N-N269D, A088T-N109G-A116T-G131H-N218S-N243V-S248N-Q275R, A088T-N109G-A116T-G131H-N218S-S248N-K256R-L257G, A088T-N109G-A116T-G131H-N243V-S248N, A088T-N109G-A116T-G131H-T158S, A088T-N109G-A116T-G131H-T158S-N218S-L257G-I268V, A088T-N109G-A116T-G131H-T158S-N218S-N243V-K256R, A088T-N109G-A116T-G131H-T158S-N218S-N243V-K256R-L257G, A088T-N109G-A116T-G131H-T158S-N218S-N243V-S248N, A088T-N109G-A116T-G131H-T158S-N218S-N243V-S248N-L257G, A088T-N109G-A116T-G131H-T158S-N218S-S248N-L257G, A088T-N109G-A116T-G131H-T158S-S248N, A088T-N109G-A116T-G131H-T158S-S248N, A088T-N109G-A116T-G131H-W241L-S248N-K256R-L257G, A088T-N109G-A116T-K256R, A088T-N109G-A116T-N218S-K256R-L257G, A088T-N109G-A116T-N218S-N243V-S248N-K256R, A088T-N109G-A116T-N218S-S248N, A088T-N109G-A116T-T158S-N218S, A088T-N109G-A116T-T158S-N218S-K256R-L257G, A088T-N109G-A116T-T158S-N218S-N243V-S248N-L257G, A088T-N109G-A116T-T158S-N243V-S248N, A088T-N109G-A116T-T158S-N243V-S248N-K256R, A088T-N109G-G131H-A138V-T158S-N218S-N243V-S248N-L257G, A088T-N109G-G131H-K256R-L257G, A088T-N109G-G131H-N218S-N243V, A088T-N109G-G131H-N218S-N243V-S248N-L257G, A088T-N109G-G131H-N218S-S248N-K256R-L257G, A088T-N109G-G131H-N218S-S248N-K256R-L257G-Q275R, A088T-N109G-G131H-N243V-S248N, A088T-N109G-G131H-N243V-S248N-K256R-L257G, A088T-N109G-G131H-T158S, A088T-N109G-G131H-T158S-L233S-N243V-S248N, A088T-N109G-G131H-T158S-N218S-N243V-K256R, A088T-N109G-G131H-T158S-N218S-N243V-K256R-L257G, A088T-N109G-G131H-T158S-N218S-N243V-S248N-K256R-L257G, A088T-N109G-G131H-T158S-N218S-N243V-S248N-K256R-L257G, A088T-N109G-G131H-T158S-N218S-N243V-S248N-L257G, A088T-N109G-

G131H-T158S-N218S-S248N-K256R, A088T-N109G-G131H-T158S-N243V-S248N-K256R, A088T-N109G-G131H-T158S-S248N-K256R, A088T-N109G-G131H-T158S-S248N-K256R-L257G, A088T-N109G-G131H-V149A-K256R-L257G, A088T-N109G-N218S-K256R-L257G, A088T-N109G-N218S-N243V-K256R, A088T-N109G-N218S-N243V-L257G, A088T-N109G-N218S-N243V-S248N, A088T-N109G-N218S-N243V-S248N-K256R-L257G, A088T-N109G-N218S-S248N-K256R, A088T-N109G-N243V-K256R, A088T-N109G-N243V-S248N-K256R, A088T-N109G-S248N-K256R-L257G, A088T-N109G-T158S, A088T-N109G-T158S-K256R-L257G, A088T-N109G-T158S-N218S-N243V-K256R, A088T-N109G-T158S-N218S-N243V-K256R-L257G, A088T-N109G-T158S-N218S-N243V-S248N-K256R, A088T-N109G-T158S-N218S-N243V-S248N-L257G, A088T-N109G-T158S-N218S-S248N, A088T-N109G-T158S-S248N, A088T-N109G-T158S-S248N, A088T-N218S-N243V-K256R, A088T-N218S-N243V-L257G, A088T-N218S-N243V-S248N, A088T-N218S-N243V-S248N-K256R, A088T-N218S-N243V-S248N-K256R, A088T-N218S-S248N, A088T-N218S-S248N-L257G, A088T-S248N-K256R-L257G, A088T-T158S-K256R, A088T-T158S-N218S-N243V-K256R, A088T-T158S-N218S-N243V-L257G, A088T-T158S-N218S-N243V-S248N, A088T-T158S-N218S-N243V-S248N-K256R, A088T-T158S-N218S-N243V-S248N-K256R-L257G, A088T-T158S-N218S-N243V-S248N-K256R-L257G, A088T-T158S-N218S-N243V-S248N-L257G, A088T-T158S-N218S-S248N, A088T-T158S-N218S-S248N-K256R, A088T-T158S-N218S-S248N-L257G, A088T-T158S-N218S-S248N-L257G-Q275K, A088T-T158S-N243V, A088T-T158S-N243V-K256R, A088T-T158S-N243V-S248N, A088T-T158S-S248N-K256R-L257G, A088T-T158S-S248N-L257G, A088T-V147I-N218S-N243V-K256R-L257G, A116T-G131H-L257G, A116T-G131H-N218S-N243V, A116T-G131H-N218S-N243V-K256R-L257G, A116T-G131H-N218S-N243V-S248N-K256R-L257G, A116T-G131H-N218S-S248N, A116T-G131H-N218S-S248N-K256R, A116T-G131H-N243V-S248N-K256R, A116T-G131H-T158S-N218S-N243V-S248N, A116T-G131H-T158S-N218S-S248N, A116T-G131H-T158S-N243V-K256R, A116T-G131H-V139I-N218S-N243V-S248N, A116T-K141E-N218S-N243V-S248N-K256R-L257G, A116T-K256R, A116T-N218S-N243V-S248N, A116T-N218T-N243V-S248N, A116T-N243V-K256R-L257G, A116T-S248N-K256R, A116T-T158S-N218S-K256R, A116T-T158S-N218S-K256R-L257G, A116T-T158S-N218S-N243V-L257G, A116T-T158S-N218S-N243V-S248N, A116T-T158S-N218S-S248N-L257G, G024S-G053S-N078S-G097A-N101S, G053S-A088T-N109G-A116T-G131H-T158S-G169S-N218S-S248N-K256R-L257G, G131H-K141R-T158S-N218S-K256R, G131H-K256R, G131H-N218S-K256R-L257G, G131H-N218S-N243V-S248N-L257G, G131H-N218S-S248N-K256R, G131H-N243V-S248N, G131H-N243V-S248N-L257G, G131H-T158S-N218S, G131H-T158S-N218S-N240H-N243V-S248N-K256R-L257G, G131H-T158S-N218S-N243V, G131H-T158S-N218S-S248N-K256R-L257G-N269S, G131H-T158S-N243V-L257G, G131H-T158S-N243V-S248N, G131H-T158S-S248N, K256R, K256R-L257G, N109G-A116T-G131H-N218S-N243V, N109G-A116T-G131H-N218S-N243V-L257G, N109G-A116T-G131H-N218S-S248N-L257G, N109G-A116T-G131H-N218S-W241R-N243V-K256R, N109G-A116T-G131H-S248N-L257G, N109G-A116T-G131H-T158S-N218S-K256R, N109G-A116T-G131H-T158S-N218S-N243V-K256R-L257G, N109G-A116T-G131H-T158S-N218S-N243V-S248N, N109G-A116T-G131H-T158S-N218S-N243V-S248N-L257G, N109G-A116T-G131H-T158S-N243V-K256R-L257G, N109G-A116T-G131H-T158S-N243V-S248N-K256R, N109G-A116T-G131H-T158S-S248N-K256R-L257G, N109G-A116T-I234T-N243V-S248N-K256R-L257G, N109G-A116T-N218S-N243V-S248N, N109G-A116T-N243V-K256R-L257G, N109G-A116T-T158S-N218S-K237R-N243V-S248N, N109G-G131H-N218S-N243V-S248N, N109G-G131H-S248N, N109G-G131H-T158S, N109G-G131H-T158S-L257G, N109G-G131H-T158S-N218S-N243V-S248N-K256R, N109G-G131H-T158S-N218S-S248N-K256R, N109G-G131H-T158S-N218S-S248N-L257G, N109G-G131H-T158S-N243V-S248N-K256R-L257G, N109G-G131H-T158S-S248N-K256R, N109G-N218S-K256R-L257G, N109G-N218S-N243V-S248N-K256R, N109G-N218S-S248N-L257G, N109G-S248N, N109G-T158S-N218S, N109G-T158S-N218S-N243V, N109G-T158S-N243V-L257G, N218S-K256R, N218S-N243V-K256R, N218S-N243V-S248N, N218S-S248N, N218S-S248N-K256R, N243V-L257G, S003P-N109G-A116T-G131H-N218S-N243V-S248N, S003P-N109G-A116T-G131H-T158S-N218S-K256R, S105H-W106G-I107L-I108S-N109A-G110A-I111S-E112N-W113G-A114P, S248N-L257G, T158S, T158S-K256R, T158S-N218S, T158S-N218S-K256R, T158S-N218S-L233S-S248N, T158S-N218S-L257G, T158S-N218S-N243V-K256R, T158S-N218S-N243V-S248N, T158S-N218S-N243V-S248N-L257G, T158S-N218S-S248N-K256R-L257G, T158S-N218S-S248N-L257G, T158S-N243V-S248N-L257G, T158S-S248N, and V004L-A088T-G131H-T158S-N218S-S248N-L257G, wherein amino acid positions of the variant are numbered by correspondence with the sequence of SEQ ID NO:2. Such variants have proteolytic activity. The invention includes a protease variant having proteolytic activity and/or a PI value of about 0.9 relative to BPN'-v36 in this assay, the variant comprising an amino acid sequence having at least 60%, 70%, 80%, 85%, 90%, 91%, 92%, 93%, 94%, 95%, 96%, 97%, or 98% identity to the sequence of SEQ ID NO:2 or SEQ ID NO:6 and comprising at least one set of acid substitutions selected from said group above, wherein amino acid positions of the variant are numbered by correspondence with amino acid positions of the SEQ ID NO:2 sequence. Also included are compositions, including, but not limited to, e.g., cleaning compositions, comprising at least one such variant and methods for cleaning utilizing at least one such variant as described in greater detail elsewhere herein.

The following BPN'-v36 variants were determined to have a PI value equal to or greater than 0.5 and less than 0.9 relative to BPN'-v36 in a BMI microswatch cleaning assay in Detergent Composition 4 at pH 8 and 16° C.: BPN'-S024G-S053G-S078N-S101N-G128A-Y217Q amino acid sequence (SEQ ID NO:6) comprising at least one set of amino acid substitutions selected from the group consisting of A015S-A088T-N109G-G131H-T158S-N218S-S248N, A088T-A098S-G131H-S248N-K256R-L257G, A088T-A116T-G131H-N218S-N243V-K256R-L257G, A088T-A116T-G131H-T158S-L257G, A088T-A116T-G131H-T158S-N218S-L257G, A088T-A116T-G131H-T158S-N218S-N243V-S248N-K256R-L257G, A088T-A116T-G131H-T158S-N218S-N243V-S248N-L257G, A088T-A116T-N218S-L257G, A088T-A116T-T158S-K256R, A088T-A116T-T158S-S248N-K256R-L257G, A088T-G131H-K141E-N218S-N243V-S248N-L257G, A088T-G131H-K256R, A088T-G131H-N218S-K256R, A088T-G131H-N218S-

N243V-S248N-K256R, A088T-G131H-N218S-N243V-S248N-L257G, A088T-G131H-N218S-S248N-K256R, A088T-G131H-N218S-S248N-K256R, A088T-G131H-T158S-S248N-K256R, A088T-G131H-T158S-S248N-K256R-L257G, A088T-I107T-N109G-G131H-N218S-S248N-K256R, A088T-N109G-A116T-G131H-D140G-T158S-N218S-N243V-K256R, A088T-N109G-A116T-G131H-N218S-N243V-K256R, A088T-N109G-A116T-G131H-N218S-N243V-S248N-K256R, A088T-N109G-A116T-G131H-T158S-N218S-S248N-L257G, A088T-N109G-A116T-G131H-T158S-N243V-S248N-K256R-I268V, A088T-N109G-A116T-G131H-V149A-N218S-S248N-K256R-L257G, A088T-N109G-A116T-N218S-N243V-S248N-K256R-L257G, A088T-N109G-A116T-T158S-K256R-L257G, A088T-N109G-A116T-T158S-N218S-N243V-L257G, A088T-N109G-D140G-N243V, A088T-N109G-G131H-D140G-T158S-N243V-S248N-K256R, A088T-N109G-G131H-K141E-T158S-N218S-K256R, A088T-N109G-G131H-N218S-S248N, A088T-N109G-G131H-N218S-S248N-K256R-Q271R, A088T-N109G-G131H-N218S-S248N-L257G, A088T-N109G-G131H-T158S-K256R, A088T-N109G-G131H-T158S-N218S-S248N-K256R, A088T-N109G-G131H-V149L-T158S-K256R-L257G, A088T-N109G-T158S-N218S, A088T-N109G-T158S-N218S-K256R-L257G-Q271K, A088T-N109G-T158S-N218S-L257G, A088T-N109G-T158S-S248N-K256R, A088T-N218S-S248N-L257G-Q271R, A088T-T158S-N218S-K256R-L257G, A088T-T158S-N218S-N243V-K256R, A088T-Y104H-A116T-G131H-N218S-N243V, A116T-G131H-K141E-N218S-N243V-S248N-L257G, A116T-G131H-N218S-N243V-S248N-K256R, A116T-G131H-T158S-N218S-S248N-L257G-N269D, A116T-G131H-T158S-N218S-S248N-Q271R, A116T-G131H-T158S-N243V-S248N, A116T-G157E-T158S-N243V-S248N-K256R, A116T-T158S-N218S, G131H-N218S-L257G, G131H-N218S-S248N, G131H-T158S-N218S-N243V-S248N-K256R-L257G, G131H-T158S-N218S-N243V-S248N-L257G, G131H-T158S-N218S-S248N-I268V, I107T-N109G-G131H-N218S-L257G, L090I-N109G-T158S-N243V, L257G, N109G-A116T-G131H-T158S-N218S-K256R-L257G-Q271R, N109G-A116T-N218S-W241R-N243V-S248N-K256R-L257G, N109G-G131H-K141E-L257G, N109G-G131H-N218S-N243V, N109G-T158S-N218S-N243V-L257G, N109G-T158S-N218S-S248N-K256R, N109G-T158S-N243V-S248N-K256R-L257G, N218S-S248N-K256R-L257G, S003P-N109G-G131H-T158S-L257G, S003P-S248N-L257G, T158S-S248N-K256R-L257G, V004A-A088T-G131H-N218S-N243V-S248N-L257G, Y006H-N218S-N243V-S248N, Y104H-N109G-G131H-N243V-S248N, A088T-A116T-T158S-N218S-N243V-S248N-K256R, A088T-A116T-T158S-N243V, A088T-G131H-T158S-N218S-I234T-S248N-L257G, A088T-G131H-T158S-N218S-N243V-S248N-K256R, A088T-G131H-V149L-T158S-N243V-S248N-K256R-L257G, A088T-I107T-N109G-G131H-N218S-A223G-S248N-K256R, A088T-K213N-N243V-S248N-K256R, A088T-K256R-L257G, A088T-N109G-A116T-G131H-A232S-N243V-K256R, A088T-N109G-A116T-G131H-D140G-S248N-L257G, A088T-N109G-A116T-G131H-N218S-N243V-S248N-K256R-L257G, A088T-N109G-A116T-G131H-T158S-N218S-N243V-S248N, A088T-N109G-A116T-G131H-T158S-N243V-S248N-L257G, A088T-N109G-A116T-M124I-G131H-T158S-N218S-S248N-L257G, A088T-N109G-A116T-V148A-N218S-N243V, A088T-N109G-G131H-N218S-N243V-S248N, A088T-N109G-N218S-S248N-T255K-K256R-L257G, A088T-T158S-N218S-L257G, A088T-T158S-N218S-Q245K-S248N-K256R, A088T-T158S-N218S-S248N-K256R, A116T-G131H-N218S-N243V-K256R, A116T-G131H-N218S-W241R-N243V-S248N-K256R-L257G, A116T-G131H-T158S-N218S-L257G, A116T-G131H-V150A-T158S-N243V-S248N-K256R-L257G, I107T-G131H-T158S-N243V-S248N-K256R-L257G, N109G-A116T-K141E-T158S-N218S-N243V-L257G, N109G-A116T-T158S-N218S-N243V-S248N, T158S-N243V-S248N-K256R, T158S-N243V-S248N-K256R-L257G, A088T-A116T-G131H-G146C, A088T-A116T-N218S, A088T-A116T-T158S-N243V-K256R-L257G, A088T-A138E-N218S-N243V-K256R, A088T-N109G-A116T-G131H-T158S-N218S-N243F-S248N, A088T-T158S-V203I-N218S-K256R-L257G, A116T-D140G-T158S-N218S-N243V-S248N, A088T-A116T-T158S-K256R-L257G, A088T-A116T-T158S-N218S-N243V-S248N-E251K-K256R-L257G, A088T-I108T-N109G-G131H-T158S-N218S-S248N-K256R-L257G, A088T-N109G-A116T-G131H-K141E-N218S, A088T-N109G-W241R-S248N-K256R, and G065D-A088T-G131H-N243V-S248N, wherein amino acid positions of the variant are numbered by correspondence with the sequence of SEQ ID NO:2. Such variants have proteolytic activity. The invention includes a protease variant having proteolytic activity and/or a PI value equal to or greater than 0.5 and less than 0.9 relative to BPN'-v36 in this assay, the variant comprising an amino acid sequence having at least 60%, 70%, 80%, 85%, 90%, 91%, 92%, 93%, 94%, 95%, 96%, 97%, or 98% identity to the sequence of SEQ ID NO:2 or SEQ ID NO:6 and comprising at least one set of acid substitutions selected from said group above, wherein amino acid positions of the variant are numbered by correspondence with amino acid positions of the SEQ ID NO:2 sequence. Also included are compositions, including, but not limited to, e.g., cleaning compositions, comprising at least one such variant and methods for cleaning utilizing at least one such variant as described in greater detail elsewhere herein.

The following BPN'-v36 variants were determined to have a PI value greater than 1.0, at least 1.1, at least 1.2, at least 1.3, at least 1.4, at least 1.5, at least 1.6, at least 1.7, at least 1.8, at least 1.9, at least 2, from greater than 1.0 to about 10, from greater than 1.0 to about 8, or from greater than 1.0 to about 5 relative to BPN'-v36 in an egg microswatch cleaning assay in Detergent Composition 4 at pH 8 and 16° C.: BPN'-S024G-S053G-S078N-S101N-G128A-Y217Q amino acid sequence (SEQ ID NO:6) comprising at least one set of amino acid substitutions selected from the group consisting of A088T-N109G-A116T-T158S-N243V-L257G, A116T-N218S-N243V-L257G-N269S, A088T-A116T-K256R, A088T-G131H-K256R, A088T-N109G-A116T-T158S-S248N-K256R-L257G, A088T-N109G-T158S-L257G, A088T-A116T-G131H-T158S-N218S-N243V-K256R-A273T, A088T-A116T-N243V-L257G, A088T-A116T-S248N-K256R-L257G, A088T-A116T-T158S-N243V-L257G, A088T-A116T-T158S-N243V-S248N-L257G, A088T-N109G-A116T-G131H-N218S-N243V-S248N-K256R-L257G, A088T-N109G-A116T-G131H-N243V-L257G, A088T-N109G-A116T-G131H-T158S-L257G, A088T-N109G-A116T-T158S-N218S-L257G, A088T-N109G-A116T-T158S-N218S-N243V-S248N-K256R-L257G, A088T-N109G-G131H-N218S-K256R-L257G, A088T-N109G-N218S-S248N-L257G, A088T-T158S-N218S-N243V-K256R-I268V, A088T-T158S-N218S-S248N-L257G, A116T-N218S-K256R-L257G, N109G-A116T, N109G-A116T-G131H-T158S-L257G, N109G-A116T-N243V, N109G-A116T-N243V-K256R, N109G-A116T-

T158S-L257G, N109G-K256R, N109G-N243V-K256R-L257G, S003P-N109G-G131H-T158S-K256R, A088T-A116T, A088T-A116T-G131H-N218S-K256R-L257G, A088T-A116T-G131H-N218S-L257G, A088T-A116T-G131H-N218S-N243V-S248N-L257G, A088T-A116T-G131H-N243V-K256R-L257G, A088T-A116T-G131H-N243V-S248N-K256R-L257G, A088T-A116T-G131H-T158S-N218S-N243V, A088T-A116T-G131H-T158S-N218S-N243V-K256R-L257G, A088T-A116T-G131H-T158S-N218S-N243V-S248N, A088T-A116T-G131H-T158S-S248N-K256R-L257G, A088T-A116T-G131H-T158S-S248N-L257G, A088T-A116T-N218S-N243V-L257G, A088T-A116T-N218S-N243V-S248N-K256R-L257G, A088T-A116T-N218S-N243V-S248N-K256R-Q275R, A088T-A116T-T158S-A216S-N218S-N243V-K256R-L257G, A088T-A116T-T158S-K256R, A088T-A116T-T158S-N218S-L257G, A088T-A116T-T158S-N218S-N243V, A088T-A116T-T158S-N218S-N243V-K256R, A088T-A116T-T158S-N218S-N243V-K256R-L257G, A088T-A116T-T158S-N218S-N243V-K256R-N269S, A088T-A116T-T158S-N243V, A088T-A116T-T158S-N243V-K256R, A088T-A116T-V147I-T158S-N218S-N243V-L257G, A088T-G131H-K256R-L257G, A088T-G131H-N218S-N243V-S248N-K256R-L257G, A088T-G131H-S248N-K256R-L257G, A088T-G131H-T158S-N218S-L257G, A088T-G131H-T158S-N218S-N243V-L257G, A088T-I107T-N109G-A116T-G131H-T158S-N218S-N243V-S248N, A088T-I107T-N109G-G131H-N218S-S248N-K256R, A088T-N109G-A116T-G131H-A153S-N218S-S248N-L257G, A088T-N109G-A116T-G131H-K256R-L257G, A088T-N109G-A116T-G131H-N218S-K256R-L257G, A088T-N109G-A116T-G131H-N218S-L257G, A088T-N109G-A116T-G131H-N218S-N243V-K256R, A088T-N109G-A116T-G131H-N218S-N243V-L257G, A088T-N109G-A116T-G131H-N243V-L257G, A088T-N109G-A116T-G131H-S248N-L257G, A088T-N109G-A116T-G131H-T158S-N218S, A088T-N109G-A116T-G131H-T158S-N218S-N243V-S248N-K256R, A088T-N109G-A116T-G131H-T158S-N218S-N243V-S248N-L257G, A088T-N109G-A116T-N218S-K256R-L257G, A088T-N109G-A116T-N218S-L257G, A088T-N109G-A116T-N218S-N243V, A088T-N109G-A116T-N218S-N243V-L257G, A088T-N109G-A116T-N218T-K256R, A088T-N109G-A116T-N218T-K256R-L257G, A088T-N109G-A116T-N243V, A088T-N109G-A116T-N243V-K256R-L257G, A088T-N109G-A116T-N243V-K256R-L257G-N269D, A088T-N109G-A116T-T158S, A088T-N109G-A116T-T158S, A088T-N109G-A116T-T158S-L257G, A088T-N109G-A116T-T158S-N218S-N243V-K256R-L257G, A088T-N109G-A116T-T158S-N218S-N243V-K256R-L257G, A088T-N109G-A116T-T158S-N218S-N243V-S248N, A088T-N109G-A116T-T158S-N243V-S248N-L257G, A088T-N109G-G131H-A138V-T158S-N218S-N243V-S248N-L257G, A088T-N109G-G131H-L257G, A088T-N109G-G131H-N218S, A088T-N109G-G131H-N218S-N243V-L257G, A088T-N109G-G131H-N218S-N243V-S248N-K256R-L257G, A088T-N109G-G131H-N218S-S248N-K256R-L257G, A088T-N109G-G131H-T158S-N218S-K256R, A088T-N109G-G131H-T158S-N218S-N243V, A088T-N109G-G131H-T158S-N243V-K256R-L257G, A088T-N109G-G131H-T158S-N243V-L257G, A088T-N109G-G131H-T158S-N243V-S248N-L257G, A088T-N109G-G131H-V149A-K256R-L257G, A088T-N109G-N218S-N243V-L257G, A088T-N109G-N218S-N243V-S248N-L257G, A088T-N109G-N218S-S248N-K256R-L257G, A088T-N109G-N243V, A088T-N109G-N243V-K256R-L257G, A088T-N109G-N243V-L257G, A088T-N109G-N243V-S248N-L257G, A088T-N109G-S248N-K256R-L257G, A088T-N109G-T158S-K256R, A088T-N109G-T158S-N218S-N243V-K256R-Q275R, A088T-N109G-T158S-N243V, A088T-N109G-T158S-N243V-K256R-I268V, A088T-N109G-T158S-N243V-L257G, A088T-N109G-T158S-N243V-S248N-L257G, A088T-N218S-N243V-L257G, A088T-N218S-N243V-S248N-K256R-L257G, A088T-N218S-S248N, A088T-T158S-N218S-N243V-K256R-L257G, A088T-V143A-T158S-K256R, A088T-V147I-N218S-N243V-K256R-L257G, A114S-A116T-N218S-N243V-S248N-K256R-L257G, A116T-G131H-N218S-N243V-S248N-K256R-L257G, A116T-G131H-N218S-N243V-S248N-L257G, A116T-G131H-N243V-K256R, A116T-G131H-N243V-L257G, A116T-G131H-N243V-S248N-K256R, A116T-G131H-S248N-L257G, A116T-G131H-T158S-N218S-I234T-N243V-S248N-K256R, A116T-G131H-T158S-N218S-N243V-S248N-L257G, A116T-N218S-L257G, A116T-T158S-N218S-K256R-L257G, A116T-T158S-N218S-S248N, A116T-T158S-N218S-S248N-L257G-Q271R, A116T-T158S-N243V-S248N-L257G, A116T-T158S-S248N-L257G, G131H-N218S-S248N-K256R-L257G, I107T-N109G-A116T-G131H-T158S-N218S-N243V-S248N-K256R-L257G, N109G-A116T-G131H-A137V-T158S-S248N-K256R-L257G, N109G-A116T-G131H-A151S-N218S-K256R-L257G, N109G-A116T-G131H-N218S-K256R-L257G, N109G-A116T-G131H-N218S-N243V-L257G, N109G-A116T-G131H-N243V-L257G, N109G-A116T-G131H-S248N-L257G, N109G-A116T-G131H-T158S-N218S-N243V-K256R-L257G, N109G-A116T-G131H-T158S-N218S-N243V-S248N-K256R-L257G, N109G-A116T-K256R-L257G, N109G-A116T-N218S-N243V-K256R, N109G-A116T-N218S-N243V-S248N-K256R-L257G, N109G-A116T-N218S-N243V-S248N-L257G, N109G-A116T-N243V-S248N-K256R, N109G-A116T-S248N-L257G, N109G-A116T-T158S-G211V-N243V-S248N-K256R, N109G-A116T-T158S-N218S, N109G-A116T-T158S-N218S-N243V-L257G, N109G-A116T-T158S-N218S-N243V-S248N, N109G-G131H-N218S-K237N, N109G-G131H-N218S-K256R-L257G, N109G-G131H-N218S-L257G, N109G-G131H-N218S-N243V-L257G, N109G-G131H-N243V-K256R-L257G, N109G-G131H-N243V-S248N-L257G, N109G-G131H-S248N-K256R, N109G-G131H-T158S-K256R-L257G, N109G-G131H-T158S-N218S-K256R-L257G, N109G-G131H-T158S-N243V, N109G-N218S, N109G-N218S-N243V-L257G, N109G-T158S-N218S-K256R-L257G, N109G-T158S-N218S-L257G, N109G-T158S-N218S-N243V-K256R, N109G-T158S-N243V-L257G, N243V-K256R-L257G, N243V-L257G, S003F-A088T-N109G-A116T-T158S-N243V-K256R-L257G, T158S-N218S-L233S, T158S-N218S-N243V-S248N-K256R, V004A-N109G-A116T-T158S-N218S-S248N-L257G, Y006H-A116T-G131H-T158S-N218S-N243V-S248N-K256R-A272G, A088T-A098S-N218S-K256R, A088T-A116T-G131H-K256R-L257G-L267M, A088T-A116T-G131H-L257G, A088T-A116T-G131H-N218S-A274T, A088T-A116T-G131H-N218S-K256R, A088T-A116T-G131H-N218S-N243V-K256R, A088T-A116T-G131H-N218S-N243V-K256R-L257G, A088T-A116T-G131H-N218S-N243V-K256R-L257G, A088T-A116T-G131H-N218S-N243V-L257G, A088T-A116T-G131H-N218S-N243V-S248N-K256R, A088T-A116T-G131H-N218S-N243V-S248N-K256R-L257G, A088T-A116T-G131H-N218S-S248N-L257G, A088T-A116T-G131H-N243V-K256R, A088T-A116T-G131H-N243V-L257G, A088T-

A116T-G131H-N243V-S248N, A088T-A116T-G131H-N243V-S248N-A274V, A088T-A116T-G131H-N243V-S248N-K256R-L257G, A088T-A116T-G131H-S248N-K256R-L257G, A088T-A116T-G131H-T158S-K256R-L257G, A088T-A116T-G131H-T158S-K256R-L257G, A088T-A116T-G131H-T158S-L257G, A088T-A116T-G131H-T158S-N218S, A088T-A116T-G131H-T158S-N218S-K256R, A088T-A116T-G131H-T158S-N218S-K256R-L257G, A088T-A116T-G131H-T158S-N218S-K256R-L257G, A088T-A116T-G131H-T158S-N218S-L257G, A088T-A116T-G131H-T158S-N218S-N243V-K256R, A088T-A116T-G131H-T158S-N218S-N243V-S248N-K256R, A088T-A116T-G131H-T158S-N218S-S248N-K256R, A088T-A116T-G131H-T158S-N218S-S248N-L257G, A088T-A116T-G131H-T158S-N243V-K256R-L257G, A088T-A116T-G131H-T158S-N243V-L257G, A088T-A116T-G131H-T158S-N243V-S248N-K256R, A088T-A116T-G131H-T158S-N243V-S248N-K256R-L257G, A088T-A116T-K256R, A088T-A116T-N218S-K256R, A088T-A116T-N218S-N243V-K256R, A088T-A116T-N218S-N243V-K256R-L257G, A088T-A116T-N218S-N243V-S248N-K256R, A088T-A116T-N218S-N243V-S248N-L257G, A088T-A116T-N243V-K256R, A088T-A116T-N243V-L257G, A088T-A116T-N243V-S248N-K256R, A088T-A116T-N243V-S248N-K256R-L257G, A088T-A116T-S248N, A088T-A116T-S248N-K256R, A088T-A116T-S248N-L257G, A088T-A116T-T158S-N218S, A088T-A116T-T158S-N218S-K256R, A088T-A116T-T158S-N218S-K256R, A088T-A116T-T158S-N218S-K256R-L257G, A088T-A116T-T158S-N218S-N243V-K256R, A088T-A116T-T158S-N218S-N243V-S248N, A088T-A116T-T158S-N218S-N243V-S248N, A088T-A116T-T158S-N218S-N243V-S248N-K256R, A088T-A116T-T158S-N218S-N243V-S248N-K256R-L257G, A088T-A116T-T158S-N218S-N243V-S248N-L257G, A088T-A116T-T158S-N218S-N243V-K256R-L257G, A088T-G131H, A088T-G131H-N218S-K256R-L257G, A088T-G131H-N218S-N243V-K256R, A088T-G131H-N218S-N243V-K256R, A088T-G131H-N218S-N243V-L257G, A088T-G131H-N218S-N243V-L257G, A088T-G131H-N218S-S248N, A088T-G131H-N218S-S248N-K256R, A088T-G131H-N218S-S248N-K256R-L257G, A088T-G131H-N218S-S248N-L257G, A088T-G131H-N218T-L257G, A088T-G131H-N243V-L257G, A088T-G131H-N243V-S248N-K256R, A088T-G131H-S248N, A088T-G131H-S248N-L257G, A088T-G131H-T158S-N218S-K256R, A088T-G131H-T158S-N218S-K256R-L257G, A088T-G131H-T158S-N218S-N243V-K256R, A088T-G131H-T158S-N218S-N243V-K256R, A088T-G131H-T158S-N218S-N243V-K256R-L257G, A088T-G131H-T158S-N218S-N243V-K256R-L257G, A088T-G131H-T158S-N218S-S248N, A088T-G131H-T158S-N218S-S248N-K256R, A088T-G131H-T158S-N218S-S248N-K256R, A088T-G131H-T158S-N218S-S248N-L257G-I268V, A088T-G131H-T158S-N243V, A088T-G131H-T158S-N243V-S248N, A088T-G131H-T158S-N243V-S248N, A088T-G131H-T158S-N243V-S248N-K256R-L257G, A088T-N109G-A116T, A088T-N109G-A116T-G131H-D140G-T158S-N218S-N243V-K256R, A088T-N109G-A116T-G131H-K256R, A088T-N109G-A116T-G131H-N218S, A088T-N109G-A116T-G131H-N218S, A088T-N109G-A116T-G131H-N218S-K256R, A088T-N109G-A116T-G131H-N218S-L257G, A088T-N109G-A116T-G131H-N218S-N243V, A088T-N109G-A116T-G131H-N218S-N243V-K256R-L257G, A088T-N109G-A116T-G131H-N218S-N243V-L257G, A088T-N109G-A116T-G131H-N218S-N243V-S248N-K256R, A088T-N109G-A116T-G131H-N218S-S248N-K256R-L257G, A088T-N109G-A116T-G131H-N218S-S248N-L257G, A088T-N109G-A116T-G131H-N218S-S248N-L257G, A088T-N109G-A116T-G131H-N243V-K256R-L257G, A088T-N109G-A116T-G131H-N243V-S248N, A088T-N109G-A116T-G131H-N243V-S248N-K256R-L257G, A088T-N109G-A116T-G131H-S248N-K256R, A088T-N109G-A116T-G131H-S248N-K256R-L257G, A088T-N109G-A116T-G131H-S248N-L257G, A088T-N109G-A116T-G131H-T158S, A088T-N109G-A116T-G131H-T158S-N218S, A088T-N109G-A116T-G131H-T158S-N218S-L257G, A088T-N109G-A116T-G131H-T158S-N218S-N243V-K256R, A088T-N109G-A116T-G131H-T158S-N218S-N243V-K256R, A088T-N109G-A116T-G131H-T158S-N218S-N243V-K256R-L257G, A088T-N109G-A116T-G131H-T158S-N218S-N243V-S248N-K256R, A088T-N109G-A116T-G131H-T158S-N218S-S248N, A088T-N109G-A116T-G131H-T158S-N218S-S248N-K256R, A088T-N109G-A116T-G131H-T158S-N218S-S248N-L257G, A088T-N109G-A116T-G131H-T158S-N218S-S248N-L257G, A088T-N109G-A116T-G131H-T158S-N218T-N243V, A088T-N109G-A116T-G131H-T158S-N243V-K256R-L257G, A088T-N109G-A116T-G131H-T158S-N243V-S248N, A088T-N109G-A116T-G131H-T158S-N243V-S248N-K256R, A088T-N109G-A116T-G131H-T158S-N243V-S248N-L257G, A088T-N109G-A116T-G131H-T158S-S248N-K256R-L257G, A088T-N109G-A116T-G131H-T158S-S248N-L257G, A088T-N109G-A116T-K256R, A088T-N109G-A116T-N218S, A088T-N109G-A116T-N218S-N243V, A088T-N109G-A116T-N218S-N243V-K256R, A088T-N109G-A116T-N218S-N243V-K256R-L257G, A088T-N109G-A116T-N218S-N243V-L257G, A088T-N109G-A116T-N218S-N243V-S248N-K256R-L257G, A088T-N109G-A116T-N243V-S248N, A088T-N109G-A116T-N243V-S248N-K256R, A088T-N109G-A116T-N243V-S248N-K256R-L257G, A088T-N109G-A116T-N243V-S248N-K256R-L257G, A088T-N109G-A116T-N243V-S248N-L257G, A088T-N109G-A116T-S248N-K256R, A088T-N109G-A116T-S248N-K256R-L257G, A088T-N109G-A116T-T158S-K256R, A088T-N109G-A116T-T158S-N218S, A088T-N109G-A116T-T158S-N218S-K256R-L257G, A088T-N109G-A116T-T158S-N218S-L257G, A088T-N109G-A116T-T158S-N218S-N243V, A088T-N109G-A116T-T158S-N218S-N243V-L257G, A088T-N109G-A116T-T158S-N218S-N243V-S248N, A088T-N109G-A116T-T158S-N218S-N243V-S248N-K256R, A088T-N109G-A116T-T158S-N218S-N243V-S248N-L257G, A088T-N109G-A116T-T158S-N218S-S248N, A088T-N109G-A116T-T158S-N218S-S248N-K256R, A088T-N109G-A116T-T158S-N218S-S248N-L257G, A088T-N109G-A116T-T158S-N243V-K256R, A088T-N109G-A116T-T158S-N243V-S248N, A088T-N109G-A116T-T158S-S248N, A088T-N109G-A116T-T158S-S248N-K256R, A088T-N109G-A116T-T158S-S248N-L257G, A088T-N109G-G131H-N218S-K256R, A088T-N109G-G131H-N218S-K256R, A088T-N109G-G131H-N218S-N243V-K256R, A088T-N109G-G131H-N218S-N243V-K256R, A088T-N109G-G131H-N218S-N243V-K256R-L257G, A088T-N109G-G131H-N218S-N243V-S248N-K256R, A088T-N109G-G131H-N218S-S248N-L257G, A088T-N109G-G131H-N243V-K256R-L257G, A088T-N109G-G131H-N243V-K256R-L257G, A088T-N109G-G131H-N243V-L257G, A088T-N109G-G131H-

N243V-L257G, A088T-N109G-G131H-N243V-S248N-K256R, A088T-N109G-G131H-N243V-S248N-K256R-L257G, A088T-N109G-G131H-N243V-S248N-L257G, A088T-N109G-G131H-S248N-L257G, A088T-N109G-G131H-T158S-K256R-L257G, A088T-N109G-G131H-T158S-N218S-L257G, A088T-N109G-G131H-T158S-N218S-L257G, A088T-N109G-G131H-T158S-N218S-N243V-S248N, A088T-N109G-G131H-T158S-N218S-N243V-S248N-K256R, A088T-N109G-G131H-T158S-N218S-S248N-K256R, A088T-N109G-G131H-T158S-N218S-S248N-L257G, A088T-N109G-G131H-T158S-N243V, A088T-N109G-G131H-T158S-N243V-S248N, A088T-N109G-G131H-T158S-N243V-S248N-K256R, A088T-N109G-G131H-T158S-N243V-S248N-K256R, A088T-N109G-G131H-T158S-N243V-S248N-K256R-L257G, A088T-N109G-G131H-T158S-S248N-K256R-L257G, A088T-N109G-G131H-T158S-W241R-S248N-K256R, A088T-N109G-G131H-V148A-N218S-N243V-K256R-L257G, A088T-N109G-G154A-N155P-E156T-G157L-T158M-S159E-G160E-S161L, A088T-N109G-N218S-K256R, A088T-N109G-N218S-N243V-L257G, A088T-N109G-N218S-N243V-S248N, A088T-N109G-N243V-K256R, A088T-N109G-N243V-S248N, A088T-N109G-N243V-S248N-K256R-L257G, A088T-N109G-S248N, A088T-N109G-T158S-N218S, A088T-N109G-T158S-N218S-K256R, A088T-N109G-T158S-N218S-K256R-L257G, A088T-N109G-T158S-N218S-L257G, A088T-N109G-T158S-N218S-N243V-S248N-K256R, A088T-N109G-T158S-N218S-N243V-S248N-K256R-L257G, A088T-N109G-T158S-N218S-S248N-K256R, A088T-N109G-T158S-N218S-S248N-K256R-L257G, A088T-N109G-T158S-N243V-K256R, A088T-N109G-T158S-N243V-K256R, A088T-N109G-T158S-N243V-S248N-L257G, A088T-N109G-T158S-S248N-K256R-L257G, A088T-N109G-T158S-S248N-L257G, A088T-N109G-T158S-S248N-L257G, A088T-N109G-V147A-N218S-N243V-K256R, A088T-N218S-L257G-I268V, A088T-N218S-N243V, A088T-N218S-N243V-S248N, A088T-N218S-N243V-S248N-N269S, A088T-N218S-S248N-K256R, A088T-N218S-S248N-L257G-Q271R, A088T-N243V, A088T-N243V, A088T-N243V-K256R, A088T-N243V-S248N-K256R, A088T-N243V-S248N-K256R-L257G, A088T-S248N, A088T-T158S-N218S-K256R-L257G, A088T-T158S-N218S-N243V-K256R, A088T-T158S-N218S-N243V-L257G, A088T-T158S-N218S-N243V-S248N-K256R-L257G, A088T-T158S-N218S-N243V-S248N-K256R-L257G, A088T-T158S-N243V-K256R-L257G, A088T-T158S-N243V-K256R-L257G-Q271H, A088T-T158S-N243V-S248N, A088T-T158S-N243V-S248N-L257G, A088T-T158S-S248N, A088T-V147A-K256R, A116T-G131H-K256R, A116T-G131H-N218S, A116T-G131H-N218S-K256R-L257G, A116T-G131H-N218S-L257G, A116T-G131H-N218S-N243V, A116T-G131H-N218S-S248N-K256R, A116T-G131H-N218S-S248N-K256R-L257G, A116T-G131H-N243V-S248N, A116T-G131H-N243V-S248N-L257G, A116T-G131H-S248N-K256R, A116T-G131H-T158S-A231V-N243V-L257G, A116T-G131H-T158S-N218S-K256R, A116T-G131H-T158S-N218S-K256R-L257G, A116T-G131H-T158S-N218S-N243V-K256R-L257G, A116T-G131H-T158S-N218S-N243V-S248N-K256R, A116T-G131H-T158S-N218S-N243V-S248N-K256R-L257G, A116T-G131H-T158S-N218S-S248N, A116T-G131H-T158S-N243V-L257G, A116T-G131H-T158S-N243V-S248N-K256R, A116T-G131H-T158S-S248N-K256R, A116T-G131H-T158S-S248N-L257G, A116T-G131H-V143F-T158S-N218S, A116T-K256R, A116T-N218S, A116T-N218S-K256R, A116T-N218S-N243V-L257G, A116T-N218S-N243V-S248N-K256R, A116T-N218S-N243V-S248N-K256R-L257G, A116T-N218S-N243V-S248N-L257G, A116T-N218S-S248N-L257G, A116T-N243V, A116T-N243V-K256R-L257G, A116T-N243V-S248N, A116T-N243V-S248N-K256R-L257G, A116T-S248N-K256R-L257G, A116T-T158S-K256R-L257G, A116T-T158S-N218S, A116T-T158S-N218S-K256R, A116T-T158S-N218S-N243V, A116T-T158S-N218S-N243V-S248N, A116T-T158S-N218S-S248N-K256R, A116T-T158S-N218S-S248N-K256R-L257G, A116T-T158S-N243V-K256R, A116T-T158S-N243V-L257G, A116T-T158S-N243V-S248N, A116T-T158S-S248N-K256R-L257G, G131H-K141R-T158S-N218S-K256R, G131H-N218S, G131H-N218S-K256R, G131H-N218S-N243V-K256R-L257G, G131H-N218S-N243V-S248N, G131H-N218S-N243V-S248N-L257G, G131H-N243V-S248N-K256R, G131H-N243V-S248N-K256R-L257G, G131H-S248N, G131H-T158S-I234T-N243V-K256R, G131H-T158S-N218S-K256R-L257G, G131H-T158S-N218S-N243V, G131H-T158S-N218S-N243V-S248N-L257G, G131H-T158S-N218S-S248N-K256R-L257G, G131H-T158S-N218S-S248N-L257G, G131H-T158S-N243V-K256R, G131H-T158S-N243V-S248N-L257G, N109G, N109G-A116T-G131H-A144V-T158S-S248N-K256R-L257G, N109G-A116T-G131H-K256R-L257G, N109G-A116T-G131H-N218S-N243V-K256R, N109G-A116T-G131H-N218S-N243V-K256R-L257G, N109G-A116T-G131H-N218S-S248N-K256R, N109G-A116T-G131H-N218S-S248N-L257G, N109G-A116T-G131H-N243V-K256R, N109G-A116T-G131H-N243V-S248N, N109G-A116T-G131H-N243V-S248N-K256R-L257G, N109G-A116T-G131H-S248N, N109G-A116T-G131H-S248N-K256R, N109G-A116T-G131H-T158S-K256R, N109G-A116T-G131H-T158S-K256R-L257G, N109G-A116T-G131H-T158S-N218S-K256R, N109G-A116T-G131H-T158S-N218S-K256R-L257G, N109G-A116T-G131H-T158S-N218S-L257G, N109G-A116T-G131H-T158S-N218S-N243V-K256R, N109G-A116T-G131H-T158S-N218S-N243V-S248N-L257G, N109G-A116T-G131H-T158S-N218S-S248N, N109G-A116T-G131H-T158S-N243V-L257G, N109G-A116T-G131H-T158S-N243V-S248N, N109G-A116T-G131H-T158S-S248N, N109G-A116T-G131H-T158S-S248N-K256R, N109G-A116T-G131H-T158S-S248N-K256R-L257G, N109G-A116T-G131H-V149A-T158S-N218S-N243V-S248N-L257G, N109G-A116T-N218S, N109G-A116T-N218S-K256R, N109G-A116T-N218S-N243V-K256R-L257G, N109G-A116T-N218S-N243V-S248N-I268V, N109G-A116T-N243V-K256R-L257G, N109G-A116T-N243V-S248N, N109G-A116T-N243V-S248N-L257G, N109G-A116T-T158S, N109G-A116T-T158S-N218S-N243V-K256R-L257G, N109G-A116T-T158S-N218S-N243V-S248N-K256R-L257G, N109G-A116T-T158S-N218S-N243V-S248N-L257G, N109G-A116T-T158S-N218S-S248N-K256R-L257G, N109G-A116T-T158S-N243V-K256R-L257G, N109G-A116T-T158S-N243V-L257G, N109G-A116T-T158S-N243V-S248N-L257G, N109G-A116T-T158S-Q275R, N109G-A116T-T158S-S248N-K256R-L257G, N109G-G131H-L257G, N109G-G131H-N218S-N243V-S248N-K256R-L257G, N109G-G131H-N218S-N243V-S248N-L257G, N109G-G131H-N218S-S248N-K256R-L257G, N109G-G131H-N243V-K256R, N109G-G131H-S145F-N218S-N243V-K256R-L257G, N109G-G131H-S248N-K256R-L257G, N109G-G131H-S248N-L257G, N109G-G131H-T158S-K256R, N109G-G131H-T158S-N218S-L257G, N109G-G131H-

T158S-N218S-N243V, N109G-G131H-T158S-N218S-N243V-K256R, N109G-G131H-T158S-N218S-N243V-K256R-L257G, N109G-G131H-T158S-N218S-N243V-S248N-L257G, N109G-G131H-T158S-N218S-S248N-K256R, N109G-G131H-T158S-N218S-S248N-K256R-L257G-A274T, N109G-G131H-T158S-N218S-S248N-L257G, N109G-G131H-T158S-N243V-S248N, N109G-G131H-T158S-N243V-S248N-K256R-L257G, N109G-G131H-T158S-S248N-K256R-L257G, N109G-G131H-T158S-S248N-L257G, N109G-N218S-K256R-L257G, N109G-N218S-L257G, N109G-N218S-N243V-K256R, N109G-N218S-N243V-S248N-S260F, N109G-N218S-S248N, N109G-N243V-K256R, N109G-N243V-L257G, N109G-N243V-S248N, N109G-N243V-S248N-K256R-L257G, N109G-S182F-S204F-S207L-N218S-S236F-S248N-L257G, N109G-S248N-K256R, N109G-T158S-K256R, N109G-T158S-N218S-N243V-K256R-L257G, N109G-T158S-N218S-S248N-L257G, N109G-T158S-N243V, N109G-T158S-N243V-K256R, N109G-T158S-N243V-S248N, N109G-T158S-N243V-S248N-K256R, N109G-T158S-S248N-K256R, N109G-T158S-S248N-L257G, N218S, N218S-N243V-S248N-K256R, N218S-S248N-L257G, N243V-K256R, N243V-S248N-K256R, N243V-S248N-K256R-L257G, N243V-S248N-L257G-Q271R, S003P-A116T-T158S-S248N-K256R, S248N, T158S-N218S, T158S-N218S-A272V, T158S-N218S-L257G, T158S-N218S-N243V-K256R-L257G, T158S-N218S-N243V-L257G, T158S-N218S-S248N-K256R-L257G, T158S-N243V-K256R, T158S-N243V-K256R-L257G, T158S-N243V-S248N-K256R, V004A-N109G-A116T-G131H-S248N-K256R-L257G, and Y006H-A116T-G131H-S248N, wherein amino acid positions of the variant are numbered by correspondence with the sequence of SEQ ID NO:2. Such variants have enhanced proteolytic activity compared to BPN', BPN'-v3, and BPN'-v36, and a greater PI value than that of BPN', BPN'-v3 and BPN'-v36 in this assay. The invention includes a protease variant having enhanced proteolytic activity compared to BPN' (SEQ ID NO:2), enhanced proteolytic activity compared to BPN', BPN'-v3, and BPN'-v36, a PI value of greater than 1.0 to about 5 relative to BPN'-v3, and/or a PI value of greater than 1.0 to about 5 relative to BPN'-v36 in this assay, the variant comprising an amino acid sequence having at least 60%, 70%, 80%, 85%, 90%, 91%, 92%, 93%, 94%, 95%, 96%, 97%, or 98% identity to the sequence of SEQ ID NO:2 or SEQ ID NO:6 and comprising at least one set of amino acid substitutions selected from said group above, wherein amino acid positions of the variant are numbered by correspondence with amino acid positions of the SEQ ID NO:2 sequence. Also included are compositions, including, but not limited to, e.g., cleaning compositions, comprising at least one such variant and methods for cleaning utilizing at least one such variant as described in greater detail elsewhere herein.

The following BPN'-v36 variants were determined to have a PI value of about 1.0 relative to BPN'-v36 in an egg microswatch cleaning assay in Detergent Composition 4 at pH 8 and 16° C.: BPN'-S024G-S053G-S078N-S101N-G128A-Y217Q amino acid sequence (SEQ ID NO:6) comprising at least one set of amino acid substitutions selected from the group consisting of A015S-A088T-N109G-G131H-T158S-N218S-S248N, A088T, A088T-A116T-G131H-N218S-N243V-S248N, A088T-A116T-G131H-N218S-S248N, A088T-A116T-G131H-N218S-S248N, A088T-A116T-G131H-N218S-S248N-K256R-L257G, A088T-A116T-G131H-N243V, A088T-A116T-G131H-N243V-K256R, A088T-A116T-G131H-N243V-S248N, A088T-A116T-G131H-S248N-K256R, A088T-A116T-G131H-T158S-N218S-N243V-S248N, A088T-A116T-G131H-T158S-N218S-N243V-S248N-K256R, A088T-A116T-G131H-T158S-N218S-N243V-S248N-L257G, A088T-A116T-G131H-T158S-N218S-N243V-S248N-L257G, A088T-A116T-G131H-T158S-N218S-S248N, A088T-A116T-G131H-T158S-N218S-S248N-K256R, A088T-A116T-G131H-T158S-N243V, A088T-A116T-G131H-T158S-N243V-K256R, A088T-A116T-G131H-T158S-N243V-S248N, A088T-A116T-G131H-T158S-N243V-S248N-K256R-L257G, A088T-A116T-G131H-T158S-S248N, A088T-A116T-G131H-T158S-S248N-K256R, A088T-A116T-G131H-T158S-S248N-L257G, A088T-A116T-G131H-V147A-T158S-N218S-N243V-S248N-L257G, A088T-A116T-N218S-I268V, A088T-A116T-N218S-L257G, A088T-A116T-N218S-N243V-N269D, A088T-A116T-N218S-S248N, A088T-A116T-N218S-S248N, A088T-A116T-N218S-S248N-L257G, A088T-A116T-N243V-K256R-L257G, A088T-A116T-N243V-S248N-K256R, A088T-A116T-S248N-K256R, A088T-A116T-T158S-N218S, A088T-A116T-T158S-N218S-N243V-S248N-K256R-L257G, A088T-A116T-T158S-N218S-S248N, A088T-A116T-T158S-N218S-S248N-K256R-L257G, A088T-A116T-T158S-N243V-S248N, A088T-A116T-T158S-N243V-S248N-K256R, A088T-A116T-T158S-N243V-S248N-K256R-L257G, A088T-A116T-T158S-N243V-S248N-L257G, A088T-A116T-T158S-S248N, A088T-A116T-T158S-S248N-K256R-L257G, A088T-A116T-T158S-S248N-L257G, A088T-A116T-V143A-N218S-S248N-K256R, A088T-G131H-A138V-N218S-L257G, A088T-G131H-K141E-N218S-N243V-S248N-L257G, A088T-G131H-K256R, A088T-G131H-N218S-K256R, A088T-G131H-N218S-N243V-K256R-L257G, A088T-G131H-N218S-N243V-S248N, A088T-G131H-N218S-N243V-S248N, A088T-G131H-N218S-N243V-S248N-K256R, A088T-G131H-N218S-N243V-S248N-K256R-L257G, A088T-G131H-N218S-S248N, A088T-G131H-N218S-S248N-K256R, A088T-G131H-N243V-K256R-L257G, A088T-G131H-N243V-S248N, A088T-G131H-N243V-S248N-K256R-L257G, A088T-G131H-S248N, A088T-G131H-S248N-K256R, A088T-G131H-T158S-K256R, A088T-G131H-T158S-L257G, A088T-G131H-T158S-N218S, A088T-G131H-T158S-N218S-N243V-S248N, A088T-G131H-T158S-N218S-N243V-S248N-K256R, A088T-G131H-T158S-N218S-N243V-S248N-K256R-L257G, A088T-G131H-T158S-N218S-N243V-S248N-L257G, A088T-G131H-T158S-N218S-S248N, A088T-G131H-T158S-N218S-S248N-K256R-L257G, A088T-G131H-T158S-N243V, A088T-G131H-T158S-N243V-K256R, A088T-G131H-T158S-N243V-S248N-K256R, A088T-G131H-T158S-N243V-S248N-L257G, A088T-G131H-T158S-S248N-K256R-L257G, A088T-G131H-T158S-S248N-L257G, A088T-I107T-N109G-G131H-N218S-A223G-S248N-K256R, A088T-L257G, A088T-L257G, A088T-N109G-A116T-G131H-A232S-N243V-K256R, A088T-N109G-A116T-G131H-K256R-L257G, A088T-N109G-A116T-G131H-L257G, A088T-N109G-A116T-G131H-N218S-K256R, A088T-N109G-A116T-G131H-N218S-N243V-S248N-K256R, A088T-N109G-A116T-G131H-N218S-N243V-S248N-N269D, A088T-N109G-A116T-G131H-N243V-K256R, A088T-N109G-A116T-G131H-S248N, A088T-N109G-A116T-G131H-T158S-L257G, A088T-N109G-A116T-G131H-T158S-N218S-N243F-S248N, A088T-N109G-A116T-G131H-T158S-N218S-N243V, A088T-N109G-A116T-G131H-T158S-N218S-N243V-S248N-K256R-L257G, A088T-N109G-A116T-G131H-T158S-N218T-K256R, A088T-N109G-A116T-G131H-T158S-

N243V, A088T-N109G-A116T-G131H-T158S-N243V-K256R, A088T-N109G-A116T-G131H-T158S-N243V-S248N, A088T-N109G-A116T-G131H-T158S-N243V-S248N-K256R-I268V, A088T-N109G-A116T-G131H-T158S-N243V-S248N-L257G, A088T-N109G-A116T-G131H-T158S-S248N, A088T-N109G-A116T-G131H-T158S-S248N-K256R-L257G, A088T-N109G-A116T-G131H-V149A-N218S-S248N-K256R-L257G, A088T-N109G-A116T-K256R, A088T-N109G-A116T-N218S-K256R, A088T-N109G-A116T-N218S-N243V-S248N-K256R, A088T-N109G-A116T-N218S-N243V-S248N-L257G, A088T-N109G-A116T-N218S-S248N, A088T-N109G-A116T-N218S-S248N-K256R, A088T-N109G-A116T-S248N, A088T-N109G-A116T-T158S-L257G, A088T-N109G-A116T-T158S-N218S, A088T-N109G-A116T-T158S-N243V, A088T-N109G-A116T-T158S-N243V-K256R, A088T-N109G-A116T-T158S-N243V-S248N-K256R, A088T-N109G-G131H-N218S-N243V-S248N, A088T-N109G-G131H-N218S-S248N-K256R, A088T-N109G-G131H-N218S-S248N-K256R-L257G, A088T-N109G-G131H-N218S-S248N-K256R-L257G-Q275R, A088T-N109G-G131H-N218S-S248N-K256R-Q271R, A088T-N109G-G131H-N243V, A088T-N109G-G131H-N243V-K256R, A088T-N109G-G131H-N243V-S248N-K256R, A088T-N109G-G131H-S248N-K256R, A088T-N109G-G131H-S248N-L257G, A088T-N109G-G131H-T158S, A088T-N109G-G131H-T158S, A088T-N109G-G131H-T158S-K256R, A088T-N109G-G131H-T158S-K256R, A088T-N109G-G131H-T158S-N218S-N243V-K256R, A088T-N109G-G131H-T158S-N218S-N243V-K256R, A088T-N109G-G131H-T158S-N218S-N243V-K256R-L257G, A088T-N109G-G131H-T158S-N218S-N243V-S248N-K256R-L257G, A088T-N109G-G131H-T158S-N218S-N243V-S248N-L257G, A088T-N109G-G131H-T158S-N243V-K256R, A088T-N109G-G131H-T158S-N243V-K256R-L257G, A088T-N109G-G131H-T158S-N243V-S248N-K256R-L257G, A088T-N109G-G131H-T158S-S248N, A088T-N109G-G131H-T158S-S248N-L257G, A088T-N109G-G131H-V149A-K256R-L257G, A088T-N109G-G131H-V149L-T158S-K256R-L257G, A088T-N109G-K256R, A088T-N109G-K256R-L257G, A088T-N109G-K256R-L257G, A088T-N109G-L257G, A088T-N109G-N218S-K256R, A088T-N109G-N218S-N243V-K256R, A088T-N109G-N218S-N243V-S248N-K256R, A088T-N109G-N218S-N243V-S248N-K256R, A088T-N109G-N218S-S248N, A088T-N109G-N218S-S248N-L257G, A088T-N109G-N243V-K256R, A088T-N109G-N243V-S248N-L257G-I268V, A088T-N109G-S248N, A088T-N109G-S248N-K256R, A088T-N109G-T158S-K256R-L257G, A088T-N109G-T158S-N218S, A088T-N109G-T158S-N218S-K256R-Q271H, A088T-N109G-T158S-N218S-N243V-K256R, A088T-N109G-T158S-N218S-N243V-K256R-L257G, A088T-N109G-T158S-N218S-N243V-L257G, A088T-N109G-T158S-N218S-N243V-S248N-K256R, A088T-N109G-T158S-N218S-S248N-N269D, A088T-N109G-T158S-N243V-K256R-L257G, A088T-N109G-T158S-N243V-S248N-A274D, A088T-N109G-T158S-N243V-S248N-K256R-L257G-N269D, A088T-N218S-K256R, A088T-N218S-N243V, A088T-N218S-N243V-K256R, A088T-N218S-N243V-K256R-L257G, A088T-N218S-N243V-S248N-K256R, A088T-N218S-N243V-S248N-L257G, A088T-N218S-S248N-L257G, A088T-N243V-S248N, A088T-N243V-S248N-K256R, A088T-N243V-S248N-L257G, A088T-S145T-T158S-S248N, A088T-S248N-K256R-L257G, A088T-S248N-L257G, A088T-T158S, A088T-T158S, A088T-T158S-K256R, A088T-T158S-L257G, A088T-T158S-N218S, A088T-T158S-N218S-K256R, A088T-T158S-N218S-N243V-K256R, A088T-T158S-N218S-N243V-K256R-L257G, A088T-T158S-N218S-N243V-L257G, A088T-T158S-N218S-S248N, A088T-T158S-N218S-S248N, A088T-T158S-N243V, A088T-T158S-N243V-K256R, A088T-T158S-N243V-S248N-L257G, A116T, A116T-G131H-L257G, A116T-G131H-N218S-K256R, A116T-G131H-N218S-N243V-K256R, A116T-G131H-N218S-N243V-K256R-L257G, A116T-G131H-N218S-N243V-S248N, A116T-G131H-N218S-N243V-S248N-K256R, A116T-G131H-N218S-S248N, A116T-G131H-T158S-K256R, A116T-G131H-T158S-N218S-L257G, A116T-G131H-T158S-N218S-N243V-K256R, A116T-G131H-T158S-N218S-N243V-L257G, A116T-G131H-T158S-N218S-N243V-S248N, A116T-G131H-T158S-N218S-S248N-L257G-N269D, A116T-G131H-T158S-N218S-S248N-Q271R, A116T-G131H-T158S-N218T-L257G, A116T-G131H-T158S-N243V-K256R, A116T-G131H-V150A-T158S-N243V-S248N-K256R-L257G, A116T-K141E-N218S-N243V-S248N-K256R-L257G, A116T-L257G, A116T-N218S-N243V-S248N, A116T-N218T-N243V-S248N, A116T-N243V-S248N-L257G, A116T-S248N, A116T-S248N-L257G, A116T-T158S-K256R, A116T-T158S-N218S-L257G, A116T-T158S-N218S-N243V-K256R, A116T-T158S-N218S-N243V-L257G, A116T-T158S-N243V, A116T-T158S-N243V-K256R-L257G, A116T-T158S-N243V-S248N-K256R, A116T-T158S-N243V-S248N-K256R-L257G, A116T-V149I-T158S-N243V-S248N-K256R-Q271H, G024S-G053S-N078G-G097A-N101S, G024S-G053S-N078G-G097A-N101S-A128S, G131H-K256R, G131H-N218S-K256R-L257G, G131H-N218S-N243V-L257G, G131H-N218S-N243V-S248N-K256R, G131H-N218S-S248N-K256R, G131H-N218S-S248N-L257G, G131H-N243V, G131H-N243V-S248N, G131H-N243V-S248N-L257G, G131H-T158S-K256R-L257G, G131H-T158S-N218S, G131H-T158S-N218S-K256R, G131H-T158S-N218S-N240H-N243V-S248N-K256R-L257G, G131H-T158S-N218S-N243V-K256R, G131H-T158S-N218S-N243V-K256R-L257G, G131H-T158S-N218S-N243V-S248N, G131H-T158S-N218S-N243V-S248N-K256R-L257G, G131H-T158S-N218S-S248N-K256R-L257G-N269S, G131H-T158S-N218S-S248N-K256R-L257G-N269S, G131H-T158S-N243V-K256R-L257G, G131H-T158S-N243V-S248N, G131H-T158S-N243V-S248N-K256R, G131H-T158S-S248N, G131H-T158S-S248N-L257G, G131H-W241L-N243V-S248N-K256R, I107T-G131H-T158S-N243V-S248N-K256R-L257G, I107T-N109G-G131H-N218S-L257G, N109G-A116T-G131H-L257G, N109G-A116T-G131H-N218S-L257G, N109G-A116T-G131H-N218S-N243V, N109G-A116T-G131H-N218S-N243V-S248N-K256R, N109G-A116T-G131H-N218S-W241R-N243V-K256R, N109G-A116T-G131H-N243V-S248N-K256R, N109G-A116T-G131H-S248N-I268V, N109G-A116T-G131H-T158S-N218S, N109G-A116T-G131H-T158S-N218S-S248N-K256R, N109G-A116T-G131H-T158S-N218S-S248N-K256R-L257G, N109G-A116T-G131H-T158S-N218S-S248N-L257G, N109G-A116T-G131H-T158S-N243V-K256R-L257G, N109G-A116T-G131H-T158S-S248N-L257G, N109G-A116T-K141E-T158S-N218S-N243V-L257G, N109G-A116T-K256R, N109G-A116T-N218S-N243V, N109G-A116T-N218S-N243V-S248N, N109G-A116T-N218S-S248N-L257G, N109G-A116T-N243V-S248N-K256R-L257G, N109G-A116T-S248N, N109G-A116T-T158S-N218S-N243V-S248N-K256R, N109G-A116T-T158S-N218S-W241R-N243V, N109G-A116T-T158S-

N243V-S248N, N109G-A116T-T158S-S248N-L257G, N109G-G131H-K256R, N109G-G131H-N218S-K256R, N109G-G131H-N218S-N243V, N109G-G131H-N218S-N243V-K256R-L257G, N109G-G131H-N218S-N243V-S248N-K256R, N109G-G131H-N218S-S248N-K256R, N109G-G131H-N243V, N109G-G131H-N243V-S248N, N109G-G131H-N243V-S248N-K256R-L257G, N109G-G131H-S248N, N109G-G131H-T158S-L257G, N109G-G131H-T158S-N218S-N243V-S248N, N109G-G131H-T158S-N218S-N243V-S248N-K256R, N109G-G131H-T158S-N218S-N243V-S248N-K256R-L257G, N109G-G131H-T158S-N243V-L257G, N109G-G131H-T158S-N243V-S248N-K256R, N109G-G131H-T158S-S248N-K256R, N109G-K141E-N218S-S248N-L257G, N109G-N218S-N243V, N109G-N218S-N243V-S248N-K256R, N109G-N218S-S248N-K256R-L257G, N109G-N218S-S248N-L257G, N109G-N243V-S248N-L257G-Q275R, N109G-T158S-I268V, N109G-T158S-N218S, N109G-T158S-N218S-N243V, N109G-T158S-N218S-N243V-S248N, N109G-T158S-N218S-S248N-K256R, N109S-A116T-S248N, N218S-K256R, N218S-N243V-K256R, N218S-N243V-L257G, N218S-N243V-S248N, N218S-S248N, N218S-S248N-K256R, N218S-S248N-K256R-L257G, S003P-N109G-G131H-N218S-N243V-S248N-K256R-L257G, S248N-K256R-L257G, T158S-K256R, T158S-K256R-L257G, T158S-N218S-K256R-L257G, T158S-N218S-L233S-S248N, T158S-N243V, T158S-N243V-S248N-K256R-N269D, T158S-N243V-S248N-L257G, V004L-A116T-N218S-N243V-S248N-L257G, and Y006H-N218S-N243V-S248N, wherein amino acid positions of the variant are numbered by correspondence with the sequence of SEQ ID NO:2. Such variants have enhanced proteolytic activity compared to BPN' (SEQ ID NO:2) and a greater PI value than that of BPN' in this assay. The invention includes a protease variant having enhanced proteolytic activity compared to BPN' (SEQ ID NO:2), a PI value of about 1.0 relative to BPN'-v3, and a PI value of 1.0 relative to BPN'-v36 in this assay, the variant comprising an amino acid sequence having at least 60%, 70%, 80%, 85%, 90%, 91%, 92%, 93%, 94%, 95%, 96%, 97%, or 98% identity to the sequence of SEQ ID NO:2 or SEQ ID NO:6 and comprising at least one set of amino acid substitutions selected from said group above, wherein amino acid positions of the variant are numbered by correspondence with amino acid positions of the SEQ ID NO:2 sequence. Also included are compositions, including, but not limited to, e.g., cleaning compositions, comprising at least one such variant and methods for cleaning utilizing at least one such variant as described in greater detail elsewhere herein.

The following BPN'-v36 variants were determined to have a PI value equal to or greater than 0.5 and less than 0.9 relative to BPN'-v36 in an egg microswatch cleaning assay in Detergent Composition 4 at pH 8 and 16° C.: BPN'-S024G-S053G-S078N-S101N-G128A-Y217Q amino acid sequence (SEQ ID NO:6) comprising at least one set of amino acid substitutions selected from the group consisting of A088T-A098S-G131H-S248N-K256R-L257G, A088T-A116T-G131H-K256R, A088T-A116T-G131H-N218S-S248N-K256R, A088T-A116T-G131H-N243V-S248N-L257G, A088T-A116T-G131H-S248N, A088T-A116T-G131H-S248N-K256R-L257G, A088T-A116T-G131H-T158S-K256R, A088T-A116T-G131H-T158S-L257G, A088T-A116T-G131H-T158S-N218S-L257G, A088T-A116T-T158S-N218S-N243V-S248N-K256R-L257G, A088T-A116T-K256R-L257G, A088T-A116T-K256R-L257G, A088T-A116T-N218S-N243V-Q271R, A088T-A116T-N218S-S248N-K256R, A088T-A116T-T158S, A088T-A116T-T158S-K256R, A088T-A116T-T158S-N218S-N243V-L257G, A088T-A116T-T158S-N218S-S248N-K256R, A088T-G131H, A088T-G131H-L257G, A088T-G131H-N218S-N243V-S248N-L257G, A088T-G131H-N243V-K256R, A088T-G131H-N243V-L257G, A088T-G131H-N243V-S248N, A088T-G131H-N243V-S248N-K256R, A088T-G131H-T158S-N218S-I234T-S248N-L257G, A088T-G131H-T158S-N218S-N243V-S248N-K256R-L257G, A088T-G131H-T158S-N243V-K256R-L257G, A088T-G131H-T158S-S248N, A088T-G131H-T158S-S248N-K256R, A088T-G131H-T158S-S248N-K256R-L257G, A088T-G131H-V149L-T158S-N243V-S248N-K256R-L257G, A088T-N109G-A116T-G131H-K141E-N218S, A088T-N109G-A116T-G131H-N218S-N243V-S248N-Q275R, A088T-N109G-A116T-G131H-N218S-S248N, A088T-N109G-A116T-G131H-N243V-S248N-K256R, A088T-N109G-A116T-G131H-S248N-K256R-L257G, A088T-N109G-A116T-G131H-T158S-K256R, A088T-N109G-A116T-G131H-T158S-N218S-N243V-S248N, A088T-N109G-A116T-G131H-T158S-N243V-S248N-K256R-L257G, A088T-N109G-A116T-G131H-T158S-S248N, A088T-N109G-A116T-G131H-V149A-T158S-N218S-K256R, A088T-N109G-A116T-G131H-S248N-K256R-L257G, A088T-N109G-A116T-N243V-K256R, A088T-N109G-A116T-N243V-S248N-L257G, A088T-N109G-A116T-S248N-L257G, A088T-N109G-A116T-T158S-N212D-N243V-K256R-L257G, A088T-N109G-A137E-T158S-N218S-N243V-S248N-K256R-L257G, A088T-N109G-D140G-N243V, A088T-N109G-G131H-A152S-T158S-N218S-S248N-K256R, A088T-N109G-G131H-D140G-T158S-N243V-S248N-K256R, A088T-N109G-G131H-K256R-L257G, A088T-N109G-G131H-N218S, A088T-N109G-G131H-N218S-N243V, A088T-N109G-G131H-T158S-L257G, A088T-N109G-G131H-T158S-N218S-N243V-S248N-K256R-L257G, A088T-N109G-G131H-T158S-N218S-W241R-S248N-L257G, A088T-N109G-G131H-T158S-S248N-K256R, A088T-N109G-N218S-S248N-K256R, A088T-N109G-N243V-S248N-K256R, A088T-N109G-T158S, A088T-N109G-T158S-N243V-S248N-K256R, A088T-N109G-T158S-N243V-S248N-Q275R, A088T-N109G-T158S-S248N, A088T-N218S-N243V-S248N-K256R-L257G, A088T-N243V-L257G, A088T-S248N, A088T-T158S-K256R, A088T-T158S-N218S-K256R, A088T-T158S-N218S-L257G, A088T-T158S-N218S-L257G, A088T-T158S-N218S-N243V-S248N, A088T-T158S-N218S-N243V-S248N-L257G, A088T-T158S-N218S-Q245K-S248N-K256R, A088T-T158S-N218S-S248N-L257G-Q275K, A088T-T158S-N243V-K256R, A088T-T158S-N243V-K256R-L257G, A088T-T158S-N243V-S248N-K256R, A088T-T158S-S248N, A088T-T158S-S248N-K256R-L257G, A088T-T158S-S248N-L257G, A088T-T158S-S248N-L257G, A098S-G131H-T158S-N218S-N243V-S248N-K256R-L257G, A116T-G131H-K141E-N218S-N243V-S248N-L257G, A116T-G131H-N218S-W241R-N243V-S248N-K256R-L257G, A116T-G131H-N243V, A116T-G131H-T158S-N218S-S248N-K256R, A116T-G131H-V139I-N218S-N243V-S248N, A116T-N218S-S248N-K256R, A116T-T158S-L257G-Q271R, A116T-T158S-N218S-N243V-K256R-L257G, G053S-A088T-N109G-A116T-G131H-T158S-G169S-N218S-S248N-K256R-L257G, G131H-N218S-L257G, G131H-T158S, G131H-T158S-K256R, K256R, L090I-N109G-T158S-N243V, L257G, N109G-A116T-G131H, N109G-A116T-G131H-N243V, N109G-A116T-G131H-T158S-N218S-N243V-S248N-K256R, N109G-A116T-S248N-K256R, N109G-A116T-

T158S-N218S-K237R-N243V-S248N, N109G-A116T-T158S-S248N, N109G-G131H-T158S, N109G-G131H-T158S-N243V-K256R-L257G, N109G-G131H-T158S-S248N-Q271R, N109G-N218S-S248N-K256R, N109G-N243V-S248N-L257G, N109G-S248N, N109G-T158S-N218S-N243V-L257G, N109G-T158S-N243V-K256R-L257G, N109G-T158S-N243V-S248N-K256R-L257G, N218S-N243V-S248N-K256R-L257G, S003P-N109G-A116T-G131H-T158S-N218S-K256R, S003P-N109G-G131H-T158S-L257G, S105H-W106G-I107L-I108S-N109A-G110A-I111S-E112N-W113G-A114P, T158S-N218S-S248N-K256R, T158S-N243V-S248N, T158S-S248N, T158S-S248N-K256R-L257G, V004A-A088T-A116T-T158S-N218S, V004A-A088T-G131H-N218S-N243V-S248N-L257G, Y006H-N109G-N218S-N243V-S248N, Y104H-A116T-T158S-S248N, A088T-A116T-G131H-N218S-S248N-L257G, A088T-A116T-G131H-T158S-N218S-N243V-L257G, A088T-A116T-G131H-T158S-N243V-K256R-L257G, A088T-A116T-N218S, A088T-G131D-T158S-N243V-S248N, A088T-G131H-N218S-K237R-K256R-L257G, A088T-G131H-N218S-K256R, A088T-K213N-N243V-S248N-K256R, A088T-K256R-L257G, A088T-N109G-A116T-G131H-D140G-S248N-L257G, A088T-N109G-A116T-G131H-L257G, A088T-N109G-A116T-G131H-N218S-N243V-S248N-K256R-L257G, A088T-N109G-A116T-G131H-T158S-N218S-N243V-S248N, A088T-N109G-A116T-M124I-G131H-T158S-N218S-S248N-L257G, A088T-N109G-A116T-T158S-N218S-N243V-K256R, A088T-N109G-A116T-T158S-N218S-N243V-L257G, A088T-N109G-A116T-T158S-N218S-S248N, A088T-N109G-G131H-K256R-L257G, A088T-N109G-G131H-N218S-N243V-S248N-L257G, A088T-N109G-G131H-N243V-S248N, A088T-N109G-G131H-T158S-L233S-N243V-S248N, A088T-N109G-G131H-T158S-N218S-S248N-K256R, A088T-N109G-L257G, A088T-N109G-N218S-K256R-L257G, A088T-N109G-N218S-S248N-T255K-K256R-L257G, A088T-N109G-S248N-K256R-L257G, A088T-N109G-T158S-N218S-N243V, A088T-N109G-T158S-N218S-N243V-L257G, A088T-N109G-T158S-N218S-N243V-S248N-L257G, A088T-N109G-T158S-N218S-S248N, A088T-S248N-K256R-L257G, A088T-S248N-L257G-I268V, A088T-T158S-N243V-L257G, A088T-T158S-V203I-N218S-K256R-L257G, A088T-Y104H-A116T-G131H-N218S-N243V, A116T-D140G-T158S-N218S-N243V-S248N, A116T-G131H-T158S-K256R-L257G, A116T-G131H-T158S-N243V-S248N, A116T-G157E-T158S-N243V-S248N-K256R, A116T-S248N-K256R, G131H-N218S-S248N, G131H-N243V-K256R, G131H-T158S-N243V-L257G, K256R-L257G, N109G-A116T-G131H-T158S-N218S-N243V-S248N, N109G-A116T-N218S-N243V-L257G, N109G-A116T-N218S-W241R-N243V-S248N-K256R-L257G, N109G-A116T-T158S-N243V, N109G-A116T-T158S-S248N-K256R, N109G-N243V, N109G-T158S-K256R-L257G, N243V, P014L-A015L-L016C-H017T-S018L-Q019K-G020A-Y021T-T022L-G023E, S003P-S248N-L257G, T158S-N218S-N243V-S248N, T158S-S248N-K256R, Y104H-N109G-G131H-N243V-S248N, A088T-A116T-G131H-L257G, A088T-A116T-G131H-N218S-N243V, A088T-A116T-G131H-N218S-S248N-K256R, A088T-A116T-G131H-T158S-N243V-S248N-L257G, A088T-A116T-L257G, A088T-A116T-N218S, A088T-A116T-N218S-N243V-S248N, A088T-A116T-T158S-N218S-S248N, A088T-A116T-T158S-N243V-S248N-K256R, A088T-A138E-N218S-N243V-K256R, A088T-G131H-N218S-N243V-S248N-K256R, A088T-G131H-T158S-S248N-K256R, A088T-N109G-A116T-G131H-N218S-S248N-K256R-L257G, A088T-N109G-A116T-G131H-N243V-S248N-K256R, A088T-N109G-A116T-G131H-T158S-N218S-L257G-I268V, A088T-N109G-A116T-G131H-W241L-S248N-K256R-L257G, A088T-N109G-A116T-N218S-N243V-S248N-K256R, A088T-N109G-A116T-T158S-N243V-K256R-L257G, A088T-N109G-A116T-T158S-N243V-S248N, A088T-N109G-G131H-N218S-L257G, A088T-N109G-G131H-N218S-S248N, A088T-N109G-G131H-T158S-N243V-S248N-L257G, A088T-N109G-N243V-K256R-L257G, A088T-N109G-T158S-S248N-K256R, A088T-N109G-W241R-S248N-K256R, A088T-N218S-S248N-L257G, A088T-T158S-N218S-S248N-K256R, A088T-T158S-N218S-S248N-L257G, A116T-G131H-T158S-N218S-N243V, A116T-N218S-S248N, A116T-N243V-K256R, A116T-T158S, G131H-S248N-K256R, N109G-A116T-G131H-N243V-K256R-L257G, N109G-A116T-I234T-N243V-S248N-K256R-L257G, N109G-A116T-T158S-K256R-L257G, N109G-A116T-T158S-N218S-S248N-K256R, N109G-G131H, N109G-G131H-A137V-T158S-N218S-S248N, N109G-G131H-K141E-L257G, N109G-G131H-T158S-N243V-S248N-L257G, T158S-N218S-N243V-K256R, A088T-A116T-T158S-N243V-K256R-L257G, A088T-N109G-A116T-T158S-K256R-L257G, A088T-N109G-T158S-N218S-S248N, A088T-S248N-L257G, A088T-Y104H-N109G-G131H-A137E-T158S-N218S-N243V-S248N-K256R, G065D-A088T-G131H-N243V-S248N, Y104H-N218S-L257G, A088T-A116T-G131H-V150A-N218S-S248N-L257G, A088T-A116T-T158S-K256R-L257G, A088T-I108T-N109G-G131H-T158S-N218S-S248N-K256R-L257G, A088T-N109G-A116T-T158S-S248N-L257G-Q271P, A088T-N109G-A116T-V148A-N218S-N243V, A088T-Y104H-N109G-A116T-A153S-N218S-N243V-S248N-L257G-N269D, and V004M-A116T-V148A-T158S-N243V-S248N-K256R, wherein amino acid positions of the variant are numbered by correspondence with the sequence of SEQ ID NO:2. Such variants have proteolytic activity. The invention includes a protease variant having proteolytic activity and/or a PI value equal to or greater than 0.5 and less than 0.9 relative to BPN'-v36 in this assay, the variant comprising an amino acid sequence having at least 60%, 70%, 80%, 85%, 90%, 91%, 92%, 93%, 94%, 95%, 96%, 97%, or 98% identity to the sequence of SEQ ID NO:2 or SEQ ID NO:6 and comprising at least one set of acid substitutions selected from said group above, wherein amino acid positions of the variant are numbered by correspondence with amino acid positions of the SEQ ID NO:2 sequence. Also included are compositions, including, but not limited to, e.g., cleaning compositions, comprising at least one such variant and methods for cleaning utilizing at least one such variant as described in greater detail elsewhere herein.

Also provided is a subtilisin protease variant having enhanced proteolytic activity compared to BPN'-v36 and/or BPN-'v3 and/or a PI value of greater than 1.0 to about 5 compared to BPN'-v36 in a BMI microswatch or egg microswatch cleaning assay in Detergent Composition 4 at pH 8 and 16° C., the variant comprising an amino acid sequence having at least 85%, 90%, 91%, 92%, 93%, 94%, 95%, 96%, 97%, 98%, or 99% identity to SEQ ID NO:2 or SEQ ID NO:6, wherein the variant comprises at least one substitution selected from the group of X001R/T, X002R, X003F/P, X004A/L/M/P, X005S, X006H, X014L, X015L/S, X016C, X017T, X018L, X019K, X020A, X021T, X022L, X023E, X024S, X034S, X053S, X057Q, X065D, X078S, X086L, X088T, X090I, X097A, X098S, X101S, X104H, X105H/P, X106G, X107L/T, X108S/T, X109A/G/S, X110A, X111S, X112N, X113G, X114P/S, X116T, X124I, X128S, X131D/H, X137E/V, X138E/V, X139I, X140G, X141E/R, X143A/F, X144V, X145F/P/T, X146C, X147A/I, X148A, X149A/I/L, X150A, X151S, X152S, X153S, X154A, X155P, X156T, X157E/L, X158M/S, X159E, X160E, X161L, X169S, X182F, X203I, X204F, X207L, X211V, X212D, X213N, X216S, X218S/T, X223G, X231V, X232S, X233S, X234T, X235P, X236F/P, X237N/R, X240H, X241L/R, X243F/V, X245K, X248N, X251K, X255K, X256R, X257G, X260F, X267M, X268V, X269D/S, X271H/K/P/R, X272G/V, X273T, X274D/L/T/V, and X275K/R/S, and optionally at least one substitution selected from the group of A001R/T, Q002R, S003F/P, V004A/L/M/P, P005S, Y006H, P014L, A015L/S, L016C, H017T, S018L, Q019K, G020A, Y021T, T022L, G023E, G024S, G034S, G053S, P057Q, G065D, N078S, P086L, A088T, L090I, G097A, A098S, N101S, Y104H, S105H/P, W106G, I107L/T, I108S/T, N109A/G/S, G110A, I111S, E112N, W113G, A114P/S, A116T, M124I, A128S, G131D/H, A137E/V, A138E/V, V139I, D140G, K141E/R, V143A/F, A144V, S145F/P/T, G146C, V147A/I, V148A, V149A/I/L, V150A, A151S, A152S, A153S, G154A, N155P, E156T, G157E/L, T158M/S, S159E, G160E, S161L, G169S, S182F, V203I, S204F, S207L, G211V, N212D, K213N, A216S, N218S/T, A223G, A231V, A232S, L233S, I234T, L235P, S236F/P, K237N/R, N240H, W241L/R, N243F/V, Q245K, S248N, E251K, T255K, K256R, L257G, S260F, L267M, I268V, N269D/S, Q271H/K/P/R, A272G/V, A273T, A274D/L/T/V, Q275K/R/S, wherein amino acid positions of the variant are numbered by correspondence with positions of the sequence of SEQ ID NO:2. Such variants have enhanced proteolytic activity compared to BPN' (SEQ ID NO:2) BPN'-v3, and BPN'-v36 and a PI value greater than that of BPN', BPN'-v3, and BPN'-v36 in this assay. Also included are compositions, including, but not limited to, e.g., cleaning compositions, comprising at least one such variant and methods for cleaning utilizing at least one such variant as described in greater detail elsewhere herein.

Example 10

Construction and Cleaning Performance of Additional Variants of BPN'-v36

The DNA from the site evaluation libraries of the BPN'-v36 (described in Example 7) was further mutagenized by error-prone PCR. These libraries were amplified with primers P4973 and P4950 (described in Example 7) using Taq DNA polymerase (Promega). Each PCR amplification reaction contained 30 pmol of each primer, 100 ng of the template DNA (SELs of the BPN'-v36) and various amount of $MnCl_2$. The PCR reaction (20 μL) was initially heated at 95° C. for 2.5 min followed by 30 cycles of denaturation at 94° C. for 15 sec., annealing at 55° C. for 15 sec. and extension at 72° C. for 2 min. The DNA fragment was gel-purified by the QIAGEN® gel-band purification kit, digested by the BamHI and HindIII restriction enzymes and ligated with the pHPLT-BPN' partial opt vector that also was digested with the same restriction enzymes. Ligation mixtures were amplified using rolling circle amplification in an Illustra Templiphi kit according to the manufacturer's recommendation (GE Healthcare) to generate multimeric DNA for transformation into *Bacillus subtilis*. For this purpose, 1 μl of the ligation mixture was mixed with 5 μl of the sample buffer, heated to 95° C. for 3 min and cooled on ice. Next, 5 μl of the reaction buffer and 0.2 μl of the enzyme were added to each tube, followed by incubation at 30° C. for 10 hours. Products of the rolling circle amplification were diluted 100 times and used to transform *B. subtilis* cells (ΔaprE, ΔnprE, amyE::xylRPxylAcomK-phleo). An aliquot of the transformation mix was plated on LB plates containing 1.6% skim milk and 10 μg/mL neomycin and incubated overnight at 37° C.

About 500,000 clones were pre-screened on skim milk plates. Very few of them formed halos (i.e., indicative of the presence of functional protease). Colonies with halos were picked, inoculated in 150 μl of LB media containing 10 μg/mL neomycin and sequenced (Quintara). Sequences of these clones were analyzed by looking for combination of mutations, which occurred in this pool multiple times and might provide performance benefits. In order to assess the performance of these mutation combinations, double mutants were created in the BPN'-v36 background by PCR fusion as described below. For this purpose, two or three partially overlapping fragments were amplified by mutagenic primers. Primer combinations used to generate the respective variants are shown in Table 10-1 and primer sequences are shown in Table 10-2.

TABLE 10-1

Primers Pairs Used to Amplify Fragments

| Variant | Mutation 1 | Mutation 2 | Fragment 1 | Fragment 2 | Fragment 3 |
|---|---|---|---|---|---|
| 1 | A45S | S236Y | P4974, P6645 | P6644, P6647 | P6646, P4976 |
| 2 | A45S | S236G | P4974, P6645 | P6644, P6649 | P6648, P4976 |
| 3 | I115T | S183T | P4974, P6651 | P6650, P6655 | P6654, P4976 |
| 4 | I115V | N184Y | P4974, P6653 | P6652, P6657 | P6656, P4976 |
| 5 | I31T | S37P | P4974, P6659 | P6658, P4976 | |
| 6 | I31T | I35L | P4974, P6661 | P6660, P4976 | |
| 7 | I31V | S38W | P4974, P6663 | P6662, P4976 | |
| 8 | N25K | P129R | P4974, P6665 | P6664, P6667 | P6666, P4976 |
| 9 | N25K | P129K | P4974, P6665 | P6664, P6669 | P6668, P4976 |
| 10 | P14T | S37T | P4974, P6671 | P6670, P6673 | P6672, P4976 |
| 11 | P5L | Q217K | P4974, P6679 | P6678, P6681 | P6680, P4976 |
| 12 | P5L | Q217G | P4974, P6679 | P6678, P6683 | P6682, P4976 |
| 13 | Q10L | S37P | P4974, P6685 | P6684, P6675 | P6674, P4976 |
| 14 | Q10R | S37T | P4974, P6687 | P6686, P6673 | P6672, P4976 |
| 15 | S37P | T254S | P4974, P6675 | P6674, P6689 | P6688, P4976 |
| 16 | N25K | S37P | P4974, P6665 | P6664, P6675 | P6674, P4976 |
| 17 | G24A | S37W | P4974, P6691 | P6690, P6677 | P6676, P4976 |
| 18 | N25K | P129R | P4974, P6665 | P6664, P6667 | P6666, P4976 |
| 20 | S161P | S162L | P4974, P6695 | P6694, P4976 | |
| 21 | S161P | T253A | P4974, P6693 | P6692, P6701 | P6700, P4976 |
| 22 | S161P | S260P | P4974, P6693 | P6692, P6703 | P6702, P4976 |

TABLE 10-1-continued

Primers Pairs Used to Amplify Fragments

| Variant | Mutation 1 | Mutation 2 | Fragment 1 | Fragment 2 | Fragment 3 |
|---|---|---|---|---|---|
| 23 | S162L | D181H | P4974, P6697 | P6696, P6711 | P6710, P4976 |
| 24 | S162L | D181G | P4974, P6697 | P6696, P6713 | P6712, P4976 |
| 25 | S18F | S162L | P4974, P6715 | P6714, P6697 | P6696, P4976 |
| 26 | S18T | S162P | P4974, P6717 | P6716, P6699 | P6698, P4976 |
| 27 | S18P | D120N | P4974, P6719 | P6718, P6727 | P6726, P4976 |
| 28 | S18Y | K213R | P4974, P6721 | P6720, P6729 | P6728, P4976 |
| 29 | S18L | Y21S | P4974, P6731 | P6730, P4976 | |
| 30 | S18T | Y21N | P4974, P6733 | P6732, P4976 | |
| 31 | S9T | K141F | P4974, P6635 | P6734, P6737 | P6736, P4976 |
| 32 | S9T | K141R | P4974, P6635 | P6734, P6739 | P6738, P4976 |
| 33 | Q19L | S260N | P4974, P6725 | P6724, P6705 | P6704, P4976 |
| 34 | Q19L | S260P | P4974, P6725 | P6724, P6703 | P6702, P4976 |
| 35 | N61S | S260P | P4974, P6741 | P6740, P6703 | P6702, P4976 |
| 36 | N61D | S260I | P4974, P6743 | P6742, P6707 | P6706, P4976 |
| 37 | T253A | S260P | P4974, P6701 | P6700, P6703 | P6702, P4976 |
| 38 | A134T | S260G | P4974, P6745 | P6744, P6709 | P6708, P4976 |
| 39 | A133V | S260N | P4974, P6648 | P6746, P6705 | P6704, P4976 |

TABLE 10-2

Primer Sequences Used for Generation of Double Mutants of BPN'-v36

| Primer Name | Primer Sequence | SEQ ID NO: |
|---|---|---|
| P6644 | CAGATCTTAAAGTCTCTGGAGGGGCTTCTATGGTGC | SEQ ID NO: 64 |
| P6645 | CATAGAAGCCCCTCCAGAGACTTTAAGATCTGGATGGCTC | SEQ ID NO: 65 |
| P6646 | GCATTGATTCTTTACAAGCACCCGAACTGGACAAAC | SEQ ID NO: 66 |
| P6647 | CAGTTCGGGTGCTTGTAAAGAATCAATGCGGCCGCCCCA | SEQ ID NO: 67 |
| P6648 | GCATTGATTCTTGGTAAGCACCCGAACTGGACAAAC | SEQ ID NO: 68 |
| P6649 | CCAGTTCGGGTGCTTACCAAGAATCAATGCGGCCGCCCCA | SEQ ID NO: 69 |
| P6650 | CATCGAATGGGCCACAGCGAATAACATGGATGTAATCAAC | SEQ ID NO: 70 |
| P6651 | CATCCATGTTATTCGCTGTGGCCCATTCGATGCCGTTGAT | SEQ ID NO: 71 |
| P6652 | CATCGAATGGGCCGTAGCGAATAACATGGATGTAATCAAC | SEQ ID NO: 72 |
| P6653 | CATCCATGTTATTCGCTACGGCCCATTCGATGCCGTTGAT | SEQ ID NO: 73 |
| P6654 | CTGTAGACTCTACAAATCAACGTGCCTCTTTTTCCT | SEQ ID NO: 74 |
| P6655 | AAAGAGGCACGTTGATTTGTAGAGTCTACAGCGCCCACTG | SEQ ID NO: 75 |
| P6656 | CTGTAGACTCTTCATACCAACGTGCCTCTTTTTCCTCC | SEQ ID NO: 76 |
| P6657 | GAAAAGAGGCACGTTGGTATGAAGAGTCTACAGCGCCCA | SEQ ID NO: 77 |
| P6658 | TAGCGGTTACAGACAGCGGTATCGACCCAAGCCATCCAGATCTTAAAGTCG | SEQ ID NO: 78 |
| P6659 | ATGGCTTGGGTCGATACCGCTGTCTGTAACCGCTACTTTAACATTGCCTC | SEQ ID NO: 79 |
| P6660 | TAAAGTAGCGGTTACAGACAGCGGTTTAGACTCGAGCCATCCAGATCTT | SEQ ID NO: 80 |
| P6661 | ATGGCTCGAGTCTAAACCGCTGTCTGTAACCGCTACTTTAACATTGCCTC | SEQ ID NO: 81 |
| P6662 | GGTTGTAGACAGCGGTATCGACTCGTGGCATCCAGATCTTAAAGTCGCTG | SEQ ID NO: 82 |
| P6663 | ATGCCACGAGTCGATACCGCTGTCTACAACCGCTACTTTAACATTGCCTC | SEQ ID NO: 83 |
| P6664 | CTACACTGGAGGCAAAGTTAAAGTAGCGGTTATCGACA | SEQ ID NO: 84 |

TABLE 10-2-continued

Primer Sequences Used for Generation of
Double Mutants of BPN'-v36

| Primer Name | Primer Sequence | SEQ ID NO: |
|---|---|---|
| P6665 | ATAACCGCTACTTTAACTTTGCCTCCAGTGTAGCCTTGAG | SEQ ID NO: 85 |
| P6666 | GAGCCTGGGAGCACGTAGCGGCAGTGCGGCACTTAAA | SEQ ID NO: 86 |
| P6667 | GTGCCGCACTGCCGCTACGTGCTCCCAGGCTCATGTTGAT | SEQ ID NO: 87 |
| P6668 | TGAGCCTGGGAGCAAAGAGCGGCAGTGCGGCACTTAAA | SEQ ID NO: 88 |
| P6669 | GTGCCGCACTGCCGCTCTTTGCTCCCAGGCTCATGTTGAT | SEQ ID NO: 89 |
| P6670 | ATCACAAATTAAAGCCACAGCTCTGCACTCTCAAGGCTAC | SEQ ID NO: 90 |
| P6671 | AGAGTGCAGAGCTGTGGCTTTAATTTGTGATACGCCGTAA | SEQ ID NO: 91 |
| P6672 | GACAGCGGTATCGACACAAGCCATCCAGATCTTAAAGTCG | SEQ ID NO: 92 |
| P6673 | TAAGATCTGGATGGCTTGTGTCGATACCGCTGTCGATAAC | SEQ ID NO: 93 |
| P6674 | GACAGCGGTATCGACCCAAGCCATCCAGATCTTAAAGTCG | SEQ ID NO: 94 |
| P6675 | TAAGATCTGGATGGCTTGGGTCGATACCGCTGTCGATAAC | SEQ ID NO: 95 |
| P6676 | GACAGCGGTATCGACTGGAGCCATCCAGATCTTAAAGTCG | SEQ ID NO: 96 |
| P6677 | TAAGATCTGGATGGCTCCAGTCGATACCGCTGTCGATAAC | SEQ ID NO: 97 |
| P6678 | ACGCGCAGTCCGTGTTATACGGCGTATCACAAATTAAAGC | SEQ ID NO: 98 |
| P6679 | ATTTGTGATACGCCGTATAACACGGACTGCGCGTACGCAT | SEQ ID NO: 99 |
| P6680 | ACAAGTATGGTGCGAAAAACGGGACTTCCATGGCCTC | SEQ ID NO: 100 |
| P6681 | CATGGAAGTCCCGTTTTTCGCACCATACTTGTTCCCTG | SEQ ID NO: 101 |
| P6682 | ACAAGTATGGTGCGGGAAACGGGACTTCCATGGCCTC | SEQ ID NO: 102 |
| P6683 | CCATGGAAGTCCCGTTTCCCGCACCATACTTGTTCCCTG | SEQ ID NO: 103 |
| P6684 | CTTACGGCGTATCATTAATTAAAGCCCCTGCTCTGCAC | SEQ ID NO: 104 |
| P6685 | GAGCAGGGGCTTTAATTAATGATACGCCGTAAGGCACGGA | SEQ ID NO: 105 |
| P6686 | CTTACGGCGTATCACGTATTAAAGCCCCTGCTCTGCAC | SEQ ID NO: 106 |
| P6687 | GAGCAGGGGCTTTAATACGTGATACGCCGTAAGGCACGGA | SEQ ID NO: 107 |
| P6688 | TTTAGAAAACACCTCTACAAAACTTGGTGATTCTTTCTAC | SEQ ID NO: 108 |
| P6689 | TCACCAAGTTTTGTAGAGGTGTTTTCTAAACTGCTGCGGA | SEQ ID NO: 109 |
| P6690 | AGGCTACACTGGAGCAAATGTTAAAGTAGCGGTTATCGAC | SEQ ID NO: 110 |
| P6691 | GCTACTTTAACATTTGCTCCAGTGTAGCCTTGAGAGTG | SEQ ID NO: 111 |
| P6692 | GAGGGAACATCCGGACCATCGAGTACCGTCGGTTATCCA | SEQ ID NO: 112 |
| P6693 | ACCGACGGTACTCGATGGTCCGGATGTTCCCTCATTCCCA | SEQ ID NO: 113 |
| P6694 | AGGGAACATCCGGACCATTAAGTACCGTCGGTTATCCAGG | SEQ ID NO: 114 |
| P6695 | ACCGACGGTACTTAATGGTCCGGATGTTCCCTCATTCCCA | SEQ ID NO: 115 |
| P6696 | GAACATCCGGATCATTAAGTACCGTCGGTTATCCAGGCA | SEQ ID NO: 116 |
| P6697 | ATAACCGACGGTACTTAATGATCCGGATGTTCCCTCATTC | SEQ ID NO: 117 |
| P6698 | GAACATCCGGATCACCAAGTACCGTCGGTTATCCAGGCA | SEQ ID NO: 118 |
| P6699 | ATAACCGACGGTACTTGGTGATCCGGATGTTCCCTCATTC | SEQ ID NO: 119 |
| P6700 | GTTTAGAAAACGCAACTACAAAACTTGGTGATTCTTTC | SEQ ID NO: 120 |
| P6701 | CACCAAGTTTTGTAGTTGCGTTTTCTAAACTGCTGCGGAC | SEQ ID NO: 121 |

TABLE 10-2-continued

Primer Sequences Used for Generation of
Double Mutants of BPN'-v36

| Primer Name | Primer Sequence | SEQ ID NO: |
|---|---|---|
| P6702 | CAAAACTTGGTGATCCATTCTACTATGGAAAAGGGCTGAT | SEQ ID NO: 122 |
| P6703 | TTTCCATAGTAGAATGGATCACCAAGTTTTGTAGTGGTGT | SEQ ID NO: 123 |
| P6704 | CAAAACTTGGTGATAACTTCTACTATGGAAAAGGGCTGAT | SEQ ID NO: 124 |
| P6705 | TTTCCATAGTAGAAGTTATCACCAAGTTTTGTAGTGGTGT | SEQ ID NO: 125 |
| P6706 | CAAAACTTGGTGATATCTTCTACTATGGAAAAGGGCTGAT | SEQ ID NO: 126 |
| P6707 | TTTCCATAGTAGAAGATATCACCAAGTTTTGTAGTGGTGT | SEQ ID NO: 127 |
| P6708 | CAAAACTTGGTGATGGATTCTACTATGGAAAAGGGCTGAT | SEQ ID NO: 128 |
| P6709 | TTTCCATAGTAGAATCCATCACCAAGTTTTGTAGTGGTGT | SEQ ID NO: 129 |
| P6710 | GTGGGCGCTGTACACTCTTCAAATCAACGTGCCTCTT | SEQ ID NO: 130 |
| P6711 | CACGTTGATTTGAAGAGTGTACAGCGCCCACTGCAATCAC | SEQ ID NO: 131 |
| P6712 | GTGGGCGCTGTAGGATCTTCAAATCAACGTGCCTCTT | SEQ ID NO: 132 |
| P6713 | CACGTTGATTTGAAGATCCTACAGCGCCCACTGCAATCAC | SEQ ID NO: 133 |
| P6714 | CCTGCTCTGCACTTCCAAGGCTACACTGGAGGCAATG | SEQ ID NO: 134 |
| P6715 | CTCCAGTGTAGCCTTGGAAGTGCAGAGCAGGGGCTTTAAT | SEQ ID NO: 135 |
| P6716 | CCTGCTCTGCACACACAAGGCTACACTGGAGGCAATG | SEQ ID NO: 136 |
| P6717 | CTCCAGTGTAGCCTTGTGTGTGCAGAGCAGGGGCTTTAAT | SEQ ID NO: 137 |
| P6718 | CCTGCTCTGCACCCACAAGGCTACACTGGAGGCAATG | SEQ ID NO: 138 |
| P6719 | CTCCAGTGTAGCCTTGTGGGTGCAGAGCAGGGGCTTTAAT | SEQ ID NO: 139 |
| P6720 | CCTGCTCTGCACTACCAAGGCTACACTGGAGGCAATG | SEQ ID NO: 140 |
| P6721 | CTCCAGTGTAGCCTTGGTAGTGCAGAGCAGGGGCTTTAAT | SEQ ID NO: 141 |
| P6722 | CCTGCTCTGCACTTACAAGGCTACACTGGAGGCAATG | SEQ ID NO: 142 |
| P6723 | CTCCAGTGTAGCCTTGTAAGTGCAGAGCAGGGGCTTTAAT | SEQ ID NO: 143 |
| P6724 | TGCTCTGCACTCTTTAGGCTACACTGGAGGCAATGTTA | SEQ ID NO: 144 |
| P6725 | TTGCCTCCAGTGTAGCCTAAAGAGTGCAGAGCAGGGGCTT | SEQ ID NO: 145 |
| P6726 | ATCGCGAATAACATGAACGTAATCAACATGAGCCTGGGA | SEQ ID NO: 146 |
| P6727 | CTCATGTTGATTACGTTCATGTTATTCGCGATGGCCCAT | SEQ ID NO: 147 |
| P6728 | CTTCCAGGGAACCGTTATGGTGCGCAAAACGGGACTT | SEQ ID NO: 148 |
| P6729 | GTTTTGCGCACCATAACGGTTCCCTGGAAGCGTCGATTG | SEQ ID NO: 149 |
| P6730 | CTGCACTTACAAGGCTCTACTGGAGGCAATGTTAAAGTAG | SEQ ID NO: 150 |
| P6731 | TAACATTGCCTCCAGTAGAGCCTTGTAAGTGCAGAGCAGGGGCTTTAAT | SEQ ID NO: 151 |
| P6732 | GCTCTGCACTTACAAGGCAACACTGGAGGCAATGTTAAAGTAG | SEQ ID NO: 152 |
| P6733 | AACATTGCCTCCAGTGTTGCCTTGTAAGTGCAGAGCAGGGCTTTAAT | SEQ ID NO: 153 |
| P6734 | CTTACGGCGTAACACAAATTAAAGCCCCTGCTCTG | SEQ ID NO: 154 |
| P6735 | AGGGGCTTTAATTTGTGTTACGCCGTAAGGCACGGACT | SEQ ID NO: 155 |
| P6736 | TTAAAGCAGCAGTTGATTTCGCTGTTGCATCTGGTGTCGT | SEQ ID NO: 156 |
| P6737 | AGATGCAACAGCGAAATCAACTGCTGCTTTAAGTGCCGCA | SEQ ID NO: 157 |

TABLE 10-2-continued

Primer Sequences Used for Generation of
Double Mutants of BPN'-v36

| Primer Name | Primer Sequence | SEQ ID NO: |
|---|---|---|
| P6738 | TTAAAGCAGCAGTTGATCGTGCTGTTGCATCTGGTGTCGT | SEQ ID NO: 158 |
| P6739 | AGATGCAACAGCACGATCAACTGCTGCTTTAAGTGCCGCA | SEQ ID NO: 159 |
| P6740 | AAACCCGTTTCAAGATTCTAATTCTCATGGCACACACGTC | SEQ ID NO: 160 |
| P6741 | TGTGCCATGAGAATTAGAATCTTGAAACGGGTTTGTTTCG | SEQ ID NO: 161 |
| P6742 | AAACCCGTTTCAAGATGATAATTCTCATGGCACACACGTC | SEQ ID NO: 162 |
| P6743 | TGTGCCATGAGAATTATCATCTTGAAACGGGTTTGTTTCG | SEQ ID NO: 163 |
| P6744 | AAGCGGCAGTGCGACACTTAAAGCAGCAGTTGATAAAGC | SEQ ID NO: 164 |
| P6745 | TCAACTGCTGCTTTAAGTGTCGCACTGCCGCTTGGTGCTC | SEQ ID NO: 165 |
| P6746 | CAAGCGGCAGTGTTGCACTTAAAGCAGCAGTTGATAA | SEQ ID NO: 166 |
| P6747 | ACTGCTGCTTTAAGTGCAACACTGCCGCTTGGTGCTCCCA | SEQ ID NO: 167 |

Each PCR amplification reaction contained 30 pmol of each primer and 100 ng of the BPN'-v36 parent template DNA (plasmid pHPLT-BPN'-v36) (see FIG. 4). Amplifications were carried out using Vent DNA polymerase (NEB). The PCR reaction (20 µL) was initially heated at 95° C. for 2.5 min followed by 30 cycles of denaturation at 94° C. for 15 sec., annealing at 55° C. for 15 sec. and extension at 72° C. for 40 sec. Following amplification, the 5' and 3' gene fragments were gel-purified by the QIAGEN® gel-band purification kit, mixed (50 ng of each fragment), mixed and amplified by PCR once again using the primers P4973 and P4950 to generate the full-length gene fragment. The PCR conditions were same as described above, except the extension phase, which was carried out at 72° C. for 2 min. The full-length DNA fragment was gel-purified by the QIAGEN® gel-band purification kit, digested by the BamHI and HindIII restriction enzymes and ligated with the pHPLT-BPN' partial opt vector that also was digested with the same restriction enzymes. Ligation mixtures were amplified using rolling circle amplification in an Illustra Templiphi kit according to the manufacturer's recommendation (GE Healthcare) to generate multimeric DNA for transformation into *Bacillus subtilis*. For this purpose, 1 µl of the ligation mixture was mixed with 5 µl of the sample buffer, heated to 95° C. for 3 min and cooled on ice. Next, 5 µl of the reaction buffer and 0.2 µl of the enzyme were added to each tube, followed by incubation at 30° C. for 10 hours. Products of the rolling circle amplification were diluted 100 times and used to transform *B. subtilis* cells (ΔaprE, ΔnprE, amyE:: xylRPxylAcomK-phleo). An aliquot of the transformation mix was plated on LB plates containing 1.6% skim milk and 10 µg/mL neomycin and incubated overnight at 37° C. Subsequently, the colonies with halos were inoculated in 150 µl of LB media containing 10 µg/mL neomycin. The next day, the cultures were either frozen with 15% glycerol or grown in MBD medium for biochemical analysis as described in Example 2.

The variants were tested for cleaning performance using BMI microswatch assay in Detergent Composition 4 at 16° C. and pH 8, BMI microswatch assay in Detergent Composition 4 at 16° C. and pH 7, and Egg microswatch assay in Detergent Composition 4 at 16° C. and pH 8. Protein content was determined using TCA assay. All assays were performed as described in Example 1 and Performance Indices were calculated relative to BPN'-v36 (i.e., BPN'-S24G-S53G-S78N-S101N-G128A-Y217Q) (with a PI value of 1.0).

The following BPN'-v36 variants were determined to have a PI value of about 1.0 relative to BPN'-v36 in a BMI microswatch cleaning assay in Detergent Composition 4 at pH 8 and 16° C.: BPN'-S024G-S053G-S078N-S101N-G128A-Y217Q amino acid sequence (SEQ ID NO:6) comprising at least one set of amino acid substitutions selected from the group consisting of A133V-S260N, N061S-S260P, P014T-S037T, S009T-K141F, S009T-K141R, S018F-S162L, S018L-Y021S, S018P-D120N, S018T-S162P, S018T-Y021N, S018Y-K213R, S161P-S162L, S161P-S260P, and T253A-S260P, wherein amino acid positions of the variant are numbered by correspondence with the sequence of SEQ ID NO:2. Such variants have enhanced proteolytic activity compared to BPN' (SEQ ID NO:2) and a greater PI value than that of BPN' in this assay. The invention includes a protease variant having enhanced proteolytic activity compared to BPN' (SEQ ID NO:2), a PI value of about 1.0 relative to BPN'-v3, and a PI value of about 1.0 relative to BPN'-v36 in this assay, the variant comprising an amino acid sequence having at least 60%, 70%, 80%, 85%, 90%, 91%, 92%, 93%, 94%, 95%, 96%, 97%, or 98% identity to the sequence of SEQ ID NO:2 or SEQ ID NO:6 and comprising at least one set of amino acid substitutions selected from said group above, wherein amino acid positions of the variant are numbered by correspondence with amino acid positions of the SEQ ID NO:2 sequence. Also included are compositions, including, but not limited to, e.g., cleaning compositions, comprising at least one such variant and methods for cleaning utilizing at least one such variant as described in greater detail elsewhere herein.

The following BPN'-v36 variants were determined to have a PI value of about 0.9 relative to BPN'-v36 in a BMI microswatch cleaning assay in Detergent Composition 4 at pH 8 and 16° C.: BPN'-S024G-S053G-S078N-S101N-G128A-Y217Q amino acid sequence (SEQ ID NO:6) comprising at least one set of amino acid substitutions selected from the group consisting of A134T-S260G, I115V-N184Y, N025K-S037P, Q010L-S037P, Q019L-S260N, Q019L-S260P, S037P-T254S, and S161P-T253A, wherein amino acid positions of the variant are numbered by correspondence with the sequence of SEQ ID NO:2. Such variants have proteolytic activity. The invention includes a protease variant having proteolytic activity and/or a PI value of about 0.9 relative to BPN'-v36 in this assay, the variant comprising an amino acid sequence having at least 60%, 70%, 80%, 85%, 90%, 91%, 92%, 93%, 94%, 95%, 96%, 97%, or 98% identity to the sequence of SEQ ID NO:2 or SEQ ID NO:6 and comprising at least one set of acid substitutions selected from said group above, wherein amino acid positions of the variant are numbered by correspondence with amino acid positions of the SEQ ID NO:2 sequence. Also included are compositions, including, but not limited to, e.g., cleaning compositions, comprising at least one such variant and methods for cleaning utilizing at least one such variant as described in greater detail elsewhere herein.

The following BPN'-v36 variants were determined to have a PI value equal to or greater than 0.5 and less than 0.9 relative to BPN'-v36 in a BMI microswatch cleaning assay in Detergent Composition 4 at pH 8 and 16° C.: BPN'-S024G-S053G-S078N-S101N-G128A-Y217Q amino acid sequence (SEQ ID NO:6) comprising at least one set of amino acid substitutions selected from the group consisting of A045S-S236G, G024A-S037W, I031V-S038W, N061D-S260I, Q010R-S037T, I115T-S183T, N025K-P129K, N025K-P129R, A045S-S236Y, and S162L-D181H, wherein amino acid positions of the variant are numbered by correspondence with the sequence of SEQ ID NO:2. Such variants have proteolytic activity. The invention includes a protease variant having proteolytic activity and/or a PI value equal to or greater than 0.5 and less than 0.9 relative to BPN'-v36 in this assay, the variant comprising an amino acid sequence having at least 60%, 70%, 80%, 85%, 90%, 91%, 92%, 93%, 94%, 95%, 96%, 97%, or 98% identity to the sequence of SEQ ID NO:2 or SEQ ID NO:6 and comprising at least one set of acid substitutions selected from said group above, wherein amino acid positions of the variant are numbered by correspondence with amino acid positions of the SEQ ID NO:2 sequence. Also included are compositions, including, but not limited to, e.g., cleaning compositions, comprising at least one such variant and methods for cleaning utilizing at least one such variant as described in greater detail elsewhere herein.

The following BPN'-v36 variants were determined to have a PI value greater than 1.0, at least 1.1, at least 1.2, at least 1.3, at least 1.4, at least 1.5, at least 1.6, at least 1.7, at least 1.8, at least 1.9, at least 2, from greater than 1.0 to about 10, from greater than 1.0 to about 8, or from greater than 1.0 to about 5 relative to BPN'-v36 in a BMI microswatch cleaning assay in Detergent Composition 4 at pH 7 and 16° C.: BPN'-S024G-S053G-S078N-S101N-G128A-Y217Q amino acid sequence (SEQ ID NO:6) comprising at least one set of amino acid substitutions selected from the group consisting of S018F-S162L, S018P-D120N, P014T-S037T, S009T-K141R, and S161P-S162L, wherein amino acid positions of the variant are numbered by correspondence with the sequence of SEQ ID NO:2. Such variants have enhanced proteolytic activity compared to BPN', BPN'-v3, and BPN'-v36, and a greater PI value than that of BPN', BPN'-v3 and BPN'-v36 in this assay. The invention includes a protease variant having enhanced proteolytic activity compared to BPN' (SEQ ID NO:2), enhanced proteolytic activity compared to BPN', BPN'-v3, and BPN'-v36, a PI value of greater than 1.0 to about 5 relative to BPN'-v3, and/or a PI value of greater than 1.0 to about 5 relative to BPN'-v36 in this assay, the variant comprising an amino acid sequence having at least 60%, 70%, 80%, 85%, 90%, 91%, 92%, 93%, 94%, 95%, 96%, 97%, or 98% identity to the sequence of SEQ ID NO:2 or SEQ ID NO:6 and comprising at least one set of amino acid substitutions selected from said group above, wherein amino acid positions of the variant are numbered by correspondence with amino acid positions of the SEQ ID NO:2 sequence. Also included are compositions, including, but not limited to, e.g., cleaning compositions, comprising at least one such variant and methods for cleaning utilizing at least one such variant as described in greater detail elsewhere herein.

The following BPN'-v36 variants were determined to have a PI value of about 1.0 relative to BPN'-v36 in a BMI microswatch cleaning assay in Detergent Composition 4 at pH 7 and 16° C.: BPN'-S024G-S053G-S078N-S101N-G128A-Y217Q amino acid sequence (SEQ ID NO:6) comprising at least one set of amino acid substitutions selected from the group consisting of N061S-S260P, Q010L-S037P, S009T-K141F, S018L-Y021S, S018T-S162P, S018T-Y021N, S018Y-K213R, S037P-T254S, S161P-S260P, S161P-T253A, and T253A-S260P, wherein amino acid positions of the variant are numbered by correspondence with the sequence of SEQ ID NO:2. Such variants have enhanced proteolytic activity compared to BPN' (SEQ ID NO:2) and a greater PI value than that of BPN' in this assay. The invention includes a protease variant having enhanced proteolytic activity compared to BPN' (SEQ ID NO:2), a PI value of about 1.0 relative to BPN'-v3, and a PI value of about 1.0 relative to BPN'-v36 in this assay, the variant comprising an amino acid sequence having at least 60%, 70%, 80%, 85%, 90%, 91%, 92%, 93%, 94%, 95%, 96%, 97%, or 98% identity to the sequence of SEQ ID NO:2 or SEQ ID NO:6 and comprising at least one set of amino acid substitutions selected from said group above, wherein amino acid positions of the variant are numbered by correspondence with amino acid positions of the SEQ ID NO:2 sequence. Also included are compositions, including, but not limited to, e.g., cleaning compositions, comprising at least one such variant and methods for cleaning utilizing at least one such variant as described in greater detail elsewhere herein.

The following BPN' variants were determined to have a PI value of about 0.9 relative to BPN'-v3 in a BMI microswatch cleaning assay in Detergent Composition 4 at pH 7 and 16° C.: BPN' amino acid sequence (SEQ ID NO:2) comprising at least one set of amino acid substitutions selected from the group consisting of A133V-S260N, A134T-S260G, I115T-S183T, I115V-N184Y, N061D-S260I, Q019L-S260N, and Q019L-S260P, wherein positions of the variant are numbered by correspondence with the sequence of SEQ ID NO:2. Such variants have proteolytic activity. The invention includes a protease variant having proteolytic activity, a PI value of about 0.9 relative to BPN'-v3, and/or an enhanced proteolytic activity compared to BPN' in this assay, the variant comprising an amino acid sequence having at least 60%, 70%, 80%, 85%, 90%, 91%, 92%, 93%, 94%, 95%, 96%, 97%, or 98% identity to the sequence of SEQ ID NO:2 or SEQ ID NO:6 and at least one set of amino acid substitutions selected from said group above, wherein amino acid positions of the variant are numbered by correspondence with positions of the SEQ ID NO:2 sequence. Also included are compositions, including, but not limited to, e.g., cleaning compositions, comprising at least one such variant and methods for cleaning utilizing at least one such variant as described in greater detail elsewhere herein.

The following BPN'-v36 variants were determined to have a PI value equal to or greater than 0.5 and less than 0.9 relative to BPN'-v36 in a BMI microswatch cleaning assay in Detergent Composition 4 at pH 7 and 16° C.: BPN'-S024G-S053G-S078N-S101N-G128A-Y217Q amino acid sequence (SEQ ID NO:6) comprising at least one set of amino acid substitutions selected from the group consisting of A045S-S236G, G024A-S037W, Q010R-S037T, A045S-S236Y, I031V-S038W, N025K-S037P, S162L-D181H, and N025K-P129R, wherein amino acid positions of the variant are numbered by correspondence with the sequence of SEQ ID NO:2. Such variants have proteolytic activity. The invention includes a protease variant having proteolytic activity and/or a PI value equal to or greater than 0.5 and less than 0.9 relative to BPN'-v36 in this assay, the variant comprising an amino acid sequence having at least 60%, 70%, 80%, 85%, 90%, 91%, 92%, 93%, 94%, 95%, 96%, 97%, or 98% identity to the sequence of SEQ ID NO:2 or SEQ ID NO:6 and comprising at least one set of acid substitutions selected from said group above, wherein amino acid positions of the variant are numbered by correspondence with amino acid positions of the SEQ ID NO:2 sequence. Also included are compositions, including, but not limited to, e.g., cleaning compositions, comprising at least one such variant and methods for cleaning utilizing at least one such variant as described in greater detail elsewhere herein.

The following BPN'-v36 variants were determined to have a PI value greater than 1.0, at least 1.1, at least 1.2, at least 1.3, at least 1.4, at least 1.5, at least 1.6, at least 1.7, at least 1.8, at least 1.9, at least 2, from greater than 1.0 to about 10, from greater than 1.0 to about 8, or from greater than 1.0 to about 5 relative to BPN'-v36 in an egg microswatch cleaning assay in Detergent Composition 4 at pH 8 and 16° C.: BPN'-S024G-S053G-S078N-S101N-G128A-Y217Q amino acid sequence (SEQ ID NO:6) comprising at least one set of amino acid substitutions selected from the group consisting of I031V-S038W, P014T-S037T, S018F-S162L, S018P-D120N, and S162L-D181H, wherein amino acid positions of the variant are numbered by correspondence with the sequence of SEQ ID NO:2. Such variants have enhanced proteolytic activity compared to BPN', BPN'-v3, and BPN'-v36, and a greater PI value than that of BPN', BPN'-v3 and BPN'-v36 in this assay. The invention includes a protease variant having enhanced proteolytic activity compared to BPN' (SEQ ID NO:2), enhanced proteolytic activity compared to BPN', BPN'-v3, and BPN'-v36, a PI value of greater than 1.0 to about 5 relative to BPN'-v3, and/or a PI value of greater than 1.0 to about 5 relative to BPN'-v36 in this assay, the variant comprising an amino acid sequence having at least 60%, 70%, 80%, 85%, 90%, 91%, 92%, 93%, 94%, 95%, 96%, 97%, or 98% identity to the sequence of SEQ ID NO:2 or SEQ ID NO:6 and comprising at least one set of amino acid substitutions selected from said group above, wherein amino acid positions of the variant are numbered by correspondence with amino acid positions of the SEQ ID NO:2 sequence. Also included are compositions, including, but not limited to, e.g., cleaning compositions, comprising at least one such variant and methods for cleaning utilizing at least one such variant as described in greater detail elsewhere herein.

The following BPN'-v36 variants were determined to have a PI value of about 1.0 relative to BPN'-v36 in an egg microswatch cleaning assay in Detergent Composition 4 at pH 8 and 16° C.: BPN'-S024G-S053G-S078N-S101N-G128A-Y217Q amino acid sequence (SEQ ID NO:6) comprising at least one set of amino acid substitutions selected from the group consisting of A133V-S260N, A134T-S260G, G024A-S037W, I115V-N184Y, N025K-P129K, N025K-P129R, N061D-S260I, Q019L-S260P, S009T-K141F, S009T-K141R, S018L-Y021S, S018T-S162P, S018T-Y021N, S018Y-K213R, S161P-S162L, S161P-T253A, and T253A-S260P, wherein amino acid positions of the variant are numbered by correspondence with the sequence of SEQ ID NO:2. Such variants have enhanced proteolytic activity compared to BPN' (SEQ ID NO:2) and a greater PI value than that of BPN' in this assay. The invention includes a protease variant having enhanced proteolytic activity compared to BPN' (SEQ ID NO:2), a PI value of about 1.0 relative to BPN'-v3, and/or a PI value of about 1.0 relative to BPN'-v36 in this assay, the variant comprising an amino acid sequence having at least 60%, 70%, 80%, 85%, 90%, 91%, 92%, 93%, 94%, 95%, 96%, 97%, or 98% identity to the sequence of SEQ ID NO:2 or SEQ ID NO:6 and comprising at least one set of amino acid substitutions selected from said group above, wherein amino acid positions of the variant are numbered by correspondence with amino acid positions of the SEQ ID NO:2 sequence. Also included are compositions, including, but not limited to, e.g., cleaning compositions, comprising at least one such variant and methods for cleaning utilizing at least one such variant as described in greater detail elsewhere herein.

The following BPN'-v36 variants were determined to have a PI value equal to or greater than 0.8 and equal to or less than 0.9 relative to BPN'-v36 in an egg microswatch cleaning assay in Detergent Composition 4 at pH 8 and 16° C.: BPN'-S024G-S053G-S078N-S101N-G128A-Y217Q amino acid sequence (SEQ ID NO:6) comprising at least one set of amino acid substitutions selected from the group consisting of A045S-S236G, A045S-S236Y, I115T-S183T, N025K-S037P, N061S-S260P, Q010L-S037P, Q010R-S037T, Q019L-S260N, S037P-T254S, and S161P-S260P, wherein amino acid positions of the variant are numbered by correspondence with the sequence of SEQ ID NO:2. Such variants have proteolytic activity. The invention includes a protease variant having proteolytic activity and/or a PI value equal to or greater than 0.8 and equal to or less than 0.9 relative to BPN'-v36 in this assay, the variant comprising an amino acid sequence having at least 60%, 70%, 80%, 85%, 90%, 91%, 92%, 93%, 94%, 95%, 96%, 97%, or 98% identity to the sequence of SEQ ID NO:2 or SEQ ID NO:6 and comprising at least one set of acid substitutions selected from said group above, wherein amino acid positions of the variant are numbered by correspondence with amino acid positions of the SEQ ID NO:2 sequence. Also included are compositions, including, but not limited to, e.g., cleaning compositions, comprising at least one such variant and methods for cleaning utilizing at least one such variant as described in greater detail elsewhere herein.

Also provided is a subtilisin protease variant having enhanced proteolytic activity compared to BPN'-v36 and/or a PI value of greater than 1.0 to about 5 compared to BPN'-v36 in a BMI or egg microswatch cleaning assay in Detergent Composition 4 at pH 8 and 16° C., the variant comprising an amino acid sequence having at least 85%, 90%, 91%, 92%, 93%, 94%, 95%, 96%, 97%, 98%, or 99% identity to SEQ ID NO:2 or SEQ ID NO:6, wherein the variant comprises at least one substitution comprising at least one substitution selected from the group of X009T, X010L/R, X014T, X018F/L/P/T/Y, X019L, X021N/S, X024A, X025K, X031V, X037P/T/W, X038W, X045S, X061D/S, X115T/V, X120N, X129K/R, X133V, X134T, X141F/R, X161P, X162L/P, X181H, X183T, X184Y, X213R, X236G/Y, X253A, X254S, and X260G/I/N/P, and optionally at least one substitution selected from the group of S009T, Q010L/R, P014T, S018F/L/P/T/Y, Q019L, Y021N/S, G024A, N025K, I031V, S037P/T/W, S038W, A045S, N061D/S, I115T/V, D120N, P129K/R, A133V, A134T, K141F/R, S161P, S162L/P, D181H, S183T, N184Y, K213R, S236G/Y, T253A, T254S, and S260G/I/N/P, wherein amino acid positions of the variant are numbered by correspondence with positions of the sequence of SEQ ID NO:2. Such variants have enhanced proteolytic activity compared to BPN' (SEQ ID NO:2) BPN'-v3, and BPN'-v36 and a PI value greater than that of BPN', BPN'-v3, and BPN'-v36 in this assay. Also included are compositions, including, but not limited to, e.g., cleaning compositions, comprising at least one such variant and methods for cleaning utilizing at least one such variant as described in greater detail elsewhere herein.

Example 11

1. Generation of Combinatorial Libraries FS1-FS3

The pHPLT-BPN'-v3 plasmid containing the BPN' expression cassette served as template DNA (parent plasmid) for cloning. Three separate combinatorial libraries (FS1, FS2, and FS3) were synthesized by DNA2.0, and were delivered as individual ligation reactions. A list of libraries and possible substitutions are shown in Table 11-1. The libraries were designed to allow the incorporation of either the wild type residues or the substitutions at each site described in Table 11-1.

For efficient transformation of *B. subtilis*, the DNA from the ligation reaction was amplified by rolling circle amplification (RCA) using the Illustra Templiphi kit (GE Healthcare). Reactions were performed according to the manufacturer's protocol. One microliter of ten-fold diluted amplified DNA was used to transform 50 μL of competent *B. subtilis* cells (ΔaprE, ΔnprE, amyE::xylRPxylAcomK-phleo). The transformation mixture was shaken at 37° C. for 1 hour. Ten microliter aliquots of the transformation mixture were plated on skim milk (1.6%) Luria Agar plates supplemented with 10 μg/ml of neomycin (Teknova).

Transformants were picked into microtiter plates containing 125-150 μl Luria broth medium supplemented with 10 μg/ml neomycin. Plates were grown overnight at 37° C. with 250-300 rpm shaking and 70-80% humidity using Enzyscreen lids for microtiter plates (Enzyscreen). Between 7 and 10 microliters from the overnight culture plate were used to inoculate a new microtiter plate containing 190 μl of MBD medium (a MOPS based defined medium) with 10 μg/ml neomycin. MBD medium was prepared essentially as known in the art (see Neidhardt et al., J. Bacteriol. 119:736-747 (1974)), except that NH$_4$Cl$_2$, FeSO$_4$, and CaCl$_2$ were omitted from the base medium, 3 mM K$_2$HPO$_4$ was used, and the base medium was supplemented with 60 mM urea, and 100 ml of a solution made of 210 g/L glucose, and 350 g/L maltodextrin. The micronutrients were made up as a 100× stock solution containing in one liter, 400 mg FeSO$_4$.7H$_2$O, 100 mg MnSO$_4$.H$_2$O, 100 mg ZnSO$_4$.7H$_2$O, 50 mg CuCl$_2$.2H$_2$O, 100 mg CoCl$_2$.6H$_2$O, 100 mg NaMoO$_4$.2H$_2$O, 100 mg Na$_2$B$_4$O$_7$.10H$_2$O, 10 ml of 1 M CaCl$_2$, and 10 ml of 0.5 M sodium citrate. The MBD medium containing microtiter plates were grown for 60-70 hours at 37° C., 250-300 rpm, and 70-80% humidity using Enzyscreen lids (Enzyscreen) for determining protein expression. The next day, cultures were filtered through a micro-filter plate (0.22 μm; Millipore) and the resulting filtrate was used for biochemical analysis.

TABLE 11-1

Possible Substitutions for Combinatorial Libraries FS1-FS3

| | FS1 | FS2 | FS3 |
|---|---|---|---|
| 1 | G102A | A97G | N61E |
| 2 | S130P | A128G | P129E |
| 3 | T55P | N123G | K213L |
| 4 | V203Y | G102A | S145D |
| 5 | N61P | L126V | Q275E |
| 6 | S101N | G100N | P40E |
| 7 | S53G | N62Q | S159K |
| 8 | S78N | M124I | S24R |
| 9 | S87T-A88L-S89G | N61P | A144K |
| 10 | S24G-N25G | S130P | N240K |
| 11 | L75S-N76Y | P129S | P239R |

2. Generation of Variants to Improve BPN' Stability

To improve BPN' stability, variants were constructed using either parent molecules pHPLT-BPN' G97A-G128A-Y217Q-S87D or pHPLT-BPN' G97A-G128A-Y217Q-P40E, both synthesized by Gene Oracle, or parent molecules pHPLT-BPN' G97A-G128A-Y217Q-S78N and pHPLT-partial opt FNA (*B. amyloliquefaciens* subtilisin BPN'-Y217L) synthesized by GeneArt.

The information listed in Tables 11-2 and 11-3 summarizes the parent molecule used, the mutations added, and the primers used to construct variants provided herein.

TABLE 11-2

Primer Sequences Used for the Generation of BPN' Stability Mutants

| Primer | Primer Sequence 5' to 3' | SEQ ID NO: |
|---|---|---|
| p31 | /5PHOS/CGGCGTTAAACAATAACATTGGCGTGCTTGGTGTAG | 169 |
| p32 | /5PHOS/ACCAAGCACGCCAATGTTATTGTTTAACGCCGCAACC | 170 |
| p25 | /5PHOS/GTATCGACTCGAGCCATGAAGATCTTAAAGTCGCTGGAG | 171 |
| p26 | /5PHOS/CAGCGACTTTAAGATCTTCATGGCTCGAGTCGATACCG | 172 |
| p33 | /5PHOS/TTGGTGTAGCCCCGGATGCTTCGCTCTACGCCGTTAAAG | 173 |
| p34 | /5PHOS/CGTAGAGCGAAGCATCCGGGGCTACACCAAGCACG | 174 |
| p29 | /5PHOS/GAACGGTTGCGGCGTTAGATAATTCTATTGGCGTGCTTG | 175 |
| p30 | /5PHOS/AGCACGCCAATAGAATTATCTAACGCCGCAACCGTTC | 176 |

TABLE 11-2-continued

Primer Sequences Used for the Generation of BPN' Stability Mutants

| Primer | Primer Sequence 5' to 3' | SEQ ID NO: |
|---|---|---|
| p27 | /5PHOS/AACGGTTGCGGCGTTAGATAATAACATTGGCGTGCTT GGTGTAG | 177 |
| p28 | /5PHOS/ACACCAAGCACGCCAATGTTATTATCTAACGCCGCAA CCGTTCCTG | 178 |
| p7 | /5PHOS/CGGCGTTAAACAATAATATTGGCGTGCTTGG | 179 |
| p8 | /5PHOS/CCAAGCACGCCAATATTATTGTTTAACGCCG | 180 |
| p21 | /5PHOS/GGTGTAGCCCCGGATGCTTCGCTCTACG | 181 |
| p22 | /5PHOS/CGTAGAGCGAAGCATCCGGGGCTACACC | 182 |
| p11 | /5PHOS/GTATCGACTCGAGCCATGAAGATCTTAAAG | 183 |
| p12 | /5PHOS/CTTTAAGATCTTCATGGCTCGAGTCGATAC | 184 |
| p13 | /5PHOS/CGCTTCCAGGGAACAACTATGGTGCGTA | 185 |
| p14 | /5PHOS/TACGCACCATAGTTGTTCCCTGGAAGCG | 186 |
| p15 | /5PHOS/CACTCTCAAGGCTACGTTGGATCAAATGTTA | 187 |
| p16 | /5PHOS/TAACATTTGATCCAACGTAGCCTTGAGAGTG | 188 |
| p17 | /5PHOS/TGGCGTTTCTATTGAATCGACGCTTCCAG | 189 |
| p18 | /5PHOS/CTGGAAGCGTCGATTCAATAGAAACGCCA | 190 |

TABLE 11-3

Templates Used, Mutations to be Incorporated, and Primers Used in the Generation of Variants for Improved Stability

| | Parent Molecules (Templates) | Mutation to Incorporate | Primers Used |
|---|---|---|---|
| 1 | pHPLT-BPN' G97A-G128A-Y217Q-S87D | S78N | p31, p32 |
| 2 | pHPLT-BPN' G97A-G128A-Y217Q-S78N | P40E | p25, p26 |
| 3 | pHPLT-BPN' G97A-G128A-Y217Q-P40E | S87D | p33, p34 |
| 4 | pHPLT-BPN' G97A-G128A-Y217Q-S78N | P40E, S87D | p25, p33 |
| 5 | pHPLT-BPN' G97A-G128A-Y217Q-S87D | N76D | p29, p30 |
| 6 | pHPLT-BPN' G97A-G128A-Y217Q-S87D | N76D, S78N | p27, p28 |
| 7 | pHPLT-partial opt FNA | S78N | p7, p8 |
| 8 | pHPLT-partial opt FNA | S87D | p21, p22 |
| 9 | pHPLT-partial opt FNA | P40E | p11, p12 |
| 10 | pHPLT-partial opt FNA | K213N | p13, p14 |
| 11 | pHPLT-partial opt FNA | T22V | p15, p16 |
| 12 | pHPLT-partial opt FNA | Q206E | p17, p18 |
| 13 | pHPLT-partial opt FNA | P40E, S87D, S78N | p11, p21, p7 |

*Bacillus subtilis* strains expressing plasmids were streaked onto 1.6% skim milk plates containing 10 ppm neomycin and grown overnight at 37° C. Single colonies from the plates were grown overnight at 37° C. with shaking at 250 rpm in 5 mL Luria broth containing 10 ppm neomycin. Plasmids were isolated using the QIAGEN® Miniprep kit protocol adding 1 microliter of Ready Lyse lysozyme (Epicentre) for 15 minutes at 37° C. in buffer P1 to aid in cell lysis. The plasmids were sequenced to ensure correct DNA sequences before proceeding. The plasmids were methylated using NEB's Dam Methylase Kit in a reaction containing 77.5 µL water+ 10 µL Buffer 10×+0.25 µL SAM+2 µL DAM methylase+10 µL miniprep DNA (~150 ng/µL) at 37° C. overnight. The methylated plasmid DNA was purified using a DNA Clean and Concentrator Kit (Zymo) or with a QIAGEN® PCR purification kit. Multi-Site QUIKCHANGE® mutagenesis reactions were set up for each of the DNA templates in a reaction mix containing 2.5 µL Buffer 5×+0.75 µL Quik Solution+0.5 µL primer 1 (25 µM) 0.5 µL primer 2 (25 µM)+ 1.5 µL dNTP's+1 µL enzyme blend+16.25 µL H₂O+2 µL DNA. The PCR program used was: 95° C. for 1 min; (95° C. for 1 min, 53° C. for 1 min, 65° C. for 10 min)×29 cycles; 65° C. for 10 min, 4° C. hold. In all reactions, PCR was performed using a MJ Research PTC-200 Peltier thermal cycler. The parental DNA from the PCR samples was removed by addition of 1 µL of DpnI to QUIKCHANGE® mutagenesis kit reactions at 37° C. overnight. To increase the transformation frequency, the DpnI digested reactions were amplified using rolling circle amplification (RCA) using the Illustra TempliPhi kit according to the manufacturer's protocol. *B. subtilis* cells (ΔaprE, ΔnprE, amyE::xylRPxylAcomK-phleo) were transformed with 1 µL each of the RCA reaction and the transformed cells were plated onto LA+1.6% skim milk plates containing 10 ppm neomycin and incubated at 37° C. overnight. Colonies from overnight growth were selected to perform colony PCR for sequencing using "puReTaq Ready-To-Go PCR Beads" (Amersham). The PCR and sequencing primers used were pHPLT F1 (SEQ ID NO:54) and pHPLT seq R1 (SEQ ID NO:55). Clones with appropriate sequences were frozen. The BPN' variant proteins were produced by growing the *B. subtilis* transformants in 96 well microtiter plates at 37° C. for 68 hours in a MOPS based medium containing urea.

3. Generation of BPN' Variants Derived From Five Different Parent Plasmids

BPN' variants were constructed using a total of five different templates: BPN'-v3 (G97A-G128A-Y217Q), BPN'-v4 (G97A-N123G-Y217Q), BPN' variant 8, (S87D-G97A-N109D-G128A-S188D-S248R-Y217Q), BPN' variant 16 (S87D-G97A-N109D-G128A-S188D-Y217Q), and BPN' variant 21 (S87R-G97A-N109R-G128A-S188R-Y217Q-

S248R) as shown in Table 11-4. The generation of BPN'-v4 and BPN'-v3 are described in PCT App. No. PCT/US09/46066 (WO 09/149,144), filed on Jun. 3, 2009, hereby incorporated herein by reference for such description. BPN' variants 8, 16, 21 were synthesized by Gene Oracle and served as parent plasmids to build additional variants. All variants were generated using QUIKCHANGE® mutagenesis kits, except two (variants 5 and 33), which were generated using fusion PCR as described below. Primers (listed in Table 11-5) for the generation of variants were synthesized at Integrated DNA Technologies. The mutations introduced (shown in bold) and the primers and template used are shown in Table 11-4.

BPN' variant 21 were streaked onto 1.6% skim milk plates containing 10 ppm neomycin and grown overnight at 37° C. Single colonies from the plates were grown overnight at 37° C. with shaking at 250 rpm in 5 mL Luria broth containing 10 ppm neomycin. Plasmids expressing BPN'-v3, BPN'-v4, BPN' variant 8, BPN' variant 16, and BPN' variant 21 were isolated using QIAGEN® Miniprep kit protocol except following cell lysis, 1 microliter of Ready Lyse lysozyme was added and incubated for 15 minutes at 37° C. The plasmids were methylated using NEB's Dam Methylase Kit in a reaction containing 77.75 µL $H_2O$+10 µL Buffer 10×+0.25 µL SAM+2 µL DAM methylase+10 µL miniprep DNA at 37° C.

TABLE 11-4

Mutations Introduced (bold) & Parent Plasmids Used to Generate BPN' Variants

| Variant | Variants Constructed | Parent Plasmid | Primers Used |
|---|---|---|---|
| 1 | G97A-N123C-Y217Q | G97A-N123G-Y217Q | N123C f, N123C r |
| 2 | N76D-G97A-G128A-Y217Q | G97A-G128A-Y217Q | N76D f, N76D r |
| 3 | G97A-N109D-G128A-Y217Q | G97A-G128A-Y217Q | N109D f1, N109D r |
| 4 | G97A-G128A-S188D-Y217Q | G97A-G128A-Y217Q | S188D f, S188D r |
| 5 | G97A-G128A-S248D-Y217Q | G97A-G128A-Y217Q | pHPLT F1, S248D forfus, pHPLT R1, S248D revfus |
| 6 | G97A-G128A-S188D-S248R-Y217Q | G97A-G128A-Y217Q | S188D f, S248R f1 |
| 7 | G97A-N109D-G128A-S188D-S248R-Y217Q | S87D-G97A-N109D-G128A-S188D-S248R-Y217Q | D87S f, D87S r |
| 8 | S87D-G97A-N109D-G128A-S188D-S248R-Y217Q | Synthesized by Gene Oracle | Synthesized by Gene Oracle |
| 9 | S87R-G97A-G128A-S188D-S248D-Y217Q | S87D-G97A-N109D-G128A-S188D-Y217Q | S87R f, S248D f1, D109N f |
| 10 | S87R-G97A-N109D-G128A-S188D-Y217Q | S87D-G97A-N109D-G128A-S188D-S248R-Y217Q | R248Sfor, R248Srev |
| 11 | G97A-N109D-G128A-S188R-Y217Q | G97A-G128A-Y217Q | N109D f2, S188R f |
| 12 | S87R-G97A-N109D-G128A-S188D-Y217Q-S248R | S87D-G97A-N109D-G128A-S188D-S248R-Y217Q | S87R f, S87R r |
| 13 | G97A-N109D-G128A-Y217Q-S248R | G97A-G128A-Y217Q | N109D f2, S248R f2 |
| 14 | S87D-G97A-G128A-Y217Q-S248R | G97A-G128A-Y217Q | S87D f, S248R f1 |
| 15 | S87D-G97A-N109D-G128A-S188D-Y217Q-S248D | S87D-G97A-N109D-G128A-S188D-Y217Q | S248D f1, S248D r |
| 16 | S87D-G97A-N109D-G128A-S188D-Y217Q | Synthesized by Gene Oracle | Synthesized by Gene Oracle |
| 17 | G97A-N109D-G128A-Y217Q-S248D | G97A-G128A-Y217Q | N109D f2, S248D f2 |
| 18 | S87R-G97A-G128A-Y217Q | G97A-G128A-Y217Q | S87R f, S87R r |
| 19 | S87R-G97A-G128A-Y217Q-S248R | G97A-G128A-Y217Q | S87R f, S248R f1 |
| 20 | S87R-G97A-G128A-S188R-Y217Q-S248R | S87R-G97A-N109R-G128A-S188R-Y217Q-S248R | D109N f, D109N r |
| 21 | S87R-G97A-N109R-G128A-S188R-Y217Q-S248R | Synthesized by Gene Oracle | Synthesized by Gene Oracle |
| 22 | G97A-G102A-G128A-Y217Q | G97A-G128A-Y217Q | G102A f, G102A r |
| 23 | G97A-G128A-S130P-Y217Q | G97A-G128A-Y217Q | S130P f, S130P r |
| 24 | G97A-S101N-G128A-Y217Q | G97A-G128A-Y217Q | S101N f, S101N r |
| 25 | G97A-G100N-G128A-Y217Q | G97A-G128A-Y217Q | G100N f, G100N r |
| 26 | N61P-G97A-G128A-Y217Q | G97A-G128A-Y217Q | N61P f, N61P r |
| 27 | G97A-G128A-A187D-Y217Q | G97A-G128A-Y217Q | A187D f, A187D r |
| 28 | G97A-G128A-F189D-Y217Q | G97A-G128A-Y217Q | f189D f, f189D r |
| 29 | G97A-G128A-A137V-Y217Q | G97A-G128A-Y217Q | A137V f, A137V r |
| 30 | S63T-G97A-G128A-Y217Q | G97A-G128A-Y217Q | S63T f, S63T r |
| 31 | G97A-Q103N-G128A-Y217Q | G97A-G128A-Y217Q | Q103N f, Q103N r |
| 32 | N62D-G97A-G128A-Y217Q | G97A-G128A-Y217Q | N62D f, N62D r |
| 33 | G97A-G100E-G128A-Y217Q | G97A-G128A-Y217Q | G100E Fsfor, pHPLT F1, G100E Fsrev, pHPLT R1 |

Generation of BPN' Variants Via QUIKCHANGE® Mutagenesis

*Bacillus subtilis* strains containing plasmids expressing BPN'-v3, BPN'-v4, BPN' variant 8, BPN' variant 16, and overnight. The methylated DNA was purified using the QIAGEN® PCR purification kit. Variants 14, 18, and 19 listed in Table 11-4 were generated using QUIKCHANGE LIGHTNING™ Multi Site-Directed Mutagenesis kits (Stratagene) in a reaction mix containing 2.5 µL Buffer 5×+0.75 µL Quik Solution+0.5 µL primer 1 (25 µM) 0.5 µL primer 2 (25 µM)+1.5 µL dNTP's+1 µL enzyme blend+16.25 µL H₂O+2 µL DNA. The PCR program used was as follows: 95° C. for 2 min; (95° C. for 20 sec, 55° C. for 30 sec, 64° C. for 2 min 30 sec)×29 cycles; 64° C. for 5 min, 4° C. hold.

The remaining variants were created using QUIKCHANGE® Multi Site-Directed Mutagenesis kits in a reaction mix containing 2.5 µL Buffer 5×+0.75 µL Quik Solution+0.5 µL primer 1 (25 µM)+0.5 µL primer 2 (25 µM)+1.5 µL dNTP's+1 µL enzyme blend+16.25 µL H2O+2 µL DNA. The PCR program used was as follows: 95° C. for 1 min; (95° C. for 1 min, 53° C. for 1 min, 65° C. for 10 min)×29 cycles; 65° C. for 10 min, 4° C. hold. In all reactions, PCR was performed using a MJ Research PTC-200 Peltier thermal cycler. The primers used for the Quik-Change reactions are provided in Table 11-5.

TABLE 11-5

Primers Used for Quik-Change Reactions

| Primer Name | Primer Sequence (5' to 3') | SEQ ID NO: |
|---|---|---|
| N76D f | /5PHOS/GAACGGTTGCGGCGTTAGATAATTCTATTGGCGTGCTTG | 191 |
| N76D r | /5PHOS/AGCACGCCAATAGAATTATCTAACGCCGCAACCGTTC | 192 |
| S87D f | /5PHOS/TTGGTGTAGCCCCGGATGCTTCGCTCTACGCCGTTAAAG | 193 |
| S87D r | /5PHOS/CGTAGAGCGAAGCATCCGGGGCTACACCAAGCACG | 194 |
| G102A f | /5PHOS/GCAGCAGACGGATCAGCACAATACTCATGGATTAT | 195 |
| G102A r | /5PHOS/ATAATCCATGAGTATTGTGCTGATCCGTCTGCTGC | 196 |
| S130P f | /5PHOS/CAACATGAGCCTGGGAGCACCACCGGGCAGTGCGGCACTTAAAGC | 197 |
| S130P r | /5PHOS/GCTTTAAGTGCCGCACTGCCCGGTGGTGCTCCCAGGCTCATGTTG | 198 |
| S101N f | /5PHOS/GTTCTTGCAGCAGACGGAAATGGCCAATACTCATGGATT | 199 |
| S101N r | /5PHOS/AATCCATGAGTATTGGCCATTTCCGTCTGCTGCAAGAAC | 200 |
| G100N f | /5PHOS/TTAAAGTTCTTGCAGCAGACAATTCAGGCCAATACTCATGGA | 201 |
| G100N r | /5PHOS/TCCATGAGTATTGGCCTGAATTGTCTGCTGCAAGAACTTTAA | 202 |
| N61P f | /5PHOS/CCGTTTCAAGATCCGAATTCTCATGGCACACACGTC | 203 |
| N61P r | /5PHOS/TGCCATGAGAATTCGGATCTTGAAACGGGTTTGTTTCG | 204 |
| A187D f | /5PHOS/TTCAAATCAACGTGATTCTTTTTCCTCCGTGGGACCGGAG | 205 |
| A187D r | /5PHOS/ACGGAGGAAAAAGAATCACGTTGATTTGAAGAGTCTACAG | 206 |
| F189D f | /5PHOS/CAAATCAACGTGCCTCTGATTCCTCCGTGGGACCGGAG | 207 |
| F189D r | /5PHOS/CTCCGGTCCCACGGAGGAATCAGAGGCACGTTGATTTG | 208 |
| A137V f | /5PHOS/AGCGGCAGTGCGGCACTTAAAGTTGCAGTTGATAAAGCTGTTGC | 209 |
| A137V r | /5PHOS/GCAACAGCTTTATCAACTGCAACTTTAAGTGCCGCACTGCCGCT | 210 |
| S63T f | /5PHOS/TCAAGATAACAATACACATGGCACACACGTCGCAGGAAC | 211 |
| S63T r | /5PHOS/ACGTGTGTGCCATGTGTATTGTTATCTTGAAACGGGTTTG | 212 |
| Q103N f | /5PHOS/AGACGGATCAGGCAATTACTCATGGATTATCAACGGCATC | 213 |
| Q103N r | /5PHOS/TAATCCATGAGTAATTGCCTGATCCGTCTGCTGCAAG | 214 |
| N62D f | /5PHOS/ACCCGTTTCAAGATAACGATTCTCATGGCACACACGTC | 215 |
| N62D r | /5PHOS/GACGTGTGTGCCATGAGAATCGTTATCTTGAAACGGGT | 216 |
| N109D f1 | /5PHOS/CAATACTCATGGATTATCGATGGCATCGAATGGGCCA | 217 |
| N109D r | /5PHOS/TGGCCCATTCGATGCCATCGATAATCCATGAGTATTG | 218 |
| S188D f | /5PHOS/CTCTTCAAATCAACGTGCCGATTTTCCTCCGTGGGACC | 219 |
| S188D r | /5PHOS/GGTCCCACGGAGGAAAATCGGCACGTTGATTTGAAGAG | 220 |
| S248R f1 | /5PHOS/CAAACACTCAAGTCCGCAGAAGTTTAGAAAACACCAC | 221 |
| S87R f | /5PHOS/GTGCTTGGTGTAGCCCCGAGAGCTTCGCTCTACGCCGT | 222 |
| S87R r | /5PHOS/ACGGCGTAGAGCGAAGCTCTCGGGGCTACACCAAGCAC | 223 |
| S248D f1 | /5PHOS/CAAACACTCAAGTCCGCGATAGTTTAGAAAACACCAC | 224 |
| S248D r | /5PHOS/GTGGTGTTTTCTAAACTATCGCGGACTTGAGTGTTTG | 225 |
| D87S f | /5PHOS/GTGCTTGGTGTAGCCCCGTCTGCTTCGCTCTACGCCGT | 226 |
| D87S r | /5PHOS/ACGGCGTAGAGCGAAGCAGACGGGGCTACACCAAGCAC | 227 |

TABLE 11-5-continued

Primers Used for Quik-Change Reactions

| Primer Name | Primer Sequence (5' to 3') | SEQ ID NO: |
|---|---|---|
| D109N f | /5PHOS/CAATACTCATGGATTATCAACGGCATCGAATGGGCCA | 228 |
| D109N r | /5PHOS/TGGCCCATTCGATGCCGTTGATAATCCATGAGTATTG | 229 |
| N109D f2 | /5PHOS/ACTCATGGATTATCGATGGCATCGAATGGGCCATCGC | 230 |
| S248R f2 | /5PHOS/CACTCAAGTCCGCAGAAGTTTAGAAAACACCACTAC | 231 |
| S248D f2 | /5PHOS/CACTCAAGTCCGCGATAGTTTAGAAAACACCACTAC | 232 |
| S188R f | /5PHOS/CAAATCAACGTGCCAGATTTTCCTCCGTGGGACCGGAG | 233 |
| QC FUSION_For1 | AAAGGGGAGGAAAATCGTGAAACA | 234 |
| QC FUSION_Rev1 | GTTCTAAATCGTGTTTTTCTTG | 235 |
| S248D forfus | GAACTGGACAAACACTCAAGTCCGCGATAGTTTAGAAAACACCACTAC | 236 |
| S248D revfus | GACTTGAGTGTTTGTCCAGTTCGGGTGCTTAGAAAG | 237 |
| R248Sfor | /5PHOS/CAAACACTCAAGTCCGCAGCAGTTTAGAAAACACCAC | 238 |
| R248S rev | /5PHOS/GTGGTGTTTTCTAAACTGCTGCGGACTTGAGTGTTTG | 239 |
| G100E_Fsfor | ACGCCGTTAAAGTTCTTGCAGCAGACGAATCAGGCCAATACTCATGGAT | 240 |
| G100E_Fsrev | TGCTGCAAGAACTTTAACGGCGTAGAGCGAAGCAGA | 241 |
| N123C f | /5PHOS/ACATGGATGTAATCTGCATGAGCCTGGGAGGACCAAG | 242 |
| N123C r | /5PHOS/TCCTCCCAGGCTCATGCAGATTACATCCATGTTATTCG | 243 |
| pHpLT R1 | /5PHOS/GTTATGAGTTAGTTCAAATTCG | 244 |

The parental DNA from the PCR samples was removed by addition of 1 μL of DpnI to Quik-Change reactions at 37° C. overnight. One micro-liter of the DpnI-digested reactions were amplified using rolling circle amplification (RCA) using the Illustra TempliPhi kit according to the manufacturer's protocol. B. subtilis cells (ΔaprE, ΔnprE, amyE::xylRPxylA-comK-phleo) were transformed with 1 μL each of the RCA reaction and the transformed cells were plated onto LA+1.6% skim milk plates containing 10 ppm neomycin and incubated at 37° C. overnight. Colonies from overnight growth were selected to perform colony PCR using "puReTaq Ready-To-Go PCR Beads" (Amersham). The PCR primers used were pHPLT F1 (SEQ ID NO:54) and pHPLT seq R1 (SEQ ID NO:55). Clones with appropriate sequences were frozen. BPN' variants were expressed by growing the B. subtilis transformants in 96 well microtiter plates at 37° C. for 68 hours in a MOPS based medium containing urea.

Generation of BPN' Variants Via Fusion PCR

Variants 5 and 33 were generated using Fusion PCR, with fragments amplified from template pHPLT-BPN'-v3. The PCR primers used to generate these variants are included in Table 11-5. For Variant 5, a 5' fragment of the BPN' gene was amplified using forward primer pHPLT F1 (SEQ ID NO:54), and reverse primer S248D revfus. The 3' fragment of the BPN' gene was amplified using the forward primer S248D forfus containing the mutation of interest and the reverse primer pHPLT R1. The two products contained 20 bp of overlapping sequence, and were fused by combining 1 μL of each fragment and fusion primers QC FUSION_For1 and QC FUSION_Rev1 in a final PCR reaction. All PCR reactions were performed using standard conditions of the Herculase II PCR Kit (Stratagene). The PCR mix contained 1 μL DNA polymerase, 1 μL plasmid DNA (or fragment DNA for fusion), 0.5 μL dNTP's, 1.25 μL 25 μM forward primer, 1.25 μL 25 μM reverse primer, 10 μL Buffer 5×, 35 μL H$_2$O and the PCR program used was as follows: 95° C. for 2 min, (95° C. for 30 sec, 55° C. for 30 sec, 72° C. for "X" sec) for 29 cycles, 72° C. for 1 min, 4° C. hold (the "X" is 15 seconds per 1 kB of DNA to amplify).

For Variant 33, a 5' fragment of the BPN' gene was amplified using the template pHPLT-BPN'-v3 and primers pHPLT F1 (SEQ ID NO:54), and G100E_Fsrev. The 3' fragment that contained the variant was amplified using primers G100E_Fsfor and pHPLT R1. The two products contained 20 bp of overlapping sequence, and were fused by combining 1 μl of each fragment and fusion primers QC FUSION_For1 and QC FUSION_Rev1 in a final PCR reaction. The PCR conditions were the same as listed above.

The two fusion products were purified using a QIAGEN® PCR purification column with conditions provided by the manufacturer, and digested overnight using Bgl I and HindIII enzymes. The plasmid pHPLT-BPN' partial opt was digested using the same enzymes and the vector band was gel extracted and purified over a QIAGEN® gel purification column using the manufacturer's recommendations. The restriction enzyme mix contained: 10 μL purified DNA, 5 μL Roche Buffer B, 0.5 μL HindIII, 0.5 μL Bgl I, 34 μL H$_2$O and the reactions were carried out at 37° C. for 8 hours followed by 65° C. for 20 min. The digest was purified using a QIAGEN® PCR purification column and ligated to the cut vector backbone overnight at 16° C. using the Mighty Mix Ligase kit (Tekara). Following incubation, 1 μL of the ligation mix was amplified using the Illustra TempliPhi kit.

For the amplification reaction, 1 μL of the ligation reaction mix was mixed with 5 μL of sample buffer from the TempliPhi kit and heated for 3 minutes at 95° C. to denature the DNA. The reaction was placed on ice to cool for 2 minutes and then spun down briefly. Five microliters of reaction buffer and 0.2 μL of phi29 polymerase from the TempliPhi kit were added, and the reactions were incubated at 30° C. in an MJ Research PCR machine for 4 hours. The phi29 enzyme was heat inactivated in the reactions by incubation at 65° C. for 10 min in the PCR machine. *Bacillus subtilis* cells (ΔaprE, ΔnprE, amyE::xylRPxylAcomK-phleo) were transformed using 1 μL of the reaction mix and the transformants were grown overnight at 37° C. on 1.6% skim milk plates containing 10 ppm neomycin. Transformants were selected to perform colony PCR and sequencing using "puReTaq Ready-To-Go PCR Beads" (Amersham) and primers pHPLT F1 (SEQ ID NO:54) and pHPLT seqR1 (SEQ ID NO:55).

4. Generation of BPN' Variants from Libraries RCL4-RCL7
RCL4 Library

"RCL4" refers to a group of site saturation libraries created by PCR fusion that simultaneously randomize three contiguous codons in the BPN'-v3-encoding (BPN"-G97A-G128A-Y217Q) gene. The amino acid positions corresponding to the three mutated codons in each library are provided in Table 11-6. Two partially overlapping, complementary mutagenic primers, each containing three degenerate codons were used to introduce mutations within each library as shown in Table 11-6 below. Only the first two nucleotides of each degenerate codon (NNX, N=A, C, T, or G and X is unchanged nucleotide) of interest were mutated in each primer (Table 11-6).

To create each library, two PCR reactions were carried out using either the common 3' gene-flanking primer (P4976, CCTCTCGGTTATGAGTTAGTTC; (SEQ ID NO:61)) and mutagenic primer, or the common 5' gene-flanking primer (P4974, GCCTCACATTTGTGCCACCTA; (SEQ ID NO:60)) and mutagenic primer as shown for each library in Table 11-6. These PCR reactions generated two PCR fragments, one encoding the 5' half of the mutant BPN'-v3 gene (5' gene fragment) and the other encoding the 3' half of the mutant BPN'-v3 gene (3' gene fragment). Each PCR amplification reaction contained 30 pmol of each primer and 100 ng of the BPN'-v3 parent template DNA (plasmid pHPLT-BPN'-v3) (see FIG. 1). Amplifications were carried out using Vent DNA polymerase (NEB). The PCR reaction (20 μL) was initially heated at 95° C. for 2.5 min followed by 30 cycles of denaturation at 94° C. for 15 sec., annealing at 55° C. for 15 sec. and extension at 72° C. for 40 sec. Following amplification, the 5' and 3' gene fragments were gel-purified by the QIAGEN® gel-band purification kit, mixed (50 ng of each fragment) and amplified by PCR once again using the primers P4973 (AAAGGATCCTAATCGGCGCTTTTC; SEQ ID NO:62) and P4950 (CTTGTCTCCAAGCT-TAAAATAAAA; SEQ ID NO:63) to generate the full-length gene fragment. The PCR conditions were same as described above, except the extension phase, which was carried out at 72° C. for 2 min. The full-length DNA fragment was gel-purified by the QIAGEN® gel-band purification kit, digested by the BamHI and HindIII restriction enzymes and ligated with the pHPLT-BPN' partial opt vector that also was digested with the same restriction enzymes. Ligation mixtures were amplified using rolling circle amplification in an Illustra Templiphi kit according to the manufacturer's recommendation (GE Healthcare) to generate multimeric DNA for transformation into *Bacillus subtilis*. For this purpose, 1 μl of the ligation mixture was mixed with 5 μl of the sample buffer, heated to 95° C. for 3 min and cooled on ice. Next, 5 μl of the reaction buffer and 0.2 μl of the enzyme were added to each tube, followed by incubation at 30° C. for 10 hours. Products of the rolling circle amplification were diluted 100 times and used to transform *B. subtilis* cells (ΔaprE, ΔnprE, amyE::xylRPxylAcomK-phleo). An aliquot of the transformation mix was plated on LB plates containing 1.6% skim milk and 10 μg/mL neomycin and incubated overnight at 37° C. Subsequently, the colonies with halos were inoculated in 120 μl of LB media containing 10 μg/mL neomycin.

TABLE 11-6

List of Primers Used to Create RCL4 Libraries

| Library # | Mutated residues in BPN'-v3 | Gene fragment | Common flanking primer names | Mutagenic primer names | Mutagenic primer sequence | SEQ ID NO: |
|---|---|---|---|---|---|---|
| 1 | 5-7 | 3' | P4976 | P5119 | TACGCGCAGTCCGT GNNTNNCNNCGTAT CACAAATTAAAGCC CCTG | 245 |
|  |  | 5' | P4974 | P5120 | TTTAATTTGTGATA CGNNGNNANNCAC GGACTGCGCGTACG CAT | 246 |
| 2 | 11-13 | 3' | P4976 | P5121 | TACGGCGTATCACA ANNTNNANNCCCTG CTCTGCACTCTCAAG | 247 |
|  |  | 5' | P4974 | P5122 | AGAGTGCAGAGCA GGGNNTNNANNTTG TGATACGCCGTAAG GCAC | 248 |
| 3 | 20-22 | 3' | P4976 | P5123 | GCTCTGCACTCTCA ANNCNNCNNTGGAT CAAATGTTAAAGTA GCGGT | 249 |
|  |  | 5' | P4974 | P5124 | TTTAACATTTGATC CANNGNNGNNTTGA | 250 |

TABLE 11-6-continued

List of Primers Used to Create RCL4 Libraries

| Library # | Mutated residues in BPN'-v3 | Gene fragment | Common flanking primer names | Mutagenic primer names | Mutagenic primer sequence | SEQ ID NO: |
|---|---|---|---|---|---|---|
| | | | | | GAGTGCAGAGCAG GGGCTT | |
| 4 | 21-23 | 3' | P4976 | P5125 | CTGCACTCTCAAGG CNNCNNTNNATCAA ATGTTAAAGTAGCG GTTATC | 251 |
| | | 5' | P4974 | P5126 | TACTTTAACATTTG ATNNANNGNNGCCT TGAGAGTGCAGAGC AG | 252 |
| 5 | 22-24 | 3' | P4976 | P5127 | CACTCTCAAGGCTA CNNTNNANNAAATG TTAAAGTAGCGGTT ATCGA | 253 |
| | | 5' | P4974 | P5128 | CGCTACTTTAACAT TTNNTNNANNGTAG CCTTGAGAGTGCAG AG | 254 |
| 6 | 23-25 | 3' | P4976 | P5129 | TCTCAAGGCTACAC TNNANNANNTGTTA AAGTAGCGGTTATC GACA | 255 |
| | | 5' | P4974 | P5130 | AACCGCTACTTTAA CANNTNNTNNAGTG TAGCCTTGAGAGTG CAG | 256 |
| 7 | 24-26 | 3' | P4976 | P5131 | CAAGGCTACACTGG ANNANNTNNTAAA GTAGCGGTTATCGA CAGC | 257 |
| | | 5' | P4974 | P5132 | GATAACCGCTACTT TANNANNTNNTCCA GTGTAGCCTTGAGA GTG | 258 |
| 8 | 25-27 | 3' | P4976 | P5133 | GGCTACACTGGATC ANNTNNTNNAGTAG CGGTTATCGACAGC GGT | 259 |
| | | 5' | P4974 | P5134 | GTCGATAACCGCTA CTNNANNANNTGAT CCAGTGTAGCCTTG AGA | 260 |
| 9 | 26-28 | 3' | P4976 | P5135 | TACACTGGATCAAA TNNTNNANNAGCGG TTATCGACAGCGGT AT | 261 |
| | | 5' | P4974 | P5136 | GCTGTCGATAACCG CTNNTNNANNATTT GATCCAGTGTAGCC TTGA | 262 |
| 10 | 27-29 | 3' | P4976 | P5137 | ACTGGATCAAATGT TNNANNANNGGTTA TCGACAGCGGTATC GAC | 263 |
| | | 5' | P4974 | P5138 | ACCGCTGTCGATAA CCNNTNNTNNAACA TTTGATCCAGTGTA GCCT | 264 |
| 11 | 28-30 | 3' | P4976 | P5139 | GGATCAAATGTTAA ANNANNGNNTATCG ACAGCGGTATCGAC TC | 265 |
| | | 5' | P4974 | P5140 | GATACCGCTGTCGA TANNCNNTNNTTA | 266 |

TABLE 11-6-continued

List of Primers Used to Create RCL4 Libraries

| Library # | Mutated residues in BPN'-v3 | Gene fragment | Common flanking primer names | Mutagenic primer names | Mutagenic primer sequence | SEQ ID NO: |
|---|---|---|---|---|---|---|
| | | | | | ACATTTGATCCAGT GTAGC | |
| 12 | 29-31 | 3' | P4976 | P5141 | TCAAATGTTAAAGT ANNGNNTNNCGAC AGCGGTATCGACTC GAGCCAT | 267 |
| | | 5' | P4974 | P5142 | GTCGATACCGCTGT CGNNANNCNNTACT TTAACATTTGATCC AGTGTA | 268 |
| 13 | 30-32 | 3' | P4976 | P5143 | AATGTTAAAGTAGC GNNTNNCNNCAGCG GTATCGACTCGAGC CAT | 269 |
| | | 5' | P4974 | P5144 | CGAGTCGATACCGC TGNNGNNANNCGCT ACTTTAACATTTGA TCCAG | 270 |
| 14 | 31-33 | 3' | P4976 | P5145 | GTTAAAGTAGCGGT TNNCNNCNNCGGTA TCGACTCGAGCCAT CCA | 271 |
| | | 5' | P4974 | P5146 | GCTCGAGTCGATAC CGNNGNNGNNAAC CGCTACTTTAACAT TTGATC | 272 |
| 15 | 32-34 | 3' | P4976 | P5147 | AAAGTAGCGGTTAT CNNCNNCNNTATCG ACTCGAGCCATCCA GAT | 273 |
| | | 5' | P4974 | P5148 | ATGGCTCGAGTCGA TANNGNNGNNGAT AACCGCTACTTTAA CATTTG | 274 |
| 16 | 33-35 | 3' | P4976 | P5149 | GTAGCGGTTATCGA CNNCNNTNNCGACT CGAGCCATCCAGAT CT | 275 |
| | | 5' | P4974 | P5150 | TGGATGGCTCGAGT CGNNANNGNNGTC GATAACCGCTACTT TAACA | 276 |
| 17 | 34-36 | 3' | P4976 | P5151 | GCGGTTATCGACAG CNNTNNCNNCTCGA GCCATCCAGATCTT AAAG | 277 |
| | | 5' | P4974 | P5152 | ATCTGGATGGCTCG AGNNGNNANNGCT GTCGATAACCGCTA CTTT | 278 |
| 18 | 35-37 | 3' | P4976 | P5153 | GTTATCGACAGCGG TNNCNNCNNGAGCC ATCCAGATCTTAAA GTC | 279 |
| | | 5' | P4974 | P5154 | AAGATCTGGATGGC TCNNGNNGNNACCG CTGTCGATAACCGC TA | 280 |
| 19 | 36-38 | 3' | P4976 | P5155 | ATCGACAGCGGTAT CNNCNNGNNCCATC CAGATCTTAAAGTC GCTG | 281 |
| | | 5' | P4974 | P5156 | TTTAAGATCTGGAT GGNNCNNGNNGAT | 282 |

TABLE 11-6-continued

List of Primers Used to Create RCL4 Libraries

| Library # | Mutated residues in BPN'-v3 | Gene fragment | Common flanking primer names | Mutagenic primer names | Mutagenic primer sequence | SEQ ID NO: |
|---|---|---|---|---|---|---|
| | | | | | ACCGCTGTCGATAACCGCTA | |
| 20 | 37-39 | 3' | P4976 | P5157 | GACAGCGGTATCGACNNGNNCNNTCCAGATCTTAAAGTCGCTGGA | 283 |
| | | 5' | P4974 | P5158 | GACTTTAAGATCTGGANNGNNCNNGTCGATACCGCTGTCGATAAC | 284 |
| 21 | 38-40 | 3' | P4976 | P5159 | AGCGGTATCGACTCGNNCNNTNNAGATCTTAAAGTCGCTGGAGG | 285 |
| | | 5' | P4974 | P5160 | AGCGACTTTAAGATCTNNANNGNNCGAGTCGATACCGCTGTCGA | 286 |
| 22 | 41-43 | 3' | P4976 | P5161 | GACTCGAGCCATCCANNTNNTNNAGTCGCTGGAGGGGCTTCTAT | 287 |
| | | 5' | P4974 | P5162 | AGCCCCTCCAGCGACTNNANNANNTGGATGGCTCGAGTCGATAC | 288 |
| 23 | 43-45 | 3' | P4976 | P5163 | AGCCATCCAGATCTTNNANNCNNTGGAGGGCTTCTATGGTCCGT | 289 |
| | | 5' | P4974 | P5164 | CATAGAAGCCCCTCCNAGCGACTTTNAAGATCTGGATGGCTGAGTC | 290 |
| 24 | 44-46 | 3' | P4976 | P5165 | CATCCAGATCTTAAANNCNNTNNAGGGGCTTCTATGGTGCCGT | 291 |
| | | 5' | P4974 | P5166 | CACCATAGAAGCCCCTNNANNGNNTTTAAGATCTGGATGGCTCGAG | 292 |
| 25 | 51-53 | 3' | P4976 | P5167 | GGAGGGGCTTCTATGNNGNNGNNCGAAACAAACCCGTTTCAAGATAA | 293 |
| | | 5' | P4974 | P5168 | AAACGGGTTTGTTTCGNNCNNCNNCATAGAAGCCCCTCCAGCGA | 294 |
| 26 | 52-54 | 3' | P4976 | P5169 | GGGGCTTCTATGGTGNNGNNCNNAACAAACCCGTTTCAAGATAACAA | 295 |
| | | 5' | P4974 | P5170 | TTGAAACGGGTTTGTTNNGNNCNNCACCATAGAAGCCCCTCCAG | 296 |
| 27 | 53-55 | 3' | P4976 | P5171 | GCTTCTATGGTGCCGNNCNNANNAAACCCGTTTCAAGATAACAATTC | 297 |
| | | 5' | P4974 | P5172 | ATCTTGAAACGGGTTTNNTNNGNNCCGGC | 298 |

TABLE 11-6-continued

List of Primers Used to Create RCL4 Libraries

| Library # | Mutated residues in BPN'-v3 | Gene fragment | Common flanking primer names | Mutagenic primer names | Mutagenic primer sequence | SEQ ID NO: |
|---|---|---|---|---|---|---|
| | | | | | ACCATAGAAGCCCCTC | |
| 28 | 54-56 | 3' | P4976 | P5173 | TCTATGGTGCCGTCCNNANNANNCCCGTTTCAAGATAACAATTCTCA | 299 |
| | | 5' | P4974 | P5174 | GTTATCTTGAAACGGGNNTNNTNNGGACGGCACCATAGAAGCCCCT | 300 |
| 29 | 55-57 | 3' | P4976 | P5175 | ATGGTGCCGTCCGAANNANNCNNGTTTCAAGATAACAATTCTCATGG | 301 |
| | | 5' | P4974 | P5176 | ATTGTTATCTTGAAACNNGNNTNNTTCGGACGGCACCATAGAAG | 302 |
| 30 | 56-58 | 3' | P4976 | P5177 | GTGCCGTCCGAAACANNCNNGNNTCAAGATAACAATTCTCATGGCAC | 303 |
| | | 5' | P4974 | P5178 | AGAATTGTTATCTTGANNCNNGNNTGTTTCGGACGGCACCATAGA | 304 |
| 31 | 57-59 | 3' | P4976 | P5179 | CCGTCCGAAACAAACNNGNNTNNAGATAACAATTCTCATGGCACAC | 305 |
| | | 5' | P4974 | P5180 | ATGAGAATTGTTATCTNNANNCNNGTTTGTTTCGGACGGCACCA | 306 |
| 32 | 58-60 | 3' | P4976 | P5181 | TCCGAAACAAACCCGNNTNNANNTAACAATTCTCATGGCACACAC | 307 |
| | | 5' | P4974 | P5182 | GCCATGAGAATTGTTANNTNNANNCGGGTTTGTTTCGGACGGCA | 308 |
| 33 | 59-61 | 3' | P4976 | P5183 | GAAACAAACCCGTTTNNANNTNNCAATTCTCATGGCACACACGTC | 309 |
| | | 5' | P4974 | P5184 | TGTGCCATGAGAATTGNNANNTNNAAACGGGTTTGTTTCGGACG | 310 |
| 34 | 60-62 | 3' | P4976 | P5185 | ACAAACCCGTTTCAANNTNNCNNTTCTCATGGCACACACGTCG | 311 |
| | | 5' | P4974 | P5186 | GTGTGTGCCATGAGAANNGNNANNTTGAAACGGGTTTGTTTCGGAC | 312 |
| 35 | 61-63 | 3' | P4976 | P5187 | AACCCGTTTCAAGATNNCNNTNNTCATGGCACACACGTCGCAG | 313 |
| | | 5' | P4974 | P5188 | GACGTGTGTGCCATGANNANNGNNATCTTGAAACGGGTTTGTTTCG | 314 |

TABLE 11-6-continued

List of Primers Used to Create RCL4 Libraries

| Library # | Mutated residues in BPN'-v3 | Gene fragment | Common flanking primer names | Mutagenic primer names | Mutagenic primer sequence | SEQ ID NO: |
|---|---|---|---|---|---|---|
| 36 | 62-64 | 3' | P4976 | P5189 | CCGTTTCAAGATAA CNNTNNTNNTGGCA CACACGTCGCAGGAA | 315 |
|  |  | 5' | P4974 | P5190 | TGCGACGTGTGTGC CANNANNANNGTTA TCTTGAAACGGGTT TGTTT | 316 |
| 37 | 67-69 | 3' | P4976 | P5191 | AATTCTCATGGCAC ANNCNNCNNAGGA ACGGTTGCGGCGTT AAA | 317 |
|  |  | 5' | P4974 | P5192 | CGCCGCAACCGTTC CTNNGNNGNNTGTG CCATGAGAATTGTT ATCTT | 318 |
| 38 | 68-70 | 3' | P4976 | P5193 | TCTCATGGCACACA CNNCNNANNAACG GTTGCGGCGTTAAA CAAT | 319 |
|  |  | 5' | P4974 | P5194 | TAACGCCGCAACCG TTNNTNNGNNGTGT GTGCCATGAGAATT GTTA | 320 |
| 39 | 71-73 | 3' | P4976 | P5195 | ACACACGTCGCAGG ANNGNNTNNGGCGT TAAACAATTCTATT GGCGT | 321 |
|  |  | 5' | P4974 | P5196 | AGAATTGTTTAACG CCNNANNCNNTCCT GCGACGTGTGTGCC AT | 322 |
| 40 | 74-76 | 3' | P4976 | P5197 | GCAGGAACGGTTGC GNNGNNANNCAATT CTATTGGCGTGCTT GGTG | 323 |
|  |  | 5' | P4974 | P5198 | CACGCCAATAGAAT TGNNTNNCNNCGCA ACCGTTCCTGCGAC GT | 324 |
| 41 | 77-79 | 3' | P4976 | P5199 | ACGGTTGCGGCGTT ANNCNNTNNTATTG GCGTGCTTGGTGTA GC | 325 |
|  |  | 5' | P4974 | P5200 | ACCAAGCACGCCAA TANNANNGNNTAAC GCCGCAACCGTTCC TG | 326 |
| 42 | 81-83 | 3' | P4976 | P5201 | AACAATTCTATTGG CNNGNNTNNTGTAG CCCCGTCTGCTTCG CT | 327 |
|  |  | 5' | P4974 | P5202 | AGCAGACGGGGCTA CANNANNCNNGCC AATAGAATTGTTTA ACGCCGCAA | 328 |
| 43 | 83-85 | 3' | P4976 | P5203 | TCTATTGGCGTGCT TNNTNNANNCCCGT CTGCTTCGCTCTACG | 329 |
|  |  | 5' | P4974 | P5204 | GAGCGAAGCAGAC GGGNNTNNANNAA GCACGCCAATAGAA TTGTTTA | 330 |
| 44 | 84-86 | 3' | P4976 | P5205 | ATTGGCGTGCTTGG TNNANNCNNGTCTG | 331 |

TABLE 11-6-continued

List of Primers Used to Create RCL4 Libraries

| Library # | Mutated residues in BPN'-v3 | Gene fragment | Common flanking primer names | Mutagenic primer names | Mutagenic primer sequence | SEQ ID NO: |
|---|---|---|---|---|---|---|
| | | 5' | P4974 | P5206 | CTTCGCTCTACGCC GT GTAGAGCGAAGCA GACNNGNNTNNACC AAGCACGCCAATAG AATTG | 332 |
| 45 | 85-87 | 3' | P4976 | P5207 | TGGCGTGCTTGGTG TANNCNNGNNTGCT TCGCTCTACGCCGT TAA | 333 |
| | | 5' | P4974 | P5208 | GGCGTAGAGCGAA GCANNCNNGNNTAC ACCAAGCACGCCAA TAGA | 334 |
| 46 | 86-88 | 3' | P4976 | P5209 | GTGCTTGGTGTAGC CNNGNNTNNTTCGC TCTACGCCGTTAAA GTT | 335 |
| | | 5' | P4974 | P5210 | AACGGCGTAGAGCG AANNANNCNNGGC TACACCAAGCACGC CAA | 336 |
| 47 | 87-89 | 3' | P4976 | P5211 | CTTGGTGTAGCCCC GNNTNNTNNGCTCT ACGCCGTTAAAGTT CTT | 337 |
| | | 5' | P4974 | P5212 | TTTAACGGCGTAGA GCNNANNANNCGG GGCTACACCAAGCA CGCCAAT | 338 |
| 48 | 88-90 | 3' | P4976 | P5213 | GGTGTAGCCCCGTC TNNTNNGNNCTACG CCGTTAAAGTTCTT GCAG | 339 |
| | | 5' | P4974 | P5214 | AACTTTAACGGCGT AGNNCNNANNAGA CGGGGCTACACCAA GCA | 340 |
| 49 | 89-91 | 3' | P4976 | P5215 | GTAGCCCCGTCTGC TNNGNNCNNCGCCG TTAAAGTTCTTGCA GCA | 341 |
| | | 5' | P4974 | P5216 | AAGAACTTTAACGG CGNNGNNCNNAGC AGACGGGGCTACAC CAA | 342 |
| 50 | 90-92 | 3' | P4976 | P5217 | GCCCCGTCTGCTTC GNNCNNCNNCGTTA AAGTTCTTGCAGCA GAC | 343 |
| | | 5' | P4974 | P5218 | TGCAAGAACTTTAA CGNNGNNGNNCGA AGCAGACGGGGCTA CAC | 344 |
| 51 | 91-93 | 3' | P4976 | P5219 | CCGTCTGCTTCGCT CNNCNNCNNTAAAG TTCTTGCAGCAGAC GGA | 345 |
| | | 5' | P4974 | P5220 | TGCTGCAAGAACTT TANNGNNGNNGAG CGAAGCAGACGGG GCT | 346 |
| 52 | 92-94 | 3' | P4976 | P5221 | TCTGCTTCGCTCTAC NNCNNTNNAGTTCT TGCAGCAGACGGATC | 347 |

TABLE 11-6-continued

List of Primers Used to Create RCL4 Libraries

| Library # | Mutated residues in BPN'-v3 | Gene fragment | Common flanking primer names | Mutagenic primer names | Mutagenic primer sequence | SEQ ID NO: |
|---|---|---|---|---|---|---|
| | | 5' | P4974 | P5222 | GTCTGCTGCAAGAA CTNNANNGNNGTAG AGCGAAGCAGACG GGGCTA | 348 |
| 53 | 93-95 | 3' | P4976 | P5223 | GCTTCGCTCTACGC CNNTNNANNTCTTG CAGCAGACGGATCAG | 349 |
| | | 5' | P4974 | P5224 | TCCGTCTGCTGCAA GANNTNNANNGGC GTAGAGCGAAGCA GACG | 350 |
| 54 | 94-96 | 3' | P4976 | P5225 | TCGCTCTACGCCGT TNNANNTNNTGCAG CAGACGGATCAGGC CA | 351 |
| | | 5' | P4974 | P5226 | TGATCCGTCTGCTG CANNANNTNNAAC GGCGTAGAGCGAA GCAG | 352 |
| 55 | 95-97 | 3' | P4976 | P5227 | CTCTACGCCGTTAA ANNTNNTNNAGCAG ACGGATCAGGCCAA TA | 353 |
| | | 5' | P4974 | P5228 | GCCTGATCCGTCTG CTNNANNANNTTTA ACGGCGTAGAGCGA AG | 354 |
| 56 | 96-98 | 3' | P4976 | P5229 | TACGCCGTTAAAGT TNNTNNANNAGACG GATCAGGCCAATAC TC | 355 |
| | | 5' | P4974 | P5230 | TTGGCCTGATCCGT CTNNTNNANNAACT TAACGGCGTAGAG CGA | 356 |
| 57 | 97-99 | 3' | P4976 | P5231 | GCCGTTAAAGTTCT TNNANNANNCGGAT CAGGCCAATACTCA TG | 357 |
| | | 5' | P4974 | P5232 | GTATTGGCCTGATC CGNNTNNTNNAAGA ACTTTAACGGCGTA GAG | 358 |
| 58 | 98-100 | 3' | P4976 | P5233 | GTTAAAGTTCTTGC ANNANNCNNATCA GGCCAATACTCATG GATTA | 359 |
| | | 5' | P4974 | P5234 | TGAGTATTGGCCTG ATNNGNNTNNTGCA AGAACTTTAACGGC GTAG | 360 |
| 59 | 99-101 | 3' | P4976 | P5235 | AAAGTTCTTGCAGC ANNCNNANNAGGC CAATACTCATGGAT TATC | 361 |
| | | 5' | P4974 | P5236 | CCATGAGTATTGGC CTNNTNNGNNTGCT GCAAGAACTTTAAC GGCGTA | 362 |
| 60 | 100-102 | 3' | P4976 | P5237 | GTTCTTGCAGCAGA CNNANNANNCCAAT ACTCATGGATTATC AAC | 363 |
| | | 5' | P4974 | P5238 | AATCCATGAGTATT GGNNTNNTNNGTCT | 364 |

TABLE 11-6-continued

List of Primers Used to Create RCL4 Libraries

| Library # | Mutated residues in BPN'-v3 | Gene fragment | Common flanking primer names | Mutagenic primer names | Mutagenic primer sequence | SEQ ID NO: |
|---|---|---|---|---|---|---|
| | | | | | GCTGCAAGAACTTT AACG | |
| 61 | 101-103 | 3' | P4976 | P5239 | CTTGCAGCAGACGG ANNANNCNNATACT CATGGATTATCAAC GGCA | 365 |
| | | 5' | P4974 | P5240 | GATAATCCATGAGT ATNNGNNTNNTCCG TCTGCTGCAAGAAC TTT | 366 |
| 62 | 102-104 | 3' | P4976 | P5241 | GCAGCAGACGGATC ANNCNNANNCTCAT GGATTATCAACGGC ATC | 367 |
| | | 5' | P4974 | P5242 | TTGATAATCCATGA GNNTNNGNNTGATC CGTCTGCTGCAAGA AC | 368 |
| 63 | 103-105 | 3' | P4976 | P5243 | GCAGACGGATCAGG CNNANNCNNATGG ATTATCAACGGCAT CGAAT | 369 |
| | | 5' | P4974 | P5244 | GCCGTTGATAATCC ATNNGNNTNNGCCT GATCCGTCTGCTGC AA | 370 |
| 64 | 104-106 | 3' | P4976 | P5245 | GACGGATCAGGCCA ANNCNNANNGATTA TCAACGGCATCGAA TGG | 371 |
| | | 5' | P4974 | P5246 | GATGCCGTTGATAA TCNNTNNGNNTTGG CCTGATCCGTCTGC TG | 372 |
| 65 | 105-107 | 3' | P4976 | P5247 | GGATCAGGCCAATA CNNANNGNNTATCA ACGGCATCGAATGG GCCAT | 373 |
| | | 5' | P4974 | P5248 | TTCGATGCCGTTGA TANNCNNTNNGTAT GGCCTGATCCGTC TG | 374 |
| 66 | 106-108 | 3' | P4976 | P5249 | TCAGGCCAATACTC ANNGNNTNNCAAC GGCATCGAATGGGC CAT | 375 |
| | | 5' | P4974 | P5250 | CCATTCGATGCCGT TGNNANNCNNTGAG TATTGGCCTGATCC GTC | 376 |
| 67 | 107-109 | 3' | P4976 | P5251 | GGCCAATACTCATG GNNTNNCNNCGGCA TCGAATGGGCCATC GCGAAT | 377 |
| | | 5' | P4974 | P5252 | GGCCCATTCGATGC CGNNGNNANNCCAT GAGTATTGGCCTGA TCC | 378 |
| 68 | 108-110 | 3' | P4976 | P5253 | CAATACTCATGGAT TNNCNNCNNCATCG AATGGGCCATCGCG AA | 379 |
| | | 5' | P4974 | P5254 | GATGGCCCATTCGA TGNNGNNGNNAATC | 380 |

TABLE 11-6-continued

List of Primers Used to Create RCL4 Libraries

| Library # | Mutated residues in BPN'-v3 | Gene fragment | Common flanking primer names | Mutagenic primer names | Mutagenic primer sequence | SEQ ID NO: |
|---|---|---|---|---|---|---|
| | | | | | CATGAGTATTGGCCTGAT | |
| 69 | 109-111 | 3' | P4976 | P5255 | TACTCATGGATTATCNNCNNCNNCGAATGGGCCATCGCGAATAA | 381 |
| | | 5' | P4974 | P5256 | CGCGATGGCCCATTCGNNGNNGNNGATAATCCATGAGTATTGGCCT | 382 |
| 70 | 110-112 | 3' | P4976 | P5257 | TCATGGATTATCAACNNCNNCNNATGGGCCATCGCGAATAACATG | 383 |
| | | 5' | P4974 | P5258 | ATTCGCGATGGCCCATNNGNNGNNGTTGATAATCCATGAGTATTGG | 384 |
| 71 | 111-113 | 3' | P4976 | P5259 | TGGATTATCAACGGCNNCNNANNGGCCATCGCGAATAACATGGA | 385 |
| | | 5' | P4974 | P5260 | GTTATTCGCGATGGCCNNTNNGNNGCCGTTGATAATCCATGAGTAT | 386 |
| 72 | 112-114 | 3' | P4976 | P5261 | ATTATCAACGGCATCNNANNGNNCATCGCGAATAACATGGATGTAA | 387 |
| | | 5' | P4974 | P5262 | CATGTTATTCGCGATGNNCNNTNNGATGCCGTTGATAATCCATGAG | 388 |
| 73 | 113-115 | 3' | P4976 | P5263 | ATCAACGGCATCGAAANNGNNCNNCGCGAATAACATGGATGTAATCAA | 389 |
| | | 5' | P4974 | P5264 | ATCCATGTTATTCGCGNNGNNCNNTTCGATGCCGTTGATAATCCAT | 390 |
| 74 | 114-116 | 3' | P4976 | P5265 | AACGGCATCGAATGGNNCNNCNNGAATAACATGGATGTAATCAACAT | 391 |
| | | 5' | P4974 | P5266 | TACATCCATGTTATTCNNGNNGNNCCATTCGATGCCGTTGATAATC | 392 |
| 75 | 115-117 | 3' | P4976 | P5267 | GGCATCGAATGGGCNNCNNGNNTAACATGGATGTAATCAACATGAG | 393 |
| | | 5' | P4974 | P5268 | GATTACATCCATGTTANNCNNGNNGGCCCATTCGATGCCGTTGA | 394 |
| 76 | 116-118 | 3' | P4976 | P5269 | ATCGAATGGGCCATCNNGNNTNNCATGGATGTAATCAACATGAGCCT | 395 |
| | | 5' | P4974 | P5270 | GTTGATTACATCCATGNNANNCNNGATG | 396 |

TABLE 11-6-continued

List of Primers Used to Create RCL4 Libraries

| Library # | Mutated residues in BPN'-v3 | Gene fragment | Common flanking primer names | Mutagenic primer names | Mutagenic primer sequence | SEQ ID NO: |
|---|---|---|---|---|---|---|
| | | | | | GCCCATTCGATGCCGT | |
| 77 | 117-119 | 3' | P4976 | P5271 | GAATGGGCCATCGCGNNTNNCNNGGATGTAATCAACATGAGCCTG | 397 |
| | | 5' | P4974 | P5272 | CATGTTGATTACATCCNNGNNANNCGCGATGGCCCATTCGATGC | 398 |
| 78 | 118-120 | 3' | P4976 | P5273 | TGGGCCATCGCGAATNNCNNGNNTGTAATCAACATGAGCCTGGGA | 399 |
| | | 5' | P4974 | P5274 | GCTCATGTTGATTACANNCNNGNNATTCGCGATGGCCCATTCGA | 400 |
| 79 | 119-121 | 3' | P4976 | P5275 | GCCATCGCGAATAACNNGNNTNNAATCAACATGAGCCTGGGAGCA | 401 |
| | | 5' | P4974 | P5276 | CAGGCTCATGTTGATTNNANNCNNGTTATTCGCGATGGCCCATTC | 402 |
| 80 | 120-122 | 3' | P4976 | P5277 | ATCGCGAATAACATGNNTNNANNCAACATGAGCCTGGGAGCAC | 403 |
| | | 5' | P4974 | P5278 | TCCCAGGCTCATGTTGNNTNNANNCATGTTATTCGCGATGGCCCAT | 404 |
| 81 | 121-123 | 3' | P4976 | P5279 | GCGAATAACATGGATNNANNCNNCATGAGCCTGGGAGCACCAAG | 405 |
| | | 5' | P4974 | P5280 | TGCTCCCAGGCTCATGNNGNNTNNATCCATGTTATTCGCGATGGCCCATT | 406 |
| 82 | 122-124 | 3' | P4976 | P5281 | AATAACATGGATGTANNCNNCNNGAGCCTGGGAGCACCAAGCGGCA | 407 |
| | | 5' | P4974 | P5282 | TGGTGCTCCCAGGCTCNNGNNGNNTACATCCATGTTATTCGCGATG | 408 |
| 83 | 123-125 | 3' | P4976 | P5283 | AACATGGATGTAATCNNCNNGNNCCTGGGAGCACCAAGCGGCA | 409 |
| | | 5' | P4974 | P5284 | GCTTGGTGCTCCCAGGNNCNNGNNGATTACATCCATGTTATTCGCGA | 410 |
| 84 | 124-126 | 3' | P4976 | P5285 | ATGGATGTAATCAACNNGNNCNNGGAGCACCAAGCGGCAGTG | 411 |
| | | 5' | P4974 | P5286 | GCCGCTTGGTGCTCCCNNGNNCNNGTTGATTACATCCATGTTATTCG | 412 |

TABLE 11-6-continued

List of Primers Used to Create RCL4 Libraries

| Library # | Mutated residues in BPN'-v3 | Gene fragment | Common flanking primer names | Mutagenic primer names | Mutagenic primer sequence | SEQ ID NO: |
|---|---|---|---|---|---|---|
| 85 | 125-127 | 3' | P4976 | P5287 | GATGTAATCAACAT GNNCNNGNNAGCA CCAAGCGGCAGTGC GGCA | 413 |
| | | 5' | P4974 | P5288 | ACTGCCGCTTGGTG CTNNCNNGNNCATG TTGATTACATCCAT GTTATT | 414 |
| 86 | 126-128 | 3' | P4976 | P5289 | GTAATCAACATGAG CNNGNNANNACCA AGCGGCAGTGCGGC ACT | 415 |
| | | 5' | P4974 | P5290 | CGCACTGCCGCTTG GTNNTNNCNNGCTC ATGTTGATTACATC CATG | 416 |
| 87 | 129-131 | 3' | P4976 | P5291 | ATGAGCCTGGGAGC ANNANNCNNCAGT GCGGCACTTAAAGC AGCA | 417 |
| | | 5' | P4974 | P5292 | TTTAAGTGCCGCAC TGNNGNNTNNTGCT CCCAGGCTCATGTT GAT | 418 |
| 88 | 132-134 | 3' | P4976 | P5293 | GGAGCACCAAGCG GCNNTNNGNNACTT AAAGCAGCAGTTGA TAAAG | 419 |
| | | 5' | P4974 | P5294 | AACTGCTGCTTTAA GTNNCNNANNGCCG CTTGGTGCTCCCAG GCT | 420 |
| 89 | 133-135 | 3' | P4976 | P5295 | GCACCAAGCGGCAG TNNGNNANNTAAA GCAGCAGTTGATAA AGCTG | 421 |
| | | 5' | P4974 | P5296 | ATCAACTGCTGCTT TANNTNNCNNACTG CCGCTTGGTGCTCC CA | 422 |
| 90 | 134-136 | 3' | P4976 | P5297 | CCAAGCGGCAGTGC GNNANNTNNAGCA GCAGTTGATAAAGC TGTTG | 423 |
| | | 5' | P4974 | P5298 | TTTATCAACTGCTG CTNNANNTNNCGCA CTGCCGCTTGGTGC TC | 424 |
| 91 | 135-137 | 3' | P4976 | P5299 | AGCGGCAGTGCGGC ANNTNNANNAGCA GTTGATAAAGCTGT TGCAT | 425 |
| | | 5' | P4974 | P5300 | AGCTTTATCAACTG CTNNTNNANNTGCC GCACTGCCGCTTGG TG | 426 |
| 92 | 136-138 | 3' | P4976 | P5301 | GGCAGTGCGGCACT TNNANNANNAGTTG ATAAAGCTGTTGCA TCTG | 427 |
| | | 5' | P4974 | P5302 | AACAGCTTTATCAA CTNNTNNTNNAAGT GCCGCACTGCCGCT TG | 428 |

TABLE 11-6-continued

List of Primers Used to Create RCL4 Libraries

| Library # | Mutated residues in BPN'-v3 | Gene fragment | Common flanking primer names | Mutagenic primer names | Mutagenic primer sequence | SEQ ID NO: |
|---|---|---|---|---|---|---|
| 93 | 137-139 | 3' | P4976 | P5303 | AGTGCGGCACTTAA ANNANNANNTGAT AAAGCTGTTGCATC TGGTG | 429 |
| | | 5' | P4974 | P5304 | TGCAACAGCTTTAT CANNTNNTNNTTTA AGTGCCGCACTGCC GCTT | 430 |
| 94 | 138-140 | 3' | P4976 | P5305 | GCGGCACTTAAAGC ANNANNTNNTAAA GCTGTTGCATCTGG TGTC | 431 |
| | | 5' | P4974 | P5306 | AGATGCAACAGCTT TANNANNTNNTGCT TTAAGTGCCGCACT GC | 432 |
| 95 | 139-141 | 3' | P4976 | P5307 | GCACTTAAAGCAGC ANNTNNTNNAGCTG TTGCATCTGGTGTC GT | 433 |
| | | 5' | P4974 | P5308 | ACCAGATGCAACAG CTNNANNANNTGCT GCTTTAAGTGCCGC AC | 434 |
| 96 | 140-142 | 3' | P4976 | P5309 | CTTAAAGCAGCAGT TNNTNNANNTGTTG CATCTGGTGTCGTC GT | 435 |
| | | 5' | P4974 | P5310 | GACACCAGATGCAA CANNTNNANNAACT GCTGCTTTAAGTGC CGCA | 436 |
| 97 | 141-143 | 3' | P4976 | P5311 | AAAGCAGCAGTTGA TNNANNTNNTGCAT CTGGTGTCGTCGTA GT | 437 |
| | | 5' | P4974 | P5312 | GACGACACCAGATG CANNANNTNNATCA ACTGCTGCTTTAAG TGC | 438 |
| 98 | 142-144 | 3' | P4976 | P5313 | GCAGCAGTTGATAA ANNTNNTNNATCTG GTGTCGTCGTAGTA GC | 439 |
| | | 5' | P4974 | P5314 | TACGACGACACCAG ATNNANNANNTTTA TCAACTGCTGCTTT AAGTG | 440 |
| 99 | 143-145 | 3' | P4976 | P5315 | GCAGTTGATAAAGC TNNTNNANNTGGTG TCGTCGTAGTAGCG GCA | 441 |
| | | 5' | P4974 | P5316 | TACTACGACGACAC CANNTNNANNAGCT TTATCAACTGCTGC TTTAA | 442 |
| 100 | 144-146 | 3' | P4976 | P5317 | GTTGATAAAGCTGT TNNANNTNNTGTCG TCGTAGTAGCGGCA GCT | 443 |
| | | 5' | P4974 | P5318 | CGCTACTACGACGA CANNANNTNNAAC AGCTTTATCAACTG CTGCT | 444 |

TABLE 11-6-continued

List of Primers Used to Create RCL4 Libraries

| Library # | Mutated residues in BPN'-v3 | Gene fragment | Common flanking primer names | Mutagenic primer names | Mutagenic primer sequence | SEQ ID NO: |
|---|---|---|---|---|---|---|
| 101 | 145-147 | 3' | P4976 | P5319 | GATAAAGCTGTTGC ANNTNNTNNCGTCG TAGTAGCGGCAGCTG | 445 |
| | | 5' | P4974 | P5320 | TGCCGCTACTACGA CGNNANNANNTGC AACAGCTTTATCAA CTGCT | 446 |
| 102 | 146-148 | 3' | P4976 | P5321 | AAAGCTGTTGCATC TNNTNNCNNCGTAG TAGCGGCAGCTGGG AA | 447 |
| | | 5' | P4974 | P5322 | AGCTGCCGCTACTA CGNNGNNANNAGA TGCAACAGCTTTAT CAACTG | 448 |
| 103 | 147-149 | 3' | P4976 | P5323 | GCTGTTGCATCTGG TNNCNNCNNAGTAG CGGCAGCTGGGAAT GA | 449 |
| | | 5' | P4974 | P5324 | CCCAGCTGCCGCTA CTNNGNNGNNACCA GATGCAACAGCTTT ATCA | 450 |
| 104 | 148-150 | 3' | P4976 | P5325 | GTTGCATCTGGTGT CNNCNNANNAGCG GCAGCTGGGAATGA GGGAA | 451 |
| | | 5' | P4974 | P5326 | ATTCCCAGCTGCCG CTNNTNNGNNGACA CCAGATGCAACAGC TTT | 452 |
| 105 | 149-151 | 3' | P4976 | P5327 | GCATCTGGTGTCGT CNNANNANNGGCA GCTGGGAATGAGGG AAC | 453 |
| | | 5' | P4974 | P5328 | CTCATTCCCAGCTG CCNNTNNTNNGACG ACACCAGATGCAAC AG | 454 |
| 106 | 150-152 | 3' | P4976 | P5329 | TCTGGTGTCGTCGT ANNANNGNNAGCT GGGAATGAGGGAA CATC | 455 |
| | | 5' | P4974 | P5330 | TCCCTCATTCCCAG CTNNCNNTNNTACG ACGACACCAGATGC AAC | 456 |
| 107 | 151-153 | 3' | P4976 | P5331 | GGTGTCGTCGTAGT ANNGNNANNTGGG AATGAGGGAACATC CGGAT | 457 |
| | | 5' | P4974 | P5332 | TGTTCCCTCATTCCC ANNTNNCNNTACTA CGACGACACCAGAT GCA | 458 |
| 108 | 158-160 | 3' | P4976 | P5333 | GCTGGGAATGAGGG ANNANNCNNATCAT CGAGTACCGTCGGT TAT | 459 |
| | | 5' | P4974 | P5334 | GACGGTACTCGATG ATNNGNNTNNCCC TCATTCCCAGCTGC CGCTA | 460 |

TABLE 11-6-continued

List of Primers Used to Create RCL4 Libraries

| Library # | Mutated residues in BPN'-v3 | Gene fragment | Common flanking primer names | Mutagenic primer names | Mutagenic primer sequence | SEQ ID NO: |
|---|---|---|---|---|---|---|
| 109 | 159-161 | 3' | P4976 | P5335 | GGGAATGAGGGAACANNCNNANNATCGAGTACCGTCGGTTATCCA | 461 |
|  |  | 5' | P4974 | P5336 | ACCGACGGTACTCGATNNTNNGNNTGTTCCCTCATTCCCAGCTG | 462 |
| 110 | 160-162 | 3' | P4976 | P5337 | AATGAGGGAACATCCNNANNANNGAGTACCGTCGGTTATCCAGG | 463 |
|  |  | 5' | P4974 | P5338 | ATAACCGACGGTACTCNNTNNTNNGGATGTTCCCTCATTCCCAG | 464 |
| 111 | 163-165 | 3' | P4976 | P5339 | ACATCCGGATCATCGNNTNNCNNCGGTTATCCAGGCAAGTACCCTT | 465 |
|  |  | 5' | P4974 | P5340 | CTTGCCTGGATAACCGNNGNNANNCGATGATCCGGATGTTCCT | 466 |
| 112 | 164-166 | 3' | P4976 | P5341 | TCCGGATCATCGAGTNNCNNCNNTTATCCAGGCAAGTACCCTTCA | 467 |
|  |  | 5' | P4974 | P5342 | GTACTTGCCTGGATAANNGNNGNNACTCGATGATCCGGATGTTCC | 468 |
| 113 | 167-169 | 3' | P4976 | P5343 | TCGAGTACCGTCGGTNNTNNANNCAAGTACCCTTCAGTGATTGCA | 469 |
|  |  | 5' | P4974 | P5344 | CACTGAAGGGTACTTGNNTNNANNACCGACGGTACTCGATGATC | 470 |
| 114 | 168-170 | 3' | P4976 | P5345 | AGTACCGTCGGTTATNNANNCNNGTACCTTCAGTGATTGCAGTG | 471 |
|  |  | 5' | P4974 | P5346 | AATCACTGAAGGGTACNNGNNTNNATAACCGACGGTACTCGATGA | 472 |
| 115 | 169-171 | 3' | P4976 | P5347 | ACCGTCGGTTATCCANNCNNGNNCCCTTCAGTGATTGCAGTGG | 473 |
|  |  | 5' | P4974 | P5348 | TGCAATCACTGAAGGGNNCNNGNNTGGATAACCGACGGTACTCGA | 474 |
| 116 | 170-172 | 3' | P4976 | P5349 | GTCGGTTATCCAGGCNNGNNCNNTTCAGTGATTGCAGTGGGCGCT | 475 |
|  |  | 5' | P4974 | P5350 | CACTGCAATCACTGAANNGNNCNNGCCTGGATAACCGACGGTAC | 476 |

TABLE 11-6-continued

List of Primers Used to Create RCL4 Libraries

| Library # | Mutated residues in BPN'-v3 | Gene fragment | Common flanking primer names | Mutagenic primer names | Mutagenic primer sequence | SEQ ID NO: |
|---|---|---|---|---|---|---|
| 117 | 171-173 | 3' | P4976 | P5351 | GGTTATCCAGGCAA GNNCNNTNNAGTGA TTGCAGTGGGCGCT GTA | 477 |
| | | 5' | P4974 | P5352 | GCCCACTGCAATCA CTNNANNGNNCTTG CCTGGATAACCGAC GGTA | 478 |
| 118 | 172-174 | 3' | P4976 | P5353 | TATCCAGGCAAGTA CNNTNNANNGATTG CAGTGGGCGCTGTA GA | 479 |
| | | 5' | P4974 | P5354 | AGCGCCCACTGCAA TCNNTNNANNGTAC TTGCCTGGATAACC GAC | 480 |
| 119 | 182-184 | 3' | P4976 | P5355 | GTGGGCGCTGTAGA CNNTNNANNTCAAC GTGCCTCTTTTCCTC | 481 |
| | | 5' | P4974 | P5356 | AAAAGAGGCACGTT GANNTNNANNGTCT ACAGCGCCCACTGC AA | 482 |
| 120 | 183-185 | 3' | P4976 | P5357 | GGCGCTGTAGACTC TNNANNTNNACGTG CCTCTTTTCCTCCGT | 483 |
| | | 5' | P4974 | P5358 | GGAAAAGAGGCA CGTNNANNTNNAGA GTCTACAGCGCCCA CTG | 484 |
| 121 | 184-186 | 3' | P4976 | P5359 | GCTGTAGACTCTTC ANNTNNANNTGCCT CTTTTCCTCCGTGG GA | 485 |
| | | 5' | P4974 | P5360 | GGAGGAAAAGAG GCANNTNNANNTGA AGAGTCTACAGCGC CCA | 486 |
| 122 | 185-187 | 3' | P4976 | P5361 | GTAGACTCTTCAAA TNNANNTNNCTCTT TTCCTCCGTGGGAC | 487 |
| | | 5' | P4974 | P5362 | CACGGAGGAAAAA GAGNNANNTNNATT TGAAGAGTCTACAG CGCCCA | 488 |
| 123 | 186-188 | 3' | P4976 | P5363 | GACTCTTCAAATCA ANNTNNCNNTTTTT CCTCCGTGGGACCG GA | 489 |
| | | 5' | P4974 | P5364 | TCCCACGGAGGAAA AANNGNNANNTTG ATTTGAAGAGTCTA CAGCGCCCA | 490 |
| 124 | 192-194 | 3' | P4976 | P5365 | GCCTCTTTTCCTCC NNGNNANNGGAGC TGGATGTCATGGCC CCT | 491 |
| | | 5' | P4974 | P5366 | CATGACATCCAGCT CCNNTNNCNNGGAG GAAAAGAGGCAC GTTG | 492 |
| 125 | 194-196 | 3' | P4976 | P5367 | TTTTCCTCCGTGGG ANNGNNGNNGGAT | 493 |

TABLE 11-6-continued

List of Primers Used to Create RCL4 Libraries

| Library # | Mutated residues in BPN'-v3 | Gene fragment | Common flanking primer names | Mutagenic primer names | Mutagenic primer sequence | SEQ ID NO: |
|---|---|---|---|---|---|---|
| | | 5' | P4974 | P5368 | GTCATGGCCCCTGGCGTT AGGGGCCATGACAT CCNNCNNCNNTCCC ACGGAGGAAAAAG AGG | 494 |
| 126 | 195-197 | 3' | P4976 | P5369 | TCCTCCGTGGGACC GNNGNNGNNTGTCA TGGCCCCTGGCGTT TCTATT | 495 |
| | | 5' | P4974 | P5370 | GCCAGGGGCCATGA CANNCNNCNNCGGT CCCACGGAGGAAA AAG | 496 |
| 127 | 196-198 | 3' | P4976 | P5371 | TCCGTGGGACCGGA GNNGNNTNNCATGG CCCCTGGCGTTTCT ATT | 497 |
| | | 5' | P4974 | P5372 | AACGCCAGGGGCCA TGNNANNCNNCTCC GGTCCCACGGAGGA AAAA | 498 |
| 128 | 197-199 | 3' | P4976 | P5373 | GTGGGACCGGAGCT GNNTNNCNNGGCCC CTGGCGTTTCTATTC AA | 499 |
| | | 5' | P4974 | P5374 | AGAAACGCCAGGG GCCNNGNNANNCA GCTCCGGTCCCACG GAGGAAA | 500 |
| 129 | 198-200 | 3' | P4976 | P5375 | GGACCGGAGCTGGA TNNCNNGNNCCCTG GCGTTTCTATTCAA TCGA | 501 |
| | | 5' | P4974 | P5376 | AATAGAAACGCCAG GGNNCNNGNNATCC AGCTCCGGTCCCAC GGA | 502 |
| 130 | 203-205 | 3' | P4976 | P5377 | GTCATGGCCCCTGG CNNTNNTNNTCAAT CGACGCTTCCAGGG AA | 503 |
| | | 5' | P4974 | P5378 | TGGAAGCGTCGATT GANNANNANNGCC AGGGGCCATGACAT CCA | 504 |
| 131 | 210-212 | 3' | P4976 | P5379 | ATTCAATCGACGCT TNNANNGNNCAAGT ATGGTGCGCAAAAC GGGA | 505 |
| | | 5' | P4974 | P5380 | TTGCGCACCATACT TGNNCNNTNNAAGC GTCGATTGAATAGA AACG | 506 |
| 132 | 211-213 | 3' | P4976 | P5381 | CAATCGACGCTTCC ANNGNNCNNGTATG GTGCGCAAAACGGG ACT | 507 |
| | | 5' | P4974 | P5382 | GTTTTGCGCACCAT ACNNGNNCNNTGG AAGCGTCGATTGAA TAGAA | 508 |
| 133 | 216-218 | 3' | P4976 | P5383 | GGGAACAAGTATGG TNNGNNANNCGGG | 509 |

TABLE 11-6-continued

List of Primers Used to Create RCL4 Libraries

| Library # | Mutated residues in BPN'-v3 | Gene fragment | Common flanking primer names | Mutagenic primer names | Mutagenic primer sequence | SEQ ID NO: |
|---|---|---|---|---|---|---|
| | | 5' | P4974 | P5384 | ACTTCCATGGCCTCGCCGCATGGCCATGGAAGTCCCGNNTNNCNNACCATACTTGTTCCCTGGAAG | 510 |
| 134 | 217-219 | 3' | P4976 | P5385 | AACAAGTATGGTGCGNNANNCNNGACTTCCATGGCCTCGCCGCAT | 511 |
| | | 5' | P4974 | P5386 | CGAGGCCATGGAAGTCNNGNNTNNCGCACCATACTTGTTCCCTG | 512 |
| 135 | 218-220 | 3' | P4976 | P5387 | AAGTATGGTGCGCAANNCNNGNNTTCCATGGCCTCGCCGCATG | 513 |
| | | 5' | P4974 | P5388 | CGGCGAGGCCATGGAANNCNNGNNTTGCGCACCATACTTGTTCCC | 514 |
| 136 | 219-221 | 3' | P4976 | P5389 | TATGGTGCGCAAAACNNGNNTNNCATGGCCTCGCCGCATGTAG | 515 |
| | | 5' | P4974 | P5390 | ATGCGGCGAGGCCATGNNANNCNNGTTTTGCGCACCATACTTGTTC | 516 |
| 137 | 230-232 | 3' | P4976 | P5391 | CCGCATGTAGCTGGGNNGNNCNNATTGATTCTTTCTAAGCACCCGAA | 517 |
| | | 5' | P4974 | P5392 | CTTAGAAAGAATCAATNNGNNCNNCCAGCTACATGCGGCGAGGCCAT | 518 |
| 138 | 231-233 | 3' | P4976 | P5393 | CATGTAGCTGGGGCGNNCNNANNGATTCTTTCTAAGCACCCGAACT | 519 |
| | | 5' | P4974 | P5394 | GTGCTTAGAAAGAATCNNTNNGNNCGCCCAGCTACATGCGGCGAGGCCAT | 520 |
| 139 | 232-234 | 3' | P4976 | P5395 | GTAGCTGGGGCGGCCNNANNGNNTCTTTCTAAGCACCCGAACTG | 521 |
| | | 5' | P4974 | P5396 | CGGGTGCTTAGAAAGANNCNNTNNGGCCGCCCCAGCTACATGC | 522 |
| 140 | 238-240 | 3' | P4976 | P5397 | TTGATTCTTTCTAAGNNCNNGNNCTGGACAAACACTCAAGTCCGCA | 523 |
| | | 5' | P4974 | P5398 | TTGAGTGTTTGTCCAGNNCNNGNNCTTAGAAAGAATCAATGCGGC | 524 |
| 141 | 240-242 | 3' | P4976 | P5399 | CTTTCTAAGCACCCGNNCNNGNNAAACACTCAAGTCCGCAGCAGT | 525 |
| | | 5' | P4974 | P5400 | GCGGACTTGAGTGTTTNNCNNGNNCGGG | 526 |

TABLE 11-6-continued

List of Primers Used to Create RCL4 Libraries

| Library # | Mutated residues in BPN'-v3 | Gene fragment | Common flanking primer names | Mutagenic primer names | Mutagenic primer sequence | SEQ ID NO: |
|---|---|---|---|---|---|---|
| | | | | | TGCTTAGAAAGAAT CAAT | |
| 142 | 246-248 | 3' | P4976 | P5401 | TGGACAAACACTCA ANNCNNCNNCAGTT TAGAAAACACCACT ACAAAA | 527 |
| | | 5' | P4974 | P5402 | GGTGTTTTCTAAAC TGNNGNNGNNTTGA GTGTTTGTCCAGTT CGGGT | 528 |
| 143 | 255-257 | 3' | P4976 | P5403 | TTAGAAAACACCAC TNNANNANNTGGTG ATTCTTTCTACTATG GAAA | 529 |
| | | 5' | P4974 | P5404 | GTAGAAAGAATCAC CANNTNNTNNAGTG GTGTTTTCTAAACT GCTG | 530 |
| 144 | 258-260 | 3' | P4976 | P5405 | ACCACTACAAAACT TNNTNNTNNTTTCT ACTATGGAAAAGGG CTGA | 531 |
| | | 5' | P4974 | P5406 | TTTTCCATAGTAGA AANNANNANNAAG TTTTGTAGTGGTGTT TTCTAA | 532 |
| 145 | 265-267 | 3' | P4976 | P5407 | GATTCTTTCTACTAT NNANNANNGCTGAT CAACGTACAGGCGG CA | 533 |
| | | 5' | P4974 | P5408 | CTGTACGTTGATCA GCNNTNNTNNATAG TAGAAAGAATCACC AAGTTT | 534 |

RCL5 Variants

"RCL5" refers to a set of combinatorial variants created by PCR fusion using several BPN' mutants as parent (template) molecules. The mutations introduced in each parent plasmid are shown in Table 11-7 and the mutagenic primers used to create the mutants are indicated in Table 11-8.

TABLE 11-7

List of Parent Plasmids and Mutations Introduced in the RCL5 Variants

| Combinatorial Variant # | Parent Plasmids | Mutations Introduced |
|---|---|---|
| 1 | G97A-G128A-Y217Q-T22N-S24A | N61P-N62S |
| 2 | G97A-G128A-Y217Q-T22N-S24A | T55P |
| 3 | G97A-G128A-Y217Q-T22N-S24A | N61P-S63H |
| 4 | G97A-G128A-Y217Q-T22N-S24A | Q59S-N61P |
| 5 | G97A-G128A-Y217Q-T22N-S24A | L75S-N76Y |
| 6 | G97A-G128A-Y217Q-T22N-S24A | P86S-S87G-A88V |
| 7 | G97A-G128A-Y217Q-T22N-S24A | S87G-A88V-S89A |
| 8 | G97A-G128A-Y217Q-T22N-S24A | S87T-A88L-S89G |
| 9 | G97A-G128A-Y217Q-T22N-S24A | P129Q-S130G-G131S |
| 10 | G97A-G128A-Y217Q-T22N-S24A | V203Y |
| 11 | G97A-G128A-Y217Q-T22N-S24A | G211R-N212S-K213V |
| 12 | G97A-G128A-Y217Q-S24G-N25G | N61P-N62S |
| 13 | G97A-G128A-Y217Q-S24G-N25G | T55P |
| 14 | G97A-G128A-Y217Q-S24G-N25G | N61P-S63H |
| 15 | G97A-G128A-Y217Q-S24G-N25G | Q59S-N61P |
| 16 | G97A-G128A-Y217Q-S24G-N25G | L75S-N76Y |
| 17 | G97A-G128A-Y217Q-S24G-N25G | P86S-S87G-A88V |
| 18 | G97A-G128A-Y217Q-S24G-N25G | S87G-A88V-S89A |
| 19 | G97A-G128A-Y217Q-S24G-N25G | S87T-A88L-S89G |
| 20 | G97A-G128A-Y217Q-S24G-N25G | P129Q-S130G-G131S |

TABLE 11-7-continued

| List of Parent Plasmids and Mutations Introduced in the RCL5 Variants | | |
|---|---|---|
| Combinatorial Variant # | Parent Plasmids | Mutations Introduced |
| 21 | G97A-G128A-Y217Q-S24G-N25G | V203Y |
| 22 | G97A-G128A-Y217Q-S24G-N25G | G211R-N212S-K213V |
| 23 | G97A-G128A-Y217Q-S24R | N61P-N62S |
| 24 | G97A-G128A-Y217Q-S24R | T55P |
| 25 | G97A-G128A-Y217Q-S24R | N61P-S63H |
| 26 | G97A-G128A-Y217Q-S24R | Q59S-N61P |
| 27 | G97A-G128A-Y217Q-S24R | L75S-N76Y |
| 28 | G97A-G128A-Y217Q-S24R | P86S-S87G-A88V |
| 29 | G97A-G128A-Y217Q-S24R | S87G-A88V-S89A |
| 30 | G97A-G128A-Y217Q-S24R | S87T-A88L-S89G |
| 31 | G97A-G128A-Y217Q-S24R | P129Q-S130G-G131S |
| 32 | G97A-G128A-Y217Q-S24R | V203Y |
| 33 | G97A-G128A-Y217Q-S24R | G211R-N212S-K213V |
| 34 | G97A-G128A-Y217Q-G23A-S24G-N25G | N61P-N62S |
| 35 | G97A-G128A-Y217Q-G23A-S24G-N25G | T55P |
| 36 | G97A-G128A-Y217Q-G23A-S24G-N25G | N61P-S63H |
| 37 | G97A-G128A-Y217Q-G23A-S24G-N25G | Q59S-N61P |
| 38 | G97A-G128A-Y217Q-G23A-S24G-N25G | L75S-N76Y |
| 39 | G97A-G128A-Y217Q-G23A-S24G-N25G | P86S-S87G-A88V |
| 40 | G97A-G128A-Y217Q-G23A-S24G-N25G | S87G-A88V-S89A |
| 41 | G97A-G128A-Y217Q-G23A-S24G-N25G | S87T-A88L-S89G |
| 42 | G97A-G128A-Y217Q-G23A-S24G-N25G | P129Q-S130G-G131S |
| 43 | G97A-G128A-Y217Q-G23A-S24G-N25G | V203Y |
| 44 | G97A-G128A-Y217Q-G23A-S24G-N25G | G211R-N212S-K213V |
| 45 | G97A-G128A-Y217Q-N61P-N62S | L75S-N76Y |
| 46 | G97A-G128A-Y217Q-N61P-N62S | P86S-S87G-A88V |
| 47 | G97A-G128A-Y217Q-N61P-N62S | S87G-A88V-S89A |
| 48 | G97A-G128A-Y217Q-N61P-N62S | S87T-A88L-S89G |
| 49 | G97A-G128A-Y217Q-N61P-N62S | P129Q-S130G-G131S |
| 50 | G97A-G128A-Y217Q-N61P-N62S | V203Y |
| 51 | G97A-G128A-Y217Q-N61P-N62S | G211R-N212S-K213V |
| 52 | G97A-G128A-Y217Q-T55P | L75S-N76Y |
| 53 | G97A-G128A-Y217Q-T55P | P86S-S87G-A88V |
| 54 | G97A-G128A-Y217Q-T55P | S87G-A88V-S89A |
| 55 | G97A-G128A-Y217Q-T55P | S87T-A88L-S89G |
| 56 | G97A-G128A-Y217Q-T55P | P129Q-S130G-G131S |
| 57 | G97A-G128A-Y217Q-T55P | V203Y |
| 58 | G97A-G128A-Y217Q-T55P | G211R-N212S-K213V |
| 59 | G97A-G128A-Y217Q-N61P-S63H | L75S-N76Y |
| 60 | G97A-G128A-Y217Q-N61P-S63H | P86S-S87G-A88V |
| 61 | G97A-G128A-Y217Q-N61P-S63H | S87G-A88V-S89A |
| 62 | G97A-G128A-Y217Q-N61P-S63H | S87T-A88L-S89G |
| 63 | G97A-G128A-Y217Q-N61P-S63H | P129Q-S130G-G131S |
| 64 | G97A-G128A-Y217Q-N61P-S63H | V203Y |
| 65 | G97A-G128A-Y217Q-N61P-S63H | G211R-N212S-K213V |
| 66 | G97A-G128A-Y217Q-Q59S-N61P | L75S-N76Y |
| 67 | G97A-G128A-Y217Q-Q59S-N61P | P86S-S87G-A88V |
| 68 | G97A-G128A-Y217Q-Q59S-N61P | S87G-A88V-S89A |
| 69 | G97A-G128A-Y217Q-Q59S-N61P | S87T-A88L-S89G |
| 70 | G97A-G128A-Y217Q-Q59S-N61P | P129Q-S130G-G131S |
| 71 | G97A-G128A-Y217Q-Q59S-N61P | V203Y |
| 72 | G97A-G128A-Y217Q-Q59S-N61P | G211R-N212S-K213V |
| 73 | G97A-G128A-Y217Q-L75S-N76Y | P86S-S87G-A88V |
| 74 | G97A-G128A-Y217Q-L75S-N76Y | S87G-A88V-S89A |
| 75 | G97A-G128A-Y217Q-L75S-N76Y | S87T-A88L-S89G |
| 76 | G97A-G128A-Y217Q-L75S-N76Y | P129Q-S130G-G131S |
| 77 | G97A-G128A-Y217Q-L75S-N76Y | V203Y |
| 78 | G97A-G128A-Y217Q-L75S-N76Y | G211R-N212S-K213V |
| 79 | G97A-G128A-Y217Q-P86S-S87G-A88V | P129Q-S130G-G131S |
| 80 | G97A-G128A-Y217Q-P86S-S87G-A88V | V203Y |
| 81 | G97A-G128A-Y217Q-P86S-S87G-A88V | G211R-N212S-K213V |
| 82 | G97A-G128A-Y217Q-S87G-A88V-S89A | P129Q-S130G-G131S |
| 83 | G97A-G128A-Y217Q-S87G-A88V-S89A | V203Y |
| 84 | G97A-G128A-Y217Q-S87G-A88V-S89A | G211R-N212S-K213V |
| 85 | G97A-G128A-Y217Q-S87T-A88L-S89G | P129Q-S130G-G131S |
| 86 | G97A-G128A-Y217Q-S87T-A88L-S89G | V203Y |
| 87 | G97A-G128A-Y217Q-S87T-A88L-S89G | G211R-N212S-K213V |
| 88 | G97A-G128A-Y217Q-P129Q-S130G-G131S | V203Y |
| 89 | G97A-G128A-Y217Q-P129Q-S130G-G131S | G211R-N212S-K213V |
| 90 | G97A-G128A-Y217Q-V203Y | G211R-N212S-K213V |

TABLE 11-8

Primers Used to Create RCL5 Combinatorial Variants

| Mutations Introduced | Gene Fragments | Common 3' & 5' Gene Flanking Primer Names | Primer Name | Primer Sequence | SEQ ID NO: |
|---|---|---|---|---|---|
| T22N-S24A | 3' | P4976 | P5432 | TCAAGGCTACAATGGAGCAAATG TTAAAGTAGCGGTTATCGA | 535 |
|  | 5' | P4974 | P5433 | TTTAACATTTGCTCCATTGTAGCC TTGAGAGTGCAGAG | 536 |
| S24G-N25G | 3' | P4976 | P5434 | CTACACTGGAGGAGGTGTTAAAG TAGCGGTTATCGACA | 537 |
|  | 5' | P4974 | P5435 | CTACTTTAACACCTCCTCCAGTGT AGCCTTGAGAGTG | 538 |
| S24R | 3' | P4976 | P5436 | AGGCTACACTGGAAGAAATGTTA AAGTAGCGGTTATCGAC | 539 |
|  | 5' | P4974 | P5437 | CTTTAACATTTCTTCCAGTGTAGC CTTGAGAGTG | 540 |
| G23A-S24G-N25G | 3' | P4976 | P5438 | AAGGCTACACTGCAGGAGGTGTT AAAGTAGCGGTTATCGACA | 541 |
|  | 5' | P4974 | P5439 | CTACTTTAACACCTCCTGCAGTGT AGCCTTGAGAGTGCAG | 542 |
| N61

TABLE 11-8-continued

Primers Used to Create RCL5 Combinatorial Variants

| Mutations Introduced | Gene Fragments | Common 3' & 5' Gene Flanking Primer Names | Primer Name | Primer Sequence | SEQ ID NO: |
|---|---|---|---|---|---|
|  | 5' | P4974 | P5459 | TCGATTGAATAGAATAGCCAGGG GCCATGACATCCA | 562 |
| G211R-N212S-K213V | 3' | P4976 | P5460 | TCGACGCTTCCAAGGTCCGTGTA TGGTGCGCAAAACGGGACT | 563 |
|  | 5' | P4974 | P5461 | TTGCGCACCATACACGGACCTTG GAAGCGTCGATTGAATAGAAA | 564 |

To create each mutant, two PCR reactions were carried out using either the common 3' gene-flanking primer (P4976, CCTCTCGGTTATGAGTTAGTTC; SEQ ID NO:61) and the mutagenic primer, or the common 5' gene-flanking primer (P4974, GCCTCACATTTGTGCCACCTA; SEQ ID NO:60) and mutagenic primer as shown for each library in Table 11-8. These PCR reactions generated two PCR fragments, one encoding the 5' half of the mutant BPN' gene (5' gene fragment) and the other encoding the 3' half of the mutant BPN' gene (3' gene fragment). Each PCR amplification reaction contained 30 pmol of each primer and 100 ng of the parent molecules listed in Table 11-7. Amplifications were carried out using Vent DNA polymerase (NEB). The PCR reaction (20 µL) was initially heated at 95° C. for 2.5 min followed by 30 cycles of denaturation at 94° C. for 15 sec., annealing at 55° C. for 15 sec. and extension at 72° C. for 40 sec. Following amplification, the 5' and 3' gene fragments were gel-purified by the QIAGEN® gel-band purification kit, mixed (50 ng of each fragment) and amplified by PCR once again using the primers P4973 (AAAGGATCCTAATCG-GCGCTTTTC; SEQ ID NO:62) and P4950 (CTTGTCTC-CAAGCTTAAAATAAAA; SEQ ID NO:63) to generate the full-length gene fragment. The PCR conditions were same as described above, except the extension phase, which was carried out at 72° C. for 2 min. The full-length DNA fragment was gel-purified by the QIAGEN® gel-band purification kit, digested by the BamHI and HindIII restriction enzymes and ligated with the pHPLT-BPN' partial opt that also was digested with the same restriction enzymes. Ligation mixtures were amplified using rolling circle amplification by Illustra Templiphi kit according to the manufacturer's instructions (GE Healthcare) to generate multimeric DNA for transformation into *Bacillus subtilis*. For this purpose, 1 µl of the ligation mixture was mixed with 5 µl of the sample buffer, heated to 95° C. for 3 min and cooled on ice. Next, 5 µl of the reaction buffer and 0.2 µl of the enzyme were added to each tube, followed by incubation at 30° C. for 10 hours. Products of the rolling circle amplification were diluted 100 times and used to transform *B. subtilis* cells (ΔaprE, ΔnprE, amyE:: xylRPxylAcomK-phleo). An aliquot of the transformation mix was plated on LB plates containing 1.6% skim milk and 10 µg/mL neomycin and incubated overnight at 37° C. Subsequently, the colonies with halos were inoculated in 120 µl of LB media containing 10 µg/mL neomycin.

RCL 6 Combinatorial Libraries

"RCL6" refers to a group of combinatorial libraries created by PCR fusion using several BPN' mutants as parent (template) molecules. A mixture of BPN' mutants were used as templates (parent molecules) in the construction of each of these libraries. The five different mixes of parent molecules used to create these libraries are provided in Table 11-9, and the mutations introduced in each library are listed in Table 11-10.

To create each mutant, two PCR reactions were carried out using either the common 3' gene-flanking primer (P4976, CCTCTCGGTTATGAGTTAGTTC; SEQ ID NO:61) and the mutagenic primer, or the common 5' gene-flanking primer (P4974, GCCTCACATTTGTGCCACCTA; SEQ ID NO:60) and mutagenic primer as shown for each library in Table 11-10. These PCR reactions generated two PCR fragments, one encoding the 5' half of the mutant BPN' gene (5' gene fragment) and the other encoding the 3' half of the mutant BPN' gene (3' gene fragment). Each PCR amplification reaction contained 30 pmol of each primer and 100 ng of the parent molecules listed in Table 11-9. Amplifications were carried out using Vent DNA polymerase (NEB). The PCR reaction (20 µL) was initially heated at 95° C. for 2.5 min followed by 30 cycles of denaturation at 94° C. for 15 sec., annealing at 55° C. for 15 sec. and extension at 72° C. for 40 sec. Following amplification, the 5' and 3' gene fragments were gel-purified by the QIAGEN® gel-band purification kit, mixed (50 ng of each fragment) and amplified by PCR once again using the primers P4973 (AAAGGATCCTAATCG-GCGCTTTTC; SEQ ID NO:62) and P4950 (CTTGTCTC-CAAGCTTAAAATAAAA; SEQ ID NO:63) to generate the full-length gene fragment. The PCR conditions were same as described above, except the extension phase, which was carried out at 72° C. for 2 min. The full-length DNA fragment was gel-purified by the QIAGEN® gel-band purification kit, digested using BamHI and HindIII restriction enzymes and ligated with the pHPLT-BPN' partial opt vector that also was digested with the same restriction enzymes. Ligation mixtures were amplified using rolling circle amplification by Illustra Templiphi kit according to the manufacturer's instructions (GE Healthcare) to generate multimeric DNA for transformation into *Bacillus subtilis*. For this purpose, 1 µl of the ligation mixture was mixed with 5 µl of the sample buffer, heated to 95° C. for 3 min and cooled on ice. Next, 5 µl of the reaction buffer and 0.2 µl of the enzyme were added to each tube, followed by incubation at 30° C. for 10 hours. Products of the rolling circle amplification were diluted 100 times and used to transform *B. subtilis* cells (ΔaprE, ΔnprE, amyE:: xylRPxylAcomK-phleo). An aliquot of the transformation mix was plated on LB plates containing 1.6% skim milk and 10 µg/mL neomycin and incubated overnight at 37° C. Subsequently, the colonies with halos were inoculated in 120 µl of LB media containing 10 µg/mL neomycin.

TABLE 11-9

Parent Molecules of BPN' Used to Create RCL6 Libraries
Mixes of Parent Molecules

| Mix 1 | Mix 2 | Mix 3 | Mix 4 | Mix 5 |
|---|---|---|---|---|
| G97A-G128A-Y217Q-S24G-N25G | G97A-G128A-Y217Q-T55P | G97A-G128A-Y217Q-L75S-N76Y | G97A-G128A-Y217Q-P86S-S87G-A88V | G97A-G128A-Y217Q-P129Q-S130G-G131S |
| G97A-G128A-Y217Q-S24R | G97A-G128A-Y217Q-N61P-S63H | | G97A-G128A-Y217Q-S87G-A88V-S89A | |
| G97A-G128A-Y217Q-G23A-S24G-N25G | G97A-G128A-Y217Q-Q59S-N61P | | G97A-G128A-Y217Q-S87T-A88L-S89G | |

TABLE 11-10

Mutations Introduced in the RCL6 Libraries

| Mutations Introduced | Gene Fragment | Common 5' & 3' Gene Flanking Primer Names | Mutagenic Primer Name | Mutagenic Primer Sequence | SEQ ID NO: |
|---|---|---|---|---|---|
| V68C, A69G | 3' | P4976 | P5462 | CATGGCACACACTGCGGAGGAACGGTTGCGGCGTTAAAC | 565 |
| | 5' | P4974 | P5463 | GCAACCGTTCCTCCGCAGTGTGTGCCATGAGAATTGTTA | 566 |
| V72I, A73G, delA74, L75S | 3' | P4976 | P5464 | GTCGCAGGAACGATTGGTTCAAACAATTCTATTGGCGTGCTTG | 567 |
| | 5' | P4974 | P5465 | CAATAGAATTGTTTGAACCAATCGTTCCTGCGACGTGTGTGCCAT | 568 |
| L75H, N76G | 3' | P4976 | P5466 | AACGGTTGCGGCGCATGGAAATTCTATTGGCGTGCTTGGTG | 569 |
| | 5' | P4974 | P5467 | CAATAGAATTTCCATGCGCCGCAACCGTTCCTGCGACGTGT | 570 |
| L75R, N76G, N77S | 3' | P4976 | P5468 | AACGGTTGCGGCGAGAGGAGGTTCTATTGGCGTGCTTGGTGTA | 571 |
| | 5' | P4974 | P5469 | CACGCCAATAGAACCTCCTCTCGCCGCAACCGTTCCTGCGACGTGT | 572 |
| L75G, N76G, N77G | 3' | P4976 | P5470 | AACGGTTGCGGCGGGAGGCGGTTCTATTGGCGTGCTTGGTGTA | 573 |
| | 5' | P4974 | P5471 | CACGCCAATAGAACCGCCTCCCGCCGCAACCGTTCCTGCGACGTGT | 574 |
| A92G | 3' | P4976 | P5472 | TGCTTCGCTCTACGGCGTTAAAGTTCTTGCAGCAGAC | 575 |
| | 5' | P4974 | P5473 | CAAGAACTTTAACGCCGTAGAGCGAAGCAGACGGGGCTA | 576 |
| delV93, K94S, V95C, L96S | 3' | P4976 | P5474 | TTCGCTCTACGCCTCATGTTCTGCAGCAGACGGATCAGGCCAA | 577 |
| | 5' | P4974 | P5475 | ATCCGTCTGCTGCAGAACATGAGGCGTAGAGCGAAGCAGACG | 578 |
| V121I_I122S_N123C | 3' | P4976 | P5476 | AATAACATGGATATATCTTGCATGAGCCTGGGAGCACCAAG | 579 |

TABLE 11-10-continued

Mutations Introduced in the RCL6 Libraries

| Mutations Introduced | Gene Fragment | Common 5' & 3' Gene Flanking Primer Names | Mutagenic Primer Name | Mutagenic Primer Sequence | SEQ ID NO: |
|---|---|---|---|---|---|
| | 5' | P4974 | P5477 | CAGGCTCATGCAAGATAT ATCCATGTTATTCGCGATG GCCCATT | 580 |
| V121L_N123C | 3' | P4976 | P5478 | CGAATAACATGGATCTTA TCTGCATGAGCCTGGGAG CACCAAG | 581 |
| | 5' | P4974 | P5479 | CCAGGCTCATGCAGATAA GATCCATGTTATTCGCGAT GGCCCATT | 582 |
| I122C_N123S_M124L | 3' | P4976 | P5480 | TAACATGGATGTATGCTC ATTGAGCCTGGGAGCACC AAGCGGCA | 583 |
| | 5' | P4974 | P5481 | TGCTCCCAGGCTCAATGA GCATACATCCATGTTATTC GCGATG | 584 |
| N123C | 3' | P4976 | P5482 | ACATGGATGTAATCTGCA TGAGCCTGGGAGCACCAAG | 585 |
| | 5' | P4974 | P5483 | TCCCAGGCTCATGCAGAT TACATCCATGTTATTCGCG AT | 586 |
| M124I | 3' | P4976 | P5484 | GGATGTAATCAACATCAG CCTGGGAGCACCAAGCGG CA | 587 |
| | 5' | P4974 | P5485 | TGCTCCCAGGCTGATGTT GATTACATCCATGTTATTCG | 588 |
| M124V | 3' | P4976 | P5486 | GGATGTAATCAACGTAAG CCTGGGAGCACCAAGCGG CA | 589 |
| | 5' | P4974 | P5487 | TGCTCCCAGGCTTACGTTG ATTACATCCATGTTATTCG | 590 |
| M124V-L126A | 3' | P4976 | P5488 | GGATGTAATCAACGTAAG CGCGGGAGCACCAAGCGG CAGTG | 591 |
| | 5' | P4974 | P5489 | TTGGTGCTCCCGCGCTTAC GTTGATTACATCCATGTTA TTCG | 592 |
| L126F, delP129 | 3' | P4976 | P5490 | AATCAACATGAGCTTCGG AGCAAGCGGCAGTGCGGC ACTTAA | 593 |
| | 5' | P4974 | P5491 | CACTGCCGCTTGCTCCGA AGCTCATGTTGATTACATC CATGT | 594 |
| G127Y | 3' | P4976 | P5492 | AACATGAGCCTGTACGCA CCAAGCGGCAGTGCGGCA CTTA | 595 |
| | 5' | P4974 | P5493 | CACTGCCGCTTGGTGCGT ACAGGCTCATGTTGATTA CATCC | 596 |
| G127S_P129D | 3' | P4976 | P5494 | CAACATGAGCCTGTCAGC AGATAGCGGCAGTGCGGC ACTTAAA | 597 |
| | 5' | P4974 | P5495 | GCACTGCCGCTATCTGCT GACAGGCTCATGTTGATT ACATCC | 598 |
| G127N, P129R | 3' | P4976 | P5496 | CAACATGAGCCTGAACGC ACGTAGCGGCAGTGCGGC ACTTAAA | 599 |
| | 5' | P4974 | P5497 | GCACTGCCGCTACGTGCG TTCAGGCTCATGTTGATTA CATCC | 600 |

TABLE 11-10-continued

Mutations Introduced in the RCL6 Libraries

| Mutations Introduced | Gene Fragment | Common 5' & 3' Gene Flanking Primer Names | Mutagenic Primer Name | Mutagenic Primer Sequence | SEQ ID NO: |
|---|---|---|---|---|---|
| G128N, insS, P129S | 3' | P4976 | P5498 | ATGAGCCTGGGAAATTCA TCTAGCGGCAGTGCGGCA CTTAAA | 601 |
| | 5' | P4974 | P5499 | GCACTGCCGCTAGATGAA TTTCCCAGGCTCATGTTGA TTAC | 602 |
| G128S_P129V | 3' | P4976 | P5500 | CATGAGCCTGGGATCAGT TAGCGGCAGTGCGGCACT TAAA | 603 |
| | 5' | P4974 | P5501 | GCACTGCCGCTAACTGAT CCCAGGCTCATGTTGATT AC | 604 |
| G128S, P129D | 3' | P4976 | P5502 | CATGAGCCTGGGATCAGA TAGCGGCAGTGCGGCACT TAAA | 605 |
| | 5' | P4974 | P5503 | GCACTGCCGCTATCTGAT CCCAGGCTCATGTTGATT AC | 606 |
| G128S, P129G | 3' | P4976 | P5504 | CATGAGCCTGGGATCAGG TAGCGGCAGTGCGGCACT TAAA | 607 |
| | 5' | P4974 | P5505 | GCACTGCCGCTACCTGAT CCCAGGCTCATGTTGATT AC | 608 |
| H128H, P129Y | 3' | P4976 | P5506 | CATGAGCCTGGGACACTA TAGCGGCAGTGCGGCACT TAAA | 609 |
| | 5' | P4974 | P5507 | GCACTGCCGCTATAGTGT CCCAGGCTCATGTTGATT AC | 610 |
| P129D | 3' | P4976 | P5508 | GAGCCTGGGAGCAGACAG CGGCAGTGCGGCACTTAA | 611 |
| | 5' | P4974 | P5509 | TGCCGCACTGCCGCTGTCT GCTCCCAGGCTCATGTTG AT | 612 |
| P129E | 3' | P4976 | P5510 | GAGCCTGGGAGCAGAAAG CGGCAGTGCGGCACTTAA | 613 |
| | 5' | P4974 | P5511 | TGCCGCACTGCCGCTTTCT GCTCCCAGGCTCATGTTG AT | 614 |
| P129V | 3' | P4976 | P5512 | GAGCCTGGGAGCAGTAAG CGGCAGTGCGGCACTTAA | 615 |
| | 5' | P4974 | P5513 | TGCCGCACTGCCGCTTACT GCTCCCAGGCTCATGTTG AT | 616 |
| P129G, delS130 | 3' | P4976 | P5514 | GAGCCTGGGAGCAGGAGG CAGTGCGGCACTTAAAGC | 617 |
| | 5' | P4974 | P5515 | AGTGCCGCACTGCCTCCT GCTCCCAGGCTCATGTTG AT | 618 |
| P129H, delS130, S132N | 3' | P4976 | P5516 | AGCCTGGGAGCACACGGC AATGCGGCACTTAAAGCA GCAGTT | 619 |
| | 5' | P4974 | P5517 | TTTAAGTGCCGCATTGCC GTGTGCTCCCAGGCTCAT GTTGAT | 620 |
| A134T | 3' | P4976 | P5518 | AAGCGGCAGTGCGACACT TAAAGCAGCAGTTGATAA AG | 621 |
| | 5' | P4974 | P5519 | AACTGCTGCTTTAAGTGTC GCACTGCCGCTTGGTGCTC | 622 |

TABLE 11-10-continued

Mutations Introduced in the RCL6 Libraries

| Mutations Introduced | Gene Fragment | Common 5' & 3' Gene Flanking Primer Names | Mutagenic Primer Name | Mutagenic Primer Sequence | SEQ ID NO: |
|---|---|---|---|---|---|
| G97R, insG, A98C | 3' | P4976 | P5520 | GTTAAAGTTCTTCGTGGTT GTGACGGATCAGGCCAAT ACTC | 623 |
| | 5' | P4974 | P5521 | CTGATCCGTCACAACCAC GAAGAACTTTAACGGCGT AGAGC | 624 |
| A98G, D99G | 3' | P4976 | P5522 | TTAAAGTTCTTGCAGGAG GCGGATCAGGCCAATACT CATG | 625 |
| | 5' | P4974 | P5523 | TATTGGCCTGATCCGCCTC CTGCAAGAACTTTAACGG CGTAG | 626 |
| A98G, insR | 3' | P4976 | P5524 | TTAAAGTTCTTGCAGGAC GTGACGGATCAGGCCAAT ACTCA | 627 |
| | 5' | P4974 | P5525 | CTGATCCGTCACGTCCTGC AAGAACTTTAACGGCGTAG | 628 |
| A98D, D99G | 3' | P4976 | P5526 | TTAAAGTTCTTGCAGACG GCGGATCAGGCCAATACT CATG | 629 |
| | 5' | P4974 | P5527 | TATTGGCCTGATCCGCCGT CTGCAAGAACTTTAACGG CGTAG | 630 |
| A98H, D99G, G100D | 3' | P4976 | P5528 | TAAAGTTCTTGCACATGG AGATTCAGGCCAATACTC ATGGATTAT | 631 |
| | 5' | P4974 | P5529 | AGTATTGGCCTGAATCTC CATGTGCAAGAACTTTAA CGGCGTAG | 632 |
| D99R, insN | 3' | P4976 | P5530 | AAGTTCTTGCAGCACGTA ACGGATCAGGCCAATACT CATG | 633 |
| | 5' | P4974 | P5531 | TATTGGCCTGATCCGTTAC GTGCTGCAAGAACTTTAA CGGCGTA | 634 |
| D99V, S101D | 3' | P4976 | P5532 | AGTTCTTGCAGCAGTAGG AGATGGCCAATACTCATG GATTATCAA | 635 |
| | 5' | P4974 | P5533 | TGAGTATTGGCCATCTCCT ACTGCTGCAAGAACTTTA ACGGCGTA | 636 |
| D99C, insS | 3' | P4976 | P5534 | TTAAAGTTCTTGCAGCAT GTAGCGGATCAGGCCAAT ACTCATG | 637 |
| | 5' | P4974 | P5535 | TATTGGCCTGATCCGCTAC ATGCTGCAAGAACTTTAA CGGCGTA | 638 |
| G100S | 3' | P4976 | P5536 | AAGTTCTTGCAGCAGACT CTTCAGGCCAATACTCAT GGATTAT | 639 |
| | 5' | P4974 | P5537 | ATGAGTATTGGCCTGAAG AGTCTGCTGCAAGAACTT TAACG | 640 |
| G100S, S101V | 3' | P4976 | P5538 | TTCTTGCAGCAGACTCTGT AGGCCAATACTCATGGAT TATCA | 641 |
| | 5' | P4974 | P5539 | CATGAGTATTGGCCTACA GAGTCTGCTGCAAGAACT TTAACG | 642 |

TABLE 11-10-continued

Mutations Introduced in the RCL6 Libraries

| Mutations Introduced | Gene Fragment | Common 5' & 3' Gene Flanking Primer Names | Mutagenic Primer Name | Mutagenic Primer Sequence | SEQ ID NO: |
|---|---|---|---|---|---|
| G100D | 3' | P4976 | P5540 | AAGTTCTTGCAGCAGACG ATTCAGGCCAATACTCAT GGATTAT | 643 |
|  | 5' | P4974 | P5541 | ATGAGTATTGGCCTGAAT CGTCTGCTGCAAGAACTT TAACG | 644 |
| G100N | 3' | P4976 | P5542 | AAGTTCTTGCAGCAGACA ATTCAGGCCAATACTCAT GGATTAT | 645 |
|  | 5' | P4974 | P5543 | ATGAGTATTGGCCTGAAT TGTCTGCTGCAAGAACTTT AACG | 646 |
| S100N, S101L | 3' | P4976 | P5544 | TTCTTGCAGCAGACAATC TAGGCCAATACTCATGGA TTATCA | 647 |
|  | 5' | P4974 | P5545 | CATGAGTATTGGCCTAGA TTGTCTGCTGCAAGAACTT TAACG | 648 |
| S101G | 3' | P4976 | P5546 | TTCTTGCAGCAGACGGAG GAGGCCAATACTCATGGA TTATCAA | 649 |
|  | 5' | P4974 | P5547 | ATGAGTATTGGCCTCCTCC GTCTGCTGCAAGAACTTTA | 650 |
| S101D | 3' | P4976 | P5548 | TTCTTGCAGCAGACGGAG ATGGCCAATACTCATGGA TTATCAA | 651 |
|  | 5' | P4974 | P5549 | ATGAGTATTGGCCATCTC CGTCTGCTGCAAGAACTT TA | 652 |
| S101V, Q103N | 3' | P4976 | P5550 | TGCAGCAGACGGAGTAGG CAACTACTCATGGATTAT CAACGGCAT | 653 |
|  | 5' | P4974 | P5551 | ATAATCCATGAGTAGTTG CCTACTCCGTCTGCTGCAA GAACTTTA | 654 |
| S101E | 3' | P4976 | P5552 | TTCTTGCAGCAGACGGAC GTGGCCAATACTCATGGA TTATCAA | 655 |
|  | 5' | P4974 | P5553 | ATGAGTATTGGCCACGTC CGTCTGCTGCAAGAACTT TA | 656 |
| A116S, N117G, N118R | 3' | P4976 | P5554 | AATGGGCCATCTCTGGTA GAATGGATGTAATCAACA TGAGCCT | 657 |
|  | 5' | P4974 | P5555 | GATTACATCCATTCTACCA GAGATGGCCCATTCGATG CCGTT | 658 |
| A116G, N117R | 3' | P4976 | P5556 | AATGGGCCATCGGACGTA ACATGGATGTAATCAACA TGAG | 659 |
|  | 5' | P4974 | P5557 | GATTACATCCATGTTACGT CCGATGGCCCATTCGATG CCGTT | 660 |
| A116N, N117S, N118G | 3' | P4976 | P5558 | AATGGGCCATCAATTCTG GAATGGATGTAATCAACA TGAGCCT | 661 |
|  | 5' | P4974 | P5559 | GATTACATCCATTCCAGA ATTGATGGCCCATTCGAT GCCGTT | 662 |
| M222Q | 3' | P4976 | P5560 | AAAACGGGACTTCCCAGG CCTCGCCGCATGTAGCTG | 663 |

TABLE 11-10-continued

Mutations Introduced in the RCL6 Libraries

| Mutations Introduced | Gene Fragment | Common 5' & 3' Gene Flanking Primer Names | Mutagenic Primer Name | Mutagenic Primer Sequence | SEQ ID NO: |
|---|---|---|---|---|---|
| | 5' | P4974 | P5561 | TACATGCGGCGAGGCCTG GGAAGTCCCGTTTTGCGC AC | 664 |
| S24R | 3' | P4976 | P5562 | AAGGCTACACTGGAAGAA ATGTTAAAGTAGCGGTTA TCGA | 665 |
| | 5' | P4974 | P5563 | CTACTTTAACATTTCTTCC AGTGTAGCCTTGAGAGTG | 666 |
| N25Y | 3' | P4976 | P5564 | CTACACTGGATCATATGTT AAAGTAGCGGTTATCGACA | 667 |
| | 5' | P4974 | P5565 | TAACCGCTACTTTAACAT ATGATCCAGTGTAGCCTT GAGA | 668 |
| P52D | 3' | P4976 | P5566 | CTTCTATGGTGGATTCCGA AACAAACCCGTTTCAAG | 669 |
| | 5' | P4974 | P5567 | GGTTTGTTTCGGAATCCAC CATAGAAGCCCCTCCAG | 670 |
| S63T | 3' | P4976 | P5568 | TTTCAAGATAACAATACA CATGGCACACACGTCGCA GGA | 671 |
| | 5' | P4974 | P5569 | TGTGTGCCATGTGTATTGT TATCTTGAAACGGGTTTGT | 672 |
| N61E | 3' | P4976 | P5570 | GTTTCAAGATGAAAATTC TCATGGCACACACGTC | 673 |
| | 5' | P4974 | P5571 | TGTGCCATGAGAATTTTC ATCTTGAAACGGGTTTGTT TCG | 674 |
| N61P | 3' | P4976 | P5572 | AACCCGTTTCAAGATCCA AATTCTCATGGCACACAC GTC | 675 |
| | 5' | P4974 | P5573 | TGCCATGAGAATTTGGAT CTTGAAACGGGTTTGTTTCG | 676 |
| N62Q | 3' | P4976 | P5574 | GTTTCAAGATAACCAATC TCATGGCACACACGTCGC AGGAA | 677 |
| | 5' | P4974 | P5575 | TGTGTGCCATGAGATTGG TTATCTTGAAACGGGTTTG TTT | 678 |
| N62D | 3' | P4976 | P5576 | GTTTCAAGATAACGATTC TCATGGCACACACGTCGC AGGAA | 679 |
| | 5' | P4974 | P5577 | TGTGTGCCATGAGAATCG TTATCTTGAAACGGGTTTG TTT | 680 |
| S63Q | 3' | P4976 | P5578 | TCAAGATAACAATCAACA TGGCACACACGTCGCAGG | 681 |
| | 5' | P4974 | P5579 | ACGTGTGTGCCATGTTGA TTGTTATCTTGAAACGGGT TTG | 682 |
| V68A | 3' | P4976 | P5580 | TCATGGCACACACGCAGC AGGAACGGTTGCGGCGTT AA | 683 |
| | 5' | P4974 | P5581 | CAACCGTTCCTGCTGCGT GTGTGCCATGAGAATTGT TA | 684 |
| S87D | 3' | P4976 | P5582 | TGTAGCCCCGGATGCTTC GCTCTACGCCGTTAA | 685 |
| | 5' | P4974 | P5583 | CGTAGAGCGAAGCATCCG GGGCTACACCAAGCACG | 686 |

TABLE 11-10-continued

Mutations Introduced in the RCL6 Libraries

| Mutations Introduced | Gene Fragment | Common 5' & 3' Gene Flanking Primer Names | Mutagenic Primer Name | Mutagenic Primer Sequence | SEQ ID NO: |
|---|---|---|---|---|---|
| L96T | 3' | P4976 | P5584 | CGTTAAAGTTACAGCAGC AGACGGATCAGGCCAATA | 687 |
| | 5' | P4974 | P5585 | TGATCCGTCTGCTGCTGTA ACTTTAACGGCGTAGAGC GAA | 688 |
| L126A | 3' | P4976 | P5586 | TAATCAACATGAGCGCGG GAGCACCAAGCGGCAGTG | 689 |
| | 5' | P4974 | P5587 | TTGGTGCTCCCGCGCTCAT GTTGATTACATCCATG | 690 |
| L126T | 3' | P4976 | P5588 | TAATCAACATGAGCACGG GAGCACCAAGCGGCAGTG | 691 |
| | 5' | P4974 | P5589 | TTGGTGCTCCCGTGCTCAT GTTGATTACATCCATG | 692 |
| S125A | 3' | P4976 | P5590 | ATGTAATCAACATGGCAC TGGGAGCACCAAGCGGCA GT | 693 |
| | 5' | P4974 | P5591 | TTGGTGCTCCCAGTGCCAT GTTGATTACATCCATGTTA TT | 694 |
| S130P | 3' | P4976 | P5592 | TGGGAGCACCACCAGGCA GTGCGGCACTTAAAGC | 695 |
| | 5' | P4974 | P5593 | GTGCCGCACTGCCTGGTG GTGCTCCCAGGCTCATGT | 696 |
| P129L | 3' | P4976 | P5594 | TGAGCCTGGGAGCACTTA GCGGCAGTGCGGCACTTAA | 697 |
| | 5' | P4974 | P5595 | TGCCGCACTGCCGCTAAG TGCTCCCAGGCTCATGTTG AT | 698 |
| P129E | 3' | P4976 | P5596 | TGAGCCTGGGAGCAGAAA GCGGCAGTGCGGCACTTAA | 699 |
| | 5' | P4974 | P5597 | TGCCGCACTGCCGCTTTCT GCTCCCAGGCTCATGTTG AT | 700 |
| P129S | 3' | P4976 | P5598 | TGAGCCTGGGAGCATCTA GCGGCAGTGCGGCACTTAA | 701 |
| | 5' | P4974 | P5599 | TGCCGCACTGCCGCTAGA TGCTCCCAGGCTCATGTTG AT | 702 |
| P40E | 3' | P4976 | P5600 | GACTCGAGCCATGAAGAT CTTAAAGTCGCTGGAGG | 703 |
| | 5' | P4974 | P5601 | GACTTTAAGATCTTCATG GCTCGAGTCGATACCGCT | 704 |
| Y6Q | 3' | P4976 | P5602 | GCAGTCCGTGCCTCAAGG CGTATCACAAATTAAAGC CCCT | 705 |
| | 5' | P4974 | P5603 | ATTTGTGATACGCCTTGA GGCACGGACTGCGCGTAC GCAT | 706 |
| G102A | 3' | P4976 | P5604 | CAGACGGATCAGCACAAT ACTCATGGATTATCAACG GCAT | 707 |
| | 5' | P4974 | P5605 | TAATCCATGAGTATTGTG CTGATCCGTCTGCTGCAA GAAC | 708 |
| S101N | 3' | P4976 | P5606 | GCAGCAGACGGAAACGGC CAATACTCATGGATTATC AA | 709 |
| | 5' | P4974 | P5607 | CATGAGTATTGGCCGTTTC CGTCTGCTGCAAGAACTT TA | 710 |

TABLE 11-10-continued

Mutations Introduced in the RCL6 Libraries

| Mutations Introduced | Gene Fragment | Common 5' & 3' Gene Flanking Primer Names | Mutagenic Primer Name | Mutagenic Primer Sequence | SEQ ID NO: |
|---|---|---|---|---|---|
| G100E | 3' | P4976 | P5608 | TTCTTGCAGCAGACGAAT CAGGCCAATACTCATGGA TTAT | 711 |
|  | 5' | P4974 | P5609 | TGAGTATTGGCCTGATTC GTCTGCTGCAAGAACTTT AACG | 712 |
| I115V | 3' | P4976 | P5610 | ATCGAATGGGCCGTAGCG AATAACATGGATGTAATC AA | 713 |
|  | 5' | P4974 | P5611 | CATCCATGTTATTCGCTAC GGCCCATTCGATGCCGTT GAT | 714 |
| A144K | 3' | P4976 | P5612 | GTTGATAAAGCTGTTAAA TCTGGTGTCGTCGTAGTA GC | 715 |
|  | 5' | P4974 | P5613 | GACGACACCAGATTTAAC AGCTTTATCAACTGCTGCTT | 716 |
| S145D | 3' | P4976 | P5614 | GATAAAGCTGTTGCAGAT GGTGTCGTCGTAGTAGCG GCA | 717 |
|  | 5' | P4974 | P5615 | TACTACGACGACACCATC TGCAACAGCTTTATCAAC TGCT | 718 |
| S159K | 3' | P4976 | P5616 | AATGAGGGAACAAAAGG ATCATCGAGTACCGTCGG TTA | 719 |
|  | 5' | P4974 | P5617 | ACGGTACTCGATGATCCT TTTGTTCCCTCATTCCCAG CTG | 720 |
| S162K | 3' | P4976 | P5618 | AACATCCGGATCAAAAAG TACCGTCGGTTATCCAGG CAA | 721 |
|  | 5' | P4974 | P5619 | ATAACCGACGGTACTTTTT GATCCGGATGTTCCCTCATT | 722 |
| V147P | 3' | P4976 | P5620 | TGTTGCATCTGGTCCAGTC GTAGTAGCGGCAGCTGGG AAT | 723 |
|  | 5' | P4974 | P5621 | TGCCGCTACTACGACTGG ACCAGATGCAACAGCTTT ATCA | 724 |
| S161P | 3' | P4976 | P5622 | AGGGAACATCCGGACCAT CGAGTACCGTCGGTTATC CA | 725 |
|  | 5' | P4974 | P5623 | ACCGACGGTACTCGATGG TCCGGATGTTCCCTCATTC CCA | 726 |
| A187D | 3' | P4976 | P5624 | CTTCAAATCAACGTGACT CTTTTTCCTCCGTGGGACC GGA | 727 |
|  | 5' | P4974 | P5625 | ACGGAGGAAAAAGAGTC ACGTTGATTTGAAGAGTC TACAG | 728 |
| F189D | 3' | P4976 | P5626 | TCAACGTGCCTCTGATTCC TCCGTGGGACCGGAGCTG GAT | 729 |
|  | 5' | P4974 | P5627 | TCCCACGGAGGAATCAGA GGCACGTTGATTTGAAGAG | 730 |
| L267V | 3' | P4976 | P5628 | TACTATGGAAAAGGGGTA ATCAACGTACAGGCGGCA GC | 731 |

TABLE 11-10-continued

Mutations Introduced in the RCL6 Libraries

| Mutations Introduced | Gene Fragment | Common 5' & 3' Gene Flanking Primer Names | Mutagenic Primer Name | Mutagenic Primer Sequence | SEQ ID NO: |
|---|---|---|---|---|---|
| | 5' | P4974 | P5629 | CTGTACGTTGATTACCCCT TTTCCATAGTAGAAAGAAT | 732 |
| Q206E | 3' | P4976 | P5630 | TGGCGTTTCTATTGAATCG ACGCTTCCAGGGAACAA | 733 |
| | 5' | P4974 | P5631 | CTGGAAGCGTCGATTCAA TAGAAACGCCAGGGGCCAT | 734 |
| K213T | 3' | P4976 | P5632 | CTTCCAGGGAACACATAT GGTGCGCAAAACGGGACT | 735 |
| | 5' | P4974 | P5633 | GTTTTGCGCACCATATGTG TTCCCTGGAAGCGTCGATT | 736 |
| K213L | 3' | P4976 | P5634 | CTTCCAGGGAACCTTTAT GGTGCGCAAAACGGGACT | 737 |
| | 5' | P4974 | P5635 | GTTTTGCGCACCATAAAG GTTCCCTGGAAGCGTCGA TT | 738 |
| K265N | 3' | P4976 | P5636 | TTTCTACTATGGAAACGG GCTGATCAACGTACAGGC GGCA | 739 |
| | 5' | P4974 | P5637 | ACGTTGATCAGCCCGTTTC CATAGTAGAAAGAATCAC CAA | 740 |
| N240K | 3' | P4976 | P5638 | TTTCTAAGCACCCGAAAT GGACAAACACTCAAGTCC GCA | 741 |
| | 5' | P4974 | P5639 | GAGTGTTTGTCCATTTCGG GTGCTTAGAAAGAATCAAT | 742 |
| P239R | 3' | P4976 | P5640 | TTCTTTCTAAGCACCGTAA CTGGACAAACACTCAAGT CC | 743 |
| | 5' | P4974 | P5641 | TGTTTGTCCAGTTACGGTG CTTAGAAAGAATCAATGCG | 744 |
| T242R | 3' | P4976 | P5642 | CACCCGAACTGGCGTAAC ACTCAAGTCCGCAGCAGT | 745 |
| | 5' | P4974 | P5643 | TGCGGACTTGAGTGTTAC GCCAGTTCGGGTGCTTAG AAAG | 746 |
| S89Y | 3' | P4976 | P5644 | CGTCTGCTTACCTCTACGC CGTTAAAGTTCTTG | 747 |
| | 5' | P4974 | P5645 | ACTTTAACGGCGTAGAGG TAAGCAGACGGGGCTACA CCAA | 748 |
| P129Q | 3' | P4976 | P5646 | AGCCTGGGAGCACAAAGC GGCAGTGCGGCACTTAAA | 749 |
| | 5' | P4974 | P5647 | CACTGCCGCTTTGTGCTCC CAGGCTCATGTTGAT | 750 |
| G211T | 3' | P4976 | P5648 | TTCAATCGACGCTTCCAA CGAACAAGTATGGTGCGC AAAAC | 751 |
| | 5' | P4974 | P5649 | CACCATACTTGTTCGTTGG AAGCGTCGATTGAATAGA AA | 752 |
| I111V | 3' | P4976 | P5650 | TGGATTATCAACGGCGTA GAATGGGCCATCGCGAAT AAC | 753 |
| | 5' | P4974 | P5651 | CGATGGCCCATTCTACGC CGTTGATAATCCATGAGT ATT | 754 |

RCL 7 Combinatorial Variants

"RCL7" refers to a set of combinatorial variants created by PCR fusion using several BPN' mutants as parent (template) plasmid. The mutations introduced in each parent plasmid are listed in Table 11-11, and the mutagenic primers used to create the mutants are described in Table 11-10.

To create each mutant, two PCR reactions were carried out using either the common 3' gene-flanking primer (P4976, CCTCTCGGTTATGAGTTAGTTC; SEQ ID NO:61) and the mutagenic primer, or the common 5' gene-flanking primer (P4974, GCCTCACATTTGTGCCACCTA; SEQ ID NO:60) and mutagenic primer as shown for each library in Table 11-10. These PCR reactions generated two PCR fragments, one encoding the 5' half of the mutant BPN' gene (5' gene fragment) and the other encoding the 3' half of the mutant BPN' gene (3' gene fragment). Each PCR amplification reaction contained 30 pmol of each primer and 100 ng of the parent molecules listed in Table 11-11. Amplifications were carried out using Vent DNA polymerase (NEB). The PCR reaction (20 μL) was initially heated at 95° C. for 2.5 min followed by 30 cycles of denaturation at 94° C. for 15 sec., annealing at 55° C. for 15 sec. and extension at 72° C. for 40 sec. Following amplification, the 5' and 3' gene fragments were gel-purified using a QIAGEN® gel-band purification kit, mixed (50 ng of each fragment) and amplified by PCR once again using the primers P4973 (AAAGGATCCTAATCGGCGCTTTTC; SEQ ID NO:62) and P4950 (CTTGTCTCCAAGCTTAAAATAAAA; SEQ ID NO:63) to generate the full-length gene fragment. The PCR conditions were same as described above, except the extension phase, which was carried out at 72° C. for 2 min. The full-length DNA fragment was gel-purified using a QIAGEN® gel-band purification kit, digested using BamHI and HindIII restriction enzymes, and ligated with the pHPLT-BPN' partial opt that also was digested with the same restriction enzymes. Ligation mixtures were amplified using rolling circle amplification by Illustra Templiphi kit according to the manufacturer's instructions (GE Healthcare) to generate multimeric DNA for transformation into *Bacillus subtilis*. For this purpose, 1 μl of the ligation mixture was mixed with 5 μl of the sample buffer, heated to 95° C. for 3 min and cooled on ice. Next, 5 μl of the reaction buffer and 0.2 μl of the enzyme were added to each tube, followed by incubation at 30° C. for 10 hours. Products of the rolling circle amplification were diluted 100 times and used to transform *B. subtilis* cells (ΔaprE, ΔnprE, amyE::xylRPxylAcomK-phleo). An aliquot of the transformation mix was plated on LB plates containing 1.6% skim milk and 10 μg/mL neomycin and incubated overnight at 37° C. Subsequently, the colonies with halos were inoculated in 120 μl of LB media containing 10 μg/mL neomycin.

TABLE 11-11

List of Parent Plasmids and Introduced Mutations in the RCL7 variants

| Combinatorial Variant # | Parent Plasmid | Mutation(s) Introduced |
|---|---|---|
| 1 | G97A-G128A-Y217Q-T55P | S24R |
| 2 | G97A-G128A-Y217Q-N61E | S24R |
| 3 | G97A-G128A-Y217Q-N61P-S63H | S24R |
| 4 | G97A-G128A-Y217Q-L75S-N76Y | S24R |
| 5 | G97A-G128A-Y217Q-S87T-A88L-S89G | S24R |
| 6 | G97A-G128A-Y217Q-S89Y | S24R |
| 7 | G97A-G128A-Y217Q-I111V | S24R |
| 8 | G97A-G128A-Y217Q-I115V | S24R |
| 9 | G97A-G128A-Y217Q-P129Q-S130G-G131S | S24R |
| 10 | G97A-G128A-Y217Q-P129Q | S24R |
| 11 | G97A-G128A-Y217Q-A134T | S24R |
| 12 | G97A-G128A-Y217Q-A144K | S24R |
| 13 | G97A-G128A-Y217Q-S145D | S24R |
| 14 | G97A-G128A-Y217Q-S159K | S24R |
| 15 | G97A-G128A-Y217Q-S162K | S24R |
| 16 | G97A-G128A-Y217Q-S161P-S78N | S24R |
| 17 | G97A-G128A-Y217Q-V203Y | S24R |
| 18 | G97A-G128A-Y217Q-G211T-S78N | S24R |
| 19 | G97A-G128A-Y217Q-K213T | S24R |
| 20 | G97A-G128A-Y217Q-P239R | S24R |
| 21 | G97A-G128A-Y217Q-N240K | S24R |
| 22 | G97A-G128A-Y217Q-L267V-S78N | S24R |
| 23 | G97A-G128A-Y217Q-A273S-S78N | S24R |
| 24 | G97A-G128A-Y217Q-L75S-N76Y | T55P |
| 25 | G97A-G128A-Y217Q-S87T-A88L-S89G | T55P |
| 26 | G97A-G128A-Y217Q-S89Y | T55P |
| 27 | G97A-G128A-Y217Q-I111V | T55P |
| 28 | G97A-G128A-Y217Q-I115V | T55P |
| 29 | G97A-G128A-Y217Q-P129Q-S130G-G131S | T55P |
| 30 | G97A-G128A-Y217Q-P129Q | T55P |
| 31 | G97A-G128A-Y217Q-A134T | T55P |
| 32 | G97A-G128A-Y217Q-A144K | T55P |
| 33 | G97A-G128A-Y217Q-S145D | T55P |
| 34 | G97A-G128A-Y217Q-S159K | T55P |
| 35 | G97A-G128A-Y217Q-S162K | T55P |
| 36 | G97A-G128A-Y217Q-S161P | T55P |
| 37 | G97A-G128A-Y217Q-V203Y | T55P |
| 38 | G97A-G128A-Y217Q-G211T | T55P |
| 39 | G97A-G128A-Y217Q-K213T | T55P |
| 40 | G97A-G128A-Y217Q-P239R | T55P |
| 41 | G97A-G128A-Y217Q-N240K | T55P |
| 42 | G97A-G128A-Y217Q-L267V | T55P |
| 43 | G97A-G128A-Y217Q-A273S | T55P |

TABLE 11-11-continued

List of Parent Plasmids and Introduced Mutations in the RCL7 variants

| Combinatorial Variant # | Parent Plasmid | Mutation(s) Introduced |
|---|---|---|
| 44 | G97A-G128A-Y217Q-L75S-N76Y | N61E |
| 45 | G97A-G128A-Y217Q-S87T-A88L-S89G | N61E |
| 46 | G97A-G128A-Y217Q-S89Y | N61E |
| 47 | G97A-G128A-Y217Q-I111V | N61E |
| 48 | G97A-G128A-Y217Q-I115V | N61E |
| 49 | G97A-G128A-Y217Q-P129Q-S130G-G131S | N61E |
| 50 | G97A-G128A-Y217Q-P129Q | N61E |
| 51 | G97A-G128A-Y217Q-A134T | N61E |
| 52 | G97A-G128A-Y217Q-A144K | N61E |
| 53 | G97A-G128A-Y217Q-S145D | N61E |
| 54 | G97A-G128A-Y217Q-S159K | N61E |
| 55 | G97A-G128A-Y217Q-S162K | N61E |
| 56 | G97A-G128A-Y217Q-S161P | N61E |
| 57 | G97A-G128A-Y217Q-V203Y | N61E |
| 58 | G97A-G128A-Y217Q-G211T | N61E |
| 59 | G97A-G128A-Y217Q-K213T | N61E |
| 60 | G97A-G128A-Y217Q-P239R | N61E |
| 61 | G97A-G128A-Y217Q-N240K | N61E |
| 62 | G97A-G128A-Y217Q-L267V | N61E |
| 63 | G97A-G128A-Y217Q-A273S | N61E |
| 64 | G97A-G128A-Y217Q-L75S-N76Y | N61P-S63H |
| 65 | G97A-G128A-Y217Q-S87T-A88L-S89G | N61P-S63H |
| 66 | G97A-G128A-Y217Q-S89Y | N61P-S63H |
| 67 | G97A-G128A-Y217Q-I111V | N61P-S63H |
| 68 | G97A-G128A-Y217Q-I115V | N61P-S63H |
| 69 | G97A-G128A-Y217Q-P129Q-S130G-G131S | N61P-S63H |
| 70 | G97A-G128A-Y217Q-P129Q | N61P-S63H |
| 71 | G97A-G128A-Y217Q-A134T | N61P-S63H |
| 72 | G97A-G128A-Y217Q-A144K | N61P-S63H |
| 73 | G97A-G128A-Y217Q-S145D | N61P-S63H |
| 74 | G97A-G128A-Y217Q-S159K | N61P-S63H |
| 75 | G97A-G128A-Y217Q-S162K | N61P-S63H |
| 76 | G97A-G128A-Y217Q-S161P | N61P-S63H |
| 77 | G97A-G128A-Y217Q-V203Y | N61P-S63H |
| 78 | G97A-G128A-Y217Q-G211T | N61P-S63H |
| 79 | G97A-G128A-Y217Q-K213T | N61P-S63H |
| 80 | G97A-G128A-Y217Q-P239R | N61P-S63H |
| 81 | G97A-G128A-Y217Q-N240K | N61P-S63H |
| 82 | G97A-G128A-Y217Q-L267V | N61P-S63H |
| 83 | G97A-G128A-Y217Q-A273S | N61P-S63H |
| 84 | G97A-G128A-Y217Q-S87T-A88L-S89G | L75S-N76Y |
| 85 | G97A-G128A-Y217Q-S89Y | L75S-N76Y |
| 86 | G97A-G128A-Y217Q-I111V | L75S-N76Y |
| 87 | G97A-G128A-Y217Q-I115V | L75S-N76Y |
| 88 | G97A-G128A-Y217Q-P129Q-S130G-G131S | L75S-N76Y |
| 89 | G97A-G128A-Y217Q-P129Q | L75S-N76Y |
| 90 | G97A-G128A-Y217Q-A134T | L75S-N76Y |
| 91 | G97A-G128A-Y217Q-A144K | L75S-N76Y |
| 92 | G97A-G128A-Y217Q-S145D | L75S-N76Y |
| 93 | G97A-G128A-Y217Q-S159K | L75S-N76Y |
| 94 | G97A-G128A-Y217Q-S162K | L75S-N76Y |
| 95 | G97A-G128A-Y217Q-S161P | L75S-N76Y |
| 96 | G97A-G128A-Y217Q-V203Y | L75S-N76Y |
| 97 | G97A-G128A-Y217Q-G211T | L75S-N76Y |
| 98 | G97A-G128A-Y217Q-K213T | L75S-N76Y |
| 99 | G97A-G128A-Y217Q-P239R | L75S-N76Y |
| 100 | G97A-G128A-Y217Q-N240K | L75S-N76Y |
| 101 | G97A-G128A-Y217Q-L267V | L75S-N76Y |
| 102 | G97A-G128A-Y217Q-A273S | L75S-N76Y |
| 103 | G97A-G128A-Y217Q-I111V | S87T-A88L-S89G |
| 104 | G97A-G128A-Y217Q-I115V | S87T-A88L-S89G |
| 105 | G97A-G128A-Y217Q-P129Q-S130G-G131S | S87T-A88L-S89G |
| 106 | G97A-G128A-Y217Q-P129Q | S87T-A88L-S89G |
| 107 | G97A-G128A-Y217Q-A134T | S87T-A88L-S89G |
| 108 | G97A-G128A-Y217Q-A144K | S87T-A88L-S89G |
| 109 | G97A-G128A-Y217Q-S145D | S87T-A88L-S89G |
| 110 | G97A-G128A-Y217Q-S159K | S87T-A88L-S89G |
| 111 | G97A-G128A-Y217Q-S162K | S87T-A88L-S89G |
| 112 | G97A-G128A-Y217Q-S161P | S87T-A88L-S89G |
| 113 | G97A-G128A-Y217Q-V203Y | S87T-A88L-S89G |
| 114 | G97A-G128A-Y217Q-G211T | S87T-A88L-S89G |
| 115 | G97A-G128A-Y217Q-K213T | S87T-A88L-S89G |
| 116 | G97A-G128A-Y217Q-P239R | S87T-A88L-S89G |
| 117 | G97A-G128A-Y217Q-N240K | S87T-A88L-S89G |
| 118 | G97A-G128A-Y217Q-L267V | S87T-A88L-S89G |

TABLE 11-11-continued

| List of Parent Plasmids and Introduced Mutations in the RCL7 variants | | |
|---|---|---|
| Combinatorial Variant # | Parent Plasmid | Mutation(s) Introduced |
| 119 | G97A-G128A-Y217Q-A273S | S87T-A88L-S89G |
| 120 | G97A-G128A-Y217Q-I111V | S89Y |
| 121 | G97A-G128A-Y217Q-I115V | S89Y |
| 122 | G97A-G128A-Y217Q-P129Q-S130G-G131S | S89Y |
| 123 | G97A-G128A-Y217Q-P129Q | S89Y |
| 124 | G97A-G128A-Y217Q-A134T | S89Y |
| 125 | G97A-G128A-Y217Q-A144K | S89Y |
| 126 | G97A-G128A-Y217Q-S145D | S89Y |
| 127 | G97A-G128A-Y217Q-S159K | S89Y |
| 128 | G97A-G128A-Y217Q-S162K | S89Y |
| 129 | G97A-G128A-Y217Q-S161P | S89Y |
| 130 | G97A-G128A-Y217Q-V203Y | S89Y |
| 131 | G97A-G128A-Y217Q-G211T | S89Y |
| 132 | G97A-G128A-Y217Q-K213T | S89Y |
| 133 | G97A-G128A-Y217Q-P239R | S89Y |
| 134 | G97A-G128A-Y217Q-N240K | S89Y |
| 135 | G97A-G128A-Y217Q-L267V | S89Y |
| 136 | G97A-G128A-Y217Q-A273S | S89Y |
| 137 | G97A-G128A-Y217Q-P129Q-S130G-G131S | I111V |
| 138 | G97A-G128A-Y217Q-P129Q | I111V |
| 139 | G97A-G128A-Y217Q-A134T | I111V |
| 140 | G97A-G128A-Y217Q-A144K | I111V |
| 141 | G97A-G128A-Y217Q-S145D | I111V |
| 142 | G97A-G128A-Y217Q-S159K | I111V |
| 143 | G97A-G128A-Y217Q-S162K | I111V |
| 144 | G97A-G128A-Y217Q-S161P | I111V |
| 145 | G97A-G128A-Y217Q-V203Y | I111V |
| 146 | G97A-G128A-Y217Q-G211T | I111V |
| 147 | G97A-G128A-Y217Q-K213T | I111V |
| 148 | G97A-G128A-Y217Q-P239R | I111V |
| 149 | G97A-G128A-Y217Q-N240K | I111V |
| 150 | G97A-G128A-Y217Q-L267V | I111V |
| 151 | G97A-G128A-Y217Q-A273S | I111V |
| 152 | G97A-G128A-Y217Q-P129Q-S130G-G131S | I115V |
| 153 | G97A-G128A-Y217Q-P129Q | I115V |
| 154 | G97A-G128A-Y217Q-A134T | I115V |
| 155 | G97A-G128A-Y217Q-A144K | I115V |
| 156 | G97A-G128A-Y217Q-S145D | I115V |
| 157 | G97A-G128A-Y217Q-S159K | I115V |
| 158 | G97A-G128A-Y217Q-S162K | I115V |
| 159 | G97A-G128A-Y217Q-S161P | I115V |
| 160 | G97A-G128A-Y217Q-V203Y | I115V |
| 161 | G97A-G128A-Y217Q-G211T | I115V |
| 162 | G97A-G128A-Y217Q-K213T | I115V |
| 163 | G97A-G128A-Y217Q-P239R | I115V |
| 164 | G97A-G128A-Y217Q-N240K | I115V |
| 165 | G97A-G128A-Y217Q-L267V | I115V |
| 166 | G97A-G128A-Y217Q-A273S | I115V |
| 167 | G97A-G128A-Y217Q-A144K | P129Q-S130G-G131S |
| 168 | G97A-G128A-Y217Q-S145D | P129Q-S130G-G131S |
| 169 | G97A-G128A-Y217Q-S159K | P129Q-S130G-G131S |
| 170 | G97A-G128A-Y217Q-S162K | P129Q-S130G-G131S |
| 171 | G97A-G128A-Y217Q-S161P | P129Q-S130G-G131S |
| 172 | G97A-G128A-Y217Q-V203Y | P129Q-S130G-G131S |
| 173 | G97A-G128A-Y217Q-G211T | P129Q-S130G-G131S |
| 174 | G97A-G128A-Y217Q-K213T | P129Q-S130G-G131S |
| 175 | G97A-G128A-Y217Q-P239R | P129Q-S130G-G131S |
| 176 | G97A-G128A-Y217Q-N240K | P129Q-S130G-G131S |
| 177 | G97A-G128A-Y217Q-L267V | P129Q-S130G-G131S |
| 178 | G97A-G128A-Y217Q-A273S | P129Q-S130G-G131S |
| 179 | G97A-G128A-Y217Q-A144K | P129Q |
| 180 | G97A-G128A-Y217Q-S145D | P129Q |
| 181 | G97A-G128A-Y217Q-S159K | P129Q |
| 182 | G97A-G128A-Y217Q-S162K | P129Q |
| 183 | G97A-G128A-Y217Q-S161P | P129Q |
| 184 | G97A-G128A-Y217Q-V203Y | P129Q |
| 185 | G97A-G128A-Y217Q-G211T | P129Q |
| 186 | G97A-G128A-Y217Q-K213T | P129Q |
| 187 | G97A-G128A-Y217Q-P239R | P129Q |
| 188 | G97A-G128A-Y217Q-N240K | P129Q |
| 189 | G97A-G128A-Y217Q-L267V | P129Q |
| 190 | G97A-G128A-Y217Q-A273S | P129Q |
| 191 | G97A-G128A-Y217Q-A144K | A134T |
| 192 | G97A-G128A-Y217Q-S145D | A134T |
| 193 | G97A-G128A-Y217Q-S159K | A134T |

TABLE 11-11-continued

| List of Parent Plasmids and Introduced Mutations in the RCL7 variants | | |
|---|---|---|
| Combinatorial Variant # | Parent Plasmid | Mutation(s) Introduced |
| 194 | G97A-G128A-Y217Q-S162K | A134T |
| 195 | G97A-G128A-Y217Q-S161P | A134T |
| 196 | G97A-G128A-Y217Q-V203Y | A134T |
| 197 | G97A-G128A-Y217Q-G211T | A134T |
| 198 | G97A-G128A-Y217Q-K213T | A134T |
| 199 | G97A-G128A-Y217Q-P239R | A134T |
| 200 | G97A-G128A-Y217Q-N240K | A134T |
| 201 | G97A-G128A-Y217Q-L267V | A134T |
| 202 | G97A-G128A-Y217Q-A273S | A134T |
| 203 | G97A-G128A-Y217Q-S159K | A144K |
| 204 | G97A-G128A-Y217Q-S162K | A144K |
| 205 | G97A-G128A-Y217Q-S161P | A144K |
| 206 | G97A-G128A-Y217Q-V203Y | A144K |
| 207 | G97A-G128A-Y217Q-G211T | A144K |
| 208 | G97A-G128A-Y217Q-K213T | A144K |
| 209 | G97A-G128A-Y217Q-P239R | A144K |
| 210 | G97A-G128A-Y217Q-N240K | A144K |
| 211 | G97A-G128A-Y217Q-L267V | A144K |
| 212 | G97A-G128A-Y217Q-A273S | A144K |
| 213 | G97A-G128A-Y217Q-S159K | S145D |
| 214 | G97A-G128A-Y217Q-S162K | S145D |
| 215 | G97A-G128A-Y217Q-S161P | S145D |
| 216 | G97A-G128A-Y217Q-V203Y | S145D |
| 217 | G97A-G128A-Y217Q-G211T | S145D |
| 218 | G97A-G128A-Y217Q-K213T | S145D |
| 219 | G97A-G128A-Y217Q-P239R | S145D |
| 220 | G97A-G128A-Y217Q-N240K | S145D |
| 221 | G97A-G128A-Y217Q-L267V | S145D |
| 222 | G97A-G128A-Y217Q-A273S | S145D |
| 223 | G97A-G128A-Y217Q-V203Y | S159K |
| 224 | G97A-G128A-Y217Q-G211T | S159K |
| 225 | G97A-G128A-Y217Q-K213T | S159K |
| 226 | G97A-G128A-Y217Q-P239R | S159K |
| 227 | G97A-G128A-Y217Q-N240K | S159K |
| 228 | G97A-G128A-Y217Q-L267V | S159K |
| 229 | G97A-G128A-Y217Q-A273S | S159K |
| 230 | G97A-G128A-Y217Q-V203Y | S162K |
| 231 | G97A-G128A-Y217Q-G211T | S162K |
| 232 | G97A-G128A-Y217Q-K213T | S162K |
| 233 | G97A-G128A-Y217Q-P239R | S162K |
| 234 | G97A-G128A-Y217Q-N240K | S162K |
| 235 | G97A-G128A-Y217Q-L267V | S162K |
| 236 | G97A-G128A-Y217Q-A273S | S162K |
| 237 | G97A-G128A-Y217Q-V203Y | S161P |
| 238 | G97A-G128A-Y217Q-G211T | S161P |
| 239 | G97A-G128A-Y217Q-K213T | S161P |
| 240 | G97A-G128A-Y217Q-239R | S161P |
| 241 | G97A-G128A-Y217Q-N240K | S161P |
| 242 | G97A-G128A-Y217Q-L267V | S161P |
| 243 | G97A-G128A-Y217Q-A273S | S161P |
| 244 | G97A-G128A-Y217Q-G211T | V203Y |
| 245 | G97A-G128A-Y217Q-K213T | V203Y |
| 246 | G97A-G128A-Y217Q-P239R | V203Y |
| 247 | G97A-G128A-Y217Q-N240K | V203Y |
| 248 | G97A-G128A-Y217Q-L267V | V203Y |
| 249 | G97A-G128A-Y217Q-A273S | V203Y |
| 250 | G97A-G128A-Y217Q-P239R | G211T |
| 251 | G97A-G128A-Y217Q-N240K | G211T |
| 252 | G97A-G128A-Y217Q-L267V | G211T |
| 253 | G97A-G128A-Y217Q-A273S | G211T |
| 254 | G97A-G128A-Y217Q-P239R | K213T |
| 255 | G97A-G128A-Y217Q-N240K | K213T |
| 256 | G97A-G128A-Y217Q-L267V | K213T |
| 257 | G97A-G128A-Y217Q-A273S | K213T |
| 258 | G97A-G128A-Y217Q-L267V | P239R |
| 259 | G97A-G128A-Y217Q-A273S | P239R |
| 260 | G97A-G128A-Y217Q-L267V | N240K |
| 261 | G97A-G128A-Y217Q-A273S | N240K |

Example 12

Table of Detergents

The compositions of the detergents used in the assays for Part I Example 12 are shown in Table 12-1. BPN' variant protein samples were added to the detergent compositions as described in Part I Example 1 to assay for the various properties listed.

TABLE 12-1

Composition of Detergents Used in the Assays to Test BPN' Variants

| Ingredient | Composition (wt % of Composition) | | |
|---|---|---|---|
| | 1 | 2 | 3 |
| $C_{12-15}$ Alkylethoxy(1.8)sulphate | 14.7 | 11.6 | |
| $C_{11.8}$ Alkylbenzene sulfonate | 4.3 | 11.6 | 8.3 |
| $C_{16-17}$ Branched alkyl sulphate | 1.7 | 1.29 | |
| $C_{12-14}$ Alkyl-9-ethoxylate | 0.9 | 1.07 | |
| $C_{12}$ dimethylamine oxide | 0.6 | 0.64 | |
| Citric acid | 3.5 | 0.65 | 3 |
| $C_{12-18}$ fatty acid | 1.5 | 2.32 | 3.6 |
| Sodium Borate (Borax) | 2.5 | 2.46 | 1.2 |
| Sodium $C_{12-14}$ alkyl ethoxy 3 sulfate | | | 2.9 |
| $C_{14-15}$ alkyl 7-ethoxylate | | | 4.2 |
| $C_{12-14}$ Alkyl-7-ethoxylate | | | 1.7 |
| Ca formate | 0.09 | 0.09 | |
| A compound having the following general structure: bis(($C_2H_5O$)($C_2H_4O$)n)($CH_3$)—$N^+$—$C_xH_{2x}$—$N^+$—($CH_3$)- bis(($C_2H_5O$)($C_2H_4O$)n), wherein n = from 20 to 30, and x = from 3 to 8, or sulphated or sulphonated variants thereof | | | 1.2 |
| Random graft co-polymer[1] | | 1.46 | 0.5 |
| Ethoxylated Polyethylenimine[2] | 1.5 | 1.29 | |
| Diethylene triamine pentaacetic acid | 0.34 | 0.64 | |
| Diethylene triamine penta(methylene phosphonic acid) | | | 0.3 |
| Tinopal AMS-GX | | 0.06 | |
| Tinopal CBS-X | 0.2 | 0.17 | |
| Amphiphilic alkoxylated grease cleaning polymer[3] | 1.28 | 1 | 0.4 |
| Ethanol | 2 | 1.58 | 1.6 |
| Propylene Glycol | 3.9 | 3.59 | 1.3 |
| Diethylene glycol | 1.05 | 1.54 | |
| Polyethylene glycol | 0.06 | 0.04 | |
| Monoethanolamine | 3.05 | 2.41 | 0.4 |
| NaOH | 2.44 | 1.8 | |
| Sodium Cumene Sulphonate | | | 1 |
| Sodium Formate | | 0.11 | |
| Water, Aesthetics (Dyes, perfumes) and Minors (Enzymes, solvents, structurants) | balance | balance | balance |

[1]"Random graft copolymer" is a polyvinyl acetate grafted polyethylene oxide copolymer having a polyethylene oxide backbone and multiple polyvinyl acetate side chains. The molecular weight of the polyethylene oxide backbone is about 6000 and the weight ratio of the polyethylene oxide to polyviny acetate is about 40 to 60 and no more than 1 grafting point per 50 ethylene oxide units.
[2]Polyethylenimine (MW = 600) with 20 ethoxylate groups per —NH.
[3]Amphiphilic alkoxylated grease cleaning polymer is a polyethylenimine (MW = 600) with 24 ethoxylate groups per —NH and 16 propoxylate groups per —NH.

Stain Removal Performance of BPN' Combinatorial Variants

Experiments to evaluate the stain removal performance of BPN' combinatorial variants generated as described in Example 11 were performed using BMI stained microswatches. The assay was performed as described in Example 1 (BMI microswatch assay). Table 12-2 provides Performance Index (PI) values of variants generated from RCL4 library using BMI microswatch assay in Detergent Composition 1 at pH 8 and 16° C. and Detergent Composition 1 at pH 8 and 32° C. and BMI microswatch assay in heat deactivated commercial TIDE® 2× Cold (Procter & Gamble) detergent at 16° C. and pH 8. Heat inactivation of commercial detergent formulas serves to destroy the endogenous enzymatic activity of any protein components while retaining the properties of nonenzymatic components. Heat inactivation of the detergents was performed by placing pre-weighed amounts of liquid detergent (in a glass bottle) in a water bath at 95° C. for 2 hours. The TIDE® 2× Cold detergent was purchased from local supermarket stores. Both unheated and heated detergents were assayed within 5 minutes of dissolving the detergent, in order to accurately determine percentage deactivated. Enzyme activity was tested by AAPF assay. Working solutions were made from the heat inactivated stock. Appropriate amounts of water hardness and buffer were added to the detergent solutions to match the desired conditions (Table 12-2). The solutions were mixed by vortexing or inverting the bottles.

TABLE 12-2

Working Detergent Solutions

| Detergent | Temp (° C.) | Detergent g/L | pH | Buffer | Hardness Gpg |
|---|---|---|---|---|---|
| TIDE® 2X Cold | 16, 32 | 0.98 | 8 | 5 mM HEPES | 6 |

The sequences of the variants listed in Table 12-3 are relative to BPN'-v3: G97A-G128A-Y217Q. The PI values are calculated relative to BPN'-v3. All mutants in this list have a PI cutoff equal or greater than 0.5 for at least one property tested. "Det. Comp." means Detergent Composition.

least one such protease variant and methods for cleaning utilizing at least one such protease variant as described in greater detail elsewhere herein.

TABLE 12-3

Performance Index Values of Variants Generated from RCL4 Library

| Sequence Relative to BPN' | Sequence Relative to BPN'-v3: G97A-G128A-Y217Q | TIDE ® Detergent pH 8, 16° C., BMI PI | Det. Comp. 1, pH 8, 16° C., BMI PI | Det. Comp. 1, pH 8, 32° C., BMI PI |
|---|---|---|---|---|
| S87T-A88L-S89G-G97A-G128A-Y217Q | S87T-A88L-S89G | 1.00 | 1.12 | 0.99 |
| N61P-S63H-G97A-G128A-Y217Q | N61P-S63H | 1.03 | 1.12 | 1.01 |
| S87G-A88V-S89A-G97A-G128A-Y217Q | S87G-A88V-S89A | 1.02 | 1.11 | 0.99 |
| P86S-S87G-A88V-G97A-G128A-Y217Q | P86S-S87G-A88V | 1.00 | 1.10 | 1.00 |
| Q59S-N61P-G97A-G128A-Y217Q | Q59S-N61P | 1.01 | 1.09 | 1.00 |
| S24G-N25G-G97A-G128A-Y217Q | S24G-N25G | 0.99 | 1.09 | 1.02 |
| N61P-N62S-G97A-G128A-Y217Q | N61P-N62S | 0.99 | 1.06 | 0.98 |
| G97A-G128A-P129Q-S130G-G131S-Y217Q | P129Q-S130G-G131S | 0.96 | 1.06 | 0.99 |
| L75S-N76Y-G97A-G128A-Y217Q | L75S-N76Y | 0.99 | 1.06 | 1.00 |
| G97A-G128A-V203Y-Y217Q | V203Y | 0.99 | 1.05 | 1.01 |
| T55P-G97A-G128A-Y217Q | T55P | 0.98 | 1.04 | 0.98 |
| A88V-L90I-G97A-G128A-Y217Q | A88V-L90I | 0.99 | 1.04 | 1.00 |
| G97A-G128A-G211R-N212S-K213V-Y217Q | G211R-N212S-K213V | 0.97 | 1.04 | 0.98 |
| G23A-S24G-N25G-G97A-G128A-Y217Q | G23A-S24G-N25G | 0.98 | 1.04 | 0.98 |
| T22N-S24A-G97A-G128A-Y217Q | T22N-S24A | 0.98 | 1.03 | 0.97 |
| S24R-G97A-G128A-Y217Q | S24R | 0.95 | 1.02 | 0.99 |
| G97A-A98S-G128A-Y217Q | A98S | 0.95 | 1.02 | 0.99 |
| BPN'-v3: G97A-G128A-Y217Q | BPN'-v3 | 1.00 | 1.00 | 1.00 |
| G97A-G128A-T158G-S159G-Y217Q | T158G-S159G | 0.95 | 0.99 | 0.97 |
| Q59E-N61P-G97A-G128A-Y217Q | Q59E-N61P | 0.90 | 0.94 | 0.90 |
| G97A-A98E-G128A-Y217Q | A98E | 0.92 | 0.91 | 0.90 |

The invention includes a protease variant having proteolytic activity, the variant comprising an amino acid sequence having at least 60%, 70%, 80%, 85%, 90%, 91%, 92%, 93%, 94%, 95%, 96%, 97%, or 98% identity to the sequence of SEQ ID NO:2 and at least one set of amino acid substitutions selected from those in Table 12-3, wherein positions of the variant are numbered by correspondence with positions of the SEQ ID NO:2 sequence. The proteolytic activity of such protease variant may be greater than that of the BPN' or BPN'-v3 protease. Each such protease variant may be an isolated, recombinant, substantially pure, or non-naturally occurring protease variant. Also included are compositions, including cleaning compositions, comprising at Table 12-4 provides Performance Index (PI) values of variants generated from RCL 5-7 and FS1-3 using BMI microswatch assay in Detergent Composition 1 at 16° C. and pH 8, BMI microswatch assay in Detergent Composition 2 at 16° C. and pH 8, and stability measured in Detergent Composition 3. PI values for specific activity by AAPF hydrolysis (Specific AAPF PI) were also determined. All assays were performed as described in Example 1. The sequences of the variants listed are relative to BPN'-v3: G97A-G128A-Y217Q. PI values were calculated relative to BPN'-v3. All mutants in this list have a PI cutoff equal or greater than 0.5 for at least one property tested. PI values less than 0.01 were modified to display 0.01 in bold italics.

TABLE 12-4

Performance Index Values of Variants Generated From RCL 5-7 and FS1-3

| Source of Variants | Sequence Relative to BPN' | Sequence Relative to BPN'-v3: G97A-G128A-Y217Q | Det. Comp. 1, pH 8, 16° C., BMI PI | Det. Comp. 2, pH 8, 16° C., BMI PI | Specific AAPF PI | Det. Comp. 3, Stability PI |
|---|---|---|---|---|---|---|
| RCL6 | G97A-G128A-Y217Q-P86S-S87G-A88V-A116N-N117S-N118G | P86S-S87G-A88V-A116N-N117S-N118G | 1.21 | 1.14 | 1.17 | 0.03 |
| FS1 | G97A-G128A-Y217Q-S24G-N25G-N61P-S101N | S24G-N25G-N61P-S101N | 1.05 | 1.12 | 1.96 | 1.00 |
| FS1 | G97A-G128A-Y217Q-S24G-N25G-S53G-T55P-S87T-A88L-S89G-S101N-V203Y | S24G-N25G-S53G-T55P-S87T-A88L-S89G-S101N-V203Y | 1.04 | 1.10 | 1.71 | 0.03 |
| FS1 | G97A-G128A-Y217Q-N61P-S78N-S101N-V203Y | N61P-S78N-S101N-V203Y | 1.03 | 1.10 | 1.73 | 0.33 |
| FS1 | G97A-G128A-Y217Q-T55P-N61P-S78N-S101N-V203Y | T55P-N61P-S78N-S101N-V203Y | 1.06 | 1.10 | 1.97 | 0.39 |
| FS1 | G97A-G128A-Y217Q-S53G-T55P-N61P-S78N-S87T-A88L-S89G-S101N | S53G-T55P-N61P-S78N-S87T-A88L-S89G-S101N | 1.03 | 1.10 | 2.22 | 0.33 |
| RCL7 | G97A-G128A-Y217Q-V203Y-L267V | V203Y-L267V | 1.10 | 1.09 | 1.12 | 0.09 |
| FS1 | G97A-G128A-Y217Q-S24G-N25G-T55P-S101N | S24G-N25G-T55P-S101N | 1.04 | 1.09 | 1.82 | 1.13 |
| RCL7 | G97A-G128A-Y217Q-A134T-L267V | A134T-L267V | 1.13 | 1.08 | 0.93 | 0.66 |
| FS1 | G97A-G128A-Y217Q-S24G-N25G-S53G-T55P-N61P-S78N-S87T-A88L-S89G | S24G-N25G-S53G-T55P-N61P-S78N-S87T-A88L-S89G | 1.01 | 1.08 | 1.10 | 0.29 |
| FS1 | G97A-G128A-Y217Q-S24G-N25G-S53G-N61P-S101N-V203Y | S24G-N25G-S53G-N61P-S101N-V203Y | 1.07 | 1.08 | 2.11 | 0.09 |
| RCL6 | G97A-G128A-Y217Q-N25Y-Q59S-N61P | N25Y-Q59S-N61P | 1.07 | 1.08 | 0.85 | 0.66 |
| RCL7 | G97A-G128A-Y217Q-I111V-S161P | I111V-S161P | 1.10 | 1.08 | 0.66 | 0.98 |
| RCL7 | G97A-G128A-Y217Q-I115V-L267V | I115V-L267V | 1.10 | 1.08 | 1.07 | 0.63 |
| FS1 | G97A-G128A-Y217Q-T55P-S78N-S87T-A88L-S89G-S101N-V203Y | T55P-S78N-S87T-A88L-S89G-S101N-V203Y | 0.99 | 1.08 | 1.39 | 0.16 |
| RCL6 | G97A-G128A-Y217Q-N25Y-P129Q-S130G-G131S-A137T | N25Y-P129Q-S130G-G131S-A137T | 1.07 | 1.08 | 0.88 | 0.67 |
| RCL7 | G97A-G128A-Y217Q-N61P-S63H-A128S-P129Q | N61P-S63H-A128S-P129Q | 1.04 | 1.08 | 1.59 | 0.78 |
| FS1 | G97A-G128A-Y217Q-S53G- | S53G-N61P-S101N-V203Y | 1.03 | 1.08 | 1.91 | 0.09 |

TABLE 12-4-continued

Performance Index Values of Variants Generated From RCL 5-7 and FS1-3

| Source of Variants | Sequence Relative to BPN' | Sequence Relative to BPN'-v3: G97A-G128A-Y217Q | Det. Comp. 1, pH 8, 16° C., BMI PI | Det. Comp. 2, pH 8, 16° C., BMI PI | Specific AAPF PI | Det. Comp. 3, Stability PI |
|---|---|---|---|---|---|---|
| | N61P-S101N-V203Y | | | | | |
| FS1 | G97A-G128A-Y217Q-S24G-N25G-S53G-S78N-S87T-A88L-S89G-S101N | S24G-N25G-S53G-S78N-S87T-A88L-S89G-S101N | 1.08 | 1.07 | 1.44 | 0.33 |
| FS1 | G97A-G128A-Y217Q-N61P-S78N-S87T-A88L-S89G-S101N | N61P-S78N-S87T-A88L-S89G-S101N | 1.07 | 1.07 | 1.80 | 0.31 |
| RCL6 | G97A-G128A-Y217Q-N25Y-N61P-S63H | N25Y-N61P-S63H | 1.06 | 1.07 | 0.74 | 0.60 |
| RCL5 | G97A-G128A-Y217Q-Q59S-N61P-V203Y | Q59S-N61P-V203Y | 0.99 | 1.07 | 0.69 | 0.09 |
| RCL6 | G97A-G128A-Y217Q-V8L-N25Y-P129Q-S130G-G131S | V8L-N25Y-P129Q-S130G-G131S | 1.08 | 1.07 | 1.22 | 0.03 |
| RCL6 | G97A-G128A-Y217Q-P86S-S87G-A88V-P239R | P86S-S87G-A88V-P239R | 1.16 | 1.07 | 1.26 | 0.03 |
| FS1 | G97A-G128A-Y217Q-S24G-N25G-S53G-T55P-N61P-S101N-V203Y | S24G-N25G-S53G-T55P-N61P-S101N-V203Y | 1.02 | 1.07 | 2.07 | 0.11 |
| RCL5 | G97A-G128A-Y217Q-S24G-N25G-P129Q-S130G-G131S | S24G-N25G-P129Q-S130G-G131S | 1.09 | 1.06 | 1.25 | 1.00 |
| FS3 | G97A-G128A-Y217Q-N240K | N240K | 1.04 | 1.06 | 0.90 | 0.94 |
| RCL5 | G97A-G128A-Y217Q-G23A-S24G-N25G-G211R-N212S-K213V | G23A-S24G-N25G-G211R-N212S-K213V | 1.06 | 1.06 | 1.05 | 0.06 |
| RCL7 | G97A-G128A-Y217Q-N61P-S63H-S78N-I111V-A134T | N61P-S63H-S78N-I111V-A134T | 1.03 | 1.06 | 0.43 | 1.14 |
| RCL6 | G97A-G128A-Y217Q-S63T-P86S-S87G-A88V | S63T-P86S-S87G-A88V | 1.17 | 1.06 | 1.46 | 0.02 |
| RCL6 | G97A-G128A-Y217Q-G23A-S24G-N25G-A116N-N117S-N118G | G23A-S24G-N25G-A116N-N117S-N118G | 1.08 | 1.06 | 0.91 | 0.21 |
| FS1 | G97A-G128A-Y217Q-S78N-S87T-A88L-S89G-S101N | S78N-S87T-A88L-S89G-S101N | 1.03 | 1.06 | 1.40 | 0.33 |
| RCL6 | G97A-G128A-Y217Q-S24G-N25G-A116N-N117S-N118G | S24G-N25G-A116N-N117S-N118G | 1.06 | 1.06 | 0.74 | 1.05 |
| RCL7 | G97A-G128A-Y217Q-T55P-N240K | T55P-N240K | 1.02 | 1.06 | 0.91 | 0.93 |
| RCL6 | G97A-G128A-Y217Q-T55P-P129V-P194S | T55P-P129V-P194S | 1.07 | 1.06 | 0.85 | 0.86 |
| RCL6 | G97A-G128A-Y217Q-N25Y-S87G-A88V-S89A | N25Y-S87G-A88V-S89A | 1.07 | 1.05 | 1.14 | 0.08 |
| FS1 | G97A-G128A-Y217Q-S24G- | S24G-N25G-S87T-A88L- | 1.02 | 1.05 | 1.19 | 0.06 |

TABLE 12-4-continued

Performance Index Values of Variants Generated From RCL 5-7 and FS1-3

| Source of Variants | Sequence Relative to BPN' | Sequence Relative to BPN'-v3: G97A-G128A-Y217Q | Det. Comp. 1, pH 8, 16° C., BMI PI | Det. Comp. 2, pH 8, 16° C., BMI PI | Specific AAPF PI | Det. Comp. 3, Stability PI |
|---|---|---|---|---|---|---|
| | N25G-S87T-A88L-S89G-S101N | S89G-S101N | | | | |
| RCL7 | G97A-G128A-Y217Q-P129Q-S130G-G131S-V203Y | P129Q-S130G-G131S-V203Y | 1.04 | 1.05 | 0.94 | 0.05 |
| RCL6 | G97A-G128A-Y217Q-Q59S-N61P-N240K | Q59S-N61P-N240K | 1.05 | 1.05 | 0.80 | 0.84 |
| FS3 | G97A-G128A-Y217Q-S24R-P40E-P129E-S159K-K265R | S24R-P40E-P129E-S159K-K265R | 1.13 | 1.05 | 1.08 | 1.31 |
| RCL7 | G97A-G128A-Y217Q-P52S-T55P-V203Y | P52S-T55P-V203Y | 1.09 | 1.05 | 0.53 | 0.15 |
| RCL6 | G97A-G128A-Y217Q-S24R-P129E | S24R-P129E | 1.11 | 1.05 | 0.88 | 0.59 |
| FS1 | G97A-G128A-Y217Q-S24G-N25G-S53G-N61P-S78N | S24G-N25G-S53G-N61P-S78N | 0.98 | 1.05 | 1.17 | 1.16 |
| FS1 | G97A-G128A-Y217Q-S24G-N25G-T55P-S78N-S101N | S24G-N25G-T55P-S78N-S101N | 1.07 | 1.05 | 1.71 | 1.29 |
| RCL6 | G97A-G128A-Y217Q-P86S-S87G-A88V-A116S-N117G-N118R | P86S-S87G-A88V-A116S-N117G-N118R | 1.10 | 1.05 | 0.76 | 0.05 |
| RCL6 | G97A-G128A-Y217Q-N61P-S87T-A88L-S89G | N61P-S87T-A88L-S89G | 1.00 | 1.05 | 1.12 | 0.05 |
| FS1 | G97A-G128A-Y217Q-S24G-N25G-S53G-T55P-S78N-S87T-A88L-S89G | S24G-N25G-S53G-T55P-S78N-S87T-A88L-S89G | 0.96 | 1.05 | 0.96 | 0.29 |
| RCL5 | G97A-G128A-Y217Q-G23A-S24G-N25G-N61P-S63H | G23A-S24G-N25G-N61P-S63H | 1.06 | 1.05 | 0.89 | 0.13 |
| RCL6 | G97A-G128A-Y217Q-S24R-Q59S-N61P | S24R-Q59S-N61P | 1.07 | 1.05 | 0.94 | 0.49 |
| RCL6 | G97A-G128A-Y217Q-N61P-P129Q-S130G-G131S | N61P-P129Q-S130G-G131S | 1.07 | 1.05 | 1.13 | 0.78 |
| FS1 | G97A-G128A-Y217Q-S24G-N25G-S53G-T55P-N61P-S78N-S87T-A88L-S89G-S101N | S24G-N25G-S53G-T55P-N61P-S78N-S87T-A88L-S89G-S101N | 1.05 | 1.04 | 1.98 | 0.32 |
| FS1 | G97A-G128A-Y217Q-S24G-N25G-S53G-T55P-S101N-V203Y | S24G-N25G-S53G-T55P-S101N-V203Y | 1.05 | 1.04 | 1.57 | 0.15 |
| FS1 | G97A-G128A-Y217Q-N61P-S78N-S87T-A88L-S89G-S101N-V203Y | N61P-S78N-S87T-A88L-S89G-S101N-V203Y | 1.02 | 1.04 | 1.60 | 0.12 |
| FS1 | G97A-G128A-Y217Q-S24G- | S24G-N25G-S53G-T55P- | 1.03 | 1.04 | 2.01 | 1.27 |

TABLE 12-4-continued

Performance Index Values of Variants Generated From RCL 5-7 and FS1-3

| Source of Variants | Sequence Relative to BPN' | Sequence Relative to BPN'-v3: G97A-G128A-Y217Q | Det. Comp. 1, pH 8, 16° C., BMI PI | Det. Comp. 2, pH 8, 16° C., BMI PI | Specific AAPF PI | Det. Comp. 3, Stability PI |
|---|---|---|---|---|---|---|
| | N25G-S53G-T55P-S78N-S101N | S78N-S101N | | | | |
| FS1 | G97A-G128A-Y217Q-S24G-N25G-S53G-S101N-V203Y | S24G-N25G-S53G-S101N-V203Y | 1.01 | 1.04 | 1.77 | 0.07 |
| FS1 | G97A-G128A-Y217Q-S24G-N25G-S78N-S101N-V203Y | S24G-N25G-S78N-S101N-V203Y | 1.09 | 1.04 | 1.54 | 0.28 |
| RCL7 | G97A-G128A-Y217Q-P129Q-S130G-G131S-A133V-L267V | P129Q-S130G-G131S-A133V-L267V | 1.14 | 1.04 | 1.37 | 0.56 |
| FS1 | G97A-G128A-Y217Q-S87T-A88L-S89G-S101N | S87T-A88L-S89G-S101N | 1.05 | 1.04 | 1.44 | 0.07 |
| RCL6 | G97A-G128A-Y217Q-G23A-S24G-N25G-P239R | G23A-S24G-N25G-P239R | 1.07 | 1.04 | 0.92 | 0.16 |
| RCL6 | G97A-G128A-Y217Q-S87G-A88V-S89A-A116N-N117S-N118G | S87G-A88V-S89A-A116N-N117S-N118G | 1.07 | 1.04 | 0.92 | 0.37 |
| RCL6 | G97A-G128A-Y217Q-Q59S-N61P-A116S-N117G-N118R | Q59S-N61P-A116S-N117G-N118R | 1.09 | 1.04 | 0.68 | 0.91 |
| RCL5 | G97A-G128A-Y217Q-Q59S-N61P-S87T-A88L-S89G | Q59S-N61P-S87T-A88L-S89G | 1.03 | 1.04 | 0.81 | 0.08 |
| FS1 | G97A-G128A-Y217Q-S24G-N25G-S53G-S87T-A88L-S89G-V203Y | S24G-N25G-S53G-S87T-A88L-S89G-V203Y | 0.96 | 1.04 | 0.73 | 0.04 |
| RCL7 | G97A-G128A-Y217Q-A134T-G211T | A134T-G211T | 1.11 | 1.04 | 0.71 | 0.35 |
| RCL7 | G97A-G128A-Y217Q-T55P-A128S-P129Q | T55P-A128S-P129Q | 1.03 | 1.04 | 2.71 | 1.02 |
| FS1 | G97A-G128A-Y217Q-T55P-S78N-S87T-A88L-S89G-S101N | T55P-S78N-S87T-A88L-S89G-S101N | 1.05 | 1.04 | 1.56 | 0.33 |
| RCL6 | G97A-G128A-Y217Q-P86S-S87G-A88V-T242R | P86S-S87G-A88V-T242R | 1.09 | 1.04 | 0.83 | 0.04 |
| RCL7 | G97A-G128A-Y217Q-S161P-V203Y | S161P-V203Y | 1.04 | 1.04 | 0.81 | 0.09 |
| FS1 | G97A-G128A-Y217Q-S24G-N25G-T55P-N61P-S78N-S101N-V203Y | S24G-N25G-T55P-N61P-S78N-S101N-V203Y | 1.05 | 1.04 | 2.01 | 0.44 |
| RCL7 | G97A-G128A-Y217Q-G211T-L267V | G211T-L267V | 1.08 | 1.03 | 1.16 | 0.30 |
| RCL6 | G97A-G128A-Y217Q-P40E-T55P-N269K | P40E-T55P-N269K | 1.08 | 1.03 | 0.71 | 0.05 |
| RCL6 | G97A-G128A-Y217Q-S24R-A128S-P129G | S24R-A128S-P129G | 1.08 | 1.03 | 1.63 | 0.64 |

TABLE 12-4-continued

Performance Index Values of Variants Generated From RCL 5-7 and FS1-3

| Source of Variants | Sequence Relative to BPN' | Sequence Relative to BPN'-v3: G97A-G128A-Y217Q | Det. Comp. 1, pH 8, 16° C., BMI PI | Det. Comp. 2, pH 8, 16° C., BMI PI | Specific AAPF PI | Det. Comp. 3, Stability PI |
|---|---|---|---|---|---|---|
| RCL6 | G97A-G128A-Y217Q-S24G-N25G-N61P-N62S-P194L-A232T | S24G-N25G-N61P-N62S-P194L-A232T | 1.15 | 1.03 | 3.06 | 0.35 |
| RCL6 | G97A-G128A-Y217Q-T55P-A116S-N117G-N118R | T55P-A116S-N117G-N118R | 1.07 | 1.03 | 0.83 | 1.06 |
| FS1 | G97A-G128A-Y217Q-S24G-N25G-S53G-S78N-S101N-V203Y | S24G-N25G-S53G-S78N-S101N-V203Y | 1.03 | 1.03 | 1.76 | 0.32 |
| RCL7 | G97A-G128A-Y217Q-P129Q-S130G-G131S-N240K | P129Q-S130G-G131S-N240K | 1.08 | 1.03 | 0.90 | 0.83 |
| FS1 | G97A-G128A-Y217Q-S53G-T55P-N61P-S78N-S87T-A88L-S89G | S53G-T55P-N61P-S78N-S87T-A88L-S89G | 0.93 | 1.03 | 1.00 | 0.33 |
| RCL6 | G97A-G128A-Y217Q-N25Y-P129Q-S130G-G131S | N25Y-P129Q-S130G-G131S | 1.08 | 1.03 | 0.93 | 0.69 |
| RCL6 | G97A-G128A-Y217Q-T55P-I115V | T55P-I115V | 1.06 | 1.03 | 1.07 | 1.07 |
| RCL6 | G97A-G128A-Y217Q-N25Y-T55P | N25Y-T55P | 1.05 | 1.03 | 1.00 | 0.80 |
| RCL6 | G97A-G128A-Y217Q-G23A-S24G-N25G-A128S-P129D | G23A-S24G-N25G-A128S-P129D | 0.97 | 1.03 | 1.75 | 0.15 |
| FS1 | G97A-G128A-Y217Q-S53G-S78N-S87T-A88L-S89G-S101N-P129S-V203Y | S53G-S78N-S87T-A88L-S89G-S101N-P129S-V203Y | 1.00 | 1.03 | 1.68 | 0.13 |
| RCL7 | G97A-G128A-Y217Q-T55P-A134T | T55P-A134T | 1.06 | 1.03 | 0.94 | 1.05 |
| RCL7 | G97A-G128A-Y217Q-N61P-S63H-S78N-I111V | N61P-S63H-S78N-I111V | 1.03 | 1.02 | 0.49 | 1.18 |
| FS2 | Y217Q-N61P-A97G-G102A-A128G-P129S | N61P-A97G-G102A-A128G-P129S | 0.98 | 1.02 | NA | NA |
| FS1 | G97A-G128A-Y217Q-S53G-N61P-S101N | S53G-N61P-S101N | 1.02 | 1.02 | 2.08 | 0.88 |
| RCL5 | G97A-G128A-Y217Q-Q59S-N61P-S87G-A88V-S89A | Q59S-N61P-S87G-A88V-S89A | 1.01 | 1.02 | 0.90 | 0.20 |
| FS1 | G97A-G128A-Y217Q-S53G-S87T-A88L-S89G-S101N-V203Y | S53G-S87T-A88L-S89G-S101N-V203Y | 0.96 | 1.02 | 1.11 | 0.04 |
| RCL6 | G97A-G128A-Y217Q-S87T-A88L-S89G-P129S | S87T-A88L-S89G-P129S | 1.06 | 1.02 | 1.21 | 0.10 |
| FS1 | G97A-G128A-Y217Q-S53G-T55P-S78N-S101N-V203Y | S53G-T55P-S78N-S101N-V203Y | 1.03 | 1.02 | 1.70 | 0.48 |
| RCL5 | G97A-G128A-Y217Q-T55P- | T55P-P129Q-S130G-G131S | 1.01 | 1.02 | 1.18 | 0.91 |

TABLE 12-4-continued

Performance Index Values of Variants Generated From RCL 5-7 and FS1-3

| Source of Variants | Sequence Relative to BPN' | Sequence Relative to BPN'-v3: G97A-G128A-Y217Q | Det. Comp. 1, pH 8, 16° C., BMI PI | Det. Comp. 2, pH 8, 16° C., BMI PI | Specific AAPF PI | Det. Comp. 3, Stability PI |
|---|---|---|---|---|---|---|
| | P129Q-S130G-G131S | | | | | |
| RCL5 | G97A-G128A-Y217Q-Q59S-N61P-P129Q-S130G-G131S | Q59S-N61P-P129Q-S130G-G131S | 0.98 | 1.02 | 0.83 | 0.80 |
| RCL7 | G97A-G128A-Y217Q-A134T-P239R | A134T-P239R | 1.03 | 1.02 | 0.53 | 0.98 |
| RCL5 | G97A-G128A-Y217Q-T55P-V203Y | T55P-V203Y | 1.01 | 1.01 | 1.02 | 0.23 |
| RCL7 | G97A-G128A-Y217Q-T55P-S78N-S89Y | T55P-S78N-S89Y | 1.03 | 1.01 | 1.05 | 1.25 |
| RCL5 | G97A-G128A-Y217Q-T22N-S24A-N61P-S63H | T22N-S24A-N61P-S63H | 1.00 | 1.01 | 0.69 | 0.46 |
| RCL7 | G97A-G128A-Y217Q-S161P-L267V | S161P-L267V | 1.05 | 1.01 | 1.00 | 0.66 |
| RCL6 | G97A-G128A-Y217Q-T55P-L75H-N76G | T55P-L75H-N76G | 1.06 | 1.01 | 0.69 | 0.59 |
| RCL7 | G97A-G128A-Y217Q-A134T-S161P | A134T-S161P | 1.07 | 1.01 | 0.73 | 1.00 |
| RCL7 | G97A-G128A-Y217Q-S87T-A88L-S89G-A134T | S87T-A88L-S89G-A134T | 1.08 | 1.01 | 0.66 | 0.13 |
| RCL6 | G97A-G128A-Y217Q-T55P-A116N-N117S-N118G | T55P-A116N-N117S-N118G | 1.06 | 1.01 | 1.06 | 1.11 |
| v12 | G97A-G128S-Y217Q | A128S | 1.02 | 1.01 | 1.65 | 1.00 |
| RCL7 | G97A-G128A-Y217Q-T55P-S78N-I115V | T55P-S78N-I115V | 1.07 | 1.00 | 1.00 | 1.32 |
| RCL6 | G97A-G128A-Y217Q-Y6Q-P129Q-S130G-G131S | Y6Q-P129Q-S130G-G131S | 1.03 | 1.00 | 0.98 | 0.23 |
| RCL7 | G97A-G128A-Y217Q-S24R-P129Q-S130G-G131S | S24R-P129Q-S130G-G131S | 1.06 | 1.00 | 1.11 | 0.61 |
| FS1 | G97A-G128A-Y217Q-S24G-N25G-S53G-S78N-S101N | S24G-N25G-S53G-S78N-S101N | 0.99 | 1.00 | 1.61 | 1.21 |
| RCL6 | G97A-G128A-Y217Q-T55P-P129V | T55P-P129V | 1.07 | 1.00 | 0.70 | 1.00 |
| v3 | G97A-G128A-Y217Q | BPN'-v3 | 1.00 | 1.00 | 1.00 | 1.00 |
| FS2 | G97A-Y217Q-N61P-N62Q-G100N-A128G | N61P-N62Q-G100N-A128G | 0.95 | 1.00 | NA | NA |
| RCL6 | G97A-G128A-Y217Q-T55P-P129Q | T55P-P129Q | 1.10 | 1.00 | 1.77 | 1.15 |
| FS1 | G97A-G128A-Y217Q-S24G-N25G-S53G-T55P-N61P-S78N-S87T-A88L-S89G-S101N-V203Y | S24G-N25G-S53G-T55P-N61P-S78N-S87T-A88L-S89G-S101N-V203Y | 1.05 | 1.00 | 1.84 | 0.12 |
| RCL6 | G97A-G128A-Y217Q-S87T- | S87T-A88L-S89G-N240K | 1.04 | 1.00 | 0.83 | 0.10 |

TABLE 12-4-continued

Performance Index Values of Variants Generated From RCL 5-7 and FS1-3

| Source of Variants | Sequence Relative to BPN' | Sequence Relative to BPN'-v3: G97A-G128A-Y217Q | Det. Comp. 1, pH 8, 16° C., BMI PI | Det. Comp. 2, pH 8, 16° C., BMI PI | Specific AAPF PI | Det. Comp. 3, Stability PI |
|---|---|---|---|---|---|---|
| RCL7 | G97A-G128A-Y217Q-A134T-N240K | A134T-N240K | 1.07 | 0.99 | 0.61 | 0.96 |
| RCL7 | G97A-G128A-Y217Q-S87T-A88L-S89G-P239R | S87T-A88L-S89G-P239R | 1.04 | 0.99 | 0.68 | 0.14 |
| RCL7 | G97A-G128A-Y217Q-P129Q-S130G-G131S-L267V | P129Q-S130G-G131S-L267V | 1.08 | 0.99 | 1.35 | 0.61 |
| RCL7 | G97A-G128A-Y217Q-P129Q-N240K | P129Q-N240K | 1.06 | 0.99 | 1.39 | 1.00 |
| FS1 | G97A-G128A-Y217Q-S78N-S87T-A88L-S89G-V203Y | S78N-S87T-A88L-S89G-V203Y | 0.93 | 0.99 | 0.74 | 0.15 |
| RCL7 | G97A-G128A-Y217Q-I111V-A273S | I111V-A273S | 1.00 | 0.99 | 0.48 | 0.27 |
| FS1 | G97A-G128A-Y217Q-S24G-N25G-T55P-S78N-A88V-S101N | S24G-N25G-T55P-S78N-A88V-S101N | 1.03 | 0.99 | 2.17 | 0.71 |
| FS1 | G97A-G128A-Y217Q-S24G-N25G-T55P-S78N | S24G-N25G-T55P-S78N | 0.96 | 0.98 | 1.15 | 1.20 |
| FS1 | G97A-G128A-Y217Q-S24G-N25G-S53G-S78N-S87T-A88L-S101N-V203Y | S24G-N25G-S53G-S78N-S87T-A88L-S101N-V203Y | 1.02 | 0.98 | 1.27 | 0.10 |
| FS1 | G97A-G128A-Y217Q-S24G-N25G-S53G-S78N-S87T-A88L-S89G-V203Y | S24G-N25G-S53G-S78N-S87T-A88L-S89G-V203Y | 0.97 | 0.98 | 0.75 | 0.14 |
| FS1 | G97A-G128A-Y217Q-S24G-N25G-S53G-S78N-S87T-A88L-S89G-S101N-V203Y | S24G-N25G-S53G-S78N-S87T-A88L-S89G-S101N-V203Y | 1.06 | 0.98 | 1.21 | 0.14 |
| RCL5 | G97A-G128A-Y217Q-S87G-A88V-S89A-P129Q-S130G-G131S | S87G-A88V-S89A-P129Q-S130G-G131S | 1.01 | 0.98 | 1.18 | 0.29 |
| RCL7 | G97A-G128A-Y217Q-N61P-S63H-S78N-S161P | N61P-S63H-S78N-S161P | 1.03 | 0.98 | 0.73 | 1.16 |
| FS1 | G97A-G128A-Y217Q-T55P-N61P-S78N-S87T-A88L-S89G-S101N-V203Y | T55P-N61P-S78N-S87T-A88L-S89G-S101N-V203Y | 1.04 | 0.98 | 1.75 | 0.14 |
| RCL7 | G97A-G128A-Y217Q-I111V-P129Q-S130G-G131S | I111V-P129Q-S130G-G131S | 1.00 | 0.98 | 0.52 | 0.97 |
| RCL5 | G97A-G128A-Y217Q-T22N-S24A-T55P | T22N-S24A-T55P | 0.96 | 0.98 | 0.94 | 0.64 |
| RCL7 | G97A-G128A-Y217Q-I115V-N240K | I115V-N240K | 1.04 | 0.98 | 0.66 | 0.90 |

TABLE 12-4-continued

Performance Index Values of Variants Generated From RCL 5-7 and FS1-3

| Source of Variants | Sequence Relative to BPN' | Sequence Relative to BPN'-v3: G97A-G128A-Y217Q | Det. Comp. 1, pH 8, 16° C., BMI PI | Det. Comp. 2, pH 8, 16° C., BMI PI | Specific AAPF PI | Det. Comp. 3, Stability PI |
|---|---|---|---|---|---|---|
| RCL6 | G97A-G128A-Y217Q-S87G-A88V-S89A-A116N-N117S-N118G-P172H | S87G-A88V-S89A-A116N-N117S-N118G-P172H | 0.98 | 0.98 | 0.66 | 0.40 |
| FS1 | G97A-G128A-Y217Q-S24G-N25G-S78N-S87T-A88L-S89G-S101N | S24G-N25G-S78N-S87T-A88L-S89G-S101N | 1.01 | 0.98 | 1.28 | 0.31 |
| RCL6 | G97A-G128A-Y217Q-S24G-N25G-I115V-A134T | S24G-N25G-I115V-A134T | 1.03 | 0.98 | 0.59 | 1.13 |
| RCL6 | G97A-G128A-Y217Q-T55P-A128S-P129D | T55P-A128S-P129D | 0.97 | 0.97 | 1.39 | 1.00 |
| RCL7 | G97A-G128A-Y217Q-I111V-S159K | I111V-S159K | 0.99 | 0.97 | 0.64 | 1.12 |
| RCL7 | G97A-G128A-Y217Q-N240K-A273S | N240K-A273S | 1.03 | 0.96 | 0.64 | 0.19 |
| RCL7 | G97A-G128A-Y217Q-S159K-L267V | S159K-L267V | 1.00 | 0.96 | 1.08 | 0.79 |
| RCL7 | G97A-G128A-Y217Q-I111V-P129Q-G211T | I111V-P129Q-G211T | 1.01 | 0.96 | 0.83 | 0.42 |
| RCL7 | G97A-G128A-Y217Q-I115V-A273S | I115V-A273S | 1.05 | 0.95 | 0.74 | 0.20 |
| RCL6 | G97A-G128A-Y217Q-S89Y | S89Y | 0.99 | 0.95 | 0.70 | 0.88 |
| RCL6 | G97A-G128A-Y217Q-S24R-A116N-N117S-N118G | S24R-A116N-N117S-N118G | 1.08 | 0.95 | 0.91 | 0.60 |
| RCL7 | G97A-G128A-Y217Q-N61E-A144K | N61E-A144K | 1.03 | 0.95 | 0.97 | 1.10 |
| RCL6 | G97A-G128A-Y217Q-P129Q-S130G-G131S-P239R | P129Q-S130G-G131S-P239R | 1.02 | 0.95 | 0.85 | 0.99 |
| RCL7 | G97A-G128A-Y217Q-S87T-A88L-S89G-I115V | S87T-A88L-S89G-I115V | 0.97 | 0.95 | 0.59 | 0.13 |
| RCL6 | G97A-G128A-Y217Q-T55P-A92G | T55P-A92G | 0.96 | 0.94 | 0.56 | 0.91 |
| FS3 | G97A-G128A-Y217Q-S145D-S159K-N240K-Q275E | S145D-S159K-N240K-Q275E | 0.98 | 0.94 | 0.76 | 1.08 |
| RCL7 | G97A-G128A-Y217Q-S89Y-P129Q-S130G-G131S | S89Y-P129Q-S130G-G131S | 1.04 | 0.94 | 0.71 | 0.70 |
| RCL7 | G97A-G128A-Y217Q-P129Q-S130G-G131S-S162K | P129Q-S130G-G131S-S162K | 1.01 | 0.94 | 1.00 | 0.93 |
| RCL7 | G97A-G128A-Y217Q-I111V-A134T | I111V-A134T | 0.98 | 0.94 | 0.37 | 1.06 |
| RCL6 | G97A-G128A-Y217Q-P40E-S53Y-S78Y-P86S-S87G-A88V | P40E-S53Y-S78Y-P86S-S87G-A88V | 0.99 | 0.94 | 0.97 | 0.35 |

TABLE 12-4-continued

Performance Index Values of Variants Generated From RCL 5-7 and FS1-3

| Source of Variants | Sequence Relative to BPN' | Sequence Relative to BPN'-v3: G97A-G128A-Y217Q | Det. Comp. 1, pH 8, 16° C., BMI PI | Det. Comp. 2, pH 8, 16° C., BMI PI | Specific AAPF PI | Det. Comp. 3, Stability PI |
|---|---|---|---|---|---|---|
| RCL6 | G97A-G128A-Y217Q-S24G-N25G-L75H-N76G | S24G-N25G-L75H-N76G | 0.93 | 0.93 | 0.58 | 0.52 |
| FS2 | G97A-Y217Q-N61P-A128G-P129S-S130P | N61P-A128G-P129S-S130P | 0.85 | 0.93 | 0.65 | 0.92 |
| RCL6 | G97A-G128A-Y217Q-S24R-S145D | S24R-S145D | 0.99 | 0.93 | 0.89 | 0.59 |
| FS3 | G97A-G128A-Y217Q-S24R-S145D-P239R-Q275E | S24R-S145D-P239R-Q275E | 0.92 | 0.92 | 0.63 | 0.68 |
| RCL7 | G97A-G128A-Y217Q-S24R-S78N-S182P-L267V | S24R-S78N-S182P-L267V | 0.95 | 0.92 | 1.16 | 0.55 |
| FS1 | G97A-G128A-Y217Q-S53G-N61P-S87T-A88L-S89G-S101N-V203Y | S53G-N61P-S87T-A88L-S89G-S101N-V203Y | 1.04 | 0.92 | 1.67 | 0.02 |
| RCL6 | G97A-G128A-Y217Q-P5S-S87G-A88V-S89A-A116G-N117R | P5S-S87G-A88V-S89A-A116G-N117R | 0.98 | 0.92 | 0.64 | 0.07 |
| FS1 | G97A-G128A-Y217Q-S53G-N61P-S78N-S87T-A88L-S89G-S101N-V203Y | S53G-N61P-S78N-S87T-A88L-S89G-S101N-V203Y | 0.99 | 0.92 | 1.65 | 0.11 |
| RCL6 | G97A-G128A-Y217Q-Q59S-N61P-A116N-N117S-N118G | Q59S-N61P-A116N-N117S-N118G | 0.93 | 0.92 | 0.42 | 1.04 |
| RCL7 | G97A-G128A-Y217Q-P239R-A273S | P239R-A273S | 0.94 | 0.91 | 0.52 | 0.23 |
| FS1 | G97A-G128A-Y217Q-S53G-S78N-S87T-A88L-S89G-S101N-V203Y | S53G-S78N-S87T-A88L-S89G-S101N-V203Y | 0.94 | 0.91 | 1.16 | 0.13 |
| RCL6 | G97A-G128A-Y217Q-S24R-P129V | S24R-P129V | 0.98 | 0.91 | 0.52 | 0.58 |
| RCL7 | G97A-G128A-Y217Q-I111V-P239R | I111V-P239R | 0.97 | 0.91 | 0.38 | 1.08 |
| FS1 | G97A-G128A-Y217Q-S87T-A88L-S89G-S101N-V203Y | S87T-A88L-S89G-S101N-V203Y | 0.90 | 0.91 | 0.79 | 0.05 |
| RCL6 | G97A-G128A-Y217Q-T55P-P129L | T55P-P129L | 0.99 | 0.91 | 0.62 | 0.98 |
| RCL7 | G97A-G128A-Y217Q-S87T-A88L-S89G-I111V | S87T-A88L-S89G-I111V | 0.92 | 0.90 | 0.42 | 0.13 |
| RCL7 | G97A-G128A-Y217Q-S145D-A273S | S145D-A273S | 0.91 | 0.90 | 0.66 | 0.17 |
| RCL6 | G97A-G128A-Y217Q-P129Q-S130G-G131S-T242R | P129Q-S130G-G131S-T242R | 0.94 | 0.90 | 0.51 | 0.89 |
| RCL7 | G97A-G128A-Y217Q-S3F-S87T-A88L-S89G- | S3F-S87T-A88L-S89G- | 0.93 | 0.89 | 0.55 | 0.07 |

TABLE 12-4-continued

Performance Index Values of Variants Generated From RCL 5-7 and FS1-3

| Source of Variants | Sequence Relative to BPN' | Sequence Relative to BPN'-v3: G97A-G128A-Y217Q | Det. Comp. 1, pH 8, 16° C., BMI PI | Det. Comp. 2, pH 8, 16° C., BMI PI | Specific AAPF PI | Det. Comp. 3, Stability PI |
|---|---|---|---|---|---|---|
| | A88L-S89G-G211T | G211T | | | | |
| RCL6 | G97A-G128A-Y217Q-S87G-A88V-S89A-S162K | S87G-A88V-S89A-S162K | 0.97 | 0.89 | 1.21 | 0.37 |
| RCL7 | G97A-G128A-Y217Q-S89Y-G211T | S89Y-G211T | 0.89 | 0.88 | 0.53 | 0.41 |
| RCL7 | G97A-G128A-Y217Q-S87T-A88L-S89G-A144K | S87T-A88L-S89G-A144K | 0.93 | 0.88 | 0.74 | 0.12 |
| RCL6 | G97A-G128A-Y217Q-P129Q-S130G-G131S-S159K | P129Q-S130G-G131S-S159K | 0.95 | 0.88 | 1.21 | 0.96 |
| RCL6 | G97A-G128A-Y217Q-A116N-N117S-N118G-P129Q-S130G-G131S | A116N-N117S-N118G-P129Q-S130G-G131S | 0.90 | 0.88 | 0.54 | 0.95 |
| RCL6 | G97A-G128A-Y217Q-S24G-N25G-P129V | S24G-N25G-P129V | 0.86 | 0.87 | 0.44 | 1.02 |
| FS1 | G97A-G128A-Y217Q-S24G-N25G-S78N-S87T-A88L-S89G-S101N-V203Y | S24G-N25G-S78N-S87T-A88L-S89G-S101N-V203Y | 0.87 | 0.86 | 0.83 | 0.12 |
| FS2 | G97A-Y217Q-N123G-A128G | N123G-A128G | 0.83 | 0.86 | 1.00 | 0.14 |
| FS2 | G97A-G128A-Y217Q-N61P-N62Q-G100N-G102A-M124I | N61P-N62Q-G100N-G102A-M124I | 0.82 | 0.86 | 5.52 | 0.40 |
| RCL6 | G97A-G128A-Y217Q-S24G-N25G-K141E-T242R | S24G-N25G-K141E-T242R | 0.90 | 0.85 | 0.65 | 1.10 |
| RCL6 | G97A-G128A-Y217Q-S87G-A88V-S89A-A116N-N117S-N118G-A144T | S87G-A88V-S89A-A116N-N117S-N118G-A144T | 0.89 | 0.85 | 0.44 | 0.32 |
| FS1 | G97A-G128A-Y217Q-T55P-N61P-S87T-A88L-S89G-G110C-S130P | T55P-N61P-S87T-A88L-S89G-G110C-S130P | 0.83 | 0.85 | 0.92 | 0.30 |
| RCL6 | G97A-G128A-Y217Q-L75S-N76Y-A116S-N117G-N118R | L75S-N76Y-A116S-N117G-N118R | 0.84 | 0.83 | 0.41 | 0.13 |
| FS3 | G97A-G128A-Y217Q-S145D-S159K-K213L-P239R-N240K | S145D-S159K-K213L-P239R-N240K | 0.74 | 0.81 | 0.38 | 0.65 |
| RCL6 | G97A-G128A-Y217Q-S24R-S87T-A88L-S89G | S24R-S87T-A88L-S89G | 0.86 | 0.80 | 0.53 | 0.08 |
| RCL6 | G97A-G128A-Y217Q-G23A-S24G-N25G-P129V | G23A-S24G-N25G-P129V | 0.88 | 0.79 | 0.53 | 0.20 |
| RCL7 | G97A-G128A-Y217Q-A134T-K213L | A134T-K213L | 0.87 | 0.79 | 0.51 | 0.81 |
| RCL7 | G97A-G128A-Y217Q-S89Y-A273S | S89Y-A273S | 0.81 | 0.79 | 0.48 | 0.19 |

TABLE 12-4-continued

Performance Index Values of Variants Generated From RCL 5-7 and FS1-3

| Source of Variants | Sequence Relative to BPN' | Sequence Relative to BPN'-v3: G97A-G128A-Y217Q | Det. Comp. 1, pH 8, 16° C., BMI PI | Det. Comp. 2, pH 8, 16° C., BMI PI | Specific AAPF PI | Det. Comp. 3, Stability PI |
|---|---|---|---|---|---|---|
| RCL7 | G97A-G128A-Y217Q-S24R-P239R | S24R-P239R | 0.90 | 0.78 | 0.71 | 0.69 |
| FS2 | G97A-Y217Q-N123G-A128G-P129S | N123G-A128G-P129S | 0.76 | 0.78 | 0.71 | 0.12 |
| RCL7 | G97A-G128A-Y217Q-S89Y-P239R | S89Y-P239R | 0.77 | 0.76 | 0.38 | 0.90 |
| RCL6 | G97A-G128A-Y217Q-S24G-N25G-A92G | S24G-N25G-A92G | 0.71 | 0.76 | 0.25 | 0.59 |
| RCL6 | G97A-G128A-Y217Q-N61P-S63H-I115V-A228V | N61P-S63H-I115V-A228V | 0.73 | 0.74 | 0.24 | 0.42 |
| FNA | Y217L | A97G-A128G-Q217L | 0.73 | 0.74 | 1.81 | 1.21 |
| RCL6 | G97A-G128A-Y217Q-L75S-N76Y-P129V | L75S-N76Y-P129V | 0.73 | 0.73 | 0.34 | 0.09 |
| RCL6 | G97A-G128A-Y217Q-S24R-P129L | S24R-P129L | 0.80 | 0.73 | 0.35 | 0.58 |
| RCL6 | G97A-G128A-Y217Q-S87G-A88V-S89A-P129Q-S182Y-S204Y-P239Q | S87G-A88V-S89A-P129Q-S182Y-S204Y-P239Q | 0.69 | 0.73 | 0.90 | 0.36 |
| RCL6 | G97A-G128A-Y217Q-S24R-A92G | S24R-A92G | 0.75 | 0.73 | 0.28 | 0.44 |
| RCL6 | G97A-G128A-Y217Q-S24R-A116S-N117G-N118R | S24R-A116S-N117G-N118R | 0.81 | 0.72 | 0.48 | 0.58 |
| RCL6 | G97A-G128A-Y217Q-G23A-S24G-N25G-A116G-N117R | G23A-S24G-N25G-A116G-N117R | 0.85 | 0.66 | 0.63 | 0.20 |
| RCL6 | G97A-G128A-Y217Q-S24G-N25G-P129L | S24G-N25G-P129L | 0.72 | 0.66 | 0.39 | 1.03 |
| RCL6 | G97A-G128A-Y217Q-S87T-A88L-S89G-S101G | S87T-A88L-S89G-S101G | 0.78 | 0.66 | 0.65 | 0.11 |
| RCL6 | G97A-G128A-Y217Q-G23A-S24G-N25G-P129L | G23A-S24G-N25G-P129L | 0.52 | 0.59 | 0.37 | 0.20 |
| FS1 | G97A-G128A-Y217Q-S53G-N61P-G102A-V203Y | S53G-N61P-G102A-V203Y | 0.55 | 0.58 | 0.29 | 0.16 |
| RCL6 | G97A-G128A-Y217Q-T55P-V147P | T55P-V147P | 0.56 | 0.57 | 0.22 | 1.09 |
| RCL6 | G97A-G128A-Y217Q-Y6Q-L75S-N76Y | Y6Q-L75S-N76Y | 0.55 | 0.52 | 0.24 | 0.17 |
| RCL6 | G97A-G128A-Y217Q-N61P-S63H-V147P | N61P-S63H-V147P | 0.36 | 0.37 | 0.14 | 0.95 |
| RCL6 | G97A-G128A-Y217Q-S24R-V147P | S24R-V147P | 0.16 | 0.22 | 0.08 | 0.85 |
| RCL6 | G97A-G128A-Y217Q-S24G- | S24G-N25G-V68C-A69G | 0.21 | 0.18 | 0.06 | 0.71 |

TABLE 12-4-continued

Performance Index Values of Variants Generated From RCL 5-7 and FS1-3

| Source of Variants | Sequence Relative to BPN' | Sequence Relative to BPN'-v3: G97A-G128A-Y217Q | Det. Comp. 1, pH 8, 16° C., BMI PI | Det. Comp. 2, pH 8, 16° C., BMI PI | Specific AAPF PI | Det. Comp. 3, Stability PI |
|---|---|---|---|---|---|---|
| FS1 | N25G-V68C-A69G G97A-G128A-Y217Q-S24G-N25G-N61P-L75S-N76Y-S101N-V203Y | S24G-N25G-N61P-L75S-N76Y-S101N-V203Y | 0.19 | 0.18 | 0.08 | 0.38 |
| FS1 | G97A-G128A-Y217Q-L75S-N76Y-S78N-S101N-V203Y | L75S-N76Y-S78N-S101N-V203Y | 0.13 | 0.12 | 0.05 | 0.72 |
| FS1 | G97A-G128A-Y217Q-L75S-N76Y-S78N-S87T-A88L-S89G-S101N-S130P | L75S-N76Y-S78N-S87T-A88L-S89G-S101N-S130P | 0.04 | 0.04 | 0.07 | 0.73 |
| FS1 | G97A-G128A-Y217Q-S24G-N25G-S53G-S101N-S130P-V203Y | S24G-N25G-S53G-S101N-S130P-V203Y | 0.06 | 0.04 | 0.06 | 0.33 |
| RCL6 | G97A-G128A-Y217Q-G47E-M50I-L75S-N76Y-S162K | G47E-M50I-L75S-N76Y-S162K | *0.01* | 0.03 | 0.02 | 1.21 |
| FS1 | G97A-G128A-Y217Q-S53G-T55P-S87T-A88L-S89G-S101N-S130P-V203Y | S53G-T55P-S87T-A88L-S89G-S101N-S130P-V203Y | *0.01* | 0.02 | 0.05 | 0.45 |
| FS1 | G97A-G128A-Y217Q-S24G-N25G-L75S-N76Y-A128T-P129T-S130G-G131Q-S132C-A133G-A134T | S24G-N25G-L75S-N76Y-A128T-P129T-S130G-G131Q-S132C-A133G-A134T | *0.01* | *0.01* | 0.02 | 1.21 |
| RCL6 | G97A-G128A-Y217Q-P129Q-S130G-G131S-V147P | P129Q-S130G-G131S-V147P | *0.01* | *0.01* | 0.03 | 1.11 |
| FS1 | G97A-G128A-Y217Q-S53G-T55P-N61P-L75S-N76Y-S87T-A88L-S89G-G102A-S130P-V203Y | S53G-T55P-N61P-L75S-N76Y-S87T-A88L-S89G-G102A-S130P-V203Y | *0.01* | *0.01* | 0.02 | 1.05 |
| FS1 | G97A-G128A-Y217Q-S53G-T55P-N61P-L75S-N76Y-S101N-S130P-V203Y | S53G-T55P-N61P-L75S-N76Y-S101N-S130P-V203Y | 0.03 | *0.01* | 0.02 | 1.03 |

The invention includes a protease variant having proteolytic activity, the variant comprising an amino acid sequence having at least 60%, 70%, 80%, 85%, 90%, 91%, 92%, 93%, 94%, 95%, 96%, 97%, or 98% identity to the sequence of SEQ ID NO:2 and at least one set of amino acid substitutions selected from those listed in Table 12-4, wherein positions of the variant are numbered by correspondence with positions of the SEQ ID NO:2 sequence. Each such protease variant may be an isolated, recombinant, substantially pure, or non-naturally occurring protease variant. Also included are compositions, including cleaning compositions, comprising at least one such protease variant and methods for cleaning utilizing at least one such protease variant as described in greater detail elsewhere herein.

Table 12-5 provides the Performance Index (PI) values of BPN' variants (generated as described in "Generation of Variants to Improve BPN' Stability"; see Table 11-3) for stain removal in BMI microswatch assay in Detergent Composition 1 at 16° C. and pH 8 (Det. Comp. 1, pH 8, 16° C., BMI PI) and for stability in LAS/EDTA (LAS/EDTA Stability PI). Assays were performed as described in Example 1 (BMI microswatch assay, LAS/EDTA stability assay). The sequences of the variants are shown relative to both BPN' and FNA. That is, each variant sequence is the BPN' or FNA sequence with the specified variant amino acid substitutions. PI values are shown relative to FNA parent, which is BPN'-Y217L.

TABLE 12-5

Performance Index of Stability-Improved BPN' Variants

| Sequence Relative to FNA: BPN' Y217L | Sequence Relative to BPN' | Det. Comp. 1 pH 8, 16° C., BMI PI | LAS/EDTA Stability PI |
|---|---|---|---|
| P40E-S78N-S87D | P40E-S78N-S87D-Y217L | 0.71 | 11.65 |
| P40E | P40E-Y217L | 0.96 | 8.33 |
| T22V-S78N-Q206E-K213N | T22V-S78N-Q206E-K213N-Y217L | 0.75 | 5.95 |
| T22V-S78N-K213N | T22V-S78N-K213N-Y217L | 0.86 | 5.71 |
| S87D | S87D-Y217L | 0.90 | 4.04 |
| S78N | S78N-Y217L | 0.87 | 3.86 |
| K213N | K213N-Y217L | 0.91 | 1.84 |
| Q206E | Q206E-Y217L | 0.86 | 1.76 |
| T22V | T22V-Y217L | 0.97 | 1.46 |
| FNA | Y217L | 1.00 | 1.00 |

The invention includes a protease variant having proteolytic activity and/or improved stability relative to FNA, the variant comprising an amino acid sequence having at least 60%, 70%, 80%, 85%, 90%, 91%, 92%, 93%, 94%, 95%, 96%, 97%, or 98% identity to the sequence of SEQ ID NO:2 and at least one set of amino acid substitutions selected from those listed in Table 12-5, wherein positions of the variant are numbered by correspondence with positions of the SEQ ID NO:2 sequence. Such protease variant may have a proteolytic activity greater than that of BPN' or BPN'-v3. Each such protease variant may be an isolated, recombinant, substantially pure, or non-naturally occurring protease variant. Also included are compositions, including cleaning compositions, comprising at least one such protease variant and methods for cleaning utilizing at least one such protease variant as described in greater detail elsewhere herein.

Table 12-6 provides the Performance Index (PI) values of BPN' variants generated from Library Parent: BPN'-v3: G97A-G128A-Y217Q (as described in "Generation of Variants to Improve BPN' Stability"; see Table 11-3) for stain removal in a BMI microswatch assay in Detergent Composition 1 at 16° C. and pH 8 and for stability in LAS/EDTA. Assays were performed as described in Example 1 (BMI microswatch assay and LAS/EDTA stability assay). The Performance Index was calculated relative to BPN'-v3: G97A-G128A-Y217Q. All mutants in this list have a PI cutoff equal or greater than 0.5 for at least one property tested.

TABLE 12-6

Performance Index of Stability-Improved BPN' Variants

| Sequence Relative to BPN'-v3: BPN' G97A-G128A-Y217Q | Sequence Relative to BPN' | Det. Comp. 1 pH 8, 16° C., BMI PI | LAS/EDTA Stability PI |
|---|---|---|---|
| S87D-N76D-S78N | S87D-N76D-S78N-G97A-G128A-Y217Q | 0.62 | 2.27 |
| P40E-S78N-S87D | P40E-S78N-S87D-G97A-G128A-Y217Q | 0.21 | 2.18 |
| P40E-S87D | P40E-S87D-G97A-G128A-Y217Q | 0.18 | 2.14 |
| S78N-P40E | S78N-P40E-G97A-G128A-Y217Q | 0.80 | 2.03 |
| S87D-N76D | S87D-N76D-G97A-G128A-Y217Q | 0.55 | 1.89 |
| P40E | P40E-G97A-G128A-Y217Q | 0.84 | 1.79 |
| S78N-S87D | S78N-S87D-G97A-G128A-Y217Q | 0.79 | 1.71 |
| S87D | S87D-G97A-G128A-Y217Q | 0.78 | 1.20 |
| S78N | S78N-G97A-G128A-Y217Q | 0.93 | 1.14 |
| BPN'-v3 | G97A-G128A-Y217Q | 1.00 | 1.00 |

The invention includes a protease variant having proteolytic activity and having improved stability relative to BPN'-v3, the variant comprising an amino acid sequence having at least 60%, 70%, 80%, 85%, 90%, 91%, 92%, 93%, 94%, 95%, 96%, 97%, or 98% identity to the sequence of SEQ ID NO:2 and at least one set of amino acid substitutions selected from those listed in Table 12-6, wherein positions of the variant are numbered by correspondence with positions of the SEQ ID NO:2 sequence. Each such protease variant may be an isolated, recombinant, substantially pure, or non-naturally occurring protease variant. Also included are compositions, including cleaning compositions, comprising at least one such protease variant and methods for cleaning utilizing at least one such protease variant as described in greater detail elsewhere herein.

Table 12-7 provides the Performance Index (PI) values of BPN' variants (generated as described in "Generation of BPN' Variants from Five Different Plasmids"; see Table 11-4) for stain removal in a BMI microswatch assay in Detergent Composition 1 at 16° C. and pH 8. Assays were performed as described in Example 1 (BMI microswatch assay). The Performance Index of each variant was calculated relative to BPN'-v3: G97A-G128A-Y217Q. All mutants in this list have a PI cutoff equal or greater than 0.5 for at least one property tested.

TABLE 12-7

Performance Index of BPN' Variants

| Sequence Relative to BPN'-v3 G97A-G128A-Y217Q | Sequence Relative to BPN' | Det. Comp. 1, pH 8, 16° C., BMI PI |
|---|---|---|
| S101N | G97A-S101N-G128A-Y217Q | 1.12 |
| A137V | G97A-G128A-A137V-Y217Q | 1.12 |
| N61P | N61P-G97A-G128A-Y217Q | 1.11 |
| S130P | G97A-G128A-S130P-Y217Q | 1.09 |
| Q103N | G97A-Q103N-G128A-Y217Q | 1.07 |
| S63T | S63T-G97A-G128A-Y217Q | 1.03 |
| G102A | G97A-G102A-G128A-Y217Q | 1.02 |
| BPN'-v3 | BPN'-v3 (G97A-G128A-Y217Q) | 1.00 |
| N109D-S248R | G97A-N109D-G128A-Y217Q-S248R | 0.96 |
| S87R | S87R-G97A-G128A-Y217Q | 0.95 |
| S188D | G97A-G128A-S188D-Y217Q | 0.95 |
| S87D-S248R | S87D-G97A-G128A-Y217Q-S248R | 0.94 |
| S188D-S248R | G97A-G128A-S188D-S248R-Y217Q | 0.93 |
| S248D | G97A-G128A-S248D-Y217Q | 0.86 |
| N109D-S188D-S248R | G97A-N109D-G128A-S188D-S248R-Y217Q | 0.83 |
| N109D | G97A-N109D-G128A-Y217Q | 0.81 |
| S87R-S248R | S87R-G97A-G128A-Y217Q-S248R | 0.79 |
| N109D-S188R | G97A-N109D-G128A-S188R-Y217Q | 0.77 |
| N76D | N76D-G97A-G128A-Y217Q | 0.75 |
| S87D-N109D-S188D-S248R | S87D-G97A-N109D-G128A-S188D-S248R-Y217Q | 0.58 |
| S87R-N109D-S188D-S248R | S87R-G97A-N109D-G128A-S188D-Y217Q-S248R | 0.55 |
| S87R-S188R-S248R | S87R-G97A-G128A-S188R-Y217Q-S248R | 0.52 |
| A187D | G97A-G128A-A187D-Y217Q | 0.48 |
| N109D-S248D | G97A-N109D-G128A-Y217Q-S248D | 0.47 |
| S87R-N109R-S188R-S248R | S87R-G97A-N109R-G128A-S188R-Y217Q-S248R | 0.39 |
| F189D | G97A-G128A-F189D-Y217Q | 0.31 |
| G100N | G97A-G100N-G128A-Y217Q | 0.28 |
| S87R-N109D-S188D | S87R-G97A-N109D-G128A-S188D-Y217Q | 0.24 |
| S87D-N109D-S188D | S87D-G97A-N109D-G128A-S188D-Y217Q | 0.12 |
| S87R-S188D-S248D | S87R-G97A-G128A-S188D-S248D-Y217Q | 0.09 |
| N62D | N62D-G97A-G128A-Y217Q | 0.09 |
| S87D-N109D-S188D-S248D | S87D-G97A-N109D-G128A-S188D-Y217Q-S248D | 0.08 |

The invention includes a protease variant having proteolytic activity, the variant comprising an amino acid sequence having at least 60%, 70%, 80%, 85%, 90%, 91%, 92%, 93%, 94%, 95%, 96%, 97%, or 98% identity to the sequence of SEQ ID NO:2 and at least one set of amino acid substitutions selected from those listed in Table 12-7, wherein positions of the variant are numbered by correspondence with positions of the SEQ ID NO:2 sequence. Each such protease variant may be an isolated, recombinant, substantially pure, or non-naturally occurring protease variant. Also included are compositions, including cleaning compositions, comprising at least one such protease variant and methods for cleaning utilizing at least one such protease variant as described in greater detail elsewhere herein.

Table 12-8 provides the Performance index (PI) values of BPN' variants (generated as described in "Generation of Combinatorial Libraries and Variants of BPN'-v3+S78N" as described in Example 3) for stain removal using a BMI microswatch assay in Detergent Composition 1 at 16° C. and pH 8. Assays were performed as described in Example 1 (BMI microswatch assay). The Performance Index of each variant was calculated relative to BPN'-S78N-G97A-G128A-Y217Q. PI values less than 0.01 were modified and are indicated as "0.01" in bold italics.

TABLE 12-8

Performance Index Values of BPN' Variants

| Variant | Sequence Relative to BPN' | Sequence Relative to BPN'-v3: G97A-G128A-Y217Q | Det. Comp. 1 pH 8, 16° C., BMI PI |
|---|---|---|---|
| v3/S78N/L267V | S78N-G97A-G128A-Y217Q-L267V | S78N-L267V | 1.12 |
| v3/S78N/S161P | S78N-G97A-G128A-Y217Q-S161P | S78N-S161P | 1.05 |
| v3/S78N/I115V | S78N-G97A-G128A-Y217Q-I115V | S78N-I115V | 1.04 |
| v3/S78N/A273S | S78N-G97A-G128A-Y217Q-A273S | S78N-A273S | 1.03 |

TABLE 12-8-continued

Performance Index Values of BPN' Variants

| Variant | Sequence Relative to BPN' | Sequence Relative to BPN'-v3: G97A-G128A-Y217Q | Det. Comp. 1 pH 8, 16° C., BMI PI |
|---|---|---|---|
| v3/S78N/G211T | S78N-G97A-G128A-Y217Q-G211T | S78N-G211T | 1.00 |
| V3 + S78N | S78N-G97A-G128A-Y217Q | S78N | 1.00 |
| v3/S78N/I111V | S78N-G97A-G128A-Y217Q-I111V | S78N-I111V | 0.98 |
| v3/S78N/V147L | S78N-G97A-G128A-Y217Q-V147L | S78N-V147L | 0.97 |
| v3/S78N/I108V | S78N-G97A-G128A-Y217Q-I108V | S78N-I108V | 0.97 |
| v3/S78N/S89Y | S78N-G97A-G128A-Y217Q-S89Y | S78N-S89Y | 0.94 |
| v3/S78N/A138T | S78N-G97A-G128A-Y217Q-A138T | S78N-A138T | 0.92 |
| v3/S78N/P172V | S78N-G97A-G128A-Y217Q-P172V | S78N-P172V | 0.74 |
| v3/S78N/Q59G | S78N-G97A-G128A-Y217Q-Q59G | S78N-Q59G | 0.64 |
| GcM96 | G97A-G128A-Y217Q-P129T-V147Q-S159D-S161P-S183T-Q185T-G211A-S224A | P129T-V147Q-S159D-S161P-S183T-Q185T-G211A-S224A | 0.57 |
| GcM91 | G97A-G128A-Y217Q-Q059V-I108V-V147Q-G211A-N252Q | Q059V-I108V-V147Q-G211A-N252Q | 0.55 |
| v3/S78N/Y167A | S78N-G97A-G128A-Y217Q-Y167A | S78N-Y167A | 0.53 |
| v3/S78N/A92G | S78N-G97A-G128A-Y217Q-A92G | S78N-A92G | 0.49 |
| v3/S78N/P129L | S78N-G97A-G128A-Y217Q-P129L | S78N-P129L | 0.48 |
| GcM92 | G97A-G128A-Y217Q-N061A-S087E-M124I-S161P-S224A | N061A-S087E-M124I-S161P-S224A | 0.36 |
| v3/S78N/N62Q | S78N-G97A-G128A-Y217Q-N62Q | S78N-N62Q | 0.27 |
| v3/S78N/V68A | S78N-G97A-G128A-Y217Q-V68A | S78N-V68A | 0.24 |
| GcM94 | G97A-G128A-Y217Q-S063T-S101A-L126V-S183T-T244N | S063T-S101A-L126V-S183T-T244N | 0.12 |
| v3/S78N/M124T | S78N-G97A-G128A-Y217Q-M124T | S78N-M124T | 0.05 |
| GcM95 | G97A-G128A-Y217Q-P040L-S053G-Q059V-N061A-N062Q-S063T-S087E-G100N | P040L-S053G-Q059V-N061A-N062Q-S063T-S087E-G100N | *0.01* |
| GcM93 | G97A-G128A-Y217Q-N062Q-G100N-S125A-S159D-N240S | N062Q-G100N-S125A-S159D-N240S | *0.01* |
| GcM100 | G97A-G128A-Y217Q-V68A-G102A-G211A-S125A | V68A-G102A-G211A-S125A | *0.01* |
| GcM90 | G97A-G128A-Y217Q-S053G-V068A-G102A-P129T-Q185T | S053G-V068A-G102A-P129T-Q185T | *0.01* |

The invention includes a protease variant having proteolytic activity, the variant comprising an amino acid sequence having at least 60%, 70%, 80%, 85%, 90%, 91%, 92%, 93%, 94%, 95%, 96%, 97%, or 98% identity to the sequence of SEQ ID NO:2 and at least one set of amino acid substitutions selected from those listed in Table 12-8, wherein positions of the variant are numbered by correspondence with positions of the SEQ ID NO:2 sequence. Each such protease variant may be an isolated, recombinant, substantially pure, or non-naturally occurring protease variant. Also included are compositions, including cleaning compositions, comprising at least one such protease variant and methods for cleaning utilizing at least one such protease variant as described in greater detail elsewhere herein.

Table 12-9 provides Performance index (PI) values of BPN' single variants (constructed using PCR fusion as described in PCT App. No. PCT/US09/46156, filed Jun. 3, 2009, which is incorporated by reference herein for such description) for stain removal in a BMI microswatch assay in Detergent Composition 2 at 16° C. and pH 8 and for stability measured in Detergent Composition 3. PI values for specific activity by AAPF hydrolysis (PI specific AAPF) were determined. All assays were performed as described in Example 1. Performance index values were calculated relative to BPN wild type. PI values less than 0.01 are indicated as "0.01" in bold italics. "Det. Comp." means Detergent Composition.

TABLE 12-9

Performance Index Values for BPN' Single Variants

| BPN' Variant | Det. Comp. 2 pH 8, 16° C., BMI PI | PI Specific AAPF | Det. Comp. 3 Stability PI |
|---|---|---|---|
| S182E | 1.34 | 1.05 | 0.50 |
| N109I | 1.28 | 1.22 | 0.20 |
| N117H | 1.15 | 0.25 | 0.20 |
| K237D | 1.15 | 0.60 | 0.70 |
| L257Q | 1.14 | 0.94 | 0.80 |
| P225N | 1.13 | 1.02 | 0.70 |
| S105H | 1.11 | 1.07 | *0.01* |
| S236I | 1.10 | 0.58 | 0.90 |
| L235H | 1.10 | 0.65 | 0.70 |
| S249E | 1.07 | 0.72 | 0.30 |
| N76E | 1.07 | 0.76 | 0.20 |
| S145N | 1.06 | 1.16 | 1.10 |
| N243D | 1.05 | 1.03 | 0.90 |
| R247N | 1.04 | 1.04 | 0.50 |
| E195N | 1.04 | 1.05 | 0.40 |
| A98K | 1.03 | 0.75 | 0.70 |
| S182N | 0.99 | 1.14 | 0.90 |
| S161H | 0.97 | 1.07 | 0.90 |
| G83H | 0.95 | 0.72 | 0.60 |
| G131D | 0.95 | 1.11 | 1.30 |
| T71C | 0.93 | 1.00 | 1.30 |
| K136Q | 0.93 | 1.02 | 0.80 |
| P40D | 0.93 | 1.20 | 1.20 |
| A187H | 0.91 | 0.95 | 0.60 |
| L250K | 0.90 | 1.02 | 0.40 |
| S9I | 0.87 | 0.20 | *0.01* |
| N76M | 0.85 | 0.60 | 0.60 |
| S132D | 0.85 | 0.88 | 0.70 |
| Q19F | 0.83 | 0.47 | 0.30 |
| E112H | 0.83 | 1.02 | *0.01* |
| S249P | 0.80 | 1.02 | 0.50 |
| S53D | 0.78 | 0.29 | 0.10 |
| V68E | 0.78 | 0.59 | 1.70 |
| D41I | 0.72 | 1.15 | 0.90 |
| K43H | 0.70 | 0.28 | 0.10 |
| V4H | 0.66 | 0.37 | 0.60 |
| A13Y | 0.64 | 0.48 | *0.01* |
| N62P | 0.61 | 0.60 | 1.30 |
| L196E | 0.56 | 0.70 | 0.70 |
| V44D | 0.51 | 0.18 | *0.01* |

The invention includes a protease variant having proteolytic activity, the variant comprising an amino acid sequence having at least 60%, 70%, 80%, 85%, 90%, 91%, 92%, 93%, 94%, 95%, 96%, 97%, or 98% identity to the sequence of SEQ ID NO:2 and at least one substitution selected from those listed in Table 12-9, wherein positions of the variant are numbered by correspondence with positions of the SEQ ID NO:2 sequence. Each such protease variant may be an isolated, recombinant, substantially pure, or non-naturally occurring protease variant. Also included are compositions, including cleaning compositions, comprising at least one such protease variant and methods for cleaning utilizing at least one such protease variant as described in greater detail elsewhere herein.

Example 13

Liquid Laundry Detergent Compositions

In this Example, various formulations for liquid laundry detergent compositions are provided. The following liquid laundry detergent compositions of the present invention are prepared as shown below. In each of these formulations, at least one protease variant provided herein is included at a concentration of from about 0.0001 to about 10 weight percent. In some alternative aspects, other concentrations will find use, as determined by the formulator, based on their needs.

TABLE 13-1

Liquid Laundry Detergent Composition

| Compound | Formulations | | | | |
|---|---|---|---|---|---|
| | I | II | III | IV | V |
| LAS | 24.0 | 32.0 | 6.0 | 3.0 | 6.0 |
| $NaC_{16}$—$C_{17}HSAS$ | — | — | — | 5.0 | — |
| $C_{12}$-$C_{15}$ $AE_{1.8}S$ | — | — | 8.0 | 7.0 | 5.0 |
| $C_8$-$C_{10}$ propyl dimethyl amine | 2.0 | 2.0 | 2.0 | 2.0 | 1.0 |
| $C_{12}$-$C_{14}$ alkyl dimethyl amine oxide | — | — | — | — | 2.0 |
| $C_{12}$-$C_{15}$ AS | — | — | 17.0 | — | 8.0 |
| CFAA | — | 5.0 | 4.0 | 4.0 | 3.0 |
| $C_{12}$-$C_{14}$ Fatty alcohol ethoxylate | 12.0 | 6.0 | 1.0 | 1.0 | 1.0 |
| $C_{12}$-$C_{18}$ Fatty acid | 3.0 | — | 4.0 | 2.0 | 3.0 |
| Citric acid (anhydrous) | 4.5 | 5.0 | 3.0 | 2.0 | 1.0 |
| DETPMP | — | — | 1.0 | 1.0 | 0.5 |
| Monoethanolamine | 5.0 | 5.0 | 5.0 | 5.0 | 2.0 |
| Sodium hydroxide | — | — | 2.5 | 1.0 | 1.5 |
| 1N HCl aqueous solution | #1 | #1 | — | — | — |
| Propanediol | 12.7 | 14.5 | 13.1 | 10. | 8.0 |
| Ethanol | 1.8 | 2.4 | 4.7 | 5.4 | 1.0 |
| DTPA | 0.5 | 0.4 | 0.3 | 0.4 | 0.5 |
| Pectin Lyase | — | — | — | 0.005 | — |
| Amylase | 0.001 | 0.002 | — | — | — |
| Cellulase | — | — | 0.0002 | — | 0.0001 |
| Lipase | 0.1 | — | 0.1 | — | 0.1 |
| NprE (optional) | 0.05 | 0.3 | — | 0.5 | 0.2 |
| PMN | — | — | 0.08 | — | — |
| Protease A (optional) | — | — | — | — | 0.1 |
| Aldose Oxidase | — | — | 0.3 | — | 0.003 |
| ZnCl2 | 0.1 | 0.05 | 0.05 | 0.05 | 0.02 |
| Ca formate | 0.05 | 0.07 | 0.05 | 0.06 | 0.07 |
| DETBCHD | — | — | 0.02 | 0.01 | — |
| SRP1 | 0.5 | 0.5 | — | 0.3 | 0.3 |
| Boric acid | — | — | — | — | 2.4 |
| Sodium xylene sulfonate | — | — | 3.0 | — | — |
| Sodium cumene sulfonate | — | — | — | 0.3 | 0.5 |
| DC 3225C | 1.0 | 1.0 | 1.0 | 1.0 | 1.0 |
| 2-butyl-octanol | 0.03 | 0.04 | 0.04 | 0.03 | 0.03 |
| Brightener 1 | 0.12 | 0.10 | 0.18 | 0.08 | 0.10 |
| Balance to 100% perfume/dye and/or water | | | | | |

1: Add 1N HCl aqueous solution to adjust the neat pH of the formula in the range from about 3 to about 5.

The pH of Formulations (I)-(II) in Table 13-1 is about 5 to about 7 and of Formulations (III)-(V) in Table 13-1 is about 7.5 to about 8.5.

Example 14

Hand Dish Liquid Detergent Compositions

In this Example, various hand dish liquid detergent formulations are provided. The following hand dish liquid detergent compositions of the present invention are provided below. In each of these formulations, at least one protease variant provided herein is included at a concentration of from about 0.0001 to about 10 weight percent. In some alternative aspects, other concentrations will find use, as determined by the formulator, based on their needs.

TABLE 14-1

Hand Dish Liquid Detergent Compositions

| Compound | I | II | III | IV | V | VI |
|---|---|---|---|---|---|---|
| $C_{12}$-$C_{15}AE_{1.8}S$ | 30.0 | 28.0 | 25.0 | — | 15.0 | 10.0 |
| LAS | — | — | — | 5.0 | 15.0 | 12.0 |
| Paraffin Sulfonate | — | — | — | 20.0 | — | — |
| $C_{10}$-$C_{18}$ Alkyl Dimethyl Amine Oxide | 5.0 | 3.0 | 7.0 | — | — | — |
| Betaine | 3.0 | — | 1.0 | 3.0 | 1.0 | — |
| $C_{12}$ poly-OH fatty acid amide | — | — | — | 3.0 | — | 1.0 |
| $C_{14}$ poly-OH fatty acid amide | — | 1.5 | — | — | — | — |
| $C_{11}E_9$ | 2.0 | — | 4.0 | — | — | 20.0 |
| DTPA | — | — | — | — | 0.2 | — |
| Tri-sodium Citrate dehydrate | 0.25 | — | — | 0.7 | — | — |
| Diamine | 1.0 | 5.0 | 7.0 | 1.0 | 5.0 | 7.0 |
| $MgCl_2$ | 0.25 | — | — | 1.0 | — | — |
| nprE (optional) | 0.02 | 0.01 | — | 0.01 | — | 0.05 |
| PMN | — | — | 0.03 | — | 0.02 | — |
| Protease A (optional) | — | 0.01 | — | — | — | — |
| Amylase | 0.001 | — | — | 0.002 | — | 0.001 |
| Aldose Oxidase | 0.03 | — | 0.02 | — | 0.05 | — |
| Sodium Cumene Sulphonate | — | — | — | 2.0 | 1.5 | 3.0 |
| PAAC | 0.01 | 0.01 | 0.02 | — | — | — |
| DETBCHD | — | — | — | 0.01 | 0.02 | 0.01 |
| Balance to 100% perfume/dye and/or water | | | | | | |

The pH of Formulations (I)-(VI) in Table 14-1 is about 8 to about 11.

Example 15

Liquid Automatic Dishwashing Detergent Compositions

In this Example, various liquid automatic dishwashing detergent formulations are provided. The following hand dish liquid detergent compositions of the present invention are provided below. In each of these formulations, at least one protease variant provided herein is included at a concentration of from about 0.0001 to about 10 weight percent. In some alternative aspects, other concentrations will find use, as determined by the formulator, based on their needs.

TABLE 15-1

Liquid Automatic Dishwashing Detergent Compositions

| Compound | I | II | III | IV | V |
|---|---|---|---|---|---|
| STPP | 16 | 16 | 18 | 16 | 16 |
| Potassium Sulfate | — | 10 | 8 | — | 10 |
| 1,2 propanediol | 6.0 | 0.5 | 2.0 | 6.0 | 0.5 |
| Boric Acid | — | — | — | 4.0 | 3.0 |
| $CaCl_2$ dihydrate | 0.04 | 0.04 | 0.04 | 0.04 | 0.04 |
| Nonionic | 0.5 | 0.5 | 0.5 | 0.5 | 0.5 |
| nprE (optional) | 0.1 | 0.03 | — | 0.03 | — |
| PMN | — | — | 0.05 | — | 0.06 |
| Protease B (optional) | — | — | — | 0.01 | — |
| Amylase | 0.02 | — | 0.02 | 0.02 | — |
| Aldose Oxidase | — | 0.15 | 0.02 | — | 0.01 |
| Galactose Oxidase | — | — | 0.01 | — | 0.01 |
| PAAC | 0.01 | — | — | 0.01 | — |
| DETBCHD | — | 0.01 | — | — | 0.01 |
| Balance to 100% perfume/dye and/or water | | | | | |

Example 16

Granular and/or Tablet Laundry Compositions

This Example provides various formulations for granular and/or tablet laundry detergents. The following laundry compositions of present invention, which may be in the form of granules or tablet, are provided below. In each of these formulations, at least one protease variant provided herein is included at a concentration of from about 0.0001 to about 10 weight percent. In some alternative aspects, other concentrations will find use, as determined by the formulator, based on their needs.

TABLE 16-1

Granular and/or Tablet Laundry Compositions

| Compound | I | II | III | IV | V |
|---|---|---|---|---|---|
| Base Product | | | | | |
| $C_{14}$-$C_{15}$AS or TAS | 8.0 | 5.0 | 3.0 | 3.0 | 3.0 |
| LAS | 8.0 | — | 8.0 | — | 7.0 |
| $C_{12}$-$C_{15}AE_3S$ | 0.5 | 2.0 | 1.0 | — | — |
| $C_{12}$-$C_{15}E_5$ or $E_3$ | 2.0 | — | 5.0 | 2.0 | 2.0 |
| QAS | — | — | — | 1.0 | 1.0 |
| Zeolite A | 20.0 | 18.0 | 11.0 | — | 10.0 |
| SKS-6 (dry add) | — | — | 9.0 | — | — |
| MA/AA | 2.0 | 2.0 | 2.0 | — | — |
| AA | — | — | — | — | 4.0 |
| 3Na Citrate•$2H_2O$ | — | 2.0 | — | — | — |
| Citric Acid (Anhydrous) | 2.0 | — | 1.5 | 2.0 | — |
| DTPA | 0.2 | 0.2 | — | — | — |
| EDDS | — | — | 0.5 | 0.1 | — |
| HEDP | — | — | 0.2 | 0.1 | — |
| PB1 | 3.0 | 4.8 | — | — | 4.0 |
| Percarbonate | — | — | 3.8 | 5.2 | — |
| NOBS | 1.9 | — | — | — | — |
| NACA OBS | — | — | 2.0 | — | — |
| TAED | 0.5 | 2.0 | 2.0 | 5.0 | 1.00 |
| BB1 | 0.06 | — | 0.34 | — | 0.14 |

TABLE 16-1-continued

Granular and/or Tablet Laundry Compositions

| Compound | I | II | III | IV | V |
|---|---|---|---|---|---|
| BB2 | — | 0.14 | — | 0.20 | — |
| Anhydrous Na Carbonate | 15.0 | 18.0 | — | 15.0 | 15.0 |
| Sulfate | 5.0 | 12.0 | 5.0 | 17.0 | 3.0 |
| Silicate | — | 1.0 | — | — | 8.0 |
| nprE (optional) | 0.03 | — | 0.1 | 0.06 | — |
| PMN | — | 0.05 | — | — | 0.1 |
| Protease B (optional) | — | 0.01 | — | — | — |
| Protease C (optional) | — | — | — | 0.01 | — |
| Lipase | — | 0.008 | — | — | — |
| Amylase | 0.001 | — | — | — | 0.001 |
| Cellulase | — | 0.0014 | — | — | — |
| Pectin Lyase | 0.001 | 0.001 | 0.001 | 0.001 | 0.001 |
| Aldose Oxidase | 0.03 | — | 0.05 | — | — |
| PAAC | — | 0.01 | — | — | 0.05 |
| Balance to 100% Moisture and/or Minors* | | | | | |

*Perfume, dye, brightener/SRP1/Na carboxymethylcellulose/photobleach/$MgSO_4$/PVPVI/suds suppressor/high molecular PEG/clay.

Example 17

Liquid Laundry Detergents

This Example provides various formulations for liquid laundry detergents. The following liquid laundry detergent formulations of the present invention are provided below. In each of these formulations, at least one protease variant provided herein is included at a concentration of from about 0.0001 to about 10 weight percent. In some alternative aspects, other concentrations will find use, as determined by the formulator, based on their needs.

TABLE 17-1

Liquid Laundry Detergents

| Compound | I | II | III | IV | V | VI |
|---|---|---|---|---|---|---|
| LAS | 11.5 | 11.5 | 9.0 | — | 4.0 | — |
| $C_{12}$-$C_{15}AE_{2.85}S$ | — | — | 3.0 | 18.0 | — | 16.0 |
| $C_{14}$-$C_{15}E_{2.5}S$ | 11.5 | 11.5 | 3.0 | — | 16.0 | — |
| $C_{12}$-$C_{13}E_9$ | — | — | 3.0 | 2.0 | 2.0 | 1.0 |
| $C_{12}$-$C_{13}E_7$ | 3.2 | 3.2 | — | — | — | — |
| CFAA | — | — | — | 5.0 | — | 3.0 |
| TPKFA | 2.0 | 2.0 | — | 2.0 | 0.5 | 2.0 |
| Citric Acid (Anhydrous) | 3.2 | 3.2 | 0.5 | 1.2 | 2.0 | 1.2 |
| Ca formate | 0.1 | 0.1 | 0.06 | 0.1 | — | — |
| Na formate | 0.5 | 0.5 | 0.06 | 0.1 | 0.05 | 0.05 |
| ZnCl2 | 0.1 | 0.05 | 0.06 | 0.03 | 0.05 | 0.05 |
| Na Culmene Sulfonate | 4.0 | 4.0 | 1.0 | 3.0 | 1.2 | — |
| Borate | 0.6 | 0.6 | 1.5 | — | — | — |
| Na Hydroxide | 6.0 | 6.0 | 2.0 | 3.5 | 4.0 | 3.0 |
| Ethanol | 2.0 | 2.0 | 1.0 | 4.0 | 4.0 | 3.0 |
| 1,2 Propanediol | 3.0 | 3.0 | 2.0 | 8.0 | 8.0 | 5.0 |
| Monoethanolamine | 3.0 | 3.0 | 1.5 | 1.0 | 2.5 | 1.0 |
| TEPAE | 2.0 | 2.0 | — | 1.0 | 1.0 | 1.0 |
| nprE (optional) | 0.03 | 0.05 | — | 0.03 | — | 0.02 |
| PMN | — | — | 0.01 | — | 0.08 | — |
| Protease A (optional) | — | — | 0.01 | — | — | — |
| Lipase | — | — | — | 0.002 | — | — |
| Amylase | — | — | — | — | 0.002 | — |
| Cellulase | — | — | — | — | — | 0.0001 |
| Pectin Lyase | 0.005 | 0.005 | — | — | — | — |
| Aldose Oxidase | 0.05 | — | — | 0.05 | — | 0.02 |
| Galactose oxidase | — | 0.04 | — | — | — | — |
| PAAC | 0.03 | 0.03 | 0.02 | — | — | — |
| DETBCHD | — | — | — | 0.02 | 0.01 | — |
| SRP 1 | 0.2 | 0.2 | — | 0.1 | — | — |
| DTPA | — | — | — | 0.3 | — | — |
| PVNO | — | — | — | 0.3 | — | 0.2 |

TABLE 17-1-continued

Liquid Laundry Detergents

| Compound | I | II | III | IV | V | VI |
|---|---|---|---|---|---|---|
| Brightener 1 | 0.2 | 0.2 | 0.07 | 0.1 | — | — |
| Silicone antifoam | 0.04 | 0.04 | 0.02 | 0.1 | 0.1 | 0.1 |
| Balance to 100% perfume/dye and/or water | | | | | | |

Example 18

High Density Dishwashing Detergents

This Example provides various formulations for high density dishwashing detergents. The following compact high density dishwashing detergents of the present invention are provided below. In each of these formulations, at least one protease variant provided herein is included at a concentration of from about 0.0001 to about 10 weight percent. In some alternative aspects, other concentrations will find use, as determined by the formulator, based on their needs.

TABLE 18-1

High Density Dishwashing Detergents

| Compound | I | II | III | IV | V | VI |
|---|---|---|---|---|---|---|
| STPP | — | 45.0 | 45.0 | — | — | 40.0 |
| 3Na Citrate•2H$_2$O | 17.0 | — | — | 50.0 | 40.2 | — |
| Na Carbonate | 17.5 | 14.0 | 20.0 | — | 8.0 | 33.6 |
| Bicarbonate | — | — | — | 26.0 | — | — |
| Silicate | 15.0 | 15.0 | 8.0 | — | 25.0 | 3.6 |
| Metasilicate | 2.5 | 4.5 | 4.5 | — | — | — |
| PB1 | — | — | 4.5 | — | — | — |
| PB4 | — | — | — | 5.0 | — | — |
| Percarbonate | — | — | — | — | — | 4.8 |
| BB1 | — | 0.1 | 0.1 | — | 0.5 | — |
| BB2 | 0.2 | 0.05 | — | 0.1 | — | 0.6 |
| Nonionic | 2.0 | 1.5 | 1.5 | 3.0 | 1.9 | 5.9 |
| HEDP | 1.0 | — | — | — | — | — |
| DETPMP | 0.6 | — | — | — | — | — |
| PAAC | 0.03 | 0.05 | 0.02 | — | — | — |
| Paraffin | 0.5 | 0.4 | 0.4 | 0.6 | — | — |
| nprE (optional) | 0.072 | 0.053 | — | 0.026 | — | 0.01 |
| PMN | — | — | 0.053 | — | 0.059 | — |
| Protease B (optional) | — | — | — | — | — | 0.01 |
| Amylase | 0.012 | — | 0.012 | — | 0.021 | 0.006 |
| Lipase | — | 0.001 | — | 0.005 | — | — |
| Pectin Lyase | 0.001 | 0.001 | 0.001 | — | — | — |
| Aldose Oxidase | 0.05 | 0.05 | 0.03 | 0.01 | 0.02 | 0.01 |
| BTA | 0.3 | 0.2 | 0.2 | 0.3 | 0.3 | 0.3 |
| Polycarboxylate | 6.0 | — | — | — | 4.0 | 0.9 |
| Perfume | 0.2 | 0.1 | 0.1 | 0.2 | 0.2 | 0.2 |
| Balance to 100% Moisture and/or Minors* | | | | | | |

*Brightener/dye/SRP1/Na carboxymethylcellulose/photobleach/MgSO$_4$/PVPVI/suds suppressor/ high molecular PEG/clay.

The pH of Formulations (I) through (VI) in Table 18-1 is from about 9.6 to about 11.3.

Example 19

Tablet Detergent Compositions

This Example provides various tablet detergent formulations. The following tablet detergent compositions of the present invention are prepared by compression of a granular dishwashing detergent composition at a pressure of 13KN/cm$^2$ using a standard 12 head rotary press. In each of these formulations, at least one protease variant provided herein is included at a concentration of from about 0.0001 to about 10 weight percent. In some alternative aspects, other concentrations will find use, as determined by the formulator, based on their needs.

TABLE 19-1

Tablet Detergent Compositions

| Compound | I | II | III | IV | V | VI | VII | VIII |
|---|---|---|---|---|---|---|---|---|
| STPP | — | 48.8 | 44.7 | 38.2 | — | 42.4 | 46.1 | 46.0 |
| 3Na Citrate•2H$_2$O | 20.0 | — | — | — | 35.9 | — | — | — |
| Na Carbonate | 20.0 | 5.0 | 14.0 | 15.4 | 8.0 | 23.0 | 20.0 | — |
| Silicate | 15.0 | 14.8 | 15.0 | 12.6 | 23.4 | 2.9 | 4.3 | 4.2 |
| Lipase | 0.001 | — | 0.01 | — | 0.02 | — | — | — |
| Protease B (optional) | 0.01 | — | — | — | — | — | — | — |
| Protease C (optional) | — | — | — | — | — | 0.01 | — | — |
| nprE (optional) | 0.01 | 0.08 | — | 0.04 | — | 0.023 | — | 0.05 |
| PMN | — | — | 0.05 | — | 0.052 | — | 0.023 | — |
| Amylase | 0.012 | 0.012 | 0.012 | — | 0.015 | — | 0.017 | 0.002 |
| Pectin Lyase | 0.005 | — | — | 0.002 | — | — | — | — |
| Aldose Oxidase | — | 0.03 | — | 0.02 | 0.02 | — | 0.03 | — |

TABLE 19-1-continued

Tablet Detergent Compositions

| Compound | Formulations | | | | | | | |
|---|---|---|---|---|---|---|---|---|
| | I | II | III | IV | V | VI | VII | VIII |
| PB1 | — | — | 3.8 | — | 7.8 | — | — | 4.5 |
| Percarbonate | 6.0 | — | — | 6.0 | — | 5.0 | — | — |
| BB1 | 0.2 | — | 0.5 | — | 0.3 | 0.2 | — | — |
| BB2 | — | 0.2 | — | 0.5 | — | — | 0.1 | 0.2 |
| Nonionic | 1.5 | 2.0 | 2.0 | 2.2 | 1.0 | 4.2 | 4.0 | 6.5 |
| PAAC | 0.01 | 0.01 | 0.02 | — | — | — | — | — |
| DETBCHD | — | — | — | 0.02 | 0.02 | — | — | — |
| TAED | — | — | — | — | — | 2.1 | — | 1.6 |
| HEDP | 1.0 | — | — | 0.9 | — | 0.4 | 0.2 | — |
| DETPMP | 0.7 | — | — | — | — | — | — | — |
| Paraffin | 0.4 | 0.5 | 0.5 | 0.5 | — | — | 0.5 | — |
| BTA | 0.2 | 0.3 | 0.3 | 0.3 | 0.3 | 0.3 | 0.3 | — |
| Polycarboxylate | 4.0 | — | — | — | 4.9 | 0.6 | 0.8 | — |
| PEG 400-30,000 | — | — | — | — | — | 2.0 | — | 2.0 |
| Glycerol | — | — | — | — | — | 0.4 | — | 0.5 |
| Perfume | — | — | — | 0.05 | 0.2 | 0.2 | 0.2 | 0.2 |
| Balance to 100% Moisture and/or Minors* | | | | | | | | |

*Brightener/SRP1/Na carboxymethylcellulose/photobleach/MgSO$_4$/PVPVI/suds suppressor/high molecular PEG/clay.

The pH of Formulations (I) through (VII) in Table 19-1 is from about 10 to about 11.5 and the pH of Formulation (VIII) in Table 19-1 is from 8-10. The tablet weight of Formulations (I) through (VIII) in Table 19-1 is from about 20 grams to about 30 grams.

Example 20

Liquid Hard Surface Cleaning Detergents

This Example provides various formulations for liquid hard surface cleaning detergents. The following liquid hard surface cleaning detergent compositions of the present invention are provided below. In each of these formulations, at least one protease variant provided herein is included at a concentration of from about 0.0001 to about 10 weight percent. In some alternative aspects, other concentrations will find use, as determined by the formulator, based on their needs.

TABLE 20-1

Liquid Hard Surface Cleaning Detergents

| Compound | Formulations | | | | | | |
|---|---|---|---|---|---|---|---|
| | I | II | III | IV | V | VI | VII |
| $C_9$-$C_{11}E_5$ | 2.4 | 1.9 | 2.5 | 2.5 | 2.5 | 2.4 | 2.5 |
| $C_{12}$-$C_{14}E_5$ | 3.6 | 2.9 | 2.5 | 2.5 | 2.5 | 3.6 | 2.5 |
| $C_7$-$C_9E_6$ | — | — | — | — | 8.0 | — | — |
| $C_{12}$-$C_{14}E_{21}$ | 1.0 | 0.8 | 4.0 | 2.0 | 2.0 | 1.0 | 2.0 |
| LAS | — | — | — | 0.8 | 0.8 | — | 0.8 |
| Sodium culmene sulfonate | 1.5 | 2.6 | — | 1.5 | 1.5 | 1.5 | 1.5 |
| Isachem ® AS | 0.6 | 0.6 | — | — | — | 0.6 | — |
| Na$_2$CO$_3$ | 0.6 | 0.13 | 0.6 | 0.1 | 0.2 | 0.6 | 0.2 |
| 3Na Citrate•2H$_2$O | 0.5 | 0.56 | 0.5 | 0.6 | 0.75 | 0.5 | 0.75 |
| NaOH | 0.3 | 0.33 | 0.3 | 0.3 | 0.5 | 0.3 | 0.5 |
| Fatty Acid | 0.6 | 0.13 | 0.6 | 0.1 | 0.4 | 0.6 | 0.4 |
| 2-butyl octanol | 0.3 | 0.3 | — | 0.3 | 0.3 | 0.3 | 0.3 |
| PEG DME-2000 ® | 0.4 | — | 0.3 | 0.35 | 0.5 | — | — |
| PVP | 0.3 | 0.4 | 0.6 | 0.3 | 0.5 | — | — |
| MME PEG (2000) ® | — | — | — | — | — | 0.5 | 0.5 |
| Jeffamine ® ED-2001 | — | 0.4 | — | — | 0.5 | — | — |
| PAAC | — | — | — | 0.03 | 0.03 | 0.03 | — |
| DETBCHD | 0.03 | 0.05 | 0.05 | — | — | — | — |
| nprE (optional) | 0.07 | — | 0.08 | 0.03 | — | 0.01 | 0.04 |
| PMN | — | 0.05 | — | — | 0.06 | — | — |
| Protease B (optional) | — | — | — | — | — | 0.01 | — |
| Amylase | 0.12 | 0.01 | 0.01 | — | 0.02 | — | 0.01 |

TABLE 20-1-continued

Liquid Hard Surface Cleaning Detergents

| Compound | Formulations | | | | | | |
|---|---|---|---|---|---|---|---|
| | I | II | III | IV | V | VI | VII |
| Lipase | — | 0.001 | — | 0.005 | — | 0.005 | — |
| Pectin Lyase | 0.001 | — | 0.001 | — | — | — | 0.002 |
| ZnCl2 | 0.02 | 0.01 | 0.03 | 0.05 | 0.1 | 0.05 | 0.02 |
| Calcium Formate | 0.03 | 0.03 | 0.01 | — | — | — | — |
| PB1 | — | 4.6 | — | 3.8 | — | — | — |
| Aldose Oxidase | 0.05 | — | 0.03 | — | 0.02 | 0.02 | 0.05 |
| Balance to 100% perfume/dye and/or water | | | | | | | |

The pH of Formulations (I) through (VII) in Table 20-1 is from about 7.4 to about 9.5.

Example 21

Cleaning Performance of BPN'-v36 Polypeptide Variants

BPN'-v36 polypeptide variants comprising two amino acid substitutions were constructed by standard PCR fusion using the BPN'-v36 variant as a backbone or parent sequence. For this purpose, two or three partially overlapping fragments were amplified by mutagenic primers prepared such that the primer encoded a desired substitution. PCR amplification reactions were carried out as described in Example 7 of Part I supra. The following BPN'-v36 double mutant variants (i.e., BPN'-v36 with the following two amino acid substitution) were constructed: Q019R-N025D, A001Y-Q275R, V004A-S249N, V004E-S260P, V004A-T55A, Y006F-S249C, Y006D-T55A, V008L-Q275R, Q010R-Q275K, L016Q-Q217H, H017R-T158A, S183D-Q206R, P210S-N212D, S018Y-V203A, S018K-V203I, Y021H-D259G, Y021H-D259R, K027R-N269D, K027R-N269T, S037P-S260F, S037T-S260P, D041E-N077D, D041G-N077E, G166V-S183T, N252S-L257H, V044A-Q206H, V044A-Q206K, V044A-Q206R, N076T-N212D, N076P-N212S, N077D-N252D, N077D-N252T, K141I-S248N, T158I-D259N, T158A-D259P, S161E-Q185H, K237M-H238R, G160A-D259G, G160R-D259V, G215R-D259R, G215D-D259V, N061D-Q206R, N061L-Q206H, S009L-N218S, S161E-S260T, Q019A-N109S, T022S-G166V, Y021H-N252H, P129S-K136R, T022S-T242S, N025K-H238R, N025D-Q185R, S037G-Q275H, K043S-N076S, K043N-Q217R, K043N-S163T, T055A-V147A, N061K-N252K, N062Y-G097D, Y021H-V084E, Y021H-S037E, N062Y-T244A, K027E-Y091F, A074S-P129Q, S249R-Q275R, I079V-Q217H, A098T-T158A, K027R-D120H, Q019R-Q185R, G131S-K265N, A133V-D259N, A144H-T244A, I035V-K043N, G160R-T244A, S161P-T253A, S163T-Q245L, K170R-D259G, S183T-S249R, N184Y-Y262N, V198L-D259G, A200T-H226L, Q206R-S260P, G211V-T244A, Q217R-T244A, L75I-N76D, S260P-Q275L, S260P-Q275R, Y262N-Q275R, V004A-Y006F, H017L-Q019A, N025D-V026A, N118G-V121A, V072F-L075I, S183T-R186K, V203A-Q217R, and S249R-Y262H. The cleaning performance of each of these variants was tested in a BMI microswatch cleaning assay in Detergent Composition 4 at pH 8 and 16° C. and egg microswatch cleaning assay in Detergent Composition 4 at pH 8 and 16° C. as described in Example 1 of Part I. Results are provided below.

The following BPN' protease variants were determined to have a PI value equal to or greater than 0.9 and equal or less than 1.0 relative to BPN'-v36 in a BMI microswatch cleaning assay in Detergent Composition 4 at pH 8 and 16° C.: BPN'-S024G-S053G-S078N-S101N-G128A-Y217Q amino acid sequence (SEQ ID NO:6) comprising at least one set of amino acid substitutions selected from the group consisting of S183T-S249R, N61D-Q206R, Y262N-Q275R, K43R-N76S, K170R-D259G, Y6F-S249C, Q19A-N109S, H17L-Q19A, Q19R-Q185R, S18Y-V203A, S161E-S260T, S18K-V203I, V4A-T55A, N252S-L257H, S249R-Y262H, N61L-Q206H, N184Y-Y262N, Q19R-N25D, A74S-P129Q, K27R-D120H, Y21H-N252H, K27R-N269D, A98T-T158A, I79V-Q217H, S9L-N218S, V4A-Y6F, S161P-T253A, V203A-Q217R, T22S-T242S, N76P-N212S, S37T-S260P, T55A-V147A, G160R-T244A, N25D-Q185R, G211V-T244A, A144H-T244A, Y21H-N252H, A1Y-Q275R, V198L-D259G, K141I-S248N, S183T-R186K, S161E-Q185H, P129S-K136R, K43N-S163T, S37G-Q275H, N62Y-T244A, and S260P-Q275R, wherein amino acid positions of the variant are numbered by correspondence with the sequence of SEQ ID NO:2. Such variants have enhanced proteolytic activity compared to BPN' (SEQ ID NO:2) and a greater PI value than that of BPN' in this assay. The invention includes a protease variant having enhanced proteolytic activity compared to BPN' (SEQ ID NO:2), a PI value of equal to or greater than 0.9 and equal to or less than 1.0 relative to BPN'-v36 in this assay, the variant comprising an amino acid sequence having at least 60%, 70%, 80%, 85%, 90%, 91%, 92%, 93%, 94%, 95%, 96%, 97%, 98%, or 99% identity to the sequence of SEQ ID NO:2 or SEQ ID NO:6 and comprising at least one set of amino acid substitutions selected from said group above, wherein amino acid positions of the variant are numbered by correspondence with amino acid positions of the SEQ ID NO:2 sequence. Also included are compositions, including, but not limited to, e.g., cleaning compositions, comprising at least one such variant and methods for cleaning utilizing at least one such protease variant as described in greater detail elsewhere herein.

Also provided is a subtilisin protease variant having enhanced proteolytic activity and a PI value of greater than 1.0 to about 5 compared to BPN' in a BMI microswatch cleaning assay in Detergent Composition 4 at pH 8 and 16° C., the variant comprising an amino acid sequence having at least 85%, 90%, 91%, 92%, 93%, 94%, 95%, 96%, 97%, 98%, or 99% identity to SEQ ID NO:2 or SEQ ID NO:6, wherein the variant comprises at least one substitution comprising at least one substitution selected from the group of X1Y, X4A, X6F, X9L, X17L, X18K/Y, X19A/R, X21H, X22S, X25D, X27R, X37G/T, X43N/R, X55A, X61D/L, X62Y, X74S, X76P/S, X79V, X98T, X109S, X120H, X129Q/S, X136R, X141I, X144H, X147A, X158A, X160R, X161E/P, X163T, X170R, X183T, X184Y, X185H/R, X186K, X198L, X203A/I, X206H/R, X211V, X212S, X217H/R, X218S, X242S, X244A, X248N, X249C/R, X252H/S, X253A, X257H, X259G, X260P/T, X262H/N, X269D, and X275H/R, and optionally at least one substitution selected from the group of A1Y, V4A, Y6F, S9L, H17L, S18K/Y, Q19A/R, Y21H, T22S, N25D, K27R, S37G/T, K43N/R, T55A, N61D/L, N62Y, A74S, N76P/S, I79V, A98T, N109S, D120H, P129Q/S, K136R, K141I, A144H, V147A, T158A, G160R, S161E/P, S163T, K170R, S183T, N184Y, Q185H/R, R186K, V198L, V203A/I, Q206H/R, G211V, N212S, Q217H/R, N218S, T242S, T244A, S248N, S249C/R, N252H/S, T253A, L257H, D259G, S260P/T, Y262H/N, N269D, and Q275H/R, wherein amino acid positions of the variant are numbered by correspondence with positions of the sequence of SEQ ID NO:2. Such variants have enhanced proteolytic activity compared to the BPN' (SEQ ID NO:2) and a PI value greater than that of BPN' in this assay. Also included are compositions, including, but not limited to, e.g., cleaning compositions, comprising at least one such variant and methods for cleaning utilizing at least one such protease variant as described in greater detail elsewhere herein.

The following BPN' subtilisin protease variants were determined to have a PI value equal or greater than 0.5 and less than 0.9 relative to BPN'-v36 in a BMI microswatch cleaning assay in Detergent Composition 4 at pH 8 and 16° C.: BPN'-S024G-S053G-S078N-S101N-G128A-Y217Q amino acid sequence (SEQ ID NO:6) comprising at least one set of amino acid substitutions selected from the group consisting of Y21H-D259G, A133V-D259N, I79V-Q217H, S18K-V203I, T158A-D259P, N61K-N252K, K43N-Q217R, T158A-D259P, Q206R-S260P, A133V-D259N, V198L-D259G, N61K-N252K, S161E-S260T, G160A-D259G, K43N-Q217R, A1Y-Q275R, A200T-H226L, Q217R-T244A, S260P-Q275R, Q206R-S260P, T158I-D259N, Q217R-T244A, L75I-N76D, S161E-Q185H, Y21H-S37E, S249R-Q275R, T158I-D259N, Y21H-S37E, N76T-N212D, S260P-Q275L, G131S-K265N, V4A-S249N, N25D-Q185N, K43R-N76S, S183D-Q206R, Q10R-Q275K, K43N-S163T, Q10R-Q275K, N25D-V26A, G131S-K265N, S260P-Q275L, K141I-S248N, L16Q-Q217H, S249R-Q275R, K27R-N269T, P210S-N212D, L75I-N76D, S183D-Q206R, N118G-V121A, G215D-D259V, N76T-N212D, K27R-N269T, N62Y-G97D, V4E-S260P, G215D-D259V, K27E-Y91F, Y6D-T55A, N77D-N252T, V4E-S260P, Y6D-T55A, N25K-H238R, V44A-Q206H, L16Q-Q217H, V44A-Q206R, V44A-Q206H, and S37P-S260F, wherein amino acid positions of the variant are numbered by correspondence with the sequence of SEQ ID NO:2. Such variants have proteolytic activity. The invention includes a protease variant having proteolytic activity, having enhanced proteolytic activity greater than that of BPN', and/or a PI value equal to or greater than 0.5 and less than 0.9 relative to BPN'-v36 in this assay, the variant comprising an amino acid sequence having at least 60%, 70%, 80%, 85%, 90%, 91%, 92%, 93%, 94%, 95%, 96%, 97%, 98%, or 99% identity to the sequence of SEQ ID NO:2 or SEQ ID NO:6 and comprising at least one set of acid substitutions selected from said group above, wherein amino acid positions of the variant are numbered by correspondence with amino acid positions of the SEQ ID NO:2 sequence. Also included are compositions, including, but not limited to, e.g., cleaning compositions, comprising at least one such variant and methods for cleaning utilizing at least one such protease variant as described in greater detail elsewhere herein.

The following BPN'-v36 variants were determined to have a PI value greater than 1.0, at least 1.1, at least 1.2, at least 1.3, at least 1.4, at least 1.5, at least 1.6, at least 1.7, at least 1.8, at least 1.9, at least 2, from greater than 1.0 to about 10, from greater than 1.0 to about 8, or from greater than 1.0 to about 5 relative to BPN'-v36 in an egg microswatch cleaning assay in Detergent Composition 4 at pH 8 and 16° C.: BPN'-S024G-S053G-S078N-S101N-G128A-Y217Q amino acid sequence (SEQ ID NO:6) comprising at least one set of amino acid substitutions selected from the group consisting of Y21H-D259G, S183T-S249R, N61D-Q206R, Y262N-Q275R, K043R-N076S, A133V-D259N, and I079V-Q217H, wherein amino acid positions of the variant are numbered by correspondence with the sequence of SEQ ID NO:2. Such variants have enhanced proteolytic activity compared to the BPN', BPN'-v3, and BPN'-v36, and a greater PI value than that of BPN', BPN'-v3 and BPN'-v36 in this assay. The invention includes a protease variant having enhanced proteolytic activity compared to BPN' (SEQ ID NO:2), enhanced proteolytic activity compared to BPN', BPN'-v3, and BPN'-v36, a PI value of greater than 1.0 to about 5 relative to BPN'-v3, and/or a PI value of greater than 1.0 to about 5 relative to BPN'-v36 in this assay, the variant comprising an amino acid sequence having at least 60%, 70%, 80%, 85%, 90%, 91%, 92%, 93%, 94%, 95%, 96%, 97%, 98%, or 99% identity to the sequence of SEQ ID NO:2 or SEQ ID NO:6 and comprising at least one set of amino acid substitutions selected from said group above, wherein amino acid positions of the variant are numbered by correspondence with amino acid positions of the SEQ ID NO:2 sequence. Also included are compositions, including, but not limited to, e.g., cleaning compositions, comprising at least one such variant and methods for cleaning utilizing at least one such protease variant as described in greater detail elsewhere herein.

Also provided is a subtilisin protease variant having enhanced proteolytic activity and/or a PI value of greater than 1.0 to about 5 compared to BPN' in a BMI microswatch cleaning assay in Detergent Composition 4 at pH 8 and 16° C., the variant comprising an amino acid sequence having at least 85%, 90%, 91%, 92%, 93%, 94%, 95%, 96%, 97%, 98%, or 99% identity to SEQ ID NO:2 or SEQ ID NO:6, wherein the variant comprises at least one substitution comprising at least one substitution selected from the group of X021H, X043R, X061D, X076S, X079V, X133V, X183T, X206R, X217H, X249R, X259G/N, X262N, and X275R, and optionally at least one substitution selected from the group of Y021H, K043R, N061D, N076S, I079V, A133V, S183T, Q206R, Q217H, S249R, D259G/N, Y262N, and Q275R, wherein amino acid positions of the variant are numbered by correspondence with positions of the sequence of SEQ ID NO:2. Such variants have enhanced proteolytic activity compared to the BPN' (SEQ ID NO:2) and a PI value greater than that of BPN' in this assay. Also included are compositions, including, but not limited to, e.g., cleaning compositions, comprising at least one such variant and methods for cleaning utilizing at least one such protease variant as described in greater detail elsewhere herein.

The following BPN'-v36 variants were determined to have a PI value equal to or greater than 0.5 and less than or equal to 1.0 relative to BPN'-v36 in an egg microswatch cleaning assay in Detergent Composition 4 at pH 8 and 16° C.: BPN'-S024G-S053G-S078N-S101N-G128A-Y217Q amino acid sequence (SEQ ID NO:6) comprising at least one set of amino acid substitutions selected from the group consisting of K170R-D259G, S18K-V203I, Y6F-S249C, Q19A-N109S, H17L-Q19A, Q19R-Q185R, S18Y-V203A, N61D-Q206R, S161E-S260T, S18K-V203I, V4A-T55A, N252S-L257H, S249R-Y262H, N61L-Q206H, N184Y-Y262N, Q19R-N25D, S249R-Y262H, A74S-P129Q, T158A-D259P, H17L-Q19A, K27R-D120H, V4A-T55A, N61K-N252K, Y21H-

N252H, K27R-N269D, K43N-Q217R, T158A-D259P, Q206R-S260P, K27R-N269D, A98T-T158A, 179V-Q217H, S9L-N218S, V4A-Y6F, S161P-T253A, V203A-Q217R, T22S-T242S, N76P-N212S, A133V-D259N, S37T-S260P, T55A-V147A, V198L-D259G, Q19R-Q185R, V4A-Y6F, Q19A-N109S, Y262N-Q275R, G160R-T244A, Q19R-N25D, N25D-Q185R, N61K-N252K, S161E-S260T, A98T-T158A, N61L-Q206H, G211V-T244A, S9L-N218S, A144H-T244A, A144H-T244A, S18Y-V203A, Y21H-N252H, A74S-P129Q, G160A-D259G, K43N-Q217R, A1Y-Q275R, A1Y-Q275R, A200T-H226L, Q217R-T244A, S260P-Q275R, Q206R-S260P, K141I-S248N, S183T-R186K, T158I-D259N, S37T-S260P, K27R-D120H, T22S-T242S, Q217R-T244A, S161E-Q185H, P129S-K136R, G211V-T244A, N76P-N212S, L75I-N76D, S161E-Q185H, Y21H-S37E, S249R-Q275R, G160A-D259G, K43N-S163T, T158I-D259N, Y21H-S37E, S37G-Q275H, S161P-T253A, N76T-N212D, S260P-Q275L, Y6F-S249C, N184Y-Y262N, G131S-K265N, V4A-S249N, N25D-Q185R, N252S-L257H, K43R-N76S, S183D-Q206R, G160R-T244A, Q10R-Q275K, S37G-Q275H, K43N-S163T, Q10R-Q275K, N25D-V26A, P129S-K136R, G131S-K265N, S260P-Q275L, K141I-S248N, T22S-G166V, N62Y-T244A, L16Q-Q217H, S249R-Q275R, S260P-Q275R, K27R-N269T, P210S-N212D, L75I-N76D, S183D-Q206R, N118G-V121A, G215D-D259V, N76T-N212D, V4A-S249N, K27R-N269T, G166V-S183T, N62Y-G97D, V4E-S260P, G215D-D259V, K27E-Y91F, Y21H-D259R, Y6D-T55A, N77D-N252T, V4E-S260P, Y6D-N252T, Y21H-D259R, N25K-H238R, N77D-N252D, V44A-Q206H, L16Q-Q217H, V72F-L75I, S37P-S260F, V72F-L75I, N77D-N252D, V44A-Q206R, S163T-Q245L, V44A-Q206H, V44A-Q206R, S37P-S260F, G215R-D259R, V44A-Q206K, and V44A-Q206K, wherein amino acid positions of the variant are numbered by correspondence with the sequence of SEQ ID NO:2. Such variants have proteolytic activity. The invention includes a protease variant having proteolytic activity and/or a PI value equal to or greater than 0.5 and equal to or less than 1.0 relative to BPN'-v36 in this assay, the variant comprising an amino acid sequence having at least 60%, 70%, 80%, 85%, 90%, 91%, 92%, 93%, 94%, 95%, 96%, 97%, 98%, or 99% identity to the sequence of SEQ ID NO:2 or SEQ ID NO:6 and comprising at least one set of acid substitutions selected from said group above, wherein amino acid positions of the variant are numbered by correspondence with amino acid positions of the SEQ ID NO:2 sequence. Also included are compositions, including, but not limited to, e.g., cleaning compositions, comprising at least one such variant and methods for cleaning utilizing at least one such protease variant as described in greater detail elsewhere herein.

Example 22

Cleaning Performance of Additional BPN'-v36 Polypeptide Variants

The following BPN'-v36 variants were synthesized at DNA2.0 (Menlo Park, Calif.) using the pHPLT-BPN'-v36 plasmid containing the BPN' expression cassette served as template DNA (parent plasmid) for cloning: N109G-A128S-S224A, N109G-A128S-S224A-N243V, A88T-N109G-A116T-A128S-S224A-N243V, N61G-N109G-A128S-S224A, N61G-N109G-A128S-S224A-N243V, N61G-A88T-N109G-A116T-A128S-S224A-N243V, N109Q-A128S-S224A, N109Q-A128S-S224A-N243V, A88T-N109Q-A116T-A128S-S224A-N243V, N109S-A128S-S224A, N109S-A128S-S224A-N243V, A88T-N109S-A116T-A128S-S224A-N243V, N109M-A128S-S224A, N109M-A128S-S224A-N243V, A88T-N109M-A116T-A128S-S224A-N243V, N109G-A114S-A128S, N109G-A114S-A128S-N243V, A88T-N109G-A114S-A116T-A128S-N243V, N109G-A114S-A128S-S224A, N109G-A114S-A128S-S224A-N243V, N109G-A128S-S183V, N109G-A128S-S183L, N109G-A128S-S183L-S224A, N109G-A114S-A128S-S183L-S224A, A88T-N109G-A114S-A116T-A128S-S183L-S224A-N243V, N76D-N109G-A128S-S224A, N101Q-N109Q-A128S-S224A-N243V, N101Q-N109Q-A128S-P129S-S130T-S224A-N243V, N109G-A128S-P129S-S130T-S224A-N243V, S33T-A128S-N218S, S33T-N109G-A128S-N218S-N243V, S33T-N61G-N109G-A128S-N218S-N243V, S33T-N109G-A128S-G169A-N218S-N243V, S33T-S63G-N109G-A128S-N218S-N243V, S33T-N76D-N109G-A128S-N218S-N243V, S33T-S63G-N109G-A128S-G169A-N218S-N243V, I31L-S33T-S63G-N109G-A128S-G169A-N218S-N243V, S33T-N61G-S63G-N109G-A128S-N218S-N243V, S33T-N61G-A88T-N109G-A116T-A128S-N218S-N243V, S33T-N61G-S63G-N109G-A128S-G131H-G169A-N218S-N243V, S33T-N61P-S63G-N109G-A128S-G131H-G169A-N218S-N243V, S33T-N109G-A128S-N218S-S224A-N243V, S63G-N109Q-A128S-S224A-N243V, S63G-N109Q-A128S-G131H-S224A-N243V, N61P-S63G-N109Q-A128S-S224A-N243V, N61P-S63G-N109Q-A128S-G131H-S224A-N243V, A1G-N61P-S63G-N109Q-A128S-G131H-S224A-N243V, I31L-N61P-S63G-N109Q-A128S-G131H-S224A-N243V, N61P-S63G-N109Q-A128S-G131H-S224A-N243V-S249Q, S33T-T55P-N61P-S63G-N109Q-A128S-G131H-S224A-N243V, S33T-T55P-N61P-S63G-A88T-N109G-A116T-A128S-G131H-S224A-N243V, S33T-T55P-N61P-S63G-A88T-N109G-A116T-A128S-G131H-S224A-N243V-S249Q, A1G-I31L-S33T-T55P-N61P-S63G-A88T-N109G-A116T-A128S-G131H-S224A-N243V-S249Q, N61P-S63G-N109Q-A128S-G131H-G169A-S224A-N243V-S249Q, and A1G-I31L-S33T-T55P-N61P-S63G-A88T-N109G-A116T-A128S-G131H-G169A-S224A-N243V-S249Q.

The variants were grown for protein expression as described in Example 11 of Part I. These variants were tested for their performance in the BMI microswatch cleaning assay in Detergent Composition 4 at pH 8 and 16° C., the egg microswatch cleaning assay in Detergent Composition 4 at pH 8 and 16° C., and the AAPF assay as described in Example 1 of Part I. Results are provided below.

The following BPN'-v36 variants were determined to have a PI value greater than 1.0, at least 1.1, at least 1.2, at least 1.3, at least 1.4, at least 1.5, at least 1.6, at least 1.7, at least 1.8, at least 1.9, at least 2, from greater than 1.0 to about 10, from greater than 1.0 to about 8, or from greater than 1.0 to about 5 relative to BPN'-v36 in a BMI microswatch cleaning assay in Detergent Composition 4 at pH 8 and 16° C.: BPN'-S024G-S053G-S078N-S101N-G128A-Y217Q amino acid sequence (SEQ ID NO:6) comprising at least one set of amino acid substitutions selected from the group consisting of N61P-S63G-N109Q-A128S-S224A-N243V, A88T-N109G-A114S-A116T-A128S-N243V, A88T-N109G-A114S-A116T-A128S-S183L-S224A-N243V, N109G-A128S-S183V, N109G-A128S-N243V-K256R, N109M-A128S-S224A, A88T-N109S-A116T-A128S-S224A-N243V, N109Q-A128S-S224A-N243V, A88T-N109M-A116T-A128S-S224A-N243V, N109S-A128S-S224A-N243V, A88T-N109G-A116T-N243V, N101Q-N109Q-A128S-S224A-N243V, N109G-A116T-N243V-K256R, N109G-A128S-P129S-S130T-S224A-N243V, and A88T-N109Q-

A116T-A128S-S224A-N243V, wherein amino acid positions of the variant are numbered by correspondence with positions of the sequence of SEQ ID NO:2. Such variants have enhanced proteolytic activity compared to the BPN', BPN'-v3, and BPN'-v36, and a greater PI value than that of BPN', BPN'-v3 and BPN'-v36 in this assay. The invention includes a protease variant having enhanced proteolytic activity compared to BPN' (SEQ ID NO:2), enhanced proteolytic activity compared to BPN', BPN'-v3, and BPN'-v36, a PI value of greater than 1.0 to about 5 relative to BPN'-v3, and/or a PI value of greater than 1.0 to about 5 relative to BPN'-v36 in this assay, the variant comprising an amino acid sequence having at least 60%, 70%, 80%, 85%, 90%, 91%, 92%, 93%, 94%, 95%, 96%, 97%, or 98% identity to the sequence of SEQ ID NO:2 or SEQ ID NO:6 and comprising at least one set of amino acid substitutions selected from said group above, wherein amino acid positions of the variant are numbered by correspondence with amino acid positions of the SEQ ID NO:2 sequence. Also included are compositions, including, but not limited to, e.g., cleaning compositions, comprising at least one such variant and methods for cleaning utilizing at least one such protease variant as described in greater detail elsewhere herein.

Also provided is a subtilisin protease variant having enhanced proteolytic activity compared to BPN'-v36 and/or a PI value of equal to or greater than 1.0 to about 5 compared to BPN'-v36 in a BMI microswatch cleaning assay in Detergent Composition 4 at pH 8 and 16° C., the variant comprising an amino acid sequence having at least 85%, 90%, 91%, 92%, 93%, 94%, 95%, 96%, 97%, 98%, or 99% identity to SEQ ID NO:2 or SEQ ID NON:6, wherein the variant comprises at least one substitution comprising at least one substitution selected from the group of X61G/P/S, X63G, X88T, X101Q, X109G/M/Q/S, X114S, X116T, X128S, X129S, X130T, X158S, X183L/V, X224A, X243V, X248A, and X256R, and optionally at least one substitution selected from the group of N61G/P/S, S63G, A88T, N101Q, N109G/M/Q/S, A114S, A116T, A128S, P129S, S130T, T158S, S183L/V, S224A, N243V, S248A, and K256R, wherein amino acid positions of the variant are numbered by correspondence with positions of the sequence of SEQ ID NO:2. Such variants have enhanced proteolytic activity compared to the BPN' (SEQ ID NO:2) BPN'-v3, and BPN'-v36 and a PI value greater than that of BPN', BPN'-v3, and BPN'-v36 in this assay. Also included are compositions, including, but not limited to, e.g., cleaning compositions, comprising at least one such variant and methods for cleaning utilizing at least one such protease variant as described in greater detail elsewhere herein.

The following BPN'-v36 variants were determined to have a PI value equal to or greater than 0.9 and equal to or less than 1.0 relative to BPN'-v36 in a BMI microswatch cleaning assay in Detergent Composition 4 at pH 8 and 16° C.: BPN'-S024G-S053G-S078N-S101N-G128A-Y217Q amino acid sequence (SEQ ID NO:6) comprising at least one set of amino acid substitutions selected from the group consisting of G24S-G53S-N78S-G97A-N101S-A128S, G24S-G53S-N78S-G97A-N101S, S33T-T55P-N61P-S63G-A88T-N109G-A116T-A128S-G131H-S224A-N243V, S33T-N61G-S63G-N109G-A128S-N218S-N243V, S33T-S63G-N109G-A128S-N218S-N243V, S33T-T55P-N61P-S63G-N109Q-A128S-G131H-S224A-N243V, N61P-S63G-N109Q-A128S-G131H-G169A-S224A-N243V-S249Q, S33T-N61G-A88T-N109G-A116T-A128S-N218S-N243V, S33T-N109G-A128S-N218S-N243V, S33T-N76D-N109G-A128S-N218S-N243V, S33T-N76D-N109G-A128S-N218S-N243V-S248N-K256R, S33T-N61G-N109G-A128S-N218S-N243V, S33T-A128S-N218S, A1G-N61P-S63G-N109Q-A128S-G131H-S224A-N243V, N61P-S63G-N109Q-A128S-G131H-S224A-N243V-S249Q, N61P-S63G-N109Q-A128S-G131H-S224A-N243V, S63G-N109Q-A128S-G131H-S224A-N243V, N109G-A114S-A128S, N109G-A114S-A128S-S183L-S224A, N109G-A114S-A128S-S224A, N109G-A114S-A128S-S224A-N243V, A88T-N109G-A116T-A128S-S224A-N243V, N61G-A88T-N109G-A116T-A128S-S224A-N243V, N109G-A114S-A128S-N243V, N109G-A128S-S224A-N243V, N109G-A128S-S224A, N109G-A128S-S183L-S224A, N61G-N109G-A128S-S224A, N109G-A128S-S183L, S33T-N76D, N109S-A128S-S224A, N101Q-N109Q-A128S-P129S-S130T-S224A-N243V, S63G-N109Q-A128S-S224A-N243V, N109M-A128S-S224A-N243V, S63G-N109G, N109G-K256R, S63G-N76D, S33T-N109G-A128S-G169A-N218S-N243V, and S33T-N109G-A128S-N218S-S224A-N243V, wherein amino acid positions of the variant are numbered by correspondence with the sequence of SEQ ID NO:2. Such variants have proteolytic activity. The invention includes a protease variant having proteolytic activity, enhanced proteolytic activity compared to BPN', and/or a PI value equal to or greater than 0.9 and less or equal to 1.0 relative to BPN'-v36 in this assay, the variant comprising an amino acid sequence having at least 60%, 70%, 80%, 85%, 90%, 91%, 92%, 93%, 94%, 95%, 96%, 97%, or 98% identity to the sequence of SEQ ID NO:2 or SEQ ID NO:6 and comprising at least one set of acid substitutions selected from said group above, wherein amino acid positions of the variant are numbered by correspondence with amino acid positions of the SEQ ID NO:2 sequence. Also included are compositions, including, but not limited to, e.g., cleaning compositions, comprising at least one such variant and methods for cleaning utilizing at least one such protease variant as described in greater detail elsewhere herein.

The following BPN'-v36 variants were determined to have a PI value equal to or greater than 0.5 and less than 0.9 relative to BPN'-v36 in a BMI microswatch cleaning assay in Detergent Composition 4 at pH 8 and 16° C.: BPN'-S024G-S053G-S078N-S101N-G128A-Y217Q amino acid sequence (SEQ ID NO:6) comprising at least one set of amino acid substitutions selected from the group consisting of I31L-S33T-S63G-N109G-A128S-G169A-N218S-N243V, A1G-I31L-S33T-T55P-N61P-S63G-A88T-N109G-A116T-A128S-G131H-G169A-S224A-N243V-S249Q, S33T-N61G-S63G-N109G-A128S-G131H-G169A-N218S-N243V, S33T-S63G-N109G-A128S-G169A-N218S-N243V, S33T-T55P-N61P-S63G-A88T-N109G-A116T-A128S-G131H-S224A-N243V-S249Q, S33T-N76D-A128S-N218S, N76D-N109G-A128S-S224A, and S33T-N61P-S63G-N109G-A128S-G131H-G169A-N218S-N243V, wherein amino acid positions of the variant are numbered by correspondence with the sequence of SEQ ID NO:2. Such variants have proteolytic activity. The invention includes a protease variant having proteolytic activity and/or a PI value equal to or greater than 0.5 and less than 0.9 relative to BPN'-v36 in this assay, the variant comprising an amino acid sequence having at least 60%, 70%, 80%, 85%, 90%, 91%, 92%, 93%, 94%, 95%, 96%, 97%, or 98% identity to the sequence of SEQ ID NO:2 or SEQ ID NO:6 and comprising at least one set of acid substitutions selected from said group above, wherein amino acid positions of the variant are numbered by correspondence with amino acid positions of the SEQ ID NO:2 sequence. Also included are compositions, including, but not limited to, e.g., cleaning compositions, comprising at least one such variant and methods for cleaning utilizing at least one such protease variant as described in greater detail elsewhere herein.

The following BPN'-v36 variants were determined to have a PI value greater than 1.0, at least 1.1, at least 1.2, at least 1.3, at least 1.4, at least 1.5, at least 1.6, at least 1.7, at least 1.8, at least 1.9, at least 2, from greater than 1.0 to about 10, from greater than 1.0 to about 8, or from greater than 1.0 to about 5 relative to BPN'-v36 in an egg microswatch cleaning assay in Detergent Composition 4 at pH 8 and 16° C.: BPN'-S024G-S053G-S078N-S101N-G128A-Y217Q amino acid sequence (SEQ ID NO:6) comprising at least one set of amino acid substitutions selected from the group consisting of S33T-T55P-N61P-S63G-A88T-N109G-A116T-A128S-G131H-S224A-N243V, S33T-N61G-S63G-N109G-A128S-N218S-N243V, S33T-S63G-N109G-A128S-N218S-N243V, N61P-S63G-N109Q-A128S-G131H-G169A-S224A-N243V-S249Q, S33T-N61G-A88T-N109G-A116T-A128S-N218S-N243V, S33T-N109G-A128S-N218S-N243V, S33T-A128S-N218S, A1G-N61P-S63G-N109Q-A128S-G131H-S224A-N243V, N61P-S63G-N109Q-A128S-G131H-S224A-N243V-S249Q, S63G-N109Q-A128S-G131H-S224A-N243V, N61P-S63G-N109Q-A128S-S224A-N243V, A88T-N109G-A114S-A116T-A128S-N243V, A88T-N109G-A114S-A116T-A128S-S183L-S224A-N243V, N109G-A114S-A128S, N109G-A114S-A128S-S183L-S224A, N109G-A114S-A128S-S224A, N109G-A114S-A128S-S224A-N243V, A88T-N109G-A116T-A128S-S224A-N243V, N61G-A88T-N109G-A116T-A128S-S224A-N243V, N109G-A128S-S183V, N109G-A114S-A128S-N243V, N109G-A128S-N243V-S248A, N109G-A128S-S224A-N243V, N109G-A128S-N243V-K256R, N109G-A128S-S224A, N109G-A128S-S183L-S224A, N61G-N109G-A128S-S224A, N109M-A128S-S224A, A88T-N109S-A116T-A128S-S224A-N243V, N109M-A128S-S224A-N243V, S63G-A128S, A88T-N109G-A116T-N243V, N101Q-N109G-A128S-S224A-N243V, N109G-A116T-N243V-K256R, N109G-A116T, S63G-N109G, A88T-N109G, N109G-K256R, N61G-N109G-N243V, S33T-N109G-A128S-G169A-N218S-N243V, S33T-N109G-A128S-N218S-S224A-N243V, N109G-A128S-P129S-S130T-S224A-N243V, and A88T-N109Q-A116T-A128S-S224A-N243V, wherein amino acid positions of the variant are numbered by correspondence with the sequence of SEQ ID NO:2. Such variants have enhanced proteolytic activity compared to the BPN', BPN'-v3, and BPN'-v36, and a greater PI value than that of BPN', BPN'-v3 and BPN'-v36 in this assay. The invention includes a protease variant having enhanced proteolytic activity compared to BPN' (SEQ ID NO:2), enhanced proteolytic activity compared to BPN', BPN'-v3, and BPN'-v36, a PI value of greater than 1.0 to about 5 relative to BPN'-v3, and/or a PI value of greater than 1.0 to about 5 relative to BPN'-v36 in this assay, the variant comprising an amino acid sequence having at least 60%, 70%, 80%, 85%, 90%, 91%, 92%, 93%, 94%, 95%, 96%, 97%, or 98% identity to the sequence of SEQ ID NO:2 or SEQ ID NO:6 and comprising at least one set of amino acid substitutions selected from said group above, wherein amino acid positions of the variant are numbered by correspondence with amino acid positions of the SEQ ID NO:2 sequence. Also included are compositions, including, but not limited to, e.g., cleaning compositions, comprising at least one such variant and methods for cleaning utilizing at least one such protease variant as described in greater detail elsewhere herein.

Also provided is a subtilisin protease variant having enhanced proteolytic activity compared to BPN'-v36 and/or a PI value of greater than 1.0 to about 5 compared to BPN'-v36 in an egg microswatch cleaning assay in Detergent Composition 4 at pH 8 and 16° C., the variant comprising an amino acid sequence having at least 85%, 90%, 91%, 92%, 93%, 94%, 95%, 96%, 97%, 98%, or 99% identity to SEQ ID NO:2 or SEQ ID NO:6, wherein the variant comprises at least one substitution comprising at least one substitution selected from the group of X1G, X33T, X55P, X61G/P/S, X63G, X76D, X88T, X101Q, X109G/M/Q/S, X114S, X116T, X128S, X129S, X130T, X131H, X158S, X169A, X183L/V, X218S, X224A, X243V, X248A/N, X249Q, X256R, and optionally at least one substitution selected from the group of A1G, S33T, T55P, N61G/P/S, S63G, N76D, A88T, N101Q, N109G/M/Q/S, A114S, A116T, A128S, P129S, S130T, G131H, T158S, G169A, S183L/V, N218S, S224A, N243V, S248A/N, S249Q, K256R, wherein amino acid positions of the variant are numbered by correspondence with positions of the sequence of SEQ ID NO:2. Such variants have enhanced proteolytic activity compared to the BPN', BPN'-v3, and BPN'-v36 and a PI value greater than that of BPN', BPN'-v3, and BPN'-v36 in this assay. Also included are compositions, including, but not limited to, e.g., cleaning compositions, comprising at least one such variant and methods for cleaning utilizing at least one such protease variant as described in greater detail elsewhere herein.

The following BPN'-v36 variant was determined to have a PI value equal to or greater than 0.5 and equal to or less than 1.0 relative to BPN'-v36 in an egg BMI microswatch cleaning assay in Detergent Composition 4 at pH 8 and 16° C.: BPN'-S024G-S053G-S078N-S101N-G128A-Y217Q amino acid sequence (SEQ ID NO:6) comprising amino acid substitutions selected from the group consisting of substitutions S33T-N76D-A128S-N218S, N76D-N109G-A128S-S224A and S063G-N76D, wherein amino acid positions of the variant are numbered by correspondence with the sequence of SEQ ID NO:2. Such variants have proteolytic activity. The invention includes a protease variant having proteolytic activity and/or a PI value equal to or greater than 0.5 and equal to or less than 1.0 relative to BPN'-v36 in this assay, the variant comprising an amino acid sequence having at least 60%, 70%, 80%, 85%, 90%, 91%, 92%, 93%, 94%, 95%, 96%, 97%, or 98% identity to the sequence of SEQ ID NO:2 or SEQ ID NO:6 and comprising amino acid substitutions selected from the group consisting of S33T-N76D-A128S-N218S, N76D-N109G-A128S-S224A, and S063G-N076D, wherein amino acid positions of the variant are numbered by correspondence with amino acid positions of the SEQ ID NO:2 sequence. Also included are compositions, including, but not limited to, e.g., cleaning compositions, comprising at least one such variant and methods for cleaning utilizing at least one such protease variant as described in greater detail elsewhere herein.

The following BPN'-v36 variants were determined to have a PI value greater than 1.0, at least 1.1, at least 1.2, at least 1.3, at least 1.4, at least 1.5, at least 1.6, at least 1.7, at least 1.8, at least 1.9, at least 2, from greater than 1.0 to about 10, from greater than 1.0 to about 8, or from greater than 1.0 to about 5 relative to BPN'-v36 in an AAPF proteolytic assay: BPN'-S024G-S053G-S078N-S101N-G128A-Y217Q amino acid sequence (SEQ ID NO:6) comprising at least one set of amino acid substitutions selected from the group consisting of G24S-G53S-N78S-G97A-N101S-A128S, I31L-S33T-S563G-N109G-A128S-G169A-N218S-N243V, A1G-I31L-S33T-T55P-N61P-S63G-A88T-N109G-A116T-A128S-G131H-G169A-S224A-N243V-S249Q, S33T-N61G-S63G-N109G-A128S-G131H-G169A-N218S-N243V, S33T-S63G-N109G-A128S-G169A-N218S-N243V, S33T-T55P-N61P-S63G-A88T-N109G-A116T-A128S-G131H-S224A-N243V, S33T-T55P-N61P-S63G-A88T-N109G-A116T-A128S-G131H-S224A-N243V-S249Q, S33T-N61G-S63G-N109G-A128S-N218S-N243V, S33T-S63G-N109G-

A128S-N218S-N243V, S33T-T55P-N61P-S63G-N109Q-A128S-G131H-S224A-N243V, N61P-S63G-N109Q-A128S-G131H-G169A-S224A-N243V-S249Q, S33T-N61G-A88T-N109G-A116T-A128S-N218S-N243V, S33T-N109G-A128S-N218S-N243V, S33T-N76D-N109G-A128S-N218S-N243V, S33T-N76D-N109G-A128S-N218S-N243V-S248N-K256R, S33T-N61G-N109G-A128S-N218S-N243V, S33T-N76D-A128S-N218S, S33T-A128S-N218S, A1G-N61P-S63G-N109Q-A128S-G131H-S224A-N243V, N61P-S63G-N109Q-A128S-G131H-S224A-N243V-S249Q, N61P-S63G-N109Q-A128S-G131H-S224A-N243V, S63G-N109Q-A128S-G131H-S224A-N243V, N61P-S63G-N109Q-A128S-S224A-N243V, A88T-N109G-A114S-A116T-A128S-N243V, A88T-N109G-A114S-A116T-A128S-S183L-S224A-N243V, N109G-A114S-A128S, N109G-A114S-A128S-S183L-S224A, N109G-A114S-A128S-S224A, N109G-A114S-A128S-S224A-N243V, A88T-N109G-A116T-A128S-S224A-N243V, N61G-A88T-N109G-A116T-A128S-S224A-N243V, N109G-A128S-S183V, N109G-A114S-A128S-N243V, N109G-A128S-N243V-S248A, N109G-A128S-S224A-N243V, N109G-A128S-N243V-K256R, N109G-A128S-S224A, N109G-A128S-S183L-S224A, N61G-N109G-A128S-S224A, N76D-N109G-A128S-S224A, N109M-A128S-S224A, N109G-A128S-S183L, S33T-N76D, A88T-N109S-A116T-A128S-S224A-N243V, N109Q-A128S-S224A-N243V, N109S-A128S-S224A, A88T-N109M-A116T-A128S-S224A-N243V, N101Q-N109Q-A128S-P129S-S130T-S224A-N243V, S63G-N109Q-A128S-S224A-N243V, N109M-A128S-S224A-N243V, S63G-A128S, N109S-A128S-S224A-N243V, A88T-N109G-A116T-N243V, N61S-N109G-N243V, N101Q-N109Q-A128S-S224A-N243V, N109G-A116T-N243V-K256R, A88T-N109G-A116T-T158S-N243V-K256R, N109G-A116T, S63G-N109G, A88T-N109G, N109G-K256R, N61G-N109G-N243V, S33T-N61P-S63G-N109G-A128S-G131H-G169A-N218S-N243V, S33T-N109G-A128S-G169A-N218S-N243V, S33T-N109G-A128S-N218S-S224A-N243V, N109G-A128S-P129S-S130T-S224A-N243V, and A88T-N109Q-A116T-A128S-S224A-N243V, wherein amino acid positions of the variant are numbered by correspondence with the sequence of SEQ ID NO:2. Such variants have enhanced proteolytic activity compared to the BPN', BPN'-v3, and BPN'-v36, and a greater PI value than that of BPN', BPN'-v3 and BPN'-v36 in this assay. The invention includes a protease variant having enhanced proteolytic activity compared to BPN' (SEQ ID NO:2), enhanced proteolytic activity compared to BPN', BPN'-v3, and BPN'-v36, a PI value of greater than 1.0 to about 5 relative to BPN'-v3, and/or a PI value of greater than 1.0 to about 5 relative to BPN'-v36 in this assay, the variant comprising an amino acid sequence having at least 60%, 70%, 80%, 85%, 90%, 91%, 92%, 93%, 94%, 95%, 96%, 97%, or 98% identity to the sequence of SEQ ID NO:2 or SEQ ID NO:6 and comprising at least one set of amino acid substitutions selected from said group above, wherein amino acid positions of the variant are numbered by correspondence with amino acid positions of the SEQ ID NO:2 sequence. Also included are compositions, including, but not limited to, e.g., cleaning compositions, comprising at least one such variant and methods for cleaning utilizing at least one such protease variant as described in greater detail elsewhere herein.

Also provided is a subtilisin protease variant having enhanced proteolytic activity compared to BPN'-v36 and/or a PI value of greater than 1.0 to about 5 compared to BPN'-v36 in An AAPF proteolytic assay, the variant comprising an amino acid sequence having at least 85%, 90%, 91%, 92%, 93%, 94%, 95%, 96%, 97%, 98%, or 99% identity to SEQ ID NO:2 or SEQ ID NO:6, wherein the variant comprises at least one substitution comprising at least one substitution selected from the group of X1G, X31L, X33T, X55P, X61G/P/S, X63G, X76D, X88T, X101Q, X109G/M/Q/S, X114S, X116T, X128S, X129S, X130T, X131H, X158S, X169A, X183L/V, X218S, X224A, X243V, X248A/N, X249Q, and X256R, and optionally at least one substitution selected from the group of A1G, I31L, S33T, T55P, N61G/P/S, S63G, N76D, A88T, N101Q, N109G/M/Q/S, A114S, A116T, A128S, P129S, S130T, G131H, T158S, G169A, S183L/V, N218S, S224A, N243V, S248A/N, S249Q, and K256R, wherein amino acid positions of the variant are numbered by correspondence with positions of the sequence of SEQ ID NO:2. Such variants have enhanced proteolytic activity compared to the BPN' (SEQ ID NO:2) BPN'-v3, and BPN'-v36 and a PI value greater than that of BPN', BPN'-v3, and BPN'-v36 in this assay. Also included are compositions, including, but not limited to, e.g., cleaning compositions, comprising at least one such variant and methods for cleaning utilizing at least one such protease variant as described in greater detail elsewhere herein.

The following BPN'-v36 variant was determined to have a PI value equal to or greater than 0.5 and equal to or less than 1.0 relative to BPN'-v36 in an AAPF proteolytic assay: BPN'-S024G-S053G-S078N-S101N-G128A-Y217Q amino acid sequence (SEQ ID NO:6) comprising amino acid substitutions G24S-G53S-N78S-G97A-N101S or S063G-N76D, wherein amino acid positions of the variant are numbered by correspondence with the sequence of SEQ ID NO:2. Such variants have proteolytic activity. The invention includes a protease variant having proteolytic activity and/or a PI value equal to or greater than 0.5 and equal to or less than 1.0 relative to BPN'-v36 in this assay, the variant comprising an amino acid sequence having at least 60%, 70%, 80%, 85%, 90%, 91%, 92%, 93%, 94%, 95%, 96%, 97%, or 98% identity to the sequence of SEQ ID NO:2 or SEQ ID NO:6 and comprising substitutions G24S-G53S-N78S-G97A-N101S or S063G-N76D, wherein amino acid positions of the variant are numbered by correspondence with amino acid positions of the SEQ ID NO:2 sequence. Also included are compositions, including, but not limited to, e.g., cleaning compositions, comprising at least one such variant and methods for cleaning utilizing at least one such protease variant as described in greater detail elsewhere herein.

Example 23

Cleaning Performance of Polypeptide BPN'-v36 Polypeptides Variants from Combinatorial Libraries Based on BPN'-v36 Polypeptide Two separate combinatorial libraries (AJ1 and AJ2) were synthesized by DNA2.0 (Menlo Park, Calif.) and were delivered as individual ligation reactions. The pHPLT-BPN'-v36 plasmid (FIG. 4) containing the BPN' expression cassette served as template DNA (parent plasmid) for library construction. A list of the possible amino acid positions and substitutions for each library is shown in Table 23-1. The ligation reactions for each library were used to transform *B. subtilis*, and the library variants were grown up for protein expression as described in Example 11. The variants were tested for performance in the BMI microswatch cleaning assay in Detergent Composition 4 at pH 8 and 16° C. as described in Example 1 of Part I.

TABLE 23-1

Possible Substitutions for Combinatorial Libraries AJ1 and AJ2

| AJ1 | | AJ2 | |
|---|---|---|---|
| Position | Possible Substitutions | Position | Possible Substitutions |
| S33 | G, S | E54 | E, Q |
| D60 | D, G | D99 | D, N |
| N62 | N, L, S | D120 | D, N |
| S63 | S, R, L, N, G | D140 | D, N |
| S125 | S, A | E156 | E, Q |
| Q217 | Q, R, E, L, G | D197 | D, N |
| M222 | M, L, S | K12 | K, T |
| | | K27 | K, S |
| | | K43 | K, T |
| | | K141 | K, Y |
| | | K213 | K, Q |
| | | K237 | K, A |
| | | K256 | K, Q |

The following BPN'-v36 variants were determined to have a PI value equal to or greater than 0.5 and less or equal to 1.0 relative to BPN'-v36 in the BMI microswatch cleaning assay in Detergent Composition 4 at pH 8 and 16° C.: BPN'-S024G-S053G-S078N-S101N-G128A-Y217Q amino acid sequence (SEQ ID NO:6) comprising at least one set of amino acid substitutions selected from the group consisting of G024S-G053S-N078S-G097A-N101S (i.e., BPN'-v3), G024S-G053S-N078S-G097A-N101S-A128S (i.e., BPN'-v12), N062L, N062L-S063G, N062S, N062S-S063G-Q217L, N062S-S063L-Q217L, N062S-S063N, N062S-S063R, Q217E, S063G, S063G-Q217L, S063G-Q217L-M222S, S063L-Q217L, S063N, S063N-Q217L, D099N-K141Y-K213Q, D099N-K141Y-K256Q, K043T, K043T-K141Y-E156Q, N062L-Q217E, N062L-Q217L, N062L-S063G-Q217E, N062L-S063L, N062L-S063N-Q217L, N062S-Q217L, N062S-S063G, N062S-S063L, N062S-S063N-Q217L, N062S-S063R-Q217E, Q217L, S063G-Q217E, S063N-Q217E, S063R, S063R-Q217E, S063R-Q217L,), D099N-K141Y-K213Q, D099N-K141Y-K256Q, K043T, K043T-K141Y-E156Q, N062L-Q217E, N062L-Q217L, N062L-S063G-Q217E, N062L-S063L, N062S-Q217L, N062S-S063G, N062S-S063L, N062S-S063N-Q217L, Q217L, S063G-Q217E, S063N-Q217E, S063R, S063R-Q217E, and S063R-Q217L, wherein amino acid positions of the variant are numbered by correspondence with the sequence of SEQ ID NO:2. Such variants have proteolytic activity. The invention includes a protease variant having proteolytic activity and/or a PI value equal to or greater than 0.5 and equal to or less than 1.0 relative to BPN'-v36 in this assay, the variant comprising an amino acid sequence having at least 60%, 70%, 80%, 85%, 90%, 91%, 92%, 93%, 94%, 95%, 96%, 97%, or 98% identity to the sequence of SEQ ID NO:2 or SEQ ID NO:6 and comprising at least one set of acid substitutions selected from said group above, wherein amino acid positions of the variant are numbered by correspondence with amino acid positions of the SEQ ID NO:2 sequence. Also included are compositions, including, but not limited to, e.g., cleaning compositions, comprising at least one such variant and methods for cleaning utilizing at least one such protease variant as described in greater detail elsewhere herein. Note that a protease variant which is BPN'-S024G-S053G-S078N-S101N-G128A-Y217Q amino acid sequence (SEQ ID NO:6) comprising the amino acid substitutions G024S-G053S-N078S-G097A-N101S is BPN'-v3 (SEQ ID NO:4), because the G at position 24, G at position 53, N at position 78, and N at position 101 of SEQ ID NO:6 have been substituted with S at each of positions 24, 53, 78, and 101 of SEQ ID NO:6. In addition, G at position 97 of SEQ ID NO:6 has been substituted with A. Thus, the resultant sequence is SEQ ID NO:4.

The following BPN'-v36 variants were determined to have a PI value equal to or greater than 0.5 and less than 0.9 relative to BPN'-v36 in the BMI microswatch cleaning assay in Detergent Composition 4 at pH 8 and 16° C.: BPN'-S024G-S053G-S078N-S101N-G128A-Y217Q amino acid sequence (SEQ ID NO:6) comprising at least one set of amino acid substitutions selected from the group consisting of D099N, K141Y-E156Q, N062L-S063L-Q217L, N062L-S063N, N062L-S063N-Q217E, N062L-S063R, N062L-S063R-Q217L, N062L-S063N-Q217E, N062L-S063R-Q217L, N062S-Q217E, N062S-S063G-Q217E, N062S-S063G-Q217R, N062S-S063N-Q217R, S063G-S125A, D060G-Q217L, D120N-K141Y-K213Q, K043T-D099N-D120N-K141Y, K043T-D099N-K141Y-K256Q, K043T-K237A, N062L-S063G-Q217R, N062L-S063G-S125A, N062L-S063L-Q217E, N062L-S063N-S125A-Q217L, N062S-Q217R, N062S-S063L-Q217E, N062S-S063R-Q217L, S063G-M222S, S063G-Q217R, D120N-E156Q-K256Q, K141Y-D197N, N062L-Q217R, N062L-S063G-Q217L-M222S, N062L-S063L-Q217R, N062L-S063N-Q217R, N062S-Q217G, N062S-S063G-Q217G, N062S-S063G-Q217L-M222L, N062S-S063G-S125A-Q217L, N062S-S063N-Q217E, Q217G, S033G-N062S-S063G, S063G-Q217G, S063G-Q217L-M222L, S063G-S125A-Q217R, S063L-Q217R, S063N-M222S, S063N-Q217R, S063N-S125A-Q217L, S063R-Q217R, S063R-S125A-Q217L, D099N-E156Q-K256Q, E156Q, K012T-D099N-K213Q, K012T-K256Q, K043T-D099N-K141Y-K213Q, K043T-E156Q, K141Y-K213Q, N062L-Q217G, N062L-Q217L-M222L, N062L-Q217L-M222S, N062L-S063G-M222S, N062L-S063G-Q217L-M222L, N062L-S063G-Q217R-M222S, N062L-S063N-Q217L-M222S, N062L-S063N-S125A, N062L-S063R-S125A, N062L-S125A, N062S-S063G-M222S, N062S-S063G-Q217G-M222S, N062S-S063G-S125A, N062S-S063N-Q217L-M222L, N062S-S063N-S125A-Q217L, N062S-S063R-Q217G, N062S-S063R-Q217L-M222S, Q217G-M222S, Q217L-M222S, Q217R, S033G-S063G-Q217R, S063G-Q217E-M222S, S063G-S125A-Q217G, S063L-Q217E, S063N-Q217G, S063N-Q217G-M222S, S063N-Q217L-M222S, S063R-Q217L-M222S, and S063R-S125A, wherein amino acid positions of the variant are numbered by correspondence with the sequence of SEQ ID NO:2. Such variants have proteolytic activity. The invention includes a protease variant having proteolytic activity and/or a PI value equal to or greater than 0.5 and less than 0.9 relative to BPN'-v36 in this assay, the variant comprising an amino acid sequence having at least 60%, 70%, 80%, 85%, 90%, 91%, 92%, 93%, 94%, 95%, 96%, 97%, 98%, or 99% identity to the sequence of SEQ ID NO:2 or SEQ ID NO:6 and comprising at least one set of acid substitutions selected from said group above, wherein amino acid positions of the variant are numbered by correspondence with amino acid positions of the SEQ ID NO:2 sequence. Also included are compositions, including, but not limited to, e.g., cleaning compositions, comprising at least one such variant and methods for cleaning utilizing at least one such protease variant as described in greater detail elsewhere herein.

Part II

Series I GG36 Cold Water Protease Variants

The amino acid sequence of wild-type mature *Bacillus lentus* GG36 protease is:

(SEQ ID NO: 755)
AQSVPWGISRVQAPAAHNRGLTGSGVKVAVLDTGISTHPDLNIRGGAS

FVPGEPSTQDGNGHGTHVAGTIAALNNSIGVLGVAPSAELYAVKVLGA

SGSGSVSSIAQGLEWAGNNGMHVANLSLGSPSPSATLEQAVNSATSRG

VLVVAASGNSGAGSISYPARYANAMAVGATDQNNNRASFSQYGAGLDI

VAPGVNVQSTYPGSTYASLNGTSMATPHVAGAAALVKQKNPSWSNVQI

RNHLKNTATSLGSTNLYGSGLVNAEAATR

As indicated herein, suitable Series I GG36 cold water protease variants include enzyme variants derived from a parent protease, said parent protease's sequence being at least 60%, 70%, 75%, 80%, 85%, 86%, 87%, 88%, 89%, 90%, 91%, 92%, 93%, 94%, 95%, 96%, 97%, 98%, 99%, 99.5%, or 100% identical to the amino acid sequence of SEQ ID NO:755, said protease variant having one or more of the following characteristics:
  a) Test Method 2 performance index of at least 1.1, at least 1.2, at least 1.3, at least 1.4, at least 1.5, at least 1.6, at least 1.7, at least 1.8, at least 1.9, at least 2, from 1.1 to about 10, from 1.1 to about 8, or even from 1.1 to about 5;
  b) a Test Method 3 performance index of at least 1.1, at least 1.2, at least 1.3, at least 1.4, at least 1.5, at least 1.6, at least 1.7, at least 1.8, at least 1.9, at least 2, from 1.1 to about 10, from 1.1 to about 8, or even from 1.1 to about 5;
  c) a Test Method 4 performance index of at least 1.0, at least 1.1, at least 1.2, at least 1.3, at least 1.4, at least 1.5, at least 1.6, at least 1.7, at least 1.8, at least 1.9, at least 2, from 1.0 to about 10, from 1.0 to about 8, or even from 1.0 to about 5.

Test Method 2, Test Method 3, and Test Method 4 are explicitly described in the "Test Methods" section of Part II Example 1. All mutations referenced herein utilize the BPN' numbering scheme as shown in FIG. 5. In some aspects, the variants referenced herein refer to variants having amino acid sequences compared to the amino acid sequence of SEQ ID NO:755, using the BPN' numbering scheme.

Suitable Series I GG36 cold water proteases can be variants of subtilisins or derived from subtilisins, particularly those derived from subtilisin Bacillus lentus GG36 of SEQ ID NO:755 and in some aspects, comprise one or more of the following mutations: A1R, Q2S, V4R, V4S, S9A, R10S, P14K, A16S, H17R, N18R, G20R, T22A, T22R, S24R, S24W, G25R, G25V, V26F, L42I, N43R, N43A, G46R, P52F, P52E, P52N, T57R, Q59A, N62E, N62Q, V68A, V68C, T71G, I72C, A74C. L75A, L75F, L75R, N76D, S78R, L82R, P86W, E89P, E89T, E89G, E89H, E89I, E89V, E89W, Y91N, K94N, G100S, S101A, S101N, S101G, S101D, S103G, S103N, V104L, V104I, S106V, S106G, A108I, L111V, E112V, G115K, G115R, N117F, G118I, V121F, S128D, S128F, S128L, S128N, P129E, S144R, L148I, A158E, G159E, S160D, S166D, N185E, N185I, R186H, S188E, S188D, D197F, V203E, Y209S, Y209N, Y209F, Y209T, Y209E, Y209H, Y209G, P210R, S212I, S212F, Y214F, A215N, A215D, A215E, L217E, L217N, T224A, A230E, A231I, Q236F, N238R, N238K, P239K, P239G, P239R, P239S, W241R, S242R, S242L, N243R, V244R, N248I, N248V, H249R, L250I, N252R, T253R, L262D, Y263F, S265F, L267V, L267N. N269I, N269R, E271F, E271I, E271H, E271P, E271T, E271V, E271L and/or A272F, wherein the variant has proteolytic activity and each amino acid position of the variant is numbered by correspondence to an amino acid position in the amino acid sequence of SEQ ID NO:2 (BPN') as determined by alignment of the amino acid sequence of the variant with SEQ ID NO:2.

In one aspect, suitable Series I GG36 cold water protease variants include subtilisins, particularly those derived from Bacillus lentus GG36 of SEQ ID NO:755, comprising one or more of the following sets of substitutions: T022R-S024R, S009A-E271L, N018R-W241R, N018R-G115R, N043R-H249R, G020R-H249R, V004R-H249R, G020R-S024R, N018R-H249R, S009A-G020R, G020R-W241R, S009A-S078R, G020R-G115R, N018R-S024R, S024R-S242R, T022R-G115R, N018R-N043R, G020R-N043R, N018R-S242R, S242R-N269R, N018R-V244R, S024R-N269R, G020R-E271L, S024R-E271L, V004R-S009A, G020R-N269R, A001R-S024R, V244R-E271L, S009A-N018R, W241R-E271L, V004R-S024R, S009A-H249R, S009A-T022R, N062E-P129E, N062E-G159E, A016S-L148I, A158E-H249R, A016S-N062E, L111V-S188D, T022A-N062E, N062E-L148I, T022A-P129E, N062E-E271F, N062E-A158E, A016S-G159E, N062E-R186H, S128N-G159E, N062E-S188D, N062E-S128N, L148I-G159E, S103G-A158E, L111V-G159E, A158E-E271F, A016S-S188D, T022A-L111V, S128N-A158E, A016S-A158E, V104L-A158E, S128N-R186H, G159E-Y209E, N062E-S101A, L111V-Y209E, L148I-S188D, S101A-Y209E, T022A-S188D, A016S-T022A, S128N-P129E, A016S-Y209E, A016S-S128N, T022A-E089P, S128N-Y209E, E089P-A158E, N062E-S103G, R186H-E271F, A016S-P129E, E089P-G159E, L111V-H249R, S101A-P129E, L148I-Y209E, T022A-G159E, P129E-H249R, P129E-Y209E, V104L-P129E, S128N-S188D, L111V-A158E, T022A-A158E, N062E-Y209E, N062E-H249R, S101A-R186H, E089P-P129E, P129E-E271, T22A-L111V-G159E, S101A-S103G-V104L-Y209E, S101A-S103G-V104L-G159E, S101A-S103G-V104L-S188D, S101G-S103A-V104I-G159D, T22A-S103G-G159E, T22A-S128N-E271F-Y209E, T22-Y209E-E271F, T22A-S101A-Y209E, S101A-Y209E-E271F, T22A-L111V-S128N, T22A-S101A-G159E, S101A-S103G-V104L, T22A-S101A-S103G-V104L, S101A-S103G-V104L, S101G-S103A-V104I, S101A-S103G-V104L-S128N, S103A-V104I-G159D-A232V-Q236H-Q245R-N248D-N252K, S101G-V104I-G159D-A232V-Q236H-Q245R-N248D-N252K, S101G-S103A-G159D-A232V-Q236H-Q245R-N248D-N252K, S101G-S103A-V104L-A232V-Q236H-Q245R-N248D-N252K, S101G-S103A-V104L-G159D-Q236H-Q245R-N248D-N252K, S101G-S103A-V104L-G159D-A232V-Q245R-N248D-N252K, S101G-S103A-V104L-G159D-A232V-Q236H-N248D-N252K, S101G-S103A-V104L-G159D-A232V-Q236H-Q245R-N252K, S101G-S103A-V104L-G159D-A232V-Q236H-Q245R-N248D, N62E-S101G-S103A-V104I-G159D-A232V-Q245R-N248D-E271F, N62E-S101G-S103A-V104I-G159D-A232V-Q245R-N248D-H249R, T22A-S101G-S103A-V104I-G159D-A232V-Q245R-N248D-H249R, S101G-S103A-V104I-G159D-A232V-Q245R-N248D-S24R, S101G-S103A-V104I-G159D-A232V-Q245R-N248D-T253R, S101G-S103A-V104I-A158E-A232V-Q245R-N248D-H249R, T22A-S101G-S103A-V104I-G159D-A232V-Q245R-N248D-E271F, S101G-S103A-V104I-G159E-A232V-Q245R-N248D-H249R, S101G-S103A-V104I-G159D-A232V-Q245R-N248D-N238R, S101G-S103A-V104I-A158E-A232V-Q245R-N248D-E271F, S101G-S103A-V104I-G159D-A232V-Q245R-N248D, S101G-S103A-V104I-G159D-A232V-Q245R-N248D-E271F, S101G-S103A-V104I-G159D-A232V-Q245R-N248D-N76D, and/or S101G-S103A-V104I-G159E-A232V-

Q245R-N248D-E271F, wherein the variant has proteolytic activity and each amino acid position of the variant is numbered by correspondence to an amino acid position in the amino acid sequence of SEQ ID NO:2 (BPN') as determined by alignment of the amino acid sequence of the variant with SEQ ID NO:2.

In another aspect, suitable Series I GG36 cold water protease variants include variants of subtilisins, particularly those derived from *Bacillus lentus* GG36 of SEQ ID NO:755, wherein the variants comprise three, four, five, six, seven, eight, nine, 10, 11, 12, 13, 14 15, 16, 17, 18, 19, 20, 21, 22, 23, 24, or even 25 mutations within the group of positions comprising positions 1, 2, 4, 9, 10, 14, 16, 17, 18, 20, 22, 24, 25, 26, 42, 43, 46, 52, 57, 59, 62, 68, 71, 72, 74, 75, 76, 78, 82, 86, 89, 91, 94, 100, 101, 103, 104, 106, 108, 111, 112, 115, 117, 118, 121, 128, 129, 144, 148, 158, 159, 160, 166, 185, 186, 188, 197, 203, 209, 210, 212, 214, 215, 217, 224, 230, 231, 236, 238, 239, 241, 242, 243, 244, 248, 249, 250, 252, 253, 262, 263, 265, 267, 269, 271 and 272.

In another aspect, suitable Series I GG36 cold water protease variants include variants of subtilisins, particularly those derived from *Bacillus lentus* GG36 of SEQ ID NO:755, wherein the variants comprise a total of three, four, five, six, seven, eight, nine, 10, 11, 12, 13, 14, 15, 16, 17, 18, 19, 20, 21, 22, 23, 24, or even 25 mutations selected from: A1R, Q2S, V4R, V4S, S9A, R10S, P14K, A16S, H17R, N18R, G20R, T22A, T22R, S24R, S24W, G25R, G25V, V26F, L42I, N43R, N43A, G46R, P52F, P52E, P52N, T57R, Q59A, N62E, N62Q, V68A, V68C, T71G, I72C, A74C. L75A, L75F, L75R, N76D, S78R, L82R, P86W, E89P, E89T, E89G, E89H, E89I, E89V, E89W, Y91N, K94N, G100S, S101A, S101N, S101G, S101D, S103G, S103N, V104L, V104I, S106V, S106G, A108I, L111V, E112V, G115K, G115R, N117F, G118I, V121F, S128D, S128F, S128L, S128N, P129E, S144R, L148I, A158E. G159E, S160D, S166D, N185E, N185I, R186H, S188E, S188D, D197F, V203E, Y209S, Y209N, Y209F, Y209T, Y209E, Y209H, Y209G, P210R, S212I, S212F, Y214F, A215N, A215D, A215E, L217E, L217N, T224A, A230E, A231I, Q236F, N238R, N238K, P239K, P239G, P239R, P239S, W241R, S242R, S242L, N243R, V244R, N248I, N248V, H249R, L250I, N252R, T253R, L262D, Y263F, S265F, L267V, L267N, N269I, N269R, E271F, E271I, E271H, E271P, E271T, E271V, E271L and A272F; and optionally one or more of the following mutations: S103A, G159D, Q236H, Q245R, N248D and N252K, wherein the variant has proteolytic activity and each amino acid position of the variant is numbered by correspondence to an amino acid position in the amino acid sequence of SEQ ID NO:2 (BPN') as determined by alignment of the amino acid sequence of the variant with SEQ ID NO:2.

In some aspects, the Series I GG36 cold water protease variant comprises one or more mutations, and having a total net charge of −5, −4, −3, −2, −1 or 0 relative to *B. lentus* subtilisin GG36 wild-type (SEQ ID NO:755).

In another aspect, the Series I GG36 cold water protease variants are low ionic strength Series I GG36 cold water protease variants. Such low ionic strength Series I GG36 cold water protease variants comprising one or more mutations, and having a total net charge of −5, −4, −3, −2, −1 or 0 relative to *B. lentus* subtilisin GG36 protease wild-type (SEQ ID NO:755). These mutations can be selected from: (a) two or more of the following mutations: A1R, Q2S, V4R, V4S, S9A, R105, P14K, A16S, T22A, T22R, S24R, G25V, V26F, L42I, P52F, P52E, P52N, N62E, N62Q, V68A, V68C, T71G, I72C, A74C. L75A, L75F, S78R, E89P, E89T, E89G, E89H, E89W, Y91N, K94N, G100S, S101A, S101N, S101G, S101D, S103G, S103N, V104L, V104I, A108I, L111V, E112V, G115K, N117F, V121F, S128D, S128F, S128L, S128N, P129E, L148I, A158E. G159E, S160D, S166D, N185E, R186H, S188E, S188D, V203E, Y209S, Y209N, Y209F, Y209T, Y209E, Y209H, Y209G, P210R, S212I, S212F, Y214F, A215N, A215D, A215E, L217E, L217N, T224A, A230E, A231I, Q236F, N238R, N238K, P239K, P239G, P239R, N248V, H249R, L250I, L262D, Y263F, S265F, L267V, L267N. N269I, N269R, E271F, E271I, E271H and A272F; and/or (b) one or more of the following sets of mutations: N062E-P129E, N062E-G159E, A016S-L148I, A158E-H249R, A016S-N062E, L111V-S188D, T022A-N062E, N062E-L148I, T022A-P129E, N062E-E271F, N062E-A158E, A016S-G159E, N062E-R186H, S128N-G159E, N062E-S188D, N062E-S128N, L148I-G159E, S103G-A158E, L111V-G159E, A158E-E271F, A016S-S188D, T022A-L111V, S128N-A158E, A016S-A158E, V104L-A158E, S128N-R186H, G159E-Y209E, N062E-S101A, L111V-Y209E, L148I-S188D, S101A-Y209E, T022A-S188D, A016S-T022A, S128N-P129E, A016S-Y209E, A016S-S128N, T022A-E089P, S128N-Y209E, E089P-A158E, N062E-S103G, R186H-E271F, A016S-P129E, E089P-G159E, L111V-H249R, S101A-P129E, L148I-Y209E, T022A-G159E, P129E-H249R, P129E-Y209E, V104L-P129E, S128N-S188D, L111V-A158E, T022A-A158E, N062E-Y209E, N062E-H249R, S101A-R186H, E089P-P129E, P129E-E271F, T22A-L111V-G159E, S101A-S103G-V104L-Y209E, S101A-S103G-V104L-G159E, S101A-S103G-V104L-S188D, S101G-S103A-V104I-G159D, T22A-S103G-G159E, T22A-S128N-E271F-Y209E, T22A-Y209E-E271F, T22A-S101A-Y209E, S101A-Y209E-E271F, T22A-L111V-S128N, T22A-S101A-G159E, S101A-S103G-V104L, T22A-S101A-S103G-V104L, S101A-S103G-V104L, S101G-S103A-V104I, S101A-S103G-V104L-S128N, S103A-V104I-G159D-A232V-Q236H-Q245R-N248D-N252K, S101G-V104I-G159D-A232V-Q236H-Q245R-N248D-N252K, S101G-S103A-G159D-A232V-Q236H-Q245R-N248D-N252K, S101G-S103A-V104L-A232V-Q236H-Q245R-N248D-N252K, S101G-S103A-V104L-G159D-Q236H-Q245R-N248D-N252K, S101G-S103A-V104L-G159D-A232V-Q245R-N248D-N252K, S101G-S103A-V104L-G159D-A232V-Q236H-N248D-N252K, S101G-S103A-V104L-G159D-A232V-Q236H-Q245R-N252K, S101G-S103A-V104L-G159D-A232V-Q236H-Q245R-N248D, N62E-S101G-S103A-V104I-G159D-A232V-Q245R-N248D-E271F, N62E-S101G-S103A-V104I-G159D-A232V-Q245R-N248D-H249R, T22A-S101G-S103A-V104I-G159D-A232V-Q245R-N248D-H249R, S101G-S103A-V104I-G159D-A232V-Q245R-N248D-S24R, S101G-S103A-V104I-G159D-A232V-Q245R-N248D-T253R, S101G-S103A-V104I-A158E-A232V-Q245R-N248D-H249R, T22A-S101G-S103A-V104I-G159D-A232V-Q245R-N248D-E271F, S101G-S103A-V104I-G159E-A232V-Q245R-N248D-H249R, S101G-S103A-V104I-G159D-A232V-Q245R-N248D-N238R, S101G-S103A-V104I-A158E-A232V-Q245R-N248D-E271F, S101G-S103A-V104I-G159D-A232V-Q245R-N248D, S101G-S103A-V104I-G159D-A232V-Q245R-N248D-E271F, S101G-S103A-V104I-G159D-A232V-Q245R-N248D-N76D and S101G-S103A-V104I-G159E-A232V-Q245R-N248D-E271F, wherein the variant has proteolytic activity and each amino acid position of the variant is numbered by correspondence to an amino acid position in the amino acid sequence of SEQ ID NO:2 (BPN').

In another aspect, the above low ionic strength Series I GG36 cold water protease variants form part of a detergent composition that is diluted in water, typically within a laundry washing machine, to form a laundry detergent wash liquor, whose conductivity is from about 0.1 mS/cm to about 3 mS/cm, from about 0.3 mS/cm to about 2.5 mS/cm, or even from about 0.5 mS/cm to about 2 mS/cm.

In another aspect, the Series I GG36 cold water protease variants are high ionic strength Series I GG36 cold water protease variants. Such high ionic strength Series I GG36 cold water protease variants comprise two or more mutations, and have a total net charge of +5, +4, +3, +2, +1 or 0 relative to B. lentus subtilisin GG36 protease wild-type (SEQ ID NO:755). These mutations can be selected from: (a) two or more of the following mutations V4R, H17R, N18R, G20R, T22R, S24R, S24W, G25R, N43R, N43A, G46R, P52F, P52N, T57R, Q59A, N62Q, T71G, L75R, N76D, S78R, L82R, P86W, E89P, E89W, E89T, E89I, E89H, E89V, V104L, S106V, S106G, G115R, G118I, V121F, S144R, N185I, D197F, Y209N, Y209S, L217E, A231I, P239R, P239S, W241R, S242R, S242L, N243R, V244R, N248I, H249R, N252R, T253R, E271T, E271V, E271L, E271H, E271F, E271P, A1R, S9A, S212F and N269R; and/or (b) one or more of the following sets of mutations T022R-S024R, S009A-E271L, N018R-W241R, N018R-G115R, N043R-H249R, G020R-H249R, V004R-H249R, G020R-S024R, N018R-H249R, S009A-G020R, G020R-W241R, S009A-S078R, G020R-G115R, N018R-S024R, S024R-S242R, T022R-G115R, N018R-N043R, G020R-N043R, N018R-S242R, S242R-N269R, N018R-V244R, S024R-N269R, G020R-E271L, S024R-E271L, V004R-S009A, G020R-N269R, A001R-S024R, V244R-E271L, S009A-N018R, W241R-E271L, V004R-S024R, S009A-H249R, S009A-T022R, S101G-S103A-V104I-G159D-A232V-Q245R-N248D-E271F, S101G-S103A-V104I-A158E-A232V-Q245R-N248D-E271F, S101G-S103A-V104I-A158E-A232V-Q245R-N248D-H249R, S101G-S103A-V104I-G159D-A232V-Q245R-N248D-S24R, S101G-S103A-V104L-G159D-A232V-Q236H-Q245R-N252K, S101G-S103A-V104L-A232V-Q236H-Q245R-N248D-N252K, wherein the variant has proteolytic activity and each amino acid position of the variant is numbered by correspondence to an amino acid position in the amino acid sequence of SEQ ID NO:2 (BPN').

In another aspect, the above high ionic strength Series I GG36 cold water protease variants form part of a detergent composition that is diluted in water, typically within a laundry washing machine, to form a laundry detergent wash liquor, whose conductivity is from about 3 mS/cm to about 30 mS/cm, from about 3.5 mS/cm to about 20 mS/cm, or even from about 4mS/cm to about 10 mS/cm.

The charge of the Series I GG36 cold water protease variants is expressed relative to B. lentus subtilisin GG36 protease wild-type having the amino acid sequence of SEQ ID NO:755. The amino acids that impart a single negative charge are D and E and those that impart a single positive charge are R, H and K. Any amino acid change versus SEQ ID NO:755 that changes a charge is used to calculate the charge of the Series I GG36 cold water protease variant. For example, introducing a negative charge mutation from a wild-type neutral position will add a net charge of −1 to the Series I GG36 cold water protease variant, whereas introducing a negative charge mutation (D or E) from a wild-type positive amino acid residue (R, H or K) will add a net charge of −2. Summing the charge changes from all the amino acid residues that are different for the Series I GG36 cold water protease variant versus B. lentus subtilisin GG36 protease wild-type having the amino acid sequence of SEQ ID NO:755 gives the charge change of the Series I GG36 cold water protease variant. Without wishing to be bound by theory, it is believed that: (a) the preferred charge range for Series I GG36 cold water protease variants to be used in low conductivity laundry detergent solutions is −5, −4, −3, −2, −1, 0, particularly −2, −1; and (b) the preferred charge range for Series I GG36 cold water protease variants to be used in high conductivity laundry detergent solutions is +5, +4, +3, +2, +1, 0, particularly +2, +1. By correctly selecting the charge unexpectedly improved levels of cold water cleaning performance can be obtained. "Low conductivity laundry detergent solutions" are defined as having a conductivity of from about 0.1 mS/cm to about 3 mS/cm, from about 0.3 mS/cm to about 2.5 mS/cm, or even from about 0.5 mS/cm to about 2 mS/cm. "High conductivity laundry detergent solutions" are defined as having a conductivity of from about 3 mS/cm to about 30 mS/cm, from about 3.5 mS/cm to about 20 mS/cm, or even from about 4 mS/cm to about 10 mS/cm. It is intended that the above examples be non-limiting. Once mutations are combined to optimize cold water performance, the enzyme charge can also be balanced by mutations in further positions.

Methods for Making GG36 Cold Water Protease Variants

A variety of methods are known in the art that are suitable for generating modified polynucleotides of the invention that encode GG36 cold water protease variants, including, but not limited to, for example, site-saturation mutagenesis, scanning mutagenesis, insertional mutagenesis, deletion mutagenesis, random mutagenesis, site-directed mutagenesis, and directed-evolution, as well as various other recombinatorial approaches. Non-limiting exemplary methods of making the Series I GG36 cold water protease variants are provided in the section above entitled "Vectors, Cells, and Methods for Making Protease Variant Polypeptides of the Invention."

For testing of enzyme activity in heat-inactivated detergents, working solutions of detergents are made from the heat inactivated stocks. Appropriate amounts of water hardness (e.g., 6 gpg or 12 gpg) and buffer are added to the detergent solutions to match the desired conditions. The solutions are mixed by vortexing or inverting the bottles. The following Table provides information regarding some of the commercially-available detergents and test conditions used herein. In some experiments, additional and/or other commercially available detergents find use in the following Examples.

TABLE A

| Laundry and Dish Washing Conditions | | | | | | | |
|---|---|---|---|---|---|---|---|
| Region | Form | Dose | Detergent* | Buffer | Gpg | pH | T (° C.) |
| Laundry (Heavy Duty Liquid and Granular) | | | | | | | |
| NA | HDL | 0.78 g/l | P&G TIDE ® 2X | 5 mM HEPES | 6 | 8.0 | 20 |
| WE | HDL | 5.0 g/L | Henkel PERSIL ™ | 5 mM HEPES | 12 | 8.2 | 40 |
| WE | HDG | 8.0 g/L | P&G ARIEL ® | 2 mM $Na_2CO_3$ | 12 | 10.5 | 40 |
| JPN | HDG | 0.7 g/L | P&G TIDE ® | 2 mM $Na_2CO_3$ | 6 | 10.0 | 20 |
| NA | HDG | 1.0 g/L | P&G TIDE ® | 2 mM $Na_2CO_3$ | 6 | 10.0 | 20 |

TABLE A-continued

Laundry and Dish Washing Conditions

| Region | Form | Dose | Detergent* | Buffer | Gpg | pH | T (° C.) |
|---|---|---|---|---|---|---|---|
| Automatic Dish Washing | | | | | | | |
| WE | ADW | 3.0 g/L | RB CALGONIT ™ | 2 mM $Na_2CO_3$ | 21 | 10.0 | 40 |
| NA | ADW | 3.0 g/L | P&G CASCADE ® | 2 mM $Na_2CO_3$ | 9 | 10.0 | 40 |

In some additional Examples, the following solutions find use:

TABLE B

Working Detergent Solutions

| Detergent | Temp (C.) | Detergent g/L | pH | Buffer | Gpg |
|---|---|---|---|---|---|
| TIDE ® 2X Cold | 16 | 0.98 | 8 | 5 mM HEPES | 6 |
| TIDE ® 2X Cold | 32 | 0.98 | 8 | 5 mM HEPES | 6 |
| TIDE ® 2X Cold | 16 | 0.98 | 7 | 5 mM MOPS | 6 |

Table C provides granular laundry detergent compositions produced in accordance with the invention suitable for laundering fabrics.

TABLE C

Granular Laundry Detergent Compositions and Their Components

| Component | Detergent Compositions | | | | | |
|---|---|---|---|---|---|---|
| | 1 | 2 | 3 | 4 | 5 | 6 |
| Linear alkylbenzenesulfonate with aliphatic carbon chain length $C_{11}$-$C_{12}$ | 15 | 12 | 20 | 10 | 12 | 13 |
| Other surfactants | 1.6 | 1.2 | 1.9 | 3.2 | 0.5 | 1.2 |
| Phosphate builder(s) | 2 | 3 | 4 | | | |
| Zeolite | | 1 | | 1 | 4 | 1 |
| Silicate | 4 | 5 | 2 | 3 | 3 | 5 |
| Sodium Carbonate | 2 | 5 | 5 | 4 | 0 | 3 |
| Polyacrylate (MW 4500) | 1 | 0.6 | 1 | 1 | 1.5 | 1 |
| Carboxymethyl cellulose (Finnfix BDA ex CPKelco) | 1 | — | 0.3 | — | 1.1 | — |
| Celluclean® (15.6 mg/g) | 0.23 | 0.17 | 0.5 | 0.2 | 0.2 | 0.6 |
| Cold Water Protease variant* | 0.23 | 0.17 | 0.05 | 0.2 | 0.03 | 0.1 |
| Stainzyme Plus® (14 mg/g) | 0.23 | 0.17 | 0.5 | 0.2 | 0.2 | 0.6 |
| Mannaway 4.0T (4 mg/g) | 0.1 | | | 0.1 | | 0.1 |
| Lipex 100T (18.6 mg/g) | 0.2 | | 0.1 | | 0.3 | |
| Fluorescent Brightener(s) | 0.16 | 0.06 | 0.16 | 0.18 | 0.16 | 0.16 |
| Diethylenetriamine pentaacetic acid or Ethylene diamine tetraacetic acid | 0.6 | | 0.6 | 0.25 | 0.6 | 0.6 |
| $MgSO_4$ | 1 | 1 | 1 | 0.5 | 1 | 1 |
| Bleach(es) and Bleach activator(s) | 6.88 | | 6.12 | 2.09 | 1.17 | 4.66 |
| Ethoxylated thiophene Hueing Dye[5] | 0.002 | 0.001 | 0.003 | 0.003 | — | — |
| Direct Violet 9 ex Ciba Specialty Chemicals | | | | 0.0006 | 0.0004 | 0.0006 |
| Sulfate/Citric Acid/Sodium Bicarbonate/Moisture/perfume | Balance to 100% | | | | | |

[1] Random graft copolymer is a polyvinyl acetate grafted polyethylene oxide copolymer having a polyethylene oxide backbone and multiple polyvinyl acetate side chains. The molecular weight of the polyethylene oxide backbone is about 6000 and the weight ratio of the polyethylene oxide to polyvinyl acetate is about 40 to 60 and no more than 1 grafting point per 50 ethylene oxide units.
[2] Polyethylenimine (MW = 600) with 20 ethoxylate groups per —NH.
[3] Amphiphilic alkoxylated grease cleaning polymer is a polyethylenimine (MW = 600) with 24 ethoxylate groups per —NH and 16 propoxylate groups per —NH
[4] Reversible protease inhibitor of structure:

TABLE C-continued

Granular Laundry Detergent Compositions and Their Components

| Component | Detergent Compositions | | | | | |
|---|---|---|---|---|---|---|
| | 1 | 2 | 3 | 4 | 5 | 6 |

[5]Ethoxylated thiophene Hueing Dye is as described in U.S. Pat. No. 7,208,459 B2.

In Table C, all enzyme levels expressed as % enzyme raw material, except for cold water protease variant (of this invention) which is expressed as % of active protein added to the product. Table D provides granular laundry detergent compositions suitable for top-loading automatic washing machines (detergent compositions 7-9) and front loading washing machines (detergent compositions 10-11). The GG36 protease variant tested and/or cold water protease variant of the present invention is added separately to these formulations.

TABLE D

Granular Laundry Detergent Compositions and Their Components

| Component | Detergent Composition | | | | |
|---|---|---|---|---|---|
| Surfactants | 7 | 8 | 9 | 10 | 11 |
| $C_{16-17}$ Branched alkyl sulfate | 3.55 | 15.8 | | | |
| $C_{12-14}$ alkyl sulphate | | | 1.5 | | |
| Sodium linear alkylbenzenesulfonate with aliphatic chain length $C_{11}$-$C_{12}$ | 9.6 | | 10.6 | 7.5 | 9 |
| Sodium $C_{14/15}$ alcohol ethoxy - 3 - sulfate | 1.15 | | | 2.88 | |
| Sodium $C_{14/15}$ alkyl sulphate | 2.37 | | | | |
| $C_{14/15}$ alcohol ethoxylate with average 7 moles of ethoxylation | | | | 1.17 | 1 |
| mono-$C_{8-10}$ alkyl mono-hydroxyethyl di-methyl quaternary ammonium chloride | | | | | 0.45 |
| Di methyl hydroxyl ethyl lauryl ammonium chloride | | | 0.18 | | |
| Zeolite A | 13.9 | 4.7 | 0.01 | 2.9 | 1.8 |
| Sodium Silicate 1.6.ratio | 4 | 0.2 | | 4 | 4 |
| Sodium Silicate 2.35.ratio | | | 8 | | |
| Citric Acid | | | | 2.5 | 1.4 |
| Sodium tripolyphosphate | | | 5 | | |
| Sodium Carbonate | 24.1 | 30 | 16.9 | 24.4 | 21 |
| Nonanoyloxybenzenesuplhonate | 5.78 | 2.81 | 0.96 | | |
| Oxaziridinium-based bleach booster | | | | 0.03 | 0.017 |
| Tetrasodium S,S,-ethylenediaminedisuccinate | | | | 0.2 | |
| Diethylenetriamine penta (methylene phosphonic acid), heptasodium salt | 0.61 | | | | 0.33 |
| Hydroxyethane dimethylene phosphonic acid | | | | 0.29 | 0.45 |
| Ethylene diamine tetraacetate | | | 0.27 | | |
| MgSO4 | | | 0.47 | 0.5994 | 0.782 |
| Sodium Percarbonate | 7 | 4.4 | | 15.9 | 19.1 |
| Tetra Acetyl Ethylene Diamine | | | | 3.3 | 4.6 |
| Sodium Perborate Monohydrate | | | 1.2 | | |
| Carboxymethyl cellulose (e.g., Finnfix BDA ex CPKelco) | 0.1 | | 0.17 | 1.69 | 0.23 |
| Sodium Acrylic acid/maleic acid co-polymer (70/30) | 0.0236 | 3.8 | | 2 | 2.5 |
| Sodium polyacrylate (Sokalan PA30 CL) | 4 | | 0.84 | | |
| Terephthalate polymer | | | | 0.23 | |
| Polyethylene glycol/vinyl acetate random graft co polymer | | | 0.89 | 0.89 | 0.91 |
| Photobleach- zinc phthalocyanine tetrasulfonate | | | 0.005 | 0.001 | 0.002 |
| C.I. Fluorescent Brightener 260 | 0.11 | 0.15 | 0.04 | 0.23 | 0.15 |
| C.I. Fluorescent Brightener 351 (Tinopal ® CBS) | | | 0.1 | | |
| Suds suppressor granule | | 0.25 | | 0.07 | 0.04 |
| Hydrophobically modified carboxy methyl cellulose (Finnifix ® SH-1) | | | | 0.019 | 0.028 |

TABLE D-continued

Granular Laundry Detergent Compositions and Their Components

| Component | Detergent Composition | | | | |
|---|---|---|---|---|---|
| Surfactants | 7 | 8 | 9 | 10 | 11 |
| Bentonite | | | 8.35 | | |
| Miscellaneous (Dyes, perfumes, process aids, moisture and sodium sulphate) | Balance | Balance | Balance | Balance | Balance |

In Table D, surfactant ingredients can be obtained from any suitable supplier, including but not limited to BASF (e.g., LUTENSOL®), Shell Chemicals, Stepan, Huntsman, and Clariant (e.g., PRAEPAGEN®). Zeolite can be obtained from sources such as Industrial Zeolite. Citric acid and sodium citrate can be obtained from sources such as Jungbunzlauer. Sodium percarbonate, sodium carbonate, sodium bicarbonate and sodium sesquicarbonate can be obtained from sources such as Solvay. Acrylate/maleate copolymers can be obtained from sources such as BASF. Carboxymethylcellulose and hydrophobically modified carboxymethyl cellulose can be obtained from sources such as CPKelco. C.I. Fluorescent Brightener 260 can be obtained from 3V Sigma (e.g., OPTI-BLANC®, OPTIBLANC® 2M/G, OPTIBLANC® 2MG/LT Extra, or OPTIBLANC® Ecobright. Tetrasodium S,S-ethylenediamine disuccinate can be obtained from sources such as Innospec. Terephthalate co-polymer can be obtained from Clariant (e.g., REPELOTEX SF 2). In addition, 1-Hydroxyethane-1,1-diphosphonic acid can be obtained from Thermphos. Oxaziridinium-based bleach booster has the following structure, where R1=2-butyloctyl, and was produced according to US 2006/0089284A1.

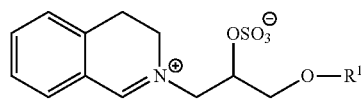

The enzymes NATALASE®, TERMAMYL®, STAINZYME PLUS®, CELLUCLEAN® and MANNAWAY® can be obtained from Novozymes. Zinc phthalocyanine tetrasulfonate can be obtained from Ciba Specialty Chemicals (e.g., TINOLUX® BMC). Suds suppressor granule can be obtained from Dow Corning. In these detergent compositions, random graft copolymer is a polyvinyl acetate grafted polyethylene oxide copolymer having a polyethylene oxide backbone and multiple polyvinyl acetate side chains The molecular weight of the polyethylene oxide backbone is about 6000 and the weight ratio of the polyethylene oxide to polyvinyl acetate is about 40 to 60 and no more than 1 grafting point per 50 ethylene oxide units.

Part II Examples

Example 1

Assays and Test Methods

This Example describes the various Test Methods and assays used in the development of the variants described in these Examples. Any deviations from the protocols provided are indicated in the pertinent Examples. The assays were performed using a Biomek FX Robot (Beckman Coulter) or a multichannel pipettor (e.g., Rainin PipetLite, Mettler-Toledo) and a SpectraMAX MTP Reader (type 340; Molecular Devices).

A. Test Methods

Test Method 1

A protocol to define whether a dye or pigment material is a fabric hueing agent for the purpose of the invention is provided below:

1) Fill two tergotometer pots with 800 ml of Newcastle upon Tyne, UK, City Water (~12 grains per US gallon total hardness, supplied by Northumbrian Water, Pity Me, Durham, Co. Durham, UK).

2) Insert pots into tergotometer, with water temperature controlled at 30° C. and agitation set at 40 rpm for the duration of the experiment.

3) Add 4.8 g of IEC-B detergent (IEC 60456 Washing Machine Reference Base Detergent Type B), supplied by wfk, Brüggen-Bracht, Germany, to each pot.

4) After two minutes, add 2.0 mg active colorant to the first pot.

5) After one minute, add 50 g of flat cotton vest (supplied by Warwick Equest, Consett, County Durham, UK), cut into 5 cm×5 cm swatches, to each pot.

6) After 10 minutes, drain the pots and re-fill with cold Water (16° C.) having a water hardness of 14.4 English Clark Degrees Hardness with a 3:1 Calcium to Magnesium molar ratio.

7) After 2 minutes rinsing, remove fabrics.

8) Repeat steps 3-7 for a further three cycles using the same treatments.

9) Collect and line dry the fabrics indoors for 12 hours.

10) Analyze the swatches using a Hunter Miniscan spectrometer fitted with D65 illuminant and UVA cutting filter, to obtain Hunter a (red-green axis) and Hunter b (yellow-blue axis) values.

11) Average the Hunter a and Hunter b values for each set of fabrics. If the fabrics treated with colorant under assessment show an average difference in hue of greater than 0.2 units on either the a axis or b axis, it is deemed to be a fabric hueing agent for the purpose of the invention.

Test Method 2

For Test Method 2, the BMI microswatch assay provided below is run using the granular detergent composition 10 (see Table D above). The laundry detergent is dissolved in water that has a hardness of 12 gpg and adjusted to a temperature of 16° C., and the protease variant enzyme of interest is added. Performance of the protease variant enzymes is then determined as per the BMI microswatch assay described. The performance index is determined by comparing the performance of the protease variant enzyme with that of the $B.$ $lentus$ GG36 subtilisin enzyme having the amino acid sequence of SEQ ID NO:755, with in all cases the enzyme dosage being 1.6 ppm. Protease variant enzymes having a performance index of 1.1 or greater are viewed to be cold water protease variants.

Test Method 3

For Test Method 3, the BMI microswatch assay provided below is run using the granular laundry detergent composition 7 (see Table D above). The laundry detergent is dissolved in water that has a hardness of 6 gpg and adjusted to a temperature of 16° C., the GG36 protease variant enzyme of interest is added. Performance of the GG36 protease variant enzymes is then determined as per the BMI microswatch assay described. The performance index is determined by comparing the performance of the GG36 protease variant enzyme with that of the *B. lentus* GG36 subtilisin enzyme having the amino acid sequence of SEQ ID NO:755, with in all cases the enzyme dosage being 4 ppm. GG36 protease variant enzymes having a performance index of 1.1 or greater are viewed to be cold water protease variants.

Test Method 4

For Test Method 4, the BMI microswatch assay provided below is run using the granular laundry detergent composition 7 (see Table D above). The laundry detergent is dissolved in water that has a hardness of 6 gpg and adjusted to a temperature of 16° C., and the GG36 protease variant enzyme of interest is added. Performance of the GG36 protease variant enzymes is then determined as per the BMI microswatch assay described. The performance index is determined by comparing the performance of the GG36 protease variant enzyme with that of a reference enzyme GG36-A158E, said GG36-A158E reference enzyme consisting of the *B. lentus* subtilisin GG36 protease amino acid sequence of SEQ ID NO:755 with a single substitution of glutamic acid for alanine at position 158 (i.e., the A158E mutation), with in all cases the enzyme dosage being 4 ppm. GG36 protease variant enzymes having a performance index of 1.0 or greater are viewed to be cold water protease variants.

Test Method 5

Electrical conductivity of an aqueous solution is assayed according to the standard method ASTM D1125 and reported in units of milliSiemens/cm, abbreviated to mS/cm herein.

B. Assays

TCA Assay for Protein Content Determination in 96-Well Microtiter Plates

For GG36 and GG36 variants, this assay was started using filtered *B. subtilis* culture supernatants from microtiter plates grown 2-3 days at 37° C. with shaking at 250 rpm and humidified aeration. A fresh 96-well flat bottom microtiter plate (MTP; Costar 9017 medium binding clear polystyrene plate) was used for the assay. First, 100 µL/well of 0.25 N HCl was placed in each well. Then, 20-25 µL of filtered culture supernatant were added and the solution was mixed on a table top mixer (e.g., Lab line Instruments, Titer plate shaker, model 4825) for 5-10 seconds. The light scattering/absorbance at 405 nm was then determined, in order to provide the "blank" reading. For the "test" reading, 100 µL/well of 30% (w/v) trichloroacetic acid (TCA) was added to each well containing the mixture of HCl and culture supernatant, and the plate was incubated for 10 minutes at room temperature. After briefly mixing the solution on a table top mixer for no more than 2-3 sec, the light scattering/absorbance at 405 nm was determined. The turbidity/light scatter increase in the samples correlates to the total amount of precipitable protein in the culture supernatant. The calculations were performed by subtracting the "blank" reading (obtained after addition of HCl only, no TCA) from the "test" reading (obtained after addition of TCA, as described above) to provide a relative measure of the protein content in the samples. If desired, a standard curve can be created by calibrating the TCA readings with AAPF assays of clones with known conversion factors. However, the TCA results are linear with respect to protein concentration from 50 to 500 parts per million (ppm) of protein (where 1 ppm corresponds to 1 mg/L) and can thus be plotted directly against enzyme performance for the purpose of choosing variants with desired performance.

AAPF Protease Assay in 96-Well Microtiter Plates

In order to determine the protease activity of the serine protease variants, the hydrolysis of N-succinyl-L-alanyl-L-alanyl-L-prolyl-L-phenyl-p-nitroanilide (suc-AAPF-pNA) was measured. The reagent solutions used were: 100 mM Tris/HCl, pH 8.6, containing 0.005% TWEEN®-80 (Tris dilution buffer); 100 mM Tris buffer, pH 8.6, containing 1 mM $CaCl_2$ and 0.005% TWEEN®-80 (Tris/Ca buffer); and 160 mM suc-AAPF-pNA in DMSO (suc-AAPF-pNA stock solution) (Sigma: S-7388). To prepare a suc-AAPF-pNA working solution, 1 ml suc-AAPF-pNA stock solution was added to 100 ml Tris/Ca buffer and mixed well for at least 10 seconds. The assay was performed by adding 10 µl of diluted protease solution to each well of a 96-well MTP, immediately followed by the addition of 190 µl of 1 mg/ml suc-AAPF-pNA working solution. The solutions were mixed for 5 sec, and the absorbance change in kinetic mode (25 readings in 5 minutes) was read at 405 nm in an MTP reader, at 25° C. The protease activity was expressed as AU (activity=$\Delta$OD min$^{-1}$ ml$^{-1}$).

Eglin C Inhibition Assay

As described herein, serine protease concentration and specific activity was determined by titration with an inhibitor called eglin c. Eglin c from the leech *Hirudo medicinalis* is a tight-binding protein inhibitor of subtilisins and ASP protease (Heinz et al., Biochemistry, 31: 8755-66 [1992]), and can therefore be used to measure protease enzyme concentration, which in turn permits specific activity to be calculated. The gene for eglin c was synthesized and expressed in *E. coli* by standard methods. Its properties and inhibitory potency were the same as eglin c purchased from Sigma.

(i) Concentration Determination of an Eglin C Stock Solution

A sample of *Bacillus lentus* subtilisin of known specific activity was diluted in 100 mM Tris buffer, pH 8.6, containing 1 mM $CaCl_2$ and 0.005% TWEEN®-80 (Tris/Ca buffer), to a concentration appropriate for AAPF protease assay described above. Several dilutions of the eglin c stock solution were also made in the Tris/Ca buffer. An aliquot of each diluted eglin c solution was mixed with an equal volume of the diluted *Bacillus lentus* subtilisin solution. An aliquot of the Tris/Ca buffer only, without eglin c, was also mixed with an equal volume of the diluted *Bacillus lentus* subtilisin solution, in order to measure uninhibited subtilisin activity in the absence of eglin c. The mixed solutions were incubated at room temperature for 15-30 minutes and the protease activity of each sample was then measured by AAPF assay described above. Using the known specific activity of *Bacillus lentus* subtilisin, the concentration of active protease in each sample was determined. The concentration of eglin c in each sample was then calculated based on the decrease of the observed protease activity as compared to the uninhibited subtilisin sample that was mixed with Tris/Ca buffer only (without eglin c). Thus, using the known dilutions and volumes of the eglin c solutions, the concentration of eglin c in the stock solution was determined.

(ii) Concentration and Specific Activity Determination of Subtilisin Variants

Samples of subtilisin variants were diluted in 100 mM Tris buffer, pH 8.6, containing 1 mM $CaCl_2$ and 0.005% TWEEN®-80 (Tris/Ca buffer). Several dilutions of the eglin c stock solution of known concentration were also made in the Tris/Ca buffer. An aliquot of each diluted eglin c solution was mixed with an equal volume of a subtilisin variant solution.

The mixed solutions were incubated at room temperature for 15-30 minutes and the protease activity of each sample was then measured by AAPF assay. Using the observed decrease of the protease activity upon addition of each eglin c sample and the known concentration of the eglin c, the concentration of the eglin c necessary for the complete inhibition of each subtilisin enzyme variant was calculated. This concentration is equivalent to the enzyme concentration in the sample. An aliquot of the Tris/Ca buffer only, without eglin c, was also mixed with each subtilisin variant sample and the protease activity in the absence of eglin c was measured by AAPF assay. The specific activity of the subtilisin variants was then calculated using the enzyme concentrations as determined above.

BMI Microswatch Assay

Blood milk and ink (BMI) stained microswatches (EMPA116) of 5.5 millimeter circular diameter were obtained from CFT. In one method, the EMPA116 BMI fabric is pre-rinsed in water prior to cutting them into a 96 well microtiter plate (Corning 3641), one microswatch per well. In the second method the EMPA 116 cloth is cut directly into a 96 well microtiter plate (Corning 3641) where the swatches are then rinsed with two water washes. The rinses are carried out by adding 200 µl of Milli Q water to each well/swatch and mixing them on a table top mixer (Lab line instruments, Titer plate shaker, model 4825) for 15 minutes at a setting of 7. The wash liquor is removed and 200 µl of water is added again to the swatch for another 15 minute rinse. The wash water is removed and the swatches are then air dried in the microtiter plate.

Detergent compositions 7-11 were diluted in Milli-Q (deionized) water to final working concentrations described in Table 1-1. These detergents were buffered with 2 mM sodium carbonate, pH 10.3. Additionally, a water hardness composition (3:1 Ca:Mg.—$CaCl_2$:$MgCl_2$.$6H_2O$) was added to each detergent solution to the final concentration described in Table 1-1. The detergent solutions were mixed at room temperature for 0.5 to 2 hours, centrifuged in 50 mL polypropylene conical tubes at 3000×g for 5-10 minutes and were kept at room temperature for the 32° C. assays or pre-equilibrated in an ice-water bath for the 16° C. assays. Then, 190 µl of the desired detergent solution was added to each well of the MTP containing BMI microswatches. To this mixture, 5-15 µl of the diluted enzyme master dilution solution were added, making the approximate concentration of enzyme in the reaction 0.25-2 µg/ml. The enzyme master dilution solution was prepared from the filtered culture supernatants (see TCA assay described above) at ~2.5-20 µg/mL. The MTP was sealed with tape and placed in the iEMS incubator/shaker (Thermo/Labsystems) pre-set at 16° C. in a refrigerator for 30 minutes or at 32° C. on the benchtop for 30 minutes, with agitation at 1400 rpm. Following incubation under the appropriate conditions, 120-125 µl of the solution from each well was transferred into a fresh MTP (Corning 9017). The new MTP containing 125 µl of solution/well was read at 600 nm (with 5 sec mixing mode in the plate reader) using the MTP SpectraMax reader. Blank controls containing a microswatch and detergent without any enzyme were also included. The absorbance value obtained was corrected for the blank value (substrate without enzyme), providing a measure of hydrolytic activity. For each sample (variant) the performance index was calculated. The performance index compares the performance of the variant (measured value) and the standard enzyme (theoretical value) at the same protein concentration. In addition, the theoretical values can be calculated, using the parameters of a performance dose response curve of the standard protease. A performance index (PI) that is greater than 1 (PI>1) identifies a better variant as compared to the standard (e.g., wild-type), while a PI of 1 (PI=1) identifies a variant that performs the same as the standard, and a PI that is less than 1 (PI<1) identifies a variant that performs worse than the standard. Thus, the PI identifies winners as well as variants that are less desirable for use under certain circumstances.

TABLE 1-1

Final Detergent, Water Hardness, and Buffer Concentrations Used for BMI Microswatch Assays

| Detergent Composition | Final Detergent Concentration (g/L) | Final Water Hardness* (gpg) | Final Sodium Carbonate Buffer Concentration (mM) |
|---|---|---|---|
| 7 | 0.808 | 6 | 2 |
| 8 | 1 | 3 | 2 |
| 9 | 2.3 | 12 | 2 |
| 10 | 5.9 | 12 | 2 |
| 11 | 8.3 | 12 | 2 |

LAS/EDTA Stability Assay

The stability of protease variants in the presence of a representative anionic surfactant (LAS=linear alkylbene sulfonate, sodium dodecylbenzenesulfonate-DOBS) and di-sodium EDTA is measured after incubation under defined conditions and the residual activity is determined using the AAPF assay described above. The reagents used were dodecylbenzene sulfonate, sodium salt (DOBS; Sigma No. D-2525), TWEEN®-80 (Sigma No. P-8074), di-sodium EDTA (Siegfried Handel No. 164599-02), HEPES (Sigma No. H-7523), unstressed buffer: 50 mM HEPES (11.9 g/l)+ 0.005% TWEEN®-80, pH 8.0, Stress buffer: 50 mM HEPES (11.9 g/l), 0.1% (w/v) DOBS (1 g/l), 10 mM EDTA (3.36 g/l), pH 8.0, reference protease and protease variant culture supernatants, containing 200-400 µg/ml protein. The equipment used is V- or U-bottom MTP as dilution plates (Greiner 651101 and 650161 respectively), F-bottom MTP (Corning 9017) for unstress and LAS/EDTA buffer as well as for suc-AAPF-pNA plates, Biomek FX (Beckman Coulter), Spectramax Plus 384 MTP Reader (Molecular Devices), and iEMS Incubator/Shaker (Thermo/Labsystems).

The iEMS incubator/shaker (Thermo/Labsystems) is set at 29° C. Culture supernatants were diluted into plates containing unstress buffer to a concentration of ~25 ppm (master dilution plate). For the assay, 20 µl of sample from the master dilution plate is added to plates containing 180 µl unstress buffer to give a final incubation concentration of 2.5 ppm. The contents were mixed and kept at room temperature and the AAPF assay is performed on this plate. In addition, 20 µl of sample from the master dilution plate is also added to plates containing 180 µl stress buffer (50 mM HEPES (11.9 g/l), 0.1% (w/v) DOBS (1 g/l), 10 mM EDTA (3.36 g/l), pH 8.0). The solutions were mixed and immediately placed in 29° C. iEMS shaker for 30 min at 400 rpm. Following 30 minutes of incubation, the AAPF assay is performed on the stress plate. The stability of the samples is determined by calculating the ratio of the residual and initial AAPF activity as follows: Residual Activity (%)=[mOD·min-1 stressed]*100/[mOD·min-1 unstressed].

The final detergent, water hardness and buffer concentrations are determined based on the assay system to be used (e.g., North American, Japanese, Western European, or Central European conditions). In some aspects, the stain removal performance of the protease variants is determined in commercially available detergents. Heat inactivation of commercial detergent formulas serves to destroy the enzymatic activity of any protein components while retaining the properties of non-enzymatic components. Thus, this method is suitable for preparing commercially purchased detergents for use in testing the enzyme variants of the present invention.

Baked Egg Microtiter Assay

For this assay, 96-well baked egg yolk substrate plates are prepared from chicken egg yolks. Chicken egg yolks are separated from the whites, released from the membrane sac, and diluted 20% (vol/weight) with Milli-Q water. The diluted yolk is stirred for 15 min at room temperature using a magnetic stirrer. Five µL are carefully pipetted into the center of each well of a 96-well V-bottom plate (Costar #3894) using an 8-channel pipette. The plates are baked at 90° C. for 1 hour and cooled at room temperature. The baked egg yolk substrate plates are stored at room temperature and used within one week of preparation. Automatic dish detergents are prepared as described herein and pre-heated to 50° C. A 190 µL aliquot of detergent is added to each well of the 96-well plate using an 8-channel pipette. Ten µL of diluted enzyme is added to each well using a 96-channel pipetting device. The plate is carefully sealed with an adhesive foil sealer and incubated at 50° C. with shaking for 30 min. 120 µL of the reaction mixture is transferred to a new 96-well flat-bottom plate, and the absorbance/light scattering is determined at 405 nm. The absorbance/light scattering at 405 nm is proportional to egg yolk removal.

Egg Yolk Microswatch Assay ("CS-38 Microswatch Assay"; or "EGG" or "Dish")

Automatic dish detergents are prepared as described herein. The equipment used included a New Brunswick Innova 4230 shaker/incubator and a SpectraMAX (type 340) MTP reader. The MTPs are obtained from Costar (type 9017). Aged egg yolk with pigment swatches (CS-38) are obtained from Center for Test Materials (Vlaardingen, Netherlands). Before cutting 0.25-inch circular microswatches, the fabric is washed with water. One microswatch is placed in each well of a 96-well microtiter plate. The test detergent is equilibrated at 50° C. 190 µl of detergent solution is added to each well of the MTP, containing microswatches. To this mixture, 10 µl of the diluted enzyme solution is added. The MTP is sealed with adhesive foil and placed in the incubator for 30 minutes, with agitation. Following incubation, 100 µl of the solution from each well is transferred into a fresh MTP. This MTP is read at 405 nm using a SpectraMax MTP reader. Blank controls, as well as controls containing microswatches and detergent but no enzyme are also included.

In some aspects, pre-washed microswatches find use. This type of microswatch is pre-washed in deionised water for 20 minutes at ambient temperature. After the pre-washing step, the swatches are put on top of paper towels to dry. The air-dried swatches are then punched using a ¼" circular die on an expulsion press. Finally two microswatches are put into each well of a 96-well MTP vertically to expose the whole surface area (i.e. not flat on the bottom of the well).

Samples of protease variants to be tested are obtained from filtered culture broth of cultures grown in MTP plates. The equipment used is a Biomek FX Robot (Beckman Coulter), a SpectraMAX MTP Reader (type 340; Molecular Devices), an iEMS incubator/shaker (Thermo/Labsystems); F-bottom MTPs (Costar type 9017 used for reading reaction plates after incubation); and V-bottom MTPs (Greiner 651101 used for pre-dilution of supernatant). In this assay, the proteases hydrolyze the substrate and liberate pigment and insoluble particles from the substrate. Thus the rate of turbidity is a measure of enzyme activity.

The stain removal performance of reference serine proteases and variants therefrom on microswatches is determined on a MTP scale in commercially available detergent (Calgonit 5 in1). CS-38 microswatches (egg-yolk with pigment, aged by heating), obtained from CFT Vlaardingen are used as substrate. Two swatches are used per well. ADW tablets from Calgonit 5 in1 are used to prepare the detergent solution. To inactivate the protease activity present in the tablets, a 21 g tablet is dissolved in Milli-Q water heated in a water bath to a temperature of 60° C. The solution is cooled to room temperature and the volume of water adjusted to 700 mL. The solution is further diluted with water to achieve a final concentration of 3 g/l. Water hardness is adjusted to 21° GH by adding 1.46 ml of the Ca/Mg-mixture (Ca/Mg mixture [(3:1), 1.92 M $CaCl_2$=282.3 g/L $CaCl_2.2H_2O$; 0.64 M $MgCl_2$=130.1 g/L $MgCl_2.6H_2O$), 15000 gpg]. The enzyme samples are prediluted in 10 mM NaCl, 0.1 mM $CaCl_2$, 0.005% TWEEN®-80 solution and tested at appropriate concentrations.

The incubator is set at the desired temperature of 50° C. 72 µl of dilution buffer is added to the empty V-bottom plate (i.e., a "dilution plate") followed by 8 µl supernatant. 9 µl from the dilution plate is added to plates containing the microswatches incubated in 171 µl detergent solution. 9 µl from the dilution plate is added to plates containing the microswatches to give a total dilution of supernatant of 200×. The microswatch plate (with detergent and enzyme) is covered with tape and placed in the incubator/shaker for 30 minutes at 1400 rpm. Following incubation, 75 µl of the reaction mixture is transferred to an empty F-bottom plate and the absorbance is read in a MTP Reader at 405 nm after de-bubbling with a hair dryer. Blank controls, containing one or two microswatches and detergent without the addition of reference protease containing samples are also included in the test.

The absorbance value obtained is corrected for the blank value (substrate without enzyme), providing a measure of hydrolytic activity. For each sample (variant) the performance index is calculated. The performance index compares the performance of the variant (actual value) and the standard enzyme (theoretical value) at the same protein concentration. In addition, the theoretical values can be calculated, using the parameters of the Langmuir equation of the standard enzyme.

Egg Yolk Stains on Stainless Steel

The stainless steel sheets (10×15 cm; brushed on one side) used in these experiments are thoroughly washed at 95° C. in a laboratory dishwasher with a high-alkalinity commercial detergent (e.g., ECOLAB® detergent; Henkel) to provide sheets that are clean and grease-free. These sheets are deburred prior to their first use. The sheets are dried for 30 minutes at 80° C. in a thermal cabinet before being soiled with egg yolk. The surfaces to be brushed are not touched prior to soiling. Also, no water stains or fluff on the surfaces are permitted. The cooled sheets are weighed before soiling.

The egg yolks are prepared by separating the yolks of approximately 10-11 eggs (200 g of egg yolk) from the whites. The yolks are stirred with a fork in a glass beaker to homogenize the yolk suspension. The yolks are then strained (approx. 0.5 mm mesh) to remove coarse particles and any egg shell fragments. A flat brush (2.5") is used to apply 1.0±0.1 g egg yolk suspension as uniformly as possible over an area of 140 $cm^2$ on the brushed sides of each of the stainless steel sheets, leaving an approx. 1 cm wide unsoiled rim (adhesive tape is used if needed). The soiled sheets are dried horizontally (to prevent formation of droplets on the edges of the sheets), at room temperature for 4 hours (max. 24 h).

For denaturation, the sheets are immersed for 30 seconds in boiling, demineralized water (using a holding device if necessary). Then, the sheets are dried again for 30 min at 80° C. After drying and cooling, the sheets are weighed. After weighing, the sheets are left for at least 24 hours (20° C., 40-60% relatively humidity) before submitting them to the wash test. In order to meet the testing requirements, only sheets with 500±100 mg/140 cm² (egg yolk after denaturation), are used in the testing. After the wash tests are conducted, the sheets are dried for 30 min at 80° C., in the thermal cabinet, and weighed again after cooling. The percent cleaning performance is determined by dividing the (mg of egg yolk released by washing×100) by the (mg of denatured egg yolk applied).

Minced Meat on Porcelain Plates

For these experiments, dessert plates (Arzberg, white, glazed porcelain) conforming to EN 50242, form 1495, No. 0219, diameter 19 cm are used. A total of 225 g lean pork and beef (half and half) is finely chopped and cooled, after removing visible fat. The mixture is twice run through a mincer. Temperatures above 35° C. are avoided. Then, 225 g of the minced meat is mixed with 75 g of egg (white and yolk mixed together). The preparation is then frozen up to three months at −18° C., prior to use. If pork is not available, beef is used.

The minced meat and egg mixture (300 g) is brought up to room temperature and mixed with 80 ml synthetic water. The mixture is then homogenized using a kitchen hand blender for 2 min. Then, a fork is used to spread 3 g of the minced meat/egg/water mixture on each white porcelain plate, leaving an approx. 2 cm wide unsoiled margin around the rim. The amount applied is 11.8±0.5 mg/cm². The plates are dried for 2 hours at 120° C. in a preheated thermal cabinet. As soon as the plates are cooled, they are ready for use. The plates are stacked with paper towels between each of the plates.

After washing, the plates are sprayed with ninhydrin solution (1% ethanol) for better identification of the minced meat residues. To promote the color reaction, the plates are heated for 10 min at 80° C. in the thermal cabinet. Evaluation of the washing performance is done by visually inspecting the color reactions of the minced meat residues with reference to the IKW photographic catalogue (IKW).

Egg/Milk Stains on Stainless Steel

The stainless steel sheets (10×15 cm; brushed on one side) used in these experiments are thoroughly washed at 95° C. in a laboratory dishwasher with a high-alkalinity commercial detergent to remove grease and clean the sheets. The sheets are polished dry with a cellulose cloth. The surfaces to be brushed are not touched prior to soiling. Also, no water stains or fluff on the surfaces are permitted. Before soiling, the sheets are placed in a thermal cabinet at 80° C., for 30 min. The cooled sheets are weighed before soiling.

The egg yolks and whites of whole raw eggs (3-4 eggs; 160 g/egg) are placed in a bowl and beaten with an egg whisk. Then, 50 ml semi-skimmed UHT (1.5% fat, ultra-high temperature, homogenized) milk are added to the mixture. The milk and egg are mixed without generating froth. A flat brush is used to uniformly distribute 1.0±0.1 g of the egg/milk mixture on the brushed side of the stainless steel sheets, using a balance to check the distribution. A margin of approximately 1.0 cm is left around the short sides of the sheets. The soiled sheets are dried horizontally (to prevent formation of droplets on the edges of the sheets), at room temperature for 4 hours (max. 24 h).

The sheets are then immersed for 30 seconds in boiling, demineralized water (using a holding device if necessary). Then, the sheets are dried again for 30 min at 80° C. After drying and cooling, the sheets are weighed. After weighing, the sheets are left for at least 24 hours (20° C., 40-60% relatively humidity), before submitting them to the wash test. In order to meet the testing requirements, only sheets with 190±10 mg egg yolk are used.

After the wash tests are conducted, the sheets are dried for 30 min at 80° C., in the thermal cabinet, and weighed again after cooling. The percentage cleaning performance is determined by dividing the (mg of egg/milk released by washing× 100) by the (mg of egg/milk applied).

Preparation of the Spaghetti Mix Stain on Porcelain Plates

Pasta sauce (390 g) is mixed with 150 g of boiled spaghetti pasta, 25 g of minced meat (improved IKW composition-a combination of 225 gram fat free minced meat and 75 gram egg yolk) and 50 g of Grozette Formaggio cheese. A spoon is used to spread 3 g of this mixture on each white porcelain plate (Arzberg, 19 cm diameter, white, glazed porcelain, conforming to EN 50242, form 1495, No. 0219) leaving an approximately 2 cm wide unsoiled margin around the rim. The plates are dried by baking them for 2 hours at 120° C. in an oven. As soon as the plates are cooled, they are ready for use. The plates are stacked with paper towels between each of the plates for storage. After washing, the plates are sprayed with iodine solution (0.05N) for better identification of the carbohydrate residues. Evaluation of the washing performance is done by visually inspecting the color reactions of the carbohydrate residues with reference to the IKW photographic catalogue (IKW) and rated on a scale of 0-10 (10 being clean).

Performance Index

The performance index compares the performance of the variant (measured value) and the standard enzyme (theoretical value) at the same protein concentration. In addition, the theoretical values can be calculated, using the parameters of a performance dose response curve of the standard protease. Various terms set forth below are used to describe the variant: non-deleterious variants have a PI>0.05; deleterious variants have a PI=0.05; combinable variants are those for which the variant has performance index values greater than or equal to 0.2 for at least one property, and >0.05 for all properties. Combinable variants are those that can be combined to deliver proteins with appropriate performance indices for one or more desired properties. These data find use in engineering any subtilisin/subtilase. Even if the subtilase to be engineered has an amino acid different from that of subtilisin GG36 at particular positions, these data find use in finding substitutions that will alter the desired properties by identifying the best choices for substitutions, including substitutions to the GG36 wild type amino acid.

Example 2

Generation of GG36 Single Mutants Using Site Evaluation Libraries (SELs)

The construction of GG36 SELs described in this example was performed by GENEART using their proprietary methods and technology platform for gene optimization, gene synthesis, library generation and analysis (WO 2004/059556A3, European Patent Nos. 0 200 362 and 0 201 184; and U.S. Pat. Nos. 4,683,195, 4,683,202 and 6,472,184). The GG36 SELs were produced at positions pre-selected by the inventors using the pHPLT-GG36 *B. subtilis* expression plasmid (see FIG. 6). This *B. subtilis* expression plasmid contains the GG36 expression cassette shown below, the *B. licheniformis* LAT promoter (Plat), and additional elements from pUB110 (McKenzie et al., Plasmid, 15:93-103, 1986) including a replicase gene (reppUB), a neomycin/kanamycin resistance gene (neo) and a bleomycin resistance marker (bleo) (FIG. 4 in U.S. Pat. No. 6,566,112). The pHPLT-GG36 plasmid map is provided at FIG. 6. The GG36 expression cassette sequence is provided below.

The DNA sequence of GG36 (the signal sequence is shown in lower case letters, propeptide in lower case, underlined text, and GG36 mature sequence in uppercase letters) is provided below:

(SEQ ID NO: 756)
Gtgagaagcaaaaaattgtggatcgtcgcgtcgaccgcactactcatttc tgttgctttcagttcatcgatcgcatcggct<u>gctgaagaagcaaaagaaa</u>

<u>aatatttaattggctttaatgagcaggaagctgtcagtgagtttgtagaa</u>

<u>caagtagaggcaaatgacgaggtcgccattctctctgaggaagaggaagt</u>

<u>cgaaattgaattgcttcatgaatttgaaacgattcctgttttatccgttg</u>

<u>agttaagcccagaagatgtggacgcgcttgagctcgatccagcgatttct</u>

<u>tatattgaagaggatgcagaagtaacgacaatg</u>GCGCAATCAGTGCCATG

GGGAATTAGCCGTGTGCAAGCCCCAGCTGCCCATAACCGTGGATTGACAG

GTTCTGGTGTAAAAGTTGCTGTCCTCGATACAGGTATTTCCACTCATCCA

GACTTAAATATTCGTGGTGGCGCTAGCTTTGTACCAGGGGAACCATCCAC

TCAAGATGGGAATGGGCATGGCACGCATGTGGCCGGGACGATTGCTGCTT

TAAACAATTCGATTGGCGTTCTTGGCGTAGCGCCGAGCGCGGAACTATAC

GCTGTTAAAGTATTAGGGGCGAGCGGTTCAGGTTCGGTCAGCTCGATTGC

CCAAGGATTGGAATGGGCAGGGAACAATGGCATGCACGTTGCTAATTTGA

GTTTAGGAAGCCCTTCGCCAAGTGCCACACTTGAGCAAGCTGTTAATAGC

GCGACTTCTAGAGGCGTTCTTGTTGTAGCGGCATCTGGAAATTCAGGTGC

AGGCTCAATCAGCTATCCGGCCCGTTATGCGAACGCAATGGCAGTCGGAG

CTACTGACCAAAACAACAACCGCGCCAGCTTTTCACAGTATGGCGCAGGG

CTTGACATTGTCGCACCAGGTGTAAACGTGCAGAGCACATACCCAGGTTC

AACGTATGCCAGCTTAAACGGTACATCGATGGCTACTCCTCATGTTGCAG

GTGCAGCAGCCCTTGTTAAACAAAAGAACCCATCTTGGTCCAATGTACAA

ATCCGCAATCATCTAAAGAATACGGCAACGAGCTTAGGAAGCACGAACTT

GTATGGAAGCGGACTTGTCAATGCAGAAGCTGCAACTCGTTAA

The protein sequence of GG36 (the signal sequence is shown in lower case letters, propeptide in lower case, underlined text, and GG36 mature protease sequence in uppercase letters) is provided below:

(SEQ ID NO: 757)
vrskklwivastallisvafsssiasa<u>aeeakekyliqfneqeavsefve</u>

<u>qveandevailseeeeveiellhefetipvlsvelspedvdaleldpais</u>

<u>yieedaevttm</u>AQSVPWGISRVQAPAAHNRGLTGSGVKVAVLDTGISTHP

DLNIRGGASFVPGEPSTQDGNGHGTHVAGTIAALNNSIGVLGVAPSAELY

AVKVLGASGSGSVSSIAQGLEWAGNNGMHVANLSLGSPSPSATLEQAVNS

ATSRGVLVVAASGNSGAGSISYPARYANAMAVGATDQNNNRASFSQYGAG

LDIVAPGVNVQSTYPGSTYASLNGTSMATPHVAGAAALVKQKNPSWSNVQ

IRNHLKNTATSLGSTNLYGSGLVNAEAATR.

The method of mutagenesis was based on the codon-specific mutation approach in which all possible amino acid substitutions are simultaneously created at a specific codon of interest using forward and reverse mutagenesis primers that contain a degenerate codon, NNS ((A, C, T or G), (A, C, T or G), (C or G)) at the site of interest. To construct each of the GG36 SELs, three PCR reactions were performed: two mutagenesis reactions (primary PCR1 and PCR2) to introduce the mutated codon of interest in the mature GG36 DNA sequence using the NNS forward and reverse mutagenesis primers (25-45 nucleotides long), and a third reaction to fuse the two mutagenesis PCR products together to construct the pHPLT-GG36 expression vector having the desired mutated codons in the mature GG36 sequence.

The primer sequences used in this Example are provided below:

TABLE 2-1

Primers

| Sequence | Primer Name |
| --- | --- |
| CGCGCTTGAGCTCGATCCAGCGATTTC (SEQ ID NO: 758) | SacI-Fw |
| GTCTCCAAGCTTTAACGAGTTGCAG (SEQ ID NO: 759) | HindIII-Rv |
| GCAATTCAGATCTTCCTTCAGGTTATGACC (SEQ ID NO: 760) | pHPLT-BglII-Fw |
| GCATCGAAGATCTGATTGCTTAACTGCTTC (SEQ ID NO: 761) | pHPLT-BglII-Rv |

The Phusion High-Fidelity DNA Polymerase (Finnzymes catalog no. F-530L) was used for all PCRs, and the reactions were executed according to manufacturer's protocols that were supplied with the polymerase. In particular, for primary PCR 1, 1 μL (10 μM) of each of the pHPLT-BglII-Fw primer and a NNS reverse mutagenesis primer were used, and for primary PCR 2, 1 μL (10 μM) of the pHPLT-BglII-Rv primer and a NNS forward mutagenesis primer were used. Each reaction also included 1 μL of the pHPLT-GG36 plasmid template DNA (0.1-1 ng/μL). An MJ Research PTC-200 Peltier thermal cycler was used for the PCRs. The reactions yielded two fragments of approximately 2 to 3 kb having approximately 30 nucleotide overlap surrounding the GG36 codon of interest. The fragments obtained were fused in a third PCR similar to the ones described above using 1 μL of primary PCR 1 reaction mix, 1 μL of primary PCR 2 reaction mix and 1 μL (10 μM) of each of the forward and reverse SacI-Fw and HindIII-Rv primers. The amplified linear 859 bp fragment encoding the GG36 variant gene was purified (using QIAGEN® Qiaquick PCR purification kit) and digested with the SacI and HindIII restriction enzymes to create cohesive ends on both sides of the fusion fragment. About 50 ng of plasmid pHPLT-GG36 was also purified after digestion with SacI and HindIII, resulting in a 3.9 kb vector backbone fragment. The digested vector fragment was ligated with 50 ng of the digested 859 bp fragment encoding the variant enzyme using the T4 DNA ligase (Invitrogen) following the manufacturer's protocol for cloning of cohesive ends. Subsequently, the ligation mixture was used to transform B. subtilis cells (ΔaprE, ΔnprE, oppA, ΔspoIIE, degUHy32, ΔamyE::[xylR, pxylA-comK]) as described (WO 2002/014490).

To express the variant proteins for further biochemical analyses, the B. subtilis strains carrying the GG36 variant plasmids were inoculated into microtiter plates containing 150 μl Luria broth medium supplemented with 10 μg/ml neomycin. Plates were grown overnight at 37° C. with 300 rpm shaking and 80% humidity using Enzyscreen lids for microtiter plates (Enzyscreen). Ten microliters from the overnight culture plate were used to inoculate a new microtiter plate containing 190 μl of MBD medium (a MOPS based defined medium) with 10 ug/ml neomycin. MBD medium was prepared essentially as known in the art (see Neidhardt et al., J. Bacteriol. 119:736-747 [1974]), except that $NH_4Cl_2$, $FeSO_4$, and $CaCl_2$ were omitted from the base medium, 3 mM $K_2HPO_4$ was used, and the base medium was supplemented with 60 mM urea, and 100 ml of a solution made of 210 g/L glucose, and 350 g/L maltodextrin. The micronutrients were made up as a 100× stock solution containing in one liter, 400 mg $FeSO_4.7H_2O$, 100 mg $MnSO_4.H_2O$, 100 mg $ZnSO_4.7H_2O$, 50 mg $CuCl_2.2H_2O$, 100 mg $CoCl_2.6H_2O$, 100 mg $NaMoO_4.2H_2O$, 100 mg $Na_2B_4O_7.10H_2O$, 10 ml of 1M $CaCl_2$, and 10 ml of 0.5 M sodium citrate. The MBD medium containing microtiter plates were grown for 68 hours at 37° C., 300 rpm, and 80% humidity using Enzyscreen lids (Enzyscreen) for determining protein expression. The next day, cultures were filtered through a micro-filter plate (0.22 μm; Millipore) and the resulting filtrate was used for biochemical analysis. The TCA and BMI microswatch assays for the detergent compositions 7-11 were carried out as described in Example 1. Performance indices were also calculated as described under the BMI assay description in Example 1, and they are shown in Table 2-2 relative to GG36. In the following Tables, the detergent compositions ("Det.") correspond to those shown in Table D, above. Also, as indicated, the amino acid position is listed according to BPN' numbering.

TABLE 2-2

Single Variants of GG36 with Performance Indices of at Least 0.2 Relative to GG36 in Either TCA or BMI Microswatch Cleaning at 16° C. in Detergents 7-11.

| GG36 Amino Acid Position (BPN' Numbering) | WT Residue | Mutant Residue |
|---|---|---|
| 1 | A | R |
| 2 | Q | A |
| 2 | Q | R |
| 2 | Q | S |
| 2 | Q | M |
| 2 | Q | W |
| 3 | S | R |
| 4 | V | R |
| 4 | V | S |
| 4 | V | C |
| 8 | I | A |
| 9 | S | W |
| 9 | S | F |
| 9 | S | A |
| 10 | R | A |
| 10 | R | M |
| 10 | R | S |
| 10 | R | H |
| 12 | Q | F |
| 12 | Q | R |
| 14 | P | F |
| 14 | P | K |
| 14 | P | Q |
| 15 | A | R |
| 15 | A | F |
| 16 | A | S |
| 17 | H | R |
| 17 | H | F |
| 17 | H | M |
| 18 | N | R |
| 18 | N | K |
| 20 | G | R |
| 20 | G | K |
| 20 | G | F |
| 22 | T | R |
| 22 | T | Q |
| 22 | T | L |
| 22 | T | V |
| 22 | T | W |
| 22 | T | Y |
| 22 | T | A |
| 23 | G | A |
| 23 | G | S |
| 23 | G | F |
| 24 | S | R |
| 24 | S | W |
| 24 | S | H |
| 24 | S | L |
| 24 | S | Q |
| 24 | S | F |
| 25 | G | R |
| 25 | G | F |
| 25 | G | V |
| 26 | V | F |
| 27 | K | R |
| 27 | K | L |
| 27 | K | V |
| 27 | K | F |
| 28 | V | A |
| 28 | V | E |
| 28 | V | N |
| 29 | A | T |
| 30 | V | E |
| 31 | L | F |
| 33 | T | S |
| 33 | T | G |
| 33 | T | D |
| 34 | G | P |
| 35 | I | M |
| 36 | S | T |
| 36 | S | F |
| 36 | S | R |
| 38 | T | R |
| 38 | T | F |
| 38 | T | L |
| 40 | P | H |
| 40 | P | W |
| 40 | P | R |
| 40 | P | N |
| 40 | P | T |
| 40 | P | L |
| 42 | L | I |
| 43 | N | R |
| 43 | N | A |
| 43 | N | S |
| 43 | N | W |
| 43 | N | F |
| 43 | N | I |
| 43 | N | D |
| 43 | N | M |
| 45 | R | T |
| 46 | G | R |
| 48 | A | R |
| 50 | F | C |
| 51 | V | W |
| 51 | V | F |
| 51 | V | H |
| 52 | P | F |
| 52 | P | N |
| 52 | P | E |
| 55 | P | Y |
| 57 | T | R |
| 59 | Q | A |
| 59 | Q | F |
| 59 | Q | R |
| 60 | D | P |
| 60 | D | A |
| 60 | D | Q |
| 62 | N | Q |
| 62 | N | E |
| 63 | G | S |

TABLE 2-2-continued

Single Variants of GG36 with Performance Indices of at Least 0.2 Relative to GG36 in Either TCA or BMI Microswatch Cleaning at 16° C. in Detergents 7-11.

| GG36 Amino Acid Position (BPN' Numbering) | WT Residue | Mutant Residue |
|---|---|---|
| 63 | G | A |
| 63 | G | M |
| 63 | G | V |
| 63 | G | T |
| 63 | G | H |
| 63 | G | Q |
| 63 | G | I |
| 63 | G | D |
| 63 | G | E |
| 63 | G | P |
| 64 | H | F |
| 64 | H | T |
| 68 | V | A |
| 68 | V | C |
| 69 | A | N |
| 69 | A | T |
| 69 | A | W |
| 69 | A | P |
| 71 | T | G |
| 72 | I | C |
| 74 | A | C |
| 75 | L | R |
| 75 | L | A |
| 75 | L | E |
| 75 | L | F |
| 78 | S | R |
| 78 | S | I |
| 78 | S | N |
| 79 | I | Q |
| 79 | I | W |
| 81 | V | R |
| 82 | L | R |
| 82 | L | T |
| 82 | L | M |
| 82 | L | F |
| 82 | L | V |
| 85 | A | M |
| 86 | P | W |
| 86 | P | I |
| 86 | P | L |
| 89 | E | P |
| 89 | E | W |
| 89 | E | T |
| 89 | E | I |
| 89 | E | H |
| 89 | E | V |
| 89 | E | F |
| 89 | E | L |
| 89 | E | W |
| 89 | E | G |
| 91 | Y | F |
| 91 | Y | N |
| 92 | A | F |
| 94 | K | N |
| 99 | S | F |
| 99 | S | T |
| 99 | S | M |
| 99 | S | G |
| 99 | S | P |
| 100 | G | I |
| 100 | G | S |
| 100 | G | N |
| 100 | G | Q |
| 101 | S | N |
| 101 | S | G |
| 101 | S | T |
| 101 | S | A |
| 101 | S | D |
| 101 | S | F |
| 101 | S | D |
| 101 | S | E |
| 101 | S | P |
| 102 | G | A |
| 102 | G | N |
| 102 | G | T |
| 102 | G | E |
| 102 | G | H |
| 103 | S | N |
| 103 | S | G |
| 103 | S | D |
| 104 | V | L |
| 104 | V | I |
| 104 | V | E |
| 104 | V | D |
| 105 | S | T |
| 105 | S | Q |
| 105 | S | E |
| 106 | S | V |
| 106 | S | G |
| 106 | S | T |
| 106 | S | A |
| 106 | S | E |
| 106 | S | D |
| 106 | S | F |
| 107 | I | F |
| 107 | I | M |
| 108 | A | I |
| 108 | A | G |
| 109 | Q | M |
| 111 | L | V |
| 111 | L | I |
| 112 | E | V |
| 112 | E | L |
| 112 | E | Q |
| 114 | A | G |
| 115 | G | R |
| 115 | G | K |
| 116 | N | L |
| 116 | N | A |
| 116 | N | K |
| 117 | N | F |
| 118 | G | I |
| 118 | G | R |
| 119 | M | C |
| 120 | H | A |
| 120 | H | F |
| 120 | H | R |
| 121 | V | E |
| 121 | V | F |
| 123 | N | G |
| 123 | N | E |
| 124 | L | S |
| 128 | S | N |
| 128 | S | M |
| 128 | S | H |
| 128 | S | Q |
| 128 | S | I |
| 128 | S | F |
| 128 | S | L |
| 128 | S | D |
| 129 | P | E |
| 132 | S | A |
| 132 | S | E |
| 138 | A | G |
| 144 | S | R |
| 147 | V | L |
| 148 | L | I |
| 158 | A | E |
| 159 | G | C |
| 159 | G | E |
| 160 | S | D |
| 166 | S | E |
| 166 | S | D |
| 167 | Y | W |
| 175 | M | V |
| 177 | V | C |

TABLE 2-2-continued

Single Variants of GG36 with Performance Indices of at Least 0.2 Relative to GG36 in Either TCA or BMI Microswatch Cleaning at 16° C. in Detergents 7-11.

| GG36 Amino Acid Position (BPN' Numbering) | WT Residue | Mutant Residue |
|---|---|---|
| 181 | D | A |
| 182 | Q | R |
| 183 | N | D |
| 183 | N | R |
| 183 | N | I |
| 183 | N | F |
| 183 | N | M |
| 185 | N | I |
| 185 | N | E |
| 185 | N | V |
| 186 | R | H |
| 186 | R | K |
| 188 | S | R |
| 188 | S | E |
| 188 | S | D |
| 192 | Y | W |
| 192 | Y | H |
| 194 | A | V |
| 194 | A | F |
| 194 | A | E |
| 197 | D | F |
| 198 | I | L |
| 198 | I | F |
| 203 | V | E |
| 203 | V | C |
| 208 | T | S |
| 209 | Y | N |
| 209 | Y | S |
| 209 | Y | F |
| 209 | Y | T |
| 209 | Y | H |
| 209 | Y | L |
| 209 | Y | G |
| 209 | Y | E |
| 210 | P | V |
| 210 | P | R |
| 210 | P | L |
| 211 | G | R |
| 211 | G | Q |
| 212 | S | I |
| 212 | S | F |
| 212 | S | M |
| 213 | T | A |
| 214 | Y | F |
| 215 | A | F |
| 215 | A | N |
| 215 | A | H |
| 215 | A | E |
| 215 | A | D |
| 216 | S | F |
| 216 | S | A |
| 217 | L | E |
| 217 | L | N |
| 217 | L | D |
| 218 | N | P |
| 218 | N | E |
| 218 | N | D |
| 224 | T | A |
| 224 | T | G |
| 227 | V | I |
| 230 | A | E |
| 231 | A | I |
| 231 | A | C |
| 233 | L | C |
| 234 | V | F |
| 235 | K | F |
| 236 | Q | N |
| 236 | Q | F |
| 238 | N | R |
| 238 | N | K |
| 238 | N | L |
| 239 | P | R |
| 239 | P | S |

TABLE 2-2-continued

Single Variants of GG36 with Performance Indices of at Least 0.2 Relative to GG36 in Either TCA or BMI Microswatch Cleaning at 16° C. in Detergents 7-11.

| GG36 Amino Acid Position (BPN' Numbering) | WT Residue | Mutant Residue |
|---|---|---|
| 239 | P | R |
| 239 | P | H |
| 239 | P | N |
| 239 | P | K |
| 239 | P | T |
| 239 | P | F |
| 239 | P | G |
| 240 | S | R |
| 241 | W | R |
| 242 | S | R |
| 242 | S | L |
| 243 | N | R |
| 243 | N | F |
| 244 | V | R |
| 246 | I | S |
| 248 | N | I |
| 248 | N | V |
| 248 | N | R |
| 249 | H | R |
| 249 | H | T |
| 250 | L | I |
| 251 | K | R |
| 251 | K | S |
| 252 | N | R |
| 252 | N | F |
| 252 | N | H |
| 252 | N | I |
| 253 | T | R |
| 253 | T | F |
| 253 | T | I |
| 254 | A | C |
| 256 | S | N |
| 258 | G | R |
| 260 | T | V |
| 260 | T | I |
| 262 | L | H |
| 262 | L | D |
| 263 | Y | F |
| 265 | S | F |
| 267 | L | N |
| 267 | L | M |
| 267 | L | V |
| 269 | N | R |
| 269 | N | I |
| 270 | A | C |
| 271 | E | T |
| 271 | E | V |
| 271 | E | L |
| 271 | E | H |
| 271 | E | F |
| 271 | E | P |
| 271 | E | A |
| 271 | E | M |
| 271 | E | I |
| 272 | A | F |
| 272 | A | R |
| 273 | A | I |
| 273 | A | F |
| 274 | T | G |

TABLE 2-3

GG36 Single Variants with Performance Indices of at Least 1.5 Relative to GG36 BMI Microswatch Cleaning at 32° C. in Detergent 7.
GG36 Variant

N62E
A158E
G159E

TABLE 2-4

GG36 Single Variants with Performance Indices of at least 1.2
Relative to GG36 BMI Microswatch Cleaning at 32° C. in Detergent 10.

GG36 Variant

A1R
S78R
V244R
N269R
E271L

Example 3

Construction and Cleaning Performance of the NHJ1 and WCE1 Sets of GG36 Variants The NHJ1 and WCE1 set of GG36 variants described herein were constructed at DNA 2.0, Inc., using the pHPLT-GG36 *B. subtilis* expression plasmid described above (FIG. 6). The variants were expressed in *B. subtilis* cells (genotype: ΔaprE, ΔnprE, amyE::xylRPxylAcomK-phleo) as described in Example 2, and were further characterized using the TCA assay for protein content determination, LAS/EDTA stability assay, and BMI microswatch cleaning assay as described in Example 1. These results are shown in Tables 3-1 and 3-2. In the following Tables, the detergent compositions ("Det.") correspond to those shown in Table D, above. Also, as indicated, the amino acid position is listed according to BPN' numbering.

TABLE 3-1

NHJ1 Variants with Performance Indices of at least 0.25
Relative to GG36 in Any One of TCA, LAS/EDTA Stability, or BMI
Microswatch Cleaning at 16° C. in Detergents 7, 8 or 9.

GG36 Variant (BPN' Numbering)

N062E-A158E
S103G-A158E
S128N-A158E
A016S-A158E
V104L-A158E
E089P-A158E
L111V-A158E
T022A-A158E
S101A-A158E
L148I-A158E
P129E-A158E
T022A-E089P
A016S-E089P
N062E-E089P
N062E-E271F
A158E-E271F
R186H-E271F
P129E-E271F
L111V-E271F
Y209E-E271F
A016S-E271F
S188D-E271F
T022A-E271F
G159E-E271F
V104L-E271F
S101A-E271F
E089P-E271F
S128N-E271F
S103G-E271F
L148I-E271F
H249R-E271F
N062E-G159E
A016S-G159E
S128N-G159E
L148I-G159E
L111V-G159E
E089P-G159E

TABLE 3-1-continued

NHJ1 Variants with Performance Indices of at least 0.25
Relative to GG36 in Any One of TCA, LAS/EDTA Stability, or BMI
Microswatch Cleaning at 16° C. in Detergents 7, 8 or 9.

GG36 Variant (BPN' Numbering)

T022A-G159E
P129E-G159E
S103G-G159E
V104L-G159E
A158E-G159E
S101A-G159E
A158E-H249R
L111V-H249R
P129E-H249R
N062E-H249R
A016S-H249R
R186H-H249R
L148I-H249R
G159E-H249R
S101A-H249R
S188D-H249R
V104L-H249R
Y209E-H249R
T022A-H249R
S128N-H249R
S103G-H249R
E089P-H249R
T022A-L111V
S101A-L111V
A016S-L111V
V104L-L111V
N062E-L111V
S103G-L111V
E089P-L111V
A016S-L148I
N062E-L148I
T022A-L148I
P129E-L148I
V104L-L148I
S103G-L148I
S128N-L148I
S101A-L148I
E089P-L148I
L111V-L148I
A016S-N062E
T022A-N062E
N062E-P129E
T022A-P129E
S128N-P129E
A016S-P129E
S101A-P129E
V104L-P129E
E089P-P129E
S103G-P129E
L111V-P129E
N062E-R186H
S128N-R186H
S101A-R186H
T022A-R186H
A016S-R186H
A158E-R186H
E089P-R186H
P129E-R186H
G159E-R186H
S103G-R186H
V104L-R186H
L111V-R186H
L148I-R186H
N062E-S101A
T022A-S101A
A016S-S101A
E089P-S101A
N062E-S103G
T022A-S103G
A016S-S103G
S101A-S103G
E089P-S103G
N062E-S128N
A016S-S128N
T022A-S128N

TABLE 3-1-continued

NHJ1 Variants with Performance Indices of at least 0.25 Relative to GG36 in Any One of TCA, LAS/EDTA Stability, or BMI Microswatch Cleaning at 16° C. in Detergents 7, 8 or 9. GG36 Variant (BPN' Numbering)

S101A-S128N
V104L-S128N
E089P-S128N
S103G-S128N
L111V-S128N
L111V-S188D
N062E-S188D
A016S-S188D
L148I-S188D
T022A-S188D
S128N-S188D
S101A-S188D
V104L-S188D
E089P-S188D
P129E-S188D
G159E-S188D
R186H-S188D
S103G-S188D
A158E-S188D
A016S-T022A
A016S-V104L
T022A-V104L
S101A-V104L
N062E-V104L
S103G-V104L
E089P-V104L
G159E-Y209E
L111V-Y209E
S101A-Y209E
A016S-Y209E
S128N-Y209E
L148I-Y209E
P129E-Y209E
N062E-Y209E
T022A-Y209E
S103G-Y209E
A158E-Y209E
S188D-Y209E
V104L-Y209E
E089P-Y209E
R186H-Y209E
GG36

TABLE 3-2

WCE1 Variants with Performance Indices of at least 0.2 Relative to GG36 in Any One of TCA, LAS/EDTA Stability, or BMI Microswatch Cleaning at 16° C. in Detergents 10 or 11. GG36 Variant (BPN' Numbering)

N018R-W241R
G020R-W241R
S024R-W241R
S009A-W241R
G020R-W241R
V004R-W241R
N043R-W241R
S078R-W241R
T022R-W241R
G115R-W241R
A001R-W241R
S212F-W241R
L082R-W241R
N018R-V244R
S024R-V244R
S078R-V244R
G020R-V244R
S212F-V244R
S009A-V244R
L082R-V244R
A001R-V244R
N043R-V244R

TABLE 3-2-continued

WCE1 Variants with Performance Indices of at least 0.2 Relative to GG36 in Any One of TCA, LAS/EDTA Stability, or BMI Microswatch Cleaning at 16° C. in Detergents 10 or 11. GG36 Variant (BPN' Numbering)

T022R-V244R
V004R-V244R
G115R-V244R
W241R-V244R
S242R-V244R
A001R-V004R
S009A-T022R
N018R-T022R
G020R-T022R
V004R-T022R
A001R-T022R
S024R-S242R
N018R-S242R
V004R-S242R
G020R-S242R
S212F-S242R
L082R-S242R
S078R-S242R
A001R-S242R
S009A-S242R
T022R-S242R
G115R-S242R
N043R-S242R
W241R-S242R
N018R-S212F
T022R-S212F
V004R-S212F
S024R-S212F
A001R-S212F
G115R-S212F
G020R-S212F
S009A-S212F
N043R-S212F
S078R-S212F
L082R-S212F
S009A-S078R
G020R-S078R
S024R-S078R
T022R-S078R
N018R-S078R
V004R-S078R
A001R-S078R
N043R-S078R
T022R-S024R
G020R-S024R
N018R-S024R
A001R-S024R
V004R-S024R
S009A-S024R
V004R-S009A
A001R-S009A
S242R-N269R
S024R-N269R
G020R-N269R
T022R-N269R
H249R-N269R
S212F-N269R
N043R-N269R
V244R-N269R
A001R-N269R
N018R-N269R
S078R-N269R
S009A-N269R
G115R-N269R
W241R-N269R
V004R-N269R
L082R-N269R
N018R-N043R
G020R-N043R
V004R-N043R
T022R-N043R
S009A-N043R
A001R-N043R
S024R-N043R
S009A-N018R

TABLE 3-2-continued

WCE1 Variants with Performance Indices of at least 0.2
Relative to GG36 in Any One of TCA, LAS/EDTA Stability, or
BMI Microswatch Cleaning at 16° C. in Detergents 10 or 11.
GG36 Variant (BPN' Numbering)

V004R-N018R
A001R-N018R
S024R-L082R
S009A-L082R
N018R-L082R
A001R-L082R
S078R-L082R
G020R-L082R
T022R-L082R
V004R-L082R
N043R-L082R
N043R-H249R
G020R-H249R
V004R-H249R
N018R-H249R
S009A-H249R
S212F-H249R
T022R-H249R
S024R-H249R
G115R-H249R
A001R-H249R
L082R-H249R
S242R-H249R
W241R-H249R
V244R-H249R
S078R-H249R
N018R-G115R
G020R-G115R
T022R-G115R
S078R-G115R
S009A-G115R
V004R-G115R
A001R-G115R
L082R-G115R
N043R-G115R
S024R-G115R
S009A-G020R
N18R-G020R
V004R-G020R
A001R-G020R
S009A-E271L
G020R-E271L
S024R-E271L
V244R-E271L
W241R-E271L
N043R-E271L
T022R-E271L
H249R-E271L
S212F-E271L
G115R-E271L
S242R-E271L
S078R-E271L
V004R-E271L
N269R-E271L
A001R-E271L
N018R-E271L
L082R-E271L
GG36

Example 4

Construction and Cleaning Performance of NHJ4 Set of GG36 Variants

The NHJ4 set of GG36 variants described in Table 4-4 below were constructed using the pHPLT-GG36 *B. subtilis* expression plasmid (FIG. 6) using PCR fusion or the QUIKCHANGE® Multi Site-directed mutagenesis kit ("QCMS kit"; Stratagene) as described below.

a) Construction of NHJ4 Variants by QUIKCHANGE® Multi Site-Directed Mutagenesis

Variants created using the QUIKCHANGE® Multi Site-Directed Mutagenesis are shown in Table 4-1. The parent plasmid pHPLT-GG36 (template DNA) was methylated using two micrograms of DNA and Dam methylase (NEB), according to the manufacturer's instructions. Site-directed mutants were made by a QuikChange® Multi Site-Directed Mutagenesis Kit ("QCMS kit"; Stratagene) following the manufacturer's protocol. The following mutations were introduced in the parent plasmid S101A-S103G-V104L, G159E, T22A, Y209E, E271F, S101A, S103G, L111V, S128N, N62E, and S188D, For efficient transformation of *B. subtilis*, DNA from the QCMS reaction mixtures was amplified by rolling circle amplification (RCA) using the Illustra Templiphi kit (GE Healthcare) and the reaction was performed according to the manufacturer's protocol. One microliter of ten-fold diluted amplified DNA was used to transform 50 µL of competent *B. subtilis* cells (genotype: ΔaprE, ΔnprE, amyE::xylRPxylA-comK-phleo). The transformation mixture was shaken at 37° C. for 1 hour. Ten microliter aliquots of the transformation mixture were plated on skim milk (1.6%) Luria agar plates supplemented with 10 µg/ml of neomycin (Teknova). Subsequently, the colonies with halos were inoculated in 120 µl of LB media containing 10 µg/mL neomycin for plasmid DNA extraction (QIAprep Spin Miniprep kit, Qiagen). The extracted plasmids were sequenced to confirm the presence of the desired mutations.

b) Construction of NHJ4 Variants by Extension PCR

Ten combinatorial mutants of GG36 were created by extension PCR. The list of mutations introduced in the GG36 gene contained in the pHPLT plasmid were T22A, N62E, S103G, S103G-L111V, S101G-S103A-V104I, S101A-S103G-V104L, S101A, S128N, G159D, G159E, Y209E, and L111V. To create each mutant, PCR fragments containing the desired mutations were amplified using mutagenic primers as well as forward and reverse primers to amplify the entire GG36 variant. Each PCR amplification reaction contained 30 pmol of each mutagenic primer and 100 ng of the DNA template, pHPLT-GG36 plasmid. Amplifications were carried out using Vent DNA polymerase (NEB). The PCR reaction (20 µL) was initially heated at 95° C. for 2.5 min followed by 30 cycles of denaturation at 94° C. for 15 sec., annealing at 55° C. for 15 sec. and extension at 72° C. for 1 min. Following amplification, 2 to 4 PCR fragments for each variant were gel-purified, using a QIAGEN® gel-band purification kit and mixed (50 ng of each fragment). These mixtures served as DNA templates for the extension PCR to generate the full-length gene fragments. The PCR conditions were same as described above, except the extension phase, which was carried out at 72° C. for 2 min. The full-length DNA fragment was gel-purified using a QIAGEN® gel-band purification kit, digested with the BamHI and HindIII restriction enzymes and ligated with the pHPLT-GG36, which was digested with the same restriction enzymes. One microliter of the ligation mixtures was amplified using rolling circle amplification by Illustra Templiphi kit according to the manufacturer's instructions (GE Healthcare) to generate multimeric DNA for transformation into *Bacillus subtilis*. Products of the rolling circle amplification were diluted 100-times and used to transform *B. subtilis* cells (genotype: ΔaprE, ΔnprE, amyE::xylRPxylA-comK-phleo). An aliquot of the transformation mix was plated on LB plates containing 1.6% skim milk and 10 µg/mL neomycin and incubated overnight at 37° C. Subsequently, the colonies with halos were inoculated in 120 µl of Luria broth medium containing 10 µg/mL neomycin for plasmid DNA extraction (QIAprep Spin Miniprep kit, Qiagen). The extracted plasmids were sequenced to confirm the presence of the desired mutations. Variants created by the extension PCR are shown in Table 4-1.

To express the NHJ4 set of variant proteins for further biochemical analyses, the *B. subtilis* strains carrying the variant plasmids were inoculated into microtiter plates containing 150 µl Luria broth medium supplemented with 10 µg/ml neomycin. The cultures were grown up for protein expression as described in Example 2, and they were filtered through a micro-filter plate (0.22 µm; Millipore) also as described in Example 2. The resulting filtrate was used for biochemical analysis. The eglin c inhibition assay for protein content determination and BMI microswatch assays tested in various detergents were carried out as described in Example 1. Performance indices are also calculated as described under the BMI assay description in Example 1. Table 4-1 provides information regarding these multiple mutation variants and the results obtained for them. The PI values are relative to GG36. In the following Tables, the detergent compositions ("Det.") correspond to those shown in Table D, above. Also, as indicated, the amino acid position is listed according to BPN' numbering.

TABLE 4-1

NHJ4 Multiple Mutation Variants with BMI Cleaning Performance Indices of at Least 0.2 Relative to GG36 in Detergents 7, 8 or 9 at 16° C.

| Variant Name | Created by | Mutations, (BPN' Numbering) |
|---|---|---|
| | | GG36 |
| NHJ4-1 | Extension PCR | S101G S103A V104I |
| NHJ4-10 | Extension PCR | T22A S101A Y209E |
| NHJ4-11 | Extension PCR | S103G L111V G159E |
| NHJ4-12 | Extension PCR | T22A S103G G159E |
| NHJ4-13 | QCMS | T22A L111V G159E |
| NHJ4-14 | QCMS | T22A S128N E271F Y209E |
| NHJ4-15 | QCMS | T22A S103G L111V |
| NHJ4-16 | QCMS | N62E L111V S128N |
| NHJ4-17 | QCMS | T22A L111V S128N |
| NHJ4-18 | Extension PCR | T22A N62E L111V |
| NHJ4-19 | QCMS | S101A S103G V104L S188D |
| NHJ4-2 | Extension PCR | S101G S103A V104I G159D |
| NHJ4-20 | Extension PCR | S101A S103G V104L S128N |
| NHJ4-24 | QCMS | T22A S101A G159E |
| NHJ4-3 | Extension PCR | S101A S103G V104L |
| NHJ4-4 | Extension PCR | S101A S103G V104L G159E |
| NHJ4-5 | Extension PCR | T22A S101A S103G V104L |
| NHJ4-6 | QCMS | S101A S103G V104L Y209E |
| NHJ4-7 | QCMS | T22A Y209E E271F |
| NHJ4-8 | QCMS | T22A S101A E271F |
| NHJ4-9 | QCMS | S101A Y209E E271F |

Example 5

Construction and Cleaning Performance of NHJ3 Set of GG36 Variants

Figure 7:
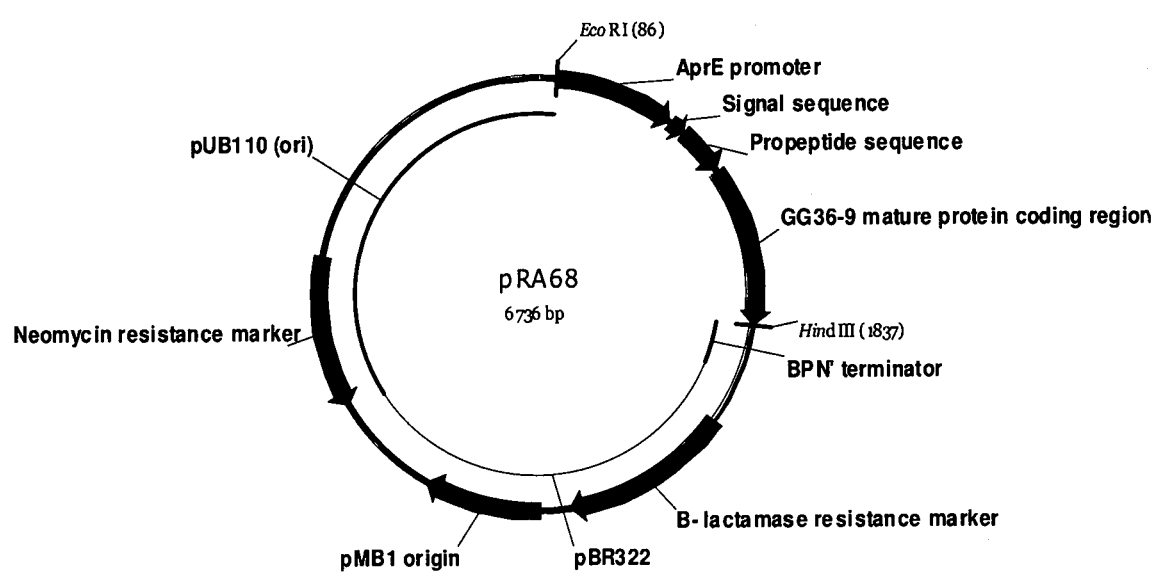
FIG. 7 provides a map of pRA68.

The NHJ3 set of variants described herein are based on a variant of GG36 (referred to as GG36-9) containing the following mutations: S101G, S103A, V104I, G159D, A232V, Q236H, Q245R, N248D, and N252K (BPN' numbering). These variants were created using the QUIKCHANGE® Lightning Site-Directed Mutagenesis Kit (QCLDS kit; Stratagene), with the pRA68 plasmid (see FIG. 7) as the DNA template. Plasmid pRA68 was derived from the pBN3 vector (see Babe et al., Biotech. Appl. Biochem. 27:117-124 [1998]).

The DNA sequence of GG36-9 variant (the signal sequence is shown in lower case letters, propeptide in lower case, underlined text, and GG36-9 mature sequence in uppercase letters) is provided below:

(SEQ ID NO: 762)
Gtgagaagcaaaaaattgtggatcgtcgcgtcgaccgcactactcatttc tgttgcttttagttcatcgatcgcatcggct<u>gctgaagaagcaaaagaaa</u>

<u>aatatttaattggctttaatgagcaggaagctgtcagtgagtttgtagaa</u>

<u>caagtagaggcaaatgacgaggtcgccattctctctgaggaagaggaagt</u>

<u>cgaaattgaattgcttcatgaatttgaaacgattcctgttttatccgttg</u>

<u>agttaagcccagaagatgtggacgcgcttgaactcgatccagcgatttct</u>

<u>tatattgaagaggatgcagaagtaacgacaatg</u>GCGCAATCAGTGCCATG

GGGAATTAGCCGTGTGCAAGCCCCGGCTGCCCATAACCGTGGATTGACAG

GTTCTGGTGTAAAAGTTGCTGTCCTCGATACAGGTATTTCCACTCATCCA

GACTTAAATATTCGTGGTGGCGCTAGCTTTGTACCAGGGGAACCATCCAC

TCAAGATGGGAATGGGCATGGCACGCATGTGGCCGGGACGATTGCTGCTC

TAAACAATTCGATTGGCGTACTTGGCGTAGCGCCGAGCGCGGAACTATAC

GCTGTTAAAGTATTAGGGGCGAGCGGTGGGGCGCCATCAGCTCGATTGC

CCAAGGATTGGAATGGGCAGGGAACAATGGCATGCACGTTGCTAATTTGA

GTTTAGGAAGCCCTTCGCCAAGTGCCACACTTGAGCAAGCTGTTAATAGC

GCGACTTCTAGGGGCGTTCTTGTTGTAGCGGCATCTGGAAATTCGGGTGC

AGACTCAATCAGCTATCCGGCCCGTTATGCGAACGCAATGGCAGTCGGAG

CTACTGACCAAAACAACAACCGCGCCAGCTTTTCACAGTATGGCGCAGGG

CTTGACATCGTCGCACCAGGTGTAAACGTGCAGAGCACATACCCAGGTTC

AACGTATGCCAGCTTAAACGGTACATCGATGGCTACTCCTCATGTTGCAG

GTGCAGCAGTCCTTGTTAAACATAAGAACCCATCTTGGTCCAATGTACGA

ATCCGCGATCATCTAAAGAAAACGGCAACGAGCTTAGGAAGCACGAACTT

GTATGGAAGCGGACTTGTCAATGCCGAAGCTGCAACTCGTTAA

The protein sequence of the GG36-9 variant (the signal sequence is shown in lower case letters, propeptide in lower case, underlined text, and GG36-9 mature protease sequence in uppercase letters) is provided below:

(SEQ ID NO: 763)
vrskklwivastallisvafsssias<u>aaeeakekyliqfneqeavsefve</u>

<u>qveandevailseeeeveiellhefetipvlsvelspedvdaleldpais</u>

<u>yieedaevttm</u>AQSVPWGISRVQAPAAHNRGLTGSGVKVAVLDTGISTHP

DLNIRGGASFVPGEPSTQDGNGHGTHVAGTIAALNNSIGVLGVAPSAELY

AVKVLGASGGGAISSIAQGLEWAGNNGMHVANLSLGSPSPSATLEQAVNS

ATSRGVLVVAASGNSGADSISYPARYANAMAVGATDQNNNRASFSQYGAG

LDIVAPGVNVQSTYPGSTYASLNGTSMATPHVAGAAVLVKHKNPSWSNVR

IRDHLKKTATSLGSTNLYGSGLVNAEAATR

To create the NHJ3 variants using the QCLSD kit, mutagenic primers were designed for each of the variants according to the manufacturer's protocol. The mutagenesis reaction for each variant consisted of 0.5 µl of 10× Buffer, 0.5 µL of pRA68 plasmid DNA (168 ng/µL), 0.5 µl forward mutagenic primer (25 µM), 0.5 µl reverse mutagenesis primer (25 μM), 1 μl dNTPs (supplied in the QCLSD kit), 1.5 μl Quik solution (supplied in the QCLMS kit), 1 μl Enzyme blend (supplied in the QCLSD kit), and 40 μl of distilled, deionized water to make up a 50 μL reaction volume as per the manufacturer's instructions. The cycling program was 1 cycle at 95° C. for 2 minutes, 18 cycles of 95° C. for 20 seconds, 60° C. for 10 seconds and 68° C. for 3 minutes, 22 seconds, and a final cycle of 68° C. for 5 minutes. Next, 1 μL of DpnI restriction enzyme supplied in the kit was used to digest the plasmid DNA in the reaction, and then 2 μL of the reaction was used to transform TOP 10 *E. coli* competent cells (Invitrogen). The *E. coli* transformants were selected on Luria broth medium plates containing 50 μg/mL (ppm) carbenicillin after overnight growth at 37° C. Plasmid DNA was extracted from 4-8 *E. coli* colonies grown in LA medium containing 50 μg/mL (ppm) carbenicillin using the QIAprep spin miniprep kit (Qiagen). The plasmids were sequenced to confirm the presence of the desired mutations. The variant plasmids were then transformed into *B. subtilis* cells as described in Example 2. The *B. subtilis* variant strains were grown up as described in Example 2 for further biochemical analysis, such as protein content determination using the eglin c inhibition assay (Example 1) and a BMI microswatch cleaning assay (Example 1). The results are provided below in Tables 5-1 and 5-2. The PIs are relative to GG36. In the following Tables, the detergent compositions ("Det.") correspond to those shown in Table D, above. Also, as indicated, the amino acid position is listed according to BPN' numbering.

TABLE 5-1

NHJ3 Multiple Mutation Variants with BMI Cleaning Performance Indices of at Least 1.1 Relative to GG36 in Detergents 7, 8, or 9 at 16° C.

| Variant | Variant Sequence Relative to GG36 (Using BPN' Numbering) |
|---|---|
| | GG36 |
| NHJ3-1 | S103A-V104I-G159D-A232V-Q236H-Q245R-N248D-N252K |
| NHJ3-2 | S101G-V104I-G159D-A232V-Q236H-Q245R-N248D-N252K |
| NHJ3-3 | S101G-S103A-G159D-A232V-Q236H-Q245R-N248D-N252K |
| NHJ3-4 | S101G-S103A-V104L-A232V-Q236H-Q245R-N248D-N252K |
| NHJ3-5 | S101G-S103A-V104L-G159D-Q236H-Q245R-N248D-N252K |
| NHJ3-6 | S101G-S103A-V104L-G159D-A232V-Q245R-N248D-N252K |
| NHJ3-7 | S101G-S103A-V104L-G159D-A232V-Q236H-N248D-N252K |
| NHJ3-8 | S101G-S103A-V104L-G159D-A232V-Q236H-Q245R-N252K |
| NHJ3-9 | S101G-S103A-V104L-G159D-A232V-Q236H-Q245R-N248D |

TABLE 5-2

NHJ3 Multiple Mutation Variants with BMI Cleaning Performance Indices of at Least 0.3 Relative to GG36 in Detergents 10 or 11 at 16° C.

| Variant | Variant Sequence Relative to GG36 (Using BPN' Numbering) |
|---|---|
| | GG36 |
| NHJ3-1 | S103A-V104I-G159D-A232V-Q236H-Q245R-N248D-N252K |
| NHJ3-2 | S101G-V104I-G159D-A232V-Q236H-Q245R-N248D-N252K |
| NHJ3-3 | S101G-S103A-G159D-A232V-Q236H-Q245R-N248D-N252K |
| NHJ3-4 | S101G-S103A-V104L-A232V-Q236H-Q245R-N248D-N252K |
| NHJ3-5 | S101G-S103A-V104L-G159D-Q236H-Q245R-N248D-N252K |
| NHJ3-6 | S101G-S103A-V104L-G159D-A232V-Q245R-N248D-N252K |
| NHJ3-7 | S101G-S103A-V104L-G159D-A232V-Q236H-N248D-N252K |
| NHJ3-8 | S101G-S103A-V104L-G159D-A232V-Q236H-Q245R-N252K |
| NHJ3-9 | S101G-S103A-V104L-G159D-A232V-Q236H-Q245R-N248D |

Example 6

Construction and Cleaning Performance of NHJ5 Set of GG36 Variants

Figure 8:
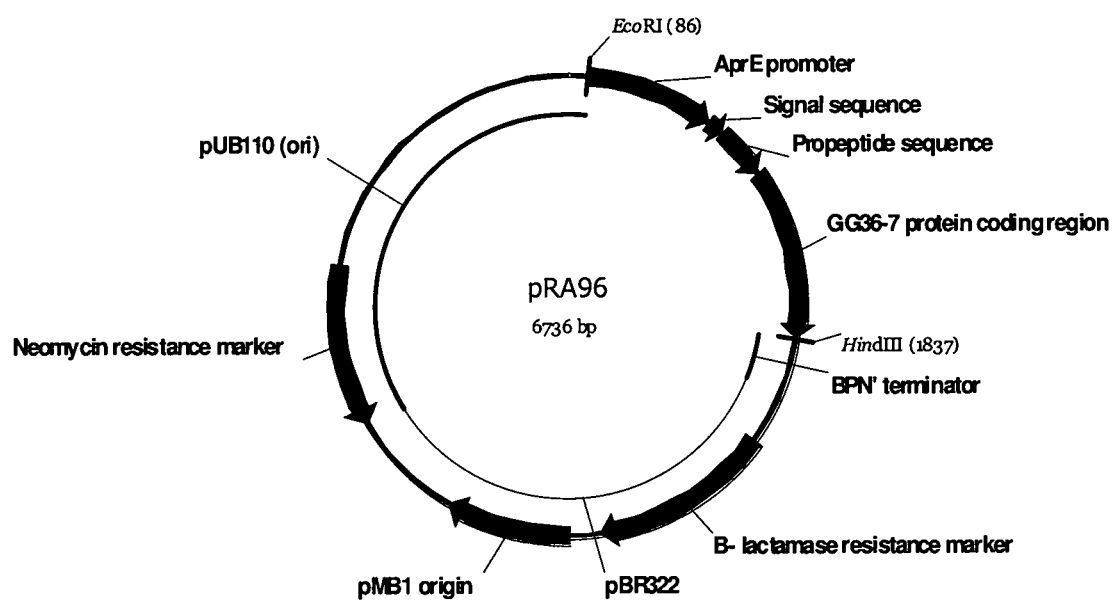
FIG. 8 provides a map of pRA96.

The NHJ5 set of variants described herein are based on a variant of GG36 (referred to as GG36-7) containing the following mutations: S101G, S103A, V104I, G159D, A232V, Q245R, N248D, and (BPN' numbering). These variants were created using the QUIKCHANGE® Lightning Multi Site-Directed Mutagenesis Kit ("QCLMS kit") with the pRA96 plasmid as the DNA template (see FIG. 8). The mutations incorporated included: H243R(H249R), E265F (E271F), D157E (D159E), A156E (A158E), A156E-D157G (A158E-D159E), T22A, N60E (N62E), N232R(N238R), D242R (D248R), T247R (T253R), S24R, N74D (N76D) {GG36 Numbering and BPN' Numbering Shown in Parentheses.

The variants were generated using the methods described in Example 5. The *B. subtilis* variant strains were grown up as described in Example 2 for further biochemical analysis, such as protein content determination using the eglin c inhibition assay (Example 1) and the BMI microswatch cleaning assay (Example 1). The results are provided below in Table 6-1. The PI values are relative to GG36. In the following Tables, the detergent compositions ("Det.") correspond to those shown in Table D, above. Also, as indicated, the amino acid position is listed according to BPN' numbering.

The DNA sequence of GG36-7 variant (the signal sequence is shown in lower case letters, propeptide in lower case, underlined text, and GG36-7 mature protease sequence in uppercase letters) is provided below:

(SEQ ID NO: 764)
gtgagaagcaaaaaattgtggatcgtcgcgtcgaccgcactactcatttc tgttgcttttagttcatcgatcgcatcggct<u>gctgaagaagcaaaagaaa</u>

<u>aatatttaattggctttaatgagcaggaagctgtcagtgagtttgtagaa</u>

<u>caagtagaggcaaatgacgaggtcgccattctctctgaggaagaggaagt</u>

<u>cgaaattgaattgcttcatgaatttgaaacgattcctgttttatccgttg</u>

<u>agttaagcccagaagatgtggacgcgcttgaactcgatccagcgatttct</u>

<u>tatattgaagaggatgcagaagtaacgacaatg</u>GCGCAATCAGTGCCATG

GGGAATTAGCCGTGTGCAAGCCCCGGCTGCCCATAACCGTGGATTGACAG

GTTCTGGTGTAAAAGTTGCTGTCCTCGATACAGGTATTTCCACTCATCCA

GACTTAAATATTCGTGGTGGCGCTAGCTTTGTACCAGGGGAACCATCCAC

TCAAGATGGGAATGGGCATGGCACGCATGTGGCCGGGACGATTGCTGCTC

TAAACAATTCGATTGGCGTACTTGGCGTAGCGCCGAGCGCGGAACTATAC

GCTGTTAAAGTATTAGGGGCGAGCGGTGGGGCGCCATCAGCTCGATTGC

CCAAGGATTGGAATGGGCAGGGAACAATGGCATGCACGTTGCTAATTTGA

GTTTAGGAAGCCCTTCGCCAAGTGCCACACTTGAGCAAGCTGTTAATAGC

GCGACTTCTAGGGGCGTTCTTGTTGTAGCGGCATCTGGAAATTCGGGTGC

AGACTCAATCAGCTATCCGGCCCGTTATGCGAACGCAATGGCAGTCGGAG

CTACTGACCAAAACAACAACCGCGCCAGCTTTTCACAGTATGGCGCAGGG

CTTGACATCGTCGCACCAGGTGTAAACGTGCAGAGCACATACCCAGGTTC

AACGTATGCCAGCTTAAACGGTACATCGATGGCTACTCCTCATGTTGCAG

-continued
```
GTGCAGCAGTCCTTGTTAAACAAAAGAACCCATCTTGGTCCAATGTACGA

ATCCGCGATCATCTAAAGAATACGGCAACGAGCTTAGGAAGCACGAACTT

GTATGGAAGCGGACTTGTCAATGCCGAAGCTGCAACTCGT
```

The protein sequence of GG36-7 variant (signal sequence is shown in lower case letters, propeptide in lower case, underlined text, and GG36-7 mature protease sequence in uppercase letters) is provided below:

(SEQ ID NO: 765)
vrskklwivastallisvafsssiasa<u>aeeakekyliqfneqeavsefve</u>

<u>qveandevailseeeeveiellhefetipvlsvelspedvdaleldpais</u>

<u>yieedaevttm</u>AQSVPWGISRVQAPAAHNRGLTGSGVKVAVLDTGISTHP

DLNIRGGASFVPGEPSTQDGNGHGTHVAGTIAALNNSIGVLGVAPSAELY

AVKVLGASGGGAISSIAQGLEWAGNNGMHVANLSLGSPSPSATLEQAVNS

ATSRGVLVVAASGNSGADSISYPARYANAMAVGATDQNNNRASFSQYGAG

LDIVAPGVNVQSTYPGSTYASLNGTSMATPHVAGAAVLVKQKNPSWSNVR

IRDHLKNTATSLGSTNLYGSGLVNAEAATR

TABLE 6-1

NHJ5 Multiple Mutation Variants with BMI Cleaning Performance Indices of at Least 0.6 Relative to GG36 in Detergents 7-11 at 16° C.

| Variant | Variant Sequence Relative to GG36 (BPN' Numbering) |
| --- | --- |
| | GG36 |
| GG36-7 | S101G-S103A-V104I-G159D-A232V-Q245R-N248D |
| NHJ5-1 | S101G-S103A-V104I-G159D-A232V-Q245R-N248D-E271F |
| NHJ5-2 | S101G-S103A-V104I-G159D-A232V-Q245R-N248D-N238D |
| NHJ5-3 | S101G-S103A-V104I-G159D-A232V-Q245R-N248D-N248R |
| NHJ5-4 | S101G-S103A-V104I-G159D-A232V-Q245R-N248D-T253R |
| NHJ5-5 | S101G-S103A-V104I-G159D-A232V-Q245R-N248D-S24R |
| NHJ5-6 | S101G-S103A-V104I-G159D-A232V-Q245R-N248D-N76D |
| NHJ5-7 | S101G-S103A-V104I-G159E-A232V-Q245R-N248D-H249R |
| NHJ5-8 | S101G-S103A-V104I-G159E-A232V-Q245R-N248D-E271F |
| NHJ5-9 | S101G-S103A-V104I-A158E-A232V-Q245R-N248D-H249R |
| NHJ5-10 | S101G-S103A-V104I-A158E-A232V-Q245R-N248D-E271F |
| NHJ5-11 | T22A-S101G-S103A-V104I-G159D-A232V-Q245R-N248D-H249R |
| NHJ5-12 | T22A-S101G-S103A-V104I-G159D-A232V-Q245R-N248D-E271F |
| NHJ5-13 | N62E-S101G-S103A-V104I-G159D-A232V-Q245R-N248D-H249R |
| NHJ5-14 | N62E-S101G-S103A-V104I-G159D-A232V-Q245R-N248D-E271F |

Example 7

Construction of NHJ2 Combinatorial Library

This Example describes the construction of a GG36 combinatorial library involving one or more of the following mutations: A16S, T22A, S101A, S103G, V104L, L111V, S128N, and L148I (BPN' numbering). The pHPLT-GG36 *B. subtilis* expression plasmid was provided to DNA 2.0 Inc. for the generation of NHJ2 combinatorial library. A ligation reaction of the constructed NHJ2 library was provided by DNA 2.0, Inc. for transformation in the *B. subtilis* strain (genotype: ΔaprE, ΔnprE, amyE::xylRPxylAcomK-phleo). The variants generated containing one or several of the mutations described herein are tested for cold water cleaning applications using methods and detergent compositions described herein.

Example 8

Construction of Additional Libraries and GG36 Variants

Additional libraries and variants are constructed using the following set of mutations: A1R, A230E, E271L, G115R, G20R, H249R, K235F, K27V/F/L, L75E, L82R, N18R, N269R, N43D, N43R, N76D, R45T, S212F, S242R, S24R, S78R, S9A, T22R, V121E, V244R, V28E, V30E, V4R, W241R (BPN' numbering). The variants generated containing one or more of these mutations are tested for cold water cleaning applications using methods and detergent compositions described herein.

Additional sets of GG36 variants are constructed and tested for cold water cleaning applications using methods and detergent compositions described herein include: G20R-N43R-H249R, G20R-T22R-N43R, G20R-N43R-S242R, G20R-N43R-E271L, G20R-N43R-V244R, G20R-S24R-N43R-S242R, S9A-T22R-S78R-S212F-W241R, S9A-G20R-N43R-S212F, S9A-N43R-S212F, G20R-N43R-S212F, G20R-T22R-N43R-S212F, S24R-S78R-S212F, S9A-N43R-S78R, S9A-N43R-S78R-S242R, S9A-G20R-N43R-S78R, G20R-S24R-N43R-S78R-S242R, T22R-S24R-S78R-S212F, S9A-G20R-N43R-S78R-S242R, G20R-N43R-S78R-H249R, G20R-N43R-S78R, S9A-S78R-S212F, S9A-T22R-N43R-S78R, S9A-G20R-S24R-N43R, S9A-T22R-S78R-S212F, V4R-S9A-T22R-S78R-S212F, G20R-S24R-N43R, A1R-S9A-N43R, G20R-S24R-N43R-G115R, S9A-S24R-N43R, G20R-T22R-S24R-N43R, A1R-S24R-N43R, S9A-G20R-S24R-N43R-S242R, S9A-G20R-T22R-S78R-S212F, S9A-S24R-N43R-V244R, S9A-S24R-N43R-S242R, V4R-S9A-T22R-S24R-S212F, and T22R-S24R-N43R (BPN' numbering).

Example 9

Construction and Cleaning Performance of the GG36 Library WCE2

The WCE2 combinatorial library was generated by DNA 2.0, Inc. using the pHPLT-GG36 *B. subtilis* expression plasmid. A ligation reaction of the constructed WCE2 library was provided by DNA 2.0, Inc. for transformation in the *B. subtilis* strain (genotype: ΔaprE, ΔnprE, amyE::xylRPxylAcomK-phleo). The set of mutations used to generate the WCE2 library are A230E, G20R, H249R, N18R, N43R/D, N76D, R45T, S242R, and S24R (BPN' numbering). The variants generated containing one or more of these mutations are tested for cold water cleaning applications using methods and detergent compositions described herein.

Example 10

Construction and Cleaning Performance of the WCE3 Set of GG36 Variants

This Example describes the WCE3 set of mutants based on the GG36 variants, GG36-7 (Example 5) and GG36-9 (Example 4). These variants are: S101G-S103A-V104I-A232V-Q245R-N248D, S101G-S103A-V104I-G159D-A232V-Q245R, S101G-S103A-V104I-G159R-A232V-Q245R-N248D, S101G-S103A-V104I-G159D-A232V-Q245R-N248R, S101G-S103A-V104I-A232V-Q245R, S101G-S103A-V104I-A232V-Q245R-N248D, S101G-S103A-V104I-G159R-A232V-Q245R-N248R, and S101G, S103A, V104I, A232V, Q236H, Q245R, and N252K. They were created using the QuikChange® Lightning Multi Site-Directed Mutagenesis Kit (QCLMS kit; Stratagene) with the pRA96 plasmid as the DNA template described in Example 5. The variants generated will be tested for cold water cleaning applications using methods and detergent compositions described in this application.

Example 11

Construction of Additional Libraries and Variants of GG36

Figure 6:
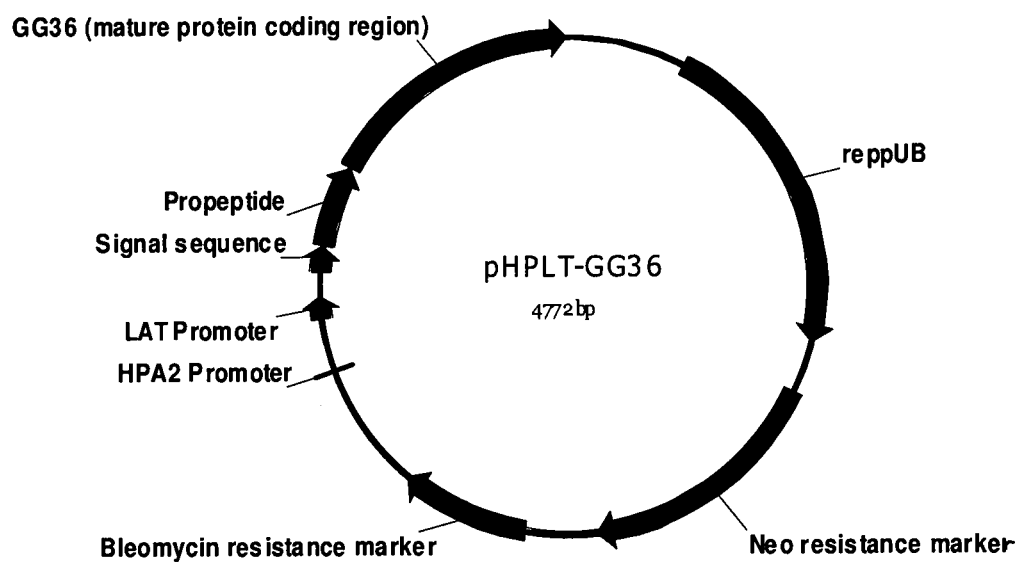
FIG. 6 provides map of pHPLT-GG36.

This Example describes the construction of GG36 variants and libraries using one or more of the following mutations: A16S, T22A, S24R, N62E, N76D, E89P, S101A/G, S103G/A, V104L/I, L111V, S128N, P129E, A232V, L148I, A158E, G159D/E, S166D, R186H, S188D, Y209E, Q236H, N238R, Q245R, N248D/R, H249R, N252K/R, T253R, E271F (BPN' numbering) using a *B. subtilis* expression plasmid (e.g., pHPLT-GG36; FIG. 6). The variants generated containing one or more of these mutations are tested for cold water cleaning applications using methods and detergent compositions described herein.

Example 12

Construction of Additional Libraries and Variants of GG36

This Example describes the construction of GG36 variants and libraries in *B. subtilis* using one or more of the following mutations (BPN' numbering): A1R, Q2S, Q2M, Q2A, Q2R, Q2W, S3R, V4R, V4S, V4C, I8A, S9A, S9F, S9W, R10S, R10A, R10H, R10M, Q12F, Q12R, P14K, P14F, P14Q, A15R, A15F, A16S, H17R, H17M, $H_{17}F$, N18R, N18K, G20F, G20K, G20R, T22A, T22R, T22Y, T22V, T22Q, T22L, T22W, G23A, G23S, G23F, S24R, S24F, S24W, S24Q, S24H, S24L, G25V, G25F, G25R, V26F, K27L, K27F, K27R, K27V, V28A, V28N, V28E, A29T, V30E, L31F, T33S, T33G, T33D, G34P, I35M, S36T, S36F, S36R, T38L, T38F, T38R, P40N, P40L, P40T, P40W, P40H, P40R, L42I, N43A, N43F, N43I, N43S, N43R, N43M, N43W, N43D, R45T, G46R, A48R, F50C, V51W, V51F, V51H, P52F, P52E, P52N, P55Y, T57R, Q59A, Q59F, Q59R, D60P, D60Q, D60A, N62E, N62Q, G63V, G63M, G63T, G63I, G63A, G63S, G63H, G63Q, G63D, G63E, G63P, H64F, H64T, V68A, V68C, A69N, A69T, A69P, A69W, T71G, I72C, A74C, L75A, L75F, L75E, L75R, N76D, S78R, S78N, S78I, I79W, I79Q, V81R, L82F, L82T, L82V, L82R, L82M, A85M, P86W, P86L, P86I, E89P, E89T, E89G, E89H, E89L, E89V, E89W, E89F, E89I, Y91N, Y91F, A92F, K94N, S99F, S99T, S99P, S99G, S99M, G100S, G100N, G100Q, G100I, S101A, S101N, S101G, S101T, S101D, S101E, S101P, S101F, G102A, G102T, G102N, G102H, G102E, S103G, S103N, S103D, S103A, V104L, V104I, V104E, V104D, S105T, S105E, S105Q, S106G, S106T, S106E, S106D, S106A, S106V, S106F, I107M, I107F, A108I, A108G, Q109M, L111V, L111I, E112V, E112L, E112Q, A114G, G115K, G115R, N116K, N116A, N116L, N117F, G118R, G118I, M119C, H120A, H120F, H120R, V121F, V121E, N123G, N123E, L124S, S128D, S128F, S128L, S128N, S128H, S128M, S128I, S128Q, P129E, S132A, S132E, A138G, S144R, V147L, L148I, A158E, G159D, G159E, G159C, S160D, S166D, S166E, Y167W, M175V, V177C, D181A, Q182R, N183I, N183D, N183M, N183F, N183R, N185E, N185V, N185I, R186H, R186K, S188E, S188D, S188R, Y192H, Y192W, A194E, A194V, A194F, D197F, I198L, I198F, V203E, V203C, T208S, Y209S, Y209N, Y209F, Y209T, Y209E, Y209H, Y209G, Y209L, P210R, P210V, P210L, G211Q, G211R, S212I, S212M, S212F, T213A, Y214F, A215N, A215D, A215E, A215H, A215F, S216F, S216A, L217E, L217N, L217D, N218D, N218P, N218E, T224A, T224G, V227I, A230E, A231I, A231C, A232V, L233C, V234F, K235F, Q236F, Q236N, Q236H, N238R, N238K, N238L, P239K, P239G, P239R, P239H, P239T, P239N, P239S, P239F, S240R, W241R, S242L, S242R, N243F, N243R, V244R, Q245R, I246S, N248D, N248V, N248I, N248R, H249R, H249T, L250I, K251R, K251S, N252I, N252F, N252R, N252K, N252H, T253I, T253R, T253F, A254C, S256N, G258R, T260V, T260I, L262D, L262H, Y263F, S265F, L267V, L267N, L267M, N269I, N269R, A270C, E271I, E271V, E271H, E271M, E271L, E271P, E271A, E271F, E271T, A272F, A272F, A272R, A273F, A273I, and T274G. The variants generated containing one or more of these mutations are tested for cold water cleaning applications using methods and detergent compositions described herein.

Example 13

Automatic Dishwash Performance Tests

In this Example, methods used to determine the wash performance of protease variants using some commercially available dish detergents are described. These protease variants are tested under various conditions. These detergents are commercially available from WFK and are referred to by the designations provided below. The protocols for each of the stain types (minced meat, egg yolk, and egg yolk with milk) are provided below. Before the individual soil types can be applied to the test dishes, the dishes must be thoroughly washed. This is particularly necessary, as residues of certain persistent stains may still be present on the dishes from previous tests. New dishes were also subjected to three thorough washes before being used for the first time in a test.

The washing tests are typically performed in an automatic dishwasher (e.g., Miele: G690SC), equipped with soiled dishes and stainless steel sheets, as described above. A defined amount of the detergent is used, as indicated in the tables of results below. In some experiments, the temperatures tested are 45° C., 55° C. and 65° C. In some experiments, the water hardness is 9° or 21° GH (German hardness) (374 ppm Ca).

As indicated above, after washing, the plates soiled with minced meat or pasta/sauce/meat/cheese are visually assessed using a photo rating scale of from 0 to 10, wherein "0" designated a completely dirty plate and "10" designated a clean plate. These values correspond to the stain or soil removal (SR) capability of the enzyme-containing detergent.

The washed stainless steel plates soiled with egg yolk and/or egg yolk milk (are analyzed gravimetrically to determine the amount of residual stain after washing.

Some exemplary detergents are provided below.

| Component | Wt % |
|---|---|
| Phosphate-Free Detergent, IEC-60436 WFK Type B (pH = 10.4 in 3 g/l) | |
| Sodium citrate dehydrate, | 30.0 |
| Maleic acid/acrylic acid copolymer sodium Salt (SOKALAN ® CP5; BASF) | 12.0 |
| Sodium perborate monohydrate, | 5.0 |

-continued

| Component | Wt % |
|---|---|
| TAED, | 2.0 |
| Sodium disilicate: Protil A (Cognis), | 25.0 |
| Linear fatty alcohol ethoxylate, | 2.0 |
| Sodium carbonate anhydrous, | add to 100 |
| Phosphate-Containing Detergent:, IEC-60436 WFK Type C (pH = 10.5 in 3 g/l)) | |
| Sodium tripolyphosphate | 23.0 |
| Sodium citrate dehydrate | 22.3 |
| Maleic acid/Acrylic Acid Copolymer Sodium Salt | 4.0 |
| Sodium perborate monohydrate | 6.0 |
| TAED | 2.0 |
| Sodium disilicate: Protil A (Cognis) | 5.0 |
| Linear Fatty Alcohol Ethoxylate | 2.0 |
| Sodium Carbonate anhydrous, | add to 100, |

Example 14

Granular and/or Tablet Laundry Compositions

This Example provides various formulations for granular and/or tablet laundry detergents. The following laundry compositions of present invention, which may be in the form of granules or tablet, are provided below. In each of these formulations, at least one protease variant provided herein is included at a concentration of from about 0.0001 to about 10 weight percent. In some alternative aspects, other concentrations will find use, as determined by the formulator, based on their needs.

TABLE 14-1

Granular and/or Tablet Laundry Compositions

| Compound | I | II | III | IV | V |
|---|---|---|---|---|---|
| Base Product | | | | | |
| $C_{14}$-$C_{15}$AS or TAS | 8.0 | 5.0 | 3.0 | 3.0 | 3.0 |
| LAS | 8.0 | — | 8.0 | — | 7.0 |
| $C_{12}$-$C_{15}$AE$_3$S | 0.5 | 2.0 | 1.0 | — | — |
| $C_{12}$-$C_{15}$E$_5$ or E$_3$ | 2.0 | — | 5.0 | 2.0 | 2.0 |
| QAS | — | — | — | 1.0 | 1.0 |
| Zeolite A | 20.0 | 18.0 | 11.0 | — | 10.0 |
| SKS-6 (dry add) | — | — | 9.0 | — | — |

TABLE 14-1-continued

Granular and/or Tablet Laundry Compositions

| Compound | I | II | III | IV | V |
|---|---|---|---|---|---|
| MA/AA | 2.0 | 2.0 | 2.0 | — | — |
| AA | — | — | — | — | 4.0 |
| 3Na Citrate 2H$_2$O | — | 2.0 | — | — | — |
| Citric Acid (Anhydrous) | 2.0 | — | 1.5 | 2.0 | — |
| DTPA | 0.2 | 0.2 | — | — | — |
| EDDS | — | — | 0.5 | 0.1 | — |
| HEDP | — | — | 0.2 | 0.1 | — |
| PB1 | 3.0 | 4.8 | — | — | 4.0 |
| Percarbonate | — | — | 3.8 | 5.2 | — |
| NOBS | 1.9 | — | — | — | — |
| NACA OBS | — | — | 2.0 | — | — |
| TAED | 0.5 | 2.0 | 2.0 | 5.0 | 1.00 |
| BB1 | 0.06 | — | 0.34 | — | 0.14 |
| BB2 | — | 0.14 | — | 0.20 | — |
| Anhydrous Na Carbonate | 15.0 | 18.0 | — | 15.0 | 15.0 |
| Sulfate | 5.0 | 12.0 | 5.0 | 17.0 | 3.0 |
| Silicate | — | 1.0 | — | — | 8.0 |
| nprE (optional) | 0.03 | — | 0.1 | 0.06 | — |
| PMN | — | 0.05 | — | — | 0.1 |
| Protease B (optional) | — | 0.01 | — | — | — |
| Protease C (optional) | — | — | — | 0.01 | — |
| Lipase | — | 0.008 | — | — | — |
| Amylase | 0.001 | — | — | — | 0.001 |
| Cellulase | — | 0.0014 | — | — | — |
| Pectin Lyase | 0.001 | 0.001 | 0.001 | 0.001 | 0.001 |
| Aldose Oxidase | 0.03 | — | 0.05 | — | — |
| PAAC | — | 0.01 | — | — | 0.05 |
| Balance to 100% Moisture and/or Minors* | | | | | |

*Perfume, dye, brightener/SRP1/Na carboxymethylcellulose/photobleach/MgSO$_4$/PVPVI/suds suppressor/high molecular PEG/clay.

Example 15

Tablet Detergent Compositions

This Example provides various tablet detergent formulations. The following tablet detergent compositions of the present invention are prepared by compression of a granular dishwashing detergent composition at a pressure of 13KN/cm$^2$ using a standard 12 head rotary press. In each of these formulations, at least one protease variant provided herein is included at a concentration of from about 0.0001 to about 10 weight percent. In some alternative aspects, other concentrations will find use, as determined by the formulator, based on their needs.

TABLE 15-1

Tablet Detergent Compositions

| Compound | I | II | III | IV | V | VI | VII | VIII |
|---|---|---|---|---|---|---|---|---|
| STPP | — | 48.8 | 44.7 | 38.2 | — | 42.4 | 46.1 | 46.0 |
| 3Na Citrate 2H$_2$O | 20.0 | — | — | — | 35.9 | — | — | — |
| Na Carbonate | 20.0 | 5.0 | 14.0 | 15.4 | 8.0 | 23.0 | 20.0 | — |
| Silicate | 15.0 | 14.8 | 15.0 | 12.6 | 23.4 | 2.9 | 4.3 | 4.2 |
| Lipase | 0.001 | — | 0.01 | — | 0.02 | — | — | — |
| Protease B (optional) | 0.01 | — | — | — | — | — | — | — |
| Protease C (optional) | — | — | — | — | — | 0.01 | — | — |
| nprE (optional) | 0.01 | 0.08 | — | 0.04 | — | 0.023 | — | 0.05 |
| PMN | — | — | 0.05 | — | 0.052 | — | 0.023 | — |
| Amylase | 0.012 | 0.012 | 0.012 | — | 0.015 | — | 0.017 | 0.002 |
| Pectin Lyase | 0.005 | — | — | 0.002 | — | — | — | — |

TABLE 15-1-continued

Tablet Detergent Compositions

| Compound | I | II | III | IV | V | VI | VII | VIII |
|---|---|---|---|---|---|---|---|---|
| Aldose Oxidase | — | 0.03 | — | 0.02 | 0.02 | — | 0.03 | — |
| PB1 | — | — | 3.8 | — | 7.8 | — | — | 4.5 |
| Percarbonate | 6.0 | — | — | 6.0 | — | 5.0 | — | — |
| BB1 | 0.2 | — | 0.5 | — | 0.3 | 0.2 | — | — |
| BB2 | — | 0.2 | — | 0.5 | — | — | 0.1 | 0.2 |
| Nonionic | 1.5 | 2.0 | 2.0 | 2.2 | 1.0 | 4.2 | 4.0 | 6.5 |
| PAAC | 0.01 | 0.01 | 0.02 | — | — | — | — | — |
| DETBCHD | — | — | — | 0.02 | 0.02 | — | — | — |
| TAED | — | — | — | — | — | 2.1 | — | 1.6 |
| HEDP | 1.0 | — | — | 0.9 | — | 0.4 | 0.2 | — |
| DETPMP | 0.7 | — | — | — | — | — | — | — |
| Paraffin | 0.4 | 0.5 | 0.5 | 0.5 | — | — | 0.5 | — |
| BTA | 0.2 | 0.3 | 0.3 | 0.3 | 0.3 | 0.3 | 0.3 | — |
| Polycarboxylate | 4.0 | — | — | — | 4.9 | 0.6 | 0.8 | — |
| PEG 400-30,000 | — | — | — | — | — | 2.0 | — | 2.0 |
| Glycerol | — | — | — | — | — | 0.4 | — | 0.5 |
| Perfume | — | — | — | 0.05 | 0.2 | 0.2 | 0.2 | 0.2 |
| Balance to 100% Moisture and/or Minors* | | | | | | | | |

*Brightener/SRP1/Na carboxymethylcellulose/photobleach/MgSO4/PVPVI/suds suppressor/high molecular PEG/clay.

The pH of Examples 14(I) through 14(VII) is from about 10 to about 11.5; pH of 14(VIII) is from 8-10. The tablet weight of Examples 14(I) through 14(VIII) is from about 20 grams to about 30 grams.

Example 16

Liquid Laundry Detergent Compositions

In this Example, various formulations for liquid laundry detergent compositions are provided. The following liquid laundry detergent compositions of the present invention are prepared as shown below. In each of these formulations, at least one protease variant provided herein is included at a concentration of from about 0.0001 to about 10 weight percent. In some alternative aspects, other concentrations will find use, as determined by the formulator, based on their needs.

TABLE 16-1

Liquid Laundry Detergent Compositions

| Compound | I | II | III | IV | V |
|---|---|---|---|---|---|
| LAS | 24.0 | 32.0 | 6.0 | 3.0 | 6.0 |
| NaC$_{16}$—C$_{17}$ HSAS | — | — | — | 5.0 | — |
| C$_{12}$-C$_{15}$ AE$_{1.8}$S | — | — | 8.0 | 7.0 | 5.0 |
| C$_8$-C$_{10}$ propyl dimethyl amine | 2.0 | 2.0 | 2.0 | 2.0 | 1.0 |
| C$_{12}$-C$_{14}$ alkyl dimethyl amine oxide | — | — | — | — | 2.0 |
| C$_{12}$-C$_{15}$ AS | — | — | 17.0 | — | 8.0 |
| CFAA | — | 5.0 | 4.0 | 4.0 | 3.0 |
| C$_{12}$-C$_{14}$ Fatty alcohol ethoxylate | 12.0 | 6.0 | 1.0 | 1.0 | 1.0 |
| C$_{12}$-C$_{18}$ Fatty acid | 3.0 | — | 4.0 | 2.0 | 3.0 |
| Citric acid (anhydrous) | 4.5 | 5.0 | 3.0 | 2.0 | 1.0 |
| DETPMP | — | — | 1.0 | 1.0 | 0.5 |
| Monoethanolamine | 5.0 | 5.0 | 5.0 | 5.0 | 2.0 |
| Sodium hydroxide | — | — | 2.5 | 1.0 | 1.5 |
| 1N HCl aqueous solution | #1 | #1 | — | — | — |
| Propanediol | 12.7 | 14.5 | 13.1 | 10. | 8.0 |
| Ethanol | 1.8 | 2.4 | 4.7 | 5.4 | 1.0 |
| DTPA | 0.5 | 0.4 | 0.3 | 0.4 | 0.5 |
| Pectin Lyase | — | — | — | 0.005 | — |
| Amylase | 0.001 | 0.002 | — | — | — |
| Cellulase | — | — | 0.0002 | — | 0.0001 |
| Lipase | 0.1 | — | 0.1 | — | 0.1 |
| NprE (optional) | 0.05 | 0.3 | — | 0.5 | 0.2 |
| PMN | — | — | 0.08 | — | — |
| Protease A (optional) | — | — | — | — | 0.1 |
| Aldose Oxidase | — | — | 0.3 | — | 0.003 |
| ZnCl2 | 0.1 | 0.05 | 0.05 | 0.05 | 0.02 |
| Ca formate | 0.05 | 0.07 | 0.05 | 0.06 | 0.07 |
| DETBCHD | — | — | 0.02 | 0.01 | — |
| SRP1 | 0.5 | 0.5 | — | 0.3 | 0.3 |
| Boric acid | — | — | — | — | 2.4 |
| Sodium xylene sulfonate | — | — | 3.0 | — | — |
| Sodium cumene sulfonate | — | — | — | 0.3 | 0.5 |
| DC 3225C | 1.0 | 1.0 | 1.0 | 1.0 | 1.0 |
| 2-butyl-octanol | 0.03 | 0.04 | 0.04 | 0.03 | 0.03 |
| Brightener 1 | 0.12 | 0.10 | 0.18 | 0.08 | 0.10 |
| Balance to 100% perfume/dye and/or water | | | | | |

1: Add 1 N HCl aqueous solution to adjust the neat pH of the formula in the range from about 3 to about 5.

The pH of Examples above 15(I)-(II) is about 5 to about 7, and of 15(III)-(V) is about 7.5 to about 8.5.

TABLE 16-2

Liquid Laundry Detergents

| Compound | I | II | III | IV | V | VI |
|---|---|---|---|---|---|---|
| LAS | 11.5 | 11.5 | 9.0 | — | 4.0 | — |
| $C_{12}$-$C_{15}AE_{2.85}S$ | — | — | 3.0 | 18.0 | — | 16.0 |
| $C_{14}$-$C_{15}E_{2.5}S$ | 11.5 | 11.5 | 3.0 | — | 16.0 | — |
| $C_{12}$-$C_{13}E_9$ | — | — | 3.0 | 2.0 | 2.0 | 1.0 |
| $C_{12}$-$C_{13}E_7$ | 3.2 | 3.2 | — | — | — | — |
| CFAA | — | — | — | 5.0 | — | 3.0 |
| TPKFA | 2.0 | 2.0 | — | 2.0 | 0.5 | 2.0 |
| Citric Acid (Anhydrous) | 3.2 | 3.2 | 0.5 | 1.2 | 2.0 | 1.2 |
| Ca formate | 0.1 | 0.1 | 0.06 | 0.1 | — | — |
| Na formate | 0.5 | 0.5 | 0.06 | 0.1 | 0.05 | 0.05 |
| $ZnCl_2$ | 0.1 | 0.05 | 0.06 | 0.03 | 0.05 | 0.05 |
| Na Culmene Sulfonate | 4.0 | 4.0 | 1.0 | 3.0 | 1.2 | — |
| Borate | 0.6 | 0.6 | 1.5 | — | — | — |
| Na Hydroxide | 6.0 | 6.0 | 2.0 | 3.5 | 4.0 | 3.0 |
| Ethanol | 2.0 | 2.0 | 1.0 | 4.0 | 4.0 | 3.0 |
| 1,2 Propanediol | 3.0 | 3.0 | 2.0 | 8.0 | 8.0 | 5.0 |
| Monoethanolamine | 3.0 | 3.0 | 1.5 | 1.0 | 2.5 | 1.0 |
| TEPAE | 2.0 | 2.0 | — | 1.0 | 1.0 | 1.0 |
| nprE (optional) | 0.03 | 0.05 | — | 0.03 | — | 0.02 |
| PMN | — | — | 0.01 | — | 0.08 | — |
| Protease A (optional) | — | — | 0.01 | — | — | — |
| Lipase | — | — | — | 0.002 | — | — |
| Amylase | — | — | — | — | 0.002 | — |
| Cellulase | — | — | — | — | — | 0.0001 |
| Pectin Lyase | 0.005 | 0.005 | — | — | — | — |
| Aldose Oxidase | 0.05 | — | — | 0.05 | — | 0.02 |
| Galactose oxidase | — | 0.04 | — | — | — | — |
| PAAC | 0.03 | 0.03 | 0.02 | — | — | — |
| DETBCHD | — | — | — | 0.02 | 0.01 | — |
| SRP 1 | 0.2 | 0.2 | — | 0.1 | — | — |
| DTPA | — | — | — | 0.3 | — | — |
| PVNO | — | — | — | 0.3 | — | 0.2 |
| Brightener 1 | 0.2 | 0.2 | 0.07 | 0.1 | — | — |
| Silicone antifoam | 0.04 | 0.04 | 0.02 | 0.1 | 0.1 | 0.1 |
| Balance to 100% perfume/dye and/or water | | | | | | |

Example 17

Hand Dish Liquid Detergent Compositions

In this Example, various hand dish liquid detergent formulations are provided. The following hand dish liquid detergent compositions of the invention are provided below. In each of these formulations, at least one protease variant provided herein is included at a concentration of from about 0.0001 to about 10 weight percent. In some alternative aspects, other concentrations will find use, as determined by the formulator, based on their needs.

TABLE 17-1

Hand Dish Liquid Detergent Compositions

| Compound | I | II | III | IV | V | VI |
|---|---|---|---|---|---|---|
| $C_{12}$-$C_{15}AE_{1.8}S$ | 30.0 | 28.0 | 25.0 | — | 15.0 | 10.0 |
| LAS | — | — | — | 5.0 | 15.0 | 12.0 |
| Paraffin Sulfonate | — | — | — | 20.0 | — | — |
| $C_{10}$-$C_{18}$ Alkyl Dimethyl Amine Oxide | 5.0 | 3.0 | 7.0 | — | — | — |
| Betaine | 3.0 | — | 1.0 | 3.0 | 1.0 | — |
| $C_{12}$ poly-OH fatty acid amide | — | — | — | 3.0 | — | 1.0 |
| $C_{14}$ poly-OH fatty acid amide | — | 1.5 | — | — | — | — |
| $C_{11}E_9$ | 2.0 | — | 4.0 | — | — | 20.0 |
| DTPA | — | — | — | — | 0.2 | — |
| Tri-sodium Citrate dehydrate | 0.25 | — | — | 0.7 | — | — |
| Diamine | 1.0 | 5.0 | 7.0 | 1.0 | 5.0 | 7.0 |
| $MgCl_2$ | 0.25 | — | — | 1.0 | — | — |
| nprE (optional) | 0.02 | 0.01 | — | 0.01 | — | 0.05 |
| PMN | — | — | 0.03 | — | 0.02 | — |
| Protease A (optional) | — | 0.01 | — | — | — | — |
| Amylase | 0.001 | — | — | 0.002 | — | 0.001 |
| Aldose Oxidase | 0.03 | — | 0.02 | — | 0.05 | — |
| Sodium Cumene Sulphonate | — | — | — | 2.0 | 1.5 | 3.0 |
| PAAC | 0.01 | 0.01 | 0.02 | — | — | — |
| DETBCHD | — | — | — | 0.01 | 0.02 | 0.01 |
| Balance to 100% perfume/dye and/or water | | | | | | |

The pH of Examples 16(I)-(VI) is about 8 to about 11.

Example 18

Liquid Automatic Dishwashing Detergent Compositions

In this Example, various liquid automatic dishwashing detergent formulations are provided. The following hand dish liquid detergent compositions of the invention are provided below. In each of these formulations, at least one protease variant provided herein is included at a concentration of from about 0.0001 to about 10 weight percent. In some aspects, other concentrations will find use, as determined by the formulator, based on their needs.

TABLE 18-1

Liquid Automatic Dishwashing Detergent Compositions

| Compound | I | II | III | IV | V |
|---|---|---|---|---|---|
| STPP | 16 | 16 | 18 | 16 | 16 |
| Potassium Sulfate | — | 10 | 8 | — | 10 |
| 1,2 propanediol | 6.0 | 0.5 | 2.0 | 6.0 | 0.5 |
| Boric Acid | — | — | — | 4.0 | 3.0 |
| CaCl$_2$ dihydrate | 0.04 | 0.04 | 0.04 | 0.04 | 0.04 |
| Nonionic | 0.5 | 0.5 | 0.5 | 0.5 | 0.5 |
| nprE (optional) | 0.1 | 0.03 | — | 0.03 | — |
| PMN | — | — | 0.05 | — | 0.06 |
| Protease B (optional) | — | — | — | 0.01 | — |
| Amylase | 0.02 | — | 0.02 | 0.02 | — |
| Aldose Oxidase | — | 0.15 | 0.02 | — | 0.01 |
| Galactose Oxidase | — | — | 0.01 | — | 0.01 |
| PAAC | 0.01 | — | — | 0.01 | — |
| DETBCHD | — | 0.01 | — | — | 0.01 |
| Balance to 100% perfume/dye and/or water | | | | | |

Example 19

High Density Dishwashing Detergents

This Example provides various formulations for high density dishwashing detergents. The following compact high density dishwashing detergents of the invention are provided below. In each formulation, at least one protease variant provided herein is included at a concentration of from about 0.0001 to about 10 weight percent. In some aspects, other concentrations will find use, as determined by the formulator, based on their needs.

TABLE 19-1

High Density Dishwashing Detergents

| Compound | I | II | III | IV | V | VI |
|---|---|---|---|---|---|---|
| STPP | — | 45.0 | 45.0 | — | — | 40.0 |
| 3Na Citrate 2H$_2$O | 17.0 | — | — | 50.0 | 40.2 | — |
| Na Carbonate | 17.5 | 14.0 | 20.0 | — | 8.0 | 33.6 |
| Bicarbonate | — | — | — | 26.0 | — | — |
| Silicate | 15.0 | 15.0 | 8.0 | — | 25.0 | 3.6 |
| Metasilicate | 2.5 | 4.5 | 4.5 | — | — | — |
| PB1 | — | — | 4.5 | — | — | — |
| PB4 | — | — | — | 5.0 | — | — |
| Percarbonate | — | — | — | — | — | 4.8 |
| BB1 | — | 0.1 | 0.1 | — | 0.5 | — |
| BB2 | 0.2 | 0.05 | — | 0.1 | — | 0.6 |
| Nonionic | 2.0 | 1.5 | 1.5 | 3.0 | 1.9 | 5.9 |
| HEDP | 1.0 | — | — | — | — | — |
| DETPMP | 0.6 | — | — | — | — | — |
| PAAC | 0.03 | 0.05 | 0.02 | — | — | — |
| Paraffin | 0.5 | 0.4 | 0.4 | 0.6 | — | — |
| nprE (optional) | 0.072 | 0.053 | — | 0.026 | — | 0.01 |
| PMN | — | — | 0.053 | — | 0.059 | — |
| Protease B (optional) | — | — | — | — | — | 0.01 |
| Amylase | 0.012 | — | 0.012 | — | 0.021 | 0.006 |
| Lipase | — | 0.001 | — | 0.005 | — | — |
| Pectin Lyase | 0.001 | 0.001 | 0.001 | — | — | — |
| Aldose Oxidase | 0.05 | 0.05 | 0.03 | 0.01 | 0.02 | 0.01 |
| BTA | 0.3 | 0.2 | 0.2 | 0.3 | 0.3 | 0.3 |
| Polycarboxylate | 6.0 | — | — | — | 4.0 | 0.9 |
| Perfume | 0.2 | 0.1 | 0.1 | 0.2 | 0.2 | 0.2 |
| Balance to 100% Moisture and/or Minors* | | | | | | |

*Brightener/dye/SRP1/Na carboxymethylcellulose/photobleach/MgSO$_4$/PVPVI/suds suppressor/high molecular PEG/clay.

The pH of Examples 18(I) through (VI) is from about 9.6 to about 11.3.

Example 20

Liquid Hard Surface Cleaning Detergents

This Example provides various formulations for liquid hard surface cleaning detergents. The following liquid hard surface cleaning detergent compositions of the invention are provided below. In each of these formulations, at least one protease variant provided herein is included at a concentration of from about 0.0001 to about 10 weight percent. In some aspects, other concentrations will find use, as determined by the formulator, based on their needs.

TABLE 20-1

Liquid Hard Surface Cleaning Detergents

| Compound | I | II | III | IV | V | VI | VII |
|---|---|---|---|---|---|---|---|
| C$_9$-C$_{11}$E$_5$ | 2.4 | 1.9 | 2.5 | 2.5 | 2.5 | 2.4 | 2.5 |
| C$_{12}$-C$_{14}$E$_5$ | 3.6 | 2.9 | 2.5 | 2.5 | 2.5 | 3.6 | 2.5 |
| C$_7$-C$_9$E$_6$ | — | — | — | — | 8.0 | — | — |
| C$_{12}$-C$_{14}$E$_{21}$ | 1.0 | 0.8 | 4.0 | 2.0 | 2.0 | 1.0 | 2.0 |
| LAS | — | — | — | 0.8 | 0.8 | — | 0.8 |
| Sodium culmene sulfonate | 1.5 | 2.6 | — | 1.5 | 1.5 | 1.5 | 1.5 |
| Isachem ® AS | 0.6 | 0.6 | — | — | — | 0.6 | — |
| Na$_2$CO$_3$ | 0.6 | 0.13 | 0.6 | 0.1 | 0.2 | 0.6 | 0.2 |
| 3Na Citrate•2H$_2$O | 0.5 | 0.56 | 0.5 | 0.6 | 0.75 | 0.5 | 0.75 |
| NaOH | 0.3 | 0.33 | 0.3 | 0.3 | 0.5 | 0.3 | 0.5 |
| Fatty Acid | 0.6 | 0.13 | 0.6 | 0.1 | 0.4 | 0.6 | 0.4 |
| 2-butyl octanol | 0.3 | 0.3 | — | 0.3 | 0.3 | 0.3 | 0.3 |
| PEG DME-2000 ® | 0.4 | — | 0.3 | 0.35 | 0.5 | — | — |

TABLE 20-1-continued

| Liquid Hard Surface Cleaning Detergents | | | | | | | |
|---|---|---|---|---|---|---|---|
| | Formulations | | | | | | |
| Compound | I | II | III | IV | V | VI | VII |
| PVP | 0.3 | 0.4 | 0.6 | 0.3 | 0.5 | — | — |
| MME PEG (2000) ® | — | — | — | — | — | 0.5 | 0.5 |
| Jeffamine ® ED-2001 | — | 0.4 | — | — | 0.5 | — | — |
| PAAC | — | — | — | 0.03 | 0.03 | 0.03 | — |
| DETBCHD | 0.03 | 0.05 | 0.05 | — | — | — | — |
| nprE (optional) | 0.07 | — | 0.08 | 0.03 | — | 0.01 | 0.04 |
| PMN | — | 0.05 | — | — | 0.06 | — | — |
| Protease B (optional) | — | — | — | — | — | 0.01 | — |
| Amylase | 0.12 | 0.01 | 0.01 | — | 0.02 | — | 0.01 |
| Lipase | — | 0.001 | — | 0.005 | — | 0.005 | — |
| Pectin Lyase | 0.001 | — | 0.001 | — | — | — | 0.002 |
| ZnCl2 | 0.02 | 0.01 | 0.03 | 0.05 | 0.1 | 0.05 | 0.02 |
| Calcium Formate | 0.03 | 0.03 | 0.01 | — | — | — | — |
| PB1 | — | 4.6 | — | 3.8 | — | — | — |
| Aldose Oxidase | 0.05 | — | 0.03 | — | 0.02 | 0.02 | 0.05 |
| Balance to 100% perfume/dye and/or water | | | | | | | |

The pH of Examples 19(I) through (VII) is from about 7.4 to about 9.5.

All publications, patent applications, and patents cited in this specification are herein incorporated by reference as if each individual publication, patent application, or patent were specifically and individually indicated to be incorporated by reference. In particular, all publications cited herein are expressly incorporated herein by reference for the purpose of describing and disclosing compositions and methodologies which might be used in connection with the invention. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. An isolated protein comprising a protease variant of the parent subtilisin protease set forth by SEQ ID NO: 2, wherein the variant comprises, compared to SEQ ID NO: 2, six amino acid substitutions selected from the group consisting of X024G/R, X053G, X078N, X101N, X128A/S, and X217L/Q,
the variant has at least 90% identity to SEQ ID NO: 2, and
the variant has enhanced proteolytic activity and/or cleaning activity, compared to the parent protease set forth in SEQ ID NO:2.

2. The protein of claim 1, wherein the protease variant comprises the amino acid substitutions S024G+S053G+S078N+S101N+G128S+Y217Q or S024G+S053G+S078N+S101N+G128A+Y217Q.

3. The protein of claim 1, wherein the protease variant consists of the amino acid sequence set forth by SEQ ID NO: 6.

* * * * *

SEQUENCE LISTING

```
<160> NUMBER OF SEQ ID NOS: 766

<210> SEQ ID NO 1
<211> LENGTH: 1146
<212> TYPE: DNA
<213> ORGANISM: Bacillus amyloliquefaciens

<400> SEQUENCE: 1
gtgagaagca aaaaattgtg gatcagtttg ctgtttgctt tagcgttaat ctttacgatg      60
gcgttcggca gcacatcctc tgcccaggcg gcagggaaat caaacgggga aaagaaatat     120
attgtcgggt ttaaacagac aatgagcacg atgagcgccg ctaagaagaa agatgtcatt     180
tctgaaaaag gcgggaaagt gcaaaagcaa ttcaaatatg tagacgcagc ttcagctaca     240
ttaaacgaaa aagctgtaaa agaattgaaa aaagacccga gcgtcgctta cgttgaagaa     300
gatcacgtag cacatgcgta cgcgcagtcc gtgccttacg gcgtatcaca aattaaagcc     360
cctgctctgc actctcaagg ctacactgga tcaaatgtta aagtagcggt tatcgacagc     420
ggtatcgact cgagccatcc agatcttaaa gtcgctggag gggcttctat ggtgccgtcc     480
gaaacaaacc cgtttcaaga taacaattct catggcacac acgtcgcagg aacggttgcg     540
gcgttaaaca attctattgg cgtgcttggt gtagcccccgt ctgcttcgct ctacgccgtt     600
aaagttcttg gcgcagacgg atcaggccaa tactcatgga ttatcaacgg catcgaatgg     660
gccatcgcga ataacatgga tgtaatcaac atgagcctgg gaggaccaag cggcagtgcg     720
gcacttaaag cagcagttga taaagctgtt gcatctggtg tcgtcgtagt agcggcagct     780
gggaatgagg gaacatccgg atcatcgagt accgtcggtt atccaggcaa gtaccttca      840 gtgattgcag tgggcgctgt agactcttca aatcaacgtg cctcttttc ctccgtggga     900
```

```
ccggagctgg atgtcatggc ccctggcgtt tctattcaat cgacgcttcc agggaacaag    960
tatggtgcgt ataacgggac ttccatggcc tcgccgcatg tagctggggc ggccgcattg   1020
attctttcta agcacccgaa ctggacaaac actcaagtcc gcagcagttt agaaaacacc   1080
actacaaaac ttggtgattc tttctactat ggaaaagggc tgatcaacgt acaggcggca   1140
gctcag                                                              1146
```

<210> SEQ ID NO 2
<211> LENGTH: 275
<212> TYPE: PRT
<213> ORGANISM: Bacillus amyloliquefaciens

<400> SEQUENCE: 2

```
Ala Gln Ser Val Pro Tyr Gly Val Ser Gln Ile Lys Ala Pro Ala Leu
1               5                   10                  15

His Ser Gln Gly Tyr Thr Gly Ser Asn Val Lys Val Ala Val Ile Asp
            20                  25                  30

Ser Gly Ile Asp Ser Ser His Pro Asp Leu Lys Val Ala Gly Gly Ala
        35                  40                  45

Ser Met Val Pro Ser Glu Thr Asn Pro Phe Gln Asp Asn Asn Ser His
    50                  55                  60

Gly Thr His Val Ala Gly Thr Val Ala Ala Leu Asn Asn Ser Ile Gly
65                  70                  75                  80

Val Leu Gly Val Ala Pro Ser Ala Ser Leu Tyr Ala Val Lys Val Leu
                85                  90                  95

Gly Ala Asp Gly Ser Gly Gln Tyr Ser Trp Ile Ile Asn Gly Ile Glu
            100                 105                 110

Trp Ala Ile Ala Asn Asn Met Asp Val Ile Asn Met Ser Leu Gly Gly
        115                 120                 125

Pro Ser Gly Ser Ala Ala Leu Lys Ala Ala Val Asp Lys Ala Val Ala
    130                 135                 140

Ser Gly Val Val Val Val Ala Ala Ala Gly Asn Glu Gly Thr Ser Gly
145                 150                 155                 160

Ser Ser Ser Thr Val Gly Tyr Pro Gly Lys Tyr Pro Ser Val Ile Ala
                165                 170                 175

Val Gly Ala Val Asp Ser Ser Asn Gln Arg Ala Ser Phe Ser Ser Val
            180                 185                 190

Gly Pro Glu Leu Asp Val Met Ala Pro Gly Val Ser Ile Gln Ser Thr
        195                 200                 205

Leu Pro Gly Asn Lys Tyr Gly Ala Tyr Asn Gly Thr Ser Met Ala Ser
    210                 215                 220

Pro His Val Ala Gly Ala Ala Leu Ile Leu Ser Lys His Pro Asn
225                 230                 235                 240

Trp Thr Asn Thr Gln Val Arg Ser Ser Leu Glu Asn Thr Thr Lys
                245                 250                 255

Leu Gly Asp Ser Phe Tyr Tyr Gly Lys Gly Leu Ile Asn Val Gln Ala
            260                 265                 270

Ala Ala Gln
        275
```

<210> SEQ ID NO 3
<211> LENGTH: 825
<212> TYPE: DNA
<213> ORGANISM: Bacillus amyloliquefaciens

<400> SEQUENCE: 3

-continued

```
gcgcagtccg tgccttacgg cgtatcacaa attaaagccc ctgctctgca ctctcaaggc      60
tacactggat caaatgttaa agtagcggtt atcgacagcg gtatcgactc gagccatcca     120
gatcttaaag tcgctggagg ggcttctatg gtgccgtccg aaacaaaccc gtttcaagat     180
aacaattctc atggcacaca cgtcgcagga acggttgcgg cgttaaacaa ttctattggc     240
gtgcttggtg tagccccgtc tgcttcgctc tacgccgtta agttcttgc agcagacgga      300
tcaggccaat actcatggat tatcaacggc atcgaatggg ccatcgcgaa taacatggat     360
gtaatcaaca tgagcctggg agcaccaagc ggcagtgcgg cacttaaagc agcagttgat     420
aaagctgttg catctggtgt cgtcgtagta gcggcagctg gaatgaggg aacatccgga      480
tcatcgagta ccgtcggtta tccaggcaag taccccttcag tgattgcagt gggcgctgta    540
gactcttcaa atcaacgtgc ctctttttcc tccgtgggac cggagctgga tgtcatggcc     600
cctggcgttt ctattcaatc gacgcttcca gggaacaagt atggtgcgca aaacgggact     660
tccatggcct cgccgcatgt agctggggcg ccgcattga ttctttctaa gcacccgaac      720
tggacaaaca ctcaagtccg cagcagttta gaaaacacca ctacaaaact tggtgattct     780
ttctactatg gaaaagggct gatcaacgta caggcggcag ctcag                     825
```

<210> SEQ ID NO 4
<211> LENGTH: 275
<212> TYPE: PRT
<213> ORGANISM: Bacillus amyloliquefaciens

<400> SEQUENCE: 4

```
Ala Gln Ser Val Pro Tyr Gly Val Ser Gln Ile Lys Ala Pro Ala Leu
1               5                   10                  15

His Ser Gln Gly Tyr Thr Gly Ser Asn Val Lys Val Ala Val Ile Asp
            20                  25                  30

Ser Gly Ile Asp Ser Ser His Pro Asp Leu Lys Val Ala Gly Gly Ala
        35                  40                  45

Ser Met Val Pro Ser Glu Thr Asn Pro Phe Gln Asp Asn Asn Ser His
    50                  55                  60

Gly Thr His Val Ala Gly Thr Val Ala Ala Leu Asn Asn Ser Ile Gly
65                  70                  75                  80

Val Leu Gly Val Ala Pro Ser Ala Ser Leu Tyr Ala Val Lys Val Leu
                85                  90                  95

Ala Ala Asp Gly Ser Gly Gln Tyr Ser Trp Ile Ile Asn Gly Ile Glu
            100                 105                 110

Trp Ala Ile Ala Asn Asn Met Asp Val Ile Asn Met Ser Leu Gly Ala
        115                 120                 125

Pro Ser Gly Ser Ala Ala Leu Lys Ala Ala Val Asp Lys Ala Val Ala
    130                 135                 140

Ser Gly Val Val Val Ala Ala Ala Gly Asn Glu Gly Thr Ser Gly
145                 150                 155                 160

Ser Ser Ser Thr Val Gly Tyr Pro Gly Lys Tyr Pro Ser Val Ile Ala
                165                 170                 175

Val Gly Ala Val Asp Ser Ser Asn Gln Arg Ala Ser Phe Ser Ser Val
            180                 185                 190

Gly Pro Glu Leu Asp Val Met Ala Pro Gly Val Ser Ile Gln Ser Thr
        195                 200                 205

Leu Pro Gly Asn Lys Tyr Gly Ala Gln Asn Gly Thr Ser Met Ala Ser
    210                 215                 220

Pro His Val Ala Gly Ala Ala Ala Leu Ile Leu Ser Lys His Pro Asn
```

```
              225                 230                 235                 240
Trp Thr Asn Thr Gln Val Arg Ser Ser Leu Glu Asn Thr Thr Thr Lys
                245                 250                 255
Leu Gly Asp Ser Phe Tyr Tyr Gly Lys Gly Leu Ile Asn Val Gln Ala
                260                 265                 270
Ala Ala Gln
        275

<210> SEQ ID NO 5
<211> LENGTH: 825
<212> TYPE: DNA
<213> ORGANISM: Artificial
<220> FEATURE:
<223> OTHER INFORMATION: synthesized BPN'-v36 variant

<400> SEQUENCE: 5
gcgcagtccg tgccttacgg cgtatcacaa attaaagccc ctgctctgca ctctcaaggc      60
tacactggag gcaatgttaa agtagcggtt atcgacagcg gtatcgactc gagccatcca     120
gatcttaaag tcgctggagg ggcttctatg gtgccgggcg aaacaaaccc gtttcaagat     180
aacaattctc atggcacaca cgtcgcagga acggttgcgg cgttaaacaa taatattggc     240
gtgcttggtg tagccccgtc tgcttcgctc tacgccgtta aagttcttgg cgcagacgga     300
aatggccaat actcatggat tatcaacggc atcgaatggg ccatcgcgaa taacatggat     360
gtaatcaaca tgagcctggg agcaccaagc ggcagtgcgg cacttaaagc agcagttgat     420
aaagctgttg catctggtgt cgtcgtagta gcggcagctg gaatgagggg aacatccgga     480
tcatcgagta ccgtcggtta tccaggcaag taccccttcag tgattgcagt gggcgctgta     540
gactcttcaa atcaacgtgc ctcttttttcc tccgtgggac cggagctgga tgtcatggcc     600
cctggcgttt ctattcaatc gacgcttcca gggaacaagt atggtgcgca aaacgggact     660
tccatggcct cgccgcatgt agctggggcg gccgcattga ttctttctaa gcacccgaac     720
tggacaaaca ctcaagtccg cagcagttta gaaaacacca ctacaaaact tggtgattct     780
ttctactatg gaaagggct gatcaacgta caggcggcag ctcag                     825

<210> SEQ ID NO 6
<211> LENGTH: 275
<212> TYPE: PRT
<213> ORGANISM: Artificial
<220> FEATURE:
<223> OTHER INFORMATION: synthesized BPN'-v36 variant

<400> SEQUENCE: 6

Ala Gln Ser Val Pro Tyr Gly Val Ser Gln Ile Lys Ala Pro Ala Leu
1               5                   10                  15

His Ser Gln Gly Tyr Thr Gly Gly Asn Val Lys Val Ala Val Ile Asp
                20                  25                  30

Ser Gly Ile Asp Ser Ser His Pro Asp Leu Lys Val Ala Gly Gly Ala
        35                  40                  45

Ser Met Val Pro Gly Glu Thr Asn Pro Phe Gln Asp Asn Asn Ser His
    50                  55                  60

Gly Thr His Val Ala Gly Thr Val Ala Ala Leu Asn Asn Asn Ile Gly
65                  70                  75                  80

Val Leu Gly Val Ala Pro Ser Ala Ser Leu Tyr Ala Val Lys Val Leu
                85                  90                  95

Gly Ala Asp Gly Asn Gly Gln Tyr Ser Trp Ile Ile Asn Gly Ile Glu
                100                 105                 110
```

```
Trp Ala Ile Ala Asn Asn Met Asp Val Ile Asn Met Ser Leu Gly Ala
            115                 120                 125
Pro Ser Gly Ser Ala Ala Leu Lys Ala Ala Val Asp Lys Ala Val Ala
        130                 135                 140
Ser Gly Val Val Val Ala Ala Ala Gly Asn Glu Gly Thr Ser Gly
145                 150                 155                 160
Ser Ser Ser Thr Val Gly Tyr Pro Gly Lys Tyr Pro Ser Val Ile Ala
                165                 170                 175
Val Gly Ala Val Asp Ser Ser Asn Gln Arg Ala Ser Phe Ser Ser Val
            180                 185                 190
Gly Pro Glu Leu Asp Val Met Ala Pro Gly Val Ser Ile Gln Ser Thr
        195                 200                 205
Leu Pro Gly Asn Lys Tyr Gly Ala Gln Asn Gly Thr Ser Met Ala Ser
210                 215                 220
Pro His Val Ala Gly Ala Ala Ala Leu Ile Leu Ser Lys His Pro Asn
225                 230                 235                 240
Trp Thr Asn Thr Gln Val Arg Ser Ser Leu Glu Asn Thr Thr Thr Lys
                245                 250                 255
Leu Gly Asp Ser Phe Tyr Tyr Gly Lys Gly Leu Ile Asn Val Gln Ala
            260                 265                 270
Ala Ala Gln
        275

<210> SEQ ID NO 7
<211> LENGTH: 825
<212> TYPE: DNA
<213> ORGANISM: Artificial
<220> FEATURE:
<223> OTHER INFORMATION: synthesized BPN'-v3+S78N variant

<400> SEQUENCE: 7
gcgcagtccg tgccttacgg cgtatcacaa attaaagccc tgctctgca ctctcaaggc      60
tacactggat caaatgttaa agtagcggtt atcgacagcg gtattgattc gagccatcca     120
gatcttaaag tcgctggagg ggcttctatg gtgccgtccg aaacaaaccc gtttcaagat     180
aacaattctc atggcacaca cgtcgcagga acggttgcgg cgttaaacaa taatattggc     240
gtgcttggtg tagccccgtc tgcttcgctc tacgccgtta agttcttgc agcagacgga     300
tcaggccaat actcatggat tatcaacggc atcgaatggg ccatcgcgaa taacatggat     360
gtaatcaaca tgagcctggg agcaccaagc ggcagtgcgg cacttaaagc agcagttgat     420
aaagctgttg catctggtgt cgtcgtagta gcggcagctg gaatgagggg aacatccgga     480
tcatcgagta ccgtcggtta tccaggcaag taccttcag tgattgcagt gggcgctgta     540
gactcttcaa atcaacgtgc ctctttttcc tccgtgggac cggagctgga tgtcatggcc     600
cctggcgttt ctattcaatc gacgcttcca gggaacaagt atggtgcgca aaacgggact     660
tccatggcct cgccgcatgt agctggggcg gccgcattga ttcttctaa gcacccgaac     720
tggacaaaca ctcaagtccg cagcagttta gaaaacacca ctacaaaact tggtgattct     780
ttctactatg gaaagggct gatcaacgta caggcggcag ctcag                     825

<210> SEQ ID NO 8
<211> LENGTH: 275
<212> TYPE: PRT
<213> ORGANISM: Artificial
<220> FEATURE:
<223> OTHER INFORMATION: synthesized BPN'-v3+S78N variant

<400> SEQUENCE: 8
```

Ala Gln Ser Val Pro Tyr Gly Val Ser Gln Ile Lys Ala Pro Ala Leu
1               5                   10                  15

His Ser Gln Gly Tyr Thr Gly Ser Asn Val Lys Val Ala Val Ile Asp
            20                  25                  30

Ser Gly Ile Asp Ser Ser His Pro Asp Leu Lys Val Ala Gly Gly Ala
        35                  40                  45

Ser Met Val Pro Ser Glu Thr Asn Pro Phe Gln Asp Asn Asn Ser His
    50                  55                  60

Gly Thr His Val Ala Gly Thr Val Ala Ala Leu Asn Asn Asn Ile Gly
65              70                  75                  80

Val Leu Gly Val Ala Pro Ser Ala Ser Leu Tyr Ala Val Lys Val Leu
                85                  90                  95

Ala Ala Asp Gly Ser Gly Gln Tyr Ser Trp Ile Ile Asn Gly Ile Glu
            100                 105                 110

Trp Ala Ile Ala Asn Asn Met Asp Val Ile Asn Met Ser Leu Gly Ala
        115                 120                 125

Pro Ser Gly Ser Ala Ala Leu Lys Ala Ala Val Asp Lys Ala Val Ala
    130                 135                 140

Ser Gly Val Val Val Ala Ala Ala Gly Asn Glu Gly Thr Ser Gly
145                 150                 155                 160

Ser Ser Ser Thr Val Gly Tyr Pro Gly Lys Tyr Pro Ser Val Ile Ala
                165                 170                 175

Val Gly Ala Val Asp Ser Ser Asn Gln Arg Ala Ser Phe Ser Ser Val
            180                 185                 190

Gly Pro Glu Leu Asp Val Met Ala Pro Gly Val Ser Ile Gln Ser Thr
        195                 200                 205

Leu Pro Gly Asn Lys Tyr Gly Ala Gln Asn Gly Thr Ser Met Ala Ser
    210                 215                 220

Pro His Val Ala Gly Ala Ala Ala Leu Ile Leu Ser Lys His Pro Asn
225                 230                 235                 240

Trp Thr Asn Thr Gln Val Arg Ser Ser Leu Glu Asn Thr Thr Thr Lys
                245                 250                 255

Leu Gly Asp Ser Phe Tyr Tyr Gly Lys Gly Leu Ile Asn Val Gln Ala
            260                 265                 270

Ala Ala Gln
    275

<210> SEQ ID NO 9
<211> LENGTH: 828
<212> TYPE: DNA
<213> ORGANISM: Artificial
<220> FEATURE:
<223> OTHER INFORMATION: synthesized GcM90 gene

<400> SEQUENCE: 9
gcgcagtccg tgccttacgg cgtatcacaa attaaagccc ctgctctgca ctctcaaggc      60
tacactggat caaatgttaa agtagcggtt atcgacagcg gtatcgactc gagccatcca     120
gatcttaaag tcgctggagg ggcttctatg gtgccgggag aaacaaaccc gtttcaagat     180
aacaattctc atggcacaca cgcagcagga acggttgcgg cgttaaacaa taatattggc     240
gtgcttggtg tagccccgtc tgcttcgctc tacgccgtta agttcttgc agcagacgga      300 tcagcacaat actcatggat tatcaacggc atcgaatggg ccatcgcgaa taacatggat     360
gtaatcaaca tgagcctggg agcaacaagc ggcagtgcgg cacttaaagc agcagttgat     420
aaagctgttg catctggtgt cgtcgtagta gcggcagctg ggaatgaggg aacatccgga     480

```
tcatcgagta ccgtcggtta tccaggcaag tacccttcag tgattgcagt gggcgctgta    540
gactcttcaa atacacgtgc ctcttttttcc tccgtgggac cggagctgga tgtcatggcc    600
cctggcgttt ctattcaatc gacgcttcca gggaacaagt atggtgcgca aaacgggact    660
tccatggcct cgccgcatgt agctggggcg gccgcattga ttctttctaa gcacccgaac    720
tggacaaaca ctcaagtccg cagcagttta gaaaacacca ctacaaaact tggtgattct    780
ttctactatg gaaaagggct gatcaacgta caggcggcag ctcagtaa                 828
```

```
<210> SEQ ID NO 10
<211> LENGTH: 275
<212> TYPE: PRT
<213> ORGANISM: Artificial
<220> FEATURE:
<223> OTHER INFORMATION: amino acid encoded by synthesized GcM90 gene

<400> SEQUENCE: 10
```

```
Ala Gln Ser Val Pro Tyr Gly Val Ser Gln Ile Lys Ala Pro Ala Leu
1               5                   10                  15

His Ser Gln Gly Tyr Thr Gly Ser Asn Val Lys Val Ala Val Ile Asp
            20                  25                  30

Ser Gly Ile Asp Ser Ser His Pro Asp Leu Lys Val Ala Gly Gly Ala
        35                  40                  45

Ser Met Val Pro Gly Glu Thr Asn Pro Phe Gln Asp Asn Asn Ser His
    50                  55                  60

Gly Thr His Ala Ala Gly Thr Val Ala Ala Leu Asn Asn Asn Ile Gly
65                  70                  75                  80

Val Leu Gly Val Ala Pro Ser Ala Ser Leu Tyr Ala Val Lys Val Leu
                85                  90                  95

Ala Ala Asp Gly Ser Ala Gln Tyr Ser Trp Ile Ile Asn Gly Ile Glu
            100                 105                 110

Trp Ala Ile Ala Asn Asn Met Asp Val Ile Asn Met Ser Leu Gly Ala
        115                 120                 125

Thr Ser Gly Ser Ala Ala Leu Lys Ala Ala Val Asp Lys Ala Val Ala
    130                 135                 140

Ser Gly Val Val Val Ala Ala Ala Gly Asn Glu Gly Thr Ser Gly
145                 150                 155                 160

Ser Ser Ser Thr Val Gly Tyr Pro Gly Lys Tyr Pro Ser Val Ile Ala
                165                 170                 175

Val Gly Ala Val Asp Ser Ser Asn Thr Arg Ala Ser Phe Ser Ser Val
            180                 185                 190

Gly Pro Glu Leu Asp Val Met Ala Pro Gly Val Ser Ile Gln Ser Thr
        195                 200                 205

Leu Pro Gly Asn Lys Tyr Gly Ala Gln Asn Gly Thr Ser Met Ala Ser
    210                 215                 220

Pro His Val Ala Gly Ala Ala Leu Ile Leu Ser Lys His Pro Asn
225                 230                 235                 240

Trp Thr Asn Thr Gln Val Arg Ser Ser Leu Glu Asn Thr Thr Thr Lys
                245                 250                 255

Leu Gly Asp Ser Phe Tyr Tyr Gly Lys Gly Leu Ile Asn Val Gln Ala
            260                 265                 270

Ala Ala Gln
        275
```

```
<210> SEQ ID NO 11
<211> LENGTH: 828
```

```
<212> TYPE: DNA
<213> ORGANISM: Artificial
<220> FEATURE:
<223> OTHER INFORMATION: synthesized GcM91 gene

<400> SEQUENCE: 11
gcgcagtccg tgccttacgg cgtatcacaa attaaagccc ctgctctgca ctctcaaggc    60
tacactggat caaatgttaa agtagcggtt atcgacagcg gtatcgactc gagccatcca   120
gatcttaaag tcgctggagg ggcttctatg gtgccgtccg aaacaaaccc gtttgtcgat   180
aacaattctc atggcacaca cgtcgcagga acggttgcgg cgttaaacaa taatattggc   240
gtgcttggtg tagccccgtc tgcttcgctc tacgccgtta agttcttgc agcagacgga    300 tcaggccaat actcatggat tgtcaacggc atcgaatggg ccatcgcgaa taacatggat   360
gtaatcaaca tgagcctggg agcaccaagc ggcagtgcgg cacttaaagc agcagttgat   420
aaagctgttg catctggtca agtcgtagta gcggcagctg ggaatgaggg aacatccgga   480
tcatcgagta ccgtcggtta ccaggcaag tacccttcag tgattgcagt gggcgctgta    540
gactcttcaa atcaacgtgc ctcttttttcc tccgtgggac cggagctgga tgtcatggcc   600
cctggcgttt ctattcaatc gacgcttcca gcaaacaagt atggtgcgca aaacgggact   660
tccatggcct cgccgcatgt agctggggcg ccgcattga ttctttctaa gcacccgaac    720
tggacaaaca ctcaagtccg cagcagttta gaacaaacca ctacaaaact tggtgattct   780
ttctactatg gaaaagggct gatcaacgta caggcggcag ctcagtaa                828

<210> SEQ ID NO 12
<211> LENGTH: 275
<212> TYPE: PRT
<213> ORGANISM: Artificial
<220> FEATURE:
<223> OTHER INFORMATION: amino acid encoded by synthesized GcM91 gene

<400> SEQUENCE: 12

Ala Gln Ser Val Pro Tyr Gly Val Ser Gln Ile Lys Ala Pro Ala Leu
1               5                   10                  15

His Ser Gln Gly Tyr Thr Gly Ser Asn Val Lys Val Ala Val Ile Asp
            20                  25                  30

Ser Gly Ile Asp Ser Ser His Pro Asp Leu Lys Val Ala Gly Gly Ala
        35                  40                  45

Ser Met Val Pro Ser Glu Thr Asn Pro Phe Val Asp Asn Asn Ser His
    50                  55                  60

Gly Thr His Val Ala Gly Thr Val Ala Ala Leu Asn Asn Asn Ile Gly
65                  70                  75                  80

Val Leu Gly Val Ala Pro Ser Ala Ser Leu Tyr Ala Val Lys Val Leu
                85                  90                  95

Ala Ala Asp Gly Ser Gly Gln Tyr Ser Trp Ile Val Asn Gly Ile Glu
            100                 105                 110

Trp Ala Ile Ala Asn Asn Met Asp Val Ile Asn Met Ser Leu Gly Ala
        115                 120                 125

Pro Ser Gly Ser Ala Ala Leu Lys Ala Ala Val Asp Lys Ala Val Ala
    130                 135                 140

Ser Gly Gln Val Val Val Ala Ala Ala Gly Asn Glu Gly Thr Ser Gly
145                 150                 155                 160

Ser Ser Ser Thr Val Gly Tyr Pro Gly Lys Tyr Pro Ser Val Ile Ala
                165                 170                 175

Val Gly Ala Val Asp Ser Ser Asn Gln Arg Ala Ser Phe Ser Ser Val
            180                 185                 190
```

```
Gly Pro Glu Leu Asp Val Met Ala Pro Gly Val Ser Ile Gln Ser Thr
            195                 200                 205

Leu Pro Ala Asn Lys Tyr Gly Ala Gln Asn Gly Thr Ser Met Ala Ser
        210                 215                 220

Pro His Val Ala Gly Ala Ala Leu Ile Leu Ser Lys His Pro Asn
225                 230                 235                 240

Trp Thr Asn Thr Gln Val Arg Ser Ser Leu Glu Gln Thr Thr Thr Lys
            245                 250                 255

Leu Gly Asp Ser Phe Tyr Tyr Gly Lys Gly Leu Ile Asn Val Gln Ala
            260                 265                 270

Ala Ala Gln
        275

<210> SEQ ID NO 13
<211> LENGTH: 828
<212> TYPE: DNA
<213> ORGANISM: Artificial
<220> FEATURE:
<223> OTHER INFORMATION: synthesized GcM92 gene

<400> SEQUENCE: 13
gcgcagtccg tgccttacgg cgtatcacaa attaaagccc ctgctctgca ctctcaaggc      60
tacactggat caaatgttaa agtagcggtt atcgacagcg gtatcgactc gagccatcca     120
gatcttaaag tcgctggagg ggcttctatg gtgccgtccg aaacaaaccc gtttcaagat     180
gcaaattctc atggcacaca cgtcgcagga acggttgcgg cgttaaacaa taatattggc     240
gtgcttggtg tagccccgga agcttcgctc tacgccgtta agttcttgc agcagacgga      300
tcaggccaat actcatggat tatcaacggc atcgaatggg ccatcgcgaa taacatggat     360
gtaatcaaca tcagcctggg agcaccaagc ggcagtgcgg cacttaaagc agcagttgat     420
aaagctgttg catctggtgt cgtcgtagta gcggcagctg ggaatgaggg aacatccgga     480
ccttcgagta ccgtcggtta tccaggcaag tacccttcag tgattgcagt gggcgctgta     540
gactcttcaa atcaacgtgc ctctttttcc tccgtgggac cggagctgga tgtcatggcc     600
cctggcgttt ctattcaatc gacgcttcca gggaacaagt atggtgcgca aaacgggact     660
tccatggccg caccgcatgt agctggggcg gccgcattga ttctttctaa gcacccgaac     720
tggacaaaca ctcaagtccg cagcagttta gaaaacacca ctacaaaact tggtgattct     780
ttctactatg gaaaagggct gatcaacgta caggcggcag ctcagtaa                  828

<210> SEQ ID NO 14
<211> LENGTH: 275
<212> TYPE: PRT
<213> ORGANISM: Artificial
<220> FEATURE:
<223> OTHER INFORMATION: amino acid encoded by synthesized GcM92 gene

<400> SEQUENCE: 14

Ala Gln Ser Val Pro Tyr Gly Val Ser Gln Ile Lys Ala Pro Ala Leu
1               5                   10                  15

His Ser Gln Gly Tyr Thr Gly Ser Asn Val Lys Val Ala Val Ile Asp
            20                  25                  30

Ser Gly Ile Asp Ser Ser His Pro Asp Leu Lys Val Ala Gly Gly Ala
        35                  40                  45

Ser Met Val Pro Ser Glu Thr Asn Pro Phe Gln Asp Ala Asn Ser His
    50                  55                  60

Gly Thr His Val Ala Gly Thr Val Ala Ala Leu Asn Asn Asn Ile Gly
```

```
                65                  70                  75                  80
Val Leu Gly Val Ala Pro Glu Ala Ser Leu Tyr Ala Val Lys Val Leu
                    85                  90                  95

Ala Ala Asp Gly Ser Gly Gln Tyr Ser Trp Ile Ile Asn Gly Ile Glu
                100                 105                 110

Trp Ala Ile Ala Asn Asn Met Asp Val Ile Asn Ile Ser Leu Gly Ala
            115                 120                 125

Pro Ser Gly Ser Ala Ala Leu Lys Ala Ala Val Asp Lys Ala Val Ala
        130                 135                 140

Ser Gly Val Val Val Ala Ala Gly Asn Glu Gly Thr Ser Gly
145                 150                 155                 160

Pro Ser Ser Thr Val Gly Tyr Pro Gly Lys Tyr Pro Ser Val Ile Ala
                165                 170                 175

Val Gly Ala Val Asp Ser Ser Asn Gln Arg Ala Ser Phe Ser Ser Val
            180                 185                 190

Gly Pro Glu Leu Asp Val Met Ala Pro Gly Val Ser Ile Gln Ser Thr
        195                 200                 205

Leu Pro Gly Asn Lys Tyr Gly Ala Gln Asn Gly Thr Ser Met Ala Ala
    210                 215                 220

Pro His Val Ala Gly Ala Ala Leu Ile Leu Ser Lys His Pro Asn
225                 230                 235                 240

Trp Thr Asn Thr Gln Val Arg Ser Ser Leu Glu Asn Thr Thr Lys
                245                 250                 255

Leu Gly Asp Ser Phe Tyr Tyr Gly Lys Gly Leu Ile Asn Val Gln Ala
            260                 265                 270

Ala Ala Gln
        275

<210> SEQ ID NO 15
<211> LENGTH: 828
<212> TYPE: DNA
<213> ORGANISM: Artificial
<220> FEATURE:
<223> OTHER INFORMATION: synthesized GcM93 gene

<400> SEQUENCE: 15
gcgcagtccg tgccttacgg cgtatcacaa attaaagccc ctgctctgca ctctcaaggc      60
tacactggat caaatgttaa agtagcggtt atcgacagcg gtatcgactc gagccatcca     120
gatcttaaag tcgctggagg ggcttctatg gtgccgtccg aaacaaaccc gtttcaagat     180
aaccaatctc atggcacaca cgtcgcagga acggttgcgg cgttaaacaa taatattggc     240
gtgcttggtg tagccccgtc tgcttcgctc tacgccgtta agttcttgc agcagacaac      300 tcaggccaat actcatggat tatcaacggc atcgaatggg ccatcgcgaa taacatggat     360
gtaatcaaca tggcactggg agcaccaagc ggcagtgcgg cacttaaagc agcagttgat     420
aaagctgttg catctggtgt cgtcgtagta gcggcagctg ggaatgaggg aacagatgga     480
tcatcgagta ccgtcggtta tccaggcaag tacccttcag tgattgcagt gggcgctgta     540
gactcttcaa atcaacgtgc ctctttttcc tccgtgggac cggagctgga tgtcatggcc     600
cctggcgttt ctattcaatc gacgcttcca gggaacaagt atggtgcgca aaacgggact     660
tccatggcct cgccgcatgt agctgggcg gccgcattga ttcttttctaa gcacccgtca     720 tggacaaaca ctcaagtccg cagcagttta gaaaacacca ctacaaaact tggtgattct     780
ttctactatg gaaagggct gatcaacgta caggcggcag ctcagtaa                   828
```

```
<210> SEQ ID NO 16
<211> LENGTH: 275
<212> TYPE: PRT
<213> ORGANISM: Artificial
<220> FEATURE:
<223> OTHER INFORMATION: amino acid encoded by synthesized GcM93 gene

<400> SEQUENCE: 16

Ala Gln Ser Val Pro Tyr Gly Val Ser Gln Ile Lys Ala Pro Ala Leu
 1               5                  10                  15

His Ser Gln Gly Tyr Thr Gly Ser Asn Val Lys Val Ala Val Ile Asp
                20                  25                  30

Ser Gly Ile Asp Ser Ser His Pro Asp Leu Lys Val Ala Gly Gly Ala
            35                  40                  45

Ser Met Val Pro Ser Glu Thr Asn Pro Phe Gln Asp Asn Gln Ser His
    50                  55                  60

Gly Thr His Val Ala Gly Thr Val Ala Ala Leu Asn Asn Ile Gly
 65                 70                  75                  80

Val Leu Gly Val Ala Pro Ser Ala Ser Leu Tyr Ala Val Lys Val Leu
                85                  90                  95

Ala Ala Asp Asn Ser Gly Gln Tyr Ser Trp Ile Ile Asn Gly Ile Glu
            100                 105                 110

Trp Ala Ile Ala Asn Asn Met Asp Val Ile Asn Met Ala Leu Gly Ala
        115                 120                 125

Pro Ser Gly Ser Ala Ala Leu Lys Ala Ala Val Asp Lys Ala Val Ala
    130                 135                 140

Ser Gly Val Val Val Ala Ala Ala Gly Asn Glu Gly Thr Asp Gly
145                 150                 155                 160

Ser Ser Ser Thr Val Gly Tyr Pro Gly Lys Tyr Pro Ser Val Ile Ala
                165                 170                 175

Val Gly Ala Val Asp Ser Ser Asn Gln Arg Ala Ser Phe Ser Ser Val
            180                 185                 190

Gly Pro Glu Leu Asp Val Met Ala Pro Gly Val Ser Ile Gln Ser Thr
        195                 200                 205

Leu Pro Gly Asn Lys Tyr Gly Ala Gln Asn Gly Thr Ser Met Ala Ser
    210                 215                 220

Pro His Val Ala Gly Ala Ala Ala Leu Ile Leu Ser Lys His Pro Ser
225                 230                 235                 240

Trp Thr Asn Thr Gln Val Arg Ser Ser Leu Glu Asn Thr Thr Thr Lys
                245                 250                 255

Leu Gly Asp Ser Phe Tyr Tyr Gly Lys Gly Leu Ile Asn Val Gln Ala
            260                 265                 270

Ala Ala Gln
        275

<210> SEQ ID NO 17
<211> LENGTH: 828
<212> TYPE: DNA
<213> ORGANISM: Artificial
<220> FEATURE:
<223> OTHER INFORMATION: synthesized GcM94 gene

<400> SEQUENCE: 17
gcgcagtccg tgccttacgg cgtatcacaa attaaagccc ctgctctgca ctctcaaggc      60
tacactggat caaatgttaa agtagcggtt atcgacagcg gtatcgactc gagccatcca     120
gatcttaaag tcgctggagg ggcttctatg gtgccgtccg aaacaaaccc gtttcaagat     180
aacaatacac atggcacaca cgtcgcagga acggttgcgg cgttaaacaa taatattggc     240
```

```
gtgcttggtg tagccccgtc tgcttcgctc tacgccgtta aagttcttgc agcagacgga      300
gcaggccaat actcatggat tatcaacggc atcgaatggg ccatcgcgaa taacatggat      360
gtaatcaaca tgagcgtcgg agcaccaagc ggcagtgcgg cacttaaagc agcagttgat      420
aaagctgttg catctggtgt cgtcgtagta gcggcagctg gaatgaggg aacatccgga       480 tcatcgagta ccgtcggtta tccaggcaag taccettcag tgattgcagt gggcgctgta      540
gactctacaa atcaacgtgc ctcttttcc tccgtgggac cggagctgga tgtcatggcc       600
cctggcgttt ctattcaatc gacgcttcca gggaacaagt atggtgcgca aaacgggact      660
tccatggcct cgccgcatgt agctggggcg ccgcattga ttctttctaa gcacccgaac       720
tggacaaaca accaagtccg cagcagttta gaaaacacca ctacaaaact tggtgattct      780
ttctactatg gaaaagggct gatcaacgta caggcggcag ctcagtaa                   828

<210> SEQ ID NO 18
<211> LENGTH: 275
<212> TYPE: PRT
<213> ORGANISM: Artificial
<220> FEATURE:
<223> OTHER INFORMATION: amino acid encoded by synthesized GcM94 gene

<400> SEQUENCE: 18

Ala Gln Ser Val Pro Tyr Gly Val Ser Gln Ile Lys Ala Pro Ala Leu
1               5                   10                  15

His Ser Gln Gly Tyr Thr Gly Ser Asn Val Lys Val Ala Val Ile Asp
            20                  25                  30

Ser Gly Ile Asp Ser Ser His Pro Asp Leu Lys Val Ala Gly Gly Ala
        35                  40                  45

Ser Met Val Pro Ser Glu Thr Asn Pro Phe Gln Asp Asn Asn Thr His
    50                  55                  60

Gly Thr His Val Ala Gly Thr Val Ala Ala Leu Asn Asn Asn Ile Gly
65                  70                  75                  80

Val Leu Gly Val Ala Pro Ser Ala Ser Leu Tyr Ala Val Lys Val Leu
                85                  90                  95

Ala Ala Asp Gly Ala Gly Gln Tyr Ser Trp Ile Ile Asn Gly Ile Glu
            100                 105                 110

Trp Ala Ile Ala Asn Asn Met Asp Val Ile Asn Met Ser Val Gly Ala
        115                 120                 125

Pro Ser Gly Ser Ala Ala Leu Lys Ala Ala Val Asp Lys Ala Val Ala
    130                 135                 140

Ser Gly Val Val Val Ala Ala Ala Gly Asn Glu Gly Thr Ser Gly
145                 150                 155                 160

Ser Ser Ser Thr Val Gly Tyr Pro Gly Lys Tyr Pro Ser Val Ile Ala
                165                 170                 175

Val Gly Ala Val Asp Ser Thr Asn Gln Arg Ala Ser Phe Ser Ser Val
            180                 185                 190

Gly Pro Glu Leu Asp Val Met Ala Pro Gly Val Ser Ile Gln Ser Thr
        195                 200                 205

Leu Pro Gly Asn Lys Tyr Gly Ala Gln Asn Gly Thr Ser Met Ala Ser
    210                 215                 220

Pro His Val Ala Gly Ala Ala Leu Ile Leu Ser Lys His Pro Asn
225                 230                 235                 240

Trp Thr Asn Asn Gln Val Arg Ser Ser Leu Glu Asn Thr Thr Thr Lys
                245                 250                 255

Leu Gly Asp Ser Phe Tyr Tyr Gly Lys Gly Leu Ile Asn Val Gln Ala
```

Ala Ala Gln
        275

<210> SEQ ID NO 19
<211> LENGTH: 828
<212> TYPE: DNA
<213> ORGANISM: Artificial
<220> FEATURE:
<223> OTHER INFORMATION: synthesized GcM95 gene

<400> SEQUENCE: 19

| | | | |
|---|---|---|---|
| gcgcagtccg tgccttacgg cgtatcacaa attaaagccc ctgctctgca ctctcaaggc | | | 60 |
| tacactggat caaatgttaa agtagcggtt atcgacagcg gtatcgactc gagccatctg | | | 120 |
| gatcttaaag tcgctggagg ggcttctatg gtgccgggag aaacaaaccc gtttgtcgat | | | 180 |
| gcacaaacac atggcacaca cgtcgcagga acggttgcgg cgttaaacaa taatattggc | | | 240 |
| gtgcttggtg tagccccgga agcttcgctc tacgccgtta agttcttgc agcagacaac | | | 300 |
| gcagcacaat actcatggat tgtcaacggc atcgaatggg ccatcgcgaa taacatggat | | | 360 |
| gtaatcaaca tgagcctggg agcaccaagc ggcagtgcgg cacttaaagc agcagttgat | | | 420 |
| aaagctgttg catctggtgt cgtcgtagta gcggcagctg gaatgaggg aacatccgga | | | 480 |
| tcatcgagta ccgtcggtta ccaggcaag taccttcag tgattgcagt gggcgctgta | | | 540 |
| gactcttcaa atcaacgtgc ctcttttcc tccgtgggac cggagctgga tgtcatggcc | | | 600 |
| cctggcgttt ctattcaatc gacgcttcca gggaacaagt atggtgcgca aaacgggact | | | 660 |
| tccatggcct cgccgcatgt agctggggcg ccgcattga ttctttctaa gcacccgaac | | | 720 |
| tggacaaaca ctcaagtccg cagcagttta gaaaacacca ctacaaaact tggtgattct | | | 780 |
| ttctactatg gaaagggct gatcaacgta caggcggcag ctcagtaa | | | 828 |

<210> SEQ ID NO 20
<211> LENGTH: 275
<212> TYPE: PRT
<213> ORGANISM: Artificial
<220> FEATURE:
<223> OTHER INFORMATION: amino acid encoded by synthesized GcM95 gene

<400> SEQUENCE: 20

Ala Gln Ser Val Pro Tyr Gly Val Ser Gln Ile Lys Ala Pro Ala Leu
1               5                   10                  15

His Ser Gln Gly Tyr Thr Gly Ser Asn Val Lys Val Ala Val Ile Asp
            20                  25                  30

Ser Gly Ile Asp Ser Ser His Leu Asp Leu Lys Val Ala Gly Gly Ala
        35                  40                  45

Ser Met Val Pro Gly Glu Thr Asn Pro Phe Val Asp Ala Gln Thr His
    50                  55                  60

Gly Thr His Val Ala Gly Thr Val Ala Ala Leu Asn Asn Asn Ile Gly
65                  70                  75                  80

Val Leu Gly Val Ala Pro Glu Ala Ser Leu Tyr Ala Val Lys Val Leu
                85                  90                  95

Ala Ala Asp Asn Ala Ala Gln Tyr Ser Trp Ile Val Asn Gly Ile Glu
            100                 105                 110

Trp Ala Ile Ala Asn Asn Met Asp Val Ile Asn Met Ser Leu Gly Ala
        115                 120                 125

Pro Ser Gly Ser Ala Ala Leu Lys Ala Ala Val Asp Lys Ala Val Ala
    130                 135                 140

Ser Gly Val Val Val Ala Ala Ala Gly Asn Glu Gly Thr Ser Gly
145                 150                 155                 160

Ser Ser Ser Thr Val Gly Tyr Pro Gly Lys Tyr Pro Ser Val Ile Ala
                165                 170                 175

Val Gly Ala Val Asp Ser Ser Asn Gln Arg Ala Ser Phe Ser Ser Val
            180                 185                 190

Gly Pro Glu Leu Asp Val Met Ala Pro Gly Val Ser Ile Gln Ser Thr
        195                 200                 205

Leu Pro Gly Asn Lys Tyr Gly Ala Gln Asn Gly Thr Ser Met Ala Ser
    210                 215                 220

Pro His Val Ala Gly Ala Ala Leu Ile Leu Ser Lys His Pro Asn
225                 230                 235                 240

Trp Thr Asn Thr Gln Val Arg Ser Ser Leu Glu Asn Thr Thr Lys
                245                 250                 255

Leu Gly Asp Ser Phe Tyr Tyr Gly Lys Gly Leu Ile Asn Val Gln Ala
            260                 265                 270

Ala Ala Gln
        275

<210> SEQ ID NO 21
<211> LENGTH: 828
<212> TYPE: DNA
<213> ORGANISM: Artificial
<220> FEATURE:
<223> OTHER INFORMATION: synthesized GcM96 gene

<400> SEQUENCE: 21
gcgcagtccg tgccttacgg cgtatcacaa attaaagccc ctgctctgca ctctcaaggc     60
tacactggat caaatgttaa agtagcggtt atcgacagcg gtatcgactc gagccatcca    120
gatcttaaag tcgctggagg ggcttctatg gtgccgtccg aaacaaaccc cgtttcaagat   180 aacaattctc atggcacaca cgtcgcagga acgttgcgg cgttaaacaa taatattggc    240
gtgcttggtg tagccccgtc tgcttcgctc tacgccgtta aagttcttgc agcagacgga    300
tcaggccaat actcatggat tatcaacggc atcgaatggg ccatcgcgaa taacatggat    360
gtaatcaaca tgagcctggg agcaacaagc ggcagtgcgg cacttaaagc agcagttgat    420
aaagctgttg catctggtca agtcgtagta gcggcagctg gaatgagggg aacagatgga    480
ccttcgagta ccgtcggtta tccaggcaag tacccttcag tgattgcagt gggcgctgta    540
gactctacaa atacacgtgc ctcttttttcc tccgtgggac cggagctgga tgtcatggcc    600
cctggcgttt ctattcaatc gacgcttcca gcaaacaagt atggtgcgca aaacgggact    660
tccatggccg caccgcatgt agctggggcg gccgcattga ttctttctaa gcacccgtca    720
tggacaaaca accaagtccg cagcagttta gaacaaacca ctacaaaact tggtgattct    780
ttctactatg gaaagggct gatcaacgta caggcggcag ctcagtaa               828

<210> SEQ ID NO 22
<211> LENGTH: 275
<212> TYPE: PRT
<213> ORGANISM: Artificial
<220> FEATURE:
<223> OTHER INFORMATION: amino acid encoded by synthesized GcM96 gene

<400> SEQUENCE: 22

Ala Gln Ser Val Pro Tyr Gly Val Ser Gln Ile Lys Ala Pro Ala Leu
1               5                   10                  15

His Ser Gln Gly Tyr Thr Gly Ser Asn Val Lys Val Ala Val Ile Asp
            20                  25                  30

Ser Gly Ile Asp Ser Ser His Pro Asp Leu Lys Val Ala Gly Gly Ala
         35                  40                  45

Ser Met Val Pro Ser Glu Thr Asn Pro Phe Gln Asp Asn Asn Ser His
 50                  55                  60

Gly Thr His Val Ala Gly Thr Val Ala Ala Leu Asn Asn Asn Ile Gly
 65                  70                  75                  80

Val Leu Gly Val Ala Pro Ser Ala Ser Leu Tyr Ala Val Lys Val Leu
                 85                  90                  95

Ala Ala Asp Gly Ser Gly Gln Tyr Ser Trp Ile Ile Asn Gly Ile Glu
                100                 105                 110

Trp Ala Ile Ala Asn Asn Met Asp Val Ile Asn Met Ser Leu Gly Ala
                115                 120                 125

Thr Ser Gly Ser Ala Ala Leu Lys Ala Ala Val Asp Lys Ala Val Ala
        130                 135                 140

Ser Gly Gln Val Val Ala Ala Ala Gly Asn Glu Gly Thr Asp Gly
145                 150                 155                 160

Pro Ser Ser Thr Val Gly Tyr Pro Gly Lys Tyr Pro Ser Val Ile Ala
                165                 170                 175

Val Gly Ala Val Asp Ser Thr Asn Thr Arg Ala Ser Phe Ser Ser Val
                180                 185                 190

Gly Pro Glu Leu Asp Val Met Ala Pro Gly Val Ser Ile Gln Ser Thr
                195                 200                 205

Leu Pro Ala Asn Lys Tyr Gly Ala Gln Asn Gly Thr Ser Met Ala Ala
        210                 215                 220

Pro His Val Ala Gly Ala Ala Ala Leu Ile Leu Ser Lys His Pro Ser
225                 230                 235                 240

Trp Thr Asn Asn Gln Val Arg Ser Ser Leu Glu Gln Thr Thr Thr Lys
                245                 250                 255

Leu Gly Asp Ser Phe Tyr Tyr Gly Lys Gly Leu Ile Asn Val Gln Ala
                260                 265                 270

Ala Ala Gln
    275

<210> SEQ ID NO 23
<211> LENGTH: 828
<212> TYPE: DNA
<213> ORGANISM: Artificial
<220> FEATURE:
<223> OTHER INFORMATION: synthesized GcM100 gene

<400> SEQUENCE: 23
gcgcagtccg tgccttacgg cgtatcacaa attaaagccc ctgctctgca ctctcaaggc      60
tacactggat caaatgttaa agtagcggtt atcgacagcg gtatcgactc gagccatcca     120
gatcttaaag tcgctggagg ggcttctatg gtgccgtccg aaacaaaccc gtttcaagat     180
aacaattctc atggcacaca cgcagcagga acggttgcgg cgttaaacaa taatattggc     240
gtgcttggtg tagccccgtc tgcttcgctc tacgccgtta agttcttgc agcagacgga      300 tcagcacaat actcatggat tatcaacggc atcgaatggg ccatcgcgaa taacatggat     360
gtaatcaaca tggcactggg agcaccaagc ggcagtgcgg cacttaaagc agcagttgat     420
aaagctgttg catctggtgt cgtcgtagta gcggcagctg gaatgagggg aacatccgga     480
tcatcgagta ccgtcggtta tccaggcaag taccctcag tgattgcagt gggcgctgta     540
gactcttcaa atcaacgtgc ctctttttcc tccgtgggac cggagctgga tgtcatggcc     600
cctggcgttt ctattcaatc gacgcttcca gcaaacaagt atggtgcgca aaacgggact     660

```
tccatggcct cgccgcatgt agctggggcg gccgcattga ttctttctaa gcacccgaac    720
tggacaaaca ctcaagtccg cagcagttta gaaaacacca ctacaaaact tggtgattct    780
ttctactatg gaaagggct gatcaacgta caggcggcag ctcagtaa                  828
```

<210> SEQ ID NO 24
<211> LENGTH: 275
<212> TYPE: PRT
<213> ORGANISM: Artificial
<220> FEATURE:
<223> OTHER INFORMATION: amino acid encoded by synthesized GcM100 gene

<400> SEQUENCE: 24

```
Ala Gln Ser Val Pro Tyr Gly Val Ser Gln Ile Lys Ala Pro Ala Leu
1               5                   10                  15

His Ser Gln Gly Tyr Thr Gly Ser Asn Val Lys Val Ala Val Ile Asp
                20                  25                  30

Ser Gly Ile Asp Ser Ser His Pro Asp Leu Lys Val Ala Gly Gly Ala
            35                  40                  45

Ser Met Val Pro Ser Glu Thr Asn Pro Phe Gln Asp Asn Asn Ser His
50                  55                  60

Gly Thr His Ala Ala Gly Thr Val Ala Ala Leu Asn Asn Ile Gly
65                  70                  75                  80

Val Leu Gly Val Ala Pro Ser Ala Ser Leu Tyr Ala Val Lys Val Leu
                85                  90                  95

Ala Ala Asp Gly Ser Ala Gln Tyr Ser Trp Ile Ile Asn Gly Ile Glu
            100                 105                 110

Trp Ala Ile Ala Asn Asn Met Asp Val Ile Asn Met Ala Leu Gly Ala
        115                 120                 125

Pro Ser Gly Ser Ala Ala Leu Lys Ala Ala Val Asp Lys Ala Val Ala
130                 135                 140

Ser Gly Val Val Val Ala Ala Ala Gly Asn Glu Gly Thr Ser Gly
145                 150                 155                 160

Ser Ser Ser Thr Val Gly Tyr Pro Gly Lys Tyr Pro Ser Val Ile Ala
                165                 170                 175

Val Gly Ala Val Asp Ser Ser Asn Gln Arg Ala Ser Phe Ser Ser Val
            180                 185                 190

Gly Pro Glu Leu Asp Val Met Ala Pro Gly Val Ser Ile Gln Ser Thr
        195                 200                 205

Leu Pro Ala Asn Lys Tyr Gly Ala Gln Asn Gly Thr Ser Met Ala Ser
    210                 215                 220

Pro His Val Ala Gly Ala Ala Ala Leu Ile Leu Ser Lys His Pro Asn
225                 230                 235                 240

Trp Thr Asn Thr Gln Val Arg Ser Ser Leu Glu Asn Thr Thr Thr Lys
                245                 250                 255

Leu Gly Asp Ser Phe Tyr Tyr Gly Lys Gly Leu Ile Asn Val Gln Ala
            260                 265                 270

Ala Ala Gln
        275
```

<210> SEQ ID NO 25
<211> LENGTH: 36
<212> TYPE: DNA
<213> ORGANISM: Artificial
<220> FEATURE:
<223> OTHER INFORMATION: synthesized primer

<400> SEQUENCE: 25

```
cttctatggt gccgtccgaa acaaacccgt ttcaag                                   36

<210> SEQ ID NO 26
<211> LENGTH: 34
<212> TYPE: DNA
<213> ORGANISM: Artificial
<220> FEATURE:
<223> OTHER INFORMATION: synthesized primer

<400> SEQUENCE: 26
tcatggcaca cacgtcgcag gaacggttgc ggcg                                     34

<210> SEQ ID NO 27
<211> LENGTH: 37
<212> TYPE: DNA
<213> ORGANISM: Artificial
<220> FEATURE:
<223> OTHER INFORMATION: synthesized primer

<400> SEQUENCE: 27
agcagacgga tcaggccaat actcatggat tatcaac                                  37

<210> SEQ ID NO 28
<211> LENGTH: 39
<212> TYPE: DNA
<213> ORGANISM: Artificial
<220> FEATURE:
<223> OTHER INFORMATION: synthesized primer

<400> SEQUENCE: 28
tgagcctggg agcaccaagc ggcagtgcgg cacttaaag                                39

<210> SEQ ID NO 29
<211> LENGTH: 38
<212> TYPE: DNA
<213> ORGANISM: Artificial
<220> FEATURE:
<223> OTHER INFORMATION: synthesized primer

<400> SEQUENCE: 29
tagactcttc aaatcaacgt gcctcttttt cctccgtg                                 38

<210> SEQ ID NO 30
<211> LENGTH: 34
<212> TYPE: DNA
<213> ORGANISM: Artificial
<220> FEATURE:
<223> OTHER INFORMATION: synthesized primer

<400> SEQUENCE: 30
gaaacaaacc cgtttcaaga taacaattct catg                                     34

<210> SEQ ID NO 31
<211> LENGTH: 37
<212> TYPE: DNA
<213> ORGANISM: Artificial
<220> FEATURE:
<223> OTHER INFORMATION: synthesized primer

<400> SEQUENCE: 31
atactcatgg attatcaacg gcatcgaatg ggccatc                                  37

<210> SEQ ID NO 32
<211> LENGTH: 36
<212> TYPE: DNA
<213> ORGANISM: Artificial
```

```
<220> FEATURE:
<223> OTHER INFORMATION: synthesized primer

<400> SEQUENCE: 32
tgttgcatct ggtgtcgtcg tagtagcggc agctgg                          36

<210> SEQ ID NO 33
<211> LENGTH: 37
<212> TYPE: DNA
<213> ORGANISM: Artificial
<220> FEATURE:
<223> OTHER INFORMATION: synthesized primer

<400> SEQUENCE: 33
atcgacgctt ccagggaaca agtatggtgc gcaaaac                         37

<210> SEQ ID NO 34
<211> LENGTH: 35
<212> TYPE: DNA
<213> ORGANISM: Artificial
<220> FEATURE:
<223> OTHER INFORMATION: synthesized primer

<400> SEQUENCE: 34
cagcagttta gaaaacacca ctacaaaact tggtg                           35

<210> SEQ ID NO 35
<211> LENGTH: 38
<212> TYPE: DNA
<213> ORGANISM: Artificial
<220> FEATURE:
<223> OTHER INFORMATION: synthesized primer

<400> SEQUENCE: 35
caaacccgtt tcaagataac aattctcatg gcacacac                        38

<210> SEQ ID NO 36
<211> LENGTH: 39
<212> TYPE: DNA
<213> ORGANISM: Artificial
<220> FEATURE:
<223> OTHER INFORMATION: synthesized primer

<400> SEQUENCE: 36
ttggtgtagc cccgtctgct tcgctctacg ccgttaaag                       39

<210> SEQ ID NO 37
<211> LENGTH: 36
<212> TYPE: DNA
<213> ORGANISM: Artificial
<220> FEATURE:
<223> OTHER INFORMATION: synthesized primer

<400> SEQUENCE: 37
tggatgtaat caacatgagc ctgggagcac caagcg                          36

<210> SEQ ID NO 38
<211> LENGTH: 39
<212> TYPE: DNA
<213> ORGANISM: Artificial
<220> FEATURE:
<223> OTHER INFORMATION: synthesized primer

<400> SEQUENCE: 38
agggaacatc cggatcatcg agtaccgtcg gttatccag                       39
```

```
<210> SEQ ID NO 39
<211> LENGTH: 36
<212> TYPE: DNA
<213> ORGANISM: Artificial
<220> FEATURE:
<223> OTHER INFORMATION: synthesized primer

<400> SEQUENCE: 39
gacttccatg gcctcgccgc atgtagctgg ggcggc                              36

<210> SEQ ID NO 40
<211> LENGTH: 36
<212> TYPE: DNA
<213> ORGANISM: Artificial
<220> FEATURE:
<223> OTHER INFORMATION: synthesized primer

<400> SEQUENCE: 40
gtttcaagat aacaattctc atggcacaca cgtcgc                              36

<210> SEQ ID NO 41
<211> LENGTH: 35
<212> TYPE: DNA
<213> ORGANISM: Artificial
<220> FEATURE:
<223> OTHER INFORMATION: synthesized primer

<400> SEQUENCE: 41
gttcttgcag cagacggatc aggccaatac tcatg                               35

<210> SEQ ID NO 42
<211> LENGTH: 37
<212> TYPE: DNA
<213> ORGANISM: Artificial
<220> FEATURE:
<223> OTHER INFORMATION: synthesized primer

<400> SEQUENCE: 42
atgtaatcaa catgagcctg ggagcaccaa gcggcag                             37

<210> SEQ ID NO 43
<211> LENGTH: 37
<212> TYPE: DNA
<213> ORGANISM: Artificial
<220> FEATURE:
<223> OTHER INFORMATION: synthesized primer

<400> SEQUENCE: 43
ggaatgaggg aacatccgga tcatcgagta ccgtcgg                             37

<210> SEQ ID NO 44
<211> LENGTH: 38
<212> TYPE: DNA
<213> ORGANISM: Artificial
<220> FEATURE:
<223> OTHER INFORMATION: synthesized primer

<400> SEQUENCE: 44
ctttctaagc acccgaactg gacaaacact caagtccg                            38

<210> SEQ ID NO 45
<211> LENGTH: 36
<212> TYPE: DNA
<213> ORGANISM: Artificial
<220> FEATURE:
<223> OTHER INFORMATION: synthesized primer

<400> SEQUENCE: 45
```

```
tcaagataac aattctcatg gcacacacgt cgcagg                                36
```

<210> SEQ ID NO 46
<211> LENGTH: 37
<212> TYPE: DNA
<213> ORGANISM: Artificial
<220> FEATURE:
<223> OTHER INFORMATION: synthesized primer

<400> SEQUENCE: 46

```
tgcagcagac ggatcaggcc aatactcatg gattatc                               37
```

<210> SEQ ID NO 47
<211> LENGTH: 35
<212> TYPE: DNA
<213> ORGANISM: Artificial
<220> FEATURE:
<223> OTHER INFORMATION: synthesized primer

<400> SEQUENCE: 47

```
aatcaacatg agcctgggag caccaagcgg cagtg                                 35
```

<210> SEQ ID NO 48
<211> LENGTH: 37
<212> TYPE: DNA
<213> ORGANISM: Artificial
<220> FEATURE:
<223> OTHER INFORMATION: synthesized primer

<400> SEQUENCE: 48

```
cgctgtagac tcttcaaatc aacgtgcctc tttttcc                               37
```

<210> SEQ ID NO 49
<211> LENGTH: 35
<212> TYPE: DNA
<213> ORGANISM: Artificial
<220> FEATURE:
<223> OTHER INFORMATION: synthesized primer

<400> SEQUENCE: 49

```
gaactggaca aacactcaag tccgcagcag tttag                                 35
```

<210> SEQ ID NO 50
<211> LENGTH: 34
<212> TYPE: DNA
<213> ORGANISM: Artificial
<220> FEATURE:
<223> OTHER INFORMATION: synthesized primer

<400> SEQUENCE: 50

```
tcatggcaca cacgtcgcag gaacggttgc ggcg                                  34
```

<210> SEQ ID NO 51
<211> LENGTH: 37
<212> TYPE: DNA
<213> ORGANISM: Artificial
<220> FEATURE:
<223> OTHER INFORMATION: synthesized primer

<400> SEQUENCE: 51

```
agcagacgga tcaggccaat actcatggat tatcaac                               37
```

<210> SEQ ID NO 52
<211> LENGTH: 37
<212> TYPE: DNA
<213> ORGANISM: Artificial

-continued

```
<220> FEATURE:
<223> OTHER INFORMATION: synthesized primer

<400> SEQUENCE: 52
atcgacgctt ccagggaaca agtatggtgc gcaaaac                              37

<210> SEQ ID NO 53
<211> LENGTH: 37
<212> TYPE: DNA
<213> ORGANISM: Artificial
<220> FEATURE:
<223> OTHER INFORMATION: synthesized primer

<400> SEQUENCE: 53
atgtaatcaa catgagcctg ggagcaccaa gcggcag                              37

<210> SEQ ID NO 54
<211> LENGTH: 22
<212> TYPE: DNA
<213> ORGANISM: Artificial
<220> FEATURE:
<223> OTHER INFORMATION: synthesized primer

<400> SEQUENCE: 54
tacatatgag ttatgcagtt tg                                              22

<210> SEQ ID NO 55
<211> LENGTH: 19
<212> TYPE: DNA
<213> ORGANISM: Artificial
<220> FEATURE:
<223> OTHER INFORMATION: synthesized primer

<400> SEQUENCE: 55
ttatccttta ccttgtctc                                                  19

<210> SEQ ID NO 56
<211> LENGTH: 35
<212> TYPE: DNA
<213> ORGANISM: Artificial
<220> FEATURE:
<223> OTHER INFORMATION: synthesized primer

<400> SEQUENCE: 56
caacatgagc ctgggatcac caagcggcag tgcgg                                35

<210> SEQ ID NO 57
<211> LENGTH: 35
<212> TYPE: DNA
<213> ORGANISM: Artificial
<220> FEATURE:
<223> OTHER INFORMATION: synthesized primer

<400> SEQUENCE: 57
ccgcactgcc gcttggtgat cccaggctca tgttg                                35

<210> SEQ ID NO 58
<211> LENGTH: 38
<212> TYPE: DNA
<213> ORGANISM: Artificial
<220> FEATURE:
<223> OTHER INFORMATION: synthesized primer

<400> SEQUENCE: 58
ctatggtgcc gggcgaaaca aacccgtttc aagatccg                             38
```

<210> SEQ ID NO 59
<211> LENGTH: 38
<212> TYPE: DNA
<213> ORGANISM: Artificial
<220> FEATURE:
<223> OTHER INFORMATION: synthesized primer

<400> SEQUENCE: 59
cggatcttga acgggtttg tttcgcccgg caccatag         38

<210> SEQ ID NO 60
<211> LENGTH: 21
<212> TYPE: DNA
<213> ORGANISM: Artificial
<220> FEATURE:
<223> OTHER INFORMATION: synthesized primer

<400> SEQUENCE: 60
gcctcacatt tgtgccacct a                          21

<210> SEQ ID NO 61
<211> LENGTH: 22
<212> TYPE: DNA
<213> ORGANISM: Artificial
<220> FEATURE:
<223> OTHER INFORMATION: synthesized primer

<400> SEQUENCE: 61
cctctcggtt atgagttagt tc                         22

<210> SEQ ID NO 62
<211> LENGTH: 24
<212> TYPE: DNA
<213> ORGANISM: Artificial
<220> FEATURE:
<223> OTHER INFORMATION: synthesized primer

<400> SEQUENCE: 62
aaaggatcct aatcggcgct tttc                       24

<210> SEQ ID NO 63
<211> LENGTH: 24
<212> TYPE: DNA
<213> ORGANISM: Artificial
<220> FEATURE:
<223> OTHER INFORMATION: synthesized primer

<400> SEQUENCE: 63
cttgtctcca agcttaaaat aaaa                       24

<210> SEQ ID NO 64
<211> LENGTH: 36
<212> TYPE: DNA
<213> ORGANISM: Artificial
<220> FEATURE:
<223> OTHER INFORMATION: synthesized primer

<400> SEQUENCE: 64
cagatcttaa agtctctgga ggggcttcta tggtgc          36

<210> SEQ ID NO 65
<211> LENGTH: 40
<212> TYPE: DNA
<213> ORGANISM: Artificial
<220> FEATURE:
<223> OTHER INFORMATION: synthesized primer

<400> SEQUENCE: 65
catagaagcc cctccagaga ctttaagatc tggatggctc                                    40

<210> SEQ ID NO 66
<211> LENGTH: 36
<212> TYPE: DNA
<213> ORGANISM: Artificial
<220> FEATURE:
<223> OTHER INFORMATION: synthesized primer

<400> SEQUENCE: 66
gcattgattc tttacaagca cccgaactgg acaaac                                        36

<210> SEQ ID NO 67
<211> LENGTH: 39
<212> TYPE: DNA
<213> ORGANISM: Artificial
<220> FEATURE:
<223> OTHER INFORMATION: synthesized primer

<400> SEQUENCE: 67
cagttcgggt gcttgtaaag aatcaatgcg ccgccccca                                     39

<210> SEQ ID NO 68
<211> LENGTH: 36
<212> TYPE: DNA
<213> ORGANISM: Artificial
<220> FEATURE:
<223> OTHER INFORMATION: synthesized primer

<400> SEQUENCE: 68
gcattgattc ttggtaagca cccgaactgg acaaac                                        36

<210> SEQ ID NO 69
<211> LENGTH: 40
<212> TYPE: DNA
<213> ORGANISM: Artificial
<220> FEATURE:
<223> OTHER INFORMATION: synthesized primer

<400> SEQUENCE: 69
ccagttcggg tgcttaccaa gaatcaatgc ggccgcccca                                    40

<210> SEQ ID NO 70
<211> LENGTH: 40
<212> TYPE: DNA
<213> ORGANISM: Artificial
<220> FEATURE:
<223> OTHER INFORMATION: synthesized primer

<400> SEQUENCE: 70
catcgaatgg gccacagcga ataacatgga tgtaatcaac                                    40

<210> SEQ ID NO 71
<211> LENGTH: 40
<212> TYPE: DNA
<213> ORGANISM: Artificial
<220> FEATURE:
<223> OTHER INFORMATION: synthesized primer

<400> SEQUENCE: 71
catccatgtt attcgctgtg gcccattcga tgccgttgat                                    40

<210> SEQ ID NO 72
<211> LENGTH: 40
<212> TYPE: DNA
<213> ORGANISM: Artificial

```
<220> FEATURE:
<223> OTHER INFORMATION: synthesized primer

<400> SEQUENCE: 72
catcgaatgg gccgtagcga ataacatgga tgtaatcaac                    40

<210> SEQ ID NO 73
<211> LENGTH: 40
<212> TYPE: DNA
<213> ORGANISM: Artificial
<220> FEATURE:
<223> OTHER INFORMATION: synthesized primer

<400> SEQUENCE: 73
catccatgtt attcgctacg gcccattcga tgccgttgat                    40

<210> SEQ ID NO 74
<211> LENGTH: 36
<212> TYPE: DNA
<213> ORGANISM: Artificial
<220> FEATURE:
<223> OTHER INFORMATION: synthesized primer

<400> SEQUENCE: 74
ctgtagactc tacaaatcaa cgtgcctctt tttcct                        36

<210> SEQ ID NO 75
<211> LENGTH: 40
<212> TYPE: DNA
<213> ORGANISM: Artificial
<220> FEATURE:
<223> OTHER INFORMATION: synthesized primer

<400> SEQUENCE: 75
aaagaggcac gttgatttgt agagtctaca gcgcccactg                    40

<210> SEQ ID NO 76
<211> LENGTH: 38
<212> TYPE: DNA
<213> ORGANISM: Artificial
<220> FEATURE:
<223> OTHER INFORMATION: synthesized primer

<400> SEQUENCE: 76
ctgtagactc ttcataccaa cgtgcctctt tttcctcc                      38

<210> SEQ ID NO 77
<211> LENGTH: 40
<212> TYPE: DNA
<213> ORGANISM: Artificial
<220> FEATURE:
<223> OTHER INFORMATION: synthesized primer

<400> SEQUENCE: 77 gaaaagagg cacgttggta tgaagagtct acagcgccca                     40

<210> SEQ ID NO 78
<211> LENGTH: 51
<212> TYPE: DNA
<213> ORGANISM: Artificial
<220> FEATURE:
<223> OTHER INFORMATION: synthesized primer

<400> SEQUENCE: 78
tagcggttac agacagcggt atcgacccaa gccatccaga tcttaaagtc g        51
```

```
<210> SEQ ID NO 79
<211> LENGTH: 50
<212> TYPE: DNA
<213> ORGANISM: Artificial
<220> FEATURE:
<223> OTHER INFORMATION: synthesized primer

<400> SEQUENCE: 79
atggcttggg tcgataccgc tgtctgtaac cgctacttta acattgcctc            50

<210> SEQ ID NO 80
<211> LENGTH: 49
<212> TYPE: DNA
<213> ORGANISM: Artificial
<220> FEATURE:
<223> OTHER INFORMATION: synthesized primer

<400> SEQUENCE: 80
taaagtagcg gttacagaca gcggtttaga ctcgagccat ccagatctt             49

<210> SEQ ID NO 81
<211> LENGTH: 50
<212> TYPE: DNA
<213> ORGANISM: Artificial
<220> FEATURE:
<223> OTHER INFORMATION: synthesized primer

<400> SEQUENCE: 81
atggctcgag tctaaaccgc tgtctgtaac cgctacttta acattgcctc            50

<210> SEQ ID NO 82
<211> LENGTH: 50
<212> TYPE: DNA
<213> ORGANISM: Artificial
<220> FEATURE:
<223> OTHER INFORMATION: synthesized primer

<400> SEQUENCE: 82
ggttgtagac agcggtatcg actcgtggca tccagatctt aaagtcgctg            50

<210> SEQ ID NO 83
<211> LENGTH: 50
<212> TYPE: DNA
<213> ORGANISM: Artificial
<220> FEATURE:
<223> OTHER INFORMATION: synthesized primer

<400> SEQUENCE: 83
atgccacgag tcgataccgc tgtctacaac cgctacttta acattgcctc            50

<210> SEQ ID NO 84
<211> LENGTH: 38
<212> TYPE: DNA
<213> ORGANISM: Artificial
<220> FEATURE:
<223> OTHER INFORMATION: synthesized primer

<400> SEQUENCE: 84
ctacactgga ggcaaagtta aagtagcggt tatcgaca                         38

<210> SEQ ID NO 85
<211> LENGTH: 40
<212> TYPE: DNA
<213> ORGANISM: Artificial
<220> FEATURE:
<223> OTHER INFORMATION: synthesized primer

<400> SEQUENCE: 85
```
ataaccgcta ctttaacttt gcctccagtg tagccttgag                              40

<210> SEQ ID NO 86
<211> LENGTH: 37
<212> TYPE: DNA
<213> ORGANISM: Artificial
<220> FEATURE:
<223> OTHER INFORMATION: synthesized primer

<400> SEQUENCE: 86
gagcctggga gcacgtagcg gcagtgcggc acttaaa                                 37

<210> SEQ ID NO 87
<211> LENGTH: 40
<212> TYPE: DNA
<213> ORGANISM: Artificial
<220> FEATURE:
<223> OTHER INFORMATION: synthesized primer

<400> SEQUENCE: 87
gtgccgcact gccgctacgt gctcccaggc tcatgttgat                              40

<210> SEQ ID NO 88
<211> LENGTH: 38
<212> TYPE: DNA
<213> ORGANISM: Artificial
<220> FEATURE:
<223> OTHER INFORMATION: synthesized primer

<400> SEQUENCE: 88
tgagcctggg agcaaagagc ggcagtgcgg cacttaaa                                38

<210> SEQ ID NO 89
<211> LENGTH: 40
<212> TYPE: DNA
<213> ORGANISM: Artificial
<220> FEATURE:
<223> OTHER INFORMATION: synthesized primer

<400> SEQUENCE: 89
gtgccgcact gccgctcttt gctcccaggc tcatgttgat                              40

<210> SEQ ID NO 90
<211> LENGTH: 40
<212> TYPE: DNA
<213> ORGANISM: Artificial
<220> FEATURE:
<223> OTHER INFORMATION: synthesized primer

<400> SEQUENCE: 90
atcacaaatt aaagccacag ctctgcactc tcaaggctac                              40

<210> SEQ ID NO 91
<211> LENGTH: 40
<212> TYPE: DNA
<213> ORGANISM: Artificial
<220> FEATURE:
<223> OTHER INFORMATION: synthesized primer

<400> SEQUENCE: 91
agagtgcaga gctgtggctt taatttgtga tacgccgtaa                              40

<210> SEQ ID NO 92
<211> LENGTH: 40
<212> TYPE: DNA
<213> ORGANISM: Artificial

```
<220> FEATURE:
<223> OTHER INFORMATION: synthesized primer

<400> SEQUENCE: 92
gacagcggta tcgacacaag ccatccagat cttaaagtcg                              40

<210> SEQ ID NO 93
<211> LENGTH: 40
<212> TYPE: DNA
<213> ORGANISM: Artificial
<220> FEATURE:
<223> OTHER INFORMATION: synthesized primer

<400> SEQUENCE: 93
taagatctgg atggcttgtg tcgataccgc tgtcgataac                              40

<210> SEQ ID NO 94
<211> LENGTH: 40
<212> TYPE: DNA
<213> ORGANISM: Artificial
<220> FEATURE:
<223> OTHER INFORMATION: synthesized primer

<400> SEQUENCE: 94
gacagcggta tcgacccaag ccatccagat cttaaagtcg                              40

<210> SEQ ID NO 95
<211> LENGTH: 40
<212> TYPE: DNA
<213> ORGANISM: Artificial
<220> FEATURE:
<223> OTHER INFORMATION: synthesized primer

<400> SEQUENCE: 95
taagatctgg atggcttggg tcgataccgc tgtcgataac                              40

<210> SEQ ID NO 96
<211> LENGTH: 40
<212> TYPE: DNA
<213> ORGANISM: Artificial
<220> FEATURE:
<223> OTHER INFORMATION: synthesized primer

<400> SEQUENCE: 96
gacagcggta tcgactggag ccatccagat cttaaagtcg                              40

<210> SEQ ID NO 97
<211> LENGTH: 40
<212> TYPE: DNA
<213> ORGANISM: Artificial
<220> FEATURE:
<223> OTHER INFORMATION: synthesized primer

<400> SEQUENCE: 97
taagatctgg atggctccag tcgataccgc tgtcgataac                              40

<210> SEQ ID NO 98
<211> LENGTH: 40
<212> TYPE: DNA
<213> ORGANISM: Artificial
<220> FEATURE:
<223> OTHER INFORMATION: synthesized primer

<400> SEQUENCE: 98
acgcgcagtc cgtgttatac ggcgtatcac aaattaaagc                              40
```

```
<210> SEQ ID NO 99
<211> LENGTH: 40
<212> TYPE: DNA
<213> ORGANISM: Artificial
<220> FEATURE:
<223> OTHER INFORMATION: synthesized primer

<400> SEQUENCE: 99
atttgtgata cgccgtataa cacggactgc gcgtacgcat                          40

<210> SEQ ID NO 100
<211> LENGTH: 37
<212> TYPE: DNA
<213> ORGANISM: Artificial
<220> FEATURE:
<223> OTHER INFORMATION: synthesized primer

<400> SEQUENCE: 100
acaagtatgg tgcgaaaaac gggacttcca tggcctc                             37

<210> SEQ ID NO 101
<211> LENGTH: 38
<212> TYPE: DNA
<213> ORGANISM: Artificial
<220> FEATURE:
<223> OTHER INFORMATION: synthesized primer

<400> SEQUENCE: 101
catggaagtc ccgttttttcg caccatactt gttccctg                           38

<210> SEQ ID NO 102
<211> LENGTH: 37
<212> TYPE: DNA
<213> ORGANISM: Artificial
<220> FEATURE:
<223> OTHER INFORMATION: synthesized primer

<400> SEQUENCE: 102
acaagtatgg tgcgggaaac gggacttcca tggcctc                             37

<210> SEQ ID NO 103
<211> LENGTH: 39
<212> TYPE: DNA
<213> ORGANISM: Artificial
<220> FEATURE:
<223> OTHER INFORMATION: synthesized primer

<400> SEQUENCE: 103
ccatggaagt cccgtttccc gcaccatact tgttccctg                           39

<210> SEQ ID NO 104
<211> LENGTH: 38
<212> TYPE: DNA
<213> ORGANISM: Artificial
<220> FEATURE:
<223> OTHER INFORMATION: synthesized primer

<400> SEQUENCE: 104
cttacggcgt atcattaatt aaagcccctg ctctgcac                            38

<210> SEQ ID NO 105
<211> LENGTH: 40
<212> TYPE: DNA
<213> ORGANISM: Artificial
<220> FEATURE:
<223> OTHER INFORMATION: synthesized primer

<400> SEQUENCE: 105
```

```
gagcaggggc tttaattaat gatacgccgt aaggcacgga                                40

<210> SEQ ID NO 106
<211> LENGTH: 38
<212> TYPE: DNA
<213> ORGANISM: Artificial
<220> FEATURE:
<223> OTHER INFORMATION: synthesized primer

<400> SEQUENCE: 106
cttacggcgt atcacgtatt aaagcccctg ctctgcac                                  38

<210> SEQ ID NO 107
<211> LENGTH: 40
<212> TYPE: DNA
<213> ORGANISM: Artificial
<220> FEATURE:
<223> OTHER INFORMATION: synthesized primer

<400> SEQUENCE: 107
gagcaggggc tttaatacgt gatacgccgt aaggcacgga                                40

<210> SEQ ID NO 108
<211> LENGTH: 40
<212> TYPE: DNA
<213> ORGANISM: Artificial
<220> FEATURE:
<223> OTHER INFORMATION: synthesized primer

<400> SEQUENCE: 108
tttagaaaac acctctacaa aacttggtga ttctttctac                                40

<210> SEQ ID NO 109
<211> LENGTH: 40
<212> TYPE: DNA
<213> ORGANISM: Artificial
<220> FEATURE:
<223> OTHER INFORMATION: synthesized primer

<400> SEQUENCE: 109
tcaccaagtt ttgtagaggt gttttctaaa ctgctgcgga                                40

<210> SEQ ID NO 110
<211> LENGTH: 40
<212> TYPE: DNA
<213> ORGANISM: Artificial
<220> FEATURE:
<223> OTHER INFORMATION: synthesized primer

<400> SEQUENCE: 110
aggctacact ggagcaaatg ttaaagtagc ggttatcgac                                40

<210> SEQ ID NO 111
<211> LENGTH: 38
<212> TYPE: DNA
<213> ORGANISM: Artificial
<220> FEATURE:
<223> OTHER INFORMATION: synthesized primer

<400> SEQUENCE: 111
gctactttaa catttgctcc agtgtagcct tgagagtg                                  38

<210> SEQ ID NO 112
<211> LENGTH: 39
<212> TYPE: DNA
<213> ORGANISM: Artificial
```

```
<220> FEATURE:
<223> OTHER INFORMATION: synthesized primer

<400> SEQUENCE: 112
gagggaacat ccggaccatc gagtaccgtc ggttatcca                                39

<210> SEQ ID NO 113
<211> LENGTH: 40
<212> TYPE: DNA
<213> ORGANISM: Artificial
<220> FEATURE:
<223> OTHER INFORMATION: synthesized primer

<400> SEQUENCE: 113
accgacggta ctcgatggtc cggatgttcc ctcattccca                               40

<210> SEQ ID NO 114
<211> LENGTH: 40
<212> TYPE: DNA
<213> ORGANISM: Artificial
<220> FEATURE:
<223> OTHER INFORMATION: synthesized primer

<400> SEQUENCE: 114
agggaacatc cggaccatta agtaccgtcg gttatccagg                               40

<210> SEQ ID NO 115
<211> LENGTH: 40
<212> TYPE: DNA
<213> ORGANISM: Artificial
<220> FEATURE:
<223> OTHER INFORMATION: synthesized primer

<400> SEQUENCE: 115
accgacggta cttaatggtc cggatgttcc ctcattccca                               40

<210> SEQ ID NO 116
<211> LENGTH: 39
<212> TYPE: DNA
<213> ORGANISM: Artificial
<220> FEATURE:
<223> OTHER INFORMATION: synthesized primer

<400> SEQUENCE: 116
gaacatccgg atcattaagt accgtcggtt atccaggca                                39

<210> SEQ ID NO 117
<211> LENGTH: 40
<212> TYPE: DNA
<213> ORGANISM: Artificial
<220> FEATURE:
<223> OTHER INFORMATION: synthesized primer

<400> SEQUENCE: 117
ataaccgacg gtacttaatg atccggatgt tccctcattc                               40

<210> SEQ ID NO 118
<211> LENGTH: 39
<212> TYPE: DNA
<213> ORGANISM: Artificial
<220> FEATURE:
<223> OTHER INFORMATION: synthesized primer

<400> SEQUENCE: 118
gaacatccgg atcaccaagt accgtcggtt atccaggca                                39
```

```
<210> SEQ ID NO 119
<211> LENGTH: 40
<212> TYPE: DNA
<213> ORGANISM: Artificial
<220> FEATURE:
<223> OTHER INFORMATION: synthesized primer

<400> SEQUENCE: 119
ataaccgacg gtacttggtg atccggatgt tccctcattc                                40

<210> SEQ ID NO 120
<211> LENGTH: 38
<212> TYPE: DNA
<213> ORGANISM: Artificial
<220> FEATURE:
<223> OTHER INFORMATION: synthesized primer

<400> SEQUENCE: 120
gtttagaaaa cgcaactaca aaacttggtg attctttc                                  38

<210> SEQ ID NO 121
<211> LENGTH: 40
<212> TYPE: DNA
<213> ORGANISM: Artificial
<220> FEATURE:
<223> OTHER INFORMATION: synthesized primer

<400> SEQUENCE: 121
caccaagttt tgtagttgcg ttttctaaac tgctgcggac                                40

<210> SEQ ID NO 122
<211> LENGTH: 40
<212> TYPE: DNA
<213> ORGANISM: Artificial
<220> FEATURE:
<223> OTHER INFORMATION: synthesized primer

<400> SEQUENCE: 122
caaaacttgg tgatccattc tactatggaa aagggctgat                                40

<210> SEQ ID NO 123
<211> LENGTH: 40
<212> TYPE: DNA
<213> ORGANISM: Artificial
<220> FEATURE:
<223> OTHER INFORMATION: synthesized primer

<400> SEQUENCE: 123
tttccatagt agaatggatc accaagtttt gtagtggtgt                                40

<210> SEQ ID NO 124
<211> LENGTH: 40
<212> TYPE: DNA
<213> ORGANISM: Artificial
<220> FEATURE:
<223> OTHER INFORMATION: synthesized primer

<400> SEQUENCE: 124
caaaacttgg tgataacttc tactatggaa aagggctgat                                40

<210> SEQ ID NO 125
<211> LENGTH: 40
<212> TYPE: DNA
<213> ORGANISM: Artificial
<220> FEATURE:
<223> OTHER INFORMATION: synthesized primer

<400> SEQUENCE: 125
```
tttccatagt agaagttatc accaagtttt gtagtggtgt            40

<210> SEQ ID NO 126
<211> LENGTH: 40
<212> TYPE: DNA
<213> ORGANISM: Artificial
<220> FEATURE:
<223> OTHER INFORMATION: synthesized primer

<400> SEQUENCE: 126
caaaacttgg tgatatcttc tactatggaa aagggctgat            40

<210> SEQ ID NO 127
<211> LENGTH: 40
<212> TYPE: DNA
<213> ORGANISM: Artificial
<220> FEATURE:
<223> OTHER INFORMATION: synthesized primer

<400> SEQUENCE: 127
tttccatagt agaagatatc accaagtttt gtagtggtgt            40

<210> SEQ ID NO 128
<211> LENGTH: 40
<212> TYPE: DNA
<213> ORGANISM: Artificial
<220> FEATURE:
<223> OTHER INFORMATION: synthesized primer

<400> SEQUENCE: 128
caaaacttgg tgatggattc tactatggaa aagggctgat            40

<210> SEQ ID NO 129
<211> LENGTH: 40
<212> TYPE: DNA
<213> ORGANISM: Artificial
<220> FEATURE:
<223> OTHER INFORMATION: synthesized primer

<400> SEQUENCE: 129
tttccatagt agaatccatc accaagtttt gtagtggtgt            40

<210> SEQ ID NO 130
<211> LENGTH: 37
<212> TYPE: DNA
<213> ORGANISM: Artificial
<220> FEATURE:
<223> OTHER INFORMATION: synthesized primer

<400> SEQUENCE: 130
gtgggcgctg tacactcttc aaatcaacgt gcctctt            37

<210> SEQ ID NO 131
<211> LENGTH: 40
<212> TYPE: DNA
<213> ORGANISM: Artificial
<220> FEATURE:
<223> OTHER INFORMATION: synthesized primer

<400> SEQUENCE: 131
cacgttgatt tgaagagtgt acagcgccca ctgcaatcac            40

<210> SEQ ID NO 132
<211> LENGTH: 37
<212> TYPE: DNA
<213> ORGANISM: Artificial

```
<220> FEATURE:
<223> OTHER INFORMATION: synthesized primer

<400> SEQUENCE: 132
gtgggcgctg taggatcttc aaatcaacgt gcctctt                                37

<210> SEQ ID NO 133
<211> LENGTH: 40
<212> TYPE: DNA
<213> ORGANISM: Artificial
<220> FEATURE:
<223> OTHER INFORMATION: synthesized primer

<400> SEQUENCE: 133
cacgttgatt tgaagatcct acagcgccca ctgcaatcac                             40

<210> SEQ ID NO 134
<211> LENGTH: 37
<212> TYPE: DNA
<213> ORGANISM: Artificial
<220> FEATURE:
<223> OTHER INFORMATION: synthesized primer

<400> SEQUENCE: 134
cctgctctgc acttccaagg ctacactgga ggcaatg                                37

<210> SEQ ID NO 135
<211> LENGTH: 40
<212> TYPE: DNA
<213> ORGANISM: Artificial
<220> FEATURE:
<223> OTHER INFORMATION: synthesized primer

<400> SEQUENCE: 135
ctccagtgta gccttggaag tgcagagcag gggctttaat                             40

<210> SEQ ID NO 136
<211> LENGTH: 37
<212> TYPE: DNA
<213> ORGANISM: Artificial
<220> FEATURE:
<223> OTHER INFORMATION: synthesized primer

<400> SEQUENCE: 136
cctgctctgc acacacaagg ctacactgga ggcaatg                                37

<210> SEQ ID NO 137
<211> LENGTH: 40
<212> TYPE: DNA
<213> ORGANISM: Artificial
<220> FEATURE:
<223> OTHER INFORMATION: synthesized primer

<400> SEQUENCE: 137
ctccagtgta gccttgtgtg tgcagagcag gggctttaat                             40

<210> SEQ ID NO 138
<211> LENGTH: 37
<212> TYPE: DNA
<213> ORGANISM: Artificial
<220> FEATURE:
<223> OTHER INFORMATION: synthesized primer

<400> SEQUENCE: 138
cctgctctgc acccacaagg ctacactgga ggcaatg                                37
```

```
<210> SEQ ID NO 139
<211> LENGTH: 40
<212> TYPE: DNA
<213> ORGANISM: Artificial
<220> FEATURE:
<223> OTHER INFORMATION: synthesized primer

<400> SEQUENCE: 139
ctccagtgta gccttgtggg tgcagagcag gggctttaat                    40

<210> SEQ ID NO 140
<211> LENGTH: 37
<212> TYPE: DNA
<213> ORGANISM: Artificial
<220> FEATURE:
<223> OTHER INFORMATION: synthesized primer

<400> SEQUENCE: 140
cctgctctgc actaccaagg ctacactgga ggcaatg                       37

<210> SEQ ID NO 141
<211> LENGTH: 40
<212> TYPE: DNA
<213> ORGANISM: Artificial
<220> FEATURE:
<223> OTHER INFORMATION: synthesized primer

<400> SEQUENCE: 141
ctccagtgta gccttggtag tgcagagcag gggctttaat                    40

<210> SEQ ID NO 142
<211> LENGTH: 37
<212> TYPE: DNA
<213> ORGANISM: Artificial
<220> FEATURE:
<223> OTHER INFORMATION: synthesized primer

<400> SEQUENCE: 142
cctgctctgc acttacaagg ctacactgga ggcaatg                       37

<210> SEQ ID NO 143
<211> LENGTH: 40
<212> TYPE: DNA
<213> ORGANISM: Artificial
<220> FEATURE:
<223> OTHER INFORMATION: synthesized primer

<400> SEQUENCE: 143
ctccagtgta gccttgtaag tgcagagcag gggctttaat                    40

<210> SEQ ID NO 144
<211> LENGTH: 38
<212> TYPE: DNA
<213> ORGANISM: Artificial
<220> FEATURE:
<223> OTHER INFORMATION: synthesized primer

<400> SEQUENCE: 144
tgctctgcac tctttaggct acactggagg caatgtta                      38

<210> SEQ ID NO 145
<211> LENGTH: 40
<212> TYPE: DNA
<213> ORGANISM: Artificial
<220> FEATURE:
<223> OTHER INFORMATION: synthesized primer

<400> SEQUENCE: 145
```

```
ttgcctccag tgtagcctaa agagtgcaga gcaggggctt                    40

<210> SEQ ID NO 146
<211> LENGTH: 39
<212> TYPE: DNA
<213> ORGANISM: Artificial
<220> FEATURE:
<223> OTHER INFORMATION: synthesized primer

<400> SEQUENCE: 146
atcgcgaata acatgaacgt aatcaacatg agcctggga                     39

<210> SEQ ID NO 147
<211> LENGTH: 39
<212> TYPE: DNA
<213> ORGANISM: Artificial
<220> FEATURE:
<223> OTHER INFORMATION: synthesized primer

<400> SEQUENCE: 147
ctcatgttga ttacgttcat gttattcgcg atggcccat                     39

<210> SEQ ID NO 148
<211> LENGTH: 37
<212> TYPE: DNA
<213> ORGANISM: Artificial
<220> FEATURE:
<223> OTHER INFORMATION: synthesized primer

<400> SEQUENCE: 148
cttccaggga accgttatgg tgcgcaaaac gggactt                       37

<210> SEQ ID NO 149
<211> LENGTH: 39
<212> TYPE: DNA
<213> ORGANISM: Artificial
<220> FEATURE:
<223> OTHER INFORMATION: synthesized primer

<400> SEQUENCE: 149
gttttgcgca ccataacggt tccctggaag cgtcgattg                     39

<210> SEQ ID NO 150
<211> LENGTH: 40
<212> TYPE: DNA
<213> ORGANISM: Artificial
<220> FEATURE:
<223> OTHER INFORMATION: synthesized primer

<400> SEQUENCE: 150
ctgcacttac aaggctctac tggaggcaat gttaaagtag                    40

<210> SEQ ID NO 151
<211> LENGTH: 49
<212> TYPE: DNA
<213> ORGANISM: Artificial
<220> FEATURE:
<223> OTHER INFORMATION: synthesized primer

<400> SEQUENCE: 151
taacattgcc tccagtagag ccttgtaagt gcagagcagg ggctttaat          49

<210> SEQ ID NO 152
<211> LENGTH: 43
<212> TYPE: DNA
<213> ORGANISM: Artificial
```

```
<220> FEATURE:
<223> OTHER INFORMATION: synthesized primer

<400> SEQUENCE: 152
gctctgcact tacaaggcaa cactggaggc aatgttaaag tag                          43

<210> SEQ ID NO 153
<211> LENGTH: 48
<212> TYPE: DNA
<213> ORGANISM: Artificial
<220> FEATURE:
<223> OTHER INFORMATION: synthesized primer

<400> SEQUENCE: 153
aacattgcct ccagtgttgc cttgtaagtg cagagcaggg gctttaat                     48

<210> SEQ ID NO 154
<211> LENGTH: 35
<212> TYPE: DNA
<213> ORGANISM: Artificial
<220> FEATURE:
<223> OTHER INFORMATION: synthesized primer

<400> SEQUENCE: 154
cttacggcgt aacacaaatt aaagcccctg ctctg                                   35

<210> SEQ ID NO 155
<211> LENGTH: 38
<212> TYPE: DNA
<213> ORGANISM: Artificial
<220> FEATURE:
<223> OTHER INFORMATION: synthesized primer

<400> SEQUENCE: 155
aggggcttta atttgtgtta cgccgtaagg cacggact                                38

<210> SEQ ID NO 156
<211> LENGTH: 40
<212> TYPE: DNA
<213> ORGANISM: Artificial
<220> FEATURE:
<223> OTHER INFORMATION: synthesized primer

<400> SEQUENCE: 156
ttaaagcagc agttgatttc gctgttgcat ctggtgtcgt                              40

<210> SEQ ID NO 157
<211> LENGTH: 40
<212> TYPE: DNA
<213> ORGANISM: Artificial
<220> FEATURE:
<223> OTHER INFORMATION: synthesized primer

<400> SEQUENCE: 157
agatgcaaca gcgaaatcaa ctgctgcttt aagtgccgca                              40

<210> SEQ ID NO 158
<211> LENGTH: 40
<212> TYPE: DNA
<213> ORGANISM: Artificial
<220> FEATURE:
<223> OTHER INFORMATION: synthesized primer

<400> SEQUENCE: 158
ttaaagcagc agttgatcgt gctgttgcat ctggtgtcgt                              40
```

```
<210> SEQ ID NO 159
<211> LENGTH: 40
<212> TYPE: DNA
<213> ORGANISM: Artificial
<220> FEATURE:
<223> OTHER INFORMATION: synthesized primer

<400> SEQUENCE: 159
agatgcaaca gcacgatcaa ctgctgcttt aagtgccgca                              40

<210> SEQ ID NO 160
<211> LENGTH: 40
<212> TYPE: DNA
<213> ORGANISM: Artificial
<220> FEATURE:
<223> OTHER INFORMATION: synthesized primer

<400> SEQUENCE: 160
aaacccgttt caagattcta attctcatgg cacacacgtc                              40

<210> SEQ ID NO 161
<211> LENGTH: 40
<212> TYPE: DNA
<213> ORGANISM: Artificial
<220> FEATURE:
<223> OTHER INFORMATION: synthesized primer

<400> SEQUENCE: 161
tgtgccatga gaattagaat cttgaaacgg gtttgtttcg                              40

<210> SEQ ID NO 162
<211> LENGTH: 40
<212> TYPE: DNA
<213> ORGANISM: Artificial
<220> FEATURE:
<223> OTHER INFORMATION: synthesized primer

<400> SEQUENCE: 162
aaacccgttt caagatgata attctcatgg cacacacgtc                              40

<210> SEQ ID NO 163
<211> LENGTH: 40
<212> TYPE: DNA
<213> ORGANISM: Artificial
<220> FEATURE:
<223> OTHER INFORMATION: synthesized primer

<400> SEQUENCE: 163
tgtgccatga gaattatcat cttgaaacgg gtttgtttcg                              40

<210> SEQ ID NO 164
<211> LENGTH: 39
<212> TYPE: DNA
<213> ORGANISM: Artificial
<220> FEATURE:
<223> OTHER INFORMATION: synthesized primer

<400> SEQUENCE: 164
aagcggcagt gcgacactta aagcagcagt tgataaagc                               39

<210> SEQ ID NO 165
<211> LENGTH: 40
<212> TYPE: DNA
<213> ORGANISM: Artificial
<220> FEATURE:
<223> OTHER INFORMATION: synthesized primer

<400> SEQUENCE: 165
```

```
tcaactgctg ctttaagtgt cgcactgccg cttggtgctc                              40
```

<210> SEQ ID NO 166
<211> LENGTH: 37
<212> TYPE: DNA
<213> ORGANISM: Artificial
<220> FEATURE:
<223> OTHER INFORMATION: synthesized primer

<400> SEQUENCE: 166

```
caagcggcag tgttgcactt aaagcagcag ttgataa                                 37
```

<210> SEQ ID NO 167
<211> LENGTH: 40
<212> TYPE: DNA
<213> ORGANISM: Artificial
<220> FEATURE:
<223> OTHER INFORMATION: synthesized primer

<400> SEQUENCE: 167

```
actgctgctt taagtgcaac actgccgctt ggtgctccca                              40
```

<210> SEQ ID NO 168
<211> LENGTH: 382
<212> TYPE: PRT
<213> ORGANISM: Bacillus amyloliquefaciens

<400> SEQUENCE: 168

Val Arg Ser Lys Lys Leu Trp Ile Ser Leu Leu Phe Ala Leu Ala Leu
1               5                   10                  15

Ile Phe Thr Met Ala Phe Gly Ser Thr Ser Ser Ala Gln Ala Ala Gly
            20                  25                  30

Lys Ser Asn Gly Glu Lys Lys Tyr Ile Val Gly Phe Lys Gln Thr Met
        35                  40                  45

Ser Thr Met Ser Ala Ala Lys Lys Lys Asp Val Ile Ser Glu Lys Gly
    50                  55                  60

Gly Lys Val Gln Lys Gln Phe Lys Tyr Val Asp Ala Ala Ser Ala Thr
65                  70                  75                  80

Leu Asn Glu Lys Ala Val Lys Glu Leu Lys Lys Asp Pro Ser Val Ala
                85                  90                  95

Tyr Val Glu Glu Asp His Val Ala His Ala Tyr Ala Gln Ser Val Pro
            100                 105                 110

Tyr Gly Val Ser Gln Ile Lys Ala Pro Ala Leu His Ser Gln Gly Tyr
        115                 120                 125

Thr Gly Ser Asn Val Lys Val Ala Val Ile Asp Ser Gly Ile Asp Ser
    130                 135                 140

Ser His Pro Asp Leu Lys Val Ala Gly Gly Ala Ser Met Val Pro Ser
145                 150                 155                 160

Glu Thr Asn Pro Phe Gln Asp Asn Asn Ser His Gly Thr His Val Ala
                165                 170                 175

Gly Thr Val Ala Ala Leu Asn Asn Ser Ile Gly Val Leu Gly Val Ala
            180                 185                 190

Pro Ser Ala Ser Leu Tyr Ala Val Lys Val Leu Gly Ala Asp Gly Ser
        195                 200                 205

Gly Gln Tyr Ser Trp Ile Ile Asn Gly Ile Glu Trp Ala Ile Ala Asn
    210                 215                 220

Asn Met Asp Val Ile Asn Met Ser Leu Gly Gly Pro Ser Gly Ser Ala
225                 230                 235                 240

-continued

```
Ala Leu Lys Ala Ala Val Asp Lys Ala Val Ala Ser Gly Val Val
            245                 250                 255
Val Ala Ala Ala Gly Asn Glu Gly Thr Ser Gly Ser Ser Thr Val
        260                 265                 270
Gly Tyr Pro Gly Lys Tyr Pro Ser Val Ile Ala Val Gly Ala Val Asp
    275                 280                 285
Ser Ser Asn Gln Arg Ala Ser Phe Ser Ser Val Gly Pro Glu Leu Asp
    290                 295                 300
Val Met Ala Pro Gly Val Ser Ile Gln Ser Thr Leu Pro Gly Asn Lys
305                 310                 315                 320
Tyr Gly Ala Tyr Asn Gly Thr Ser Met Ala Ser Pro His Val Ala Gly
            325                 330                 335
Ala Ala Ala Leu Ile Leu Ser Lys His Pro Asn Trp Thr Asn Thr Gln
        340                 345                 350
Val Arg Ser Ser Leu Glu Asn Thr Thr Thr Lys Leu Gly Asp Ser Phe
    355                 360                 365
Tyr Tyr Gly Lys Gly Leu Ile Asn Val Gln Ala Ala Gln
    370                 375                 380

<210> SEQ ID NO 169
<211> LENGTH: 36
<212> TYPE: DNA
<213> ORGANISM: Artificial
<220> FEATURE:
<223> OTHER INFORMATION: synthesized primer

<400> SEQUENCE: 169
cggcgttaaa caataacatt ggcgtgcttg gtgtag                            36

<210> SEQ ID NO 170
<211> LENGTH: 37
<212> TYPE: DNA
<213> ORGANISM: Artificial
<220> FEATURE:
<223> OTHER INFORMATION: synthesized primer

<400> SEQUENCE: 170
accaagcacg ccaatgttat tgtttaacgc cgcaacc                           37

<210> SEQ ID NO 171
<211> LENGTH: 39
<212> TYPE: DNA
<213> ORGANISM: Artificial
<220> FEATURE:
<223> OTHER INFORMATION: synthesized primer

<400> SEQUENCE: 171
gtatcgactc gagccatgaa gatcttaaag tcgctggag                         39

<210> SEQ ID NO 172
<211> LENGTH: 38
<212> TYPE: DNA
<213> ORGANISM: Artificial
<220> FEATURE:
<223> OTHER INFORMATION: synthesized primer

<400> SEQUENCE: 172
cagcgacttt aagatcttca tggctcgagt cgataccg                          38

<210> SEQ ID NO 173
<211> LENGTH: 39
<212> TYPE: DNA
<213> ORGANISM: Artificial
```

-continued

<220> FEATURE:
<223> OTHER INFORMATION: synthesized primer

<400> SEQUENCE: 173
ttggtgtagc cccggatgct tcgctctacg ccgttaaag    39

<210> SEQ ID NO 174
<211> LENGTH: 35
<212> TYPE: DNA
<213> ORGANISM: Artificial
<220> FEATURE:
<223> OTHER INFORMATION: synthesized primer

<400> SEQUENCE: 174
cgtagagcga agcatccggg gctacaccaa gcacg    35

<210> SEQ ID NO 175
<211> LENGTH: 39
<212> TYPE: DNA
<213> ORGANISM: Artificial
<220> FEATURE:
<223> OTHER INFORMATION: synthesized primer

<400> SEQUENCE: 175
gaacggttgc ggcgttagat aattctattg gcgtgcttg    39

<210> SEQ ID NO 176
<211> LENGTH: 37
<212> TYPE: DNA
<213> ORGANISM: Artificial
<220> FEATURE:
<223> OTHER INFORMATION: synthesized primer

<400> SEQUENCE: 176
agcacgccaa tagaattatc taacgccgca accgttc    37

<210> SEQ ID NO 177
<211> LENGTH: 44
<212> TYPE: DNA
<213> ORGANISM: Artificial
<220> FEATURE:
<223> OTHER INFORMATION: synthesized primer

<400> SEQUENCE: 177
aacggttgcg gcgttagata taacattgg cgtgcttggt gtag    44

<210> SEQ ID NO 178
<211> LENGTH: 46
<212> TYPE: DNA
<213> ORGANISM: Artificial
<220> FEATURE:
<223> OTHER INFORMATION: synthesized primer

<400> SEQUENCE: 178
acaccaagca cgccaatgtt attatctaac gccgcaaccg ttcctg    46

<210> SEQ ID NO 179
<211> LENGTH: 31
<212> TYPE: DNA
<213> ORGANISM: Artificial
<220> FEATURE:
<223> OTHER INFORMATION: synthesized primer

<400> SEQUENCE: 179
cggcgttaaa caataatatt ggcgtgcttg g    31

```
<210> SEQ ID NO 180
<211> LENGTH: 31
<212> TYPE: DNA
<213> ORGANISM: Artificial
<220> FEATURE:
<223> OTHER INFORMATION: synthesized primer

<400> SEQUENCE: 180
ccaagcacgc caatattatt gtttaacgcc g                           31

<210> SEQ ID NO 181
<211> LENGTH: 28
<212> TYPE: DNA
<213> ORGANISM: Artificial
<220> FEATURE:
<223> OTHER INFORMATION: synthesized primer

<400> SEQUENCE: 181
ggtgtagccc cggatgcttc gctctacg                              28

<210> SEQ ID NO 182
<211> LENGTH: 28
<212> TYPE: DNA
<213> ORGANISM: Artificial
<220> FEATURE:
<223> OTHER INFORMATION: synthesized primer

<400> SEQUENCE: 182
cgtagagcga agcatccggg gctacacc                              28

<210> SEQ ID NO 183
<211> LENGTH: 30
<212> TYPE: DNA
<213> ORGANISM: Artificial
<220> FEATURE:
<223> OTHER INFORMATION: synthesized primer

<400> SEQUENCE: 183
gtatcgactc gagccatgaa gatcttaaag                            30

<210> SEQ ID NO 184
<211> LENGTH: 30
<212> TYPE: DNA
<213> ORGANISM: Artificial
<220> FEATURE:
<223> OTHER INFORMATION: synthesized primer

<400> SEQUENCE: 184
ctttaagatc ttcatggctc gagtcgatac                            30

<210> SEQ ID NO 185
<211> LENGTH: 28
<212> TYPE: DNA
<213> ORGANISM: Artificial
<220> FEATURE:
<223> OTHER INFORMATION: synthesized primer

<400> SEQUENCE: 185
cgcttccagg gaacaactat ggtgcgta                              28

<210> SEQ ID NO 186
<211> LENGTH: 28
<212> TYPE: DNA
<213> ORGANISM: Artificial
<220> FEATURE:
<223> OTHER INFORMATION: synthesized primer

<400> SEQUENCE: 186
```
tacgcaccat agttgttccc tggaagcg                                              28

<210> SEQ ID NO 187
<211> LENGTH: 31
<212> TYPE: DNA
<213> ORGANISM: Artificial
<220> FEATURE:
<223> OTHER INFORMATION: synthesized primer

<400> SEQUENCE: 187
cactctcaag gctacgttgg atcaaatgtt a                                          31

<210> SEQ ID NO 188
<211> LENGTH: 31
<212> TYPE: DNA
<213> ORGANISM: Artificial
<220> FEATURE:
<223> OTHER INFORMATION: synthesized primer

<400> SEQUENCE: 188
taacatttga tccaacgtag ccttgagagt g                                          31

<210> SEQ ID NO 189
<211> LENGTH: 29
<212> TYPE: DNA
<213> ORGANISM: Artificial
<220> FEATURE:
<223> OTHER INFORMATION: synthesized primer

<400> SEQUENCE: 189
tggcgtttct attgaatcga cgcttccag                                             29

<210> SEQ ID NO 190
<211> LENGTH: 29
<212> TYPE: DNA
<213> ORGANISM: Artificial
<220> FEATURE:
<223> OTHER INFORMATION: synthesized primer

<400> SEQUENCE: 190
ctggaagcgt cgattcaata gaaacgcca                                             29

<210> SEQ ID NO 191
<211> LENGTH: 39
<212> TYPE: DNA
<213> ORGANISM: Artificial
<220> FEATURE:
<223> OTHER INFORMATION: synthesized primer

<400> SEQUENCE: 191
gaacggttgc ggcgttagat aattctattg gcgtgcttg                                  39

<210> SEQ ID NO 192
<211> LENGTH: 37
<212> TYPE: DNA
<213> ORGANISM: Artificial
<220> FEATURE:
<223> OTHER INFORMATION: synthesized primer

<400> SEQUENCE: 192
agcacgccaa tagaattatc taacgccgca accgttc                                    37

<210> SEQ ID NO 193
<211> LENGTH: 39
<212> TYPE: DNA
<213> ORGANISM: Artificial

```
<220> FEATURE:
<223> OTHER INFORMATION: synthesized primer

<400> SEQUENCE: 193
ttggtgtagc cccggatgct tcgctctacg ccgttaaag                    39

<210> SEQ ID NO 194
<211> LENGTH: 35
<212> TYPE: DNA
<213> ORGANISM: Artificial
<220> FEATURE:
<223> OTHER INFORMATION: synthesized primer

<400> SEQUENCE: 194
cgtagagcga agcatccggg gctacaccaa gcacg                        35

<210> SEQ ID NO 195
<211> LENGTH: 35
<212> TYPE: DNA
<213> ORGANISM: Artificial
<220> FEATURE:
<223> OTHER INFORMATION: synthesized primer

<400> SEQUENCE: 195
gcagcagacg gatcagcaca atactcatgg attat                        35

<210> SEQ ID NO 196
<211> LENGTH: 35
<212> TYPE: DNA
<213> ORGANISM: Artificial
<220> FEATURE:
<223> OTHER INFORMATION: synthesized primer

<400> SEQUENCE: 196
ataatccatg agtattgtgc tgatccgtct gctgc                        35

<210> SEQ ID NO 197
<211> LENGTH: 45
<212> TYPE: DNA
<213> ORGANISM: Artificial
<220> FEATURE:
<223> OTHER INFORMATION: synthesized primer

<400> SEQUENCE: 197
caacatgagc ctgggagcac caccgggcag tgcggcactt aaagc             45

<210> SEQ ID NO 198
<211> LENGTH: 45
<212> TYPE: DNA
<213> ORGANISM: Artificial
<220> FEATURE:
<223> OTHER INFORMATION: synthesized primer

<400> SEQUENCE: 198
gctttaagtg ccgcactgcc cggtggtgct cccaggctca tgttg             45

<210> SEQ ID NO 199
<211> LENGTH: 39
<212> TYPE: DNA
<213> ORGANISM: Artificial
<220> FEATURE:
<223> OTHER INFORMATION: synthesized primer

<400> SEQUENCE: 199
gttcttgcag cagacggaaa tggccaatac tcatggatt                    39
```

```
<210> SEQ ID NO 200
<211> LENGTH: 39
<212> TYPE: DNA
<213> ORGANISM: Artificial
<220> FEATURE:
<223> OTHER INFORMATION: synthesized primer

<400> SEQUENCE: 200
aatccatgag tattggccat ttccgtctgc tgcaagaac                              39

<210> SEQ ID NO 201
<211> LENGTH: 42
<212> TYPE: DNA
<213> ORGANISM: Artificial
<220> FEATURE:
<223> OTHER INFORMATION: synthesized primer

<400> SEQUENCE: 201
ttaaagttct tgcagcagac aattcaggcc aatactcatg ga                          42

<210> SEQ ID NO 202
<211> LENGTH: 42
<212> TYPE: DNA
<213> ORGANISM: Artificial
<220> FEATURE:
<223> OTHER INFORMATION: synthesized primer

<400> SEQUENCE: 202
tccatgagta ttggcctgaa ttgtctgctg caagaacttt aa                          42

<210> SEQ ID NO 203
<211> LENGTH: 36
<212> TYPE: DNA
<213> ORGANISM: Artificial
<220> FEATURE:
<223> OTHER INFORMATION: synthesized primer

<400> SEQUENCE: 203
ccgtttcaag atccgaattc tcatggcaca cacgtc                                 36

<210> SEQ ID NO 204
<211> LENGTH: 38
<212> TYPE: DNA
<213> ORGANISM: Artificial
<220> FEATURE:
<223> OTHER INFORMATION: synthesized primer

<400> SEQUENCE: 204
tgccatgaga attcggatct tgaaacgggt tgtttcg                                38

<210> SEQ ID NO 205
<211> LENGTH: 40
<212> TYPE: DNA
<213> ORGANISM: Artificial
<220> FEATURE:
<223> OTHER INFORMATION: synthesized primer

<400> SEQUENCE: 205
ttcaaatcaa cgtgattctt tttcctccgt gggaccggag                             40

<210> SEQ ID NO 206
<211> LENGTH: 40
<212> TYPE: DNA
<213> ORGANISM: Artificial
<220> FEATURE:
<223> OTHER INFORMATION: synthesized primer

<400> SEQUENCE: 206
```
acggaggaaa aagaatcacg ttgatttgaa gagtctacag                                40

<210> SEQ ID NO 207
<211> LENGTH: 38
<212> TYPE: DNA
<213> ORGANISM: Artificial
<220> FEATURE:
<223> OTHER INFORMATION: synthesized primer

<400> SEQUENCE: 207
caaatcaacg tgcctctgat tcctccgtgg gaccggag                                  38

<210> SEQ ID NO 208
<211> LENGTH: 38
<212> TYPE: DNA
<213> ORGANISM: Artificial
<220> FEATURE:
<223> OTHER INFORMATION: synthesized primer

<400> SEQUENCE: 208
ctccggtccc acggaggaat cagaggcacg ttgatttg                                  38

<210> SEQ ID NO 209
<211> LENGTH: 44
<212> TYPE: DNA
<213> ORGANISM: Artificial
<220> FEATURE:
<223> OTHER INFORMATION: synthesized primer

<400> SEQUENCE: 209
agcggcagtg cggcacttaa agttgcagtt gataaagctg ttgc                           44

<210> SEQ ID NO 210
<211> LENGTH: 44
<212> TYPE: DNA
<213> ORGANISM: Artificial
<220> FEATURE:
<223> OTHER INFORMATION: synthesized primer

<400> SEQUENCE: 210
gcaacagctt tatcaactgc aactttaagt gccgcactgc cgct                           44

<210> SEQ ID NO 211
<211> LENGTH: 39
<212> TYPE: DNA
<213> ORGANISM: Artificial
<220> FEATURE:
<223> OTHER INFORMATION: synthesized primer

<400> SEQUENCE: 211
tcaagataac aatacacatg gcacacacgt cgcaggaac                                 39

<210> SEQ ID NO 212
<211> LENGTH: 40
<212> TYPE: DNA
<213> ORGANISM: Artificial
<220> FEATURE:
<223> OTHER INFORMATION: synthesized primer

<400> SEQUENCE: 212
acgtgtgtgc catgtgtatt gttatcttga aacgggtttg                                40

<210> SEQ ID NO 213
<211> LENGTH: 40
<212> TYPE: DNA
<213> ORGANISM: Artificial

```
<220> FEATURE:
<223> OTHER INFORMATION: synthesized primer

<400> SEQUENCE: 213
agacggatca ggcaattact catggattat caacggcatc                                40

<210> SEQ ID NO 214
<211> LENGTH: 37
<212> TYPE: DNA
<213> ORGANISM: Artificial
<220> FEATURE:
<223> OTHER INFORMATION: synthesized primer

<400> SEQUENCE: 214
taatccatga gtaattgcct gatccgtctg ctgcaag                                   37

<210> SEQ ID NO 215
<211> LENGTH: 38
<212> TYPE: DNA
<213> ORGANISM: Artificial
<220> FEATURE:
<223> OTHER INFORMATION: synthesized primer

<400> SEQUENCE: 215
acccgtttca agataacgat tctcatggca cacacgtc                                  38

<210> SEQ ID NO 216
<211> LENGTH: 38
<212> TYPE: DNA
<213> ORGANISM: Artificial
<220> FEATURE:
<223> OTHER INFORMATION: synthesized primer

<400> SEQUENCE: 216
gacgtgtgtg ccatgagaat cgttatcttg aaacgggt                                  38

<210> SEQ ID NO 217
<211> LENGTH: 37
<212> TYPE: DNA
<213> ORGANISM: Artificial
<220> FEATURE:
<223> OTHER INFORMATION: synthesized primer

<400> SEQUENCE: 217
caatactcat ggattatcga tggcatcgaa tgggcca                                   37

<210> SEQ ID NO 218
<211> LENGTH: 37
<212> TYPE: DNA
<213> ORGANISM: Artificial
<220> FEATURE:
<223> OTHER INFORMATION: synthesized primer

<400> SEQUENCE: 218
tggcccattc gatgccatcg ataatccatg agtattg                                   37

<210> SEQ ID NO 219
<211> LENGTH: 39
<212> TYPE: DNA
<213> ORGANISM: Artificial
<220> FEATURE:
<223> OTHER INFORMATION: synthesized primer

<400> SEQUENCE: 219
ctcttcaaat caacgtgccg attttttcctc cgtgggacc                                39
```

```
<210> SEQ ID NO 220
<211> LENGTH: 39
<212> TYPE: DNA
<213> ORGANISM: Artificial
<220> FEATURE:
<223> OTHER INFORMATION: synthesized primer

<400> SEQUENCE: 220
ggtcccacgg aggaaaaatc ggcacgttga tttgaagag                              39

<210> SEQ ID NO 221
<211> LENGTH: 37
<212> TYPE: DNA
<213> ORGANISM: Artificial
<220> FEATURE:
<223> OTHER INFORMATION: synthesized primer

<400> SEQUENCE: 221
caaacactca agtccgcaga agtttagaaa acaccac                                37

<210> SEQ ID NO 222
<211> LENGTH: 38
<212> TYPE: DNA
<213> ORGANISM: Artificial
<220> FEATURE:
<223> OTHER INFORMATION: synthesized primer

<400> SEQUENCE: 222
gtgcttggtg tagccccgag agcttcgctc tacgccgt                               38

<210> SEQ ID NO 223
<211> LENGTH: 38
<212> TYPE: DNA
<213> ORGANISM: Artificial
<220> FEATURE:
<223> OTHER INFORMATION: synthesized primer

<400> SEQUENCE: 223
acggcgtaga gcgaagctct cggggctaca ccaagcac                               38

<210> SEQ ID NO 224
<211> LENGTH: 37
<212> TYPE: DNA
<213> ORGANISM: Artificial
<220> FEATURE:
<223> OTHER INFORMATION: synthesized primer

<400> SEQUENCE: 224
caaacactca agtccgcgat agtttagaaa acaccac                                37

<210> SEQ ID NO 225
<211> LENGTH: 37
<212> TYPE: DNA
<213> ORGANISM: Artificial
<220> FEATURE:
<223> OTHER INFORMATION: synthesized primer

<400> SEQUENCE: 225
gtggtgtttt ctaaactatc gcggacttga gtgtttg                                37

<210> SEQ ID NO 226
<211> LENGTH: 38
<212> TYPE: DNA
<213> ORGANISM: Artificial
<220> FEATURE:
<223> OTHER INFORMATION: synthesized primer

<400> SEQUENCE: 226
```
gtgcttggtg tagccccgtc tgcttcgctc tacgccgt 38

<210> SEQ ID NO 227
<211> LENGTH: 38
<212> TYPE: DNA
<213> ORGANISM: Artificial
<220> FEATURE:
<223> OTHER INFORMATION: synthesized primer

<400> SEQUENCE: 227
acggcgtaga gcgaagcaga cggggctaca ccaagcac 38

<210> SEQ ID NO 228
<211> LENGTH: 37
<212> TYPE: DNA
<213> ORGANISM: Artificial
<220> FEATURE:
<223> OTHER INFORMATION: synthesized primer

<400> SEQUENCE: 228
caatactcat ggattatcaa cggcatcgaa tgggcca 37

<210> SEQ ID NO 229
<211> LENGTH: 37
<212> TYPE: DNA
<213> ORGANISM: Artificial
<220> FEATURE:
<223> OTHER INFORMATION: synthesized primer

<400> SEQUENCE: 229
tggcccattc gatgccgttg ataatccatg agtattg 37

<210> SEQ ID NO 230
<211> LENGTH: 37
<212> TYPE: DNA
<213> ORGANISM: Artificial
<220> FEATURE:
<223> OTHER INFORMATION: synthesized primer

<400> SEQUENCE: 230
actcatggat tatcgatggc atcgaatggg ccatcgc 37

<210> SEQ ID NO 231
<211> LENGTH: 36
<212> TYPE: DNA
<213> ORGANISM: Artificial
<220> FEATURE:
<223> OTHER INFORMATION: synthesized primer

<400> SEQUENCE: 231
cactcaagtc cgcagaagtt tagaaaacac cactac 36

<210> SEQ ID NO 232
<211> LENGTH: 36
<212> TYPE: DNA
<213> ORGANISM: Artificial
<220> FEATURE:
<223> OTHER INFORMATION: synthesized primer

<400> SEQUENCE: 232
cactcaagtc cgcgatagtt tagaaaacac cactac 36

<210> SEQ ID NO 233
<211> LENGTH: 38
<212> TYPE: DNA
<213> ORGANISM: Artificial

```
<220> FEATURE:
<223> OTHER INFORMATION: synthesized primer

<400> SEQUENCE: 233
caaatcaacg tgccagattt tcctccgtgg gaccggag                                38

<210> SEQ ID NO 234
<211> LENGTH: 24
<212> TYPE: DNA
<213> ORGANISM: Artificial
<220> FEATURE:
<223> OTHER INFORMATION: synthesized primer

<400> SEQUENCE: 234 aaagggagg aaaatcgtga aaca                                                24

<210> SEQ ID NO 235
<211> LENGTH: 22
<212> TYPE: DNA
<213> ORGANISM: Artificial
<220> FEATURE:
<223> OTHER INFORMATION: synthesized primer

<400> SEQUENCE: 235
gttctaaatc gtgtttttct tg                                                 22

<210> SEQ ID NO 236
<211> LENGTH: 48
<212> TYPE: DNA
<213> ORGANISM: Artificial
<220> FEATURE:
<223> OTHER INFORMATION: synthesized primer

<400> SEQUENCE: 236
gaactggaca aacactcaag tccgcgatag tttagaaaac accactac                     48

<210> SEQ ID NO 237
<211> LENGTH: 36
<212> TYPE: DNA
<213> ORGANISM: Artificial
<220> FEATURE:
<223> OTHER INFORMATION: synthesized primer

<400> SEQUENCE: 237
gacttgagtg tttgtccagt tcgggtgctt agaaag                                  36

<210> SEQ ID NO 238
<211> LENGTH: 37
<212> TYPE: DNA
<213> ORGANISM: Artificial
<220> FEATURE:
<223> OTHER INFORMATION: synthesized primer

<400> SEQUENCE: 238
caaacactca agtccgcagc agtttagaaa acaccac                                 37

<210> SEQ ID NO 239
<211> LENGTH: 37
<212> TYPE: DNA
<213> ORGANISM: Artificial
<220> FEATURE:
<223> OTHER INFORMATION: synthesized primer

<400> SEQUENCE: 239
gtggtgtttt ctaaactgct gcggacttga gtgtttg                                 37
```

<210> SEQ ID NO 240
<211> LENGTH: 49
<212> TYPE: DNA
<213> ORGANISM: Artificial
<220> FEATURE:
<223> OTHER INFORMATION: synthesized primer

<400> SEQUENCE: 240
acgccgttaa agttcttgca gcagacgaat caggccaata ctcatggat            49

<210> SEQ ID NO 241
<211> LENGTH: 36
<212> TYPE: DNA
<213> ORGANISM: Artificial
<220> FEATURE:
<223> OTHER INFORMATION: synthesized primer

<400> SEQUENCE: 241
tgctgcaaga actttaacgg cgtagagcga agcaga                          36

<210> SEQ ID NO 242
<211> LENGTH: 37
<212> TYPE: DNA
<213> ORGANISM: Artificial
<220> FEATURE:
<223> OTHER INFORMATION: synthesized primer

<400> SEQUENCE: 242
acatggatgt aatctgcatg agcctgggag gaccaag                         37

<210> SEQ ID NO 243
<211> LENGTH: 38
<212> TYPE: DNA
<213> ORGANISM: Artificial
<220> FEATURE:
<223> OTHER INFORMATION: synthesized primer

<400> SEQUENCE: 243
tcctcccagg ctcatgcaga ttacatccat gttattcg                        38

<210> SEQ ID NO 244
<211> LENGTH: 22
<212> TYPE: DNA
<213> ORGANISM: Artificial
<220> FEATURE:
<223> OTHER INFORMATION: synthesized primer

<400> SEQUENCE: 244
gttatgagtt agttcaaatt cg                                         22

<210> SEQ ID NO 245
<211> LENGTH: 46
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 245
tacgcgcagt ccgtgnntnn cnncgtatca caaattaaag cccctg        46

<210> SEQ ID NO 246
<211> LENGTH: 44
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 246
tttaatttgt gatacgnngn nanncacgga ctgcgcgtac gcat        44

<210> SEQ ID NO 247
<211> LENGTH: 43
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 247
tacggcgtat cacaanntnn annccctgct ctgcactctc aag        43

<210> SEQ ID NO 248
<211> LENGTH: 45
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 248
agagtgcaga gcagggnntn nannttgtga tacgccgtaa ggcac        45

<210> SEQ ID NO 249
<211> LENGTH: 47
<212> TYPE: DNA
<213> ORGANISM: Artificial

```
<220> FEATURE:
<223> OTHER INFORMATION: synthesized primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 249
gctctgcact ctcaanncnn cnntggatca aatgttaaag tagcggt            47

<210> SEQ ID NO 250
<211> LENGTH: 47
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 250
tttaacattt gatccanngn ngnnttgaga gtgcagagca ggggctt            47

<210> SEQ ID NO 251
<211> LENGTH: 48
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 251
ctgcactctc aaggcnncnn tnnatcaaat gttaaagtag cggttatc           48

<210> SEQ ID NO 252
<211> LENGTH: 44
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
```

```
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 252
tactttaaca tttgatnnan ngnngccttg agagtgcaga gcag                           44

<210> SEQ ID NO 253
<211> LENGTH: 47
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 253
cactctcaag gctacnntnn annaaatgtt aaagtagcgg ttatcga                        47

<210> SEQ ID NO 254
<211> LENGTH: 44
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 254
cgctacttta acatttnntn nanngtagcc ttgagagtgc agag                           44

<210> SEQ ID NO 255
<211> LENGTH: 46
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 255
```
tctcaaggct acactnnann anntgttaaa gtagcggtta tcgaca       46

<210> SEQ ID NO 256
<211> LENGTH: 45
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 256
aaccgctact ttaacanntn ntnnagtgta gccttgagag tgcag       45

<210> SEQ ID NO 257
<211> LENGTH: 45
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 257
caaggctaca ctggannann tnntaaagta gcggttatcg acagc       45

<210> SEQ ID NO 258
<211> LENGTH: 45
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 258
gataaccgct actttannan ntnntccagt gtagccttga gagtg       45

<210> SEQ ID NO 259
<211> LENGTH: 45
<212> TYPE: DNA
<213> ORGANISM: Artificial

```
<220> FEATURE:
<223> OTHER INFORMATION: synthesized primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 259
ggctacactg gatcanntnn tnnagtagcg gttatcgaca gcggt                45

<210> SEQ ID NO 260
<211> LENGTH: 45
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 260
gtcgataacc gctactnnan nanntgatcc agtgtagcct tgaga                45

<210> SEQ ID NO 261
<211> LENGTH: 44
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 261
tacactggat caaatnntnn annagcggtt atcgacagcg gtat                 44

<210> SEQ ID NO 262
<211> LENGTH: 46
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
```

```
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 262
gctgtcgata accgctnntn nannatttga tccagtgtag ccttga          46

<210> SEQ ID NO 263
<211> LENGTH: 45
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 263
actggatcaa atgttnnann anggttatc gacagcggta tcgac            45

<210> SEQ ID NO 264
<211> LENGTH: 46
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 264
accgctgtcg ataaccnntn ntnnaacatt tgatccagtg tagcct          46

<210> SEQ ID NO 265
<211> LENGTH: 44
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 265
```

```
ggatcaaatg ttaaannann gnntatcgac agcggtatcg actc                    44
```

<210> SEQ ID NO 266
<211> LENGTH: 47
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 266

```
gataccgctg tcgatanncn ntnntttaac atttgatcca gtgtagc                 47
```

<210> SEQ ID NO 267
<211> LENGTH: 48
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 267

```
tcaaatgtta aagtanngnn tnncgacagc ggtatcgact cgagccat                48
```

<210> SEQ ID NO 268
<211> LENGTH: 48
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 268

```
gtcgataccg ctgtcgnnan ncnntacttt aacatttgat ccagtgta                48
```

<210> SEQ ID NO 269
<211> LENGTH: 45
<212> TYPE: DNA
<213> ORGANISM: Artificial

<220> FEATURE:
<223> OTHER INFORMATION: synthesized primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 269
aatgttaaag tagcgnntnn cnncagcggt atcgactcga gccat        45

<210> SEQ ID NO 270
<211> LENGTH: 47
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 270
cgagtcgata ccgctgnngn nanncgctac tttaacattt gatccag        47

<210> SEQ ID NO 271
<211> LENGTH: 45
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 271
gttaaagtag cggttnncnn cnncggtatc gactcgagcc atcca        45

<210> SEQ ID NO 272
<211> LENGTH: 47
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 272
gctcgagtcg ataccgnngn ngnnaaccgc tactttaaca tttgatc        47

<210> SEQ ID NO 273
<211> LENGTH: 45
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 273
aaagtagcgg ttatcnncnn cnntatcgac tcgagccatc cagat        45

<210> SEQ ID NO 274
<211> LENGTH: 47
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 274
atggctcgag tcgatanngn ngnngataac cgctacttta acatttg        47

<210> SEQ ID NO 275
<211> LENGTH: 44
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 275
gtagcggtta tcgacnncnn tnncgactcg agccatccag atct            44

<210> SEQ ID NO 276
<211> LENGTH: 46
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 276
tggatggctc gagtcgnnan ngnngtcgat aaccgctact ttaaca          46

<210> SEQ ID NO 277
<211> LENGTH: 46
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 277
gcggttatcg acagcnntnn cnnctcgagc catccagatc ttaaag          46

<210> SEQ ID NO 278
<211> LENGTH: 45
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 278
atctggatgg ctcgagnngn nanngctgtc gataaccgct acttt           45

<210> SEQ ID NO 279
<211> LENGTH: 45
<212> TYPE: DNA
<213> ORGANISM: Artificial

```
<220> FEATURE:
<223> OTHER INFORMATION: synthesized primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 279
gttatcgaca gcggtnncnn cnngagccat ccagatctta aagtc              45

<210> SEQ ID NO 280
<211> LENGTH: 44
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 280
aagatctgga tggctcnngn ngnnaccgct gtcgataacc gcta               44

<210> SEQ ID NO 281
<211> LENGTH: 46
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 281
atcgacagcg gtatcnncnn gnnccatcca gatcttaaag tcgctg             46

<210> SEQ ID NO 282
<211> LENGTH: 47
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
```

<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 282
tttaagatct ggatggnncn ngnngatacc gctgtcgata accgcta        47

<210> SEQ ID NO 283
<211> LENGTH: 45
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 283
gacagcggta tcgacnngnn cnntccagat cttaaagtcg ctgga        45

<210> SEQ ID NO 284
<211> LENGTH: 45
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 284
gactttaaga tctgganngn ncnngtcgat accgctgtcg ataac        45

<210> SEQ ID NO 285
<211> LENGTH: 44
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 285
agcggtatcg actcgnncnn tnnagatctt aaagtcgctg gagg    44

<210> SEQ ID NO 286
<211> LENGTH: 44
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 286
agcgacttta agatctnnan ngnncgagtc gataccgctg tcga    44

<210> SEQ ID NO 287
<211> LENGTH: 44
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 287
gactcgagcc atccanntnn tnnagtcgct ggagggctt ctat    44

<210> SEQ ID NO 288
<211> LENGTH: 44
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 288
agcccctcca gcgactnnan nanntggatg gctcgagtcg atac    44

<210> SEQ ID NO 289
<211> LENGTH: 46
<212> TYPE: DNA
<213> ORGANISM: Artificial

```
<220> FEATURE:
<223> OTHER INFORMATION: synthesized primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 289
agccatccag atcttnnann cnntggaggg gcttctatgg tgccgt            46

<210> SEQ ID NO 290
<211> LENGTH: 47
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (16)..(16)
<223> OTHER INFORMATION: n is a, c, g, or t
<220> FEATURE:
<221> NAME/KEY: misc_feature
<222> LOCATION: (26)..(26)
<223> OTHER INFORMATION: n is a, c, g, or t

<400> SEQUENCE: 290
catagaagcc cctccnagcg actttnaaga tctggatggc tcgagtc            47

<210> SEQ ID NO 291
<211> LENGTH: 43
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 291
catccagatc ttaaanncnn tnnaggggct tctatggtgc cgt            43

<210> SEQ ID NO 292
<211> LENGTH: 46
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
```

```
<222> LOCATION: (23)..(24)
<223> OTHER INFORMATION: n is a, c, g, or t

<400> SEQUENCE: 292
caccatagaa gcccctnnan ngnntttaag atctggatgg ctcgag            46

<210> SEQ ID NO 293
<211> LENGTH: 47
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 293
ggaggggctt ctatgnngnn gnncgaaaca aacccgtttc aagataa           47

<210> SEQ ID NO 294
<211> LENGTH: 44
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 294
aaacgggttt gtttcgnncn ncnncataga agcccctcca gcga              44

<210> SEQ ID NO 295
<211> LENGTH: 47
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 295
ggggcttcta tggtgnngnn cnnaacaaac ccgtttcaag ataacaa           47
```

-continued

```
<210> SEQ ID NO 296
<211> LENGTH: 44
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 296
ttgaaacggg tttgttnngn ncnncaccat agaagcccct ccag          44

<210> SEQ ID NO 297
<211> LENGTH: 47
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 297
gcttctatgg tgccgnncnn annaaacccg tttcaagata acaattc          47

<210> SEQ ID NO 298
<211> LENGTH: 44
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 298
atcttgaaac gggttttnntn ngnncggcac catagaagcc cctc          44

<210> SEQ ID NO 299
<211> LENGTH: 47
<212> TYPE: DNA
<213> ORGANISM: Artificial
<220> FEATURE:
<223> OTHER INFORMATION: synthesized primer
<220> FEATURE:
<221> NAME/KEY: misc_feature
```

```
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 299
tctatggtgc cgtccnnann annccccgttt caagataaca attctca          47

<210> SEQ ID NO 300
<211> LENGTH: 46
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 300
gttatcttga aacgggnntn ntnnggacgg caccatagaa gcccct            46

<210> SEQ ID NO 301
<211> LENGTH: 47
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 301
atggtgccgt ccgaannann cnngtttcaa gataacaatt ctcatgg           47

<210> SEQ ID NO 302
<211> LENGTH: 44
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
```

```
<222> LOCATION: (23)..(24)
<223> OTHER INFORMATION: n is a, c, g, or t

<400> SEQUENCE: 302
attgttatct tgaaacnngn ntnnttcgga cggcaccata gaag          44

<210> SEQ ID NO 303
<211> LENGTH: 47
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 303
gtgccgtccg aaacanncnn gnntcaagat aacaattctc atggcac       47

<210> SEQ ID NO 304
<211> LENGTH: 45
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 304
agaattgtta tcttganncn ngnntgtttc ggacggcacc ataga         45

<210> SEQ ID NO 305
<211> LENGTH: 46
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 305
ccgtccgaaa caaacnngnn tnnagataac aattctcatg gcacac        46
```

-continued

```
<210> SEQ ID NO 306
<211> LENGTH: 44
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 306
atgagaattg ttatctnnan ncnngtttgt tcggacggc acca                44

<210> SEQ ID NO 307
<211> LENGTH: 45
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 307
tccgaaacaa acccgnntnn anntaacaat tctcatggca cacac             45

<210> SEQ ID NO 308
<211> LENGTH: 44
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 308
gccatgagaa ttgttanntn nanncgggtt tgtttcggac ggca              44

<210> SEQ ID NO 309
<211> LENGTH: 45
<212> TYPE: DNA
<213> ORGANISM: Artificial
<220> FEATURE:
<223> OTHER INFORMATION: synthesized primer
<220> FEATURE:
<221> NAME/KEY: misc_feature
```

```
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 309
gaaacaaacc cgttttnnann tnncaattct catggcacac acgtc            45

<210> SEQ ID NO 310
<211> LENGTH: 44
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 310
tgtgccatga gaattgnnan ntnnaaacgg gtttgtttcg gacg              44

<210> SEQ ID NO 311
<211> LENGTH: 43
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 311
acaaacccgt ttcaanntnn cnnttctcat ggcacacacg tcg               43

<210> SEQ ID NO 312
<211> LENGTH: 46
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
```

```
<222> LOCATION: (23)..(24)
<223> OTHER INFORMATION: n is a, c, g, or t

<400> SEQUENCE: 312
gtgtgtgcca tgagaanngn nannttgaaa cgggtttgtt tcggac          46

<210> SEQ ID NO 313
<211> LENGTH: 43
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 313
aacccgtttc aagatnncnn tnntcatggc acacacgtcg cag          43

<210> SEQ ID NO 314
<211> LENGTH: 46
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 314
gacgtgtgtg ccatgannan ngnnatcttg aaacgggttt gtttcg          46

<210> SEQ ID NO 315
<211> LENGTH: 43
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 315
ccgtttcaag ataacnntnn tnntggcaca cacgtcgcag gaa          43
```

```
<210> SEQ ID NO 316
<211> LENGTH: 47
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 316
tgcgacgtgt gtgccannan nanngttatc ttgaaacggg tttgttt            47

<210> SEQ ID NO 317
<211> LENGTH: 44
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 317
aattctcatg gcacanncnn cnnaggaacg gttgcggcgt taaa               44

<210> SEQ ID NO 318
<211> LENGTH: 47
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 318
cgccgcaacc gttcctnngn ngnntgtgcc atgagaattg ttatctt            47

<210> SEQ ID NO 319
<211> LENGTH: 45
<212> TYPE: DNA
<213> ORGANISM: Artificial
<220> FEATURE:
<223> OTHER INFORMATION: synthesized primer
<220> FEATURE:
<221> NAME/KEY: misc_feature
```

<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 319
tctcatggca cacacnncnn annaacggtt gcggcgttaa acaat          45

<210> SEQ ID NO 320
<211> LENGTH: 46
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 320
taacgccgca accgttnntn ngnngtgtgt gccatgagaa ttgtta         46

<210> SEQ ID NO 321
<211> LENGTH: 47
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 321
acacacgtcg cagganngnn tnnggcgtta aacaattcta ttggcgt        47

<210> SEQ ID NO 322
<211> LENGTH: 44
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 322
agaattgttt aacgccnnan ncnntcctgc gacgtgtgtg ccat        44

<210> SEQ ID NO 323
<211> LENGTH: 46
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 323
gcaggaacgg ttgcgnngnn anncaattct attggcgtgc ttggtg    46

<210> SEQ ID NO 324
<211> LENGTH: 44
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 324
cacgccaata gaattgnntn ncnncgcaac cgttcctgcg acgt        44

<210> SEQ ID NO 325
<211> LENGTH: 44
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 325
acggttgcgg cgttanncnn tnntattggc gtgcttggtg tagc        44

```
<210> SEQ ID NO 326
<211> LENGTH: 44
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 326
accaagcacg ccaatannan ngnntaacgc cgcaaccgtt cctg                44

<210> SEQ ID NO 327
<211> LENGTH: 44
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 327
aacaattcta ttggcnngnn tnntgtagcc ccgtctgctt cgct                44

<210> SEQ ID NO 328
<211> LENGTH: 50
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 328
agcagacggg gctacannan ncnngccaat agaattgttt aacgccgcaa          50

<210> SEQ ID NO 329
<211> LENGTH: 43
<212> TYPE: DNA
<213> ORGANISM: Artificial
<220> FEATURE:
<223> OTHER INFORMATION: synthesized primer
<220> FEATURE:
<221> NAME/KEY: misc_feature
```

```
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 329
tctattggcg tgcttnntnn annccctgtct gcttcgctct acg         43

<210> SEQ ID NO 330
<211> LENGTH: 47
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 330
gagcgaagca gacgggnntn nannaagcac gccaatagaa ttgttta       47

<210> SEQ ID NO 331
<211> LENGTH: 44
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 331
attggcgtgc ttggtnnann cnngtctgct tcgctctacg ccgt          44

<210> SEQ ID NO 332
<211> LENGTH: 46
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
```

-continued

<222> LOCATION: (23)..(24)
<223> OTHER INFORMATION: n is a, c, g, or t

<400> SEQUENCE: 332
gtagagcgaa gcagacnngn ntnnaccaag cacgccaata gaattg    46

<210> SEQ ID NO 333
<211> LENGTH: 45
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 333
tggcgtgctt ggtgtanncn ngnntgcttc gctctacgcc gttaa    45

<210> SEQ ID NO 334
<211> LENGTH: 45
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 334
ggcgtagagc gaagcanncn ngnntacacc aagcacgcca ataga    45

<210> SEQ ID NO 335
<211> LENGTH: 45
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 335
gtgcttggtg tagccnngnn tnnttcgctc tacgccgtta aagtt    45

```
<210> SEQ ID NO 336
<211> LENGTH: 44
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 336
aacggcgtag agcgaannan ncnnggctac accaagcacg ccaa          44

<210> SEQ ID NO 337
<211> LENGTH: 45
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 337
cttggtgtag ccccgnntnn tnngctctac gccgttaaag ttctt         45

<210> SEQ ID NO 338
<211> LENGTH: 48
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 338
tttaacggcg tagagcnnan nanncggggc tacaccaagc acgccaat      48

<210> SEQ ID NO 339
<211> LENGTH: 46
<212> TYPE: DNA
<213> ORGANISM: Artificial
<220> FEATURE:
<223> OTHER INFORMATION: synthesized primer
<220> FEATURE:
<221> NAME/KEY: misc_feature
```

<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 339
ggtgtagccc cgtctnntnn gnnctacgcc gttaaagttc ttgcag          46

<210> SEQ ID NO 340
<211> LENGTH: 44
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 340
aactttaacg gcgtagnncn nannagacgg ggctacacca agca            44

<210> SEQ ID NO 341
<211> LENGTH: 45
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 341
gtagccccgt ctgctnngnn cnncgccgtt aaagttcttg cagca           45

<210> SEQ ID NO 342
<211> LENGTH: 44
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature

```
<222> LOCATION: (23)..(24)
<223> OTHER INFORMATION: n is a, c, g, or t

<400> SEQUENCE: 342
aagaacttta acggcgnngn ncnnagcaga cggggctaca ccaa          44

<210> SEQ ID NO 343
<211> LENGTH: 45
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 343
gccccgtctg cttcgnncnn cnncgttaaa gttcttgcag cagac         45

<210> SEQ ID NO 344
<211> LENGTH: 44
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 344
tgcaagaact ttaacgnngn ngnncgaagc agacggggct acac          44

<210> SEQ ID NO 345
<211> LENGTH: 45
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 345
ccgtctgctt cgctcnncnn cnntaaagtt cttgcagcag acgga         45
```

```
<210> SEQ ID NO 346
<211> LENGTH: 43
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 346
tgctgcaaga actttanngn ngnngagcga agcagacggg gct                 43

<210> SEQ ID NO 347
<211> LENGTH: 44
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 347
tctgcttcgc tctacnncnn tnnagttctt gcagcagacg gatc                44

<210> SEQ ID NO 348
<211> LENGTH: 47
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 348
gtctgctgca agaactnnan ngnngtagag cgaagcagac ggggcta             47

<210> SEQ ID NO 349
<211> LENGTH: 43
<212> TYPE: DNA
<213> ORGANISM: Artificial
<220> FEATURE:
<223> OTHER INFORMATION: synthesized primer
<220> FEATURE:
<221> NAME/KEY: misc_feature
```

<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 349
gcttcgctct acgccnntnn anntcttgca gcagacggat cag        43

<210> SEQ ID NO 350
<211> LENGTH: 44
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 350
tccgtctgct gcaaganntn nannggcgta gagcgaagca gacg        44

<210> SEQ ID NO 351
<211> LENGTH: 44
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 351
tcgctctacg ccgttnnann tnntgcagca gacggatcag gcca        44

<210> SEQ ID NO 352
<211> LENGTH: 44
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature

```
<222> LOCATION: (23)..(24)
<223> OTHER INFORMATION: n is a, c, g, or t

<400> SEQUENCE: 352
tgatccgtct gctgcannan ntnnaacggc gtagagcgaa gcag          44

<210> SEQ ID NO 353
<211> LENGTH: 44
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 353
ctctacgccg ttaaanntnn tnnagcagac ggatcaggcc aata          44

<210> SEQ ID NO 354
<211> LENGTH: 44
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 354
gcctgatccg tctgctnnan nanntttaac ggcgtagagc gaag          44

<210> SEQ ID NO 355
<211> LENGTH: 44
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 355
tacgccgtta agttnntnn annagacgga tcaggccaat actc          44
```

```
<210> SEQ ID NO 356
<211> LENGTH: 45
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 356
ttggcctgat ccgtctnntn nannaacttt aacggcgtag agcga          45

<210> SEQ ID NO 357
<211> LENGTH: 44
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 357
gccgttaaag ttcttnnann anncggatca ggccaatact catg           44

<210> SEQ ID NO 358
<211> LENGTH: 45
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 358
gtattggcct gatccgnntn ntnnaagaac tttaacggcg tagag          45

<210> SEQ ID NO 359
<211> LENGTH: 46
<212> TYPE: DNA
<213> ORGANISM: Artificial
<220> FEATURE:
<223> OTHER INFORMATION: synthesized primer
<220> FEATURE:
<221> NAME/KEY: misc_feature
```

<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 359
gttaaagttc ttgcannann cnnatcaggc caatactcat ggatta         46

<210> SEQ ID NO 360
<211> LENGTH: 46
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 360
tgagtattgg cctgatnngn ntnntgcaag aactttaacg gcgtag         46

<210> SEQ ID NO 361
<211> LENGTH: 45
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 361
aaagttcttg cagcanncnn annaggccaa tactcatgga ttatc         45

<210> SEQ ID NO 362
<211> LENGTH: 48
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature

```
<222> LOCATION: (23)..(24)
<223> OTHER INFORMATION: n is a, c, g, or t

<400> SEQUENCE: 362
ccatgagtat tggcctnntn ngnntgctgc aagaacttta acggcgta          48

<210> SEQ ID NO 363
<211> LENGTH: 45
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 363
gttcttgcag cagacnnann anccaatac tcatggatta tcaac             45

<210> SEQ ID NO 364
<211> LENGTH: 46
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 364
aatccatgag tattggnntn ntnngtctgc tgcaagaact ttaacg           46

<210> SEQ ID NO 365
<211> LENGTH: 46
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 365
cttgcagcag acggannann cnnatactca tggattatca acggca           46
```

```
<210> SEQ ID NO 366
<211> LENGTH: 45
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 366
gataatccat gagtatnngn ntnntccgtc tgctgcaaga acttt          45

<210> SEQ ID NO 367
<211> LENGTH: 45
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 367
gcagcagacg gatcanncnn annctcatgg attatcaacg gcatc          45

<210> SEQ ID NO 368
<211> LENGTH: 44
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 368
ttgataatcc atgagnntnn gnntgatccg tctgctgcaa gaac          44

<210> SEQ ID NO 369
<211> LENGTH: 46
<212> TYPE: DNA
<213> ORGANISM: Artificial
<220> FEATURE:
<223> OTHER INFORMATION: synthesized primer
<220> FEATURE:
<221> NAME/KEY: misc_feature
```

```
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 369
gcagacggat caggcnnann cnnatggatt atcaacggca tcgaat            46

<210> SEQ ID NO 370
<211> LENGTH: 44
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 370
gccgttgata atccatnngn ntnngcctga tccgtctgct gcaa              44

<210> SEQ ID NO 371
<211> LENGTH: 45
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 371
gacggatcag gccaanncnn anngattatc aacggcatcg aatgg             45

<210> SEQ ID NO 372
<211> LENGTH: 44
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
```

<222> LOCATION: (23)..(24)
<223> OTHER INFORMATION: n is a, c, g, or t

<400> SEQUENCE: 372
gatgccgttg ataatcnntn ngnnttggcc tgatccgtct gctg                44

<210> SEQ ID NO 373
<211> LENGTH: 47
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 373
ggatcaggcc aatacnnann gnntatcaac ggcatcgaat gggccat            47

<210> SEQ ID NO 374
<211> LENGTH: 44
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 374
ttcgatgccg ttgatanncn ntnngtattg gcctgatccg tctg               44

<210> SEQ ID NO 375
<211> LENGTH: 44
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 375
tcaggccaat actcanngnn tnncaacggc atcgaatggg ccat               44

```
<210> SEQ ID NO 376
<211> LENGTH: 45
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 376
ccattcgatg ccgttgnnan ncnntgagta ttggcctgat ccgtc           45

<210> SEQ ID NO 377
<211> LENGTH: 48
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 377
ggccaatact catggnntnn cnncggcatc gaatgggcca tcgcgaat        48

<210> SEQ ID NO 378
<211> LENGTH: 45
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 378
ggcccattcg atgccgnngn nanncatga gtattggcct gatcc            45

<210> SEQ ID NO 379
<211> LENGTH: 44
<212> TYPE: DNA
<213> ORGANISM: Artificial
<220> FEATURE:
<223> OTHER INFORMATION: synthesized primer
<220> FEATURE:
<221> NAME/KEY: misc_feature
```

```
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 379
caatactcat ggattnncnn cnncatcgaa tgggccatcg cgaa                    44

<210> SEQ ID NO 380
<211> LENGTH: 46
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 380
gatggcccat tcgatgnngn ngnnaatcca tgagtattgg cctgat                  46

<210> SEQ ID NO 381
<211> LENGTH: 44
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 381
tactcatgga ttatcnncnn cnncgaatgg gccatcgcga ataa                    44

<210> SEQ ID NO 382
<211> LENGTH: 46
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
```

```
<222> LOCATION: (23)..(24)
<223> OTHER INFORMATION: n is a, c, g, or t

<400> SEQUENCE: 382
cgcgatggcc cattcgnngn ngnngataat ccatgagtat tggcct          46

<210> SEQ ID NO 383
<211> LENGTH: 45
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 383
tcatggatta tcaacnncnn cnnatgggcc atcgcgaata acatg           45

<210> SEQ ID NO 384
<211> LENGTH: 46
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 384
attcgcgatg gcccatnngn ngnngttgat aatccatgag tattgg          46

<210> SEQ ID NO 385
<211> LENGTH: 44
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 385
tggattatca acggcnncnn annggccatc gcgaataaca tgga            44
```

```
<210> SEQ ID NO 386
<211> LENGTH: 46
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 386
gttattcgcg atggccnntn ngnngccgtt gataatccat gagtat          46

<210> SEQ ID NO 387
<211> LENGTH: 46
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 387
attatcaacg gcatcnnann gnncatcgcg aataacatgg atgtaa           46

<210> SEQ ID NO 388
<211> LENGTH: 46
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 388
catgttattc gcgatgnncn ntnngatgcc gttgataatc catgag           46

<210> SEQ ID NO 389
<211> LENGTH: 47
<212> TYPE: DNA
<213> ORGANISM: Artificial
<220> FEATURE:
<223> OTHER INFORMATION: synthesized primer
<220> FEATURE:
<221> NAME/KEY: misc_feature
```

```
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 389
atcaacggca tcgaanngnn cnncgcgaat aacatggatg taatcaa          47

<210> SEQ ID NO 390
<211> LENGTH: 46
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 390
atccatgtta ttcgcgnngn ncnnttcgat gccgttgata atccat           46

<210> SEQ ID NO 391
<211> LENGTH: 47
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 391
aacggcatcg aatggnncnn cnngaataac atggatgtaa tcaacat          47

<210> SEQ ID NO 392
<211> LENGTH: 46
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
```

```
<222> LOCATION: (23)..(24)
<223> OTHER INFORMATION: n is a, c, g, or t

<400> SEQUENCE: 392
tacatccatg ttattcnngn ngnnccattc gatgccgttg ataatc              46

<210> SEQ ID NO 393
<211> LENGTH: 47
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 393
ggcatcgaat gggccnncnn gnntaacatg gatgtaatca acatgag             47

<210> SEQ ID NO 394
<211> LENGTH: 44
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 394
gattacatcc atgttanncn ngnnggccca ttcgatgccg ttga                44

<210> SEQ ID NO 395
<211> LENGTH: 47
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 395
atcgaatggg ccatcnngnn tnncatggat gtaatcaaca tgagcct             47
```

```
<210> SEQ ID NO 396
<211> LENGTH: 44
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 396
gttgattaca tccatgnnan ncnngatggc ccattcgatg ccgt                44

<210> SEQ ID NO 397
<211> LENGTH: 45
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 397
gaatgggcca tcgcgnntnn cnnggatgta atcaacatga gcctg               45

<210> SEQ ID NO 398
<211> LENGTH: 44
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 398
catgttgatt acatccnngn nanncgcgat ggcccattcg atgc                44

<210> SEQ ID NO 399
<211> LENGTH: 45
<212> TYPE: DNA
<213> ORGANISM: Artificial
<220> FEATURE:
<223> OTHER INFORMATION: synthesized primer
<220> FEATURE:
<221> NAME/KEY: misc_feature
```

<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 399
tgggccatcg cgaatnncnn gnntgtaatc aacatgagcc tggga          45

<210> SEQ ID NO 400
<211> LENGTH: 44
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 400
gctcatgttg attacanncn ngnnattcgc gatggcccat tcga          44

<210> SEQ ID NO 401
<211> LENGTH: 45
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 401
gccatcgcga ataacnngnn tnnaatcaac atgagcctgg gagca          45

<210> SEQ ID NO 402
<211> LENGTH: 45
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature

```
<222> LOCATION: (23)..(24)
<223> OTHER INFORMATION: n is a, c, g, or t

<400> SEQUENCE: 402
caggctcatg ttgattnnan ncnngttatt cgcgatggcc cattc          45

<210> SEQ ID NO 403
<211> LENGTH: 43
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 403
atcgcgaata acatgnntnn anncaacatg agcctgggag cac            43

<210> SEQ ID NO 404
<211> LENGTH: 46
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 404
tcccaggctc atgttgnntn nanncatgtt attcgcgatg gcccat         46

<210> SEQ ID NO 405
<211> LENGTH: 44
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 405
gcgaataaca tggatnnann cnncatgagc ctgggagcac caag           44
```

```
<210> SEQ ID NO 406
<211> LENGTH: 50
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 406
tgctcccagg ctcatgnngn ntnnatccat gttattcgcg atggcccatt            50

<210> SEQ ID NO 407
<211> LENGTH: 46
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 407
aataacatgg atgtanncnn cnngagcctg ggagcaccaa gcggca                46

<210> SEQ ID NO 408
<211> LENGTH: 46
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 408
tggtgctccc aggctcnngn ngnntacatc catgttattc gcgatg                46

<210> SEQ ID NO 409
<211> LENGTH: 43
<212> TYPE: DNA
<213> ORGANISM: Artificial
<220> FEATURE:
<223> OTHER INFORMATION: synthesized primer
<220> FEATURE:
<221> NAME/KEY: misc_feature
```

```
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 409
aacatggatg taatcnncnn gnncctggga gcaccaagcg gca                43

<210> SEQ ID NO 410
<211> LENGTH: 47
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 410
gcttggtgct cccaggnncn ngnngattac atccatgtta ttcgcga          47

<210> SEQ ID NO 411
<211> LENGTH: 43
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 411
atggatgtaa tcaacnngnn cnngggagca ccaagcggca gtg                43

<210> SEQ ID NO 412
<211> LENGTH: 47
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
```

```
<222> LOCATION: (23)..(24)
<223> OTHER INFORMATION: n is a, c, g, or t

<400> SEQUENCE: 412
gccgcttggt gctcccnngn ncnngttgat tacatccatg ttattcg         47

<210> SEQ ID NO 413
<211> LENGTH: 45
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 413
gatgtaatca acatgnncnn gnnagcacca agcggcagtg cggca           45

<210> SEQ ID NO 414
<211> LENGTH: 48
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 414
actgccgctt ggtgctnncn ngnncatgtt gattacatcc atgttatt        48

<210> SEQ ID NO 415
<211> LENGTH: 44
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 415
gtaatcaaca tgagcnngnn annaccaagc ggcagtgcgg cact            44
```

```
<210> SEQ ID NO 416
<211> LENGTH: 46
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 416
cgcactgccg cttggtnntn ncnngctcat gttgattaca tccatg          46

<210> SEQ ID NO 417
<211> LENGTH: 45
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 417
atgagcctgg gagcannann cnncagtgcg gcacttaaag cagca           45

<210> SEQ ID NO 418
<211> LENGTH: 45
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 418
tttaagtgcc gcactgnngn ntnntgctcc caggctcatg ttgat           45

<210> SEQ ID NO 419
<211> LENGTH: 46
<212> TYPE: DNA
<213> ORGANISM: Artificial
<220> FEATURE:
<223> OTHER INFORMATION: synthesized primer
<220> FEATURE:
<221> NAME/KEY: misc_feature
```

```
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 419
ggagcaccaa gcggcnntnn gnnacttaaa gcagcagttg ataaag         46

<210> SEQ ID NO 420
<211> LENGTH: 45
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 420
aactgctgct ttaagtnncn nanngccgct tggtgctccc aggct          45

<210> SEQ ID NO 421
<211> LENGTH: 46
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 421
gcaccaagcg gcagtnngnn anntaaagca gcagttgata aagctg         46

<210> SEQ ID NO 422
<211> LENGTH: 44
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
```

<222> LOCATION: (23)..(24)
<223> OTHER INFORMATION: n is a, c, g, or t

<400> SEQUENCE: 422
atcaactgct gctttanntn ncnnactgcc gcttggtgct ccca                44

<210> SEQ ID NO 423
<211> LENGTH: 46
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 423
ccaagcggca gtgcgnnann tnnagcagca gttgataaag ctgttg              46

<210> SEQ ID NO 424
<211> LENGTH: 44
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 424
tttatcaact gctgctnnan ntnncgcact gccgcttggt gctc                44

<210> SEQ ID NO 425
<211> LENGTH: 46
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 425
agcggcagtg cggcanntnn annagcagtt gataaagctg ttgcat              46

```
<210> SEQ ID NO 426
<211> LENGTH: 44
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 426
agctttatca actgctnntn nanntgccgc actgccgctt ggtg              44

<210> SEQ ID NO 427
<211> LENGTH: 46
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 427
ggcagtgcgg cacttnnann annagttgat aaagctgttg catctg            46

<210> SEQ ID NO 428
<211> LENGTH: 44
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 428
aacagcttta tcaactnntn ntnnaagtgc cgcactgccg cttg              44

<210> SEQ ID NO 429
<211> LENGTH: 46
<212> TYPE: DNA
<213> ORGANISM: Artificial
<220> FEATURE:
<223> OTHER INFORMATION: synthesized primer
<220> FEATURE:
<221> NAME/KEY: misc_feature
```

```
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 429
agtgcggcac ttaaannann anntgataaa gctgttgcat ctggtg          46

<210> SEQ ID NO 430
<211> LENGTH: 46
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 430
tgcaacagct ttatcanntn ntnntttaag tgccgcactg ccgctt          46

<210> SEQ ID NO 431
<211> LENGTH: 45
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 431
gcggcactta aagcannann tnntaaagct gttgcatctg gtgtc          45

<210> SEQ ID NO 432
<211> LENGTH: 44
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
```

```
<222> LOCATION: (23)..(24)
<223> OTHER INFORMATION: n is a, c, g, or t

<400> SEQUENCE: 432
agatgcaaca gctttannan ntnntgcttt aagtgccgca ctgc        44

<210> SEQ ID NO 433
<211> LENGTH: 44
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 433
gcacttaaag cagcanntnn tnnagctgtt gcatctggtg tcgt        44

<210> SEQ ID NO 434
<211> LENGTH: 44
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 434
accagatgca acagctnnan nanntgctgc tttaagtgcc gcac        44

<210> SEQ ID NO 435
<211> LENGTH: 44
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 435
cttaaagcag cagttnntnn anntgttgca tctggtgtcg tcgt        44
```

```
<210> SEQ ID NO 436
<211> LENGTH: 46
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 436
gacaccagat gcaacanntn nannaactgc tgctttaagt gccgca          46

<210> SEQ ID NO 437
<211> LENGTH: 44
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 437
aaagcagcag ttgatnnann tnntgcatct ggtgtcgtcg tagt            44

<210> SEQ ID NO 438
<211> LENGTH: 45
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 438
gacgacacca gatgcannan ntnnatcaac tgctgcttta agtgc           45

<210> SEQ ID NO 439
<211> LENGTH: 44
<212> TYPE: DNA
<213> ORGANISM: Artificial
<220> FEATURE:
<223> OTHER INFORMATION: synthesized primer
<220> FEATURE:
<221> NAME/KEY: misc_feature
```

```
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 439
gcagcagttg ataaanntnn tnnatctggt gtcgtcgtag tagc                44

<210> SEQ ID NO 440
<211> LENGTH: 47
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 440
tacgacgaca ccagatnnan nanntttatc aactgctgct ttaagtg             47

<210> SEQ ID NO 441
<211> LENGTH: 45
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 441
gcagttgata aagctnnntnn anntggtgtc gtcgtagtag cggca              45

<210> SEQ ID NO 442
<211> LENGTH: 47
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
```

```
<222> LOCATION: (23)..(24)
<223> OTHER INFORMATION: n is a, c, g, or t

<400> SEQUENCE: 442
tactacgacg acaccanntn nannagcttt atcaactgct gctttaa            47

<210> SEQ ID NO 443
<211> LENGTH: 45
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 443
gttgataaag ctgttnnann tnntgtcgtc gtagtagcgg cagct              45

<210> SEQ ID NO 444
<211> LENGTH: 46
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 444
cgctactacg acgacannan ntnnaacagc tttatcaact gctgct             46

<210> SEQ ID NO 445
<211> LENGTH: 43
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 445
gataaagctg ttgcanntnn tnncgtcgta gtagcggcag ctg                43
```

```
<210> SEQ ID NO 446
<211> LENGTH: 46
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 446
tgccgctact acgacgnnan nanntgcaac agctttatca actgct        46

<210> SEQ ID NO 447
<211> LENGTH: 44
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 447
aaagctgttg catctnntnn cnncgtagta gcggcagctg ggaa        44

<210> SEQ ID NO 448
<211> LENGTH: 47
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 448
agctgccgct actacgnngn nannagatgc aacagcttta tcaactg        47

<210> SEQ ID NO 449
<211> LENGTH: 44
<212> TYPE: DNA
<213> ORGANISM: Artificial
<220> FEATURE:
<223> OTHER INFORMATION: synthesized primer
<220> FEATURE:
<221> NAME/KEY: misc_feature
```

```
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 449
gctgttgcat ctggtnncnn cnnagtagcg gcagctggga atga                    44

<210> SEQ ID NO 450
<211> LENGTH: 46
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 450
cccagctgcc gctactnngn ngnnaccaga tgcaacagct ttatca                  46

<210> SEQ ID NO 451
<211> LENGTH: 46
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 451
gttgcatctg gtgtcnncnn annagcggca gctgggaatg agggaa                  46

<210> SEQ ID NO 452
<211> LENGTH: 45
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
```

```
<222> LOCATION: (23)..(24)
<223> OTHER INFORMATION: n is a, c, g, or t

<400> SEQUENCE: 452
attcccagct gccgctnntn ngnngacacc agatgcaaca gcttt          45

<210> SEQ ID NO 453
<211> LENGTH: 44
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 453
gcatctggtg tcgtcnnann annggcagct gggaatgagg gaac          44

<210> SEQ ID NO 454
<211> LENGTH: 44
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 454
ctcattccca gctgccnntn ntnngacgac accagatgca acag          44

<210> SEQ ID NO 455
<211> LENGTH: 44
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 455
tctggtgtcg tcgtannann gnnagctggg aatgagggaa catc          44
```

```
<210> SEQ ID NO 456
<211> LENGTH: 45
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 456
tccctcattc ccagctnncn ntnntacgac gacaccagat gcaac              45

<210> SEQ ID NO 457
<211> LENGTH: 46
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 457
ggtgtcgtcg tagtanngnn anntgggaat gagggaacat ccggat             46

<210> SEQ ID NO 458
<211> LENGTH: 46
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 458
tgttccctca ttcccanntn ncnntactac gacgacacca gatgca             46

<210> SEQ ID NO 459
<211> LENGTH: 45
<212> TYPE: DNA
<213> ORGANISM: Artificial
<220> FEATURE:
<223> OTHER INFORMATION: synthesized primer
<220> FEATURE:
<221> NAME/KEY: misc_feature
```

```
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 459
gctgggaatg agggannann cnnatcatcg agtaccgtcg gttat          45

<210> SEQ ID NO 460
<211> LENGTH: 47
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 460
gacggtactc gatgatnngn ntnntccctc attcccagct gccgcta       47

<210> SEQ ID NO 461
<211> LENGTH: 45
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 461
gggaatgagg gaacanncnn annatcgagt accgtcggtt atcca          45

<210> SEQ ID NO 462
<211> LENGTH: 44
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
```

<222> LOCATION: (23)..(24)
<223> OTHER INFORMATION: n is a, c, g, or t

<400> SEQUENCE: 462
accgacggta ctcgatnntn ngnntgttcc ctcattccca gctg            44

<210> SEQ ID NO 463
<211> LENGTH: 44
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 463
aatgagggaa catccnnann anngagtacc gtcggttatc cagg            44

<210> SEQ ID NO 464
<211> LENGTH: 44
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 464
ataaccgacg gtactcnntn ntnnggatgt tccctcattc ccag            44

<210> SEQ ID NO 465
<211> LENGTH: 46
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 465
acatccggat catcgnntnn cnncggttat ccaggcaagt acccttt          46

```
<210> SEQ ID NO 466
<211> LENGTH: 44
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 466
cttgcctgga taaccgnngn nanncgatga tccggatgtt ccct              44

<210> SEQ ID NO 467
<211> LENGTH: 45
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 467
tccggatcat cgagtnncnn cnnttatcca ggcaagtacc cttca             45

<210> SEQ ID NO 468
<211> LENGTH: 45
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 468
gtacttgcct ggataanngn ngnnactcga tgatccggat gttcc             45

<210> SEQ ID NO 469
<211> LENGTH: 45
<212> TYPE: DNA
<213> ORGANISM: Artificial
<220> FEATURE:
<223> OTHER INFORMATION: synthesized primer
<220> FEATURE:
<221> NAME/KEY: misc_feature
```

```
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 469
tcgagtaccg tcggtnntnn anncaagtac ccttcagtga ttgca          45

<210> SEQ ID NO 470
<211> LENGTH: 44
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 470
cactgaaggg tacttgnntn nannaccgac ggtactcgat gatc           44

<210> SEQ ID NO 471
<211> LENGTH: 45
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 471
agtaccgtcg gttatnnann cnngtaccct tcagtgattg cagtg          45

<210> SEQ ID NO 472
<211> LENGTH: 45
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
```

```
<222> LOCATION: (23)..(24)
<223> OTHER INFORMATION: n is a, c, g, or t

<400> SEQUENCE: 472
aatcactgaa gggtacnngn ntnnataacc gacggtactc gatga        45

<210> SEQ ID NO 473
<211> LENGTH: 43
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 473
accgtcggtt atccanncnn gnnccttca gtgattgcag tgg           43

<210> SEQ ID NO 474
<211> LENGTH: 45
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 474
tgcaatcact gaagggnncn ngnntggata accgacggta ctcga        45

<210> SEQ ID NO 475
<211> LENGTH: 45
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 475
gtcggttatc caggcnngnn cnnttcagtg attgcagtgg gcgct        45
```

```
<210> SEQ ID NO 476
<211> LENGTH: 44
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 476
cactgcaatc actgaanngn ncnngcctgg ataaccgacg gtac                44

<210> SEQ ID NO 477
<211> LENGTH: 45
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 477
ggttatccag gcaagnncnn tnnagtgatt gcagtgggcg ctgta              45

<210> SEQ ID NO 478
<211> LENGTH: 46
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 478
gcccactgca atcactnnan ngnncttgcc tggataaccg acggta             46

<210> SEQ ID NO 479
<211> LENGTH: 44
<212> TYPE: DNA
<213> ORGANISM: Artificial
<220> FEATURE:
<223> OTHER INFORMATION: synthesized primer
<220> FEATURE:
<221> NAME/KEY: misc_feature
```

```
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 479
tatccaggca agtacnntnn anngattgca gtgggcgctg taga                    44

<210> SEQ ID NO 480
<211> LENGTH: 45
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 480
agcgcccact gcaatcnntn nanngtactt gcctggataa ccgac                   45

<210> SEQ ID NO 481
<211> LENGTH: 44
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 481
gtgggcgctg tagacnntnn anntcaacgt gcctctttt cctc                     44

<210> SEQ ID NO 482
<211> LENGTH: 44
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
```

```
<222> LOCATION: (23)..(24)
<223> OTHER INFORMATION: n is a, c, g, or t

<400> SEQUENCE: 482
aaaagaggca cgttganntn nanngtctac agcgcccact gcaa         44

<210> SEQ ID NO 483
<211> LENGTH: 44
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 483
ggcgctgtag actctnnann tnnacgtgcc tcttttttcct ccgt        44

<210> SEQ ID NO 484
<211> LENGTH: 44
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 484
ggaaaaagag gcacgtnnan ntnnagagtc tacagcgccc actg         44

<210> SEQ ID NO 485
<211> LENGTH: 45
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 485
gctgtagact cttcanntnn anntgcctct ttttcctccg tggga        45
```

```
<210> SEQ ID NO 486
<211> LENGTH: 44
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 486
ggaggaaaaa gaggcanntn nanntgaaga gtctacagcg ccca                44

<210> SEQ ID NO 487
<211> LENGTH: 43
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 487
gtagactctt caaatnnann tnnctctttt tcctccgtgg gac                 43

<210> SEQ ID NO 488
<211> LENGTH: 47
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 488
cacggaggaa aaagagnnan ntnnatttga agagtctaca gcgccca             47

<210> SEQ ID NO 489
<211> LENGTH: 44
<212> TYPE: DNA
<213> ORGANISM: Artificial
<220> FEATURE:
<223> OTHER INFORMATION: synthesized primer
<220> FEATURE:
<221> NAME/KEY: misc_feature
```

```
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 489
gactcttcaa atcaanntnn cnnttttcc tccgtgggac cgga           44

<210> SEQ ID NO 490
<211> LENGTH: 50
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 490
tcccacggag gaaaaanngn nannttgatt tgaagagtct acagcgccca           50

<210> SEQ ID NO 491
<211> LENGTH: 45
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 491
gcctcttttt cctccnngnn annggagctg gatgtcatgg cccct           45

<210> SEQ ID NO 492
<211> LENGTH: 45
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
```

```
<222> LOCATION: (23)..(24)
<223> OTHER INFORMATION: n is a, c, g, or t

<400> SEQUENCE: 492
catgacatcc agctccnntn ncnnggagga aaaagaggca cgttg          45

<210> SEQ ID NO 493
<211> LENGTH: 45
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 493
ttttcctccg tggganngnn gnnggatgtc atggcccctg gcgtt          45

<210> SEQ ID NO 494
<211> LENGTH: 44
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 494
aggggccatg acatccnncn ncnntcccac ggaggaaaaa gagg           44

<210> SEQ ID NO 495
<211> LENGTH: 48
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 495
tcctccgtgg gaccgnngnn gnntgtcatg gcccctggcg tttctatt       48
```

```
<210> SEQ ID NO 496
<211> LENGTH: 44
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 496
gccaggggcc atgacanncn ncnncggtcc cacggaggaa aaag            44

<210> SEQ ID NO 497
<211> LENGTH: 45
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 497
tccgtgggac cggagnngnn tnncatggcc cctggcgttt ctatt           45

<210> SEQ ID NO 498
<211> LENGTH: 46
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 498
aacgccaggg gccatgnnan ncnnctccgg tcccacggag gaaaaa          46

<210> SEQ ID NO 499
<211> LENGTH: 45
<212> TYPE: DNA
<213> ORGANISM: Artificial
<220> FEATURE:
<223> OTHER INFORMATION: synthesized primer
<220> FEATURE:
<221> NAME/KEY: misc_feature
```

<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 499
gtgggaccgg agctgnntnn cnnggcccct ggcgtttcta ttcaa            45

<210> SEQ ID NO 500
<211> LENGTH: 47
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 500
agaaacgcca ggggccnngn nanncagctc cggtcccacg gaggaaa          47

<210> SEQ ID NO 501
<211> LENGTH: 46
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 501
ggaccggagc tggatnncnn gnnccctggc gtttctattc aatcga           46

<210> SEQ ID NO 502
<211> LENGTH: 45
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature

```
<222> LOCATION: (23)..(24)
<223> OTHER INFORMATION: n is a, c, g, or t

<400> SEQUENCE: 502
aatagaaacg ccagggnncn ngnnatccag ctccggtccc acgga              45

<210> SEQ ID NO 503
<211> LENGTH: 44
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 503
gtcatggccc ctggcnntnn tnntcaatcg acgcttccag ggaa               44

<210> SEQ ID NO 504
<211> LENGTH: 44
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 504
tggaagcgtc gattgannan nanngccagg ggccatgaca tcca               44

<210> SEQ ID NO 505
<211> LENGTH: 46
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 505
attcaatcga cgcttnnann gnncaagtat ggtgcgcaaa acggga             46
```

```
<210> SEQ ID NO 506
<211> LENGTH: 46
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 506
ttgcgcacca tacttgnncn ntnnaagcgt cgattgaata gaaacg         46

<210> SEQ ID NO 507
<211> LENGTH: 45
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 507
caatcgacgc ttccanngnn cnngtatggt gcgcaaaacg ggact          45

<210> SEQ ID NO 508
<211> LENGTH: 46
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 508
gttttgcgca ccatacnngn ncnntggaag cgtcgattga atagaa         46

<210> SEQ ID NO 509
<211> LENGTH: 48
<212> TYPE: DNA
<213> ORGANISM: Artificial
<220> FEATURE:
<223> OTHER INFORMATION: synthesized primer
<220> FEATURE:
<221> NAME/KEY: misc_feature
```

```
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 509
gggaacaagt atggtnngnn anncgggact tccatggcct cgccgcat         48

<210> SEQ ID NO 510
<211> LENGTH: 45
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 510
ggccatggaa gtcccgnntn ncnnaccata cttgttccct ggaag              45

<210> SEQ ID NO 511
<211> LENGTH: 45
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 511
aacaagtatg gtgcgnnann cnngacttcc atggcctcgc cgcat              45

<210> SEQ ID NO 512
<211> LENGTH: 44
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
```

```
<222> LOCATION: (23)..(24)
<223> OTHER INFORMATION: n is a, c, g, or t

<400> SEQUENCE: 512
cgaggccatg gaagtcnngn ntnncgcacc atacttgttc cctg                44

<210> SEQ ID NO 513
<211> LENGTH: 43
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 513
aagtatggtg cgcaanncnn gnnttccatg gcctcgccgc atg                 43

<210> SEQ ID NO 514
<211> LENGTH: 45
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 514
cggcgaggcc atggaanncn ngnnttgcgc accatacttg ttccc               45

<210> SEQ ID NO 515
<211> LENGTH: 43
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 515
tatggtgcgc aaaacnngnn tnncatggcc tcgccgcatg tag                 43
```

```
<210> SEQ ID NO 516
<211> LENGTH: 46
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 516
atgcggcgag gccatgnnan ncnngttttg cgcaccatac ttgttc         46

<210> SEQ ID NO 517
<211> LENGTH: 47
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 517
ccgcatgtag ctgggnngnn cnnattgatt ctttctaagc acccgaa       47

<210> SEQ ID NO 518
<211> LENGTH: 48
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 518
cttagaaaga atcaatnngn ncnncccagc tacatgcggc gaggccat      48

<210> SEQ ID NO 519
<211> LENGTH: 46
<212> TYPE: DNA
<213> ORGANISM: Artificial
<220> FEATURE:
<223> OTHER INFORMATION: synthesized primer
<220> FEATURE:
<221> NAME/KEY: misc_feature
```

```
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 519
catgtagctg gggcgnncnn anngattctt tctaagcacc cgaact                    46

<210> SEQ ID NO 520
<211> LENGTH: 51
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 520
gtgcttagaa agaatcnntn ngnncgcccc agctacatgc ggcgaggcca t              51

<210> SEQ ID NO 521
<211> LENGTH: 44
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 521
gtagctgggg cggccnnann gnntctttct aagcacccga actg                      44

<210> SEQ ID NO 522
<211> LENGTH: 43
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
```

```
<222> LOCATION: (23)..(24)
<223> OTHER INFORMATION: n is a, c, g, or t

<400> SEQUENCE: 522
cgggtgctta gaaagannen ntnnggccgc cccagctaca tgc                43

<210> SEQ ID NO 523
<211> LENGTH: 46
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 523
ttgattcttt ctaagnncnn gnnctggaca aacactcaag tccgca            46

<210> SEQ ID NO 524
<211> LENGTH: 45
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 524
ttgagtgttt gtccagnncn ngnncttaga aagaatcaat gcggc             45

<210> SEQ ID NO 525
<211> LENGTH: 45
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 525
ctttctaagc acccgnncnn gnnaaacact caagtccgca gcagt             45
```

```
<210> SEQ ID NO 526
<211> LENGTH: 46
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 526
gcggacttga gtgttnncn ngnncgggtg cttagaaaga atcaat                 46

<210> SEQ ID NO 527
<211> LENGTH: 48
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 527
tggacaaaca ctcaanncnn cnncagttta gaaaacacca ctacaaaa              48

<210> SEQ ID NO 528
<211> LENGTH: 47
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 528
ggtgttttct aaactgnngn ngnnttgagt gtttgtccag ttcgggt               47

<210> SEQ ID NO 529
<211> LENGTH: 47
<212> TYPE: DNA
<213> ORGANISM: Artificial
<220> FEATURE:
<223> OTHER INFORMATION: synthesized primer
<220> FEATURE:
<221> NAME/KEY: misc_feature
```

```
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 529
ttagaaaaca ccactnnann anntggtgat tctttctact atggaaa            47

<210> SEQ ID NO 530
<211> LENGTH: 46
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 530
gtagaaagaa tcaccanntn ntnnagtggt gttttctaaa ctgctg             46

<210> SEQ ID NO 531
<211> LENGTH: 46
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 531
accactacaa aacttnntnn tnntttctac tatggaaaag ggctga             46

<210> SEQ ID NO 532
<211> LENGTH: 48
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
```

-continued

```
<222> LOCATION: (23)..(24)
<223> OTHER INFORMATION: n is a, c, g, or t

<400> SEQUENCE: 532 tttccatag tagaaannan nannaagttt tgtagtggtg ttttctaa         48

<210> SEQ ID NO 533
<211> LENGTH: 45
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 533
gattctttct actatnnann anngctgatc aacgtacagg cggca          45

<210> SEQ ID NO 534
<211> LENGTH: 48
<212> TYPE: DNA
<213> ORGANISM: Artificial
<220> FEATURE:
<223> OTHER INFORMATION: synthesized primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 534
ctgtacgttg atcagcnntn ntnnatagta gaaagaatca ccaagttt       48

<210> SEQ ID NO 535
<211> LENGTH: 42
<212> TYPE: DNA
<213> ORGANISM: Artificial
<220> FEATURE:
<223> OTHER INFORMATION: synthesized primer

<400> SEQUENCE: 535
tcaaggctac aatggagcaa atgttaaagt agcggttatc ga             42

<210> SEQ ID NO 536
<211> LENGTH: 38
<212> TYPE: DNA
<213> ORGANISM: Artificial
<220> FEATURE:
<223> OTHER INFORMATION: synthesized primer

<400> SEQUENCE: 536
tttaacattt gctccattgt agccttgaga gtgcagag                  38
```

<210> SEQ ID NO 537
<211> LENGTH: 38
<212> TYPE: DNA
<213> ORGANISM: Artificial
<220> FEATURE:
<223> OTHER INFORMATION: synthesized primer

<400> SEQUENCE: 537
ctacactgga ggaggtgtta aagtagcggt tatcgaca                              38

<210> SEQ ID NO 538
<211> LENGTH: 37
<212> TYPE: DNA
<213> ORGANISM: Artificial
<220> FEATURE:
<223> OTHER INFORMATION: synthesized primer

<400> SEQUENCE: 538
ctactttaac acctcctcca gtgtagcctt gagagtg                               37

<210> SEQ ID NO 539
<211> LENGTH: 40
<212> TYPE: DNA
<213> ORGANISM: Artificial
<220> FEATURE:
<223> OTHER INFORMATION: synthesized primer

<400> SEQUENCE: 539
aggctacact ggaagaaatg ttaaagtagc ggttatcgac                            40

<210> SEQ ID NO 540
<211> LENGTH: 34
<212> TYPE: DNA
<213> ORGANISM: Artificial
<220> FEATURE:
<223> OTHER INFORMATION: synthesized primer

<400> SEQUENCE: 540
ctttaacatt tcttccagtg tagccttgag agtg                                  34

<210> SEQ ID NO 541
<211> LENGTH: 42
<212> TYPE: DNA
<213> ORGANISM: Artificial
<220> FEATURE:
<223> OTHER INFORMATION: synthesized primer

<400> SEQUENCE: 541
aaggctacac tgcaggaggt gttaaagtag cggttatcga ca                         42

<210> SEQ ID NO 542
<211> LENGTH: 40
<212> TYPE: DNA
<213> ORGANISM: Artificial
<220> FEATURE:
<223> OTHER INFORMATION: synthesized primer

<400> SEQUENCE: 542
ctactttaac acctcctgca gtgtagcctt gagagtgcag                            40

<210> SEQ ID NO 543
<211> LENGTH: 37
<212> TYPE: DNA
<213> ORGANISM: Artificial
<220> FEATURE:
<223> OTHER INFORMATION: synthesized primer

<400> SEQUENCE: 543
cgtttcaaga tccctcttct catggcacac acgtcgc       37

<210> SEQ ID NO 544
<211> LENGTH: 40
<212> TYPE: DNA
<213> ORGANISM: Artificial
<220> FEATURE:
<223> OTHER INFORMATION: synthesized primer

<400> SEQUENCE: 544
tgtgccatga agagggat cttgaaacgg gtttgtttcg       40

<210> SEQ ID NO 545
<211> LENGTH: 38
<212> TYPE: DNA
<213> ORGANISM: Artificial
<220> FEATURE:
<223> OTHER INFORMATION: synthesized primer

<400> SEQUENCE: 545
tgccgtccga accaaacccg tttcaagata acaattct       38

<210> SEQ ID NO 546
<211> LENGTH: 37
<212> TYPE: DNA
<213> ORGANISM: Artificial
<220> FEATURE:
<223> OTHER INFORMATION: synthesized primer

<400> SEQUENCE: 546
tcttgaaacg ggtttggttc ggacggcacc atagaag       37

<210> SEQ ID NO 547
<211> LENGTH: 40
<212> TYPE: DNA
<213> ORGANISM: Artificial
<220> FEATURE:
<223> OTHER INFORMATION: synthesized primer

<400> SEQUENCE: 547
ccgtttcaag atcccaatca tcatggcaca cacgtcgcag       40

<210> SEQ ID NO 548
<211> LENGTH: 42
<212> TYPE: DNA
<213> ORGANISM: Artificial
<220> FEATURE:
<223> OTHER INFORMATION: synthesized primer

<400> SEQUENCE: 548
tgtgtgccat gatgattggg atcttgaaac gggtttgttt cg       42

<210> SEQ ID NO 549
<211> LENGTH: 45
<212> TYPE: DNA
<213> ORGANISM: Artificial
<220> FEATURE:
<223> OTHER INFORMATION: synthesized primer

<400> SEQUENCE: 549
acaaacccgt tttcagatcc caattctcat ggcacacacg tcgca       45

<210> SEQ ID NO 550
<211> LENGTH: 43
<212> TYPE: DNA
<213> ORGANISM: Artificial

```
<220> FEATURE:
<223> OTHER INFORMATION: synthesized primer

<400> SEQUENCE: 550
ccatgagaat tgggatctga aacgggttt gtttcggacg gca                    43

<210> SEQ ID NO 551
<211> LENGTH: 38
<212> TYPE: DNA
<213> ORGANISM: Artificial
<220> FEATURE:
<223> OTHER INFORMATION: synthesized primer

<400> SEQUENCE: 551
ggttgcggcg tcatacaatt ctattggcgt gcttggtg                         38

<210> SEQ ID NO 552
<211> LENGTH: 38
<212> TYPE: DNA
<213> ORGANISM: Artificial
<220> FEATURE:
<223> OTHER INFORMATION: synthesized primer

<400> SEQUENCE: 552
gccaatagaa ttgtatgacg ccgcaaccgt tcctgcga                         38

<210> SEQ ID NO 553
<211> LENGTH: 40
<212> TYPE: DNA
<213> ORGANISM: Artificial
<220> FEATURE:
<223> OTHER INFORMATION: synthesized primer

<400> SEQUENCE: 553
tggtgtagcc tcgggtgttt cgctctacgc cgttaaagtt                       40

<210> SEQ ID NO 554
<211> LENGTH: 39
<212> TYPE: DNA
<213> ORGANISM: Artificial
<220> FEATURE:
<223> OTHER INFORMATION: synthesized primer

<400> SEQUENCE: 554
cgtagagcga aacacccgag gctacaccaa gcacgccaa                        39

<210> SEQ ID NO 555
<211> LENGTH: 42
<212> TYPE: DNA
<213> ORGANISM: Artificial
<220> FEATURE:
<223> OTHER INFORMATION: synthesized primer

<400> SEQUENCE: 555
gtgtagcccc gggtgttgca ctctacgccg ttaaagttct tg                    42

<210> SEQ ID NO 556
<211> LENGTH: 43
<212> TYPE: DNA
<213> ORGANISM: Artificial
<220> FEATURE:
<223> OTHER INFORMATION: synthesized primer

<400> SEQUENCE: 556
acggcgtaga gtgcaacacc cggggctaca ccaagcacgc caa                   43
```

```
<210> SEQ ID NO 557
<211> LENGTH: 44
<212> TYPE: DNA
<213> ORGANISM: Artificial
<220> FEATURE:
<223> OTHER INFORMATION: synthesized primer

<400> SEQUENCE: 557
tggtgtagcc ccgactcttg gactctacgc cgttaaagtt cttg            44

<210> SEQ ID NO 558
<211> LENGTH: 43
<212> TYPE: DNA
<213> ORGANISM: Artificial
<220> FEATURE:
<223> OTHER INFORMATION: synthesized primer

<400> SEQUENCE: 558
acggcgtaga gtccaagagt cggggctaca ccaagcacgc caa             43

<210> SEQ ID NO 559
<211> LENGTH: 41
<212> TYPE: DNA
<213> ORGANISM: Artificial
<220> FEATURE:
<223> OTHER INFORMATION: synthesized primer

<400> SEQUENCE: 559
gcctgggagc acaaggctct agtgcggcac ttaaagcagc a               41

<210> SEQ ID NO 560
<211> LENGTH: 41
<212> TYPE: DNA
<213> ORGANISM: Artificial
<220> FEATURE:
<223> OTHER INFORMATION: synthesized primer

<400> SEQUENCE: 560
agtgccgcac tagagccttg tgctcccagg ctcatgttga t               41

<210> SEQ ID NO 561
<211> LENGTH: 37
<212> TYPE: DNA
<213> ORGANISM: Artificial
<220> FEATURE:
<223> OTHER INFORMATION: synthesized primer

<400> SEQUENCE: 561
atggcccctg gctattctat tcaatcgacg cttccag                    37

<210> SEQ ID NO 562
<211> LENGTH: 36
<212> TYPE: DNA
<213> ORGANISM: Artificial
<220> FEATURE:
<223> OTHER INFORMATION: synthesized primer

<400> SEQUENCE: 562
tcgattgaat agaatagcca ggggccatga catcca                     36

<210> SEQ ID NO 563
<211> LENGTH: 42
<212> TYPE: DNA
<213> ORGANISM: Artificial
<220> FEATURE:
<223> OTHER INFORMATION: synthesized primer

<400> SEQUENCE: 563
```
tcgacgcttc caaggtccgt gtatggtgcg caaaacggga ct        42

<210> SEQ ID NO 564
<211> LENGTH: 44
<212> TYPE: DNA
<213> ORGANISM: Artificial
<220> FEATURE:
<223> OTHER INFORMATION: synthesized primer

<400> SEQUENCE: 564
ttgcgcacca tacacggacc ttggaagcgt cgattgaata gaaa        44

<210> SEQ ID NO 565
<211> LENGTH: 39
<212> TYPE: DNA
<213> ORGANISM: Artificial
<220> FEATURE:
<223> OTHER INFORMATION: synthesized primer

<400> SEQUENCE: 565
catggcacac actgcggagg aacggttgcg gcgttaaac        39

<210> SEQ ID NO 566
<211> LENGTH: 39
<212> TYPE: DNA
<213> ORGANISM: Artificial
<220> FEATURE:
<223> OTHER INFORMATION: synthesized primer

<400> SEQUENCE: 566
gcaaccgttc ctccgcagtg tgtgccatga gaattgtta        39

<210> SEQ ID NO 567
<211> LENGTH: 43
<212> TYPE: DNA
<213> ORGANISM: Artificial
<220> FEATURE:
<223> OTHER INFORMATION: synthesized primer

<400> SEQUENCE: 567
gtcgcaggaa cgattggttc aaacaattct attggcgtgc ttg        43

<210> SEQ ID NO 568
<211> LENGTH: 45
<212> TYPE: DNA
<213> ORGANISM: Artificial
<220> FEATURE:
<223> OTHER INFORMATION: synthesized primer

<400> SEQUENCE: 568
caatagaatt gtttgaacca atcgttcctg cgacgtgtgt gccat        45

<210> SEQ ID NO 569
<211> LENGTH: 41
<212> TYPE: DNA
<213> ORGANISM: Artificial
<220> FEATURE:
<223> OTHER INFORMATION: synthesized primer

<400> SEQUENCE: 569
aacggttgcg gcgcatggaa attctattgg cgtgcttggt g        41

<210> SEQ ID NO 570
<211> LENGTH: 41
<212> TYPE: DNA
<213> ORGANISM: Artificial

```
<220> FEATURE:
<223> OTHER INFORMATION: synthesized primer

<400> SEQUENCE: 570
caatagaatt ccatgcgcc gcaaccgttc ctgcgacgtg t                    41

<210> SEQ ID NO 571
<211> LENGTH: 43
<212> TYPE: DNA
<213> ORGANISM: Artificial
<220> FEATURE:
<223> OTHER INFORMATION: synthesized primer

<400> SEQUENCE: 571
aacggttgcg gcgagaggag gttctattgg cgtgcttggt gta                 43

<210> SEQ ID NO 572
<211> LENGTH: 46
<212> TYPE: DNA
<213> ORGANISM: Artificial
<220> FEATURE:
<223> OTHER INFORMATION: synthesized primer

<400> SEQUENCE: 572
cacgccaata gaacctcctc tcgccgcaac cgttcctgcg acgtgt              46

<210> SEQ ID NO 573
<211> LENGTH: 43
<212> TYPE: DNA
<213> ORGANISM: Artificial
<220> FEATURE:
<223> OTHER INFORMATION: synthesized primer

<400> SEQUENCE: 573
aacggttgcg gcgggaggcg gttctattgg cgtgcttggt gta                 43

<210> SEQ ID NO 574
<211> LENGTH: 46
<212> TYPE: DNA
<213> ORGANISM: Artificial
<220> FEATURE:
<223> OTHER INFORMATION: synthesized primer

<400> SEQUENCE: 574
cacgccaata gaaccgcctc ccgccgcaac cgttcctgcg acgtgt              46

<210> SEQ ID NO 575
<211> LENGTH: 37
<212> TYPE: DNA
<213> ORGANISM: Artificial
<220> FEATURE:
<223> OTHER INFORMATION: synthesized primer

<400> SEQUENCE: 575
tgcttcgctc tacggcgtta agttcttgc agcagac                         37

<210> SEQ ID NO 576
<211> LENGTH: 39
<212> TYPE: DNA
<213> ORGANISM: Artificial
<220> FEATURE:
<223> OTHER INFORMATION: synthesized primer

<400> SEQUENCE: 576
caagaacttt aacgccgtag agcgaagcag acggggcta                      39
```

```
<210> SEQ ID NO 577
<211> LENGTH: 43
<212> TYPE: DNA
<213> ORGANISM: Artificial
<220> FEATURE:
<223> OTHER INFORMATION: synthesized primer

<400> SEQUENCE: 577
ttcgctctac gcctcatgtt ctgcagcaga cggatcaggc caa            43

<210> SEQ ID NO 578
<211> LENGTH: 42
<212> TYPE: DNA
<213> ORGANISM: Artificial
<220> FEATURE:
<223> OTHER INFORMATION: synthesized primer

<400> SEQUENCE: 578
atccgtctgc tgcagaacat gaggcgtaga gcgaagcaga cg             42

<210> SEQ ID NO 579
<211> LENGTH: 41
<212> TYPE: DNA
<213> ORGANISM: Artificial
<220> FEATURE:
<223> OTHER INFORMATION: synthesized primer

<400> SEQUENCE: 579
aataacatgg atatatcttg catgagcctg ggagcaccaa g              41

<210> SEQ ID NO 580
<211> LENGTH: 44
<212> TYPE: DNA
<213> ORGANISM: Artificial
<220> FEATURE:
<223> OTHER INFORMATION: synthesized primer

<400> SEQUENCE: 580
caggctcatg caagatatat ccatgttatt cgcgatggcc catt           44

<210> SEQ ID NO 581
<211> LENGTH: 43
<212> TYPE: DNA
<213> ORGANISM: Artificial
<220> FEATURE:
<223> OTHER INFORMATION: synthesized primer

<400> SEQUENCE: 581
cgaataacat ggatcttatc tgcatgagcc tgggagcacc aag            43

<210> SEQ ID NO 582
<211> LENGTH: 45
<212> TYPE: DNA
<213> ORGANISM: Artificial
<220> FEATURE:
<223> OTHER INFORMATION: synthesized primer

<400> SEQUENCE: 582
ccaggctcat gcagataaga tccatgttat tcgcgatggc ccatt          45

<210> SEQ ID NO 583
<211> LENGTH: 44
<212> TYPE: DNA
<213> ORGANISM: Artificial
<220> FEATURE:
<223> OTHER INFORMATION: synthesized primer

<400> SEQUENCE: 583
```

```
taacatggat gtatgctcat tgagcctggg agcaccaagc ggca                    44
```

<210> SEQ ID NO 584
<211> LENGTH: 43
<212> TYPE: DNA
<213> ORGANISM: Artificial
<220> FEATURE:
<223> OTHER INFORMATION: synthesized primer

<400> SEQUENCE: 584

```
tgctcccagg ctcaatgagc atacatccat gttattcgcg atg                    43
```

<210> SEQ ID NO 585
<211> LENGTH: 37
<212> TYPE: DNA
<213> ORGANISM: Artificial
<220> FEATURE:
<223> OTHER INFORMATION: synthesized primer

<400> SEQUENCE: 585

```
acatggatgt aatctgcatg agcctgggag caccaag                           37
```

<210> SEQ ID NO 586
<211> LENGTH: 39
<212> TYPE: DNA
<213> ORGANISM: Artificial
<220> FEATURE:
<223> OTHER INFORMATION: synthesized primer

<400> SEQUENCE: 586

```
tcccaggctc atgcagatta catccatgtt attcgcgat                         39
```

<210> SEQ ID NO 587
<211> LENGTH: 38
<212> TYPE: DNA
<213> ORGANISM: Artificial
<220> FEATURE:
<223> OTHER INFORMATION: synthesized primer

<400> SEQUENCE: 587

```
ggatgtaatc aacatcagcc tgggagcacc aagcggca                          38
```

<210> SEQ ID NO 588
<211> LENGTH: 38
<212> TYPE: DNA
<213> ORGANISM: Artificial
<220> FEATURE:
<223> OTHER INFORMATION: synthesized primer

<400> SEQUENCE: 588

```
tgctcccagg ctgatgttga ttacatccat gttattcg                          38
```

<210> SEQ ID NO 589
<211> LENGTH: 38
<212> TYPE: DNA
<213> ORGANISM: Artificial
<220> FEATURE:
<223> OTHER INFORMATION: synthesized primer

<400> SEQUENCE: 589

```
ggatgtaatc aacgtaagcc tgggagcacc aagcggca                          38
```

<210> SEQ ID NO 590
<211> LENGTH: 38
<212> TYPE: DNA
<213> ORGANISM: Artificial

```
<220> FEATURE:
<223> OTHER INFORMATION: synthesized primer

<400> SEQUENCE: 590
tgctcccagg cttacgttga ttacatccat gttattcg                                38

<210> SEQ ID NO 591
<211> LENGTH: 41
<212> TYPE: DNA
<213> ORGANISM: Artificial
<220> FEATURE:
<223> OTHER INFORMATION: synthesized primer

<400> SEQUENCE: 591
ggatgtaatc aacgtaagcg cgggagcacc aagcggcagt g                            41

<210> SEQ ID NO 592
<211> LENGTH: 42
<212> TYPE: DNA
<213> ORGANISM: Artificial
<220> FEATURE:
<223> OTHER INFORMATION: synthesized primer

<400> SEQUENCE: 592
ttggtgctcc cgcgcttacg ttgattacat ccatgttatt cg                           42

<210> SEQ ID NO 593
<211> LENGTH: 42
<212> TYPE: DNA
<213> ORGANISM: Artificial
<220> FEATURE:
<223> OTHER INFORMATION: synthesized primer

<400> SEQUENCE: 593
aatcaacatg agcttcggag caagcggcag tgcggcactt aa                           42

<210> SEQ ID NO 594
<211> LENGTH: 42
<212> TYPE: DNA
<213> ORGANISM: Artificial
<220> FEATURE:
<223> OTHER INFORMATION: synthesized primer

<400> SEQUENCE: 594
cactgccgct tgctccgaag ctcatgttga ttacatccat gt                           42

<210> SEQ ID NO 595
<211> LENGTH: 40
<212> TYPE: DNA
<213> ORGANISM: Artificial
<220> FEATURE:
<223> OTHER INFORMATION: synthesized primer

<400> SEQUENCE: 595
aacatgagcc tgtacgcacc aagcggcagt gcggcactta                              40

<210> SEQ ID NO 596
<211> LENGTH: 41
<212> TYPE: DNA
<213> ORGANISM: Artificial
<220> FEATURE:
<223> OTHER INFORMATION: synthesized primer

<400> SEQUENCE: 596
cactgccgct tggtgcgtac aggctcatgt tgattacatc c                            41
```

```
<210> SEQ ID NO 597
<211> LENGTH: 43
<212> TYPE: DNA
<213> ORGANISM: Artificial
<220> FEATURE:
<223> OTHER INFORMATION: synthesized primer

<400> SEQUENCE: 597
caacatgagc ctgtcagcag atagcggcag tgcggcactt aaa          43

<210> SEQ ID NO 598
<211> LENGTH: 42
<212> TYPE: DNA
<213> ORGANISM: Artificial
<220> FEATURE:
<223> OTHER INFORMATION: synthesized primer

<400> SEQUENCE: 598
gcactgccgc tatctgctga caggctcatg ttgattacat cc           42

<210> SEQ ID NO 599
<211> LENGTH: 43
<212> TYPE: DNA
<213> ORGANISM: Artificial
<220> FEATURE:
<223> OTHER INFORMATION: synthesized primer

<400> SEQUENCE: 599
caacatgagc ctgaacgcac gtagcggcag tgcggcactt aaa          43

<210> SEQ ID NO 600
<211> LENGTH: 42
<212> TYPE: DNA
<213> ORGANISM: Artificial
<220> FEATURE:
<223> OTHER INFORMATION: synthesized primer

<400> SEQUENCE: 600
gcactgccgc tacgtgcgtt caggctcatg ttgattacat cc           42

<210> SEQ ID NO 601
<211> LENGTH: 42
<212> TYPE: DNA
<213> ORGANISM: Artificial
<220> FEATURE:
<223> OTHER INFORMATION: synthesized primer

<400> SEQUENCE: 601
atgagcctgg gaaattcatc tagcggcagt gcggcactta aa            42

<210> SEQ ID NO 602
<211> LENGTH: 41
<212> TYPE: DNA
<213> ORGANISM: Artificial
<220> FEATURE:
<223> OTHER INFORMATION: synthesized primer

<400> SEQUENCE: 602
gcactgccgc tagatgaatt tcccaggctc atgttgatta c             41

<210> SEQ ID NO 603
<211> LENGTH: 40
<212> TYPE: DNA
<213> ORGANISM: Artificial
<220> FEATURE:
<223> OTHER INFORMATION: synthesized primer

<400> SEQUENCE: 603
```
catgagcctg ggatcagtta gcggcagtgc ggcacttaaa        40

<210> SEQ ID NO 604
<211> LENGTH: 38
<212> TYPE: DNA
<213> ORGANISM: Artificial
<220> FEATURE:
<223> OTHER INFORMATION: synthesized primer

<400> SEQUENCE: 604
gcactgccgc taactgatcc caggctcatg ttgattac          38

<210> SEQ ID NO 605
<211> LENGTH: 40
<212> TYPE: DNA
<213> ORGANISM: Artificial
<220> FEATURE:
<223> OTHER INFORMATION: synthesized primer

<400> SEQUENCE: 605
catgagcctg ggatcagata gcggcagtgc ggcacttaaa        40

<210> SEQ ID NO 606
<211> LENGTH: 38
<212> TYPE: DNA
<213> ORGANISM: Artificial
<220> FEATURE:
<223> OTHER INFORMATION: synthesized primer

<400> SEQUENCE: 606
gcactgccgc tatctgatcc caggctcatg ttgattac          38

<210> SEQ ID NO 607
<211> LENGTH: 40
<212> TYPE: DNA
<213> ORGANISM: Artificial
<220> FEATURE:
<223> OTHER INFORMATION: synthesized primer

<400> SEQUENCE: 607
catgagcctg ggatcaggta gcggcagtgc ggcacttaaa        40

<210> SEQ ID NO 608
<211> LENGTH: 38
<212> TYPE: DNA
<213> ORGANISM: Artificial
<220> FEATURE:
<223> OTHER INFORMATION: synthesized primer

<400> SEQUENCE: 608
gcactgccgc tacctgatcc caggctcatg ttgattac          38

<210> SEQ ID NO 609
<211> LENGTH: 40
<212> TYPE: DNA
<213> ORGANISM: Artificial
<220> FEATURE:
<223> OTHER INFORMATION: synthesized primer

<400> SEQUENCE: 609
catgagcctg ggacactata gcggcagtgc ggcacttaaa        40

<210> SEQ ID NO 610
<211> LENGTH: 38
<212> TYPE: DNA
<213> ORGANISM: Artificial

```
<220> FEATURE:
<223> OTHER INFORMATION: synthesized primer

<400> SEQUENCE: 610
gcactgccgc tatagtgtcc caggctcatg ttgattac                        38

<210> SEQ ID NO 611
<211> LENGTH: 36
<212> TYPE: DNA
<213> ORGANISM: Artificial
<220> FEATURE:
<223> OTHER INFORMATION: synthesized primer

<400> SEQUENCE: 611
gagcctggga gcagacagcg gcagtgcggc acttaa                          36

<210> SEQ ID NO 612
<211> LENGTH: 39
<212> TYPE: DNA
<213> ORGANISM: Artificial
<220> FEATURE:
<223> OTHER INFORMATION: synthesized primer

<400> SEQUENCE: 612
tgccgcactg ccgctgtctg ctcccaggct catgttgat                       39

<210> SEQ ID NO 613
<211> LENGTH: 36
<212> TYPE: DNA
<213> ORGANISM: Artificial
<220> FEATURE:
<223> OTHER INFORMATION: synthesized primer

<400> SEQUENCE: 613
gagcctggga gcagaaagcg gcagtgcggc acttaa                          36

<210> SEQ ID NO 614
<211> LENGTH: 39
<212> TYPE: DNA
<213> ORGANISM: Artificial
<220> FEATURE:
<223> OTHER INFORMATION: synthesized primer

<400> SEQUENCE: 614
tgccgcactg ccgctttctg ctcccaggct catgttgat                       39

<210> SEQ ID NO 615
<211> LENGTH: 36
<212> TYPE: DNA
<213> ORGANISM: Artificial
<220> FEATURE:
<223> OTHER INFORMATION: synthesized primer

<400> SEQUENCE: 615
gagcctggga gcagtaagcg gcagtgcggc acttaa                          36

<210> SEQ ID NO 616
<211> LENGTH: 39
<212> TYPE: DNA
<213> ORGANISM: Artificial
<220> FEATURE:
<223> OTHER INFORMATION: synthesized primer

<400> SEQUENCE: 616
tgccgcactg ccgcttactg ctcccaggct catgttgat                       39
```

<210> SEQ ID NO 617
<211> LENGTH: 36
<212> TYPE: DNA
<213> ORGANISM: Artificial
<220> FEATURE:
<223> OTHER INFORMATION: synthesized primer

<400> SEQUENCE: 617
gagcctggga gcaggaggca gtgcggcact taaagc    36

<210> SEQ ID NO 618
<211> LENGTH: 38
<212> TYPE: DNA
<213> ORGANISM: Artificial
<220> FEATURE:
<223> OTHER INFORMATION: synthesized primer

<400> SEQUENCE: 618
agtgccgcac tgcctcctgc tcccaggctc atgttgat    38

<210> SEQ ID NO 619
<211> LENGTH: 42
<212> TYPE: DNA
<213> ORGANISM: Artificial
<220> FEATURE:
<223> OTHER INFORMATION: synthesized primer

<400> SEQUENCE: 619
agcctgggag cacacggcaa tgcggcactt aaagcagcag tt    42

<210> SEQ ID NO 620
<211> LENGTH: 42
<212> TYPE: DNA
<213> ORGANISM: Artificial
<220> FEATURE:
<223> OTHER INFORMATION: synthesized primer

<400> SEQUENCE: 620
tttaagtgcc gcattgccgt gtgctcccag gctcatgttg at    42

<210> SEQ ID NO 621
<211> LENGTH: 38
<212> TYPE: DNA
<213> ORGANISM: Artificial
<220> FEATURE:
<223> OTHER INFORMATION: synthesized primer

<400> SEQUENCE: 621
aagcggcagt gcgacactta aagcagcagt tgataaag    38

<210> SEQ ID NO 622
<211> LENGTH: 38
<212> TYPE: DNA
<213> ORGANISM: Artificial
<220> FEATURE:
<223> OTHER INFORMATION: synthesized primer

<400> SEQUENCE: 622
aactgctgct ttaagtgtcg cactgccgct tggtgctc    38

<210> SEQ ID NO 623
<211> LENGTH: 41
<212> TYPE: DNA
<213> ORGANISM: Artificial
<220> FEATURE:
<223> OTHER INFORMATION: synthesized primer

<400> SEQUENCE: 623

```
gttaaagttc ttcgtggttg tgacggatca ggccaatact c                          41
```

<210> SEQ ID NO 624
<211> LENGTH: 41
<212> TYPE: DNA
<213> ORGANISM: Artificial
<220> FEATURE:
<223> OTHER INFORMATION: synthesized primer

<400> SEQUENCE: 624

```
ctgatccgtc acaaccacga agaactttaa cggcgtagag c                          41
```

<210> SEQ ID NO 625
<211> LENGTH: 40
<212> TYPE: DNA
<213> ORGANISM: Artificial
<220> FEATURE:
<223> OTHER INFORMATION: synthesized primer

<400> SEQUENCE: 625

```
ttaaagttct tgcaggaggc ggatcaggcc aatactcatg                            40
```

<210> SEQ ID NO 626
<211> LENGTH: 42
<212> TYPE: DNA
<213> ORGANISM: Artificial
<220> FEATURE:
<223> OTHER INFORMATION: synthesized primer

<400> SEQUENCE: 626

```
tattggcctg atccgcctcc tgcaagaact ttaacggcgt ag                         42
```

<210> SEQ ID NO 627
<211> LENGTH: 41
<212> TYPE: DNA
<213> ORGANISM: Artificial
<220> FEATURE:
<223> OTHER INFORMATION: synthesized primer

<400> SEQUENCE: 627

```
ttaaagttct tgcaggacgt gacggatcag gccaatactc a                          41
```

<210> SEQ ID NO 628
<211> LENGTH: 38
<212> TYPE: DNA
<213> ORGANISM: Artificial
<220> FEATURE:
<223> OTHER INFORMATION: synthesized primer

<400> SEQUENCE: 628

```
ctgatccgtc acgtcctgca agaactttaa cggcgtag                              38
```

<210> SEQ ID NO 629
<211> LENGTH: 40
<212> TYPE: DNA
<213> ORGANISM: Artificial
<220> FEATURE:
<223> OTHER INFORMATION: synthesized primer

<400> SEQUENCE: 629

```
ttaaagttct tgcagacggc ggatcaggcc aatactcatg                            40
```

<210> SEQ ID NO 630
<211> LENGTH: 42
<212> TYPE: DNA
<213> ORGANISM: Artificial

```
<220> FEATURE:
<223> OTHER INFORMATION: synthesized primer

<400> SEQUENCE: 630
tattggcctg atccgccgtc tgcaagaact ttaacggcgt ag                42

<210> SEQ ID NO 631
<211> LENGTH: 45
<212> TYPE: DNA
<213> ORGANISM: Artificial
<220> FEATURE:
<223> OTHER INFORMATION: synthesized primer

<400> SEQUENCE: 631
taaagttctt gcacatggag attcaggcca atactcatgg attat            45

<210> SEQ ID NO 632
<211> LENGTH: 44
<212> TYPE: DNA
<213> ORGANISM: Artificial
<220> FEATURE:
<223> OTHER INFORMATION: synthesized primer

<400> SEQUENCE: 632
agtattggcc tgaatctcca tgtgcaagaa ctttaacggc gtag              44

<210> SEQ ID NO 633
<211> LENGTH: 40
<212> TYPE: DNA
<213> ORGANISM: Artificial
<220> FEATURE:
<223> OTHER INFORMATION: synthesized primer

<400> SEQUENCE: 633
aagttcttgc agcacgtaac ggatcaggcc aatactcatg                   40

<210> SEQ ID NO 634
<211> LENGTH: 44
<212> TYPE: DNA
<213> ORGANISM: Artificial
<220> FEATURE:
<223> OTHER INFORMATION: synthesized primer

<400> SEQUENCE: 634
tattggcctg atccgttacg tgctgcaaga actttaacgg cgta              44

<210> SEQ ID NO 635
<211> LENGTH: 45
<212> TYPE: DNA
<213> ORGANISM: Artificial
<220> FEATURE:
<223> OTHER INFORMATION: synthesized primer

<400> SEQUENCE: 635
agttcttgca gcagtaggag atggccaata ctcatggatt atcaa             45

<210> SEQ ID NO 636
<211> LENGTH: 45
<212> TYPE: DNA
<213> ORGANISM: Artificial
<220> FEATURE:
<223> OTHER INFORMATION: synthesized primer

<400> SEQUENCE: 636
tgagtattgg ccatctccta ctgctgcaag aactttaacg gcgta             45
```

```
<210> SEQ ID NO 637
<211> LENGTH: 43
<212> TYPE: DNA
<213> ORGANISM: Artificial
<220> FEATURE:
<223> OTHER INFORMATION: synthesized primer

<400> SEQUENCE: 637
ttaaagttct tgcagcatgt agcggatcag gccaatactc atg        43

<210> SEQ ID NO 638
<211> LENGTH: 44
<212> TYPE: DNA
<213> ORGANISM: Artificial
<220> FEATURE:
<223> OTHER INFORMATION: synthesized primer

<400> SEQUENCE: 638
tattggcctg atccgctaca tgctgcaaga actttaacgg cgta       44

<210> SEQ ID NO 639
<211> LENGTH: 43
<212> TYPE: DNA
<213> ORGANISM: Artificial
<220> FEATURE:
<223> OTHER INFORMATION: synthesized primer

<400> SEQUENCE: 639
aagttcttgc agcagactct tcaggccaat actcatggat tat        43

<210> SEQ ID NO 640
<211> LENGTH: 41
<212> TYPE: DNA
<213> ORGANISM: Artificial
<220> FEATURE:
<223> OTHER INFORMATION: synthesized primer

<400> SEQUENCE: 640
atgagtattg gcctgaagag tctgctgcaa gaactttaac g          41

<210> SEQ ID NO 641
<211> LENGTH: 42
<212> TYPE: DNA
<213> ORGANISM: Artificial
<220> FEATURE:
<223> OTHER INFORMATION: synthesized primer

<400> SEQUENCE: 641
ttcttgcagc agactctgta ggccaatact catggattat ca         42

<210> SEQ ID NO 642
<211> LENGTH: 42
<212> TYPE: DNA
<213> ORGANISM: Artificial
<220> FEATURE:
<223> OTHER INFORMATION: synthesized primer

<400> SEQUENCE: 642
catgagtatt ggcctacaga gtctgctgca agaactttaa cg         42

<210> SEQ ID NO 643
<211> LENGTH: 43
<212> TYPE: DNA
<213> ORGANISM: Artificial
<220> FEATURE:
<223> OTHER INFORMATION: synthesized primer

<400> SEQUENCE: 643
```
aagttcttgc agcagacgat tcaggccaat actcatggat tat    43

<210> SEQ ID NO 644
<211> LENGTH: 41
<212> TYPE: DNA
<213> ORGANISM: Artificial
<220> FEATURE:
<223> OTHER INFORMATION: synthesized primer

<400> SEQUENCE: 644
atgagtattg gcctgaatcg tctgctgcaa gaactttaac g    41

<210> SEQ ID NO 645
<211> LENGTH: 43
<212> TYPE: DNA
<213> ORGANISM: Artificial
<220> FEATURE:
<223> OTHER INFORMATION: synthesized primer

<400> SEQUENCE: 645
aagttcttgc agcagacaat tcaggccaat actcatggat tat    43

<210> SEQ ID NO 646
<211> LENGTH: 41
<212> TYPE: DNA
<213> ORGANISM: Artificial
<220> FEATURE:
<223> OTHER INFORMATION: synthesized primer

<400> SEQUENCE: 646
atgagtattg gcctgaattg tctgctgcaa gaactttaac g    41

<210> SEQ ID NO 647
<211> LENGTH: 42
<212> TYPE: DNA
<213> ORGANISM: Artificial
<220> FEATURE:
<223> OTHER INFORMATION: synthesized primer

<400> SEQUENCE: 647
ttcttgcagc agacaatcta ggccaatact catggattat ca    42

<210> SEQ ID NO 648
<211> LENGTH: 42
<212> TYPE: DNA
<213> ORGANISM: Artificial
<220> FEATURE:
<223> OTHER INFORMATION: synthesized primer

<400> SEQUENCE: 648
catgagtatt ggcctagatt gtctgctgca agaactttaa cg    42

<210> SEQ ID NO 649
<211> LENGTH: 43
<212> TYPE: DNA
<213> ORGANISM: Artificial
<220> FEATURE:
<223> OTHER INFORMATION: synthesized primer

<400> SEQUENCE: 649
ttcttgcagc agacggagga ggccaatact catggattat caa    43

<210> SEQ ID NO 650
<211> LENGTH: 38
<212> TYPE: DNA
<213> ORGANISM: Artificial

```
<220> FEATURE:
<223> OTHER INFORMATION: synthesized primer

<400> SEQUENCE: 650
atgagtattg gcctcctccg tctgctgcaa gaacttta                              38

<210> SEQ ID NO 651
<211> LENGTH: 43
<212> TYPE: DNA
<213> ORGANISM: Artificial
<220> FEATURE:
<223> OTHER INFORMATION: synthesized primer

<400> SEQUENCE: 651
ttcttgcagc agacggagat ggccaatact catggattat caa                       43

<210> SEQ ID NO 652
<211> LENGTH: 38
<212> TYPE: DNA
<213> ORGANISM: Artificial
<220> FEATURE:
<223> OTHER INFORMATION: synthesized primer

<400> SEQUENCE: 652
atgagtattg gccatctccg tctgctgcaa gaacttta                              38

<210> SEQ ID NO 653
<211> LENGTH: 45
<212> TYPE: DNA
<213> ORGANISM: Artificial
<220> FEATURE:
<223> OTHER INFORMATION: synthesized primer

<400> SEQUENCE: 653
tgcagcagac ggagtaggca actactcatg gattatcaac ggcat                     45

<210> SEQ ID NO 654
<211> LENGTH: 45
<212> TYPE: DNA
<213> ORGANISM: Artificial
<220> FEATURE:
<223> OTHER INFORMATION: synthesized primer

<400> SEQUENCE: 654
ataatccatg agtagttgcc tactccgtct gctgcaagaa cttta                     45

<210> SEQ ID NO 655
<211> LENGTH: 43
<212> TYPE: DNA
<213> ORGANISM: Artificial
<220> FEATURE:
<223> OTHER INFORMATION: synthesized primer

<400> SEQUENCE: 655
ttcttgcagc agacggacgt ggccaatact catggattat caa                       43

<210> SEQ ID NO 656
<211> LENGTH: 38
<212> TYPE: DNA
<213> ORGANISM: Artificial
<220> FEATURE:
<223> OTHER INFORMATION: synthesized primer

<400> SEQUENCE: 656
atgagtattg gccacgtccg tctgctgcaa gaacttta                              38
```

```
<210> SEQ ID NO 657
<211> LENGTH: 43
<212> TYPE: DNA
<213> ORGANISM: Artificial
<220> FEATURE:
<223> OTHER INFORMATION: synthesized primer

<400> SEQUENCE: 657
aatgggccat ctctggtaga atggatgtaa tcaacatgag cct          43

<210> SEQ ID NO 658
<211> LENGTH: 42
<212> TYPE: DNA
<213> ORGANISM: Artificial
<220> FEATURE:
<223> OTHER INFORMATION: synthesized primer

<400> SEQUENCE: 658
gattacatcc attctaccag agatggccca ttcgatgccg tt           42

<210> SEQ ID NO 659
<211> LENGTH: 40
<212> TYPE: DNA
<213> ORGANISM: Artificial
<220> FEATURE:
<223> OTHER INFORMATION: synthesized primer

<400> SEQUENCE: 659
aatgggccat cggacgtaac atggatgtaa tcaacatgag              40

<210> SEQ ID NO 660
<211> LENGTH: 42
<212> TYPE: DNA
<213> ORGANISM: Artificial
<220> FEATURE:
<223> OTHER INFORMATION: synthesized primer

<400> SEQUENCE: 660
gattacatcc atgttacgtc cgatggccca ttcgatgccg tt           42

<210> SEQ ID NO 661
<211> LENGTH: 43
<212> TYPE: DNA
<213> ORGANISM: Artificial
<220> FEATURE:
<223> OTHER INFORMATION: synthesized primer

<400> SEQUENCE: 661
aatgggccat caattctgga atggatgtaa tcaacatgag cct          43

<210> SEQ ID NO 662
<211> LENGTH: 42
<212> TYPE: DNA
<213> ORGANISM: Artificial
<220> FEATURE:
<223> OTHER INFORMATION: synthesized primer

<400> SEQUENCE: 662
gattacatcc attccagaat tgatggccca ttcgatgccg tt           42

<210> SEQ ID NO 663
<211> LENGTH: 36
<212> TYPE: DNA
<213> ORGANISM: Artificial
<220> FEATURE:
<223> OTHER INFORMATION: synthesized primer

<400> SEQUENCE: 663
```
aaaacgggac ttcccaggcc tcgccgcatg tagctg                     36

<210> SEQ ID NO 664
<211> LENGTH: 38
<212> TYPE: DNA
<213> ORGANISM: Artificial
<220> FEATURE:
<223> OTHER INFORMATION: synthesized primer

<400> SEQUENCE: 664
tacatgcggc gaggcctggg aagtcccgtt ttgcgcac                   38

<210> SEQ ID NO 665
<211> LENGTH: 40
<212> TYPE: DNA
<213> ORGANISM: Artificial
<220> FEATURE:
<223> OTHER INFORMATION: synthesized primer

<400> SEQUENCE: 665
aaggctacac tggaagaaat gttaaagtag cggttatcga                 40

<210> SEQ ID NO 666
<211> LENGTH: 37
<212> TYPE: DNA
<213> ORGANISM: Artificial
<220> FEATURE:
<223> OTHER INFORMATION: synthesized primer

<400> SEQUENCE: 666
ctactttaac atttcttcca gtgtagcctt gagagtg                    37

<210> SEQ ID NO 667
<211> LENGTH: 38
<212> TYPE: DNA
<213> ORGANISM: Artificial
<220> FEATURE:
<223> OTHER INFORMATION: synthesized primer

<400> SEQUENCE: 667
ctacactgga tcatatgtta agtagcggt tatcgaca                    38

<210> SEQ ID NO 668
<211> LENGTH: 40
<212> TYPE: DNA
<213> ORGANISM: Artificial
<220> FEATURE:
<223> OTHER INFORMATION: synthesized primer

<400> SEQUENCE: 668
taaccgctac tttaacatat gatccagtgt agccttgaga                 40

<210> SEQ ID NO 669
<211> LENGTH: 36
<212> TYPE: DNA
<213> ORGANISM: Artificial
<220> FEATURE:
<223> OTHER INFORMATION: synthesized primer

<400> SEQUENCE: 669
cttctatggt ggattccgaa acaaacccgt ttcaag                     36

<210> SEQ ID NO 670
<211> LENGTH: 36
<212> TYPE: DNA
<213> ORGANISM: Artificial

```
<220> FEATURE:
<223> OTHER INFORMATION: synthesized primer

<400> SEQUENCE: 670
ggtttgtttc ggaatccacc atagaagccc ctccag                              36

<210> SEQ ID NO 671
<211> LENGTH: 39
<212> TYPE: DNA
<213> ORGANISM: Artificial
<220> FEATURE:
<223> OTHER INFORMATION: synthesized primer

<400> SEQUENCE: 671
tttcaagata acaatacaca tggcacacac gtcgcagga                            39

<210> SEQ ID NO 672
<211> LENGTH: 38
<212> TYPE: DNA
<213> ORGANISM: Artificial
<220> FEATURE:
<223> OTHER INFORMATION: synthesized primer

<400> SEQUENCE: 672
tgtgtgccat gtgtattgtt atcttgaaac gggtttgt                             38

<210> SEQ ID NO 673
<211> LENGTH: 34
<212> TYPE: DNA
<213> ORGANISM: Artificial
<220> FEATURE:
<223> OTHER INFORMATION: synthesized primer

<400> SEQUENCE: 673
gtttcaagat gaaaattctc atggcacaca cgtc                                 34

<210> SEQ ID NO 674
<211> LENGTH: 40
<212> TYPE: DNA
<213> ORGANISM: Artificial
<220> FEATURE:
<223> OTHER INFORMATION: synthesized primer

<400> SEQUENCE: 674
tgtgccatga gaattttcat cttgaaacgg gtttgtttcg                           40

<210> SEQ ID NO 675
<211> LENGTH: 39
<212> TYPE: DNA
<213> ORGANISM: Artificial
<220> FEATURE:
<223> OTHER INFORMATION: synthesized primer

<400> SEQUENCE: 675
aacccgtttc aagatccaaa ttctcatggc acacacgtc                            39

<210> SEQ ID NO 676
<211> LENGTH: 38
<212> TYPE: DNA
<213> ORGANISM: Artificial
<220> FEATURE:
<223> OTHER INFORMATION: synthesized primer

<400> SEQUENCE: 676
tgccatgaga atttggatct tgaaacgggt tgtttcg                              38
```

```
<210> SEQ ID NO 677
<211> LENGTH: 41
<212> TYPE: DNA
<213> ORGANISM: Artificial
<220> FEATURE:
<223> OTHER INFORMATION: synthesized primer

<400> SEQUENCE: 677
gtttcaagat aaccaatctc atggcacaca cgtcgcagga a                41

<210> SEQ ID NO 678
<211> LENGTH: 40
<212> TYPE: DNA
<213> ORGANISM: Artificial
<220> FEATURE:
<223> OTHER INFORMATION: synthesized primer

<400> SEQUENCE: 678
tgtgtgccat gagattggtt atcttgaaac gggtttgttt                 40

<210> SEQ ID NO 679
<211> LENGTH: 41
<212> TYPE: DNA
<213> ORGANISM: Artificial
<220> FEATURE:
<223> OTHER INFORMATION: synthesized primer

<400> SEQUENCE: 679
gtttcaagat aacgattctc atggcacaca cgtcgcagga a                41

<210> SEQ ID NO 680
<211> LENGTH: 40
<212> TYPE: DNA
<213> ORGANISM: Artificial
<220> FEATURE:
<223> OTHER INFORMATION: synthesized primer

<400> SEQUENCE: 680
tgtgtgccat gagaatcgtt atcttgaaac gggtttgttt                 40

<210> SEQ ID NO 681
<211> LENGTH: 36
<212> TYPE: DNA
<213> ORGANISM: Artificial
<220> FEATURE:
<223> OTHER INFORMATION: synthesized primer

<400> SEQUENCE: 681
tcaagataac aatcaacatg gcacacacgt cgcagg                     36

<210> SEQ ID NO 682
<211> LENGTH: 40
<212> TYPE: DNA
<213> ORGANISM: Artificial
<220> FEATURE:
<223> OTHER INFORMATION: synthesized primer

<400> SEQUENCE: 682
acgtgtgtgc catgttgatt gttatcttga aacgggtttg                 40

<210> SEQ ID NO 683
<211> LENGTH: 38
<212> TYPE: DNA
<213> ORGANISM: Artificial
<220> FEATURE:
<223> OTHER INFORMATION: synthesized primer

<400> SEQUENCE: 683
```
tcatggcaca cacgcagcag gaacggttgc ggcgttaa  38

<210> SEQ ID NO 684
<211> LENGTH: 38
<212> TYPE: DNA
<213> ORGANISM: Artificial
<220> FEATURE:
<223> OTHER INFORMATION: synthesized primer

<400> SEQUENCE: 684
caaccgttcc tgctgcgtgt gtgccatgag aattgtta  38

<210> SEQ ID NO 685
<211> LENGTH: 33
<212> TYPE: DNA
<213> ORGANISM: Artificial
<220> FEATURE:
<223> OTHER INFORMATION: synthesized primer

<400> SEQUENCE: 685
tgtagccccg gatgcttcgc tctacgccgt taa  33

<210> SEQ ID NO 686
<211> LENGTH: 35
<212> TYPE: DNA
<213> ORGANISM: Artificial
<220> FEATURE:
<223> OTHER INFORMATION: synthesized primer

<400> SEQUENCE: 686
cgtagagcga agcatccggg gctacaccaa gcacg  35

<210> SEQ ID NO 687
<211> LENGTH: 36
<212> TYPE: DNA
<213> ORGANISM: Artificial
<220> FEATURE:
<223> OTHER INFORMATION: synthesized primer

<400> SEQUENCE: 687
cgttaaagtt acagcagcag acggatcagg ccaata  36

<210> SEQ ID NO 688
<211> LENGTH: 40
<212> TYPE: DNA
<213> ORGANISM: Artificial
<220> FEATURE:
<223> OTHER INFORMATION: synthesized primer

<400> SEQUENCE: 688
tgatccgtct gctgctgtaa ctttaacggc gtagagcgaa  40

<210> SEQ ID NO 689
<211> LENGTH: 36
<212> TYPE: DNA
<213> ORGANISM: Artificial
<220> FEATURE:
<223> OTHER INFORMATION: synthesized primer

<400> SEQUENCE: 689
taatcaacat gagcgcggga gcaccaagcg gcagtg  36

<210> SEQ ID NO 690
<211> LENGTH: 35
<212> TYPE: DNA
<213> ORGANISM: Artificial

```
<220> FEATURE:
<223> OTHER INFORMATION: synthesized primer

<400> SEQUENCE: 690
ttggtgctcc cgcgctcatg ttgattacat ccatg                                35

<210> SEQ ID NO 691
<211> LENGTH: 36
<212> TYPE: DNA
<213> ORGANISM: Artificial
<220> FEATURE:
<223> OTHER INFORMATION: synthesized primer

<400> SEQUENCE: 691
taatcaacat gagcacggga gcaccaagcg gcagtg                               36

<210> SEQ ID NO 692
<211> LENGTH: 35
<212> TYPE: DNA
<213> ORGANISM: Artificial
<220> FEATURE:
<223> OTHER INFORMATION: synthesized primer

<400> SEQUENCE: 692
ttggtgctcc cgtgctcatg ttgattacat ccatg                                35

<210> SEQ ID NO 693
<211> LENGTH: 38
<212> TYPE: DNA
<213> ORGANISM: Artificial
<220> FEATURE:
<223> OTHER INFORMATION: synthesized primer

<400> SEQUENCE: 693
atgtaatcaa catggcactg ggagcaccaa gcggcagt                             38

<210> SEQ ID NO 694
<211> LENGTH: 40
<212> TYPE: DNA
<213> ORGANISM: Artificial
<220> FEATURE:
<223> OTHER INFORMATION: synthesized primer

<400> SEQUENCE: 694
ttggtgctcc cagtgccatg ttgattacat ccatgttatt                           40

<210> SEQ ID NO 695
<211> LENGTH: 34
<212> TYPE: DNA
<213> ORGANISM: Artificial
<220> FEATURE:
<223> OTHER INFORMATION: synthesized primer

<400> SEQUENCE: 695
tgggagcacc accaggcagt gcggcactta aagc                                 34

<210> SEQ ID NO 696
<211> LENGTH: 36
<212> TYPE: DNA
<213> ORGANISM: Artificial
<220> FEATURE:
<223> OTHER INFORMATION: synthesized primer

<400> SEQUENCE: 696
gtgccgcact gcctggtggt gctcccaggc tcatgt                               36
```

```
<210> SEQ ID NO 697
<211> LENGTH: 37
<212> TYPE: DNA
<213> ORGANISM: Artificial
<220> FEATURE:
<223> OTHER INFORMATION: synthesized primer

<400> SEQUENCE: 697
tgagcctggg agcacttagc ggcagtgcgg cacttaa                              37

<210> SEQ ID NO 698
<211> LENGTH: 39
<212> TYPE: DNA
<213> ORGANISM: Artificial
<220> FEATURE:
<223> OTHER INFORMATION: synthesized primer

<400> SEQUENCE: 698
tgccgcactg ccgctaagtg ctcccaggct catgttgat                            39

<210> SEQ ID NO 699
<211> LENGTH: 37
<212> TYPE: DNA
<213> ORGANISM: Artificial
<220> FEATURE:
<223> OTHER INFORMATION: synthesized primer

<400> SEQUENCE: 699
tgagcctggg agcagaaagc ggcagtgcgg cacttaa                              37

<210> SEQ ID NO 700
<211> LENGTH: 39
<212> TYPE: DNA
<213> ORGANISM: Artificial
<220> FEATURE:
<223> OTHER INFORMATION: synthesized primer

<400> SEQUENCE: 700
tgccgcactg ccgctttctg ctcccaggct catgttgat                            39

<210> SEQ ID NO 701
<211> LENGTH: 37
<212> TYPE: DNA
<213> ORGANISM: Artificial
<220> FEATURE:
<223> OTHER INFORMATION: synthesized primer

<400> SEQUENCE: 701
tgagcctggg agcatctagc ggcagtgcgg cacttaa                              37

<210> SEQ ID NO 702
<211> LENGTH: 39
<212> TYPE: DNA
<213> ORGANISM: Artificial
<220> FEATURE:
<223> OTHER INFORMATION: synthesized primer

<400> SEQUENCE: 702
tgccgcactg ccgctagatg ctcccaggct catgttgat                            39

<210> SEQ ID NO 703
<211> LENGTH: 35
<212> TYPE: DNA
<213> ORGANISM: Artificial
<220> FEATURE:
<223> OTHER INFORMATION: synthesized primer

<400> SEQUENCE: 703
```
gactcgagcc atgaagatct aaagtcgct ggagg                      35

<210> SEQ ID NO 704
<211> LENGTH: 36
<212> TYPE: DNA
<213> ORGANISM: Artificial
<220> FEATURE:
<223> OTHER INFORMATION: synthesized primer

<400> SEQUENCE: 704
gactttaaga tcttcatggc tcgagtcgat accgct                    36

<210> SEQ ID NO 705
<211> LENGTH: 40
<212> TYPE: DNA
<213> ORGANISM: Artificial
<220> FEATURE:
<223> OTHER INFORMATION: synthesized primer

<400> SEQUENCE: 705
gcagtccgtg cctcaaggcg tatcacaaat taaagcccct                40

<210> SEQ ID NO 706
<211> LENGTH: 40
<212> TYPE: DNA
<213> ORGANISM: Artificial
<220> FEATURE:
<223> OTHER INFORMATION: synthesized primer

<400> SEQUENCE: 706
atttgtgata cgccttgagg cacggactgc gcgtacgcat                40

<210> SEQ ID NO 707
<211> LENGTH: 40
<212> TYPE: DNA
<213> ORGANISM: Artificial
<220> FEATURE:
<223> OTHER INFORMATION: synthesized primer

<400> SEQUENCE: 707
cagacggatc agcacaatac tcatggatta tcaacggcat                40

<210> SEQ ID NO 708
<211> LENGTH: 40
<212> TYPE: DNA
<213> ORGANISM: Artificial
<220> FEATURE:
<223> OTHER INFORMATION: synthesized primer

<400> SEQUENCE: 708
taatccatga gtattgtgct gatccgtctg ctgcaagaac                40

<210> SEQ ID NO 709
<211> LENGTH: 38
<212> TYPE: DNA
<213> ORGANISM: Artificial
<220> FEATURE:
<223> OTHER INFORMATION: synthesized primer

<400> SEQUENCE: 709
gcagcagacg gaaacggcca atactcatgg attatcaa                  38

<210> SEQ ID NO 710
<211> LENGTH: 39
<212> TYPE: DNA
<213> ORGANISM: Artificial

```
<220> FEATURE:
<223> OTHER INFORMATION: synthesized primer

<400> SEQUENCE: 710
catgagtatt ggccgtttcc gtctgctgca agaacttta                                  39

<210> SEQ ID NO 711
<211> LENGTH: 40
<212> TYPE: DNA
<213> ORGANISM: Artificial
<220> FEATURE:
<223> OTHER INFORMATION: synthesized primer

<400> SEQUENCE: 711
ttcttgcagc agacgaatca ggccaatact catggattat                                 40

<210> SEQ ID NO 712
<211> LENGTH: 40
<212> TYPE: DNA
<213> ORGANISM: Artificial
<220> FEATURE:
<223> OTHER INFORMATION: synthesized primer

<400> SEQUENCE: 712
tgagtattgg cctgattcgt ctgctgcaag aactttaacg                                 40

<210> SEQ ID NO 713
<211> LENGTH: 38
<212> TYPE: DNA
<213> ORGANISM: Artificial
<220> FEATURE:
<223> OTHER INFORMATION: synthesized primer

<400> SEQUENCE: 713
atcgaatggg ccgtagcgaa taacatggat gtaatcaa                                   38

<210> SEQ ID NO 714
<211> LENGTH: 40
<212> TYPE: DNA
<213> ORGANISM: Artificial
<220> FEATURE:
<223> OTHER INFORMATION: synthesized primer

<400> SEQUENCE: 714
catccatgtt attcgctacg gcccattcga tgccgttgat                                 40

<210> SEQ ID NO 715
<211> LENGTH: 38
<212> TYPE: DNA
<213> ORGANISM: Artificial
<220> FEATURE:
<223> OTHER INFORMATION: synthesized primer

<400> SEQUENCE: 715
gttgataaag ctgttaaatc tggtgtcgtc gtagtagc                                   38

<210> SEQ ID NO 716
<211> LENGTH: 38
<212> TYPE: DNA
<213> ORGANISM: Artificial
<220> FEATURE:
<223> OTHER INFORMATION: synthesized primer

<400> SEQUENCE: 716
gacgacacca gatttaacag ctttatcaac tgctgctt                                   38
```

```
<210> SEQ ID NO 717
<211> LENGTH: 39
<212> TYPE: DNA
<213> ORGANISM: Artificial
<220> FEATURE:
<223> OTHER INFORMATION: synthesized primer

<400> SEQUENCE: 717
gataaagctg ttgcagatgg tgtcgtcgta gtagcggca                                39

<210> SEQ ID NO 718
<211> LENGTH: 40
<212> TYPE: DNA
<213> ORGANISM: Artificial
<220> FEATURE:
<223> OTHER INFORMATION: synthesized primer

<400> SEQUENCE: 718
tactacgacg acaccatctg caacagcttt atcaactgct                               40

<210> SEQ ID NO 719
<211> LENGTH: 38
<212> TYPE: DNA
<213> ORGANISM: Artificial
<220> FEATURE:
<223> OTHER INFORMATION: synthesized primer

<400> SEQUENCE: 719
aatgagggaa caaaaggatc atcgagtacc gtcggtta                                 38

<210> SEQ ID NO 720
<211> LENGTH: 40
<212> TYPE: DNA
<213> ORGANISM: Artificial
<220> FEATURE:
<223> OTHER INFORMATION: synthesized primer

<400> SEQUENCE: 720
acggtactcg atgatccttt tgttccctca ttcccagctg                               40

<210> SEQ ID NO 721
<211> LENGTH: 39
<212> TYPE: DNA
<213> ORGANISM: Artificial
<220> FEATURE:
<223> OTHER INFORMATION: synthesized primer

<400> SEQUENCE: 721
aacatccgga tcaaaaagta ccgtcggtta tccaggcaa                                39

<210> SEQ ID NO 722
<211> LENGTH: 39
<212> TYPE: DNA
<213> ORGANISM: Artificial
<220> FEATURE:
<223> OTHER INFORMATION: synthesized primer

<400> SEQUENCE: 722
ataaccgacg gtactttttg atccggatgt tccctcatt                                39

<210> SEQ ID NO 723
<211> LENGTH: 40
<212> TYPE: DNA
<213> ORGANISM: Artificial
<220> FEATURE:
<223> OTHER INFORMATION: synthesized primer

<400> SEQUENCE: 723
```
tgttgcatct ggtccagtcg tagtagcggc agctgggaat                                  40

<210> SEQ ID NO 724
<211> LENGTH: 40
<212> TYPE: DNA
<213> ORGANISM: Artificial
<220> FEATURE:
<223> OTHER INFORMATION: synthesized primer

<400> SEQUENCE: 724
tgccgctact acgactggac cagatgcaac agctttatca                                  40

<210> SEQ ID NO 725
<211> LENGTH: 38
<212> TYPE: DNA
<213> ORGANISM: Artificial
<220> FEATURE:
<223> OTHER INFORMATION: synthesized primer

<400> SEQUENCE: 725
agggaacatc cggaccatcg agtaccgtcg gttatcca                                    38

<210> SEQ ID NO 726
<211> LENGTH: 40
<212> TYPE: DNA
<213> ORGANISM: Artificial
<220> FEATURE:
<223> OTHER INFORMATION: synthesized primer

<400> SEQUENCE: 726
accgacggta ctcgatggtc cggatgttcc ctcattccca                                  40

<210> SEQ ID NO 727
<211> LENGTH: 40
<212> TYPE: DNA
<213> ORGANISM: Artificial
<220> FEATURE:
<223> OTHER INFORMATION: synthesized primer

<400> SEQUENCE: 727
cttcaaatca acgtgactct ttttcctccg tgggaccgga                                  40

<210> SEQ ID NO 728
<211> LENGTH: 40
<212> TYPE: DNA
<213> ORGANISM: Artificial
<220> FEATURE:
<223> OTHER INFORMATION: synthesized primer

<400> SEQUENCE: 728
acggaggaaa aagagtcacg ttgatttgaa gagtctacag                                  40

<210> SEQ ID NO 729
<211> LENGTH: 40
<212> TYPE: DNA
<213> ORGANISM: Artificial
<220> FEATURE:
<223> OTHER INFORMATION: synthesized primer

<400> SEQUENCE: 729
tcaacgtgcc tctgattcct ccgtgggacc ggagctggat                                  40

<210> SEQ ID NO 730
<211> LENGTH: 37
<212> TYPE: DNA
<213> ORGANISM: Artificial

```
<220> FEATURE:
<223> OTHER INFORMATION: synthesized primer

<400> SEQUENCE: 730
tcccacggag gaatcagagg cacgttgatt tgaagag                      37

<210> SEQ ID NO 731
<211> LENGTH: 38
<212> TYPE: DNA
<213> ORGANISM: Artificial
<220> FEATURE:
<223> OTHER INFORMATION: synthesized primer

<400> SEQUENCE: 731
tactatggaa aagggtaat caacgtacag gcggcagc                      38

<210> SEQ ID NO 732
<211> LENGTH: 38
<212> TYPE: DNA
<213> ORGANISM: Artificial
<220> FEATURE:
<223> OTHER INFORMATION: synthesized primer

<400> SEQUENCE: 732
ctgtacgttg attaccccctt ttccatagta gaaagaat                    38

<210> SEQ ID NO 733
<211> LENGTH: 36
<212> TYPE: DNA
<213> ORGANISM: Artificial
<220> FEATURE:
<223> OTHER INFORMATION: synthesized primer

<400> SEQUENCE: 733
tggcgtttct attgaatcga cgcttccagg gaacaa                       36

<210> SEQ ID NO 734
<211> LENGTH: 37
<212> TYPE: DNA
<213> ORGANISM: Artificial
<220> FEATURE:
<223> OTHER INFORMATION: synthesized primer

<400> SEQUENCE: 734
ctggaagcgt cgattcaata gaaacgccag gggccat                      37

<210> SEQ ID NO 735
<211> LENGTH: 36
<212> TYPE: DNA
<213> ORGANISM: Artificial
<220> FEATURE:
<223> OTHER INFORMATION: synthesized primer

<400> SEQUENCE: 735
cttccaggga acacatatgg tgcgcaaaac gggact                       36

<210> SEQ ID NO 736
<211> LENGTH: 38
<212> TYPE: DNA
<213> ORGANISM: Artificial
<220> FEATURE:
<223> OTHER INFORMATION: synthesized primer

<400> SEQUENCE: 736
gttttgcgca ccatatgtgt tccctggaag cgtcgatt                     38
```

-continued

<210> SEQ ID NO 737
<211> LENGTH: 36
<212> TYPE: DNA
<213> ORGANISM: Artificial
<220> FEATURE:
<223> OTHER INFORMATION: synthesized primer

<400> SEQUENCE: 737
cttccaggga acctttatgg tgcgcaaaac gggact        36

<210> SEQ ID NO 738
<211> LENGTH: 38
<212> TYPE: DNA
<213> ORGANISM: Artificial
<220> FEATURE:
<223> OTHER INFORMATION: synthesized primer

<400> SEQUENCE: 738
gttttgcgca ccataaaggt tccctggaag cgtcgatt        38

<210> SEQ ID NO 739
<211> LENGTH: 40
<212> TYPE: DNA
<213> ORGANISM: Artificial
<220> FEATURE:
<223> OTHER INFORMATION: synthesized primer

<400> SEQUENCE: 739
tttctactat ggaaacgggc tgatcaacgt acaggcggca        40

<210> SEQ ID NO 740
<211> LENGTH: 40
<212> TYPE: DNA
<213> ORGANISM: Artificial
<220> FEATURE:
<223> OTHER INFORMATION: synthesized primer

<400> SEQUENCE: 740
acgttgatca gcccgtttcc atagtagaaa gaatcaccaa        40

<210> SEQ ID NO 741
<211> LENGTH: 39
<212> TYPE: DNA
<213> ORGANISM: Artificial
<220> FEATURE:
<223> OTHER INFORMATION: synthesized primer

<400> SEQUENCE: 741
tttctaagca cccgaaatgg acaaacactc aagtccgca        39

<210> SEQ ID NO 742
<211> LENGTH: 38
<212> TYPE: DNA
<213> ORGANISM: Artificial
<220> FEATURE:
<223> OTHER INFORMATION: synthesized primer

<400> SEQUENCE: 742
gagtgtttgt ccatttcggg tgcttagaaa gaatcaat        38

<210> SEQ ID NO 743
<211> LENGTH: 39
<212> TYPE: DNA
<213> ORGANISM: Artificial
<220> FEATURE:
<223> OTHER INFORMATION: synthesized primer

<400> SEQUENCE: 743

```
ttctttctaa gcaccgtaac tggacaaaca ctcaagtcc                    39

<210> SEQ ID NO 744
<211> LENGTH: 38
<212> TYPE: DNA
<213> ORGANISM: Artificial
<220> FEATURE:
<223> OTHER INFORMATION: synthesized primer

<400> SEQUENCE: 744
tgtttgtcca gttacggtgc ttagaaagaa tcaatgcg                     38

<210> SEQ ID NO 745
<211> LENGTH: 36
<212> TYPE: DNA
<213> ORGANISM: Artificial
<220> FEATURE:
<223> OTHER INFORMATION: synthesized primer

<400> SEQUENCE: 745
cacccgaact ggcgtaacac tcaagtccgc agcagt                       36

<210> SEQ ID NO 746
<211> LENGTH: 40
<212> TYPE: DNA
<213> ORGANISM: Artificial
<220> FEATURE:
<223> OTHER INFORMATION: synthesized primer

<400> SEQUENCE: 746
tgcggacttg agtgttacgc cagttcgggt gcttagaaag                   40

<210> SEQ ID NO 747
<211> LENGTH: 33
<212> TYPE: DNA
<213> ORGANISM: Artificial
<220> FEATURE:
<223> OTHER INFORMATION: synthesized primer

<400> SEQUENCE: 747
cgtctgctta cctctacgcc gttaaagttc ttg                          33

<210> SEQ ID NO 748
<211> LENGTH: 40
<212> TYPE: DNA
<213> ORGANISM: Artificial
<220> FEATURE:
<223> OTHER INFORMATION: synthesized primer

<400> SEQUENCE: 748
actttaacgg cgtagaggta agcagacggg gctacaccaa                   40

<210> SEQ ID NO 749
<211> LENGTH: 36
<212> TYPE: DNA
<213> ORGANISM: Artificial
<220> FEATURE:
<223> OTHER INFORMATION: synthesized primer

<400> SEQUENCE: 749
agcctgggag cacaaagcgg cagtgcggca cttaaa                       36

<210> SEQ ID NO 750
<211> LENGTH: 34
<212> TYPE: DNA
<213> ORGANISM: Artificial
```

<220> FEATURE:
<223> OTHER INFORMATION: synthesized primer

<400> SEQUENCE: 750
cactgccgct ttgtgctccc aggctcatgt tgat 34

<210> SEQ ID NO 751
<211> LENGTH: 41
<212> TYPE: DNA
<213> ORGANISM: Artificial
<220> FEATURE:
<223> OTHER INFORMATION: synthesized primer

<400> SEQUENCE: 751
ttcaatcgac gcttccaacg aacaagtatg gtgcgcaaaa c 41

<210> SEQ ID NO 752
<211> LENGTH: 39
<212> TYPE: DNA
<213> ORGANISM: Artificial
<220> FEATURE:
<223> OTHER INFORMATION: synthesized primer

<400> SEQUENCE: 752
caccatactt gttcgttgga agcgtcgatt gaatagaaa 39

<210> SEQ ID NO 753
<211> LENGTH: 39
<212> TYPE: DNA
<213> ORGANISM: Artificial
<220> FEATURE:
<223> OTHER INFORMATION: synthesized primer

<400> SEQUENCE: 753
tggattatca acggcgtaga atgggccatc gcgaataac 39

<210> SEQ ID NO 754
<211> LENGTH: 39
<212> TYPE: DNA
<213> ORGANISM: Artificial
<220> FEATURE:
<223> OTHER INFORMATION: synthesized primer

<400> SEQUENCE: 754
cgatggccca ttctacgccg ttgataatcc atgagtatt 39

<210> SEQ ID NO 755
<211> LENGTH: 269
<212> TYPE: PRT
<213> ORGANISM: Bacillus lentus

<400> SEQUENCE: 755

```
Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

```
Ser Gly Ser Gly Ser Val Ser Ser Ile Ala Gln Gly Leu Glu Trp Ala
            100                 105                 110
Gly Asn Asn Gly Met His Val Ala Asn Leu Ser Leu Gly Ser Pro Ser
        115                 120                 125
Pro Ser Ala Thr Leu Glu Gln Ala Val Asn Ser Thr Ser Arg Gly
    130                 135                 140
Val Leu Val Val Ala Ala Ser Gly Asn Ser Gly Ala Gly Ser Ile Ser
145                 150                 155                 160
Tyr Pro Ala Arg Tyr Ala Asn Ala Met Ala Val Gly Ala Thr Asp Gln
                165                 170                 175
Asn Asn Asn Arg Ala Ser Phe Ser Gln Tyr Gly Ala Gly Leu Asp Ile
            180                 185                 190
Val Ala Pro Gly Val Asn Val Gln Ser Thr Tyr Pro Gly Ser Thr Tyr
        195                 200                 205
Ala Ser Leu Asn Gly Thr Ser Met Ala Thr Pro His Val Ala Gly Ala
    210                 215                 220
Ala Ala Leu Val Lys Gln Lys Asn Pro Ser Trp Ser Asn Val Gln Ile
225                 230                 235                 240
Arg Asn His Leu Lys Asn Thr Ala Thr Ser Leu Gly Ser Thr Asn Leu
                245                 250                 255
Tyr Gly Ser Gly Leu Val Asn Ala Glu Ala Ala Thr Arg
            260                 265

<210> SEQ ID NO 756
<211> LENGTH: 1143
<212> TYPE: DNA
<213> ORGANISM: Bacillus lentus

<400> SEQUENCE: 756
gtgagaagca aaaaattgtg gatcgtcgcg tcgaccgcac tactcatttc tgttgctttc      60
agttcatcga tcgcatcggc tgctgaagaa gcaaaagaaa atatttaat tggctttaat     120
gagcaggaag ctgtcagtga gtttgtagaa caagtagagg caaatgacga ggtcgccatt     180
ctctctgagg aagaggaagt cgaaattgaa ttgcttcatg aatttgaaac gattcctgtt     240
ttatccgttg agttaagccc agaagatgtg gacgcgcttg agctcgatcc agcgatttct     300
tatattgaag aggatgcaga agtaacgaca atggcgcaat cagtgccatg ggaattagc     360
cgtgtgcaag ccccagctgc ccataaccgt ggattgacag gttctggtgt aaaagttgct     420
gtcctcgata caggtatttc cactcatcca gacttaaata ttcgtggtgg cgctagcttt     480
gtaccagggg aaccatccac tcaagatggg aatgggcatg gcacgcatgt ggccgggacg     540
attgctgctt taaacaattc gattggcgtt cttggcgtag cgccgagcgc ggaactatac     600
gctgttaaag tattaggggc gagcggttca ggttcggtca gctcgattgc ccaaggattg     660
gaatgggcag gaacaatgg catgcacgtt gctaatttga gtttaggaag cccttcgcca     720
agtgccacac ttgagcaagc tgttaatagc gcgacttcta gaggcgttct tgttgtagcg     780
gcatctggaa attcaggtgc aggctcaatc agctatccgg cccgttatgc gaacgcaatg     840
gcagtcggag ctactgacca aaacaacaac cgcgccagct tttcacagta tggcgcaggg     900
cttgacattg tcgcaccagg tgtaaacgtg cagagcacat acccaggttc aacgtatgcc     960
agcttaaacg gtacatcgat ggctactcct catgttgcag gtgcagcagc ccttgtaaaa    1020
caaaagaacc catcttggtc caatgtacaa atccgcaatc atctaaagaa tacggcaacg    1080
agcttaggaa gcacgaactt gtatggaagc ggacttgtca atgcagaagc tgcaactcgt    1140
```

-continued

```
taa                                                              1143
```

<210> SEQ ID NO 757
<211> LENGTH: 380
<212> TYPE: PRT
<213> ORGANISM: Bacillus lentus

<400> SEQUENCE: 757

```
Val Arg Ser Lys Lys Leu Trp Ile Val Ala Ser Thr Ala Leu Leu Ile
1               5                   10                  15

Ser Val Ala Phe Ser Ser Ser Ile Ala Ser Ala Ala Glu Glu Ala Lys
            20                  25                  30

Glu Lys Tyr Leu Ile Gly Phe Asn Glu Gln Glu Ala Val Ser Glu Phe
        35                  40                  45

Val Glu Gln Val Glu Ala Asn Asp Gl 370 375 380

<210> SEQ ID NO 758
<211> LENGTH: 27
<212> TYPE: DNA
<213> ORGANISM: Artificial
<220> FEATURE:
<223> OTHER INFORMATION: synthesized primer

<400> SEQUENCE: 758
cgcgcttgag ctcgatccag cgatttc 27

<210> SEQ ID NO 759
<211> LENGTH: 25
<212> TYPE: DNA
<213> ORGANISM: Artificial
<220> FEATURE:
<223> OTHER INFORMATION: synthesized primer

<400> SEQUENCE: 759
gtctccaagc tttaacgagt tgcag 25

<210> SEQ ID NO 760
<211> LENGTH: 30
<212> TYPE: DNA
<213> ORGANISM: Artificial
<220> FEATURE:
<223> OTHER INFORMATION: synthesized primer

<400> SEQUENCE: 760
gcaattcaga tcttccttca ggttatgacc 30

<210> SEQ ID NO 761
<211> LENGTH: 30
<212> TYPE: DNA
<213> ORGANISM: Artificial
<220> FEATURE:
<223> OTHER INFORMATION: synthesized primer

<400> SEQUENCE: 761
gcatcgaaga tctgattgct taactgcttc 30

<210> SEQ ID NO 762
<211> LENGTH: 1143
<212> TYPE: DNA
<213> ORGANISM: Artificial
<220> FEATURE:
<223> OTHER INFORMATION: synthesized Bacillus lentus variant

<400> SEQUENCE: 762
gtgagaagca aaaaattgtg gatcgtcgcg tcgaccgcac tactcatttc tgttgctttt 60
agttcatcga tcgcatcggc tgctgaagaa gcaaaagaaa aatatttaat tggctttaat 120
gagcaggaag ctgtcagtga gtttgtagaa caagtagagg caaatgacga ggtcgccatt 180
ctctctgagg aagaggaagt cgaaattgaa ttgcttcatg aatttgaaac gattcctgtt 240
ttatccgttg agttaagccc agaagatgtg gacgcgcttg aactcgatcc agcgatttct 300
tatattgaag aggatgcaga agtaacgaca atggcgcaat cagtgccatg gggaattagc 360
cgtgtgcaag ccccggctgc ccataaccgt ggattgacag gttctggtgt aaaagttgct 420
gtcctcgata caggtatttc cactcatcca gacttaaata ttcgtggtgg cgctagcttt 480
gtaccagggg aaccatccac tcaagatggg aatgggcatg gcacgcatgt ggccgggacg 540
attgctgctc taaacaattc gattggcgta cttggcgtag cgccgagcgc ggaactatac 600

-continued

```
gctgttaaag tattaggggc gagcggtggg ggcgccatca gctcgattgc ccaaggattg    660
gaatgggcag ggaacaatgg catgcacgtt gctaatttga gtttaggaag cccttcgcca    720
agtgccacac ttgagcaagc tgttaatagc gcgacttcta ggggcgttct tgttgtagcg    780
gcatctggaa attcgggtgc agactcaatc agctatccgg cccgttatgc gaacgcaatg    840
gcagtcggag ctactgacca aaacaacaac cgcgccagct tttcacagta tggcgcaggg    900
cttgacatcg tcgcaccagg tgtaaacgtg cagagcacat acccaggttc aacgtatgcc    960
agcttaaacg gtacatcgat ggctactcct catgttgcag gtgcagcagt ccttgttaaa   1020
cataagaacc catcttggtc caatgtacga atccgcgatc atctaaagaa aacggcaacg   1080
agcttaggaa gcacgaactt gtatggaagc ggacttgtca atgccgaagc tgcaactcgt   1140
taa                                                                 1143
```

<210> SEQ ID NO 763
<211> LENGTH: 380
<212> TYPE: PRT
<213> ORGANISM: Artificial
<220> FEATURE:
<223> OTHER INFORMATION: synthesized Bacillus lentus variant

<400> SEQUENCE: 763

```
Val Arg Ser Lys Lys Leu Trp Ile Val Ala Ser Thr Ala Leu Leu Ile
1               5                   10                  15

Ser Val Ala Phe Ser Ser Ser Ile Ala Ser Ala Ala Glu Glu Ala Lys
            20                  25                  30

Glu Lys Tyr Leu Ile Gly Phe Asn Glu Gln Glu Ala Val Ser Glu Phe
        35                  40                  45

Val Glu Gln Val Glu Ala Asn Asp Glu Val Ala Ile Leu Ser Glu Glu
    50                  55                  60

Glu Glu Val Glu Ile Glu Leu Leu His Glu Phe Glu Thr Ile Pro Val
65                  70                  75                  80

Leu Ser Val Glu Leu Ser Pro Glu Asp Val Asp Ala Leu Glu Leu Asp
                85                  90                  95

Pro Ala Ile Ser Tyr Ile Glu Glu Asp Ala Glu Val Thr Thr Met Ala
            100                 105                 110

Gln Ser Val Pro Trp Gly Ile Ser Arg Val Gln Ala Pro Ala Ala His
        115                 120                 125

Asn Arg Gly Leu Thr Gly Ser Gly Val Lys Val Ala Val Leu Asp Thr
    130                 135                 140

Gly Ile Ser Thr His Pro Asp Leu Asn Ile Arg Gly Gly Ala Ser Phe
145                 150                 155                 160

Val Pro Gly Glu Pro Ser Thr Gln Asp Gly Asn Gly His Gly Thr His
                165                 170                 175

Val Ala Gly Thr Ile Ala Ala Leu Asn Asn Ser Ile Gly Val Leu Gly
            180                 185                 190

Val Ala Pro Ser Ala Glu Leu Tyr Ala Val Lys Val Leu Gly Ala Ser
        195                 200                 205

Gly Gly Gly Ala Ile Ser Ser Ile Ala Gln Gly Leu Glu Trp Ala Gly
    210                 215                 220

Asn Asn Gly Met His Val Ala Asn Leu Ser Leu Gly Ser Pro Ser Pro
225                 230                 235                 240

Ser Ala Thr Leu Glu Gln Ala Val Asn Ser Ala Thr Ser Arg Gly Val
                245                 250                 255

Leu Val Val Ala Ala Ser Gly Asn Ser Gly Ala Asp Ser Ile Ser Tyr
            260                 265                 270
```

```
Pro Ala Arg Tyr Ala Asn Ala Met Ala Val Gly Ala Thr Asp Gln Asn
        275                 280                 285

Asn Asn Arg Ala Ser Phe Ser Gln Tyr Gly Ala Gly Leu Asp Ile Val
    290                 295                 300

Ala Pro Gly Val Asn Val Gln Ser Thr Tyr Pro Gly Ser Thr Tyr Ala
305                 310                 315                 320

Ser Leu Asn Gly Thr Ser Met Ala Thr Pro His Val Ala Gly Ala Ala
                325                 330                 335

Val Leu Val Lys His Lys Asn Pro Ser Trp Ser Asn Val Arg Ile Arg
            340                 345                 350

Asp His Leu Lys Lys Thr Ala Thr Ser Leu Gly Ser Thr Asn Leu Tyr
        355                 360                 365

Gly Ser Gly Leu Val Asn Ala Glu Ala Ala Thr Arg
    370                 375                 380

<210> SEQ ID NO 764
<211> LENGTH: 1140
<212> TYPE: DNA
<213> ORGANISM: Artificial
<220> FEATURE:
<223> OTHER INFORMATION: synthesized Bacillus lentus variant

<400> SEQUENCE: 764
gtgagaagca aaaaattgtg atcgtcgcg tcgaccgcac tactcatttc tgttgctttt      60
agttcatcga tcgcatcggc tgctgaagaa gcaaaagaaa atatttaat tggctttaat    120
gagcaggaag ctgtcagtga gtttgtagaa caagtagagg caaatgacga ggtcgccatt    180
ctctctgagg aagaggaagt cgaaattgaa ttgcttcatg aatttgaaac gattcctgtt    240
ttatccgttg agttaagccc agaagatgtg gacgcgcttg aactcgatcc agcgatttct    300
tatattgaag aggatgcaga agtaacgaca atggcgcaat cagtgccatg gggaattagc    360
cgtgtgcaag ccccggctgc ccataaccgt ggattgacag gttctggtgt aaaagttgct    420
gtcctcgata caggtatttc cactcatcca gacttaaata ttcgtggtgg cgctagcttt    480
gtaccagggg aaccatccac tcaagatggg aatgggcatg gcacgcatgt ggccgggacg    540
attgctgctc taaacaattc gattggcgta cttggcgtag cgccgagcgc ggaactatac    600
gctgttaaag tattaggggc gagcggtggg gcgccatca gctcgattgc ccaaggattg    660
gaatgggcag ggaacaatgg catgcacgtt gctaatttga gtttaggaag cccttcgcca    720
agtgccacac ttgagcaagc tgttaatagc gcgacttcta ggggcgttct tgttgtagcg    780
gcatctggaa attcgggtgc agactcaatc agctatccgg cccgttatgc gaacgcaatg    840
gcagtcggag ctactgacca aaacaacaac cgcgccagct tttcacagta tggcgcaggg    900
cttgacatcg tcgcaccagg tgtaaacgtg cagagcacat acccaggttc aacgtatgcc    960
agcttaaacg gtacatcgat ggctactcct catgttgcag gtgcagcagt ccttgttaaa   1020
caaaagaacc catcttggtc caatgtacga atccgcgatc atctaaagaa tacggcaacg   1080
agcttaggaa gcacgaactt gtatggaagc ggacttgtca atgccgaagc tgcaactcgt   1140

<210> SEQ ID NO 765
<211> LENGTH: 380
<212> TYPE: PRT
<213> ORGANISM: Artificial
<220> FEATURE:
<223> OTHER INFORMATION: synthesized Bacillus lentus variant

<400> SEQUENCE: 765
```

```
Val Arg Ser Lys Lys Leu Trp Ile Val Ala Ser Thr Ala Leu Leu Ile
1               5                   10                  15

Ser Val Ala Phe Ser Ser Ile Ala Ser Ala Glu Glu Ala Lys
            20              25              30

Glu Lys Tyr Leu Ile Gly Phe Asn Glu Gln Glu Ala Val Ser Glu Phe
        35                  40                  45

Val Glu Gln Val Glu Ala Asn Asp Glu Val Ala Ile Leu Ser Glu Glu
50                  55                  60

Glu Glu Val Glu Ile Glu Leu Leu His Glu Phe Glu Thr Ile Pro Val
65                  70                  75                  80

Leu Ser Val Glu Leu Ser Pro Glu Asp Val Asp Ala Leu Glu Leu Asp
                85                  90                  95

Pro Ala Ile Ser Tyr Ile Glu Glu Asp Ala Glu Val Thr Thr Met Ala
                100                 105                 110

Gln Ser Val Pro Trp Gly Ile Ser Arg Val Gln Ala Pro Ala Ala His
            115                 120                 125

Asn Arg Gly Leu Thr Gly Ser Gly Val Lys Val Ala Val Leu Asp Thr
    130                 135                 140

Gly Ile Ser Thr His Pro Asp Leu Asn Ile Arg Gly Gly Ala Ser Phe
145                 150                 155                 160

Val Pro Gly Glu Pro Ser Thr Gln Asp Gly Asn Gly His Gly Thr His
                165                 170                 175

Val Ala Gly Thr Ile Ala Ala Leu Asn Asn Ser Ile Gly Val Leu Gly
                180                 185                 190

Val Ala Pro Ser Ala Glu Leu Tyr Ala Val Lys Val Leu Gly Ala Ser
                195                 200                 205

Gly Gly Gly Ala Ile Ser Ser Ile Ala Gln Gly Leu Glu Trp Ala Gly
210                 215                 220

Asn Asn Gly Met His Val Ala Asn Leu Ser Leu Gly Ser Pro Ser Pro
225                 230                 235                 240

Ser Ala Thr Leu Glu Gln Ala Val Asn Ser Ala Thr Ser Arg Gly Val
                245                 250                 255

Leu Val Val Ala Ala Ser Gly Asn Ser Gly Ala Asp Ser Ile Ser Tyr
                260                 265                 270

Pro Ala Arg Tyr Ala Asn Ala Met Ala Val Gly Ala Thr Asp Gln Asn
            275                 280                 285

Asn Asn Arg Ala Ser Phe Ser Gln Tyr Gly Ala Gly Leu Asp Ile Val
    290                 295                 300

Ala Pro Gly Val Asn Val Gln Ser Thr Tyr Pro Gly Ser Thr Tyr Ala
305                 310                 315                 320

Ser Leu Asn Gly Thr Ser Met Ala Thr Pro His Val Ala Gly Ala Ala
                325                 330                 335

Val Leu Val Lys Gln Lys Asn Pro Ser Trp Ser Asn Val Arg Ile Arg
            340                 345                 350

Asp His Leu Lys Asn Thr Ala Thr Ser Leu Gly Ser Thr Asn Leu Tyr
                355                 360                 365

Gly Ser Gly Leu Val Asn Ala Glu Ala Ala Thr Arg
    370                 375                 380

<210> SEQ ID NO 766
<211> LENGTH: 4
<212> TYPE: PRT
<213> ORGANISM: Artificial
<220> FEATURE:
<223> OTHER INFORMATION: synthetic reagent
```

```
<400> SEQUENCE: 766

Ala Ala Pro Phe
1
```